United States Patent
Blaquiere et al.

(10) Patent No.: US 9,546,178 B2
(45) Date of Patent: Jan. 17, 2017

(54) BENZOXAZEPIN PI3K INHIBITOR COMPOUNDS AND METHODS OF USE

(71) Applicant: Genentech, Inc., South San Francisco, CA (US)

(72) Inventors: Nicole Blaquiere, San Francisco, CA (US); Steven Do, San Jose, CA (US); Danette Dudley, Pacifica, CA (US); Adrian Folkes, Slough (GB); Robert Heald, Harlow (GB); Timothy Heffron, Burlingame, CA (US); Mark Jones, Harlow (GB); Aleksandr Kolesnikov, San Francisco, CA (US); Chudi Ndubaku, San Francisco, CA (US); Alan G. Olivero, Half Moon Bay, CA (US); Stephen Price, Harlow (GB); Steven Staben, San Francisco, CA (US); Lan Wang, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/930,929

(22) Filed: Nov. 3, 2015

(65) Prior Publication Data
US 2016/0052933 A1    Feb. 25, 2016

Related U.S. Application Data

(60) Continuation of application No. 14/297,142, filed on Jun. 5, 2014, now Pat. No. 9,198,918, which is a continuation of application No. 14/047,206, filed on Oct. 7, 2013, now Pat. No. 8,785,626, which is a continuation of application No. 13/681,763, filed on Nov. 20, 2012, now Pat. No. 8,586,574, which is a continuation of application No. 13/477,587, filed on May 22, 2012, now Pat. No. 8,343,955, which is a division of application No. 12/890,812, filed on Sep. 27, 2010, now Pat. No. 8,242,104.

(60) Provisional application No. 61/246,381, filed on Sep. 28, 2009, provisional application No. 61/330,685, filed on May 3, 2010.

(51) Int. Cl.
C07D 491/044 (2006.01)
C07D 498/04 (2006.01)
C07D 498/14 (2006.01)
C07D 519/00 (2006.01)
A61K 31/553 (2006.01)
A61K 45/06 (2006.01)

(52) U.S. Cl.
CPC ......... *C07D 491/044* (2013.01); *A61K 31/553* (2013.01); *A61K 45/06* (2013.01); *C07D 498/04* (2013.01); *C07D 498/14* (2013.01); *C07D 519/00* (2013.01)

(58) Field of Classification Search
CPC .. C07D 491/044; C07D 498/04; C07D 498/14
See application file for complete search history.

(56) References Cited

PUBLICATIONS

Meier et al. Helvetica Chimica Acta—vol. 68 (1985), pp. 1283-1300.*

* cited by examiner

*Primary Examiner* — Rebecca Anderson
(74) *Attorney, Agent, or Firm* — Alex Andrus

(57) ABSTRACT

Benzoxazepin compounds of Formula I, including stereoisomers, geometric isomers, tautomers, solvates, metabolites and pharmaceutically acceptable salts thereof, wherein: $Z^1$ is $CR^1$ or N; $Z^2$ is $CR^2$ or N; $Z^3$ is $CR^3$ or N; $Z^4$ is $CR^4$ or N; and B is a pyrazolyl, imidazolyl, or triazolyl ring fused to the benzoxepin ring, are useful for inhibiting lipid kinases including p110 alpha and other isoforms of PI3K, and for treating disorders such as cancer mediated by lipid kinases. Methods of using compounds of Formula I for in vitro, in situ, and in vivo diagnosis, prevention or treatment of such disorders in mammalian cells, or associated pathological conditions, are disclosed.

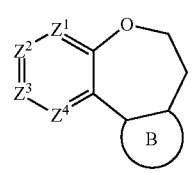

8 Claims, 16 Drawing Sheets

BENZOXAZEPIN PI3K INHIBITOR COMPOUNDS AND METHODS OF USE

CROSS REFERENCE TO RELATED APPLICATIONS

This application is a continuation of U.S. Ser. No. 14/297,142, filed 5 Jun. 2014, which is a continuation of U.S. Ser. No. 14/047,206, filed 7 Oct. 2013, now U.S. Pat. No. 8,785,626, which is a continuation of U.S. Ser. No. 13/681,763, filed 20 Nov. 2012, now U.S. Pat. No. 8,586,574, issued 19 Nov. 2013, which is a continuation of U.S. Ser. No. 13/477,587, filed 22 May 2012, now U.S. Pat. No. 8,343,955, issued 1 Jan. 2013, which is a divisional of U.S. Ser. No. 12/890,812, filed 27 Sep. 2010, now U.S. Pat. No. 8,242,104, issued 14 Aug. 2012, and claims the benefit under 35 USC §119(e) of U.S. Provisional Application Ser. No. 61/246,381 filed on 28 Sep. 2009 and U.S. Provisional Application Ser. No. 61/330,685 filed on 3 May 2010, all of which are incorporated by reference in entireties.

FIELD OF THE INVENTION

The invention relates generally to compounds with anti-cancer activity and more specifically to compounds which inhibit PI3 kinase activity. The invention also relates to methods of using the compounds for in vitro, in situ, and in vivo diagnosis or treatment of mammalian cells, or associated pathological conditions.

BACKGROUND OF THE INVENTION

Phosphatidylinositol (hereinafter abbreviated as "PI") is one of a number of phospholipids found in cell membranes. In recent years it has become clear that PI plays an important role in intracellular signal transduction. Cell signaling via 3'-phosphorylated phosphoinositides has been implicated in a variety of cellular processes, e.g., malignant transformation, growth factor signaling, inflammation, and immunity (Rameh et al (1999) J. Biol Chem, 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al (1992) Trends Cell Biol 2:358-60).

Phosphoinositide 3-kinases (PI3K) are lipid kinases that phosphorylate lipids at the 3-hydroxyl residue of an inositol ring (Whitman et al (1988) Nature, 332:664). The 3-phosphorylated phospholipids (PIP3s) generated by PI3-kinases act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al (2002) Nature Rev. Cancer 2:489; Phillips et al (1998) Cancer 83:41).

The main PI3-kinase isoform in cancer is the Class I PI3-kinase, p110α (alpha) (U.S. Pat. No. 5,824,492; U.S. Pat. No. 5,846,824; U.S. Pat. No. 6,274,327). Other isoforms are implicated in cardiovascular and immune-inflammatory disease (Workman P (2004) Biochem Soc Trans 32:393-396; Patel et al (2004) Proceedings of the American Association of Cancer Research (Abstract LB-247) 95th Annual Meeting, March 27-31, Orlando, Fla., USA; Ahmadi K and Waterfield MD (2004) Encyclopedia of Biological Chemistry (Lennarz W J, Lane M D eds) Elsevier/Academic Press).

The PI3 kinase/Akt/PTEN pathway is an attractive target for cancer drug development since such agents would be expected to inhibit proliferation, reverse the repression of apoptosis and surmount resistance to cytotoxic agents in cancer cells. PI3 kinase inhibitors have been reported (Folkes et al (2008) J. Med. Chem. 51:5522-5532; Yaguchi et al (2006) Jour. of the Nat. Cancer Inst. 98(8):545-556; U.S. Pat. Nos. 7,173,029; 7,037,915 ; 6,608,056; 6,608,053; 6,838,457; 6,770,641; 6,653,320; 6,403,588; 6,703,414; WO 97/15658; WO 2006/046031; WO 2006/046035; WO 2006/046040; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070), including p110 alpha binding activity (US 2008/0207611; US 2008/0039459; US 2008/0076768; WO 2008/073785; WO 2008/070740).

SUMMARY OF THE INVENTION

The invention relates generally to benzoxazepin compounds of Formula I with anti-cancer activity, and more specifically with PI3 kinase inhibitory activity. Certain hyperproliferative disorders are characterized by the modulation of PI3 kinase function, e.g. by mutations or overexpression of the proteins. Accordingly, the compounds of the invention may be useful in the treatment of hyperproliferative disorders such as cancer. The compounds may inhibit tumor growth in mammals and may be useful for treating human cancer patients.

The invention also relates to methods of using the benzoxazepin compounds of Formula I for in vitro, in situ, and in vivo diagnosis or treatment of mammalian cells, organisms, or associated pathological conditions.

Formula I compounds include:

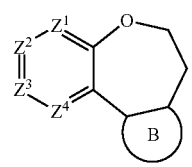

I

Formula I compounds include stereoisomers, geometric isomers, tautomers, or pharmaceutically acceptable salts thereof, wherein: Z1 is CR1 or N; Z2 is CR2 or N; Z3 is CR3 or N; Z4 is CR4 or N; B is a pyrazolyl, imidazolyl, or triazolyl ring fused to the benzoxepin ring. The various substituents are as defined herein.

Another aspect of the invention provides a pharmaceutical composition comprising a benzoxazepin compound of Formula I and a pharmaceutically acceptable carrier. The pharmaceutical composition may further comprise one or more additional therapeutic agent.

Another aspect of the invention provides methods of inhibiting PI3 kinase activity, comprising contacting a PI3 kinase with an effective inhibitory amount of a compound of Formula I.

Another aspect of the invention provides methods of preventing or treating a hyperproliferative disease or disorder modulated by PI3 kinases, comprising administering to a mammal in need of such treatment an effective amount of a compound of Formula I. Examples of such hyperproliferative disease or disorder include, but are not limited to, cancer.

Another aspect of the invention provides methods of preventing or treating a hyperproliferative disorder, comprising administering to a mammal in need of such treatment an effective amount of a compound of Formula I, alone or in combination with one or more additional compounds having anti-hyperproliferative properties.

In a further aspect the present invention provides a method of using a compound of this invention to treat a hyperproliferative disease or condition modulated by PI3 kinase in a mammal.

An additional aspect of the invention is the use of a compound of this invention for treating cancer modulated by PI3 kinase in a mammal.

Another aspect of the invention includes kits comprising a compound of Formula I, a container, and optionally a package insert or label indicating a treatment.

Another aspect of the invention includes methods of preparing, methods of separating, and methods of purifying compounds of Formula I.

Another aspect of the invention includes novel intermediates useful for preparing Formula I compounds.

DETAILED DESCRIPTION OF EXEMPLARY EMBODIMENTS

Figure 1:
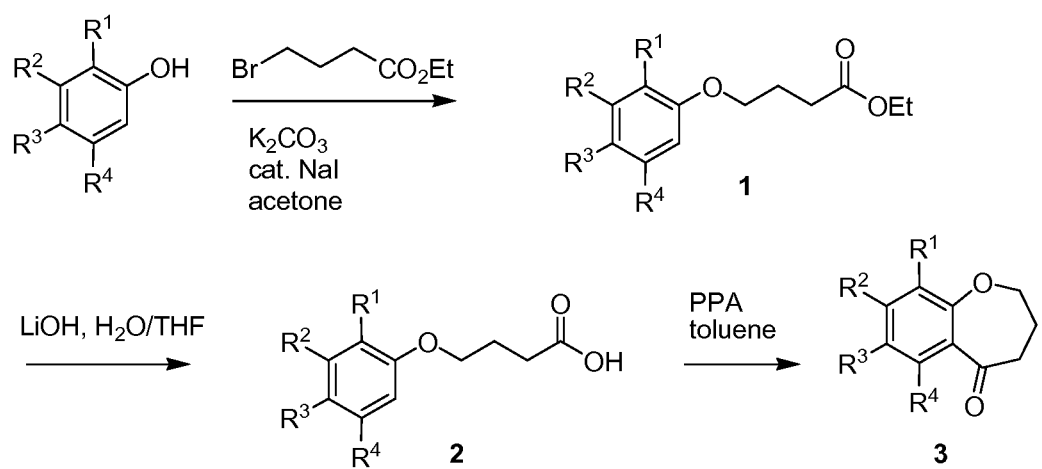
FIG. 1 shows a general exemplary route to benzoxepinone compounds 3

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

Definitions

The term "alkyl" as used herein refers to a saturated linear or branched-chain monovalent hydrocarbon radical of one to twelve carbon atoms (C1-C12), wherein the alkyl radical may be optionally substituted independently with one or more substituents described below. In another embodiment, an alkyl radical is one to eight carbon atoms (C1-C8), or one to six carbon atoms (C1-C6). Examples of alkyl groups include, but are not limited to, methyl (Me, —CH3), ethyl (Et, —CH2CH3), 1-propyl (n-Pr, n-propyl, —CH2CH2CH3), 2-propyl (i-Pr, i-propyl, —CH(CH3)2), 1-butyl (n-Bu, n-butyl, —CH2CH2CH2CH3), 2-methyl-1-propyl (i-Bu, i-butyl, —CH2CH(CH3)2), 2-butyl (s-Bu, s-butyl, —CH(CH3)CH2CH3), 2-methyl-2-propyl (t-Bu, t-butyl, —C(CH3)3), 1-pentyl (n-pentyl, —CH2CH2CH2CH2CH3), 2-pentyl (—CH(CH3)CH2CH2CH3), 3-pentyl (—CH(CH2CH3)2), 2-methyl-2-butyl (—C(CH3)2CH2CH3), 3-methyl-2-butyl (—CH(CH3)CH(CH3)2), 3-methyl-1-butyl (—CH2CH2CH(CH3)2), 2-methyl-1-butyl (—CH2CH(CH3)CH2CH3), 1-hexyl (—CH2CH2CH2CH2CH2CH3), 2-hexyl (—CH(CH3)CH2CH2CH2CH3), 3-hexyl (—CH(CH2CH3)(CH2CH2CH3)), 2-methyl-2-pentyl (—C(CH3)2CH2CH2CH3), 3-methyl-2-pentyl (—CH(CH3)CH(CH3)CH2CH3), 4-methyl-2-pentyl (—CH(CH3)CH2CH(CH3)2), 3-methyl-3-pentyl (—C(CH3)(CH2CH3)2), 2-methyl-3-pentyl (—CH(CH2CH3)CH(CH3)2), 2,3-dimethyl-2-butyl (—C(CH3)2CH(CH3)2), 3,3-dimethyl-2-butyl (—CH(CH3)C(CH3)3, 1-heptyl, 1-octyl, and the like.

The term "alkylene" as used herein refers to a saturated linear or branched-chain divalent hydrocarbon radical of one to twelve carbon atoms (C1-C12), wherein the alkylene radical may be optionally substituted independently with one or more substituents described below. In another embodiment, an alkylene radical is one to eight carbon atoms (C1-C8), or one to six carbon atoms (C1-C6). Examples of alkylene groups include, but are not limited to, methylene (—CH2-), ethylene (—CH2CH2-), propylene (—CH2CH2CH2-), and the like.

The term "alkenyl" refers to linear or branched-chain monovalent hydrocarbon radical of two to eight carbon atoms (C2-C8) with at least one site of unsaturation, i.e., a carbon-carbon, sp2 double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=CH2), allyl (—CH2CH=CH2), and the like.

The term "alkenylene" refers to linear or branched-chain divalent hydrocarbon radical of two to eight carbon atoms (C2-C8) with at least one site of unsaturation, i.e., a carbon-carbon, sp2 double bond, wherein the alkenyl radical may be optionally substituted, and includes radicals having "cis" and "trans" orientations, or alternatively, "E" and "Z" orientations. Examples include, but are not limited to, ethylenylene or vinylene (—CH=CH—), allyl (—CH2CH=CH—), and the like.

The term "alkynyl" refers to a linear or branched monovalent hydrocarbon radical of two to eight carbon atoms (C2-C8) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —CH2C≡CH), and the like.

The term "alkynylene" refers to a linear or branched divalent hydrocarbon radical of two to eight carbon atoms (C2-C8) with at least one site of unsaturation, i.e., a carbon-carbon, sp triple bond, wherein the alkynyl radical may be optionally. Examples include, but are not limited to, ethynylene (—C≡C—), propynylene (propargylene, —CH2C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms (C3-C12) as a monocyclic ring or 7 to 12 carbon atoms as a bicyclic ring. Bicyclic carbocycles having 7 to 12 atoms can be arranged, e.g., as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo [2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-20 carbon atoms (C6-C20) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms (C6-C20) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), e.g.: a bicyclo [4,5], [5,5], [5,6], or [6,6] system. Heterocycles are described in Paquette, Leo A.;

"Principles of Modern Heterocyclic Chemistry" (W.A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, e.g., 2-hydroxypyridinyl), imidazolyl, imidazopyridinyl, pyrimidinyl (including, e.g., 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, e.g., by assessing the time to disease progression (TTP) and/or determining the response rate (RR).

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer, regardless of mechanism of action. Classes of chemotherapeutic agents include, but are not limited to: alkyating agents, antimetabolites, spindle poison plant alkaloids, cytoxic/antitumor antibiotics, topoisomerase inhibitors, antibodies, photosensitizers, and kinase inhibitors. Chemotherapeutic agents include compounds used in "targeted therapy" and conventional chemotherapy.

Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), pemetrexed (ALIMTA®, Eli Lilly), trastuzumab (HERCEPTIN®, Genentech), temozolomide (4-methyl-5-oxo-2,3,4,6,8-pentazabicyclo[4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCINO), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclophosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1I (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-1-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, e.g., tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, e.g., 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, e.g., PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, e.g., ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the PI3K inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

A "metabolite" is a product produced through metabolism in the body of a specified compound or salt thereof. Metabolites of a compound may be identified using routine techniques known in the art and their activities determined using tests such as those described herein. Such products may result e.g. from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, e.g., treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, e.g., treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The terms "compound of this invention," and "compounds of the present invention" and "compounds of Formula I" include compounds of Formulas I and stereoisomers, geometric isomers, tautomers, solvates, metabolites, and pharmaceutically acceptable salts and prodrugs thereof.

Any formula or structure given herein, including Formula I compounds, is also intended to represent hydrates, solvates, and polymorphs of such compounds, and mixtures thereof.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I. Various isotopically labeled compounds of the present invention, e.g. those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, e.g. increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, e.g. increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

Benzoxazepin Compounds

The present invention provides benzoxazepin compounds, and pharmaceutical formulations thereof, which are potentially useful in the treatment of diseases, conditions and/or disorders modulated by PI3 kinases. More specifically, the present invention provides compounds of Formula I:

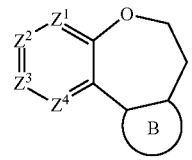

stereoisomers, geometric isomers, tautomers, and pharmaceutically acceptable salts thereof, wherein:

$Z^1$ is $CR^1$ or N;
$Z^2$ is $CR^2$ or N;
$Z^3$ is $CR^3$ or N;
$Z^4$ is $CR^4$ or N;
B is a pyrazolyl, imidazolyl, or triazolyl ring fused to the benzoxepin ring and selected from the structures:

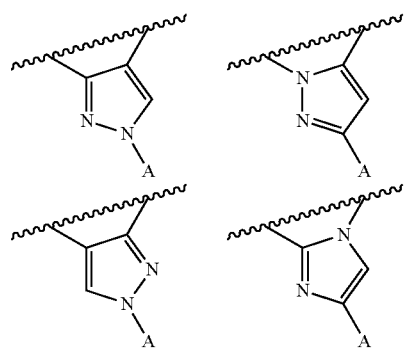

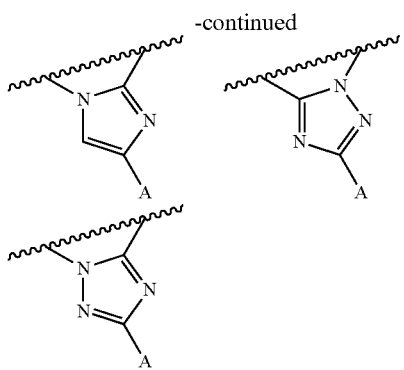

$R^1$, $R^2$, $R^3$, and $R^4$ are independently selected from H, F, Cl, Br, I, —CN, —COR$^{10}$, —CO$_2$R$^{10}$, —C(=O)N(R$^{10}$)OR$^{11}$, —C(=NR$^{10}$)NR$^{10}$R$^{11}$, —C(=O)NR$^{10}$R$^{11}$, —NO$_2$, —NR$^{10}$R$^{11}$, —NR$^{12}$C(=O)R$^{10}$, —NR$^{12}$C(=O)OR$^{11}$, —NR$^{12}$C(=O)NR$^{10}$R$^{11}$, —NR$^{12}$C(=O)(C$_1$-C$_{12}$ alkylene)NR$^{10}$R$^{11}$, —NR$^{12}$(C$_1$-C$_{12}$ alkylene)NR$^{10}$R$^{11}$, —NR$^{12}$(C$_1$-C$_{12}$ alkylene)OR$^{10}$, —NR$^{12}$(C$_1$-C$_{12}$ alkylene)C(=O)NR$^{10}$R$^{11}$, —OR$^{10}$, —SR$^{10}$, —S(O)$_2$R$^{10}$, —C(=O)NR$^{10}$(C$_1$-C$_{12}$ alkylene)NR$^{10}$R$^{11}$,
—C(=O)NR$^{10}$(C$_1$-C$_{12}$ alkylene)NR$^{10}$C(=O)OR$^{11}$,
—C(=O)NR$^{10}$(C$_1$-C$_{12}$ alkylene)NR$^{10}$C(=O)R$^{11}$,
—C(=O)NR$^{10}$(C$_1$-C$_{12}$ alkylene)R$^{10}$,
C$_1$-C$_{12}$ alkyl,
C$_2$-C$_8$ alkenyl,
C$_2$-C$_8$ alkynyl,
C$_3$-C$_{12}$ carbocyclyl,
C$_2$-C$_{20}$ heterocyclyl,
C$_6$-C$_{20}$ aryl,
C$_1$-C$_{20}$ heteroaryl,
—(C$_3$-C$_{12}$ carbocyclyl)-(C$_1$-C$_{12}$ alkyl),
—(C$_2$-C$_{20}$ heterocyclyl)-(C$_1$-C$_{12}$ alkyl),
—(C$_6$-C$_{20}$ aryl)-(C$_1$-C$_{12}$ alkyl),
—(C$_1$-C$_{20}$ heteroaryl)-(C$_1$-C$_{12}$ alkyl),
—(C$_1$-C$_{12}$ alkylene)-(C$_3$-C$_{12}$ carbocyclyl),
—(C$_1$-C$_{12}$ alkylene)-(C$_2$-C$_{20}$ heterocyclyl),
—(C$_1$-C$_{12}$ alkylene)-(C$_2$-C$_{20}$ heterocyclyl)-(C$_2$-C$_{20}$ heterocyclyl),
—(C$_1$-C$_{12}$ alkylene)-(C$_2$-C$_{20}$ heterocyclyl)-(C$_3$-C$_{12}$ carbocyclyl),
—(C$_1$-C$_{12}$ alkylene)-(C$_2$-C$_{20}$ heterocyclyl)-C(=O)—(C$_2$-C$_{20}$ heterocyclyl),
—(C$_1$-C$_{12}$ alkylene)-(C$_1$-C$_{20}$ heteroaryl),
—(C$_1$-C$_{12}$ alkylene)-(C$_2$-C$_{20}$ heterocyclyl)-(C$_1$-C$_{12}$ alkyl),
—(C$_1$-C$_{12}$ alkylene)-(C$_6$-C$_{20}$ aryl)-(C$_1$-C$_{12}$ alkyl),
—(C$_1$-C$_{12}$ alkylene)-(C$_1$-C$_{20}$ heteroaryl)-(C$_1$-C$_{12}$ alkyl),
—(C$_1$-C$_{12}$ alkylene)-C(=O)—(C$_2$-C$_{20}$ heterocyclyl),
—(C$_1$-C$_{12}$ alkylene)C(=O)OR$^{10}$,
—(C$_1$-C$_{12}$ alkylene)C(=O)NR$^{10}$R$^{11}$,
—(C$_1$-C$_{12}$ alkylene)-NR$^{10}$R$^{11}$,
—(C$_1$-C$_{12}$ alkylene)NR$^{12}$C(=O)R$^{10}$,
—(C$_1$-C$_{12}$ alkylene)OR$^{10}$,
—(C$_1$-C$_{12}$ alkylene)-NR$^{10}$—(C$_1$-C$_{12}$ alkylene)-(C$_1$-C$_{20}$ heteroaryl),
—(C$_1$-C$_{12}$ alkylene)-NR$^{10}$—(C$_1$-C$_{12}$ alkylene)-(C$_1$-C$_{20}$ heterocyclyl),
—(C$_1$-C$_{12}$ alkylene)-NR$^{10}$—(C$_1$-C$_{12}$ alkylene)-NHC(=O)—(C$_1$-C$_{20}$ heteroaryl),
—(C$_1$-C$_{12}$ alkylene)-(C$_2$-C$_{20}$ heterocyclyl)-NR$^{10}$R$^{11}$, and
—(C$_1$-C$_{12}$ alkylene)-(C$_2$-C$_{20}$ heterocyclyl)-(C$_1$-C$_{12}$ alkyl)-NR$^{10}$R$^{11}$, where alkyl, alkenyl, alkynyl, alkylene, carbocyclyl, heterocyclyl, aryl, and heteroaryl are optionally substituted with one or more groups independently selected from F, Cl, Br, I, R$^{10}$, —SR$^{10}$, —S(O)$_2$R$^{10}$, —S(O)$_2$NR$^{10}$R$^{11}$, —NR$^{10}$R$^{11}$, —NR$^{12}$C(O)R$^{10}$, —CO$_2$R$^{10}$, C(O)R$^{10}$, —CONR$^{10}$R$^{11}$, oxo, and —OR$^{10}$;

A is selected from —C(=O)NR$^5$R$^6$, —NR$^5$R$^6$, C$_6$-C$_{20}$ aryl, C$_2$-C$_{20}$ heterocyclyl and C$_1$-C$_{20}$ heteroaryl wherein aryl, heterocyclyl and heteroaryl are optionally substituted with one or more groups independently selected from F, Cl, Br, I, —CN, —COR$^{10}$, —CO$_2$R$^{10}$, —C(=O)N(R$^{10}$)OR$^{11}$, —C(=NR$^{10}$)NR$^{10}$R$^{11}$, —C(=O)NR$^{10}$R$^{11}$, —NO$_2$, —NR$^{10}$R$^{11}$, —NR$^{12}$C(=O)R$^{10}$, —NR$^{12}$C(=O)OR$^{11}$, —NR$^{12}$C(=O)NR$^{10}$R$^{11}$, —NR$^{12}$C(=O)(C$_1$-C$_{12}$ alkylene)NR$^{10}$R$^{11}$, —NR$^{12}$(C$_1$-C$_{12}$ alkylene)NR$^{10}$R$^{11}$, —NR$^{12}$(C$_1$-C$_{12}$ alkylene)OR$^{10}$, —NR$^{12}$(C$_1$-C$_{12}$ alkylene)C(=O)NR$^{10}$R$^{11}$, —OR$^{10}$, —S(O)$_2$R$^{10}$, —C(=O)NR$^{10}$(C$_1$-C$_{12}$ alkylene)NR$^{10}$R$^{11}$,
—C(=O)NR$^{10}$(C$_1$-C$_{12}$ alkylene)NR$^{10}$C(=O)OR$^{11}$,
—C(=O)NR$^{10}$(C$_1$-C$_{12}$ alkylene)NR$^{10}$C(=O)R$^{11}$,
—C(=O)NR$^{10}$(C$_1$-C$_{12}$ alkylene)R$^{10}$,
C$_1$-C$_{12}$ alkyl,
C$_2$-C$_8$ alkenyl,
C$_2$-C$_8$ alkynyl,
C$_3$-C$_{12}$ carbocyclyl,
C$_2$-C$_{20}$ heterocyclyl,
C$_6$-C$_{20}$ aryl,
C$_1$-C$_{20}$ heteroaryl,
—(C$_3$-C$_{12}$ carbocyclyl)-(C$_1$-C$_{12}$ alkyl),
—(C$_2$-C$_{20}$ heterocyclyl)-(C$_1$-C$_{12}$ alkyl),
—(C$_6$-C$_{20}$ aryl)-(C$_1$-C$_{12}$ alkyl),
—(C$_1$-C$_{20}$ heteroaryl)-(C$_1$-C$_{12}$ alkyl),
—(C$_1$-C$_{12}$ alkylene)-(C$_3$-C$_{12}$ carbocyclyl),
—(C$_1$-C$_{12}$ alkylene)-(C$_2$-C$_{20}$ heterocyclyl),
—(C$_1$-C$_{12}$ alkylene)-(C$_2$-C$_{20}$ heterocyclyl)-(C$_2$-C$_{20}$ heterocyclyl),
—(C$_1$-C$_{12}$ alkylene)-(C$_2$-C$_{20}$ heterocyclyl)-(C$_3$-C$_{12}$ carbocyclyl),
—(C$_1$-C$_{12}$ alkylene)-(C$_2$-C$_{20}$ heterocyclyl)-C(=O)—(C$_2$-C$_{20}$ heterocyclyl),
—(C$_1$-C$_{12}$ alkylene)-(C$_1$-C$_{20}$ heteroaryl),
—(C$_1$-C$_{12}$ alkylene)-(C$_2$-C$_{20}$ heterocyclyl)-(C$_1$-C$_{12}$ alkyl),
—(C$_1$-C$_{12}$ alkylene)-(C$_6$-C$_{20}$ aryl)-(C$_1$-C$_{12}$ alkyl),
—(C$_1$-C$_{12}$ alkylene)-(C$_1$-C$_{20}$ heteroaryl)-(C$_1$-C$_{12}$ alkyl),
—(C$_1$-C$_{12}$ alkylene)-C(=O)—(C$_2$-C$_{20}$ heterocyclyl),
—(C$_1$-C$_{12}$ alkylene)C(=O)OR$^{10}$,
—(C$_1$-C$_{12}$ alkylene)-NR$^{10}$R$^{11}$,
—(C$_1$-C$_{12}$ alkylene)NR$^{12}$C(=O)R$^{10}$,
—(C$_1$-C$_{12}$ alkylene)OR$^{10}$,
—(C$_1$-C$_{12}$ alkylene)-NR$^{10}$—(C$_1$-C$_{12}$ alkylene)-(C$_1$-C$_{20}$ heteroaryl),
—(C$_1$-C$_{12}$ alkylene)-NR$^{10}$—(C$_1$-C$_{12}$ alkylene)-(C$_1$-C$_{20}$ heterocyclyl),
—(C$_1$-C$_{12}$ alkylene)-NR$^{10}$—(C$_1$-C$_{12}$ alkylene)-NHC(=O)—(C$_1$-C$_{20}$ heteroaryl),
—(C$_1$-C$_{12}$ alkylene)-(C$_2$-C$_{20}$ heterocyclyl)-NR$^{10}$R$^{11}$, and
—(C$_1$-C$_{12}$ alkylene)-(C$_2$-C$_{20}$ heterocyclyl)-(C$_1$-C$_{12}$ alkyl)-NR$^{10}$R$^{11}$, where alkyl, alkenyl, alkynyl, alkylene, carbocyclyl, heterocyclyl, aryl, and heteroaryl are optionally substituted with one or more groups independently selected from F, Cl, Br, I, R$^{10}$, —SR$^{10}$, —S(O)$_2$R$^{10}$, —NR$^{10}$R$^{11}$, —NR$^{12}$C(O)R$^{10}$, —CO$_2$R$^{10}$, —C(O)R$^{10}$, —CONR$^{10}$R$^{11}$, and —OR$^{10}$;

R$^5$ is selected from H, and C$_1$-C$_{12}$ alkyl, optionally substituted with one or more groups independently selected from F, Cl, Br, I, —CN, —CO$_2$H, —CONH$_2$, —CONHCH$_3$, —NH₂, —NO₂, —N(CH₃)₂, —NHCOCH₃, —NHS(O)₂CH₃, —OH, —OCH₃, —OCH₂CH₃, —S(O)₂NH₂, and —S(O)₂CH₃;

R⁶ is selected from C₁-C₁₂ alkyl, C₃-C₁₂ carbocyclyl, C₂-C₂₀ heterocyclyl, C₁-C₂₀ heteroaryl, and C₆-C₂₀ aryl, each optionally substituted with one or more groups independently selected from F, Cl, Br, I, —CH₃, —CH₂OH, —CH₂C₆H₅, —CN, —CF₃, —CO₂H, —C(O)CH₃, —NH₂, —NO₂, —N(CH₃)₂, —NHCOCH₃, —NHS(O)₂CH₃, —OH, oxo, —OCH₃, —OCH₂CH₃, —S(O)₂NH₂, —S(O)₂CH₃, —C(=O)NR¹⁰(C₁-C₁₂ alkylene)NR¹⁰R¹¹, phenyl, pyridinyl, tetrahydro-furan-2-yl, 2,3-dihydro-benzofuran-2-yl, 1-isopropyl-pyrrolidin-3-ylmethyl, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, —C≡CR¹³, —CH=CHR¹³, and —C(=O)NR¹⁰R¹¹;

or R⁵ and R⁶ together with the nitrogen atom to which they are attached form C₂-C₂₀ heterocyclyl or C₁-C₂₀ heteroaryl, optionally substituted with one or more groups selected from F, Cl, Br, I, CH₃, C(CH₃)₃, —CH₂OH, —CH₂CH₂OH, —CH₂C₆H₅, pyridin-2-yl, 6-methyl-pyridin-2-yl, pyridin-4-yl, pyridin-3-yl, pyrimidin-2-yl, pyrazin-2-yl, tetrahydro-furan-carbonyl, 2-methoxy-phenyl, benzoyl, cyclopropylmethyl, (tetrahydrofuran-2-yl)methyl, 2,6-dimethyl-morpholin-4-yl, 4-methyl-piperazine-carbonyl, pyrrolidine-1-carbonyl, cyclopropanecarbonyl, 2,4-difluoro-phenyl, pyridin-2-ylmethyl, morpholin-4-yl, —CN, —CF₃, —CO₂H, —CONH₂, —CONHCH₃, —CON(CH₃)₂, —COCF₃, —COCH₃, —COCH(CH₃)₂, —NO₂, NHCH₃, —N(CH₃)₂, —N(CH₂CH₃)₂, —NHCOCH₃, —NCH₃COCH₃, —NHS(O)₂CH₃, —OH, —OCH₃, —OCH₂CH₃, —CH₂OCH₃, —CH₂CH₂OCH₃, —CH₂S(O)₂NHCH₃, —CH₂S(O)₂CH₂CH₃, —S(O)₂NHCH₃, —S(O)₂CH₂CH₃, —S(O)₂NH₂, —S(O)₂N(CH₃)₂ and —S(O)₂CH₃;

R¹⁰, R¹¹ and R¹² are independently selected from H, C₁-C₁₂ alkyl, —(C₁-C₁₂ alkylene)-(C₂-C₂₀ heterocyclyl), —(C₁-C₁₂ alkylene)-(C₆-C₂₀ aryl), —(C₁-C₁₂ alkylene)-(C₃-C₁₂ carbocyclyl), C₂-C₈ alkenyl, C₂-C₈ alkynyl, C₃-C₁₂ carbocyclyl, C₂-C₂₀ heterocyclyl, C₆-C₂₀ aryl, and C₁-C₂₀ heteroaryl, each of which are optionally substituted with one or more groups independently selected from F, Cl, Br, I, —CH₃, —CH₂CH₃, —CH(CH₃)₂, —CH₂OH, —CH₂OCH₃, —CH₂CH₂OH, —C(CH₃)₂OH, —CH₂C (CH₃)₂OH, —CH₂CH(CH₃)OH, —CH₂CO₂H, —CH₂CO₂CH₃, —CH₂NH₂, —(CH₂)₂N(CH₃)₂, —CH₂C₆H₅, —CN, —CF₃, —CO₂H, —C(O)CH₃, —C(O)CH(OH)CH₃, —CO₂CH₃, —CONH₂, —CONHCH₃, —CON(CH₃)₂, —C(CH₃)₂CONH₂, —NH₂, —NO₂, —N(CH₃)₂, —N(CH₃)C(CH₃)₂CONH₂, —N(CH₃)CH₂CH₂S(O)₂CH₃, —NHCOCH₃, —NHS(O)₂CH₃, =O(oxo), —OH, —OCH₃, —OCH₂CH₃, —OCH₂CH₂OH, —OP(O)(OH)₂, —SCH₃, —S(O)₂CH₃, —S(O)₂NH₂, —S(O)₂N(CH₃)₂, —CH₂S(O)₂NHCH₃, —CH₂S(O)₂CH₂CH₃, —S(O)₂NHCH₃, —S(O)₂CH₂CH₃, pyrrolidin-1-yl, 2-oxopyrrolidin-1-yl, cyclopropyl, cyclopentyl, oxetanyl, 4-methylpiperazin-1-yl, and 4-morpholinyl;

or R¹⁰ and R¹¹ together with the nitrogen atom to which they are attached form a C₂-C₂₀ heterocyclyl ring or C₁-C₂₀ heteroaryl each of which are optionally substituted with one or more groups independently selected from F, Cl, Br, I, —CH₃, —CH₂OH, —CH₂C₆H₅, —CN, —CF₃, —CO₂H, —CONH₂, —CONHCH₃, —NO₂, —N(CH₃)₂, —NHCOCH₃, —NHS(O)₂CH₃, —OH, oxo, —OCH₃, —OCH₂CH₃, —S(O)₂NH₂, —S(O)₂CH₃, —CH(CH₃)₂, —CH₂CF₃, —CH₂CH₂OH and —C(CH₃)₂OH; and R¹³ is selected from H, F, Cl, Br, I, —CH₃, —CH₂CH₃, —CN, —CF₃, —CH₂N(CH₃)₂, —CH₂OH, —CO₂H, —CONH₂, —CON(CH₃)₂, —NO₂, and —S(O)₂CH₃.

Exemplary embodiments include Formula Ia compounds wherein B is:

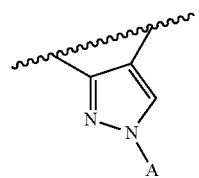

and has the structure:

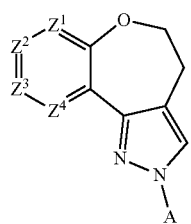

Ia

Exemplary embodiments include Formula Ib compounds wherein B is:

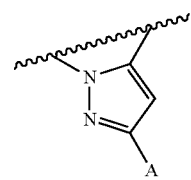

and has the structure:

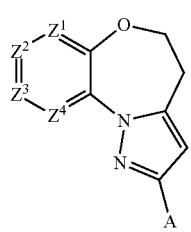

Ib

Exemplary embodiments include Formula Ic compounds wherein B is:

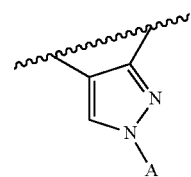

and has the structure:

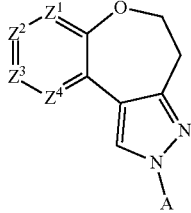

Ic

Exemplary embodiments include Formula Id compounds wherein B is:

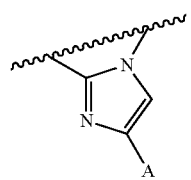

and has the structure:

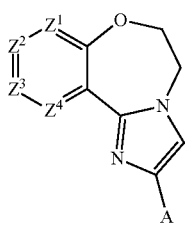

Id

Exemplary embodiments include Formula Ie compounds wherein B is:

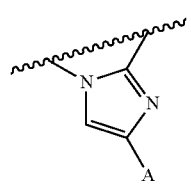

and has the structure:

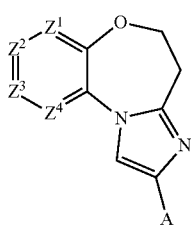

Ie

Exemplary embodiments include Formula If compounds wherein B is:

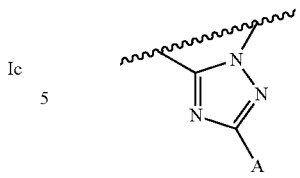

and has the structure:

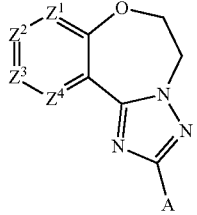

If

Exemplary embodiments include Formula Ig compounds wherein B is:

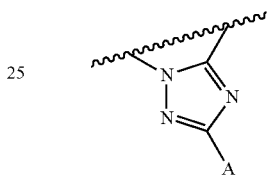

and has the structure:

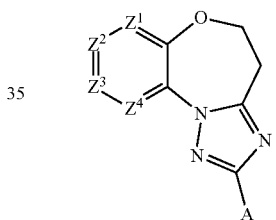

Ig

Exemplary embodiments of Formula I compounds include wherein $Z^1$ is $CR^1$; $Z^2$ is $CR^2$; $Z^3$ is $CR^3$; and $Z^4$ is $CR^4$.

Exemplary embodiments of Formula I compounds include wherein $Z^1$ is N; $Z^2$ is $CR^2$; $Z^3$ is $CR^3$; and $Z^4$ is $CR^4$.

Exemplary embodiments of Formula I compounds include wherein $Z^1$ is $CR^1$; $Z^2$ is N; $Z^3$ is $CR^3$; and $Z^4$ is $CR^4$.

Exemplary embodiments of Formula I compounds include wherein $Z^1$ is $CR^1$; $Z^2$ is $CR^2$; $Z^3$ is N; and $Z^4$ is $CR^4$.

Exemplary embodiments of Formula I compounds include wherein $Z^1$ is $CR^1$; $Z^2$ is $CR^2$; $Z^3$ is $CR^3$; and $Z^4$ is N.

Exemplary embodiments include Formula Ih compounds:

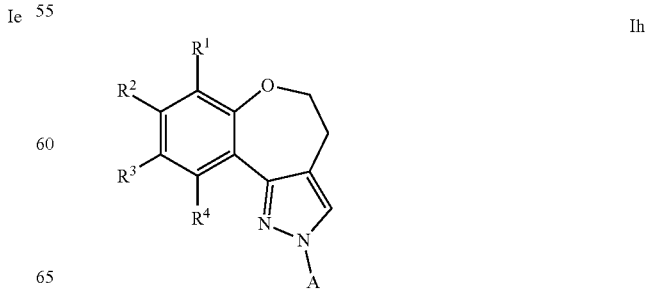

Ih

Exemplary embodiments include Formula Ii compounds:

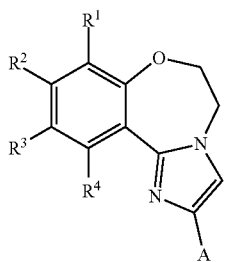

Exemplary embodiments include Formula Ij compounds:

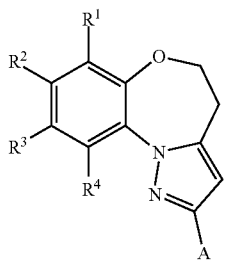

Exemplary embodiments include wherein $R^1$, $R^2$, $R^3$ and $R^4$ are independently selected from H, F, Cl, Br, I, CN, $NO_2$, and $C_1$-$C_6$ alkyl.

Exemplary embodiments include wherein $R^2$ and $R^3$ are independently selected from —$NR^{10}R^{11}$, —C(=O)$NR^{10}R^{11}$ and —($C_1$-$C_{12}$ alkylene)C(=O)$NR^{10}R^{11}$.

Exemplary embodiments include wherein $R^2$ and $R^3$ are independently selected from optionally substituted $C_3$-$C_{12}$ carbocyclyl, $C_2$-$C_{20}$ heterocyclyl, $C_6$-$C_{20}$ aryl, and $C_1$-$C_{20}$ heteroaryl.

Exemplary embodiments include wherein $R^2$ and $R^3$ are independently selected from optionally substituted azabicyclo[3.2.1]octanyl, azetidinyl, cyclopropyl, 3,8-diazabicyclo[3.2.1]octanyl, dihydropyrrolidinyl, imidazolyl, morpholinyl, oxetanyl, phenyl, piperazinone, piperazinyl, piperidyl, pyrazinyl, pyrazolyl, pyridinyl, pyridinone, pyrimidinyl, pyrrolidinyl, tetrahydropyranyl, and tetrahydropyridinyl.

Exemplary embodiments include wherein $R^2$ and $R^3$ are independently —$OR^{10}$.

Exemplary embodiments include wherein $R^2$ is —$OR^{10}$ and $Z^3$ is N.

Exemplary embodiments include wherein A is —C(=O)$NR^5R^6$.

Exemplary embodiments include wherein $R^5$ is $CH_3$.

Exemplary embodiments include wherein $R^6$ is phenyl substituted with one or more groups independently selected from F, Cl, Br, I, —$CH_2OH$, —$CH_2C_6H_5$, —CN, —$CF_3$, —$CO_2H$, —$CONH_2$, —$CONHCH_3$, —$NO_2$, —$N(CH_3)_2$, —$NHCOCH_3$, —$NHS(O)_2CH_3$, —OH, —$OCH_3$, —$OCH_2CH_3$, —$S(O)_2NH_2$, —$S(O)_2CH_3$, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, —C≡$CR^{13}$, and —CH=$CHR^{13}$.

Exemplary embodiments include wherein $R^5$ and $R^6$ together with the nitrogen atom to which they are attached form morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, or indolinyl.

Exemplary embodiments include wherein A is $C_2$-$C_{20}$ heterocyclyl or $C_1$-$C_{20}$ heteroaryl substituted with —$CH_2OH$, —$CH_2CO_2H$, —$CH(CH_3)CH_2OCH_3$, —$CH_3$, —$CH(CH_3)_2$, —$CH_2CH(CH_3)_2$, —$CH_2CF_3$, —C(=O)$CH_3$, —C(=O)$NHCH_3$, —C(=O)$N(CH_3)_2$, —$CO_2H$, —$CO_2CH_3$, —$CH_2CO_2CH_3$, —$NH_2$, —NHC(=O)$CH_3$, —OH, —$OCH_3$, —$S(O)_2CH_3$, 1-methylpiperid-4-yl, 4-methylpiperazin-1-yl, 4-morpholinyl, (4-methylpiperazin-1 yl)carboxamide, —$CH_2$(1H-1,2,4-triazol-5-yl), cyclopropyl, cyclopropylmethyl, or cyclobutyl.

Exemplary embodiments include wherein A is a $C_1$-$C_{20}$ heteroaryl selected from pyridyl, isoxazolyl, imidazolyl, pyrazolyl, pyrrolyl, thiazolyl, pyridazinyl, pyrimidinyl, pyrazinyl, oxazolyl, oxadiazolyl, 1,3,4-oxadiazol-2(3H)-one, furanyl, thienyl, 1,2,3-triazolyl, 1,2,4-triazolyl, 1,2,4-triazol-5(4H)-one, 4,5-dihydro-1,2,4-triazin-6(1H)-one, tetrazolyl, pyrrolo[2,3-b]pyridinyl, indazolyl, 3,4-dihydroquinolinyl, and benzo[d]thiazole.

Exemplary embodiments include wherein A is selected from the structures:

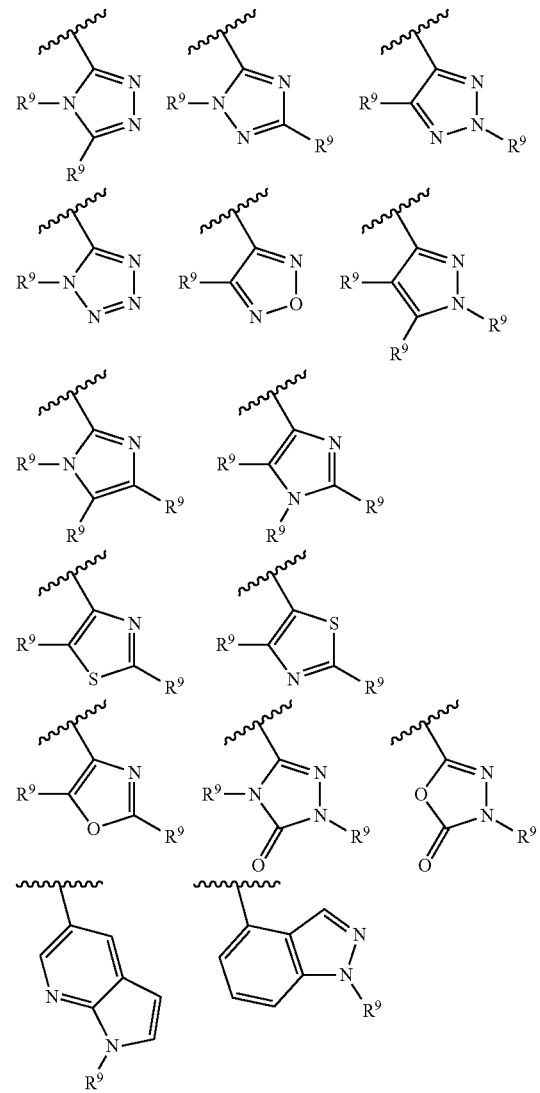

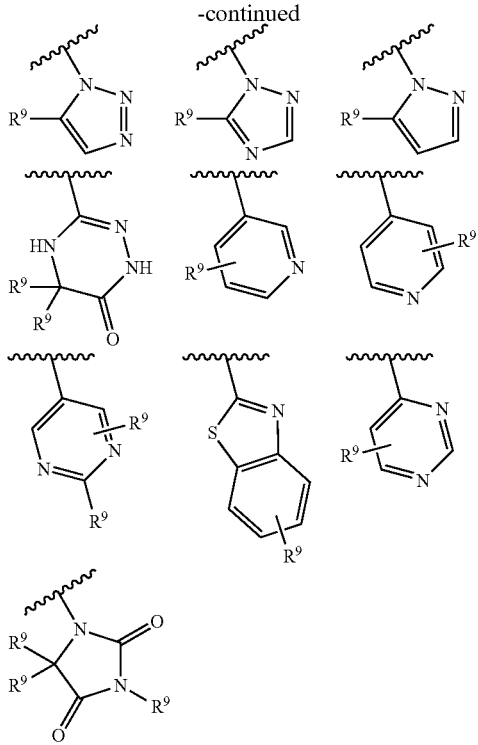

where $R^9$ is independently selected from H, F, Cl, Br, I, —CH₃, —CH₂CH₃, —CH(CH₃)₂, —C(CH₃)₃, —CH₂CH(CH₃)₂, —CH₂OH, —CH₂CO₂H, —CH(CH₃)CH₂OCH₃, —CN, —CF₃, —CH₂CF₃, —CH₂NH₂, —CH₂CH₂NH₂, —C(=O)CH₃, —CH₂C(=O)NHCH₃, —C(=O)NHCH₃, —CO₂H, —CH₂CO₂CH₃, —NH₂, —OH, —OCH₃, —SCH₃, —S(O)₂CH₃, cyclopropyl, cyclopropylmethyl, 1-methylpiperid-4-yl, 4-methylpiperazin-1-yl, 4-morpholinyl, morpholin-4-yl-ethyl, benzyl, and phenyl, where benzyl and phenyl are optionally substituted with one or more groups selected from F, Cl, Br, I, —CH₂OH, —CH₂CO₂H, —CN, —CH₂NH₂, —CH₃, —C(=O)CH₃, —C(=O)NHCH₃, —CO₂H, —CH₂CO₂CH₃, —NH₂, —OCH₃, —S(O)₂CH₃, 1-methylpiperid-4-yl, 4-methylpiperazin-1-yl, and 4-morpholinyl; and where the wavy line indicates the site of attachment.

Exemplary embodiments include wherein A is selected from the structures:

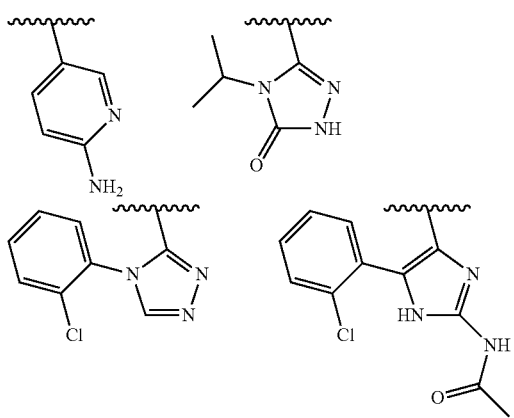

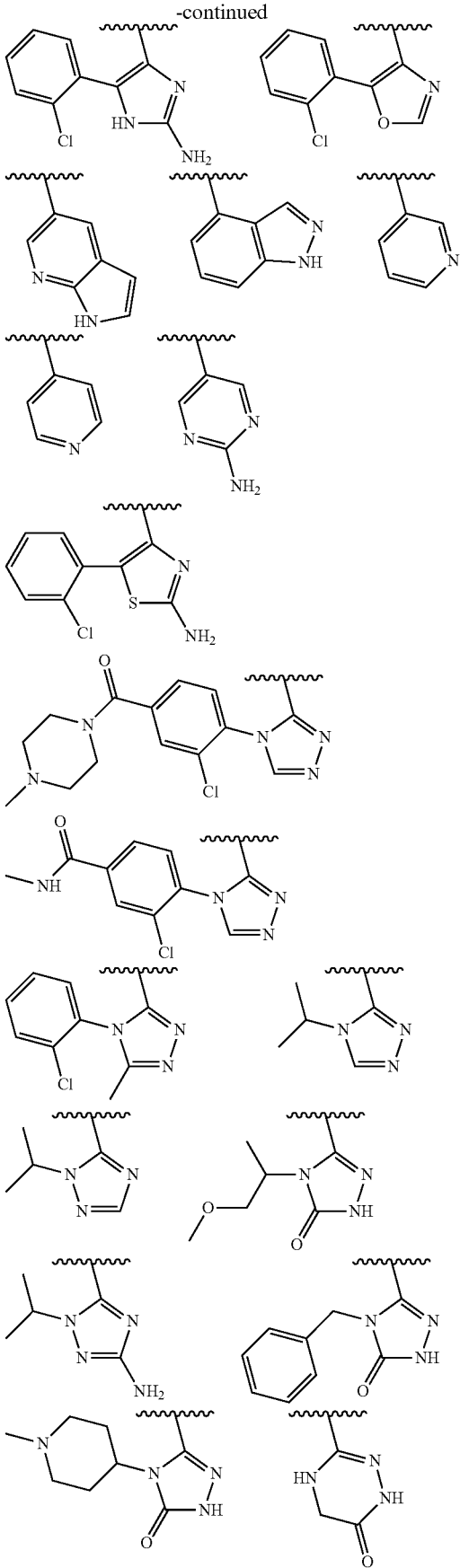

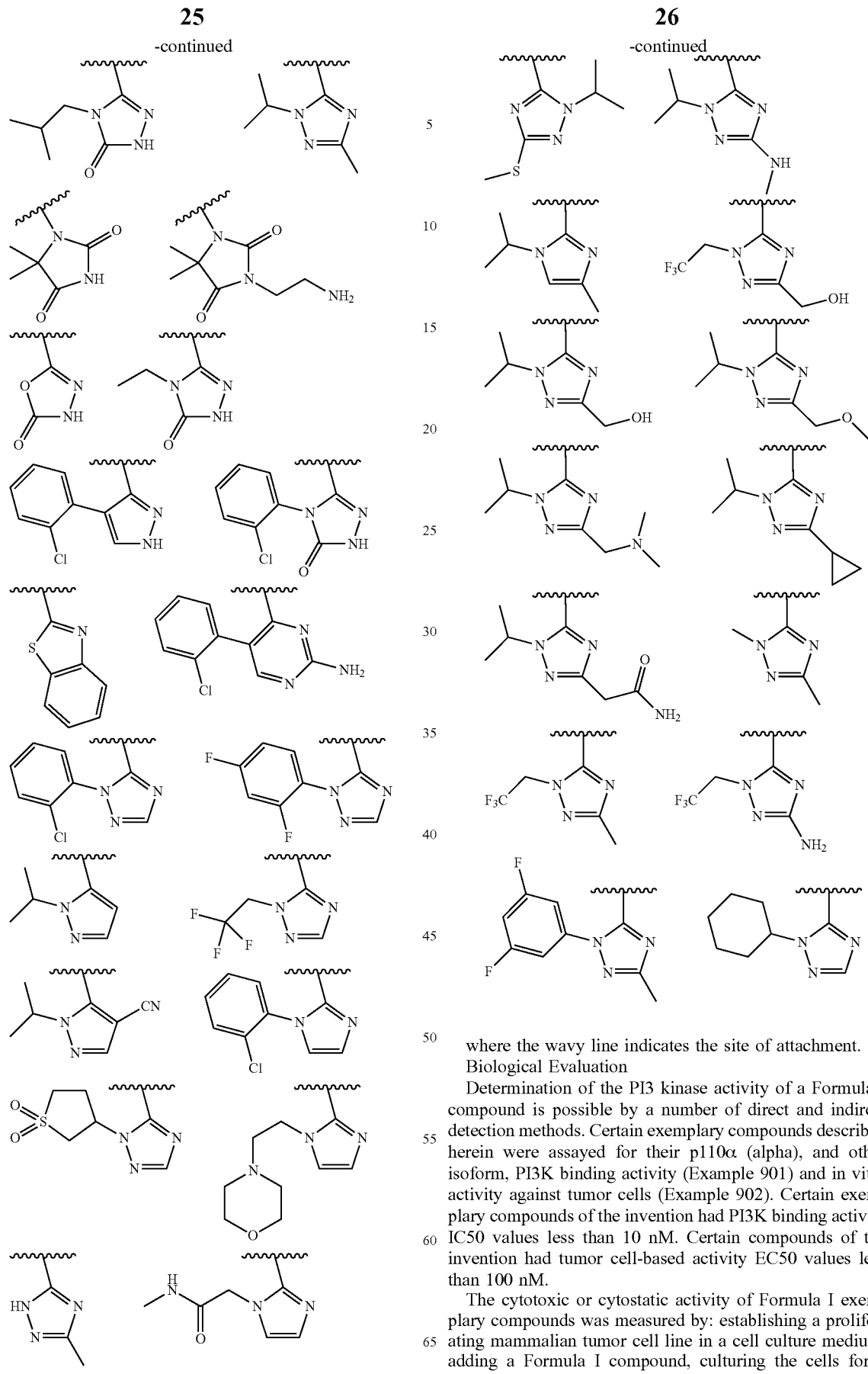

where the wavy line indicates the site of attachment.

Biological Evaluation

Determination of the PI3 kinase activity of a Formula I compound is possible by a number of direct and indirect detection methods. Certain exemplary compounds described herein were assayed for their p110α (alpha), and other isoform, PI3K binding activity (Example 901) and in vitro activity against tumor cells (Example 902). Certain exemplary compounds of the invention had PI3K binding activity IC50 values less than 10 nM. Certain compounds of the invention had tumor cell-based activity EC50 values less than 100 nM.

The cytotoxic or cytostatic activity of Formula I exemplary compounds was measured by: establishing a proliferating mammalian tumor cell line in a cell culture medium, adding a Formula I compound, culturing the cells for a period from about 6 hours to about 5 days; and measuring cell viability (Example 902). Cell-based in vitro assays were used to measure viability, i.e. proliferation (IC50), cytotoxicity (EC50), and induction of apoptosis (caspase activation).

The in vitro potency of Formula I exemplary compounds was measured by the cell proliferation assay, CellTiter-Glo® Luminescent Cell Viability Assay, commercially available from Promega Corp., Madison, Wis. (Example 902). This homogeneous assay method is based on the recombinant expression of Coleoptera luciferase (U.S. Pat. No. 5,583,024; U.S. Pat. No. 5,674,713; U.S. Pat. No. 5,700,670) and determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay was conducted in 96 or 384 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g. 96 or 384 well format. Data can be recorded by luminometer or CCD camera imaging device. The luminescence output is presented as relative light units (RLU), measured over time.

The anti-proliferative effects of Formula I exemplary compounds were measured by the CellTiter-Glo® Assay (Example 902) against several tumor cell lines. Potency EC50 values were established for the tested compounds. The range of in vitro cell potency activities was about 100 nM to about 10 µM. Certain tested compounds had EC50 values of less than 1 micromolar (1 µM) in stopping proliferation of certain tumor cell lines.

Certain ADME properties were measured for certain exemplary compounds by assays including: Caco-2 Permeability (Example 903), Hepatocyte Clearance (Example 904), Cytochrome P450 Inhibition (Example 905), Cytochrome P450 Induction (Example 906), Plasma Protein Binding (Example 907), and hERG channel blockage (Example 908).

Certain exemplary compounds were tested for efficacy by a dose escalation studies by administration in tumor xenograft Taconic nude mouse models (Example 909). The breast cancer cell line MDA-MB-361.1 mouse model was administered certain exemplary Formula I compounds along with Vehicle (MCT, negative control). The tumor growth delay was measured when dosed orally daily for 21 days at 50 and 100 mg/kg. Body weight change over the course of treatment was measured as an indicator of safety. Treatment of the MDA-MB-361.1 mouse model with certain exemplary Formula I compounds caused tumor growth stasis, inhibition, or regression when dosed orally daily for 21 days.

Exemplary Formula I compounds No. 101-294 in Table 1, No. 295-533 in Table 2, and No. 534-570 in Table 3 were made, characterized, and tested for inhibition of PI3K alpha ($IC_{50}$ or $K_i$ binding to p110 alpha less than 1 micromolar, µM) and selectivity according to the methods of this invention, and have the following structures and corresponding names (ChemDraw Ultra, Version 9.0.1, CambridgeSoft Corp., Cambridge Mass.). For example, compound 101 had an $IC_{50}$ of 0.77 micromole; compound 102 had an $IC_{50}$ of 0.0030 micromole; compound 103 had an $IC_{50}$ of 0.058 micromole; compound 154 had an $IC_{50}$ of 0.00091 micromole; compound 170 had an $IC_{50}$ of 0.022 micromole; compound 171 had an $IC_{50}$ of 0.00066 micromole; compound 180 had an $IC_{50}$ of 0.00018 micromole; compound 196 had an $IC_{50}$ of 0.00050 micromole; compound 200 had an $IC_{50}$ of 0.0020 micromole; compound 248 had an $IC_{50}$ of 0.00037 micromole; compound 251 had an $IC_{50}$ of 0.0014 micromole; compound 253 had an $IC_{50}$ of 0.0044 micromole; compound 280 had an $IC_{50}$ of 0.20 micromole; compound 338 had an $IC_{50}$ of 0.00032 micromole; compound 436 had a $K_i$ of 0.00024 micromole; and compound 520 had a $K_i$ of 0.0021 micromole.

TABLE 1

| No. | Structure | Name |
|---|---|---|
| 101 | 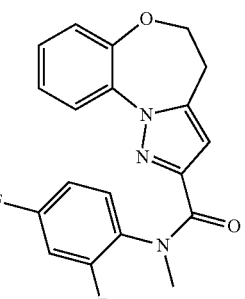 | N-(2,4-difluorophenyl)-N-methyl-4,5-dihydrobenzo[b]pyrazolo[1,5-d][1,4]oxazepine-2-carboxamide |

TABLE 1-continued

| No. | Structure | Name |
|-----|-----------|------|
| 102 | 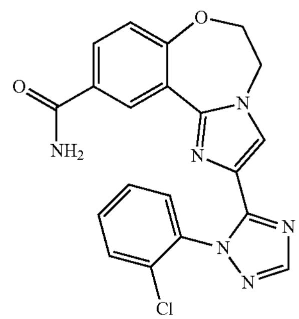 [SMILES: NC(=O)c1ccc2c(c1)-c1nc(-c3ncnn3-c3ccccc3Cl)cn1CCO2] | 2-(1-(2-chlorophenyl)-1H-1,2,4-triazol-5-yl)-5,6-dihydrobenzo[f]imidazo[1,2-d][1,4]oxazepine-10-carboxamide |
| 103 | 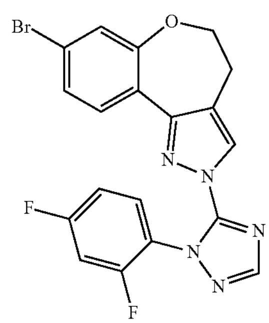 [SMILES: Fc1ccc(-n2ncnc2-n2cc3c(n2)-c2ccc(Br)cc2OCC3)c(F)c1] | 2-(1-(2,4-difluorophenyl)-1H-1,2,4-triazol-5-yl)-8-bromo-4,5-dihydrobenzo-2H-oxepino[4,5-d]pyrazole |
| 104 | 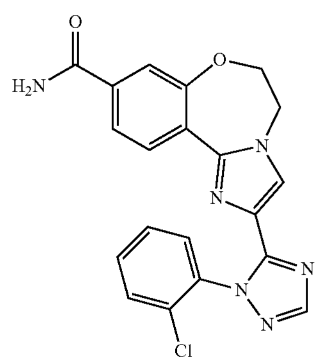 [SMILES: NC(=O)c1ccc2c(c1)OCCn1cc(-c3ncnn3-c3ccccc3Cl)nc1-2] | 2-(1-(2-chlorophenyl)-1H-1,2,4-triazol-5-yl)-5,6-dihydrobenzo[f]imidazo[1,2-d][1,4]oxazepine-9-carboxamide |
| 105 | 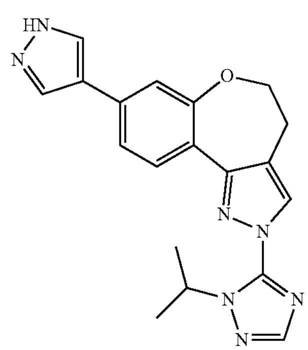 [SMILES: CC(C)n1ncnc1-n1cc2c(n1)-c1ccc(-c3cn[nH]c3)cc1OCC2] | 2-(1-isopropyl-1H-1,2,4-triazol-5-yl)-8-(pyrazol-4-yl)-4,5-dihydrobenzo-2H-oxepino[4,5-d]pyrazole |

TABLE 1-continued

| No. | Structure | Name |
|---|---|---|
| 106 | 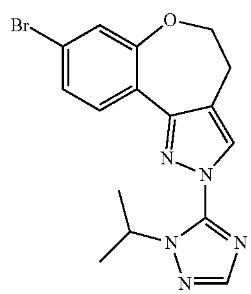 [SMILES: CC(C)n1ncnc1-n1cc2c(n1)-c1ccc(Br)cc1OCC2] | 2-(1-isopropyl-1H-1,2,4-triazol-5-yl)-8-bromo-4,5-dihydrobenzo-2H-oxepino[4,5-d]pyrazole |
| 107 | 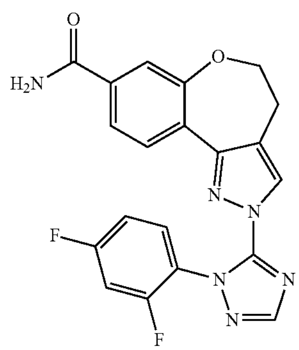 [SMILES: NC(=O)c1ccc2c(c1)OCCc1cn(-c3ncnn3-c3ccc(F)cc3F)nc1-2] | 2-(1-(2,4-difluorophenyl)-1H-1,2,4-triazol-5-yl)-4,5-dihydrobenzo-2H-oxepino[4,5-d]pyrazole-8-carboxamide |
| 108 | 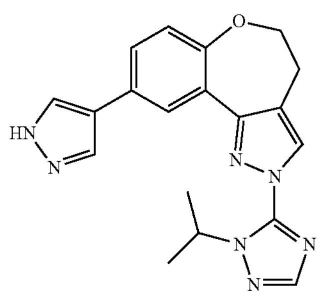 [SMILES: CC(C)n1ncnc1-n1cc2c(n1)-c1cc(-c3cn[nH]c3)ccc1OCC2] | 2-(4-isopropyl-4H-1,2,4-triazol-5-yl)-9-(pyrazol-4yl)-4,5-dihydrobenzo-2H-oxepino[4,5-d]pyrazole |
| 109 | 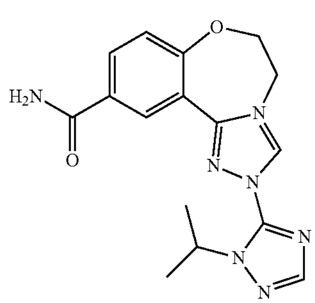 | 2-(1-isopropyl-1H-1,2,4-triazol-5-yl)-5,6-dihydrobenzo[f]imidazo[1,2-d][1,4]oxazepine-10-carboxamide |
| 110 | 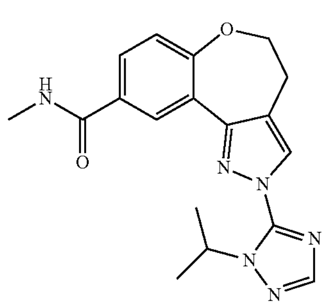 [SMILES: CNC(=O)c1ccc2c(c1)-c1nn(-c3ncnn3C(C)C)cc1CCO2] | 2-(1-isopropyl-1H-1,2,4-triazol-5-yl)-9-N-methyl-4,5-dihydrobenzo-2H-oxepino[4,5-d]pyrazole-9-carboxamide |

TABLE 1-continued

| No. | Structure | Name |
|---|---|---|
| 111 | 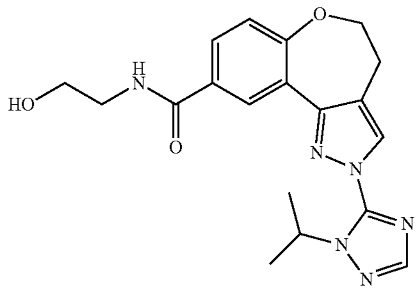 [SMILES: CC(C)n1ncnc1-n1cc2c(n1)-c1cc(C(=O)NCCO)ccc1OCC2] | 2-(1-isopropyl-1H-1,2,4-triazol-5-yl)-9-N-(2-hydroxyethyl)-4,5-dihydrobenzo-2H-oxepino[4,5-d]pyrazole-9-carboxamide |
| 112 | 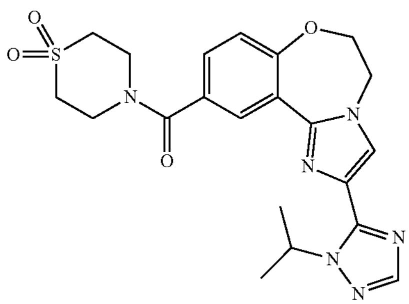 [SMILES: CC(C)n1ncnc1-c1cn2c(n1)-c1cc(C(=O)N3CCS(=O)(=O)CC3)ccc1OCC2] | (2-(1-isopropyl-1H-1,2,4-triazol-5-yl)-5,6-dihydrobenzo[f]imidazo[1,2-d][1,4]oxazepin-10-yl)(S-dioxothiomorpholino)methanone |
| 113 | 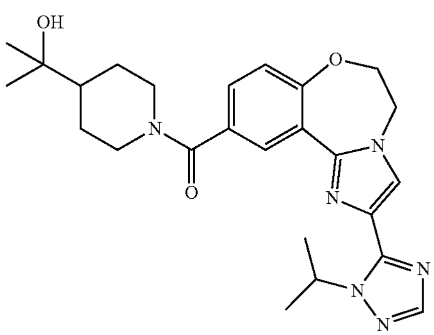 [SMILES: CC(C)n1ncnc1-c1cn2c(n1)-c1cc(C(=O)N3CCC(C(C)(C)O)CC3)ccc1OCC2] | (4-(2-hydroxypropan-2-yl)piperidin-1-yl)(2-(1-isopropyl-1H-1,2,4-triazol-5-yl)-5,6-dihydrobenzo[f]imidazo[1,2-d][1,4]oxazepin-10-yl)methanone |
| 114 | 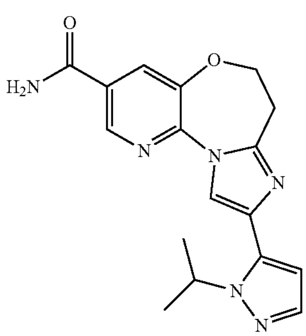 [SMILES: CC(C)n1nccc1-c1cn2c(n1)CCOc1cc(C(N)=O)cnc1-2] | 9-(1-isopropyl-1H-pyrazol-5-yl)-6,7-dihydroimidazo[1,2-d]pyrido[3,2-b][1,4]oxazepine-3-carboxamide |
| 115 | 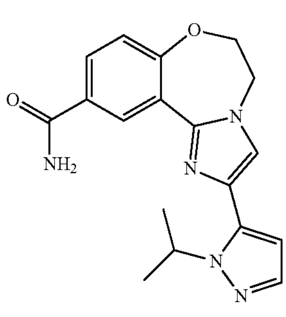 [SMILES: CC(C)n1nccc1-c1cn2c(n1)-c1cc(C(N)=O)ccc1OCC2] | 2-(1-isopropyl-1H-pyrazol-5-yl)-5,6-dihydrobenzo[f]imidazo[1,2-d][1,4]oxazepine-10-carboxamide |

TABLE 1-continued

| No. | Structure | Name |
|---|---|---|
| 116 | 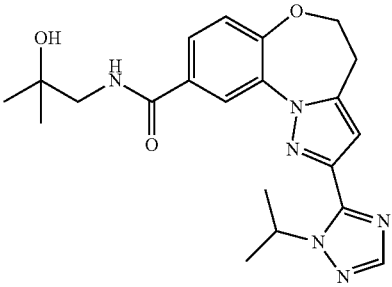 [SMILES: CC(C)n1ncnc1-c1cc2n(n1)-c1cc(C(=O)NCC(C)(C)O)ccc1OCC2] | N-(2-hydroxy-2-methylpropyl)-2-(1-isopropyl-1H-1,2,4-triazol-5-yl)-4,5-dihydrobenzo[b]pyrazolo[1,5-d][1,4]oxazepine-9-carboxamide |
| 117 | 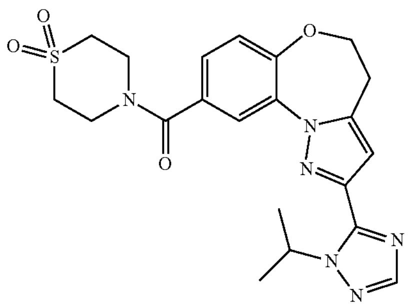 [SMILES: CC(C)n1ncnc1-c1cc2n(n1)-c1cc(C(=O)N3CCS(=O)(=O)CC3)ccc1OCC2] | (2-(1-isopropyl-1H-1,2,4-triazol-5-yl)-4,5-dihydrobenzo[b]pyrazolo[1,5-d][1,4]oxazepin-9-yl)(S-dioxothiomorpholino)methanone |
| 118 | 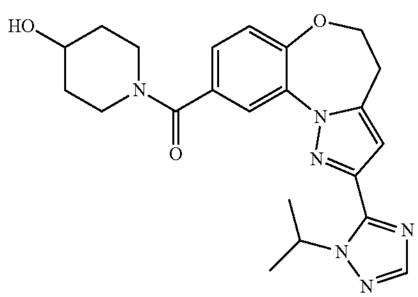 [SMILES: CC(C)n1ncnc1-c1cc2n(n1)-c1cc(C(=O)N3CCC(O)CC3)ccc1OCC2] | (4-hydroxypiperidin-1-yl)(2-(1-isopropyl-1H-1,2,4-triazol-5-yl)-4,5-dihydrobenzo[b]pyrazolo[1,5-d][1,4]oxazepin-9-yl)methanone |
| 119 | 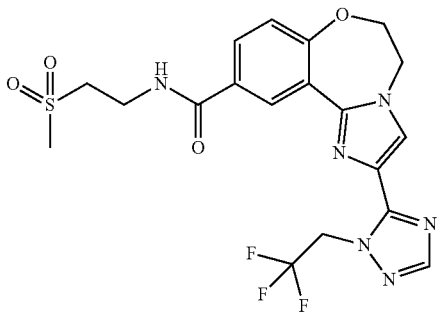 [SMILES: CS(=O)(=O)CCNC(=O)c1ccc2c(c1)-c1nc(-c3ncnn3CC(F)(F)F)cn1CCO2] | N-(2-(methylsulfonyl)ethyl)-2-(1-(2,2,2-trifluoroethyl)-1H-1,2,4-triazol-5-yl)-5,6-dihydrobenzo[f]imidazo[1,2-d][1,4]oxazepine-10-carboxamide |
| 120 | 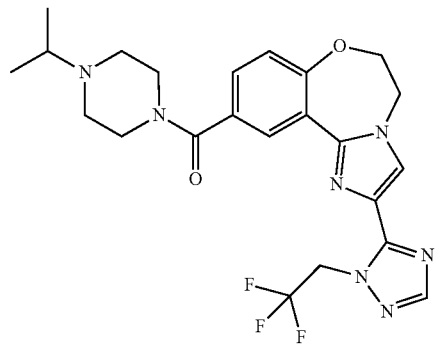 [SMILES: CC(C)N1CCN(C(=O)c2ccc3c(c2)-c2nc(-c4ncnn4CC(F)(F)F)cn2CCO3)CC1] | (4-isopropylpiperazin-1-yl)(2-(1-(2,2,2-trifluoroethyl)-1H-1,2,4-triazol-5-yl)-5,6-dihydrobenzo[f]imidazo[1,2-d][1,4]oxazepin-10-yl)methanone |

TABLE 1-continued

| No. | Structure | Name |
|---|---|---|
| 121 | 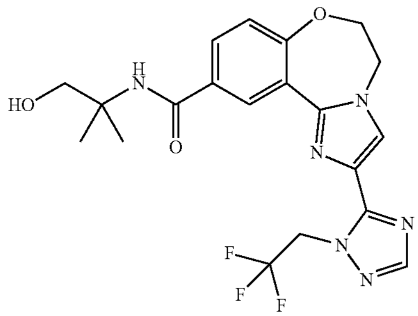 [SMILES: CC(C)(CO)NC(=O)c1ccc2c(c1)-c1nc(-c3ncnn3CC(F)(F)F)cn1CCO2] | N-(1-hydroxy-2-methylpropan-2-yl)-2-(1-(2,2,2-trifluoroethyl)-1H-1,2,4-triazol-5-yl)-5,6-dihydrobenzo[f]imidazo[1,2-d][1,4]oxazepine-10-carboxamide |
| 122 | 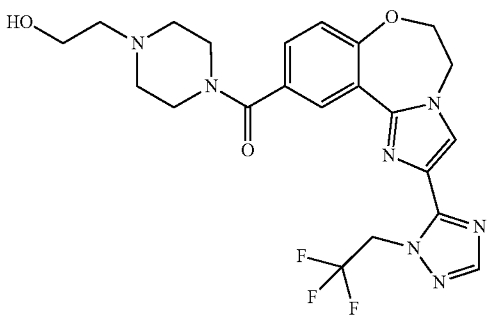 [SMILES: O=C(c1ccc2c(c1)-c1nc(-c3ncnn3CC(F)(F)F)cn1CCO2)N1CCN(CCO)CC1] | (4-(2-hydroxyethyl)piperazin-1-yl)(2-(1-(2,2,2-trifluoroethyl)-1H-1,2,4-triazol-5-yl)-5,6-dihydrobenzo[f]imidazo[1,2-d][1,4]oxazepin-10-yl)methanone |
| 123 | 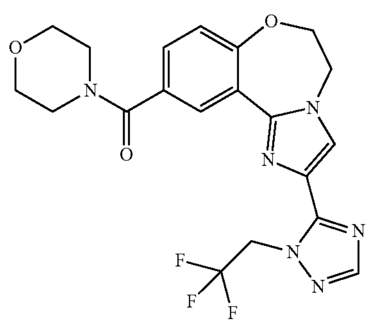 [SMILES: O=C(c1ccc2c(c1)-c1nc(-c3ncnn3CC(F)(F)F)cn1CCO2)N1CCOCC1] | morpholino(2-(1-(2,2,2-trifluoroethyl)-1H-1,2,4-triazol-5-yl)-5,6-dihydrobenzo[f]imidazo[1,2-d][1,4]oxazepin-10-yl)methanone |
| 124 | 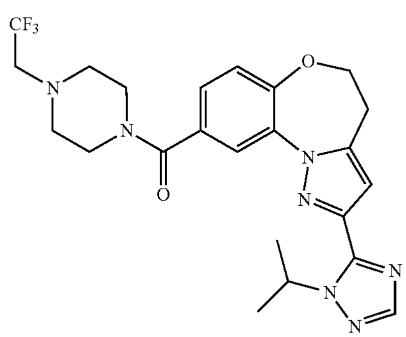 [SMILES: CC(C)n1ncnc1-c1cc2n(n1)-c1cc(C(=O)N3CCN(CC(F)(F)F)CC3)ccc1OCC2] | (2-(1-isopropyl-1H-1,2,4-triazol-5-yl)-4,5-dihydrobenzo[b]pyrazolo[1,5-d][1,4]oxazepin-9-yl)(4-(2,2,2-trifluoroethyl)piperazin-1-yl)methanone |
| 125 | 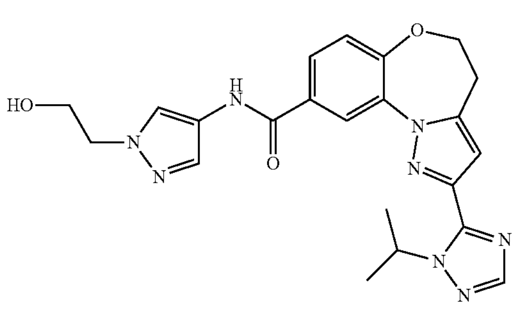 [SMILES: CC(C)n1ncnc1-c1cc2n(n1)-c1cc(C(=O)Nc3cnn(CCO)c3)ccc1OCC2] | N-(1-(2-hydroxyethyl)-1H-pyrazol-4-yl)-2-(1-isopropyl-1H-1,2,4-triazol-5-yl)-4,5-dihydrobenzo[b]pyrazolo[1,5-d][1,4]oxazepine-9-carboxamide |

TABLE 1-continued

| No. | Structure | Name |
|---|---|---|
| 126 | 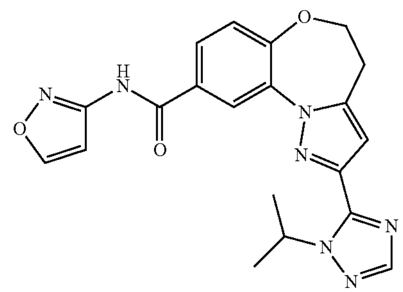 [SMILES: CC(C)n1ncnc1-c1cc2n(n1)-c1cc(C(=O)Nc3ccon3)ccc1OCC2] | 2-(1-isopropyl-1H-1,2,4-triazol-5-yl)-N-(isoxazol-3-yl)-4,5-dihydrobenzo[b]pyrazolo[1,5-d][1,4]oxazepine-9-carboxamide |
| 127 | 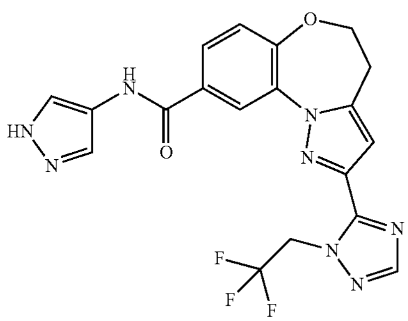 [SMILES: O=C(Nc1cn[nH]c1)c1ccc2c(c1)-n1nc(-c3ncnn3CC(F)(F)F)cc1CCO2] | N-(1H-pyrazol-4-yl)-2-(1-(2,2,2-trifluoroethyl)-1H-1,2,4-triazol-5-yl)-4,5-dihydrobenzo[b]pyrazolo[1,5-d][1,4]oxazepine-9-carboxamide |
| 128 | 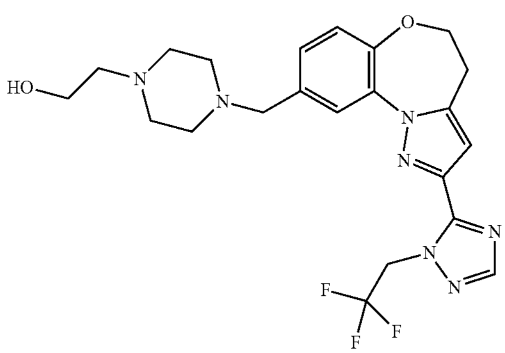 [SMILES: OCCN1CCN(Cc2ccc3c(c2)-n2nc(-c4ncnn4CC(F)(F)F)cc2CCO3)CC1] | 2-(4-((2-(1-(2,2,2-trifluoroethyl)-1H-1,2,4-triazol-5-yl)-4,5-dihydrobenzo[b]pyrazolo[1,5-d][1,4]oxazepin-9-yl)methyl)piperazin-1-yl)ethanol |
| 129 | 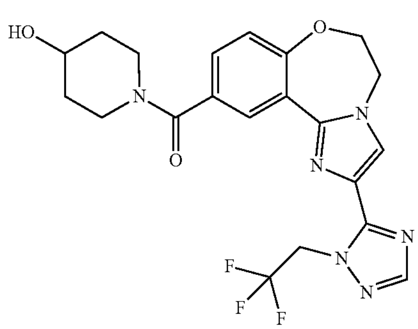 [SMILES: O=C(c1ccc2c(c1)-c1nc(-c3ncnn3CC(F)(F)F)cn1CCO2)N1CCC(O)CC1] | (4-hydroxypiperidin-1-yl)(2-(1-(2,2,2-trifluoroethyl)-1H-1,2,4-triazol-5-yl)-5,6-dihydrobenzo[f]imidazo[1,2-d][1,4]oxazepin-10-yl)methanone |

TABLE 1-continued

| No. | Structure | Name |
|---|---|---|
| 130 | 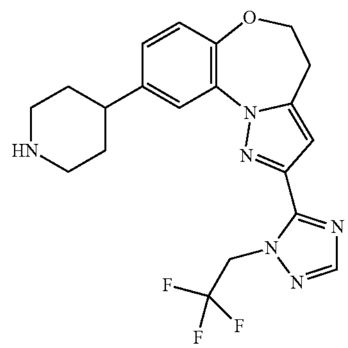 [SMILES: FC(F)(F)Cn1ncnc1-c1cc2n(n1)-c1cc(C3CCNCC3)ccc1OCC2] | 9-(piperidin-4-yl)-2-(1-(2,2,2-trifluoroethyl)-1H-1,2,4-triazol-5-yl)-4,5-dihydrobenzo[b]pyrazolo[1,5-d][1,4]oxazepine |
| 131 | 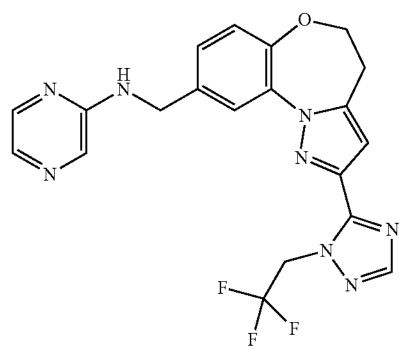 [SMILES: FC(F)(F)Cn1ncnc1-c1cc2n(n1)-c1cc(CNc3cnccn3)ccc1OCC2] | N-((2-(1-(2,2,2-trifluoroethyl)-1H-1,2,4-triazol-5-yl)-4,5-dihydrobenzo[b]pyrazolo[1,5-d][1,4]oxazepin-9-yl)methyl)pyrazin-2-amine |
| 132 | 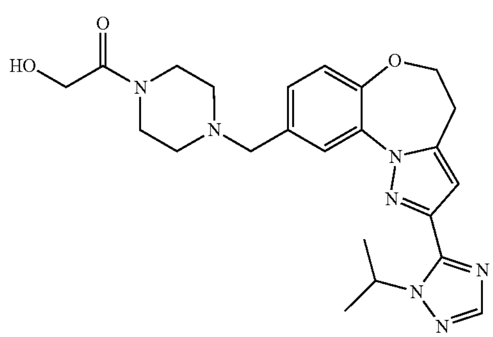 [SMILES: CC(C)n1ncnc1-c1cc2n(n1)-c1cc(CN3CCN(C(=O)CO)CC3)ccc1OCC2] | 2-hydroxy-1-(4-((2-(1-isopropyl-1H-1,2,4-triazol-5-yl)-4,5-dihydrobenzo[b]pyrazolo[1,5-d][1,4]oxazepin-9-yl)methyl)piperazin-1-yl)ethanone |
| 133 | 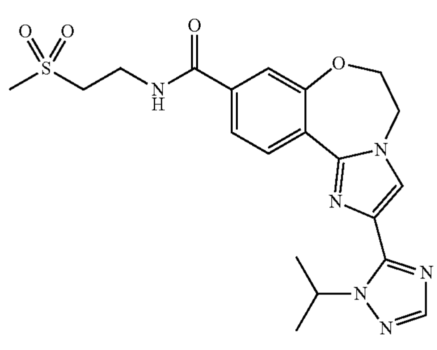 [SMILES: CC(C)n1ncnc1-c1cn2c(n1)-c1ccc(C(=O)NCCS(C)(=O)=O)cc1OCC2] | 2-(1-isopropyl-1H-1,2,4-triazol-5-yl)-N-(2-(methylsulfonyl)ethyl)-5,6-dihydrobenzo[f]imidazo[1,2-d][1,4]oxazepine-9-carboxamide |

TABLE 1-continued

| No. | Structure | Name |
|---|---|---|
| 134 | 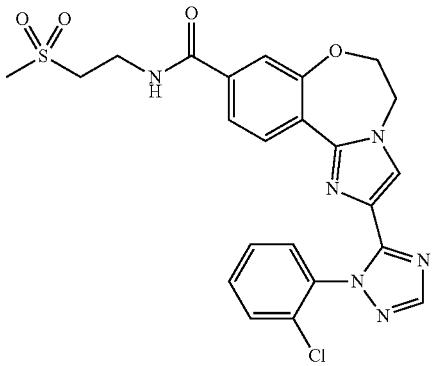 [SMILES: CS(=O)(=O)CCNC(=O)c1ccc2c(c1)OCCn1cc(-c3ncnn3-c3ccccc3Cl)nc1-2] | 2-(1-(2-chlorophenyl)-1H-1,2,4-triazol-5-yl)-N-(2-(methylsulfonyl)ethyl)-5,6-dihydrobenzo[f]imidazo[1,2-d][1,4]oxazepine-9-carboxamide |
| 135 | 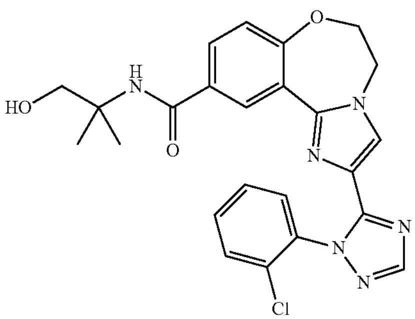 [SMILES: CC(C)(CO)NC(=O)c1ccc2c(c1)-c1nc(-c3ncnn3-c3ccccc3Cl)cn1CCO2] | 2-(1-(2-chlorophenyl)-1H-1,2,4-triazol-5-yl)-N-(1-hydroxy-2-methylpropan-2-yl)-5,6-dihydrobenzo[f]imidazo[1,2-d][1,4]oxazepine-10-carboxamide |
| 136 | 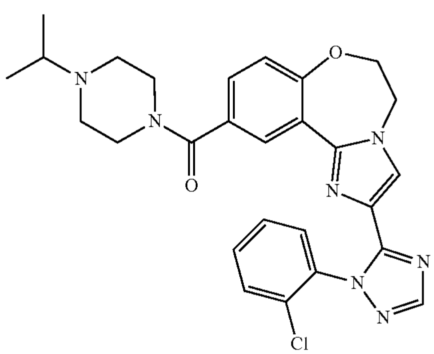 [SMILES: CC(C)N1CCN(C(=O)c2ccc3c(c2)-c2nc(-c4ncnn4-c4ccccc4Cl)cn2CCO3)CC1] | (2-(1-(2-chlorophenyl)-1H-1,2,4-triazol-5-yl)-5,6-dihydrobenzo[f]imidazo[1,2-d][1,4]oxazepin-10-yl)(4-isopropylpiperazin-1-yl)methanone |
| 137 | 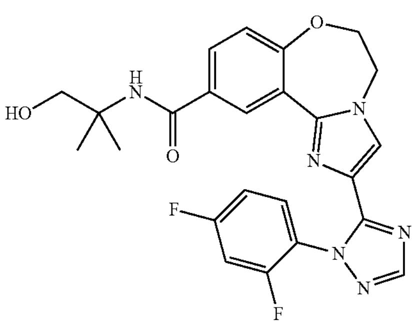 [SMILES: CC(C)(CO)NC(=O)c1ccc2c(c1)-c1nc(-c3ncnn3-c3ccc(F)cc3F)cn1CCO2] | 2-(1-(2,4-difluorophenyl)-1H-1,2,4-triazol-5-yl)-N-(1-hydroxy-2-methylpropan-2-yl)-5,6-dihydrobenzo[f]imidazo[1,2-d][1,4]oxazepine-10-carboxamide |

TABLE 1-continued

| No. | Structure | Name |
|---|---|---|
| 138 | 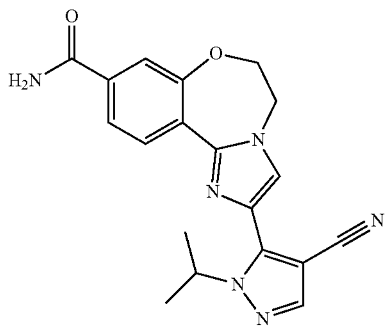 [SMILES: CC(C)n1ncc(C#N)c1-c1cn2c(n1)-c1ccc(C(N)=O)cc1OCC2] | 2-(4-cyano-1-isopropyl-1H-pyrazol-5-yl)-5,6-dihydrobenzo[f]imidazo[1,2-d][1,4]oxazepine-9-carboxamide |
| 139 | 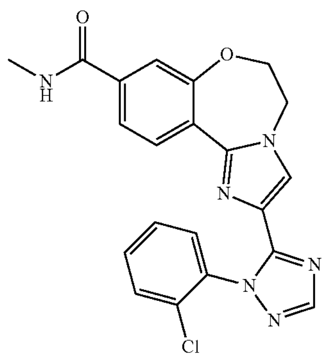 [SMILES: CNC(=O)c1ccc2c(c1)OCCn1cc(-c3ncnn3-c3ccccc3Cl)nc1-2] | 2-(1-(2-chlorophenyl)-1H-1,2,4-triazol-5-yl)-N-methyl-5,6-dihydrobenzo[f]imidazo[1,2-d][1,4]oxazepine-9-carboxamide |
| 140 | 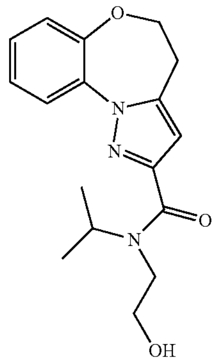 [SMILES: CC(C)N(CCO)C(=O)c1cc2n(n1)-c1ccccc1OCC2] | N-(2-hydroxyethyl)-N-isopropyl-4,5-dihydrobenzo[b]pyrazolo[1,5-d][1,4]oxazepine-2-carboxamide |
| 141 | 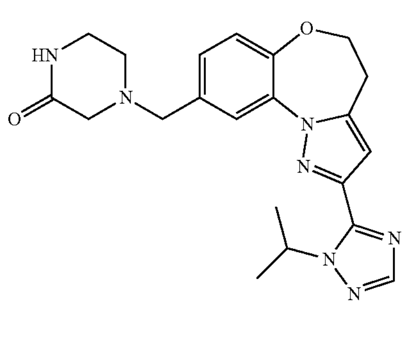 [SMILES: CC(C)n1ncnc1-c1cc2n(n1)-c1cc(CN3CCNC(=O)C3)ccc1OCC2] | 4-((2-(1-isopropyl-1H-1,2,4-triazol-5-yl)-4,5-dihydrobenzo[b]pyrazolo[1,5-d][1,4]oxazepin-9-yl)methyl)piperazin-2-one |

TABLE 1-continued

| No. | Structure | Name |
|---|---|---|
| 142 | 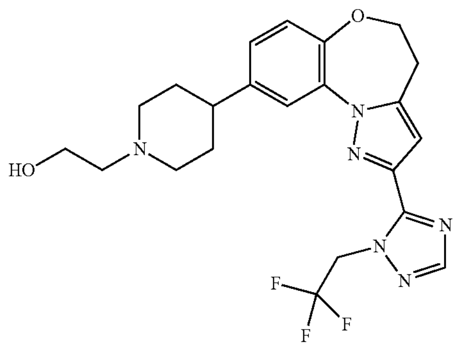 [SMILES: OCCN1CCC(c2ccc3c(c2)-n2nc(-c4ncnn4CC(F)(F)F)cc2CCO3)CC1] | 2-(4-(2-(1-(2,2,2-trifluoroethyl)-1H-1,2,4-triazol-5-yl)-4,5-dihydrobenzo[b]pyrazolo[1,5-d][1,4]oxazepin-9-yl)piperidin-1-yl)ethanol |
| 143 | 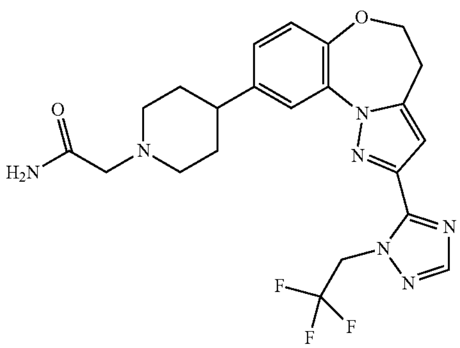 [SMILES: NC(=O)CN1CCC(c2ccc3c(c2)-n2nc(-c4ncnn4CC(F)(F)F)cc2CCO3)CC1] | 2-(4-(2-(1-(2,2,2-trifluoroethyl)-1H-1,2,4-triazol-5-yl)-4,5-dihydrobenzo[b]pyrazolo[1,5-d][1,4]oxazepin-9-yl)piperidin-1-yl)acetamide |
| 144 | 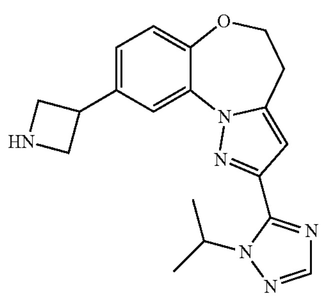 [SMILES: CC(C)n1ncnc1-c1cc2n(n1)-c1cc(C3CNC3)ccc1OCC2] | 9-(azetidin-3-yl)-2-(1-isopropyl-1H-1,2,4-triazol-5-yl)-4,5-dihydrobenzo[b]pyrazolo[1,5-d][1,4]oxazepine |
| 145 | 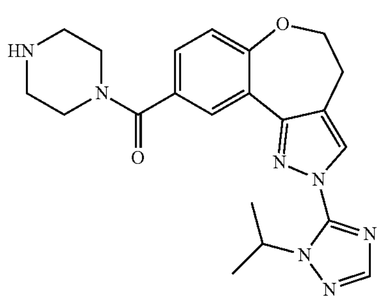 [SMILES: CC(C)n1ncnc1-n1cc2c(n1)-c1cc(C(=O)N3CCNCC3)ccc1OCC2] | 2-(1-isopropyl-1H-1,2,4-triazol-5-yl)-9-(piperazine-1-carbonyl)-4,5-dihydrobenzo-2H-oxepino[4,5-d]pyrazole |
| 146 | 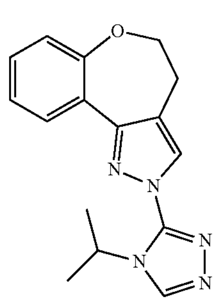 [SMILES: CC(C)n1cnnc1-n1cc2c(n1)-c1ccccc1OCC2] | 2-(4-isopropyl-4H-1,2,4-triazol-5-yl)-4,5-dihydrobenzo-2H-oxepino[4,5-d]pyrazole |

TABLE 1-continued

| No. | Structure | Name |
|---|---|---|
| 147 | 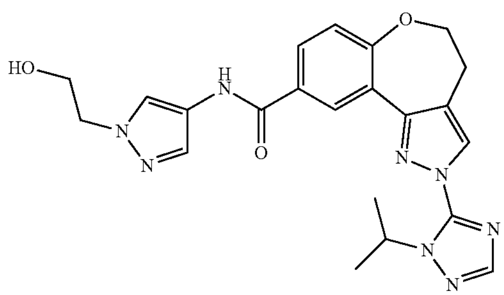 [SMILES: CC(C)n1ncnc1-n1cc2c(n1)-c1cc(C(=O)Nc3cnn(CCO)c3)ccc1OCC2] | 2-(1-isopropyl-1H-1,2,4-triazol-5-yl)-9-N-(1-(2-hydroxyethyl)-1H-pyrazol-4-yl)-4,5-dihydrobenzo-2H-oxepino[4,5-d]pyrazole-9-carboxamide |
| 148 | 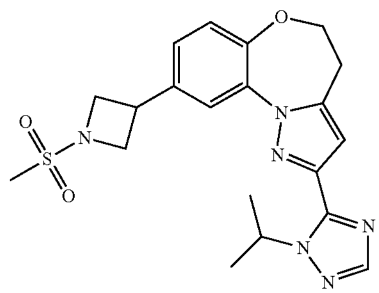 [SMILES: CC(C)n1ncnc1-c1cc2n(n1)-c1cc(C3CN(S(C)(=O)=O)C3)ccc1OCC2] | 2-(1-isopropyl-1H-1,2,4-triazol-5-yl)-9-(1-(methylsulfonyl)azetidin-3-yl)-4,5-dihydrobenzo[b]pyrazolo[1,5-d][1,4]oxazepine |
| 149 | 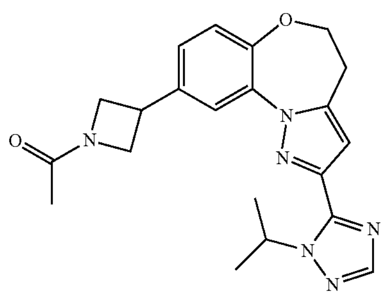 [SMILES: CC(=O)N1CC(c2ccc3c(c2)-n2nc(-c4ncnn4C(C)C)cc2CCO3)C1] | 1-(3-(2-(1-isopropyl-1H-1,2,4-triazol-5-yl)-4,5-dihydrobenzo[b]pyrazolo[1,5-d][1,4]oxazepin-9-yl)azetidin-1-yl)ethanone |
| 150 | 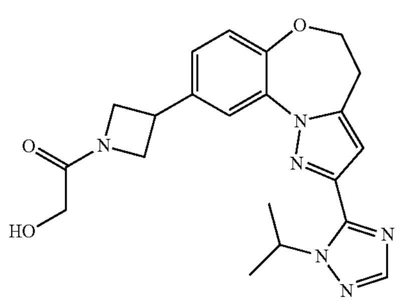 [SMILES: CC(C)n1ncnc1-c1cc2n(n1)-c1cc(C3CN(C(=O)CO)C3)ccc1OCC2] | 2-hydroxy-1-(3-(2-(1-isopropyl-1H-1,2,4-triazol-5-yl)-4,5-dihydrobenzo[b]pyrazolo[1,5-d][1,4]oxazepin-9-yl)azetidin-1-yl)ethanone |
| 151 | 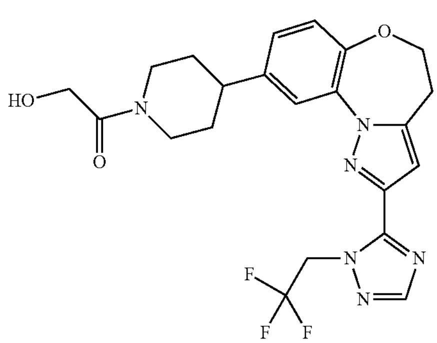 [SMILES: O=C(CO)N1CCC(c2ccc3c(c2)-n2nc(-c4ncnn4CC(F)(F)F)cc2CCO3)CC1] | 2-hydroxy-1-(4-(2-(1-(2,2,2-trifluoroethyl)-1H-1,2,4-triazol-5-yl)-4,5-dihydrobenzo[b]pyrazolo[1,5-d][1,4]oxazepin-9-yl)piperidin-1-yl)ethanone |

TABLE 1-continued

| No. | Structure | Name |
|---|---|---|
| 152 | 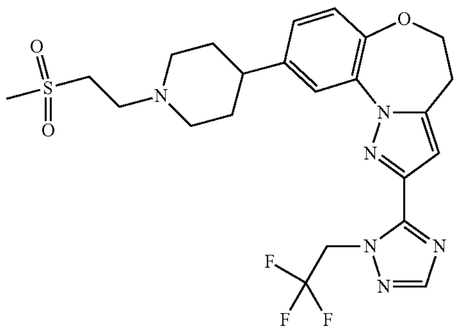 [SMILES: CS(=O)(=O)CCN1CCC(c2ccc3c(c2)-n2nc(-c4ncnn4CC(F)(F)F)cc2CCO3)CC1] | 9-(1-(2-(methylsulfonyl)ethyl)piperidin-4-yl)-2-(1-(2,2,2-trifluoroethyl)-1H-1,2,4-triazol-5-yl)-4,5-dihydrobenzo[b]pyrazolo[1,5-d][1,4]oxazepine |
| 153 | 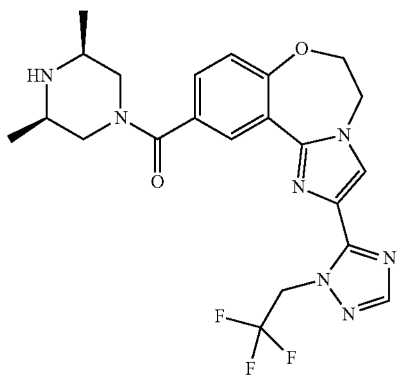 [SMILES: C[C@@H]1CN(C(=O)c2ccc3c(c2)-c2nc(-c4ncnn4CC(F)(F)F)cn2CCO3)C[C@H](C)N1] | ((3S,5R)-3,5-dimethylpiperazin-1-yl)(2-(1-(2,2,2-trifluoroethyl)-1H-1,2,4-triazol-5-yl)-5,6-dihydrobenzo[f]imidazo[1,2-d][1,4]oxazepin-10-yl)methanone |
| 154 | 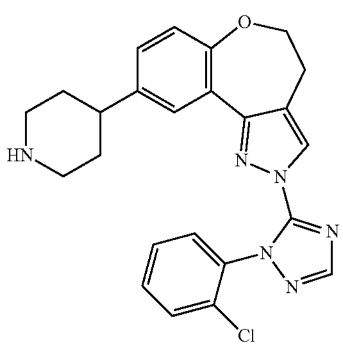 [SMILES: Clc1ccccc1-n1ncnc1-n1cc2c(n1)-c1cc(C3CCNCC3)ccc1OCC2] | 2-(1-(2-chlorophenyl)-1H-1,2,4-triazol-5-yl)-9-piperid-4-yl-4,5-dihydrobenzo-2H-oxepino[4,5-d]pyrazole |
| 155 | 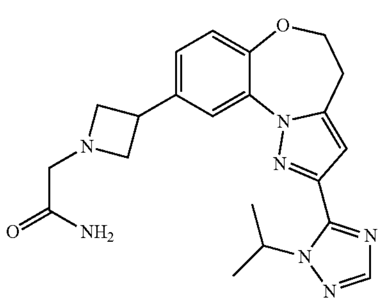 [SMILES: CC(C)n1ncnc1-c1cc2n(n1)-c1cc(C3CN(CC(N)=O)C3)ccc1OCC2] | 2-(3-(2-(1-isopropyl-1H-1,2,4-triazol-5-yl)-4,5-dihydrobenzo[b]pyrazolo[1,5-d][1,4]oxazepin-9-yl)azetidin-1-yl)acetamide |

TABLE 1-continued

| No. | Structure | Name |
|---|---|---|
| 156 | 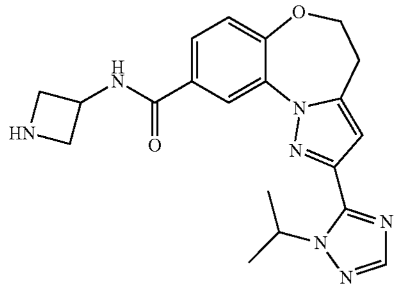 [SMILES: CC(C)n1ncnc1-c1cc2n(n1)-c1cc(C(=O)NC3CNC3)ccc1OCC2] | N-(azetidin-3-yl)-2-(1-isopropyl-1H-1,2,4-triazol-5-yl)-4,5-dihydrobenzo[b]pyrazolo[1,5-d][1,4]oxazepine-9-carboxamide |
| 157 | 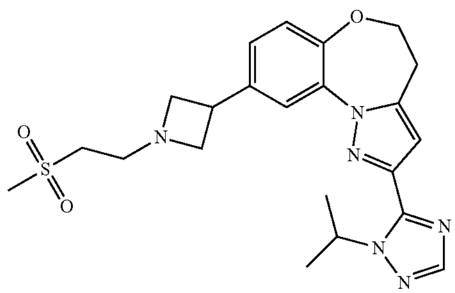 [SMILES: CC(C)n1ncnc1-c1cc2n(n1)-c1cc(C3CN(CCS(C)(=O)=O)C3)ccc1OCC2] | 2-(1-isopropyl-1H-1,2,4-triazol-5-yl)-9-(1-(2-(methylsulfonyl)ethyl)azetidin-3-yl)-4,5-dihydrobenzo[b]pyrazolo[1,5-d][1,4]oxazepine |
| 158 | 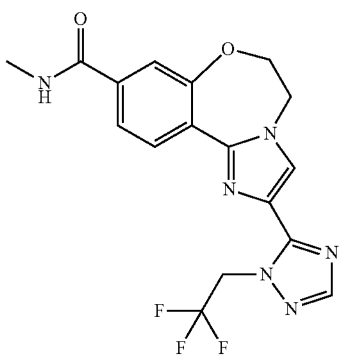 [SMILES: CNC(=O)c1ccc2c(c1)OCCn1cc(-c3ncnn3CC(F)(F)F)nc1-2] | N-methyl-2-(1-(2,2,2-trifluoroethyl)-1H-1,2,4-triazol-5-yl)-5,6-dihydrobenzo[f]imidazo[1,2-d][1,4]oxazepine-9-carboxamide |
| 159 | 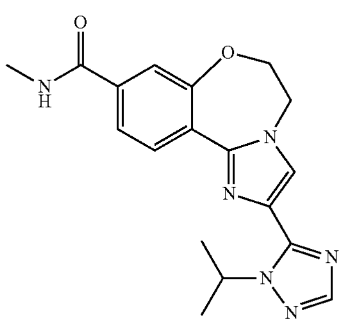 [SMILES: CNC(=O)c1ccc2c(c1)OCCn1cc(-c3ncnn3C(C)C)nc1-2] | 2-(1-isopropyl-1H-1,2,4-triazol-5-yl)-N-methyl-5,6-dihydrobenzo[f]imidazo[1,2-d][1,4]oxazepine-9-carboxamide |
| 160 | 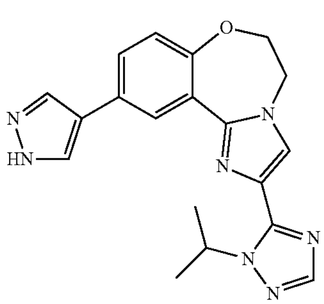 [SMILES: CC(C)n1ncnc1-c1cn2c(n1)-c1cc(-c3cn[nH]c3)ccc1OCC2] | 2-(1-isopropyl-1H-1,2,4-triazol-5-yl)-10-(1H-pyrazol-4-yl)-5,6-dihydrobenzo[f]imidazo[1,2-d][1,4]oxazepine |

TABLE 1-continued

| No. | Structure | Name |
|---|---|---|
| 161 | 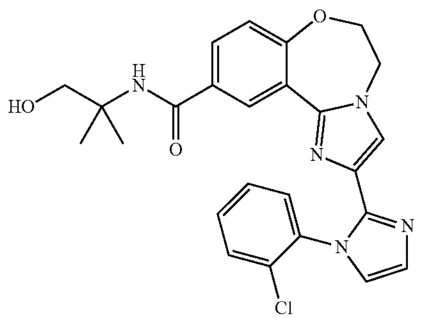 | 2-(1-(2-chlorophenyl)-1H-imidazol-2-yl)-N-(1-hydroxy-2-methylpropan-2-yl)-5,6-dihydrobenzo[f]imidazo[1,2-d][1,4]oxazepine-10-carboxamide |
| 162 | 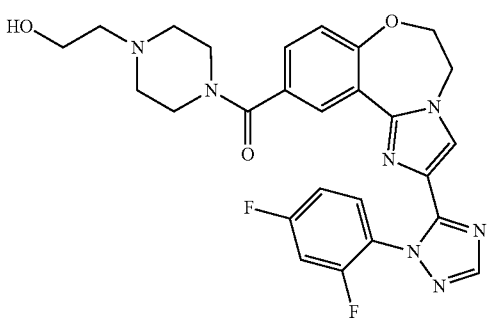 [SMILES: O=C(c1ccc2c(c1)-c1nc(-c3ncnn3-c3ccc(F)cc3F)cn1CCO2)N1CCN(CCO)CC1] | (2-(1-(2,4-difluorophenyl)-1H-1,2,4-triazol-5-yl)-5,6-dihydrobenzo[f]imidazo[1,2-d][1,4]oxazepin-10-yl)(4-(2-hydroxyethyl)piperazin-1-yl)methanone |
| 163 | 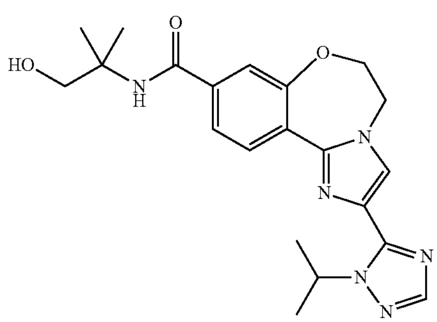 [SMILES: CC(C)n1ncnc1-c1cn2c(n1)-c1ccc(C(=O)NC(C)(C)CO)cc1OCC2] | N-(1-hydroxy-2-methylpropan-2-yl)-2-(1-isopropyl-1H-1,2,4-triazol-5-yl)-5,6-dihydrobenzo[f]imidazo[1,2-d][1,4]oxazepine-9-carboxamide |
| 164 | 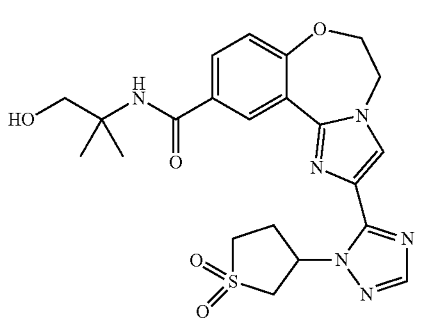 [SMILES: CC(C)(CO)NC(=O)c1ccc2c(c1)-c1nc(-c3ncnn3C3CCS(=O)(=O)C3)cn1CCO2] | N-(1-hydroxy-2-methylpropan-2-yl)-2-(1-(S-dioxo-tetrahydrothiophen-3-yl)-1H-1,2,4-triazol-5-yl)-5,6-dihydrobenzo[f]imidazo[1,2-d][1,4]oxazepine-10-carboxamide |

TABLE 1-continued

| No. | Structure | Name |
|---|---|---|
| 165 | 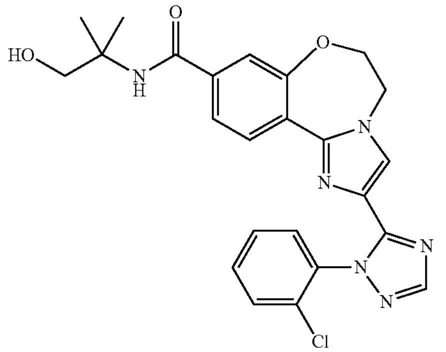 [SMILES: CC(C)(CO)NC(=O)c1ccc2c(c1)OCCn1cc(-c3ncnn3-c3ccccc3Cl)nc1-2] | 2-(1-(2-chlorophenyl)-1H-1,2,4-triazol-5-yl)-N-(1-hydroxy-2-methylpropan-2-yl)-5,6-dihydrobenzo[f]imidazo[1,2-d][1,4]oxazepine-9-carboxamide |
| 166 | 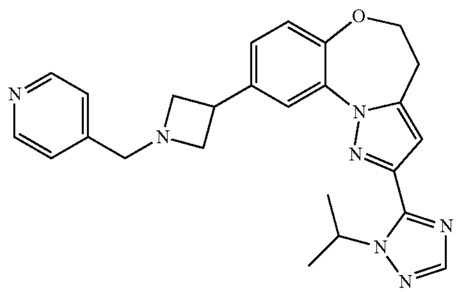 [SMILES: CC(C)n1ncnc1-c1cc2n(n1)-c1cc(C3CN(Cc4ccncc4)C3)ccc1OCC2] | 2-(1-isopropyl-1H-1,2,4-triazol-5-yl)-9-(1-(pyridin-4-ylmethyl)azetidin-3-yl)-4,5-dihydrobenzo[b]pyrazolo[1,5-d][1,4]oxazepine |
| 167 | 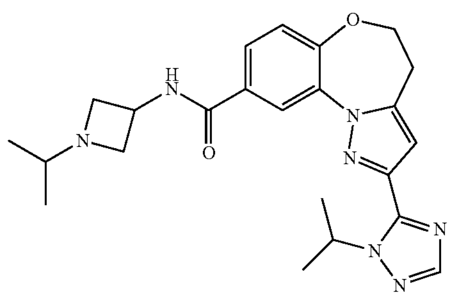 [SMILES: CC(C)N1CC(NC(=O)c2ccc3c(c2)-n2nc(-c4ncnn4C(C)C)cc2CCO3)C1] | 2-(1-isopropyl-1H-1,2,4-triazol-5-yl)-N-(1-isopropylazetidin-3-yl)-4,5-dihydrobenzo[b]pyrazolo[1,5-d][1,4]oxazepine-9-carboxamide |
| 168 | 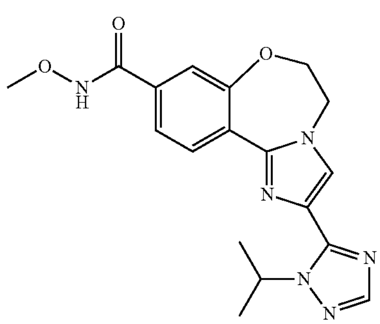 [SMILES: CONC(=O)c1ccc2c(c1)OCCn1cc(-c3ncnn3C(C)C)nc1-2] | 2-(1-isopropyl-1H-1,2,4-triazol-5-yl)-N-methoxy-5,6-dihydrobenzo[f]imidazo[1,2-d][1,4]oxazepine-9-carboxamide |
| 169 | 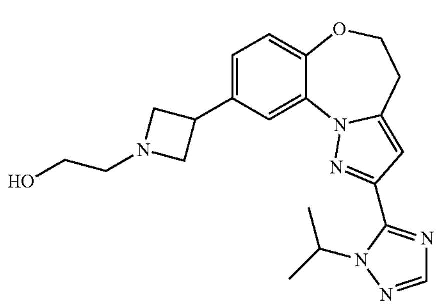 [SMILES: CC(C)n1ncnc1-c1cc2n(n1)-c1cc(C3CN(CCO)C3)ccc1OCC2] | 2-(3-(2-(1-isopropyl-1H-1,2,4-triazol-5-yl)-4,5-dihydrobenzo[b]pyrazolo[1,5-d][1,4]oxazepin-9-yl)azetidin-1-yl)ethanol |

TABLE 1-continued

| No. | Structure | Name |
|---|---|---|
| 170 | 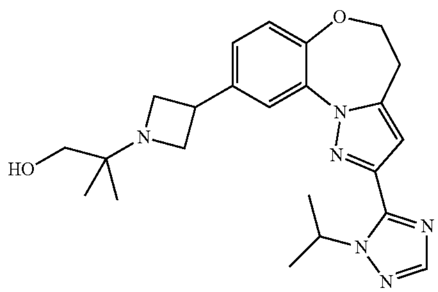 [SMILES: CC(C)n1ncnc1-c1cc2n(n1)-c1cc(C3CN(C(C)(C)CO)C3)ccc1OCC2] | 2-(3-(2-(1-isopropyl-1H-1,2,4-triazol-5-yl)-4,5-dihydrobenzo[b]pyrazolo[1,5-d][1,4]oxazepin-9-yl)azetidin-1-yl)-2-methylpropan-1-ol |
| 171 | 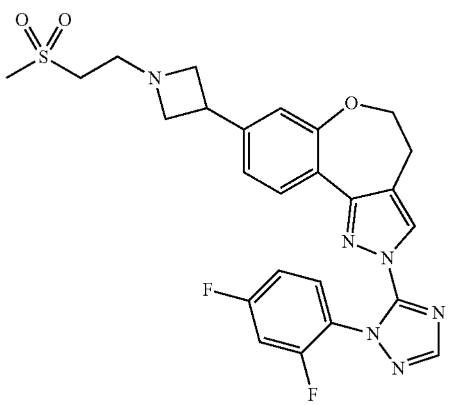 [SMILES: CS(=O)(=O)CCN1CC(c2ccc3c(c2)OCCc2cn(-c4ncnn4-c4ccc(F)cc4F)nc2-3)C1] | 2-(1-(2,4-difluorophenyl)-1H-1,2,4-triazol-5-yl)-8-(1-(2-(methylsulfonyl)ethyl)azetidin-3-yl)-4,5-dihydrobenzo-2H-oxepino[4,5-d]pyrazole |
| 172 | 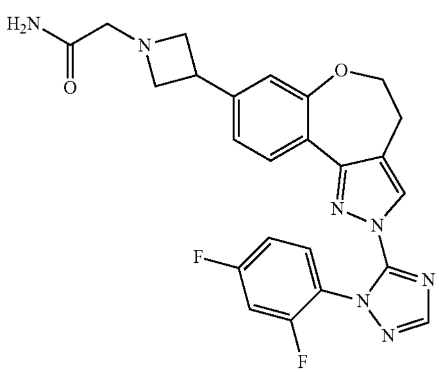 [SMILES: NC(=O)CN1CC(c2ccc3c(c2)OCCc2cn(-c4ncnn4-c4ccc(F)cc4F)nc2-3)C1] | 2-(3-{2-[2-(2,4-Difluoro-phenyl)-2H-[1,2,4]triazol-3-yl]-4,5-dihydro-2H-6-oxa-1,2-diaza-benzo[e]azulen-8-yl}-azetidin-1-yl)-acetamide |
| 173 | 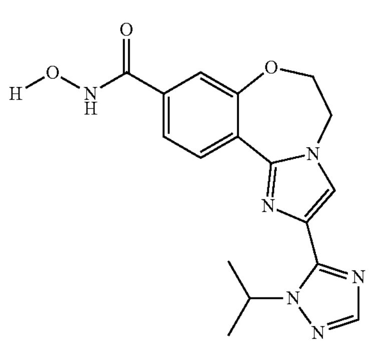 [SMILES: CC(C)n1ncnc1-c1cn2c(n1)-c1ccc(C(=O)NO)cc1OCC2] | N-hydroxy-2-(1-isopropyl-1H-1,2,4-triazol-5-yl)-5,6-dihydrobenzo[f]imidazo[1,2-d][1,4]oxazepine-9-carboxamide |

TABLE 1-continued

| No. | Structure | Name |
|---|---|---|
| 174 | 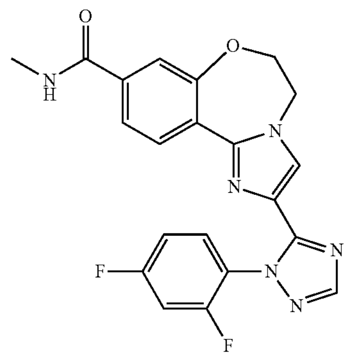 [SMILES: CNC(=O)c1ccc2c(c1)OCCn1cc(-c3ncnn3-c3ccc(F)cc3F)nc1-2] | 2-(1-(2,4-difluorophenyl)-1H-1,2,4-triazol-5-yl)-N-methyl-5,6-dihydrobenzo[f]imidazo[1,2-d][1,4]oxazepine-9-carboxamide |
| 175 | 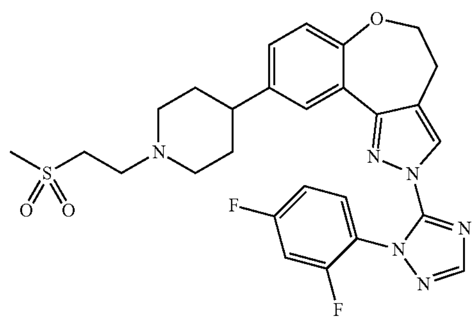 [SMILES: CS(=O)(=O)CCN1CCC(c2ccc3c(c2)-c2nn(-c4ncnn4-c4ccc(F)cc4F)cc2CCO3)CC1] | 2-[2-(2,4-Difluoro-phenyl)-2H-[1,2,4]triazol-3-yl]-[1-(2-methanesulfonyl-ethyl)-piperidin-4-yl]-4,5-dihydro-2H-6-oxa-1,2-diaza-benzo[e]azulene |
| 176 | 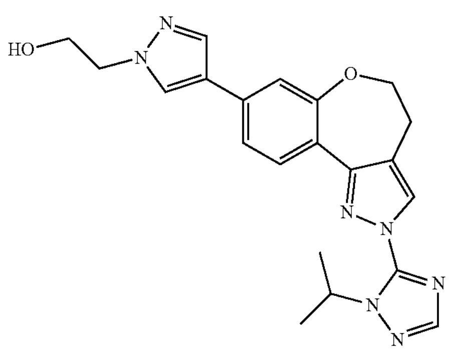 [SMILES: CC(C)n1ncnc1-n1cc2c(n1)-c1ccc(-c3cnn(CCO)c3)cc1OCC2] | 2-{4-[2-(2-Isopropyl-2H-[1,2,4]triazol-3-yl)-4,5-dihydro-2H-6-oxa-1,2-diaza-benzo[e]azulen-8-yl]-pyrazol-1-yl}-ethanol |
| 177 | 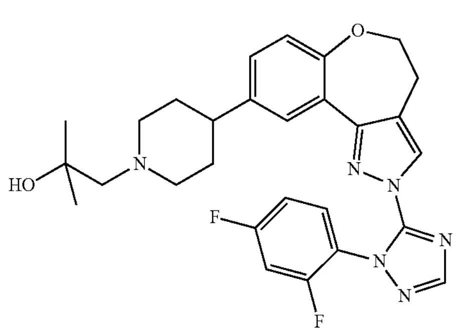 [SMILES: CC(C)(O)CN1CCC(c2ccc3c(c2)-c2nn(-c4ncnn4-c4ccc(F)cc4F)cc2CCO3)CC1] | 1-(4-{2-[2-(2,4-Difluoro-phenyl)-2H-[1,2,4]triazol-3-yl]-4,5-dihydro-2H-6-oxa-1,2-diaza-benzo[e]azulen-9-yl}-piperidin-1-yl)-2-methyl-propan-2-ol |

TABLE 1-continued

| No. | Structure | Name |
|---|---|---|
| 178 | 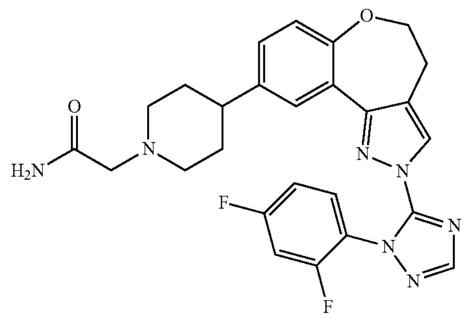 [SMILES: NC(=O)CN1CCC(c2ccc3c(c2)-c2nn(-c4ncnn4-c4ccc(F)cc4F)cc2CCO3)CC1] | 2-(4-{2-[2-(2,4-Difluoro-phenyl)-2H-[1,2,4]triazol-3-yl]-4,5-dihydro-2H-6-oxa-1,2-diaza-benzo[e]azulen-9-yl}-piperidin-1-yl)-acetamide |
| 179 | 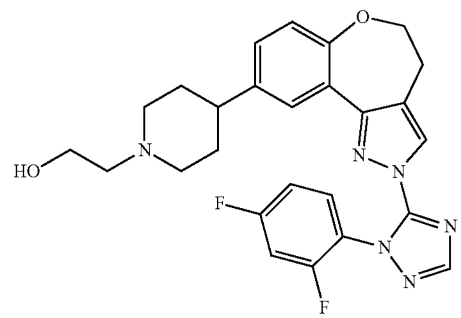 [SMILES: OCCN1CCC(c2ccc3c(c2)-c2nn(-c4ncnn4-c4ccc(F)cc4F)cc2CCO3)CC1] | 2-(4-{2-[2-(2,4-Difluoro-phenyl)-2H-[1,2,4]triazol-3-yl]-4,5-dihydro-2H-6-oxa-1,2-diaza-benzo[e]azulen-9-yl}-piperidin-1-yl)-ethanol |
| 180 | 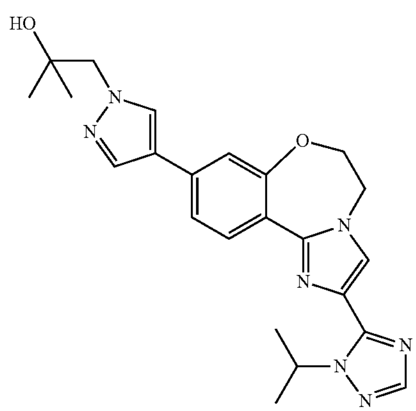 [SMILES: CC(C)n1ncnc1-c1cn2c(n1)-c1ccc(-c3cnn(CC(C)(C)O)c3)cc1OCC2] | 1-(4-(2-(1-isopropyl-1H-1,2,4-triazol-5-yl)-5,6-dihydrobenzo[f]imidazo[1,2-d][1,4]oxazepin-9-yl)-1H-pyrazol-1-yl)-2-methylpropan-2-ol |
| 181 | 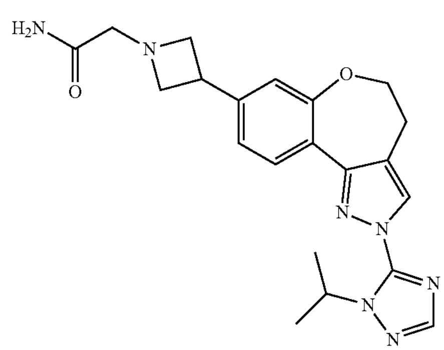 [SMILES: CC(C)n1ncnc1-n1cc2c(n1)-c1ccc(C3CN(CC(N)=O)C3)cc1OCC2] | 2-{3-[2-(2-Isopropyl-2H-[1,2,4]triazol-3-yl)-4,5-dihydro-2H-6-oxa-1,2-diaza-benzo[e]azulen-8-yl]-azetidin-1-yl}-acetamide |

TABLE 1-continued

| No. | Structure | Name |
|---|---|---|
| 182 | 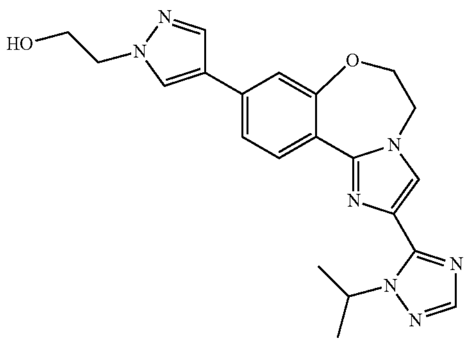 [SMILES: CC(C)n1ncnc1-c1cn2c(n1)-c1ccc(-c3cnn(CCO)c3)cc1OCC2] | 2-(4-(2-(1-isopropyl-1H-1,2,4-triazol-5-yl)-5,6-dihydrobenzo[f]imidazo[1,2-d][1,4]oxazepin-9-yl)-1H-pyrazol-1-yl)ethanol |
| 183 | 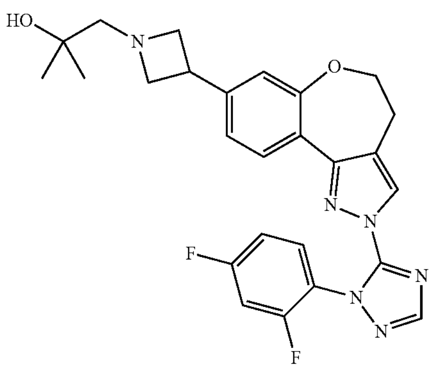 [SMILES: CC(C)(O)CN1CC(c2ccc3c(c2)OCCc2cn(-c4ncnn4-c4ccc(F)cc4F)nc2-3)C1] | 1-(3-{2-[2-(2,4-Difluoro-phenyl)-2H-[1,2,4]triazol-3-yl]-4,5-dihydro-2H-6-oxa-1,2-diaza-benzo[e]azulen-8-yl}-azetidin-1-yl)-2-methyl-propan-2-ol |
| 184 | 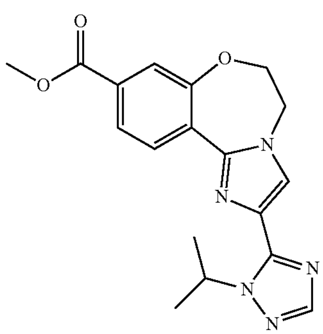 [SMILES: COC(=O)c1ccc2c(c1)OCCn1cc(-c3ncnn3C(C)C)nc1-2] | methyl 2-(1-isopropyl-1H-1,2,4-triazol-5-yl)-5,6-dihydrobenzo[f]imidazo[1,2-d][1,4]oxazepine-9-carboxylate |
| 185 | 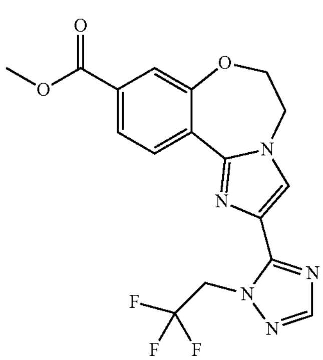 [SMILES: COC(=O)c1ccc2c(c1)OCCn1cc(-c3ncnn3CC(F)(F)F)nc1-2] | methyl 2-(1-(2,2,2-trifluoroethyl)-1H-1,2,4-triazol-5-yl)-5,6-dihydrobenzo[f]imidazo[1,2-d][1,4]oxazepine-9-carboxylate |

TABLE 1-continued

| No. | Structure | Name |
|---|---|---|
| 186 | 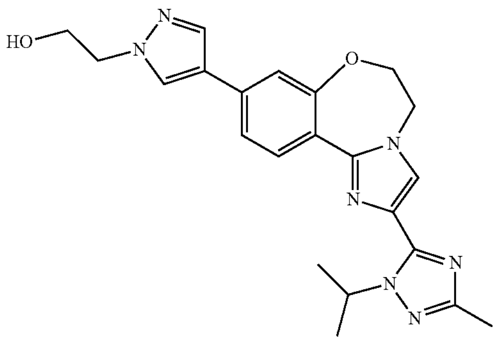 [SMILES: Cc1nc(-c2cn3c(n2)-c2ccc(-c4cnn(CCO)c4)cc2OCC3)n(C(C)C)n1] | 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)ethanol |
| 187 | 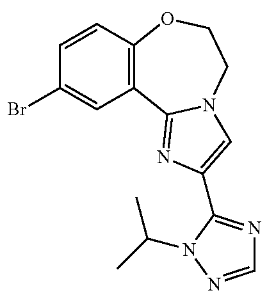 [SMILES: CC(C)n1ncnc1-c1cn2c(n1)-c1cc(Br)ccc1OCC2] | 10-bromo-2-(1-isopropyl-1H-1,2,4-triazol-5-yl)-5,6-dihydrobenzo[f]imidazo[1,2-d][1,4]oxazepine |
| 188 | 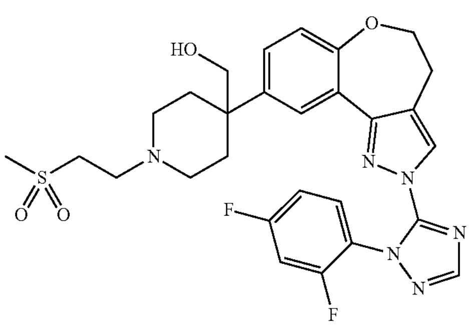 [SMILES: CS(=O)(=O)CCN1CCC(CO)(c2ccc3c(c2)-c2nn(-c4ncnn4-c4ccc(F)cc4F)cc2CCO3)CC1] | [4-{2-[2-(2,4-Difluoro-phenyl)-2H-[1,2,4]triazol-3-yl]-4,5-dihydro-2H-6-oxa-1,2-diaza-benzo[e]azulen-9-yl}-1-(2-methanesulfonyl-ethyl)-piperidin-4-yl]-methanol |
| 189 | 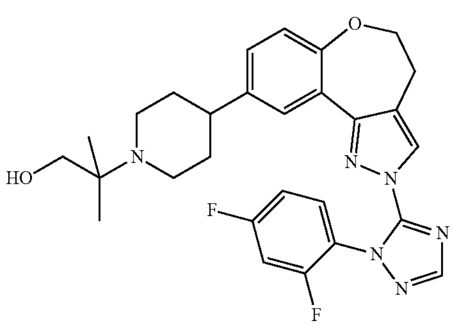 [SMILES: CC(C)(CO)N1CCC(c2ccc3c(c2)-c2nn(-c4ncnn4-c4ccc(F)cc4F)cc2CCO3)CC1] | 2-(4-{2-[2-(2,4-Difluoro-phenyl)-2H-[1,2,4]triazol-3-yl]-4,5-dihydro-2H-6-oxa-1,2-diaza-benzo[e]azulen-9-yl}-piperidin-1-yl)-2-methyl-propan-1-ol |

TABLE 1-continued

| No. | Structure | Name |
|---|---|---|
| 190 | 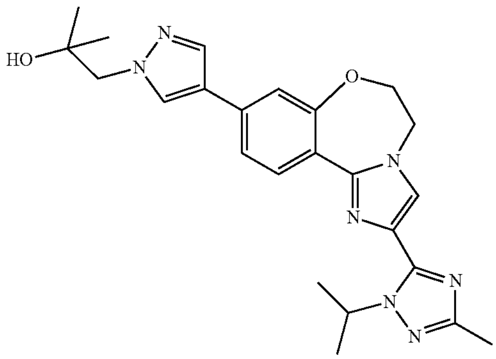 [SMILES: Cc1nc(-c2cn3c(n2)-c2ccc(-c4cnn(CC(C)(C)O)c4)cc2OCC3)n(C(C)C)n1] | 1-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropan-2-ol |
| 191 | 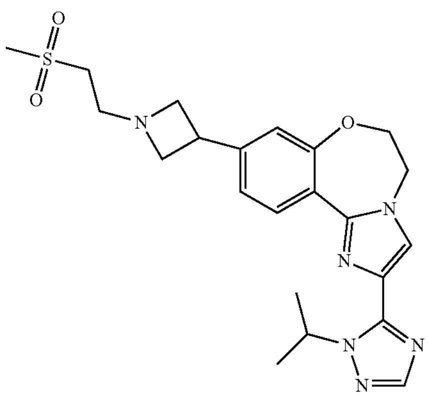 [SMILES: CC(C)n1ncnc1-c1cn2c(n1)-c1ccc(C3CN(CCS(C)(=O)=O)C3)cc1OCC2] | 2-(1-isopropyl-1H-1,2,4-triazol-5-yl)-9-(1-(2-(methylsulfonyl)ethyl)azetidin-3-yl)-5,6-dihydrobenzo[f]imidazo[1,2-d][1,4]oxazepine |
| 192 | 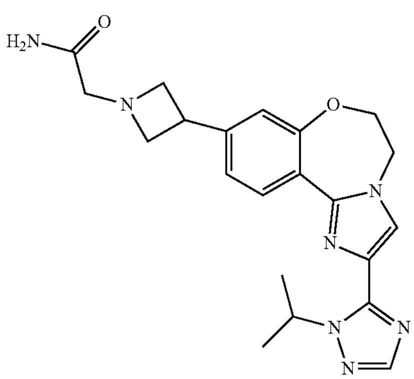 [SMILES: CC(C)n1ncnc1-c1cn2c(n1)-c1ccc(C3CN(CC(N)=O)C3)cc1OCC2] | 2-(3-(2-(1-isopropyl-1H-1,2,4-triazol-5-yl)-5,6-dihydrobenzo[f]imidazo[1,2-d][1,4]oxazepin-9-yl)azetidin-1-yl)acetamide |
| 193 | 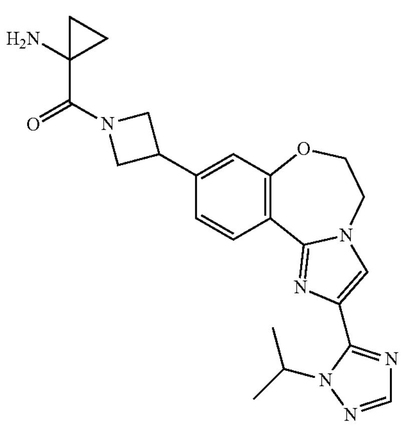 [SMILES: CC(C)n1ncnc1-c1cn2c(n1)-c1ccc(C3CN(C(=O)C4(N)CC4)C3)cc1OCC2] | (1-aminocyclopropyl)(3-(2-(1-isopropyl-1H-1,2,4-triazol-5-yl)-5,6-dihydrobenzo[f]imidazo[1,2-d][1,4]oxazepin-9-yl)azetidin-1-yl)methanone |

TABLE 1-continued

| No. | Structure | Name |
|---|---|---|
| 194 | 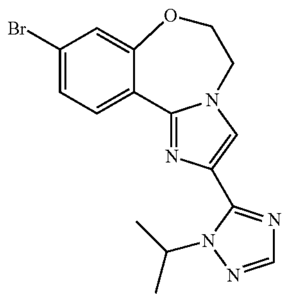 [SMILES: CC(C)n1ncnc1-c1cn2c(n1)-c1ccc(Br)cc1OCC2] | 9-bromo-2-(1-isopropyl-1H-1,2,4-triazol-5-yl)-5,6-dihydrobenzo[f]imidazo[1,2-d][1,4]oxazepine |
| 195 | 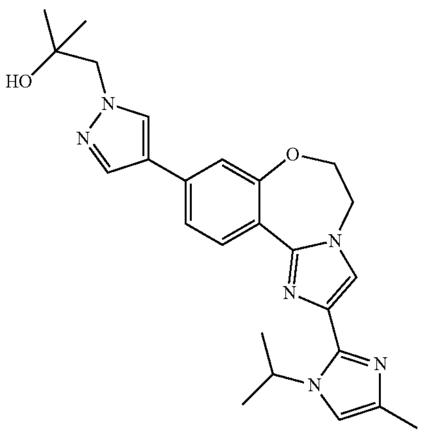 [SMILES: Cc1cn(C(C)C)c(-c2cn3c(n2)-c2ccc(-c4cnn(CC(C)(C)O)c4)cc2OCC3)n1] | 1-(4-(2-(1-isopropyl-4-methyl-1H-imidazol-2-yl)-5,6-dihydrobenzo[f]imidazo[1,2-d][1,4]oxazepin-9-yl)-1H-pyrazol-1-yl)-2-methylpropan-2-ol |
| 196 | 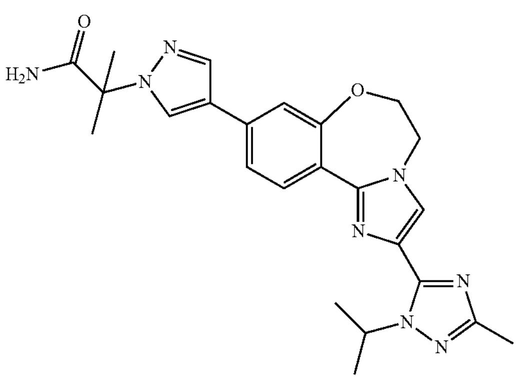 [SMILES: Cc1nc(-c2cn3c(n2)-c2ccc(-c4cnn(C(C)(C)C(N)=O)c4)cc2OCC3)n(C(C)C)n1] | 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide |
| 197 | 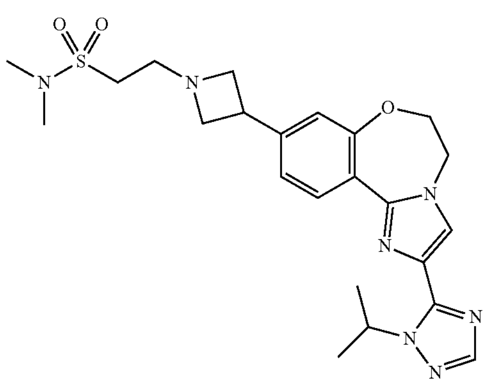 [SMILES: CC(C)n1ncnc1-c1cn2c(n1)-c1ccc(C3CN(CCS(=O)(=O)N(C)C)C3)cc1OCC2] | 2-(3-(2-(1-isopropyl-1H-1,2,4-triazol-5-yl)-5,6-dihydrobenzo[f]imidazo[1,2-d][1,4]oxazepin-9-yl)azetidin-1-yl)-N,N-dimethylethanesulfonamide |

TABLE 1-continued

| No. | Structure | Name |
|---|---|---|
| 198 | 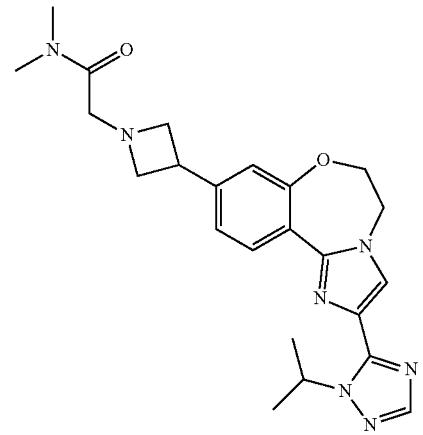 [SMILES: CC(C)n1ncnc1-c1cn2c(n1)-c1ccc(C3CN(CC(=O)N(C)C)C3)cc1OCC2] | 2-(3-(2-(1-isopropyl-1H-1,2,4-triazol-5-yl)-5,6-dihydrobenzo[f]imidazo[1,2-d][1,4]oxazepin-9-yl)azetidin-1-yl)-N,N-dimethylacetamide |
| 199 | 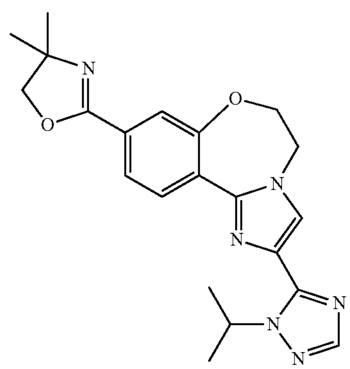 [SMILES: CC(C)n1ncnc1-c1cn2c(n1)-c1ccc(C3=NC(C)(C)CO3)cc1OCC2] | 9-(4,4-dimethyl-4,5-dihydrooxazol-2-yl)-2-(1-isopropyl-1H-1,2,4-triazol-5-yl)-5,6-dihydrobenzo[f]imidazo[1,2-d][1,4]oxazepine |
| 200 | 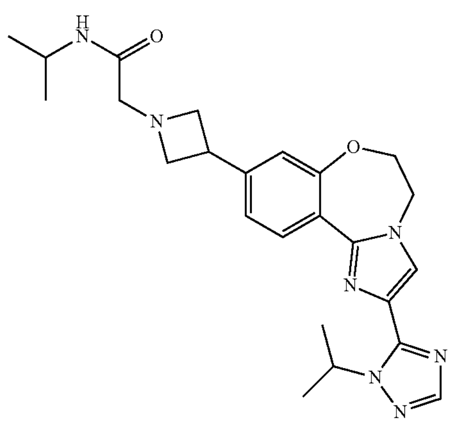 [SMILES: CC(C)NC(=O)CN1CC(c2ccc3c(c2)OCCn2cc(-c4ncnn4C(C)C)nc2-3)C1] | N-isopropyl-2-(3-(2-(1-isopropyl-1H-1,2,4-triazol-5-yl)-5,6-dihydrobenzo[f]imidazo[1,2-d][1,4]oxazepin-9-yl)azetidin-1-yl)acetamide |
| 201 | 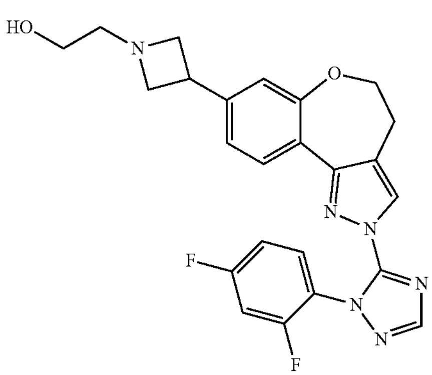 [SMILES: OCCN1CC(c2ccc3c(c2)OCCc2cn(-c4ncnn4-c4ccc(F)cc4F)nc2-3)C1] | 2-(3-{2-[2-(2,4-Difluoro-phenyl)-2H-[1,2,4]triazol-3-yl]-4,5-dihydro-2H-6-oxa-1,2-diaza-benzo[e]azulen-8-yl}-azetidin-1-yl)-ethanol |

TABLE 1-continued

| No. | Structure | Name |
|---|---|---|
| 202 | 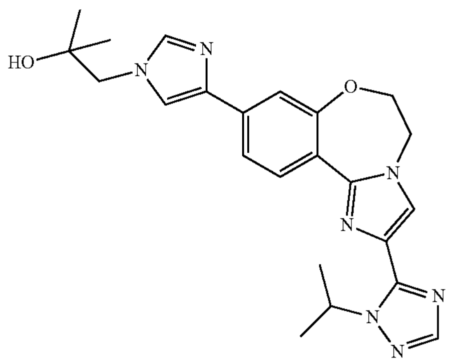 [SMILES: CC(C)n1ncnc1-c1cn2c(n1)-c1ccc(-c3cn(CC(C)(C)O)cn3)cc1OCC2] | 1-(4-(2-(1-isopropyl-1H-1,2,4-triazol-5-yl)-5,6-dihydrobenzo[f]imidazo[1,2-d][1,4]oxazepin-9-yl)-1H-imidazol-1-yl)-2-methylpropan-2-ol |
| 203 | 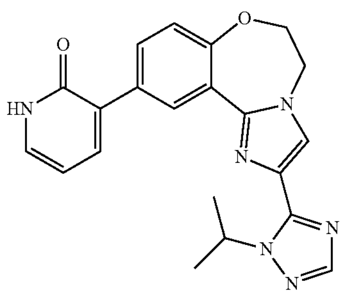 [SMILES: CC(C)n1ncnc1-c1cn2c(n1)-c1cc(-c3ccc[nH]c3=O)ccc1OCC2] | 3-(2-(1-isopropyl-1H-1,2,4-triazol-5-yl)-5,6-dihydrobenzo[f]imidazo[1,2-d][1,4]oxazepin-10-yl)pyridin-2(1H)-one |
| 204 | 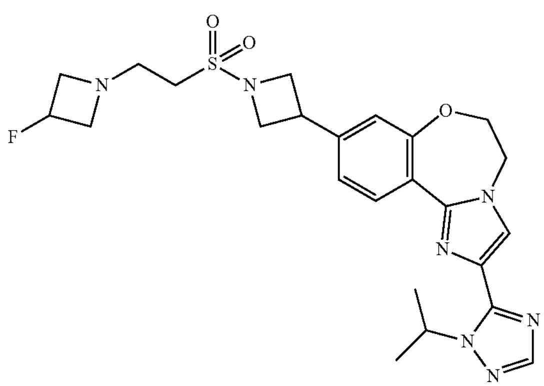 [SMILES: CC(C)n1ncnc1-c1cn2c(n1)-c1ccc(C3CN(S(=O)(=O)CCN4CC(F)C4)C3)cc1OCC2] | 9-(1-(2-(3-fluoroazetidin-1-yl)ethylsulfonyl)azetidin-3-yl)-2-(1-isopropyl-1H-1,2,4-triazol-5-yl)-5,6-dihydrobenzo[f]imidazo[1,2-d][1,4]oxazepine |
| 205 | 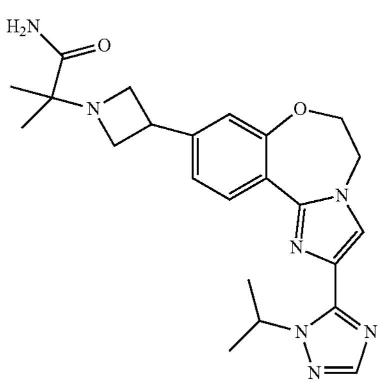 [SMILES: CC(C)n1ncnc1-c1cn2c(n1)-c1ccc(C3CN(C(C)(C)C(N)=O)C3)cc1OCC2] | 2-(3-(2-(1-isopropyl-1H-1,2,4-triazol-5-yl)-5,6-dihydrobenzo[f]imidazo[1,2-d][1,4]oxazepin-9-yl)azetidin-1-yl)-2-methylpropanamide |

| No. | Structure | Name |
| --- | --- | --- |
| 206 | 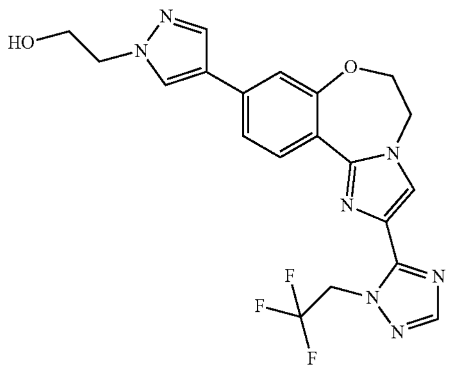 [SMILES: OCCn1cc(-c2ccc3c(c2)OCCn2cc(-c4ncnn4CC(F)(F)F)nc2-3)cn1] | 2-(4-(2-(1-(2,2,2-trifluoroethyl)-1H-1,2,4-triazol-5-yl)-5,6-dihydrobenzo[f]imidazo[1,2-d][1,4]oxazepin-9-yl)-1H-pyrazol-1-yl)ethanol |
| 207 | 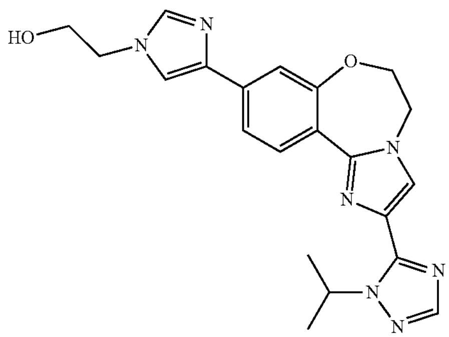 [SMILES: CC(C)n1ncnc1-c1cn2c(n1)-c1ccc(-c3cn(CCO)cn3)cc1OCC2] | 2-(4-(2-(1-isopropyl-1H-1,2,4-triazol-5-yl)-5,6-dihydrobenzo[f]imidazo[1,2-d][1,4]oxazepin-9-yl)-1H-imidazol-1-yl)ethanol |
| 208 | 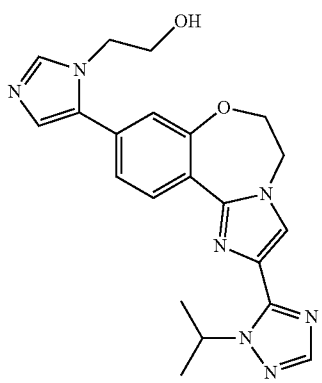 [SMILES: CC(C)n1ncnc1-c1cn2c(n1)-c1ccc(-c3cncn3CCO)cc1OCC2] | 2-(5-(2-(1-isopropyl-1H-1,2,4-triazol-5-yl)-5,6-dihydrobenzo[f]imidazo[1,2-d][1,4]oxazepin-9-yl)-1H-imidazol-1-yl)ethanol |
| 209 | 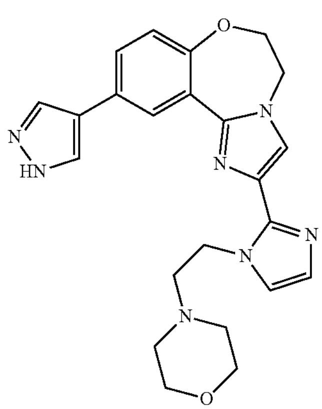 [SMILES: c1cn(CCN2CCOCC2)c(-c2cn3c(n2)-c2cc(-c4cn[nH]c4)ccc2OCC3)n1] | 2-(1-(2-morpholinoethyl)-1H-imidazol-2-yl)-10-(1H-pyrazol-4-yl)-5,6-dihydrobenzo[f]imidazo[1,2-d][1,4]oxazepine |

TABLE 1-continued

| No. | Structure | Name |
| --- | --- | --- |
| 210 | 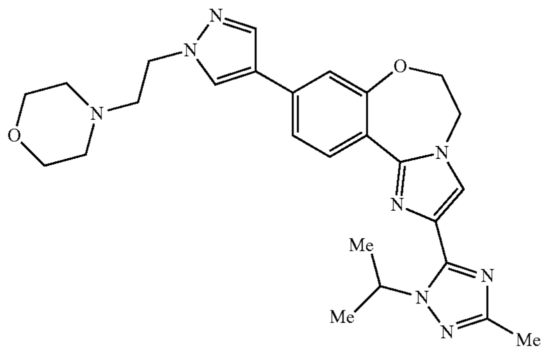 [SMILES: Cc1nc(-c2cn3c(n2)-c2ccc(-c4cnn(CCN5CCOCC5)c4)cc2OCC3)n(C(C)C)n1] | 2-(1-isopropyl-3-methyl-1H-1,2,4-triazol-5-yl)-9-(1-(2-morpholinoethyl)-1H-pyrazol-4-yl)-5,6-dihydrobenzo[f]imidazo[1,2-d][1,4]oxazepine |
| 211 | 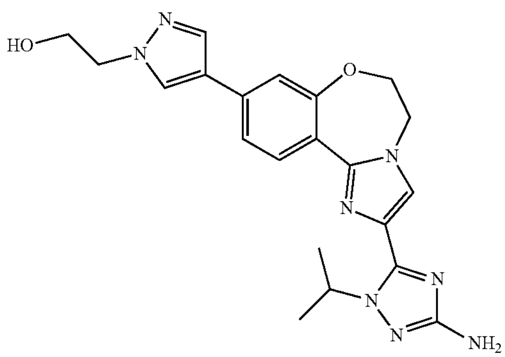 [SMILES: CC(C)n1nc(N)nc1-c1cn2c(n1)-c1ccc(-c3cnn(CCO)c3)cc1OCC2] | 2-(4-(2-(3-amino-1-isopropyl-1H-1,2,4-triazol-5-yl)-5,6-dihydrobenzo[f]imidazo[1,2-d][1,4]oxazepin-9-yl)-1H-pyrazol-1-yl)ethanol |
| 212 | 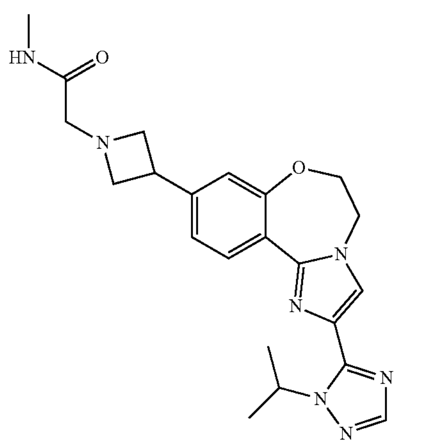 [SMILES: CNC(=O)CN1CC(c2ccc3c(c2)OCCn2cc(-c4ncnn4C(C)C)nc2-3)C1] | 2-(3-(2-(1-isopropyl-1H-1,2,4-triazol-5-yl)-5,6-dihydrobenzo[f]imidazo[1,2-d][1,4]oxazepin-9-yl)azetidin-1-yl)-N-methylacetamide |
| 213 | 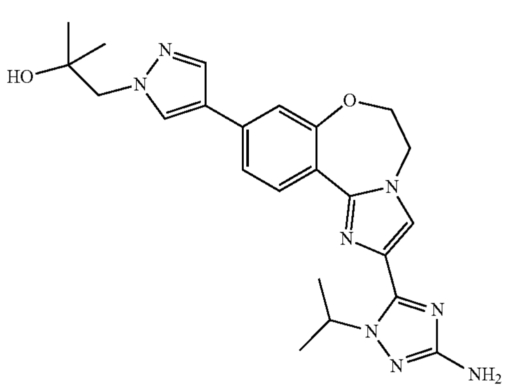 [SMILES: CC(C)n1nc(N)nc1-c1cn2c(n1)-c1ccc(-c3cnn(CC(C)(C)O)c3)cc1OCC2] | 1-(4-(2-(3-amino-1-isopropyl-1H-1,2,4-triazol-5-yl)-5,6-dihydrobenzo[f]imidazo[1,2-d][1,4]oxazepin-9-yl)-1H-pyrazol-1-yl)-2-methylpropan-2-ol |

TABLE 1-continued

| No. | Structure | Name |
|-----|-----------|------|
| 214 | 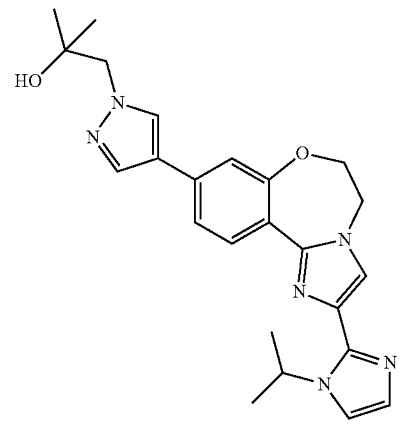 [SMILES: CC(C)n1ccnc1-c1cn2c(n1)-c1ccc(-c3cnn(CC(C)(C)O)c3)cc1OCC2] | 1-(4-(2-(1-isopropyl-1H-imidazol-2-yl)-5,6-dihydrobenzo[f]imidazo[1,2-d][1,4]oxazepin-9-yl)-1H-pyrazol-1-yl)-2-methylpropan-2-ol |
| 215 | 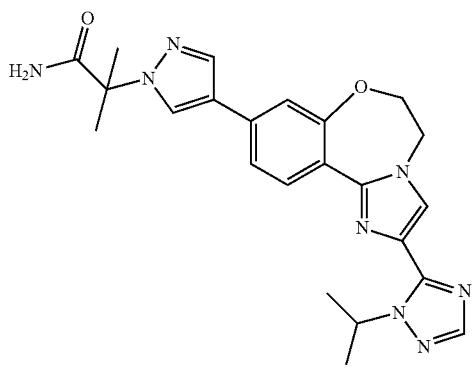 [SMILES: CC(C)n1ncnc1-c1cn2c(n1)-c1ccc(-c3cnn(C(C)(C)C(N)=O)c3)cc1OCC2] | 2-(4-(2-(1-isopropyl-1H-1,2,4-triazol-5-yl)-5,6-dihydrobenzo[f]imidazo[1,2-d][1,4]oxazepin-9-yl)-1H-pyrazol-1-yl)-2-methylpropanamide |
| 216 | 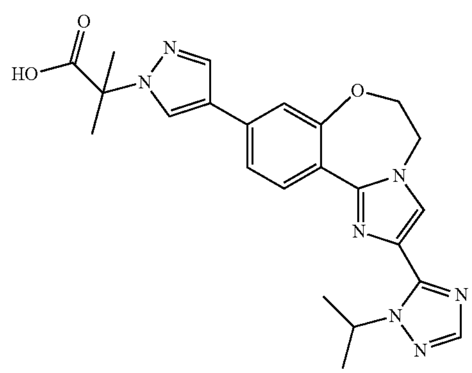 [SMILES: CC(C)n1ncnc1-c1cn2c(n1)-c1ccc(-c3cnn(C(C)(C)C(=O)O)c3)cc1OCC2] | 2-(4-(2-(1-isopropyl-1H-1,2,4-triazol-5-yl)-5,6-dihydrobenzo[f]imidazo[1,2-d][1,4]oxazepin-9-yl)-1H-pyrazol-1-yl)-2-methylpropanoic acid |
| 217 | 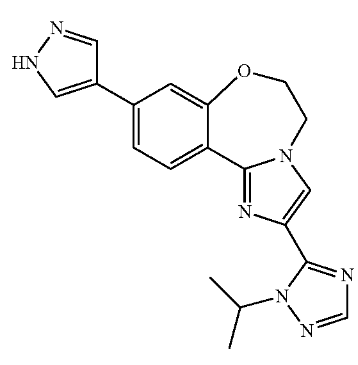 [SMILES: CC(C)n1ncnc1-c1cn2c(n1)-c1ccc(-c3cn[nH]c3)cc1OCC2] | 2-(1-isopropyl-1H-1,2,4-triazol-5-yl)-9-(1H-pyrazol-4-yl)-5,6-dihydrobenzo[f]imidazo[1,2-d][1,4]oxazepine |

TABLE 1-continued

| No. | Structure | Name |
|---|---|---|
| 218 | 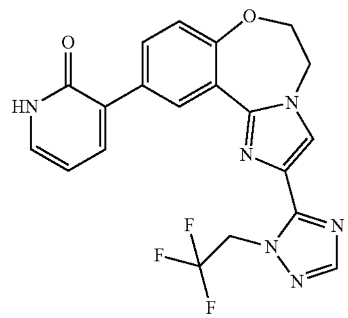 [SMILES: O=c1[nH]cccc1-c1ccc2c(c1)-c1nc(-c3ncnn3CC(F)(F)F)cn1CCO2] | 3-(2-(1-(2,2,2-trifluoroethyl)-1H-1,2,4-triazol-5-yl)-5,6-dihydrobenzo[f]imidazo[1,2-d][1,4]oxazepin-10-yl)pyridin-2(1H)-one |
| 219 | 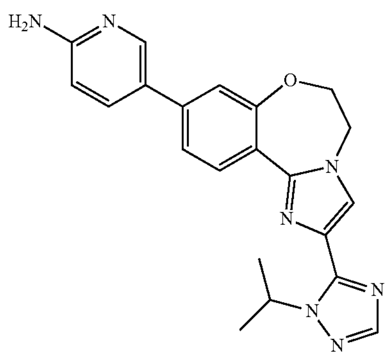 [SMILES: CC(C)n1ncnc1-c1cn2c(n1)-c1ccc(-c3ccc(N)nc3)cc1OCC2] | 5-(2-(1-isopropyl-1H-1,2,4-triazol-5-yl)-5,6-dihydrobenzo[f]imidazo[1,2-d][1,4]oxazepin-9-yl)pyridin-2-amine |
| 220 | 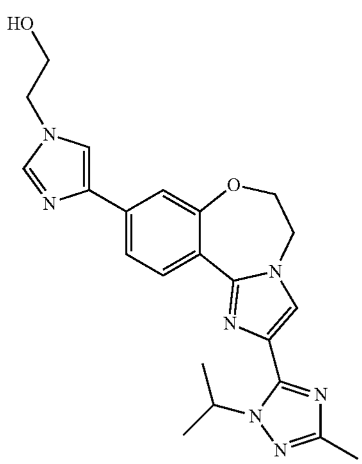 [SMILES: Cc1nc(-c2cn3c(n2)-c2ccc(-c4cn(CCO)cn4)cc2OCC3)n(C(C)C)n1] | 2-(4-(2-(1-isopropyl-3-methyl-1H-1,2,4-triazol-5-yl)-5,6-dihydrobenzo[f]imidazo[1,2-d][1,4]oxazepin-9-yl)-1H-imidazol-1-yl)ethanol |
| 221 | 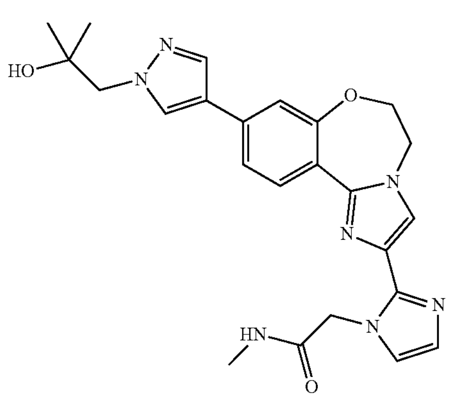 [SMILES: CNC(=O)Cn1ccnc1-c1cn2c(n1)-c1ccc(-c3cnn(CC(C)(C)O)c3)cc1OCC2] | 2-(2-(9-(1-(2-hydroxy-2-methylpropyl)-1H-pyrazol-4-yl)-5,6-dihydrobenzo[f]imidazo[1,2-d][1,4]oxazepin-2-yl)-1H-imidazol-1-yl)-N-methylacetamide |

TABLE 1-continued

| No. | Structure | Name |
|---|---|---|
| 222 | 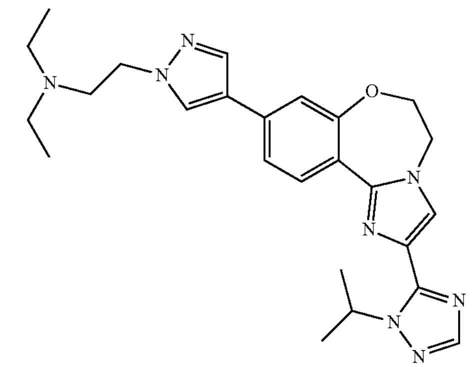 [SMILES: CCN(CC)CCn1cc(-c2ccc3c(c2)OCCn2cc(-c4ncnn4C(C)C)nc2-3)cn1] | N,N-diethyl-2-(4-(2-(1-isopropyl-1H-1,2,4-triazol-5-yl)-5,6-dihydrobenzo[f]imidazo[1,2-d][1,4]oxazepin-9-yl)-1H-pyrazol-1-yl)ethanamine |
| 223 | 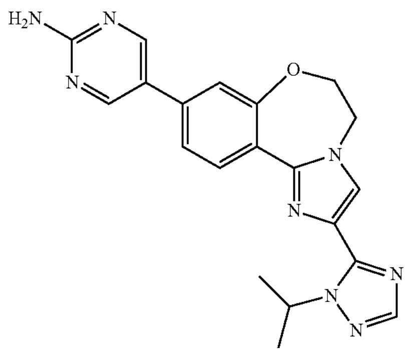 [SMILES: CC(C)n1ncnc1-c1cn2c(n1)-c1ccc(-c3cnc(N)nc3)cc1OCC2] | 5-(2-(1-isopropyl-1H-1,2,4-triazol-5-yl)-5,6-dihydrobenzo[f]imidazo[1,2-d][1,4]oxazepin-9-yl)pyrimidin-2-amine |
| 224 | 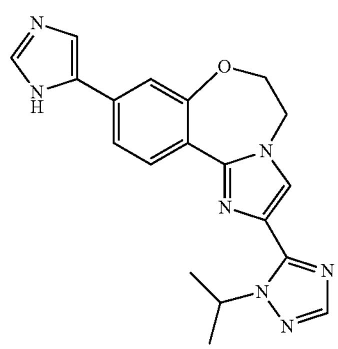 [SMILES: CC(C)n1ncnc1-c1cn2c(n1)-c1ccc(-c3cnc[nH]3)cc1OCC2] | 9-(1H-imidazol-5-yl)-2-(1-isopropyl-1H-1,2,4-triazol-5-yl)-5,6-dihydrobenzo[f]imidazo[1,2-d][1,4]oxazepine |
| 225 | 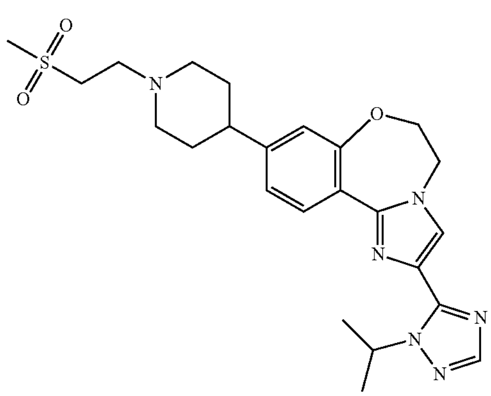 [SMILES: CC(C)n1ncnc1-c1cn2c(n1)-c1ccc(C3CCN(CCS(C)(=O)=O)CC3)cc1OCC2] | 2-(1-isopropyl-1H-1,2,4-triazol-5-yl)-9-(1-(2-(methylsulfonyl)ethyl)piperidin-4-yl)-5,6-dihydrobenzo[f]imidazo[1,2-d][1,4]oxazepine |

TABLE 1-continued

| No. | Structure | Name |
|---|---|---|
| 226 | 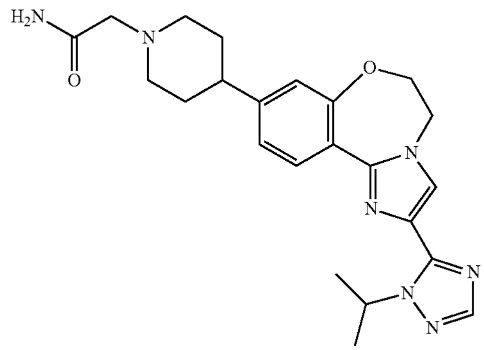 [SMILES: CC(C)n1ncnc1-c1cn2c(n1)-c1ccc(C3CCN(CC(N)=O)CC3)cc1OCC2] | 2-(4-(2-(1-isopropyl-1H-1,2,4-triazol-5-yl)-5,6-dihydrobenzo[f]imidazo[1,2-d][1,4]oxazepin-9-yl)piperidin-1-yl)acetamide |
| 227 | 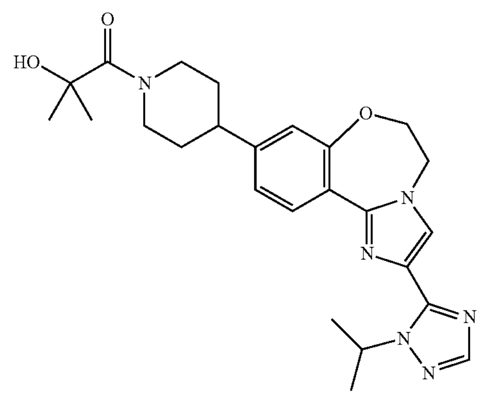 [SMILES: CC(C)n1ncnc1-c1cn2c(n1)-c1ccc(C3CCN(C(=O)C(C)(C)O)CC3)cc1OCC2] | 2-hydroxy-1-(4-(2-(1-isopropyl-1H-1,2,4-triazol-5-yl)-5,6-dihydrobenzo[f]imidazo[1,2-d][1,4]oxazepin-9-yl)piperidin-1-yl)-2-methylpropan-1-one |
| 228 | 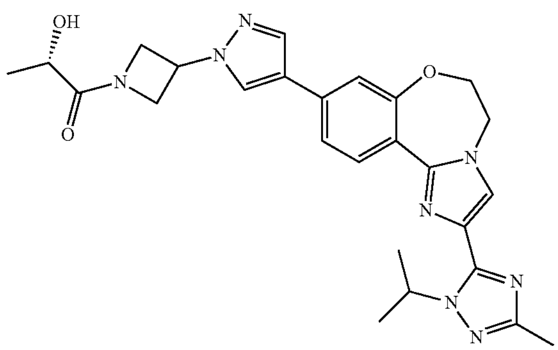 [SMILES: Cc1nc(-c2cn3c(n2)-c2ccc(-c4cnn(C5CN(C(=O)[C@H](C)O)C5)c4)cc2OCC3)n(C(C)C)n1] | (2S)-2-hydroxy-1-(3-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)azetidin-1-yl)propan-1-one |
| 229 | 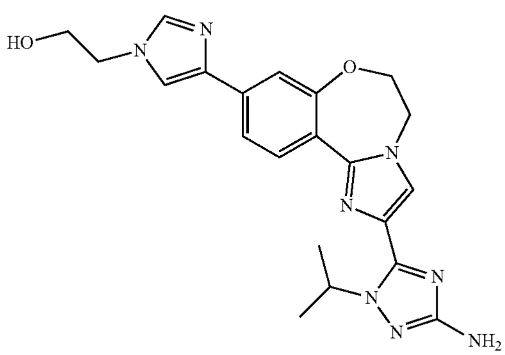 [SMILES: CC(C)n1nc(N)nc1-c1cn2c(n1)-c1ccc(-c3cn(CCO)cn3)cc1OCC2] | 2-(4-(2-(3-amino-1-isopropyl-1H-1,2,4-triazol-5-yl)-5,6-dihydrobenzo[f]imidazo[1,2-d][1,4]oxazepin-9-yl)-1H-imidazol-1-yl)ethanol |

TABLE 1-continued

| No. | Structure | Name |
|---|---|---|
| 230 | 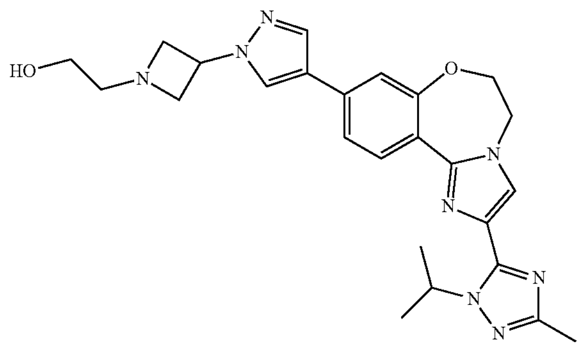 [SMILES: Cc1nc(-c2cn3c(n2)-c2ccc(-c4cnn(C5CN(CCO)C5)c4)cc2OCC3)n(C(C)C)n1] | 2-(3-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)azetidin-1-yl)ethanol |
| 231 | 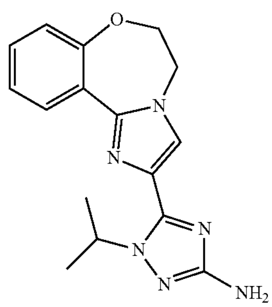 [SMILES: CC(C)n1nc(N)nc1-c1cn2c(n1)-c1ccccc1OCC2] | 5-(5,6-dihydrobenzo[f]imidazo[1,2-d][1,4]oxazepin-2-yl)-1-isopropyl-1H-1,2,4-triazol-3-amine |
| 232 | 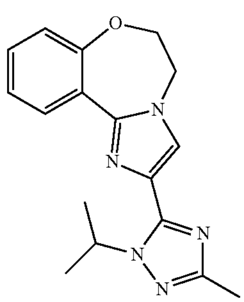 [SMILES: Cc1nc(-c2cn3c(n2)-c2ccccc2OCC3)n(C(C)C)n1] | 2-(1-isopropyl-3-methyl-1H-1,2,4-triazol-5-yl)-5,6-dihydrobenzo[f]imidazo[1,2-d][1,4]oxazepine |
| 233 | 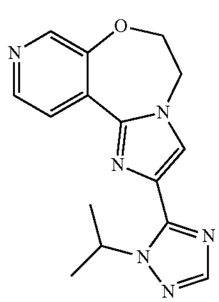 [SMILES: CC(C)n1ncnc1-c1cn2c(n1)-c1ccncc1OCC2] | 2-(1-isopropyl-1H-1,2,4-triazol-5-yl)-5,6-dihydroimidazo[1,2-d]pyrido[4,3-f][1,4]oxazepine |
| 234 | 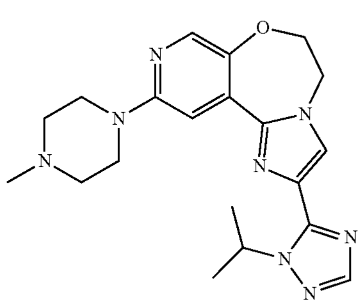 [SMILES: CC(C)n1ncnc1-c1cn2c(n1)-c1cc(N3CCN(C)CC3)ncc1OCC2] | 2-(1-isopropyl-1H-1,2,4-triazol-5-yl)-10-(4-methylpiperazin-1-yl)-5,6-dihydroimidazo[1,2-d]pyrido[4,3-f][1,4]oxazepine |

TABLE 1-continued

| No. | Structure | Name |
|---|---|---|
| 235 | 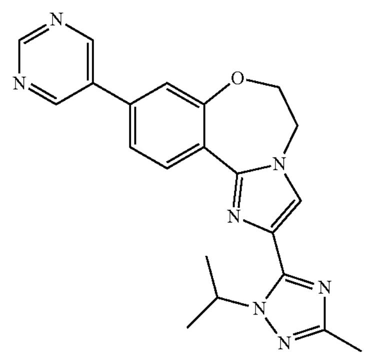 [SMILES: Cc1nc(-c2cn3c(n2)-c2ccc(-c4cncnc4)cc2OCC3)n(C(C)C)n1] | 2-(1-isopropyl-3-methyl-1H-1,2,4-triazol-5-yl)-9-(pyrimidin-5-yl)-5,6-dihydrobenzo[f]imidazo[1,2-d][1,4]oxazepine |
| 236 | 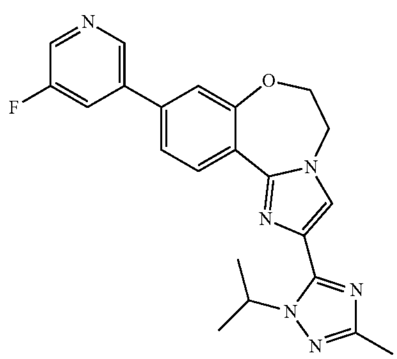 [SMILES: Cc1nc(-c2cn3c(n2)-c2ccc(-c4cncc(F)c4)cc2OCC3)n(C(C)C)n1] | 9-(5-fluoropyridin-3-yl)-2-(1-isopropyl-3-methyl-1H-1,2,4-triazol-5-yl)-5,6-dihydrobenzo[f]imidazo[1,2-d][1,4]oxazepine |
| 237 | 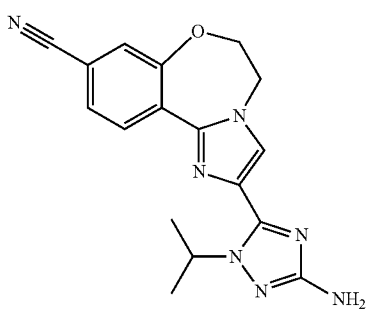 [SMILES: CC(C)n1nc(N)nc1-c1cn2c(n1)-c1ccc(C#N)cc1OCC2] | 2-(3-amino-1-isopropyl-1H-1,2,4-triazol-5-yl)-5,6-dihydrobenzo[f]imidazo[1,2-d][1,4]oxazepine-9-carbonitrile |
| 238 | 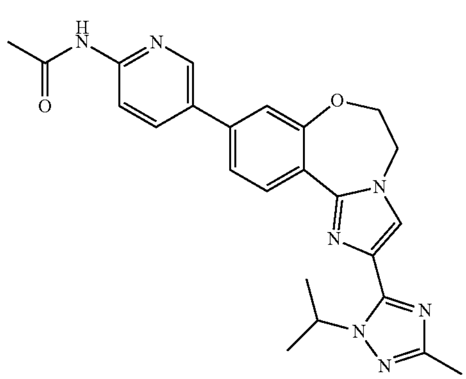 [SMILES: CC(=O)Nc1ccc(-c2ccc3c(c2)OCCn2cc(-c4nc(C)nn4C(C)C)nc2-3)cn1] | N-(5-(2-(1-isopropyl-3-methyl-1H-1,2,4-triazol-5-yl)-5,6-dihydrobenzo[f]imidazo[1,2-d][1,4]oxazepin-9-yl)pyridin-2-yl)acetamide |

TABLE 1-continued

| No. | Structure | Name |
|---|---|---|
| 239 | 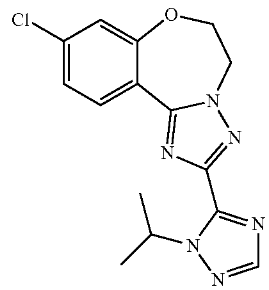 [SMILES: CC(C)n1ncnc1-c1nc2n(n1)CCOc1cc(Cl)ccc1-2] | 9-chloro-2-(1-isopropyl-1H-1,2,4-triazol-5-yl)-5,6-dihydrobenzo[f][1,2,4]triazolo[1,5-d][1,4]oxazepine |
| 240 | 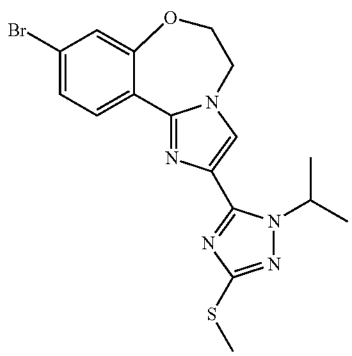 [SMILES: CSc1nc(-c2cn3c(n2)-c2ccc(Br)cc2OCC3)n(C(C)C)n1] | 9-bromo-2-(1-isopropyl-3-(methylthio)-1H-1,2,4-triazol-5-yl)-5,6-dihydrobenzo[f]imidazo[1,2-d][1,4]oxazepine |
| 241 | 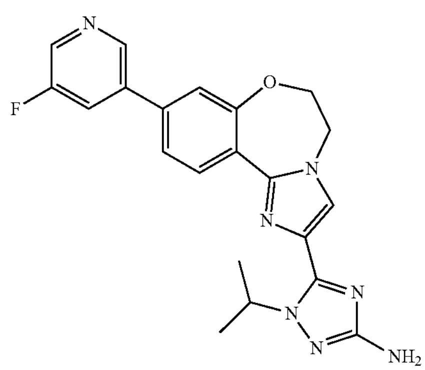 [SMILES: CC(C)n1nc(N)nc1-c1cn2c(n1)-c1ccc(-c3cncc(F)c3)cc1OCC2] | 5-(9-(5-fluoropyridin-3-yl)-5,6-dihydrobenzo[f]imidazo[1,2-d][1,4]oxazepin-2-yl)-1-isopropyl-1H-1,2,4-triazol-3-amine |
| 242 | 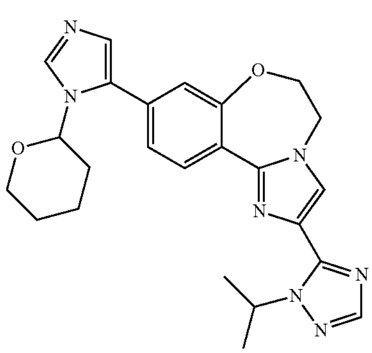 [SMILES: CC(C)n1ncnc1-c1cn2c(n1)-c1ccc(-c3cncn3C3CCCCO3)cc1OCC2] | 2-(1-isopropyl-1H-1,2,4-triazol-5-yl)-9-(1-(tetrahydro-2H-pyran-2-yl)-1H-imidazol-5-yl)-5,6-dihydrobenzo[f]imidazo[1,2-d][1,4]oxazepine |

TABLE 1-continued

| No. | Structure | Name |
|---|---|---|
| 243 | 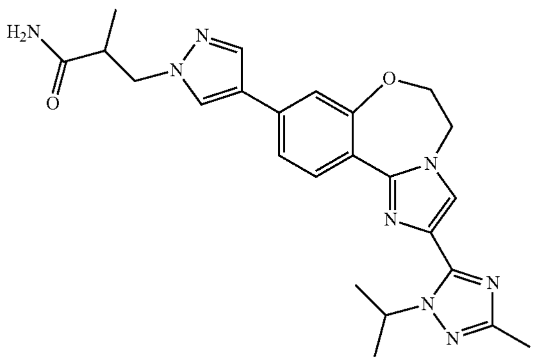 [SMILES: Cc1nc(-c2cn3c(n2)-c2ccc(-c4cnn(CC(C)C(N)=O)c4)cc2OCC3)n(C(C)C)n1] | 3-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide |
| 244 | 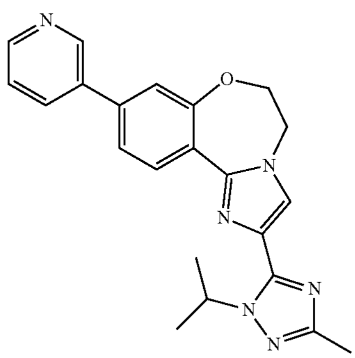 [SMILES: Cc1nc(-c2cn3c(n2)-c2ccc(-c4cccnc4)cc2OCC3)n(C(C)C)n1] | 2-(1-isopropyl-3-methyl-1H-1,2,4-triazol-5-yl)-9-(pyridin-3-yl)-5,6-dihydrobenzo[f]imidazo[1,2-d][1,4]oxazepine |
| 245 | 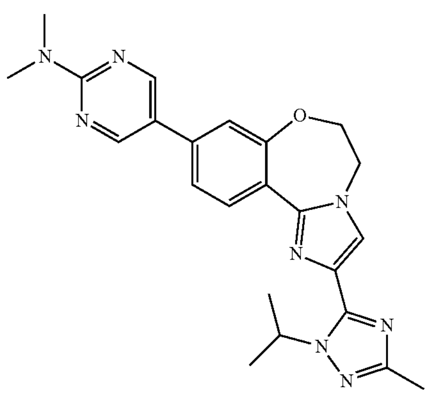 | 5-(2-(1-isopropyl-3-methyl-1H-1,2,4-triazol-5-yl)-5,6-dihydrobenzo[f]imidazo[1,2-d][1,4]oxazepin-9-yl)-N,N-dimethylpyrimidin-2-amine |
| 246 | 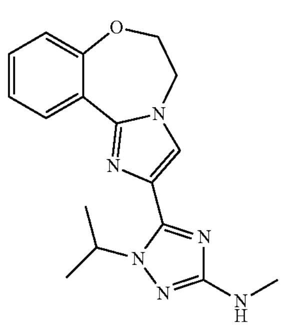 [SMILES: CNc1nc(-c2cn3c(n2)-c2ccccc2OCC3)n(C(C)C)n1] | 5-(5,6-dihydrobenzo[f]imidazo[1,2-d][1,4]oxazepin-2-yl)-1-isopropyl-N-methyl-1H-1,2,4-triazol-3-amine |

TABLE 1-continued

| No. | Structure | Name |
|---|---|---|
| 247 | 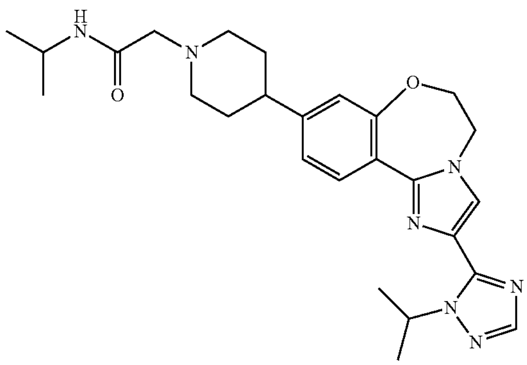 [SMILES: CC(C)NC(=O)CN1CCC(c2ccc3c(c2)OCCn2cc(-c4ncnn4C(C)C)nc2-3)CC1] | N-isopropyl-2-(4-(2-(1-isopropyl-1H-1,2,4-triazol-5-yl)-5,6-dihydrobenzo[f]imidazo[1,2-d][1,4]oxazepin-9-yl)piperidin-1-yl)acetamide |
| 248 | 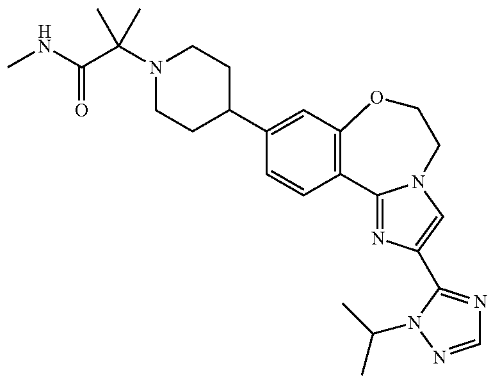 [SMILES: CNC(=O)C(C)(C)N1CCC(c2ccc3c(c2)OCCn2cc(-c4ncnn4C(C)C)nc2-3)CC1] | 2-(4-(2-(1-isopropyl-1H-1,2,4-triazol-5-yl)-5,6-dihydrobenzo[f]imidazo[1,2-d][1,4]oxazepin-9-yl)piperidin-1-yl)-N,2-dimethylpropanamide |
| 249 | 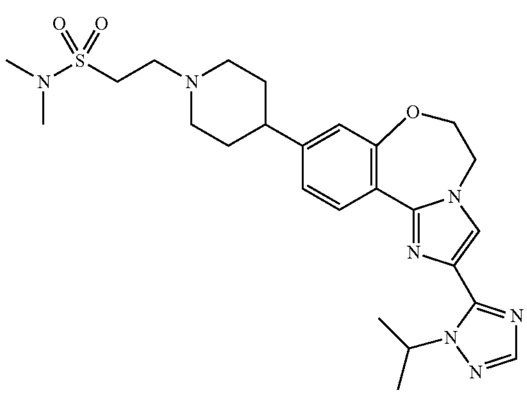 [SMILES: CC(C)n1ncnc1-c1cn2c(n1)-c1ccc(C3CCN(CCS(=O)(=O)N(C)C)CC3)cc1OCC2] | 2-(4-(2-(1-isopropyl-1H-1,2,4-triazol-5-yl)-5,6-dihydrobenzo[f]imidazo[1,2-d][1,4]oxazepin-9-yl)piperidin-1-yl)-N,N-dimethylethanesulfonamide |
| 250 | 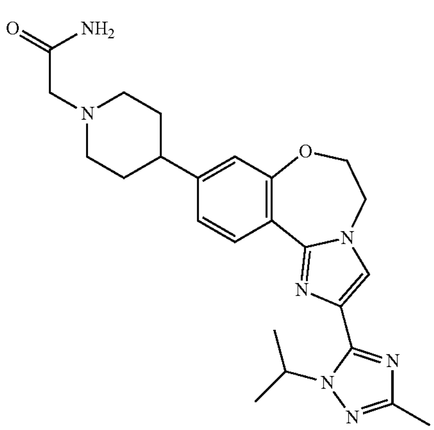 [SMILES: Cc1nc(-c2cn3c(n2)-c2ccc(C4CCN(CC(N)=O)CC4)cc2OCC3)n(C(C)C)n1] | 2-(4-(2-(1-isopropyl-3-methyl-1H-1,2,4-triazol-5-yl)-5,6-dihydrobenzo[f]imidazo[1,2-d][1,4]oxazepin-9-yl)piperidin-1-yl)acetamide |

TABLE 1-continued

| No. | Structure | Name |
|---|---|---|
| 251 | 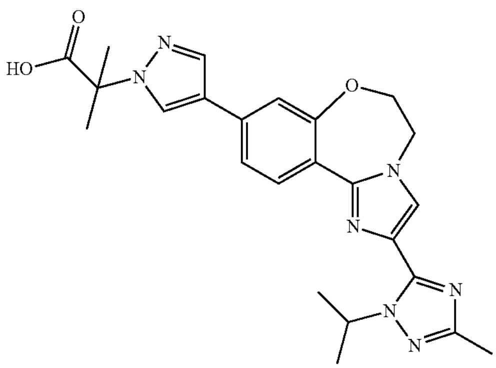 [SMILES: Cc1nc(-c2cn3c(n2)-c2ccc(-c4cnn(C(C)(C)C(=O)O)c4)cc2OCC3)n(C(C)C)n1] | 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoic acid |
| 252 | 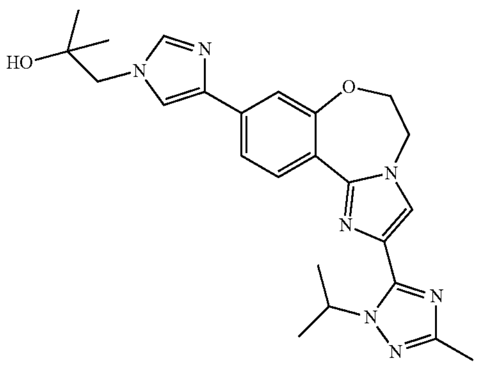 [SMILES: Cc1nc(-c2cn3c(n2)-c2ccc(-c4cn(CC(C)(C)O)cn4)cc2OCC3)n(C(C)C)n1] | 1-(4-(2-(1-isopropyl-3-methyl-1H-1,2,4-triazol-5-yl)-5,6-dihydrobenzo[f]imidazo[1,2-d][1,4]oxazepin-9-yl)-1H-imidazol-1-yl)-2-methylpropan-2-ol |
| 253 | 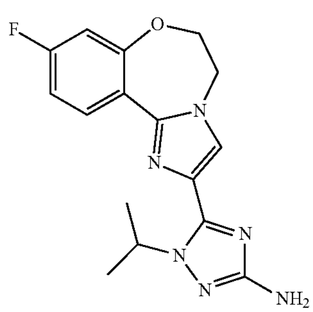 [SMILES: CC(C)n1nc(N)nc1-c1cn2c(n1)-c1ccc(F)cc1OCC2] | 5-(9-fluoro-5,6-dihydrobenzo[f]imidazo[1,2-d][1,4]oxazepin-2-yl)-1-isopropyl-1H-1,2,4-triazol-3-amine |
| 254 | 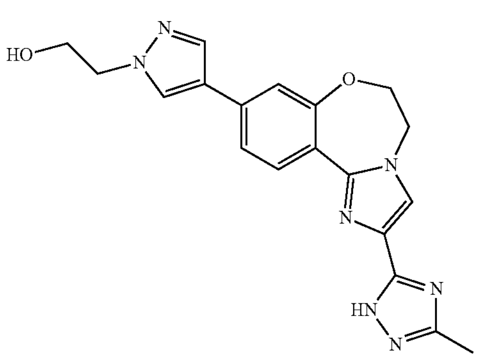 [SMILES: Cc1n[nH]c(-c2cn3c(n2)-c2ccc(-c4cnn(CCO)c4)cc2OCC3)n1] | 2-(4-(2-(3-methyl-1H-1,2,4-triazol-5-yl)-5,6-dihydrobenzo[f]imidazo[1,2-d][1,4]oxazepin-9-yl)-1H-pyrazol-1-yl)ethanol |

TABLE 1-continued

| No. | Structure | Name |
|---|---|---|
| 255 | 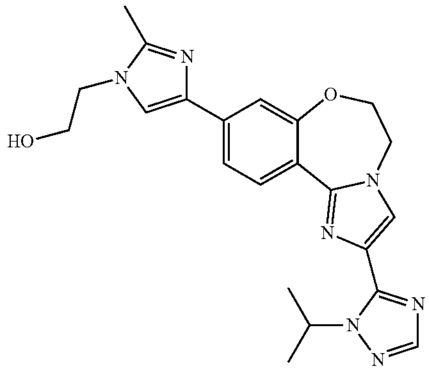 [SMILES: Cc1nc(-c2ccc3c(c2)OCCn2cc(-c4ncnn4C(C)C)nc2-3)cn1CCO] | 2-(4-(2-(1-isopropyl-1H-1,2,4-triazol-5-yl)-5,6-dihydrobenzo[f]imidazo[1,2-d][1,4]oxazepin-9-yl)-2-methyl-1H-imidazol-1-yl)ethanol |
| 256 | 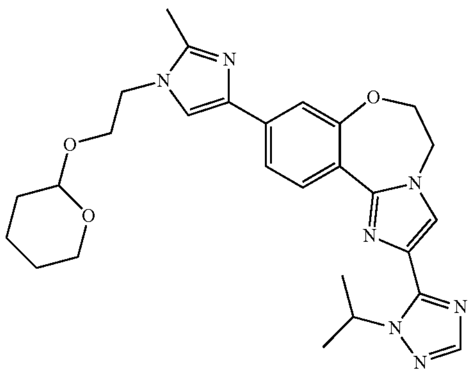 [SMILES: Cc1nc(-c2ccc3c(c2)OCCn2cc(-c4ncnn4C(C)C)nc2-3)cn1CCOC1CCCCO1] | 2-(1-isopropyl-1H-1,2,4-triazol-5-yl)-9-(2-methyl-1-(2-(tetrahydro-2H-pyran-2-yloxy)ethyl)-1H-imidazol-4-yl)-5,6-dihydrobenzo[f]imidazo[1,2-d][1,4]oxazepine |
| 257 | 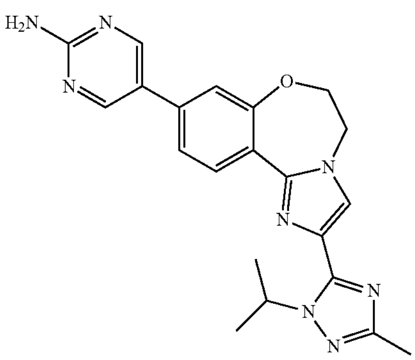 [SMILES: Cc1nc(-c2cn3c(n2)-c2ccc(-c4cnc(N)nc4)cc2OCC3)n(C(C)C)n1] | 5-(2-(1-isopropyl-3-methyl-1H-1,2,4-triazol-5-yl)-5,6-dihydrobenzo[f]imidazo[1,2-d][1,4]oxazepin-9-yl)pyrimidin-2-amine |
| 258 | 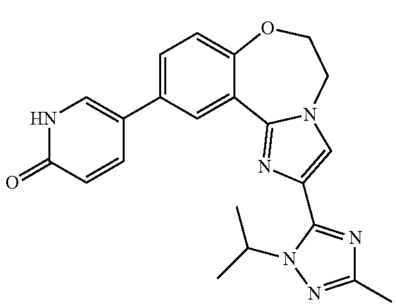 [SMILES: Cc1nc(-c2cn3c(n2)-c2cc(-c4ccc(=O)[nH]c4)ccc2OCC3)n(C(C)C)n1] | 5-(2-(1-isopropyl-3-methyl-1H-1,2,4-triazol-5-yl)-5,6-dihydrobenzo[f]imidazo[1,2-d][1,4]oxazepin-10-yl)pyridin-2(1H)-one |
| 259 | | |
| 260 | | |

TABLE 1-continued

| No. | Structure | Name |
|---|---|---|
| 261 | 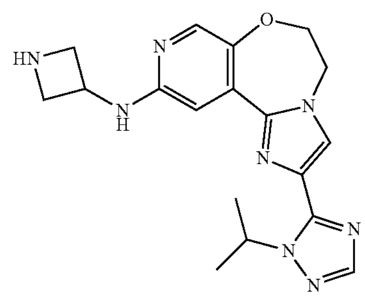 [SMILES: CC(C)n1ncnc1-c1cn2c(n1)-c1cc(NC3CNC3)ncc1OCC2] | N-(azetidin-3-yl)-2-(1-isopropyl-1H-1,2,4-triazol-5-yl)-5,6-dihydroimidazo[1,2-d]pyrido[4,3-f][1,4]oxazepin-10-amine |
| 262 | 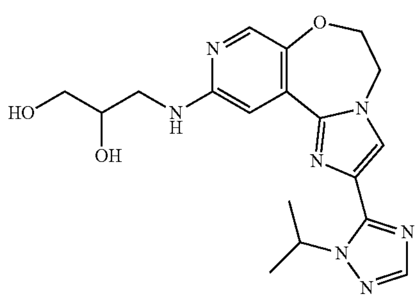 [SMILES: CC(C)n1ncnc1-c1cn2c(n1)-c1cc(NCC(O)CO)ncc1OCC2] | 3-(2-(1-isopropyl-1H-1,2,4-triazol-5-yl)-5,6-dihydroimidazo[1,2-d]pyrido[4,3-f][1,4]oxazepin-10-ylamino)propane-1,2-diol |
| 263 | 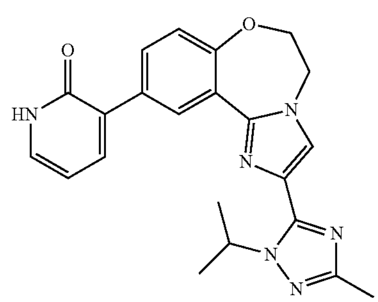 [SMILES: Cc1nc(-c2cn3c(n2)-c2cc(-c4ccc[nH]c4=O)ccc2OCC3)n(C(C)C)n1] | 3-(2-(1-isopropyl-3-methyl-1H-1,2,4-triazol-5-yl)-5,6-dihydrobenzo[f]imidazo[1,2-d][1,4]oxazepin-10-yl)pyridine-2(1H)-one |
| 264 | | |
| 265 | 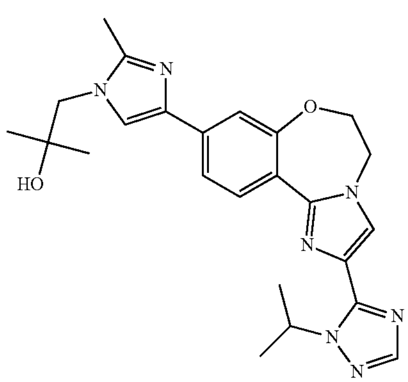 [SMILES: Cc1nc(-c2ccc3c(c2)OCCn2cc(-c4ncnn4C(C)C)nc2-3)cn1CC(C)(C)O] | 1-(4-(2-(1-isopropyl-1H-1,2,4-triazol-5-yl)-5,6-dihydrobenzo[f]imidazo[1,2-d][1,4]oxazepin-9-yl)-2-methyl-1H-imidazol-1-yl)-2-methylpropan-2-ol |
| 266 | | |
| 267 | | |
| 268 | | |

TABLE 1-continued

| No. | Structure | Name |
|---|---|---|
| 269 | 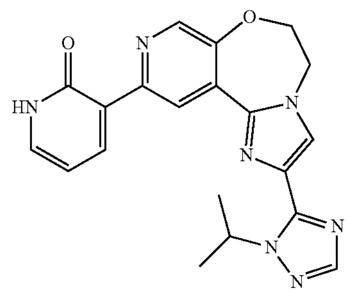 [SMILES: CC(C)n1ncnc1-c1cn2c(n1)-c1cc(-c3ccc[nH]c3=O)ncc1OCC2] | 3-(2-(1-isopropyl-1H-1,2,4-triazol-5-yl)-5,6-dihydroimidazo[1,2-d]pyrido[4,3-f][1,4]oxazepin-10-yl)pyridin-2(1H)-one |
| 270 | 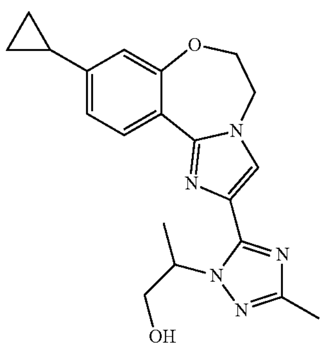 [SMILES: Cc1nc(-c2cn3c(n2)-c2ccc(C4CC4)cc2OCC3)n(C(C)CO)n1] | 2-(5-(9-cyclopropyl-5,6-dihydrobenzo[f]imidazo[1,2-d][1,4]oxazepin-2-yl)-3-methyl-1H-1,2,4-triazol-1-yl)propan-1-ol |
| 271 | 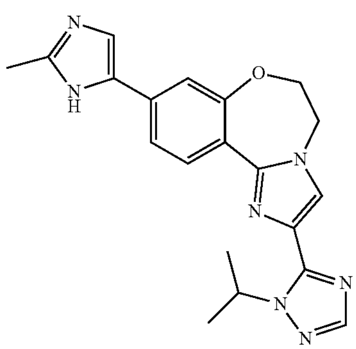 [SMILES: Cc1ncc(-c2ccc3c(c2)OCCn2cc(-c4ncnn4C(C)C)nc2-3)[nH]1] | 2-(1-isopropyl-1H-1,2,4-triazol-5-yl)-9-(2-methyl-1H-imidazol-5-yl)-5,6-dihydrobenzo[f]imidazo[1,2-d][1,4]oxazepine |
| 272 | 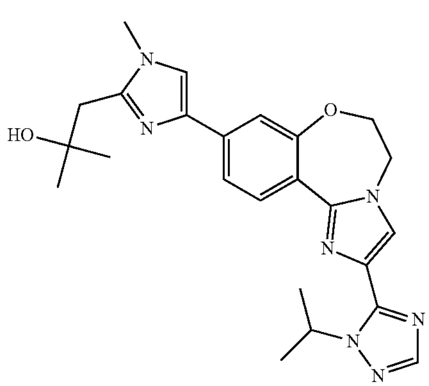 [SMILES: CC(C)n1ncnc1-c1cn2c(n1)-c1ccc(-c3cn(C)c(CC(C)(C)O)n3)cc1OCC2] | 1-(4-(2-(1-isopropyl-1H-1,2,4-triazol-5-yl)-5,6-dihydrobenzo[f]imidazo[1,2-d][1,4]oxazepin-9-yl)-1-methyl-1H-imidazol-2-yl)-2-methylpropan-2-ol |

TABLE 1-continued

| No. | Structure | Name |
|---|---|---|
| 273 | 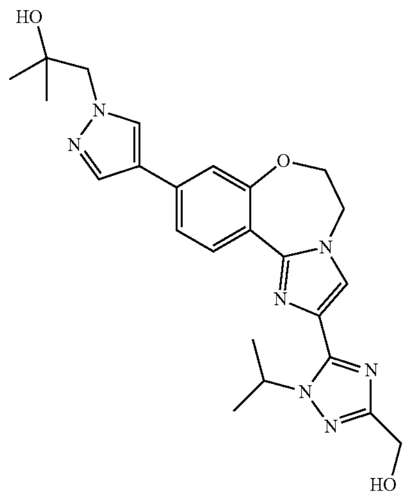 [SMILES: CC(C)n1nc(CO)nc1-c1cn2c(n1)-c1ccc(-c3cnn(CC(C)(C)O)c3)cc1OCC2] | 1-(4-(2-(3-(hydroxymethyl)-1-isopropyl-1H-1,2,4-triazol-5-yl)-5,6-dihydrobenzo[f]imidazo[1,2-d][1,4]oxazepin-9-yl)-1H-pyrazol-1-yl)-2-methylpropan-2-ol |
| 274 | 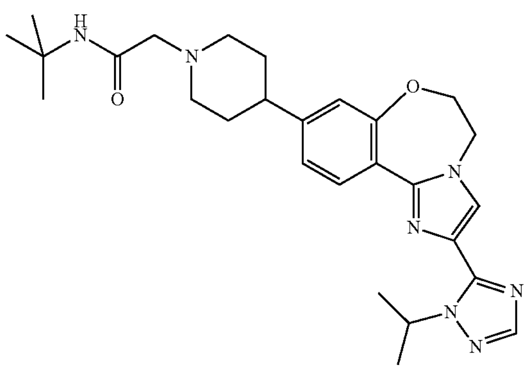 [SMILES: CC(C)n1ncnc1-c1cn2c(n1)-c1ccc(C3CCN(CC(=O)NC(C)(C)C)CC3)cc1OCC2] | N-tert-butyl-2-(4-(2-(1-isopropyl-1H-1,2,4-triazol-5-yl)-5,6-dihydrobenzo[f]imidazo[1,2-d][1,4]oxazepin-9-yl)piperidin-1-yl)acetamide |
| 275 | 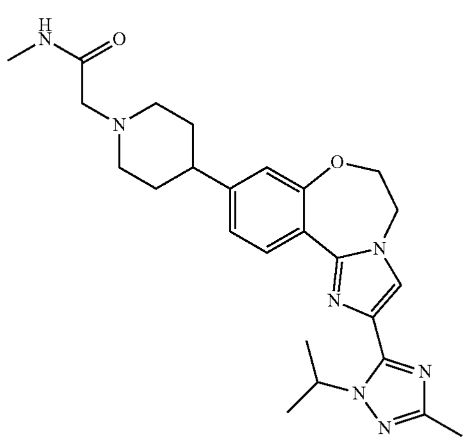 | 2-(4-(2-(1-isopropyl-3-methyl-1H-1,2,4-triazol-5-yl)-5,6-dihydrobenzo[f]imidazo[1,2-d][1,4]oxazepin-9-yl)piperidin-1-yl)-N-methylacetamide |

TABLE 1-continued

| No. | Structure | Name |
|---|---|---|
| 276 | 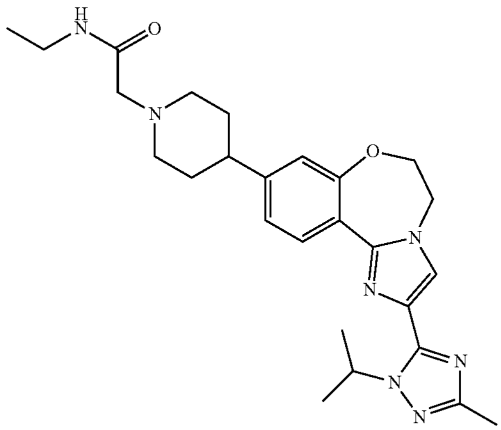 [SMILES: CCNC(=O)CN1CCC(c2ccc3c(c2)OCCn2cc(-c4nc(C)nn4C(C)C)nc2-3)CC1] | N-ethyl-2-(4-(2-(1-isopropyl-3-methyl-1H-1,2,4-triazol-5-yl)-5,6-dihydrobenzo[f]imidazo[1,2-d][1,4]oxazepin-9-yl)piperidin-1-yl)acetamide |
| 277 | 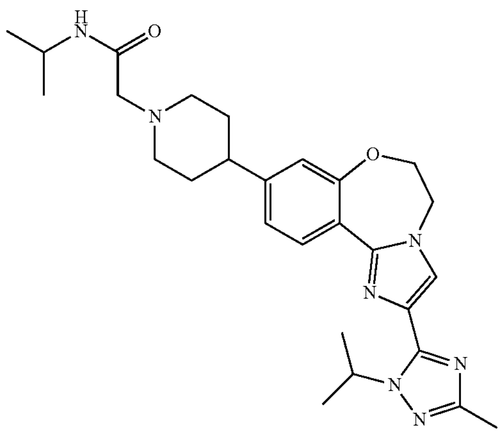 [SMILES: Cc1nc(-c2cn3c(n2)-c2ccc(C4CCN(CC(=O)NC(C)C)CC4)cc2OCC3)n(C(C)C)n1] | N-isopropyl-2-(4-(2-(1-isopropyl-3-methyl-1H-1,2,4-triazol-5-yl)-5,6-dihydrobenzo[f]imidazo[1,2-d][1,4]oxazepin-9-yl)piperidin-1-yl)acetamide |
| 278 | 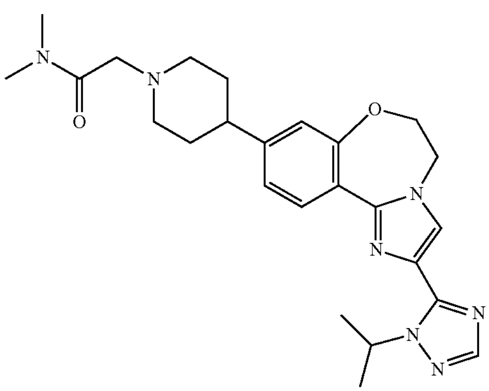 [SMILES: CC(C)n1ncnc1-c1cn2c(n1)-c1ccc(C3CCN(CC(=O)N(C)C)CC3)cc1OCC2] | 2-(4-(2-(1-isopropyl-1H-1,2,4-triazol-5-yl)-5,6-dihydrobenzo[f]imidazo[1,2-d][1,4]oxazepin-9-yl)piperidin-1-yl)-N,N-dimethylacetamide |
| 279 | 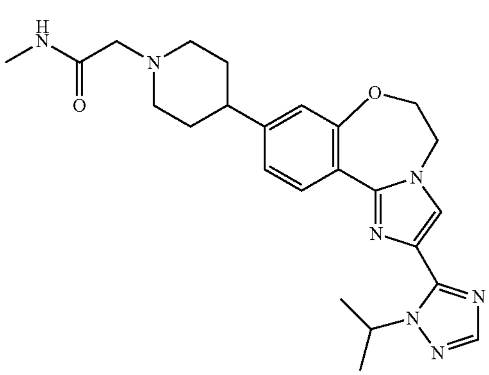 [SMILES: CNC(=O)CN1CCC(c2ccc3c(c2)OCCn2cc(-c4ncnn4C(C)C)nc2-3)CC1] | 2-(4-(2-(1-isopropyl-1H-1,2,4-triazol-5-yl)-5,6-dihydrobenzo[f]imidazo[1,2-d][1,4]oxazepin-9-yl)piperidin-1-yl)-N-methylacetamide |

TABLE 1-continued

| No. | Structure | Name |
|---|---|---|
| 280 | 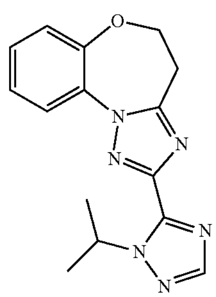 [SMILES: CC(C)n1ncnc1-c1nc2n(n1)-c1ccccc1OCC2] | 2-(1-isopropyl-1H-1,2,4-triazol-5-yl)-4,5-dihydrobenzo[b][1,2,4]triazolo[1,5-d][1,4]oxazepine |
| 281 | 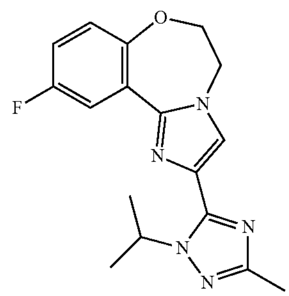 [SMILES: Cc1nc(-c2cn3c(n2)-c2cc(F)ccc2OCC3)n(C(C)C)n1] | 10-fluoro-2-(1-isopropyl-3-methyl-1H-1,2,4-triazol-5-yl)-5,6-dihydrobenzo[f]imidazo[1,2-d][1,4]oxazepine |
| 282 | 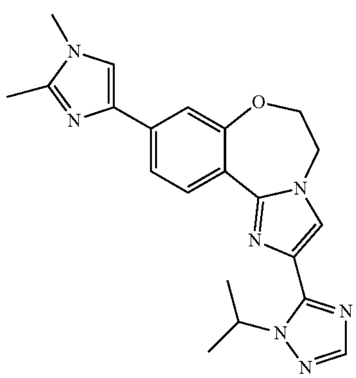 [SMILES: Cc1nc(-c2ccc3c(c2)OCCn2cc(-c4ncnn4C(C)C)nc2-3)cn1C] | 9-(1,2-dimethyl-1H-imidazol-4-yl)-2-(1-isopropyl-1H-1,2,4-triazol-5-yl)-5,6-dihydrobenzo[f]imidazo[1,2-d][1,4]oxazepine |
| 283 | 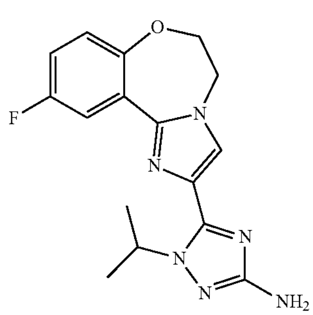 [SMILES: CC(C)n1nc(N)nc1-c1cn2c(n1)-c1cc(F)ccc1OCC2] | 5-(10-fluoro-5,6-dihydrobenzo[f]imidazo[1,2-d][1,4]oxazepin-2-yl)-1-isopropyl-1H-1,2,4-triazol-3-amine |
| 284 | 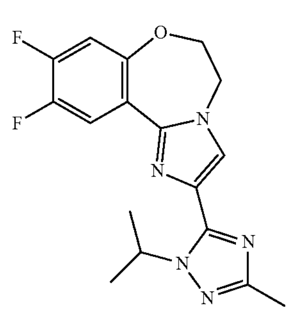 [SMILES: Cc1nc(-c2cn3c(n2)-c2cc(F)c(F)cc2OCC3)n(C(C)C)n1] | 9,10-difluoro-2-(1-isopropyl-3-methyl-1H-1,2,4-triazol-5-yl)-5,6-dihydrobenzo[f]imidazo[1,2-d][1,4]oxazepine |

TABLE 1-continued

| No. | Structure | Name |
|---|---|---|
| 285 | 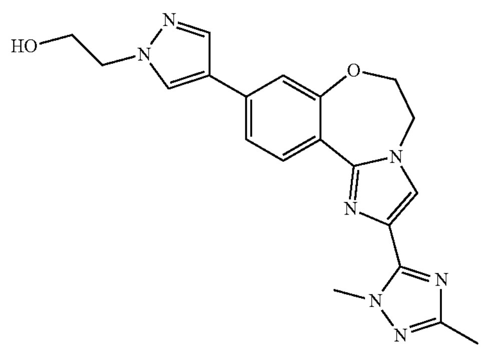 [SMILES: Cc1nc(-c2cn3c(n2)-c2ccc(-c4cnn(CCO)c4)cc2OCC3)n(C)n1] | 2-(4-(2-(1,3-dimethyl-1H-1,2,4-triazol-5-yl)-5,6-dihydrobenzo[f]imidazo[1,2-d][1,4]oxazepin-9-yl)-1H-pyrazol-1-yl)ethanol |
| 286 | 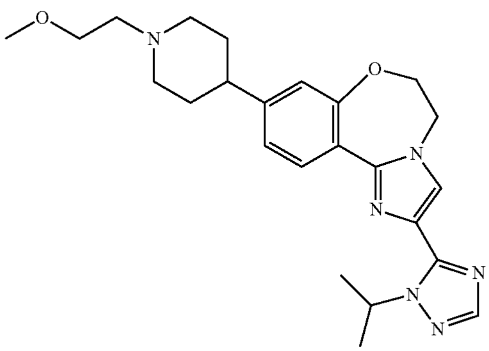 [SMILES: COCCN1CCC(c2ccc3c(c2)OCCn2cc(-c4ncnn4C(C)C)nc2-3)CC1] | 2-(1-isopropyl-1H-1,2,4-triazol-5-yl)-9-(1-(2-methoxyethyl)piperidin-4-yl)-5,6-dihydrobenzo[f]imidazo[1,2-d][1,4]oxazepine |
| 287 | 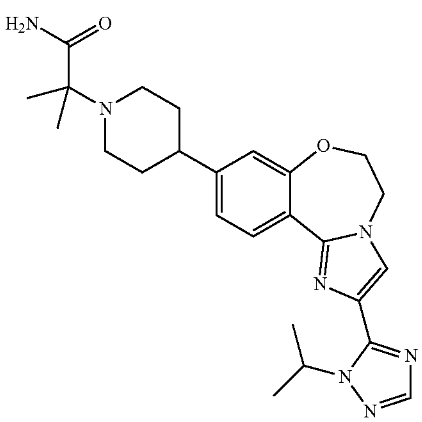 [SMILES: CC(C)n1ncnc1-c1cn2c(n1)-c1ccc(C3CCN(C(C)(C)C(N)=O)CC3)cc1OCC2] | 2-(4-(2-(1-isopropyl-1H-1,2,4-triazol-5-yl)-5,6-dihydrobenzo[f]imidazo[1,2-d][1,4]oxazepin-9-yl)piperidin-1-yl)-2-methylpropanamide |
| 288 | 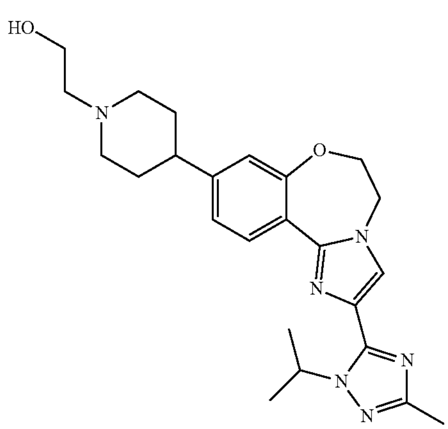 [SMILES: Cc1nc(-c2cn3c(n2)-c2ccc(C4CCN(CCO)CC4)cc2OCC3)n(C(C)C)n1] | 2-(4-(2-(1-isopropyl-3-methyl-1H-1,2,4-triazol-5-yl)-5,6-dihydrobenzo[f]imidazo[1,2-d][1,4]oxazepin-9-yl)piperidin-1-yl)ethanol |

TABLE 1-continued

| No. | Structure | Name |
| --- | --- | --- |
| 289 | 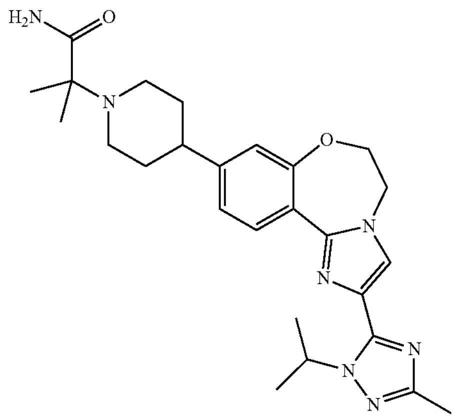 [SMILES: Cc1nc(-c2cn3c(n2)-c2ccc(C4CCN(C(C)(C)C(N)=O)CC4)cc2OCC3)n(C(C)C)n1] | 2-(4-(2-(1-isopropyl-3-methyl-1H-1,2,4-triazol-5-yl)-5,6-dihydrobenzo[f]imidazo[1,2-d][1,4]oxazepin-9-yl)piperidin-1-yl)-2-methylpropanamide |
| 290 | 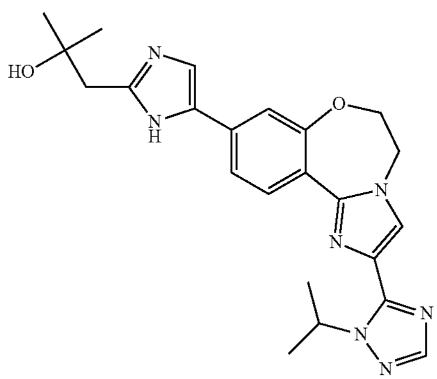 [SMILES: CC(C)n1ncnc1-c1cn2c(n1)-c1ccc(-c3cnc(CC(C)(C)O)[nH]3)cc1OCC2] | 1-(5-(2-(1-isopropyl-1H-1,2,4-triazol-5-yl)-5,6-dihydrobenzo[f]imidazo[1,2-d][1,4]oxazepin-9-yl)-1H-imidazol-2-yl)-2-methylpropan-2-ol |
| 291 | 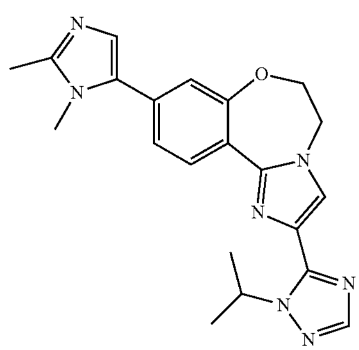 [SMILES: Cc1ncc(-c2ccc3c(c2)OCCn2cc(-c4ncnn4C(C)C)nc2-3)n1C] | 9-(1,2-dimethyl-1H-imidazol-5-yl)-2-(1-isopropyl-1H-1,2,4-triazol-5-yl)-5,6-dihydrobenzo[f]imidazo[1,2-d][1,4]oxazepine |
| 292 | 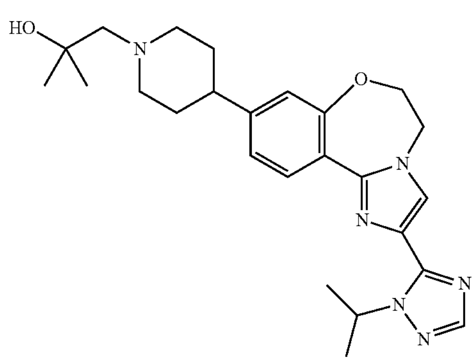 [SMILES: CC(C)n1ncnc1-c1cn2c(n1)-c1ccc(C3CCN(CC(C)(C)O)CC3)cc1OCC2] | 1-(4-(2-(1-isopropyl-1H-1,2,4-triazol-5-yl)-5,6-dihydrobenzo[f]imidazo[1,2-d][1,4]oxazepin-9-yl)piperidin-1-yl)-2-methylpropan-2-ol |

TABLE 1-continued

| No. | Structure | Name |
|---|---|---|
| 293 | 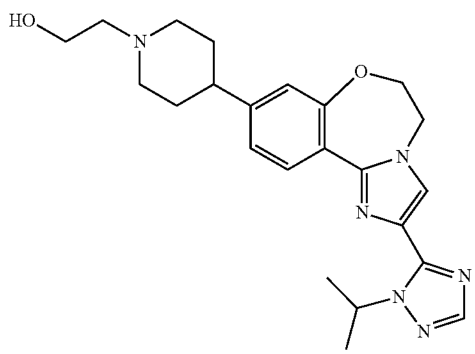 [SMILES: CC(C)n1ncnc1-c1cn2c(n1)-c1ccc(C3CCN(CCO)CC3)cc1OCC2] | 2-(4-(2-(1-isopropyl-1H-1,2,4-triazol-5-yl)-5,6-dihydrobenzo[f]imidazo[1,2-d][1,4]oxazepin-9-yl)piperidin-1-yl)ethanol |
| 294 | 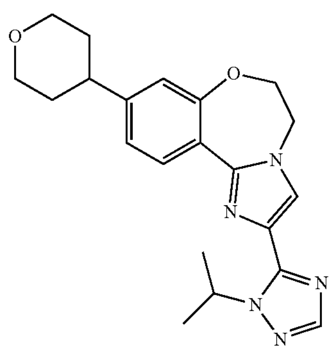 [SMILES: CC(C)n1ncnc1-c1cn2c(n1)-c1ccc(C3CCOCC3)cc1OCC2] | 2-(1-isopropyl-1H-1,2,4-triazol-5-yl)-9-(tetrahydro-2H-pyran-4-yl)-5,6-dihydrobenzo[f]imidazo[1,2-d][1,4]oxazepine |

TABLE 2

| No. | Structure | Name |
|---|---|---|
| 295 | 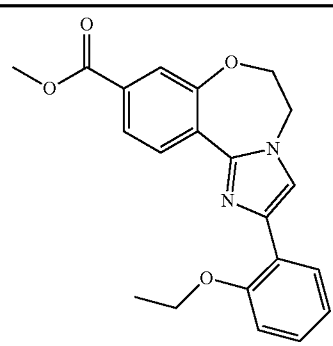 | methyl 2-(2-ethoxyphenyl)-5,6-dihydrobenzo[f]imidazo[1,2-d][1,4]oxazepine-9-carboxylate |
| 296 | 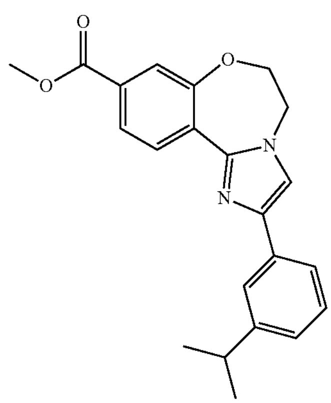 [SMILES: COC(=O)c1ccc2c(c1)OCCn1cc(-c3cccc(C(C)C)c3)nc1-2] | methyl 2-(3-isopropylphenyl)-5,6-dihydrobenzo[f]imidazo[1,2-d][1,4]oxazepine-9-carboxylate |

TABLE 2-continued

| No. | Structure | Name |
|---|---|---|
| 297 | 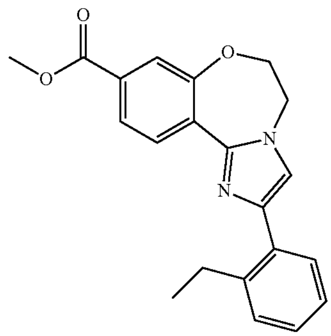 [SMILES: CCc1ccccc1-c1cn2c(n1)-c1ccc(C(=O)OC)cc1OCC2] | methyl 2-(2-ethylphenyl)-5,6-dihydrobenzo[f]imidazo[1,2-d][1,4]oxazepine-9-carboxylate |
| 298 | 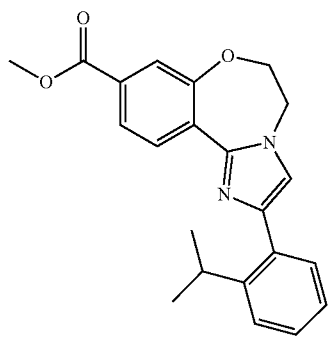 [SMILES: COC(=O)c1ccc2c(c1)OCCn1cc(-c3ccccc3C(C)C)nc1-2] | methyl 2-(2-isopropylphenyl)-5,6-dihydrobenzo[f]imidazo[1,2-d][1,4]oxazepine-9-carboxylate |
| 299 | 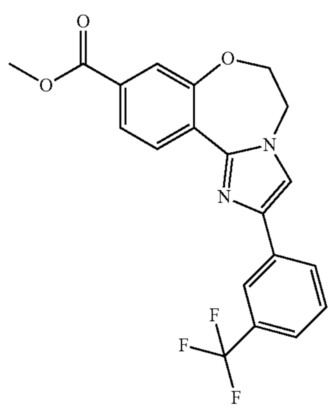 [SMILES: COC(=O)c1ccc2c(c1)OCCn1cc(-c3cccc(C(F)(F)F)c3)nc1-2] | methyl 2-(3-(trifluoromethyl)phenyl)-5,6-dihydrobenzo[f]imidazo[1,2-d][1,4]oxazepine-9-carboxylate |
| 300 | 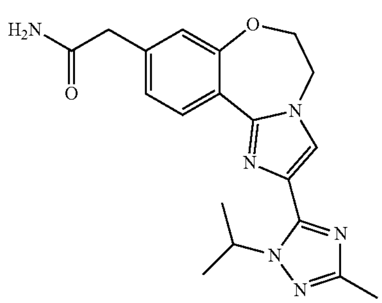 [SMILES: Cc1nc(-c2cn3c(n2)-c2ccc(CC(N)=O)cc2OCC3)n(C(C)C)n1] | 2-(2-(1-isopropyl-3-methyl-1H-1,2,4-triazol-5-yl)-5,6-dihydrobenzo[f]imidazo[1,2-d][1,4]oxazepin-9-yl)acetamide |

TABLE 2-continued

| No. | Structure | Name |
| --- | --- | --- |
| 301 | 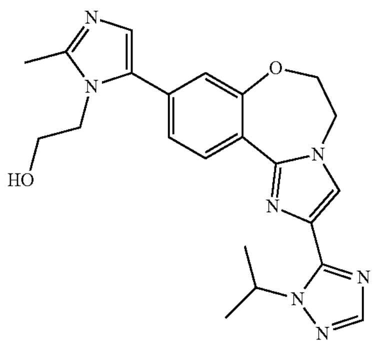 [SMILES: Cc1ncc(-c2ccc3c(c2)OCCn2cc(-c4ncnn4C(C)C)nc2-3)n1CCO] | 2-(5-(2-(1-isopropyl-1H-1,2,4-triazol-5-yl)-5,6-dihydrobenzo[f]imidazo[1,2-d][1,4]oxazepin-9-yl)-2-methyl-1H-imidazol-1-yl)ethanol |
| 302 | 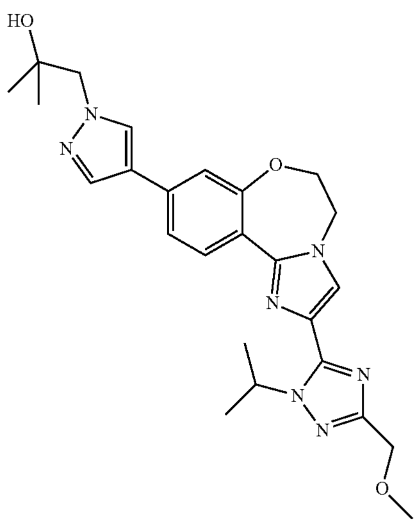 [SMILES: COCc1nc(-c2cn3c(n2)-c2ccc(-c4cnn(CC(C)(C)O)c4)cc2OCC3)n(C(C)C)n1] | 1-(4-(2-(1-isopropyl-3-(methoxymethyl)-1H-1,2,4-triazol-5-yl)-5,6-dihydrobenzo[f]imidazo[1,2-d][1,4]oxazepin-9-yl)-1H-pyrazol-1-yl)-2-methylpropan-2-ol |
| 303 | 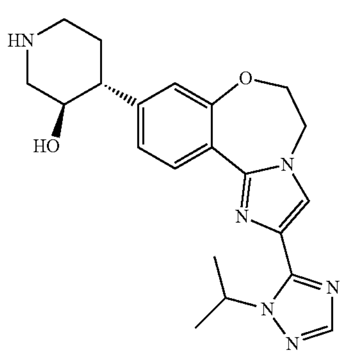 [SMILES: CC(C)n1ncnc1-c1cn2c(n1)-c1ccc([C@H]3CCNC[C@@H]3O)cc1OCC2] | (3R,4R)-4-(2-(1-isopropyl-1H-1,2,4-triazol-5-yl)-5,6-dihydrobenzo[f]imidazo[1,2-d][1,4]oxazepin-9-yl)piperidin-3-ol |

TABLE 2-continued

| No. | Structure | Name |
|---|---|---|
| 304 | 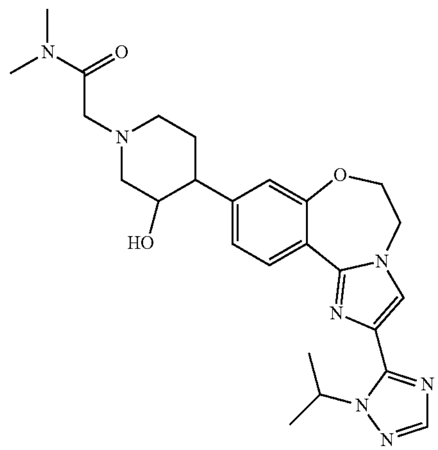 [SMILES: CC(C)n1ncnc1-c1cn2c(n1)-c1ccc(C3CCN(CC(=O)N(C)C)CC3O)cc1OCC2] | racemic-trans-2-(3-hydroxy-4-(2-(1-isopropyl-1H-1,2,4-triazol-5-yl)-5,6-dihydrobenzo[f]imidazo[1,2-d][1,4]oxazepin-9-yl)piperidin-1-yl)-N,N-dimethylacetamide |
| 305 | 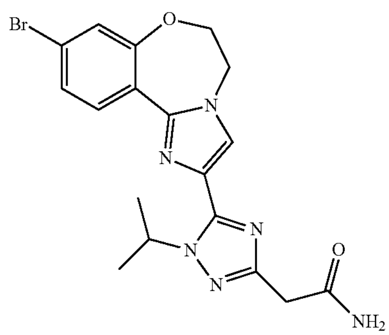 [SMILES: CC(C)n1nc(CC(N)=O)nc1-c1cn2c(n1)-c1ccc(Br)cc1OCC2] | 2-(5-(9-bromo-5,6-dihydrobenzo[f]imidazo[1,2-d][1,4]oxazepin-2-yl)-1-isopropyl-1H-1,2,4-triazol-3-yl)acetamide |
| 306 | 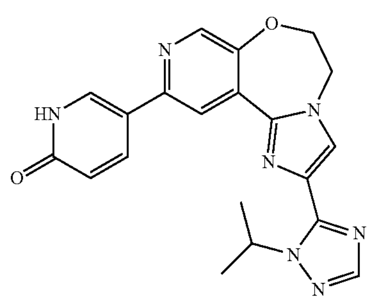 [SMILES: CC(C)n1ncnc1-c1cn2c(n1)-c1cc(-c3ccc(=O)[nH]c3)ncc1OCC2] | 5-(2-(1-isopropyl-1H-1,2,4-triazol-5-yl)-5,6-dihydrobenzoimidazo[1,2-d]pyrido[4,3-f][1,4]oxazepin-10-yl)pyridin-2(1H)-one |
| 307 | 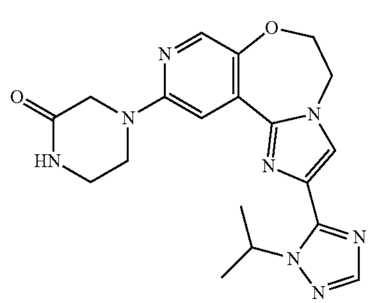 [SMILES: CC(C)n1ncnc1-c1cn2c(n1)-c1cc(N3CCNC(=O)C3)ncc1OCC2] | 4-(2-(1-isopropyl-1H-1,2,4-triazol-5-yl)-5,6-dihydroimidazo[1,2-d]pyrido[4,3-f][1,4]oxazepin-10-yl)piperazin-2-one |

TABLE 2-continued

| No. | Structure | Name |
|---|---|---|
| 308 | 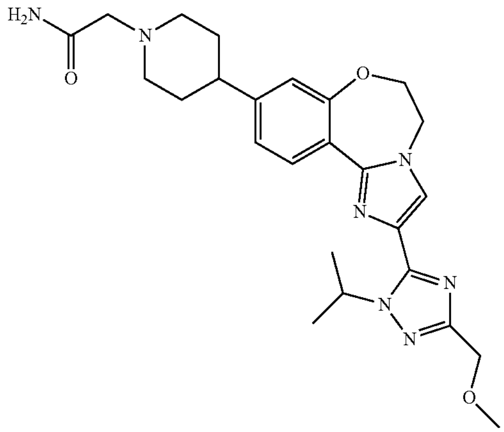 [SMILES: COCc1nc(-c2cn3c(n2)-c2ccc(C4CCN(CC(N)=O)CC4)cc2OCC3)n(C(C)C)n1] | 2-(4-(2-(1-isopropyl-3-(methoxymethyl)-1H-1,2,4-triazol-5-yl)-5,6-dihydrobenzo[f]imidazo[1,2-d][1,4]oxazepin-9-yl)piperidin-1-yl)acetamide |
| 309 | 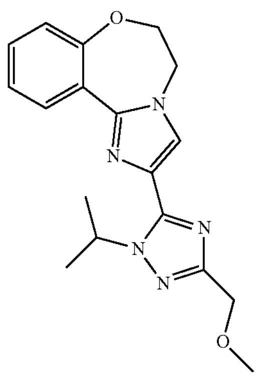 [SMILES: COCc1nc(-c2cn3c(n2)-c2ccccc2OCC3)n(C(C)C)n1] | 2-(1-isopropyl-3-(methoxymethyl)-1H-1,2,4-triazol-5-yl)-5,6-dihydrobenzo[f]imidazo[1,2-d][1,4]oxazepine |
| 310 | 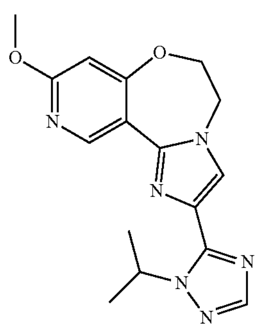 [SMILES: COc1cc2c(cn1)-c1nc(-c3ncnn3C(C)C)cn1CCO2] | 2-(1-isopropyl-1H-1,2,4-triazol-5-yl)-9-methoxy-5,6-dihydroimidazo[1,2-d]pyrido[3,4-f][1,4]oxazepine |
| 311 | 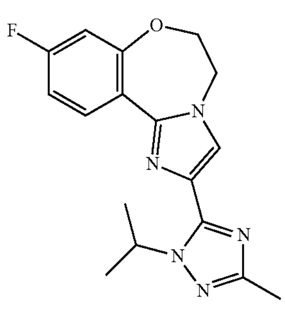 [SMILES: Cc1nc(-c2cn3c(n2)-c2ccc(F)cc2OCC3)n(C(C)C)n1] | 9-fluoro-2-(1-isopropyl-3-methyl-1H-1,2,4-triazol-5-yl)-5,6-dihydrobenzo[f]imidazo[1,2-d][1,4]oxazepine |

TABLE 2-continued

| No. | Structure | Name |
| --- | --- | --- |
| 312 | 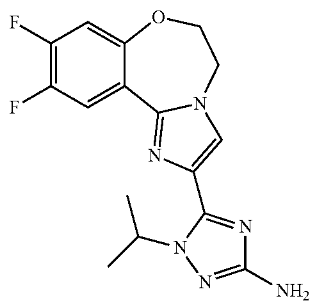 [SMILES: CC(C)n1nc(N)nc1-c1cn2c(n1)-c1cc(F)c(F)cc1OCC2] | 5-(9,10-difluoro-5,6-dihydrobenzo[f]imidazo[1,2-d][1,4]oxazepin-2-yl)-1-isopropyl-1H-1,2,4-triazol-3-amine |
| 313 | 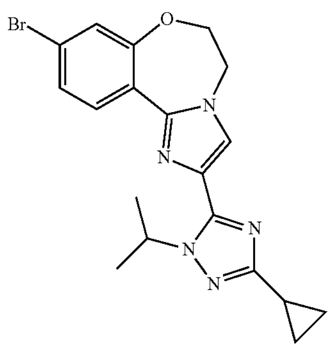 [SMILES: CC(C)n1nc(C2CC2)nc1-c1cn2c(n1)-c1ccc(Br)cc1OCC2] | 9-bromo-2-(3-cyclopropyl-1-isopropyl-1H-1,2,4-triazol-5-yl)-5,6-dihydrobenzo[f]imidazo[1,2-d][1,4]oxazepine |
| 314 | 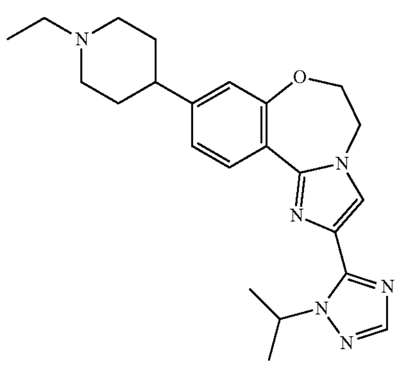 [SMILES: CCN1CCC(c2ccc3c(c2)OCCn2cc(-c4ncnn4C(C)C)nc2-3)CC1] | 9-(1-ethylpiperidin-4-yl)-2-(1-isopropyl-1H-1,2,4-triazol-5-yl)-5,6-dihydrobenzo[f]imidazo[1,2-d][1,4]oxazepine |
| 315 | 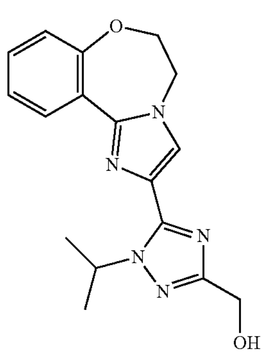 [SMILES: CC(C)n1nc(CO)nc1-c1cn2c(n1)-c1ccccc1OCC2] | (5-(5,6-dihydrobenzo[f]imidazo[1,2-d][1,4]oxazepin-2-yl)-1-isopropyl-1H-1,2,4-triazol-3-yl)methanol |

TABLE 2-continued

| No. | Structure | Name |
|---|---|---|
| 316 | 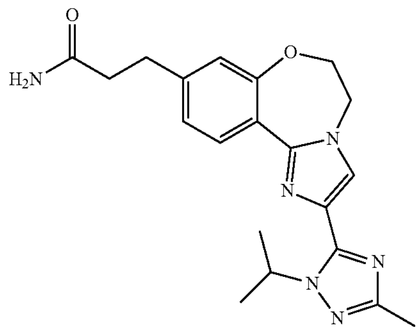 [SMILES: Cc1nc(-c2cn3c(n2)-c2ccc(CCC(N)=O)cc2OCC3)n(C(C)C)n1] | 3-(2-(1-isopropyl-3-methyl-1H-1,2,4-triazol-5-yl)-5,6-dihydrobenzo[f]imidazo[1,2-d][1,4]oxazepin-9-yl)propanamide |
| 317 | 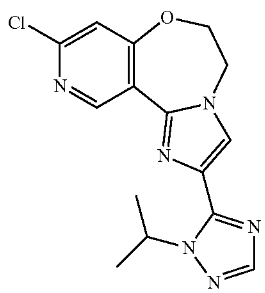 [SMILES: CC(C)n1ncnc1-c1cn2c(n1)-c1cnc(Cl)cc1OCC2] | 9-chloro-2-(1-isopropyl-1H-1,2,4-triazol-5-yl)-5,6-dihydroimidazo[1,2-d]pyrido[3,4-f][1,4]oxazepine |
| 318 | 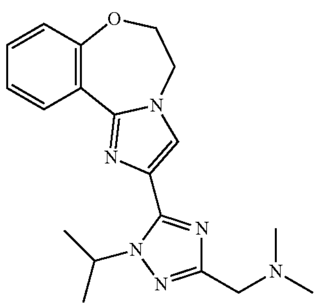 [SMILES: CC(C)n1nc(CN(C)C)nc1-c1cn2c(n1)-c1ccccc1OCC2] | 1-(5-(5,6-dihydrobenzo[f]imidazo[1,2-d][1,4]oxazepin-2-yl)-1-isopropyl-1H-1,2,4-triazol-3-yl)-N,N-dimethylmethanamine |
| 319 | 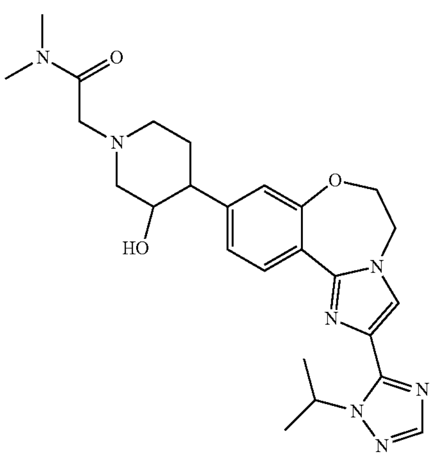 [SMILES: CC(C)n1ncnc1-c1cn2c(n1)-c1ccc(C3CCN(CC(=O)N(C)C)CC3O)cc1OCC2] | racemic-cis-2-(3-hydroxy-4-(2-(1-isopropyl-1H-1,2,4-triazol-5-yl)-5,6-dihydrobenzo[f]imidazo[1,2-d][1,4]oxazepin-9-yl)piperidin-1-yl)-N,N-dimethylacetamide |

TABLE 2-continued

| No. | Structure | Name |
|---|---|---|
| 320 | 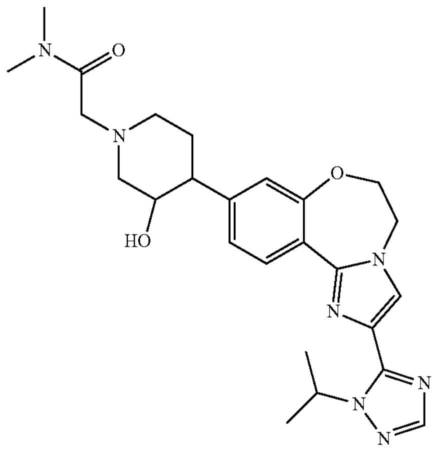 [SMILES: CC(C)n1ncnc1-c1cn2c(n1)-c1ccc(C3CCN(CC(=O)N(C)C)CC3O)cc1OCC2] | racemic-cis-2-(3-hydroxy-4-(2-(1-isopropyl-1H-1,2,4-triazol-5-yl)-5,6-dihydrobenzo[f]imidazo[1,2-d][1,4]oxazepin-9-yl)piperidin-1-yl)-N,N-dimethylacetamide |
| 321 | 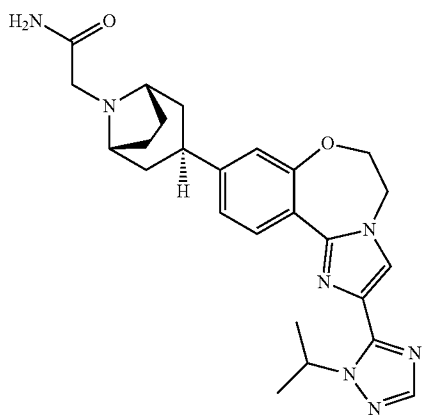 [SMILES: CC(C)n1ncnc1-c1cn2c(n1)-c1ccc([C@H]3C[C@H]4CC[C@@H](C3)N4CC(N)=O)cc1OCC2] | 2-((1R,3r,5S)-3-(2-(1-isopropyl-1H-1,2,4-triazol-5-yl)-5,6-dihydrobenzo[f]imidazo[1,2-d][1,4]oxazepin-9-yl)-8-azabicyclo[3.2.1]octan-8-yl)acetamide |
| 322 | 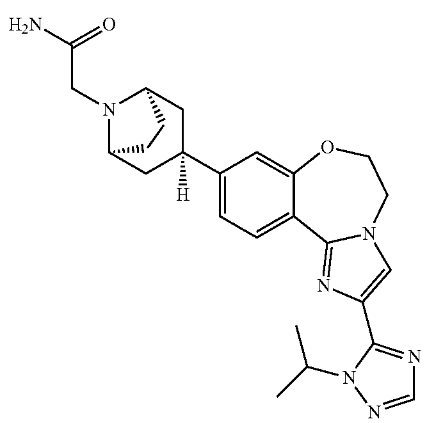 [SMILES: CC(C)n1ncnc1-c1cn2c(n1)-c1ccc([C@@H]3C[C@H]4CC[C@@H](C3)N4CC(N)=O)cc1OCC2] | 2-((1R,3S,5S)-3-(2-(1-isopropyl-1H-1,2,4-triazol-5-yl)-5,6-dihydrobenzo[f]imidazo[1,2-d][1,4]oxazepin-9-yl)-8-azabicyclo[3.2.1]octan-8-yl)acetamide |
| 323 | 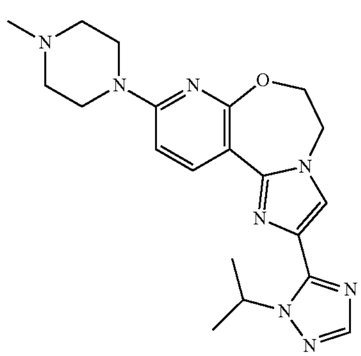 [SMILES: CC(C)n1ncnc1-c1cn2c(n1)-c1ccc(N3CCN(C)CC3)nc1OCC2] | 2-(1-isopropyl-1H-1,2,4-triazol-5-yl)-9-(4-methylpiperazin-1-yl)-5,6-dihydroimidazo[1,2-d]pyrido[3,2-f][1,4]oxazepine |

TABLE 2-continued

| No. | Structure | Name |
|---|---|---|
| 324 | 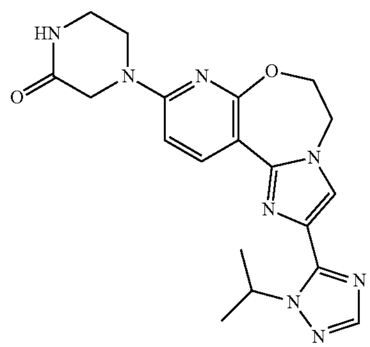 [SMILES: CC(C)n1ncnc1-c1cn2c(n1)-c1ccc(N3CCNC(=O)C3)nc1OCC2] | 4-(2-(1-isopropyl-1H-1,2,4-triazol-5-yl)-5,6-dihydroimidazo[1,2-d]pyrido[3,2-f][1,4]oxazepin-9-yl)piperazin-2-one |
| 325 | 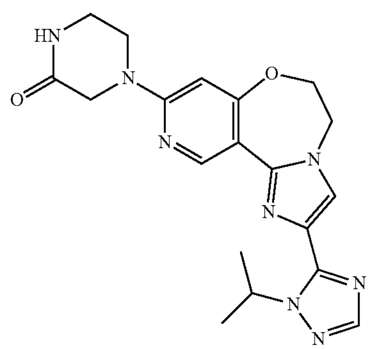 [SMILES: CC(C)n1ncnc1-c1cn2c(n1)-c1cnc(N3CCNC(=O)C3)cc1OCC2] | 4-(2-(1-isopropyl-1H-1,2,4-triazol-5-yl)-5,6-dihydroimidazo[1,2-d]pyrido[3,4-f][1,4]oxazepin-9-yl)piperazin-2-one |
| 326 | | |
| 327 | 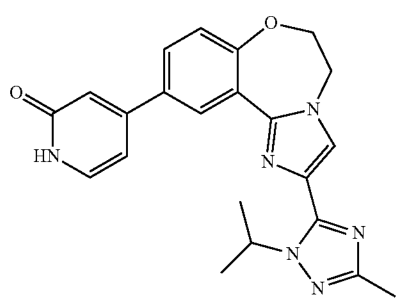 [SMILES: Cc1nc(-c2cn3c(n2)-c2cc(-c4cc[nH]c(=O)c4)ccc2OCC3)n(C(C)C)n1] | 4-(2-(1-isopropyl-3-methyl-1H-1,2,4-triazol-5-yl)-5,6-dihydrobenzo[f]imidazo[1,2-d][1,4]oxazepin-10-yl)pyridin-2(1H)-one |
| 328 | 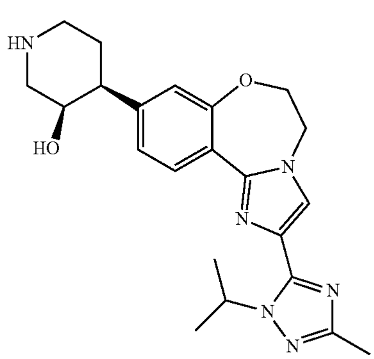 [SMILES: Cc1nc(-c2cn3c(n2)-c2ccc([C@@H]4CCNC[C@@H]4O)cc2OCC3)n(C(C)C)n1] | (3R,4S)-4-(2-(1-isopropyl-3-methyl-1H-1,2,4-triazol-5-yl)-5,6-dihydrobenzo[f]imidazo[1,2-d][1,4]oxazepin-9-yl)piperidin-3-ol |

TABLE 2-continued

| No. | Structure | Name |
|---|---|---|
| 329 | 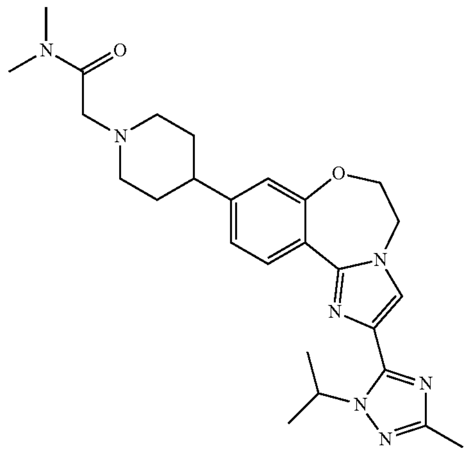 | 2-(4-(2-(1-isopropyl-3-methyl-1H-1,2,4-triazol-5-yl)-5,6-dihydrobenzo[f]imidazo[1,2-d][1,4]oxazepin-9-yl)piperidin-1-yl)-N,N-dimethylacetamide |
| 330 | 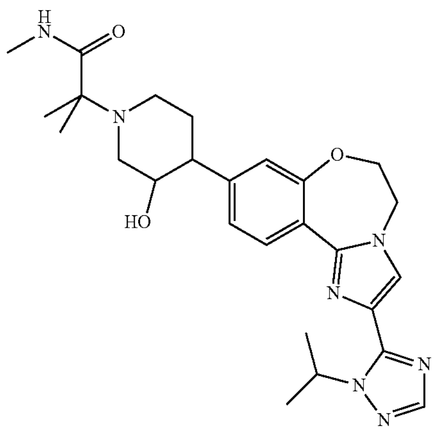 [SMILES: CNC(=O)C(C)(C)N1CCC(c2ccc3c(c2)OCCn2cc(-c4ncnn4C(C)C)nc2-3)C(O)C1] | trans-racemic-2-(3-hydroxy-4-(2-(1-isopropyl-1H-1,2,4-triazol-5-yl)-5,6-dihydrobenzo[f]imidazo[1,2-d][1,4]oxazepin-9-yl)piperidin-1-yl)-N,2-dimethylpropanamide |
| 331 | 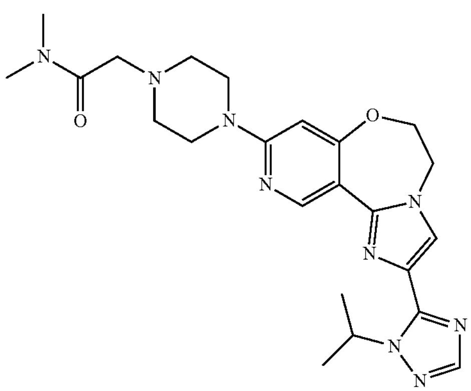 [SMILES: CC(C)n1ncnc1-c1cn2c(n1)-c1cnc(N3CCN(CC(=O)N(C)C)CC3)cc1OCC2] | 2-(4-(2-(1-isopropyl-1H-1,2,4-triazol-5-yl)-5,6-dihydroimidazo[1,2-d]pyrido[3,4-f][1,4]oxazepin-9-yl)piperidin-1-yl)-N,N-dimethylacetamide |
| 332 | 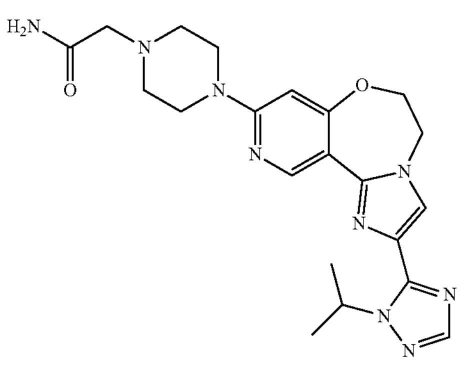 [SMILES: CC(C)n1ncnc1-c1cn2c(n1)-c1cnc(N3CCN(CC(N)=O)CC3)cc1OCC2] | 2-(4-(2-(1-isopropyl-1H-1,2,4-triazol-5-yl)-5,6-dihydroimidazo[1,2-d]pyrido[3,4-f][1,4]oxazepin-9-yl)piperazin-1-yl)acetamide |

TABLE 2-continued

| No. | Structure | Name |
|---|---|---|
| 333 | 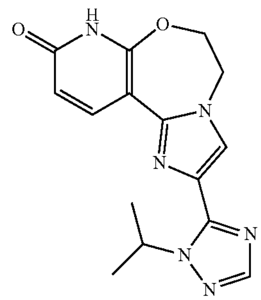 [SMILES: CC(C)n1ncnc1-c1cn2c(n1)-c1ccc(=O)[nH]c1OCC2] | 2-(1-isopropyl-1H-1,2,4-triazol-5-yl)-5,6-dihydroimidazo[1,2-d]pyrido[3,2-f][1,4]oxazepin-9(8H)-one |
| 334 | 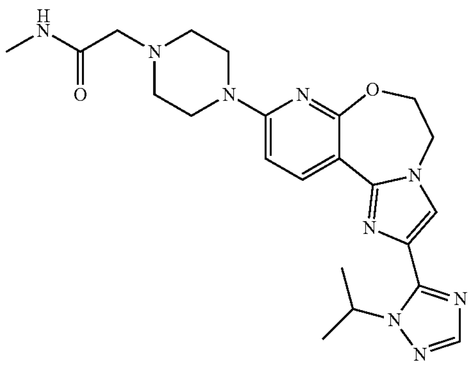 [SMILES: CNC(=O)CN1CCN(c2ccc3c(n2)OCCn2cc(-c4ncnn4C(C)C)nc2-3)CC1] | 2-(4-(2-(1-isopropyl-1H-1,2,4-triazol-5-yl)-5,6-dihydroimidazo[1,2-d]pyrido[3,2-f][1,4]oxazepin-9-yl)piperazin-1-yl)-N-methylacetamide |
| 335 | 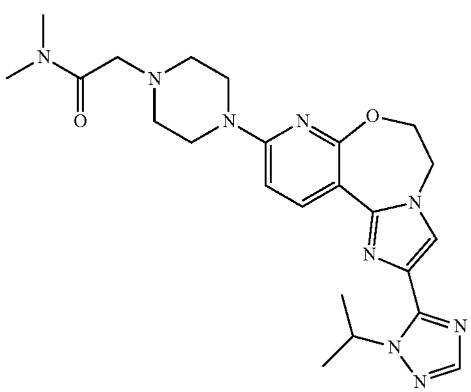 [SMILES: CC(C)n1ncnc1-c1cn2c(n1)-c1ccc(N3CCN(CC(=O)N(C)C)CC3)nc1OCC2] | 2-(4-(2-(1-isopropyl-1H-1,2,4-triazol-5-yl)-5,6-dihydroimidazo[1,2-d]pyrido[3,2-f][1,4]oxazepin-9-yl)piperazin-1-yl)-N,N-dimethylacetamide |
| 336 | 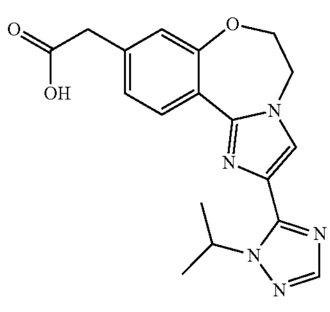 [SMILES: CC(C)n1ncnc1-c1cn2c(n1)-c1ccc(CC(=O)O)cc1OCC2] | 2-(2-(1-isopropyl-1H-1,2,4-triazol-5-yl)-5,6-dihydrobenzo[f]imidazo[1,2-d][1,4]oxazepin-9-yl)acetic acid |

TABLE 2-continued

| No. | Structure | Name |
|---|---|---|
| 337 | 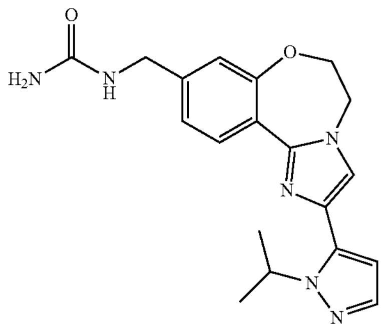 [SMILES: CC(C)n1nccc1-c1cn2c(n1)-c1ccc(CNC(N)=O)cc1OCC2] | 1-((2-(1-isopropyl-1H-pyrazol-5-yl)-5,6-dihydrobenzo[f]imidazo[1,2-d][1,4]oxazepin-9-yl)methyl)urea |
| 338 | 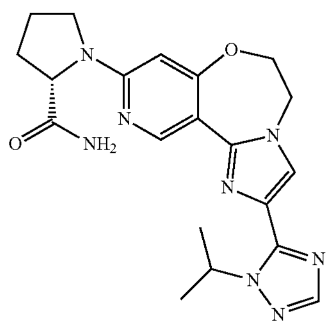 [SMILES: CC(C)n1ncnc1-c1cn2c(n1)-c1cnc(N3CCC[C@H]3C(N)=O)cc1OCC2] | (2S)-1-(2-(1-isopropyl-1H-1,2,4-triazol-5-yl)-5,6-dihydroimidazo[1,2-d]pyrido[3,4-f][1,4]oxazepin-9-yl)pyrrolidine-2-carboxamide |
| 339 | 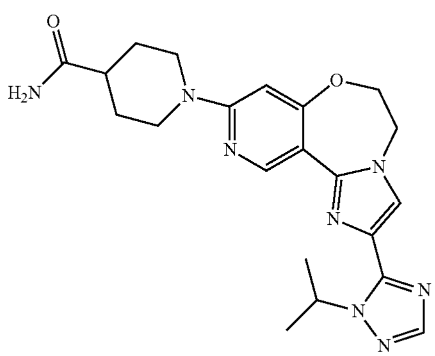 [SMILES: CC(C)n1ncnc1-c1cn2c(n1)-c1cnc(N3CCC(C(N)=O)CC3)cc1OCC2] | 1-(2-(1-isopropyl-1H-1,2,4-triazol-5-yl)-5,6-dihydroimidazo[1,2-d]pyrido[3,4-f][1,4]oxazepin-9-yl)piperidine-4-carboxamide |
| 340 | 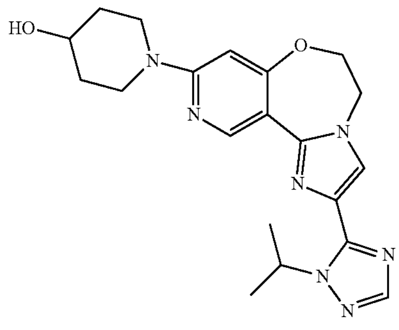 [SMILES: CC(C)n1ncnc1-c1cn2c(n1)-c1cnc(N3CCC(O)CC3)cc1OCC2] | 1-(2-(1-isopropyl-1H-1,2,4-triazol-5-yl)-5,6-dihydroimidazo[1,2-d]pyrido[3,4-f][1,4]oxazepin-9-yl)piperidin-4-ol |

TABLE 2-continued

| No. | Structure | Name |
|---|---|---|
| 341 | 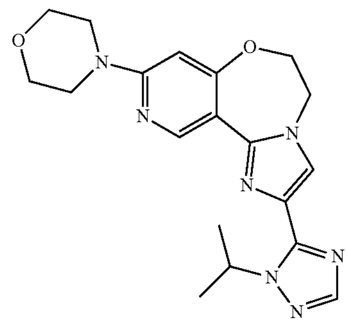 [SMILES: CC(C)n1ncnc1-c1cn2c(n1)-c1cnc(N3CCOCC3)cc1OCC2] | 2-(1-isopropyl-1H-1,2,4-triazol-5-yl)-9-morpholino-5,6-dihydroimidazo[1,2-d]pyrido[3,4-f][1,4]oxazepine |
| 342 | 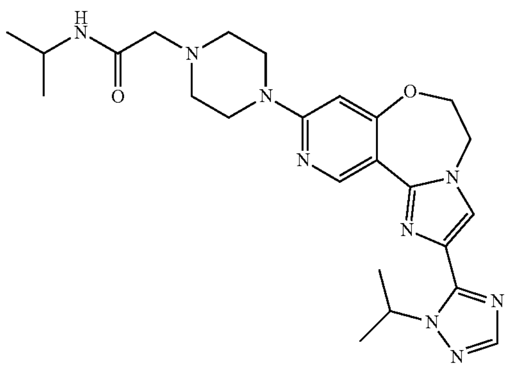 [SMILES: CC(C)NC(=O)CN1CCN(c2cc3c(cn2)-c2nc(-c4ncnn4C(C)C)cn2CCO3)CC1] | N-isopropyl-2-(4-(2-(1-isopropyl-1H-1,2,4-triazol-5-yl)-5,6-dihydroimidazo[1,2-d]pyrido[3,4-f][1,4]oxazepin-9-yl)piperazin-1-yl)acetamide |
| 343 | 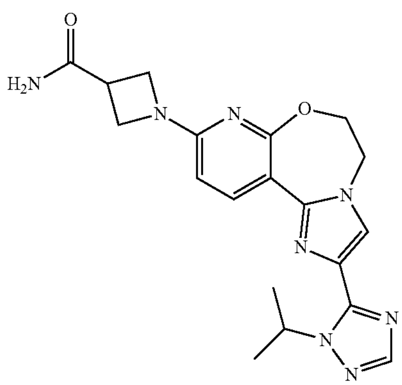 [SMILES: CC(C)n1ncnc1-c1cn2c(n1)-c1ccc(N3CC(C(N)=O)C3)nc1OCC2] | 1-(2-(1-isopropyl-1H-1,2,4-triazol-5-yl)-5,6-dihydroimidazo[1,2-d]pyrido[3,2-f][1,4]oxazepin-9-yl)azetidine-3-carboxamide |
| 344 | 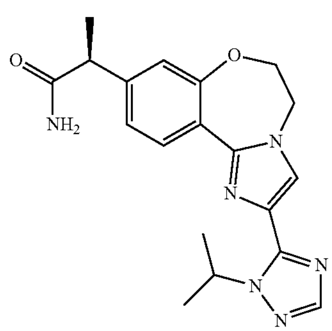 [SMILES: CC(C)n1ncnc1-c1cn2c(n1)-c1ccc([C@H](C)C(N)=O)cc1OCC2] | (2S)-2-(2-(1-isopropyl-1H-1,2,4-triazol-5-yl)-5,6-dihydrobenzo[f]imidazo[1,2-d][1,4]oxazepin-9-yl)propanamide |

TABLE 2-continued

| No. | Structure | Name |
| --- | --- | --- |
| 345 | 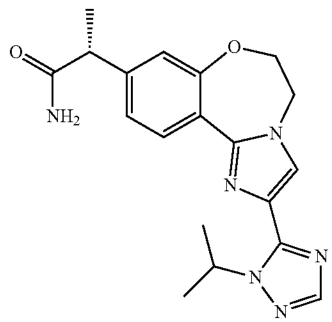 [SMILES: CC(C)n1ncnc1-c1cn2c(n1)-c1ccc([C@@H](C)C(N)=O)cc1OCC2] | (2R)-2-(2-(1-isopropyl-1H-1,2,4-triazol-5-yl)-5,6-dihydrobenzo[f]imidazo[1,2-d][1,4]oxazepin-9-yl)propanamide |
| 346 | 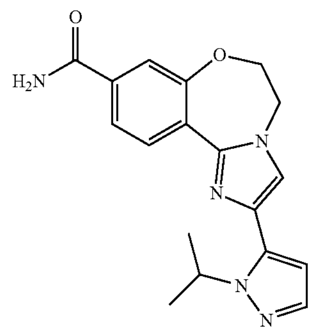 [SMILES: CC(C)n1nccc1-c1cn2c(n1)-c1ccc(C(N)=O)cc1OCC2] | 2-(1-isopropyl-1H-pyrazol-5-yl)-5,6-dihydrobenzo[f]imidazo[1,2-d][1,4]oxazepine-9-carboxamide |
| 347 | 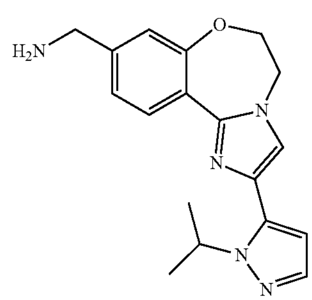 [SMILES: CC(C)n1nccc1-c1cn2c(n1)-c1ccc(CN)cc1OCC2] | (2-(1-isopropyl-1H-pyrazol-5-yl)-5,6-dihydrobenzo[f]imidazo[1,2-d][1,4]oxazepin-9-yl)methanamine |
| 348 | 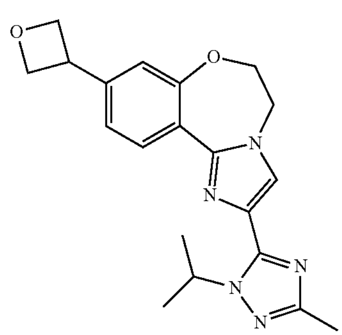 [SMILES: Cc1nc(-c2cn3c(n2)-c2ccc(C4COC4)cc2OCC3)n(C(C)C)n1] | 2-(1-isopropyl-3-methyl-1H-1,2,4-triazol-5-yl)-9-(oxetan-3-yl)-5,6-dihydrobenzo[f]imidazo[1,2-d][1,4]oxazepine |

TABLE 2-continued

| No. | Structure | Name |
| --- | --- | --- |
| 349 | 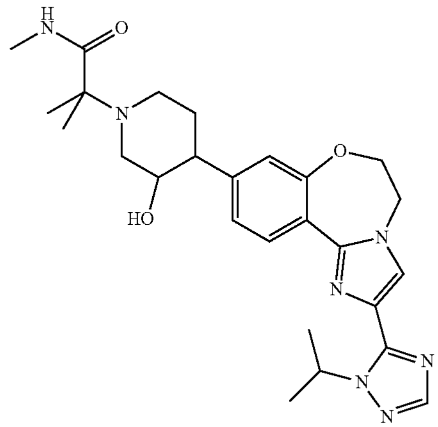 [SMILES: CNC(=O)C(C)(C)N1CCC(c2ccc3c(c2)OCCn2cc(-c4ncnn4C(C)C)nc2-3)C(O)C1] | 2-(3-hydroxy-4-(2-(1-isopropyl-1H-1,2,4-triazol-5-yl)-5,6-dihydrobenzo[f]imidazo[1,2-d][1,4]oxazepin-9-yl)piperidin-1-yl)-N,2-dimethylpropanamide |
| 350 | 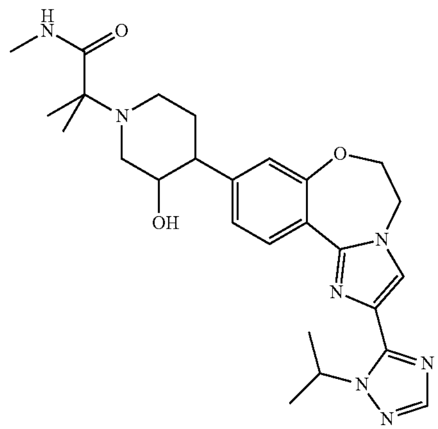 [SMILES: CNC(=O)C(C)(C)N1CCC(c2ccc3c(c2)OCCn2cc(-c4ncnn4C(C)C)nc2-3)C(O)C1] | 2-(3-hydroxy-4-(2-(1-isopropyl-1H-1,2,4-triazol-5-yl)-5,6-dihydrobenzo[f]imidazo[1,2-d][1,4]oxazepin-9-yl)piperidin-1-yl)-N,2-dimethylpropanamide |
| 351 | 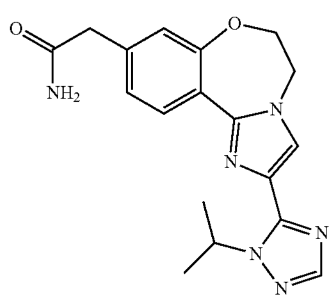 [SMILES: CC(C)n1ncnc1-c1cn2c(n1)-c1ccc(CC(N)=O)cc1OCC2] | 2-(2-(1-isopropyl-1H-1,2,4-triazol-5-yl)-5,6-dihydrobenzo[f]imidazo[1,2-d][1,4]oxazepin-9-yl)acetamide |
| 352 | 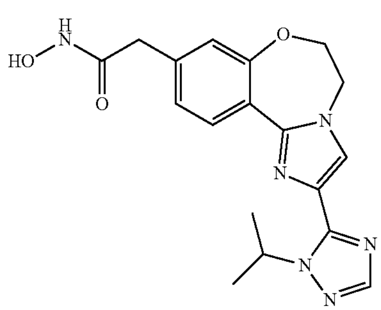 [SMILES: CC(C)n1ncnc1-c1cn2c(n1)-c1ccc(CC(=O)NO)cc1OCC2] | N-hydroxy-2-(2-(1-isopropyl-1H-1,2,4-triazol-5-yl)-5,6-dihydrobenzo[f]imidazo[1,2-d][1,4]oxazepin-9-yl)acetamide |

| No. | Structure | Name |
| --- | --- | --- |
| 353 | 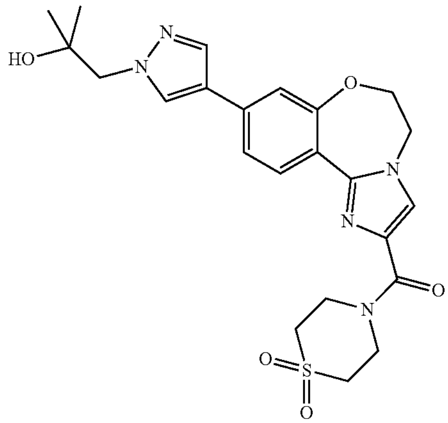 [SMILES: CC(C)(O)Cn1cc(-c2ccc3c(c2)OCCn2cc(C(=O)N4CCS(=O)(=O)CC4)nc2-3)cn1] | (9-(1-(2-hydroxy-2-methylpropyl)-1H-pyrazol-4-yl)-5,6-dihydrobenzo[f]imidazo[1,2-d][1,4]oxazepin-2-yl)(S-dioxothiomorpholino)methanone |
| 354 | 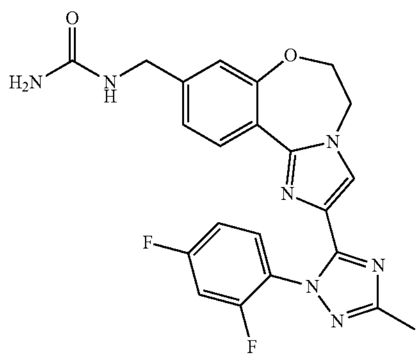 [SMILES: Cc1nc(-c2cn3c(n2)-c2ccc(CNC(N)=O)cc2OCC3)n(-c2ccc(F)cc2F)n1] | 1-((2-(1-(2,4-difluorophenyl)-3-methyl-1H-1,2,4-triazol-5-yl)-5,6-dihydrobenzo[f]imidazo[1,2-d][1,4]oxazepin-9-yl)methyl)urea |
| 355 | 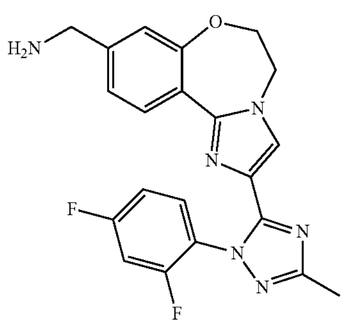 [SMILES: Cc1nc(-c2cn3c(n2)-c2ccc(CN)cc2OCC3)n(-c2ccc(F)cc2F)n1] | (2-(1-(2,4-difluorophenyl)-3-methyl-1H-1,2,4-triazol-5-yl)-5,6-dihydrobenzo[f]imidazo[1,2-d][1,4]oxazepin-9-yl)methanamine |
| 356 | 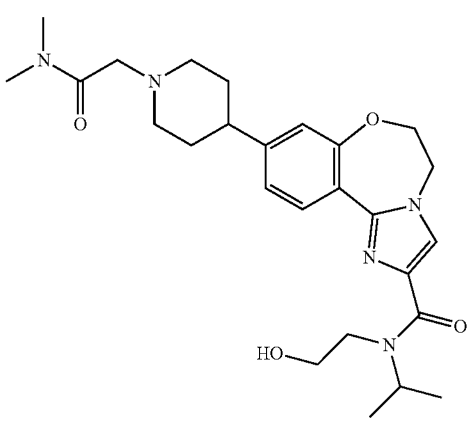 [SMILES: CC(C)N(CCO)C(=O)c1cn2c(n1)-c1ccc(C3CCN(CC(=O)N(C)C)CC3)cc1OCC2] | 9-(1-(2-(dimethylamino)-2-oxoethyl)piperidin-4-yl)-N-(2-hydroxyethyl)-N-isopropyl-5,6-dihydrobenzo[f]imidazo[1,2-d][1,4]oxazepine-2-carboxamide |

TABLE 2-continued

| No. | Structure | Name |
|---|---|---|
| 357 | 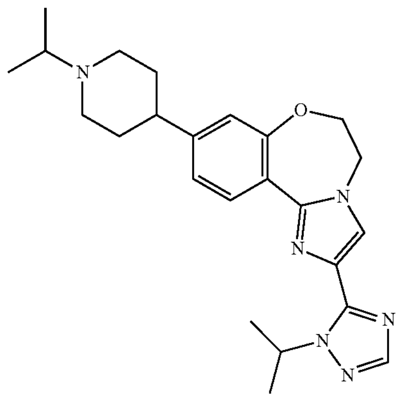 [SMILES: CC(C)N1CCC(c2ccc3c(c2)OCCn2cc(-c4ncnn4C(C)C)nc2-3)CC1] | 2-(1-isopropyl-1H-1,2,4-triazol-5-yl)-9-(1-isopropylpiperidin-4-yl)-5,6-dihydrobenzo[f]imidazo[1,2-d][1,4]oxazepine |
| 358 | 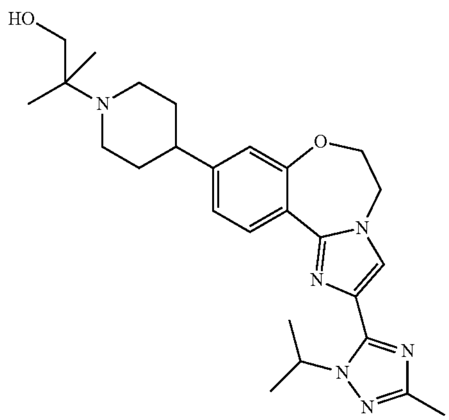 [SMILES: Cc1nc(-c2cn3c(n2)-c2ccc(C4CCN(C(C)(C)CO)CC4)cc2OCC3)n(C(C)C)n1] | 2-(4-(2-(1-isopropyl-3-methyl-1H-1,2,4-triazol-5-yl)-5,6-dihydrobenzo[f]imidazo[1,2-d][1,4]oxazepin-9-yl)piperidin-1-yl)-2-methylpropan-1-ol |
| 359 | 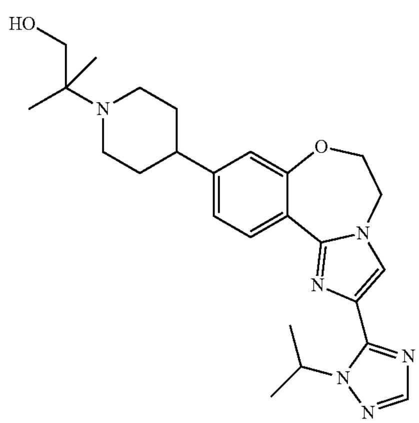 [SMILES: CC(C)n1ncnc1-c1cn2c(n1)-c1ccc(C3CCN(C(C)(C)CO)CC3)cc1OCC2] | 2-(4-(2-(1-isopropyl-1H-1,2,4-triazol-5-yl)-5,6-dihydrobenzo[f]imidazo[1,2-d][1,4]oxazepin-9-yl)piperidin-1-yl)-2-methylpropan-1-ol |
| 360 | 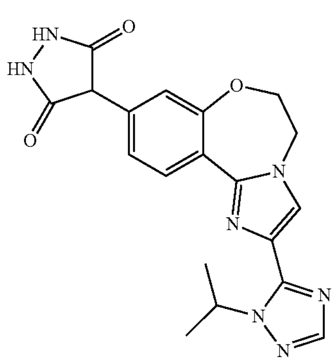 [SMILES: CC(C)n1ncnc1-c1cn2c(n1)-c1ccc(C3C(=O)NNC3=O)cc1OCC2] | 4-(2-(1-isopropyl-1H-1,2,4-triazol-5-yl)-5,6-dihydrobenzo[f]imidazo[1,2-d][1,4]oxazepin-9-yl)pyrazolidine-3,5-dione |

TABLE 2-continued

| No. | Structure | Name |
|---|---|---|
| 361 | 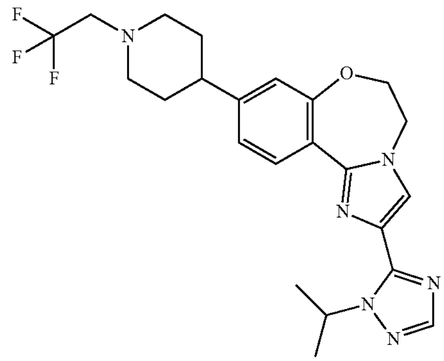 [SMILES: CC(C)n1ncnc1-c1cn2c(n1)-c1ccc(C3CCN(CC(F)(F)F)CC3)cc1OCC2] | 2-(1-isopropyl-1H-1,2,4-triazol-5-yl)-9-(1-(2,2,2-trifluoroethyl)piperidin-4-yl)-5,6-dihydrobenzo[f]imidazo[1,2-d][1,4]oxazepine |
| 362 | 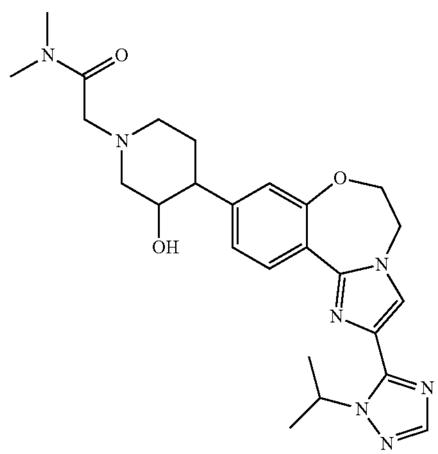 [SMILES: CC(C)n1ncnc1-c1cn2c(n1)-c1ccc(C3CCN(CC(=O)N(C)C)CC3O)cc1OCC2] | 2-(3-hydroxy-4-(2-(1-isopropyl-1H-1,2,4-triazol-5-yl)-5,6-dihydrobenzo[f]imidazo[1,2-d][1,4]oxazepin-9-yl)piperidin-1-yl)-N,N-dimethylacetamide |
| 363 | 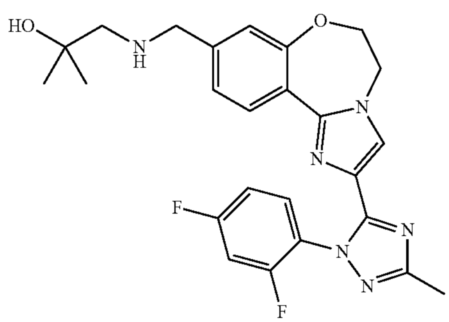 [SMILES: Cc1nc(-c2cn3c(n2)-c2ccc(CNCC(C)(C)O)cc2OCC3)n(-c2ccc(F)cc2F)n1] | 1-(((2-(1-(2,4-difluorophenyl)-3-methyl-1H-1,2,4-triazol-5-yl)-5,6-dihydrobenzo[f]imidazo[1,2-d][1,4]oxazepin-9-yl)methylamino)-2-methylpropan-2-ol |
| 364 | 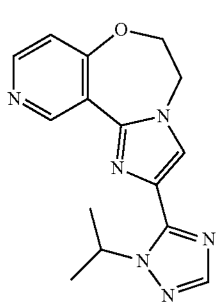 [SMILES: CC(C)n1ncnc1-c1cn2c(n1)-c1cnccc1OCC2] | 2-(1-isopropyl-1H-1,2,4-triazol-5-yl)-5,6-dihydroimidazo[1,2-d]pyrido[3,4-f][1,4]oxazepine |

TABLE 2-continued

| No. | Structure | Name |
| --- | --- | --- |
| 365 | 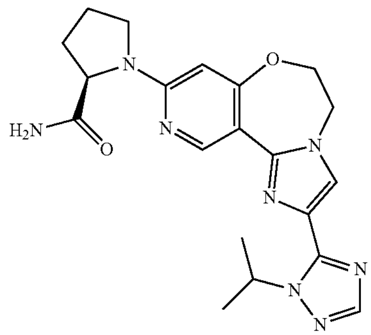 [SMILES: CC(C)n1ncnc1-c1cn2c(n1)-c1cnc(N3CCC[C@@H]3C(N)=O)cc1OCC2] | (2R)-1-(2-(1-isopropyl-1H-1,2,4-triazol-5-yl)-5,6-dihydroimidazo[1,2-d]pyrido[3,4-f][1,4]oxazepin-9-yl)pyrrolidine-2-carboxamide |
| 366 | 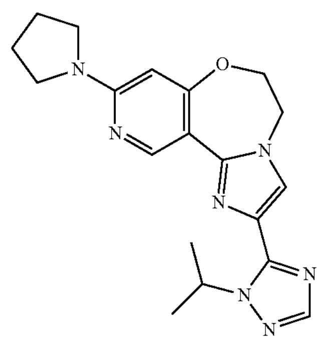 [SMILES: CC(C)n1ncnc1-c1cn2c(n1)-c1cnc(N3CCCC3)cc1OCC2] | 2-(1-isopropyl-1H-1,2,4-triazol-5-yl)-9-(pyrrolidin-1-yl)-5,6-dihydroimidazo[1,2-d]pyrido[3,4-f][1,4]oxazepine |
| 367 | 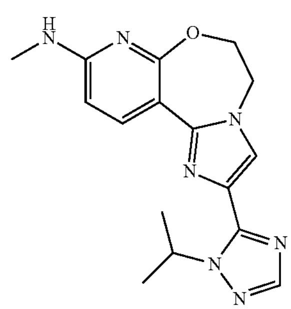 [SMILES: CNc1ccc2c(n1)OCCn1cc(-c3ncnn3C(C)C)nc1-2] | 2-(1-isopropyl-1H-1,2,4-triazol-5-yl)-N-methyl-5,6-dihydroimidazo[1,2-d]pyrido[3,2-f][1,4]oxazepin-9-amine |
| 368 | 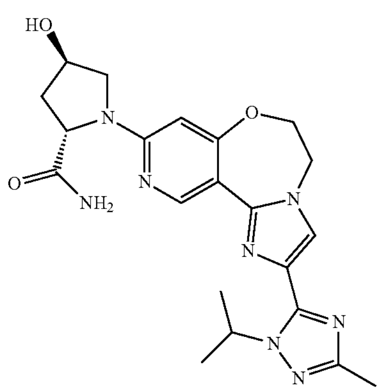 [SMILES: Cc1nc(-c2cn3c(n2)-c2cnc(N4C[C@H](O)C[C@H]4C(N)=O)cc2OCC3)n(C(C)C)n1] | (2S,4R)-4-hydroxy-1-(2-(1-isopropyl-3-methyl-1H-1,2,4-triazol-5-yl-5,6-dihydroimidazo[1,2-d]pyrido[3,4-f][1,4]oxazepin-9-yl)pyrrolidine-2-carboxamide |

TABLE 2-continued

| No. | Structure | Name |
|---|---|---|
| 369 | 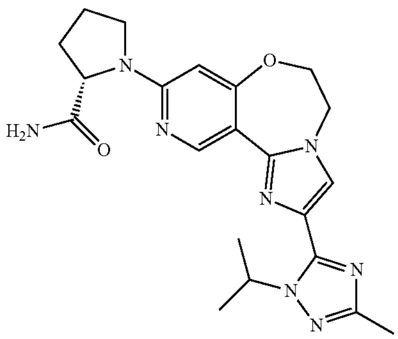 [SMILES: Cc1nc(-c2cn3c(n2)-c2cnc(N4CCC[C@H]4C(N)=O)cc2OCC3)n(C(C)C)n1] | (2S)-1-(2-(1-isopropyl-3-methyl-1H-1,2,4-triazol-5-yl)-5,6-dihydroimidazo[1,2-d]pyrido[3,4-f][1,4]oxazepin-9-yl)pyrrolidine-2-carboxamide |
| 370 | 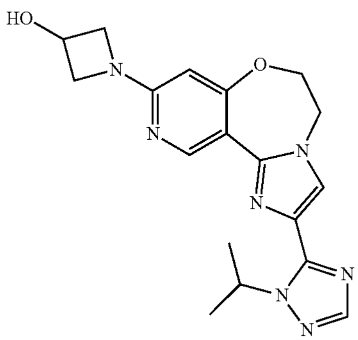 [SMILES: CC(C)n1ncnc1-c1cn2c(n1)-c1cnc(N3CC(O)C3)cc1OCC2] | 1-(2-(1-isopropyl-1H-1,2,4-triazol-5-yl)-5,6-dihydroimidazo[1,2-d]pyrido[3,4-f][1,4]oxazepin-9-yl)azetidin-3-ol |
| 371 | 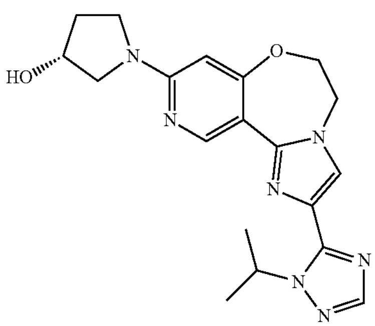 [SMILES: CC(C)n1ncnc1-c1cn2c(n1)-c1cnc(N3CC[C@@H](O)C3)cc1OCC2] | (3R)-1-(2-(1-isopropyl-1H-1,2,4-triazol-5-yl)-5,6-dihydroimidazo[1,2-d]pyrido[3,4-f][1,4]oxazepin-9-yl)pyrrolidin-3-ol |
| 372 | 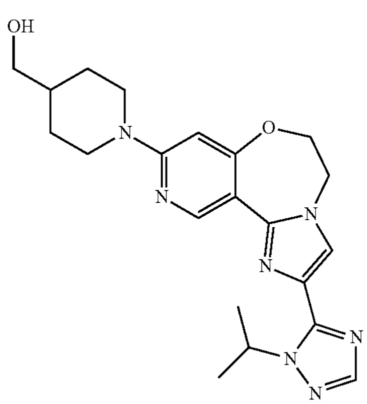 [SMILES: CC(C)n1ncnc1-c1cn2c(n1)-c1cnc(N3CCC(CO)CC3)cc1OCC2] | (1-(2-(1-isopropyl-1H-1,2,4-triazol-5-yl)-5,6-dihydroimidazo[1,2-d]pyrido[3,4-f][1,4]oxazepin-9-yl)piperidin-4-yl)methanol |

TABLE 2-continued

| No. | Structure | Name |
|---|---|---|
| 373 | 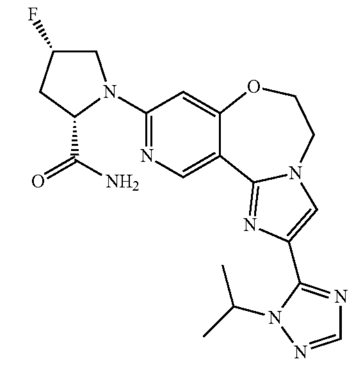 [SMILES: CC(C)n1ncnc1-c1cn2c(n1)-c1cnc(N3C[C@@H](F)C[C@H]3C(N)=O)cc1OCC2] | (2S,4S)-4-fluoro-1-(2-(1-isopropyl-1H-1,2,4-triazol-5-yl)-5,6-dihydroimidazo[1,2-d]pyrido[3,4-f][1,4]oxazepin-9-yl)pyrrolidine-2-carboxamide |
| 374 | 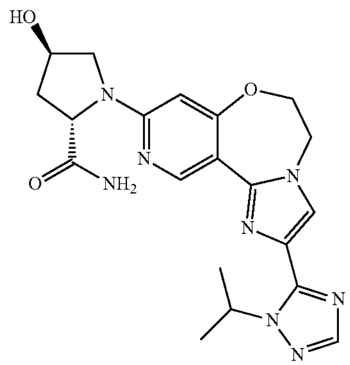 [SMILES: CC(C)n1ncnc1-c1cn2c(n1)-c1cnc(N3C[C@H](O)C[C@H]3C(N)=O)cc1OCC2] | (2S,4R)-4-hydroxy-1-(2-(1-isopropyl-1H-1,2,4-triazol-5-yl)-5,6-dihydroimidazo[1,2-d]pyrido[3,4-f][1,4]oxazepin-9-yl)pyrrolidine-2-carboxamide |
| 375 | 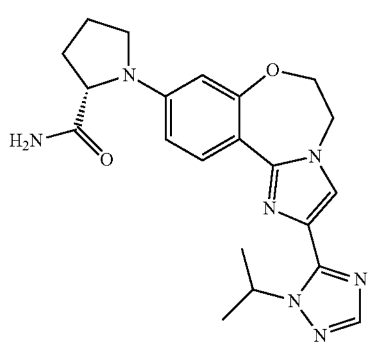 [SMILES: CC(C)n1ncnc1-c1cn2c(n1)-c1ccc(N3CCC[C@H]3C(N)=O)cc1OCC2] | (2S)-1-(2-(1-isopropyl-1H-1,2,4-triazol-5-yl)-5,6-dihydrobenzo[f]imidazo[1,2-d][1,4]oxazepin-9-yl)pyrrolidine-2-carboxamide |
| 376 | 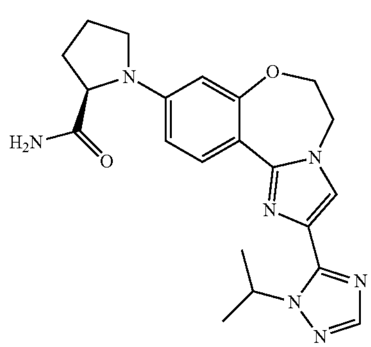 [SMILES: CC(C)n1ncnc1-c1cn2c(n1)-c1ccc(N3CCC[C@@H]3C(N)=O)cc1OCC2] | (2R)-1-(2-(1-isopropyl-1H-1,2,4-triazol-5-yl)-5,6-dihydrobenzo[f]imidazo[1,2-d][1,4]oxazepin-9-yl)pyrrolidine-2-carboxamide |

TABLE 2-continued

| No. | Structure | Name |
|-----|-----------|------|
| 377 | 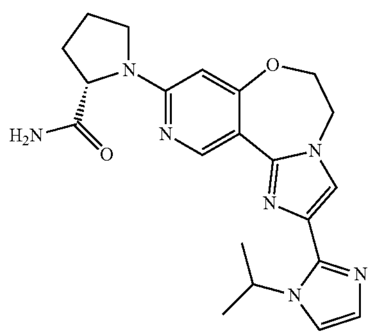 [SMILES: CC(C)n1ccnc1-c1cn2c(n1)-c1cnc(N3CCC[C@H]3C(N)=O)cc1OCC2] | (2S)-1-(2-(1-isopropyl-1H-imidazol-2-yl)-5,6-dihydroimidazo[1,2-d]pyrido[3,4-f][1,4]oxazepin-9-yl)pyrrolidine-2-carboxamide |
| 378 | 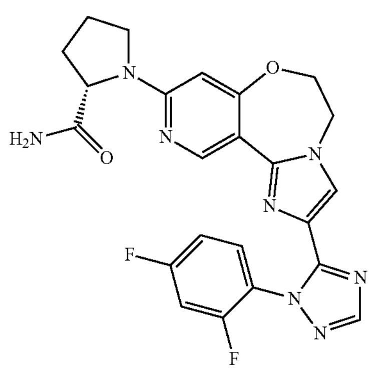 [SMILES: NC(=O)[C@@H]1CCCN1c1cc2c(cn1)-c1nc(-c3ncnn3-c3ccc(F)cc3F)cn1CCO2] | (2S)-1-(2-(1-(2,4-difluorophenyl)-1H-1,2,4-triazol-5-yl)-5,6-dihydroimidazo[1,2-d]pyrido[3,4-f][1,4]oxazepin-9-yl)pyrrolidine-2-carboxamide |
| 379 | 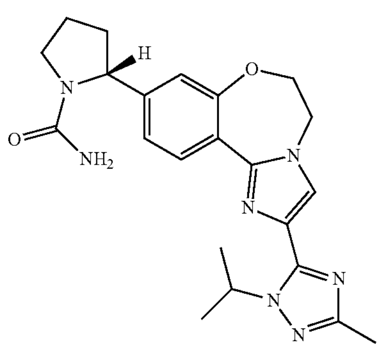 [SMILES: Cc1nc(-c2cn3c(n2)-c2ccc([C@H]4CCCN4C(N)=O)cc2OCC3)n(C(C)C)n1] | (2R)-2-(2-(1-isopropyl-3-methyl-1H-1,2,4-triazol-5-yl)-5,6-dihydrobenzo[f]imidazo[1,2-d][1,4]oxazepin-9-yl)pyrrolidine-1-carboxamide |
| 380 | 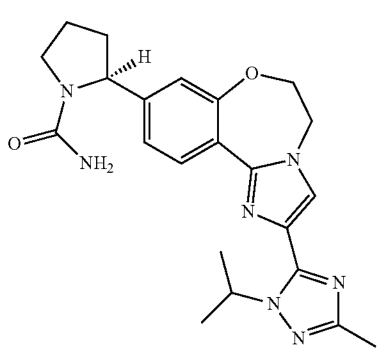 [SMILES: Cc1nc(-c2cn3c(n2)-c2ccc([C@@H]4CCCN4C(N)=O)cc2OCC3)n(C(C)C)n1] | (2S)-2-(2-(1-isopropyl-3-methyl-1H-1,2,4-triazol-5-yl)-5,6-dihydrobenzo[f]imidazo[1,2-d][1,4]oxazepin-9-yl)pyrrolidine-1-carboxamide |

TABLE 2-continued

| No. | Structure | Name |
| --- | --- | --- |
| 381 | 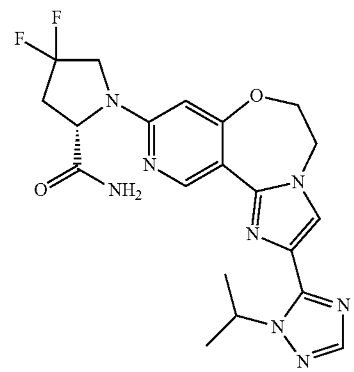 [SMILES: CC(C)n1ncnc1-c1cn2c(n1)-c1cnc(N3CC(F)(F)C[C@H]3C(N)=O)cc1OCC2] | (2S)-4,4-difluoro-1-(2-(1-isopropyl-1H-1,2,4-triazol-5-yl)-5,6-dihydroimidazo[1,2-d]pyrido[3,4-f][1,4]oxazepin-9-yl)pyrrolidine-2-carboxamide |
| 382 | 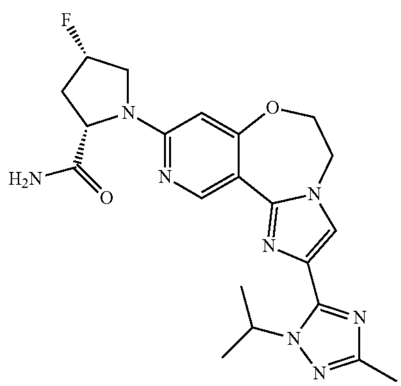 [SMILES: Cc1nc(-c2cn3c(n2)-c2cnc(N4C[C@@H](F)C[C@H]4C(N)=O)cc2OCC3)n(C(C)C)n1] | (2S,4S)-4-fluoro-1-(2-(1-isopropyl-3-methyl-1H-1,2,4-triazol-5-yl)-5,6-dihydroimidazo[1,2-d]pyrido[3,4-f][1,4]oxazepin-9-yl)pyrrolidine-2-carboxamide |
| 383 | 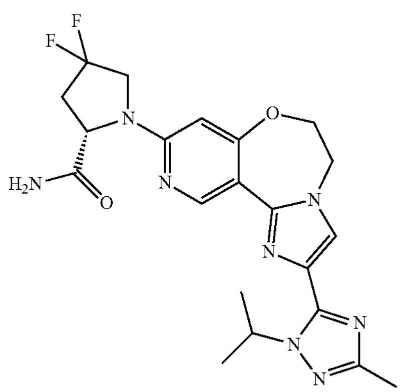 [SMILES: Cc1nc(-c2cn3c(n2)-c2cnc(N4CC(F)(F)C[C@H]4C(N)=O)cc2OCC3)n(C(C)C)n1] | (2S)-4,4-difluoro-1-(2-(1-isopropyl-3-methyl-1H-1,2,4-triazol-5-yl)-5,6-dihydroimidazo[1,2-d]pyrido[3,4-f][1,4]oxazepin-9-yl)pyrrolidine-2-carboxamide |
| 384 | 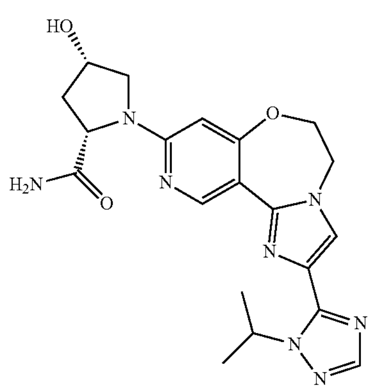 [SMILES: CC(C)n1ncnc1-c1cn2c(n1)-c1cnc(N3C[C@@H](O)C[C@H]3C(N)=O)cc1OCC2] | (2S,4S)-4-hydroxy-1-(2-(1-isopropyl-1H-1,2,4-triazol-5-yl)-5,6-dihydroimidazo[1,2-d]pyrido[3,4-f][1,4]oxazepin-9-yl)pyrrolidine-2-carboxamide |

TABLE 2-continued

| No. | Structure | Name |
|---|---|---|
| 385 | 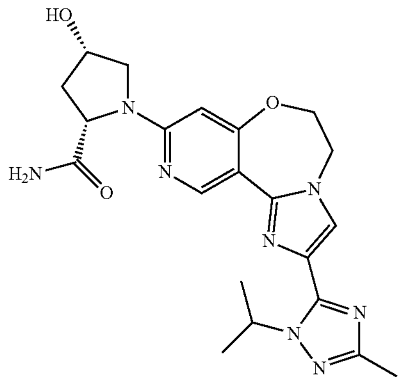 [SMILES: Cc1nc(-c2cn3c(n2)-c2cnc(N4C[C@@H](O)C[C@H]4C(N)=O)cc2OCC3)n(C(C)C)n1] | (2S,4S)-4-hydroxy-1-(2-(1-isopropyl-3-methyl-1H-1,2,4-triazol-5-yl)-5,6-dihydroimidazo[1,2-d]pyrido[3,4-f][1,4]oxazepin-9-yl)pyrrolidine-2-carboxamide |
| 386 | 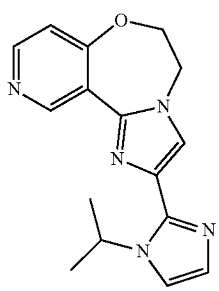 [SMILES: CC(C)n1ccnc1-c1cn2c(n1)-c1cnccc1OCC2] | 2-(1-isopropyl-1H-imidazol-2-yl)-5,6-dihydroimidazo[1,2-d]pyrido[3,4-f][1,4]oxazepine |
| 387 | 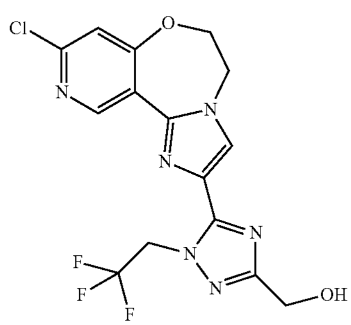 [SMILES: OCc1nc(-c2cn3c(n2)-c2cnc(Cl)cc2OCC3)n(CC(F)(F)F)n1] | (5-(9-chloro-5,6-dihydroimidazo[1,2-d]pyrido[3,4-f][1,4]oxazepin-2-yl)-1-(2,2,2-trifluoroethyl)-1H-1,2,4-triazol-3-yl)methanol |
| 388 | 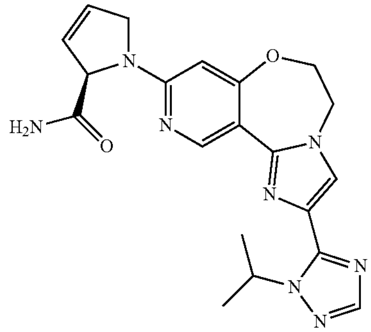 [SMILES: CC(C)n1ncnc1-c1cn2c(n1)-c1cnc(N3CC=C[C@@H]3C(N)=O)cc1OCC2] | (2R)-1-(2-(1-isopropyl-1H-1,2,4-triazol-5-yl)-5,6-dihydroimidazo[1,2-d]pyrido[3,4-f][1,4]oxazepin-9-yl)-2,5-dihydro-1H-pyrrole-2-carboxamide |

TABLE 2-continued

| No. | Structure | Name |
|---|---|---|
| 389 | 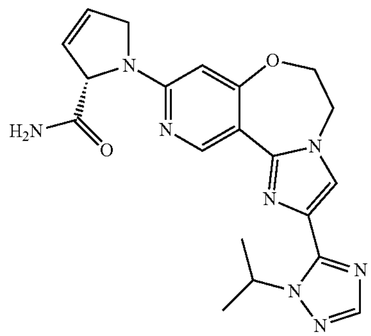 [SMILES: CC(C)n1ncnc1-c1cn2c(n1)-c1cnc(N3CC=C[C@H]3C(N)=O)cc1OCC2] | (2S)-1-(2-(1-isopropyl-1H-1,2,4-triazol-5-yl)-5,6-dihydroimidazo[1,2-d]pyrido[3,4-f][1,4]oxazepin-9-yl)-2,5-dihydro-1H-pyrrole-2-carboxamide |
| 390 | 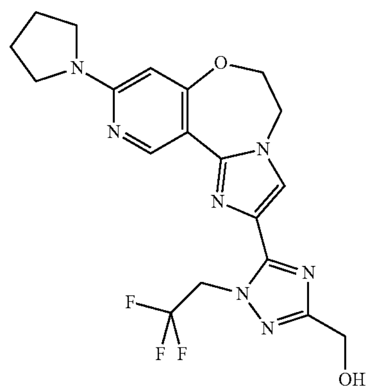 [SMILES: OCc1nc(-c2cn3c(n2)-c2cnc(N4CCCC4)cc2OCC3)n(CC(F)(F)F)n1] | (5-(9-(pyrrolidin-1-yl)-5,6-dihydroimidazo[1,2-d]pyrido[3,4-f][1,4]oxazepin-2-yl)-1-(2,2,2-trifluoroethyl)-1H-1,2,4-triazol-3-yl)methanol |
| 391 | 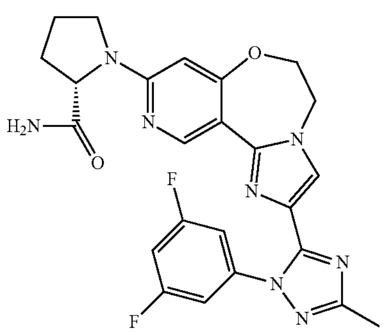 [SMILES: Cc1nc(-c2cn3c(n2)-c2cnc(N4CCC[C@H]4C(N)=O)cc2OCC3)n(-c2cc(F)cc(F)c2)n1] | (2S)-1-(2-(1-(3,5-difluorophenyl)-3-methyl-1H-1,2,4-triazol-5-yl)-5,6-dihydroimidazo[1,2-d]pyrido[3,4-f][1,4]oxazepin-9-yl)pyrrolidine-2-carboxamide |
| 392 | 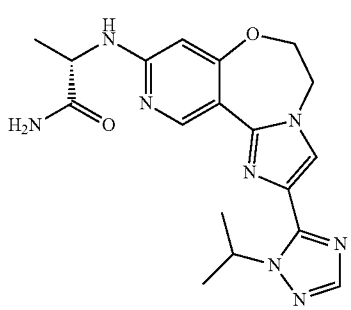 [SMILES: CC(C)n1ncnc1-c1cn2c(n1)-c1cnc(N[C@@H](C)C(N)=O)cc1OCC2] | (2S)-2-(2-(1-isopropyl-1H-1,2,4-triazol-5-yl)-5,6-dihydroimidazo[1,2-d]pyrido[3,4-f][1,4]oxazepin-9-ylamino)propanamide |

TABLE 2-continued

| No. | Structure | Name |
|---|---|---|
| 393 | 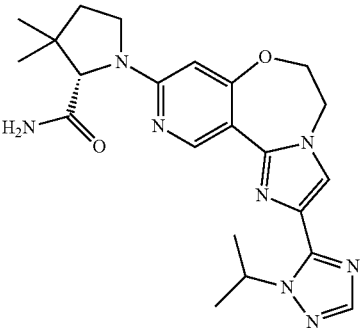 [SMILES: CC(C)n1ncnc1-c1cn2c(n1)-c1cnc(N3CCC(C)(C)[C@H]3C(N)=O)cc1OCC2] | (2S)-1-(2-(1-isopropyl-1H-1,2,4-triazol-5-yl)-5,6-dihydroimidazo[1,2-d]pyrido[3,4-f][1,4]oxazepin-9-yl)-3,3-dimethylpyrrolidine-2-carboxamide |
| 394 | 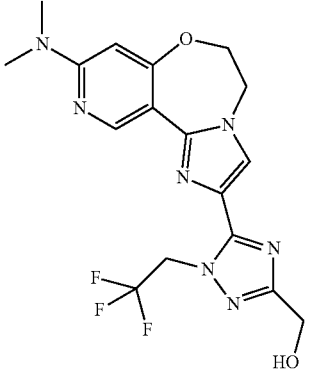 [SMILES: CN(C)c1cc2c(cn1)-c1nc(-c3nc(CO)nn3CC(F)(F)F)cn1CCO2] | (5-(9-(dimethylamino)-5,6-dihydroimidazo[1,2-d]pyrido[3,4-f][1,4]oxazepin-2-yl)-1-(2,2,2-trifluoroethyl)-1H-1,2,4-triazol-3-yl)methanol |
| 395 | 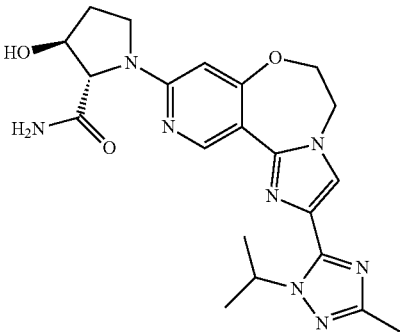 [SMILES: Cc1nc(-c2cn3c(n2)-c2cnc(N4CC[C@H](O)[C@H]4C(N)=O)cc2OCC3)n(C(C)C)n1] | (2S,3S)-3-hydroxy-1-(2-(1-isopropyl-3-methyl-1H-1,2,4-triazol-5-yl)-5,6-dihydroimidazo[1,2-d]pyrido[3,4-f][1,4]oxazepin-9-yl)pyrrolidine-2-carboxamide |
| 396 | 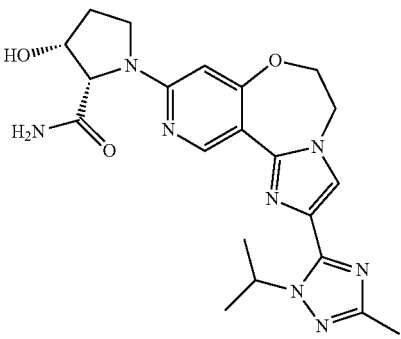 [SMILES: Cc1nc(-c2cn3c(n2)-c2cnc(N4CC[C@@H](O)[C@H]4C(N)=O)cc2OCC3)n(C(C)C)n1] | (2S,3R)-3-hydroxy-1-(2-(1-isopropyl-3-methyl-1H-1,2,4-trazol-5-yl)-5,6-dihydroimidazo[1,2-d]pyrido[3,4-f][1,4]oxazepin-9-yl)pyrrolidine-2-carboxamide |

TABLE 2-continued

| No. | Structure | Name |
|---|---|---|
| 397 | 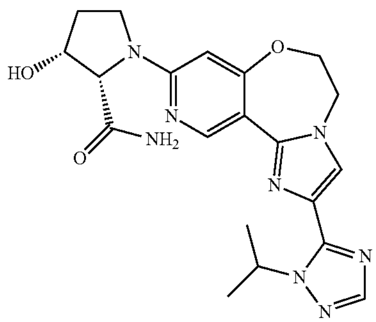 [SMILES: CC(C)n1ncnc1-c1cn2c(n1)-c1cnc(N3CC[C@@H](O)[C@H]3C(N)=O)cc1OCC2] | (2S,3R)-3-hydroxy-1-(2-(1-isopropyl-1H-1,2,4-triazol-5-yl)-5,6-dihydroimidazo[1,2-d]pyrido[3,4-f][1,4]oxazepin-9-yl)pyrrolidine-2-carboxamide |
| 398 | 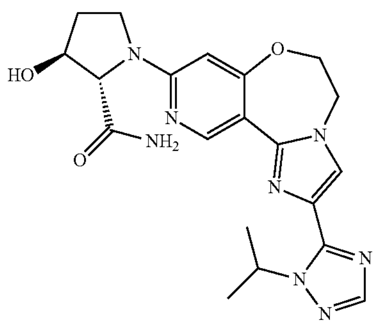 [SMILES: CC(C)n1ncnc1-c1cn2c(n1)-c1cnc(N3CC[C@H](O)[C@H]3C(N)=O)cc1OCC2] | (2S,3S)-3-hydroxy-1-(2-(1-isopropyl-1H-1,2,4-triazol-5-yl)-5,6-dihydroimidazo[1,2-d]pyrido[3,4-f][1,4]oxazepin-9-yl)pyrrolidine-2-carboxamide |
| 399 | 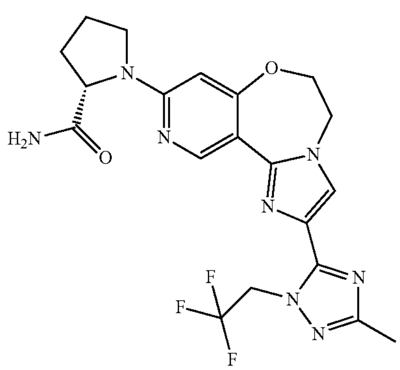 [SMILES: Cc1nc(-c2cn3c(n2)-c2cnc(N4CCC[C@H]4C(N)=O)cc2OCC3)n(CC(F)(F)F)n1] | (2S)-1-(2-(3-methyl-1-(2,2,2-trifluoromethyl)-1H-1,2,4-triazol-5-yl)-5,6-dihydroimidazo[1,2-d]pyrido[3,4-f][1,4]oxazepin-9-yl)pyrrolidine-2-carboxamide |
| 400 | 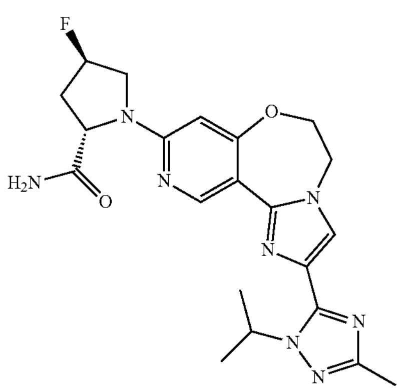 [SMILES: Cc1nc(-c2cn3c(n2)-c2cnc(N4C[C@H](F)C[C@H]4C(N)=O)cc2OCC3)n(C(C)C)n1] | (2S,4R)-4-fluoro-1-(2-(1-isopropyl-3-methyl-1H-1,2,4-triazol-5-yl)-5,6-dihydroimidazo[1,2-d]pyrido[3,4-f][1,4]oxazepin-9-yl)pyrrolidine-2-carboxamide |

TABLE 2-continued

| No. | Structure | Name |
|---|---|---|
| 401 | 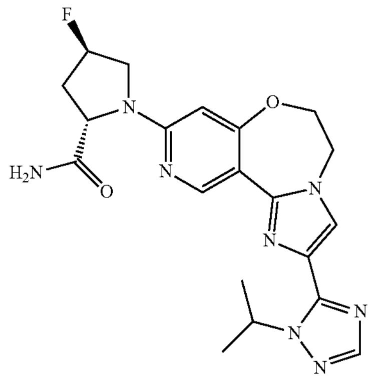 [SMILES: CC(C)n1ncnc1-c1cn2c(n1)-c1cnc(N3C[C@H](F)C[C@H]3C(N)=O)cc1OCC2] | (2S,4R)-4-fluoro-1-(2-(1-isopropyl-1H-1,2,4-triazol-5-yl)-5,6-dihydroimidazo[1,2-d]pyrido[3,4-f][1,4]oxazepin-9-yl)pyrrolidine-2-carboxamide |
| 402 | 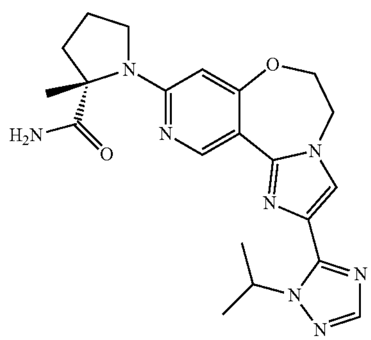 [SMILES: CC(C)n1ncnc1-c1cn2c(n1)-c1cnc(N3CCC[C@@]3(C)C(N)=O)cc1OCC2] | (2S)-1-(2-(1-isopropyl-1H-1,2,4-triazol-5-yl)-5,6-dihydroimidazo[1,2-d]pyrido[3,4-f][1,4]oxazepin-9-yl)-2-methylpyrrolidine-2-carboxamide |
| 403 | 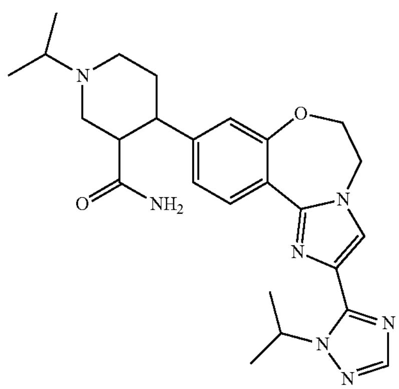 [SMILES: CC(C)N1CCC(c2ccc3c(c2)OCCn2cc(-c4ncnn4C(C)C)nc2-3)C(C(N)=O)C1] | racemic-cis-1-isopropyl-4-(2-(1-isopropyl-1H-1,2,4-triazol-5-yl)-5,6-dihydrobenzo[f]imidazo[1,2-d][1,4]oxazepin-9-yl)piperidine-3-carboxamide |
| 404 | 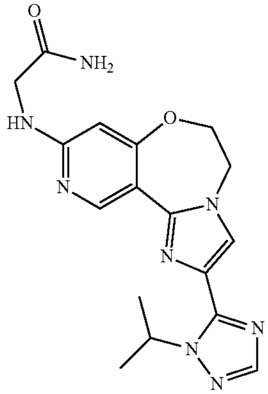 [SMILES: CC(C)n1ncnc1-c1cn2c(n1)-c1cnc(NCC(N)=O)cc1OCC2] | 2-(2-(1-isopropyl-1H-1,2,4-triazol-5-yl)-5,6-dihydroimidazo[1,2-d]pyrido[3,4-f][1,4]oxazepin-9-ylamino)acetamide |

TABLE 2-continued

| No. | Structure | Name |
|---|---|---|
| 405 | 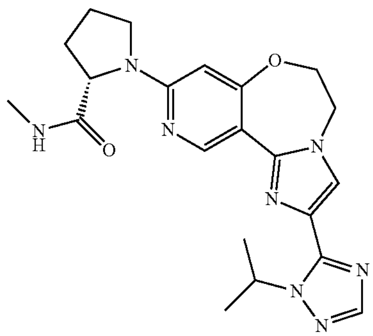 [SMILES: CNC(=O)[C@@H]1CCCN1c1cc2c(cn1)-c1nc(-c3ncnn3C(C)C)cn1CCO2] | (2S)-1-(2-(1-isopropyl-1H-1,2,4-triazol-5-yl)-5,6-dihydroimidazo[1,2-d]pyrido[3,4-f][1,4]oxazepin-9-yl)-N-methylpyrrolidine-2-carboxamide |
| 406 | 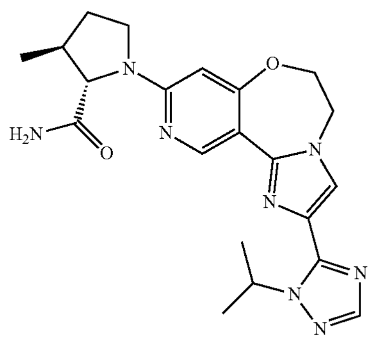 [SMILES: CC(C)n1ncnc1-c1cn2c(n1)-c1cnc(N3CC[C@H](C)[C@H]3C(N)=O)cc1OCC2] | (2S,3S)-1-(2-(1-isopropyl-1H-1,2,4-triazol-5-yl)-5,6-dihydroimidazo[1,2-d]pyrido[3,4-d][1,4]oxazepin-9-yl)-3-methylpyrrolidine-2-carboxamide |
| 407 | 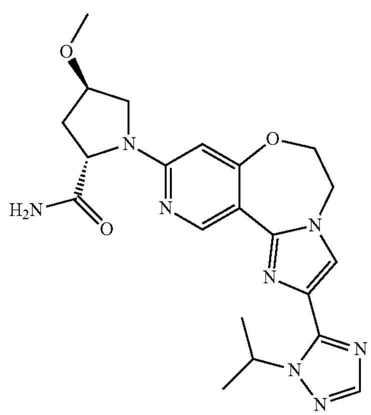 [SMILES: CO[C@@H]1C[C@@H](C(N)=O)N(c2cc3c(cn2)-c2nc(-c4ncnn4C(C)C)cn2CCO3)C1] | (2S,4R)-1-(2-(1-isopropyl-1H-1,2,4-triazol-5-yl)-5,6-dihydroimidazo[1,2-d]pyrido[3,4-f][1,4]oxazepin-9-yl)-4-methoxypyrrolidine-2-carboxamide |
| 408 | 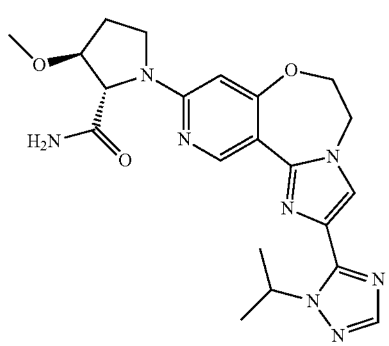 [SMILES: CO[C@H]1CCN(c2cc3c(cn2)-c2nc(-c4ncnn4C(C)C)cn2CCO3)[C@@H]1C(N)=O] | (2S,3S)-1-(2-(1-isopropyl-1H-1,2,4-triazol-5-yl)-5,6-dihydroimidazo[1,2-d]pyrido[3,4-f][1,4]oxazepin-9-yl)-3-methoxypyrrolidine-2-carboxamide |

TABLE 2-continued

| No. | Structure | Name |
|---|---|---|
| 409 | 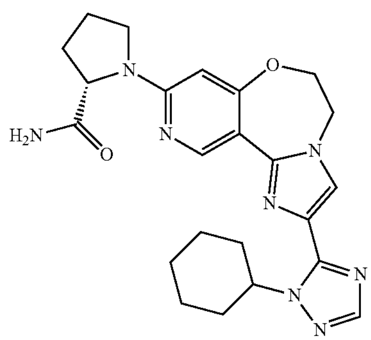 [SMILES: NC(=O)[C@@H]1CCCN1c1cc2c(cn1)-c1nc(-c3ncnn3C3CCCCC3)cn1CCO2] | (2S)-1-(2-(1-cyclohexyl-1H-1,2,4-triazol-5-yl)-5,6-dihydroimidazo[1,2-d]pyrido[3,4-f][1,4]oxazepin-9-yl)pyrrolidine-2-carboxamide |
| 410 | 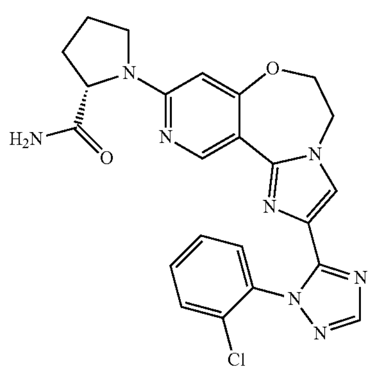 [SMILES: NC(=O)[C@@H]1CCCN1c1cc2c(cn1)-c1nc(-c3ncnn3-c3ccccc3Cl)cn1CCO2] | (2S)-1-(2-(1-(2-chlorophenyl)-1H-1,2,4-triazol-5-yl)-5,6-dihydroimidazo[1,2-d]pyrido[3,4-f][1,4]oxazepin-9-yl)pyrrolidine-2-carboxamide |
| 411 | 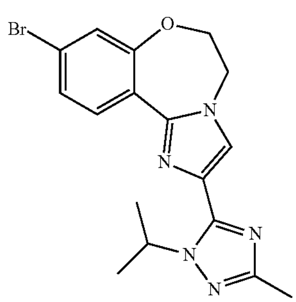 [SMILES: Cc1nc(-c2cn3c(n2)-c2ccc(Br)cc2OCC3)n(C(C)C)n1] | 9-bromo-2-(1-isopropyl-3-methyl-1H-1,2,4-triazol-5-yl)-5,6-dihydrobenzo[f]imidazo[1,2-d][1,4]oxazepine |
| 412 | 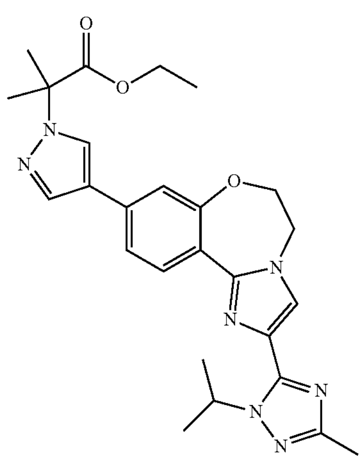 [SMILES: CCOC(=O)C(C)(C)n1cc(-c2ccc3c(c2)OCCn2cc(-c4nc(C)nn4C(C)C)nc2-3)cn1] | ethyl 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoate |

TABLE 2-continued

| No. | Structure | Name |
|-----|-----------|------|
| 413 | 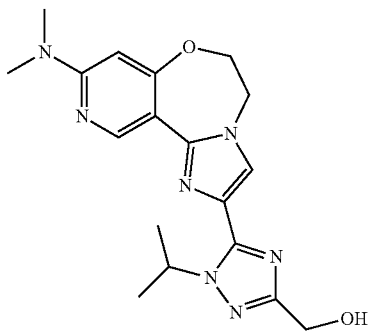 [SMILES: CC(C)n1nc(CO)nc1-c1cn2c(n1)-c1cnc(N(C)C)cc1OCC2] | (5-(9-(dimethylamino)-5,6-dihydroimidazo[1,2-d]pyrido[3,4-f][1,4]oxazepin-2-yl)-1-isopropyl-1H-1,2,4-triazol-3-yl)methanol |
| 414 | 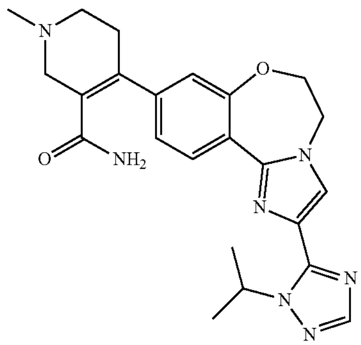 [SMILES: CC(C)n1ncnc1-c1cn2c(n1)-c1ccc(C3=C(C(N)=O)CN(C)CC3)cc1OCC2] | 4-(2-(1-isopropyl-1H-1,2,4-triazol-5-yl)-5,6-dihydrobenzo[f]imidazo[1,2-d][1,4]oxazepin-9-yl)-1-methyl-1,2,5,6-tetrahydropyridine-3-carboxamide |
| 415 | 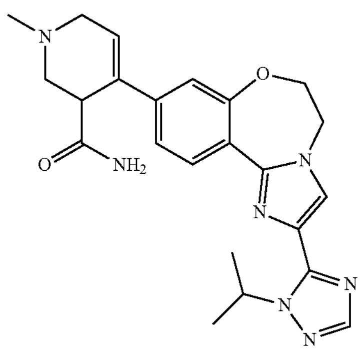 [SMILES: CC(C)n1ncnc1-c1cn2c(n1)-c1ccc(C3=CCN(C)CC3C(N)=O)cc1OCC2] | 4-(2-(1-isopropyl-1H-1,2,4-triazol-5-yl)-5,6-dihydrobenzo[f]imidazo[1,2-d][1,4]oxazepin-9-yl)-1-methyl-1,2,3,6-tetrahydropyridine-3-carboxamide |
| 416 | 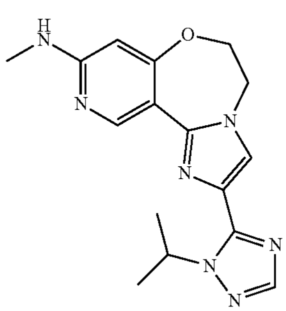 [SMILES: CNc1cc2c(cn1)-c1nc(-c3ncnn3C(C)C)cn1CCO2] | 2-(1-isopropyl-1H-1,2,4-triazol-5-yl)-N-methyl-5,6-dihydroimidazo[1,2-d]pyrido[3,4-f][1,4]oxazepin-9-amine |

TABLE 2-continued

| No. | Structure | Name |
|---|---|---|
| 417 | 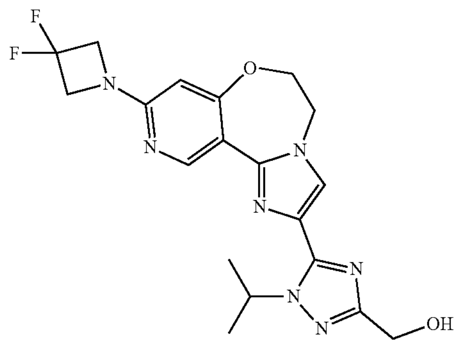 [SMILES: CC(C)n1nc(CO)nc1-c1cn2c(n1)-c1cnc(N3CC(F)(F)C3)cc1OCC2] | (5-(9-(3,3-difluoroazetidin-1-yl)-5,6-dihydroimidazo[1,2-d]pyrido[3,4-f][1,4]oxazepin-2-yl)-1-isopropyl-1H-1,2,4-triazol-3-yl)methanol |
| 418 | 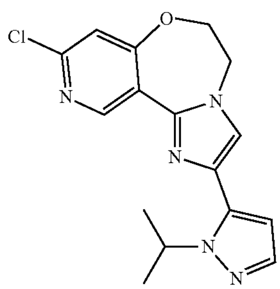 [SMILES: CC(C)n1nccc1-c1cn2c(n1)-c1cnc(Cl)cc1OCC2] | 9-chloro-2-(1-isopropyl-1H-pyrazol-5-yl)-5,6-hydroxyimidazo[1,2-d]pyrido[3,4-f][1,4]oxazepine |
| 419 | 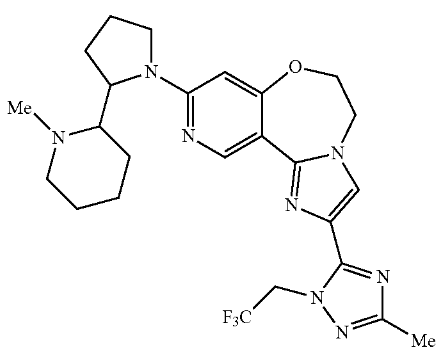 [SMILES: Cc1nc(-c2cn3c(n2)-c2cnc(N4CCCC4C4CCCCN4C)cc2OCC3)n(CC(F)(F)F)n1] | 2-(3-methyl-1-(2,2,2-trifluoroethyl)-1H-1,2,4-triazol-5-yl)-9-(2-(1-methylpiperidin-2-yl)pyrrolidin-1-yl)-5,6-dihydroimidazo[1,2-d]pyrido[3,4-f][1,4]oxazepine |
| 420 | 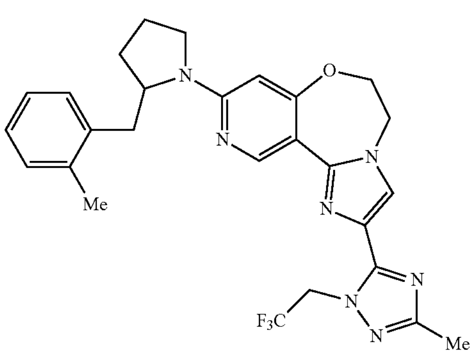 [SMILES: Cc1nc(-c2cn3c(n2)-c2cnc(N4CCCC4Cc4ccccc4C)cc2OCC3)n(CC(F)(F)F)n1] | 2-(3-methyl-1-(2,2,2-trifluoromethyl)-1H-1,2,4-triazol-5-yl)-9-(2-(2-methylbenzyl)pyrrolidin-1-yl)-5,6-dihydroimidazo[1,2-d]pyrido[3,4-f][1,4]oxazepine |

TABLE 2-continued

| No. | Structure | Name |
|---|---|---|
| 421 | 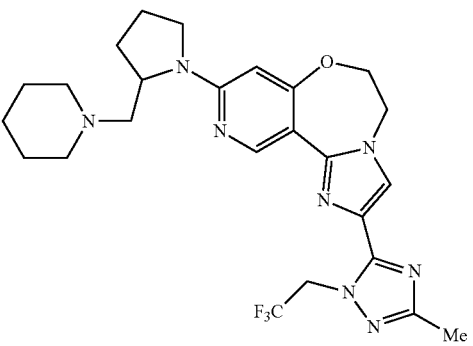 [SMILES: Cc1nc(-c2cn3c(n2)-c2cnc(N4CCCC4CN4CCCCC4)cc2OCC3)n(CC(F)(F)F)n1] | 2-(3-methyl-1-(2,2,2-trifluoromethyl)-1H-1,2,4-triazol-5-yl)-9-(2-(piperidin-1-ylmethyl)pyrrolidin-1-yl)-5,6-dihydroimidazo[1,2-d]pyrido[3,4-f][1,4]oxazepine |
| 422 | 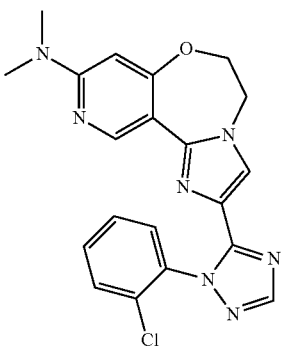 [SMILES: CN(C)c1cc2c(cn1)-c1nc(-c3ncnn3-c3ccccc3Cl)cn1CCO2] | 2-(1-(2-chlorophenyl)-1H-1,2,4-triazol-5-yl)-N,N-dimethyl-5,6-dihydroimidazo[1,2-d]pyrido[3,4-f][1,4]oxazepin-9-amine |
| 423 | 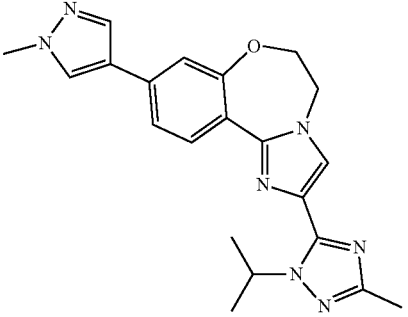 | 2-(1-isopropyl-3-methyl-1H-1,2,4-triazol-5-yl)-9-(1-methyl-1H-pyrazol-4-yl)-5,6-dihydrobenzo[f]imidazo[1,2-d][1,4]oxazepine |
| 424 | 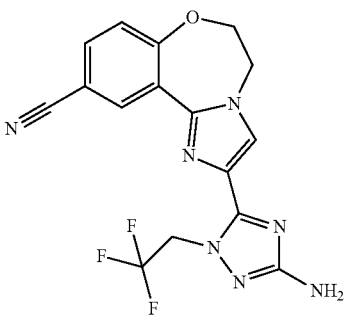 [SMILES: N#Cc1ccc2c(c1)-c1nc(-c3nc(N)nn3CC(F)(F)F)cn1CCO2] | 2-(3-amino-1-(2,2,2-trifluoroethyl)-1H-1,2,4-triazol-5-yl)-5,6-dihydrobenzo[f]imidazo[1,2-d][1,4]oxazepine-10-carbonitrile |

TABLE 2-continued

| No. | Structure | Name |
|---|---|---|
| 425 | 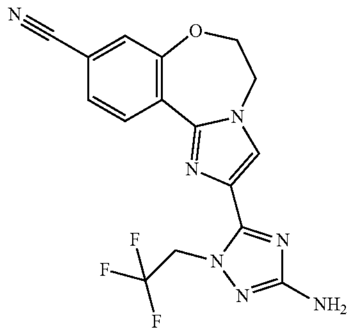 [SMILES: N#Cc1ccc2c(c1)OCCn1cc(-c3nc(N)nn3CC(F)(F)F)nc1-2] | 2-(3-amino-1-(2,2,2-trifluoroethyl)-1H-1,2,4-triazol-5-yl)-5,6-dihydrobenzo[f]imidazo[1,2-d][1,4]oxazepine-9-carbonitrile |
| 426 | 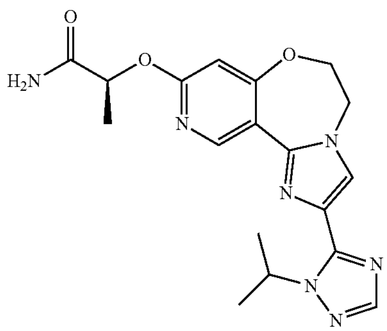 [SMILES: CC(C)n1ncnc1-c1cn2c(n1)-c1cnc(O[C@@H](C)C(N)=O)cc1OCC2] | (2S)-2-(2-(1-isopropyl-1H-1,2,4-triazol-5-yl)-5,6-dihydroimidazo[1,2-d]pyrido[3,4-f][1,4]oxazepin-9-yloxy)propanamide |
| 427 | 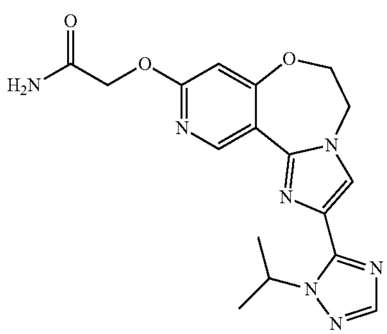 [SMILES: CC(C)n1ncnc1-c1cn2c(n1)-c1cnc(OCC(N)=O)cc1OCC2] | 2-(2-(1-isopropyl-1H-1,2,4-triazol-5-yl)-5,6-dihydroimidazo[1,2-d]pyrido[3,4-f][1,4]oxazepin-9-yloxy)acetamide |
| 428 | 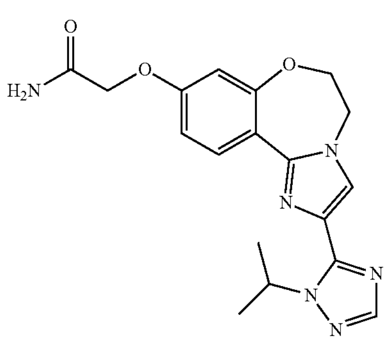 [SMILES: CC(C)n1ncnc1-c1cn2c(n1)-c1ccc(OCC(N)=O)cc1OCC2] | 2-(2-(1-isopropyl-1H-1,2,4-triazol-5-yl)-5,6-dihydrobenzo[f]imidazo[1,2-d][1,4]oxazepin-9-yloxy)acetamide |

TABLE 2-continued

| No. | Structure | Name |
|---|---|---|
| 429 | 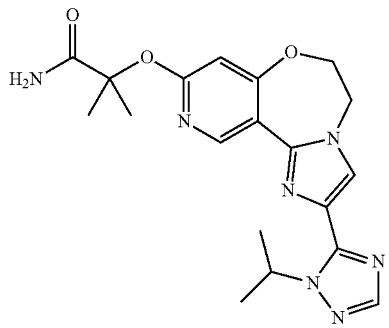 [SMILES: CC(C)n1ncnc1-c1cn2c(n1)-c1cnc(OC(C)(C)C(N)=O)cc1OCC2] | 2-(2-(1-isopropyl-1H-1,2,4-triazol-5-yl)-5,6-dihydroimidazo[1,2-d]pyrido[3,4-f][1,4]oxazepin-9-yloxy)-2-methylpropanamide |
| 430 | 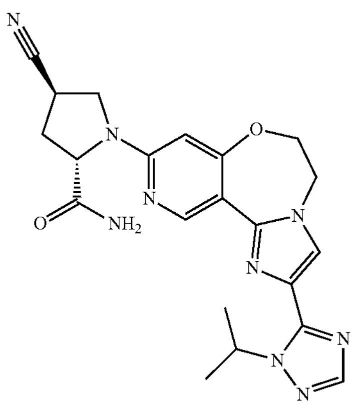 [SMILES: CC(C)n1ncnc1-c1cn2c(n1)-c1cnc(N3C[C@H](C#N)C[C@H]3C(N)=O)cc1OCC2] | (2S,4R)-4-cyano-1-(2-(1-isopropyl-1H-1,2,4-triazol-5-yl)-5,6-dihydroimidazo[1,2-d]pyrido[3,4-f][1,4]oxazepin-9-yl)pyrrolidine-2-carboxamide |
| 431 | 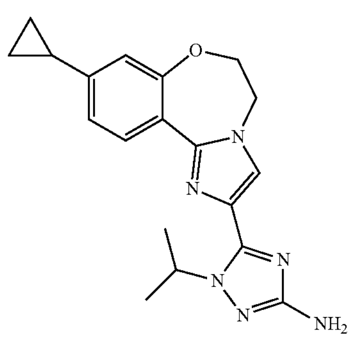 [SMILES: CC(C)n1nc(N)nc1-c1cn2c(n1)-c1ccc(C3CC3)cc1OCC2] | 5-(9-cyclopropyl-5,6-dihydrobenzo[f]imidazo[1,2-d][1,4]oxazepin-2-yl)-1-isopropyl-1H-1,2,4-triazol-3-amine |
| 432 | 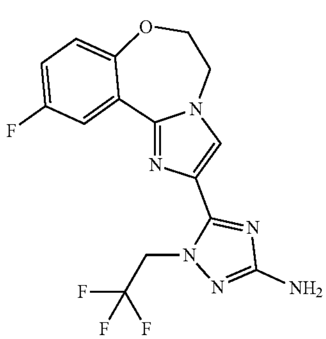 [SMILES: Nc1nc(-c2cn3c(n2)-c2cc(F)ccc2OCC3)n(CC(F)(F)F)n1] | 5-(10-fluoro-5,6-dihydrobenzo[f]imidazo[1,2-d][1,4]oxazepin-2-yl)-1-(2,2,2-trifluoroethyl)-1H-1,2,4-triazol-3-amine |

TABLE 2-continued

| No. | Structure | Name |
|---|---|---|
| 433 | 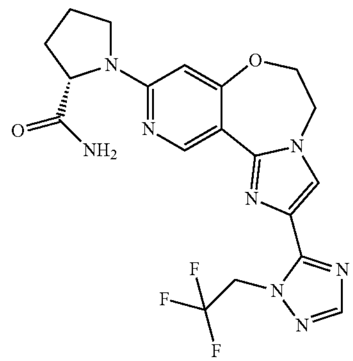 [SMILES: NC(=O)[C@@H]1CCCN1c1cc2c(cn1)-c1nc(-c3ncnn3CC(F)(F)F)cn1CCO2] | (2S)-1-(2-(1-(2,2,2-trifluoroethyl)-1H-1,2,4-triazol-5-yl)-5,6-dihydroimidazo[1,2-d]pyrido[3,4-f][1,4]oxazepin-9-yl)pyrrolidine-2-carboxamide |
| 434 | 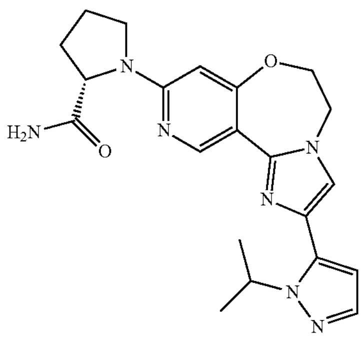 [SMILES: CC(C)n1nccc1-c1cn2c(n1)-c1cnc(N3CCC[C@H]3C(N)=O)cc1OCC2] | (2S)-1-(2-(1-isopropyl-1H-pyrazol-5-yl)-5,6-dihydroimidazo[1,2-d]pyrido[3,4-f][1,4]oxazepin-9-yl)pyrrolidine-2-carboxamide |
| 435 | 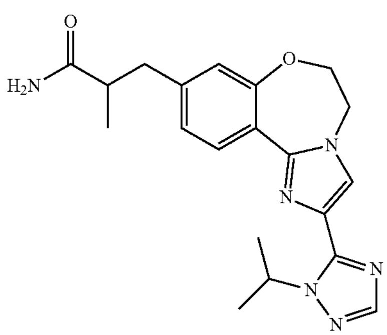 [SMILES: CC(Cc1ccc2c(c1)OCCn1cc(-c3ncnn3C(C)C)nc1-2)C(N)=O] | 3-(2-(1-isopropyl-1H-1,2,4-triazol-5-yl)-5,6-dihydrobenzo[f]imidazo[1,2-d][1,4]oxazepin-9-yl)-2-methylpropanamide |
| 436 | 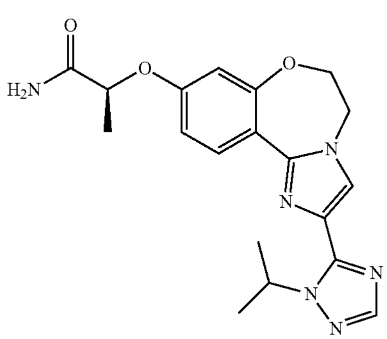 [SMILES: CC(C)n1ncnc1-c1cn2c(n1)-c1ccc(O[C@@H](C)C(N)=O)cc1OCC2] | (2S)-2-(2-(1-isopropyl-1H-1,2,4-triazol-5-yl)-5,6-dihydrobenzo[f]imidazo[1,2-d][1,4]oxazepin-9-yloxy)propanamide |

TABLE 2-continued

| No. | Structure | Name |
|---|---|---|
| 437 | 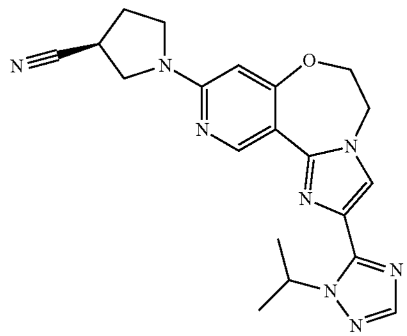 [SMILES: CC(C)n1ncnc1-c1cn2c(n1)-c1cnc(N3CC[C@H](C#N)C3)cc1OCC2] | (3S)-1-(2-(1-isopropyl-1H-1,2,4-triazol-5-yl)-5,6-dihydroimidazo[1,2-d]pyrido[3,4-f][1,4]oxazepin-9-yl)pyrrolidine-2-carbonitrile |
| 438 | 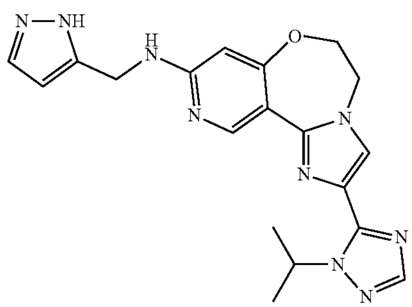 [SMILES: CC(C)n1ncnc1-c1cn2c(n1)-c1cnc(NCc3ccn[nH]3)cc1OCC2] | N-((1H-pyrazol-5-yl)methyl)-2-(1-isopropyl-1H-1,2,4-triazol-5-yl)-5,6-dihydroimidazo[1,2-d]pyrido[3,4-f][1,4]oxazepin-9-amine |
| 439 | 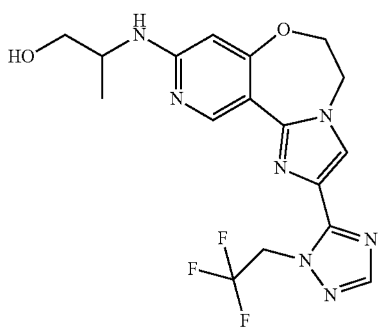 [SMILES: CC(CO)Nc1cc2c(cn1)-c1nc(-c3ncnn3CC(F)(F)F)cn1CCO2] | 2-(2-(1-(2,2,2-trifluoroethyl)-1H-1,2,4-triazol-5-yl)-5,6-dihydroimidazo[1,2-d]pyrido[3,4-f][1,4]oxazepin-9-ylamino)propan-1-ol |
| 440 | 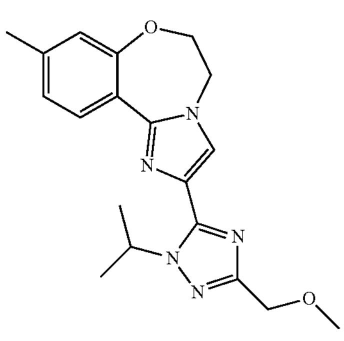 | 2-(1-isopropyl-3-(methoxymethyl)-1H-1,2,4-triazol-5-yl)-9-methyl-5,6-dihydrobenzo[f]imidazo[1,2-d][1,4]oxazepine |

TABLE 2-continued

| No. | Structure | Name |
|---|---|---|
| 441 | 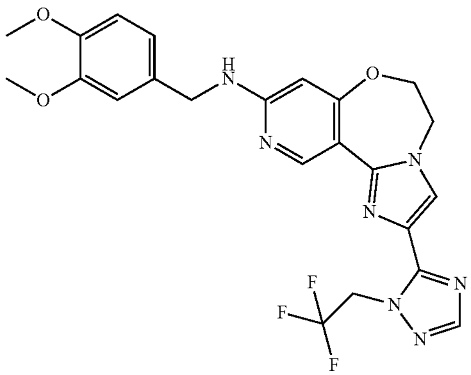 [SMILES: COc1ccc(CNc2cc3c(cn2)-c2nc(-c4ncnn4CC(F)(F)F)cn2CCO3)cc1OC] | N-(3,4-dimethoxybenzyl)-2-(1-(2,2,2-trifluoroethyl)-1H-1,2,4-triazol-5-yl)-5,6-dihydroimidazo[1,2-d]pyrido[3,4-f][1,4]oxazepin-9-amine |
| 442 | 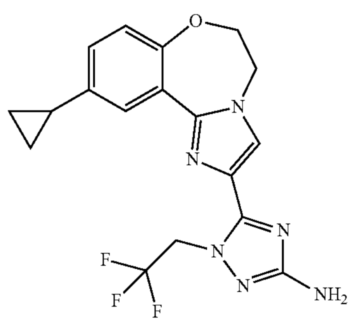 [SMILES: Nc1nc(-c2cn3c(n2)-c2cc(C4CC4)ccc2OCC3)n(CC(F)(F)F)n1] | 5-(1-cyclopropyl-6-dihydrobenzo[f]imidazo[1,2-d][1,4]oxazepin-2-yl)-1-(2,2,2-trifluoroethyl)-1H-1,2,4-triazol-3-amine |
| 443 | 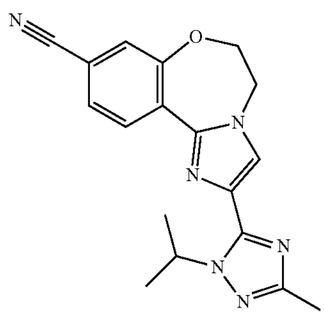 [SMILES: Cc1nc(-c2cn3c(n2)-c2ccc(C#N)cc2OCC3)n(C(C)C)n1] | 2-(1-isopropyl-3-methyl-1H-1,2,4-triazol-5-yl)-5,6-dihydrobenzo[f]imidazo[1,2-d][1,4]oxazepine-9-carbonitrile |
| 444 | 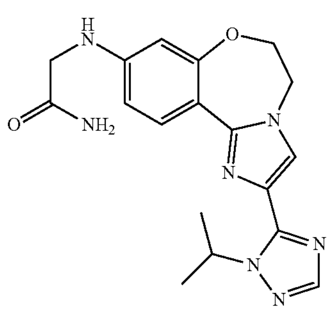 [SMILES: CC(C)n1ncnc1-c1cn2c(n1)-c1ccc(NCC(N)=O)cc1OCC2] | 2-(2-(1-isopropyl-1H-1,2,4-triazol-5-yl)-5,6-dihydrobenzo[f]imidazo[1,2-d][1,4]oxazepin-9-ylamino)acetamide |

TABLE 2-continued

| No. | Structure | Name |
|---|---|---|
| 445 | 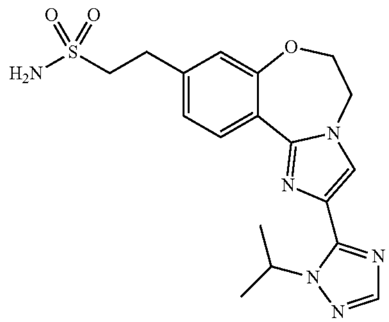 [SMILES: CC(C)n1ncnc1-c1cn2c(n1)-c1ccc(CCS(N)(=O)=O)cc1OCC2] | 2-(2-(1-isopropyl-1H-1,2,4-triazol-5-yl)-5,6-dihydrobenzo[f]imidazo[1,2-d][1,4]oxazepin-9-yl)ethanesulfonamide |
| 446 | 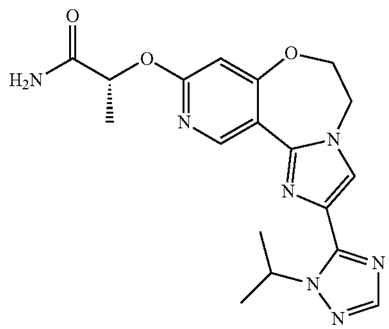 [SMILES: CC(C)n1ncnc1-c1cn2c(n1)-c1cnc(O[C@H](C)C(N)=O)cc1OCC2] | (R)-2-(2-(1-isopropyl-1H-1,2,4-triazol-5-yl)-5,6-dihydroimidazo[1,2-d]pyrido[3,4-f][1,4]oxazepin-9-yloxy)propanamide |
| 447 | 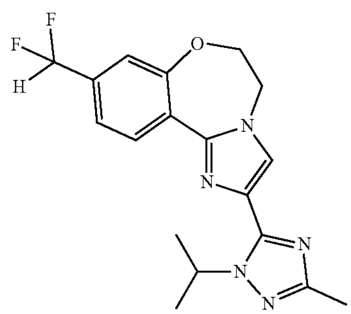 [SMILES: Cc1nc(-c2cn3c(n2)-c2ccc(C(F)F)cc2OCC3)n(C(C)C)n1] | 9-(difluoromethyl)-2-(1-isopropyl-3-methyl-1H-1,2,4-triazol-5-yl)-5,6-dihydrobenzo[f]imidazo[1,2-d][1,4]oxazepine |
| 448 | 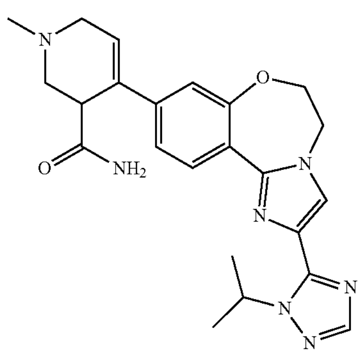 [SMILES: CC(C)n1ncnc1-c1cn2c(n1)-c1ccc(C3=CCN(C)CC3C(N)=O)cc1OCC2] | 4-(2-(1-isopropyl-1H-1,2,4-triazol-5-yl)-5,6-dihydrobenzo[f]imidazo[1,2-d][1,4]oxazepin-9-yl)-1-methyl-1,2,3,6-tetrahydropyridine-3-carboxamide |

TABLE 2-continued

| No. | Structure | Name |
|---|---|---|
| 449 | 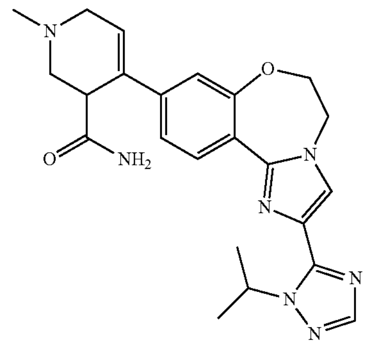 [SMILES: CC(C)n1ncnc1-c1cn2c(n1)-c1ccc(C3=CCN(C)CC3C(N)=O)cc1OCC2] | 4-(2-(1-isopropyl-1H-1,2,4-triazol-5-yl)-5,6-dihydrobenzo[f]imidazo[1,2-d][1,4]oxazepin-9-yl)-1-methyl-1,2,3,6-tetrahydropyridine-3-carboxamide |
| 450 | 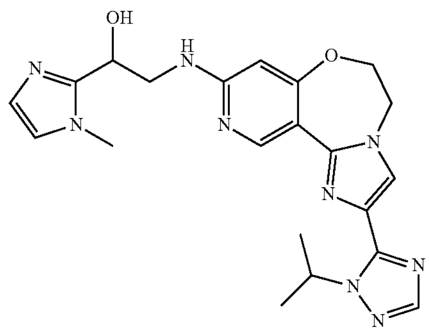 [SMILES: CC(C)n1ncnc1-c1cn2c(n1)-c1cnc(NCC(O)c3nccn3C)cc1OCC2] | 2-(2-(1-isopropyl-1H-1,2,4-triazol-5-yl)-5,6-dihydroimidazo[1,2-d]pyrido[3,4-f][1,4]oxazepin-9-ylamino)-1-(1-methyl-1H-imidazol-2-yl)ethanol |
| 451 | 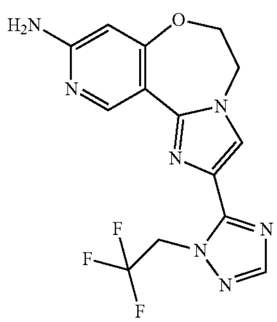 [SMILES: Nc1cc2c(cn1)-c1nc(-c3ncnn3CC(F)(F)F)cn1CCO2] | 2-(1-(2,2,2-trifluoroethyl)-1H-1,2,4-triazol-5-yl)-5,6-dihydroimidazo[1,2-d]pyrido[3,4-f][1,4]oxazepin-9-amine |
| 452 | 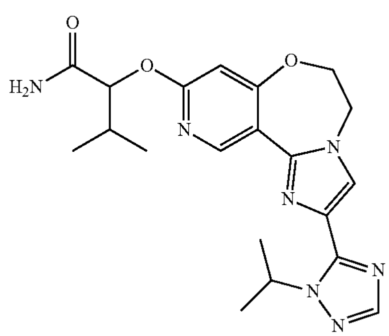 [SMILES: CC(C)C(Oc1cc2c(cn1)-c1nc(-c3ncnn3C(C)C)cn1CCO2)C(N)=O] | 2-(2-(1-isopropyl-1H-1,2,4-triazol-5-yl)-5,6-dihydroimidazo[1,2-d]pyrido[3,4-f][1,4]oxazepin-9-yloxy)-3-methylbutanamide |
| 453 | 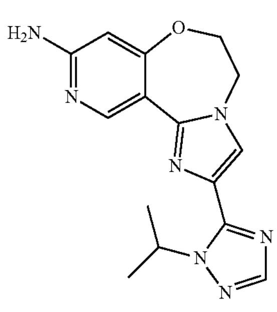 [SMILES: CC(C)n1ncnc1-c1cn2c(n1)-c1cnc(N)cc1OCC2] | 2-(1-isopropyl-1H-1,2,4-triazol-5-yl)-5,6-dihydroimidazo[1,2-d]pyrido[3,4-f][1,4]oxazepin-9-amine |

TABLE 2-continued

| No. | Structure | Name |
|---|---|---|
| 454 | 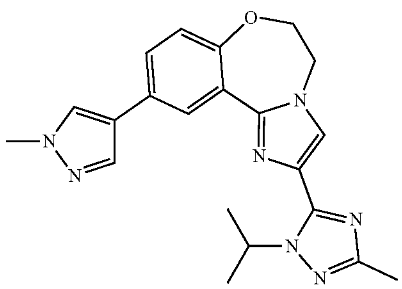 | 2-(1-isopropyl-3-methyl-1H-1,2,4-triazol-5-yl)-10-(1-methyl-1H-pyrazol-4-yl)-5,6-dihydrobenzo[f]imidazo[1,2-d][1,4]oxazepine |
| 455 | 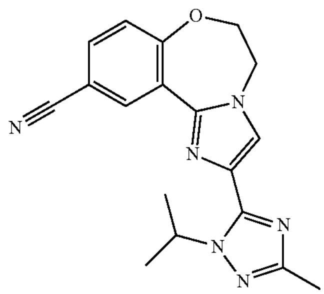 [SMILES: Cc1nc(-c2cn3c(n2)-c2cc(C#N)ccc2OCC3)n(C(C)C)n1] | 2-(1-isopropyl-3-methyl-1H-1,2,4-triazol-5-yl)-5,6-dihydrobenzo[f]imidazo[1,2-d][1,4]oxazepin-10-carbonitrile |
| 456 | 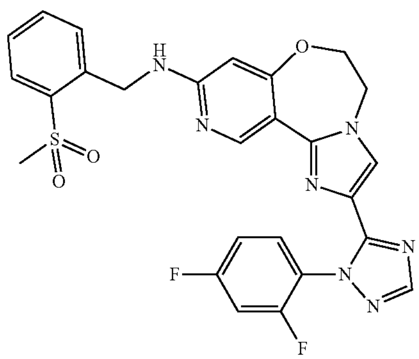 [SMILES: CS(=O)(=O)c1ccccc1CNc1cc2c(cn1)-c1nc(-c3ncnn3-c3ccc(F)cc3F)cn1CCO2] | 2-(1-(2,4-difluorophenyl)-1H-1,2,4-triazol-5-yl)-N-(2-(methylsulfonyl)benzyl)-5,6-dihydroimidazo[1,2-d]pyrido[3,4-f][1,4]oxazepin-9-amine |
| 457 | 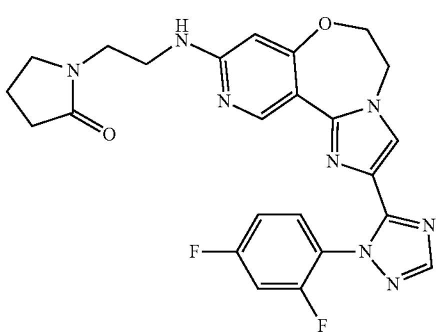 [SMILES: O=C1CCCN1CCNc1cc2c(cn1)-c1nc(-c3ncnn3-c3ccc(F)cc3F)cn1CCO2] | 1-(2-(2-(1-(2,4-difluorophenyl)-1H-1,2,4-triazol-5-yl)-5,6-dihydroimidazo[1,2-d]pyrido[3,4-f][1,4]oxazepin-9-ylamino)ethyl)pyrrolidin-2-one |
| 458 | 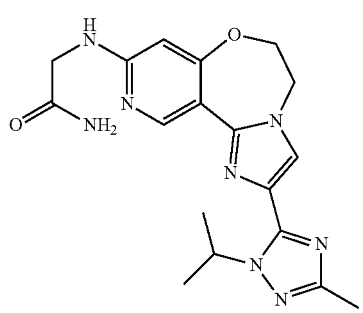 [SMILES: Cc1nc(-c2cn3c(n2)-c2cnc(NCC(N)=O)cc2OCC3)n(C(C)C)n1] | 2-(2-(1-isopropyl-3-methyl-1H-1,2,4-triazol-5-yl)-5,6-dihydroimidazo[1,2-d]pyrido[3,4-f][1,4]oxazepin-9-ylamino)acetamide |

TABLE 2-continued

| No. | Structure | Name |
| --- | --- | --- |
| 459 | 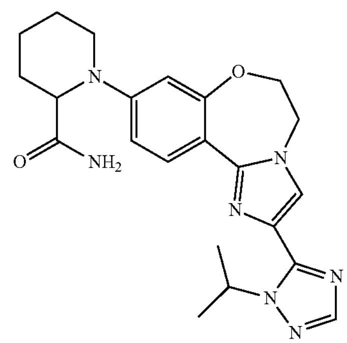 [SMILES: CC(C)n1ncnc1-c1cn2c(n1)-c1ccc(N3CCCCC3C(N)=O)cc1OCC2] | 1-(2-(1-isopropyl-1H-1,2,4-triazol-5-yl)-5,6-dihydrobenzo[f]imidazo[1,2-d][1,4]oxazepin-9-yl)piperidine-2-carboxamide |
| 460 | 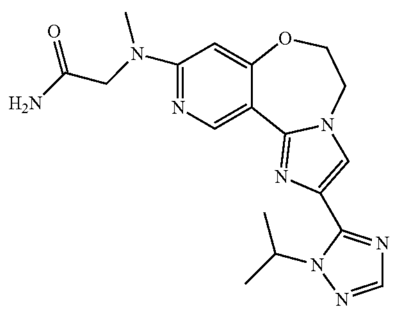 [SMILES: CC(C)n1ncnc1-c1cn2c(n1)-c1cnc(N(C)CC(N)=O)cc1OCC2] | 2-((2-(1-isopropyl-1H-1,2,4-triazol-5-yl)-5,6-dihydroimidazo[1,2-d]pyrido[3,4-f][1,4]oxazepin-9-yl)(methyl)amino)acetamide |
| 461 | 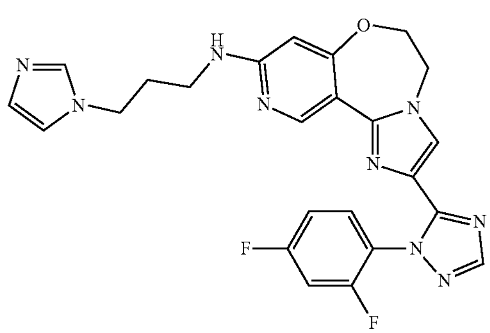 [SMILES: Fc1ccc(-n2ncnc2-c2cn3c(n2)-c2cnc(NCCCn4ccnc4)cc2OCC3)c(F)c1] | N-(3-(1H-imidazol-1-yl)propyl)-2-(1-(2,4-difluorophenyl)-1H-1,2,4-triazol-5-yl)-5,6-dihydroimidazo[1,2-d]pyrido[3,4-f][1,4]oxazepin-9-amine |
| 462 | 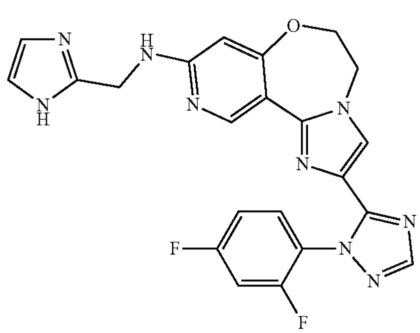 [SMILES: Fc1ccc(-n2ncnc2-c2cn3c(n2)-c2cnc(NCc4ncc[nH]4)cc2OCC3)c(F)c1] | N-((1H-imidazol-2-yl)methyl)-2-(1-(2,4-difluorophenyl)-1H-1,2,4-triazol-5-yl)-5,6-dihydroimidazo[1,2-d]pyrido[3,4-f][1,4]oxazepin-9-amine |
| 463 | 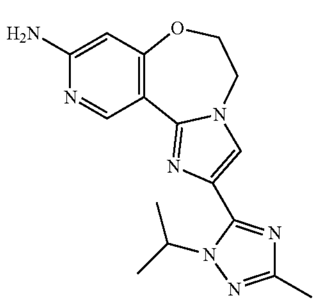 [SMILES: Cc1nc(-c2cn3c(n2)-c2cnc(N)cc2OCC3)n(C(C)C)n1] | 2-(1-isopropyl-3-methyl-1H-1,2,4-triazol-5-yl)-5,6-dihydroimidazo[1,2-d]pyrido[3,4-f][1,4]oxazepin-9-amine |

TABLE 2-continued

| No. | Structure | Name |
|---|---|---|
| 464 | 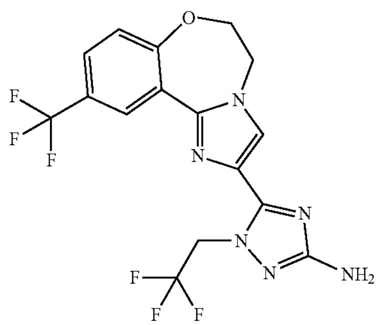 [SMILES: Nc1nc(-c2cn3c(n2)-c2cc(C(F)(F)F)ccc2OCC3)n(CC(F)(F)F)n1] | 1-(2,2,2-trifluoroethyl)-5-(10-(trifluoromethyl)-5,6-dihydrobenzo[f]imidazo[1,2-d][1,4]oxazepin-2-yl)-1H-1,2,4-triazol-3-amine |
| 465 | 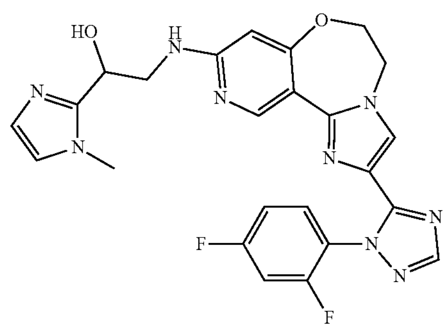 [SMILES: Cn1ccnc1C(O)CNc1cc2c(cn1)-c1nc(-c3ncnn3-c3ccc(F)cc3F)cn1CCO2] | 2-(2-(1-(2,4-difluorophenyl)-1H-1,2,4-triazol-5-yl)-5,6-dihydroimidazo[1,2-d]pyrido[3,4-f][1,4]oxazepin-9-ylamino)-1-(1-methyl-1H-imidazol-2-yl)ethanol |
| 466 | 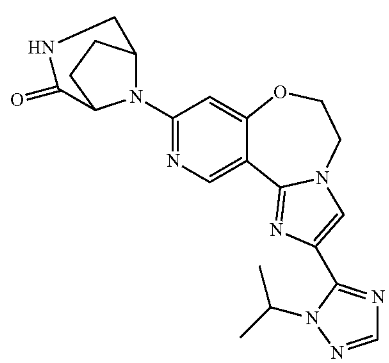 [SMILES: CC(C)n1ncnc1-c1cn2c(n1)-c1cnc(N3C4CCC3C(=O)NC4)cc1OCC2] | 8-(2-(1-isopropyl-1H-1,2,4-triazol-5-yl)-5,6-dihydroimidazo[1,2-d]pyrido[3,4-f][1,4]oxazepin-9-yl)-3,8-azabicyclo[3.2.1]octan-2-one |
| 467 | 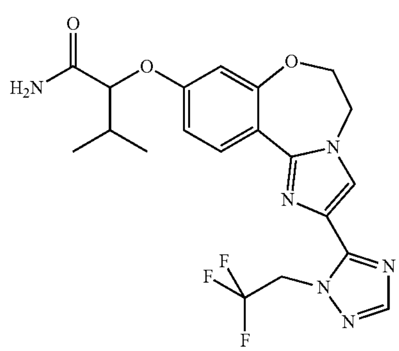 | 3-methyl-2-(2-(1-(2,2,2-trifluoroethyl)-1H-1,2,4-triazol-5-yl)-5,6-dihydrobenzo[f]imidazo[1,2-d][1,4]oxazepin-9-yloxy)butanamide |

TABLE 2-continued

| No. | Structure | Name |
|---|---|---|
| 468 | 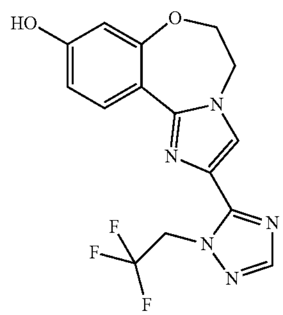 [SMILES: Oc1ccc2c(c1)OCCn1cc(-c3ncnn3CC(F)(F)F)nc1-2] | 2-(1-(2,2,2-trifluoroethyl)-1H-1,2,4-triazol-5-yl)-5,6-dihydrobenzo[f]imidazo[1,2-d][1,4]oxazepin-9-ol |
| 469 | 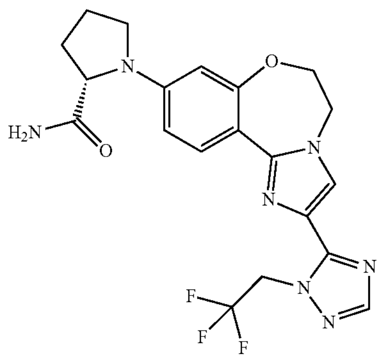 [SMILES: NC(=O)[C@@H]1CCCN1c1ccc2c(c1)OCCn1cc(-c3ncnn3CC(F)(F)F)nc1-2] | (2S)-1-(2-(1-(2,2,2-trifluoroethyl)-1H-1,2,4-triazol-5-yl)-5,6-dihydrobenzo[f]imidazo[1,2-d][1,4]oxazepin-9-yl)pyrrolidine-2-carboxamide |
| 470 | 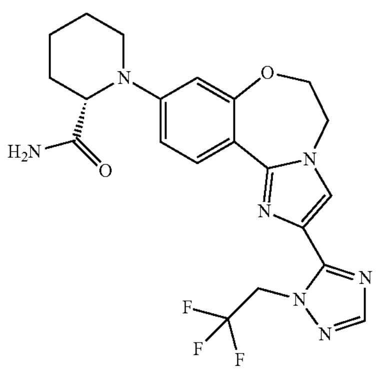 [SMILES: NC(=O)[C@@H]1CCCCN1c1ccc2c(c1)OCCn1cc(-c3ncnn3CC(F)(F)F)nc1-2] | (2S)-1-(2-(1-(2,2,2-trifluoroethyl)-1H-1,2,4-triazol-5-yl)-5,6-dihydrobenzo[f]imidazo[1,2-d][1,4]oxazepin-9-yl)piperidine-2-carboxamide |
| 471 | 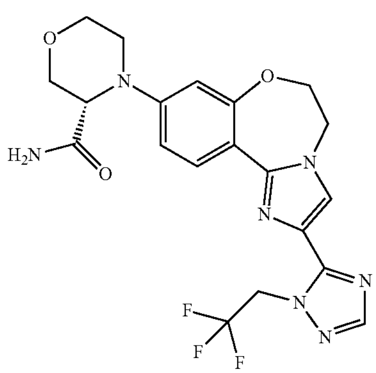 [SMILES: NC(=O)[C@@H]1COCCN1c1ccc2c(c1)OCCn1cc(-c3ncnn3CC(F)(F)F)nc1-2] | (3S)-4-(2-(1-(2,2,2-trifluoroethyl)-1H-1,2,4-triazol-5-yl)-5,6-dihydrobenzo[f]imidazo[1,2-d][1,4]oxazepin-9-yl)morpholine-3-carboxamide |

TABLE 2-continued

| No. | Structure | Name |
|---|---|---|
| 472 | 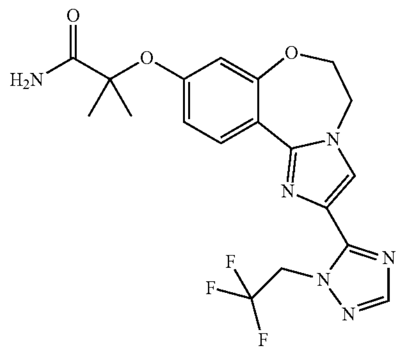 [SMILES: CC(C)(Oc1ccc2c(c1)OCCn1cc(-c3ncnn3CC(F)(F)F)nc1-2)C(N)=O] | 2-methyl-2-(2-(1-(2,2,2-trifluoroethyl)-1H-1,2,4-triazol-5-yl)-5,6-dihydrobenzo[f]imidazo[1,2-d][1,4]oxazepin-9-yloxy)propanamide |
| 473 | 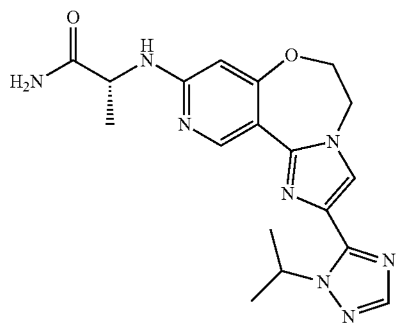 [SMILES: CC(C)n1ncnc1-c1cn2c(n1)-c1cnc(N[C@H](C)C(N)=O)cc1OCC2] | (2R)-2-(2-(1-isopropyl-1H-1,2,4-triazol-5-yl)-5,6-dihydroimidazo[1,2-d]pyrido[3,4-f][1,4]oxazepin-9-ylamino)propanamide |
| 474 | 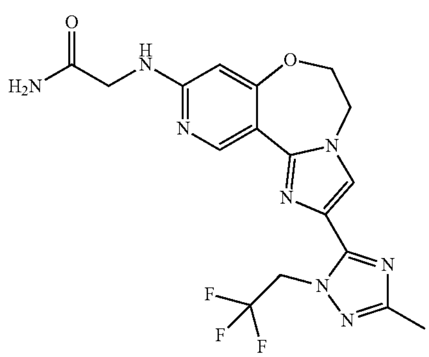 [SMILES: Cc1nc(-c2cn3c(n2)-c2cnc(NCC(N)=O)cc2OCC3)n(CC(F)(F)F)n1] | 2-(2-(3-methyl-1-(2,2,2-trifluoroethyl)-1H-1,2,4-triazol-5-yl)-5,6-dihydroimidazo[1,2-d]pyrido[3,4-f][1,4]oxazepin-9-ylamino)acetamide |
| 475 | 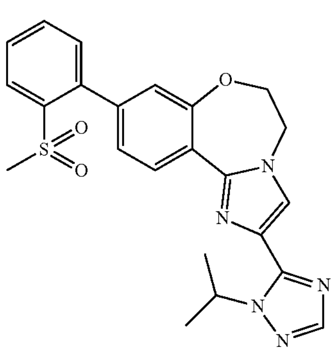 [SMILES: CC(C)n1ncnc1-c1cn2c(n1)-c1ccc(-c3ccccc3S(C)(=O)=O)cc1OCC2] | 2-(1-isopropyl-1H-1,2,4-triazol-5-yl)-9-(2-(methylsulfonyl)phenyl)-5,6-dihydrobenzo[f]imidazo[1,2-d][1,4]oxazepine |

TABLE 2-continued

| No. | Structure | Name |
|---|---|---|
| 476 | 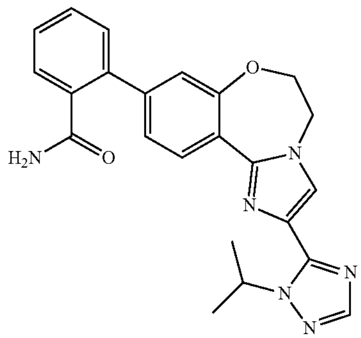 [SMILES: CC(C)n1ncnc1-c1cn2c(n1)-c1ccc(-c3ccccc3C(N)=O)cc1OCC2] | 2-(2-(1-isopropyl-1H-1,2,4-triazol-5-yl)-5,6-dihydrobenzo[f]imidazo[1,2-d][1,4]oxazepin-9-yl)benzamide |
| 477 | 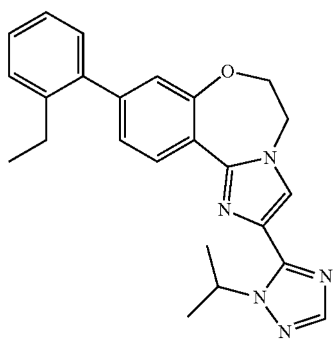 [SMILES: CCc1ccccc1-c1ccc2c(c1)OCCn1cc(-c3ncnn3C(C)C)nc1-2] | 9-(2-ethylphenyl)-2-(1-isopropyl-1H-1,2,4-triazol-5-yl)-5,6-dihydrobenzo[f]imidazo[1,2-d][1,4]oxazepine |
| 478 | 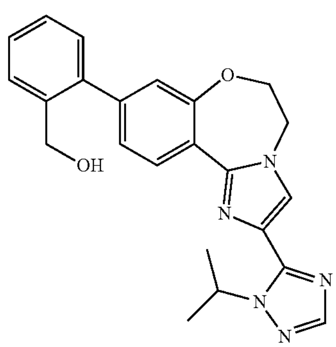 [SMILES: CC(C)n1ncnc1-c1cn2c(n1)-c1ccc(-c3ccccc3CO)cc1OCC2] | (2-(2-(1-isopropyl-1H-1,2,4-triazol-5-yl)-5,6-dihydrobenzo[f]imidazo[1,2-d][1,4]oxazepin-9-yl)phenyl)methanol |
| 479 | 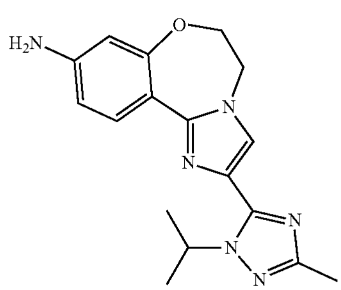 [SMILES: Cc1nc(-c2cn3c(n2)-c2ccc(N)cc2OCC3)n(C(C)C)n1] | 2-(1-isopropyl-3-methyl-1H-1,2,4-triazol-5-yl)-5,6-dihydrobenzo[f]imidazo[1,2-d][1,4]oxazepin-9-amine |
| 480 | 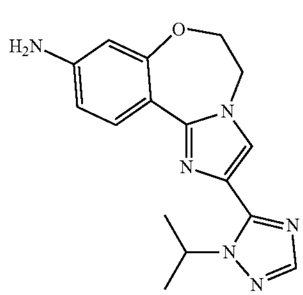 [SMILES: CC(C)n1ncnc1-c1cn2c(n1)-c1ccc(N)cc1OCC2] | 2-(1-isopropyl-1H-1,2,4-triazol-5-yl)-5,6-dihydrobenzo[f]imidazo[1,2-d][1,4]oxazepin-9-amine |

TABLE 2-continued

| No. | Structure | Name |
|---|---|---|
| 481 | 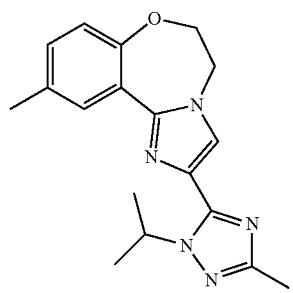 | 2-(1-isopropyl-3-methyl-1H-1,2,4-triazol-5-yl)-10-methyl-5,6-dihydrobenzo[f]imidazo[1,2-d][1,4]oxazepine |
| 482 | 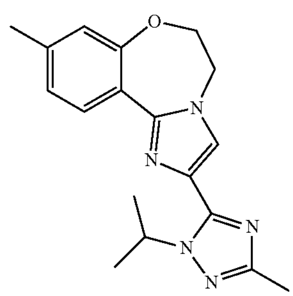 | 2-(1-isopropyl-3-methyl-1H-1,2,4-triazol-5-yl)-9-methyl-5,6-dihydrobenzo[f]imidazo[1,2-d][1,4]oxazepine |
| 483 | 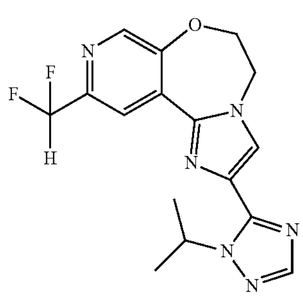 [SMILES: CC(C)n1ncnc1-c1cn2c(n1)-c1cc(C(F)F)ncc1OCC2] | 10-(difluoromethyl)-2-(1-isopropyl-1H-1,2,4-triazol-5-yl)-5,6-dihydroimidazo[1,2-d]pyrido[3,4-f][1,4]oxazepine |
| 484 | 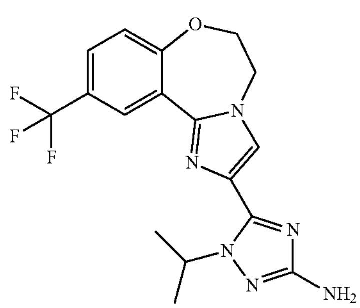 [SMILES: CC(C)n1nc(N)nc1-c1cn2c(n1)-c1cc(C(F)(F)F)ccc1OCC2] | 1-isopropyl-5-(10-(trifluoromethyl)-5,6-dihydrobenzo[f]imidazo[1,2-d][1,4]oxazepin-2-yl)-1H-1,2,4-triazol-3-amine |
| 485 | 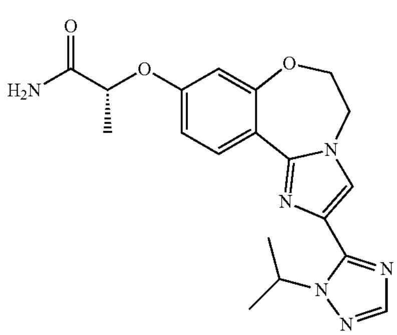 [SMILES: CC(C)n1ncnc1-c1cn2c(n1)-c1ccc(O[C@H](C)C(N)=O)cc1OCC2] | (2R)-2-(2-(1-isopropyl-1H-1,2,4-triazol-5-yl)-5,6-dihydrobenzo[f]imidazo[1,2-d][1,4]oxazepin-9-yloxy)propanamide |

TABLE 2-continued

| No. | Structure | Name |
|---|---|---|
| 486 | 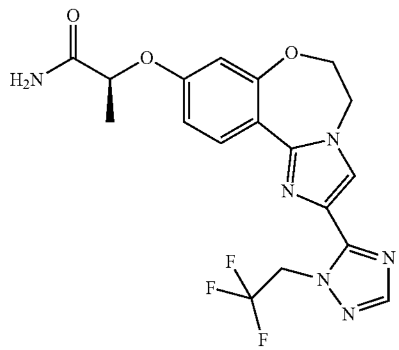 [SMILES: C[C@H](Oc1ccc2c(c1)OCCn1cc(-c3ncnn3CC(F)(F)F)nc1-2)C(N)=O] | (2S)-2-(2-(1-(2,2,2-trifluoroethyl)-1H-1,2,4-triazol-5-yl)-5,6-dihydrobenzo[f]imidazo[1,2-d][1,4]oxazepin-9-yloxy)propanamide |
| 487 | 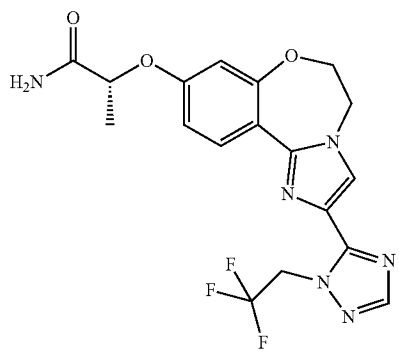 [SMILES: C[C@@H](Oc1ccc2c(c1)OCCn1cc(-c3ncnn3CC(F)(F)F)nc1-2)C(N)=O] | (2R)-2-(2-(1-(2,2,2-trifluoroethyl)-1H-1,2,4-triazol-5-yl)-5,6-dihydrobenzo[f]imidazo[1,2-d][1,4]oxazepin-9-yloxy)propanamide |
| 488 | 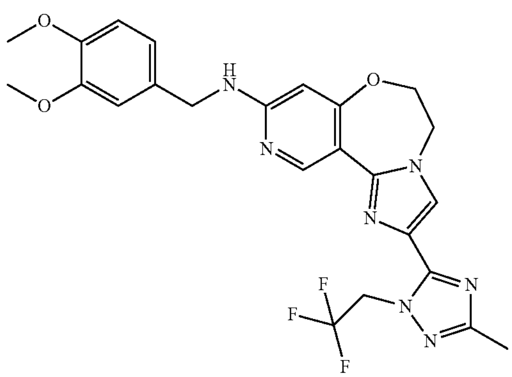 | N-(3,4-dimethoxybenzyl)-2-(3-methyl-1-(2,2,2-trifluoroethyl)-1H-1,2,4-triazol-5-yl)-5,6-dihydroimidazo[1,2-d]pyrido[3,4-f][1,4]oxazepin-9-amine |
| 489 | 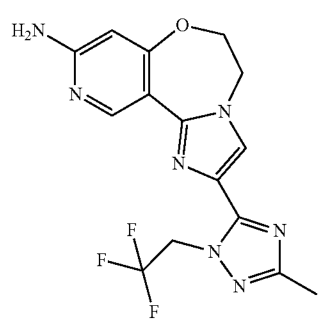 [SMILES: Cc1nc(-c2cn3c(n2)-c2cnc(N)cc2OCC3)n(CC(F)(F)F)n1] | 2-(3-methyl-1-(2,2,2-trifluoroethyl)-1H-1,2,4-triazol-5-yl)-5,6-dihydroimidazo[1,2-d]pyrido[3,4-f][1,4]oxazepin-9-amine |

TABLE 2-continued

| No. | Structure | Name |
|---|---|---|
| 490 | 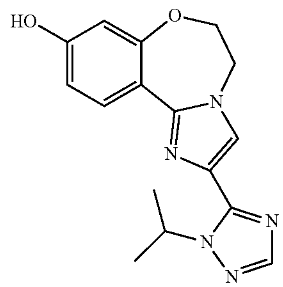 [SMILES: CC(C)n1ncnc1-c1cn2c(n1)-c1ccc(O)cc1OCC2] | 2-(1-isopropyl-1H-1,2,4-triazol-5-yl)-5,6-dihydrobenzo[f]imidazo[1,2-d][1,4]oxazepin-9-ol |
| 491 | 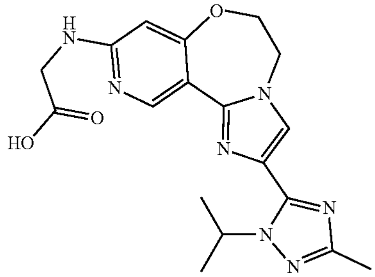 [SMILES: Cc1nc(-c2cn3c(n2)-c2cnc(NCC(=O)O)cc2OCC3)n(C(C)C)n1] | 2-(2-(1-isopropyl-3-methyl-1H-1,2,4-triazol-5-yl)-5,6-dihydroimidazo[1,2-d]pyrido[3,4-f][1,4]oxazepin-9-ylamino)acetic acid |
| 492 | 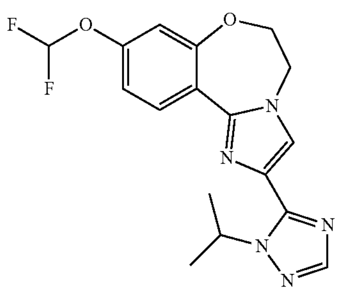 [SMILES: CC(C)n1ncnc1-c1cn2c(n1)-c1ccc(OC(F)F)cc1OCC2] | 9-(difluoromethoxy)-2-(1-isopropyl-1H-1,2,4-triazol-5-yl)-5,6-dihydrobenzo[f]imidazo[1,2-d][1,4]oxazepine |
| 493 | 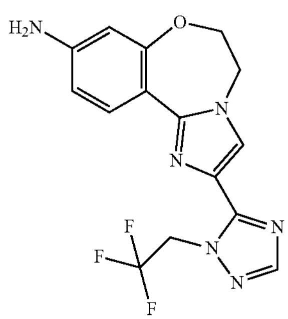 [SMILES: Nc1ccc2c(c1)OCCn1cc(-c3ncnn3CC(F)(F)F)nc1-2] | 2-(1-(2,2,2-trifluoroethyl)-1H-1,2,4-triazol-5-yl)-5,6-dihydrobenzo[f]imidazo[1,2-d][1,4]oxazepin-9-amine |
| 494 | 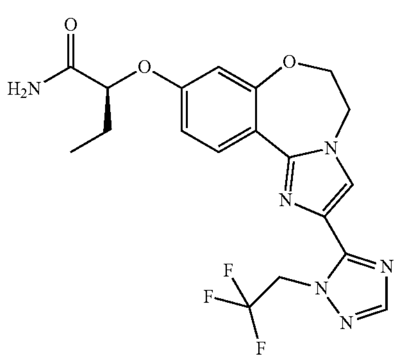 [SMILES: CC[C@H](Oc1ccc2c(c1)OCCn1cc(-c3ncnn3CC(F)(F)F)nc1-2)C(N)=O] | (2S)-2-(2-(1-(2,2,2-trifluoroethyl)-1H-1,2,4-triazol-5-yl)-5,6-dihydrobenzo[f]imidazo[1,2-d][1,4]oxazepin-9-yloxy)butanamide |

TABLE 2-continued

| No. | Structure | Name |
|---|---|---|
| 495 | 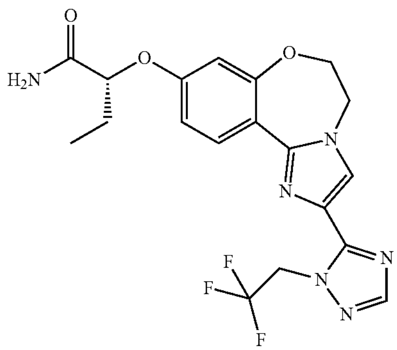 [SMILES: CC[C@@H](Oc1ccc2c(c1)OCCn1cc(-c3ncnn3CC(F)(F)F)nc1-2)C(N)=O] | (2R)-2-(2-(1-(2,2,2-trifluoroethyl)-1H-1,2,4-triazol-5-yl)-5,6-dihydrobenzo[f]imidazo[1,2-d][1,4]oxazepin-9-yloxy)butanamide |
| 496 | 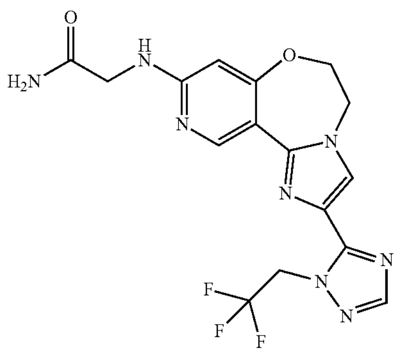 [SMILES: NC(=O)CNc1cc2c(cn1)-c1nc(-c3ncnn3CC(F)(F)F)cn1CCO2] | 2-(2-(1-(2,2,2-trifluoroethyl)-1H-1,2,4-triazol-5-yl)-5,6-dihydroimidazo[1,2-d]pyrido[3,4-f][1,4]oxazepin-9-ylamino)acetamide |
| 497 | 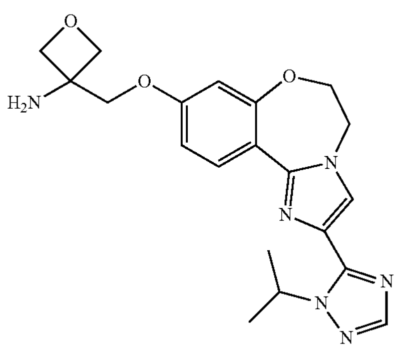 [SMILES: CC(C)n1ncnc1-c1cn2c(n1)-c1ccc(OCC3(N)COC3)cc1OCC2] | 3-((2-(1-isopropyl-1H-1,2,4-triazol-5-yl)-5,6-dihydrobenzo[f]imidazo[1,2-d][1,4]oxazepin-9-yloxy)methyl)oxetan-3-amine |
| 498 | 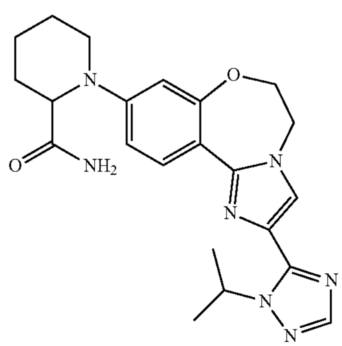 [SMILES: CC(C)n1ncnc1-c1cn2c(n1)-c1ccc(N3CCCCC3C(N)=O)cc1OCC2] | 1-(2-(1-isopropyl-1H-1,2,4-triazol-5-yl)-5,6-dihydrobenzo[f]imidazo[1,2-d][1,4]oxazepin-9-yl)piperidine-2-carboxamide |

TABLE 2-continued

| No. | Structure | Name |
|---|---|---|
| 499 | 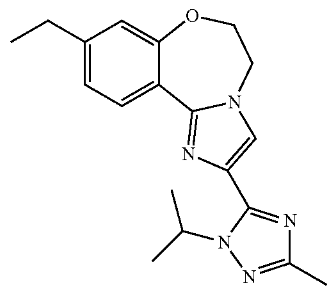 [SMILES: CCc1ccc2c(c1)OCCn1cc(-c3nc(C)nn3C(C)C)nc1-2] | 9-ethyl-2-(1-isopropyl-3-methyl-1H-1,2,4-triazol-5-yl)-5,6-dihydrobenzo[f]imidazo[1,2-d][1,4]oxazepine |
| 500 | 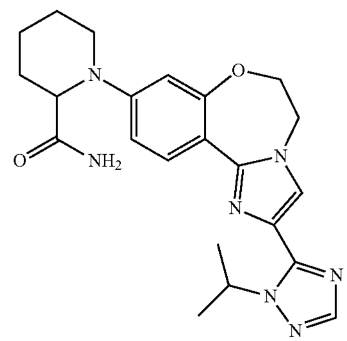 [SMILES: CC(C)n1ncnc1-c1cn2c(n1)-c1ccc(N3CCCCC3C(N)=O)cc1OCC2] | 1-(2-(1-isopropyl-1H-1,2,4-triazol-5-yl)-5,6-dihydrobenzo[f]imidazo[1,2-d][1,4]oxazepin-9-yl)piperidine-2-carboxamide |
| 501 | 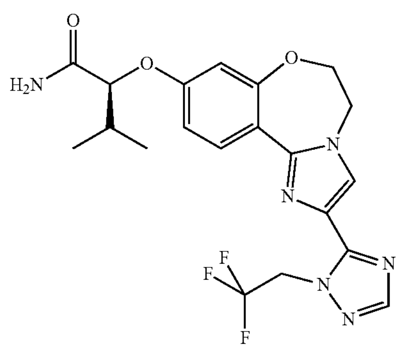 [SMILES: CC(C)[C@H](Oc1ccc2c(c1)OCCn1cc(-c3ncnn3CC(F)(F)F)nc1-2)C(N)=O] | (2S)-3-methyl-2-(2-(1-(2,2,2-trifluoroethyl)-1H-1,2,4-triazol-5-yl)-5,6-dihydrobenzo[f]imidazo[1,2-d][1,4]oxazepin-9-yloxy)butanamide |
| 502 | 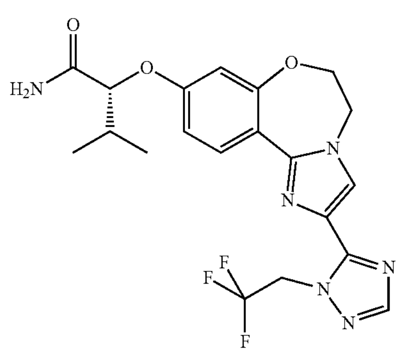 [SMILES: CC(C)[C@@H](Oc1ccc2c(c1)OCCn1cc(-c3ncnn3CC(F)(F)F)nc1-2)C(N)=O] | (2R)-3-methyl-2-(2-(1-(2,2,2-trifluoroethyl)-1H-1,2,4-triazol-5-yl)-5,6-dihydrobenzo[f]imidazo[1,2-d][1,4]oxazepin-9-yloxy)butanamide |

TABLE 2-continued

| No. | Structure | Name |
|-----|-----------|------|
| 503 | 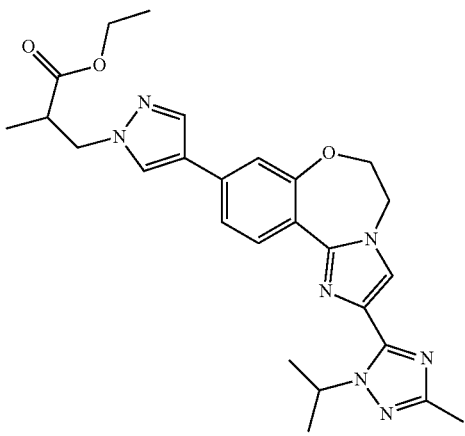 [SMILES: CCOC(=O)C(C)Cn1cc(-c2ccc3c(c2)OCCn2cc(-c4nc(C)nn4C(C)C)nc2-3)cn1] | ethyl 3-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoate |
| 504 | 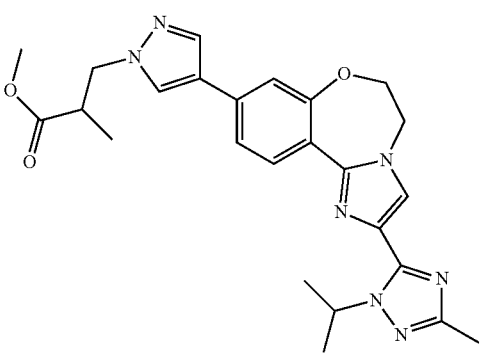 [SMILES: COC(=O)C(C)Cn1cc(-c2ccc3c(c2)OCCn2cc(-c4nc(C)nn4C(C)C)nc2-3)cn1] | methyl 3-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoate |
| 505 | 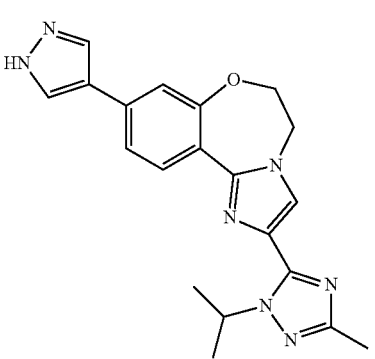 [SMILES: Cc1nc(-c2cn3c(n2)-c2ccc(-c4cn[nH]c4)cc2OCC3)n(C(C)C)n1] | 2-(1-isopropyl-3-methyl-1H-1,2,4-triazol-5-yl)-9-(1H-pyrazol-4-yl)-5,6-dihydrobenzo[f]imidazo[1,2-d][1,4]oxazepine |
| 506 | 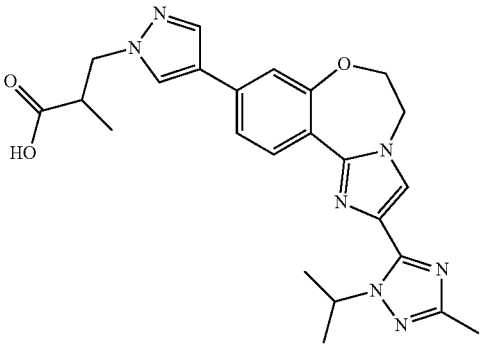 [SMILES: Cc1nc(-c2cn3c(n2)-c2ccc(-c4cnn(CC(C)C(=O)O)c4)cc2OCC3)n(C(C)C)n1] | 3-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoic acid |

TABLE 2-continued

| No. | Structure | Name |
|---|---|---|
| 507 | 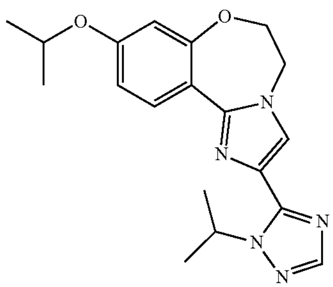 [SMILES: CC(C)Oc1ccc2c(c1)OCCn1cc(-c3ncnn3C(C)C)nc1-2] | 9-isopropoxy-2-(1-isopropyl-1H-1,2,4-triazol-5-yl)-5,6-dihydrobenzo[f]imidazo[1,2-d][1,4]oxazepine |
| 508 | 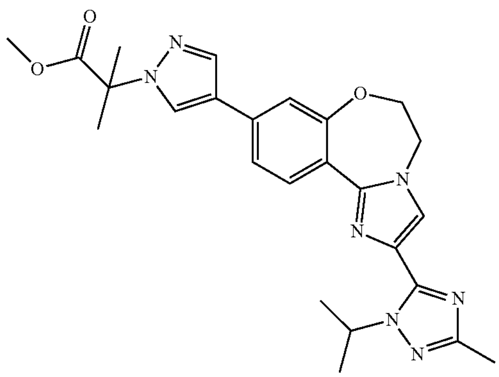 | methyl 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoate |
| 509 | 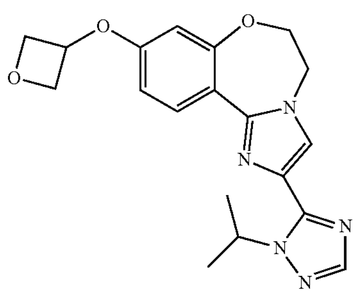 [SMILES: CC(C)n1ncnc1-c1cn2c(n1)-c1ccc(OC3COC3)cc1OCC2] | 2-(1-isopropyl-1H-1,2,4-triazol-5-yl)-9-(oxetan-3-yloxy)-5,6-dihydrobenzo[f]imidazo[1,2-d][1,4]oxazepine |
| 510 | 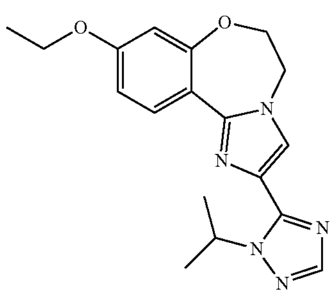 [SMILES: CCOc1ccc2c(c1)OCCn1cc(-c3ncnn3C(C)C)nc1-2] | 9-ethoxy-2-(1-isopropyl-1H-1,2,4-triazol-5-yl)-5,6-dihydrobenzo[f]imidazo[1,2-d][1,4]oxazepine |
| 511 | 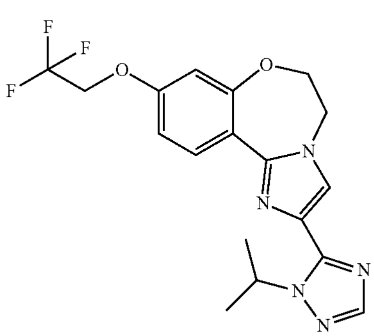 [SMILES: CC(C)n1ncnc1-c1cn2c(n1)-c1ccc(OCC(F)(F)F)cc1OCC2] | 2-(1-isopropyl-1H-1,2,4-triazol-5-yl)-9-(2,2,2-trifluoroethoxy)-5,6-dihydrobenzo[f]imidazo[1,2-d][1,4]oxazepine |

TABLE 2-continued

| No. | Structure | Name |
|---|---|---|
| 512 | 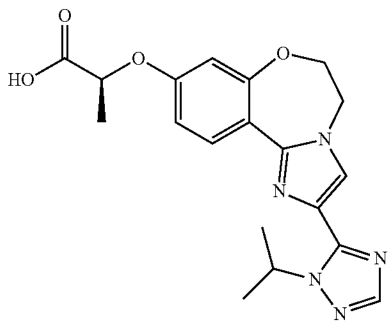 [SMILES: CC(C)n1ncnc1-c1cn2c(n1)-c1ccc(O[C@@H](C)C(=O)O)cc1OCC2] | (2S)-2-(2-(1-isopropyl-1H-1,2,4-triazol-5-yl)-5,6-dihydrobenzo[f]imidazo[1,2-d][1,4]oxazepin-9-yloxy)propanoic acid |
| 513 | 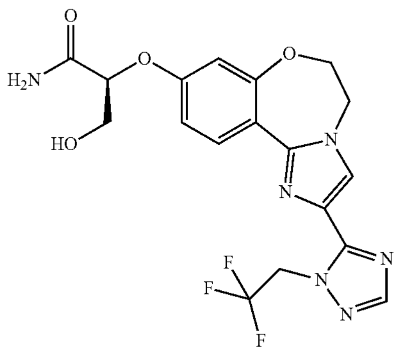 [SMILES: NC(=O)[C@H](CO)Oc1ccc2c(c1)OCCn1cc(-c3ncnn3CC(F)(F)F)nc1-2] | (2S)-3-hydroxy-2-(2-(1-(2,2,2-trifluoroethyl)-1H-1,2,4-triazol-5-yl)-5,6-dihydrobenzo[f]imidazo[1,2-d][1,4]oxazepin-9-yloxy)propanamide |
| 514 | 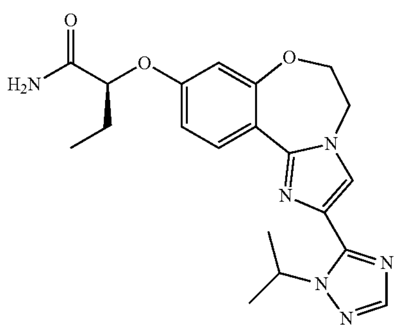 [SMILES: CC[C@H](Oc1ccc2c(c1)OCCn1cc(-c3ncnn3C(C)C)nc1-2)C(N)=O] | (2S)-2-(2-(1-isopropyl-1H-11580493,2,4-triazol-5-yl)-5,6-dihydrobenzo[f]imidazo[1,2-d][1,4]oxazepin-9-yloxy)butanamide |
| 515 | 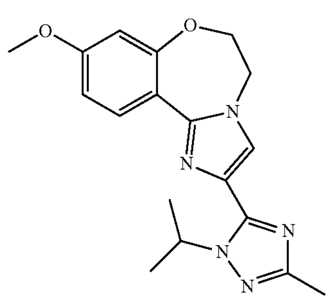 | 2-(1-isopropyl-3-methyl-1H-1,2,4-triazol-5-yl)-9-methoxy-5,6-dihydrobenzo[f]imidazo[1,2-d][1,4]oxazepine |
| 516 | 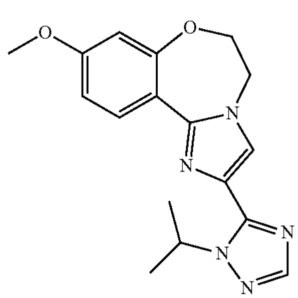 [SMILES: COc1ccc2c(c1)OCCn1cc(-c3ncnn3C(C)C)nc1-2] | 2-(1-isopropyl-1H-1,2,4-triazol-5-yl)-9-methoxy-5,6-dihydrobenzo[f]imidazo[1,2-d][1,4]oxazepine |

TABLE 2-continued

| No. | Structure | Name |
| --- | --- | --- |
| 517 | 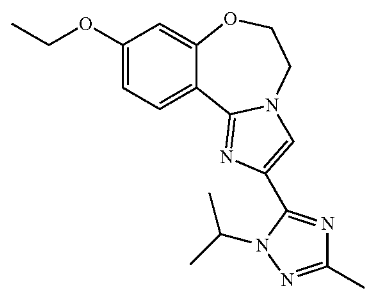 [SMILES: CCOc1ccc2c(c1)OCCn1cc(-c3nc(C)nn3C(C)C)nc1-2] | 9-ethoxy-2-(1-isopropyl-3-methyl-1H-1,2,4-triazol-5-yl)-5,6-dihydrobenzo[f]imidazo[1,2-d][1,4]oxazepine |
| 518 | 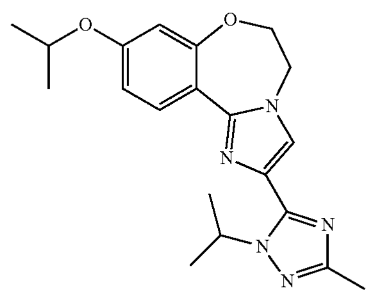 [SMILES: Cc1nc(-c2cn3c(n2)-c2ccc(OC(C)C)cc2OCC3)n(C(C)C)n1] | 9-isopropoxy-2-(1-isopropyl-3-methyl-1H-1,2,4-triazol-5-yl)-5,6-dihydrobenzo[f]imidazo[1,2-d][1,4]oxazepine |
| 519 | 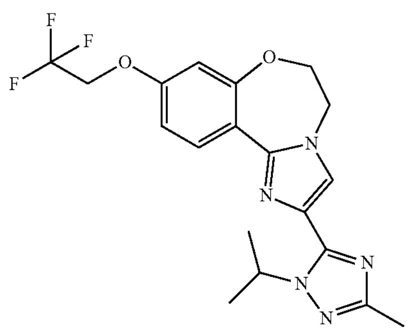 [SMILES: Cc1nc(-c2cn3c(n2)-c2ccc(OCC(F)(F)F)cc2OCC3)n(C(C)C)n1] | 2-(1-isopropyl-3-methyl-1H-1,2,4-triazol-5-yl)-9-(2,2,2-trifluoroethoxy)-5,6-dihydrobenzo[f]imidazo[1,2-d][1,4]oxazepine |
| 520 | 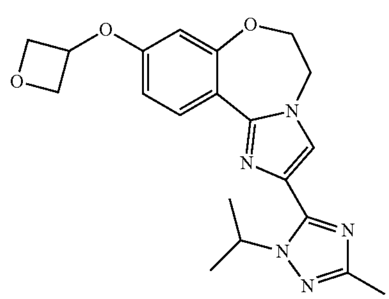 [SMILES: Cc1nc(-c2cn3c(n2)-c2ccc(OC4COC4)cc2OCC3)n(C(C)C)n1] | 2-(1-isopropyl-3-methyl-1H-1,2,4-triazol-5-yl)-9-(oxetan-3-yloxy)-5,6-dihydrobenzo[f]imidazo[1,2-d][1,4]oxazepine |
| 521 | 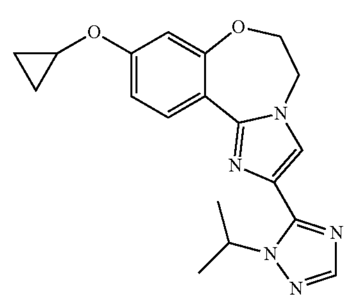 [SMILES: CC(C)n1ncnc1-c1cn2c(n1)-c1ccc(OC3CC3)cc1OCC2] | 9-cyclopropoxy-2-(1-isopropyl-1H-1,2,4-triazol-5-yl)-5,6-dihydrobenzo[f]imidazo[1,2-d][1,4]oxazepine |

TABLE 2-continued

| No. | Structure | Name |
|---|---|---|
| 522 | 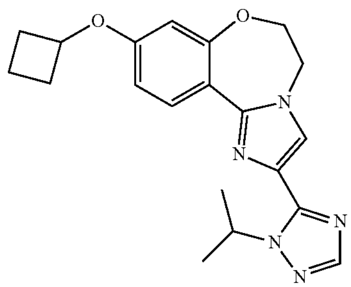 [SMILES: CC(C)n1ncnc1-c1cn2c(n1)-c1ccc(OC3CCC3)cc1OCC2] | 9-cyclobutyloxy-2-(1-isopropyl-1H-1,2,4-triazol-5-yl)-5,6-dihydrobenzo[f]imidazo[1,2-d][1,4]oxazepine |
| 523 | 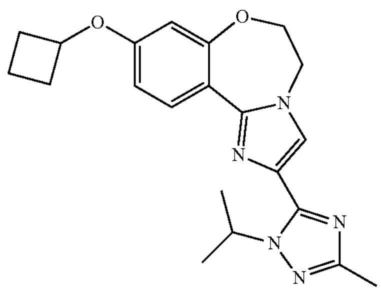 [SMILES: Cc1nc(-c2cn3c(n2)-c2ccc(OC4CCC4)cc2OCC3)n(C(C)C)n1] | 9-cyclobutoxy-2-(1-isopropyl-3-methyl-1H-1,2,4-triazol-5-yl)-5,6-dihydrobenzo[f]imidazo[1,2-d][1,4]oxazepine |
| 524 | 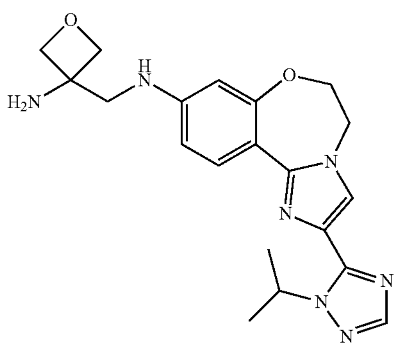 [SMILES: CC(C)n1ncnc1-c1cn2c(n1)-c1ccc(NCC3(N)COC3)cc1OCC2] | N-((3-aminooxetan-3-yl)methyl)-2-(1-isopropyl-1H-1,2,4-triazol-5-yl)-5,6-dihydrobenzo[f]imidazo[1,2-d][1,4]oxazepin-9-amine |
| 525 | 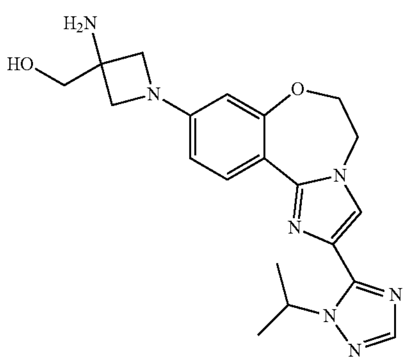 [SMILES: CC(C)n1ncnc1-c1cn2c(n1)-c1ccc(N3CC(N)(CO)C3)cc1OCC2] | (3-amino-1-(2-(1-isopropyl-1H-1,2,4-triazol-5-yl)-5,6-dihydrobenzo[f]imidazo[1,2-d][1,4]oxazepin-9-yl)azetidin-3-yl)methanol |
| 526 | 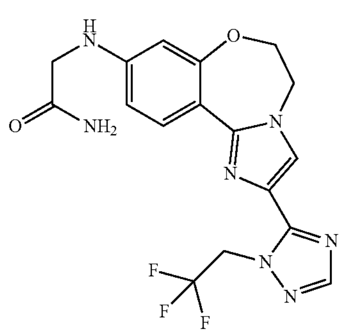 [SMILES: NC(=O)CNc1ccc2c(c1)OCCn1cc(-c3ncnn3CC(F)(F)F)nc1-2] | 2-(2-(1-(2,2,2-trifluoroethyl)-1H-1,2,4-triazol-5-yl)-5,6-dihydrobenzo[f]imidazo[1,2-d][1,4]oxazepin-9-ylamino)acetamide |

TABLE 2-continued

| No. | Structure | Name |
|---|---|---|
| 527 | 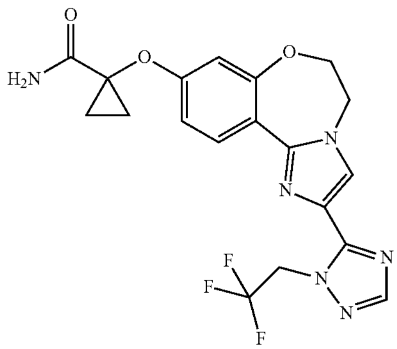 [SMILES: NC(=O)C1(Oc2ccc3c(c2)OCCn2cc(-c4ncnn4CC(F)(F)F)nc2-3)CC1] | 1-(2-(1-(2,2,2-trifluoroethyl)-1H-1,2,4-triazol-5-yl)-5,6-dihydrobenzo[f]imidazo[1,2-d][1,4]oxazepin-9-yloxy)cyclopropanecarboxamide |
| 528 | 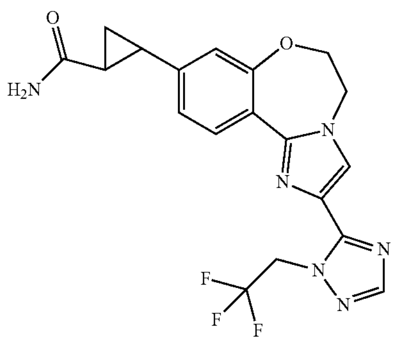 [SMILES: NC(=O)C1CC1c1ccc2c(c1)OCCn1cc(-c3ncnn3CC(F)(F)F)nc1-2] | cis-2-(2-(1-(2,2,2-trifluoroethyl)-1H-1,2,4-triazol-5-yl)-5,6-dihydrobenzo[f]imidazo[1,2-d][1,4]oxazepin-9-yl)cyclopropanecarboxamide |
| 529 | 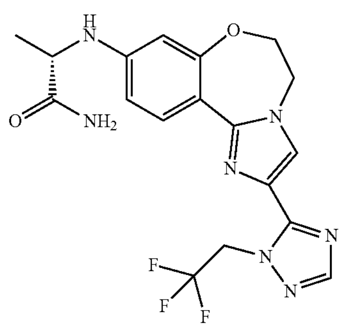 [SMILES: C[C@H](Nc1ccc2c(c1)OCCn1cc(-c3ncnn3CC(F)(F)F)nc1-2)C(N)=O] | (2S)-2-(2-(1-(2,2,2-trifluoroethyl)-1H-1,2,4-triazol-5-yl)-5,6-dihydrobenzo[f]imidazo[1,2-d][1,4]oxazepin-9-ylamino)propanamide |
| 530 | 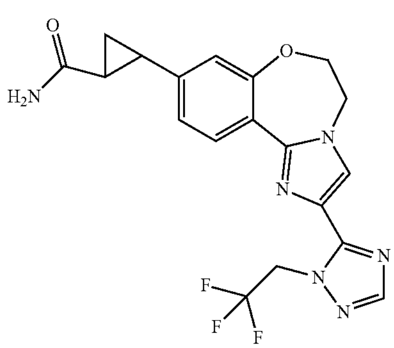 [SMILES: NC(=O)C1CC1c1ccc2c(c1)OCCn1cc(-c3ncnn3CC(F)(F)F)nc1-2] | trans-2-(2-(1-(2,2,2-trifluoroethyl)-1H-1,2,4-triazol-5-yl)-5,6-dihydrobenzo[f]imidazo[1,2-d][1,4]oxazepin-9-yl)cyclopropanecarboxamide |

TABLE 2-continued

| No. | Structure | Name |
|---|---|---|
| 531 | 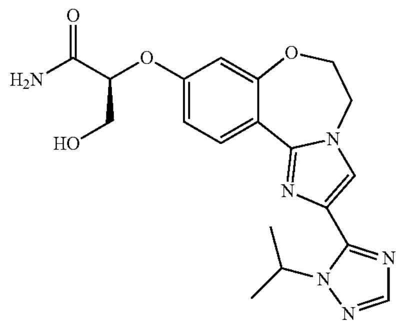 [SMILES: CC(C)n1ncnc1-c1cn2c(n1)-c1ccc(O[C@@H](CO)C(N)=O)cc1OCC2] | (2S)-3-hydroxy-2-(2-(1-isopropyl-1H-1,2,4-triazol-5-yl)-5,6-dihydrobenzo[f]imidazo[1,2-d][1,4]oxazepin-9-yloxy)propanamide |
| 532 | 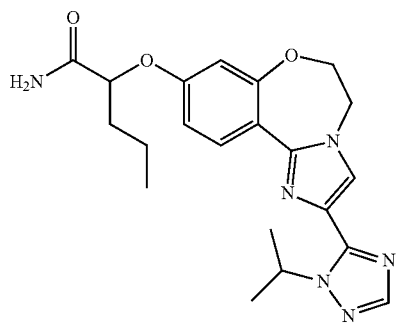 [SMILES: CCCC(Oc1ccc2c(c1)OCCn1cc(-c3ncnn3C(C)C)nc1-2)C(N)=O] | 2-(2-(1-isopropyl-1H-1,2,4-triazol-5-yl)-5,6-dihydrobenzo[f]imidazo[1,2-d][1,4]oxazepin-9-yloxy)pentanamide |
| 533 | 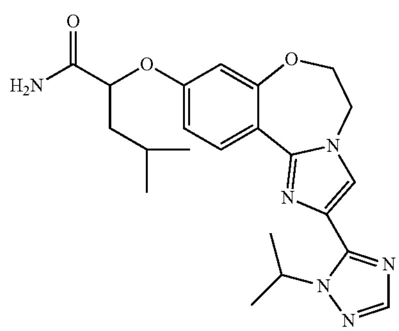 [SMILES: CC(C)CC(Oc1ccc2c(c1)OCCn1cc(-c3ncnn3C(C)C)nc1-2)C(N)=O] | 2-(2-(1-isopropyl-1H-1,2,4-triazol-5-yl)-5,6-dihydrobenzo[f]imidazo[1,2-d][1,4]oxazepin-9-yloxy)-4-methylpentanamide |

TABLE 3

| No. | Structure | Name |
|---|---|---|
| 534 | 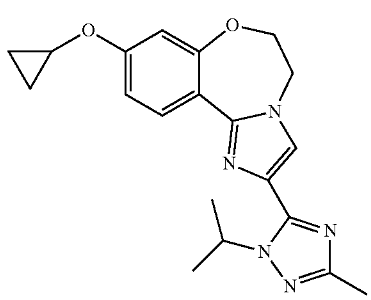 [SMILES: Cc1nc(-c2cn3c(n2)-c2ccc(OC4CC4)cc2OCC3)n(C(C)C)n1] | 9-cyclopropyl-2-(1-isopropyl-3-methyl-1H-1,2,4-triazol-5-yl)-5,6-dihydrobenzo[f]imidazo[1,2-d][1,4]oxazepine |

TABLE 3-continued

| No. | Structure | Name |
|---|---|---|
| 535 | 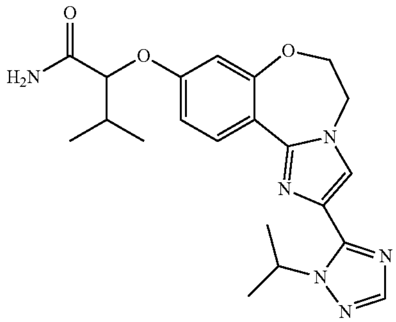 [SMILES: CC(C)C(Oc1ccc2c(c1)OCCn1cc(-c3ncnn3C(C)C)nc1-2)C(N)=O] | 2-(2-(1-isopropyl-1H-1,2,4-triazol-5-yl)-5,6-dihydrobenzo[f]imidazo[1,2-d][1,4]oxazepin-9-yloxy)-3-methylbutanamide |
| 536 | 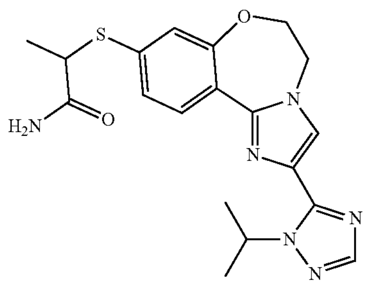 [SMILES: CC(Sc1ccc2c(c1)OCCn1cc(-c3ncnn3C(C)C)nc1-2)C(N)=O] | 2-(2-(1-isopropyl-1H-1,2,4-triazol-5-yl)-5,6-dihydrobenzo[f]imidazo[1,2-d][1,4]oxazepin-9-ylthio)propanamide |
| 537 | 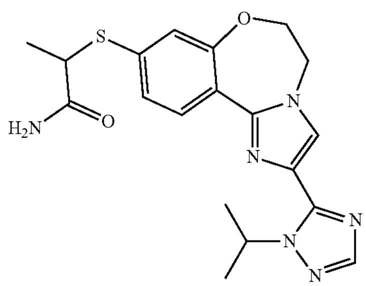 [SMILES: CC(Sc1ccc2c(c1)OCCn1cc(-c3ncnn3C(C)C)nc1-2)C(N)=O] | 2-(2-(1-isopropyl-1H-1,2,4-triazol-5-yl)-5,6-dihydrobenzo[f]imidazo[1,2-d][1,4]oxazepin-9-ylthio)propanamide |
| 538 | 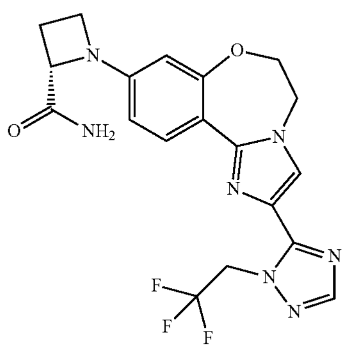 [SMILES: NC(=O)[C@@H]1CCN1c1ccc2c(c1)OCCn1cc(-c3ncnn3CC(F)(F)F)nc1-2] | (2S)-1-(2-(1-(2,2,2-trifluoroethyl)-1H-1,2,4-triazol-5-yl)-5,6-dihydrobenzo[f]imidazo[1,2-d][1,4]oxazepin-9-yl)azetidine-2-carboxamide |
| 539 | 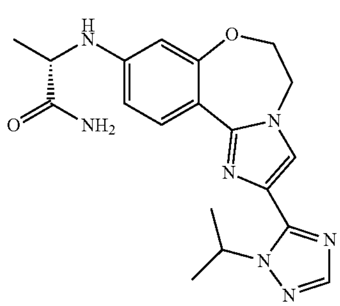 [SMILES: CC(C)n1ncnc1-c1cn2c(n1)-c1ccc(N[C@@H](C)C(N)=O)cc1OCC2] | (2S)-2-(2-(1-isopropyl-1H-1,2,4-triazol-5-yl)-5,6-dihydrobenzo[f]imidazo[1,2-d][1,4]oxazepin-9-ylamino)propanamide |

TABLE 3-continued

| No. | Structure | Name |
|---|---|---|
| 540 | 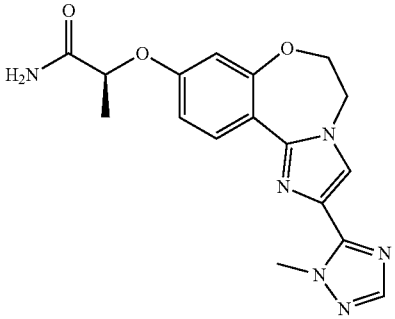 [SMILES: C[C@H](Oc1ccc2c(c1)OCCn1cc(-c3ncnn3C)nc1-2)C(N)=O] | (2S)-2-(2-(1-methyl-1H-1,2,4-triazol-5-yl)-5,6-dihydrobenzo[f]imidazo[1,2-d][1,4]oxazepin-9-yloxy)propanamide |
| 541 | 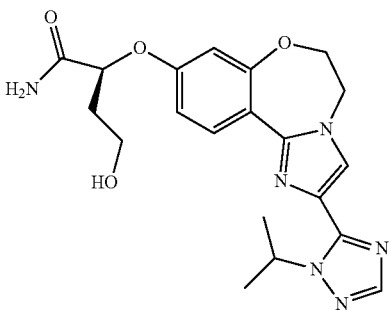 [SMILES: CC(C)n1ncnc1-c1cn2c(n1)-c1ccc(O[C@@H](CCO)C(N)=O)cc1OCC2] | (2S)-4-hydroxy-2-(2-(1-isopropyl-1H-1,2,4-triazol-5-yl)-5,6-dihydrobenzo[f]imidazo[1,2-d][1,4]oxazepin-9-yloxy)butanamide |
| 542 | 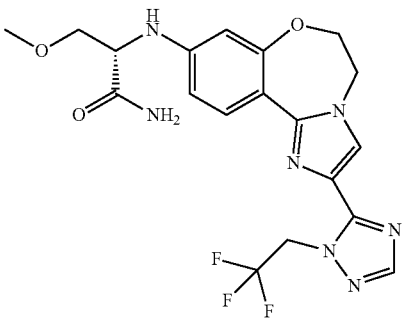 [SMILES: COC[C@H](Nc1ccc2c(c1)OCCn1cc(-c3ncnn3CC(F)(F)F)nc1-2)C(N)=O] | (2S)-3-methoxy-2-(2-(1-(2,2,2-trifluoroethyl)-1H-1,2,4-triazol-5-yl)-5,6-dihydrobenzo[f]imidazo[1,2-d][1,4]oxazepin-9-ylamino)propanamide |
| 543 | 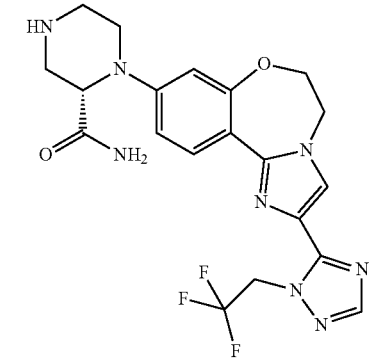 [SMILES: NC(=O)[C@@H]1CNCCN1c1ccc2c(c1)OCCn1cc(-c3ncnn3CC(F)(F)F)nc1-2] | (2S)-1-(2-(1-(2,2,2-trifluoroethyl)-1H-1,2,4-triazol-5-yl)-5,6-dihydrobenzo[f]imidazo[1,2-d][1,4]oxazepin-9-yl)piperazine-2-carboxamide |

TABLE 3-continued

| No. | Structure | Name |
| --- | --- | --- |
| 544 | 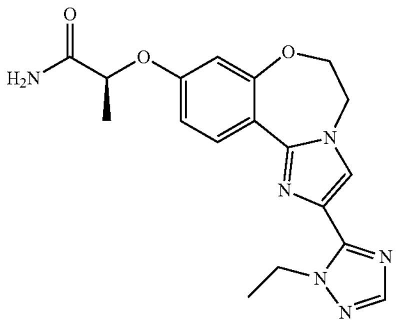 [SMILES: CCn1ncnc1-c1cn2c(n1)-c1ccc(O[C@@H](C)C(N)=O)cc1OCC2] | (1S)-2-(2-(1-ethyl-1H-1,2,4-triazol-5-yl)-5,6-dihydrobenzo[f]imidazo[1,2-d][1,4]oxazepin-9-yloxy)propanamide |
| 545 | 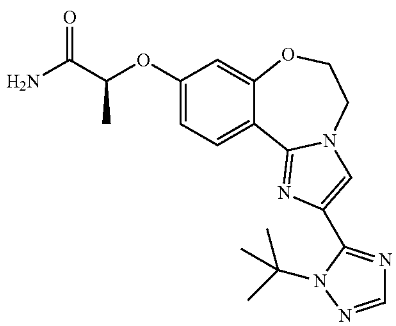 [SMILES: C[C@H](Oc1ccc2c(c1)OCCn1cc(-c3ncnn3C(C)(C)C)nc1-2)C(N)=O] | (2S)-2-(2-(1-tert-butyl-1H-1,2,4-triazol-5-yl)-5,6-dihydrobenzo[f]imidazo[1,2-d][1,4]oxazepin-9-yloxy)propanamide |
| 546 | 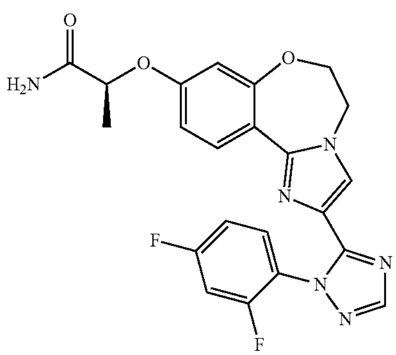 [SMILES: C[C@H](Oc1ccc2c(c1)OCCn1cc(-c3ncnn3-c3ccc(F)cc3F)nc1-2)C(N)=O] | (2S)-2-(2-(1-(2,4-difluorophenyl)-1H-1,2,4-triazol-5-yl)-5,6-dihydrobenzo[f]imidazo[1,2-d][1,4]opxazepin-9-yloxy)propanamide |
| 547 | 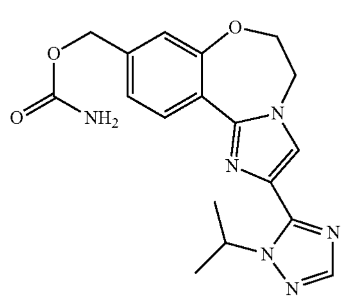 [SMILES: CC(C)n1ncnc1-c1cn2c(n1)-c1ccc(COC(N)=O)cc1OCC2] | (2-(1-isopropyl-1H-1,2,4-triazol-5-yl)-5,6-dihydrobenzo[f]imidazo[1,2-d][1,4]oxazepin-9-yl)methyl carbamate |

TABLE 3-continued

| No. | Structure | Name |
|---|---|---|
| 548 | 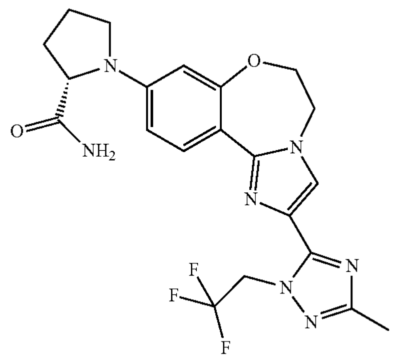 [SMILES: Cc1nc(-c2cn3c(n2)-c2ccc(N4CCC[C@H]4C(N)=O)cc2OCC3)n(CC(F)(F)F)n1] | (2S)-1-(2-(3-methyl-1-(2,2,2-trifluoroethyl)-1H-1,2,4-triazol-5-yl)-5,6-dihydrobenzo[f]imidazo[1,2-d][1,4]oxazepin-9-yl)pyrrolidine-2-carboxamide |
| 549 | 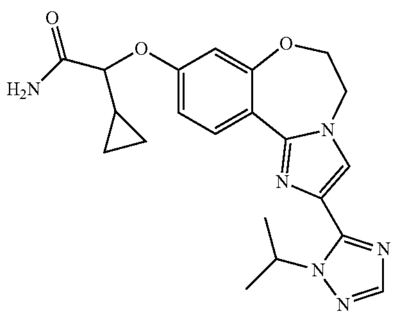 [SMILES: CC(C)n1ncnc1-c1cn2c(n1)-c1ccc(OC(C(N)=O)C3CC3)cc1OCC2] | 2-cyclopropyl-2-(2-(1-isopropyl-1H-1,2,4-triazol-5-yl)-5,6-dihydrobenzo[f]imidazo[1,2-d][1,4]oxazepin-9-yloxy)acetamide |
| 550 | 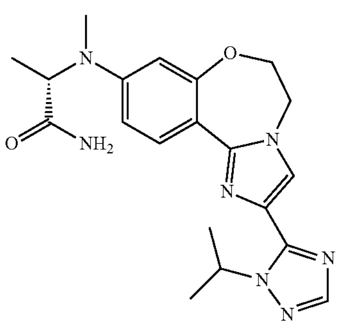 [SMILES: CC(C)n1ncnc1-c1cn2c(n1)-c1ccc(N(C)[C@@H](C)C(N)=O)cc1OCC2] | (2S)-2-((2-(1-isopropyl-1H-1,2,4-triazol-5-yl)-5,6-dihydrobenzo[f]imidazo[1,2-d][1,4]oxazepin-9-yl)(methyl)amino)propanamide |
| 551 | 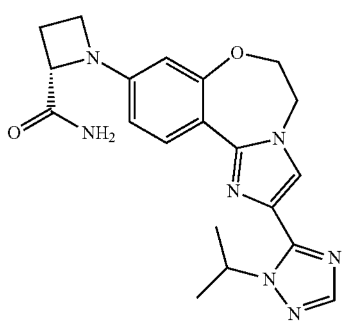 [SMILES: CC(C)n1ncnc1-c1cn2c(n1)-c1ccc(N3CC[C@H]3C(N)=O)cc1OCC2] | (2S)-1-(2-(1-isopropyl-1H-1,2,4-triazol-5-yl)-5,6-dihydrobenzo[f]imidazo[1,2-d][1,4]oxazepin-9-yl)azetidine-2-carboxamide |
| 552 | 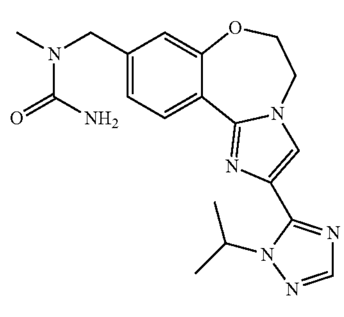 [SMILES: CC(C)n1ncnc1-c1cn2c(n1)-c1ccc(CN(C)C(N)=O)cc1OCC2] | 1-((2-(1-isopropyl-1H-1,2,4-triazol-5-yl)-5,6-dihydrobenzo[f]imidazo[1,2-d][1,4]oxazepin-9-yl)methyl)-1-methylurea |

TABLE 3-continued

| No. | Structure | Name |
|---|---|---|
| 553 | 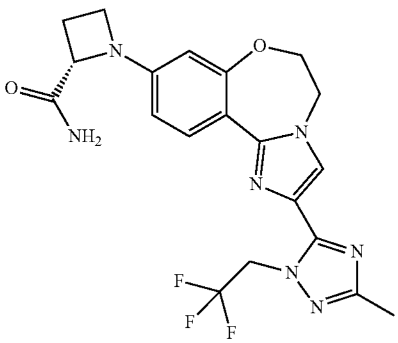 [SMILES: Cc1nc(-c2cn3c(n2)-c2ccc(N4CC[C@H]4C(N)=O)cc2OCC3)n(CC(F)(F)F)n1] | (2S)-1-(2-(3-methyl-1-(2,2,2-trifluoroethyl)-1H-1,2,4-triazol-5-yl)-5,6-dihydrobenzo[f]imidazo[1,2-d][1,4]oxazepin-9-yl)azetidine-2-carboxamide |
| 554 | 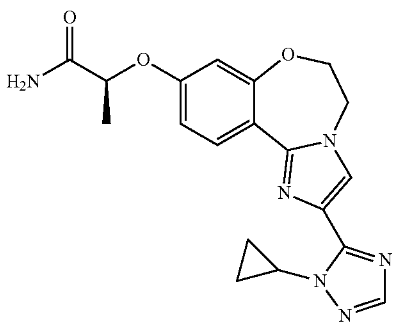 [SMILES: C[C@H](Oc1ccc2c(c1)OCCn1cc(-c3ncnn3C3CC3)nc1-2)C(N)=O] | (2S)-2-(2-(1-cyclopropyl-1H-1,2,4-triazol-5-yl)-5,6-dihydrobenzo[f]imidazo[1,2-d][1,4]oxazepin-9-yloxy)propanamide |
| 555 | 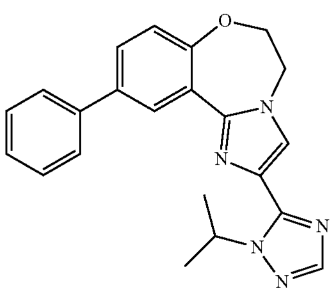 [SMILES: CC(C)n1ncnc1-c1cn2c(n1)-c1cc(-c3ccccc3)ccc1OCC2] | 2-(1-isopropyl-1H-1,2,4-triazol-5-yl)-10-phenyl-5,6-dihydrobenzo[f]imidazo[1,2-d][1,4]oxazepine |
| 556 | 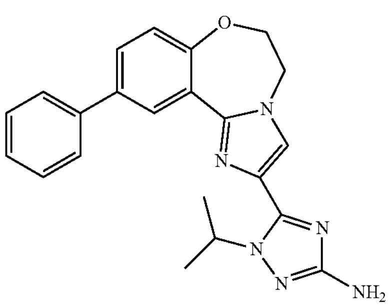 [SMILES: CC(C)n1nc(N)nc1-c1cn2c(n1)-c1cc(-c3ccccc3)ccc1OCC2] | 1-isopropyl-5-(10-phenyl-5,6-dihydrobenzo[f]imidazo[1,2-d][1,4]oxazepin-2-yl)-1H-1,2,4-triazol-3-amine |
| 557 | 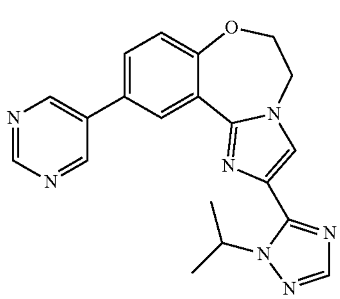 [SMILES: CC(C)n1ncnc1-c1cn2c(n1)-c1cc(-c3cncnc3)ccc1OCC2] | 2-(1-isopropyl-1H-1,2,4-triazol-5-yl)-10-(pyrimidin-5-yl)-5,6-dihydrobenzo[f]imidazo[1,2-d][1,4]oxazepine |

TABLE 3-continued

| No. | Structure | Name |
|---|---|---|
| 558 | 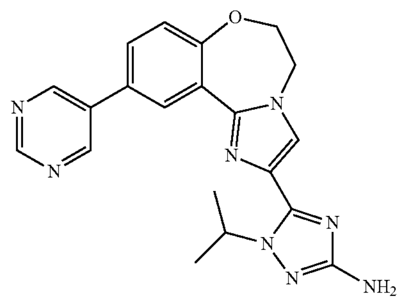 [SMILES: CC(C)n1nc(N)nc1-c1cn2c(n1)-c1cc(-c3cncnc3)ccc1OCC2] | 1-isopropyl-5-(10-(pyrimidin-5-yl)-5,6-dihydrobenzo[f]imidazo[1,2-d][1,4]oxazepin-2-yl)-1H-1,2,4-triazol-3-amine |
| 559 | 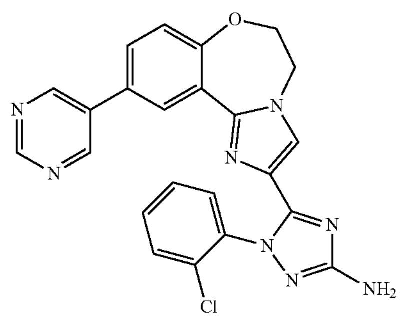 [SMILES: Nc1nc(-c2cn3c(n2)-c2cc(-c4cncnc4)ccc2OCC3)n(-c2ccccc2Cl)n1] | 1-(2-chlorophenyl)-5-(10-(pyrimidin-5-yl)-5,6-dihydrobenzo[f]imidazo[1,2-d][1,4]oxazepin-2-yl)-1H-1,2,4-triazol-3-amine |
| 560 | 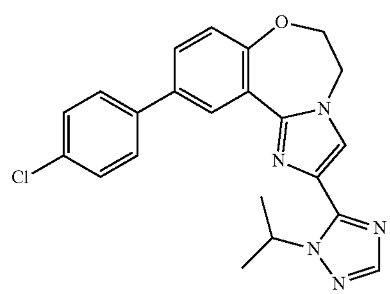 [SMILES: CC(C)n1ncnc1-c1cn2c(n1)-c1cc(-c3ccc(Cl)cc3)ccc1OCC2] | 10-(4-chlorophenyl)-2-(1-isopropyl-1H-1,2,4-triazol-5-yl)-5,6-dihydrobenzo[f]imidazo[1,2-d][1,4]oxazepine |
| 561 | 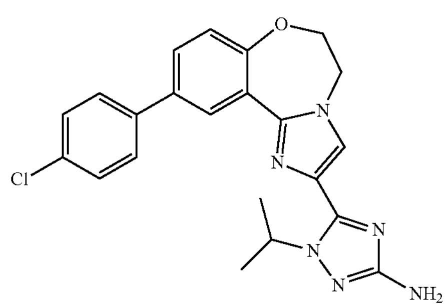 [SMILES: CC(C)n1nc(N)nc1-c1cn2c(n1)-c1cc(-c3ccc(Cl)cc3)ccc1OCC2] | 5-(10-(4-chlorophenyl)-5,6-dihydrobenzo[f]imidazo[1,2-d][1,4]oxazepin-2-yl)-1-isopropyl-1H-1,2,4-triazol-3-amine |
| 562 | 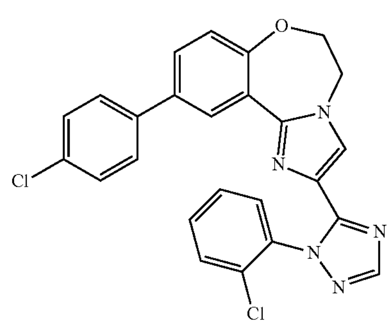 [SMILES: Clc1ccc(-c2ccc3c(c2)-c2nc(-c4ncnn4-c4ccccc4Cl)cn2CCO3)cc1] | 10-(4-chlorophenyl)-2-(1-(2-chlorophenyl)-1H-1,2,4-triazol-5-yl)-5,6-dihydrobenzo[f]imidazo[1,2-d][1,4]oxazepine |

TABLE 3-continued
| No. | Structure | Name |
| --- | --- | --- |
| 563 | 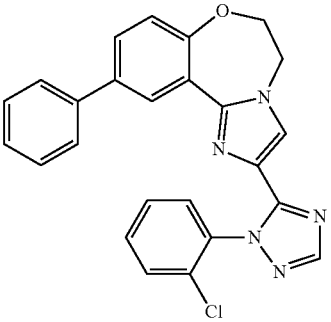 [SMILES: Clc1ccccc1-n1ncnc1-c1cn2c(n1)-c1cc(-c3ccccc3)ccc1OCC2] | 2-(1-(2-chlorophenyl)-1H-1,2,4-triazol-5-yl)-10-phenyl-5,6-dihydrobenzo[f]imidazo[1,2-d][1,4]oxazepine |
| 564 | 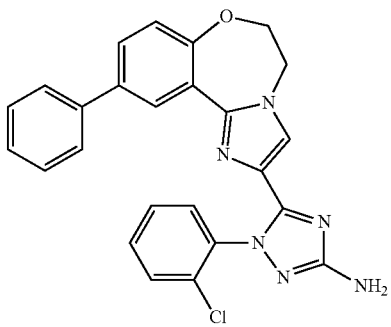 [SMILES: Nc1nc(-c2cn3c(n2)-c2cc(-c4ccccc4)ccc2OCC3)n(-c2ccccc2Cl)n1] | 1-(2-chlorophenyl)-5-(10-phenyl-45,6-dihydrobenzo[f]imidazo[1,2-d][1,4]oxazepin-2-yl)-1H-1,2,4-triazol-3-amine |
| 565 | 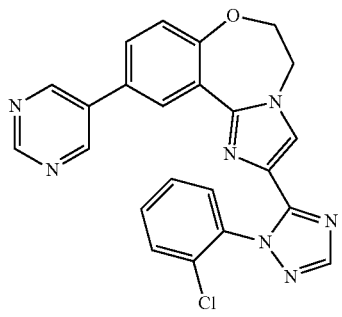 [SMILES: Clc1ccccc1-n1ncnc1-c1cn2c(n1)-c1cc(-c3cncnc3)ccc1OCC2] | 2-(1-(2-chlorophenyl)-1H-1,2,4-triazol-5-yl)-10-(pyrimidin-5-yl)-5,6-dihydrobenzo[f]imidazo[1,2-d][1,4]oxazepine |
| 566 | 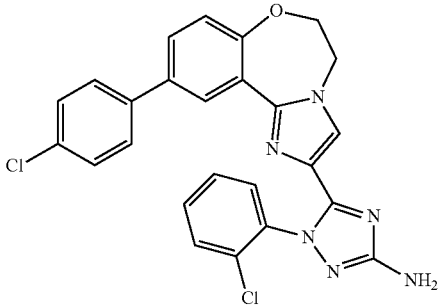 [SMILES: Nc1nc(-c2cn3c(n2)-c2cc(-c4ccc(Cl)cc4)ccc2OCC3)n(-c2ccccc2Cl)n1] | 1-(2-chlorophenyl)-5-(10-(4-chlorophenyl)-5,6-dihydrobenzo[f]imidazo[1,2-d][1,4]oxazepin-2-yl)-1H-1,2,4-triazol-3-amine |

TABLE 3-continued

| No. | Structure | Name |
|---|---|---|
| 567 | 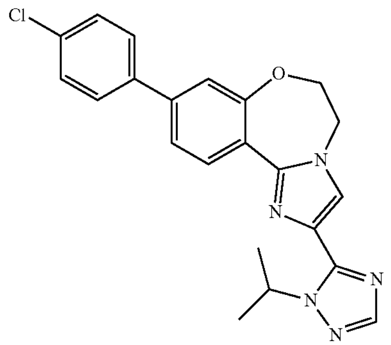 [SMILES: CC(C)n1ncnc1-c1cn2c(n1)-c1ccc(-c3ccc(Cl)cc3)cc1OCC2] | 9-(4-chlorophenyl)-2-(1-isopropyl-1H-1,2,4-triazol-5-yl)-5,6-dihydrobenzo[f]imidazo[1,2-d][1,4]oxazepine |
| 568 | 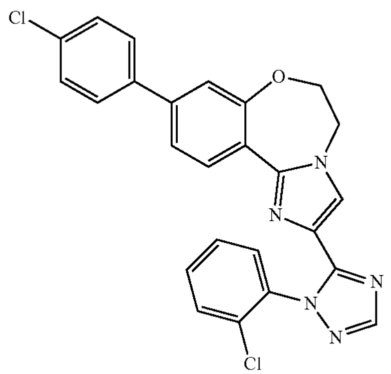 [SMILES: Clc1ccc(-c2ccc3c(c2)OCCn2cc(-c4ncnn4-c4ccccc4Cl)nc2-3)cc1] | 9-(4-chlorophenyl)-2-(1-(2-chlorophenyl)-1H-1,2,4-triazol-5-yl)-5,6-dihydrobenzo[f]imidazo[1,2-d][1,4]oxazepine |
| 569 | 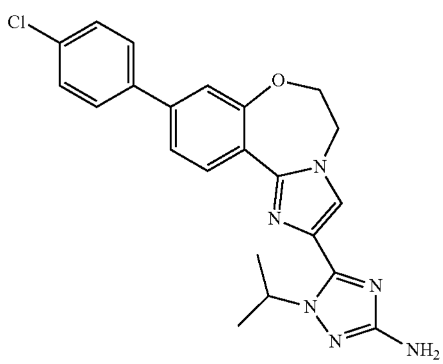 [SMILES: CC(C)n1nc(N)nc1-c1cn2c(n1)-c1ccc(-c3ccc(Cl)cc3)cc1OCC2] | 5-(9-(4-chlorophenyl)-5,6-dihydrobenzo[f]imidazo[1,2-d][1,4]oxazepin-2-yl)-1-isopropyl-1H-1,2,4-triazol-3-amine |
| 570 | 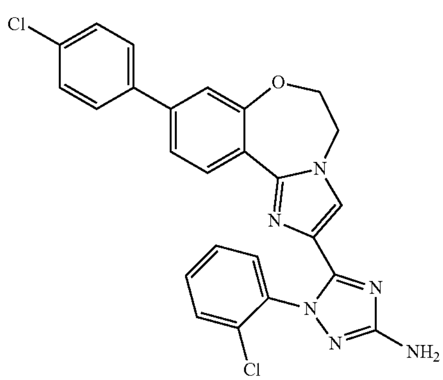 [SMILES: Nc1nc(-c2cn3c(n2)-c2ccc(-c4ccc(Cl)cc4)cc2OCC3)n(-c2ccccc2Cl)n1] | 1-(2-chlorophenyl)-5-(9-(4-chlorophenyl)-5,6-dihydrobenzo[f]imidazo[1,2-d][1,4]oxazepin-2-yl)-1H-1,2,4-triazol-3-amine |

Administration of Formula I Compounds

The Formula I compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with e.g. the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I Compounds

Formula I compounds of the present invention are useful for treating hyperproliferative diseases, conditions and/or disorders including, but not limited to, those characterized by over expression of lipid kinases, e.g. PI3 kinase. Accordingly, an aspect of this invention includes methods of treating or preventing diseases or conditions that can be treated or prevented by inhibiting lipid kinases, including PI3. In one embodiment, the method comprises administering to a mammal in need thereof a therapeutically effective amount of a compound of Formula I, or a stereoisomer, geometric isomer, tautomer, or pharmaceutically acceptable salt thereof. In one embodiment, a human patient is treated with a compound of Formula I and a pharmaceutically acceptable carrier, adjuvant, or vehicle, wherein said compound of Formula I is present in an amount to detectably inhibit PI3 kinase activity.

Formula I compounds may also be useful for treating hyperproliferative diseases characterized by over expression of protein kinases such as those encoded by PIM; the genes Pim-1, Pim-2, and Pim-3 (Proviral Insertion, Moloney) which are implicated in lymphoma and solid-tumor development (Cuypers et al. (1984) Cell, vol. 37 (1) pp. 141-50; Selten et al. (1985) EMBO J. vol. 4 (7) pp. 1793-8; van der Lugt et al. (1995) EMBO J. vol. 14 (11) pp. 2536-44; Mikkers et al. (2002) Nature Genetics, vol. 32 (1) pp. 153-9; van Lohuizen et al. (1991) Cell, vol. 65 (5) pp. 737-52.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Formula I compounds may be useful for in vitro, in situ, and in vivo diagnosis or treatment of mammalian cells, organisms, or associated pathological conditions, such as systemic and local inflammation, immune-inflammatory diseases such as rheumatoid arthritis, immune suppression, organ transplant rejection, allergies, ulcerative colitis, Crohn's disease, dermatitis, asthma, systemic lupus erythematosus, Sjögren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD), psoriasis, and for general joint protective effects.

Formula I compounds may be useful for treating conditions of the brain and central nervous system which require transport across the blood-brain barrier. Certain Formula I compounds have favorable penetrant properties for delivery to the brain. Disorders of the brain which may be effectively treated with Formula I compounds include metastatic and primary brain tumors, such as glioblastoma and melanoma.

Formula I compounds may be useful for treating ocular disorders such as wet and dry Age-related Macular Degeneration (AMD) and retina edema, by localized delivery to the eye. Certain Formula I compounds have favorable properties for delivery to, and uptake into, the eye. Certain Formula I compounds may enhance efficacy and extend duration of response for treatment of wet AMD in combination with ranibizumab (LUCENTIS®, Genentech, Inc.) and bevacizumab (AVASTIN®, Genentech, Inc.).

Another aspect of this invention provides a compound of this invention for use in the treatment of the diseases or conditions described herein in a mammal, e.g., a human, suffering from such disease or condition. Also provided is the use of a compound of this invention in the preparation of a medicament for the treatment of the diseases and conditions described herein in a warm-blooded animal, such as a mammal, e.g. a human, suffering from such disorder.

Pharmaceutical Formulations

In order to use a Formula I compound for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a Formula I compound and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the Formula I compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound of this invention for use herein is preferably sterile. In particular, formulations to be used for in vivo administration must be sterile. Such sterilization is readily accomplished by filtration through sterile filtration membranes.

The compound ordinarily can be stored as a solid composition, a lyophilized formulation or as an aqueous solution.

The pharmaceutical compositions of the invention comprising a Formula I compound will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the Formula I compound administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, e.g., by coacervation techniques or by interfacial polymerization, e.g., hydroxymethylcellulose or gelatin-microcapsules and poly-(methylmethacylate) microcapsules, respectively, in colloidal drug delivery systems (e.g., liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of Formula I compounds may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (e.g., poly(2-hydroxyethylmethacrylate), or poly(vinyl alcohol)), polylactides (U.S. Pat. No. 3,773,919), copolymers of L-glutamic acid and gamma-ethyl-1-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, e.g., inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations may be applied as a topical ointment or cream containing the active ingredient(s) in an amount of, e.g., 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, about 0.5 to 10% w/w, or about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising e.g. cocoa butter or a salicylate.

Formulations suitable for intrapulmonary or nasal administration have a particle size e.g. in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, e.g. sealed ampoules and vials, and may be stored in a freeze-dried (lyophilized) condition requiring only the addition of the sterile liquid carrier, e.g. water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with other therapeutic agents for the treatment of a disease or disorder described herein, such as a hyperproliferative disorder (e.g., cancer). In certain embodiments, a compound of Formula I is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, in combination with a chemotherapeutic agent such as described herein.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of anti-cancer therapy, a compound of Formula I, or a stereoisomer, geometric isomer, tautomer, solvate, metabolite, or pharmaceutically acceptable salt or prodrug thereof, may be combined with other chemotherapeutic, hormonal or antibody agents such as those described herein, as well as combined with surgical therapy and radiotherapy. Combination therapies according to the present invention thus comprise the administration of at least one compound of Formula I, or a stereoisomer, geometric isomer, tautomer, solvate, metabolite, or pharmaceutically acceptable salt or prodrug thereof, and the use of at least one other cancer treatment method. The amounts of the compound(s) of Formula I and the other pharmaceutically active chemotherapeutic agent(s) and the relative timings of administration will be selected in order to achieve the desired combined therapeutic effect.

Metabolites of Formula I Compounds

Also falling within the scope of this invention are the in vivo metabolic products of Formula I described herein. Such products may result e.g. from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., 14C or 3H) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, may be useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. The kit comprises a container comprising a compound of Formula I. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, e.g., bottles, vials, syringes, blister pack, etc. The container may be formed from a variety of materials such as glass or plastic. The container may hold a compound of Formula I or II or a formulation thereof which is effective for treating the condition and may have a sterile access port (e.g., the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I, and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I or II, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, e.g. in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula I Compounds

Benzoxazepin compounds of Formula I may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-23, Wiley, N.Y. (1967-2006 ed.), or Beilsteins Handbuch der organischen Chemie, 4, Aufl. ed. Springer-Verlag, Berlin, including supplements (also available via the Beilstein online database).

In certain embodiments, compounds of Formula I may be readily prepared using well-known procedures to prepare benzoxepin compounds (Sekhar et al (1989) Sulfur Letters 9(6):271-277; Katsura et al (2000 J. Med. Chem. 43:3315-3321; Rueeger et al (2004) Biorganic & Med. Chem. Letters 14:2451-2457; Reiter et al (2007) Biorganic & Med. Chem. Letters 17:5447-5454; Banaszak et al (2006) Tetrahedron Letters 47:6235-6238;) and other heterocycles, which are described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990).

Compounds of Formula I may be prepared singly or as compound libraries comprising at least 2, e.g. 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

For illustrative purposes, the General Procedures show general methods which may be applied for preparation of Formula I compounds, as well as key intermediates. The Figures and Examples sections contain more detailed description of individual reaction steps. Those skilled in the art will appreciate that other synthetic routes may be used to synthesize the inventive compounds. Although certain starting materials and routes are depicted in the Schemes, General Procedures and Examples, other similar starting materials and routes can be substituted to provide a variety of derivatives and/or reaction conditions. In addition, many of the compounds prepared by the methods described below can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, Third Ed., 1999.

Methods of Separation

In the methods of preparing the compounds of this invention, it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, e.g.: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the 1H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

GENERAL PREPARATIVE PROCEDURES

FIGS. 1-20 show general methods for preparation of Formula I benzoxazepin compounds and intermediates.

FIG. 1 shows a general exemplary route to benzoxepin compounds 3

Figure 2:
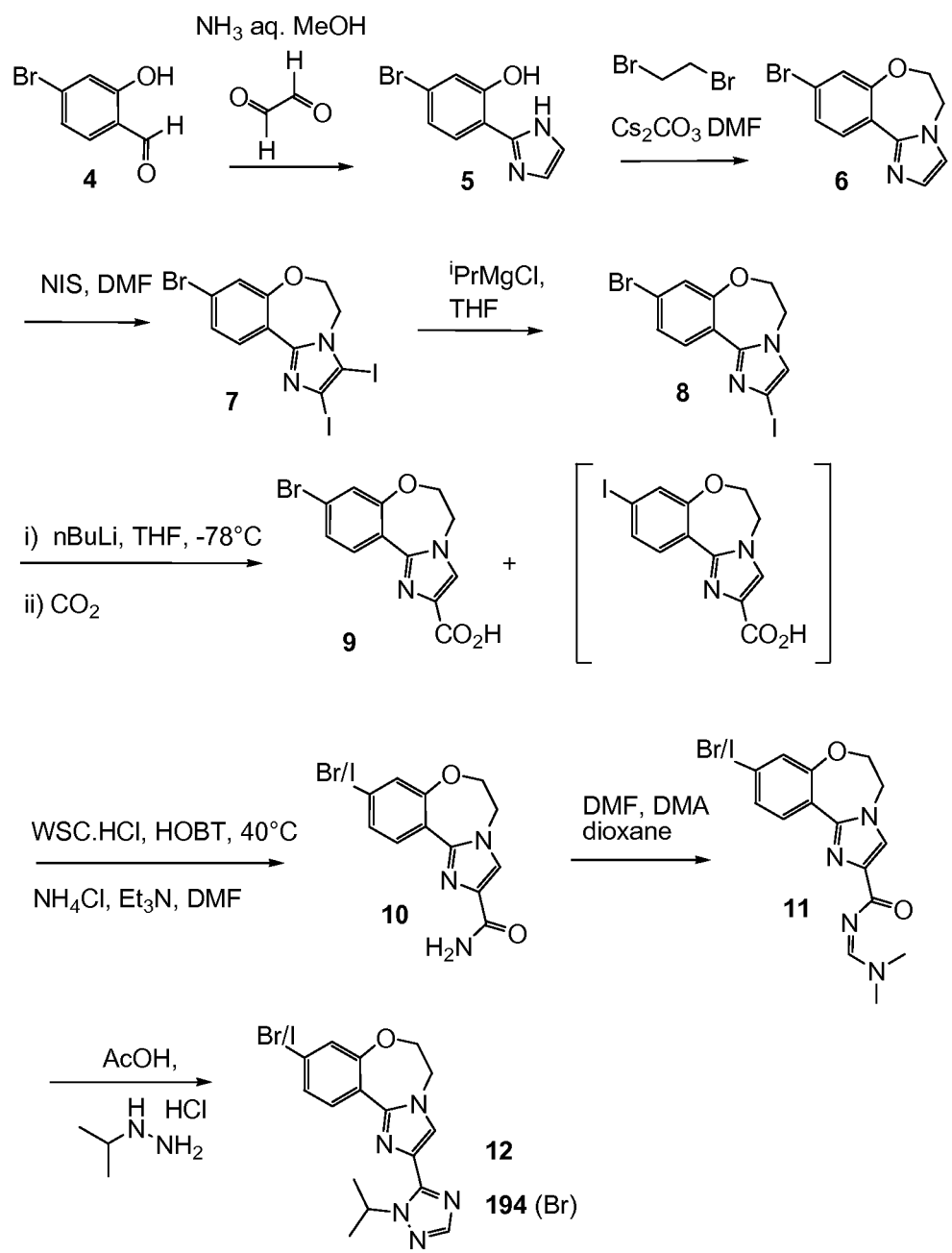
FIG. 2 shows a synthetic route to 9-halo-2-(1-isopropyl-1H-1,2,4-triazol-5-yl)-5,6-dihydrobenzo[f]imidazo[1,2-d][1,4]oxazepine compounds 12 from 4-bromo-2-hydroxybenzaldehyde 4.

FIG. 2 shows a synthetic route to 9-halo-2-(1-isopropyl-1H-1,2,4-triazol-5-yl)-5,6-dihydrobenzo[f]imidazo[1,2-d][1,4]oxazepine compounds 12 from 4-bromo-2-hydroxybenzaldehyde 4.

Figure 3:
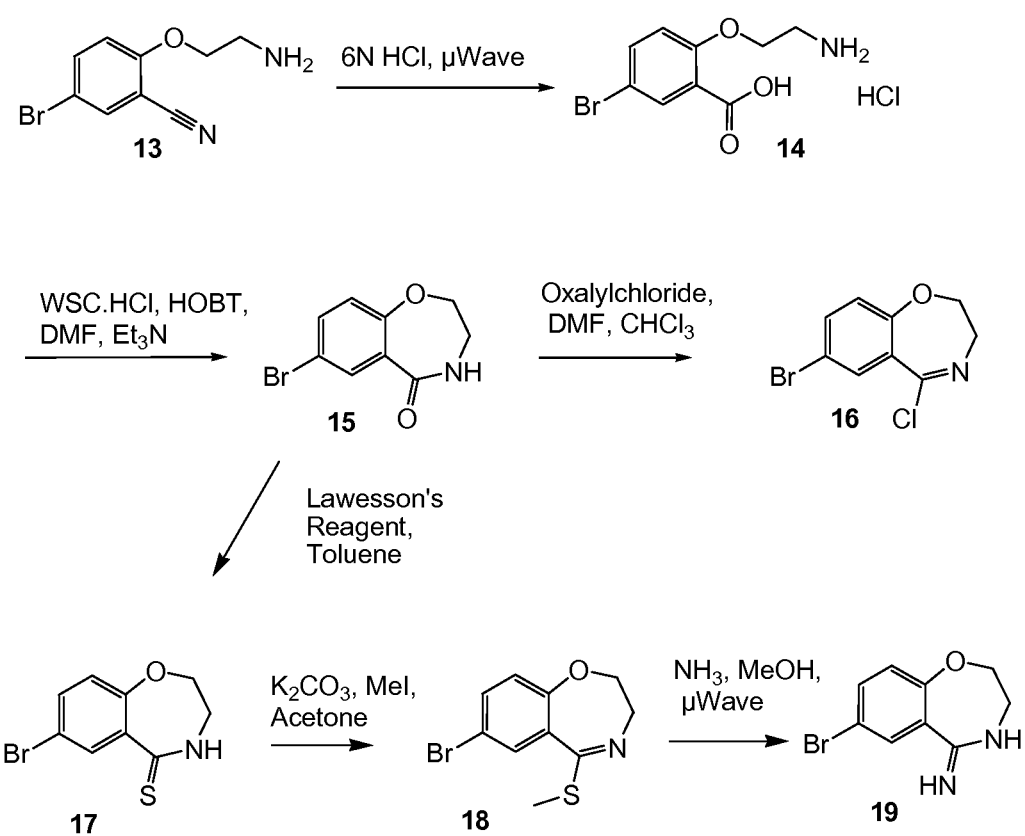
FIG. 3 shows a synthetic route to 7-bromo-5-chloro-2,3-dihydrobenzo[f][1,4]oxazepine 16 and 7-bromo-3,4-dihydrobenzo[f][1,4]oxazepin-5(2H)-imine 19

FIG. 3 shows a synthetic route to 7-bromo-5-chloro-2,3-dihydrobenzo[f][1,4]oxazepine 16 and 7-bromo-3,4-dihydrobenzo[f][1,4]oxazepin-5(2H)-imine 19

Figure 4:
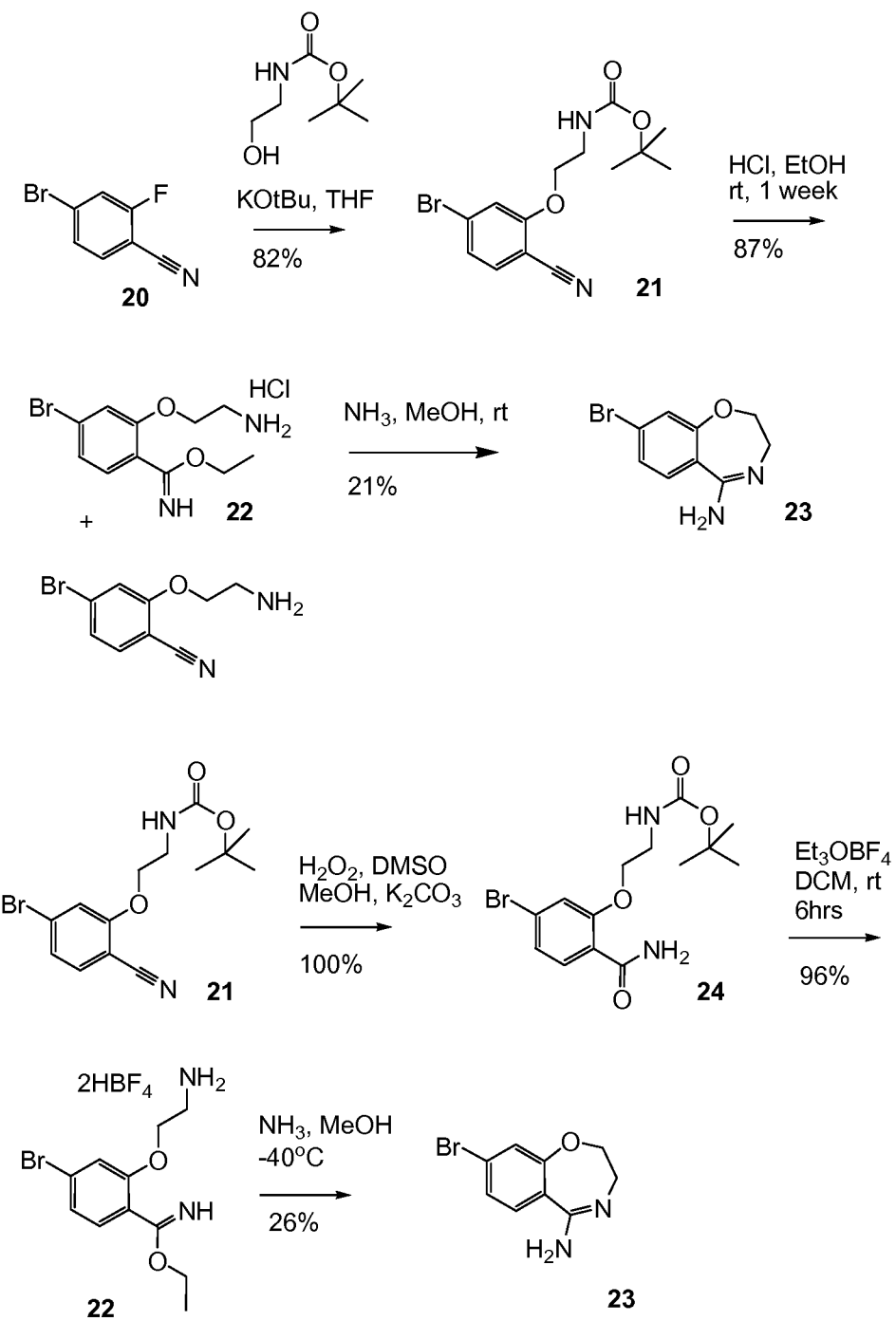
FIG. 4 shows synthetic routes to (E)-8-bromo-2,3-dihydrobenzo[f][1,4]oxazepin-5-amine 23

FIG. 4 shows synthetic routes to (E)-8-bromo-2,3-dihydrobenzo[f][1,4]oxazepin-5-amine 23

Figure 5:
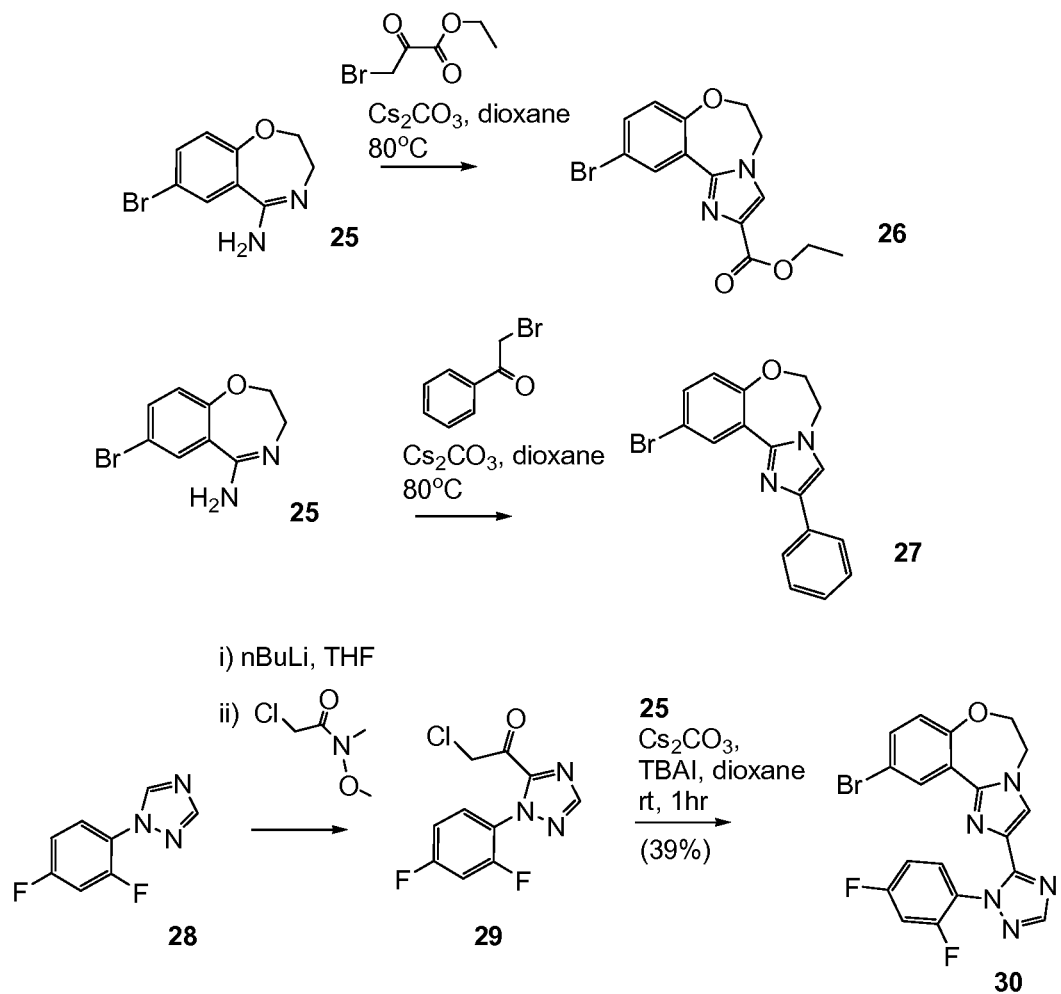
FIG. 5 shows synthetic routes to 10-bromo-2-phenyl-5,6-dihydrobenzo[f]imidazo[1,2-d][1,4]oxazepine 27 and 10-bromo-2-(1-(2,4-difluorophenyl)-1H-1,2,4-triazol-5-yl)-5,6-dihydrobenzo[f]imidazo[1,2-d][1,4]oxazepine 30

FIG. 5 shows synthetic routes to 10-bromo-2-phenyl-5,6-dihydrobenzo[f]imidazo[1,2-d][1,4]oxazepine 27 and 10-bromo-2-(1-(2,4-difluorophenyl)-1H-1,2,4-triazol-5-yl)-5,6-dihydrobenzo[f]imidazo[1,2-d][1,4]oxazepine 30

Figure 6:
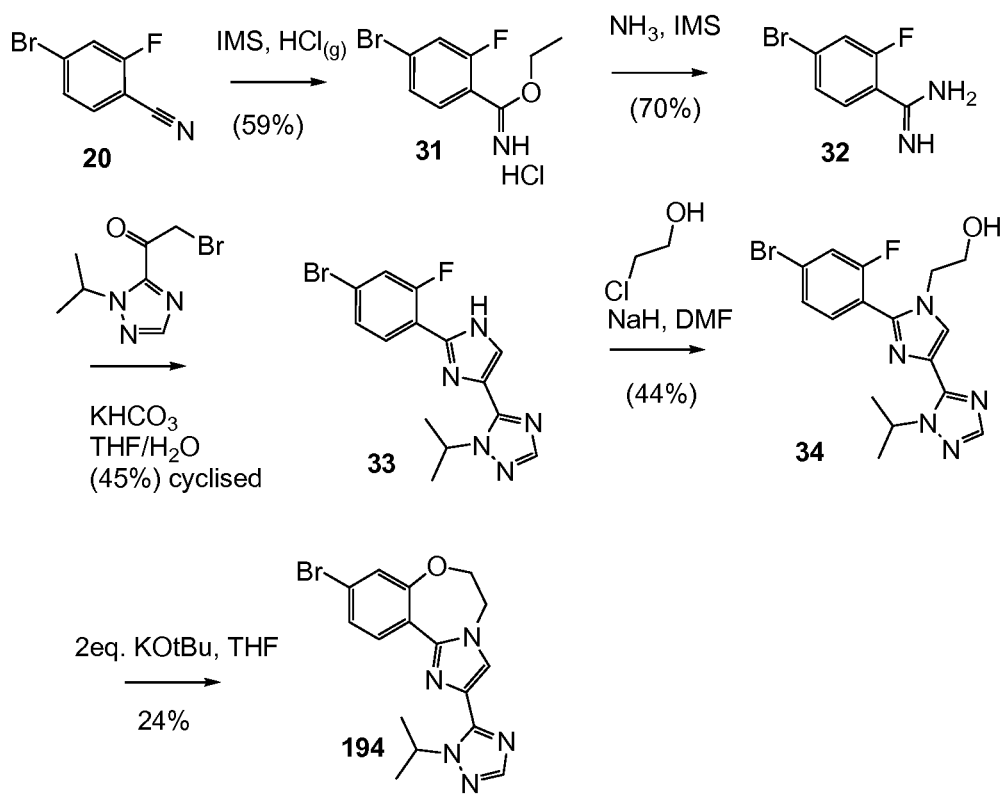
FIG. 6 shows a synthetic route to 9-halo-2-(1-isopropyl-1H-1,2,4-triazol-5-yl)-5,6-dihydrobenzo[f]imidazo[1,2-d][1,4]oxazepine compounds 12 from 4-bromo-2-fluorobenzonitrile 20.

FIG. 6 shows a synthetic route to 9-halo-2-(1-isopropyl-1H-1,2,4-triazol-5-yl)-5,6-dihydrobenzo[f]imidazo[1,2-d][1,4]oxazepine compounds 12 from 4-bromo-2-fluorobenzonitrile 20.

Figure 7:
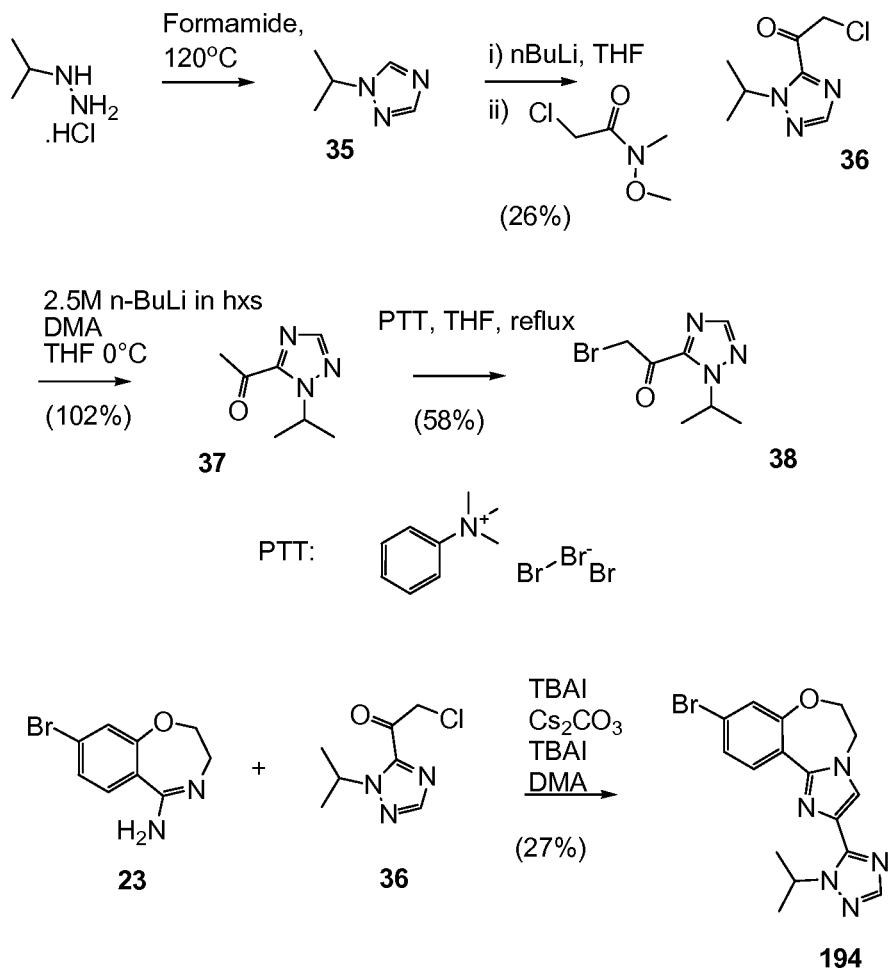
FIG. 7 shows a synthetic route to 9-halo-2-(1-isopropyl-1H-1,2,4-triazol-5-yl)-5,6-dihydrobenzo[f]imidazo[1,2-d][1,4]oxazepine compounds 12 from the reaction of (E)-8-bromo-2,3-dihydrobenzo[f][1,4]oxazepin-5-amine 23 and 2-chloro-1-(1-isopropyl-1H-1,2,4-triazol-5-yl)ethanone 36.

FIG. 7 shows a synthetic route to 9-halo-2-(1-isopropyl-1H-1,2,4-triazol-5-yl)-5,6-dihydrobenzo[f]imidazo[1,2-d][1,4]oxazepine compounds 12 from the reaction of (E)-8-bromo-2,3-dihydrobenzo[f][1,4]oxazepin-5-amine 23 and 2-chloro-1-(1-isopropyl-1H-1,2,4-triazol-5-yl)ethanone 36.

Figure 8:
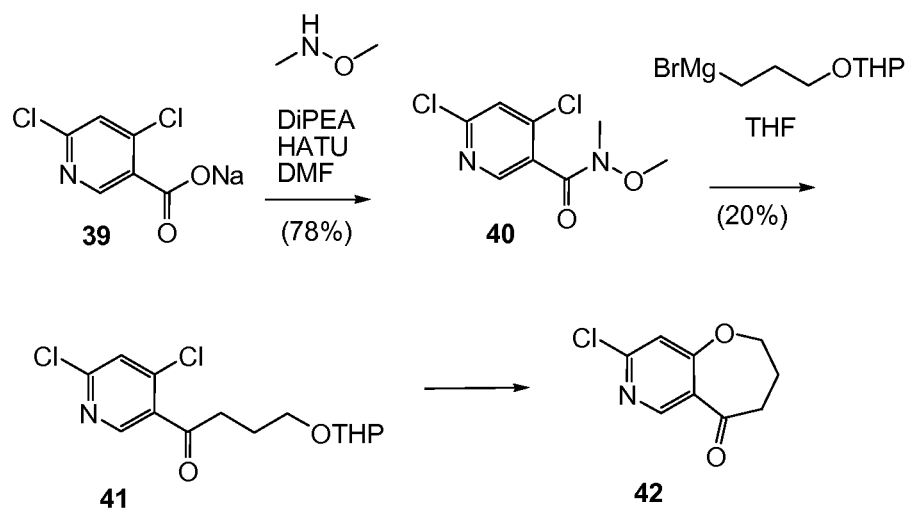
FIG. 8 shows a synthetic route to 8-chloro-3,4-dihydrooxepino[3,2-c]pyridin-5(2H)-one 42

FIG. 8 shows a synthetic route to 8-chloro-3,4-dihydrooxepino[3,2-c]pyridin-5(2H)-one 42

Figure 9:
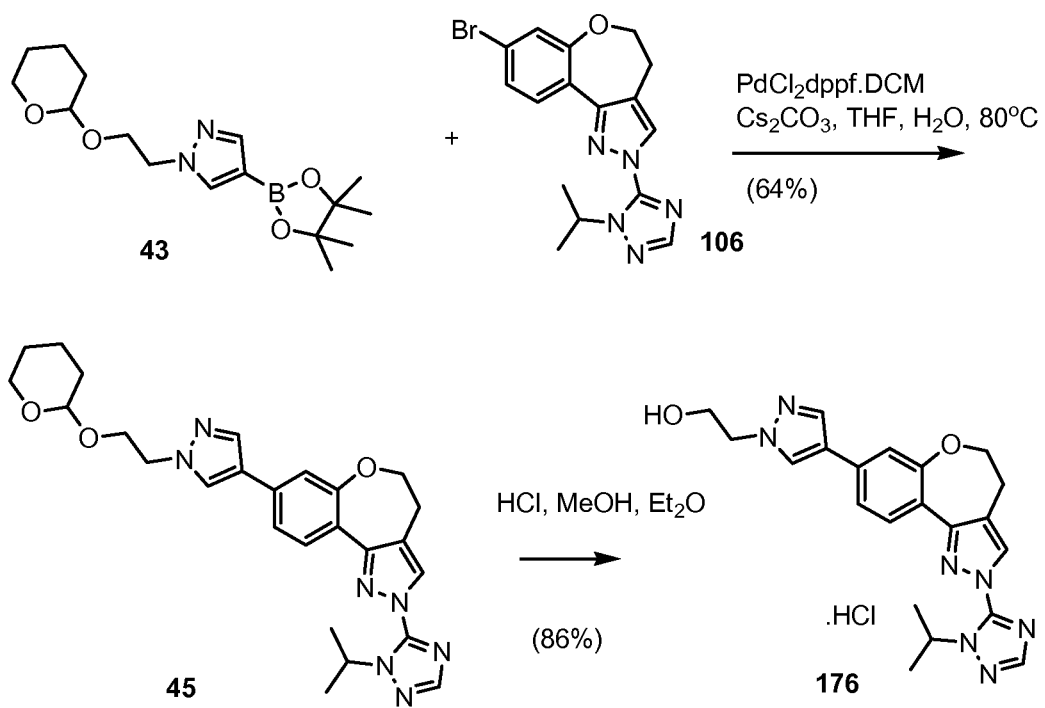
FIG. 9 shows a synthetic route to 2-{4-[2-(2-Isopropyl-2H-[1,2,4]triazol-3-yl)-4,5-dihydro-2H-6-oxa-1,2-diaza-benzo[e]azulen-8-yl]-pyrazol-1-yl}-ethanol 176

FIG. 9 shows a synthetic route to 2-{4-[2-(2-Isopropyl-2H-[1,2,4]triazol-3-yl)-4,5-dihydro-2H-6-oxa-1,2-diaza-benzo[e]azulen-8-yl]-pyrazol-1-yl}-ethanol 176

Figure 10:
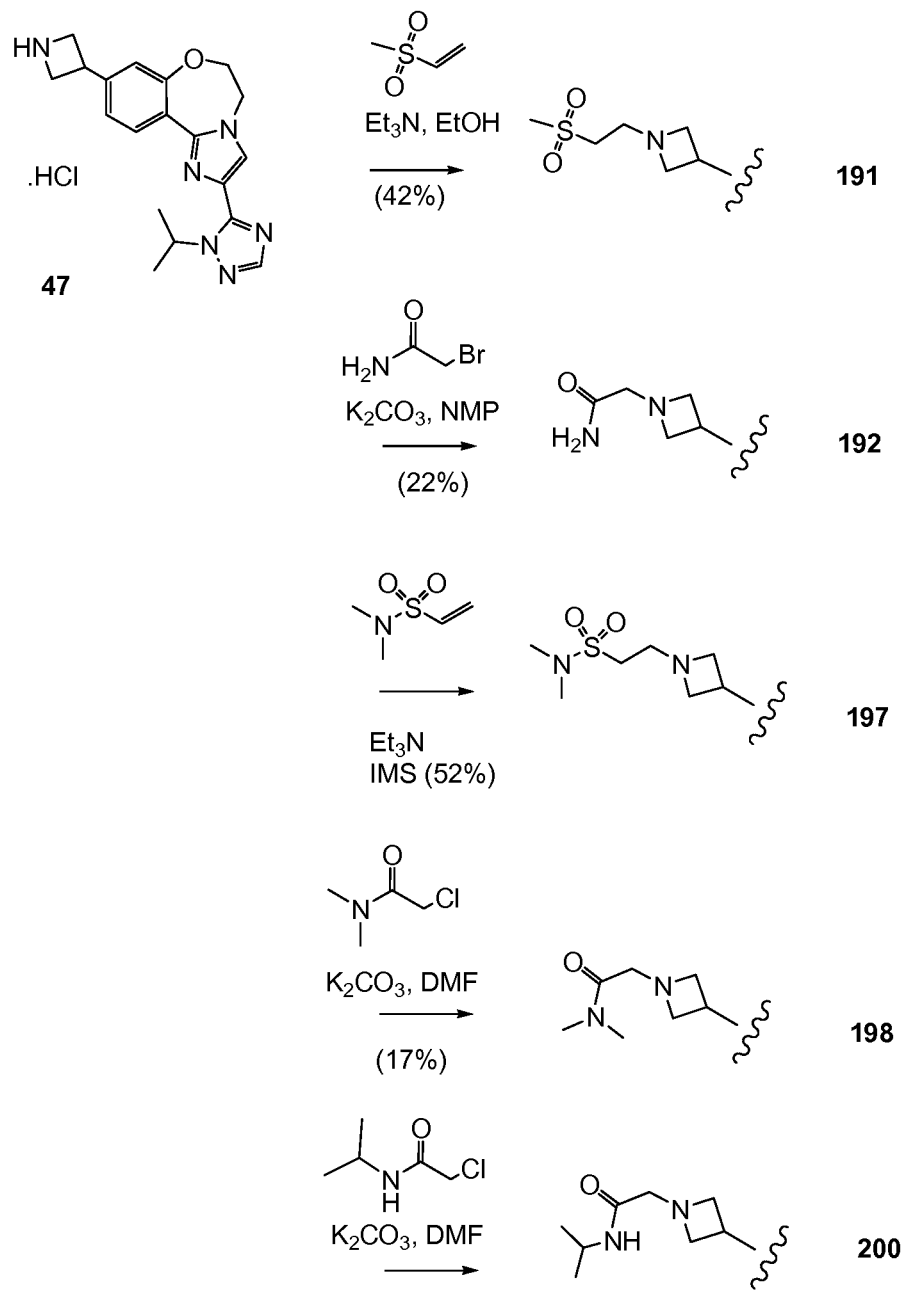
FIG. 10 shows conversion of 8-azetidin-3-yl-2-(2-isopropyl-2H-[1,2,4]triazol-3-yl)-4,5-dihydro-6-oxa-1,3a-diaza-benzo[e]azulene hydrochloride 47 to 191, 192, 197, 198, 200.

FIG. 10 shows conversion of 8-azetidin-3-yl-2-(2-isopropyl-2H-[1,2,4]triazol-3-yl)-4,5-dihydro-6-oxa-1,3a-diaza-benzo[e]azulene hydrochloride 47 to 191, 192, 197, 198, 200.

Figure 11:
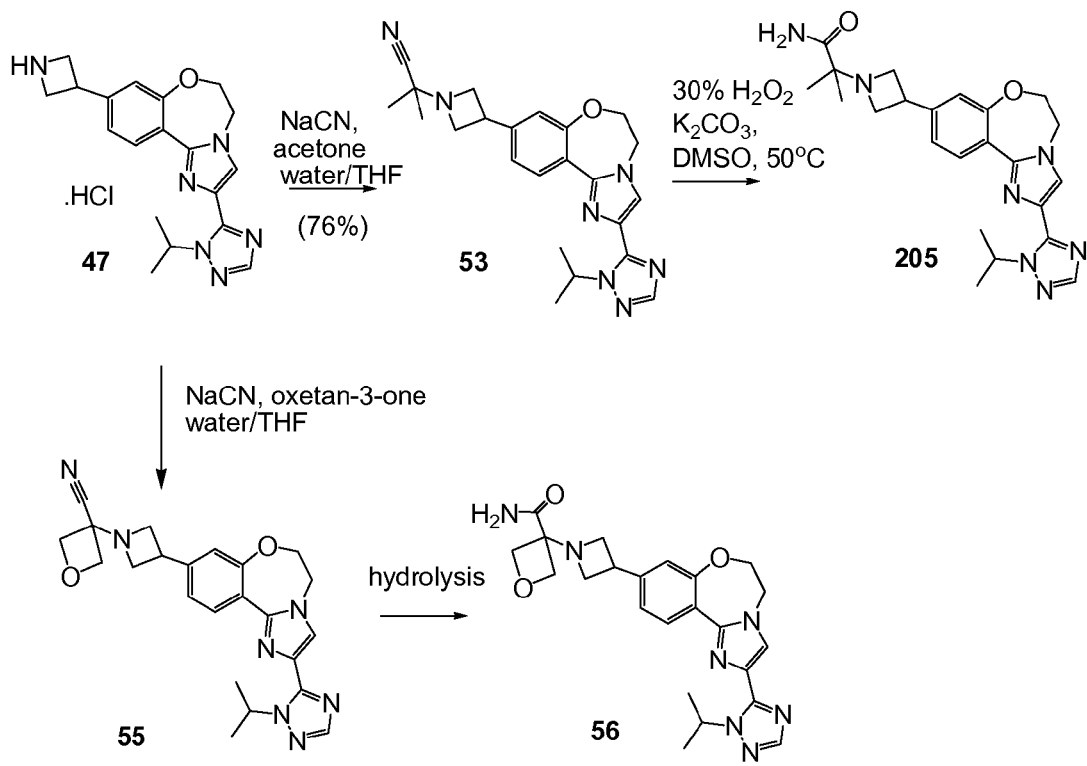
FIG. 11 shows a synthetic route to 2-(3-(2-(1-isopropyl-1H-1,2,4-triazol-5-yl)-5,6-dihydrobenzo[f]imidazo[1,2-d][1,4]oxazepin-9-yl)azetidin-1-yl)-2-methylpropanamide 205 and 3-(3-(2-(1-isopropyl-1H-1,2,4-triazol-5-yl)-5,6-dihydrobenzo[f]imidazo[1,2-d][1,4]oxazepin-9-yl)azetidin-1-yl)oxetane-3-carboxamide 56 from 8-azetidin-3-yl-2-(2-isopropyl-2H-[1,2,4]triazol-3-yl)-4,5-dihydro-6-oxa-1,3a-diaza-benzo[e]azulene hydrochloride 47.

FIG. 11 shows a synthetic route to 2-(3-(2-(1-isopropyl-1H-1,2,4-triazol-5-yl)-5,6-dihydrobenzo[f]imidazo[1,2-d][1,4]oxazepin-9-yl)azetidin-1-yl)-2-methylpropanamide 205 and 3-(3-(2-(1-isopropyl-1H-1,2,4-triazol-5-yl)-5,6-dihydrobenzo[f]imidazo[1,2-d][1,4]oxazepin-9-yl)azetidin-1-yl)oxetane-3-carboxamide 56 from 8-azetidin-3-yl-2-(2-isopropyl-2H-[1,2,4]triazol-3-yl)-4,5-dihydro-6-oxa-1,3a-diaza-benzo[e]azulene hydrochloride 47

Figure 12:
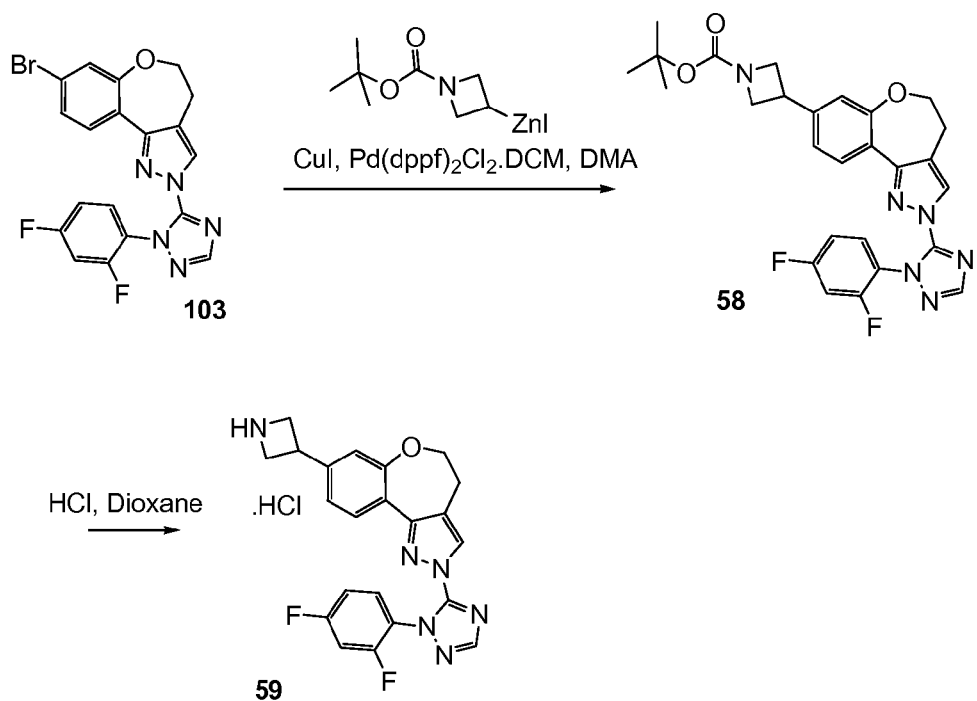
FIG. 12 shows a synthetic route to 8-Azetidin-3-yl-2-[2-(2,4-difluoro-phenyl)-2H-[1,2,4]triazol-3-yl]-4,5-dihydro-2H-6-oxa-1,2-diaza-benzo[e]azulene 59.

FIG. 12 shows a synthetic route to 8-Azetidin-3-yl-2-[2-(2,4-difluoro-phenyl)-2H-[1,2,4]triazol-3-yl]-4,5-dihydro-2H-6-oxa-1,2-diaza-benzo[e]azulene 59

Figure 13:
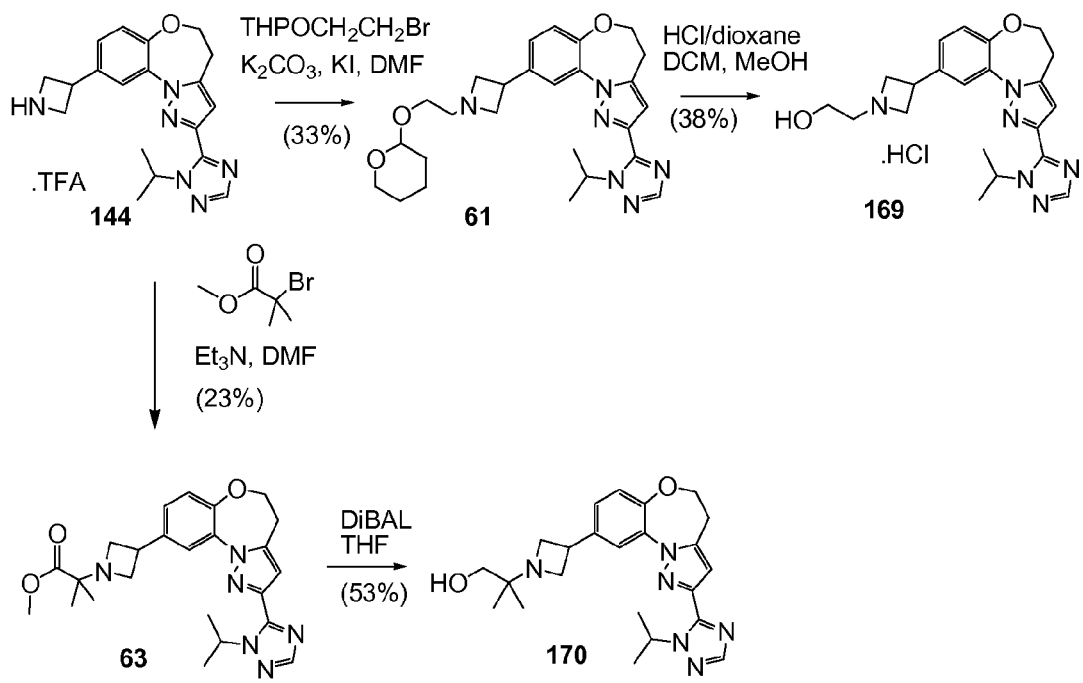
FIG. 13 shows a synthetic route to 2-(3-(2-(1-isopropyl-1H-1,2,4-triazol-5-yl)-4,5-dihydrobenzo[b]pyrazolo[1,5-d][1,4]oxazepin-9-yl)azetidin-1-yl)ethanol 169 and 2-(3-(2-(1-isopropyl-1H-1,2,4-triazol-5-yl)-4,5-dihydrobenzo[b]pyrazolo[1,5-d][1,4]oxazepin-9-yl)azetidin-1-yl)-2-methylpropan-1-ol 170 from 9-(azetidin-3-yl)-2-(1-isopropyl-1H-1,2,4-triazol-5-yl)-4,5-dihydrobenzo[b]pyrazolo[1,5-d][1,4]oxazepine 144.

FIG. 13 shows a synthetic route to 2-(3-(2-(1-isopropyl-1H-1,2,4-triazol-5-yl)-4,5-dihydrobenzo[b]pyrazolo[1,5-d][1,4]oxazepin-9-yl)azetidin-1-yl)ethanol 169 and 2-(3-(2-(1-isopropyl-1H-1,2,4-triazol-5-yl)-4,5-dihydrobenzo[b]pyrazolo[1,5-d][1,4]oxazepin-9-yl)azetidin-1-yl)-2-methylpropan-1-ol 170 from 9-(azetidin-3-yl)-2-(1-isopropyl-1H-1,2,4-triazol-5-yl)-4,5-dihydrobenzo[b]pyrazolo[1,5-d][1,4]oxazepine 144.

Figure 14:
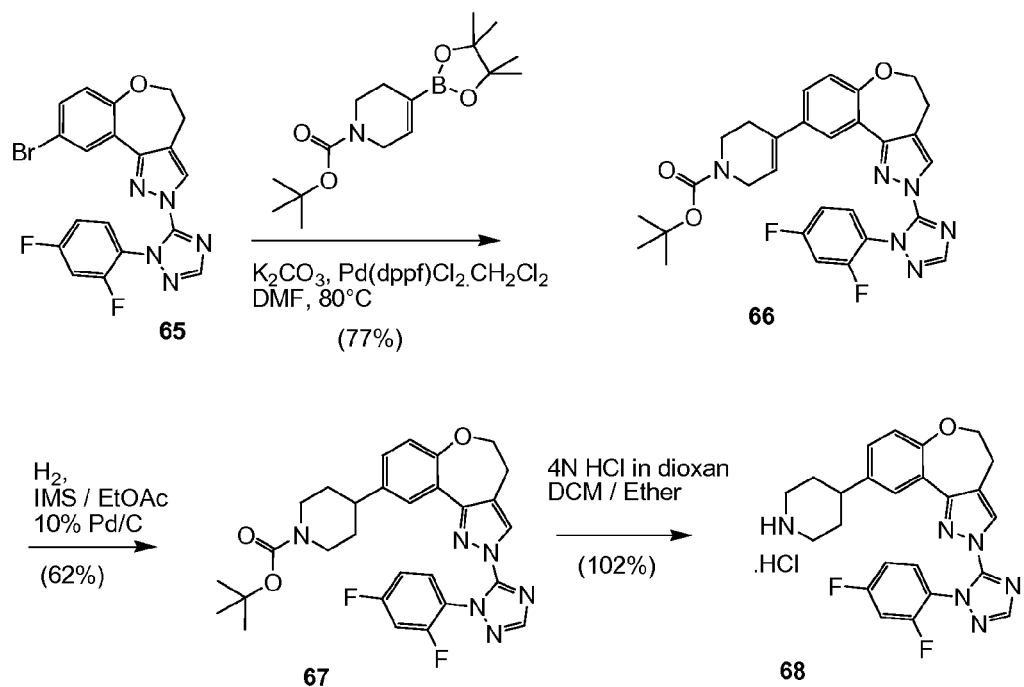
FIG. 14 shows a synthetic route to 2-[2-(2,4-Difluoro-phenyl)-2H-[1,2,4]triazol-3-yl]-9-piperidin-4-yl-4,5-dihydro-2H-6-oxa-1,2-diaza-benzo[e]azulene 68

FIG. 14 shows a synthetic route to 2-[2-(2,4-Difluoro-phenyl)-2H-[1,2,4]triazol-3-yl]-9-piperidin-4-yl-4,5-dihydro-2H-6-oxa-1,2-diaza-benzo[e]azulene 68

Figure 15:
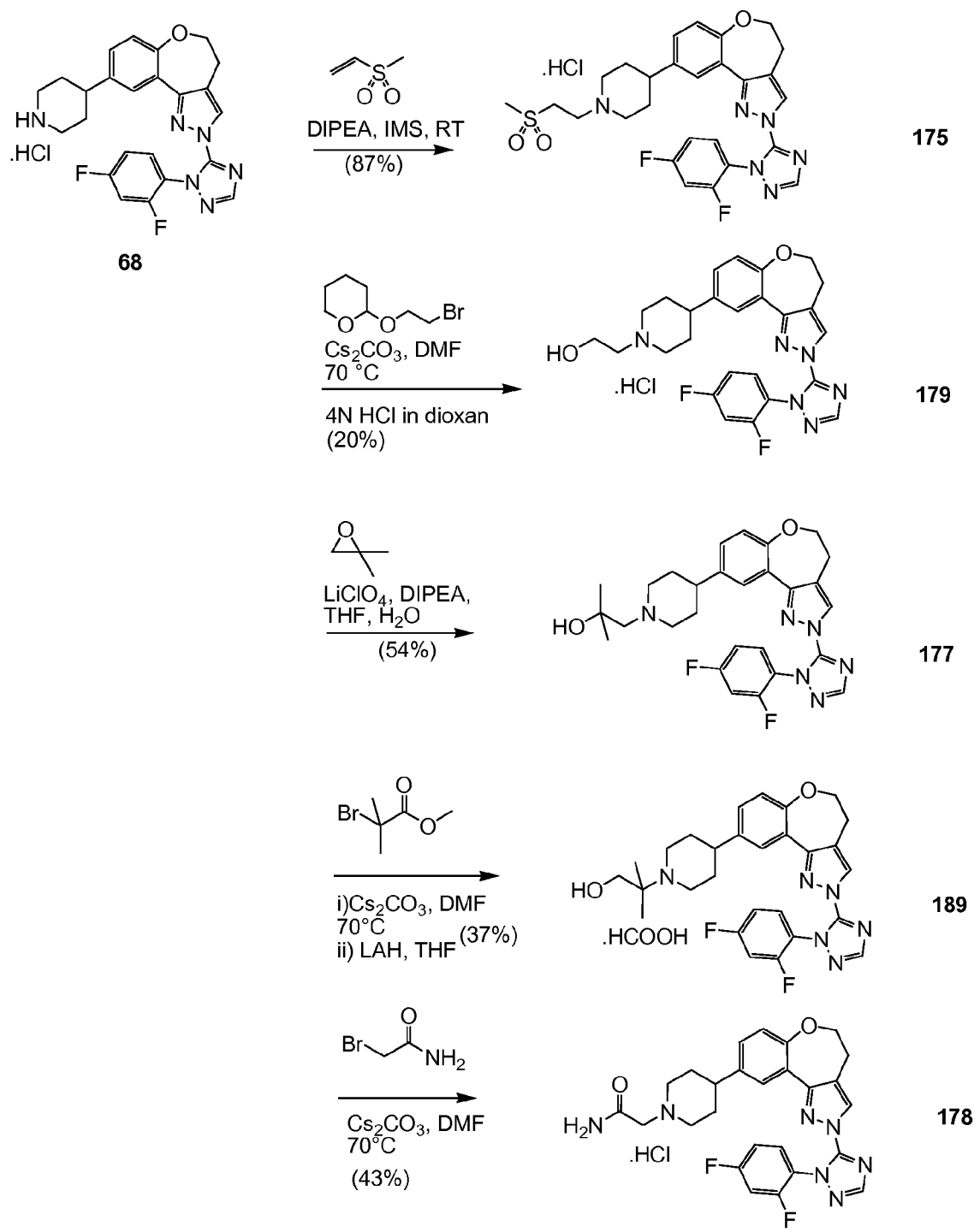
FIG. 15 shows conversion of 68 to 175, 177, 178, 179, 189.

FIG. 15 shows conversion of 68 to 175, 177, 178, 179, 189.

Figure 16:
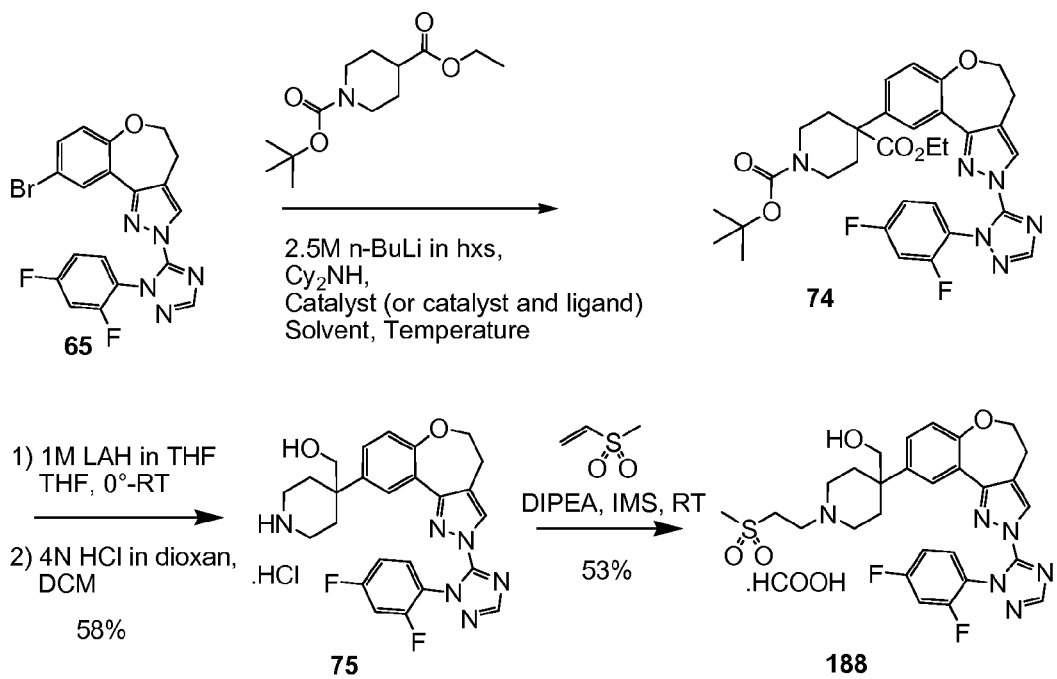
FIG. 16 shows a synthetic route to [4-{2-[2-(2,4-Difluoro-phenyl)-2H-[1,2,4]triazol-3-yl]-4,5-dihydro-2H-6-oxa-1,2-diaza-benzo[e]azulen-9-yl}-1-(2-methanesulfonyl-ethyl)-piperidin-4-yl]-methanol 188.
Figure 16:
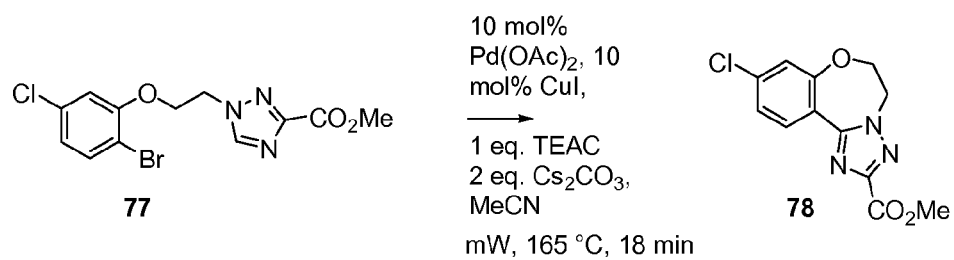

FIG. 16 shows a synthetic route to [4-{2-[2-(2,4-Difluoro-phenyl)-2H-[1,2,4]triazol-3-yl]-4,5-dihydro-2H-6-oxa-1,2-diaza-benzo[e]azulen-9-yl}-1-(2-methanesulfonyl-ethyl)-piperidin-4-yl]-methanol 188

Figure 17:
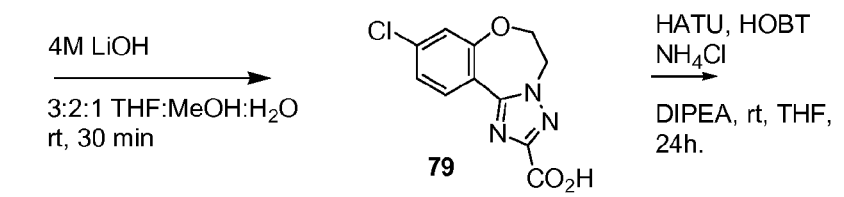
FIG. 17 shows a synthetic route to 9-chloro-2-(1-isopropyl-1H-1,2,4-triazol-5-yl)-5,6-dihydrobenzo[f][1,2,4]triazolo[1,5-d][1,4]oxazepine 239.
Figure 17:
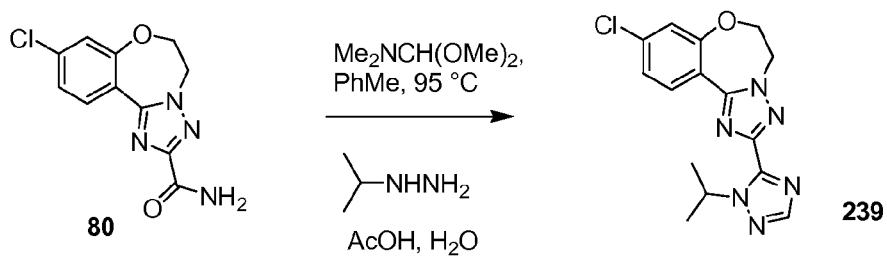

FIG. 17 shows a synthetic route to 9-chloro-2-(1-isopropyl-1H-1,2,4-triazol-5-yl)-5,6-dihydrobenzo[f][1,2,4]triazolo[1,5-d][1,4]oxazepine 239

Figure 18:
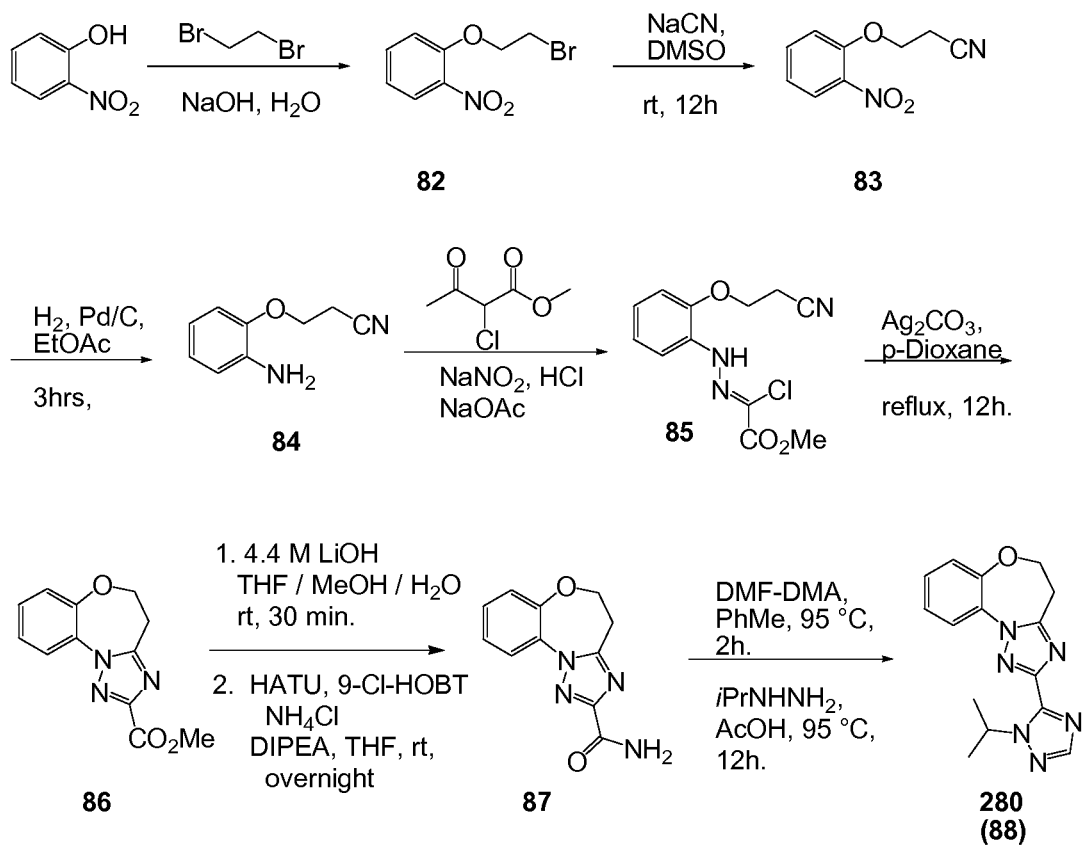
FIG. 18 shows a synthetic route to 2-(1-isopropyl-1H-1,2,4-triazol-5-yl)-4,5-dihydrobenzo[b][1,2,4]triazolo[1,5-d][1,4]oxazepine 88 (280).

FIG. 18 shows a synthetic route to 2-(1-isopropyl-1H-1,2,4-triazol-5-yl)-4,5-dihydrobenzo[b][1,2,4]triazolo[1,5-d][1,4]oxazepine 88 (280)

Figure 19:
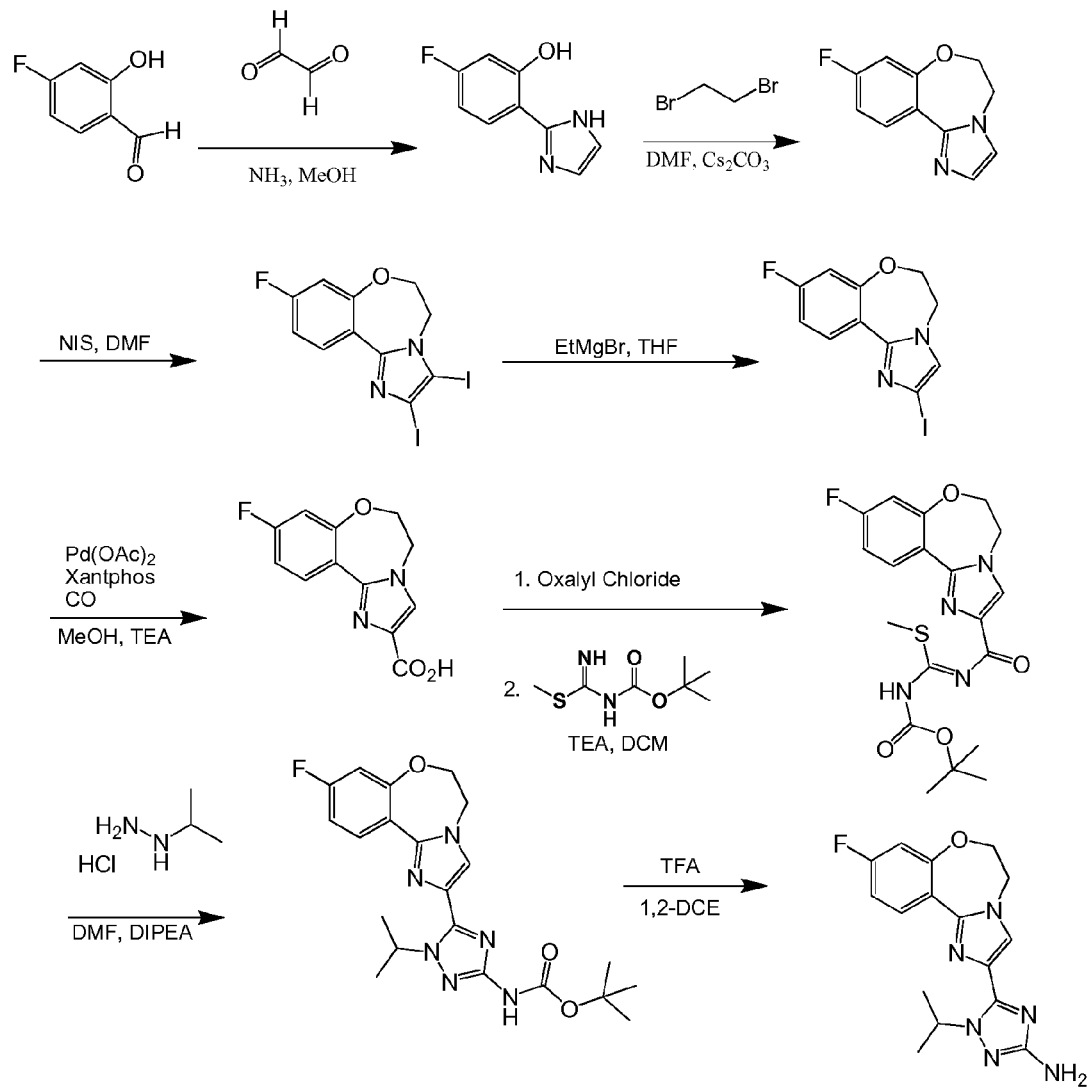
FIG. 19 shows a synthetic route to tert-butyl 5-(9-fluoro-5,6-dihydrobenzo[f]imidazo[1,2-d][1,4]oxazepin-2-yl)-1-isopropyl-1H-1,2,4-triazol-3-ylcarbamate from 4-fluoro-2-hydroxybenzaldehyde.
Figure 20:
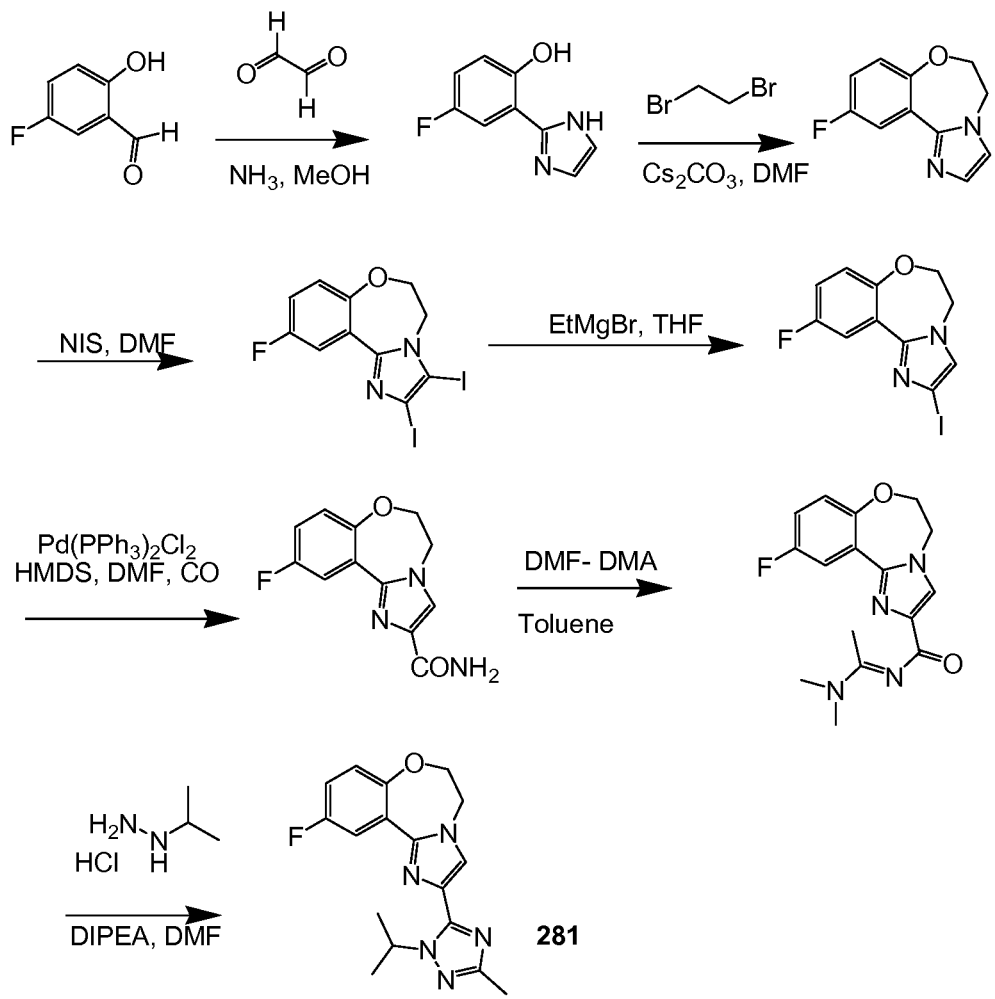
FIG. 20 shows a synthetic route to 10-fluoro-2-(1-isopropyl-3-methyl-1H-1,2,4-triazol-5-yl)-5,6-dihydrobenzo[f]imidazo[1,2-d][1,4]oxazepine 281 from 5-fluoro-2-hydroxybenzaldehyde.

FIG. 19 shows a synthetic route to tert-butyl 5-(9-fluoro-5,6-dihydrobenzo[f]imidazo[1,2-d][1,4]oxazepin-2-yl)-1-isopropyl-1H-1,2,4-triazol-3-ylcarbamate from 4-fluoro-2-hydroxybenzaldehyde FIG. 20 shows a synthetic route to 10-fluoro-2-(1-isopropyl-3-methyl-1H-1,2,4-triazol-5-yl)-5,6-dihydrobenzo[f]imidazo[1,2-d][1,4]oxazepine 281 from 5-fluoro-2-hydroxybenzaldehyde

EXAMPLES

The chemical reactions described in the Examples may be readily adapted to prepare a number of other PI3K inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the Examples described below, unless otherwise indicated all temperatures are set forth in degrees Celsius. Reagents were purchased from commercial suppliers such as Sigma Aldrich Chemical Company, and were used without further purification unless otherwise indicated. The reactions set forth below were conducted generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Column chromatography was conducted on a Biotage system (Manufacturer: Dyax Corporation) having a silica gel column or on a silica SEP PAK® cartridge (Waters). 1H NMR spectra were obtained at 400 MHz in deuterated CDCl3, d6-DMSO, CH3OD or d6-acetone solutions (reported in ppm), using chloroform as the reference standard (7.25 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Liquid Chromatography Mass Spectrometry (LCMS) experiments to determine retention times (RT) and associated mass ions were performed using various methods familiar to those skilled in the art of analytical methods of organic compounds.

Chemical structures were named according to: vendor designation; IUPAC convention; ChemDraw Ultra, Version 9.0.1, CambridgeSoft Corp., Cambridge Mass.; or Autonom 2000 Name, MDL Inc. It is recognized by those skilled in the art that a compound may have more than one name, according to different conventions.

Example 1

8-bromo-3,4-dihydrobenzo[b]oxepin-5(2H)-one

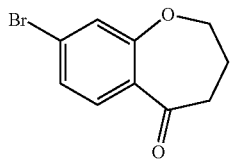 [SMILES: O=C1CCCOc2cc(Br)ccc21]

Step 1: ethyl 4-(3-bromophenoxy)butanoate

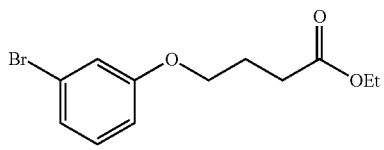 [SMILES: CCOC(=O)CCCOc1cccc(Br)c1]

Solid 3-bromophenol (10.0 g, 58 mmol) was added portion wise to a stirred suspension of K2CO3 in acetone (100 mL) at room temperature. see FIG. 1. Sodium iodide (NaI, 1.0 g) was added, followed by ethyl-4-bromobutyrate (9.2 mL, 64 mmol). The reaction mixture was heated at 80° C. overnight, cooled to room temperature, diluted with water and extracted with ethylacetate to give ethyl 4-(3-bromophenoxy)butanoate.

Step 2: 4-(3-bromophenoxy)butanoic acid

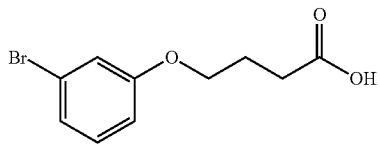 [SMILES: O=C(O)CCCOc1cccc(Br)c1]

Ethyl 4-(3-bromophenoxy)butanoate 6 from Example 5 was taken up in 100 mL THF and 50 mL water and treated with lithium hydroxide LiOH (hydrate, 4.9 g). see FIG. 1. The whole was heated at 50° C. for 2 days. The mixture was cooled to room temperature and acidified to pH 1 with 2N HCl. The aqueous was extracted with ethylacetate. The combined organics were washed with brine and dried over sodium sulfate to give crude 4-(3-Bromophenoxy)butanoic acid as a sticky solid. 1H NMR (DMSO-d6, 500 MHz) 7.24 (m, 1H), 7.13 (m, 1H), 7.11 (m, 1H), 6.95 (m, 1H), 3.99 (m, 2H), 2.37 (m, 2H), 1.94 (m, 2H).

Step 3: 8-bromo-3,4-dihydrobenzo[b]oxepin-5(2H)-one

To a stirred suspension of polyphosphoric acid (PPA, ca. 60 g) and celite (ca. 40 g) in 100 mL toluene was added crude 4-(3-bromophenoxy)butanoic acid 7 (ca. 58 mmol) in one portion, 10 mL toluene rinse (FIG. 1). The resultant suspension was heated at 110° C. for 5 hr. The toluene was decanted through a plug of celite and the remaining slurry was washed repeatedly with toluene and ethylacetate. The eluent was concentrated and purified by flash column chromatography (4:1 hex:EtOAc) to give 8-bromo-3,4-dihydrobenzo[b]oxepin-5(2H)-one (7 g, ca. 50% y). 1H NMR (DMSO-d6, 500 MHz) 7.55 (d, J=8.5 Hz, 1H), 7.37 (d, J=1.5 Hz, 1H), 7.35 (dd, J=8.5, 1.5 Hz, 1H), 4.24 (t, J=6.5 Hz, 2H), 2.79 (t, J=7.0 Hz, 2H), 2.14 (m, 2H).

Example 2

(Z)-8-bromo-5-chloro-2,3-dihydrobenzo[b]oxepine-4-carbaldehyde

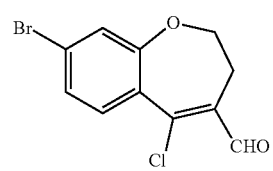 [SMILES: O=CC1=C(Cl)c2ccc(Br)cc2OCC1]

Phosphorus oxychloride, POCl3 (1.88 mL, 20.8 mmol) was added dropwise to DMF (5 mL) at 0° C. After 30 min a solution of 8-bromo-3,4-dihydrobenzo[b]oxepin-5(2H)-one 8 (2.0 g, 8.3 mmol) in 8 mL DMF was added dropwise. The reaction mixture was allowed to reach room temperature to stir 2 hr, then poured slowly over rapidly stirred ice water. The aqueous phase was extracted with ethylacetate and the combined organics were washed with brine, dried over sodium sulfate and concentrated to give (Z)-8-bromo-5-chloro-2,3-dihydrobenzo[b]oxepine-4-carbaldehyde.

Example 3

7-bromo-3,4-dihydrobenzo[b]oxepin-5(2H)-one

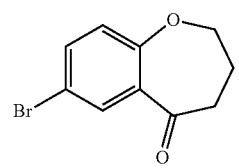

To a slurry of NaH (60% dispersion in mineral oil) (1.48 g, 37.1 mmol) in THF (~50 mL) at room temperature was added 1-(5-bromo-2-(2-bromoethoxy)phenyl)ethanone (8.07 g, 25.1 mmol). The reaction mixture was slowly heated to reflux and allowed to stir for 20 h. The solvent was removed under vacuum pressure and the concentrated residue was absorbed onto silica gel and purified by column chromatography (4:1 ethyl acetate/petroleum ether). The product was afforded as a yellow oil after the solvents were removed, providing 4.22 g (70%) of 7-bromo-3,4-dihydrobenzo[b]oxepin-5(2H)-one. 1H NMR (CDCl3) 7.87 (d, J=2.6 Hz, 1H), 7.50 (dd, J=2.6, 8.1 Hz, 1H), 6.97 (d, J=8.8 Hz, 2H), 4.24 (t, J=6.6 Hz, 2H), 2.89 (t, J=7.0 Hz, 2H), 2.15-2.29 (m, 2H).

Example 4

4,7-dibromo-3,4-dihydrobenzo[b]oxepin-5(2H)-one

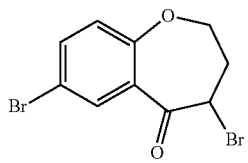 [SMILES: O=C1c2cc(Br)ccc2OCCC1Br]

To 7-bromo-3,4-dihydrobenzo[b]oxepin-5(2H)-one (3 g, 12 mmol) in ether (110 mL) was added bromine (0.7 mL, 14 mmol) and allowed to stir at room temperature overnight. The reaction mixture was concentrated under reduced pressure and purified via ISCO chromatography (hexane to 20% hexane in EtOAc over 45 minutes). Collected fractions and concentrated to give 4,7-dibromo-3,4-dihydrobenzo[b]oxepin-5(2H)-one (3.53 g, 89%). 1H NMR (500 MHz, CDCl3) δ 7.86 (d, J=2.5, 1H), 7.52 (dt, J=28.5, 14.2, 1H), 6.97 (d, J=8.7, 1H), 4.95 (dd, J=7.6, 6.8, 1H), 4.53-4.36 (m, 1H), 4.17 (ddd, J=12.8, 9.9, 4.4, 1H), 3.04-2.84 (m, 1H), 2.52 (ddt, J=14.7, 7.8, 4.5, 1H)

Example 5

3-isopropyl-1-methyl-1H-1,2,4-triazol-5(4H)-one

Step 1: 1-methylhydrazinecarboxamide

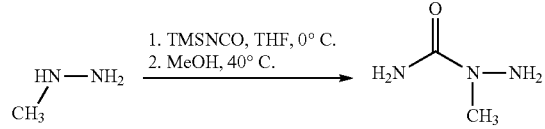

Methylhydrazine and trimethylsilylisocyanate were reacted in tetrahydrofuran at 0 C and then quenched and hydrolyzed with methanol to give 1-methylhydrazinecarboxamide.

Step 2: 2-isobutyryl-1-methylhydrazinecarboxamide

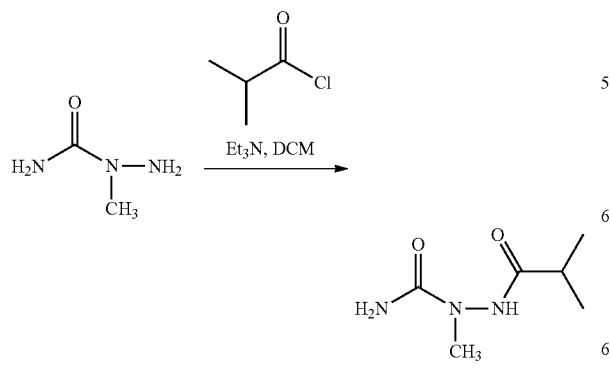

1-Methylhydrazinecarboxamide was acylated with isobutyryl chloride in triethylamine and dichloromethane to give 2-isobutyryl-1-methylhydrazinecarboxamide.

Step 3: 3-isopropyl-1-methyl-1H-1,2,4-triazol-5(4H)-one

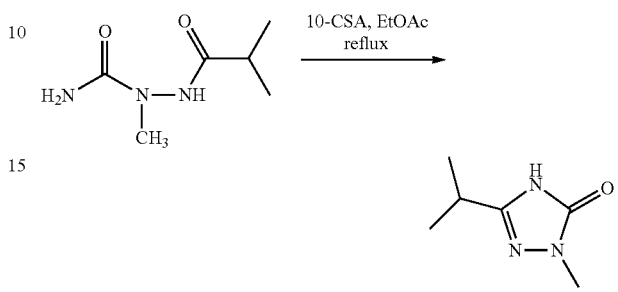

2-Isobutyryl-1-methylhydrazinecarboxamide was cyclized with 10-camphorsulfonic acid at reflux in ethylacetate to give 3-isopropyl-1-methyl-1H-1,2,4-triazol-5(4H)-one.

Example 6

1,3-dimethyl-1H-1,2,4-triazol-5(4H)-one and 1-isopropyl-3-methyl-1H-1,2,4-triazol-5(4H)-one

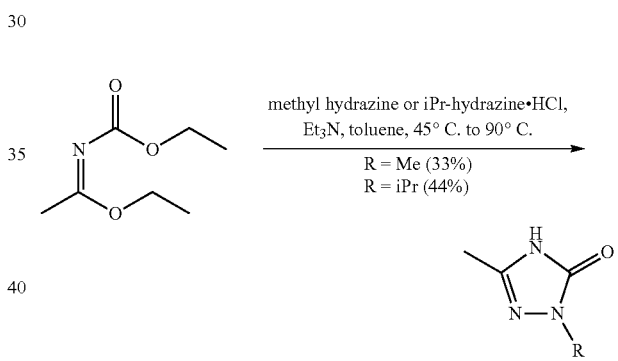

Acetamide and ethyl chloroformate were mixed at 45 C to give the hydrochloride salt of ethyl acetimidate which was further reacted with ethyl chloroformate, diisopropylethylamine, and dichloromethane at 0 C to give ethyl N-ethoxycarbonylacetimidate which was reacted with methyl hydrazine or isopropyl hydrazine hydrochloride in triethylamine and toluene to give 1,3-dimethyl-1H-1,2,4-triazol-5(4H)-one and 1-isopropyl-3-methyl-1H-1,2,4-triazol-5(4H)-one, respectively.

Example 7

4-isopropyl-1-(4-methoxybenzyl)-1H-imidazol-2(3H)-one

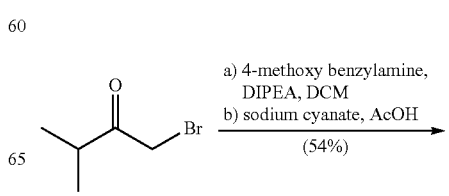

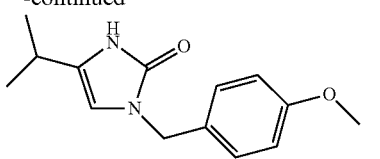

3-Methylbutan-2-one was brominated with bromine in methanol to give 1-bromo-3-methylbutan-2-one which was reacted with 4-methoxybenzylamine and cyclized with sodium cyanate to give 4-isopropyl-1-(4-methoxybenzyl)-1H-imidazol-2(3H)-one.

Example 8

Methyl 6,7-dihydroimidazo[1,2-d]pyrido[3,2-b][1,4]oxazepine-3-carboxylate

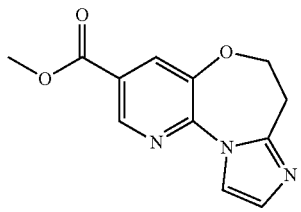 [SMILES: COC(=O)c1cnc2c(c1)OCCc1nccn1-2]

Step 1: 2-Methyl-1-trityl-1H-imidazole

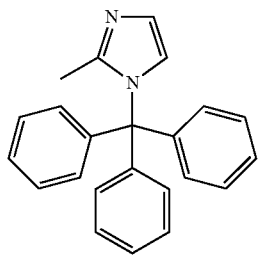 [SMILES: Cc1nccn1C(c1ccccc1)(c1ccccc1)c1ccccc1]

Triphenylmethyl chloride (16.0 g, 57.5 mmol) was added portionwise to a solution of 2-methylimidazole (4.10 g, 50.0 mmol) and Triethylamine (9.02 mL, 64.7 mmol) in 20 ml of N,N-dimethylformamide. The mixture was stirred for 18 hours, mixed with 300 ml of water and extracted with 1000 ml of ethyl acetate. The organic extract was washed with 1 L of water, brine, dried over MgSO4 and concentrate in vacuum to 50 ml volume. A precipitate was collected, washed with ethyl acetate and dried in high vacuum for 18 hours. Weight 15.0 g (92.5%). 1H NMR (400 MHz, CDCl3) δ 7.34-7.29 (m, 9H), 7.16-7.11 (m, 6H), 6.90 (d, J=1.5, 1H), 6.71 (d, J=1.5, 1H), 1.65 (s, 3H).

Step 2: 2-(1-trityl-1H-imidazol-2-yl)acetaldehyde

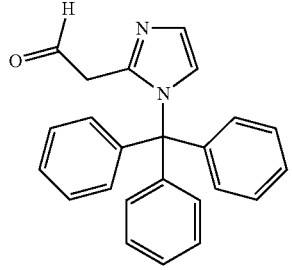 [SMILES: O=CCc1nccn1C(c1ccccc1)(c1ccccc1)c1ccccc1]

1.6 M of n-Butyllithium in hexane (7.5 mL) was added dropwise to a solution of 2-Methyl-1-trityl-1H-imidazole (3.244 g, 10.00 mmol) in Tetrahydrofuran (100.0 mL, 1233 mmol) at −76° C. The dark red mixture was stirred for 45 min. Ethyl formate (4.039 mL, 50.00 mmol) was added quickly and the mixture (turned yellowish) was stirred for 20 min. 6 ml of 5% aq. citric acid were added and the mixture was mixed with 60 ml of aq citric acid and extracted with ethyl acetate. The organic layer was washed with water, brine, dried over MgSO4 and concentrated in vacuum. Pale yellow semisolid material (2.025 g, 57.5%) was used in the next step without further purification.

Step 3: 2-(1-trityl-1H-imidazol-2-yl)ethanol

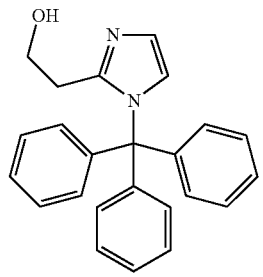 [SMILES: OCCc1nccn1C(c1ccccc1)(c1ccccc1)c1ccccc1]

Crude 2-(1-trityl-1H-imidazol-2-yl)acetaldehyde (2.025 g (5.75 mmol) was dissolved in MeOH/THF (1:1, 40 ml) and NaBH4 (0.435 g, 11.5 mmol) was added portionwise to the above mixture. The mixture was stirred for 18 hours, diluted with 100 ml of water and extracted with 2×DCM. The combined organic extracts were washed with water, brine, dried over Na2SO4 and concentrated in vacuum. Weight of the residue 1.915 g (94%). 1H NMR (500 MHz, CDCl3) δ 7.35-7.31 (m, 9H), 7.12 (dd, J=6.7, 2.7, 6H), 6.93 (d, J=1.0, 1H), 6.74 (d, J=1.0, 1H), 5.04 (br, 1H), 3.46 (t, J=5.4, 2H), 2.00 (t, J=5.4, 2H).

Step 4: Methyl 6-iodo-5-(2-(1-trityl-1H-imidazol-2-yl)ethoxy)nicotinate

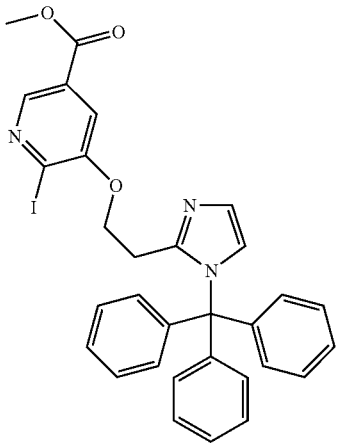 [SMILES: COC(=O)c1cnc(I)c(OCCc2nccn2C(c2ccccc2)(c2ccccc2)c2ccccc2)c1]

Diisopropyl azodicarboxylate (1160 uL, 5.90 mmol) was added dropwise to a mixture of 2-(1-trityl-1H-imidazol-2-yl)ethanol (1900 mg, 5.4 mmol), methyl 5-hydroxy-6-iodonicotinate (1570 mg, 5.63 mmol) and Triphenylphosphine (1550 mg, 5.90 mmol) in Tetrahydrofuran (45.0 mL, 555 mmol) at 00 C. After stirring for 3 hours the mixture was mixed with water and extracted with ethyl acetate. The organic layer was washed with water, brine, dried over MgSO4 and concentrated in vacuum. The residue was purified on 40 g silica column eluting with 50% ethyl acetate in DCM to give 1.45 g (44%) of methyl 6-iodo-5-(2-(1-trityl-1H-imidazol-2-yl)ethoxy)nicotinate. MS(ESI+): 616.0. 1H NMR (400 MHz, CDCl3) δ 8.52 (d, J=1.9, 1H), 7.40-7.28 (m, 10H), 7.20-7.16 (m, 6H), 6.99 (d, J=1.5, 1H), 6.81 (d, J=1.5, 1H), 3.98-3.91 (m, 5H), 2.46 (t, J=7.3, 2H).

Step 5: Methyl 5-(2-(1H-imidazol-2-yl)ethoxy)-6-iodonicotinate

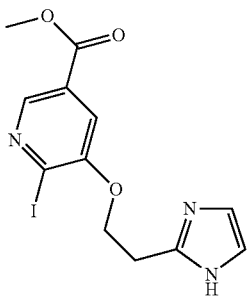 [SMILES: COC(=O)c1cnc(I)c(OCCc2ncc[nH]2)c1]

Triethylsilane (0.160 mL, 1.00 mmol) was added to a solution of 1.45 g (2.36 mmol) of methyl 6-iodo-5-(2-(1-trityl-1H-imidazol-2-yl)ethoxy)nicotinate in trifluoroacetic acid (30.0 mL, 389 mmol). The mixture was stirred for 4 hours, concentrated in vacuum and triturated with 50 ml of anhydrous ethyl ether. The solid material was collected, washed with several portions of ether and partitioned between 1 M of aqueous sodium carbonate and ethyl acetate. The organic extracts were washed with water, brine, dried over magnesium sulfate and concentrated in vacuum to give a residue (0.55 g, 62%) of methyl 5-(2-(1H-imidazol-2-yl)ethoxy)-6-iodonicotinate. MS(ESI+): 374.0

Step 6: Methyl 6,7-dihydroimidazo[1,2-d]pyrido[3,2-b][1,4]oxazepine-3-carboxylate A mixture of methyl 5-(2-(1H-imidazol-2-yl)ethoxy)-6-iodonicotinate (373 mg, 1.00 mmol), Copper(I) oxide (14.3 mg, 0.10 mmol), Ninhydrin (35.6 mg, 0.20 mmol) and potassium carbonate (290 mg, 2.10 mmol) in dimethyl sulfoxide (10.0 mL) was heated at 110° C. for 2 hours. The mixture was poured into 20 ml of water and extracted with ethyl acetate (3×15 ml). The organic extracts were washed with water (3×15 ml), brine, dried over MgSO4 and concentrated. The residue (0.220 g, 90%) was used without further purification in the next step. MS(ESI+): 246.0. 1H NMR (500 MHz, CDCl3) δ 8.77 (d, J=1.9, 1H), 8.10 (s, 1H), 8.04 (d, J=1.9, 1H), 7.08 (s, 1H), 4.47 (t, J=5.1, 2H), 3.97 (s, 3H), 3.46 (t, J=5.1, 2H).

Example 9

Methyl 9,10-diiodo-6,7-dihydroimidazo[1,2-d]pyrido[3,2-b][1,4]oxazepine-3-carboxylate

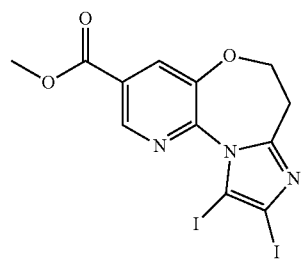 [SMILES: COC(=O)c1cnc2c(c1)OCCc1nc(I)c(I)n1-2]

N-Iodosuccinimide (394 mg, 1.75 mmol) was added to a solution of methyl 5-(2-(1H-imidazol-2-yl)ethoxy)-6-iodonicotinate (220 mg, 0.90 mmol) in N,N-Dimethylformamide (8.0 mL, 1.0E2 mmol). The mixture was stirred for 6 hours at room temperature and 18 hours at 60° C. The mixture was concentrated in vacuum and the residue was partitioned between ethyl acetate and 1M aq Na2CO3. The organic layer was washed with water, brine, dried over Na2SO4 and concentrated. The residue was purified on a 4 g silica column eluting with 40% of ethyl acetate in heptane. Weight 130 mg. MS(ESI+): 497.9. 1H NMR (500 MHz, CDCl3) δ 9.02 (d, J=1.9, 1H), 8.21 (d, J=1.9, 1H), 4.65 (t, J=6.4, 2H), 4.00 (s, 3H), 3.14 (t, J=6.4, 2H).

Example 10

Methyl 10-iodo-6,7-dihydroimidazo[1,2-d]pyrido[3,2-b][1,4]oxazepine-3-carboxylate

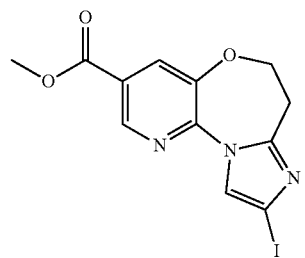 [SMILES: COC(=O)c1cnc2c(c1)OCCc1nc(I)cn1-2]

Ethylmagnesium bromide in ethyl ether (3.0 M, 0.104 mL, 0.31 mmol)) was added dropwise to a suspension of methyl 9,10-diiodo-6,7-dihydroimidazo[1,2-d]pyrido[3,2-b][1,4]oxazepine-3-carboxylate (130 mg, 0.26 mmol) in Tetrahydrofuran (5.0 mL, 62 mmol) at −15° C. The mixture was stirred for 15-20 min (a completion was monitored by LCMS), pour into 20 ml of sat. aq. NH4Cl and extracted with ethyl acetate. The organic extracts were washed with water (2×20 ml), brine, dried over MgSO4 and concentrated in vacuum. Weight 92 mg (94%). MS(ESI+): 372.0.

Example 11

Methyl 9-(1-isopropyl-1H-pyrazol-5-yl)-6,7-dihydroimidazo[1,2-d]pyrido[3,2-b][1,4]oxazepine-3-carboxylate

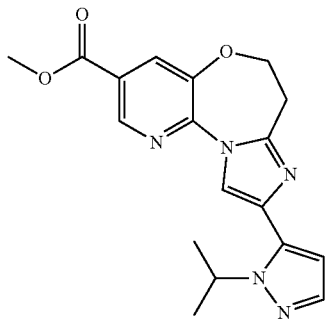 [SMILES: COC(=O)c1cnc2c(c1)OCCc1nc(-c3ccnn3C(C)C)cn1-2]

A mixture of 1-isopropyl-5-(4,4,5,5-tetramethyl-1,3,2-dioxaborolan-2-yl)-1H-pyrazole (117.1 mg, 0.4958 mmol), methyl 10-iodo-6,7-dihydroimidazo[1,2-d]pyrido[3,2-b][1,4]oxazepine-3-carboxylate (92.0 mg, 0.248 mmol), [1,1'-Bis(diphenylphosphino)ferrocene]dichloropalladium(II), complex with dichloromethane (1:1) (20.24 mg, 0.02479 mmol) and 1.0 M of Potassium acetate in water (0.49 mL) in 1,2-Dimethoxyethane (5.0 mL, 48 mmol) was degassed. The reaction was microwaved on 200 watts, 140° C. for 40 minutes. The reaction mixture was filtered, washed with DME, mixed with water and extracted with EtOAc. Combined organic extracts were washed with 1% aq NaOH to remove a phenolic byproduct, then 5% aq citric acid, water, brine, dried over Na2SO4 and concentrated in vacuum. The residue was purified on 4 g silica column, eluting with 60-70% of EtOAc in heptane. Yield 21 mg. MS(ESI+): 354.2.

Example 12

9-(1-Isopropyl-1H-pyrazol-5-yl)-6,7-dihydroimidazo[1,2-d]pyrido[3,2-b][1,4]oxazepine-3-carboxylic acid

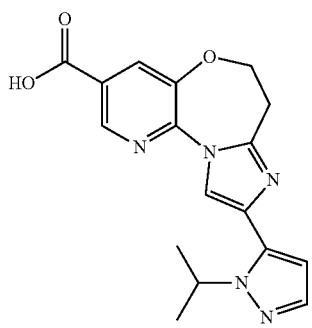 [SMILES: CC(C)n1nccc1-c1cn2c(n1)CCOc1cc(C(=O)O)cnc1-2]

A mixture of 21 mg (0.06 mmol) of methyl 9-(1-isopropyl-1H-pyrazol-5-yl)-6,7-dihydroimidazo[1,2-d]pyrido[3,2-b][1,4]oxazepine-3-carboxylate and 1.0 ml of 1 N aq LiOH in 4 ml of methanol and 4 ml of tetrahydrofuran was stirred for 6 hours. The mixture was acidified to pH 3 by addition of 1 N HCl and concentrated in vacuum. The residue was partitioned between ethyl acetate and water, the organic layer was washed with brine, dried over Na2SO4 and concentrated. Yield 17 mg. MS(ESI+): 340.1

Example 13

Methyl 2-(1-isopropyl-1H-pyrazol-5-yl)-5,6-dihydrobenzo[f]imidazo[1,2-d][1,4]oxazepine-10-carboxylate

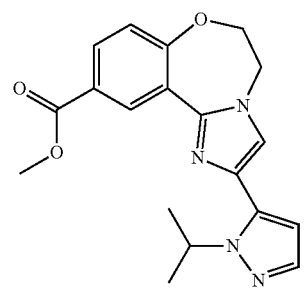 [SMILES: COC(=O)c1ccc2c(c1)-c1nc(-c3ccnn3C(C)C)cn1CCO2]

A mixture of methyl 2-iodo-5,6-dihydrobenzo[f]imidazo[1,2-d][1,4]oxazepine-10-carboxylate (370.1 mg, 1.000 mmol), 1-isopropyl-5-(4,4,5,5-tetramethyl-1,3,2-dioxaborolan-2-yl)-1H-pyrazole (354 mg, 1.50 mmol), [1,1'-Bis(diphenylphosphino)ferrocene]dichloropalladium(II), complex with dichloromethane (1:1) (40.8 mg, 0.0500 mmol) and 2.0 M of Potassium acetate in water (1.00 mL) in Acetonitrile (12 mL, 230 mmol) was degassed. The reaction was microwaved on 200 watts, 140° C. for 30 minutes. The reaction mixture was partitioned between water and ethyl acetate, filtered, the organic layer was washed with water, brine, dried over MgSO4 and concentrated in vacuum. The residue was purified on 12 g silica column eluting with 35-40% ethyl acetate in heptane. Yield 119 mg (34%). MS: (ESI+): 353.1.

Example 14

2-(1-Isopropyl-1H-pyrazol-5-yl)-5,6-dihydrobenzo[f]imidazo[1,2-d][1,4]oxazepine-10-carboxylic acid

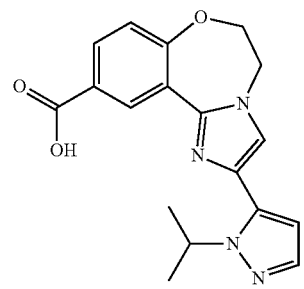 [SMILES: CC(C)n1nccc1-c1cn2c(n1)-c1cc(C(=O)O)ccc1OCC2]

Following the procedure in Example 10, methyl 2-(1-isopropyl-1H-pyrazol-5-yl)-5,6-dihydrobenzo[f]imidazo[1,2-d][1,4]oxazepine-10-carboxylate was hydrolyzed to give 2-(1-isopropyl-1H-pyrazol-5-yl)-5,6-dihydrobenzo[f]imidazo[1,2-d][1,4]oxazepine-10-carboxylic acid. MS(ESI+): 339.4.

Example 15

Methyl 2-(4-cyano-1-isopropyl-1H-pyrazol-5-yl)-5,6-dihydrobenzo[f]imidazo[1,2-d][1,4]oxazepine-9-carboxylate

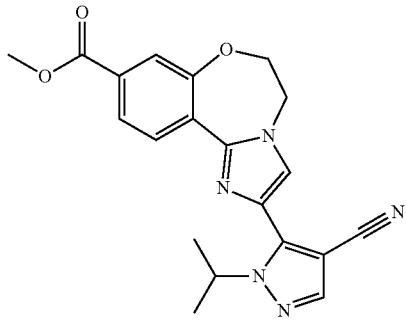 [SMILES: COC(=O)c1ccc2c(c1)OCCn1cc(-c3c(C#N)cnn3C(C)C)nc1-2]

Step 1:
5-Amino-1-isopropyl-1H-pyrazole-4-carbonitrile

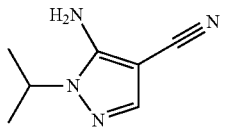

Sodium methoxide (2.139 g, 39.60 mmol) was added to a solution of ethoxymethylenemalonitrile (2.198 g, 18.00 mmol) and isopropylhydrazine hydrochloride (2.212 g, 20.00 mmol) in Ethanol (50 mL, 800 mmol). The mixture was heated under reflux for 18 hours. The solvent was removed in vacuum, the residue partitioned between ethyl acetate and water. The organic layer was washed with water, brine, dried over Na2SO4, concentrated in vacuum and purified on 25 g silica column, eluting with 25-30% of ethyl acetate in heptane, to give 5-Amino-1-isopropyl-1H-pyrazole-4-carbonitrile (yield 1.77 g, 65%). MS(ESI+): 151.2. 1H NMR (400 MHz, CDCl3) δ 7.51 (d, J=6.4, 1H), 4.23 (ddd, J=19.8, 16.6, 9.8, 3H), 1.46 (d, J=6.6, 7H).

Step 2:
5-Iodo-1-isopropyl-1H-pyrazole-4-carbonitrile

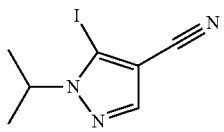

Amyl nitrite (13.00 g, 111.0 mmol) was added to a suspension of 5-amino-1-isopropyl-1H-pyrazole-4-carbonitrile (1.77 g, 11.8 mmol) in Diiodomethane (56.0 mL, 695 mmol) at −10° C. in 30 min. The mixture was stirred for 30 min at room temperature and then heated at 100° C. for 2 hours. The mixture was then cooled and concentrated in high vacuum to give a residue which was partitioned between ethyl acetate and 5% Na2S2O5. The organic layer was washed with water, 0.1% of aq HCl, water, brine, dried and concentrated in vacuum. The residue was purified on silica column eluting with 20-30% ethyl acetate in heptane. Yield 1.68 g (55%). MS(ESI+): 262.2

Step 3: Methyl 2-(tributylstannyl)-5,6-dihydrobenzo[f]imidazo[1,2-d][1,4]oxazepine-9-carboxylate

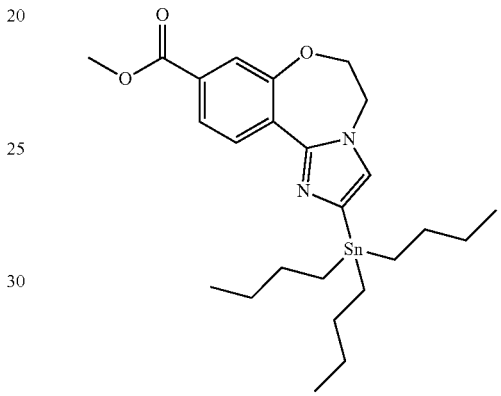

Isopropylmagnesium chloride in tetrahydrofuran (2.0 M, 1.5 mL, 3.00 mmol) was added dropwise to a solution of methyl 2-iodo-5,6-dihydrobenzo[f]imidazo[1,2-d][1,4]oxazepine-9-carboxylate (740 mg, 2.00 mmol) in Tetrahydrofuran (12 mL, 150 mmol) at room temperature. The mixture was stirred for 2.5 hours. Tributyltin chloride (0.8138 mL, 3.000 mmol) was added and the mixture was stirred for 18 hours. The mixture was mixed with sat aq. NH4Cl and extracted with ethyl acetate. The organic layer was washed with brine, dried over Na2SO4 and purified on 25 g silica column eluting with 15-20% ethyl acetate in heptane. Yield 160 mg (15%). MS(ESI+): 535.2

Step 4: Methyl 2-(4-cyano-1-isopropyl-1H-pyrazol-5-yl)-5,6-dihydrobenzo[f]imidazo[1,2-d][1,4]oxazepine-9-carboxylate A mixture of methyl 2-(tributylstannyl)-5,6-dihydrobenzo[f]imidazo[1,2-d][1,4]oxazepine-9-carboxylate (155 mg, 0.291 mmol), 5-amino-1-isopropyl-1H-pyrazole-4-carbonitrile (133 mg, 0.509 mmol) and Tetrakis(triphenylphosphine)palladium(0) (16.8 mg, 0.0145 mmol) in Toluene (6.0 mL, 56 mmol) was heated for 18 hours. The mixture was concentrated in vacuum, the residue purified on 4 g silica column eluting with 30% ethyl acetate in heptane. Yield 65 mg (59%). MS(ESI+): 378.2

Example 16

2-(4-cyano-1-isopropyl-1H-pyrazol-5-yl)-5,6-dihydrobenzo[f]imidazo[1,2-d][1,4]oxazepine-9-carboxylic acid

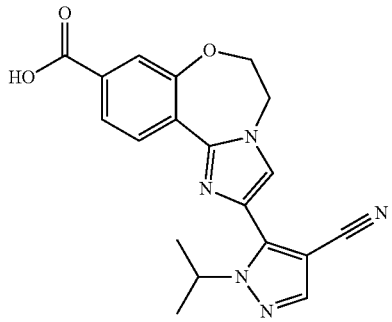 [SMILES: CC(C)n1ncc(C#N)c1-c1cn2c(n1)-c1ccc(C(=O)O)cc1OCC2]

Following the procedure in Example 10, methyl 2-(4-cyano-1-isopropyl-1H-pyrazol-5-yl)-5,6-dihydrobenzo[f]imidazo[1,2-d][1,4]oxazepine-9-carboxylate was hydrolyzed to give 2-(4-cyano-1-isopropyl-1H-pyrazol-5-yl)-5,6-dihydrobenzo[f]imidazo[1,2-d][1,4]oxazepine-9-carboxylic acid. MS(ESI+): 364.3

Example 17

10-Chloro-5,6-dihydroimidazo[1,2-d]pyrido[4,3-f][1,4]oxazepine

Step 1: 2-Chloro-5-(methoxymethoxy)pyridine

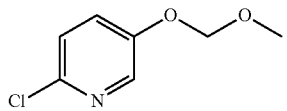

Sodium hydride, 60% dispension in mineral oil (3:2, Sodium hydride:Mineral Oil, 2.32 g) was added portion wise to a solution of 6-Chloro-pyridin-3-ol (5.00 g, 38.6 mmol) in a mixture of Tetrahydrofuran (10.0 mL, 123 mmol) and N,N-Dimethylformamide (20.0 mL, 258 mmol). The mixture formed was stirred for 15 min and Chloromethyl Methyl Ether (3.66 mL, 48.2 mmol) was added dropwise. The above mixture was stirred for 6 hours (monitored by LCMS), poured into water and extracted with ethyl acetate. The organic extracts were washed with water, brine, dried over MgSO4 and concentrated in vacuum. Purified on 40 g silica column eluting with 10-40% ethyl acetate in heptane to give 6.33 g of 2-chloro-5-(methoxymethoxy)pyridine.

Step 2: 2-Chloro-5-(methoxymethoxy)isonicotinaldehyde

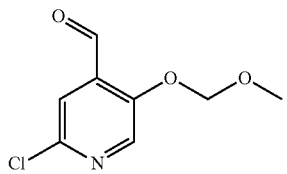

tert-Butyllithium in pentane (1.7 M, 19.0 mL) was added dropwise to a solution of 2-chloro-5-(methoxymethoxy)pyridine (4.880 g, 28.11 mmol) in 100 ml of ethyl ether at −76° C. Some precipitate appeared. The mixture was kept at −76° C. for 20 min then N,N-dimethylformamide (2.938 mL, 37.95 mmol) was added dropwise. The mixture was stirred for 10 min at −76° C. and then allowed to warm to at 0° C. for 1 h period. 10% aq NH4Cl was added and the mixture was extracted with ethyl acetate. The organic solution was washed with water, brine and dried over Na2SO4. After concentration in vacuum the yield of the crude 2-chloro-5-(methoxymethoxy)isonicotinaldehyde 5.49 g. MS: 202.0, 172.0. Without further purification was used in the next step.

Step 3: 2-chloro-4-(1H-imidazol-2-yl)-5-(methoxymethoxy)pyridine

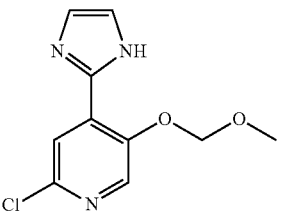 [SMILES: COCOc1cnc(Cl)cc1-c1ncc[nH]1]

Crude 2-chloro-5-(methoxymethoxy)isonicotinaldehyde (5.20 g, 25.87 mmol) was dissolved in 60 ml of methanol and mixed with 40% aqueous ethanedial (16.31 g, 112.4 mmol) and aqueous ammonia (19.15 g, 337.3 mmol). The mixture was stirred for 3 hours, concentrated in vacuum and acidified to pH<1 with 60 ml of 1 N aq HCl. The aqueous solution was extracted with ethyl acetate (3×30 ml). The organic extracts were discarded while aqueous was basified by addition of sat NaHCO3. The mixture was extracted with ethyl acetate (3×30 ml), combined organic extracts were washed with water, brine, dried and concentrated in vacuum. The residue (crude 4.185 g) was purified on 40 g silica column eluting with 60-70% of ethyl acetate in heptane to yield 2.06 g of 2-chloro-4-(1H-imidazol-2-yl)-5-(methoxymethoxy)pyridine (33%). MS(ESI+): 208 (loss of HOMe). 1H NMR (500 MHz, CDCl3) δ 10.56 (s, 1H), 8.35 (s, 1H), 8.23 (s, 1H), 7.30 (s, 1H), 7.22 (s, 1H), 5.43 (s, 2H), 3.54 (d, J=14.0, 3H).

Step 4: 6-Chloro-4-(1H-imidazol-2-yl)pyridin-3-ol

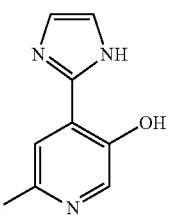

Hydrogen chloride in dioxane (4 M, 40 mL) was added dropwise to a solution of 2.06 g (8.60 mmol) of 2-chloro-4-(1H-imidazol-2-yl)-5-(methoxymethoxy)pyridine in Methylene chloride (40 mL, 600 mmol). The suspension was stirred for 2 hours and filtered. The solid was washed with DCM, ether and dried in vacuum. Yield of 6-chloro-4-(1H-imidazol-2-yl)pyridin-3-ol dihydrochloride 2.31 g (100%). MS(ESI+): 196.2. 1H NMR (400 MHz, DMSO) δ 13.20 (s, 1H), 8.14 (s, 1H), 7.96 (s, 1H), 7.42 (s, 2H).

Step 5: 10-Chloro-5,6-dihydroimidazo[1,2-d]pyrido[4,3-f][1,4]oxazepine

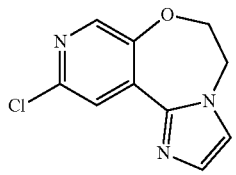 [SMILES: Clc1cc2c(cn1)OCCn1ccnc1-2]

A mixture of 2.30 g (8.55 mmol) of 6-chloro-4-(1H-imidazol-2-yl)pyridin-3-ol dihydrochloride, 1,2-dibromoethane (1.842 mL, 21.37 mmol) and Cesium Carbonate (19.46 g, 59.74 mmol) in 120 ml of N,N-Dimethylformamide was heated for 3 hours at 90° C. The mixture was filtered and concentrated in high vacuum to give 10-Chloro-5,6-dihydroimidazo[1,2-d]pyrido[4,3-f][1,4]oxazepine. Weight 1.88 g (99%) MS(ESI+): 222.2. 1H NMR (400 MHz, CDCl3) δ 8.37 (s, 1H), 8.17 (s, 1H), 7.24 (d, J=1.0, 1H), 7.10 (d, J=0.9, 1H), 4.51-4.45 (m, 4H).

Example 18

10-chloro-2,3-diiodo-5,6-dihydroimidazo[1,2-d]pyrido[4,3-f][1,4]oxazepine

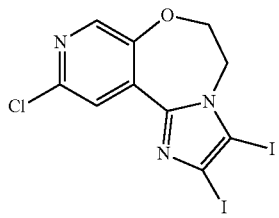 [SMILES: Clc1cc2c(cn1)OCCn1c-2nc(I)c1I]

N-Iodosuccinimide (5.771 g, 25.65 mmol) was added to 1.89 g (8.55 mmol) of 10-chloro-5,6-dihydroimidazo[1,2-d]pyrido[4,3-f][1,4]oxazepine in N,N-dimethylformamide (28 mL, 360 mmol) and the mixture was heated at 80° C. for 48 hours. A precipitate was collected, washed with DMF and ethyl ether and dried on air and then in high vacuum. Weight 2.85 g (70%). MS: 473.9. 1H NMR (500 MHz, CDCl3) δ 8.33 (s, 1H), 8.19 (s, 1H), 4.53-4.46 (m, 2H), 4.45-4.38 (m, 2H).

Example 19

10-chloro-2-iodo-5,6-dihydroimidazo[1,2-d]pyrido[4,3-f][1,4]oxazepine

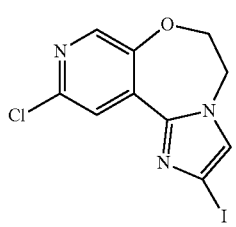 [SMILES: Clc1cc2c(cn1)OCCn1cc(I)nc1-2]

Isopropylmagnesium chloride in tetrahydrofuran (2.0 M, 3.311 mL) was added dropwise to a solution of 10-chloro-2,3-diiodo-5,6-dihydroimidazo[1,2-d]pyrido[4,3-f][1,4]oxazepine (2.850 g, 6.020 mmol) in 110 ml of tetrahydrofuran at −10° C. The mixture was allowed to warm to 10° C. in 45 min and then mixed with 250 ml of cold 10% NH4Cl. The organic layer was washed with brine and dried over Na2SO4. Concentration in vacuum afforded 2.06 g of 10-chloro-2-iodo-5,6-dihydroimidazo[1,2-d]pyrido[4,3-f][1,4]oxazepine (98.5%). MS: 348.0. 1H NMR (500 MHz, CDCl3) δ 8.33 (d, J=10.1, 1H), 8.18 (s, 1H), 7.18 (s, 1H), 4.46 (q, J=5.8, 4H).

Example 20

10-Chloro-5,6-dihydroimidazo[1,2-d]pyrido[4,3-f][1,4]oxazepine-2-carboxamide

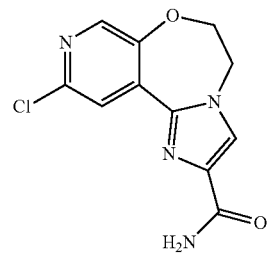 [SMILES: NC(=O)c1cn2c(n1)-c1cc(Cl)ncc1OCC2]

A mixture of 10-chloro-2-iodo-5,6-dihydroimidazo[1,2-d]pyrido[4,3-f][1,4]oxazepine (2056 mg, 5.916 mmol), bis(triphenylphosphine)palladium(II) chloride (2.10E2 mg, 0.300 mmol) and hexamethyldisilazane (7.488 mL, 35.50 mmol) in 60 ml of N,N-Dimethylformamide was subjected to carbonylation at 1 atm with CO from balloon. The reaction mixture was heated at 70° C. for 1 h. The mixture was concentrated in vacuum, the residue partitioned between ethyl acetate and 1 M aqueous sodium carbonate. The organic extracts were washed with water, brine, dried over magnesium sulfate, concentrated in vacuum and purified on a 12 g silica column eluting with 0-5% MeOH in DCM to give 1300 mg (83%). MS(ESI+): 265.0. 1H NMR (500 MHz, DMSO) δ 8.37 (s, 1H), 8.22 (s, 1H), 7.93 (s, 1H), 7.70 (s, 1H), 7.25 (s, 1H), 4.56 (s, 4H).

Example 21

10-Chloro-N-((dimethylamino)methylene)-5,6-dihydroimidazo[1,2-d]pyrido[4,3-f][1,4]oxazepine-2-carboxamide

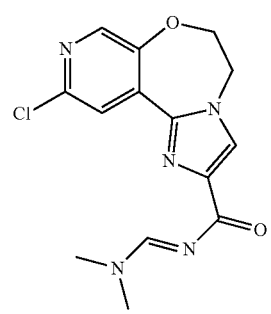 [SMILES: CN(C)/C=N/C(=O)c1cn2c(n1)-c1cc(Cl)ncc1OCC2]

A mixture of 10-chloro-5,6-dihydroimidazo[1,2-d]pyrido[4,3-f][1,4]oxazepine-2-carboxamide (1.290 g, 4.875 mmol) and 1,1-Dimethoxy-N,N-dimethylmethanamine (3.238 mL, 24.37 mmol) in 70 ml of toluene was heated under reflux for 1 hour. After cooling the product precipitated from the reaction mixture, collected, washed with ethyl ether and dried on air. Weight 0.705 g (85%). MS(ESI+): 320.1

Example 22

10-chloro-2-(1-isopropyl-1H-1,2,4-triazol-5-yl)-5,6-dihydroimidazo[1,2-d]pyrido[4,3-f][1,4]oxazepine

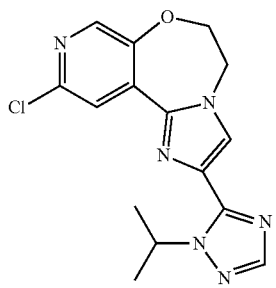 [SMILES: CC(C)n1ncnc1-c1cn2c(n1)-c1cc(Cl)ncc1OCC2]

A mixture of 660 mg (2.06 mmol) of 10-chloro-N-((dimethylamino)methylene)-5,6-dihydroimidazo[1,2-d]pyrido[4,3-f][1,4]oxazepine-2-carboxamide and isopropylhydrazine hydrochloride (0.332 g, 3.00 mmol) in 44 ml of acetic acid was heated at 85° C. for 3 hours. The mixture was cooled, filtered and mixed with 15 ml of water. A precipitate was filtered out, washed with water and dried in high vacuum. The above solid was triturated with 1o ml of ethyl acetate, filtered out, washed with ethyl acetate, ethyl ether and dried on air. Yield 0.710 g. MS: 331.2. 1H NMR (500 MHz, DMSO) δ 8.26 (s, 1H), 8.20 (s, 1H), 8.11 (s, 1H), 7.96 (s, 1H), 5.76 (dt, J=13.1, 6.6, 1H), 4.62 (q, J=5.6, 4H), 1.50 (d, J=6.6, 6H).

Example 23 methyl 4-hydroxy-3-(1H-imidazol-2-yl)benzoate

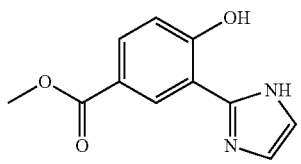 [SMILES: COC(=O)c1ccc(O)c(-c2ncc[nH]2)c1]

Following the procedure in Example 22, methyl 3-formyl-4-hydroxybenzoate was coupled with ethanal and ammonia to give methyl 4-hydroxy-3-(1H-imidazol-2-yl)benzoate. Yield 78%. MS(ESI+): 219.1

Example 24 methyl 5,6-dihydrobenzo[f]imidazo[1,2-d][1,4]oxazepine-10-carboxylate

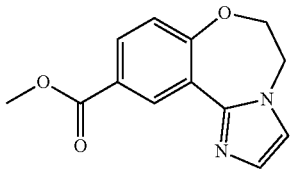 [SMILES: COC(=O)c1ccc2c(c1)-c1nccn1CCO2]

Following the procedure in Example 17, methyl 4-hydroxy-3-(1H-imidazol-2-yl)benzoate reacted with 1,2-dibromoethane to give methyl 5,6-dihydrobenzo[f]imidazo[1,2-d][1,4]oxazepine-10-carboxylate. Yield 76%. MS(ESI+): 245.0. 1H NMR (400 MHz, CDCl3) δ 9.21 (d, J=2.2, 1H), 7.91 (dd, J=8.6, 2.2, 1H), 7.20 (t, J=4.8, 1H), 7.05 (d, J=8.6, 1H), 7.00 (d, J=0.8, 1H), 4.53-4.48 (m, 2H), 4.43-4.39 (m, 2H), 3.91 (d, J=5.9, 3H).

Example 25 methyl 2,3-diiodo-5,6-dihydrobenzo[f]imidazo[1,2-d][1,4]oxazepine-10-carboxylate

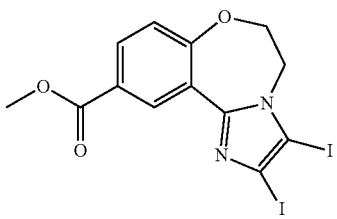 [SMILES: COC(=O)c1ccc2c(c1)-c1nc(I)c(I)n1CCO2]

A mixture of methyl 5,6-dihydrobenzo[f]imidazo[1,2-d][1,4]oxazepine-10-carboxylate (2670 mg, 9.29 mmol) and N-Iodosuccinimide (5230 mg, 23.2 mmol) in 100 ml of N,N-Dimethylformamide was heated at 80° C. for 3 hours. The mixture was mixed 300 ml of water and extracted 3×120 ml of methylene chloride. The combined organic extracts were washed with 5% aq sodium bicarbonate, 2×50 ml of 10% aq sodium thiosulfate, water, brine, dried over MgSO4 and concentrated in vacuum to a small volume. The precipitate was filtered, washed with methylene chloride and dried in vacuum. Yield 3.86 g (84%). MS 497.0. 1H NMR (500 MHz, CDCl3) δ 9.12 (d, J=2.0, 1H), 7.93 (dd, J=8.6, 2.1, 1H), 7.05 (d, J=8.6, 1H), 4.55-4.46 (m, 2H), 4.38 (dd, J=5.0, 2.9, 2H), 3.92 (s, 3H).

Example 26 methyl 2-iodo-5,6-dihydrobenzo[f]imidazo[1,2-d][1,4]oxazepine-10-carboxylate

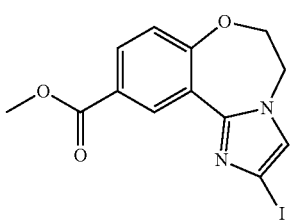 [SMILES: COC(=O)c1ccc2c(c1)-c1nc(I)cn1CCO2]

Following the procedure in Example 26, methyl 2,3-diiodo-5,6-dihydrobenzo[f]imidazo[1,2-d][1,4]oxazepine-10-carboxylate was converted to methyl 2-iodo-5,6-dihydrobenzo[f]imidazo[1,2-d][1,4]oxazepine-10-carboxylate. Yield 95%. MS(ESI+): 370.9. 1H NMR (400 MHz, CDCl3) δ 9.15 (d, J=2.1, 1H), 7.92 (dd, J=8.6, 2.2, 1H), 7.08 (s, 1H), 7.04 (t, J=7.9, 1H), 4.48 (dd, J=9.5, 5.5, 2H), 4.40 (dd, J=9.4, 5.5, 2H), 3.92 (s, 3H).

Example 27 methyl 2-cyano-5,6-dihydrobenzo[f]imidazo[1,2-d][1,4]oxazepine-10-carboxylate

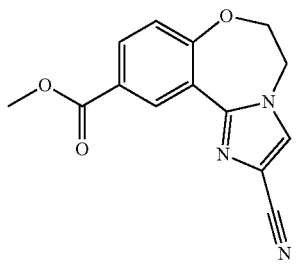 [SMILES: COC(=O)c1ccc2c(c1)-c1nc(C#N)cn1CCO2]

2-iodo-5,6-dihydrobenzo[f]imidazo[1,2-d][1,4]oxazepine-10-carboxylate (370.1 mg, 1.0 mmol) and Copper cyanide (268.6 mg, 3.000 mmol) were mixed in 8 ml of N,N-Dimethylformamide. The reaction was microwaved on 200 watts, 150° C., for 40 minutes. The reaction mixture was partitioned between 25 ml of 5% ammonia in water and 25 ml of EtOAc. The aqueous layer was additionally extracted with 3×20 ml EtOAc, combined extracts were washed with water, brine and dried over MgSO4 to afford 225 mg of methyl 2-cyano-5,6-dihydrobenzo[f]imidazo[1,2-d][1,4]oxazepine-10-carboxylate. Yield 81%. (MS: 270.0).

Example 28 methyl 2-carbamoyl-5,6-dihydrobenzo[f]imidazo[1,2-d][1,4]oxazepine-10-carboxylate

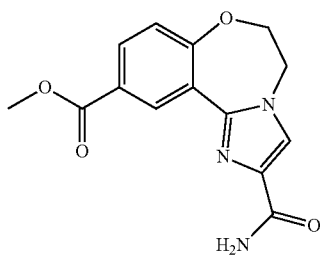 [SMILES: COC(=O)c1ccc2c(c1)-c1nc(C(N)=O)cn1CCO2]

Methyl 2-cyano-5,6-dihydrobenzo[f]imidazo[1,2-d][1,4]oxazepine-10-carboxylate (220 mg, 0.82 mmol) was dissolved in 4.0 ml of dimethyl sulfoxide and treated with a solution of potassium carbonate (136 mg, 0.980 mmol) in water (1.60 mL, 88.8 mmol). After cooling at 0° C., hydrogen peroxide (0.751 mL, 9.80 mmol) was added slowly. The mixture was stirred at room temperature for 2 hours. The mixture was diluted with 20 ml of water and extracted with ethyl acetate (3×20 ml). The organic extracts were washed with 5% sodium thiosufate, sat. NaHCO3, brine, dried over sodium sulfate and concentrated to give 180 mg (77%) of crude methyl 2-carbamoyl-5,6-dihydrobenzo[f]imidazo[1,2-d][1,4]oxazepine-10-carboxylate. MS(ESI+): 288.0.

Example 29 methyl 2-((dimethylamino)methylenecarbamoyl)-5,6-dihydrobenzo[f]imidazo[1,2-d][1,4]oxazepine-10-carboxylate

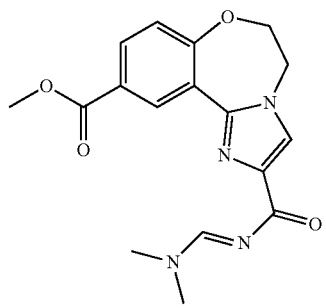 [SMILES: COC(=O)c1ccc2c(c1)-c1nc(C(=O)/N=C/N(C)C)cn1CCO2]

Following the procedure in Example 21, methyl 2-carbamoyl-5,6-dihydrobenzo[f]imidazo[1,2-d][1,4]oxazepine-10-carboxylate was converted to methyl 2-((dimethylamino)methylenecarbamoyl)-5,6-dihydrobenzo[f]imidazo[1,2-d][1,4]oxazepine-10-carboxylate Yield 82%. MS(ESI+): 343.1

Example 30 methyl 2-(1-(2-chlorophenyl)-1H-1,2,4-triazol-5-yl)-5,6-dihydrobenzo[f]imidazo[1,2-d][1,4]oxazepine-10-carboxylate

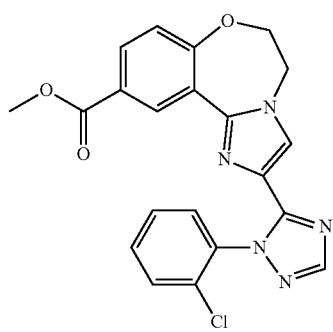 [SMILES: COC(=O)c1ccc2c(c1)-c1nc(-c3ncnn3-c3ccccc3Cl)cn1CCO2]

Following the procedure in Example 22, methyl 2-((dimethylamino)methylenecarbamoyl)-5,6-dihydrobenzo[f]imidazo[1,2-d][1,4]oxazepine-10-carboxylate was coupled with 2-chlorophenylhydrazine hydrochloride to give methyl 2-(1-(2-chlorophenyl)-1H-1,2,4-triazol-5-yl)-5,6-dihydrobenzo[f]imidazo[1,2-d][1,4]oxazepine-10-carboxylate. Yield 59%. MS(ESI+): 422.1

Example 31

2-(1-(2-chlorophenyl)-1H-1,2,4-triazol-5-yl)-5,6-dihydrobenzo[f]imidazo[1,2-d][1,4]oxazepine-10-carboxylic acid

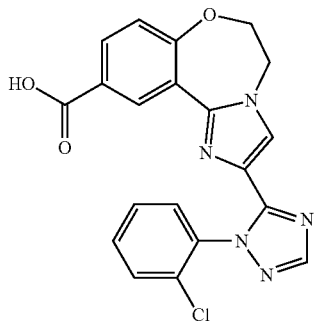 [SMILES: O=C(O)c1ccc2c(c1)-c1nc(-c3ncnn3-c3ccccc3Cl)cn1CCO2]

Following the procedure in Example 12, methyl 2-(1-(2-chlorophenyl)-1H-1,2,4-triazol-5-yl)-5,6-dihydrobenzo[f]imidazo[1,2-d][1,4]oxazepine-10-carboxylate was hydrolyzed to give 2-(1-(2-chlorophenyl)-1H-1,2,4-triazol-5-yl)-5,6-dihydrobenzo[f]imidazo[1,2-d][1,4]oxazepine-10-carboxylic acid. Yield 75%. MS(ESI+): 408.1

Example 33

9-bromo-5,6-dihydrobenzo[f]imidazo[1,2-d][1,4]oxazepine-2-carbaldehyde

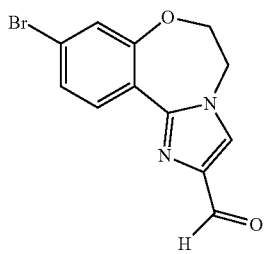 [SMILES: O=Cc1cn2c(n1)-c1ccc(Br)cc1OCC2]

Ethylmagnesium bromide in ethyl ether (3.0 M, 3.472 mL) was added dropwise to a solution of 9-bromo-2-iodo-5,6-dihydrobenzo[f]imidazo[1,2-d][1,4]oxazepine (1173 mg, 3.000 mmol) in 20 ml of tetrahydrofuran at −30° C. The mixture was stirred at this temperature for 20 min and allowed to warm to 15° C. The mixture was cooled to −25° C. again and N,N-dimethylformamide (929.2 uL, 12.00 mmol) was added. The mixture was left for 18 hours. The mixture was quenched with sat. aq. NH4Cl and extracted with ethyl acetate. The organic extracts were washed with water, brine, dried over mgSO4 and concentrated in vacuum. Yield 0.92 g. MS: 293.1

Example 34

9-bromo-2-(4-methyl-1H-imidazol-2-yl)-5,6-dihydrobenzo[f]imidazo[1,2-d][1,4]oxazepine

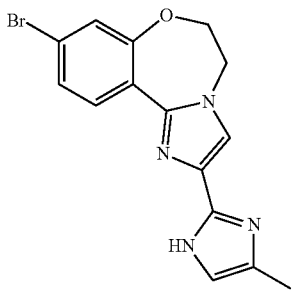 [SMILES: Cc1c[nH]c(-c2cn3c(n2)-c2ccc(Br)cc2OCC3)n1]

Ammonia in water (16.0 M, 0.819 mL) was added to a solution of 9-bromo-5,6-dihydrobenzo[f]imidazo[1,2-d][1,4]oxazepine-2-carbaldehyde (640 mg, 2.2 mmol) and pyruvaldehyde (0.787 g, 4.37 mmol) in methanol (17 mL, 420 mmol) and Tetrahydrofuran (6 mL, 70 mmol). After 1 hour the same amount of pyruvaldehyde and 16.0 M of Ammonia in water were added again. The mixture was stirred for 2 h, concentrated in vacuum and the residue partitioned between ethyl acetate and water. The organic extract was washed with water, brine, dried over MgSO4 and concentrated. The residue was purified on 4 g silica column using ethyl acetate gradient in dichloromethane. Weight 0.417 g. MS: 344.9.

Example 35

9-bromo-2-(1H-imidazol-2-yl)-5,6-dihydrobenzo[f]imidazo[1,2-d][1,4]oxazepine

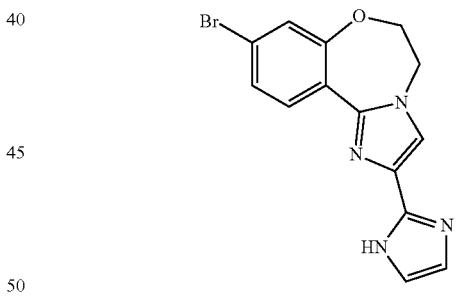

Ethanedial (0.689 mL, 6.01 mmol) and 16.0 M of Ammonia in water (1.50 mL) were added to a 9-bromo-5,6-dihydrobenzo[f]imidazo[1,2-d][1,4]oxazepine-2-carbaldehyde (550 mg, 1.5 mmol) in Methanol (30.0 mL, 742 mmol) After 1 hour, additional quantity of Ethanedial and ammonia were added and the mixture was stirred for 4 hours. The mixture then was concentrated in vacuum and partitioned between 0.5 N HCl and ethyl acetate. The organic extract was discarded, the acidic aqueous basified by careful addition of sat. NaHCO3. The mixture was extracted with ethyl acetate, the organic extracts were washed with water, brine, dried and concentrated. The residue was triturated with DCM to produce a precipitate which was collected, washed with cold DCM and dried to give 9-bromo-2-(1H-imidazol-2-yl)-5,6-dihydrobenzo[f]imidazo[1,2-d][1,4]oxazepine. MS: (ESI+)=331.2

Example 36

9-bromo-2-(1-isopropyl-1H-imidazol-2-yl)-5,6-dihydrobenzo[f]imidazo[1,2-d][1,4]oxazepine

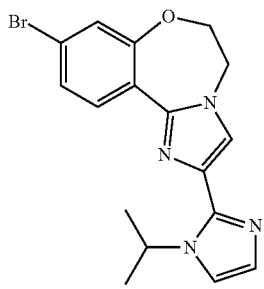 [SMILES: CC(C)n1ccnc1-c1cn2c(n1)-c1ccc(Br)cc1OCC2]

To a solution of 9-bromo-2-(1H-imidazol-2-yl)-5,6-dihydrobenzo[f]imidazo[1,2-d][1,4]oxazepine (0.237 g, 0.716 mmol) and Cesium Carbonate (0.280 g, 0.859 mmol) in N,N-Dimethylformamide (4.74 mL, 61.2 mmol) was added Isopropyl iodide (0.0859 mL, 0.859 mmol). The reaction was stirred 18 h at 50 C. The reaction was quenched with water then extracted EtOAc 2x. The crude product was purified to give 9-bromo-2-(1-isopropyl-1H-imidazol-2-yl)-5,6-dihydrobenzo[f]imidazo[1,2-d][1,4]oxazepine. MS: (ESI+)=373.1

Example 37 methyl 3-hydroxy-4-(1H-imidazol-2-yl)benzoate

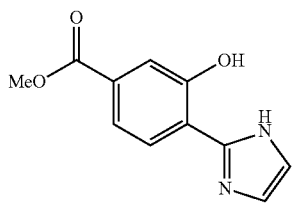 [SMILES: COC(=O)c1ccc(-c2ncc[nH]2)c(O)c1]

4-Formyl-3-hydroxybenzoic acid (5 g, 30 mmol) was suspended in methanol (70 mL), and treated with thionyl chloride (3.29 mL 45 mmol) dropwise. The mixture was heated to reflux overnight. Concentrated to dryness, and 50 mL of toluene was added, and concentrated again. The residue was recrystallized from ethyl acetate-hexane. A total of 4.8 g (85%) of methyl 4-formyl-3-hydroxybenzoate was obtained.

A mixture of methyl 4-formyl-3-hydroxybenzoate (4.8 g, 27 mmol), 40% aqueous solution of ethanedial (11.6 g, 79.93 mmol) and 50% aqueous ammonia (6.8 g, 399 mmol) in methanol (50 mL) was stirred for 2 hours or longer until the reaction is done. The solvent was removed by rotary evaporation, and the residue was partitioned between ethyl acetate and water. The mixture was filtered to remove the precipitates. pH was adjusted to 5-6 by careful addition of 1 N HCl. The aqueous layer was extracted with EtOAc three times. The combined organic layer was washed with water, brine and dried over MgSO4. The residue was purified by flash chromatography to yield methyl 3-hydroxy-4-(1H-imidazol-2-yl)benzoate as a yellow solid (4 g, 71%)

Example 38 methyl 5,6-dihydrobenzo[f]imidazo[1,2-d][1,4]oxazepine-9-carboxylate

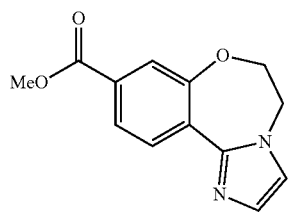 [SMILES: COC(=O)c1ccc2c(c1)OCCn1ccnc1-2]

A mixture of methyl 3-hydroxy-4-(1H-imidazol-2-yl)benzoate (2.2 g, 10 mmol), 1,2-dibromoethane (3.12 mL, 36 mmol) and cesium carbonate (13.14 g, 40 mmol) in DMF (100 mL) was heated at 90° C. for 12 hours. The mixture was filtered, the mother liquor was concentrated in vacuo, and the residue was partitioned between water and ethyl acetate. The suspension was filtered and the solid was pure byproduct. The organic layer was washed with water, brine and dried over MgSO4 and concentrated to give crude methyl 5,6-dihydrobenzo[f]imidazo[1,2-d][1,4]oxazepine-9-carboxylate (2 g, 80%).

Example 38a 10-bromo-5,6-dihydrobenzo[f]imidazo[1,2-d][1,4]oxazepine

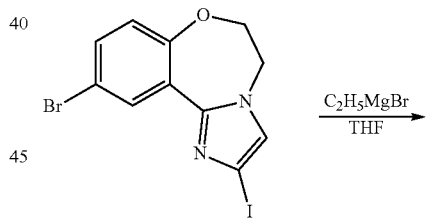

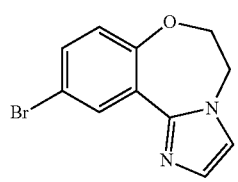

To a solution of 10-bromo-2-iodo-5,6-dihydrobenzo[f]imidazo[1,2-d][1,4]oxazepine (9 g, 20 mmol) in THF (40 mL) was added Ethylmagnesium bromide in Ethyl ether (22 mL) at −20° C. The mixture was allowed to warm to room temperature and in one and half hour the completion was showed by LCMS. The reaction mixture was poured into 10% NH4Cl and extracted by EtOAc. Organic layer was washed by brine, dried by MgSO4 and concentrated. The crude was purified by Isco chromatography to afford 10-bromo-5,6-dihydrobenzo[f]imidazo[1,2-d][1,4]oxazepine. LC/MS(ESI+): m/z 265 (M+H).

Example 38b 10-(2-fluoropyridin-3-yl)-5,6-dihydrobenzo[f]imidazo[1,2-d][1,4]oxazepine

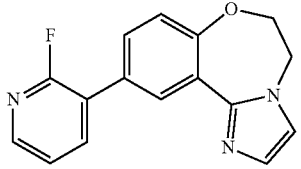 [SMILES: Fc1ncccc1-c1ccc2c(c1)-c1nccn1CCO2]

To 10-bromo-5,6-dihydrobenzo[f]imidazo[1,2-d][1,4]oxazepine (140 mg, 0.53 mmol) in DMF (20 mL) and water (2 mL) was added 2-Fluoropyridine-3-boronic acid (89 mg, 0.632 mmol), Potassium acetate (207 mg, 2.11 mmol) and Tetrakis(triphenylphosphine)palladium (30 mg, 0.0264 mmol). The reaction mixture was degassed for 5 minutes, and heated at 100° C. overnight. LCMS showed desired product peak. The reaction was allowed to cool to room temperature, diluted with EtOAc, and filtered through a thin pad of celite. The filtrate was washed with water followed by brine, dried over MgSO4 and concentrated. The crude residue was purified by Prep HPLC to provide 10-(2-fluoropyridin-3-yl)-5,6-dihydrobenzo[f]imidazo[1,2-d][1,4]oxazepine. LC/MS(ESI+): m/z 282 (M+H)

Example 38c 3-(5,6-dihydrobenzo[f]imidazo[1,2-d][1,4]oxazepin-10-yl)pyridin-2(1H)-one

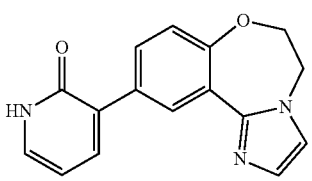 [SMILES: O=c1[nH]cccc1-c1ccc2c(c1)-c1nccn1CCO2]

To a solution of 10-(2-fluoropyridin-3-yl)-5,6-dihydrobenzo[f]imidazo[1,2-d][1,4]oxazepine (100 mg, 0.4 mmol) in DME (4 mL) was added 10% aqueous HCl (4 mL). The reaction was allowed to stir and heated at 80° C. overnight. The reaction was allowed to cool to room temperature and concentrated under reduced pressure. The crude was purified by Prep HPLC to provide 3-(5,6-dihydrobenzo[f]imidazo[1,2-d][1,4]oxazepin-10-yl)pyridin-2(1H)-one. LC/MS(ESI+): m/z 280 (M+H). 1H NMR (500 MHz, DMSO) δ 11.73 (s, 1H), 8.71 (d, J=2.3, 1H), 7.72-7.50 (m, 1H), 7.47-7.21 (m, 1H), 7.15-6.86 (m, 2H), 6.29 (t, J=6.6, 1H), 4.44 (d, J=6.1, 4H).

Example 38d 4-(5,6-dihydrobenzo[f]imidazo[1,2-d][1,4]oxazepin-10-yl)pyridin-2(1H)-one

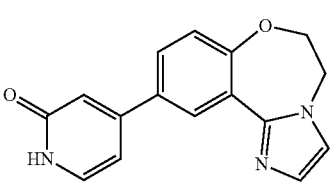 [SMILES: O=c1cc(-c2ccc3c(c2)-c2nccn2CCO3)cc[nH]1]

Following the procedures of Examples 38a-c, 4-(5,6-dihydrobenzo[f]imidazo[1,2-d][1,4]oxazepin-10-yl)pyridin-2(1H)-one was prepared. LC/MS (ESI+): m/z 280 (M+H). H NMR (500 MHz, DMSO) δ 8.70 (d, J=2.5, 1H), 7.59 (dd, J=8.5, 2.5, 1H), 7.45 (d, J=6.8, 1H), 7.35 (s, 1H), 7.09 (dd, J=16.9, 4.7, 2H), 6.57-6.36 (m, 2H), 4.47 (dd, J=11.6, 5.6, 4H).

Example 38e 5-(5,6-dihydrobenzo[f]imidazo[1,2-d][1,4]oxazepin-10-yl)pyridin-2(1H)-one

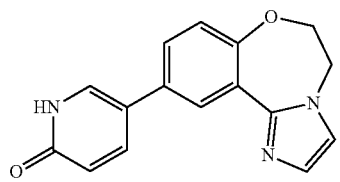 [SMILES: O=c1ccc(-c2ccc3c(c2)-c2nccn2CCO3)c[nH]1]

Following the procedures of Examples 38a-c, 5-(5,6-dihydrobenzo[f]imidazo[1,2-d][1,4]oxazepin-10-yl)pyridin-2(1H)-one was prepared. LC/MS (ESI+): m/z 280 (M+H). 1H NMR (500 MHz, DMSO) δ 8.48 (s, 1H), 8.03 (s, 1H), 7.94 (s, 1H), 7.83 (d, J=10.8, 1H), 7.77 (d, J=8.7, 1H), 7.21 (d, J=8.7, 2H), 6.46 (d, J=9.8, 1H), 4.65 (dd, J=24.3, 4.8, 4H).

Example 39 methyl 2,3-diiodo-5,6-dihydrobenzo[f]imidazo[1,2-d][1,4]oxazepine-9-carboxylate

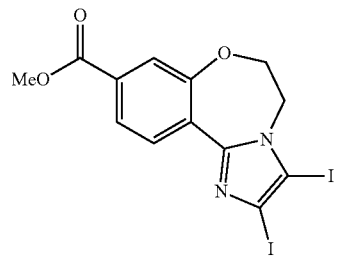 [SMILES: COC(=O)c1ccc2c(c1)OCCn1c-2nc(I)c1I]

A mixture of methyl 5,6-dihydrobenzo[f]imidazo[1,2-d][1,4]oxazepine-9-carboxylate (2 g, 8 mmol) and NIS (9.2 g, 41 mmol) in DMF was heated at 80° C. overnight. The mixture was diluted with ethyl acetate and water. The thick suspension was filtered through a glass filter. The solid was washed with ethyl acetate, then further diluted with THF, and dried over MgSO4. LCMS indicated that this solution contained pure product. The brown solution was washed with 10% sodium thiosulfate, water, brine dried over MgSO4 and concentrated to small volume. The precipitate was filtered and dried to give methyl 2,3-diiodo-5,6-dihydrobenzo[f]imidazo[1,2-d][1,4]oxazepine-9-carboxylate (3.4 g, 81% yield).

Example 40 methyl 2-iodo-5,6-dihydrobenzo[f]imidazo[1,2-d][1,4]oxazepine-9-carboxylate

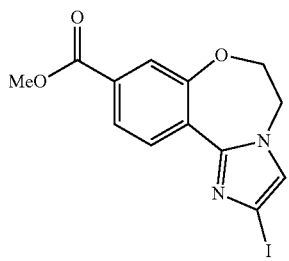 [SMILES: COC(=O)c1ccc2c(c1)OCCn1cc(C#N)nc1-2]

Fresh ethyl magnesium bromide in ethyl ether (3.0 M 1.1 mL) was added dropwise to a suspension of methyl 2,3-diiodo-5,6-dihydrobenzo[f]imidazo[1,2-d][1,4]oxazepine-9-carboxylate (1.1 g, 2.2 mmol) in THF at −15° C. The mixture was stirred and monitored using LC/MS. After 1 hour, there was no remaining starting material and the reaction was poured into sat. NH4Cl and extracted with EtOAc. The organic extracts were washed with water, brine, dried over MgSO4 and concentrated. At the end of this process, 0.7 g (80%) of methyl 2-iodo-5,6-dihydrobenzo[f]imidazo[1,2-d][1,4]oxazepine-9-carboxylate was obtained.

Example 41 methyl 2-cyano-5,6-dihydrobenzo[f]imidazo[1,2-d][1,4]oxazepine-9-carboxylate

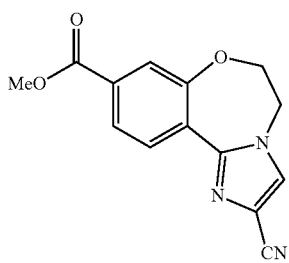

Methyl 2-iodo-5,6-dihydrobenzo[f]imidazo[1,2-d][1,4]oxazepine-9-carboxylate (740, 2.3 mmol) and copper cyanide (537 mg, 6.9 mmol) were mixed in DMF (8 mL). The reaction was microwaved on 200 watts, 150° C. for 40 minutes. The reaction mixture was partitioned between 15% ammonia in water and EtOAc. The aqueous layer was extracted with EtOAc three times, combined organic extracts were washed with water, brine and dried over MgSO4 to produce 0.46 g (74% yield) of methyl 2-cyano-5,6-dihydrobenzo[f]imidazo[1,2-d][1,4]oxazepine-9-carboxylate.

Example 42 methyl 2-carbamoyl-5,6-dihydrobenzo[f]imidazo[1,2-d][1,4]oxazepine-9-carboxylate

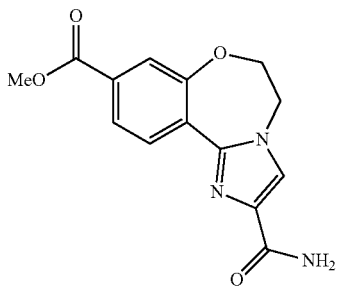 [SMILES: COC(=O)c1ccc2c(c1)OCCn1cc(C(N)=O)nc1-2]

Methyl 2-cyano-5,6-dihydrobenzo[f]imidazo[1,2-d][1,4]oxazepine-9-carboxylate (0.46 g, 1.7 mmol) was stirred with potassium carbonate (469 mg, 3.4 mmol), water (1.2 mL) and hydrogen peroxide (408 mg, 6 mmol) in DMSO (7 mL) for 4 hours. The mixture was diluted with 70 mL of water and extracted with ethyl acetate. Ethyl acetate solution was washed with water, 5% Na2S2O3, water, brine, dried over MgSO4 and concentrated under vacuum to give methyl 2-carbamoyl-5,6-dihydrobenzo[f]imidazo[1,2-d][1,4]oxazepine-9-carboxylate (0.37 g).

Example 43

9-bromo-5,6-dihydrobenzo[f]imidazo[1,2-d][1,4]oxazepine-2-carboxamide

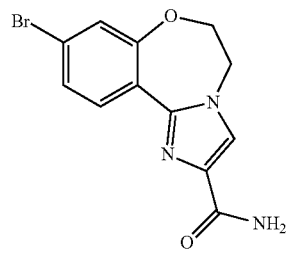 [SMILES: NC(=O)c1cn2c(n1)-c1ccc(Br)cc1OCC2]

Step 1: 5-bromo-2-(1H-imidazol-2-yl)phenol

4-Bromo-2-hydroxybenzaldehyde (1.0 g, 5 mmol), 40% aqueous solution of ethanedial (3.6 g, 24.87 mmol) and 50% aqueous ammonia (2.5 g) in methanol (20 mL) was stirred for 2 h or longer until the reaction is done. The solvent was concentrated by rotary evaporation and the residue was partitioned between EtOAc and water. The mixture was filtered to remove the precipitate. pH was adjusted to 5-6 by careful addition of 1 N HCl. The aqueous layer was extracted with EtOAc three times. The combined organic layer was washed with water, brine and dried over MgSO4. Purified by ISCO chromatography (30% EtOAc/DCM) yielded 5-bromo-2-(1H-imidazol-2-yl)phenol as yellow solid 0.9 g.

Step 2: 9-bromo-5,6-dihydrobenzo[f]imidazo[1,2-d][1,4]oxazepine

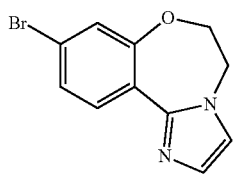 [SMILES: Brc1ccc2c(c1)OCCn1ccnc1-2]

A mixture of 5-bromo-2-(1H-imidazol-2-yl)phenol (0.9 g, 4 mmol), 1,2-dibromoethane (1.3 mL, 15 mmol) and cesium carbonate (4.9 g, 15 mmol) in DMF (20 mL) was heated to 90° C. for 12 h. The mixture was partitioned between water and ethyl acetate. The organic layer was washed with water, brine and dried over MgSO4 and concentrated to give 9-bromo-5,6-dihydrobenzo[f]imidazo[1,2-d][1,4]oxazepine (0.8 g).

Step 3: 9-bromo-2,3-diiodo-5,6-dihydrobenzo[f]imidazo[1,2-d][1,4]oxazepine

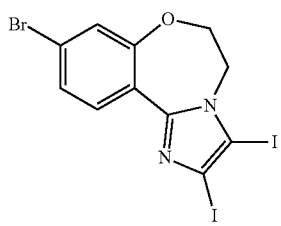 [SMILES: Brc1ccc2c(c1)OCCn1c-2nc(I)c1I]

A mixture of 9-bromo-5,6-dihydrobenzo[f]imidazo[1,2-d][1,4]oxazepine (0.8 g, 3 mmol) and NIS (1.87 g, 8.3 mmol) in DMF was stirred at room temperature for 48 h. The mixture was diluted with ethyl acetate, washed with 5% sodium bicarbonate, 10% sodium thiosulfate, water and brine and the organic layer was dried over MgSO4 and concentrated to a solid residue. Purified by ISCO chromatography (30% EtOAc/Heptane) yielded 9-bromo-2,3-diiodo-5,6-dihydrobenzo[f]imidazo[1,2-d][1,4]oxazepine 1.2 g.

Step 4: 9-bromo-2-iodo-5,6-dihydrobenzo[f]imidazo[1,2-d][1,4]oxazepine

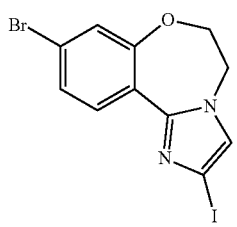 [SMILES: Brc1ccc2c(c1)OCCn1cc(I)nc1-2]

A 3.0 M solution of ethylmagnesium bromide in ethyl ether (1.1 mL) was added dropwise to a suspension of 9-bromo-2,3-diiodo-5,6-dihydrobenzo[f]imidazo[1,2-d][1,4]oxazepine (1.1 g, 2.2 mmol) in THF at −15° C. The mixture was stirred and followed by LC/MS. After 1 hour, there is no starting material left and the reaction was poured into sat. NH4Cl and extracted with ethyl acetate. The organic extracts were washed with water, brine, dried over MgSO4 and concentrated. The crude residue was purified by flash column chromatography to provide 9-bromo-2-iodo-5,6-dihydrobenzo[f]imidazo[1,2-d][1,4]oxazepine as white solid (0.7 g).

Step 5: 9-bromo-5,6-dihydrobenzo[f]imidazo[1,2-d][1,4]oxazepine-2-carboxamide

9-Bromo-2-iodo-5,6-dihydrobenzo[f]imidazo[1,2-d][1,4]oxazepine (1.5 g, 3.8 mmol) and bis(triphenylphosphine)palladium(II) chloride (142 mg, 0.202 mmol), DMF (45 mL) and hexamethyldisilazane (4.34 mL, 20.6 mmol) were mixed. The entire solution was purged with a CO balloon and sealed with the CO balloon attached. The reaction flask was heated at 70° C. for 2 h. LC/MS indicated clean conversion. Cooled to room temp and poured into 1 N HCl (30 mL). Stirred for 5 min and neutralized with sat. aq. NaHCO3 soln. Extracted three times with EtOAc, dried over MgSO4, filtered and concentrated in vacuo. Triturated with IPA and the solids were collected after filtration and EtOAc wash. This provided 734 mg (62% yield) of 9-bromo-5,6-dihydrobenzo[f]imidazo[1,2-d][1,4]oxazepine-2-carboxamide as a tan solid. LC/MS(ESI+): m/z 310 (M+H). 1H NMR (400 MHz, CDCl3) δ 8.36 (d, J=8.5, 1H), 7.63 (s, 1H), 7.24 (dd, J=7.2, 4.2, 1H), 7.09-6.99 (m, 1H), 4.51-4.36 (m, 4H).

Example 44

9-bromo-N-formyl-5,6-dihydrobenzo[f]imidazo[1,2-d][1,4]oxazepine-2-carboxamide

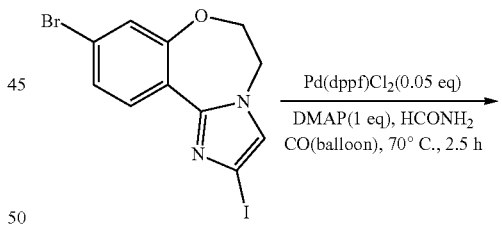

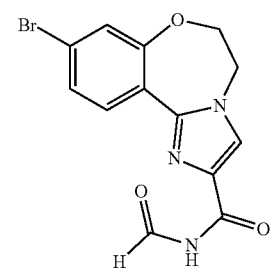

9-Bromo-2-iodo-5,6-dihydrobenzo[f]imidazo[1,2-d][1,4]oxazepine (10 g, 25.6 mmol) was heated in formamide (200 mL) with Pd(dppf)Cl2 (0.94 g, 1.28 mmol) and DMAP (3.13 g, 25.6 mmol) under CO balloon at 70° C. for 2.5 h. The mixture was cooled to room temperature, diluted with EtOAc and filtered. The resulting precipitate was dried to obtain 9-bromo-N-formyl-5,6-dihydrobenzo[f]imidazo[1,2-d][1,4]oxazepine-2-carboxamide (6.7 g, 78%). 1H NMR (DMSO-d6, 400 MHz): δ 11.10 (d, J=9.6 Hz, 1H), 9.21 (d, J=9.6 Hz, 1H), 8.53 (d, J=8.8 Hz, 1H), 8.24 (s, 1H), 7.34-7.28 (m, 2H), 4.53-4.50 (m, 4H). LC-MS: (ESI, m/z) =336 [M+H]+

Example 46

8-Bromo-4,5-dihydro-6-oxa-1,3a-diaza-benzo[e]azulene-2-carboxylic acid [1-dimethylamino-eth-(E)-ylidene]-amide

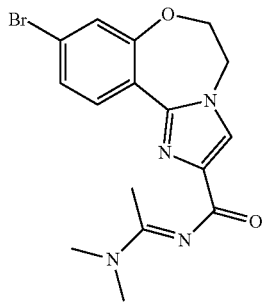 [SMILES: C/C(=N\C(=O)c1cn2c(n1)-c1ccc(Br)cc1OCC2)N(C)C]

To a solution of 8-Bromo-4,5-dihydro-6-oxa-1,3a-diaza-benzo[e]azulene-2-carboxylic acid amide (0.280 g, 0.000909 mol) in toluene (5 mL) was added dimethylacetamide-dimethylacetal (0.405 mL, 0.00273 mol). The solution was stirred at 95° C. for 4 h. The toluene was removed in vacuo to give 8-Bromo-4,5-dihydro-6-oxa-1,3a-diaza-benzo[e]azulene-2-carboxylic acid [1-dimethylamino-eth-(E)-ylidene]-amide. MS(ESI+) 377.1/379.1.

Example 47

[5-(8-Bromo-4,5-dihydro-6-oxa-1,3a-diaza-benzo[e]azulen-2-yl)-1-isopropyl-1H-[1,2,4]triazol-3-yl]-carbamic acid tert-butyl ester

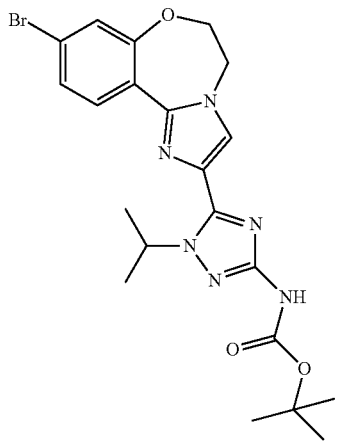 [SMILES: CC(C)n1nc(NC(=O)OC(C)(C)C)nc1-c1cn2c(n1)-c1ccc(Br)cc1OCC2]

Step 1: 8-Bromo-4,5-dihydro-6-oxa-1,3a-diaza-benzo[e]azulene-2-carboxylic acid methyl ester

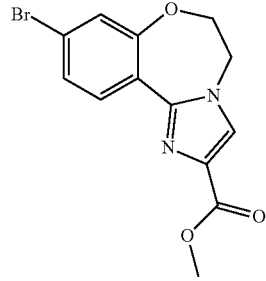 [SMILES: COC(=O)c1cn2c(n1)-c1ccc(Br)cc1OCC2]

8-Bromo-2-iodo-4,5-dihydro-6-oxa-1,3a-diaza-benzo[e]azulene (6.000 g, 0.01534 mol) followed by palladium acetate (0.1722 g, 0.0007672 mol) and 4,5-bis(diphenylphosphino)-9,9-dimethylxanthene (0.8879 g, 0.001534 mol) were added sequentially to a dry nitrogen-filled flask. Degassed triethylamine (180 mL, 1.3 mol) and methanol (60 mL) were added, and the reaction mixture was thoroughly purged with a carbon monoxide balloon for about 3 minutes. Two carbon monoxide balloons were fixed to the flask and the reaction was heated to 50° C. for 3 hours. The reaction was purged with nitrogen, concentrated in vacuo, and dry loaded onto silica gel. The crude was purified by flash chromatography (40-100% ethyl acetate in hexanes followed by 5-15% MeOH in DCM) to give 8-Bromo-4,5-dihydro-6-oxa-1,3a-diaza-benzo[e]azulene-2-carboxylic acid methyl ester (4.242 g) as a light brown solid. MS(ESI+) 323.0/325.0

Step 2: 8-Bromo-4,5-dihydro-6-oxa-1,3a-diaza-benzo[e]azulene-2-carboxylic acid

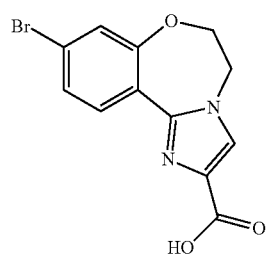 [SMILES: O=C(O)c1cn2c(n1)-c1ccc(Br)cc1OCC2]

To a solution of 8-Bromo-4,5-dihydro-6-oxa-1,3a-diaza-benzo[e]azulene-2-carboxylic acid methyl ester (1.000 g, 0.003095 mol) in tetrahydrofuran (7.50 mL) and water (4.5 mL) was added lithium hydroxide (0.2964 g, 0.01238 mol). The reaction was stirred at 45° C. for 2 h. The mixture was acidified to pH=1 with 2N HCl. The resulting precipitate was filtered and rinsed with cold water to obtain 8-Bromo-4,5-dihydro-6-oxa-1,3a-diaza-benzo[e]azulene-2-carboxylic acid (860 mg) as an off-white solid. MS(ESI+) 309.0/311.0

Alternatively, to a solution of 8-bromo-2-iodo-4,5-dihydro-6-oxa-1,3a-diaza-enzo[e]azulene (10 g, 25.6 mmol) in THF (120 mL) at −78° C. was added nBuLi (19.2 mL, 1.6 M in hexanes, 30.7 mmol) at such a rate that Tmax<−73° C. During the addition the purple colour faded and a tan precipitate formed. The reaction mixture was stirred at −78°

C. for 20 min. CO2 generated from dry-ice and passed over drying silica was bubbled through the reaction for 30 min. The temperature rose to −55° C. before dropping back to −78° C. A thick precipitate formed quickly during the addition of CO2. The reaction was stirred at −78° C. for 1 h. The reaction was quenched by pouring onto 20 mL water (CARE:effervescent). The mixture was allowed to warm to RT. The pH of the mixture was adjusted to ~pH 8 by addition of saturated aqueous NaHCO3 and the aqueous layer washed with ethyl acetate. The aqueous fraction was collected and the pH adjusted to ~pH 4 by addition of AcOH. The precipitate formed was collected by filtration, washed with water and dried in vacuo to give 8-Bromo-4,5-dihydro-6-oxa-1,3a-diaza-benzo[e]azulene-2-carboxylic acid as a beige solid (4.38 g, 55%). 1H NMR (400 MHz, d6-DMSO) 8.31 (1H, d, J=8.5 Hz), 7.98 (1H, s), 7.32 (1H, dd, J=8.5, 2.2 Hz), 7.27 (1H, d, J=2.2 Hz), 4.51-4.47 (4H, m). LCMS: RT=3.67 min, M+H+=309/311 (40%), M+Na+=323/325 (100%). 1H NMR showed product to contain ~5% 8-iodo-4,5-dihydro-6-oxa-1,3a-diaza-benzo[e]azulene-2-carboxylic acid.

Step 3: {[(E)-8-Bromo-4,5-dihydro-6-oxa-1,3a-diaza-benzo[e]azulene-2-carbonylimino]-methylthiomethyl}-carbamic acid tert-butyl ester

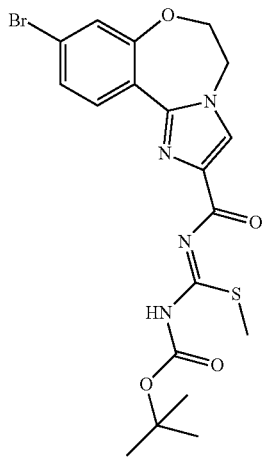 [SMILES: CS/C(=N\C(=O)c1cn2c(n1)-c1ccc(Br)cc1OCC2)NC(=O)OC(C)(C)C]

To a solution of 8-Bromo-4,5-dihydro-6-oxa-1,3a-diaza-benzo[e]azulene-2-carboxylic acid (0.839 g, 0.00271 mol) and oxalyl chloride (2M in DCM, 1.36 mL, 0.002714 mol), in methylene chloride (16.70 mL) under nitrogen atmosphere was added 1 drop of N,N-dimethylformamide. The solution was stirred at room temperature for 2 h. The reaction was concentrated in vacuo and the acid chloride was redissolved in methylene chloride (9.0 mL). The solution was added dropwise to a solution of N-tertbutoxycarbonyl-S-methylpseudothiourea (0.5164 g, 0.002714 mol) and triethylamine (1.173 mL, 0.008414 mol) in methylene chloride (9.0 mL). The reaction was stirred at room temperature for 1.5 h. Methylene chloride and water were added and the mixture was extracted 3× with methylene chloride. Saturated sodium carbonate was then added and the mixture was extracted with chloroform. The organic layers were combined and concentrated. The product was redissolved in methylene chloride and methanol and filtered. The filtrate was collected, concentrated and dry loaded onto silica gel and purified by flash chromatography (0-15% MeOH in DCM) to give {[(E)-8-Bromo-4,5-dihydro-6-oxa-1,3a-diaza-benzo[e]azulene-2-carbonylimino]-methylthiomethyl}-carbamic acid tert-butyl ester (658 mg) as an off-white solid. MS(ESI+) 481.0/483.0

Step 4: [5-(8-Bromo-4,5-dihydro-6-oxa-1,3a-diaza-benzo[e]azulen-2-yl)-1-isopropyl-1H-[1,2,4]triazol-3-yl]-carbamic acid tert-butyl ester To a solution of {[(E)-8-Bromo-4,5-dihydro-6-oxa-1,3a-diaza-benzo[e]azulene-2-carbonylimino]-methylthiomethyl}-carbamic acid tert-butyl ester (0.658 g, 0.00137 mol) in N,N-dimethylformamide (7.50 mL) was added N,N-Diisopropylethylamine (0.9524 mL, 0.005468 mol) then isopropylhydrazine hydrochloride (0.2267 g, 0.002050 mol). The reaction was stirred at room temperature for 4 h. Water and methylene chloride were added and the mixture was extracted 3× with methylene chloride. The organic layers were combined, dried with MgSO4 and concentrated. The crude was purified by flash chromatography (0-10% MeOH in DCM) to give [5-(8-Bromo-4,5-dihydro-6-oxa-1,3a-diaza-benzo[e]azulen-2-yl)-1-isopropyl-1H-[1,2,4]triazol-3-yl]-carbamic acid tert-butyl ester (642 mg) a sticky light yellow solid. The material was carried forward without any further purification. MS(ESI+) 489.1/491.1

Example 48

8-Bromo-2-(2-isopropyl-5-methyl-2H-[1,2,4]triazol-3-yl)-4,5-dihydro-6-oxa-1,3a-diaza-benzo[e]azulene

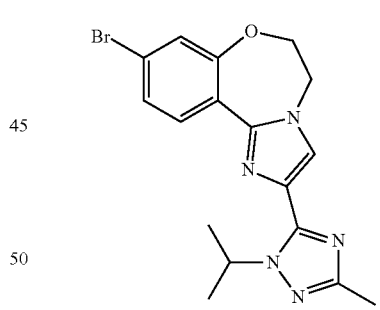

To a solution of 8-Bromo-4,5-dihydro-6-oxa-1,3a-diaza-benzo[e]azulene-2-carboxylic acid [1-dimethylamino-eth-(E)-ylidene]-amide (0.340 g, 0.000901 mol) in acetic acid (3.0 mL, 0.053 mol) was added isopropylhydrazine hydrochloride (0.1196 g, 0.001082 mol). The reaction was heated to 95° C. for 3 h. The acetic acid was removed in vacuo and the product was loaded as a solid onto silica and purified by flash chromatography (0-10% MeOH in DCM) to give 8-Bromo-2-(2-isopropyl-5-methyl-2H-[1,2,4]triazol-3-yl)-4,5-dihydro-6-oxa-1,3a-diaza-benzo[e]azulene (293 mg) as an orange solid. MS(ESI+) 388.1/390.1

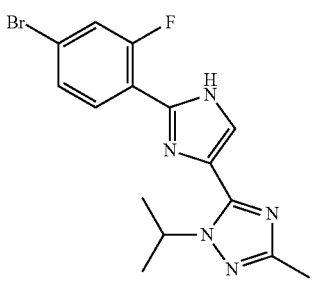 [SMILES: Cc1nc(-c2c[nH]c(-c3ccc(Br)cc3F)n2)n(C(C)C)n1]

Alternatively, 8-Bromo-2-(2-isopropyl-5-methyl-2H-[1,2,4]triazol-3-yl)-4,5-dihydro-6-oxa-1,3a-diaza-benzo[e]azulene may be prepared whereby a mixture of 4-bromo-2-fluoro-benzamidine hydrochloride (5.67 g, 22.3 mmol), potassium hydrogen carbonate (8.95 g, 89.4 mmol), THF (45 mL) and water (10 mL) was heated to reflux and a solution of 2-bromo-1-(2-isopropyl-5-methyl-2H-[1,2,4]triazol-3-yl)-ethanone (5.5 g, 22.3 mmol) in THF (15 mL) added dropwise. The reaction mixture was heated at reflux for 18 h before removal of volatile solvent in vacuo. The resultant suspension was filtered and the residue triturated in hot diethyl ether to give 5-[2-(4-Bromo-2-fluoro-phenyl)-1H-imidazol-4-yl]-1-isopropyl-3-methyl-1H-[1,2,4]triazole as an off-white solid (6.4 g, 79%). $^1$H NMR 400 MHz (DMSO-d) δ: 7.97 (1 H, t, J=8.30 Hz), 7.81 (1 H, s), 7.76 (1 H, dd, J=10.68, 1.92 Hz), 7.58 (1 H, dd, J=8.42, 1.93 Hz), 5.79 (1 H, br, m), 2.26 (3 H, s), 1.44 (6 H, d, J=6.60 Hz).

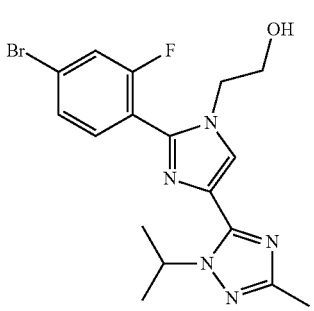 [SMILES: Cc1nc(-c2cn(CCO)c(-c3ccc(Br)cc3F)n2)n(C(C)C)n1]

A suspension of 5-[2-(4-bromo-2-fluoro-phenyl)-1H-imidazol-4-yl]-1-isopropyl-3-methyl-1H-[1,2,4]triazole (2.9 g, 7.96 mmol) in toluene (50 mL) was treated with ethylene carbonate (25 mL) and heated at reflux for 5 h. The cooled reaction mixture was diluted with DCM and passed through a pad of silica eluting with DCM then 20% methanol in DCM. Methanolic fractions were combined and concentrated in vacuo to give a pale tan solid. The solid was triturated in diethyl ether to give 2-[2-(4-Bromo-2-fluorophenyl)-4-(2-isopropyl-5-methyl-2H-[1,2,4]triazol-3-yl)-imidazol-1-yl]-ethanol as a white solid (2.3 g, 71%). LCMS: RT=2.85 min, [M+H]+=408/410. 1H NMR 400 MHz (CDCl3) δ: 8.16 (1 H, s), 7.67-7.20 (3 H, m), 5.83 (1 H, m), 4.05 (2 H, t, J=5.10 Hz), 3.92 (2 H, t, J=5.10 Hz), 2.44 (3 H, s), 1.50 (6 H, d, J=6.65 Hz).

A suspension of 2-[2-(4-bromo-2-fluoro-phenyl)-4-(2-isopropyl-5-methyl-2H-[1,2,4]triazol-3-yl)-imidazol-1-yl]-ethanol (2.3 g, 5.6 mmol) in DMF (50 mL) was treated with sodium hydride (60% dispersion, 247 mg, 6.2 mmol) portionwise over 5 min and the mixture stirred at RT for 1 h. The reaction was quenched by the slow addition of water (200 mL). The precipitate formed was filtered off, washed with water to give 8-Bromo-2-(2-isopropyl-5-methyl-2H-[1,2,4]triazol-3-yl)-4,5-dihydro-6-oxa-1,3a-diaza-benzo[e]azulene as a white solid (1.64 g, 53%). LCMS: RT=3.43 min, [M+H]+=388/390. 1H NMR 400 MHz (CDCl3) δ: 8.37 (1 H, d, J=8.61 Hz), 7.70 (1 H, s), 7.26-7.25 (2 H, m), 5.87-5.86 (1 H, m), 4.50-4.48 (2 H, m), 4.46-4.42 (2 H, m), 2.42 (3 H, s), 1.57 (6 H, d, J=6.64 Hz)

Example 49

9-Bromo-4,5-dihydro-2H-6-oxa-1,2-diaza-benzo[e]azulene

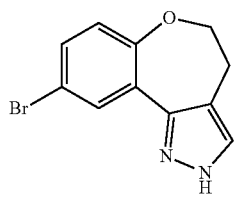 [SMILES: Brc1ccc2c(c1)-c1n[nH]cc1CCO2]

Step 1:
7-Bromo-3,4-dihydro-2H-benzo[b]oxepin-5-one

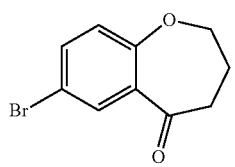

To a stirred solution of 5'-bromo-2'-hydroxyacetophenone (10 g, 46.5 mmol) in methyl ethyl ketone (100 mL) was added K2CO3 (13.5 g, 97.7 mmol) followed by 1,2-dibromoethane (20 mL, 232.5 mmol). The reaction mixture was heated at a mild reflux temperature for 16 h then cooled to room temperature. The reaction mixture was filtered and then concentrated in vacuo. The resultant residue was dissolved in diethyl ether/ethyl acetate (4:1, 500 mL) and the precipitated solid was removed by filtration. The filtrate was washed with 2 N NaOH (100 mL) and the organic portion was dried over Na2SO4 and concentrated in vacuo to give 1-[5-bromo-2-(2-bromo-ethoxy)-phenyl]-ethanone (8.07 g, 55%) which was used in the subsequent step without further purification.

To a slurry of NaH (60% dispersion in mineral oil) (1.48 g, 37.1 mmol) in THF (50 mL) at room temperature was added [5-bromo-2-(2-bromo-ethoxy)-phenyl]-ethanone (8.07 g, 25.1 mmol). The reaction mixture was slowly heated to reflux and allowed to stir for 20 h. The solvent was removed in vacuo and the residue subjected to flash chromatography (SiO2, 4:1 ethyl acetate/petroleum ether) to give 7-Bromo-3,4-dihydro-2H-benzo[b]oxepin-5-one as a yellow oil (4.22 g, 70%). 1H NMR (CDCl3) δ 2.15-2.29 (2H, m), 2.89 (2H, t, J=7.0 Hz), 4.24 (2H, t, J=6.6 Hz), 6.97 (1H, d, J=8.8 Hz), 7.50 (1H, dd, J=2.6, 8.1 Hz), 7.87 (1H, d, J=2.6 Hz).

Step 2: 7-Bromo-4-[1-dimethylamino-meth-(E)-ylidene]-3,4-dihydro-2H-benzo[b]-oxepin-5-one

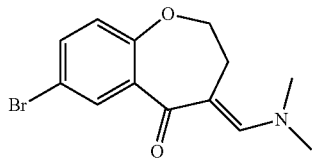 [SMILES: CN(C)/C=C1\CCOc2ccc(Br)cc2C1=O]

7-Bromo-3,4-dihydro-2H-benzo[b]oxepin-5-one (10.0 g, 41.5 mmol) in dimethylformamide dimethylacetal (100 mL) was heated at 110° C. for 18 h. The reaction was allowed to cool to room temperature and cyclohexane (100 mL) was added. The resulting solid precipitate was collected by filtration, washed with cyclohexane and then dried under vacuum at 40° C. to yield 7-Bromo-4-[1-dimethylamino-meth-(E)-ylidene]-3,4-dihydro-2H-benzo[b]-oxepin-5-one as yellow crystals (8.19 g, 67%). ¹H NMR δ (ppm) (CDCl3): 7.83 (1 H, d, J=2.59 Hz), 7.74 (1 H, s), 7.46 (1 H, dd, J=8.51, 2.58 Hz), 6.88 (1 H, d, J=8.52 Hz), 4.27-4.19 (2 H, m), 3.14 (6 H, s), 2.76-2.69 (2 H, m).

Step 3: 9-Bromo-4,5-dihydro-2H-6-oxa-1,2-diaza-benzo[e]azulene

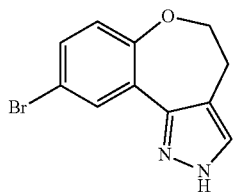 [SMILES: Brc1ccc2c(c1)-c1n[nH]cc1CCO2]

To a suspension of 8-bromo-4-[1-dimethylamino-meth-(E)-ylidene]-3,4-dihydro-2H-benzo[b]-oxepin-5-one (8.19 g, 27.7 mmol) in ethanol (100 mL) was added powdered hydrazine dihydrochloride (5.81 g, 55.3 mmol) at room temperature and the mixture stirred for 3 h. The reaction mixture was concentrated to near dryness in vacuo and isopropyl alcohol (200 mL) and water (100 mL) added. The resultant mixture was heated at reflux for 3 h them allowed to cool to room temperature. The mixture was concentrated in vacuo to remove the volatile solvent then diluted to 400 mL with water. The resulting solid precipitate was collected by filtration, washed with water and dried under vacuum at 40° C. to yield 9-Bromo-4,5-dihydro-2H-6-oxa-1,2-diaza-benzo[e]azulene as a pale yellow solid (7.8 g, 106%). ¹H NMR δ (ppm)(CDCl3): 8.27 (1 H, d, J=2.45 Hz), 7.59 (1 H, s), 7.32 (1 H, dd, J=8.64, 2.41 Hz), 6.94 (1 H, d, J=8.64 Hz), 4.34-4.28 (2 H, m), 3.15-3.09 (2 H, m).

Example 50

8-Bromo-4,5-dihydro-2H-6-oxa-1,2-diaza-benzo[e]azulene

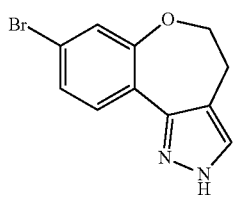 [SMILES: Brc1ccc2c(c1)OCCc1c[nH]nc1-2]

Step 1: 8-Bromo-4-[1-dimethylamino-meth-(E)-ylidene]-3,4-dihydro-2H-benzo[b]-oxepin-5-one

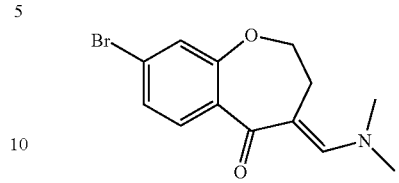

8-Bromo-3,4-dihydro-2H-benzo[b]oxepin-5-one (5.0 g, 20.7 mmol) in dimethylformamide dimethylacetal (15 mL) was heated at 110° C. for 18 h. The reaction was allowed to cool to room temperature and cyclohexane (20 mL) was added. The resulting solid precipitate was collected by filtration, washed with cyclohexane and then dried under vacuum at 40° C. to yield 8-Bromo-4-[1-dimethylamino-meth-(E)-ylidene]-3,4-dihydro-2H-benzo[b]-oxepin-5-one as yellow crystals (5.32 g, 86%). ¹H NMR δ (ppm) (CDCl3): 7.73 (1 H, s), 7.61 (1 H, d, J=8.29 Hz), 7.29 (1 H, dd, J=8.29, 1.94 Hz), 7.18 (1 H, d, J=1.91 Hz), 4.28-4.21 (2 H, m), 3.14 (6 H, s), 2.77-2.70 (2 H, m).

Step 2: 8-Bromo-4,5-dihydro-2H-6-oxa-1,2-diaza-benzo[e]azulene

To a suspension of 8-bromo-4-[1-dimethylamino-meth-(E)-ylidene]-3,4-dihydro-2H-benzo[b]-oxepin-5-one (5.32 g, 17.9 mmol) in isopropyl alcohol (50 mL) was added powdered hydrazine dihydrochloride (3.77 g, 35.9 mmol) at room temperature, then the mixture stirred for 2 h. The reaction mixture was diluted with water (20 mL) and then heated at 100° C. for 2 h before cooling to room temperature. The reaction mixture was concentrated in vacuo to remove the volatile solvent. The resulting suspension was filtered and the filtrate washed with water and dried under vacuum at 40° C. to yield 8-Bromo-4,5-dihydro-2H-6-oxa-1,2-diaza-benzo[e]azulene as a pale yellow solid (4.28 g, 90%). ¹H NMR δ (ppm)(DMSO-d): 8.07 (1 H, d, J=8.52 Hz), 7.64 (1 H, s), 7.30-7.24 (1 H, m), 7.21 (1 H, d, J=2.07 Hz), 4.24 (2 H, dd, J=5.63, 4.50 Hz), 3.00 (2 H, t, J=5.09 Hz).

Example 51

8-Bromo-4,5-dihydro-6-oxa-1,3a-diaza-benzo[e]azulene-2-carboxylic acid amide

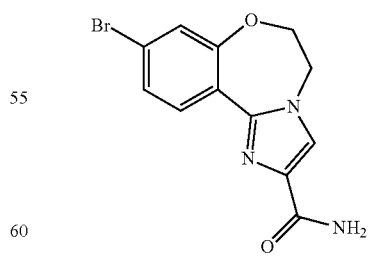

To a solution of 8-bromo-4,5-dihydro-6-oxa-1,3a-diaza-benzo[e]azulene-2-carboxylic acid (8.27 g, 26.7 mmol), EDCI (6.66 g, 34.8 mmol), HOBt (4.69 g, 34.8 mmol) and ammonium chloride (4.29 g, 80.2 mmol) in DMF (80 mL) was added triethylamine (7.49 mL, 53.5 mmol) and the reaction mixture stirred at 45° C. for 1.5 h. The reaction mixture was concentrated in vacuo and the residue triturated with water (250 mL). The precipitated product was collected by filtration and dried in vacuo at 45° C. for 16 h to give 8-Bromo-4,5-dihydro-6-oxa-1,3a-diaza-benzo[e]azulene-2-carboxylic acid amide as a buff coloured solid (7.67 g, 93%). 1H NMR (400 MHz, d6-DMSO) 8.40 (1H, d, J=8.7 Hz), 7.80 (1H, s), 7.42 (1H, br s), 7.32 (1H, dd, J=8.7, 2.0 Hz), 7.27 (1H, d, J=2.1 Hz), 7.15 (1H, br s), 4.50-4.46 (4H, m). LCMS: RT=3.07 min, M+H+=308/310. 1H NMR showed product to contain 5% 8-iodo-4,5-dihydro-6-oxa-1,3a-diaza-benzo[e]azulene-2-carboxylic acid amide.

Alternatively, a solution of 8-Bromo-2-iodo-4,5-dihydro-6-oxa-1,3a-diaza-benzo[e]azulene (10.00 g, 0.02558 mol) in N,N-Dimethylformamide (250 mL) was thoroughly degassed with N2. Bis(triphenylphosphine)palladium(II) chloride (0.807 g, 0.00115 mol) was added followed by Hexamethyldisilazane (21.58 mL, 0.1023 mol). The solution was flushed with CO for 2 minutes and then sealed with a CO balloon attached. The reaction was heated to 70° C. for 2.5 hours. Methylene chloride and saturated NH4Cl were added and the mixture was extracted 4 times with methylene chloride. The organic phases were combined, dried with MgSO4 and concentrated. A small amount of isopropanol was added and the mixture was triturated overnight. The mixture was filtered to yield 5.97 g (76% yield) of 8-Bromo-4,5-dihydro-6-oxa-1,3a-diaza-benzo[e]azulene-2-carboxylic acid amide as a fine brown powder. MS(ESI+) 308.0/310.0

Example 52

8-Bromo-2-(2-isopropyl-2H-[1,2,4]triazol-3-yl)-4,5-dihydro-6-oxa-1,3a-diaza-benzo[e]azulene

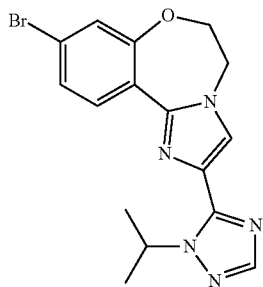 [SMILES: CC(C)n1ncnc1-c1cn2c(n1)-c1ccc(Br)cc1OCC2]

Step 1: 8-Bromo-4,5-dihydro-6-oxa-1,3a-diaza-benzo[e]azulene-2-carboxylic acid 1-dimethyl-amino-meth-(Z)-ylideneamide

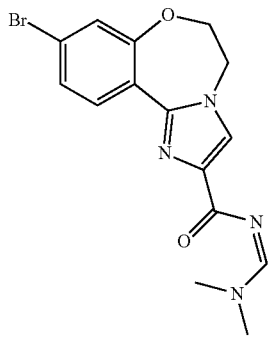 [SMILES: CN(C)/C=N\C(=O)c1cn2c(n1)-c1ccc(Br)cc1OCC2]

To a suspension of 8-bromo-4,5-dihydro-6-oxa-1,3a-diaza-benzo[e]azulene-2-carboxylic acid amide (7.67 g, 24.9 mmol) in dioxane (150 mL) was added DMF-DMA (9.92 mL, 74.7 mmol) and the reaction mixture heated at 100° C. for 1 h. During the reaction the solids dissolved to give a brown solution. The reaction mixture was concentrated in vacuo and the solid residue triturated with diethyl ether (~150 mL). The product was collected by filtration and dried in vacuo at 45° C. for 3 h to yield 8-Bromo-4,5-dihydro-6-oxa-1,3a-diaza-benzo[e]azulene-2-carboxylic acid 1-dimethylamino-meth-(Z)-ylideneamide as a buff coloured solid (8.52 g, 94%). 1H NMR (400 MHz, d6-DMSO) 8.56 (1H, s), 8.34 (1H, d, J=8.6 Hz), 7.96 (1H, s), 7.32 (1H, dd, J=8.6, 2.0 Hz), 7.26 (1H, d, J=2.1 Hz), 4.51-4.46 (4H, m), 3.16 (3H, s), 3.08 (3H, s). 1H NMR showed product to contain 5% 8-iodo-4,5-dihydro-6-oxa-1,3a-diaza-benzo[e]azulene-2-carboxylic acid 1-dimethylamino-meth-(Z)-ylideneamide.

Step 2

To a solution of 8-bromo-4,5-dihydro-6-oxa-1,3a-diaza-benzo[e]azulene-2-carboxylic acid 1-dimethylamino-meth-(Z)-ylideneamide in acetic acid was added isopropylhydrazine hydrochloride. The reaction was heated to 95° C. for 3 h. The acetic acid was removed in vacuo and the product was loaded as a solid onto silica and purified by flash chromatography (0-10% MeOH in DCM) to give 8-Bromo-4,5-dihydro-6-oxa-1,3a-diaza-benzo[e]azulene-2-carboxylic acid 1-dimethylamino-meth-(Z)-ylideneamide.

Example 53

1-(2-(tetrahydro-2H-pyran-2-yloxy)ethyl)-4-(tributylstannyl)-1H-imidazole and 1-(2-(tetrahydro-2H-pyran-2-yloxy)ethyl)-5-(tributylstannyl)-1H-imidazole

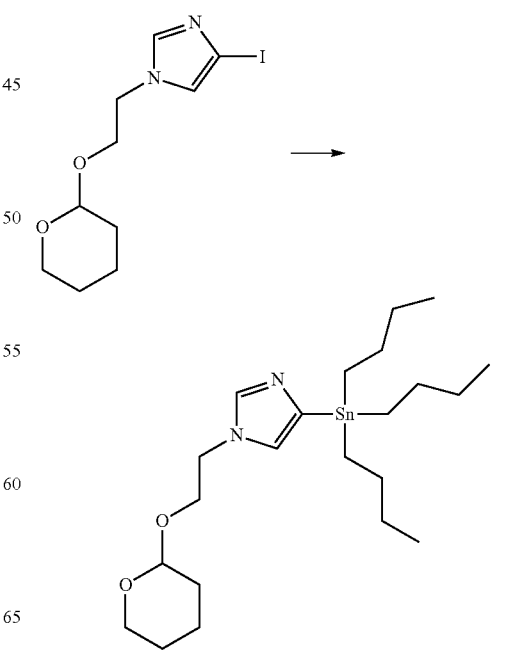

-continued

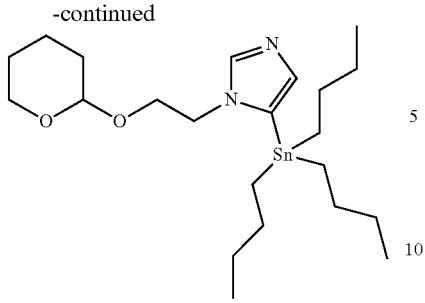

Isopropylmagnesium chloride (iPrMgCl—LiCl, 4.3 mL of 1.3 M) in THF was added dropwise to a solution of 4-iodo-1-(2-(tetrahydro-2H-pyran-2-yloxy)ethyl)-1H-imidazole (1.50 g, 4.66 mmol, mixture of regioisomers) in tetrahydrofuran (20 mL, 0.3 mol) at 0° C. The reaction mixture was stirred at 0° C. for 1 hour. Tributyltin chloride (1.64 mL, 6.05 mmol) was added and the mixture warmed to room temperature and stirred overnite. The reaction mixture was rotovapped and quenched with water, diluted with dichloromethane and filtered over celite. The aqueous layer was extracted and the crude, concentrated organic purified by flash column chromatography 50-100% ethylacetate in hexanes. NMR showed a 2:1 ratio of 1-(2-(tetrahydro-2H-pyran-2-yloxy)ethyl)-4-(tributylstannyl)-1H-imidazole and 1-(2-(tetrahydro-2H-pyran-2-yloxy)ethyl)-5-(tributylstannyl)-1H-imidazole (assumed by literature references of similar imidazole substitutions). Regioisomers were not separated.

Example 54

1-(4-bromo-1H-imidazol-1-yl)-2-methylpropan-2-ol and 1-(5-bromo-1H-imidazol-1-yl)-2-methylpropan-2-ol

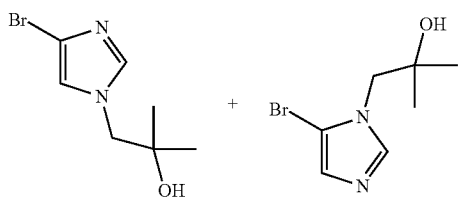

To a suspension of 4-bromo-1H-imidazole (1.0 g, 6.8 mmol) and isobutylene oxide (0.665 mL, 7.48 mmol) in methanol (0.331 mL, 8.16 mmol) was added cesium carbonate (0.63 g, 1.9 mmol). The reaction mixture was heated in a sealed vessel cautiously at 110° C. for 1.5 hrs. The reaction was cooled to room temperature, diluted with diethylether and washed 2 times with water. The organics were washed with brine, dried over magnesium sulfate and concentrated in vacuo to give a white solid which was flash purified with 100% ethyl acetate to get the two distinct intermediates. The major regioisomer was 1-(4-bromo-1H-imidazol-1-yl)-2-methylpropan-2-ol (0.8 g, 54% yield, M+1 220) while the minor regioisomer was 1-(5-bromo-1H-imidazol-1-yl)-2-methylpropan-2-ol (0.32 g, 21% yield M+1 220).

Example 55

N,N-diethyl-2-(4-(4,4,5,5-tetramethyl-1,3,2-dioxaborolan-2-yl)-1H-pyrazol-1-yl)ethanamine

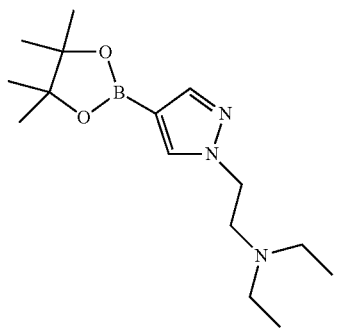 [SMILES: CCN(CC)CCn1cc(B2OC(C)(C)C(C)(C)O2)cn1]

To a solution of 4,4,5,5-tetramethyl-2-(1H-pyrazol-4-yl)-1,3,2-dioxaborolane (250 mg, 1.29 mmol) and sodium hydride (61.8 mg, 2.58 mmol) in tetrahydrofuran at 0° C. was added 2-bromo-N,N-diethylethanamine (558 mg, 2.58 mmol). The reaction was allowed to warm up to room temperature and was monitored by LCMS. After 90 minutes there was still no reaction and potassium iodide (1.71 g, 10.3 mmol) was added and the reaction was heated at 50° C. overnight. The reaction mixture was diluted with a large volume of ethyl acetate and water and partitioned. The organic layer containing the product was washed with brine and concentrated in vacuo to give clear thick oil confirmed by LCMS to be 100% pure N,N-diethyl-2-(4-(4,4,5,5-tetramethyl-1,3,2-dioxaborolan-2-yl)-1H-pyrazol-1-yl)ethanamine (340 mg, yield 90%, M+1 294.2)

Example 56

1-(2-(tert-butyldimethylsilyloxy)-2-methylpropyl)-4-(trimethylstannyl)-1H-imidazole

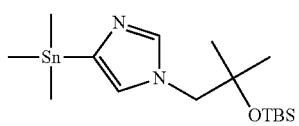 [SMILES: CC(C)(Cn1cn[c]([Sn]([CH3])([CH3])[CH3])c1)O[Si](C)(C)C(C)(C)C]

Step 1: 2,4,5-triiodo-1H-imidazole

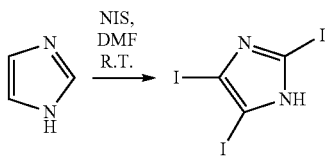 [SMILES: c1c[nH]cn1 ; Ic1nc(I)c(I)[nH]1]

To a mixture of 1H-Imidazole (50 g, 0.73 mol) in DMF (200 mL) was added NIS (328 g, 1.46 mol) portionwise, the reaction mixture was stirred at room temperature for 4 hours. The reaction mixture was poured in sat. Na2CO3 solution, filtered, the residue was washed with water and dried to give 150 g of 2,4,5-triiodo-1H-imidazole (Yield=46%).

Step 2: 4-iodo-1H-imidazole

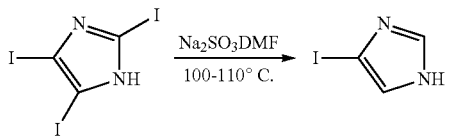

2,4,5-triiodo-1H-imidazole was reacted with Na2SO3 in DMF (250 mL) and stirring at 110° C. for over night under N2 atmosphere. The reaction mixture was filtered, the filtrate was concentrated and poured into water, then extracted with EtOAc, the organic was washed with water, dried over Na2SO4, concentrated and purified by silica gel column to give 4-iodo-1H-imidazole (Yield=55%). LC-MS: m/z=195 [M+H+]

Step 3: 1-(4-iodo-1H-imidazol-1-yl)-2-methylpropan-2-ol

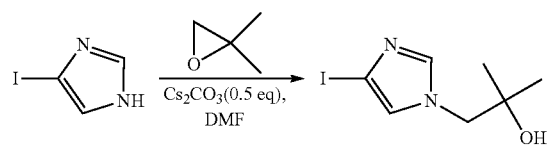

A mixture of 4-iodo-1H-imidazole, Cs2CO3 in 2,2-dimethyl oxirane was stirred at 120° C. for 20 min under irradiation with microwave. The reaction mixture was concentrated, and purified to give 1-(4-iodo-1H-imidazol-1-yl)-2-methylpropan-2-ol (Yield=71%). LC-MS: m/z=266 [M+H+] 1H NMR (CDCl3, 400 MHz): δ7.36 (s, 1 H), 7.06 (s, 1 H), 3.84 (s, 2 H), 1.22 (s, 6 H).

Step 4: 1-(2-(tert-butyldimethylsilyloxy)-2-methylpropyl)-4-iodo-1H-imidazole

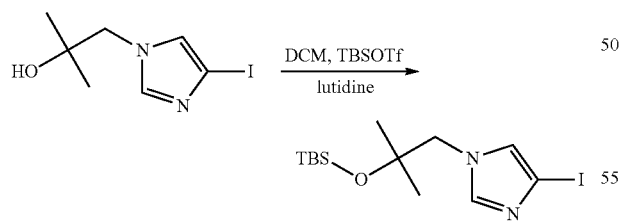

1-(4-iodo-1H-imidazol-1-yl)-2-methylpropan-2-ol was dissolved in DCm and lutidine was added dropwise at 0° C. The mixture was stirred at 0° C. for 30 min then tert-butyldimethylsilyl triflate (TBSOTf) was added dropwise. The mixture was warmed to room temperature and sitted for about an hour, then quenched with 30% acetic acid, extracted ethylacetate, dried, and concentrated to give 1-(2-(tert-butyldimethylsilyloxy)-2-methylpropyl)-4-iodo-1H-imidazole (Yield=74%). LC-MS: m/z=381[M+H+]

Step 5: 1-(2-(tert-butyldimethylsilyloxy)-2-methylpropyl)-4-(trimethylstannyl)-1H-imidazole

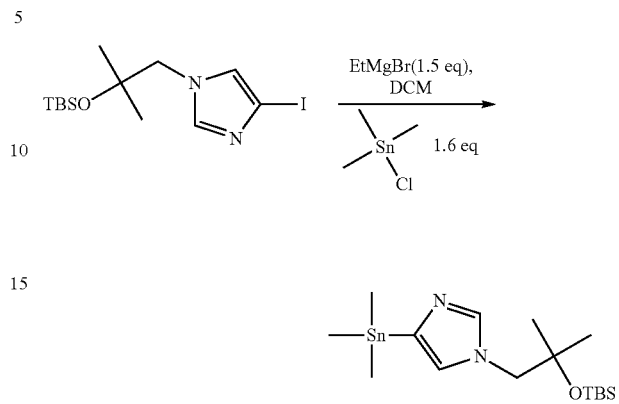

To a mixture of 1-(2-(tert-butyldimethylsilyloxy)-2-methylpropyl)-4-iodo-1H-imidazole in DCM was added ethylmagnesium bromide at −78° C. The temperature of the mixture was allowed to warm up to about 10° C. slowly and cooled again. Trimethyltin chloride was added dropwise at −78° C. After the addition, the temperature was allowed to slowly warm up to room temperature. The reaction mixture was pouted into saturate NH4Cl solution, then extracted with DCM. The organic phase was washed with water twice, dried over anhydrous Na2SO4, and concentrated to give 1-(2-(tert-butyldimethylsilyloxy)-2-methylpropyl)-4-(trimethylstannyl)-1H-imidazole (Yield=74%). LC-MS: m/z=419[M+H+] 1H NMR (CDCl3, 400 MHz): δ 7.63 (s, 1 H), 7.00 (s, 1 H), 3.79 (s, 2 H), 1.22-1.19 (s, 6 H), 0.86 (s, 9 H), 0.27 (s, 6 H), 0.02 (s, 6 H)

Example 57

2-(1-isopropyl-3-methyl-1H-1,2,4-triazol-5-yl)-9-(4,4,5,5-tetramethyl-1,3,2-dioxaborolan-2-yl)-5,6-dihydrobenzo[f]imidazo[1,2-d][1,4]oxazepine

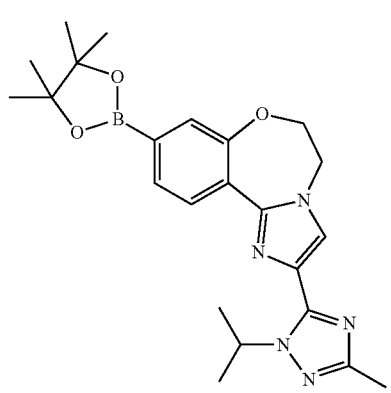

Step 1: 9-bromo-2-(1-isopropyl-4-methyl-1H-imidazol-2-yl)-5,6-dihydrobenzo[f]imidazo[1,2-d][1,4]oxazepine

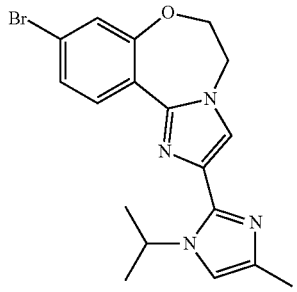 [SMILES: Cc1cn(C(C)C)c(-c2cn3c(n2)-c2ccc(Br)cc2OCC3)n1]

Isopropyl iodide (165 uL, 1.65 mmol) was added to a mixture of 417 mg (1.21 mmol) of 9-bromo-2-(4-methyl-1H-imidazol-2-yl)-5,6-dihydrobenzo[f]imidazo[1,2-d][1,4]oxazepine and cesium carbonate (538 mg, 1.65 mmol) in 3 ml of N,N-dimethylformamide. The reaction mixture was stirred at room temperature for 18 hours, mixed with water and extracted with ethyl acetate. The organic extract was washed with water, brine, dried over MgSO4, concentrated, and purified on 4 g silica column eluting with 4-5% methanol in DCM to give 210 mg of 9-bromo-2-(1-isopropyl-4-methyl-1H-imidazol-2-yl)-5,6-dihydrobenzo[f]imidazo[1,2-d][1,4]oxazepine. MS: 387.1.

Step 2

A solution of 9-bromo-2-(1-isopropyl-4-methyl-1H-imidazol-2-yl)-5,6-dihydrobenzo[f]imidazo[1,2-d][1,4]oxazepine (1.00 g, 0.00258 mol) and potassium acetate (0.758 g, 0.00773 mol) in dimethyl sulfoxide (8.5 mL, 0.12 mol) in a round bottom flask equipped with a magnetic stir bar was thoroughly purged with nitrogen. Bispinacol ester boronate (0.719 g, 0.00283 mol) and [1,1'-Bis(diphenylphosphino)ferrocene]dichloropalladium(II), complex with dichloromethane (1:1) (0.210 g, 0.258 mmol) was added and the reaction was heated to 85° C. under inert atmosphere. The reaction was monitored by LC/MS and was complete after 6 hr. The mixture was partitioned between water and methylene chloride and the mixture was extracted 3× with methylene chloride. The organic phases were combined, dried with MgSO4 and concentrated. The whole was loaded onto silica and purified by flash chromatography (0-10% MeOH in DCM followed by 100% EtOAC) to give 2-(1-isopropyl-3-methyl-1H-1,2,4-triazol-5-yl)-9-(4,4,5,5-tetramethyl-1,3,2-dioxaborolan-2-yl)-5,6-dihydrobenzo[f]imidazo[1,2-d][1,4]oxazepine (488 mg) as a beige solid. MS(ESI+) 436.2.

Example 58

9-Bromo-2-(2-isopropyl-2H-[1,2,4]triazol-3-yl)-4,5-dihydro-2H-6-oxa-1,2-diaza-benzo[e]azulene

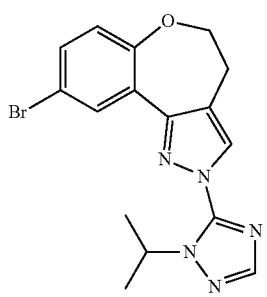 [SMILES: CC(C)n1ncnc1-n1cc2c(n1)-c1cc(Br)ccc1OCC2]

9-Bromo-2-(2-isopropyl-2H-[1,2,4]triazol-3-yl)-4,5-dihydro-2H-6-oxa-1,2-diaza-benzo[e]azulene was prepared from 9-bromo-4,5-dihydro-2H-6-oxa-1,2-diaza-benzo[e]azulene (450 mg, 1.7 mmol) and 5-chloro-1-isopropyl-1H-[1,2,4]triazole (369 mg, 2.55 mmol) to give 9-Bromo-2-(2-isopropyl-2H-[1,2,4]triazol-3-yl)-4,5-dihydro-2H-6-oxa-1,2-diaza-benzo[e]azulene as a white solid (375 mg, 59%). LCMS RT=5.05 min M+H+=374/376

Example 59

9-Bromo-2-[2-(2,4-difluoro-phenyl)-2H-[1,2,4]triazol-3-yl]-4,5-dihydro-2H-6-oxa-1,2-diaza-benzo[e]azulene

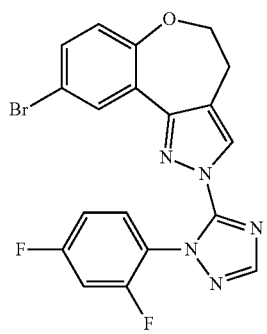 [SMILES: Fc1ccc(-n2ncnc2-n2cc3c(n2)-c2cc(Br)ccc2OCC3)c(F)c1]

9-Bromo-2-[2-(2,4-difluoro-phenyl)-2H-[1,2,4]triazol-3-yl]-4,5-dihydro-2H-6-oxa-1,2-diaza-benzo[e]azulene was prepared similarly to 8-bromo-2-[2-(2,4-difluoro-phenyl)-2H-[1,2,4]triazol-3-yl]-4,5-dihydro-2H-6-oxa-1,2-diaza-benzo[e]azulene from 5-chloro-1-(2,4-difluoro-phenyl)-1H-[1,2,4]triazole (1.33 g, 6.16 mmol) and 9-bromo-4,5-dihydro-2H-6-oxa-1,2-diaza-benzo[e]azulene (1.36 g, 5.13 mmol), the crude product was subjected to flash chromatography (SiO2, gradient 0 to 35% ethyl acetate in cyclohexane) to give 9-Bromo-2-[2-(2,4-difluoro-phenyl)-2H-[1,2,4]triazol-3-yl]-4,5-dihydro-2H-6-oxa-1,2-diaza-benzo[e]azulen (1.42 g, 62%). LCMS RT=4.80 M+H+=444/446.

Example 60

9-Bromo-2-[2-(2-chloro-phenyl)-2H-[1,2,4]triazol-3-yl]-4,5-dihydro-2H-6-oxa-1,2-diaza-benzo[e]azulene

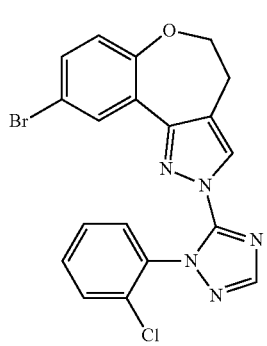 [SMILES: Clc1ccccc1-n1ncnc1-n1cc2c(n1)-c1cc(Br)ccc1OCC2]

Following the procedures in Example 103, 2,4-dichlorophenyl hydrazine hydrochloride was reacted with formamide to give 1-(2-Chloro-phenyl)-1H-[1,2,4]triazole as an off-white solid. ¹H NMR δ (ppm)(CDCl3): 8.54 (1 H, s), 8.14 (1 H, s), 7.61-7.54 (2 H, m), 7.46-7.39 (2 H, m).

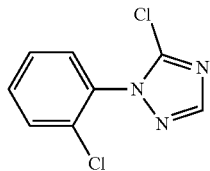

Following the procedure for 5-chloro-1-(2,4-difluoro-phenyl)-1H-[1,2,4]triazole, 1-(2-chloro-phenyl)-1H-[1,2,4]triazole was reacted with n-butyllithium and hexachloroethane to give 5-Chloro-1-(2-chloro-phenyl)-1H-[1,2,4]triazole as a white solid.

¹H NMR δ (ppm)(CDCl3): 8.05 (1 H, s), 7.61-7.58 (1 H, m), 7.55-7.48 (1 H, m), 7.46-7.43 (2 H, m).

9-Bromo-2-[2-(2-chloro-phenyl)-2H-[1,2,4]triazol-3-yl]-4,5-dihydro-2H-6-oxa-1,2-diaza-benzo[e]azulene was prepared similarly to 8-bromo-2-[2-(2,4-difluoro-phenyl)-2H-[1,2,4]triazol-3-yl]-4,5-dihydro-2H-6-oxa-1,2-diaza-benzo[e]azulene from 5-chloro-1-(2-chloro-phenyl)-1H-[1,2,4]triazole (2.25 g, 10.5 mmol) and 9-bromo-4,5-dihydro-2H-6-oxa-1,2-diaza-benzo[e]azulene (1.9 g, 7 mmol), the crude product was subjected to flash chromatography (SiO2, gradient 0 to 60% DCM (+10% ethyl acetate) in cyclohexane) to give 9-Bromo-2-[2-(2-chloro-phenyl)-2H-[1,2,4]triazol-3-yl]-4,5-dihydro-2H-6-oxa-1,2-diaza-benzo[e]azulene (1.3 g, 33%). LCMS RT=4.82 M+H+=442/444

Example 61

9-Bromo-2-(2-isopropyl-2H-[1,2,4]triazol-3-yl)-4,5-dihydro-6-oxa-1,10b-diaza-benzo[e]azulene

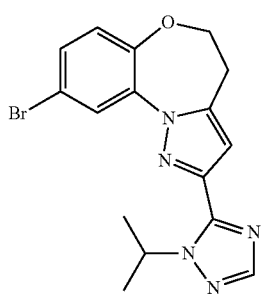 [SMILES: CC(C)n1ncnc1-c1cc2n(n1)-c1cc(Br)ccc1OCC2]

Step 1: 4-Bromo-1-but-3-ynyloxy-2-nitro-benzene

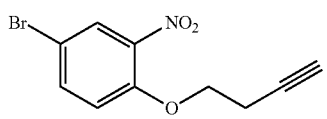

A mixture of 4-bromo-1-fluoro-2-nitrobenzene (20.0 g, 90 mmol), 3-butyn-1-ol (7.0 g, 99.8 mmol) and potassium carbonate (13.8 g, 99.8 mmol) in dry DMF (20 mL) was heated with 4 Å molecular sieves for 43 h. The mixture was cooled, diluted with water to approximately 500 mL and extracted three times with ethyl acetate. The combined organic extracts were washed with water and then brine, dried and concentrated in vacuo. The resultant residue was subjected to flash chromatography (SiO2, gradient 5 to 10% ethyl acetate in cyclohexane) to give 4-Bromo-1-but-3-ynyloxy-2-nitro-benzene as a yellow solid (17.35 g, 71%). NMR showed an impurity (19%) which was not removed at this stage. LCMS: RT=4.41 min, [M+Na]+=292/294.

Step 2: 5-Bromo-2-but-3-ynyloxy-phenylamine

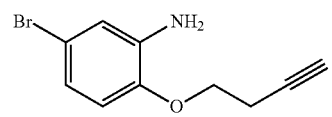

4-Bromo-1-but-3-ynyloxy-2-nitro-benzene (82% pure, 4.22 g, 12.5 mmol) was heated in a mixture of IMS (Industrial Methylated Spirits, 40 mL) and glacial acetic acid (2 mL) at approx. 50° C. until a solution was formed. Iron powder (5.05 g, 89.8 mmol) and iron (III) chloride hexahydrate (0.56 g, 1.56 mmol) were added and the mixture was heated under reflux for 18 h. The cooled mixture was filtered through Celite®, and washed through with ethyl acetate. The filtrate was washed with water, followed by brine, dried (Na2SO4), filtered and concentrated in vacuo. The resultant residue was subjected to flash chromatography (SiO2, gradient 10 to 20% ethyl acetate in cyclohexane) to give 5-Bromo-2-but-3-ynyloxy-phenylamine as an orange oil (2.68 g, 89%). LCMS: RT=4.10 min, M+H+=240/242.

Step 3: Chloro-(5-bromo-2-but-3-ynyloxyphenylhydrazono)acetic acid ethyl ester

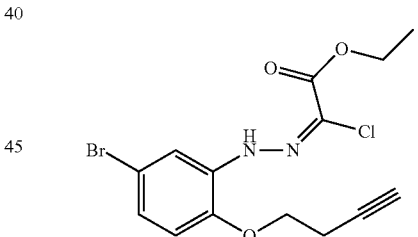

2-Chloro-3-oxo-butyric acid ethyl ester (1.94 g, 11.2 mmol) and sodium acetate (1.45 g, 17.8 mmol) were stirred in IMS (100 mL) to give a clear solution, then cooled to 0° C. Separately, 5-bromo-2-but-3-ynyloxy-phenylamine (2.68 g, 11.2 mmol) in 6M hydrochloric acid (6.8 mL) was cooled to 0° C. and a solution of sodium nitrite (0.77 g, 11.2 mmol) in water (11.2 mL) was added dropwise with stirring, keeping the temperature below 5° C. The aqueous acidic solution was added to the IMS solution, washed in with a little water, keeping the temperature below 5° C. After 1 h at 0-5° C., the mixture was diluted with water and extracted several times with ethyl acetate. The combined organic extracts were washed with water, dried (Na2SO4), filtered and concentrated in vacuo to give Chloro-(5-bromo-2-but-3-ynyloxyphenylhydrazono)acetic acid ethyl ester as a pale brown solid (3.96 g, 95%). LCMS: RT=4.97 min, [M+Na]+=395/397/399.

Step 4: 9-Bromo-4,5-dihydro-6-oxa-1,10b-diaza-benzo[e]azulene-2-carboxylic acid ethyl ester

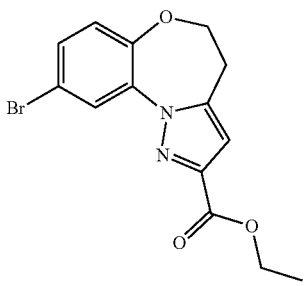 [SMILES: CCOC(=O)c1cc2n(n1)-c1cc(Br)ccc1OCC2]

A mixture of chloro-(5-bromo-2-but-3-ynyloxyphenylhydrazono)acetic acid ethyl ester (3.28 g, 8.78 mmol) and triethylamine (12.2 mL, 88 mmol) in dry toluene (900 mL) was heated at gentle reflux (120° C.) for 54 h. The cooled mixture was filtered, the residue washed with ethyl acetate and the filtrate concentrated in vacuo. The resultant residue was subjected to flash chromatography (SiO2, gradient 10 to 15% ethyl acetate in cyclohexane) to give 9-Bromo-4,5-dihydro-6-oxa-1,10b-diaza-benzo[e]azulene-2-carboxylic acid ethyl ester as a yellow solid (2.52 g, 85%). LCMS: RT=4.52 min, M+H+=337/339, [M+Na]+=359/361.

Step 5: 9-Bromo-4,5-dihydro-6-oxa-1,10b-diaza-benzo[e]azulene-2-carboxylic acid amide

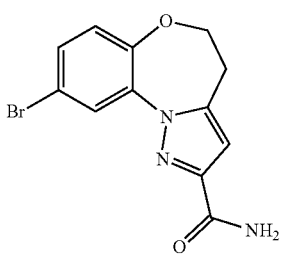 [SMILES: NC(=O)c1cc2n(n1)-c1cc(Br)ccc1OCC2]

9-Bromo-4,5-dihydro-6-oxa-1,10b-diaza-benzo[e]azulene-2-carboxylic acid ethyl ester (1.51 g, 4.48 mmol) in 2M ammonia/methanol solution (70 mL) was heated in a pressure bomb at approximately 120° C. (external temperature) for 30 h, then allowed to cool. The mixture was filtered and concentrated in vacuo. The resultant residue was subjected to flash chromatography (SiO2, gradient 50 to 100% ethyl acetate in cyclohexane) to give 9-Bromo-4,5-dihydro-6-oxa-1,10b-diaza-benzo[e]azulene-2-carboxylic acid amide as a pale yellow solid (1.11 g, 80%). LCMS: RT=4.00 min, M+H+=308/310, [M+Na]+=330/332.

Step 6: 9-Bromo-4,5-dihydro-6-oxa-1,10b-diaza-benzo[e]azulene-2-carboxylic acid 1-dimethylaminomethylideneamide

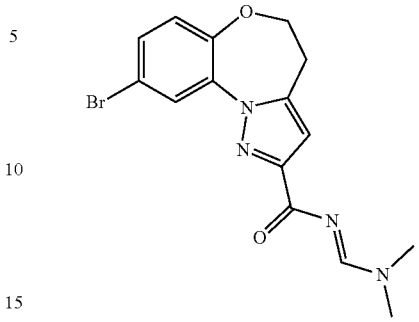

A mixture of 9-bromo-4,5-dihydro-6-oxa-1,10b-diaza-benzo[e]azulene-2-carboxylic acid amide (1.11 g, 3.60 mmol) and dimethylformamide dimethylacetal (1.44 mL, 10.8 mmol) in dry 1,4-dioxane (25 mL) was heated at 100° C. for 2 h, then concentrated in vacuo. The resultant residue was triturated in diethyl ether to give 9-Bromo-4,5-dihydro-6-oxa-1,10b-diaza-benzo[e]azulene-2-carboxylic acid 1-dimethylaminomethylideneamide as a yellow solid (1.27 g, 97%). LCMS: RT=3.27 min, M+H+=363/365.

Step 7: 9-Bromo-2-(2-isopropyl-2H-[1,2,4]triazol-3-yl)-4,5-dihydro-6-oxa-1,10b-diaza-benzo[e]azulene A mixture of 9-bromo-4,5-dihydro-6-oxa-1,10b-diaza-benzo[e]azulene-2-carboxylic acid 1-dimethylaminomethylideneamide (1.27 g, 3.5 mmol), isopropylhydrazine hydrochloride (0.48 g, 4.37 mmol) and glacial acetic acid (6 mL) was heated at 110° C. for 6.5 h, then cooled and concentrated in vacuo. The resultant residue was dissolved in aqueous sodium bicarbonate and DCM and the phases were separated. The aqueous phase was extracted several times with DCM, the combined organic extracts dried (MgSO4) and concentrated in vacuo. The resultant residue was subjected to flash chromatography (SiO2, gradient 30 to 70% ethyl acetate in cyclohexane) to give 9-Bromo-2-(2-isopropyl-2H-[1,2,4]triazol-3-yl)-4,5-dihydro-6-oxa-1,10b-diaza-benzo[e]azulene (0.99 g, 76%). LCMS: RT=5.07 min, M+H+=374/376. $^1$H NMR δ (ppm)(CDCl3): 8.07 (1 H, d, J=2.41 Hz), 7.96 (1 H, s), 7.39 (1 H, dd, J=8.63, 2.43 Hz), 7.08 (1 H, d, J=8.63 Hz), 6.91 (1 H, s), 5.73-5.65 (1 H, m), 4.53 (2 H, t, J=5.91 Hz), 3.18 (2 H, t, J=5.91 Hz), 1.60 (6 H, d, J=6.62 Hz)

Example 62

9-Bromo-2-[2-(2,2,2-trifluoro-ethyl)-2H-[1,2,4]triazol-3-yl]-4,5-dihydro-6-oxa-1,10b-diaza-benzo[e]azulene

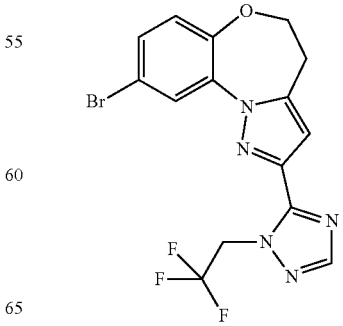

Following the procedure for 9-bromo-2-(2-isopropyl-2H-[1,2,4]triazol-3-yl)-4,5-dihydro-6-oxa-1,10b-diaza-benzo[e]azulene, 9-bromo-4,5-dihydro-6-oxa-1,10b-diaza-benzo[e]azulene-2-carboxylic acid 1-dimethylaminomethylideneamide was reacted with trifluoroethyl hydrazine (70% aqueous) to give 9-Bromo-2-[2-(2,2,2-trifluoro-ethyl)-2H-[1,2,4]triazol-3-yl]-4,5-dihydro-6-oxa-1,10b-diaza-benzo[e]azulene as a white solid. LCMS RT=4.49 min, M+H+=414/416.

Example 63

8-Azetidin-3-yl-2-[2-(2,4-difluoro-phenyl)-2H-[1,2,4]triazol-3-yl]-4,5-dihydro-2H-6-oxa-1,2-diaza-benzo[e]azulene hydrochloride

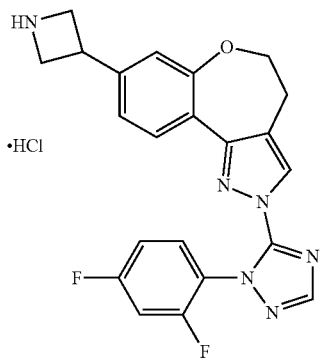 [SMILES: Cl ; Fc1ccc(-n2ncnc2-n2cc3c(n2)-c2ccc(C4CNC4)cc2OCC3)c(F)c1]

Step 1: 3-Azetidine-1-carboxylic acid tert-butyl ester zinc iodide

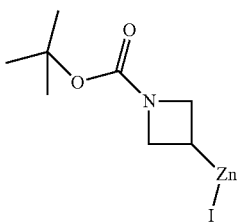

In a sealed flask were placed zinc dust (276 mg, 4.22 mmol) and Celpure P65 filter agent (60 mg) and the mixture heated at 300° C. under vacuum for 10 min. The flask was purged with argon and allowed to cool to RT. To the mixture was added DMA (2.4 mL), followed by dropwise addition of a mixture of chlorotrimethylsilane (TMSCl) and 1,2-dibromoethane (84 µL, 7:5 v:v), causing a slight exotherm and a small amount of effervescence. The reaction mixture was aged at RT for 15 minutes before the dropwise addition of 3-iodo-azetidine-1-carboxylic acid tert-butyl ester (0.96 g, 3.38 mmol) as a solution in DMA (2 mL). The reaction mixture was stirred at RT for 1.5 h before being filtered to give 3-Azetidine-1-carboxylic acid tert-butyl ester zinc iodide as a colourless solution in DMA.

Step 2: 3-{2-[2-(2,4-Difluoro-phenyl)-2H-[1,2,4]triazol-3-yl]-4,5-dihydro-2H-6-oxa-1,2-diaza-benzo[e]azulen-8-yl}-azetidine-1-carboxylic acid tert-butyl ester

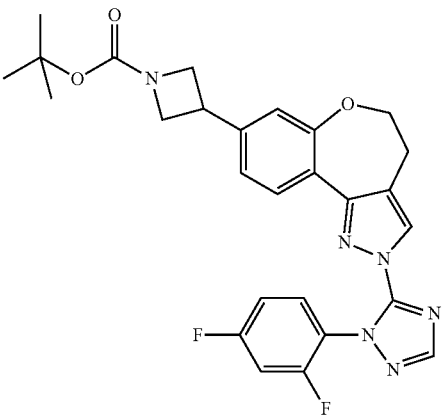 [SMILES: CC(C)(C)OC(=O)N1CC(c2ccc3c(c2)OCCc2cn(-c4ncnn4-c4ccc(F)cc4F)nc2-3)C1]

A solution of 8-bromo-2-[2-(2,4-difluoro-phenyl)-2H-[1,2,4]triazol-3-yl]-4,5-dihydro-2H-6-oxa-1,2-diaza-benzo[e]azulene (1 g, 2.25 mmol), [1,1'-bis(diphenylphosphino)ferrocene]dichloropalladium(II), complex with dichloromethane (183 mg, 0.22 mmol) and copper (I) iodide (56 mg, 0.29 mmol) in DMA (10 mL) was degassed by vacuum purging then bubbling argon through the mixture (×3). To the dark red mixture was added 3-azetidine-1-carboxylic acid tert-butyl ester zinc iodide (1.17 g, 3.38 mmol) as a solution in DMA (4.4 mL) and the mixture heated at 85° C. for 2 h. During the reaction the mixture turned green, then pale orange before finally turning black. The reaction mixture was diluted with water (20 mL) and ethyl acetate (20 mL) and the mixture filtered through Celite 0. The organic portion of the filtrate was separated and the aqueous extracted with ethyl acetate (2×20 mL). The combined organic fractions were washed with brine (100 mL), dried (MgSO4) and then concentrated in vacuo. The resultant residue was subjected to flash chromatography (SiO2, gradient 0 to 100% ethyl acetate in cyclohexane) to give 3-{2-[2-(2,4-Difluoro-phenyl)-2H-[1,2,4]triazol-3-yl]-4,5-dihydro-2H-6-oxa-1,2-diaza-benzo[e]azulen-8-yl}-azetidine-1-carboxylic acid tert-butyl ester as a yellow oil (1.1 g, 94%). LCMS: RT=4.81 min, M+H+=521 (100%), M+H+-OtBu=465 (60%), M+H+-Boc=421 (20%).

Step 3: 8-Azetidin-3-yl-2-[2-(2,4-difluoro-phenyl)-2H-[1,2,4]triazol-3-yl]-4,5-dihydro-2H-6-oxa-1,2-diaza-benzo[e]azulene hydrochloride 3-{2-[2-(2,4-Difluoro-phenyl)-2H-[1,2,4]triazol-3-yl]-4,5-dihydro-2H-6-oxa-1,2-diaza-benzo[e]azulen-8-yl}-azetidine-1-carboxylic acid tert-butyl ester (1.1 g, 2.11 mmol) was dissolved in hydrochloric acid in dioxane (10 mL, 4N) and the reaction stirred at RT for 1 h. After approximately 5 min a thick white precipitate formed. The reaction was concentrated in vacuo to yield 8-Azetidin-3-yl-2-[2-(2,4-difluoro-phenyl)-2H-[1,2,4]triazol-3-yl]-4,5-dihydro-2H-6-oxa-1,2-diaza-benzo[e]azulene hydrochloride as a yellow solid (1.0 g, 100%). LCMS: RT=3.00 min, M+H+=421.

Example 64

8-Azetidin-3-yl-2-(2-isopropyl-2H-[1,2,4]triazol-3-yl)-4,5-dihydro-2H-6-oxa-1,2-diaza-benzo[e]azulene hydrochloride

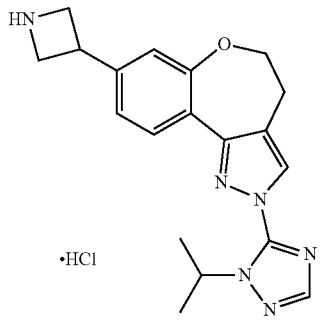 [SMILES: CC(C)n1ncnc1-n1cc2c(n1)-c1ccc(C3CNC3)cc1OCC2 ; Cl]

Step 1: 3-[2-(2-Isopropyl-2H-[1,2,4]triazol-3-yl)-4,5-dihydro-2H-6-oxa-1,2-diaza-benzo[e]azulen-8-yl]-azetidine-1-carboxylic acid tert-butyl ester

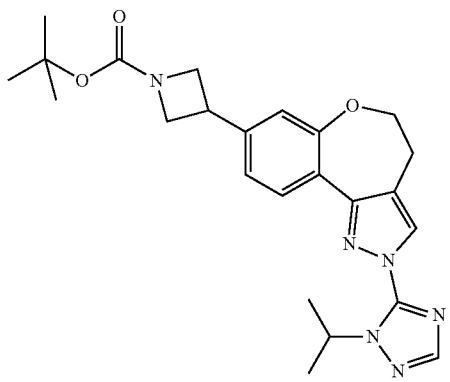 [SMILES: CC(C)n1ncnc1-n1cc2c(n1)-c1ccc(C3CN(C(=O)OC(C)(C)C)C3)cc1OCC2]

3-[2-(2-Isopropyl-2H-[1,2,4]triazol-3-yl)-4,5-dihydro-2H-6-oxa-1,2-diaza-benzo[e]azulen-8-yl]-azetidine-1-carboxylic acid tert-butyl ester was prepared similarly to 3-{2-[2-(2,4-difluoro-phenyl)-2H-[1,2,4]triazol-3-yl]-4,5-dihydro-2H-6-oxa-1,2-diaza-benzo[e]azulen-8-yl}-azetidine-1-carboxylic acid tert-butyl ester from 8-bromo-2-(2-isopropyl-2H-[1,2,4]triazol-3-yl)-4,5-dihydro-2H-6-oxa-1,2-diaza-benzo[e]azulene and 3-azetidine-1-carboxylic acid tert-butyl ester zinc iodide. LCMS: RT=4.85 min, M+H+=451 (40%), M+H+-OtBu=395 (100%), M+H+-Boc=351 (10%).

Step 2: 8-Azetidin-3-yl-2-(2-isopropyl-2H-[1,2,4]triazol-3-yl)-4,5-dihydro-2H-6-oxa-1,2-diaza-benzo[e]azulene hydrochloride 8-Azetidin-3-yl-2-(2-isopropyl-2H-[1,2,4]triazol-3-yl)-4,5-dihydro-2H-6-oxa-1,2-diaza-benzo[e]azulene hydrochloride was prepared similarly to 8-azetidin-3-yl-2-[2-(2,4-difluoro-phenyl)-2H-[1,2,4]triazol-3-yl]-4,5-dihydro-2H-6-oxa-1,2-diaza-benzo[e]azulene hydrochloride from 3-[2-(2-isopropyl-2H-[1,2,4]triazol-3-yl)-4,5-dihydro-2H-6-oxa-1,2-diaza-benzo[e]azulen-8-yl]-azetidine-1-carboxylic acid tert-butyl ester. LCMS: RT=2.86 min, M+H+=351 (20%), M+H+-iPr=308 (100%).

Example 65

8-Azetidin-3-yl-2-(2-isopropyl-2H-[1,2,4]triazol-3-yl)-4,5-dihydro-6-oxa-1,3a-diaza-benzo[e]azulene hydrochloride

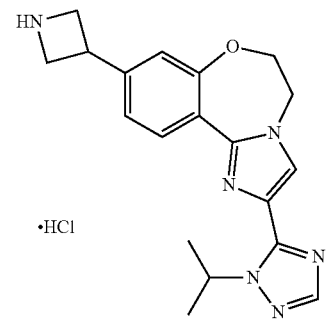 [SMILES: CC(C)n1ncnc1-c1cn2c(n1)-c1ccc(C3CNC3)cc1OCC2 ; Cl]

Step 1: 3-[2-(2-Isopropyl-2H-[1,2,4]triazol-3-yl)-4,5-dihydro-6-oxa-1,3a-diaza-benzo[e]azulen-8-yl]-azetidine-1-carboxylic acid tert-butyl ester

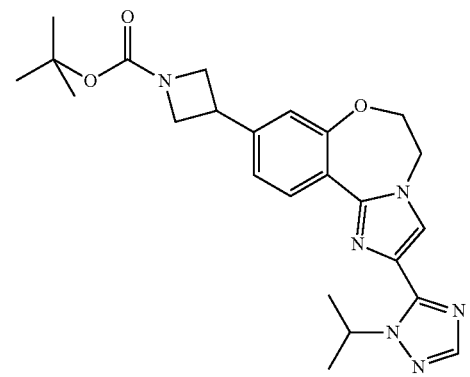 [SMILES: CC(C)n1ncnc1-c1cn2c(n1)-c1ccc(C3CN(C(=O)OC(C)(C)C)C3)cc1OCC2]

3-[2-(2-Isopropyl-2H-[1,2,4]triazol-3-yl)-4,5-dihydro-6-oxa-1,3a-diaza-benzo[e]azulen-8-yl]-azetidine-1-carboxylic acid tert-butyl ester was prepared similarly to 3-{2-[2-(2,4-difluoro-phenyl)-2H-[1,2,4]triazol-3-yl]-4,5-dihydro-2H-6-oxa-1,2-diaza-benzo[e]azulen-8-yl}-azetidine-1-carboxylic acid tert-butyl ester from 8-bromo-2-(2-isopropyl-2H-[1,2,4]triazol-3-yl)-4,5-dihydro-6-oxa-1,3a-diaza-benzo[e]azulene and 3-azetidine-1-carboxylic acid tert-butyl ester zinc iodide. LCMS: RT=4.61 min, M+H+=451.

Step 2: 8-Azetidin-3-yl-2-(2-isopropyl-2H-[1,2,4]triazol-3-yl)-4,5-dihydro-6-oxa-1,3a-diaza-benzo[e]azulene hydrochloride 8-Azetidin-3-yl-2-(2-isopropyl-2H-[1,2,4]triazol-3-yl)-4,5-dihydro-6-oxa-1,3a-diaza-benzo[e]azulene hydrochloride was prepared similarly to 8-azetidin-3-yl-2-[2-(2,4-difluoro-phenyl)-2H-[1,2,4]triazol-3-yl]-4,5-dihydro-2H-6-oxa-1,2-diaza-benzo[e]azulene hydrochloride from 3-[2-(2-isopropyl-2H-[1,2,4]triazol-3-yl)-4,5-dihydro-6-oxa-1,3a-diaza-benzo[e]azulen-8-yl]-azetidine-1-carboxylic acid tert-butyl ester. LCMS: RT=2.44 min, M+H+=351

Example 66

2-(2-Isopropyl-2H-[1,2,4]triazol-3-yl)-8-piperidin-4-yl-4,5-dihydro-6-oxa-1,3a-diaza-benzo[e]azulene trifluoroacetic acid salt

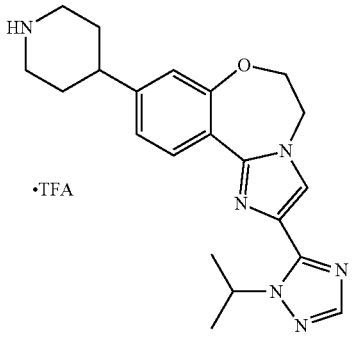 [SMILES: CC(C)n1ncnc1-c1cn2c(n1)-c1ccc(C3CCNCC3)cc1OCC2]

Step 1: 4-[2-(2-Isopropyl-2H-[1,2,4]triazol-3-yl)-4,5-dihydro-6-oxa-1,3a-diaza-benzo[e]azulen-8-yl]-piperidine-1-carboxylic acid tert-butyl ester

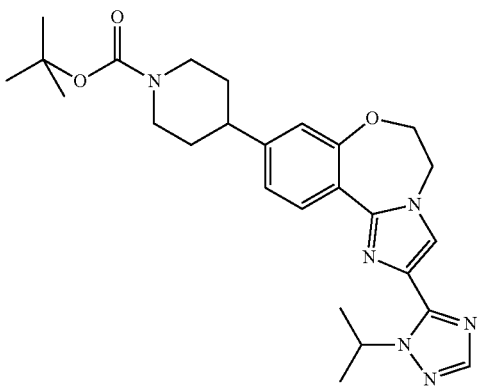 [SMILES: CC(C)n1ncnc1-c1cn2c(n1)-c1ccc(C3CCN(C(=O)OC(C)(C)C)CC3)cc1OCC2]

4-[2-(2-Isopropyl-2H-[1,2,4]triazol-3-yl)-4,5-dihydro-6-oxa-1,3a-diaza-benzo[e]azulen-8-yl]-piperidine-1-carboxylic acid tert-butyl ester was prepared similarly to 3-{2-[2-(2,4-difluoro-phenyl)-2H-[1,2,4]triazol-3-yl]-4,5-dihydro-2H-6-oxa-1,2-diaza-benzo[e]azulen-8-yl}-azetidine-1-carboxylic acid tert-butyl ester from 8-bromo-2-(2-isopropyl-2H-[1,2,4]triazol-3-yl)-4,5-dihydro-6-oxa-1,3a-diaza-benzo[e]azulene (3.0 g, 8.0 mmol) and 4-piperidine-1-carboxylic acid tert-butyl ester zinc iodide (12 mmol) (prepared similarly to 3-azetidine-1-carboxylic acid tert-butyl ester zinc iodide) to give 4-[2-(2-Isopropyl-2H-[1,2,4]triazol-3-yl)-4,5-dihydro-6-oxa-1,3a-diaza-benzo[e]azulen-8-yl]-piperidine-1-carboxylic acid tert-butyl ester (1.2 g, 31%). LCMS: RT=5.06 min, M+H+=479

Step 2: 2-(2-Isopropyl-2H-[1,2,4]triazol-3-yl)-8-piperidin-4-yl-4,5-dihydro-6-oxa-1,3a-diaza-benzo[e]azulene trifluoroacetic acid salt To a solution of 4-[2-(2-isopropyl-2H-[1,2,4]triazol-3-yl)-4,5-dihydro-6-oxa-1,3a-diaza-benzo[e]azulen-8-yl]-piperidine-1-carboxylic acid tert-butyl ester (1.2 g, 2.51 mmol) in DCM (12 mL) was added TFA (8 mL) and the reaction mixture stirred at RT for 1 h. The reaction mixture was concentrated in vacuo, the residue titrated in diethyl ether to give 2-(2-Isopropyl-2H-[1,2,4]triazol-3-yl)-8-piperidin-4-yl-4,5-dihydro-6-oxa-1,3a-diaza-benzo[e]azulene trifluoroacetic acid salt as a grey solid (1.34 g, 100%). LCMS: RT=2.88 min, M+H+=379

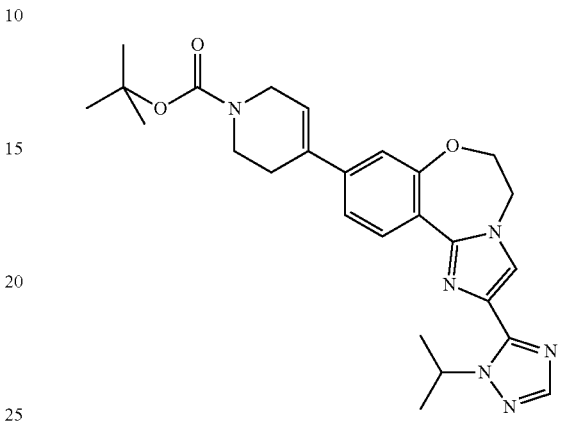

Alternatively, 2-(2-Isopropyl-2H-[1,2,4]triazol-3-yl)-8-piperidin-4-yl-4,5-dihydro-6-oxa-1,3a-diaza-benzo[e]azulene hydrochloride can be prepared whereby 8-Bromo-2-(2-isopropyl-2H-[1,2,4]triazol-3-yl)-4,5-dihydro-6-oxa-1,3a-diaza-benzo[e]azulene (2.1 g, 5.4 mmol), 3,6-dihydro-2H-pyridine-1-N-Boc-4-boronic acid pinacol ester (2.59 g, 8.3 mmol) and potassium carbonate (1.92 g, 13.9 mmol) were mixed with DMF (13 mL) and purged with argon. PdCl2dppf.DCM (310 mg, 0.42 mmol) was added, purging repeated and the mixture heated to 80° C. for 18 h. After cooling the reaction mixture was filtered through Celite®, washing with ethyl acetate, and the filtrate concentrated in vacuo. The residue was partitioned between ethyl acetate and water, the organic layer separated, dried (Na2SO4), filtered and concentrated in vacuo. The resultant residue was subjected to flash chromatography (SiO2, gradient 0 to 2% methanol in ethyl acetate) to give 4-[2-(2-Isopropyl-2H-[1,2,4]triazol-3-yl)-4,5-dihydro-6-oxa-1,3a-diaza-benzo[e]azulen-8-yl]-3,6-dihydro-2H-pyridine-1-carboxylic acid tert-butyl ester (2.56 g, 96%). LCMS RT=4.79, [M+H]+=477. 1H NMR 400 MHz (CDCl3) δ: 8.45 (1 H, d, J=8.46 Hz), 7.89 (1 H, s), 7.73 (1 H, s), 7.19 (1 H, dd, J=8.37, 1.80 Hz), 7.04 (1 H, d, J=1.87 Hz), 6.15 (1 H, s), 6.04-5.96 (1 H, m), 4.51-4.43 (4 H, m), 4.09 (2 H, d, J=3.68 Hz), 3.64 (2 H, t, J=5.64 Hz), 2.52 (2 H, s), 1.59 (6 H, d, J=6.63 Hz), 1.49 (9 H, s)

4-[2-(2-Isopropyl-2H-[1,2,4]triazol-3-yl)-4,5-dihydro-6-oxa-1,3a-diaza-benzo[e]azulen-8-yl]-3,6-dihydro-2H-pyridine-1-carboxylic acid tert-butyl ester was treated with hydrochloric acid to give 2-(2-Isopropyl-2H-[1,2,4]triazol-3-yl)-8-piperidin-4-yl-4,5-dihydro-6-oxa-1,3a-diaza-benzo[e]azulene hydrochloride. 1H NMR 400 MHz (DMSO-d) δ: 9.08 (2 H, s), 8.37 (1 H, d, J=8.30 Hz), 8.18 (1 H, s), 8.07 (1 H, s), 7.06 (1 H, dd, J=8.35, 1.80 Hz), 6.91 (1 H, d, J=1.80 Hz), 5.85 (1 H, m), 4.53 (4 H, m), 3.35 (2 H, d, J=12.46 Hz), 2.98 (2 H, m), 2.87 (1 H, m), 1.93 (4 H, m), 1.50 (6 H, d, J=6.57 Hz)

Example 67

2-[2-(2,4-Difluoro-phenyl)-2H-[1,2,4]triazol-3-yl]-9-piperidin-4-yl-4,5-dihydro-2H-6-oxa-1,2-diaza-benzo[e]azulene hydrochloride

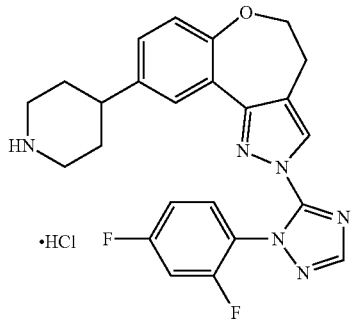 [SMILES: Fc1ccc(-n2ncnc2-n2cc3c(n2)-c2cc(C4CCNCC4)ccc2OCC3)c(F)c1 ; Cl]

Step 1: 4-{2-[2-(2,4-Difluoro-phenyl)-2H-[1,2,4]triazol-3-yl]-4,5-dihydro-2H-6-oxa-1,2-diaza-benzo[e]azulen-9-yl}-3,6-dihydro-2H-pyridine-1-carboxylic acid tert-butyl ester

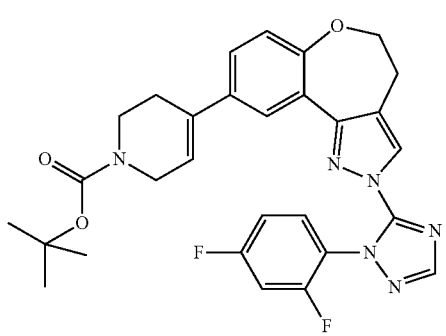 [SMILES: CC(C)(C)OC(=O)N1CC=C(c2ccc3c(c2)-c2nn(-c4ncnn4-c4ccc(F)cc4F)cc2CCO3)CC1]

4-{2-[2-(2,4-Difluoro-phenyl)-2H-[1,2,4]triazol-3-yl]-4,5-dihydro-2H-6-oxa-1,2-diaza-benzo[e]azulen-9-yl}-3,6-dihydro-2H-pyridine-1-carboxylic acid tert-butyl ester was prepared similarly to 4-{2-[2-(2,2,2-trifluoro-ethyl)-2H-[1,2,4]triazol-3-yl]-4,5-dihydro-6-oxa-1,10b-diaza-benzo[e]azulen-9-yl}-3,6-dihydro-2H-pyridine-1-carboxylic acid tert-butyl ester from 9-bromo-2-[2-(2,4-difluoro-phenyl)-2H-[1,2,4]triazol-3-yl]-4,5-dihydro-2H-6-oxa-1,2-diaza-benzo[e]azulene (1.55 mg, 1.13 mmol) to give the title compound as a colourless gum (1.47 g, 77%). LCMS RT=5.01 min, M+H+=547

Step 2: 2-[2-(2,4-Difluoro-phenyl)-2H-[1,2,4]triazol-3-yl]-9-piperidin-4-yl-4,5-dihydro-2H-6-oxa-1,2-diaza-benzo[e]azulene hydrochloride 2-[2-(2,4-Difluoro-phenyl)-2H-[1,2,4]triazol-3-yl]-9-piperidin-4-yl-4,5-dihydro-2H-6-oxa-1,2-diaza-benzo[e]azulene hydrochloride was prepared similarly to 9-piperidin-4-yl-2-[2-(2,2,2-trifluoro-ethyl)-2H-[1,2,4]triazol-3-yl]-4,5-dihydro-6-oxa-1,10b-diaza-benzo[e]azulene from 4-{2-[2-(2,4-difluoro-phenyl)-2H-[1,2,4]triazol-3-yl]-4,5-dihydro-2H-6-oxa-1,2-diaza-benzo[e]azulen-9-yl}-3,6-dihydro-2H-pyridine-1-carboxylic acid tert-butyl ester (2.06 g, 3.77 mmol) to give the title compound as a white solid (1.15 g, 62%). LCMS RT=3.04 min, M+H+=449

Example 68

(4-{2-[2-(2,4-Difluoro-phenyl)-2H-[1,2,4]triazol-3-yl]-4,5-dihydro-2H-6-oxa-1,2-diaza-benzo[e]azulen-9-yl}-piperidin-4-yl)-methanol hydrochloride

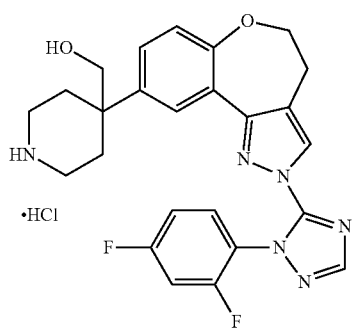 [SMILES: Cl ; OCC1(c2ccc3c(c2)-c2nn(-c4ncnn4-c4ccc(F)cc4F)cc2CCO3)CCNCC1]

Step 1: 4-{2-[2-(2,4-Difluoro-phenyl)-2H-[1,2,4]triazol-3-yl]-4,5-dihydro-2H-6-oxa-1,2-diaza-benzo[e]azulen-9-yl}-piperidine-1,4-dicarboxylic acid 1-tert-butyl ester 4-ethyl ester

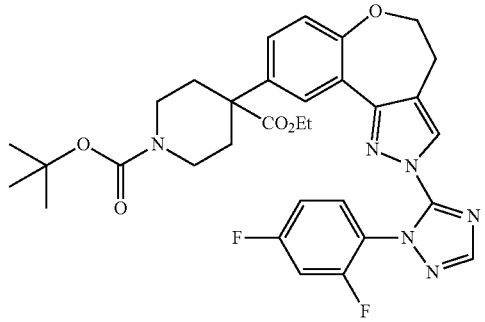 [SMILES: CCOC(=O)C1(c2ccc3c(c2)-c2nn(-c4ncnn4-c4ccc(F)cc4F)cc2CCO3)CCN(C(=O)OC(C)(C)C)CC1]

To a solution of dicyclohexylamine (291 L, 1.463 mmol) in anhydrous toluene (3 mL) was added 2.5M n-butyllithium in hexanes (563 L, 1.575 mmol) dropwise at RT under nitrogen. After complete addition the mixture was stirred at RT for 10 min then ethyl N-Boc-piperidine-4-carboxylate (305 L, 1.24 mmol) was added drop wise at RT and the mixture was stirred for 30 min. The mixture was added to 9-bromo-2-[2-(2,4-difluoro-phenyl)-2H-[1,2,4]triazol-3-yl]-4,5-dihydro-2H-6-oxa-1,2-diaza-benzo[e]azulene (500 mg, 1.13 mmol), di(dibenzylideneacetone)-palladium (35 mg, 0.06 mmol), tri-tert-butylphosphonium tetrafluoroborate (17.4 mg, 0.06 mmol) at RT under nitrogen then heated to 100° C. After heating for 17 hr the mixture was allowed to cool to RT and subjected to flash chromatography (SiO2, gradient 0 to 50% ethyl acetate in cyclohexane) to afford the title compound (200 mg, 29%). LCMS RT=4.93 min, M+H+=621.

Step 2: (4-{2-[2-(2,4-difluoro-phenyl)-2H-[1,2,4]triazol-3-yl]-4,5-dihydro-2H-6-oxa-1,2-diaza-benzo[e]azulen-9-yl}-piperidin-4-yl)-methanol hydrochloride To a solution of 4-{2-[2-(2,4-difluoro-phenyl)-2H-[1,2,4]triazol-3-yl]-4,5-dihydro-2H-6-oxa-1,2-diaza-benzo[e]azulen-9-yl}-piperidine-1,4-dicarboxylic acid 1-tert-butyl ester 4-ethyl ester (200 mg, 0.323 mmol) in anhydrous THF (10 mL) at 0° C. under nitrogen was added 1M lithium aluminum hydride in THF (485 L, 0.485 mmol) dropwise. The mixture was stirred at 0° C. for 15 min then allowed to warm to RT. After 60 min additional 1M lithium aluminum hydride in THF (485 L, 0.485 mmol) was added and stirring continued. After 2 h the mixture was cooled to 0° C. and carefully quenched with saturated NH4Cl solution. The mixture was extracted with DCM and the organic layer washed with water then brine, dried (Na2SO4), and the solvents removed in vacuo. The resultant residue was dissolved in DCM (10 mL) and treated with 4N HCl in dioxane (2 mL) at RT. After stirring for 5 h the solvent was removed in vacuo, the solid triturated with diethyl ether and collected by filtration to afford the title compound (97 mg, 58%). LCMS RT=2.84 min, M+H+=479

Example 69

2-[2-(2,2,2-Trifluoro-ethyl)-2H-[1,2,4]triazol-3-yl]-4,5-dihydro-6-oxa-1,10b-diaza-benzo[e]azulene-9-carbaldehyde

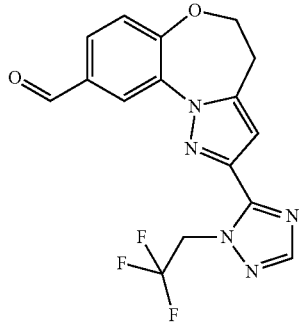 [SMILES: O=Cc1ccc2c(c1)-n1nc(-c3ncnn3CC(F)(F)F)cc1CCO2]

Step 1: 2-[2-(2,2,2-Trifluoro-ethyl)-2H-[1,2,4]triazol-3-yl]-4,5-dihydro-6-oxa-1,10b-diaza-benzo[e]azulene-9-carboxylic acid methyl ester

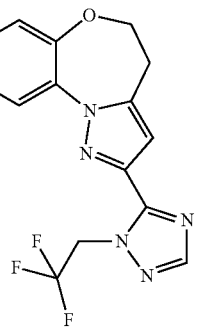

A suspension of 9-bromo-2-[2-(2,2,2-trifluoro-ethyl)-2H-[1,2,4]triazol-3-yl]-4,5-dihydro-6-oxa-1,10b-diaza-benzo[e]azulene (2.18 g, 5.28 mmol), molybdenum hexacarbonyl (696 mg, 2.64 mmol), trans-di(mu-acetato)bis[o-(di-o-tolyl-phosphino)benzyl]dipalladium (II) (240 mg, 0.24 mmol), tri-tert-butylphosphonium tetrafluoroborate (156 mg, 0.52 mmol) and DBU (792 μL, 5.28 mmol) in methanol (15 mL) and dioxane (15 mL) was degassed, then heated at 150° C. for 30 min using microwave irradiation. The reaction mixture was diluted with ethyl acetate (20 mL), filtered and the filtrate concentrated in vacuo. The resultant residue was subjected to flash chromatography (SiO2, gradient 30 to 60% ethyl acetate in cyclohexane) to yield the title compound (1.02 g, 49%). $^1$H NMR δ (ppm)(CDCl3): 8.69 (1 H, d, J=2.12 Hz), 8.03 (1 H, s), 7.96 (1 H, dd, J=8.48, 2.12 Hz), 7.22 (1 H, d, J=8.50 Hz), 6.94 (1 H, s), 5.57 (2 H, dd, J=16.24, 8.12 Hz), 4.62-4.56 (2 H, m), 3.94 (3 H, s), 3.29-3.23 (2 H, m).

Step 2: 2-[2-(2,2,2-Trifluoro-ethyl)-2H-[1,2,4]triazol-3-yl]-4,5-dihydro-6-oxa-1,10b-diaza-benzo[e]azulene-9-carboxylic acid


To a solution of 2-[2-(2,2,2-trifluoro-ethyl)-2H-[1,2,4]triazol-3-yl]-4,5-dihydro-6-oxa-1,10b-diaza-benzo[e]azulene-9-carboxylic acid methyl ester (553 mg, 1.4 mmol) in dioxane (12.5 mL) and water (12.5 mL) was added lithium hydroxide (67 mg, 2.8 mmol) and the reaction mixture stirred at RT for 2 h. The reaction mixture was concentrated in vacuo to remove the dioxane and the resultant solution acidified to pH 1 by the addition of HCl (12 N). The precipitate formed was collected by filtration, washed with water and dried in vacuo at 40° C. to give the title compound (519 mg, 98%). LCMS: RT=4.04 min, M+H+=380

Step 3: {2-[2-(2,2,2-Trifluoro-ethyl)-2H-[1,2,4]triazol-3-yl]-4,5-dihydro-6-oxa-1,10b-diaza-benzo[e]azulen-9-yl}-methanol

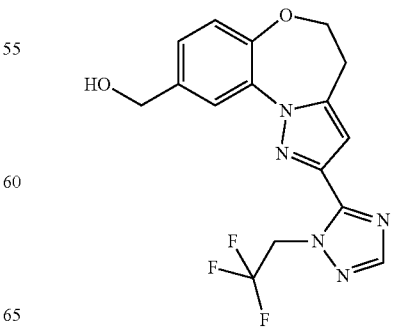

To a solution of 2-[2-(2,2,2-trifluoro-ethyl)-2H-[1,2,4]triazol-3-yl]-4,5-dihydro-6-oxa-1,10b-diaza-benzo[e]azulene-9-carboxylic acid methyl ester (393 mg, 1 mmol) in THF (10 mL) at −70° C. was added DIBAL (3 mL, 1 M solution in toluene, 3 mmol) and the reaction mixture stirred at 0° C. for 1 h. The reaction mixture was diluted with methanol (5 mL), then with saturated aqueous sodium potassium tartrate solution. The resultant mixture was extracted with ethyl acetate (3×20 mL), then the combined organic fractions dried (MgSO4) and concentrated in vacuo to give the title compound (370 mg, 100%).

Step 4: 2-[2-(2,2,2-Trifluoro-ethyl)-2H-[1,2,4]triazol-3-yl]-4,5-dihydro-6-oxa-1,10b-diaza-benzo[e]azulene-9-carbaldehyde To a solution of {2-[2-(2,2,2-trifluoro-ethyl)-2H-[1,2,4]triazol-3-yl]-4,5-dihydro-6-oxa-1,10b-diaza-benzo[e]azulen-9-yl}-methanol (370 mg, 1 mmol) in DCM (20 mL) was added Dess-Martin periodinane (467 mg, 1.1 mmol) and the reaction mixture stirred at RT for 30 minutes. The reaction mixture was diluted with DCM (20 mL) and the solution washed with sodium hydroxide solution (1 M, aqueous). The organic layer was separated, dried (MgSO4) and then concentrated in vacuo. The resultant residue was subjected to flash chromatography (SiO2, gradient 0 to 90% ethyl acetate in cyclohexane) to yield the title compound as a white solid (253 mg, 70%). LCMS: RT=4.10, M+H+=364

Example 70

2-(2-Isopropyl-2H-[1,2,4]triazol-3-yl)-4,5-dihydro-6-oxa-1,10b-diaza-benzo[e]azulene-9-carboxylic acid

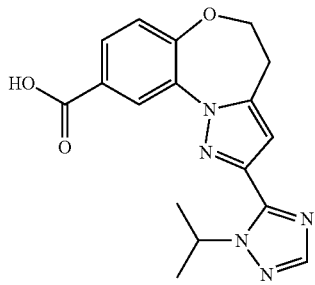 [SMILES: CC(C)n1ncnc1-c1cc2n(n1)-c1cc(C(=O)O)ccc1OCC2]

Step 1: 2-(2-Isopropyl-2H-[1,2,4]triazol-3-yl)-4,5-dihydro-6-oxa-1,10b-diaza-benzo[e]azulene-9-carboxylic acid methyl ester

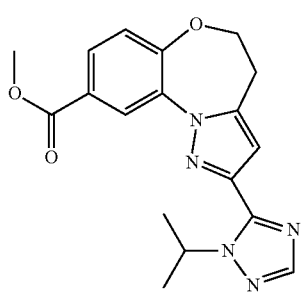 [SMILES: COC(=O)c1ccc2c(c1)-n1nc(-c3ncnn3C(C)C)cc1CCO2]

Following Example 69, 2-(2-Isopropyl-2H-[1,2,4]triazol-3-yl)-4,5-dihydro-6-oxa-1,10b-diaza-benzo[e]azulene-9-carboxylic acid methyl ester was prepared from 9-bromo-2-(2-isopropyl-2H-[1,2,4]triazol-3-yl)-4,5-dihydro-6-oxa-1,10b-diaza-benzo[e]azulene (0.99 g, 2.65 mmol). The reaction mixture was diluted with ethyl acetate (20 mL), filtered and the filtrate concentrated in vacuo. The resultant residue was subjected to flash chromatography (SiO2, gradient 50 to 100% ethyl acetate in cyclohexane) to give the title compound (0.32 g, 34%). LCMS: RT=4.73, M+H+=354.

Step 2: [2-(2-Isopropyl-2H-[1,2,4]triazol-3-yl)-4,5-dihydro-6-oxa-1,10b-diaza-benzo[e]azulen-9-yl]-methanol

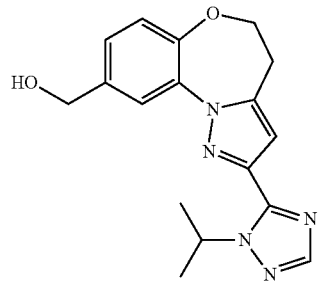 [SMILES: CC(C)n1ncnc1-c1cc2n(n1)-c1cc(CO)ccc1OCC2]

Following Example 69, [2-(2-Isopropyl-2H-[1,2,4]triazol-3-yl)-4,5-dihydro-6-oxa-1,10b-diaza-enzo[e]azulen-9-yl]-methanol was prepared from 2-(2-isopropyl-2H-[1,2,4]triazol-3-yl)-4,5-dihydro-6-oxa-1,10b-diaza-benzo[e]azulene-9-carboxylic acid methyl ester (0.50 g, 1.42 mmol) to give the title compound (360 mg, 78%). LCMS: RT=3.81, M+H+=326.

Step 3: 2-(2-Isopropyl-2H-[1,2,4]triazol-3-yl)-4,5-dihydro-6-oxa-1,10b-diaza-benzo[e]azulene-9-carbaldehyde

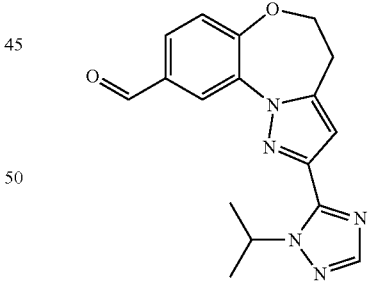

Following Example 69, 2-(2-Isopropyl-2H-[1,2,4]triazol-3-yl)-4,5-dihydro-6-oxa-1,10b-diaza-benzo[e]azulene-9-carbaldehyde was prepared from [2-(2-isopropyl-2H-[1,2,4]triazol-3-yl)-4,5-dihydro-6-oxa-1,10b-diaza-benzo[e]azulen-9-yl]-methanol (360 mg, 1.11 mmol). The reaction mixture was diluted with DCM (20 mL) and the solution washed with sodium hydroxide solution (1 M, aqueous). The organic layer was separated, dried (MgSO4) and concentrated in vacuo. The resultant residue was subjected to flash chromatography (SiO2, 100% ethyl acetate) to yield the title compound as a white solid (410 mg, 114%). LCMS: RT=4.15, M+H+=324.

325

Step 4: 2-(2-Isopropyl-2H-[1,2,4]triazol-3-yl)-4,5-dihydro-6-oxa-1,10b-diaza-benzo[e]azulene-9-carboxylic acid Following Example 69, 2-(2-Isopropyl-2H-[1,2,4]triazol-3-yl)-4,5-dihydro-6-oxa-1,10b-diaza-benzo[e]azulene-9-carboxylic acid was prepared from 2-(2-isopropyl-2H-[1,2,4]triazol-3-yl)-4,5-dihydro-6-oxa-1,10b-diaza-benzo[e]azulene-9-carboxylic acid methyl ester (720 mg, 2.04 mmol). The reaction mixture was concentrated in vacuo to remove dioxane and the resultant solution acidified to pH 1 by the addition of HCl (12 N). The precipitate that formed was collected by filtration, washed with water and dried in vacuo at 50° C. to give the title compound (584 mg, 84%). LCMS: RT=4.61 min, M+H+=340.

Example 72

2-(1-(2-chlorophenyl)-1H-imidazol-2-yl)-5,6-dihydrobenzo[f]imidazo[1,2-d][1,4]oxazepine-10-carboxylic acid

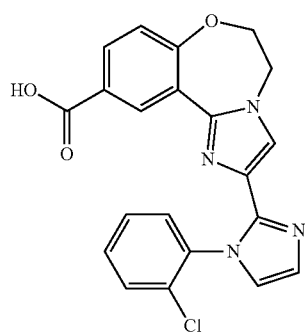 [SMILES: O=C(O)c1ccc2c(c1)-c1nc(-c3nccn3-c3ccccc3Cl)cn1CCO2]

Step 1: methyl 2-(1-(2-chlorophenyl)-1H-imidazol-2-yl)-5,6-dihydrobenzo[f]imidazo[1,2-d][1,4]oxazepine-10-carboxylate

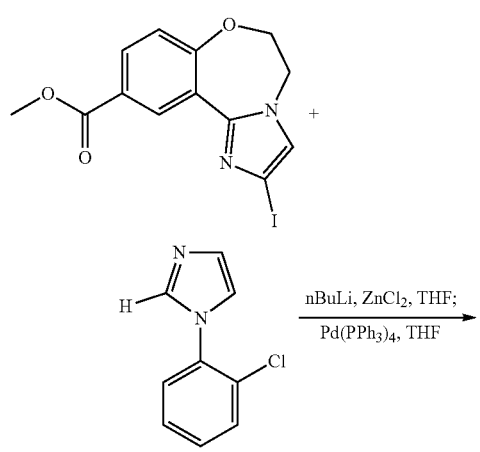

326

-continued

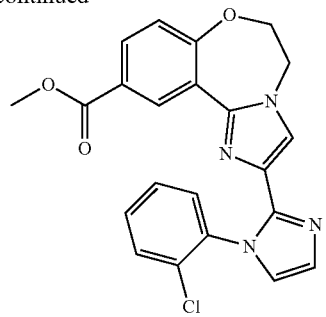

To a solution of 1-(2-chlorophenyl)-1H-imidazole (0.133 g, 0.743 mmol) in tetrahydrofuran (5.43 mL, 66.9 mmol) at −78° C. was added 1.60 M of n-Butyllithium in Hexane (0.464 mL) dropwise. The reaction mixture was stirred at −78° C. for 1 h then 0.50 M of Zinc dichloride in Tetrahydrofuran (1.48 mL) was added. The reaction mixture was warmed to RT 30 min then added Tetrakis(triphenylphosphine)palladium(0) (0.0780 g, 0.0675 mmol), solution of methyl 2-iodo-5,6-dihydrobenzo[f]imidazo[1,2-d][1,4]oxazepine-10-carboxylate (0.250 g, 0.675 mmol) in 2 ml THF. The reaction was reflux for 2 h followed by treating with additional 0.50 M of Zinc dichloride in Tetrahydrofuran 2.2 ml and refluxed 3 h. The mixture was diluted with EtOAc then washed with sat. Na2CO3, and brine. The organic layer was dried over Na2SO4, concentrated in vacuo. The crude product, methyl 2-(1-(2-chlorophenyl)-1H-imidazol-2-yl)-5,6-dihydrobenzo[f]imidazo[1,2-d][1,4]oxazepine-10-carboxylate, was purified by chromatography. MS: (ESI+)=421.2

Step 2: 2-(1-(2-chlorophenyl)-1H-imidazol-2-yl)-5,6-dihydrobenzo[f]imidazo[1,2-d][1,4]oxazepine-10-carboxylic acid To a solution of methyl 2-(1-(2-chlorophenyl)-1H-imidazol-2-yl)-5,6-dihydrobenzo[f]imidazo[1,2-d][1,4]oxazepine-10-carboxylate (0.100 g, 0.238 mmol) in tetrahydrofuran (5.56 mL, 68.5 mmol) and Water (5.56 mL, 308 mmol) was added Lithium hydroxide, monohydrate (0.0399 g, 0.950 mmol). The reaction mixture was stirred at rt o/n. The reaction mixture was concentrated. The reaction mixture was acidified with 1M HCl then extracted with DCM (3×). The combined organics were dried over Na2SO4, filtered and concentrated to give 2-(1-(2-chlorophenyl)-1H-imidazol-2-yl)-5,6-dihydrobenzo[f]imidazo[1,2-d][1,4]oxazepine-10-carboxylic acid. MS: (ESI+)=407.2

Example 74

10-bromo-2-(1H-imidazol-2-yl)-5,6-dihydrobenzo[f]imidazo[1,2-d][1,4]oxazepine

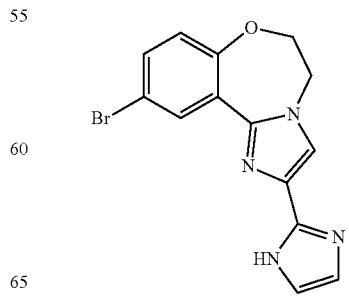

Step 1: 10-bromo-5,6-dihydrobenzo[f]imidazo[1,2-d][1,4]oxazepine-2-carbaldehyde

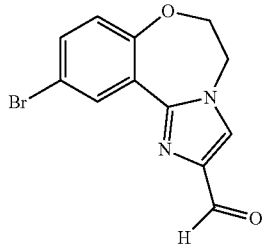 [SMILES: O=Cc1cn2c(n1)-c1cc(Br)ccc1OCC2]

10-bromo-2-iodo-5,6-dihydrobenzo[f]imidazo[1,2-d][1,4]oxazepine was formylated to give 10-bromo-5,6-dihydrobenzo[f]imidazo[1,2-d][1,4]oxazepine-2-carbaldehyde. Yield 84%. MS: 293.1

Step 2: 10-bromo-5,6-dihydrobenzo[f]imidazo[1,2-d][1,4]oxazepine-2-carbaldehyde was coupled with ethanedial in the presence of ammonia to give 10-bromo-2-(1H-imidazol-2-yl)-5,6-dihydrobenzo[f]imidazo[1,2-d][1,4]oxazepine.

Yield 37%. MS: 331.0

Example 82

1-(2-bromoethoxy)-2-nitrobenzene 82

To 2-nitrophenol (25.0 g, 0.180 mol) in sodium hydroxide (14.4 g, 359 mmol) and Water (6.0 mL, 330 mmol) in a 500 mL flask at 107° C. with a reflux condenser was added 1,2-dibromoethane (61.9 mL, 719 mmol), and the flask was heated at 107° C. for three days (FIG. 18). Then, the product was extracted twice with 100 mL DCM, washed with 2M NaOH and brine, dried with sodium sulfate, and concentrated. Silica gel chromatography eluting with hexanes and ethyl acetate provided the bromide 82 in 63% yield. 1H NMR (500 MHz, CDCl3) δ 7.83 (dd, J=8.4, 1.6 Hz, 1H), 7.53 (td, J=8.1, 1.6 Hz, 1H), 7.12-7.01 (m, 2H), 4.45-4.34 (m, 2H), 3.67 (t, J=6.5 Hz, 2H), according to: WO 2002076926

Example 83

3-(2-nitrophenoxy)propanenitrile 83

To sodium cyanide (0.398 g, 8.13 mmol) in dimethyl sulfoxide (29.0 mL, 409 mmol) at 45° C. was added bromide 84 (2.00 g, 8.13 mmol) in one portion, and the reaction was stirred for 4 hours at 70° C. (FIG. 18). Then, the reaction was extracted with ethyl acetate, and the organic layers were dried with sodium sulfate, and concentrated. Silica gel chromatography eluting with hexanes and ethyl acetate provided the nitrile 83 in 43% yield. 1H NMR (400 MHz, CDCl3) δ 7.89 (dd, J=8.1, 1.7 Hz, 1H), 7.62-7.55 (m, 1H), 7.19-7.13 (m, 1H), 7.11 (dd, J=8.4, 0.8 Hz, 1H), 4.36 (t, J=6.6 Hz, 2H), 2.94 (t, J=6.6 Hz, 2H), according to Vitale et al (1994) Anales de la Asociacion Quimica Argentina 82(1): 19-23.

Example 84

3-(2-aminophenoxy)propanenitrile 84

To palladium (0.00748 g, 0.0702 mmol) in a 50 mL flask with stirbar was added ethyl acetate (11.7 g, 133 mmol) under nitrogen, and then nitrile 83 (0.675 g, 3.51 mmol) was added (FIG. 18). The flask was fitted with a balloon containing hydrogen, and the nitrogen inlet was removed. The reaction was stirred vigorously for 4 hours, and then was filtered through celite, washing with ethyl acetate. The product 84 required no further purification, 98% yield. 1H NMR (500 MHz, CDCl3) δ 6.85-6.77 (m, 1H), 6.74-6.62 (m, 3H), 4.08 (t, J=6.1 Hz, 2H), 3.94-3.74 (m, 2H), 2.72 (t, J=6.1 Hz, 2H). LRMS m/z Calcd. for C9H10N2O: 162.07931, found: 163.1 [M+1].

Example 85

(E/Z)-Methyl 2-chloro-2-(2-(2-(2-cyanoethoxy)phenyl)hydrazono)acetate 85

To aniline 84 (1.65 g, 10.2 mmol) in acetic acid (6.80 mL, 120 mmol) and 2 M of Hydrogen chloride in water (13.59 mL), then sodium nitrite (1.0290 g, 14.914 mmol) was added while stirring vigorously at 0° C. (FIG. 18). After 20 minutes, 2-chloroacetoacetate methyl ester (1.5317 g, 10.173 mmol) was added dropwise via syringe and the mixture was warmed to room temperature over 5 hours. Then, the organic layer was extracted twice with 100 mL diethyl ether and dried with sodium sulfate, and concentrated. The crude product 85 was taken forward for next step. LRMS m/z Calcd. for C12H12ClN3O3: 281.05672, found: 282.1 [M+1].

Example 86

Methyl 4,5-dihydrobenzo[b][1,2,4]triazolo[1,5-d][1,4]oxazepine-2-carboxylate 86

To chlorohydrazone 85 (2.87 g, 10.2 mmol) in a 200 mL flask was added 1,4-dioxane (100 mL) and silver carbonate (4.22 g, 15.3 mmol) under nitrogen (FIG. 18). The flask was fitted with a reflux condenser, and wrapped in tin foil (to keep in the dark). Next, the reaction was refluxed while stirring for 4 hours. Then, the reaction was filtered, concentrated, and purified by silica gel chromatography to provide ester 86 in 7% yield over two steps. 1H NMR (500 MHz, CDCl3) δ 8.19 (dd, J=8.2, 1.4 Hz, 1H), 7.31 (td, J=8.0, 1.6 Hz, 1H), 7.25-7.20 (m, 1H), 7.18 (dd, J=8.1, 1.3 Hz, 1H), 4.50 (t, J=5.7 Hz, 2H), 4.03 (s, 3H), 3.50 (t, J=5.7 Hz, 2H). LRMS m/z Calcd. for C12H11N3O3: 245.08004, found: 246.1 [M+1].

Example 87

4,5-dihydrobenzo[b][1,2,4]triazolo[1,5-d][1,4]oxazepine-2-carboxamide 87

Ester 86 (0.166 g, 0.677 mmol) was dissolved in 3:2:1 THF:MeOH:H2O (31.2 mL), treated with 4 N aqueous lithium hydroxide (1.32 mL), and the mixture was stirred for 30 min at 25° C. (FIG. 18). The reaction was quenched with 1 N aq. HCl (20 mL) and the solution was extracted three times with 20 mL EtOAc. The combined organic extracts were dried with sodium sulfate, and concentrated to give crude 4,5-dihydrobenzo[b][1,2,4]triazolo[1,5-d][1,4]oxazepine-2-carboxylic acid which was taken forward to the next step. LRMS m/z Calcd. for C12H9N3O3: 231.06439, found: 232.1 [M+1].

To crude 4,5-dihydrobenzo[b][1,2,4]triazolo[1,5-d][1,4]oxazepine-2-carboxylic acid (0.177 g) in N,N-dimethylformamide (1.55 mL, 20.0 mmol) was added N,N,N',N'-tetramethyl-O-(7-azabenzotriazol-1-yl)uronium hexafluorophosphate (0.761 g, 2.00 mmol) and 6-chloro-1-hydroxybenzotriazole (0.339 g, 2.00 mmol) (FIG. 18). The reaction was stirred vigorously, and to the reaction was added ammonium chloride (0.285 g, 5.34 mmol). Then, N,N-diisopropylethylamine (0.465 mL, 2.67 mmol) was added after 10 minutes. After 3 hours the reaction was taken to dryness. Preparative HPLC (acetonitrile/water) gave amide 87 (0.0485 grams, 31% over two steps). 1H NMR (500 MHz, CDCl3) δ 8.22 (d, J=8.2 Hz, 1H), 7.30 (t, J=7.7 Hz, 1H), 7.22 (t, J=7.7 Hz, 1H), 7.18 (d, J=8.0 Hz, 1H), 6.97 (s, 1H), 5.75 (s, 1H), 4.49 (t, J=5.7 Hz, 2H), 3.48 (t, J=4.0 Hz, 2H). LRMS m/z Calcd. for C12H10N4O2: 230.08038, found: 231.08 [M+1].

Example 89 tert-butyl 5-(9-fluoro-5,6-dihydrobenzo[f]imidazo[1,2-d][1,4]oxazepin-2-yl)-1-isopropyl-1H-1,2,4-triazol-3-ylcarbamate

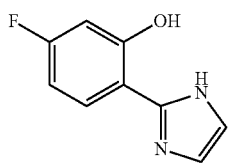 [SMILES: Oc1cc(F)ccc1-c1ncc[nH]1]

Step 1

4-Fluoro-2-hydroxybenzaldehyde (1.918 g, 0.01369 mol), ethanedial (1.884 mL, 0.04107 mol), 14.8 M ammonium hydroxide in water (14 mL, 0.21 mol) and methanol (34 mL, 0.84 mol) were combined in a round bottom flask and the reaction mixture stirred overnight at room temperature. Complete by LCMS. Concentrated in vacuo and the crude solid was dissolved in 1 M HCl until pH was ~8 with pH paper. Extracted the product with ethyl acetate, washed with brine, dried over magnesium sulfate and concentrated in vacuo again. Purified by flash chromatography in the ISCO 0% to 50% ethyl acetate in heptanes and concentrated in vacuo to give 5-fluoro-2-(1H-imidazol-2-yl)phenol (0.92 g, 37.7% yield).

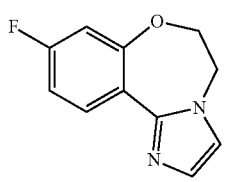 [SMILES: Fc1ccc2c(c1)OCCn1ccnc1-2]

Step 2

5-fluoro-2-(1H-imidazole-2-yl)phenol (0.90 g, 5.0 mmol) was dissolved in N,N-Dimethylformamide (40 mL, 500 mmol). Cesium carbonate (6.6 g, 20 mmol) was added, followed by 1,2-Dibromoethane (1.7 mL, 20 mmol) and heated at 90° C. with a vigreux condensation column attached for 3 hours. Complete by LCMS. Diluted with water and extracted with ethyl acetate. Acidified the aqueous layer to pH ~5 with HCl and extracted with ethyl acetate. The combined organics were concentrated in vacuo and purified by flash chromatography on the ISCO 0-50% ethyl acetate in hexanes and concentrated in vacuo to give 9-fluoro-5,6-dihydrobenzo[f]imidazo[1,2-d][1,4]oxazepine (0.69 g, 67% yield)

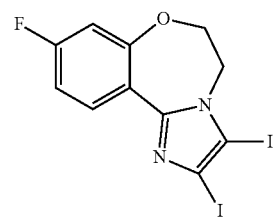 [SMILES: Fc1ccc2c(c1)OCCn1c-2nc(I)c1I]

Step 3

9-fluoro-5,6-dihydrobenzo[f]imidazo[1,2-d][1,4]oxazepine (0.69 g, 3.4 mmol), N-Iodosuccinimide (2.83 g, 12.6 mmol), and N,N-Dimethylformamide in a round bottom flask and let stir for four days. Diluted with ethyl acetate and partitioned with Sat. Sodium bicarbonate and water (50/50). The aqueous layer was extracted once more with ethyl acetate and the combined organics were dried over magnesium sulfate and concentrated in vacuo and purified by flash chromatography on the ISCO 0-40% ethyl acetate in hexanes to give 9-fluoro-2,3-diiodo-5,6-dihydrobenzo[f]imidazo[1,2-d][1,4]oxazepine (1.25 g, 81% yield)

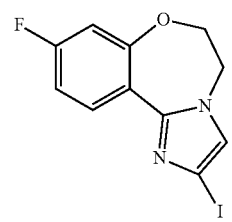 [SMILES: Fc1ccc2c(c1)OCCn1cc(I)nc1-2]

Step 4

9-fluoro-2,3-diiodo-5,6-dihydrobenzo[f]imidazo[1,2-d][1,4]oxazepine (1.24 g, 2.74 mmol) was dissolved in tetrahydrofuran (25 mL, 310 mmol) and cooled to −78° C. in a dry ice/acetone bath. Added 3.0 M ethylmagnesium bromide in ether (1.37 mL and allowed the reaction to warm up to −40° C. and stir for 4 hours. Complete by LCMS. Diluted with 100 mL of saturated ammonium chloride and extracted with ethyl acetate. Dried over magnesium sulfate, concentrated in vacuo and purified by flash chromatography on the ISCO 0-40% ethyl acetate in hexanes to give 9-fluoro-2-iodo-5,6-dihydrobenzo[f]imidazo[1,2-d][1,4]oxazepine (0.794 g, 88% yield)

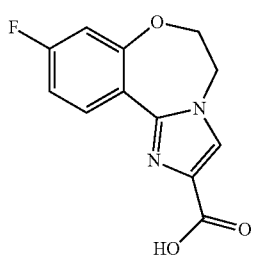 [SMILES: O=C(O)c1cn2c(n1)-c1ccc(F)cc1OCC2]

Step 5

A round bottom flask containing 9-fluoro-2-iodo-5,6-dihydrobenzo[f]imidazo[1,2-d][1,4]oxazapine (0.794 g, 2.40 mmol) was purged thoroughly with nitrogen. Palladium (II) acetate (27 mg, 0.12 mmol) and 4,5-bis(diphenylphosphino)-9,9-dimethylxanthene (139 mg, 0.24 mmol) was added sequentially with more purging. Methanol (10 mL, 200 mmol) and triethylamine (30 mL, 200 mmol) purged with nitrogen were added and the reaction mixture was purged with Carbon monoxide for 5 minutes. Two Carbon monoxide balloons were attached and the reaction mixture was heated at 50° C. for 4.5 hours. Complete formation of the methyl ester was confirmed by LCMS. Purged reaction with nitrogen and concentrated in vacuo. Purified the ester by flash chromatography on the ISCO 0 to 50% ethyl acetate in heptane and concentrated in vacuo. The ester was dissolved in tetrahydrofuran and (20 mL, 200 mmol) and 1 M Lithium hydroxide was added (7.22 mL) and the reaction was stirred for three days. Complete hydrolysis by LCMS. Adjusted to pH ~5 with 1 M HCl and extracted off the product with dichloromethane and 5% methanol to give 9-fluoro-5,6-dihydrobenzo[f]imidazo[1,2-d][1,4]oxazepine-2-carboxylic acid (0.386 g, 64.6% yield)

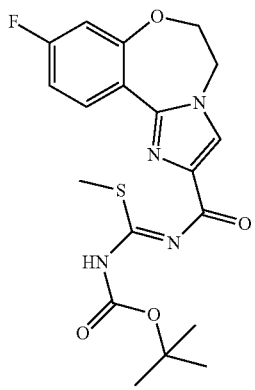 [SMILES: CS/C(=N\C(=O)c1cn2c(n1)-c1ccc(F)cc1OCC2)NC(=O)OC(C)(C)C]

Step 6

Suspended 9-fluoro-5,6-dihydrobenzo[f]imidazo[1,2-d][1,4]oxazepine-2-carboxylic acid (0.65 g, 2.6 mmol) in dichloromethane (15 mL, 230 mmol) and added 2.0 M oxalyl chloride in dichloromethane (2.0 mL) followed by N,N-Dimethylformamide (81 uL) and since the reaction still was not in solution toluene was added (15 mL, 140 mmol) and the mixture heated with a heat gun until about half was dissolved. Let stir 30 minutes and concentrated in vacuo to get the acid chloride. This was dissolved in 20 mL dichloromethane and the intermediate was added (0.50 g, 2.6 mmol) and triethylamine (1.1 mL, 7.8 mmol) in dichloromethane (50 mL, 800 mmol). The reaction mixture was stirred for 3 hours and was mostly complete by LCMS. Added water and extracted with dichloromethane 3×. Washed with brine, dried over magnesium sulfate and concentrated in vacuo and purified by flash chromatography on the ISCO 0-50% ethyl acetate in heptane to give acylthiourea intermediate (0.20 g, 18% yield).

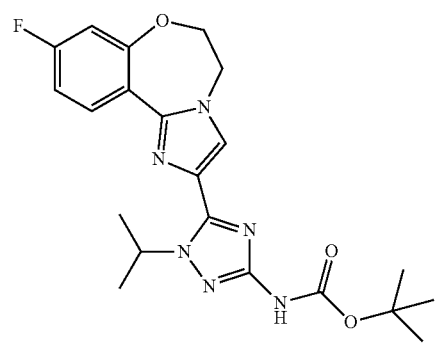 [SMILES: CC(C)n1nc(NC(=O)OC(C)(C)C)nc1-c1cn2c(n1)-c1ccc(F)cc1OCC2]

Step 7

Acylthiourea intermediate (200 mg, 0.4 mmol) was dissolved in N,N-Dimethylformamide (10 mL, 100 mmol) and N,N-Diisopropylamine (0.29 mL, 1.662 mmol) was added followed by isopropylhydrazine hydrochloride (68.92 mg, 0.62 mmol). The reaction was stirred at room temperature overnight. Complete reaction confirmed by LCMS. Diluted with water and extracted with DCM 3 times. The combined organic layers were dried over dried over magnesium sulfate and concentrated in vacuo. The product was purified by flash chromatography on the ISCO 0 to 10% methanol in dichloromethane to give tert-butyl 5-(9-fluoro-5,6-dihydrobenzo[f]imidazo[1,2-d][1,4]oxazepin-2-yl)-1-isopropyl-1H-1,2,4-triazol-3-ylcarbamate (200 mg, 100% yield)

Example 90

10-fluoro-5,6-dihydrobenzo[f]imidazo[1,2-d][1,4]oxazepine-2-carboxamide

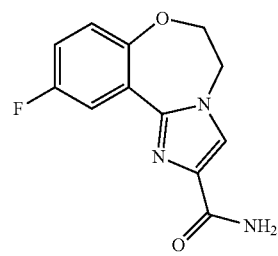 [SMILES: NC(=O)c1cn2c(n1)-c1cc(F)ccc1OCC2]

Step 1: 4-fluoro-2-(1H-imidazol-2-yl)phenol

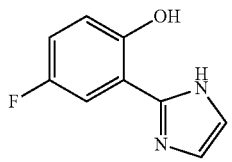 [SMILES: Oc1ccc(F)cc1-c1ncc[nH]1]

5-fluoro-2-hydroxybenzaldehyde (5.0 g, 36 mmol), ethanedial (4.912 mL, 107 mmol), 14.8 M ammonium hydroxide in water (40 mL, 600 mmol), and methanol (90 mL, 2000 mmol) were combined in a round bottom flask and let stir at room temperature overnight. Complete reaction was confirmed by LCMS. Concentrated in vacuo and added 1 M HCL until pH was ~8. Extracted with ethyl acetate, washed with brine, dried over magnesium sulfate and concentrated in vacuo. Purified by flash chromatography 0 to 50% ethyl acetate in heptane to give 4-fluoro-2-(1H-imidazol-2-yl) phenol (2.24 g, 35% yield)

Step 2

Following the procedures of Example 89, 4-fluoro-2-(1H-imidazol-2-yl)phenol was converted to 10-fluoro-5,6-dihydrobenzo[f]imidazo[1,2-d][1,4]oxazepine-2-carboxamide.

Example 91

2-Bromo-1-(2-isopropyl-5-methyl-2H-[1,2,4]triazol-3-yl)-ethanone

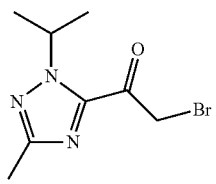

Step 1

Acetic acid hydrazide (100 g, 1.35 mol) was suspended in acetone (991 mL, 13.5 mol) and cyclohexane (1.5 L). The reaction mixture was heated at 55° C. for 16 h, during which the solids dissolved to give a colourless solution. The reaction mixture was concentrated in vacuo to give Acetic acid isopropylidenehydrazide as a white solid (153 g, 100%). 1H NMR 400 MHz (CDCl3) δ: 8.25 (1H, br s), 2.26 (3H, s), 2.00 (3H, s), 1.83 (3H, s)

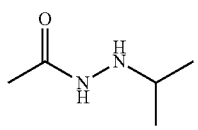

Step 2

To a solution of acetic acid isopropylidenehydrazide (153 g, 1.35 mol) in IMS (1.5 L) was added platinum oxide (0.66 g) and the reaction mixture stirred under an atmosphere of hydrogen at RT until 1H NMR showed complete consumption of acetic acid isopropylidenehydrazide (~48 h). The reaction mixture was filtered through a plug of Celite® and the filtrate concentrated in vacuo to give Acetic acid N'-isopropylhydrazide as a colourless oil which crystallised on standing (154.6 g). 1H NMR 400 MHz (CDCl3) δ: 3.12 (1H, sept, J=6.3 Hz), 1.96 (3H, s), 1.04 (6H, d, J=6.3 Hz)

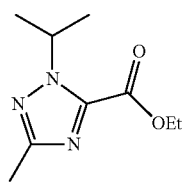

Step 3

To a solution of ethyl thiooxamate (29.6 g, 0.22 mol) in DCM (260 mL) at RT was added trimethyloxonium tetrafluroborate (34.5 g, 0.23 mol) and the mixture stirred at RT for 2 h. During this time the yellow colour faded and a thick white precipitate was formed. Acetic acid N'-isopropylhydrazide (27.1 g, 0.23 mol) and TEA (30.9 mL, 0.22 mol) were added as a solution in DCM (75 mL) causing the precipitate to dissolve. The reaction mixture was stirred at reflux for 5 h then at RT for 10 h. The reaction mixture was washed with water, and the aqueous layer extracted with DCM (2×50 mL). The combined organic extracts were washed with brine, dried (MgSO4) and concentrated in vacuo. The resultant residue was subjected to flash chromatography (SiO2, gradient 0-100% ethyl acetate in cyclohexane) to give 2-Isopropyl-5-methyl-2H-[1,2,4]triazole-3-carboxylic acid ethyl ester as a pale yellow oil which crystallised on standing (15.6 g, 32%). 1H NMR 400 MHz (CDCl3) δ: 5.49 (1H, sept, J=6.7 Hz), 4.45 (2H, t, J=7.2 Hz), 2.43 (3H, s), 1.50 (6H, d, J=6.7 Hz), 1.44 (3H, t, J=7.2 Hz)

Step 4

To a solution of 2-isopropyl-5-methyl-2H-[1,2,4]triazole-3-carboxylic acid ethyl ester (12.09 g, 61.3 mmol) and dibromomethane (8.63 mL, 122.6 mmol) in THF (500 mL) at −78° C. was added methyllithium (40.9 mL, 122.6 mmol, 3M solution in diethoxymethane) dropwise. The reaction mixture was stirred at −78° C. for 15 min. Acetic acid (3 mL) was added and the reaction mixture allowed to warm to RT. The reaction mixture was diluted with water and extracted with ethyl acetate (3×30 mL). The combined organic extracts were washed with brine, dried (MgSO4) and concentrated in vacuo. The resultant residue was subjected to flash chromatography (SiO2, gradient 0-100% ethyl acetate in cyclohexane) to give 2-Bromo-1-(2-isopropyl-5-methyl-2H-[1,2,4]triazol-3-yl)-ethanone as a colourless oil which crystallised on standing (11.26 g, 75%). 1H NMR 400 MHz (CDCl3) δ: 5.41 (1H, sept, J=6.6 Hz), 4.67 (2H, s), 2.44 (3H, s), 1.49 (6H, d, J=6.6 Hz)

Example 92

2-(2-Isopropyl-5-methyl-2H-[1,2,4]triazol-3-yl)-4,5-dihydro-6-oxa-1,3a,9-triaza-benzo[e]azulen-8-ol

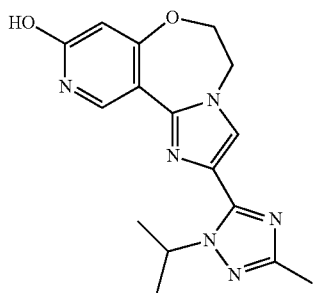 [SMILES: Cc1nc(-c2cn3c(n2)-c2cnc(O)cc2OCC3)n(C(C)C)n1]

Step 1: 4-Chloro-5-iodo-pyridin-2-ylamine

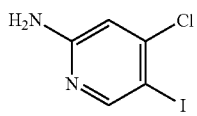

To a solution of 2-amino-4-chloropyridine (150 g, 0.78 mol) in DMF (1.5 L) was added NIS (341 g, 1.52 mol) and the reaction mixture stirred at RT for 18 h before being concentrated in vacuo to 300 mL volume. The resultant residue was poured into 10% aqueous sodium thiosulfate solution (1.2 L), stirred for 15 min and the precipitate formed collected by filtration, washed with water then dried at 35° C. in vacuo to give the title compound as a pale brown solid (185 g, 62%). 1H NMR 400 MHz (CDCl3) δ: 8.33 (1 H, s), 6.68 (1 H, s), 4.52 (2 H, s).

Step 2: 4-Chloro-5-iodo-2-methoxy-pyridine

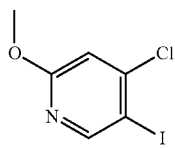

To a solution of 4-chloro-5-iodo-pyridin-2-ylamine (64.2 g, 0.25 mol) in methanol (1.1 L) and TFA (93.7 mL, 1.26 mol) was added tert-butyl nitrite (150 mL, 1.26 mol) so as to maintain temperature less than 3° C. The resultant mixture was stirred at RT for 1 h then allowed to warm to RT and stirred for 16 h. The reaction was quenched by the careful addition of water then concentrated in vacuo to ¼ volume. The resultant residue was treated with water (1 L) and the precipitate formed collected by filtration and dried in vacuo at 35° C. to give the title compound (62.3 g, 92%). Contains 16% impurity. $^1$H NMR 400 MHz (DMSO-d) δ: 8.56 (1 H, s), 7.20 (1 H, s), 3.86 (3 H, s).

Step 3: 4-Chloro-6-methoxy-nicotinonitrile

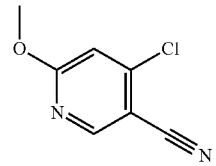

A suspension of 4-chloro-5-iodo-2-methoxy-pyridine (30.5 g, 0.11 mol), zinc (II) cyanide (7.97 g, 68 mmol), Pd(PPh3)4 (6.56 g, 5.66 mmol) and DMF (450 mL) was degassed and then heated at 120° C. for 1 h before being concentrated in vacuo. The resultant residue was treated with water then extracted with DCM, the organic extract dried (MgSO4), filtered, then concentrated in vacuo. The resultant residue was crystallized from DCM to give the title compound (10.1 g, 54%). The mother liquors were concentrated in vacuo and the residue subjected to flash chromatography (SiO2 gradient 0 to 100% ethyl acetate in cyclohexane) then crystallization from cyclohexane to give the further title compound (5.16 g, 28%, 82% total). 1H NMR 400 MHz (CDCl3) δ: 8.45 (1 H, s), 6.90 (1 H, s), 4.01 (3 H, s).

Step 4: 4-Chloro-6-methoxy-nicotinamidine hydrochloride

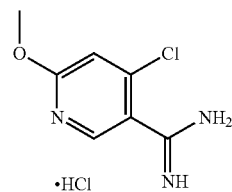

To a solution of 4-chloro-6-methoxy-nicotinonitrile (10.1 g, 59.7 mmol) in THF (300 mL) at −78° C. was added LiHMDS (65.7 mL) dropwise and the reaction mixture stirred for 30 min before allowing to warm to RT and stirring for a further 1 h. The reaction was quenched by the addition of 1N HCl (to pH ~1) and then extracted three times with ethyl acetate. The aqueous layer was concentrated in vacuo to give brown solid which was azeotroped with toluene to give the title compound as a tan solid. Mixture with ammonium chloride, 72% title compound by weight. (15.2 g, 83%). $^1$H NMR 400 MHz (DMSO-d) δ: 9.68 (4 H, d, J=15.79 Hz), 8.46 (1 H, s), 7.47 (5 H, t, J=50.66 Hz), 7.27 (1 H, s), 3.95 (3 H, s).

Step 5: 4-Chloro-5-[4-(2-isopropyl-5-methyl-2H-[1,2,4]triazol-3-yl)-1H-imidazol-2-yl]-2-methoxy-pyridine

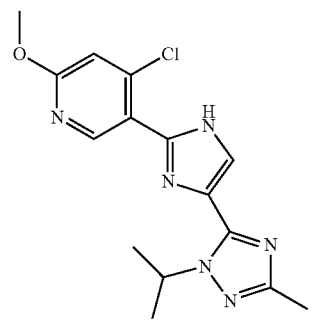 [SMILES: COc1cc(Cl)c(-c2nc(-c3nc(C)nn3C(C)C)c[nH]2)cn1]

A suspension of 4-chloro-6-methoxy-nicotinamidine hydrochloride (18.4 mmol) and potassium bicarbonate (7.37 g, 73.6 mmol) in THF (42 mL) and water (8.5 mL) was heated to reflux and treated with a solution of 2-bromo-1-(2-isopropyl-5-methyl-2H-[1,2,4]triazol-3-yl)-ethanone (4.53 g, 18.4 mmol) in THF (14 mL) added dropwise. The reaction mixture was heated at reflux for 18 h before removal of volatile solvent in vacuo. The resultant suspension was filtered and the residue washed with water then dried to give the title compound as a brown solid (5.91 g, 97%). LCMS: RT=2.68 min, [M+H]+=333/335. 1H NMR 400 MHz (CDCl3) δ: 10.41 (1 H, s), 9.02 (1 H, s), 7.81 (1 H, s), 6.87 (1 H, s), 5.91 (1 H, m), 4.00 (3 H, s), 2.41 (3 H, s), 1.55 (6 H, d, J=6.71 Hz).

Step 6: 2-[2-(4-Chloro-6-methoxy-pyridin-3-yl)-4-(2-isopropyl-5-methyl-2H-[1,2,4]triazol-3-yl)-imidazol-1-yl]-ethanol

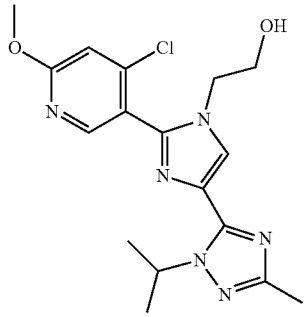 [SMILES: COc1cc(Cl)c(-c2nc(-c3nc(C)nn3C(C)C)cn2CCO)cn1]

A suspension of 4-chloro-5-[4-(2-isopropyl-5-methyl-2H-[1,2,4]triazol-3-yl)-1H-imidazol-2-yl]-2-methoxy-pyridine (5.9 g, 17.7 mmol) in toluene (20 mL) was treated with ethylene carbonate (50 mL) and heated at 130° C. for 2.5 h. The cooled reaction mixture was concentrated in vacuo then diluted with DCM and passed through a pad of silica eluting with DCM then 20% methanol in DCM. Methanolic fractions were combined and concentrated in vacuo and the resultant residue subjected to recrystallisation from acetonitrile to give the title compound as a pale tan solid (2.27 g, 34%). LCMS: RT=2.53 min [M+H]+=377/379. 1H NMR 400 MHz (CDCl3) δ: 8.25 (1H, s), 8.05 (1H, s), 6.92 (1H, s), 5.82-5.80 (1H, m), 4.00 (3H, s), 3.97 (2H, t, J=4.92 Hz), 3.88 (2H, t, J=4.92 Hz), 2.38 (3H, s), 1.48 (6H, d, J=6.63 Hz).

Step 7: 2-(2-Isopropyl-5-methyl-2H-[1,2,4]triazol-3-yl)-8-methoxy-4,5-dihydro-6-oxa-1,3a,9-triaza-benzo[e]azulene

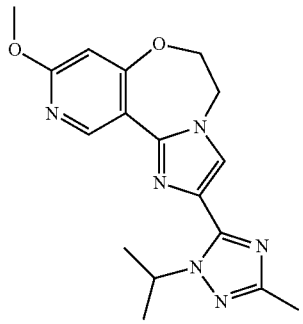 [SMILES: COc1cc2c(cn1)-c1nc(-c3nc(C)nn3C(C)C)cn1CCO2]

A solution of 2-[2-(4-chloro-6-methoxy-pyridin-3-yl)-4-(2-isopropyl-5-methyl-2H-[1,2,4]triazol-3-yl)-imidazol-1-yl]-ethanol (2.25 g, 5.97 mmol) in DMF (30 mL) was cooled to 0° C. and treated with sodium hydride (239 mg, 5.97 mmol), the reaction mixture stirred at 0° C. for 30 min then allowed to warm to RT and stirred for 2 h. The reaction mixture was re-cooled to 0° C. and treated with water (400 mL), the precipitated product filtered off and washed with water then dried in vacuo to give the title compound as a white solid (1.02 g, 50%). LCMS RT=2.68 min, [M+H]+=341. 1H NMR 400 MHz (DMSO-d) δ: 9.15 (1 H, s), 7.87 (1 H, s), 6.42 (1 H, s), 5.84 (1 H, m), 4.57-4.56 (4 H, m), 3.89 (3 H, s), 2.25 (3 H, s), 1.46 (6 H, d, J=6.60 Hz).

Step 8

A solution of 2-(2-isopropyl-5-methyl-2H-[1,2,4]triazol-3-yl)-8-methoxy-4,5-dihydro-6-oxa-1,3a,9-triaza-benzo[e]azulene (1.0 g, 2.97 mmol) in 48% aqueous HBr (5 mL) and acetic acid (5 mL) was heated at 80° C. for 7.5 h before being concentrated in vacuo. The resultant residue was suspended in water (10 mL) and pH adjusted to ~6 using 5N aqueous NaOH. The precipitate formed was filtered off, washed with water then dried in vacuo to give 2-(2-Isopropyl-5-methyl-2H-[1,2,4]triazol-3-yl)-4,5-dihydro-6-oxa-1,3a,9-triaza-benzo[e]azulen-8-ol as a white solid (1.01 g, 100%). LCMS RT=2.01 min, [M+H]+=327. 1H NMR 400 MHz (DMSO-d) δ: 8.42 (1 H, s), 7.85 (1 H, s), 5.85 (1 H, s), 5.69-5.65 (1 H, m), 4.55-4.54 (2 H, m), 4.50-4.46 (2 H, m), 2.27 (3 H, s), 1.44 (6 H, d, J=6.59 Hz).

Example 93

2-(2-Isopropyl-2H-[1,2,4]triazol-3-yl)-4,5-dihydro-6-oxa-1,3a,9-triaza-benzo[e]azulen-8-ol

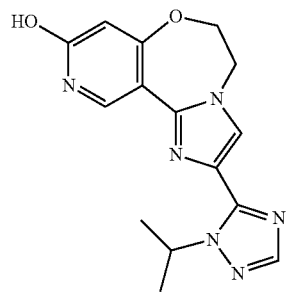 [SMILES: CC(C)n1ncnc1-c1cn2c(n1)-c1cnc(O)cc1OCC2]

Step 1: 4-Chloro-5-[4-(2-isopropyl-2H-[1,2,4]triazol-3-yl)-1H-imidazol-2-yl]-2-methoxy-pyridine

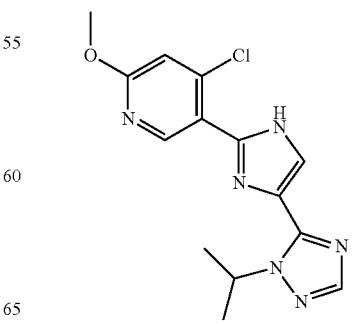

A suspension of 4-chloro-6-methoxy-nicotinamidine hydrochloride (50.9 mmol) and potassium bicarbonate (20.4 g, 202.5 mmol) in THF (128 mL) and water (21 mL) was heated to reflux and treated with a solution of 2-chloro-1-(2-isopropyl-2H-[1,2,4]triazol-3-yl)-ethanone (9.55 g, 50.9 mmol) in THF (25 mL) added dropwise. The reaction mixture was heated at reflux for 24 h before removal of volatile solvent in vacuo. The resultant residue was diluted with water and extracted with ethyl acetate. The combined extracts were dried (Na2SO4), treated with charcoal (15 g), filtered and concentrated in vacuo to give a solid. The solid was triturated with 10% diethyl ether in pentane then dried at 50° C. in vacuo to give 4-Chloro-5-[4-(2-isopropyl-2H-[1,2,4]triazol-3-yl)-1H-imidazol-2-yl]-2-methoxy-pyridine as a pale brown solid (8.74 g, 54%). LCMS RT=2.86 min, [M+H]+=319/321. 1H NMR 400 MHz (CDCl3) δ: 9.03 (1 H, s), 7.89 (1 H, s), 7.83 (1 H, s), 7.26 (1 H, s) 6.88 (1 H, s), 4.01 (3 H, s), 1.58 (6 H, d, J=6.63 Hz).

Step 2: 2-[2-(4-Chloro-6-methoxy-pyridin-3-yl)-4-(2-isopropyl-2H-[1,2,4]triazol-3-yl)-imidazol-1-yl]-ethanol

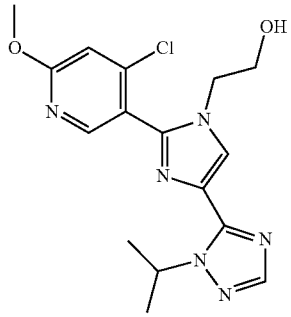 [SMILES: COc1cc(Cl)c(-c2nc(-c3ncnn3C(C)C)cn2CCO)cn1]

To warmed ethylene carbonate (34 g) was added 4-chloro-5-[4-(2-isopropyl-2H-[1,2,4]triazol-3-yl)-1H-imidazol-2-yl]-2-methoxy-pyridine (8.74 g, 27.4 mmol) and the mixture heated at 130° C. for 3 h. The cooled reaction mixture was diluted with DCM and loaded onto silica (150 g). The silica was washed with DCM then 5% methanol in DCM. Methanolic fractions were combined and concentrated in vacuo to give the title compound as a brown foam (7.52 g, 75%). LCMS RT=2.65, [M+H]+=363/365. 1H NMR 400 MHz (CDCl3) δ: 8.27 (1 H, s), 8.02 (1 H, s), 7.85 (1 H, s), 6.93 (1 H, s), 5.98-5.82 (1 H, m), 4.00 (5 H, m), 3.88 (2 H, t, J=5.11 Hz), 1.51 (6 H, d, J=6.62 Hz).

Step 3: 2-(2-Isopropyl-2H-[1,2,4]triazol-3-yl)-8-methoxy-4,5-dihydro-6-oxa-1,3a,9-triaza-benzo[e]azulene

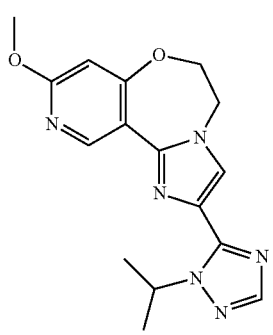 [SMILES: COc1cc2c(cn1)-c1nc(-c3ncnn3C(C)C)cn1CCO2]

A solution of 2-[2-(4-chloro-6-methoxy-pyridin-3-yl)-4-(2-isopropyl-2H-[1,2,4]triazol-3-yl)-imidazol-1-yl]-ethanol (7.52 g, 20.7 mmol) in DMF (100 mL) was cooled to 0° C. and treated with sodium hydride (804 mg, 20.1 mmol), the reaction mixture stirred at 0° C. for 10 min then allowed to warm to RT and stirred for 72 h. Further sodium hydride (150 mg) was added and stirring continued until no starting material remained before removal of solvent in vacuo. The residue was dissolved in ethyl acetate and the resultant solution washed three times with saturated brine then dried (Na2SO4), filtered and concentrated in vacuo. The resultant residue was triturated in pentane/diethyl ether (5:1) to give the title compound as a brown solid (5.38 g, 79%). LCMS RT=2.86, [M+H]+=327. 1H NMR 400 MHz (CDCl3) δ: 9.35 (1 H, s), 7.87 (1 H, s), 7.63 (1 H, s), 6.37 (1 H, s), 6.03-6.02 (1 H, m), 4.54-4.53 (2 H, m), 4.53-4.33 (2 H, m), 3.99 (3 H, s), 1.57 (6 H, d, J=6.63 Hz).

Step 4

A solution of 2-(2-isopropyl-2H-[1,2,4]triazol-3-yl)-8-methoxy-4,5-dihydro-6-oxa-1,3a,9-triaza-benzo[e]azulene (1.0 g, 2.97 mmol) in acetic acid (40 mL) was treated with 48% aqueous HBr (37.7 mL) and heated at 80° C. for 5 h before being concentrated in vacuo. The resultant residue was suspended in water (60 mL) and pH adjusted to ~6 using 5N aqueous NaOH. The precipitate formed was filtered off, washed with water then dried in vacuo. The resultant solid was triturated in acetone to give 2-(2-Isopropyl-2H-[1,2,4]triazol-3-yl)-4,5-dihydro-6-oxa-1,3a,9-triaza-benzo[e]azulen-8-ol as a beige solid (3.58 g, 69%). LCMS RT=2.04 min, [M+H]+=313. ¹H NMR 400 MHz (DMSO-d) δ: 8.42 (1 H, s), 7.90 (1 H, s), 7.83 (1 H, s), 5.84 (1 H, s), 5.78 (1 H, m), 4.71-4.30 (4 H, m), 1.45 (6 H, d, J=6.60 Hz).

Example 94

2-(2-Isopropyl-2H-[1,2,4]triazol-3-yl)-8-piperidin-4-yl-4,5-dihydro-6-oxa-1,3a,9-triaza-benzo[e]azulene hydrochloride

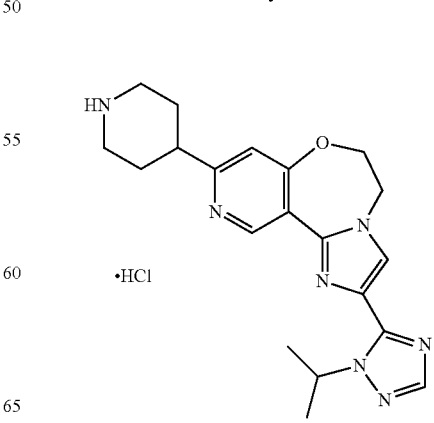

Step 1: Trifluoro-methanesulfonic acid 2-(2-isopropyl-2H-[1,2,4]triazol-3-yl)-4,5-dihydro-6-oxa-1,3a,9-triaza-benzo[e]azulen-8-yl ester

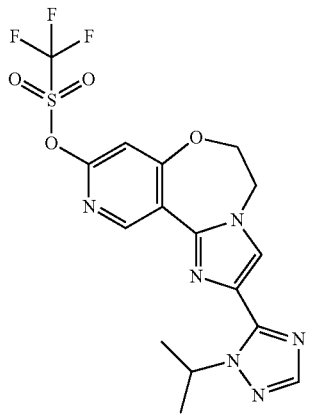 [SMILES: CC(C)n1ncnc1-c1cn2c(n1)-c1cnc(OS(=O)(=O)C(F)(F)F)cc1OCC2]

A suspension of 2-(2-isopropyl-2H-[1,2,4]triazol-3-yl)-4,5-dihydro-6-oxa-1,3a,9-triaza-benzo[e]azulen-8-ol (238 mg, 0.76 mmol) in DMF (2.2 mL) was treated with sodium hydride (65% dispersion in mineral oil, 34 mg, 0.91 mmol), the reaction mixture heated at 40° C. for 1.5 h then cooled to RT. Benzenebis(trifluoromethane) sulfonamide (327 mg, 0.91 mmol) was added and the reaction mixture stirred at RT for 24 h before being diluted with ethyl acetate (60 mL) and washed with brine (4×20 mL). The resultant solution was dried (MgSO4), filtered and concentrated in vacuo to give a solid which was triturated in diethyl ether to give Trifluoro-methanesulfonic acid 2-(2-isopropyl-2H-[1,2,4]triazol-3-yl)-4,5-dihydro-6-oxa-1,3a,9-triaza-benzo[e]azulen-8-yl ester as a white solid (44 mg). The mother liquors from trituration were concentrated in vacuo, the resultant residue recrystallised from methanol to give further compound (39 mg, 25% total). LCMS RT=3.27 min, [M+H]+=445. $^1$H NMR 400 MHz (DMSO-d6) δ: 9.32 (1 H, s), 8.04 (1 H, s), 7.93 (1 H, s), 7.36 (1 H, s), 5.89 (1 H, m), 4.74 (2 H, m), 4.63 (2 H, m), 1.48 (6 H, d, J=6.58 Hz)

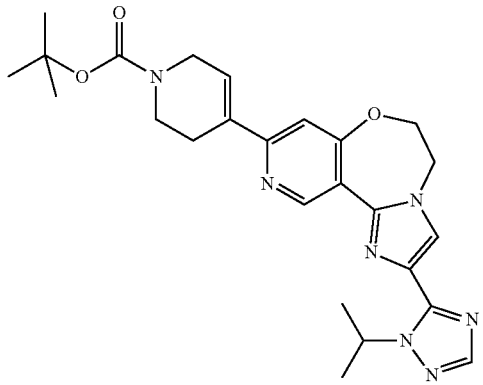 [SMILES: CC(C)n1ncnc1-c1cn2c(n1)-c1cnc(C3=CCN(C(=O)OC(C)(C)C)CC3)cc1OCC2]

Step 2

To a mixture of trifluoro-methanesulfonic acid 2-(2-isopropyl-2H-[1,2,4]triazol-3-yl)-4,5-dihydro-6-oxa-1,3a,9-triaza-benzo[e]azulen-8-yl ester (83 mg, 0.19 mmol) and 2N aqueous sodium carbonate (600 L) in DMF (1.2 mL) was added palladium bis(dibenzylideneacetone) (6 mg, 0.01 mmol), triphenylphosphine (4 mg, 0.015 mmol) and 4-(4,4,5,5-tetramethyl-[1,3,2]dioxaborolan-2-yl)-3,6-dihydro-2H-pyridine-1-carboxylic acid tert-butyl ester (75 mg, 0.24 mmol). The reaction mixture was degassed and then heated at 90° C. under an atmosphere of argon for 2 h before being concentrated in vacuo. The resultant residue was partitioned between ethyl acetate and water, the aqueous extracted with ethyl acetate (×3) and the combined organic extracts dried (MgSO4), filtered and concentrated in vacuo. The resultant residue was subjected to flash chromatography (SiO2, gradient 0 to 10% methanol in ethyl acetate) to give 4-[2-(2-Isopropyl-2H-[1,2,4]triazol-3-yl)-4,5-dihydro-6-oxa-1,3a,9-triaza-benzo[e]azulen-8-yl]-3,6-dihydro-2H-pyridine-1-carboxylic acid tert-butyl ester as a white solid (41 mg, 45%). LCMS (*) RT=3.24 min, [M+H]+=478. 1H NMR 400 MHz (CDCl3) δ: 9.65 (1 H, s), 7.94 (1 H, s), 7.89 (1H, s), 7.00 (1 H, s), 6.84 (1 H, s), 4.60 (2 H, s), 4.50 (2 H, s), 4.18 (2 H, s), 3.67 (2 H, s), 2.62 (2 H, s), 1.59 (6 H, d, J=6.62 Hz), 1.50 (9 H, s)

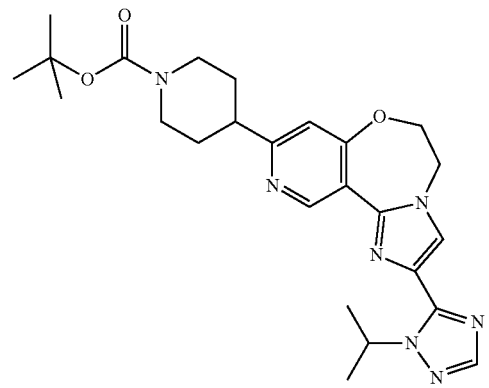 [SMILES: CC(C)n1ncnc1-c1cn2c(n1)-c1cnc(C3CCN(C(=O)OC(C)(C)C)CC3)cc1OCC2]

Step 3

A mixture of 4-[2-(2-isopropyl-2H-[1,2,4]triazol-3-yl)-4,5-dihydro-6-oxa-1,3a,9-triaza-benzo[e]azulen-8-yl]-3,6-dihydro-2H-pyridine-1-carboxylic acid tert-butyl ester (89 mg, 0.19 mmol) in IMS (10 mL) was treated with platinum oxide (10 mg), the reaction mixture degassed and stirred at RT under an atmosphere of hydrogen for 72 h. Further platinum oxide (10 mg) was added and stirring continued at RT for 18 h before the filtering through Celite® and concentrating in vacuo. The resultant residue was subjected to flash chromatography (SiO2, gradient 0 to 5% methanol in DCM) to give 4-[2-(2-Isopropyl-2H-[1,2,4]triazol-3-yl)-4,5-dihydro-6-oxa-1,3a,9-triaza-benzo[e]azulen-8-yl]-piperidine-1-carboxylic acid tert-butyl ester (58 g, 64%). LCMS RT=2.72, [M+H]+=480

Step 4

A solution of 4-[2-(2-isopropyl-2H-[1,2,4]triazol-3-yl)-4,5-dihydro-6-oxa-1,3a,9-triaza-benzo[e]azulen-8-yl]-piperidine-1-carboxylic acid tert-butyl ester (58 mg, 0.12 mmol) in DCM (0.5 mL) and methanol (0.3 mL) was treated with 4M HCl in dioxane (0.8 mL) and the reaction mixture stirred at RT for 1.5 h before being concentrated in vacuo. The resultant residue was triturated with diethyl ether to give 2-(2-Isopropyl-2H-[1,2,4]triazol-3-yl)-8-piperidin-4-yl-4,5- dihydro-6-oxa-1,3a,9-triaza-benzo[e]azulene hydrochloride (66 mg, 100%). LCMS RT=1.68 min, [M+H]+=380

Example 102

2-(1-(2-chlorophenyl)-1H-1,2,4-triazol-5-yl)-5,6-dihydrobenzo[f]imidazo[1,2-d][1,4]oxazepine-10-carboxamide 102

Oxalyl chloride in methylene chloride (2.00 M, 3.0 mL) was added to a suspension of 2-(1-(2-chlorophenyl)-1H-1, 2,4-triazol-5-yl)-5,6-dihydrobenzo[f]imidazo[1,2-d][1,4] oxazepine-10-carboxylic acid (112 mg, 0.178 mmol) in 30 ml of methylene chloride. Catalytic amount of N,N-Dimethylformamide (1.0 uL, 0.013 mmol) was added and the mixture was stirred for 2 hours. The mixture was filtered, the filtrate was concentrated in vacuum and the residue dried in high vacuum for 1 hour. The above residue was dissolved in N,N-dimethylacetamide (3.0 mL, 32 mmol) and saturated with gaseous ammonia. The mixture was stirred for 20 min, concentrated in vacuum, dissolved in aqueous methanol and subjected to RP HPLC purification to yield 18.5 mg of 102 (26%), MS: 407.1. 1H NMR (400 MHz, DMSO) δ 8.26 (d, J=2.2, 1H), 8.20 (s, 1H), 7.80 (s, 1H), 7.72-7.51 (m, 6H), 7.29 (s, 1H), 7.00 (d, J=8.5, 1H).

Example 103

2-(1-(2,4-difluorophenyl)-1H-1,2,4-triazol-5-yl)-8-bromo-4,5-dihydrobenzo-2H-oxepino[4,5-d]pyrazole 103

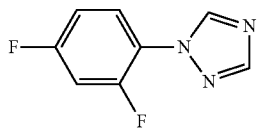 [SMILES: Fc1ccc(-n2cncn2)c(F)c1]

A solution of 2,4-difluorophenyl hydrazine (20 g, 0.14 mol) in formamide (60 mL) was heated at 120° C. for 18 h. The cooled reaction mixture was diluted with saturated aqueous sodium hydrogen carbonate and ethyl acetate forming an emulsion. The emulsion was filtered through Celite®, the aqueous extracted with ethyl acetate. The combined organic extracts were dried (Na2SO4), filtered and concentrated in vacuo and the resultant solid subjected to flash chromatography (SiO2, gradient 0 to 100% ethyl acetate in cyclohexane) to give 1-(2,4-Difluoro-phenyl)-1H-[1,2,4]triazole as a white solid (15.7 g, 62%). ¹H NMR δ (ppm) (CDCl3): 8.60 (1 H, d, J=2.83 Hz), 8.12 (1 H, s), 7.91-7.83 (1 H, m), 7.10-7.04 (2 H, m).

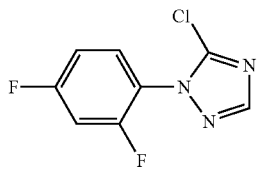 [SMILES: Fc1ccc(-n2ncnc2Cl)c(F)c1]

Under an atmosphere of nitrogen a solution of 1-(2,4-difluoro-phenyl)-1H-[1,2,4]triazole (15.7 g, 86.7 mmol) in THF (300 mL) at −78° C. was treated with n-butyllithium (38 mL, 2.5 M, 95.3 mmol) dropwise. After stirring for 1.5 h a solution of hexachloroethane (22.6 g, 95.3 mmol) in THF (30 mL) was added dropwise. The resultant reaction mixture was stirred for 1.5 h before allowing to warm to RT and quenching with water. The resultant mixture was diluted with water and extracted with ethyl acetate, the combined organic extracts were dried (Na2SO4), filtered and concentrated in vacuo to give an oil which crystallised on standing. The solid was recrystallised from cyclohexane to give 5-Chloro-1-(2,4-difluoro-phenyl)-1H-[1,2,4]triazole (12.4 g, 66%). ¹H NMR δ (ppm)(CDCl3): 8.04 (1 H, s), 7.51-7.43 (1 H, m), 7.10-7.04 (2 H, m).

To a solution of 8-bromo-4,5-dihydro-2H-6-oxa-1,2-diaza-benzo[e]azulene (2.12 g, 7.99 mmol) and 5-chloro-1-(2,4-difluoro-phenyl)-1H-[1,2,4]triazole (2.58 g, 12.0 mmol) in THF (10 mL) was added cesium carbonate (3.9 g, 12.0 mmol) and the reaction mixture heated at 180° C. for 60 min using microwave irradition. The cooled reaction mixture was diluted with water and extracted with ethyl acetate, the combined organic extracts were washed with brine, then dried (MgSO4), filtered and concentrated in vacuo. The resultant residue was triturated in hot cyclohexane to give 103 (1.62 g, 46%). ¹H NMR (DMSO-d6, 400 MHz): δ 8.45 (s, 1 H); 8.30 (s, 1 H); 7.84-7.77 (m, 1 H); 7.66-7.58 (m, 1 H); 7.37-7.30 (m, 1 H); 7.27 (d, J=8.6 Hz, 1 H); 7.22 (d, J=2.0 Hz, 1 H); 7.13 (dd, J=8.6, 2.1 Hz, 1 H); 4.26 (t, J=5.0 Hz, 2 H); 3.06 (t, J=5.0 Hz, 2 H)

Example 104

2-(1-(2-chlorophenyl)-1H-1,2,4-triazol-5-yl)-5,6-dihydrobenzo[f]imidazo[1,2-d][1,4]oxazepine-9-carboxamide 104

Following the procedure for 243, 2-(1-(2-chlorophenyl)-1H-1,2,4-triazol-5-yl)-5,6-dihydrobenzo[f]imidazo[1,2-d][1,4]oxazepine-9-carboxylic acid, ammonium chloride, HATU, diisopropylethylamine and DMF were reacted to give 104. Yield 51%. MS: 407.0. 1H NMR (400 MHz, DMSO) δ 8.21 (s, 1H), 7.99 (s, 1H), 7.95 (s, 1H), 7.74 (d, J=7.0, 1H), 7.69-7.54 (m, 4H), 7.47 (s, 1H), 7.44-7.36 (m, 2H), 4.48 (d, J=7.6, 4H)

Example 105

2-(1-isopropyl-1H-1,2,4-triazol-5-yl)-8-(pyrazol-4-yl)-4,5-dihydrobenzo-2H-oxepino[4,5-d]pyrazole 105

8-Bromo-2-(2-isopropyl-2H-[1,2,4]triazol-3-yl)-4,5-dihydro-2H-6-oxa-1,2-diaza-benzo[e]azulene (53 mg, 0.14 mmol), 4-(4,4,5,5-tetramethyl-[1,3,2]dioxaborolan-2-yl)-1H-pyrazole (36 mg, 0.18 mmol), tris(dibenzylidineacetone) di-palladium (0) (2.2 mg, 1.7 mol %), 2,4',6'-diisopropyl-1, 1'-biphenyl-2-yldicyclohexylphosphine (5.3 mg, 9 mol %) and K3PO4 (89 mg, 0.42 mmol) were combined in a reaction vial, the atmosphere evacuated and back-filled with nitrogen. Dioxane (1 mL) and water (0.1 mL) were added and the reaction mixture heated at reflux for 18 h. Further 4-(4,4,5,5-tetramethyl-[1,3,2]dioxaborolan-2-yl)-1H-pyrazole (36 mg, 0.18 mmol), tris(dibenzylidineacetone)di-palladium (0) (2.2 mg, 1.7 mol %), and 2,4',6'-diisopropyl-1, 1'-biphenyl-2-yldicyclohexylphosphine (5.3 mg, 9 mol %) were added and heating continued for a further 18 h. The reaction mixture was diluted with ethyl acetate, decanted and then concentrated in vacuo. The resultant residue was subjected to flash chromatography (SiO2, gradient 10 to 60% ethyl acetate in cyclohexane) to give 105 as a white solid (12 mg, 24%). ¹H NMR (CDCl3, 400 MHz): δ 8.28 (d, J=8.2 Hz, 1 H); 8.08 (s, 1 H); 7.90 (s, 2 H); 7.80 (s, 1 H); 7.30 (dd, J=8.2, 1.8 Hz, 1 H); 7.23 (d, J=1.8 Hz, 1 H); 5.73-5.59 (m, 1 H); 4.42-4.35 (m, 2 H); 3.20-3.13 (m, 2 H); 1.62 (d, J=6.6 Hz, 6 H). 1 Exchangeable proton not observed. LCMS: RT=9.48 min, M+H+=362

Example 106

2-(1-isopropyl-1H-1,2,4-triazol-5-yl)-8-bromo-4,5-dihydrobenzo-2H-oxepino[4,5-d]pyrazole 106

Step 1: 1-Isopropyl-1H-[1,2,4]triazole

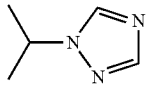

A solution of isopropyl hydrazine hydrochloride (60 g, 0.54 mmol) in formamide (270 mL) was heated at 130° C. for 3 days. The cooled solution was diluted with saturated brine (700 mL) and extracted with ethyl acetate (4×1 L). The combined organics were dried (Na2SO4), filtered and concentrated in vacuo to give an oil. The oil was subjected to distillation under reduced pressure (25 mbar by 85-90° C.) to give 1-Isopropyl-1H-[1,2,4]triazole as a colourless oil (54 g, 90%). ¹H NMR δ (ppm) (CDCl3): 8.10 (1 H, s), 7.95 (1 H, s), 4.63-4.50 (1 H, m), 1.56 (6 H, d, J=6.69 Hz).

Step 2: 5-Chloro-1-isopropyl-1H-[1,2,4]triazole

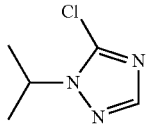

Under an atmosphere of nitrogen a solution of 1-isopropyl-1H-[1,2,4]triazole (19 mmol) in THF (50 mL) at −78° C. was treated with n-butyllithium (11.4 mL, 2.5 M, 28.5 mmol) dropwise giving a cream yellow suspension. Further n-butyllithium (3.8 mL, 2.5 M, 9.5 mmol) was added after 1 h and stirring continued for a further 1.5 h. 1,1,2-trichlorotrifluoroethane (4.57 mL, 38 mmol) was added dropwise giving a dark brown solution. The resultant reaction mixture was stirred for 15 min before being quenched by the addition of saturated aqueous NaHCO3 (20 mL) then allowed to warm to RT. The resultant mixture was extracted twice with diethyl ether, the combined organic extracts dried (Na2SO4), filtered and concentrated in vacuo to give 5-Chloro-1-isopropyl-1H-[1,2,4]triazole as a dark oil (3.9 g) which was used in the subsequent step without further purification. ¹H NMR δ (ppm) (CDCl3): 7.85 (1 H, s), 4.73-4.63 (1 H, m), 1.54-1.46 (6 H, m).

An ice-cooled suspension of sodium hydride (60% dispersion 1.09 g, 38 mmol) was treated portionwise with 8-bromo-4,5-dihydro-2H-6-oxa-1,2-diaza-benzo[e]azulene (3.6 g, 13.6 mmol) giving a deep red suspension. 5-Chloro-1-isopropyl-1H-[1,2,4]triazole (19 mmol) was added and the mixture heated at 80° C. under nitrogen for 72 h. The cooled reaction mixture was quenched with water and extracted twice with ethyl acetate. The combined organic extracts were dried (Na2SO4), filtered and then concentrated in vacuo. The resultant residue was subjected to flash chromatography (SiO2, gradient 0 to 15% ethyl acetate in cyclohexane). Appropriate fractions were combined and recrystallised from methanol and cyclohexane/ethyl acetate to give 106 as a tan solid (789 mg, 16%). ¹H NMR (CDCl3, 400 MHz): δ 8.15-8.11 (m, 1 H); 8.08 (s, 1 H); 7.80 (s, 1 H); 7.28-7.23 (m, 2 H); 5.65-5.53 (m, 1 H); 4.38-4.31 (m, 2 H); 3.18-3.10 (m, 2 H); 1.60 (d, J=6.6 Hz, 6 H).

Example 107

2-(1-(2,4-difluorophenyl)-1H-1,2,4-triazol-5-yl)-4,5-dihydrobenzo-2H-oxepino[4,5-d]pyrazole-8-carboxamide 107

To a suspension of 8-bromo-2-[2-(2,4-difluoro-phenyl)-2H-[1,2,4]triazol-3-yl]-4,5-dihydro-2H-6-oxa-1,2-diazabenzo[e]azulene (80 mg, 0.18 mmol), hydroxylamine hydrochloride (25 mg, 0.36 mmol), molybdenum hexacarbonyl (24 mg, 0.09 mmol), tri-tert-butylphosphine tetrafluoroborate (5 mg, 10 mol %), trans-di-g-acetatobis[2-(di-o-tolylphosphino)benzyl]dipalladium(II) (8.4 mg, 5 mol %) in dioxane (4 mL) were added 1,8-diazabicyclo[5.4.0]undec-7-ene (27 μL, 0.18 mmol) and DIPEA (62 μL, 0.36 mmol). The reaction mixture was heated at 150° C. under microwave irradiation for 30 mins, and diluted with ethyl acetate. The organic layer was washed with water, saturated aqueous sodium bicarbonate solution followed by brine, dried (Na2SO4) and concentrated in vacuo. The resultant residue was subjected flash chromatography (SiO2, 20 to 90% ethyl acetate in cyclohexane) to give an solid, which was recrystallised from methanol to give 107 as a white solid (17 mg, 23%). ¹H NMR (DMSO-d6, 400 MHz) δ 8.48 (s, 1 H); 8.31 (s, 1 H); 7.98 (s, 1 H); 7.87-7.79 (m, 1 H); 7.69-7.61 (m, 1 H); 7.49 (d, J=1.7 Hz, 1 H); 7.43 (dd, J=8.3, 1.8 Hz, 1 H); 7.40-7.32 (m, 3 H); 4.27 (t, J=5.0 Hz, 2 H); 3.09 (t, J=5.0 Hz, 2 H). LCMS: RT=8.72 min, M+H+=409

Example 108

2-(4-isopropyl-4H-1,2,4-triazol-5-yl)-9-(pyrazol-4yl)-4,5-dihydrobenzo-2H-oxepino[4,5-d]pyrazole 108

A suspension of 9-bromo-2-(2-isopropyl-2H-[1,2,4]triazol-3-yl)-4,5-dihydro-2H-6-oxa-1,2-diaza-benzo[e]azulene (78 mg, 0.21 mmol), 4,4,5,5-tetramethyl-2-(1H-pyrazol-4-yl)-1,3,2-dioxaborolane (61 mg, 0.31 mmol), tetrakis (triphenylphosphine) palladium (0) (24 mg, 0.021 mmol) and sodium carbonate (45 mg, 0.42 mmol) in acetonitrile (6 mL) and water (3 mL) under nitrogen was heated at 140° C. for 25 min using microwave irradiation. The reaction mixture was diluted with ethyl acetate and water, the organic layer was isolated and washed with brine, dried (Na2SO4), concentrated in vacuo. The resultant residue was subjected to flash chromatography (SiO2, gradient 0 to 50% ethyl acetate in cyclohexane) followed by recrystallisation from acetonitrile and trituration in pentane to afford 108 as an off-white solid (16 mg, 20%). (67261) ¹H NMR (DMSO-d6, 400 MHz): δ 12.91 (s, 1 H); 8.38 (d, J=2.3 Hz, 1 H); 8.32 (s, 1 H); 8.03 (s, 1 H); 7.97 (s, 2 H); 7.52 (dd, J=8.4, 2.3 Hz, 1 H); 7.05 (d, J=8.4 Hz, 1 H); 5.41-5.26 (m, 1 H); 4.35-4.26 (m, 2 H); 3.17-3.08 (m, 2 H); 1.55 (d, J=6.6 Hz, 6 H). LCMS: RT=9.38 min, M+H+=362

Example 109

2-(1-isopropyl-1H-1,2,4-triazol-5-yl)-5,6-dihydrobenzo[f]imidazo[1,2-d][1,4]oxazepine-10-carboxamide 109

To a solution of 2-(1-isopropyl-1H-1,2,4-triazol-5-yl)-5,6-dihydrobenzo[f]imidazo[1,2-d][1,4]oxazepine-10-carboxylic acid (0.170 g, 0.000501 mol) dissolved in N,N-Dimethylformamide (7.84 mL, 0.101 mol) and treated sequentially with N,N-Diisopropylethylamine (0.524 mL, 0.00300 mol) Ammonium chloride (0.107 g, 0.00200 mol) then N,N,N',N'-Tetramethyl-O-(7-azabenzotriazol-1-yl)uronium Hexafluorophosphate (0.228 g, 0.000601 mol). The reaction was stirred at r.t. overnight. The reaction was quenched with sat. sodium bicarbonate then extract with ethyl acetate (3×). The organic layers was dried (Na2SO4) and concentrated in vacuo to give 109 purified on reverse HPLC. MS: (ESI+)=339.1. 1H NMR (400 MHz, DMSO) δ 8.93 (d, J=2.2 Hz, 1H), 7.95 (s, 2H), 7.92 (s, 1H), 7.79 (dd, J=8.5, 2.2 Hz, 1H), 7.10 (d, J=8.5 Hz, 1H), 5.82 (dt, J=13.2, 6.6 Hz, 1H), 4.56 (s, 4H), 1.49 (d, J=6.6 Hz, 6H)

Example 110

2-(1-isopropyl-1H-1,2,4-triazol-5-yl)-9-N-methyl-4,5-dihydrobenzo-2H-oxepino[4,5-d]pyrazole-9-carboxamide 110

Following Example 107, 9-bromo-2-(2-isopropyl-2H-[1,2,4]triazol-3-yl)-4,5-dihydro-2H-6-oxa-1,2-diaza-benzo[e]azulene was reacted with N,O-dimethylhydroxylamine hydrochloride molybdenum hexacarbonyl, tri-tert-butylphosphine tetrafluoroborate, trans-di-μ-acetatobis[2-(di-o-tolylphosphino)benzyl]dipalladium(II) in dioxane. 1,8-Diazabicyclo[5.4.0]undec-7-ene (DBU) and DIPEA were added. The reaction mixture was heated at 150° C. under microwave irradiation for 30 mins, then diluted with ethyl acetate. The organic layer was washed with water, saturated aqueous sodium bicarbonate solution followed by brine, dried (Na2SO4) and concentrated in vacuo. The resultant residue was subjected flash chromatography to give 110 as a white solid (29 mg, 31%). 1H NMR (DMSO-d6, 400 MHz): δ 8.75 (d, J=2.3 Hz, 1 H); 8.44-8.38 (m, 1 H); 8.33 (s, 1 H); 8.05 (d, J=0.6 Hz, 1 H); 7.73 (dd, J=8.5, 2.3 Hz, 1 H); 7.10 (d, J=8.5 Hz, 1 H); 5.31-5.21 (m, 1 H); 4.35 (t, J=5.0 Hz, 2 H); 3.13 (t, J=5.0 Hz, 2 H); 2.78 (d, J=4.5 Hz, 3 H); 1.51 (d, J=6.6 Hz, 6 H). LCMS: RT=8.24 min, M+H+=353

Example 111

2-(1-isopropyl-1H-1,2,4-triazol-5-yl)-9-N-(2-hydroxyethyl)-4,5-dihydrobenzo-2H-oxepino[4,5-d]pyrazole-9-carboxamide 111

Following the procedure for 107, 9-bromo-2-(2-isopropyl-2H-[1,2,4]triazol-3-yl)-4,5-dihydro-2H-6-oxa-1,2-diaza-benzo[e]azulene was reacted with ethanolamine to give 111 as a white solid (23 mg, 22%). 1H NMR (400 MHz, DMSO-d6): δ 8.71 (d, J=2.29 Hz, 1 H); 8.35 (t, J=5.57 Hz, 1 H); 8.29 (s, 1 H); 8.00 (d, J=0.60 Hz, 1 H); 7.71 (dd, J=8.51, 2.33 Hz, 1 H); 7.06 (d, J=8.49 Hz, 1 H); 5.29-5.21 (m, 1 H); 4.65 (t, J=5.60 Hz, 1 H); 4.30 (t, J=4.98 Hz, 2 H); 3.47 (q, J=5.99 Hz, 2 H); 3.28 (t, J=4.93 Hz, 2 H); 3.09 (t, J=4.98 Hz, 2 H); 1.46 (d, J=6.59 Hz, 6 H). LCMS RT=7.41 min, M+H+=383

Example 112

(2-(1-isopropyl-1H-1,2,4-triazol-5-yl)-5,6-dihydrobenzo[f]imidazo[1,2-d][1,4]oxazepin-10-yl)(S-dioxothiomorpholino)methanone 112

Following the procedure for 116, 2-(2-isopropyl-2H-[1,2,4]triazol-3-yl)-4,5-dihydro-6-oxa-1,10b-diaza-benzo[e]azulene-9-carboxylic acid was reacted with thiomorpholine dioxide to give 112. 1H NMR (DMSO-d6, 400 MHz): δ 8.06 (d, J=2.1 Hz, 1 H); 8.04 (d, J=0.6 Hz, 1 H); 7.50 (dd, J=8.3, 2.1 Hz, 1 H); 7.34 (d, J=8.3 Hz, 1 H); 6.92 (s, 1 H); 5.67-5.54 (m, 1 H); 4.57 (t, J=5.9 Hz, 2 H); 3.35-3.26 (br m, 8H); 3.24 (t, J=6.0 Hz, 2 H); 1.48 (d, J=6.6 Hz, 6 H). LCMS: RT=8.24 min, M+H+=457

Example 113

(4-(2-hydroxypropan-2-yl)piperidin-1-yl)(2-(1-isopropyl-1H-1,2,4-triazol-5-yl)-5,6-dihydrobenzo[f]imidazo[1,2-d][1,4]oxazepin-10-yl)methanone 113

Following the procedure for 109, 2-(1-isopropyl-1H-1,2,4-triazol-5-yl)-5,6-dihydrobenzo[f]imidazo[1,2-d][1,4]oxazepine-10-carboxylic acid and 2-(piperidin-4-yl)propan-2-ol gave 113. MS: (ESI+)=465.2. 1H NMR (400 MHz, DMSO) δ 8.40 (d, J=1.6 Hz, 1H), 7.96 (s, 1H), 7.92 (s, 1H), 7.35 (dd, J=8.4, 1.9 Hz, 1H), 7.11 (d, J=8.4 Hz, 1H), 5.87-5.69 (m, 1H), 4.56 (s, 4H), 4.15 (s, 1H), 1.75 (s, 2H), 1.48 (d, J=6.6 Hz, 7H), 1.19 (dd, J=23.3, 11.1 Hz, 2H), 1.05 (s, 7H)

Example 114

9-(1-Isopropyl-1H-pyrazol-5-yl)-6,7-dihydroimidazo[1,2-d]pyrido[3,2-b][1,4]oxazepine-3-carboxamide 114

A mixture of 17 mg (0.05 mmol) of 9-(1-isopropyl-1H-pyrazol-5-yl)-6,7-dihydroimidazo[1,2-d]pyrido[3,2-b][1,4]oxazepine-3-carboxylic acid, 30 mg, (0.061 mmol) of HATU and 0.022 ml (0.155 mmol) of triethylamine in 2 ml of DMF was stirred for 10 min. Ammonia (gas) was bubbled through the mixture for 5 min. The mixture was stirred for 1 hour, concentrated in vacuum and partitioned between ethyl acetate and 0.01 N aqueous HCl. The organic layer was concentrated and the residue purified on 4 g silica column eluting with 7-8% Methanol in DCM to give 114. Yield 2.4 mg. MS(ESI+) 339.2. 1H NMR (400 MHz, CH3OH+D2O) δ 8.70 (d, J=1.8, 1H), 8.33 (s, 1H), 8.05 (d, J=1.8, 1H), 7.52 (s, 1H), 6.48 (d, J=1.6, 1H), 5.16 (dd, J=13.2, 6.6, 1H), 4.56 (t, J=5.1, 2H), 3.52-3.45 (m, 2H), 1.49 (d, J=6.6, 6H).

Example 115

2-(1-isopropyl-1H-pyrazol-5-yl)-5,6-dihydrobenzo[f]imidazo[1,2-d][1,4]oxazepine-10-carboxamide 115

Following the procedure in Example 51, 2-(1-Isopropyl-1H-pyrazol-5-yl)-5,6-dihydrobenzo[f]imidazo[1,2-d][1,4]oxazepine-10-carboxylic acid was coupled with ammonia to give 115. MS(ESI+): 338.1. 1H NMR (400 MHz, DMSO) δ 8.94 (d, J=2.2, 1H), 7.94 (s, 1H), 7.77 (dd, J=8.5, 2.2, 1H), 7.69 (s, 1H), 7.44 (d, J=1.4, 1H), 7.25 (s, 1H), 7.08 (d, J=8.5,

Example 116

N-(2-hydroxy-2-methylpropyl)-2-(1-isopropyl-1H-1,2,4-triazol-5-yl)-4,5-dihydrobenzo[b]pyrazolo[1,5-d][1,4]oxazepine-9-carboxamide 116

2-(2-Isopropyl-2H-[1,2,4]triazol-3-yl)-4,5-dihydro-6-oxa-1,10b-diaza-benzo[e]azulene-9-carboxylic acid (0.2 g, 0.59 mmol) was suspended in DMF (5 mL) and DIPEA (0.21 mL, 1.2 mmol) added. The resultant solution was treated with HATU (0.23 g, 0.6 mmol) and HOBT (81 mg, 0.6 mmol) before the addition of 1-amino-2-methyl-propan-2-ol (52.5 mg, 0.59 mmol) then stirred for 18 h at RT. The reaction mixture was concentrated in vacuo and the resultant residue partitioned between DCM and water. The aqueous layer was extracted three times with DCM and the combined organic extracts washed with water, dried (Na2SO4), filtered and concentrated in vacuo. The resultant residue was subjected to flash chromatography (SiO2, gradient 0 to 10% MeOH in ethyl acetate) and recrystallisation from ethyl acetate to give 116 (163 mg, 67%). $^1$H NMR (CDCl3, 400 MHz): δ 8.46 (d, J=2.2 Hz, 1 H); 7.94 (s, 1 H); 7.72 (dd, J=8.4, 2.2 Hz, 1 H); 7.22 (d, J=8.4 Hz, 1 H); 6.86 (s, 1 H); 6.66 (s, 1 H); 5.74-5.61 (m, 1 H); 4.57 (t, J=5.7 Hz, 2 H); 3.50 (d, J=5.9 Hz, 2 H); 3.22 (t, J=5.7 Hz, 2 H); 2.18 (s, 1 H); 1.59 (d, J=6.6 Hz, 6 H); 1.31 (s, 6 H). LCMS: RT=9.53 min, M+H+=411

Example 117

(2-(1-isopropyl-1H-1,2,4-triazol-5-yl)-4,5-dihydrobenzo[b]pyrazolo[1,5-d][1,4]oxazepin-9-yl)(S-dioxothiomorpholino)methanone 117

2-(2-Isopropyl-2H-[1,2,4]triazol-3-yl)-4,5-dihydro-6-oxa-1,10b-diaza-benzo[e]azulene-9-carboxylic acid was reacted with thiomorpholine dioxide to give 117. $^1$H NMR (DMSO-d6, 400 MHz): δ 8.06 (d, J=2.1 Hz, 1 H); 8.04 (d, J=0.6 Hz, 1 H); 7.50 (dd, J=8.3, 2.1 Hz, 1 H); 7.34 (d, J=8.3 Hz, 1 H); 6.92 (s, 1 H); 5.67-5.54 (m, 1 H); 4.57 (t, J=5.9 Hz, 2 H); 3.35-3.26 (br m, 8H); 3.24 (t, J=6.0 Hz, 2 H); 1.48 (d, J=6.6 Hz, 6 H). LCMS: RT=8.24 min, M+H+=457

Example 118

(4-hydroxypiperidin-1-yl)(2-(1-isopropyl-1H-1,2,4-triazol-5-yl)-4,5-dihydrobenzo[b]pyrazolo[1,5-d][1,4]oxazepin-9-yl)methanone 118

Following the procedure for 116, 2-(2-isopropyl-2H-[1,2,4]triazol-3-yl)-4,5-dihydro-6-oxa-1,10b-diaza-benzo[e]azulene-9-carboxylic acid was reacted with 4-hydroxy piperidine to give 118 as a white solid. $^1$H NMR (CDCl3, 400 MHz): δ 8.02 (d, J=2.1 Hz, 1 H); 7.94 (s, 1 H); 7.35 (dd, J=8.3, 2.1 Hz, 1 H); 7.23 (d, J=8.3 Hz, 1 H); 6.88 (s, 1 H); 5.76-5.62 (m, 1 H); 4.58 (t, J=5.8 Hz, 2 H); 4.19 (br s, 1 H); 4.07-3.98 (m, 1 H); 3.82 (br s, 1 H); 3.37 (br s, 1 H); 3.20 (t, J=5.8 Hz, 2H); 1.95 (br s, 2 H); 1.70 (d, J=3.9 Hz, 1 H); 1.67-1.54 (d, J=6.6 Hz, 8 H). LCMS: RT=8.77 min, M+H+=423

Example 119

N-(2-(methylsulfonyl)ethyl)-2-(1-(2,2,2-trifluoroethyl)-1H-1,2,4-triazol-5-yl)-5,6-dihydrobenzo[f]imidazo[1,2-d][1,4]oxazepine-10-carboxamide 119

Following the procedure for 109, 2-(1-(2,2,2-trifluoroethyl)-1H-1,2,4-triazol-5-yl)-5,6-dihydrobenzo[f]imidazo[1,2-d][1,4]oxazepine-10-carboxylic acid and 2-(methylsulfonyl)ethanamine gave 119. MS: (ESI+)=485.1. 1H NMR (400 MHz, DMSO) δ 8.93 (d, J=2.1 Hz, 1H), 8.72 (t, J=5.4 Hz, 1H), 8.10 (s, 2H), 7.78 (dd, J=8.6, 2.2 Hz, 1H), 7.14 (d, J=8.5 Hz, 1H), 5.94 (q, J=8.9 Hz, 2H), 4.58 (s, 4H), 3.69 (dd, J=12.7, 6.5 Hz, 2H), 3.38 (t, J=6.8 Hz, 2H), 3.04 (s, 3H)

Example 120

(4-isopropylpiperazin-1-yl)(2-(1-(2,2,2-trifluoroethyl)-1H-1,2,4-triazol-5-yl)-5,6-dihydrobenzo[f]imidazo[1,2-d][1,4]oxazepin-10-yl)methanone 120

Following the procedure for 109, 2-(1-(2,2,2-trifluoroethyl)-1H-1,2,4-triazol-5-yl)-5,6-dihydrobenzo[f]imidazo[1,2-d][1,4]oxazepine-10-carboxylic acid and 1-isopropylpiperazine gave 120. MS: (ESI+)=490.2. 1H NMR (400 MHz, DMSO) δ 8.38 (d, J=2.0 Hz, 1H), 8.10 (d, J=5.4 Hz, 2H), 7.37 (dd, J=8.4, 2.1 Hz, 1H), 7.12 (d, J=8.4 Hz, 1H), 5.87 (q, J=8.8 Hz, 2H), 4.57 (s, 4H), 3.49 (s, 4H), 2.68 (dt, J=13.0, 6.6 Hz, 1H), 2.45 (s, 4H), 0.97 (d, J=6.5 Hz, 6H)

Example 121

N-(1-hydroxy-2-methylpropan-2-yl)-2-(1-(2,2,2-trifluoroethyl)-1H-1,2,4-triazol-5-yl)-5,6-dihydrobenzo[f]imidazo[1,2-d][1,4]oxazepine-10-carboxamide 121

Following the procedure for 109, 2-(1-(2,2,2-trifluoroethyl)-1H-1,2,4-triazol-5-yl)-5,6-dihydrobenzo[f]imidazo[1,2-d][1,4]oxazepine-10-carboxylic acid and 2-amino-2-methylpropan-1-ol gave 121. MS: (ESI+)=451.1. 1H NMR (400 MHz, DMSO) δ 8.82 (d, J=2.2 Hz, 1H), 8.09 (d, J=2.9 Hz, 2H), 7.74 (dd, J=8.6, 2.3 Hz, 1H), 7.58 (s, 1H), 7.10 (d, J=8.5 Hz, 1H), 5.94 (q, J=8.9 Hz, 2H), 4.91 (t, J=5.9 Hz, 1H), 4.57 (dd, J=10.9, 5.6 Hz, 4H), 3.51 (d, J=5.9 Hz, 2H), 1.32 (s, 6H)

Example 122

(4-(2-hydroxyethyl)piperazin-1-yl)(2-(1-(2,2,2-trifluoroethyl)-1H-1,2,4-triazol-5-yl)-5,6-dihydrobenzo[f]imidazo[1,2-d][1,4]oxazepin-10-yl)methanone 122

Following the procedure for 109, 2-(1-(2,2,2-trifluoroethyl)-1H-1,2,4-triazol-5-yl)-5,6-dihydrobenzo[f]imidazo[1,2-d][1,4]oxazepine-10-carboxylic acid and 2-(piperazin-1-yl)ethanol gave 122. MS: (ESI+)=492.2. 1H NMR (400 MHz, DMSO) δ 8.39 (d, J=2.0 Hz, 1H), 8.10 (d, J=5.4 Hz, 2H), 7.38 (dd, J=8.4, 2.1 Hz, 1H), 7.13 (d, J=8.4 Hz, 1H), 5.89 (q, J=8.7 Hz, 2H), 4.57 (s, 4H), 4.40 (t, J=5.4 Hz, 1H), 4.06 (q, J=5.3 Hz, 1H), 3.51 (dd, J=11.6, 6.0 Hz, 4H), 3.17 (d, J=5.2 Hz, 1H), 2.46-2.39 (m, 5H)

Example 123 morpholino(2-(1-(2,2,2-trifluoroethyl)-1H-1,2,4-triazol-5-yl)-5,6-dihydrobenzo[f]imidazo[1,2-d][1,4]oxazepin-10-yl)methanone 123

Following the procedure for 109, 2-(1-(2,2,2-trifluoroethyl)-1H-1,2,4-triazol-5-yl)-5,6-dihydrobenzo[f]imidazo[1,2-d][1,4]oxazepine-10-carboxylic acid and morpholine gave 123. MS: (ESI+)=449.1. 1H NMR (400 MHz, DMSO) δ 8.42 (d, J=2.0 Hz, 1H), 8.10 (d, J=5.6 Hz, 2H), 7.40 (dt, J=21.4, 10.7 Hz, 1H), 7.13 (d, J=8.4 Hz, 1H), 5.89 (q, J=8.8 Hz, 2H), 4.57 (s, 4H), 3.61 (s, 4H), 3.52 (s, 4H)

Example 124

(2-(1-isopropyl-1H-1,2,4-triazol-5-yl)-4,5-dihydrobenzo[b]pyrazolo[1,5-d][1,4]oxazepin-9-yl)(4-(2,2,2-trifluoroethyl)piperazin-1-yl)methanone 124

Following the procedure for 116, 2-(2-isopropyl-2H-[1,2,4]triazol-3-yl)-4,5-dihydro-6-oxa-1,10b-diaza-benzo[e]azulene-9-carboxylic acid was reacted with 1-(2,2,2-trifluoroethyl)piperazine dihydrochloride to give 124 as a white solid. $^1$H NMR (CDCl3, 400 MHz): δ 8.02 (d, J=2.1 Hz, 1 H); 7.95 (s, 1 H); 7.35 (dd, J=8.3, 2.1 Hz, 1 H); 7.23 (d, J=8.3 Hz, 1 H); 6.88 (s, 1 H); 5.73-5.60 (m, 1 H); 4.58 (t, J=5.8 Hz, 2 H); 3.94-3.44 (br m, 4H); 3.20 (t, J=5.8 Hz, 2 H); 3.04 (q, J=9.4 Hz, 2 H); 2.74 (br s, 4 H); 1.58 (d, J=6.6 Hz, 6 H). LCMS: RT=10.93 min, M+H+=490

Example 125

N-(1-(2-hydroxyethyl)-1H-pyrazol-4-yl)-2-(1-isopropyl-1H-1,2,4-triazol-5-yl)-4,5-dihydrobenzo[b]pyrazolo[1,5-d][1,4]oxazepine-9-carboxamide 125

Following the procedure for 126, 2-(2-isopropyl-2H-[1,2,4]triazol-3-yl)-4,5-dihydro-6-oxa-1,10b-diaza-benzo[e]azulene-9-carboxylic acid was reacted with 4-amino-1-(2-hydroxyethyl)pyrazole to give 125 as a white solid. $^1$H NMR (CDCl3, 400 MHz): δ 8.50 (d, J=2.2 Hz, 1 H); 8.38 (s, 1 H); 8.10 (s, 1 H); 7.96 (s, 1 H); 7.78-7.73 (m, 1 H); 7.56 (s, 1 H); 7.22 (d, J=8.4 Hz, 1 H); 6.81 (s, 1 H); 5.60-5.47 (m, 1 H); 4.57 (t, J=5.7 Hz, 2 H); 4.23 (t, J=4.8 Hz, 2 H); 4.01 (t, J=4.8 Hz, 2 H); 3.20 (t, J=5.7 Hz, 2 H); 1.57 (d, J=6.6 Hz, 6 H). 1 Exchangeable proton not observed. LCMS: RT=9.27 min, M+H+=449

Example 126

2-(1-isopropyl-1H-1,2,4-triazol-5-yl)-N-(isoxazol-3-yl)-4,5-dihydrobenzo[b]pyrazolo[1,5-d][1,4]oxazepine-9-carboxamide 126

To an ice-cooled suspension of 2-(2-isopropyl-2H-[1,2,4]triazol-3-yl)-4,5-dihydro-6-oxa-1,10b-diaza-benzo[e]azulene-9-carboxylic acid (0.15 g, 0.44 mmol) in DCM (3.5 mL) was added oxalyl chloride (79 L, 0.93 mmol) and DMF (25 L) and the mixture stirred at RT for 2 h. 3-Amino-isoxazole (185 mg, 2.2 mmol) and triethylamine (0.12 mL, 0.88 mmol) were added and the mixture stirred at RT for 18 h before the addition of saturated aqueous sodium hydrogen carbonate. The resultant mixture was extracted with DCM then 5% MeOH in DCM and the combined extracts dried (Na2SO4), filtered and concentrated in vacuo. The resultant residue was subjected to flash chromatography (SiO2, gradient 0 to 10% MeOH in DCM) followed by trituration in diethyl ether to give 126 as a white solid. $^1$H NMR (CDCl3, 400 MHz): δ 9.49 (s, 1 H); 8.65 (d, J=2.3 Hz, 1 H); 8.30 (d, J=1.8 Hz, 1 H); 7.96 (d, J=0.7 Hz, 1 H); 7.86 (dd, J=8.5, 2.3 Hz, 1 H); 7.30 (d, J=8.5 Hz, 1 H); 7.23 (d, J=1.8 Hz, 1 H); 6.88 (s, 1 H); 5.72-5.59 (m, 1 H); 4.61 (t, J=5.6 Hz, 2 H); 3.25 (t, J=5.6 Hz, 2 H); 1.58 (d, J=6.6 Hz, 6 H). LCMS: RT=10.24 min, M+H+=406

Example 127

N-(1H-pyrazol-4-yl)-2-(1-(2,2,2-trifluoroethyl)-1H-1,2,4-triazol-5-yl)-4,5-dihydrobenzo[b]pyrazolo[1,5-d][1,4]oxazepine-9-carboxamide 127

Following the procedure for 126, 2-[2-(2,2,2-trifluoro-ethyl)-2H-[1,2,4]triazol-3-yl]-4,5-dihydro-6-oxa-1,10b-diaza-benzo[e]azulene-9-carboxylic acid was reacted with 4-amino-pyrazole-1-carboxylic acid tert-butyl ester. The intermediate carboxylic acid tert-butyl ester was dissolved in DCM (5 mL) and treated with TFA (2 mL) before the reaction mixture was stirred at RT for 2 h. The reaction mixture was concentrated in vacuo and the resultant residue triturated in water to give 127 as a white solid. $^1$H NMR (DMSO-d6, 400 MHz): δ 10.53 (s, 1 H); 8.51 (d, J=2.2 Hz, 1 H); 8.23 (s, 1 H); 7.96 (dd, J=8.5, 2.2 Hz, 1 H); 7.84 (s, 2 H); 7.39 (d, J=8.5 Hz, 1 H); 7.02 (s, 1 H); 5.77 (q, J=8.7 Hz, 2 H); 4.59 (t, J=5.8 Hz, 2 H). 3 Protons obscured by water peak. LCMS: RT=9.11 min, M+H+=445

Example 128

2-(4-((2-(1-(2,2,2-trifluoroethyl)-1H-1,2,4-triazol-5-yl)-4,5-dihydrobenzo[b]pyrazolo[1,5-d][1,4]oxazepin-9-yl)methyl)piperazin-1-yl)ethanol 128

A solution of 2-[2-(2,2,2-trifluoro-ethyl)-2H-[1,2,4]triazol-3-yl]-4,5-dihydro-6-oxa-1,10b-diaza-benzo[e]azulene-9-carbaldehyde (175 mg, 0.48 mmol) and piperazine ethanol in DCE (15 mL) was treated with sodium triacetoxyborohydride (153 mg, 0.72 mmol) and catalytic acetic acid and then stirred at RT for 72 h. The resultant mixture was diluted with DCM and washed with saturated aqueous sodium hydrogen carbonate then dried (Na2SO4), filtered and concentrated in vacuo to give a colourless gum which was subjected to flash chromatography (SiO2, gradient 0-10% MeOH in DCM). The appropriate fractions were combined, concentrated in vacuo and the resultant residue dissolved in diethyl ether and treated with 1M HCl in diethyl ether (2 mL, 2 mmol). The resultant precipitate was filtered off, washed with ether and dried in vacuo to give 128 as a white solid. $^1$H NMR (DMSO-d6 plus deuterated TFA, 400 MHz): δ 8.22 (s, 1 H); 8.16-8.12 (m, 1 H); 7.66-7.60 (m, 1 H); 7.39 (d, J=8.3 Hz, 1 H); 7.02 (s, 1 H); 5.75 (q, J=8.7 Hz, 2 H); 4.57 (t, J=5.9 Hz, 2 H); 4.52 (s, 2 H); 3.76 (t, J=5.0 Hz, 2 H); 3.61 (br s, 8 H); 3.32 (s, 2 H); 3.24 (t, J=5.9 Hz, 2 H). 1 Exchangeable not observed. LCMS: RT=6.56 min, M+H+=478

Example 129

(4-hydroxypiperidin-1-yl)(2-(1-(2,2,2-trifluoroethyl)-1H-1,2,4-triazol-5-yl)-5,6-dihydrobenzo[f]imidazo[1,2-d][1,4]oxazepin-10-yl)methanone 129

Following the procedure for 109, 2-(1-(2,2,2-trifluoroethyl)-1H-1,2,4- triazol-5-yl)-5,6-dihydrobenzo[f]imidazo

[1,2-d][1,4]oxazepine-10-carboxylic acid and 4-hydroxypiperidine gave 129. MS: (ESI+)=463.1. 1H NMR (400 MHz, DMSO) δ 8.39 (d, J=2.0 Hz, 1H), 8.09 (d, J=4.4 Hz, 2H), 7.37 (dd, J=8.4, 2.1 Hz, 1H), 7.12 (d, J=8.4 Hz, 1H), 5.87 (q, J=8.5 Hz, 2H), 4.76 (d, J=3.8 Hz, 1H), 4.57 (s, 4H), 3.76 (d, J=3.6 Hz, 2H), 1.74 (s, 2H), 1.39 (s, 2H)

Example 130

9-(piperidin-4-yl)-2-(1-(2,2,2-trifluoroethyl)-1H-1,2,4-triazol-5-yl)-4,5-dihydrobenzo[b]pyrazolo[1,5-d][1,4]oxazepine 130

Step 1: 4-{2-[2-(2,2,2-Trifluoro-ethyl)-2H-[1,2,4]triazol-3-yl]-4,5-dihydro-6-oxa-1,10b-diaza-benzo[e]azulen-9-yl}-3,6-dihydro-2H-pyridine-1-carboxylic acid tert butyl ester

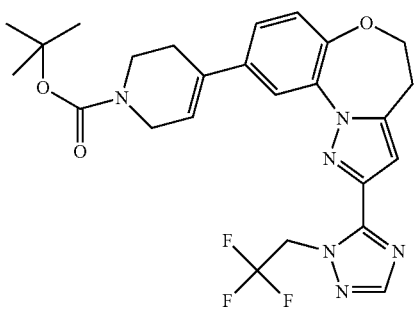 [SMILES: CC(C)(C)OC(=O)N1CC=C(c2ccc3c(c2)-n2nc(-c4ncnn4CC(F)(F)F)cc2CCO3)CC1]

9-Bromo-2-[2-(2,2,2-trifluoro-ethyl)-2H-[1,2,4]triazol-3-yl]-4,5-dihydro-6-oxa-1,10b-diaza-benzo[e]azulene (207 mg, 0.5 mmol), 4-(4,4,5,5-tetramethyl-[1,3,2]dioxaborolan-2-yl)-3,6-dihydro-2H-pyridine-1-carboxylic acid tert-butyl ester (232 mg, 0.75 mmol), [1,1'-bis(diphenylphosphino)ferrocene]dichloropalladium(II) dichloromethane (10 mol %), and potassium carbonate (138 mg, 1.0 mmol) were charged to a reaction vial, the atmosphere evacuated and back-filled with nitrogen. DMF (1 mL) was added, degassing repeated, and the mixture heated at 80° C. for 18 h. The cooled reaction mixture was diluted with ethyl acetate and washed with water then dried (Na2SO4), filtered and concentrated in vacuo. The resultant residue was subjected to flash chromatography (SiO2, gradient 20 to 60% ethyl acetate in cyclohexane) to give 4-{2-[2-(2,2,2-Trifluoro-ethyl)-2H-[1,2,4]triazol-3-yl]-4,5-dihydro-6-oxa-1,10b-diaza-benzo[e]azulen-9-yl}-3,6-dihydro-2H-pyridine-1-carboxylic acid tert butyl ester as a white crystalline solid (232 mg, 90%). LCMS: RT=4.87 min, M+H+=517.

A solution of 4-{2-[2-(2,2,2-trifluoro-ethyl)-2H-[1,2,4]triazol-3-yl]-4,5-dihydro-6-oxa-1,10b-diaza-benzo[e]azulen-9-yl}-3,6-dihydro-2H-pyridine-1-carboxylic acid tert butyl ester (232 mg, 0.41 mmol) in IMS (10 mL) was treated with a slurry of Pd/C (170 mg, 10% wt Pd on carbon, 50% water) in IMS. The mixture was degassed then the atmosphere evacuated and back-filled with hydrogen and then stirred at RT for 18 h. The reaction mixture was filtered through Celite® with ethyl acetate washings and the filtrate concentrated in vacuo. The resultant residue was dissolved in methanol (5 mL), treated with 1M HCl in diethyl ether (2 mL, 2 mmol) and the mixture stirred at RT for 18 h. Solvent was removed in vacuo and residue triturated in diethyl ether to give 130 as a pale yellow solid (127 mg, 74%). ¹H NMR (DMSO-d6, 400 MHz): δ 9.08-8.97 (br m, 1 H); 8.96-8.81 (br m, 1 H); 8.22 (s, 1 H); 7.69 (s, 1 H); 7.31-7.23 (m, 2 H); 6.99 (s, 1 H); 5.72 (q, J=8.8 Hz, 2 H); 4.51 (t, J=6.1 Hz, 2 H); 3.42-3.32 (m, 2 H); 3.22-3.15 (m, 2 H); 3.08-2.88 (m, 3 H); 2.04-1.95 (m, 2 H); 1.94-1.80 (m, 2 H). LCMS: RT=6.75 min, M+H+=419.2

Example 131

N-((2-(1-(2,2,2-trifluoroethyl)-1H-1,2,4-triazol-5-yl)-4,5-dihydrobenzo[b]pyrazolo[1,5-d][1,4]oxazepin-9-yl)methyl)pyrazin-2-amine 131

Following the procedure for 128 without the use of HCl in diethyl ether, 2-[2-(2,2,2-trifluoro-ethyl)-2H-[1,2,4]triazol-3-yl]-4,5-dihydro-6-oxa-1,10b-diaza-benzo[e]azulene-9-carbaldehyde was reacted with 2-amino pyrazine to give 131 as a white solid. ¹H NMR (CDCl3, 400 MHz): δ 8.03-7.99 (m, 3 H); 7.87 (d, J=2.6 Hz, 1 H); 7.84 (d, J=2.2 Hz, 1 H); 7.31 (dd, J=8.3, 2.2 Hz, 1 H); 7.20 (d, J=8.3 Hz, 1 H); 6.92 (s, 1 H); 5.49 (q, J=8.2 Hz, 2 H); 5.42 (br s, 1 H); 4.66 (d, J=5.4 Hz, 2 H); 4.55 (t, J=6.0 Hz, 2 H); 3.16 (t, J=6.0 Hz, 2 H). LCMS: RT=9.93 min, M+H+=443

Example 132

2-hydroxy-1-(4-((2-(1-isopropyl-1H-1,2,4-triazol-5-yl)-4,5-dihydrobenzo[b]pyrazolo[1,5-d][1,4]oxazepin-9-yl)methyl)piperazin-1-yl)ethanone 132

Following the procedure for 128 without the use of HCl in diethyl ether, 2-(2-isopropyl-2H-[1,2,4]triazol-3-yl)-4,5-dihydro-6-oxa-1,10b-diaza-benzo[e]azulene-9-carbaldehyde was reacted with 2-hydroxy-1-piperazin-1-yl-ethanone to give 132 as a white solid. ¹H NMR (CDCl3, 400 MHz): δ 7.95 (s, 1 H); 7.86 (d, J=2.0 Hz, 1 H); 7.28-7.23 (m, 1 H); 7.17 (d, J=8.2 Hz, 1 H); 6.86 (s, 1 H); 5.73-5.60 (m, 1 H); 4.55 (t, J=6.0 Hz, 2 H); 4.15 (s, 2 H); 3.69 (t, J=4.8 Hz, 2 H); 3.64-3.55 (m, 3 H); 3.29 (t, J=4.8 Hz, 2 H); 3.16 (t, J=6.0 Hz, 2 H); 2.55-2.46 (m, 4 H); 1.58 (d, J=6.6 Hz, 6 H). LCMS: RT=5.70 min, M+H+=452

Example 133

2-(1-isopropyl-1H-1,2,4-triazol-5-yl)-N-(2-(methylsulfonyl)ethyl)-5,6-dihydrobenzo[f]imidazo[1,2-d][1,4]oxazepine-9-carboxamide 133

Methyl 2-(1-isopropyl-1H-1,2,4-triazol-5-yl)-5,6-dihydrobenzo[f]imidazo[1,2-d][1,4]oxazepine-9-carboxylate 184 was saponified to give the corresponding acid, 2-(1-isopropyl-1H-1,2,4-triazol-5-yl)-5,6-dihydrobenzo[f]imidazo[1,2-d][1,4]oxazepine-9-carboxylic acid (30 mg, 0.09 mmol) which was dissolved in DMF (0.5 mL) and treated with diisopropylethylamine (0.077 mL, 0.44 mmol), 2-(methylsulfonyl)ethanamine (22 mg, 0.18 mmol) followed by HATU (67 mg, 0.18 mmol). The resulting mixture was stirred 12 h at ambient temperature. Diluted with EtOAc and H2O, extracted the aqueous layer with EtOAc (2×) and the combined organic portions were washed with brine, dried over MgSO4, filtered and concentrated in vacuo. The residue was purified by Prep HPLC to give 133. LC/MS (ESI+): m/z 462 (M+H). 1H NMR (400 MHz, DMSO) δ 8.76 (t, J=5.1, 1H), 8.48 (d, J=8.4, 1H), 7.99 (s, 1H), 7.92 (s, 1H), 7.59 (d, J=8.4, 1H), 7.53 (s, 1H), 5.86 (dt, J=13.0, 6.6, 1H), 4.56 (d, J=1.9, 4H), 3.69 (dd, J=12.7, 6.5, 2H), 3.39 (t, J=6.7, 2H), 3.05 (d, J=9.0, 3H), 1.49 (d, J=6.6, 5H)

Example 134

2-(1-(2-chlorophenyl)-1H-1,2,4-triazol-5-yl)-N-(2-(methylsulfonyl)ethyl)-5,6-dihydrobenzo[f]imidazo[1,2-d][1,4]oxazepine-9-carboxamide 134

2-(1-(2-Chlorophenyl)-1H-1,2,4-triazol-5-yl)-5,6-dihydrobenzo[f]imidazo[1,2-d][1,4]oxazepine-9-carboxylic acid (40 mg, 0.1 mmol) was reacted with 2-(methylsulfonyl)ethanamine to provide 2-(1-(2-chlorophenyl)-1H-1,2,4-triazol-5-yl)-N-(2-(methylsulfonyl)ethyl)-5,6-dihydrobenzo[f]imidazo[1,2-d][1,4]oxazepine-9-carboxamide 134. LC/MS (ESI+): m/z 514 (M+H). 1H NMR (400 MHz, DMSO) δ 8.72 (s, 1H), 8.56 (s, OH), 8.20 (s, 1H), 7.94 (s, 1H), 7.73 (d, J=7.0, 1H), 7.71-7.52 (m, 3H), 7.43 (s, 1H), 7.36 (d, J=8.9, 1H), 4.48 (d, J=6.6, 3H), 3.73-3.58 (m, 2H), 3.02 (s, 3H)

Example 135

2-(1-(2-chlorophenyl)-1H-1,2,4-triazol-5-yl)-N-(1-hydroxy-2-methylpropan-2-yl)-5,6-dihydrobenzo[f]imidazo[1,2-d][1,4]oxazepine-10-carboxamide 135

Following the procedure for 109, 2-(1-(2-chlorophenyl)-1H-imidazol-2-yl)-5,6-dihydrobenzo[f]imidazo[1,2-d][1,4]oxazepine-10-carboxylic acid and 2-amino-2-methylpropan-1-ol gave 135. MS: (ESI+)=479.1. 1H NMR (400 MHz, DMSO) δ 8.19 (s, 1H), 8.11 (d, J=2.2 Hz, 1H), 7.78 (s, 1H), 7.71-7.66 (m, 1H), 7.63 (dd, J=7.2, 2.1 Hz, 1H), 7.60-7.50 (m, 3H), 7.37 (s, 1H), 6.98 (d, J=8.5 Hz, 1H), 4.99 (t, J=5.9 Hz, 1H), 4.46 (d, J=3.7 Hz, 4H), 3.54 (d, J=5.9 Hz, 2H), 1.36 (s, 6H)

Example 136

(2-(1-(2-chlorophenyl)-1H-1,2,4-triazol-5-yl)-5,6-dihydrobenzo[f]imidazo[1,2-d][1,4]oxazepin-10-yl)(4-isopropylpiperazin-1-yl)methanone 136

Following the procedure for 109, 2-(1-(2-chlorophenyl)-1H-imidazol-2-yl)-5,6-dihydrobenzo[f]imidazo[1,2-d][1,4]oxazepine-10-carboxylic acid and 4-isopropylpiperazine gave 136. MS: (ESI+)=518.2. 1H NMR (400 MHz, DMSO) δ 8.20 (s, 1H), 7.84 (s, 1H), 7.70 (s, 2H), 7.64 (d, J=7.4 Hz, 1H), 7.62-7.51 (m, 2H), 7.36 (d, J=8.5 Hz, 1H), 7.06 (d, J=8.5 Hz, 1H), 4.48 (s, 4H), 3.57 (s, 2H), 3.04 (s, 2H), 1.29 (d, J=6.5 Hz, 6H)

Example 137

2-(1-(2,4-difluorophenyl)-1H-1,2,4-triazol-5-yl)-N-(1-hydroxy-2-methylpropan-2-yl)-5,6-dihydrobenzo[f]imidazo[1,2-d][1,4]oxazepine-10-carboxamide 137

Following the procedure for 109, 2-(1-(2,4-difluorophenyl)-1H-1,2,4-triazol-5-yl)-5,6-dihydrobenzo[f]imidazo[1,2-d][1,4]oxazepine-10-carboxylic acid and 2-amino-2-methylpropan-1-ol gave 137. MS: (ESI+)=481.1. 1H NMR (400 MHz, DMSO) δ 8.26 (d, J=2.2 Hz, 1H), 8.21 (s, 1H), 7.94 (s, 1H), 7.73-7.65 (m, 1H), 7.62 (dd, J=8.5, 2.3 Hz, 1H), 7.51-7.42 (m, 1H), 7.39 (s, 1H), 7.25 (t, J=7.7 Hz, 1H), 7.00 (d, J=8.5 Hz, 1H), 4.96 (t, J=6.0 Hz, 1H), 4.49 (d, J=6.1 Hz, 4H), 3.52 (d, J=5.8 Hz, 2H), 1.35 (s, 6H)

Example 138

2-(4-Cyano-1-isopropyl-1H-pyrazol-5-yl)-5,6-dihydrobenzo[f]imidazo[1,2-d][1,4]oxazepine-9-carboxamide 138

Following Example 109, 2-(4-Cyano-1-isopropyl-1H-pyrazol-5-yl)-5,6-dihydrobenzo[f]imidazo[1,2-d][1,4]oxazepine-9-carboxylic acid from Example 16 was coupled with ammonia to give 138. Yield 27.8 mg (44%). MS (ESI): 363.1. 1H NMR (400 MHz, DMSO) δ 8.46 (d, J=8.4, 1H), 8.11 (s, 1H), 8.00 (d, J=4.7, 2H), 7.62 (dd, J=8.4, 1.5, 1H), 7.57 (d, J=1.4, 1H), 7.44 (s, 1H), 5.46 (dt, J=13.1, 6.5, 1H), 4.59 (dd, J=17.5, 4.8, 4H), 1.48 (d, J=6.6, 6H).

Example 139

2-(1-(2-chlorophenyl)-1H-1,2,4-triazol-5-yl)-N-methyl-5,6-dihydrobenzo[f]imidazo[1,2-d][1,4]oxazepine-9-carboxamide 139

Following the same procedure as for 133, 2-(1-(2-chlorophenyl)-1H-1,2,4-triazol-5-yl)-5,6-dihydrobenzo[f]imidazo[1,2-d][1,4]oxazepine-9-carboxylic acid (40 mg, 0.1 mmol) was reacted with methylamine (2M, 0.2 mL) in THF to provide 2-(1-(2-chlorophenyl)-1H-1,2,4-triazol-5-yl)-N-methyl-5,6-dihydrobenzo[f]imidazo[1,2-d][1,4]oxazepine-9-carboxamide 139. LC/MS(ESI+): m/z 422 (M+H). 1H NMR (400 MHz, DMSO) δ 8.43 (d, J=4.5, 1H), 8.19 (s, 1H), 7.93 (s, 1H), 7.72 (t, J=10.9, 1H), 7.68-7.51 (m, 4H), 7.47-7.28 (m, 2H), 4.50 (t, J=15.6, 4H), 2.76 (d, J=4.5, 3H)

Example 140

N-(2-hydroxyethyl)-N-isopropyl-4,5-dihydrobenzo[b]pyrazolo[1,5-d][1,4]oxazepine-2-carboxamide 140

Following the procedure for 116, 8-bromo-4,5-dihydro-6-oxa-1,10b-diaza-benzo[e]azulene-2-carboxylic acid was reacted with 2-isopropylamino-ethanol. The intermediate formed (145 mg, 0.37 mmol) was dissolved in IMS (10 mL) and triethylamine (50 L, 0.37 mmol) then 10% Pd/C (20 mg) added before the reaction mixture stirred under hydrogen (1 atmosphere) for 2.75 h. The reaction mixture was filtered through Celite® and the filtrate concentrated in vacuo. The resultant residue was partitioned between DCM and water, the aqueous layer was isolated and extracted with DCM. The combined organic extracts dried (Na2SO4), filtered and concentrated in vacuo. The resultant residue was dissolved in diethyl ether and the solution washed with water, dried (Na2SO4), filtered and then concentrated in vacuo to give 140 (79 mg, 68%). $^1$H NMR (DMSO-d6, 400 MHz): δ 7.83 (dd, J=8.0, 1.6 Hz, 1 H); 7.30 (td, J=7.6, 1.8 Hz, 1 H); 7.26-7.16 (m, 2 H); 6.54 (s, 1 H); 4.67-4.53 (m, 1 H); 4.46 (t, J=6.0 Hz, 2 H); 4.35-4.27 (m, 1 H); 3.64-3.56 (m, 2 H); 3.55-3.46 (m, 2 H); 3.13 (t, J=6.0 Hz, 2 H); 1.22 (d, J=6.8 Hz, 6 H). LCMS: RT=9.00 min, M+H+=316

Example 141

4-((2-(1-isopropyl-1H-1,2,4-triazol-5-yl)-4,5-dihydrobenzo[b]pyrazolo[1,5-d][1,4]oxazepin-9-yl)methyl)piperazin-2-one 141

Following the procedure for 128 without the use of HCl in diethyl ether, 2-(2-isopropyl-2H-[1,2,4]triazol-3-yl)-4,5- dihydro-6-oxa-1,10b-diaza-benzo[e]azulene-9-carbaldehyde was reacted with 2-hydroxy-1-piperazin-1-yl-ethanone to give 141 as a white solid. ¹H NMR (MeOD, 400 MHz): δ 8.00 (s, 1 H); 7.92 (d, J=2.1 Hz, 1 H); 7.34 (dd, J=8.3, 2.1 Hz, 1 H); 7.22 (d, J=8.3 Hz, 1 H); 6.88 (s, 1 H); 5.80-5.67 (m, 1 H); 4.54 (t, J=6.1 Hz, 2 H); 3.69 (s, 2 H); 3.36-3.28 (m, 2 H); 3.19 (t, J=6.1 Hz, 2 H); 3.13 (s, 2 H); 2.76-2.70 (m, 2 H); 1.56 (d, J=6.6 Hz, 6H). 1 Exchangeable proton not observed. LCMS: RT=7.45 min, M+H+=408

Example 142

2-(4-(2-(1-(2,2,2-trifluoroethyl)-1H-1,2,4-triazol-5-yl)-4,5-dihydrobenzo[b]pyrazolo[1,5-d][1,4]oxazepin-9-yl)piperidin-1-yl)ethanol 142

A mixture of 9-piperidin-4-yl-2-[2-(2,2,2-trifluoro-ethyl)-2H-[1,2,4]triazol-3-yl]-4,5-dihydro-6-oxa-1,10b-diaza-benzo[e]azulene (180 mg, 0.43 mmol) in DMF (1 mL), potassium carbonate (89 mg, 0.65 mmol) and 2-(2-bromo-ethoxy)-tetrahydro-pyran (97 L, 0.65 mmol) was heated at 50° C. for 18 h. The cooled reaction mixture was partitioned between ethyl acetate and water, the aqueous layer extracted with ethyl acetate and the combined organic extracts dried (Na2SO4), filtered and concentrated in vacuo. The resultant residue was subjected to flash chromatography (SiO2, gradient 0 to 10% MeOH (+2M NH3) in DCM) to give a colourless oil. The oil was dissolved in methanol and treated with 1M HCl in methanol (2 mL, 2 mmol) and the reaction mixture stirred for 2 h at RT before concentrating in vacuo. The resultant residue was triturated in a mixture of diethyl ether and methanol to give 142 as a pale yellow solid (115 mg, 54%). ¹H NMR (DMSO-d6, 400 MHz): δ 9.81 (br s, 1 H); 8.22 (s, 1 H); 7.70 (s, 1 H); 7.32-7.24 (m, 2 H); 6.99 (s, 1 H); 5.72 (q, J=8.7 Hz, 2 H); 5.36 (br s, 1 H); 4.51 (t, J=6.0 Hz, 2 H); 3.80 (t, J=4.9 Hz, 2 H); 3.67-3.57 (m, 2 H); 3.22-3.06 (m, 6 H); 2.97-2.85 (m, 1 H); 2.10-2.00 (m, 4 H). LCMS: RT=6.62 min, M+H+=463.1

Example 143

2-(4-(2-(1-(2,2,2-trifluoroethyl)-1H-1,2,4-triazol-5-yl)-4,5-dihydrobenzo[b]pyrazolo[1,5-d][1,4]oxazepin-9-yl)piperidin-1-yl)acetamide 143

A mixture of 9-piperidin-4-yl-2-[2-(2,2,2-trifluoro-ethyl)-2H-[1,2,4]triazol-3-yl]-4,5-dihydro-6-oxa-1,10b-diaza-benzo[e]azulene (180 mg, 0.43 mmol) in DMF (1 mL) was treated with potassium carbonate (89 mg, 0.65 mmol) and bromo acetamide (77 mg, 0.56 mmol) and then stirred at RT for 18 h. The reaction mixture was partitioned between ethyl acetate and water, the aqueous layer extracted with ethyl acetate and the combined organic extracts dried (Na2SO4), filtered and concentrated in vacuo. The resultant residue was triturated in diethyl ether to give 143 as a pale yellow solid (115 mg, 54%). ¹H NMR (DMSO-d6, 400 MHz): δ 8.21 (s, 1 H); 7.75 (d, J=2.2 Hz, 1 H); 7.28 (dd, J=8.4, 2.2 Hz, 1 H); 7.20 (d, J=8.3 Hz, 1 H); 7.15 (s, 2 H); 6.97 (s, 1 H); 5.73 (q, J=8.8 Hz, 2 H); 4.49 (t, J=6.0 Hz, 2 H); 3.20 (t, J=6.0 Hz, 2 H); 2.96-2.85 (m, 4 H); 2.62-2.52 (m, 1 H); 2.24-2.14 (m, 2 H); 1.84-1.66 (m, 4 H). LCMS: RT=6.55 min, M+H+=476

Example 144

9-(azetidin-3-yl)-2-(1-isopropyl-1H-1,2,4-triazol-5-yl)-4,5-dihydrobenzo[b]pyrazolo[1,5-d][1,4]oxazepine 144

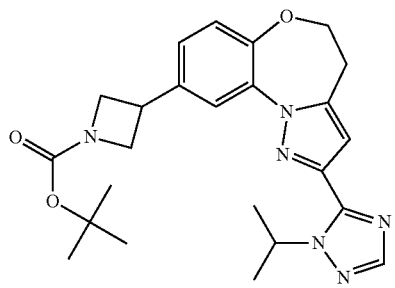 [SMILES: CC(C)n1ncnc1-c1cc2n(n1)-c1cc(C3CN(C(=O)OC(C)(C)C)C3)ccc1OCC2]

9-bromo-2-(2-isopropyl-2H-[1,2,4]triazol-3-yl)-4,5-dihydro-6-oxa-1,10b-diaza-benzo[e]azulene (0.52 g, 1.40 mmol) and 3-azetidine-1-carboxylic acid tert-butyl ester zinc iodide (2.0 mmol) were reacted to give 3-[2-(2-Isopropyl-2H-[1,2,4]triazol-3-yl)-4,5-dihydro-6-oxa-1,10b-diaza-benzo[e]azulen-9-yl]-azetidine-1-carboxylic acid tert-butyl ester (0.47 g, 49%). LCMS RT=4.70 M+H+=451.

9-Azetidin-3-yl-2-(2-isopropyl-2H-[1,2,4]triazol-3-yl)-4,5-dihydro-6-oxa-1,10b-diaza-benzo[e]azulene (0.41 g, 0.76 mmol) was treated with acid to give the crude hydrochloride salt which was partitioned between ethyl acetate and saturated aqueous sodium hydrogen carbonate and extracted three times with DCM. The combined extracts were dried (Na2SO4), filtered and concentrated in vacuo. The resultant residue was subjected to flash chromatography (SiO2, gradient 0 to 10% 2M NH3 (in MeOH) in DCM) to give 144 (162 mg, 31%). ¹H NMR (400 MHz, CDCl3): δ 7.97-7.93 (m, 1 H); 7.82 (d, J=2.19 Hz, 1 H); 7.29 (dd, J=8.36, 2.25 Hz, 1 H); 7.19 (d, J=8.32 Hz, 1 H); 6.87 (s, 1 H); 5.74-5.66 (m, 1 H); 4.57-4.50 (m, 2 H); 4.12-4.02 (m, 1 H); 4.00 (t, J=7.46 Hz, 2 H); 3.87 (t, J=7.27 Hz, 2 H); 3.16 (t, J=6.02 Hz, 2 H); 1.62 (d, 6 H). LCMS: RT=6.01 min, M+H+=351

Example 145

2-(1-isopropyl-1H-1,2,4-triazol-5-yl)-9-(piperazine-1-carbonyl)-4,5-dihydrobenzo-2H-oxepino[4,5-d]pyrazole 145

A mixture of N-Boc piperazine (101 mg, 0.54 mmol), 2-(2-isopropyl-2H-[1,2,4]triazol-3-yl)-4,5-dihydro-2H-6-oxa-1,2-diaza-benzo[e]azulene-9-carboxylic acid (180 mg, 0.53 mmol), EDCI (151 mg, 0.79 mmol), HOBt (107 mg, 0.795 mmol) and triethylamine (216 L, 1.54 mmol) in DMF (2 mL) was stirred at RT for 20 h. The mixture was diluted with ethyl acetate and washed (water, saturated aqueous sodium hydrogen carbonate and then brine), dried (Na2SO4), filtered and concentrated in vacuo. The resultant residue was subjected to flash chromatography (SiO2, gradient 0 to 10% MeOH in DCM) to give 4-[2-(2-isopropyl-2H-[1,2,4]triazol-3-yl)-4,5-dihydro-2H-6-oxa-1,2-diaza-benzo[e]azulene-9-carbonyl]-piperazine-1-carboxylic acid tert-butyl ester (258 mg, 96%). The intermediate carboxylic acid tert-butyl ester was dissolved in DCM (20 mL) and treated with 4N HCl in dioxane (4 mL) and stirred for 3 h at RT before adding diethyl ether (20 mL). The resultant precipitate was collected by filtration and washed with diethyl ether to give 145 as a white solid (209 mg, 93%). ¹H NMR (400 MHz, DMSO-d): δ 9.32 (s, 2 H); 8.37 (s, 1 H); 8.31 (d, J=2.20 Hz, 1 H); 8.06 (s, 1 H); 7.44 (dd, J=8.37, 2.21 Hz, 1 H); 7.15 (d, J=8.37 Hz, 1 H); 5.32-5.23 (m, 1 H); 4.37 (t, J=4.98 Hz, 2 H); 3.77 (s, 4 H); 3.15 (t, J=6.94 Hz, 6 H); 1.51 (d, J=6.59 Hz, 6 H). LCMS: RT=6.02 min, M+H+=408

Example 146

2-(4-isopropyl-4H-1,2,4-triazol-5-yl)-4,5-dihydrobenzo-2H-oxepino[4,5-d]pyrazole 146

Step 1:
4-Isopropyl-3-methylsulfanyl-4H-[1,2,4]triazole

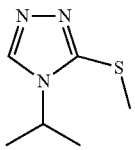

To a solution of 4-isopropyl-3-thiosemicarbazide (7.0 g, 52.54 mmol) in dioxane (50 ml) was added DMF-DMA (14.1 ml, 105.08 mmol) and the mixture heated to 100° C. After 3 h additional DMF-DMA (52.54 mmol) was added and heating was continued. After 18 h the mixture was allowed to cool to RT and the solvent removed in vacuo. The resultant residue was subjected to flash chromatography (SiO2, gradient 0 to 100% ethyl acetate in cyclohexane) to afford 4-Isopropyl-3-methylsulfanyl-4H-[1,2,4]triazole (4.05 g, 49%) LCMS RT=2.55 min, M+H+=158.

Step 2:
4-Isopropyl-3-methanesulfonyl-4H-[1,2,4]triazole

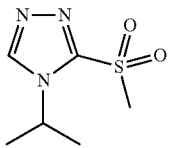

To a solution of 4-isopropyl-3-methylsulfanyl-4H-[1,2,4]triazole (3.05 g, 19.43 mmol) in DCM (30 ml) was added formic acid (2.9 ml, 76.36 mmol) and ammonium molybdate tetrahydrate (56 mg, 0.047 mmol). To the rapidly stirring mixture was carefully added hydrogen peroxide solution (50 wt. % in H2O, 8 mL, 116.58 mmol) in portions to avoid uncontrolled exotherm. After complete addition the mixture was stirred at RT for 18 h. The mixture was cooled in an ice bath and carefully quenched with saturated sodium sulfite solution, then extracted with DCM (3×100 mL). The organic extracts were combined and dried (Na2SO4), filtered and concentrated in vacuo to afford 4-Isopropyl-3-methanesulfonyl-4H-[1,2,4]triazole (3.29 g, 90%) LCMS RT=2.02 min, M+H+=190.

Step 3: 9-bromo-2-(4-isopropyl-4H-[1,2,4]triazol-3-yl)-4,5-dihydro-2H-6-oxa-1,2-diaza-benzo[e]azulene

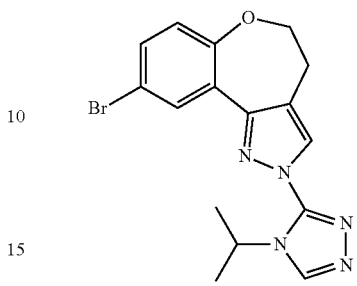

To a microwave vial were charged 9-bromo-4,5-dihydro-2H-6-oxa-1,2-diaza-benzo[e]azulene (200 mg, 0.755 mmol), 4-isopropyl-3-methanesulfonyl-4H-[1,2,4]triazole (143 mg, 0.755 mmol), cesium carbonate (246 mg, 0.755 mmol) and THF (2 mL). The reaction mixture was heated to 150° C. for 2 h then extracted with ethyl acetate (20 mL), washed with water (20 mL), dried (Na2SO4), filtered and concentrated in vacuo. The resultant residue was subjected to flash chromatography (SiO2, gradient 0 to 100% ethyl acetate in cyclohexane) to afford 9-bromo-2-(4-isopropyl-4H-[1,2,4]triazol-3-yl)-4,5-dihydro-2H-6-oxa-1,2-diaza-benzo[e]azulene (122 mg, 43%). LCMS RT=4.34 min, M+H+=374/376.

Step 4: 2-(4-Isopropyl-4H-[1,2,4]triazol-3-yl)-4,5-dihydro-2H-6-oxa-1,2-diaza-benzo[e]azulene To a degassed solution of 9-bromo-2-(4-isopropyl-4H-[1,2,4]triazol-3-yl)-4,5-dihydro-2H-6-oxa-1,2-diaza-benzo[e]azulene (122 mg, 0.326 mmol) in IMS (10 mL) was added TEA (51 L, 0.359 mmol) and 10% Pd/C (15 mg). The mixture was stirred under hydrogen (1 atmosphere) for 60 min then filtered, and the filtrate concentrated in vacuo. The resultant residue was dissolved in DCM (20 mL) and washed with water (20 mL), the organic layer dried (Na2SO4), filtered and concentrated in vacuo. The resultant residue was freeze dried from acetonitrile and water to afford 146 (54 mg, 56%). LCMS: RT=10.29 min, M+H+=296.

Alternatively, a degassed solution of 8-bromo-2-(4-isopropyl-4H-[1,2,4]triazol-3-yl)-4,5-dihydro-2H-6-oxa-1,2-diaza-benzo[e]azulene (122 mg, 0.326 mmol) in IMS (10 mL) was added 10% Pd/C (15 mg), the reaction mixture stirred under an atmosphere of hydrogen for 1 h before the reaction mixture was filtered and the filtrate concentrated in vacuo. The resultant residue was dissolved in DCM and the solution washed with water, the organic layer dried (Na2SO4), filtered and concentrated in vacuo to give a residue. The residue was dissolved in acetonitrile and water and the solution freeze dried to give 2-(4-Isopropyl-4H-[1,2,4]triazol-3-yl)-4,5-dihydro-2H-6-oxa-1,2-diaza-benzo[e]azulene as a white solid (54 mg, 56%). ¹H NMR (400 MHz, CDCl3): δ 8.27-8.23 (m, 2 H); 8.12 (t, J=1.02 Hz, 1 H); 7.30-7.24 (m, 1 H); 7.14-7.06 (m, 2 H); 5.38-5.29 (m, 1 H); 4.36 (t, J=5.10 Hz, 2 H); 3.16 (td, J=5.10, 1.06 Hz, 2 H); 1.63-1.54 (d, J=6.59 Hz, 6 H). LCMS: RT=10.29 min, M+H+=296

Example 147

2-(1-isopropyl-1H-1,2,4-triazol-5-yl)-9-N-(1-(2-hydroxyethyl)-1H-pyrazol-4-yl)-4,5-dihydrobenzo-2H-oxepino[4,5-d]pyrazole-9-carboxamide 147

Following the procedure for 116, 2-(2-isopropyl-2H-[1,2,4]triazol-3-yl)-4,5-dihydro-2H-6-oxa-1,2-diaza-benzo[e]azulene-9-carboxylic acid was reacted with 4-amino-1-(2-hydroxyethyl)pyrazole to give 147 as a white solid. $^1$H NMR (400 MHz, DMSO-d): δ 10.45 (s, 1 H); 8.85 (d, J=2.32 Hz, 1 H); 8.36 (s, 1 H); 8.08-8.05 (m, 2 H); 7.87 (dd, J=8.53, 2.35 Hz, 1 H); 7.58 (d, J=0.69 Hz, 1 H); 7.18 (d, J=8.50 Hz, 1 H); 5.36-5.28 (m, 1 H); 4.88 (t, J=5.31 Hz, 1 H); 4.39 (t, J=4.97 Hz, 2 H); 4.13 (t, J=5.61 Hz, 2 H); 3.73 (q, J=5.51 Hz, 2 H); 3.16 (t, J=4.96 Hz, 2 H); 1.53 (d, J=6.59 Hz, 6 H). LCMS: RT=9.63 min, M+H+=449

Example 148

2-(1-isopropyl-1H-1,2,4-triazol-5-yl)-9-(1-(methylsulfonyl)azetidin-3-yl)-4,5-dihydrobenzo[b]pyrazolo[1,5-d][1,4]oxazepine 148

An ice-cooled solution of 9-azetidin-3-yl-2-(2-isopropyl-2H-[1,2,4]triazol-3-yl)-4,5-dihydro-6-oxa-1,10b-diaza-benzo[e]azulene (0.16 g, 0.46 mmol) in DCM (5 mL) was treated with triethylamine (0.14 mL, 1.0 mmol) then methanesulfonyl chloride (40 L, 0.51 mmol) and the mixture stirred at RT for 2 h. The reaction mixture was washed with water and the aqueous layer extracted with DCM, the combined organic extracts were combined, dried (Na2SO4), filtered and concentrated in vacuo. The resultant residue was subjected to flash chromatography (SiO2, gradient 50 to 100% ethyl acetate in cyclohexane) to give 148 as a white solid (126 mg, 64%). $^1$H NMR (400 MHz, CDCl3): δ 7.95 (d, J=2.49 Hz, 2 H); 7.31 (dd, J=8.35, 2.29 Hz, 1 H); 7.21 (d, J=8.32 Hz, 1 H); 6.89 (s, 1 H); 5.75-5.66 (m, 1 H); 4.56 (t, J=5.89 Hz, 2 H); 4.32 (t, J=8.24 Hz, 2 H); 4.12 (t, J=7.34 Hz, 2 H); 3.92-3.82 (m, 1 H); 3.20 (t, J=5.89 Hz, 2 H); 2.93 (s, 3 H); 1.62 (d, 6 H). LCMS: RT=9.68 min, M+H+=429

Example 149

1-(3-(2-(1-isopropyl-1H-1,2,4-triazol-5-yl)-4,5-dihydrobenzo[b]pyrazolo[1,5-d][1,4]oxazepin-9-yl)azetidin-1-yl)ethanone 149

Following the procedure for 148, 9-azetidin-3-yl-2-(2-isopropyl-2H-[1,2,4]triazol-3-yl)-4,5-dihydro-6-oxa-1,10b-diaza-benzo[e]azulene was reacted with acetic anhydride to give 149 as a white solid. $^1$H NMR (400 MHz, CDCl3): δ 7.93 (s, 1 H); 7.85 (d, J=2.17 Hz, 1 H); 7.27-7.20 (m, 1 H); 7.19 (d, J=8.32 Hz, 1 H); 6.85 (s, 1H); 5.68-5.59 (m, 1 H); 4.59-4.50 (m, 3 H); 4.44 (t, J=9.38 Hz, 1 H); 4.18-4.11 (m, 1H); 4.13-4.05 (m, 1 H); 3.89-3.80 (m, 1 H); 3.16 (t, J=5.93 Hz, 2 H); 1.91 (s, 3 H); 1.57 (d, J=6.62 Hz, 6 H). LCMS: RT=9.50 min, M+H+=393

Example 150

2-hydroxy-1-(3-(2-(1-isopropyl-1H-1,2,4-triazol-5-yl)-4,5-dihydrobenzo[b]pyrazolo[1,5-d][1,4]oxazepin-9-yl)azetidin-1-yl)ethanone 150

Following the procedure for 116, 9-azetidin-3-yl-2-(2-isopropyl-2H-[1,2,4]triazol- 3-yl)-4,5-dihydro-6-oxa-1,10b-diaza-benzo[e]azulene was reacted with glycolic acid to give 150 as a white solid. $^1$H NMR (400 MHz, CDCl3): δ 7.95 (s, 1 H); 7.87 (d, J=2.09 Hz, 1 H); 7.28-7.21 (m, 1 H); 7.24-7.19 (m, 1 H); 6.87 (s, 1 H); 5.68-5.59 (m, 1 H); 4.60-4.48 (m, 4 H); 4.20 (dd, J=9.89, 6.11 Hz, 1 H); 4.16-4.07 (m, 1 H); 4.05 (d, J=3.28 Hz, 2 H); 4.03-3.96 (m, 1 H); 3.18 (t, J=5.91 Hz, 2 H); 1.58 (d, J=6.62 Hz, 6 H). 1 Exchangeable proton not observed. LCMS: RT=8.95 min, M+H+=409

Example 151

2-hydroxy-1-(4-(2-(1-(2,2,2-trifluoroethyl)-1H-1,2,4-triazol-5-yl)-4,5-dihydrobenzo[b]pyrazolo[1,5-d][1,4]oxazepin-9-yl)piperidin-1-yl)ethanone 151

Following the procedure for 116, 9-piperidin-4-yl-2-[2-(2,2,2-trifluoro-ethyl)-2H-[1,2,4]triazol-3-yl]-4,5-dihydro-6-oxa-1,10b-diaza-benzo[e]azulene was reacted with glycolic acid to give 151 as a white solid. $^1$H NMR (400 MHz, DMSO-d): δ 8.21 (s, 1 H); 7.73 (d, J=2.16 Hz, 1 H); 7.29 (dd, J=8.37, 2.17 Hz, 1 H); 7.21 (d, J=8.32 Hz, 1 H); 6.97 (s, 1 H); 5.72 (q, J=8.78 Hz, 2 H); 4.55-4.43 (m, 4 H); 4.13-4.05 (m, 2 H); 3.79 (d, J=13.44 Hz, 1 H); 3.23-3.15 (m, 3 H); 3.09 (t, J=12.91 Hz, 1 H); 2.91-2.82 (m, 1 H); 2.77-2.65 (m, 1 H); 1.86 (d, J=12.87 Hz, 2 H). LCMS: RT=9.76 min, M+H+=477

Example 152

9-(1-(2-(methylsulfonyl)ethyl)piperidin-4-yl)-2-(1-(2,2,2-trifluoroethyl)-1H-1,2,4-triazol-5-yl)-4,5-dihydrobenzo[b]pyrazolo[1,5-d][1,4]oxazepine 152

A mixture of 9-piperidin-4-yl-2-[2-(2,2,2-trifluoro-ethyl)-2H-[1,2,4]triazol-3-yl]-4,5-dihydro-6-oxa-1,10b-diaza-benzo[e]azulene (90 mg, 0.22 mmol), triethylamine (150 L, and IMS (0.6 mL) was treated with vinyl sulfone (48 mL, 0.54 mmol) then diluted with DCM and stirred for 18 h at RT. The reaction mixture was concentrated in vacuo and the residue triturated in diethyl ether to provide a solid which was subjected to flash chromatography (SiO2, gradient 0 to 5% MeOH in DCM) to give 152 as a white solid (96 mg, 85%). $^1$H NMR (400 MHz, CDCl3): δ 8.01 (s, 1 H); 7.69 (s, 1 H); 7.19-7.08 (m, 2 H); 6.92 (s, 1 H); 5.53 (q, J=8.15 Hz, 2 H); 4.54 (t, J=6.01 Hz, 2 H); 3.21-3.12 (m, 4 H); 3.21-2.92 (m, 5 H); 2.93 (t, J=6.33 Hz, 2 H); 2.63-2.54 (m, 1 H); 2.21 (t, J=11.57 Hz, 2 H); 1.94 (d, J=12.96 Hz, 2 H); 1.81-1.66 (m, 2 H). LCMS: RT=6.57 min, M+H+=525

Example 153

((3S,5R)-3,5-dimethylpiperazin-1-yl)(2-(1-(2,2,2-trifluoroethyl)-1H-1,2,4-triazol-5-yl)-5,6-dihydrobenzo[f]imidazo[1,2-d][1,4]oxazepin-10-yl)methanone 153

Following the procedure for 109, 2-(1-(2,2,2-trifluoroethyl)-1H-1,2,4-triazol-5-yl)-5,6-dihydrobenzo[f]imidazo[1,2-d][1,4]oxazepine-10-carboxylic acid and 3S,5R-dimethylpiperazine gave 153. MS: (ESI+)=476.1. 1H NMR (400 MHz, DMSO) δ 8.39 (d, J=2.0 Hz, 1H), 8.10 (d, J=4.9 Hz, 2H), 7.37 (dd, J=8.4, 2.1 Hz, 1H), 7.12 (d, J=8.4 Hz, 1H), 5.88 (s, 2H), 4.57 (s, 4H), 4.06 (q, J=5.3 Hz, 2H), 3.17 (d, J=5.2 Hz, 2H), 2.67 (s, 2H), 0.92 (s, 6H)

Example 154

2-(1-(2-chlorophenyl)-1H-1,2,4-triazol-5-yl)-9-piperid-4-yl-4,5-dihydrobenzo-2H-oxepino[4,5-d]pyrazole 154

Step 1: 4-{2-[2-(2-Chloro-phenyl)-2H-[1,2,4]triazol-3-yl]-4,5-dihydro-2H-6-oxa-1,2-diaza-benzo[e]azulen-9-yl}-3,6-dihydro-2H-pyridine-1-carboxylic acid tert-butyl ester

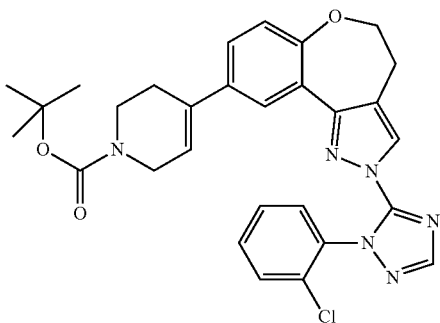 [SMILES: CC(C)(C)OC(=O)N1CC=C(c2ccc3c(c2)-c2nn(-c4ncnn4-c4ccccc4Cl)cc2CCO3)CC1]

4-{2-[2-(2-Chloro-phenyl)-2H-[1,2,4]triazol-3-yl]-4,5-dihydro-2H-6-oxa-1,2-diaza-benzo[e]azulen-9-yl}-3,6-dihydro-2H-pyridine-1-carboxylic acid tert-butyl ester was prepared similarly to 4-{2-[2-(2,2,2-trifluoro-ethyl)-2H-[1,2,4]triazol-3-yl]-4,5-dihydro-6-oxa-1,10b-diaza-benzo[e]azulen-9-yl}-3,6-dihydro-2H-pyridine-1-carboxylic acid tert-butyl ester from 9-bromo-2-[2-(2-chloro-phenyl)-2H-[1,2,4]triazol-3-yl]-4,5-dihydro-2H-6-oxa-1,2-diaza-benzo[e]azulene (500 mg, 1.13 mmol) to give 4-{2-[2-(2-Chloro-phenyl)-2H-[1,2,4]triazol-3-yl]-4,5-dihydro-2H-6-oxa-1,2-diaza-benzo[e]azulen-9-yl}-3,6-dihydro-2H-pyridine-1-carboxylic acid tert-butyl ester as a colourless gum (490 mg, 80%). LCMS RT=5.14 min, M+Na+=567

Step 2: 2-[2-(2-Chloro-phenyl)-2H-[1,2,4]triazol-3-yl]-9-piperidin-4-yl-4,5-dihydro-2H-6-oxa-1,2-diaza-benzo[e]azulene 2-[2-(2-Chloro-phenyl)-2H-[1,2,4]triazol-3-yl]-9-piperidin-4-yl-4,5-dihydro-2H-6-oxa-1,2-diaza-benzo[e]azulene was prepared similarly to 9-piperidin-4-yl-2-[2-(2,2,2-trifluoro-ethyl)-2H-[1,2,4]triazol-3-yl]-4,5-dihydro-6-oxa-1,10b-diaza-benzo[e]azulene from 4-{2-[2-(2-chloro-phenyl)-2H-[1,2,4]triazol-3-yl]-4,5-dihydro-2H-6-oxa-1,2-diaza-benzo[e]azulen-9-yl}-3,6-dihydro-2H-pyridine-1-carboxylic acid tert-butyl ester (490 mg, 0.9 mmol). The crude salt was partitioned between DCM and saturated aqueous sodium hydrogen carbonate, then the aqueous layer was extracted with DCM. The combined organic extracts were dried (Na2SO4), filtered and concentrated in vacuo. The resultant residue was subjected to reverse phase HPLC (Gemini C18 column, gradient MeOH in H₂O+0.1% HCO2H) to give 154 (80 mg, 18%) as the mono formate salt. ¹H NMR (400 MHz, DMSO-d6): δ 8.44 (s, 1 H); 8.39 (s, 1 H); 8.27 (s, 1 H); 7.81-7.68 (m, 3 H); 7.64 (td, J=7.60, 1.51 Hz, 1 H); 7.09-7.03 (m, 2 H); 6.90 (d, J=8.28 Hz, 1 H); 4.19 (t, J=5.06 Hz, 2 H); 3.32 (d, J=12.42 Hz, 2 H); 3.04 (t, J=5.01 Hz, 2 H); 2.89 (dd, J=13.45, 11.09 Hz, 2 H); 2.54-2.56 (m, 1 H); 1.69 (d, J=13.20 Hz, 2 H); 1.58-1.45 (m, 2 H). LCMS: RT=7.99 min, M+H+=447

Example 155

2-(3-(2-(1-isopropyl-1H-1,2,4-triazol-5-yl)-4,5-dihydrobenzo[b]pyrazolo[1,5-d][1,4]oxazepin-9-yl)azetidin-1-yl)acetamide 155

Following the procedure for 143, 9-azetidin-3-yl-2-(2-isopropyl-2H-[1,2,4]triazol-3-yl)-4,5-dihydro-6-oxa-1,10b-diaza-benzo[e]azulene was reacted with bromo acetamide and the crude product subjected flash chromatography (SiO2, gradient 0 to 10% MeOH in DCM) to give 155 as a white solid. ¹H NMR (400 MHz, CDCl3): δ 7.95 (s, 1 H); 7.83 (d, J=2.18 Hz, 1 H); 7.24 (d, J=2.21 Hz, 1 H); 7.18 (d, J=8.31 Hz, 1 H); 6.86 (s, 1 H); 5.71-5.63 (m, 1 H); 5.45 (s, 1 H); 4.54 (t, J=5.98 Hz, 2 H); 3.87 (t, J=7.28 Hz, 2 H); 3.81-3.72 (m, 1 H); 3.38 (t, J=6.84 Hz, 2 H); 3.22 (s, 2 H); 3.16 (t, J=5.99 Hz, 2 H); 1.59 (d, J=6.62 Hz, 6 H). 1 Exchangeable proton not observed. LCMS: RT=5.84 min, M+H+=408

Example 156

N-(azetidin-3-yl)-2-(1-isopropyl-1H-1,2,4-triazol-5-yl)-4,5-dihydrobenzo[b]pyrazolo[1,5-d][1,4]oxazepine-9-carboxamide 156

Following the procedure for 126, 2-(2-isopropyl-2H-[1,2,4]triazol-3-yl)-4,5-dihydro-6-oxa-1,10b-diaza-benzo[e]azulene-9-carboxylic acid was reacted with 1,1-dimethylethyl 3-aminoazetidine-1-carboxylate then the crude product was suspended in DCM and treated with MP carbonate resin and stirred for 1.5 h. The mixture was filtered, the filtrate concentrated in vacuo and the resultant residue triturated in diethyl ether to give 156 as a white solid. ¹H NMR (400 MHz, DMSO-d6): δ 9.11 (d, J=6.84 Hz, 1 H); 8.46 (d, J=2.18 Hz, 1 H); 8.05 (t, J=0.64 Hz, 1 H); 7.90-7.85 (m, 1 H); 7.37-7.30 (m, 1 H); 6.92 (s, 1 H); 5.62-5.53 (m, 1 H); 4.82-4.73 (m, 1 H); 4.57 (t, J=5.76 Hz, 2 H); 3.95-3.81 (m, 4 H); 3.25 (t, J=5.78 Hz, 2 H); 1.50 (d, J=6.58 Hz, 6 H). LCMS RT=6.45 min, M+H+=394

Example 157

2-(1-isopropyl-1H-1,2,4-triazol-5-yl)-9-(1-(2-(methylsulfonyl)ethyl)azetidin-3-yl)-4,5-dihydrobenzo[b]pyrazolo[1,5-d][1,4]oxazepine 157

Following the procedure for 152, 9-azetidin-3-yl-2-(2-isopropyl-2H-[1,2,4]triazol-3-yl)-4,5-dihydro-6-oxa-1,10b-diaza-benzo[e]azulene was reacted with vinyl sulfone to give 157 as a white solid. ¹H NMR (400 MHz, DMSO-d6): δ 8.01 (d, J=0.64 Hz, 1 H); 7.84 (d, J=2.19 Hz, 1 H); 7.36 (dd, J=8.32, 2.21 Hz, 1 H); 7.21 (d, J=8.30 Hz, 1 H); 6.87 (s, 1 H); 5.60-5.51 (m, 1 H); 4.48 (t, J=6.03 Hz, 2 H); 3.67 (s, 3 H); 3.20-3.10 (m, 6 H); 3.03 (s, 3 H); 2.83 (t, J=6.83 Hz, 2 H); 1.48 (d, J=6.58 Hz, 6 H). LCMS: RT=5.99 min, M+H+=457

Example 158

N-methyl-2-(1-(2,2,2-trifluoroethyl)-1H-1,2,4-triazol-5-yl)-5,6-dihydrobenzo[f]imidazo[1,2-d][1,4]oxazepine-9-carboxamide 158

Following the same procedure as for 133, 2-(1-(2,2,2-trifluoroethyl)-1H-1,2,4-triazol-5-yl)-5,6-dihydrobenzo[f]imidazo[1,2-d][1,4]oxazepine-9-carboxylic acid (60 mg, 0.1 mmol) was reacted with 2M methylamine (0.26 mL) in THF to provide 158. LC/MS(ESI+): m/z 393 (M+H). 1H NMR (400 MHz, DMSO) δ 8.49 (d, J=4.2, 1H), 8.42 (s, 1H), 8.11 (d, J=9.8, 1H), 7.60 (dd, J=8.4, 1.6, 1H), 7.52 (d, J=1.4, 1H), 5.90 (q, J=8.8, 2H), 4.57 (dd, J=11.5, 5.4, 4H), 2.79 (d, J=4.5, 3H).

Example 159

2-(1-isopropyl-1H-1,2,4-triazol-5-yl)-N-methyl-5,6-dihydrobenzo[f]imidazo[1,2-d][1,4]oxazepine-9-carboxamide 159

Following the same procedure as for 133, 2-(1-isopropyl-1H-1,2,4-triazol-5-yl)-5,6-dihydrobenzo[f]imidazo[1,2-d][1,4]oxazepine-9-carboxylic acid (100 mg, 0.3 mmol) was reacted with 2M methylamine (0.59 mL) in THF to provide 159. LC/MS(ESI+): m/z 353 (M+H). 1H NMR (400 MHz, DMSO) δ 8.54-8.39 (m, 1H), 7.93 (dd, J=18.0, 11.2, 1H), 7.67-7.46 (m, −1H), 6.47 (d, J=33.7, −2H), 5.94-5.78 (m, −2H), 4.68-4.47 (m, −4H), 3.52-3.55 (s, −3H), 2.90-2.68 (m, 1H), 1.47 (t, J=13.6, 6H).

Example 160

2-(1-isopropyl-1H-1,2,4-triazol-5-yl)-10-(1H-pyrazol-4-yl)-5,6-dihydrobenzo[f]imidazo[1,2-d][1,4]oxazepine 160

Following Example 182, 10-bromo-2-(1-isopropyl-1H-1,2,4-triazol-5-yl)-5,6-dihydrobenzo[f]imidazo[1,2-d][1,4]oxazepine 187 was coupled with tert-butyl 4-(4,4,5,5-tetramethyl-1,3,2-dioxaborolan-2-yl)-1H-pyrazole-1-carboxylate to give 160. MS: 362.3. 1H NMR (400 MHz, DMSO) δ 8.57 (t, J=4.0, 1H), 7.99-7.94 (m, 4H), 7.56 (dt, J=11.2, 5.6, 1H), 7.06 (t, J=8.6, 1H), 5.81 (p, J=6.6, 1H), 4.53 (d, J=9.5, 4H), 1.53 (d, J=6.6, 7H).

Example 161

2-(1-(2-chlorophenyl)-1H-imidazol-2-yl)-N-(1-hydroxy-2-methylpropan-2-yl)-5,6-dihydrobenzo[f]imidazo[1,2-d][1,4]oxazepine-10-carboxamide 161

Following the procedure for 109, 2-(1-(2-chlorophenyl)-1H-imidazol-2-yl)-5,6-dihydrobenzo[f]imidazo[1,2-d][1,4]oxazepine-10-carboxylic acid and 2-amino-2-methylpropan-1-ol gave 161. MS: (ESI+)=478.1. 1H NMR (400 MHz, DMSO) δ 8.12 (d, J=2.1 Hz, 1H), 7.63 (dd, J=6.0, 3.4 Hz, 1H), 7.53 (dd, J=6.1, 3.2 Hz, 2H), 7.50-7.44 (m, 3H), 7.36 (s, 1H), 7.28 (d, J=1.1 Hz, 1H), 7.12 (s, 1H), 6.96 (d, J=8.4 Hz, 1H), 5.00 (s, 1H), 4.41 (s, 4H), 3.55 (d, J=5.1 Hz, 2H), 1.36 (s, 6H)

Example 162

(2-(1-(2,4-difluorophenyl)-1H-1,2,4-triazol-5-yl)-5,6-dihydrobenzo[f]imidazo[1,2-d][1,4]oxazepin-10-yl)(4-(2-hydroxyethyl)piperazin-1-yl)methanone 162

Following the procedure for 109, 2-(1-(2,4-difluorophenyl)-1H-1,2,4-triazol-5-yl)-5,6-dihydrobenzo[f]imidazo[1,2-d][1,4]oxazepine-10-carboxylic acid and 2-(piperazin-1-yl)ethanol gave 162. MS: (ESI+)=522.2

Example 163

N-(1-hydroxy-2-methylpropan-2-yl)-2-(1-isopropyl-1H-1,2,4-triazol-5-yl)-5,6-dihydrobenzo[f]imidazo[1,2-d][1,4]oxazepine-9-carboxamide 163

Following the same procedure as for 133, 2-(1-isopropyl-1H-1,2,4-triazol-5-yl)-5,6-dihydrobenzo[f]imidazo[1,2-d][1,4]oxazepine-9-carboxylic acid (20 mg, 0.06 mmol) was reacted with 2-amino-2-methyl-1-propanol (11 mg, 0.12 mmol) in THF to provide N-(1-hydroxy-2-methylpropan-2-yl)-2-(1-isopropyl-1H-1,2,4-triazol-5-yl)-5,6-dihydrobenzo[f]imidazo[1,2-d][1,4]oxazepine-9-carboxamide 163. LC/MS(ESI+): m/z 411 (M+H). 1H NMR (400 MHz, DMSO) δ 8.45 (d, J=8.4, 1H), 7.95 (d, J=22.3, 2H), 7.64-7.45 (m, 3H), 5.86 (dt, J=13.1, 6.5, 1H), 4.88 (t, J=6.0, 1H), 4.63-4.44 (m, 4H), 3.58-3.45 (m, 3H), 1.49 (d, J=6.6, 6H), 1.32 (s, 6H)

Example 164

N-(1-hydroxy-2-methylpropan-2-yl)-2-(1-(S-dioxo-tetrahydrothiophen-3-yl)-1H-1,2,4-triazol-5-yl)-5,6-dihydrobenzo[f]imidazo[1,2-d][1,4]oxazepine-10-carboxamide 164

Following the procedure for 109, 2-(1-(S-dioxo-tetrahydrothiophen-3-yl)-1H-1,2,4-triazol-5-yl)-5,6-dihydrobenzo[f]imidazo[1,2-d][1,4]oxazepine-10-carboxylic acid and 2-amino-2-methylpropan-1-ol gave 164. MS: (ESI+)=487.1

Example 165

2-(1-(2-chlorophenyl)-1H-1,2,4-triazol-5-yl)-N-(1-hydroxy-2-methylpropan-2-yl)-5,6-dihydrobenzo[f]imidazo[1,2-d][1,4]oxazepine-9-carboxamide 165

Following the same procedure as for 133, 2-(1-(2-chlorophenyl)-1H-1,2,4-triazol-5-yl)-5,6-dihydrobenzo[f]imidazo[1,2-d][1,4]oxazepine-9-carboxylic acid (20 mg, 0.06 mmol) was reacted with 2-amino-2-methyl-1-propanol (11 mg, 0.12 mmol) in THF to provide 165. LC/MS(ESI+): m/z 480 (M+H). 1H NMR (400 MHz, DMSO) δ 8.19 (s, 1H), 7.93 (s, 1H), 7.78-7.48 (m, 6H), 7.43-7.26 (m, 2H), 4.85 (t, J=6.1, 1H), 4.47 (d, J=9.0, 4H), 3.49 (d, J=6.0, 2H), 1.29 (s, 6H)

Example 166

2-(1-isopropyl-1H-1,2,4-triazol-5-yl)-9-(1-(pyridin-4-ylmethyl)azetidin-3-yl)-4,5-dihydrobenzo[b]pyrazolo[1,5-d][1,4]oxazepine 166

Following the procedure for 128, 9-azetidin-3-yl-2-(2-isopropyl-2H-[1,2,4]triazol-3-yl)-4,5-dihydro-6-oxa-1,10b-diaza-benzo[e]azulene was reacted with pyridine 4-carboxaldehyde, the crude product subjected flash chromatography (SiO2, gradient 0 to 20% MeOH in ethyl acetate) then trituration in cyclohexane to give 166 as a white solid. ¹H NMR (400 MHz, CDCl3): δ 8.55 (d, J=5.20 Hz, 2 H); 7.95 (s, 1 H); 7.86 (d, J=2.20 Hz, 1 H); 7.30-7.24 (m, 3 H); 7.21-7.12 (m, 1 H); 6.88-6.83 (m, 1 H); 5.73-5.65 (m, 1 H); 4.54 (t, J=5.99 Hz, 2 H); 3.89-3.74 (m, 3 H); 3.71 (s, 2 H);

3.30 (s, 2 H); 3.16 (t, J=5.99 Hz, 2 H); 1.58 (d, J=6.62 Hz, 6 H). LCMS: RT=6.07 min, M+H+=442

Example 167

2-(1-isopropyl-1H-1,2,4-triazol-5-yl)-N-(1-isopropylazetidin-3-yl)-4,5-dihydrobenzo[b]pyrazolo[1,5-d][1,4]oxazepine-9-carboxamide 167

A solution of 2-(2-isopropyl-2H-[1,2,4]triazol-3-yl)-4,5-dihydro-6-oxa-1,10b-diaza-benzo[e]azulene-9-carboxylic acid azetidin-3-ylamide (0.15 g, 0.38 mmol), acetone (84 L, 1.14 mmol), acetic acid (22 L), methanol (1 mL) and DCM (1 mL) was stirred at RT for 1 h. Sodium triacetoxyborohydride (0.2 g, 0.95 mmol) was added and the resultant mixture stirred at RT for 72 h. Further acetone (84 L) and 4 Å molecular sieves were added then stirring continued for 1 h before the addition of further sodium triacetoxyborohydride (0.2 g, 0.95 mmol). The reaction mixture was stirred at RT for 18 h before the addition of saturated aqueous sodium hydrogen carbonate. The resultant mixture was extracted with 10% MeOH in DCM. The combined extracts were dried (Na2SO4), filtered and concentrated in vacuo. The resultant residue was subjected to flash chromatography (SiO2, gradient 0 to 10% MeOH in DCM) followed by trituration in diethyl ether and recrystallisation in ethyl acetate to give 167 as a white solid. $^1$H NMR (400 MHz, CDCl3): δ 8.47 (d, J=2.22 Hz, 1 H); 7.95 (s, 1 H); 7.71 (dd, J=8.44, 2.24 Hz, 1 H); 7.23 (d, J=8.43 Hz, 1 H); 6.87 (s, 1 H); 5.72-5.64 (m, 1 H); 4.74-4.67 (m, 1 H); 4.58 (t, J=5.67 Hz, 2 H); 3.68 (t, J=7.42 Hz, 2 H); 3.22 (t, J=5.69 Hz, 2 H); 3.12 (s, 2 H); 2.38 (t, J=7.02 Hz, 1 H); 1.61 (d, J=6.61 Hz, 6 H); 0.98 (d, J=6.21 Hz, 6 H). LCMS: RT=6.82 min, M+H+=436

Example 168

2-(1-isopropyl-1H-1,2,4-triazol-5-yl)-N-methoxy-5,6-dihydrobenzo[f]imidazo[1,2-d][1,4]oxazepine-9-carboxamide 168

Following the same procedure as for 133, 2-(1-isopropyl-1H-1,2,4-triazol-5-yl)-5,6-dihydrobenzo[f]imidazo[1,2-d][1,4]oxazepine-9-carboxylic acid (20 mg, 0.06 mmol) was reacted with Methoxylamine hydrochloride (9.8 mg, 0.12 mmol) in THF to provide 168. LC/MS(ESI+): m/z 369 (M+H). 1H NMR (400 MHz, DMSO) δ 8.45 (t, J=16.8, 1H), 7.95 (d, J=26.9, 2H), 7.49 (dd, J=20.1, 18.6, 2H), 5.86 (dt, J=13.1, 6.4, 1H), 4.56 (d, J=2.8, 4H), 3.72 (s, 2H), 1.61-1.32 (m, 5H)

Example 169

2-(3-(2-(1-isopropyl-1H-1,2,4-triazol-5-yl)-4,5-dihydrobenzo[b]pyrazolo[1,5-d][1,4]oxazepin-9-yl)azetidin-1-yl)ethanol 169

Following the procedures of Example 142, 9-azetidin-3-yl-2-(2-isopropyl-2H-[1,2,4]triazol-3-yl)-4,5-dihydro-6-oxa-1,10b-diaza-benzo[e]azulene 144 was reacted with 2-(2-bromoethoxy)-tetrahydropyran followed by acidic hydrolysis of the THP group to give 169 as a white solid, as illustrated in FIG. 13. $^1$H NMR (400 MHz, DMSO-d6): δ 8.03 (s, 1 H); 7.88 (d, J=2.22 Hz, 1 H); 7.42 (dd, J=8.35, 2.22 Hz, 1 H); 7.26 (d, J=8.32 Hz, 1 H); 6.89 (s, 1 H); 5.62-5.54 (m, 1 H); 4.83 (s, 1 H); 4.50 (t, J=6.03 Hz, 2 H); 4.06 (s, 2 H); 3.94 (t, J=8.52 Hz, 1 H); 3.70 (s, 2 H); 3.51 (s, 3 H); 3.18 (t, J=6.05 Hz, 2 H); 2.94 (s, 2 H); 1.49 (d, J=6.58 Hz, 6 H). LCMS: RT=6.01 min, M+H+=395

Example 170

2-(3-(2-(1-isopropyl-1H-1,2,4-triazol-5-yl)-4,5-dihydrobenzo[b]pyrazolo[1,5-d][1,4]oxazepin-9-yl)azetidin-1-yl)-2-methylpropan-1-ol 170

A mixture of 9-azetidin-3-yl-2-(2-isopropyl-2H-[1,2,4]triazol-3-yl)-4,5-dihydro-6-oxa-1,10b-diaza-benzo[e]azulene (200 mg, 0.55 mmol), 2-bromo-2-methyl propionate (71 L, 0.55 mmol), triethylamine (75 L, 0.55 mmol) in DMF was heated at 55° C. for 30 h before concentrating in vacuo. The residue was partitioned between 10% MeOH in DCM and water, the aqueous extracted with 10% MeOH in DCM and the combined organic extracts dried (Na2SO4), filtered and concentrated in vacuo. The resultant residue was subjected to flash chromatography (SiO2, gradient 0 to 10% MeOH in DCM) to give 2-{3-[2-(2-isopropyl-2H-[1,2,4]triazol-3-yl)-4,5-dihydro-6-oxa-1,10b-diaza-benzo[e]azulen-9-yl]-azetidin-1-yl}-2-methyl-propionic acid methyl ester 63 (56 mg, 23%). To a solution of 2-{3-[2-(2-isopropyl-2H-[1,2,4]triazol-3-yl)-4,5-dihydro-6-oxa-1,10b-diaza-benzo[e]azulen-9-yl]-azetidin-1-yl}-2-methyl-propionic acid methyl ester 63 (56 mg, 0.12 mmol) in THF (1.5 mL) at −78° C. was added DIBAL (1.5 M solution in toluene, 0.24 mL, 0.36 mmol) and the mixture allowed to warm to RT over 18 h. The mixture was cooled to 0° C., further DIBAL (0.12 mL, 0.18 mmol) added dropwise and stirring continued for 45 min. The reaction was quenched by the addition of MeOH (0.5 mL) followed by Rochelle's salt saturated aqueous solution (0.5 mL), then diluted with ethyl acetate and filtered through Celite®, washing with ethyl acetate. The filtrate was concentrated in vacuo and the residue subjected to flash chromatography (SiO2, gradient 0 to 5% MeOH (+2M NH3) in DCM) to give 170 as a white solid, as illustrated in FIG. 13 (27 mg, 53%). $^1$H NMR (400 MHz, CDCl3): δ 7.95 (s, 1 H); 7.85 (d, J=2.18 Hz, 1 H); 7.23 (d, J=2.23 Hz, 1 H); 7.17 (d, J=8.29 Hz, 1 H); 6.87 (s, 1 H); 5.74-5.66 (m, 1 H); 4.55 (t, J=6.02 Hz, 2 H); 3.71 (s, 3 H); 3.43 (s, 2 H); 3.28 (s, 2 H); 3.16 (t, J=6.03 Hz, 2 H); 1.59 (d, J=6.62 Hz, 6 H); 1.04 (s, 6 H). 1 Exchangeable proton not observed. LCMS: RT=6.43 min, M+H+=423

Example 171

2-(1-(2,4-difluorophenyl)-1H-1,2,4-triazol-5-yl)-8-(1-(2-(methylsulfonyl)ethyl)azetidin-3-yl)-4,5-dihydrobenzo-2H-oxepino[4,5-d]pyrazole 171

Following the procedure for 152, 8-azetidin-3-yl-2-[2-(2,4-difluoro-phenyl)-2H-[1,2,4]triazol-3-yl]-4,5-dihydro-2H-6-oxa-1,2-diaza-benzo[e]azulene hydrochloride was reacted with vinyl sulfone. The crude product was subjected to reverse phase HPLC (Gemini C6-phenyl column, gradient 40 to 90% methanol in water+0.1% HCO2H) to give 171 as a white solid. $^1$H NMR (400 MHz, DMSO-d6): δ 8.42 (s, 1 H); 8.29 (s, 1 H); 8.14 (s, 1 H); 7.81 (td, J=8.75, 5.92 Hz, 1 H); 7.64 (ddd, J=10.33, 9.02, 2.80 Hz, 1 H); 7.38-7.32 (m, 1 H); 7.29 (d, J=8.17 Hz, 1 H); 6.96 (d, J=1.71 Hz, 1 H); 6.91 (dd, J=8.25, 1.80 Hz, 1 H); 4.23 (t, J=5.01 Hz, 2 H); 3.66 (t, J=7.11 Hz, 2 H); 3.76-3.41 (m, 1 H); 3.16 (t, J=7.36 Hz, 5 H); 3.05 (s, 4 H); 2.88 (t, J=6.91 Hz, 2 H). LCMS: RT=7.25 min, M+H+=527

Example 172

2-(3-{2-[2-(2,4-Difluoro-phenyl)-2H-[1,2,4]triazol-3-yl]-4,5-dihydro-2H-6-oxa-1,2-diaza-benzo[e]azulen-8-yl}-azetidin-1-yl)-acetamide 172

Following the procedure for 143, 8-azetidin-3-yl-2-[2-(2,4-difluoro-phenyl)-2H-[1,2,4]triazol-3-yl]-4,5-dihydro-2H-6-oxa-1,2-diaza-benzo[e]azulene hydrochloride was reacted with bromo acetamide, the crude product was subjected to flash chromatography (SiO2, gradient 0 to 10% MeOH in DCM) to give 172 as a white solid. $^1$H NMR (400 MHz, DMSO-d): δ 8.42 (s, 1 H); 8.28 (s, 1 H); 7.81 (td, J=8.75, 5.92 Hz, 1 H); 7.63 (ddd, J=10.33, 9.01, 2.79 Hz, 1 H); 7.39-7.27 (m, 2 H); 7.11 (s, 1 H); 7.03 (s, 1 H); 6.96-6.89 (m, 2 H); 4.23 (t, J=5.01 Hz, 2 H); 3.66 (t, J=7.02 Hz, 2 H); 3.62-3.52 (m, 1 H); 3.16 (t, J=6.65 Hz, 2 H); 3.10-2.98 (m, 4 H). LCMS: RT=7.00 min, M+H+=478

Example 173

N-hydroxy-2-(1-isopropyl-1H-1,2,4-triazol-5-yl)-5,6-dihydrobenzo[f]imidazo[1,2-d][1,4]oxazepine-9-carboxamide 173

Following the same procedure as for 133, 2-(1-isopropyl-1H-1,2,4-triazol-5-yl)-5,6-dihydrobenzo[f]imidazo[1,2-d][1,4]oxazepine-9-carboxylic acid (20 mg, 0.06 mmol) was reacted with hydroxylamine hydrochloride (8 mg, 0.1 mmol) in THF to provide 173. LC/MS(ESI+): m/z 355 (M+H)

Example 174

2-(1-(2,4-difluorophenyl)-1H-1,2,4-triazol-5-yl)-N-methyl-5,6-dihydrobenzo[f]imidazo[1,2-d][1,4]oxazepine-9-carboxamide 174

Following the same procedure as for 133, 2-(1-(2,4-difluorophenyl)-1H-1,2,4-triazol-5-yl)-5,6-dihydrobenzo[f]imidazo[1,2-d][1,4]oxazepine-9-carboxylic acid (30 mg, 0.07 mmol) was reacted with 2M methylamine (0.06 mL) in THF to provide 174. LC/MS (ESI+): m/z 422 (M+H). 1H NMR (400 MHz, DMSO) δ 8.52 (t, J=9.7, 1H), 8.23 (s, 1H), 8.03 (s, 1H), 7.80-7.67 (m, 2H), 7.67-7.55 (m, 1H), 7.47-7.38 (m, 2H), 7.33 (t, J=8.4, 1H), 4.50 (d, J=7.7, 3H), 2.74 (t, J=17.2, 3H)

Example 175

2-[2-(2,4-Difluoro-phenyl)-2H-[1,2,4]triazol-3-yl]-9-[1-(2-methanesulfonyl-ethyl)-piperidin-4-yl]-4,5-dihydro-2H-6-oxa-1,2-diaza-benzo[e]azulene 175

Following the procedure for 152, 2-[2-(2,4-difluoro-phenyl)-2H-[1,2,4]triazol-3-yl]-9-piperidin-4-yl-4,5-dihydro-2H-6-oxa-1,2-diaza-benzo[e]azulene hydrochloride was reacted with vinyl sulfone. The crude product was dissolved in DCM and treated with 4N HCl. After stirring for 10 min diethyl ether was added and the solid precipitate collected by filtration to give 175 as a white solid. $^1$H NMR (400 MHz, DMSO-d): δ 10.63 (s, 1 H); 8.45 (s, 1 H); 8.30 (s, 1 H); 7.85 (td, J=8.75, 5.90 Hz, 1 H); 7.72 (t, J=9.62 Hz, 1 H); 7.42 (t, J=8.57 Hz, 1 H); 7.22 (d, J=2.33 Hz, 1 H); 7.11 (dd, J=8.45, 2.37 Hz, 1 H); 6.97 (d, J=8.34 Hz, 1 H); 4.22 (t, J=5.02 Hz, 2H); 3.82 (t, J=7.50 Hz, 2 H); 3.76-3.63 (m, 2 H); 3.59 (d, J=9.30 Hz, 2 H); 3.16 (s, 3 H); 3.14 (m, 2 H); 3.06 (t, J=5.04 Hz, 2 H); 2.66 (s, 1 H); 1.96-1.76 (m, 4 H). LCMS: RT=7.54 min, M+H+=555

Example 176

2-{4-[2-(2-Isopropyl-2H-[1,2,4]triazol-3-yl)-4,5-dihydro-2H-6-oxa-1,2-diaza-benzo[e]azulen-8-yl]-pyrazol-1-yl}-ethanol 176

As shown in FIG. 9, 8-Bromo-2-(2-isopropyl-2H-[1,2,4]triazol-3-yl)-4,5-dihydro-2H-6-oxa-1,2-diaza-benzo[e]azulene 106 (160 mg, 0.43 mmol), 1-[2-(tetrahydro-pyran-2-yloxy)-ethyl]-4-(4,4,5,5-tetramethyl-[1,3,2]dioxaborolan-2-yl)-1H-pyrazole 43 (165 mg, 0.51 mmol), cesium carbonate (279 mg, 0.85 mmol), 1,1'-bis(diphenylphosphino)ferrocenepalladium(II) dichloride, dichloromethane (17 mg, 5 mol %) were combined in a reaction vial, the atmosphere evacuated and back-filled with nitrogen. THF (5 mL) and water (1 mL) were added and the reaction mixture heated at 85° C. for 4 h. The reaction mixture was diluted with ethyl acetate and water, the organic layer separated, dried (Na2SO4), filtered and concentrated in vacuo. The resultant residue was subjected to flash chromatography (SiO2, gradient 0 to 30% ethyl acetate in cyclohexane) to give 2-(2-isopropyl-2H-[1,2,4]triazol-3-yl)-8-{1-[2-(tetrahydro-pyran-2-yloxy)-ethyl]-1H-pyrazol-4-yl}-4,5-dihydro-2H-6-oxa-1,2-diaza-benzo[e]azulene 45 (134 mg, 64%).

2-(2-Isopropyl-2H-[1,2,4]triazol-3-yl)-8-{1-[2-(tetrahydro-pyran-2-yloxy)-ethyl]-1H-pyrazol-4-yl}-4,5-dihydro-2H-6-oxa-1,2-diaza-benzo[e]azulene 45 (134 mg, 0.27 mmol) was dissolved in diethyl ether (5 mL) and treated with 1M HCl in diethyl ether (1 mL) then methanol (5 mL). After 30 min the reaction mixture was concentrated to dryness and the resultant residue triturated in diethyl ether to give 176 as a pale cream solid (105 mg, 86%). $^1$H NMR (400 MHz, DMSO-d6): δ 8.32 (s, 1 H); 8.23 (s, 1 H); 8.19 (d, J=8.23 Hz, 1 H); 8.03 (s, 1 H); 7.96 (s, 1 H); 7.39 (dd, J=8.24, 1.74 Hz, 1 H); 7.29 (d, J=1.68 Hz, 1 H); 5.46-5.36 (m, 1 H); 4.34 (t, 2 H); 4.17 (t, J=5.61 Hz, 2 H); 3.78 (t, J=5.58 Hz, 2 H); 3.13 (t, J=4.91 Hz, 2 H); 1.52 (d, J=6.57 Hz, 6 H). 1 Exchangeable proton not observed. LCMS: RT=10.68 min, M+H+=406

Example 177

1-(4-{2-[2-(2,4-Difluoro-phenyl)-2H-[1,2,4]triazol-3-yl]-4,5-dihydro-2H-6-oxa-1,2-diaza-benzo[e]azulen-9-yl}-piperidin-1-yl)-2-methyl-propan-2-ol 177

A mixture of 2-[2-(2,4-difluoro-phenyl)-2H-[1,2,4]triazol-3-yl]-9-piperidin-4-yl-4,5-dihydro-2H-6-oxa-1,2-diaza-benzo[e]azulene hydrochloride (100 mg, 0.21 mmol), lithium perchlorate (22 mg, 0.21 mmol) and DIPEA (72 L, 0.41 mmol) in THF (3 mL) was treated with 2,2-dimethyl-oxirane (183 L, 2.06 mmol) and then water (150 L). The reaction mixture was stirred at RT for 18 h before being concentrated in vacuo. The resultant residue was partitioned between DCM and water, the organic layer separated and concentrated in vacuo. The resultant residue was subjected to flash chromatography (SiO2, gradient 40 to 100% ethyl acetate in cyclohexane) followed by trituration in a mixture MeOH and water to give 177 as a white solid (58 mg, 54%). $^1$H NMR (400 MHz, DMSO-d): δ 8.44 (s, 1 H); 8.28 (s, 1 H); 7.85 (td, J=8.76, 5.90 Hz, 1 H); 7.61 (ddd, J=10.27, 8.88, 2.78 Hz, 1 H); 7.36-7.30 (m, 1 H); 7.22 (d, J=2.31 Hz, 1 H); 7.08 (dd, J=8.38, 2.35 Hz, 1 H); 6.89 (d, J=8.34 Hz, 1 H);

4.21 (t, J=5.02 Hz, 2 H); 4.06 (s, 1 H); 3.12-3.02 (m, 4 H); 2.31-2.19 (m, 5 H); 1.60-1.48 (m, 4 H); 1.15 (s, 6 H). LCMS: RT=7.75 min, M+H+=521

Example 178

2-(4-{2-[2-(2,4-Difluoro-phenyl)-2H-[1,2,4]triazol-3-yl]-4,5-dihydro-2H-6-oxa-1,2-diaza-benzo[e]azulen-9-yl}-piperidin-1-yl)-acetamide 178

Following the procedure for 143, 2-[2-(2,4-difluoro-phenyl)-2H-[1,2,4]triazol-3-yl]-9-piperidin-4-yl-4,5-dihydro-2H-6-oxa-1,2-diaza-benzo[e]azulene hydrochloride was reacted with bromo acetamide. The crude product was subjected flash chromatography (SiO2, gradient 50 to 100% ethyl acetate in cyclohexane). Pure fractions were combined and concentrated in vacuo and the resultant residue dissolved in DCM and treated with 4M HCl in dioxane then diethyl ether. The resultant precipitate was collected by filtration to give 178 as a white solid. $^1$H NMR (400 MHz, DMSO-d6): δ 9.86 (s, 1 H); 8.48-8.43 (m, 1 H); 8.30 (s, 1 H); 8.05 (s, 1 H); 7.85 (td, J=8.75, 5.93 Hz, 1 H); 7.74-7.63 (m, 2 H); 7.41-7.34 (m, 1 H); 7.22 (d, J=2.30 Hz, 1 H); 7.10 (dd, J=8.45, 2.35 Hz, 1 H); 6.97 (d, J=8.39 Hz, 1 H); 4.22 (t, J=5.00 Hz, 2 H); 3.98 (d, J=4.37 Hz, 2 H); 3.60 (t, J=12.26 Hz, 2H); 3.24-3.13 (m, 2 H); 3.06 (t, J=4.95 Hz, 2 H); 2.69-2.61 (m, 1 H); 1.87 (s, 4 H). LCMS: RT=7.46 min, M+H+=506

Example 179

2-(4-{2-[2-(2,4-Difluoro-phenyl)-2H-[1,2,4]triazol-3-yl]-4,5-dihydro-2H-6-oxa-1,2-diaza-benzo[e]azulen-9-yl}-piperidin-1-yl)-ethanol 179

Following the procedure for 142, 2-[2-(2,4-difluoro-phenyl)-2H-[1,2,4]triazol-3-yl]-9-piperidin-4-yl-4,5-dihydro-2H-6-oxa-1,2-diaza-benzo[e]azulene hydrochloride was reacted with 2-(2-bromo-ethoxy)-tetrahydro-pyran to give 179 as a white solid. $^1$H NMR (400 MHz, DMSO-d): δ 9.86 (s, 1 H); 8.44 (s, 1 H); 8.29 (s, 1 H); 7.84 (td, J=8.75, 5.94 Hz, 1 H); 7.72 (td, J=9.64, 2.83 Hz, 1 H); 7.43-7.37 (m, 1 H); 7.21 (d, J=2.28 Hz, 1 H); 7.09 (dd, J=8.45, 2.36 Hz, 1 H); 6.96 (d, J=8.40 Hz, 1 H); 5.37 (t, J=4.89 Hz, 1 H); 4.21 (t, J=5.01 Hz, 2 H); 3.83 (d, J=5.48 Hz, 2 H); 3.65 (d, J=12.04 Hz, 2 H); 3.23 (m, 2 H); 3.10 (m, 4 H); 2.69-2.60 (m, 1 H); 2.01-1.80 (m, 4 H). LCMS: RT=7.55 min, M+H+=493

Example 180

1-(4-(2-(1-isopropyl-1H-1,2,4-triazol-5-yl)-5,6-dihydrobenzo[f]imidazo[1,2-d][1,4]oxazepin-9-yl)-1H-pyrazol-1-yl)-2-methylpropan-2-ol 180

Following the procedure as for 182, a solution of 8-bromo-2-(2-isopropyl-2H-[1,2,4]triazol-3-yl)-4,5-dihydro-6-oxa-1,3a-diaza-benzo[e]azulene 194 (7.84 g, 20.95 mmol), 2-methyl-1-[4-(4,4,5,5-tetramethyl-[1,3,2]dioxaborolan-2-yl)-pyrazol-1-yl]-propan-2-ol (11.15 g, 41.90 mmol) and cesium carbonate (20.47 g, 62.8 mmol) in dioxan (380 mL) and water (38 mL) was degassed by evacuation/bubbling argon (×3). 1,1'-bis(diphenylphosphino)ferrocenepalladium(II) dichloride, dichloromethane (1.71 g, 2.09 mmol) was added and the reaction mixture heated at reflux for 2 h. The reaction mixture was diluted with water (250 mL) and extracted with ethyl acetate (3×100 mL). The combined organic fractions were washed with brine (100 mL), dried (MgSO4), and concentrated in vacuo to give a dark brown slurry. The slurry was triturated with hot IPA (~50 mL), allowed to cool to RT and filtered. The solid was washed with cold IPA (~30 mL) and dried in vacuo to give 180 as an off-white solid (6.6 g, 73%). LS/MS(ESI+): m/z 434 (M+H). 1H NMR (400 MHz, DMSO) δ 8.37 (d, J=8.4, 1H), 8.16 (s, 1H), 7.95 (s, 1H), 7.91 (s, 2H), 7.39 (dd, J=8.4, 1.7, 1H), 7.28 (d, J=1.7, 1H), 5.90 (dt, J=13.0, 6.5, 1H), 4.72 (s, 1H), 4.52 (q, J=6.2, 4H), 4.04 (s, 2H), 1.49 (d, J=6.6, 6H), 1.10 (s, 6H)

Example 181

2-{3-[2-(2-Isopropyl-2H-[1,2,4]triazol-3-yl)-4,5-dihydro-2H-6-oxa-1,2-diaza-benzo[e]azulen-8-yl]-azetidin-1-yl}-acetamide 181

Following the procedure for 143, 8-azetidin-3-yl-2-(2-isopropyl-2H-[1,2,4]triazol-3-yl)-4,5-dihydro-2H-6-oxa-1,2-diaza-benzo[e]azulene hydrochloride was reacted with bromo acetamide, the crude product was subjected to reverse phase HPLC (Gemini C18 column gradient 10 to 90% MeOH in water+0.1% HCO2H) to give 181 as a white solid. $^1$H NMR (400 MHz, DMSO-d): δ 8.33 (s, 1 H); 8.21-8.14 (m, 2 H); 8.04 (s, 1 H); 7.21 (dd, J=8.42, 1.92 Hz, 2 H); 7.12-7.02 (m, 2 H); 5.44-5.36 (m, 1 H); 4.32 (t, J=5.05 Hz, 2 H); 3.80-3.61 (m, 3 H); 3.30 (t, J=7.44 Hz, 2 H); 3.16-3.09 (m, 4 H); 1.52 (d, J=6.59 Hz, 6 H). LCMS: RT=6.49 min, M+H+=408

Example 182

2-(4-(2-(1-isopropyl-1H-1,2,4-triazol-5-yl)-5,6-dihydrobenzo[f]imidazo[1,2-d][1,4]oxazepin-9-yl)-1H-pyrazol-1-yl)ethanol 182

To a 10-mL microwave vial was added 9-bromo-2-(1-isopropyl-1H-1,2,4-triazol-5-yl)-5,6-dihydrobenzo[f]imidazo[1,2-d][1,4]oxazepine 194 (0.210 g, 0.56 mmol) and potassium acetate (0.17 g, 1.68 mmol), MeCN (1 mL) and water (2 mL). The mixture was thoroughly purged with N2. A solution of 1-(2-(tetrahydro-2H-pyran-2-yloxy)ethyl)-4-(4,4,5,5-tetramethyl-1,3,2-dioxaborolan-2-yl)-1H-pyrazole (0.271 g, 0.84 mmol) in MeCN (1 mL) was added, followed by tetrakis(triphenylphosphine) palladium (65 mg, 0.056 mmol) and the vial was sealed immediately. The mixture was irradiated with microwave at 150° C. for 20 minutes. Complete conversion was observed by LC/MS (a small amount of des-THP product was observed). The reaction mixture was diluted with EtOAc and water and extracted three times with EtOAc. The organic phases were combined, dried with MgSO4 and concentrated. The residue was purified using ISCO chromatography using 10% MeOH/EtOAc, which gave 170 mg, 0.35 mmol (62%) a white foaming solid as product which was immediately dissolved in DCM (2 mL) and treated with 4 M hydrogen chloride in 1,4-dioxane (0.35 mL). A white precipitate developed during the addition. The reaction was stirred at room temperature for 1 h. The reaction mixture was concentrated to dryness and dissolved in DMF/H2O. This mixture was purified by rp-HPLC to provide 105 mg (74% yield) of 182 as a white, partially crystalline solid. LS/MS(ESI+): m/z 406 (M+H). 1H NMR (400 MHz, DMSO) δ 8.37 (d, J=8.4, 1H), 8.22 (s, 1H), 7.95 (s, 1H), 7.91 (s, 2H), 7.38 (dd, J=8.4, 1.8, 1H), 7.27 (d, J=1.7, 1H), 5.91 (dq, J=13.3, 6.7, 1H), 4.91 (t, J=5.3, 1H), 4.58-4.44 (m, 4H), 4.16 (t, J=5.6, 2H), 3.77 (q, J=5.4, 2H), 1.49 (d, J=6.6, 6H)

Example 183

1-(3-{2-[2-(2,4-Difluoro-phenyl)-2H-[1,2,4]triazol-3-yl]-4,5-dihydro-2H-6-oxa-1,2-diaza-benzo[e]azulen-8-yl}-azetidin-1-yl)-2-methyl-propan-2-ol 183

Following the procedure for 177, 8-azetidin-3-yl-2-[2-(2,4-difluoro-phenyl)-2H-[1,2,4]triazol-3-yl]-4,5-dihydro-2H-6-oxa-1,2-diaza-benzo[e]azulene hydrochloride was reacted with 2,2-dimethyl-oxirane to give 183 as a white solid. $^1$H NMR (400 MHz, DMSO-d): δ 8.45 (s, 1 H); 8.31 (s, 1 H); 8.17 (s, 1 H); 7.84 (td, J=8.75, 5.92 Hz, 1 H); 7.66 (ddd, J=10.33, 9.02, 2.79 Hz, 1 H); 7.40-7.34 (m, 1 H); 7.31 (d, J=8.17 Hz, 1 H); 7.00 (d, J=1.69 Hz, 1 H); 6.93 (dd, J=8.25, 1.78 Hz, 1 H); 4.26 (t, J=5.06 Hz, 2 H); 3.79 (t, J=7.52 Hz, 2 H); 3.64 (t, J=7.75 Hz, 1 H); 3.35 (t, 2 H); 3.08 (t, J=5.05 Hz, 2 H); 2.35 (t, 2 H); 1.10 (s, 6 H). LCMS: RT=7.45 min, M+H+=493

Example 184 methyl 2-(1-isopropyl-1H-1,2,4-triazol-5-yl)-5,6-dihydrobenzo[f]imidazo[1,2-d][1,4]oxazepine-9-carboxylate 184

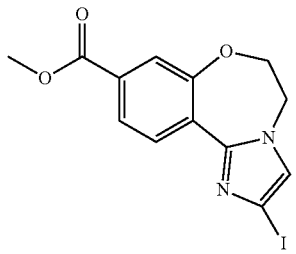 [SMILES: COC(=O)c1ccc2c(c1)OCCn1cc(I)nc1-2]

To methyl 2-iodo-5,6-dihydrobenzo[f]imidazo[1,2-d][1,4]oxazepine-9-carboxylate (1.0 g, 2.7 mmol), 1-isopropyl-1H-1,2,4-triazole (0.30 g, 2.7 mmol), CuI (1.5 g, 8.1 mmol), Pd(OAc)2 (0.061 g, 0.27 mmol), and cesium carbonate (2.2 g, 6.8 mmol) was added DMF (26 mL). The reaction mixture was allowed to stir and heat at 100° C. for 24 hours in a sealed vial. The reaction mixture was cooled to room temperature and poured into a mixture of ammonium hydroxide/water (1:2) and EtOAc and filtered through a pad of silica. The layers were separated and the aqueous portion was extracted with EtOAc. The combined organic extracts were washed with ammonium hydroxide (1:2), water, brine, dried over MgSO4, and concentrated under reduced pressure. The crude material was purified by column chromatography on silica gel eluting with EtOAc to provide 184 (0.270 g, 28%). 1H NMR (400 MHz, DMSO) δ 8.54 (d, J=8.4, 1H), 7.97 (d, J=35.2, 2H), 7.70 (dd, J=8.4, 1.7, 1H), 7.57 (d, J=1.7, 1H), 5.99-5.70 (m, 1H), 4.57 (q, J=5.9, 4H), 3.87 (s, 3H), 1.49 (d, J=6.6, 6H). MS (ESI(+)): m/z 354.1 (M+H).

Alternatively, methyl 2-carbamoyl-5,6-dihydrobenzo[f]imidazo[1,2-d][1,4]oxazepine-9-carboxylate (370 mg, 1.3 mmol) in dimethoxyethane (3 mL) was treated with 1,1-dimethoxy-N,N-dimethylmethanamine (1 mL, 7.5 mmol) and heated to 90° C. for 0.5 h. LC/MS indicated major desired product. After cooling, the reaction was concentrated to give the crude acylamidine and then suspended in acetic acid (2.3 mL), treated with isopropylhydrazine hydrochloride (0.29 g, 2.5 mmol). The mixture was heated at 75° C. for 30 min., cooled to room temperature and concentrated. Purification by ISCO using 100% EtOAc gave 184 (0.32 g, 70% yield). 1H NMR (400 MHz, DMSO) δ 8.54 (d, J=8.4, 1H), 8.02 (s, 1H), 7.93 (s, 1H), 7.70 (dd, J=8.4, 1.7, 1H), 7.57 (d, J=1.7, 1H), 5.85 (dq, J=13.3, 6.6, 1H), 4.57 (q, J=6.0, 4H), 3.87 (s, 3H), 1.49 (d, J=6.6, 6H).

Example 185 methyl 2-(1-(2,2,2-trifluoroethyl)-1H-1,2,4-triazol-5-yl)-5,6-dihydrobenzo[f]imidazo[1,2-d][1,4]oxazepine-9-carboxylate 185

Following the procedure for 184, methyl 2-iodo-5,6-dihydrobenzo[f]imidazo[1,2-d][1,4]oxazepine-9-carboxylate and trifluoroethyltriazole (1-(2,2,2-trifluoroethyl)-1H-1,2,4-triazole) were reacted. The product precipitated out of EtOAc and was collected by filtration to provide 185 (393 mg, 40%). 1H NMR (400 MHz, DMSO) δ 8.51 (d, J=8.4, 1H), 8.15 (s, 1H), 8.10 (s, 1H), 7.71 (dd, J=8.4, 1.7, 1H), 7.58 (d, J=1.6, 1H), 5.89 (q, J=8.8, 2H), 4.64-4.49 (m, 4H), 3.87 (s, 3H). MS (ESI(+)): m/z 394.0 (M+H).

Alternatively, and following the procedure for 184, methyl 2-carbamoyl-5,6-dihydrobenzo[f]imidazo[1,2-d][1,4]oxazepine-9-carboxylate was reacted with 1,1-dimethoxy-N,N-dimethylmethanamine, followed by treatment of trifluoroethylhydrazine hydrochloride in acetic acid to provide 185 (65% yield). 1H NMR (400 MHz, DMSO) δ 8.51 (d, J=8.4, 1H), 8.15 (s, 1H), 8.10 (s, 1H), 7.71 (dd, J=8.4, 1.7, 1H), 7.58 (d, J=1.6, 1H), 5.89 (q, J=8.8, 2H), 4.65-4.45 (m, 5H), 3.87 (s, 3H), 3.58-3.37 (m, 7H)

Example 186

2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)ethanol 186

Following the same procedure as for 182, Suzuki reaction of 9-bromo-2-(1-isopropyl-4-methyl-1H-imidazol-2-yl)-5,6-dihydrobenzo[f]imidazo[1,2-d][1,4]oxazepine and 1-(2-(tetrahydro-2H-pyran-2-yloxy)ethyl)-4-(4,4,5,5-tetramethyl-1,3,2-dioxaborolan-2-yl)-1H-pyrazole afforded 186 as a white crystalline solid in 72% yield after acidic removal of the THP group. LS/MS(ESI+): m/z 420 (M+H). 1H NMR (400 MHz, DMSO) δ 8.36 (d, J=8.4, 1H), 8.22 (s, 1H), 7.95 (s, 1H), 7.87 (s, 1H), 7.38 (dd, J=8.4, 1.7, 1H), 7.27 (d, J=1.7, 1H), 5.83 (dt, J=13.2, 6.6, 1H), 4.91 (t, J=5.3, 1H), 4.51 (s, 4H), 4.16 (t, J=5.6, 2H), 3.77 (q, J=5.6, 2H), 1.48 (t, J=9.0, 6H)

Example 187

10-bromo-2-(1-isopropyl-1H-1,2,4-triazol-5-yl)-5,6-dihydrobenzo[f]imidazo[1,2-d][1,4]oxazepine 187

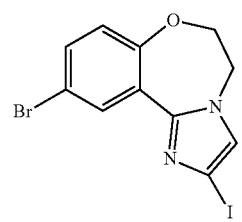

To 10-bromo-2-iodo-5,6-dihydrobenzo[f]imidazo[1,2-d][1,4]oxazepine (1.5 g, 3.8 mmol), 1-isopropyl-1H-1,2,4-triazole (0.40 g, 3.0 mmol), CuI (1.8 g, 9.5 mmol), Pd(OAc)2 (0.071 g, 0.32 mmol), and cesium carbonate (2.6 g, 7.9 mmol) was added DMF (20 mL). The reaction mixture was allowed to stir and heat at 100° C. for 24 hours in a sealed vial. The reaction mixture was cooled to room temperature, diluted with EtOAc, and filtered through celite. The filtrate was concentrated under reduced pressure. To the crude residue was added EtOAc and the solid was collected by filtration. The filtrate was concentrated and the crude material was dissolved in DMF and purified by reverse phase HPLC to provide 187 (64 mg, 5%). 1H NMR (400 MHz, DMSO) δ 8.43 (dd, J=47.5, 31.0, 1H), 7.97 (s, 1H), 7.92 (s, 1H), 7.60-7.39 (m, 1H), 7.04 (d, J=8.7, 1H), 5.74 (dt, J=13.2, 6.6, 1H), 4.76-4.33 (m, 4H), 1.49 (d, J=6.6, 6H). MS (ESI(+)): m/z 374.0 (M+H).

Example 188

[4-{2-[2-(2,4-Difluoro-phenyl)-2H-[1,2,4]triazol-3-yl]-4,5-dihydro-2H-6-oxa-1,2-diaza-benzo[e]azulen-9-yl}-1-(2-methanesulfonyl-ethyl)-piperidin-4-yl]-methanol 188

To a stirring mixture of (4-{2-[2-(2,4-difluoro-phenyl)-2H-[1,2,4]triazol-3-yl]-4,5-dihydro-2H-6-oxa-1,2-diaza-benzo[e]azulen-9-yl}-piperidin-4-yl)-methanol hydrochloride 75 (97 mg, 0.1873 mmol) in IMS (3 mL) was added DIPEA (165 L, 0.94 mmol) followed by vinyl sulfone (18 ul, 0.206 mmol) at RT, as illustrated in FIG. 16. After 3 h the solvent was removed in vacuo and the residue was subjected to HPLC (Gemini C6-Phenyl column, gradient 10 to 60%, 20 min ramp) to afford 188 (63 mg, 53%). ¹H NMR δ ppm (DMSO-d6): 8.42-8.39 (1 H, m), 8.23 (1 H, s), 8.19 (1 H, s), 7.80 (1 H, td, J=8.77, 5.87 Hz), 7.53 (1 H, ddd, J=10.34, 8.85, 2.77 Hz), 7.36 (1 H, d, J=2.40 Hz), 7.33-7.27 (1 H, m), 7.12 (1 H, dd, J=8.59, 2.48 Hz), 6.85 (1 H, dd, J=8.55, 4.83 Hz), 4.17 (2 H, t, J=5.04 Hz), 3.22-3.14 (6 H, m), 3.02 (2 H, t, J=5.09 Hz), 2.98 (3 H, s), 2.02 (2 H, s), 1.72 (4 H, s). 2 Protons obscured by water peak. LCMS: RT=6.57 min, M+H+=585

Example 189

2-(4-{2-[2-(2,4-Difluoro-phenyl)-2H-[1,2,4]triazol-3-yl]-4,5-dihydro-2H-6-oxa-1,2-diaza-benzo[e]azulen-9-yl}-piperidin-1-yl)-2-methyl-propan-1-ol 189

2-[2-(2,4-Difluoro-phenyl)-2H-[1,2,4]triazol-3-yl]-9-piperidin-4-yl-4,5-dihydro-2H-6-oxa-1,2-diaza-benzo[e]azulene hydrochloride (250 mg, 0.52 mmol) was dissolved in DMF (3 mL) and treated with cesium carbonate (336 mg, 1.03 mmol) and 2-bromo-2-methyl propionate (333 L, 2.58 mmol) then heated at 80° C. for 20 h. The cooled reaction mixture was diluted with ethyl acetate and washed with water and then brine, dried (Na2SO4), filtered and concentrated in vacuo. The resultant residue was subjected to flash chromatography (SiO2, gradient 20 to 70% ethyl acetate in cyclohexane) to give 2-(4-{2-[2-(2,4-difluoro-phenyl)-2H-[1,2,4]triazol-3-yl]-4,5-dihydro-2H-6-oxa-1,2-diaza-benzo[e]azulen-9-yl}-piperidin-1-yl)-2-methyl-propionic acid methyl ester. The intermediate 2-methyl-propionic acid methyl ester (195 mg, 0.355 mmol) was dissolved in THF (5 mL) and the solution cooled to 0° C. Lithium aluminum hydride (0.533 mL, 1M solution in THF) was added dropwise and the reaction mixture stirred at 0° C. for 15 min then at RT for 90 min. The reaction mixture was cooled to 0° C. and water added, the mixture extracted with ethyl acetate and the organic extract washed with brine, dried (Na2SO4), filtered and then concentrated in vacuo. The resultant residue was subjected to reverse phase HPLC (Gemini C6-Phenyl column, gradient 30 to 60% methanol in water+0.1% HCO2H) to give 189 as a white solid (123 mg, 70%). ¹H NMR δ (ppm) (DMSO-d6): 8.40 (1 H, s), 8.24 (1 H, s), 8.17 (1 H, s), 7.79 (1 H, td, J=8.76, 5.90 Hz), 7.64-7.57 (1 H, m), 7.34-7.28 (1 H, m), 7.18 (1 H, d, J=2.29 Hz), 7.03 (1 H, dd, J=8.38, 2.33 Hz), 6.84 (1 H, d, J=8.33 Hz), 4.16 (2 H, t, J=5.02 Hz), 3.35 (2 H, s), 3.14 (3 H, d, J=11.68 Hz), 3.00 (2 H, t, J=5.05 Hz), 2.38-2.23 (3 H, m), 1.63 (2 H, d, J=12.48 Hz), 1.53-1.39 (2 H, m), 1.03 (6 H, s). LCMS: RT=7.89 min, M+H+=521

Example 190

1-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropan-2-ol 190

Following the same procedure as for 182, Suzuki reaction of 9-bromo-2-(1-isopropyl-4-methyl-1H-imidazol-2-yl)-5,6-dihydrobenzo[f]imidazo[1,2-d][1,4]oxazepine and 2-methyl-1-(4-(4,4,5,5-tetramethyl-1,3,2-dioxaborolan-2-yl)-1H-pyrazol-1-yl)propan-2-ol provided 190. LS/MS (ESI+): m/z 448 (M+H). 1H NMR (400 MHz, DMSO) δ 8.36 (d, J=8.4, 1H), 8.16 (s, 1H), 7.94 (s, 1H), 7.87 (s, 1H), 7.39 (dd, J=8.4, 1.8, 1H), 7.27 (d, J=1.7, 1H), 5.90-5.70 (m, 1H), 4.72 (s, 1H), 4.51 (s, 4H), 4.04 (s, 2H), 2.25 (s, 3H), 1.47 (d, J=6.6, 6H), 1.10 (s, 6H)

Example 191

2-(1-isopropyl-1H-1,2,4-triazol-5-yl)-9-(1-(2-(methylsulfonyl)ethyl)azetidin-3-yl)-5,6-dihydrobenzo[f]imidazo[1,2-d][1,4]oxazepine 191

Following the procedure for 152, 8-azetidin-3-yl-2-(2-isopropyl-2H-[1,2,4]triazol-3-yl)-4,5-dihydro-6-oxa-1,3a-diaza-benzo[e]azulene hydrochloride (Example 65) was reacted with vinyl sulfone to give 191 as a white solid. ¹H NMR δ (ppm)(CDCl3): 8.44 (1 H, d, J=8.28 Hz), 7.84 (1 H, s), 7.60 (1 H, s), 7.05 (1 H, dd, J=8.32, 1.83 Hz), 6.94 (1 H, d, J=1.78 Hz), 5.99-5.89 (1 H, m), 4.48-4.39 (4 H, m), 3.78-3.70 (2 H, m), 3.71-3.62 (1 H, m), 3.25-3.18 (2 H, m), 3.04 (3 H, s), 3.02-2.95 (4 H, m), 1.56 (6 H, d, J=6.64 Hz). LCMS: RT=5.58 min, M+H+=457

Example 192

2-(3-(2-(1-isopropyl-1H-1,2,4-triazol-5-yl)-5,6-dihydrobenzo[f]imidazo[1,2-d][1,4]oxazepin-9-yl)azetidin-1-yl)acetamide 192

Following the procedure for 143, 8-azetidin-3-yl-2-(2-isopropyl-2H-[1,2,4]triazol-3-yl)-4,5-dihydro-6-oxa-1,3a-diaza-benzo[e]azulene hydrochloride (Example 65) was reacted with bromo acetamide. The crude product was subjected to flash chromatography (SiO2, gradient 0 to 10% MeOH in DCM) then trituration in diethyl ether to give 192 as a white solid. ¹H NMR δ (ppm)(CDCl3): 8.46 (1 H, d, J=8.28 Hz), 7.84 (1 H, s), 7.61 (1 H, s), 7.07 (1 H, dd, J=8.32, 1.84 Hz), 6.95 (1 H, d, J=1.79 Hz), 6.89 (1 H, s), 5.99-5.90 (1 H, m), 5.44 (1 H, s), 4.48-4.45 (2 H, m), 4.43-4.40 (2 H, m), 3.86-3.78 (2 H, m), 3.73-3.63 (1 H, m), 3.38-3.31 (2 H, m), 3.20 (2 H, s), 1.56 (6 H, d, J=6.64 Hz). LCMS: RT=5.45 min, M+H+=408

Example 193

(1-aminocyclopropyl)(3-(2-(1-isopropyl-1H-1,2,4-triazol-5-yl)-5,6-dihydrobenzo[f]imidazo[1,2-d][1,4]oxazepin-9-yl)azetidin-1-yl)methanone 193

Following the procedure for 127, 8-azetidin-3-yl-2-(2-isopropyl-2H-[1,2,4]triazol-3-yl)-4,5-dihydro-6-oxa-1,3a-diaza-benzo[e]azulene hydrochloride (Example 65) was reacted with 1-tert-butoxycarbonylamino-cyclopropanecarboxylic acid. The crude product was subjected to reverse phase HPLC (Gemini C18 column, gradient 20 to 95% MeOH in H₂O+0.1% HCO2H) to give 193 as a white solid. ¹H NMR δ (ppm)(DMSO-d): 8.36 (1 H, d, J=8.28 Hz), 8.09 (1 H, s), 7.88-7.86 (2 H, m), 7.14 (1 H, dd, J=8.35, 1.82 Hz), 7.01 (1 H, d, J=1.78 Hz), 5.88-5.80 (1 H, m), 4.50-4.44 (4 H, m), 3.83-3.71 (2 H, m), 1.44 (6 H, d, J=6.60 Hz), 1.05 (2 H, d, J=4.13 Hz), 0.67 (2 H, d, J=4.01 Hz). 2 Exchangeable protons not seen. 4 protons obscured by water peak. LCMS: RT=6.73 min, M+H+=434

Example 194

9-bromo-2-(1-isopropyl-1H-1,2,4-triazol-5-yl)-5,6-dihydrobenzo[f]imidazo[1,2-d][1,4]oxazepine 194

9-Bromo-5,6-dihydrobenzo[f]imidazo[1,2-d][1,4]oxazepine-2-carboxamide (4.93 g, 16.0 mmol) was taken up in 1,1-dimethoxy-N,N-dimethylmethanamine (25 mL, 0.18 mol) and 1,2-dimethoxyethane (66.5 mL, 0.640 mol). The heterogeneous mixture was stirred very vigorously and heated at 65° C. for 1 h. LC/MS showed complete consumption of starting material at the end of this period. The reaction mixture was concentrated in vacuo and carried on to the subsequent reaction with no further purification steps applied. The crude product from the previous reaction (5.8 g, 16.0 mmol) was suspended in glacial acetic acid (53.2 mL) and isopropylhydrazine hydrochloride (4.36 g, 39.4 mmol) was added. The mixture was heated at 100° C. for 2 h. The reaction vessel was cooled to room temp and the solvent was removed in vacuo. The resultant residue was dry loaded onto silica gel and purified by ISCO chromatography (120 g column, 100% EtOAc). In total, 2.3 g (39% yield) of 194 was isolated over the two steps. LC/MS(ESI+): m/z 376 (M+H, with halide isotope). 1H NMR (400 MHz, DMSO) δ 8.34 (d, J=8.6, 1H), 7.95 (s, 1H), 7.91 (s, 1H), 7.36 (dd, J=8.7, 2.0, 1H), 7.30 (d, J=2.0, 1H), 5.85 (dt, J=13.3, 6.6, 1H), 4.55 (d, J=15.5, 4H), 1.48 (d, J=6.6, 6H)

Alternatively, to a suspension of 8-bromo-4,5-dihydro-6-oxa-1,3a-diaza-benzo[e]azulene-2-carboxylic acid 1-dimethylamino-meth-(Z)-ylideneamide (8.52 g, 23.5 mmol) in acetic acid (50 mL) was added isopropylhydrazine hydrochloride (3.37 g, 30.5 mmol) and the reaction mixture heated at 100° C. for 1 h. The reaction mixture was allowed to cool to RT and was poured onto water (500 mL) causing the product to precipitate as an off-white solid. The product was collected by filtration, washed with water (~200 mL) and dried in vacuo at 45° C. for 16 h to yield 194 as an off-white solid (7.88 g, 86%). 1H NMR (400 MHz, d6-DMSO) 8.43 (1H, d, J=8.6 Hz), 7.97 (1H, s), 7.92 (1H, d, J=0.6 Hz), 7.36 (1H, dd, J=8.6, 2.0 Hz), 7.30 (1H, d, J=2.0 Hz), 5.86 (1H, sept, J=6.6 Hz), 4.56-4.52 (4H, m), 1.48 (6H, d, J=6.6 Hz). LCMS: RT=4.69 min, M+H+=374/376. 1H NMR showed product to contain ~5% 8-iodo-2-(2-isopropyl-2H-[1,2,4]triazol-3-yl)-4,5-dihydro-6-oxa-1,3a-diaza-benzo[e]azulene.

Also alternatively:

Step 1: 4-Bromo-2-fluoro-benzimidic acid ethyl ester hydrochloride

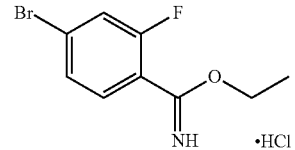

A suspension of 4-bromo-2-fluorobenzonitrile (25.0 g, 125 mmol) in IMS (88 mL) at 0-5° C. and treated dropwise with acetyl chloride (71 mL, 1 mol) maintaining the temperature below 10° C. The reaction vessel was sealed and the mixture stirred at RT for 18 h before concentrating in vacuo. The resultant residue was triturated in diethyl ether to give 4-Bromo-2-fluoro-benzimidic acid ethyl ester hydrochloride as a white solid (20.3 g, 57%). ¹H NMR δ (ppm)(DMSO-d): 7.93-7.88 (1 H, m), 7.85-7.76 (1 H, m), 7.72-7.64 (1 H, m), 4.60 (2 H, q, J=7.02 Hz), 1.47-1.38 (3 H, m).

Step 2: 4-Bromo-2-fluoro-benzamidine hydrochloride

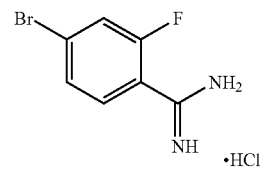 [SMILES: N=C(N)c1ccc(Br)cc1F ; Cl]

A mixture of 4-bromo-2-fluoro-benzimidic acid ethyl ester hydrochloride (20.3 g, 72 mmol) in IMS (250 mL) at 0-5° C. was saturated with NH3 (gas), and the flask sealed before allowing to warm to RT and stirring for 18 h. Solvent was removed in vacuo and the residue triturated in diethyl ether to give 4-Bromo-2-fluoro-benzamidine hydrochloride as a white solid (18.1 g, 100%). ¹H NMR δ (ppm)(DMSO-d): 9.26 (4 H, s), 7.92-7.87 (1 H, m), 7.71-7.62 (2 H, m).

Step 3: 1-(2-Isopropyl-2H-[1,2,4]triazol-3-yl)-ethanone

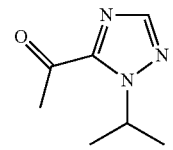

To a solution of 1-isopropyl-1H-[1,2,4]triazole (33 g, 300 mmol) in THF at −10° C. was added n-butyllithium (145 mL, 2.5M, 360 mmol) dropwise over 45 min, and then the mixture stirred at 0° C. for 30 min. DMA (35 mL) was added, the mixture allowed to warm to RT and stirred for 1 h. The resultant suspension was treated with saturated aqueous ammonium chloride (300 mL). The aqueous phase was extracted with ethyl acetate and the combined organic extracts dried (Na2SO4), filtered and concentrated in vacuo to give 1-(2-Isopropyl-2H-[1,2,4]triazol-3-yl)-ethanone as a pale orange oil (40.1 g, 87%). ¹H NMR δ (ppm)(CDCl3): 7.93 (1 H, s), 5.58-5.46 (1 H, m), 2.72 (3 H, d, J=0.78 Hz), 1.49 (6 H, dd, J=6.61, 0.78 Hz).

Step 4: 2-Bromo-1-(2-isopropyl-2H-[1,2,4]triazol-3-yl)-ethanone

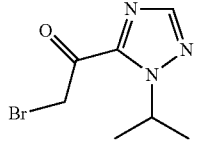

To a solution of 1-(2-isopropyl-2H-[1,2,4]triazol-3-yl)-ethanone (10 g, 65.3 mmol) in acetic acid (1 mL) and THF (100 mL) was added a solution of PTT (phenyltrimethylammonium tribromide, 24.5 g, 65.3 mmol) in THF (100 mL) over 20 min. The reaction mixture was heated at 75° C. before cooling to RT. The resultant mixture was concentrated in vacuo and the products partitioned between ethyl acetate and saturated aqueous sodium bicarbonate solution. The organic layer was separated, dried (Na2SO4), filtered and concentrated in vacuo to give a residue which was subjected to flash chromatography (SiO2, gradient 0 to 20% ethyl acetate in cyclohexane) to give 2-Bromo-1-(2-isopropyl-2H-[1,2,4]triazol-3-yl)-ethanone as an oil (5.4 g, 36%). ¹H NMR δ (ppm)(CDCl3): 7.98 (1 H, s), 5.53-5.42 (1 H, m), 4.69 (2 H, s), 1.52 (6 H, d, J=6.63 Hz).

Step 5: 5-[2-(4-Bromo-2-fluoro-phenyl)-1H-imidazol-4-yl]-1-isopropyl-1H-[1,2,4]triazole

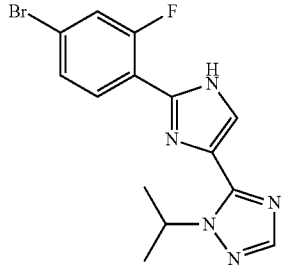 [SMILES: CC(C)n1ncnc1-c1c[nH]c(-c2ccc(Br)cc2F)n1]

To a rapidly stirred mixture of 4-bromo-2-fluoro-benzamidine hydrochloride (9.84 g, 38.8 mmol), potassium hydrogen carbonate (15.6 g, 154.8 mmol), THF (98 mL) and water (16 mL) at reflux was added a solution of 2-bromo-1-(2-isopropyl-2H-[1,2,4]triazol-3-yl)-ethanone (9.0 g, 38.8 mmol) in THF (19 mL) over 15 min. The resulting mixture was stirred for 18 h at reflux before concentrating in vacuo. The resultant residue was treated with water and the solid formed collected by filtration, washed (water, then 1:1 diethyl ether: cyclohexane then diethyl ether) to give 5-[2-(4-Bromo-2-fluoro-phenyl)-1H-imidazol-4-yl]-1-isopropyl-1H-[1,2,4]triazole as a brown solid (10.1 g, 74%). ¹H NMR δ (ppm)(CDCl3): 8.21-8.14 (1 H, m), 7.90 (1 H, s), 7.80 (1 H, s), 7.47-7.38 (2 H, m), 7.26 (1 H, s), 5.91 (1 H, br, s), 1.59 (6 H, d, J=6.63 Hz).

A solution of 5-[2-(4-bromo-2-fluoro-phenyl)-1H-imidazol-4-yl]-1-isopropyl-1H-[1,2,4]triazole (10.0 g, 28.6 mmol) in DMF (100 mL) was treated with ethylene carbonate (5.3 g, 60.1 mmol) and cesium carbonate (13.9 g, 42.5 mmol) and then heated at 100° C. for 72 h. Further cesium carbonate (9.0 g, 27.5 mmol) and water (0.5 mL) were added and heating continued for 24 h before concentrating the reaction mixture in vacuo. The resultant residue was partitioned between DCM and water, the organic layer was isolated, washed with water then brine, dried (Na2SO4), filtered and concentrated in vacuo. The resultant residue was subjected to flash chromatography (SiO2, 1% MeOH in DCM) to give 194 as an off-white solid (5.78 g, 58%). ¹H NMR δ (ppm) (CDCl3): 8.04 (1 H, s), 7.83 (1 H, s), 7.50-7.38 (3 H, m), 5.93-5.84 (1 H, m), 4.07-4.02 (2 H, m), 3.93-3.88 (2 H, m), 1.53-1.46 (6 H, m)

Example 195

1-(4-(2-(1-isopropyl-4-methyl-1H-imidazol-2-yl)-5,6-dihydrobenzo[f]imidazo[1,2-d][1,4]oxazepin-9-yl)-1H-pyrazol-1-yl)-2-methylpropan-2-ol 195

Following the procedure in Example 182, 9-bromo-2-(1-isopropyl-4-methyl-1H-imidazol-2-yl)-5,6-dihydrobenzo[f]imidazo[1,2-d][1,4]oxazepine was coupled with 2-methyl-1-(4-(4,4,5,5-tetramethyl-1,3,2-dioxaborolan-2-yl)-1H-pyrazol-1-yl)propan-2-ol to give 195. Yield 22%. MS(ESI+): 447.1. 1H NMR (400 MHz, DMSO) δ 8.34 (d, J=8.4, 1H), 8.14 (s, 1H), 7.93 (s, 1H), 7.63 (s, 1H), 7.36 (dd, J=8.4, 1.7, 1H), 7.25 (d, J=1.7, 1H), 7.00 (d, J=0.6, 1H), 5.68-5.57 (m, 1H), 4.72 (s, 1H), 4.48 (s, 4H), 4.03 (s, 2H), 2.10 (s, 3H), 2.07 (s, 1H), 1.42 (d, J=6.7, 6H), 1.09 (s, 6H).

Example 196

2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide 196

Step 1: ethyl 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoate

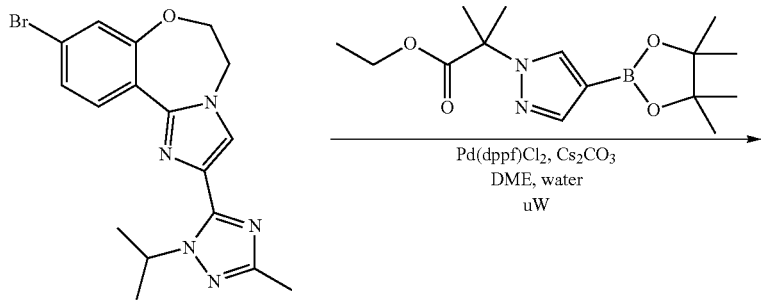

-continued

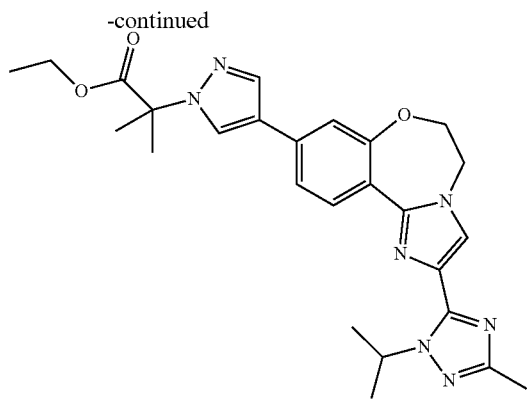

9-Bromo-2-(1-isopropyl-3-methyl-1H-1,2,4-triazol-5-yl)-5,6-dihydrobenzo[f]imidazo[1,2-d][1,4]oxazepine 411 (500 mg, 0.001 mol) and ethyl 2-methyl-2-(4-(4,4,5,5-tetramethyl-1,3,2-dioxaborolan-2-yl)-1H-pyrazol-1-yl)propanoate (594 mg, 0.0015 mol) were reacted under palladium catalyzed Suzuki coupling conditions with Pd(dppf)Cl2 and Cs2CO3 water and dimethoxyethane to give ethyl 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoate together with the corresponding acid. LC/MS(ESI+): m/z 490 (M+H)

Step 2: 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoic acid 251

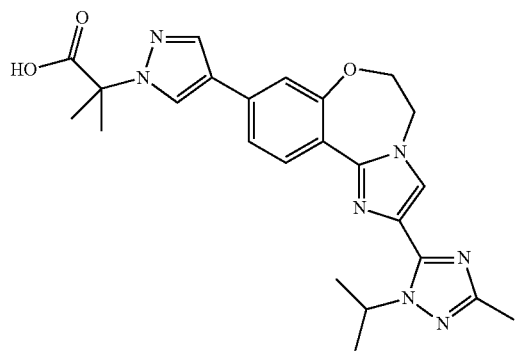 [SMILES: Cc1nc(-c2cn3c(n2)-c2ccc(-c4cnn(C(C)(C)C(=O)O)c4)cc2OCC3)n(C(C)C)n1]

(250 mg, 0.5 mmol) was treated with 1 M of lithium hydroxide in water (2 mL) and methanol (1 mL). The reaction was stirred at room temperature for 12 h. Acidified by 10% aqueous citric acid to pH=5 and extracted with EtOAc twice. The combined organic layers were washed with brine, dried and concentrated. The resultant 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoic acid 251 was used as is with no further purification steps. LC/MS(ESI+): m/z 462 (M+H). 1H NMR (500 MHz, DMSO) δ 8.44 (s, 1H), 8.36 (d, J=8.4, 1H), 7.97 (s, 1H), 7.86 (s, 1H), 7.44 (dd, J=8.4, 1.7, 1H), 7.35 (d, J=1.7, 1H), 5.82 (dt, J=13.1, 6.6, 1H), 4.52 (s, 4H), 2.25 (s, 3H), 1.78 (s, 6H), 1.45 (t, J=13.9, 6H)

Step 3

2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoic acid 251 (90 mg, 0.2 mmol) was dissolved in DMF (2 mL) and treated with NH4Cl (40 mg, 0.8 mmol), DIPEA (0.3 mL, 2 mmol) followed by N,N,N',N'-tetramethyl-O-(7-azabenzotriazol-1-yl)uronium hexafluorophosphate (HATU, 100 mg, 0.4 mmol). The mixture was stirred at room temperature for 2 hours. Saturated sodium bicarbonate was added, and the mixture was extracted with EtOAc. The combined organics were dried over sodium sulfate and concentrated. The crude was purified by 10% MeOH/EtOAc following by trituration with minimal EtOAc to provide 74 mg (82% yield) of 196. LC/MS(ESI+): m/z 463 (M+H). 1H NMR (500 MHz, DMSO) δ 8.44-8.26 (m, 2H), 8.01 (s, 1H), 7.86 (s, 1H), 7.44 (dd, J=8.4, 1.8, 1H), 7.35 (d, J=1.7, 1H), 7.15 (s, 1H), 6.79 (s, 1H), 5.82 (dt, J=13.3, 6.6, 1H), 4.52 (s, 4H), 2.25 (s, 3H), 1.75 (s, 6H), 1.47 (d, J=6.6, 6H)

Example 197

2-(3-(2-(1-isopropyl-1H-1,2,4-triazol-5-yl)-5,6-dihydrobenzo[f]imidazo[1,2-d][1,4]oxazepin-9-yl)azetidin-1-yl)-N,N-dimethylethanesulfonamide 197

Following the procedure of Example 152, 8-azetidin-3-yl-2-(2-isopropyl-2H-[1,2,4]triazol-3-yl)-4,5-dihydro-6-oxa-1,3a-diaza-benzo[e]azulene hydrochloride (Example 65) was reacted with N,N-dimethylethenesulfonamide to give 197 as a white solid. $^1$H NMR δ (ppm)(CDCl3): 8.44 (1 H, d, J=8.28 Hz), 7.84 (1 H, d, J=0.67 Hz), 7.61 (1 H, s), 7.05 (1 H, dd, J=8.32, 1.83 Hz), 6.95 (1H, d, J=1.78 Hz), 6.00-5.90 (1 H, m), 4.48-4.39 (4 H, m), 3.80-3.72 (2 H, m), 3.72-3.64 (1 H, m), 3.27-3.19 (2 H, m), 3.02-2.89 (4 H, m), 2.87 (6 H, s), 1.56 (6 H, d, J=6.63 Hz). LCMS: RT=6.35 min, M+H+=486

Example 198

2-(3-(2-(1-isopropyl-1H-1,2,4-triazol-5-yl)-5,6-dihydrobenzo[f]imidazo[1,2-d][1,4]oxazepin-9-yl)azetidin-1-yl)-N,N-dimethylacetamide 198

Following the procedure for 143, 8-azetidin-3-yl-2-(2-isopropyl-2H-[1,2,4]triazol-3-yl)-4,5-dihydro-6-oxa-1,3a-diaza-benzo[e]azulene hydrochloride (Example 65) was reacted with 2-chloro-N,N-dimethylacetamide, the crude product subjected to flash chromatography (SiO2, gradient 0 to 6% MeOH in DCM) to give 198 as a white solid. $^1$H NMR δ (ppm)(CDCl3): 8.44 (1 H, d, J=8.28 Hz), 7.84 (1 H, d, J=0.71 Hz), 7.60 (1 H, s), 7.10 (1 H, dd, J=8.33, 1.81 Hz), 6.97 (1 H, d, J=1.72 Hz), 6.01-5.91 (1 H, m), 4.48-4.39 (4 H, m), 3.99-3.90 (2 H, m), 3.86-3.77 (1 H, m), 3.46-3.38 (4 H, m), 3.00 (3 H, s), 2.93 (3 H, s), 1.56 (6 H, d, J=6.63 Hz). LCMS: RT=5.87 min, M+H+=436.

Example 199

9-(4,4-dimethyl-4,5-dihydrooxazol-2-yl)-2-(1-isopropyl-1H-1,2,4-triazol-5-yl)-5,6-dihydrobenzo[f]imidazo[1,2-d][1,4]oxazepine 199

2-Amino-2-methyl-1-propanol (0.20 g, 2.3 mmol) was dissolved in tetrahydrofuran (2.2 mL) and NaH (60% in mineral oil, 0.0942 g) was added. The resulting mixture was stirred for 1 h at room temp. To this mixture was added methyl 2-(1-isopropyl-1H-1,2,4-triazol-5-yl)-5,6-dihydrobenzo[f]imidazo[1,2-d][1,4]oxazepine-9-carboxylate 184 (0.40 g, 1.1 mmol) in THF/DMF (1:1, 10 mL). The entire reaction mixture was stirred at ambient temperature overnight. The reaction was quenched with water and diluted with EtOAc. Extracted, dried over MgSO4, filtered and concentrated. Dissolved in Methylene chloride (10 mL, 200 mmol) and cooled to at 0° C. and treated with thionyl chloride (0.314 mL, 4.30 mmol) dropwise. Following the addition, the reaction was warmed to room temp and stirred for 3 h. Concentrated in vacuo and purified by reverse phase HPLC to provide 199 (209 mg, 48% yield). LC/MS(ESI+): m/z 393 (M+H). 1H NMR (400 MHz, DMSO) δ 8.47 (d, J=8.4, 1H), 7.99 (s, 1H), 7.92 (d, J=3.5, 1H), 7.59 (dd, J=8.4, 1.6, 1H), 7.45 (d, J=1.6, 1H), 5.85 (dt, J=13.2, 6.6, 1H), 4.55 (dd, J=10.6, 6.4, 4H), 4.12 (s, 2H), 1.49 (d, J=6.6, 6H), 1.30 (s, 6H)

Example 200

N-isopropyl-2-(3-(2-(1-isopropyl-1H-1,2,4-triazol-5-yl)-5,6-dihydrobenzo[f]imidazo[1,2-d][1,4]oxazepin-9-yl)azetidin-1-yl)acetamide 200

Following the procedure for 143, 8-azetidin-3-yl-2-(2-isopropyl-2H-[1,2,4]triazol-3-yl)-4,5-dihydro-6-oxa-1,3a-diaza-benzo[e]azulene hydrochloride (Example 65) was reacted with 2-chloro-N-isopropyl acetamide. The crude product was subjected to reverse phase HPLC (Gemini C18 column gradient 0 to 70% MeOH in H2O+0.1% HCO2H) to give 200 as a white solid. $^1$H NMR δ (ppm)(CDCl3): 8.46 (1 H, d, J=8.28 Hz), 7.85 (1 H, s), 7.63 (1 H, s), 7.05 (1 H, dd, J=8.32, 1.82 Hz), 6.94-6.92 (1 H, m), 6.00-5.90 (1 H, m), 4.49-4.40 (4 H, m), 4.12-4.02 (1 H, m), 3.88 (2 H, t, J=7.51 Hz), 3.82-3.71 (1 H, m), 3.41 (2 H, t, J=7.23 Hz), 3.23 (2 H, s), 1.56 (6 H, d, J=6.63 Hz), 1.16 (6 H, d, J=6.57 Hz). 1 Exchangeable proton not seen. LCMS: RT=6.8 min, M+H+=450

Example 201

2-(3-{2-[2-(2,4-Difluoro-phenyl)-2H-[1,2,4]triazol-3-yl]-4,5-dihydro-2H-6-oxa-1,2-diaza-benzo[e]azulen-8-yl}-azetidin-1-yl)-ethanol 201

Following the procedure for 142, 8-azetidin-3-yl-2-[2-(2,4-difluoro-phenyl)-2H-[1,2,4]triazol-3-yl]-4,5-dihydro-2H-6-oxa-1,2-diaza-benzo[e]azulene hydrochloride was reacted with 2-(2-bromo-ethoxy)-tetrahydro-pyran, the crude product subjected to reverse phase HPLC (Gemini C18 column, gradient 10 to 90% MeOH in water+0.1% HCO2H) to give 201 as a white solid. $^1$H NMR (400 MHz, DMSO-d): δ 8.41 (s, 1 H); 8.28 (s, 1 H); 8.16 (s, 1H); 7.80 (td, J=8.75, 5.92 Hz, 1 H); 7.62 (ddd, J=10.34, 9.02, 2.81 Hz, 1 H); 7.37-7.31 (m, 1 H); 7.28 (d, J=8.17 Hz, 1 H); 6.95 (d, J=1.73 Hz, 1H); 6.89 (dd, J=8.25, 1.81 Hz, 1 H); 4.22 (t, J=5.03 Hz, 2 H); 3.69 (t, J=7.37 Hz, 2 H); 3.60 (dt, J=15.08, 7.40 Hz, 1 H); 3.39 (t, J=6.62 Hz, 1 H); 3.23 (t, J=7.74 Hz, 2 H); 3.14 (s, 2 H); 3.05 (t, J=5.14 Hz, 2 H); 2.61 (t, J=5.95 Hz, 2 H). LCMS: RT=7.11 min, M+H+=465

Example 202

1-(4-(2-(1-isopropyl-1H-1,2,4-triazol-5-yl)-5,6-dihydrobenzo[f]imidazo[1,2-d][1,4]oxazepin-9-yl)-1H-imidazol-1-yl)-2-methylpropan-2-ol 202

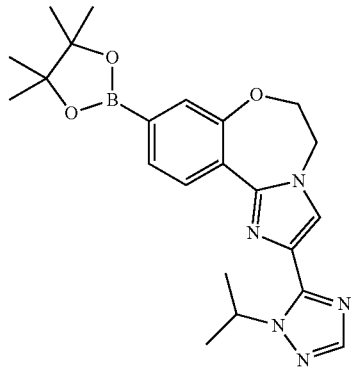 [SMILES: CC(C)n1ncnc1-c1cn2c(n1)-c1ccc(B3OC(C)(C)C(C)(C)O3)cc1OCC2]

To a microwave vial containing 9-bromo-2-(1-isopropyl-1H-1,2,4-triazol-5-yl)-5,6-dihydrobenzo[f]imidazo[1,2-d][1,4]oxazepine (402 mg, 1.07 mmol) was added potassium acetate (316 mg, 3.22 mmol) and dimethyl sulfoxide (8 mL, 100 mmol). The reaction mixture was purged with nitrogen thoroughly and bispinacol ester boronate (310 mg, 3.22 mmol) was added followed by [1,1'-bis(diphenylphosphino)ferrocene]dichloropalladium(II), complex with dichloromethane (1:1) (87.7 mg, 0.107 mmol) and the vial was sealed. The vial was heated in an oil bath for 24 hours. Complete conversion by LCMS. Filtered through celite with 8/2 dichlomethane/methanol and concentrated in vacuo. Flashed 0 to 5% methanol/dichloromethane. Concentrated in vacuo to give 2-(1-isopropyl-1H-1,2,4-triazol-5-yl)-9-(4,4,5,5-tetramethyl-1,3,2-dioxaborolan-2-yl)-5,6-dihydrobenzo[f]imidazo[1,2-d][1,4]oxazepine (117 mg, 26% yield)

2-(1-Isopropyl-1H-1,2,4-triazol-5-yl)-9-(4,4,5,5-tetramethyl-1,3,2-dioxaborolan-2-yl)-5,6-dihydrobenzo[f]imidazo[1,2-d][1,4]oxazepine (113 mg, 0.268 mmol), 1-(4-bromo-1H-imidazol-1-yl)-2-methylpropan-2-ol and 1-(5-bromo-1H-imidazol-1-yl)-2-methylpropan-2-ol (88.14 mg, 0.40 mmol), 1,1'-Bis(diphenylphosphino)ferrocenepalladium(II) chloride (21.90 mg, 0.027 mmol), 1,2-dimethoxyethane (3.0 mL, 29 mmol), and 1 M Cesium carbonate in water (0.54 mL, 0.5 mmol) were mixed in a microwave vial and microwaved at 140° C. for 15 minutes. Complete reaction by LCMS. Filtered through a paper filter followed by a silica plug. Concentrated in vacuo and purified by HPLC to give 202 (13.7 mg, 12% yield)

Alternatively, to a mixture of 224 (300 mg, 0.75 mmol) and Cs2CO3 (733 mg, 2.25 mmol) in DMF (15 mL) under nitrogen was added 2, 2-dimethyl-oxirane (2 mL, 22.4 mmol). The reaction mixture was heated at 80° C. for 8 h. Cooled to room temperature, the resulting mixture was poured into water and extracted with EtOAc. Dried organics over sodium sulfate and purified by pre-TLC (DCM/ MeOH=10:1) to give 202 as a white solid (75.3 mg, yield: 23%). 1H NMR (DMSO-d6, 400 MHz): δ 68.37 (d, J=8.4 Hz, 1H), 7.92 (s, 2H), 7.67 (s, 1H), 7.64 (s 1H), 7.53 (dd, J 1=1.6 Hz, J 2=8.4 Hz, 1H), 7.42 (d, J=1.6 Hz, 1H), 5.94-5.88 (m, 1H), 4.79 (s, 1H), 4.54-4.50 (m, 4H), 3.89 (s, 2H), 1.49 (d, J=6.4 Hz, 6H), 1.09 (s, 6H). MS: (ESI, m/z)=434 [M+H]+

Example 203

3-(2-(1-isopropyl-1H-1,2,4-triazol-5-yl)-5,6-dihydrobenzo[f]imidazo[1,2-d][1,4]oxazepin-10-yl)pyridin-2(1H)-one 203

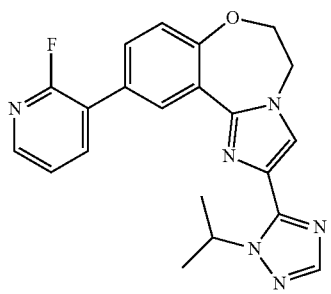 [SMILES: CC(C)n1ncnc1-c1cn2c(n1)-c1cc(-c3cccnc3F)ccc1OCC2]

10-bromo-2-(1-isopropyl-1H-1,2,4-triazol-5-yl)-5,6-dihydrobenzo[f]imidazo[1,2-d][1,4]oxazepine 187 (0.057 g, 0.15 mmol), 2-fluoropyridin-3-ylboronic acid (0.026 g, 0.183 mmol), potassium acetate (0.059 g, 0.609 mmol), and tetrakis(triphenylphosphine)palladium(0) (8.8 mg, 0.007 mmol), DMF (6 mL) and water (0.6 mL) were mixed. Nitrogen was bubbled through the reaction mixture for 5 minutes. The reaction mixture was allowed to stir and heat at 105° C. for 24 hours before cooling, diluting with EtOAc, and filtering through a pad of celite. The filtrate was concentrated under reduced pressure and diluted with EtOAc. The solution was washed sequentially with water, and brine, before drying over MgSO4 and concentrating under reduced pressure. The crude material was dissolved in DMF and purified by reverse phase HPLC to provide 10-(2-fluoropyridin-3-yl)-2-(1-isopropyl-1H-1,2,4-triazol-5-yl)-5,6-dihydrobenzo[f]imidazo[1,2-d][1,4]oxazepine (47 mg, 80%). MS (ESI(+)): m/z 391.1 (M+H)

To a solution of 10-(2-fluoropyridin-3-yl)-2-(1-isopropyl-1H-1,2,4-triazol-5-yl)-5,6-dihydrobenzo[f]imidazo[1,2-d] [1,4]oxazepine (0.047 g, 0.12 mmol) in DME (2 mL) was added 10% aq HCl (2 mL). The reaction mixture was allowed to stir and heat at 80° C. for 18 hours before cooling and concentrating under reduced pressure. The crude material was dissolved in DMF and purified by reverse phase HPLC to provide 203 (25 mg, 55%). 1H NMR (400 MHz, DMSO) δ 11.82 (s, 1H), 8.88 (d, J=2.3, 1H), 7.92 (d, J=6.7, 2H), 7.67 (ddd, J=9.0, 7.7, 2.2, 2H), 7.38 (d, J=4.8, 1H), 7.07 (d, J=8.6, 1H), 6.31 (t, J=6.7, 1H), 5.81 (dt, J=13.2, 6.6, 1H), 4.54 (q, J=5.8, 4H), 1.48 (d, J=6.6, 6H). MS (ESI(+)): m/z 389.1 (M+H)

Example 204

9-(1-(2-(3-fluoroazetidin-1-yl)ethylsulfonyl)azetidin-3-yl)-2-(1-isopropyl-1H-1,2,4-triazol-5-yl)-5,6-dihydrobenzo[f]imidazo[1,2-d][1,4]oxazepine 204

8-Azetidin-3-yl-2-(2-isopropyl-2H-[1,2,4]triazol-3-yl)-4, 5-dihydro-6-oxa-1,3a-diaza-benzo[e]azulene hydrochloride from Example 65 (200 mg, 0.517 mmol) was stirred in DCM (2 mL) with triethylamine (145 L, 1.04 mmol) for 1 h before the addition of 2-chloroethanesulfonyl chloride (84 mg, 0.52 mmol). After stirring for 1 h further triethylamine (73 L, 0.52 mmol) was added and the mixture stirred for 18 h before diluting with DCM and washing with water followed by brine. The resultant solution was concentrated in vacuo to give a brown oil which was used in the subsequent step without purification. A portion of the brown oil (81 mg, 0.18 mmol) was stirred in 3 mL IMS at RT with 3-fluoroazetidine hydrochloride (22 mg, 0.22 mmol) and triethylamine (56 L, 0.4 mmol) for 18 h before being concentrated in vacuo. The resultant residue was dissolved in DCM and the solution washed with water then brine, dried (Na2SO4), filtered and concentrated in vacuo. The resultant light brown oil was subjected to flash chromatography (SiO2, gradient 0 to 2% MeOH in DCM) to give 204 as a white solid (37 mg, 40%). $^1$H NMR δ (ppm)(CDCl3): 8.49 (1 H, d, J=8.30 Hz), 7.84 (1 H, d, J=0.64 Hz), 7.62 (1 H, s), 7.12 (1 H, dd, J=8.34, 1.88 Hz), 7.00 (1 H, d, J=1.83 Hz), 5.99-5.91 (1 H, m), 5.19-5.13 (0.5 H, m), 5.05-4.99 (0.5 H, m), 4.49-4.46 (2 H, m), 4.45-4.41 (2 H, m), 4.26 (2 H, t, J=8.24 Hz), 4.06 (2 H, t, J=7.28 Hz), 3.80-3.63 (3 H, m), 3.27-3.22 (1 H, m), 3.21-3.16 (1 H, m), 3.06-3.00 (2 H, m), 2.97-2.90 (2 H, m), 1.60-1.54 (6 H, m). LCMS: RT=2.94 min, M+H+=516

Example 205

2-(3-(2-(1-isopropyl-1H-1,2,4-triazol-5-yl)-5,6-dihydrobenzo[f]imidazo[1,2-d][1,4]oxazepin-9-yl)azetidin-1-yl)-2-methylpropanamide 205

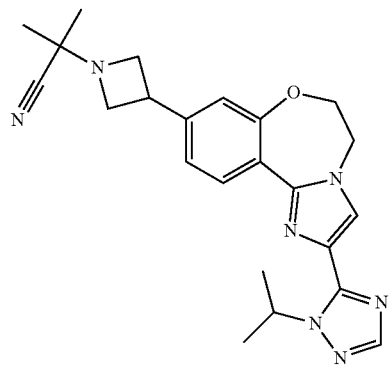 [SMILES: CC(C)n1ncnc1-c1cn2c(n1)-c1ccc(C3CN(C(C)(C)C#N)C3)cc1OCC2]

A suspension of 8-azetidin-3-yl-2-(2-isopropyl-2H-[1, 2,4]triazol-3-yl)-4,5-dihydro-6-oxa-1,3a-diaza-benzo[e]azulene hydrochloride from Example 65 (0.23 g, 0.6 mmol) in water (2.5 mL) was treated with sodium cyanide (49.5 mg, 0.6 mmol) followed by acetone (60 mg, 0.91 mmol) in water (0.25 mL) and the mixture stirred at RT for 18 h. The mixture was extracted four times with DCM and the combined extracts were dried (Na2SO4), filtered and concentrated in vacuo to give 2-{3-[2-(2-Isopropyl-2H-[1,2,4]triazol-3-yl)-4,5-dihydro-6-oxa-1,3a-diaza-benzo[e]azulen-8- yl]-azetidin-1-yl}-2-methyl-propionitrile (0.19 g, 76%). LCMS: RT=3.76 min, M+H+=418.

2-{3-[2-(2-Isopropyl-2H-[1,2,4]triazol-3-yl)-4,5-di-hydro-6-oxa-1,3a-diaza-benzo[e]azulen-8-yl]-azetidin-1-yl}-2-methyl-propionitrile (0.17 g, 0.41 mmol) was dissolved in conc. H2SO4, (2 mL) and the mixture allowed to stand at room temperature for 3.25 hr before adding to ice. The resultant solution was basified with Na2CO3, further water added, and the mixture extracted with 10% MeOH in DCM. The combined extracts were dried (Na2SO4), filtered and concentrated in vacuo. The resultant residue was subjected to flash chromatography (SiO2, gradient 0 to 10% MeOH in DCM) to give 205 as a white solid (97 mg, 54%). $^1$H NMR δ (ppm)(CDCl3): 8.46 (1 H, d, J=8.29 Hz), 7.84 (1 H, s), 7.61 (1 H, s), 7.13 (1 H, s), 7.08 (1 H, d, J=8.39 Hz), 6.95 (1 H, s), 6.01-5.91 (1 H, m), 5.27 (1 H, s), 4.50-4.40 (4 H, m), 3.62 (3 H, s), 3.33 (2 H, s), 1.56 (6 H, d, J=6.63 Hz), 1.23 (6 H, s). LCMS: RT=2.53 min, M+H+=436

Example 206

2-(4-(2-(1-(2,2,2-trifluoroethyl)-1H-1,2,4-triazol-5-yl)-5,6-dihydrobenzo[f]imidazo[1,2-d][1,4]oxazepin-9-yl)-1H-pyrazol-1-yl)ethanol 206

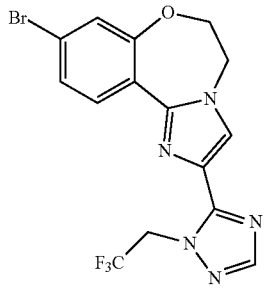 [SMILES: FC(F)(F)Cn1ncnc1-c1cn2c(n1)-c1ccc(Br)cc1OCC2]

Following the procedure for 184, 9-bromo-2-iodo-5,6-dihydrobenzo[f]imidazo[1,2-d][1,4]oxazepine and 1-(2,2,2-trifluoroethyl)-1H-1,2,4-triazole were reacted to give 9-bromo-2-(1-(2,2,2-trifluoroethyl)-1H-1,2,4-triazol-5-yl)-5,6-dihydrobenzo[f]imidazo[1,2-d][1,4]oxazepine (0.109 g, 10%). 1H NMR (400 MHz, DMSO) δ 8.28 (t, J=21.9, 1H), 8.11 (t, J=7.9, 2H), 7.51-7.35 (m, 1H), 7.32 (d, J=2.0, 1H), 5.88 (q, J=8.8, 2H), 4.76-4.29 (m, 4H). MS (ESI(+)): m/z 413.9 (M+H).

Following the procedure for 182, 9-bromo-2-(1-(2,2,2-trifluoroethyl)-1H-1,2,4-triazol-5-yl)-5,6-dihydrobenzo[f]imidazo[1,2-d][1,4]oxazepine and 1-(2-(tetrahydro-2H-pyran-2-yloxy)ethyl)-4-(4,4,5,5-tetramethyl-1,3,2-dioxaborolan-2-yl)-1H-pyrazole were reacted to give 206 (0.056 g, 48%). 1H NMR (400 MHz, DMSO) δ 8.33 (d, J=8.4, 1H), 8.24 (s, 1H), 8.07 (d, J=11.7, 2H), 7.95 (d, J=8.9, 1H), 7.41 (dd, J=8.4, 1.7, 1H), 7.28 (d, J=1.7, 1H), 5.91 (q, J=8.8, 2H), 4.91 (t, J=5.3, 1H), 4.54 (dd, J=10.8, 5.6, 4H), 4.16 (t, J=5.6, 2H), 3.87-3.69 (m, 2H). MS (ESI(+)): m/z 446.1 (M+H)

Example 207

2-(4-(2-(1-isopropyl-1H-1,2,4-triazol-5-yl)-5,6-dihydrobenzo[f]imidazo[1,2-d][1,4]oxazepin-9-yl)-1H-imidazol-1-yl)ethanol 207

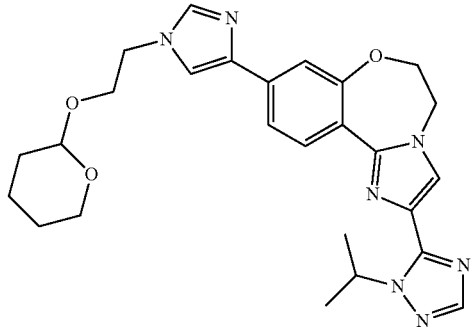 [SMILES: CC(C)n1ncnc1-c1cn2c(n1)-c1ccc(-c3cn(CCOC4CCCCO4)cn3)cc1OCC2]

Tetrakis(triphenylphosphine)palladium(0) (84.0 mg 0.0727 mmol) was added last to a degassed solution of 9-bromo-2-(1-isopropyl-1H-1,2,4-triazol-5-yl)-5,6-dihydrobenzo[f]imidazo[1,2-d][1,4]oxazepine (272 mg, 0.727 mmol) and regioisomers 1-(2-(tetrahydro-2H-pyran-2-yloxy)ethyl)-4-(tributylstannyl)-1H-imidazole and 1-(2-(tetrahydro-2H-pyran-2-yloxy)ethyl)-5-(tributylstannyl)-1H-imidazole (600 mg, 1 mmol) in acetonitrile (5 mL, 100 mmol). The reaction was heated in the CEM microwave at 140° C. for 30 minutes with complete conversion by LCMS. Concentrated in vacuo and flash purified 0 to 100% methanol/dichloromethane. The product tubes were concentrated in vacuo to give 270 mg of the regioisomers 2-(1-isopropyl-1H-1,2,4-triazol-5-yl)-9-(1-(2-(tetrahydro-2H-pyran-2-yloxy)ethyl)-1H-imidazol-4-yl)-5,6-dihydrobenzo[f]imidazo[1,2-d][1,4]oxazepine and 2-(1-isopropyl-1H-1,2,4-triazol-5-yl)-9-(1-(2-(tetrahydro-2H-pyran-2-yloxy)ethyl)-1H-imidazol-5-yl)-5,6-dihydrobenzo[f]imidazo[1,2-d][1,4]oxazepine. These inseparable compounds were dissolved in 4 N HCl in dioxane (10 mL) and the solution was stirred for 30 minutes at room temperature. Complete deprotection was confirmed by LCMS to give the final compounds which were purified by SFC to separate the regioisomer 207 (159.8 mg, 54% yield, M+1 406.1)

Alternatively, to a mixture of 224 (300 mg, 0.75 mmol) and Cs2CO3 (733 mg, 2.25 mmol) in DMF (15 mL) under nitrogen was added 2-(2-bromo-ethoxy)-tetrahydro-pyran (0.68 mL, 4.52 mmol). The reaction mixture was heated at 80° C. for 5 h. Cooled to room temperature, the resulting mixture was poured into water and extracted with EtOAc. Dried organics over sodium sulfate and purified by pre-TLC (DCM/MeOH=10:1) to give 2-(1-isopropyl-1H-1,2,4-triazol-5-yl)-9-(1-(2-(tetrahydro-2H-pyran-2-yloxy)ethyl)-1H-imidazol-4-yl)-5,6-dihydrobenzo[f]imidazo[1,2-d][1,4]oxazepine as a yellow oil (250 mg, yield: 68%). LCMS: (ESI, m/z)=490 [M+H]+

To a solution of 2-(1-isopropyl-1H-1,2,4-triazol-5-yl)-9-(1-(2-(tetrahydro-2H-pyran-2-yloxy)ethyl)-1H-imidazol-4-yl)-5,6-dihydrobenzo[f]imidazo[1,2-d][1,4]oxazepine (250 mg, 0.51 mmol) in EtOH (15 mL) was added a solution of hydrogen chloride in dioxane (1.28 mL, 5.1 mmol). The mixture was refluxed for 2 h, cooled to room temperature and concentrated. The resulting precipitates were washed with EtOAc to give 207 as a yellow solid (115.2 mg, yield 56%). 1H NMR (Methane-d4, 400 MHz): δ 9.12 (d, J=1.2 Hz, 1H), 8.78 (s, 1H), 8.65 (d, J=8.4 Hz, 1H), 8.28 (s, 1H), 8.17 (d, J=1.2 Hz, 1H), 7.58-7.53 (m, 2H), 5.85-5.78 (m, 1H), 4.71-4.63 (m, 4H), 4.41 (t, J=5.2 Hz, 2H), 3.96 (t, J=5.2 Hz, 2H), 1.66 (d, J=6.8 Hz, 6H). MS: (ESI, m/z)=406 [M+H]+

Example 208

2-(5-(2-(1-isopropyl-1H-1,2,4-triazol-5-yl)-5,6-dihydrobenzo[f]imidazo[1,2-d][1,4]oxazepin-9-yl)-1H-imidazol-1-yl)ethanol 208

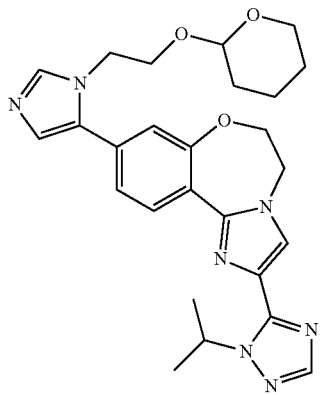 [SMILES: CC(C)n1ncnc1-c1cn2c(n1)-c1ccc(-c3cncn3CCOC3CCCCO3)cc1OCC2]

Tetrakis(triphenylphosphine)palladium(0) (84.0 mg 0.0727 mmol) was added last to a degassed solution of 9-bromo-2-(1-isopropyl-1H-1,2,4-triazol-5-yl)-5,6-dihydrobenzo[f]imidazo[1,2-d][1,4]oxazepine (272 mg, 0.727 mmol) and regioisomers 1-(2-(tetrahydro-2H-pyran-2-yloxy)ethyl)-4-(tributylstannyl)-1H-imidazole and 1-(2-(tetrahydro-2H-pyran-2-yloxy)ethyl)-5-(tributylstannyl)-1H-imidazole (600 mg, 1 mmol) in acetonitrile (5 mL, 100 mmol). The reaction was heated in the CEM microwave at 140° C. for 30 minutes with complete conversion by LCMS. Concentrated in vacuo and flash purified 0 to 100% methanol/dichloromethane. The product tubes were concentrated in vacuo to give 270 mg of the regioisomers 2-(1-isopropyl-1H-1,2,4-triazol-5-yl)-9-(1-(2-(tetrahydro-2H-pyran-2-yloxy)ethyl)-1H-imidazol-4-yl)-5,6-dihydrobenzo[f]imidazo[1,2-d][1,4]oxazepine and 2-(1-isopropyl-1H-1,2,4-triazol-5-yl)-9-(1-(2-(tetrahydro-2H-pyran-2-yloxy)ethyl)-1H-imidazol-5-yl)-5,6-dihydrobenzo[f]imidazo[1,2-d][1,4]oxazepine. These inseparable compounds were dissolved in 4 N HCl in dioxane (10 mL) and the solution was stirred for 30 minutes at room temperature. Complete deprotection was confirmed by LCMS to give the final compounds which were purified by SFC to separate the regioisomer 208 (27 mg, 9% yield, M+1 406.1)

Example 209

2-(1-(2-morpholinoethyl)-1H-imidazol-2-yl)-10-(1H-pyrazol-4-yl)-5,6-dihydrobenzo[f]imidazo[1,2-d][1,4]oxazepine 209

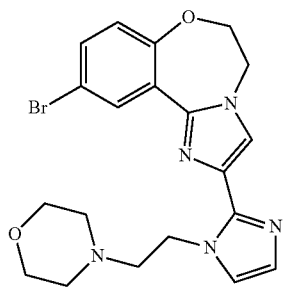 [SMILES: Brc1ccc2c(c1)-c1nc(-c3nccn3CCN3CCOCC3)cn1CCO2]

9-Bromo-2-(1H-imidazol-2-yl)-5,6-dihydrobenzo[f]imidazo[1,2-d][1,4]oxazepine was alkylated with 4-(2-chloroethyl)morpholine to give 9-bromo-2-[1-(2-morpholinoethyl)-1H-imidazol-2-yl]-5,6-dihydrobenzo[f]imidazo[1,2-d][1,4]oxazepine (yield 51%. MS: 444.2) which was coupled under Suzuki palladium coupling conditions of Example 182 with tert-butyl 4-(4,4,5,5-tetramethyl-1,3,2-dioxaborolan-2-yl)-1H-pyrazole-1-carboxylate to give 209. Yield 24%. MS: 432.1. 1H NMR (400 MHz, DMSO) δ 12.95 (s, 1H), 8.56 (d, J=2.3, 1H), 8.09 (s, 1H), 7.87 (s, 1H), 7.72 (s, 1H), 7.51 (dd, J=8.4, 2.3, 1H), 7.21 (d, J=1.0, 1H), 7.04 (d, J=8.4, 1H), 6.89 (d, J=1.0, 1H), 4.72 (t, J=7.1, 2H), 4.50 (q, J=5.6, 4H), 3.48-3.40 (m, 4H), 2.73 (t, J=7.1, 2H), 2.46-2.36 (m, 4H)

Example 210

2-(1-isopropyl-3-methyl-1H-1,2,4-triazol-5-yl)-9-(1-(2-morpholinoethyl)-1H-pyrazol-4-yl)-5,6-dihydrobenzo[f]imidazo[1,2-d][1,4]oxazepine 210

Similarly to as described in General Procedure C, 8-Bromo-2-(2-isopropyl-5-methyl-2H-[1,2,4]triazol-3-yl)-4,5-dihydro-6-oxa-1,3a-diaza-benzo[e]azulene was reacted with 4-(2-(4-(4,4,5,5-tetramethyl-1,3,2-dioxaborolan-2-yl)-1H-pyrazol-1-yl)ethyl)morpholine. Purification of the crude reaction mixture by reverse phase HPLC gave 210. LCMS: 489.2

Example 211

2-(4-(2-(3-amino-1-isopropyl-1H-1,2,4-triazol-5-yl)-5,6-dihydrobenzo[f]imidazo[1,2-d][1,4]oxazepin-9-yl)-1H-pyrazol-1-yl)ethanol 211

To a microwave vial was added 5-(8-Bromo-4,5-dihydro-6-oxa-1,3a-diaza-benzo[e]azulen-2-yl)-1-isopropyl-1H-[1,2,4]triazol-3-ylamine (0.180 g, 0.000462 mol) and potassium carbonate (0.1917 g, 0.001387 mol) in acetonitrile (2.0 mL, 0.038 mol) and water (2.0 mL, 0.11 mol). The reaction was thoroughly degassed and purged with N2 for 5 minutes. Tetrakis(triphenylphosphine)palladium(0) (0.05344 g, 4.624E-5 mol) and Acetic acid 2-[4-(4,4,5,5-tetramethyl-[1,3,2]dioxaborolan-2-yl)-pyrazol-1-yl]-ethyl ester (0.1554 g, 0.0005549 mol) were added and the vial was sealed immediately. The reaction was heated to 140° C. for 20 minutes in the microwave. The mixture was diluted with methylene chloride and filtered through celite. Saturated NH4Cl was added and the mixture was extracted 3 times with methylene chloride. The organic layers were combined, dried with MgSO4 and concentrated. The crude was purified by reverse-phase HPLC to give 211 (34.6 mg) as a colorless solid. MS(ESI+) 421.1. 1H NMR (400 MHz, DMSO) δ 8.35 (d, J=8.4, 1H), 8.22 (s, 1H), 7.95 (s, 1H), 7.73 (s, 1H), 7.38 (dd, J=8.4, 1.8, 1H), 7.27 (d, J=1.7, 1H), 5.84-5.69 (m, 1H), 5.19 (s, 2H), 4.93 (t, J=5.3, 1H), 4.50 (s, 4H), 4.16 (t, J=5.6, 2H), 3.77 (q, J=5.6, 2H), 1.42 (d, J=6.6, 6H)

Example 212

2-(3-(2-(1-isopropyl-1H-1,2,4-triazol-5-yl)-5,6-dihydrobenzo[f]imidazo[1,2-d][1,4]oxazepin-9-yl)azetidin-1-yl)-N-methylacetamide 212

A solution of 8-azetidin-3-yl-2-(2-isopropyl-2H-[1,2,4]triazol-3-yl)-4,5-dihydro-6-oxa-1,3a-diaza-benzo[e]azulene hydrochloride from Example 65 (70 mg, 0.2 mmol) in NMP (2 mL) was treated with sodium phosphate tribasic (85 mg, 0.6 mmol) then N-methyl-2-chloro acetamide (24 mg, 0.22 mmol) in NMP (0.2 mL) and the mixture stirred at RT for 18 h. The mixture was loaded onto an Isolute® SCX-2 cartridge eluting with MeOH then 2M NH3 in MeOH. Appropriate fractions were combined and concentrated in vacuo, the resultant residue was subjected to flash chromatography (SiO2, gradient 0 to 10% MeOH in DCM) to give 212 (24 mg, 29%). $^1$H NMR δ (ppm)(CDCl3): 8.50 (1 H, d, J=8.29 Hz), 7.89 (1 H, s), 7.68 (1 H, s), 7.22 (1 H, s), 7.10 (1 H, dd, J=8.33, 1.81 Hz), 6.99-6.96 (1 H, m), 6.03-5.94 (1 H, m), 4.53-4.49 (2 H, m), 4.48-4.44 (2 H, m), 3.96 (2 H, t, J=7.77 Hz), 3.81 (1 H, t, J=7.74 Hz), 3.54 (2 H, t, J=7.43 Hz), 3.35 (2 H, s), 2.86 (3 H, d, J=4.93 Hz), 1.60 (6 H, d, J=6.63 Hz). LCMS: RT=2.53 min, M+H+=422

Example 213

1-(4-(2-(3-amino-1-isopropyl-1H-1,2,4-triazol-5-yl)-5,6-dihydrobenzo[f]imidazo[1,2-d][1,4]oxazepin-9-yl)-1H-pyrazol-1-yl)-2-methylpropan-2-ol 213

To a microwave vial was added 5-(8-Bromo-4,5-dihydro-6-oxa-1,3a-diaza-benzo[e]azulen-2-yl)-1-isopropyl-1H-[1,2,4]triazol-3-ylamine (0.180 g, 0.000462 mol) and potassium acetate (0.1362 g, 0.001387 mol) in acetonitrile (2.0 mL, 0.038 mol) and water (2.0 mL, 0.11 mol). The reaction was thoroughly degassed and purged with N2 for 5 minutes. Tetrakis(triphenylphosphine)palladium(0) (0.05344 g, 4.624E-5 mol) and 2-Methyl-1-[4-(4,4,5,5-tetramethyl-[1,3,2]dioxaborolan-2-yl)-pyrazol-1-yl]-propan-2-ol (0.1477 g, 0.0005549 mol) were added and the vial was sealed immediately. The reaction was heated to 140° C. for 20 minutes in the microwave. The mixture was diluted with methylene chloride and filtered through celite. Saturated NH4Cl was added and the mixture was extracted 3 times with methylene chloride. The organic layers were combined, dried with MgSO4 and concentrated. The crude was purified by reverse-phase HPLC to give 213 (68.2 mg) as a colorless solid. MS(ESI+) 449.2. 1H NMR (400 MHz, DMSO) δ 8.35 (d, J=8.4, 1H), 8.16 (s, 1H), 7.95 (s, 1H), 7.73 (s, 1H), 7.38 (dd, J=8.4, 1.7, 1H), 7.27 (d, J=1.7, 1H), 5.82-5.68 (m, 1H), 5.19 (s, 2H), 4.74 (s, 1H), 4.50 (br, 4H), 4.04 (s, 2H), 1.42 (d, J=6.6, 6H), 1.09 (s, 6H)

Example 214

1-(4-(2-(1-isopropyl-1H-imidazol-2-yl)-5,6-dihydrobenzo[f]imidazo[1,2-d][1,4]oxazepin-9-yl)-1H-pyrazol-1-yl)-2-methylpropan-2-ol 214

9-bromo-2-(1-isopropyl-1H-imidazol-2-yl)-5,6-dihydrobenzo[f]imidazo[1,2-d][1,4]oxazepine (157 mg, 0.421 mmol), 2-methyl-1-(4-(4,4,5,5-tetramethyl-1,3,2-dioxaborolan-2-yl)-1H-pyrazol-1-yl)propan-2-ol (139.9 mg, 0.5258 mmol), and Tetrakis(triphenylphosphine)palladium (0) (68.05 mg, 0.05889 mmol) dissolved in Acetonitrile (2.66 mL, 50.9 mmol) and with dissolved 2.00 M of Potassium carbonate in Water (0.421 mL). The reaction mixture was degasssed. The reaction was microwaved on 150 watts, 140° C. for 10 minutes. The reaction was cooled to r.t., extracted with ethyl acetate to give crude product purified by rHPLC to give 214. MS: (ESI+)=433.2. 1H NMR (400 MHz, DMSO) δ 8.36 (d, J=8.4 Hz, 1H), 8.15 (s, 1H), 7.94 (s, 1H), 7.68 (s, 1H), 7.42-7.31 (m, 2H), 7.26 (d, J=1.7 Hz, 1H), 6.94 (s, 1H), 5.66 (dt, J=13.5, 6.7 Hz, 1H), 4.74 (s, 1H), 4.50 (s, 4H), 4.03 (s, 2H), 1.46 (d, J=6.7 Hz, 6H), 1.09 (s, 6H)

Example 215

2-(4-(2-(1-isopropyl-1H-1,2,4-triazol-5-yl)-5,6-dihydrobenzo[f]imidazo[1,2-d][1,4]oxazepin-9-yl)-1H-pyrazol-1-yl)-2-methylpropanamide 215

Step 1: methyl 2-(4-(2-(1-isopropyl-1H-1,2,4-triazol-5-yl)-5,6-dihydrobenzo[f]imidazo[1,2-d][1,4]oxazepin-9-yl)-1H-pyrazol-1-yl)-2-methylpropanoate

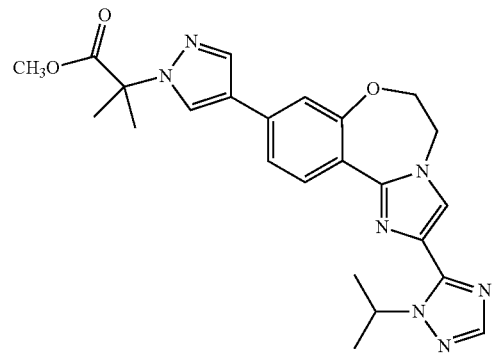

Following the procedures as Example 182, 9-bromo-2-(1-isopropyl-1H-1,2,4-triazol-5-yl)-5,6-dihydrobenzo[f]imidazo[1,2-d][1,4]oxazepine 194 and 2-methyl-2-(4-(4,4,5,5-tetramethyl-1,3,2-dioxaborolan-2-yl)-1H-pyrazol-1-yl)propanamide were coupled under Suzuki conditions to give methyl 2-(4-(2-(1-isopropyl-1H-1,2,4-triazol-5-yl)-5,6-dihydrobenzo[f]imidazo[1,2-d][1,4]oxazepin-9-yl)-1H-pyrazol-1-yl)-2-methylpropanoate (plus the corresponding acid) in 62% yield. LS/MS(ESI+): m/z 388 (M+H)

Step 2

The mixture of methyl 2-(4-(2-(1-isopropyl-1H-1,2,4-triazol-5-yl)-5,6-dihydrobenzo[f]imidazo[1,2-d][1,4]oxazepin-9-yl)-1H-pyrazol-1-yl)-2-methylpropanoate and corresponding acid (100 mg, 0.22 mmol) was treated with 1 M of lithium hydroxide in water (2 mL) and methanol (0.37 mL). The reaction was stirred at room temp for 12 h. Acidified by 10% aqueous citric acid to pH=5 and extracted with EtOAc twice. The combined organic layers were washed with brine, dried and concentrated to give 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoic acid 216. 1H NMR (400 MHz, DMSO) δ 8.44 (s, 1H), 8.39 (s, OH), 8.37 (s, 1H), 7.98 (s, 1H), 7.92 (s, 2H), 7.45 (dd, J=8.4, 1.8, 1H), 7.36 (d, J=1.7, 1H), 5.90 (dt, J=13.2, 6.6, 1H), 4.53 (q, J=6.0, 4H), 1.72 (d, J=42.8, 6H), 1.50 (d, J=6.6, 6H).

Step 3

2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoic acid (100 mg, 0.22 mmol) was dissolved in DMF (1 mL) and treated sequentially with N,N-diisopropylethylamine (0.3 mL, 2.0 mmol), ammonium chloride (50 mg, 0.9 mmol) and N,N,N',N'-tetramethyl-O-(7-azabenzotriazol-1-yl)uronium hexafluorophosphate (HATU, 200 mg, 0.6 mmol). The resulting mixture was stirred at room temp for an overnight period. Saturated sodium bicarbonate was added, and the mixture was extracted with EtOAc. The combined organics were dried over sodium sulfate, concentrated, and purified by rp-HPLC to provide 53 mg (54% yield) of 215. LC/MS(ESI+): m/z 447 (M+H). 1H NMR (400 MHz, DMSO) δ 8.41 (s, 1H), 8.39 (s, OH), 8.37 (s, 1H), 8.02 (s, 1H), 7.46 (dd, J=8.4, 1.7, 1H), 7.35 (t, J=7.2, 1H), 7.20 (s, 1H), 6.85 (s, 1H), 5.90 (hept, J=6.6, 1H), 4.53 (q, J=5.9, 4H), 1.74 (s, 6H), 1.50 (d, J=6.6, 6H)

Example 216

2-(4-(2-(1-isopropyl-1H-1,2,4-triazol-5-yl)-5,6-dihydrobenzo[f]imidazo[1,2-d][1,4]oxazepin-9-yl)-1H-pyrazol-1-yl)-2-methylpropanoic acid 216

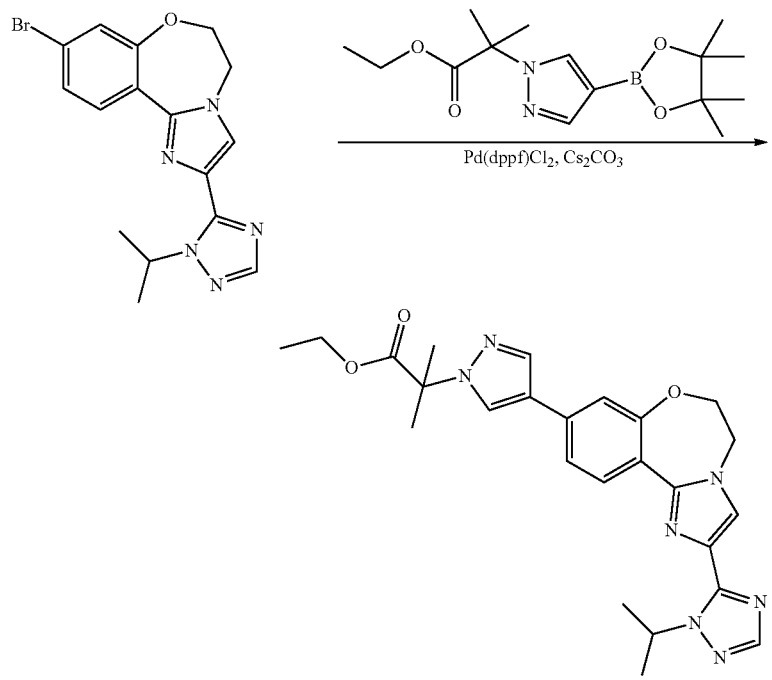

9-Bromo-2-(1-isopropyl-1H-1,2,4-triazol-5-yl)-5,6-dihydrobenzo[f]imidazo[1,2-d][1,4]oxazepine 194 and ethyl 2-methyl-2-(4-(4,4,5,5-tetramethyl-1,3,2-dioxaborolan-2-yl)-1H-pyrazol-1-yl)propanoate were reacted under Suzuki palladium conditions to give ethyl 2-(4-(2-(1-isopropyl-1H-1,2,4-triazol-5-yl)-5,6-dihydrobenzo[f]imidazo[1,2-d][1,4]oxazepin-9-yl)-1H-pyrazol-1-yl)-2-methylpropanoate. LC/MS(ESI+): m/z 476 (M+H)

Ethyl 2-(4-(2-(1-isopropyl-1H-1,2,4-triazol-5-yl)-5,6-dihydrobenzo[f]imidazo[1,2-d][1,4]oxazepin-9-yl)-1H-pyrazol-1-yl)-2-methylpropanoate was treated with lithium hydroxide in water to give 216. LC/MS(ESI+): m/z 448 (M+H). 1H NMR (400 MHz, DMSO) δ 8.44 (s, 1H), 8.38 (d, J=8.4, 1H), 7.98 (s, 1H), 7.92 (s, 2H), 7.45 (dd, J=8.4, 1.8, 1H), 7.36 (d, J=1.7, 1H), 5.90 (dt, J=13.2, 6.6, 1H), 4.53 (q, J=6.0, 4H), 1.77 (s, 6H), 1.50 (d, J=6.6, 6H)

Example 217

2-(1-isopropyl-1H-1,2,4-triazol-5-yl)-9-(1H-pyrazol-4-yl)-5,6-dihydrobenzo[f]imidazo[1,2-d][1,4]oxazepine 217

Following the same procedure as for 182, 9-bromo-2-(1-isopropyl-1H-1,2,4-triazol-5-yl)-5,6-dihydrobenzo[f]imidazo[1,2-d][1,4]oxazepine 194 and 4-(4,4,5,5-tetramethyl-1,3,2-dioxaborolan-2-yl)-1H-pyrazole provided 217 in 78% yield. LS/MS (ESI+): m/z 362 (M+H). 1H NMR (400 MHz, DMSO) δ 13.02 (s, 1H), 8.37 (d, J=8.4, 1H), 8.29 (s, 1H), 8.00 (s, 1H), 7.54-7.38 (m, 1H), 7.30 (t, J=12.5, 1H), 5.91 (dt, J=13.2, 6.6, 1H), 4.57-4.46 (m, 4H), 1.50 (d, J=6.6, 6H)

Example 218

3-(2-(1-(2,2,2-trifluoroethyl)-1H-1,2,4-triazol-5-yl)-5,6-dihydrobenzo[f]imidazo[1,2-d][1,4]oxazepin-10-yl)pyridin-2(1H)-one 218

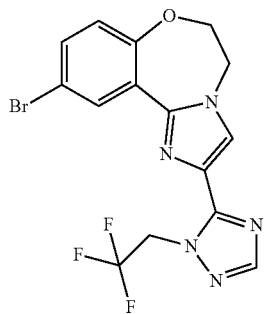 [SMILES: FC(F)(F)Cn1ncnc1-c1cn2c(n1)-c1cc(Br)ccc1OCC2]

Step 1

Following the procedure for 187,10-bromo-2-iodo-5,6-dihydrobenzo[f]imidazo[1,2-d][1,4]oxazepine and trifluoroethyltriazole (1-(2,2,2-trifluoroethyl)-1H-1,2,4-triazole) were reacted. The crude mixture was purified by column chromatography on silica gel eluting with EtOAc prior to concentrating under reduced pressure, dissolving in DMF, and purifying by reverse phase HPLC to provide 10-bromo-2-(1-(2,2,2-trifluoroethyl)-1H-1,2,4-triazol-5-yl)-5,6-dihydrobenzo[f]imidazo[1,2-d][1,4]oxazepine (0.027 g, 2%). 1H NMR (400 MHz, DMSO) δ 8.48 (d, J=2.6, 1H), 8.10 (d, J=5.5, 2H), 7.49 (dd, J=8.7, 2.6, 1H), 7.04 (t, J=7.5, 1H), 5.86 (q, J=8.8, 2H), 4.54 (dt, J=7.4, 3.7, 4H). MS (ESI(+)): m/z 413.9 (M+H)

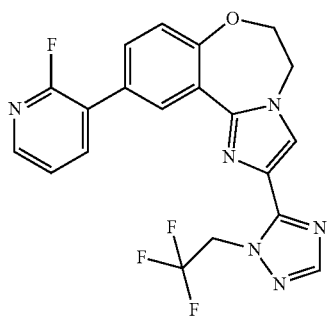 [SMILES: Fc1ncccc1-c1ccc2c(c1)-c1nc(-c3ncnn3CC(F)(F)F)cn1CCO2]

Step 2

Following the procedure for 203, 10-bromo-2-(1-(2,2,2-trifluoroethyl)-1H-1,2,4-triazol-5-yl)-5,6-dihydrobenzo[f]imidazo[1,2-d][1,4]oxazepine was reacted with 2-fluoropyridin-3-ylboronic acid to give 10-(2-fluoropyridin-3-yl)-2-(1-(2,2,2-trifluoroethyl)-1H-1,2,4-triazol-5-yl)-5,6-dihydrobenzo[f]imidazo[1,2-d][1,4]oxazepine (0.108 g, 55%), 1H NMR (400 MHz, DMSO) δ 8.71 (t, J=2.0, 1H), 8.57-7.83 (m, 4H), 7.80-7.39 (m, 2H), 7.22 (d, J=8.5, 1H), 5.88 (q, J=8.8, 2H), 4.79-4.38 (m, 4H). MS (ESI(+)): m/z 431.1 (M+H), which was hydrolyzed with HCl to give 218 (0.072 g, 72%). 1H NMR (400 MHz, DMSO) δ 11.85 (s, 1H), 8.78 (d, J=2.3, 1H), 8.09 (d, J=2.8, 2H), 7.69 (ddd, J=8.9, 7.7, 2.2, 2H), 7.36 (t, J=23.8, 1H), 7.08 (d, J=8.6, 1H), 6.30 (t, J=6.7, 1H), 5.91 (q, J=8.8, 2H), 4.56 (dd, J=13.5, 5.5, 4H). MS (ESI(+)): m/z 429.1 (M+H)

Example 219

5-(2-(1-isopropyl-1H-1,2,4-triazol-5-yl)-5,6-dihydrobenzo[f]imidazo[1,2-d][1,4]oxazepin-9-yl)pyridin-2-amine 219

Following the same procedure as for 182, 9-bromo-2-(1-isopropyl-1H-1,2,4-triazol-5-yl)-5,6-dihydrobenzo[f]imidazo[1,2-d][1,4]oxazepine 194 and 5-(4,4,5,5-tetramethyl-1,3,2-dioxaborolan-2-yl)pyridin-2-amine provided 219 in 62% yield. LS/MS (ESI+): m/z 388 (M+H). 1H NMR (400 MHz, DMSO) δ 8.42 (d, J=8.4, 1H), 8.33 (d, J=2.4, 1H), 7.93 (d, J=6.5, 2H), 7.77 (dd, J=8.7, 2.5, 1H), 7.41 (dd, J=8.5, 1.9, 1H), 7.26 (d, J=1.8, 1H), 6.53 (d, J=8.6, 1H), 6.16 (s, 2H), 5.92 (dt, J=13.2, 6.6, 1H), 4.60-4.44 (m, 4H), 1.50 (d, J=6.6, 6H)

Example 220

2-(4-(2-(1-isopropyl-3-methyl-1H-1,2,4-triazol-5-yl)-5,6-dihydrobenzo[f]imidazo[1,2-d][1,4]oxazepin-9-yl)-1H-imidazol-1-yl)ethanol 220

1-[2-(Tetrahydro-pyran-2-yloxy)-ethyl]-4-tributylstannanyl-1H-imidazole (0.690 g, 0.00142 mol) was added to a solution of 8-Bromo-2-(2-isopropyl-5-methyl-2H-[1,2,4]triazol-3-yl)-4,5-dihydro-6-oxa-1,3a-diaza-benzo[e]azulene (0.293 g, 0.000755 mol) in acetonitrile (4.5 mL, 0.086 mol). The mixture was thoroughly degassed with nitrogen and tetrakis(triphenylphosphine)palladium(0) (0.0872 g, 0.0000755 mol) was added. The vial was sealed and heated in the microwave to 140° C. for 30 minutes. Methylene chloride and water were added and the mixture was filtered through celite. The aqueous phase was extracted 3× with methylene chloride. The organic phases were combined, dried with MgSO4 and concentrated.

The crude was redissolved in methylene chloride (8.0 mL, 0.12 mol). Hydrogen chloride (4N in dioxane, 0.47 mL, 0.00189 mol) was added dropwise and the reaction was stirred at room temperature for 1 h. The reaction was concentrated in vacuo. Methylene chloride and saturated sodium carbonate were added causing the product to precipitate in the aqueous phase. The aqueous phase was filtered and the solid was purified by reverse-phase HPLC to give 220 (42 mg) as a colorless solid. MS(ESI+) 420.2

Example 221

2-(2-(9-(1-(2-hydroxy-2-methylpropyl)-1H-pyrazol-4-yl)-5,6-dihydrobenzo[f]imidazo[1,2-d][1,4]oxazepin-2-yl)-1H-imidazol-1-yl)-N-methylacetamide 221

Following the procedure for 214, 2-(2-(9-bromo-5,6-dihydrobenzo[f]imidazo[1,2-d][1,4]oxazepin-2-yl)-1H-imidazol-1-yl)-N-methylacetamide and 2-methyl-1-(4-(4,4,5,5-tetramethyl-1,3,2-dioxaborolan-2-yl)-1H-pyrazol-1-yl)propan-2-ol were reacted under Suzuki conditions to give 221. MS: (ESI+)=462.2. 1H NMR (400 MHz, DMSO) δ 8.38 (d, J=8.4 Hz, 1H), 8.18 (s, 1H), 8.06-7.99 (m, 1H), 7.96 (s, 1H), 7.69 (s, 1H), 7.33 (dd, J=8.4, 1.8 Hz, 1H), 7.26 (d, J=1.7 Hz, 1H), 7.11 (d, J=1.1 Hz, 1H), 6.90 (d, J=1.1 Hz, 1H), 5.18 (s, 2H), 4.76 (s, 1H), 4.49 (s, 4H), 4.04 (s, 2H), 2.65 (d, J=4.6 Hz, 3H), 1.10 (s, 6H).

Example 222

N,N-diethyl-2-(4-(2-(1-isopropyl-1H-1,2,4-triazol-5-yl)-5,6-dihydrobenzo[f]imidazo[1,2-d][1,4]oxazepin-9-yl)-1H-pyrazol-1-yl)ethanamine 222

A 5 mL microwave vial was charged with 9-bromo-2-(1-isopropyl-1H-1,2,4-triazol-5-yl)-5,6-dihydrobenzo[f]imidazo[1,2-d][1,4]oxazepine (347 mg, 0.928 mmol), N,N-diethyl-2-(4-(4,4,5,5-tetramethyl-1,3,2-dioxaborolan-2-yl)-1H-pyrazol-1-yl)ethanamine (340 mg, 1.16 mmol), 2 M potassium carbonate in water (0.9 mL, 2 mmol), and acetonitrile (1.52 g, 37.1 mmol) and 1,1-bis(diphenylphosphino)ferrocenepalladium(II) chloride (45.4 mg, 0.056 mmol) was added prior to sealing the vial. The reaction was placed on the microwave at 140° C. for 10 minutes. The cooled reaction mixture was diluted with ethyl acetate and water and partitioned. The organic layer was washed with brine and, dried over sodium sulfate, concentrated in vacuo and purified by HPLC to give 222 (140 mg, 33% yield, M+1 461.6)

Example 223

5-(2-(1-isopropyl-1H-1,2,4-triazol-5-yl)-5,6-dihydrobenzo[f]imidazo[1,2-d][1,4]oxazepin-9-yl)pyrimidin-2-amine 223

Following the same procedure as for 182, 9-bromo-2-(1-isopropyl-1H-1,2,4-triazol-5-yl)-5,6-dihydrobenzo Wimidazo[1,2-d][1,4]oxazepine 194 and 5-(4,4,5,5-tetramethyl- 1,3,2-dioxaborolan-2-yl)pyrimidin-2-amine provided 223 in 73% yield. LS/MS (ESI+): m/z 389 (M+H). 1H NMR (400 MHz, DMSO) δ 8.66 (s, 1H), 8.45 (d, J=8.4, 1H), 7.93 (d, J=9.7, 2H), 7.46 (dd, J=8.5, 1.9, 1H), 7.35 (d, J=1.8, 1H), 6.86 (s, 1H), 5.91 (hept, J=6.4, 1H), 4.61-4.44 (m, 4H), 1.50 (d, J=6.6, 6H)

Example 224

9-(1H-imidazol-5-yl)-2-(1-isopropyl-1H-1,2,4-triazol-5-yl)-5,6-dihydrobenzo[f]imidazo[1,2-d][1,4] oxazepine 224

To a solution of 242 (120 mg, 0.27 mmol) in dioxane (4 mL) was added a solution of hydrochloride in dioxane (0.34 mL, 1.35 mmol). The whole was heated at 60° C. for 2 h, cooled to room temperature and concentrated. To the mixture was added sat. sodium bicarbonate and extracted with EtOAc. Dried organics over sodium sulfate and purified concentrated residue by pre-TLC (DCM/MeOH=8:1) to give 224 as a yellow solid (36 mg, yield: 37%). 1H NMR (DMSO-d6, 400 MHz): δ 12.29 (s, 1H), 8.37 (d, J=8.4 Hz, 1H), 7.91 (s, 2H), 7.75 (s, 1H), 7.69 (s, 1H), 7.55 (d, J=8.0 Hz, 1H), 7.45 (s, 1H), 5.94-5.88 (m, 1H), 4.53 (br s, 4H), 1.49 (d, J=6.4 Hz, 6H). MS: (ESI, m/z)=362 [M+H]+

Example 225

2-(1-isopropyl-1H-1,2,4-triazol-5-yl)-9-(1-(2-(methylsulfonyl)ethyl)piperidin-4-yl)-5,6-dihydrobenzo[f] imidazo[1,2-d][1,4]oxazepine 225

Following the procedure for 152, 2-(2-isopropyl-2H-[1,2,4]triazol-3-yl)-8-piperidin-4-yl-4,5-dihydro-6-oxa-1,3a-diaza-benzo[e]azulene trifluoroacetic acid salt was reacted with vinyl sulfone to give 225 as a white solid. ¹H NMR δ (ppm)(DMSO-d): 8.27 (1 H, d, J=8.29 Hz), 7.86-7.84 (2 H, m), 7.00 (1 H, dd, J=8.37, 1.76 Hz), 6.85 (1 H, d, J=1.70 Hz), 5.88-5.78 (1 H, m), 4.44 (4 H, q, J=5.99 Hz), 3.26 (3 H, m), 3.00 (3 H, s), 2.95 (2 H, d, J=11.00 Hz), 2.68 (2 H, t, J=6.79 Hz), 2.02 (2 H, t, J=11.39 Hz), 1.72 (2 H, d, J=12.62 Hz), 1.57 (2 H, qd, J=12.27, 3.58 Hz), 1.42 (6 H, d, J=6.60 Hz). LCMS: RT=2.68 min, M+H+=485

Example 226

2-(4-(2-(1-isopropyl-1H-1,2,4-triazol-5-yl)-5,6-dihydrobenzo[f]imidazo[1,2-d][1,4]oxazepin-9-yl)piperidin-1-yl)acetamide 226

Following the procedure for 143, 2-(2-isopropyl-2H-[1,2,4]triazol-3-yl)-8-piperidin-4-yl-4,5-dihydro-6-oxa-1,3a-diaza-benzo[e]azulene trifluoroacetic acid salt was reacted with 2-bromo acetamide to give 226 as a white solid. ¹H NMR δ (ppm)(DMSO-d): 8.27 (1 H, d, J=8.27 Hz), 7.84 (2 H, d, J=2.70 Hz), 7.15 (1 H, s), 7.06 (1 H, s), 7.01 (1 H, d, J=8.43 Hz), 6.87 (1 H, s), 5.87-5.78 (1 H, m), 4.44 (4 H, d, J=6.92 Hz), 2.90-2.78 (4 H, m), 2.15-2.06 (2 H, m), 1.68 (5 H, s), 1.42 (6 H, d, J=6.59 Hz). LCMS: RT=2.57 min, M+H+=436

Example 227

2-hydroxy-1-(4-(2-(1-isopropyl-1H-1,2,4-triazol-5-yl)-5,6-dihydrobenzo[f]imidazo[1,2-d][1,4]oxazepin-9-yl)piperidin-1-yl)-2-methylpropan-1-one 227

A solution of 2-(2-isopropyl-2H-[1,2,4]triazol-3-yl)-8-piperidin-4-yl-4,5-dihydro-6-oxa-1,3a-diaza-benzo[e]azulene trifluoroacetic acid salt (350 mg, 0.71 mmol), 2-hydroxy-isobutyric acid (111 mg, 1.07 mmol), EDCI (327 mg, 1.7 mmol), HOBt (230 mg, 1.7 mmol) and DIPEA (0.36 mL, 2.13 mmol) was stirred at RT for 5 h before the addition of saturated aqueous sodium bicarbonate. The resultant mixture was extracted with DCM (2×30 mL), the combined extracts washed with brine then dried (MgSO4), filtered and concentrated in vacuo. The resultant residue was subjected to flash chromatography (SiO2, gradient 0 to 5% MeOH in DCM) then freeze dried to give 227 as a white solid (141 mg, 43%). ¹H NMR δ (ppm) (DMSO-d): 8.31 (1 H, d, J=8.29 Hz), 7.82 (1 H, s), 7.78 (1 H, s), 7.03 (1 H, d, J=8.38 Hz), 6.90 (1 H, s), 5.85-5.77 (1 H, m), 4.69 (2 H, d, J=13.25 Hz), 4.48 (4 H, t, J=7.99 Hz), 2.91-2.74 (4 H, m), 1.85 (2 H, d, J=13.04 Hz), 1.63-1.49 (2 H, m), 1.49 (6 H, d, J=6.64 Hz), 1.37 (6 H, s). LCMS: RT=3.92 min, M+H+=465

Example 228

(2S)-2-hydroxy-1-(3-(4-(2-(1-isopropyl-3-methyl-1H-1,2,4-triazol-5-yl)-5,6-dihydrobenzo[f]imidazo [1,2-d][1,4]oxazepin-9-yl)-1H-pyrazol-1-yl)azetidin-1-yl)propan-1-one 228

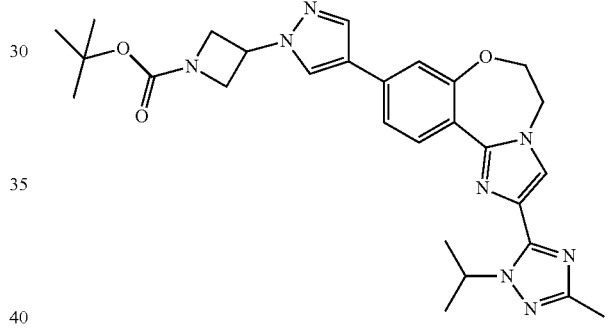

8-Bromo-2-(2-isopropyl-5-methyl-2H-[1,2,4]triazol-3-yl)-4,5-dihydro-6-oxa-1,3a-diaza-benzo[e]azulene was reacted under palladium catalyzed, Suzuki conditions with 3-[4-(4,4,5,5-Tetramethyl-[1,3,2]dioxaborolan-2-yl)-pyrazol-1-yl]-azetidine-1-carboxylic acid tert-butyl ester to give 3-{4-[2-(2-Isopropyl-5-methyl-2H-[1,2,4]triazol-3-yl)-4,5-dihydro-6-oxa-1,3a-diaza-benzo[e]azulen-8-yl]-pyrazol-1-yl}-azetidine-1-carboxylic acid tert-butyl ester. MS(ESI+) 531.2.

3-{4-[2-(2-Isopropyl-5-methyl-2H-[1,2,4]triazol-3-yl)-4,5-dihydro-6-oxa-1,3a-diaza-benzo[e]azulen-8-yl]-pyrazol-1-yl}-azetidine-1-carboxylic acid tert-butyl ester was reacted with acid to give 8-(1-Azetidin-3-yl-1H-pyrazol-4-yl)-2-(2-isopropyl-5-methyl-2H-[1,2,4]triazol-3-yl)-4,5-dihydro-6-oxa-1,3a-diaza-benzo[e]azulene. MS(ESI+) 431.2.

8-(1-Azetidin-3-yl-1H-pyrazol-4-yl)-2-(2-isopropyl-5-methyl-2H-[1,2,4]triazol-3-yl)-4,5-dihydro-6-oxa-1,3a-diaza-benzo[e]azulene was coupled with DIPEA, HATU, and L-lactic acid to give 228. MS(ESI+) 503.2. 1H NMR (400 MHz, DMSO) δ 8.45 (d, J=1.7, 1H), 8.37 (d, J=8.4, 1H), 8.12 (s, 1H), 7.89 (s, 1H), 7.42 (dd, J=8.4, 1.7, 1H), 7.32 (d, J=1.7, 1H), 5.92-5.74 (m, 1H), 5.34-5.25 (m, 1H), 5.21 (t, J=5.5, 1H), 4.84-4.66 (m, 1H), 4.60-4.53 (m, 1H), 4.52 (s, 4H), 4.40-4.31 (m, 1H), 4.26-4.09 (m, 2H), 2.25 (s, 3H), 1.47 (d, J=6.6, 6H), 1.22 (d, J=6.7, 3H)

Example 229

2-(4-(2-(3-amino-1-isopropyl-1H-1,2,4-triazol-5-yl)-5,6-dihydrobenzo[f]imidazo[1,2-d][1,4]oxazepin-9-yl)-1H-imidazol-1-yl)ethanol 229

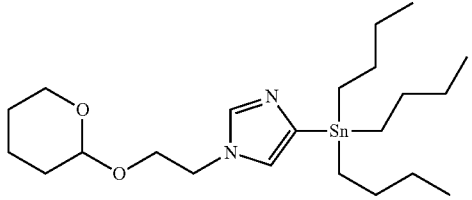 [SMILES: CCC[CH2][Sn]([CH2]CCC)([CH2]CCC)[c]1cn(CCOC2CCCCO2)cn1]

5-(8-Bromo-4,5-dihydro-6-oxa-1,3a-diaza-benzo[e]azulen-2-yl)-1-isopropyl-1H-[1,2,4]triazol-3-ylamine was reacted with 1-(2-(tetrahydro-2H-pyran-2-yloxy)ethyl)-4-(tributylstannyl)-1H-imidazole to give 229 after THP-removal with aqueous HCl purification by reverse phase HPLC (49 mg). LCMS: 421.2

Example 230

2-(3-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)azetidin-1-yl)ethanol 230

To a solution of 8-(1-Azetidin-3-yl-1H-pyrazol-4-yl)-2-(2-isopropyl-5-methyl-2H-[1,2,4]triazol-3-yl)-4,5-dihydro-6-oxa-1,3a-diaza-benzo[e]azulene in methylene chloride was added (tert-butyl-dimethyl-silanyloxy)-acetaldehyde and acetic acid followed by sodium triacetoxyborohydride. The reaction was stirred at room temperature for about 5 hours and quenched with 1N NaOH. Methylene chloride was added and the mixture was extracted 3 times with methylene chloride. The organic phases were combined, dried with MgSO4 and concentrated. The mixture was purified by flash chromatography (0-10% MeOH in DCM) to afford 8-(1-{1-[2-(tert-Butyl-dimethyl-silanyloxy)-ethyl]-azetidin-3-yl}-1H-pyrazol-4-yl)-2-(2-isopropyl-5-methyl-2H-[1,2,4]triazol-3-yl)-4,5-dihydro-6-oxa-1,3a-diaza-benzo[e]azulene MS(ESI+) 589.3, which was treated with acid to give 230. 1H NMR (400 MHz, DMSO) δ 8.45 (s, 1H), 8.36 (d, J=8.4, 1H), 8.03 (s, 1H), 7.88 (s, 1H), 7.41 (d, J=8.3, 1H), 7.32 (d, J=1.6, 1H), 5.90-5.78 (m, 1H), 4.97 (quin, J=6.9, 1H), 4.52 (s, 4H), 4.47 (t, J=5.4, 1H), 3.73 (t, J=7.6, 2H), 3.47-3.37 (m, 4H), 2.58 (t, J=7.7, 2H), 2.25 (s, 3H), 1.47 (d, J=6.6, 6H)

Example 231

5-(5,6-dihydrobenzo[f]imidazo[1,2-d][1,4]oxazepin-2-yl)-1-isopropyl-1H-1,2,4-triazol-3-amine 231

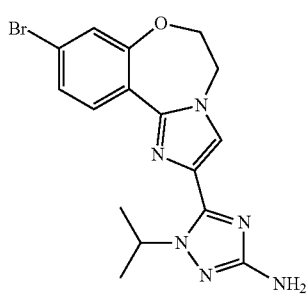 [SMILES: CC(C)n1nc(N)nc1-c1cn2c(n1)-c1ccc(Br)cc1OCC2]

5-(8-Bromo-4,5-dihydro-6-oxa-1,3a-diaza-benzo[e]azulen-2-yl)-1-isopropyl-1H-[1,2,4]triazol-3-ylamine was hydrogenated in the presence of 10% Pd on carbon to give 231 after reverse phase HPLC. LCMS: 311.2.

Example 232

2-(1-isopropyl-3-methyl-1H-1,2,4-triazol-5-yl)-5,6-dihydrobenzo[f]imidazo[1,2-d][1,4]oxazepine 232

A 25-mL round-bottomed flask was charged with 9-bromo-2-(1-isopropyl-3-methyl-1H-1,2,4-triazol-5-yl)-5,6-dihydrobenzo[f]imidazo[1,2-d][1,4]oxazepine 411 (1.0 g, 2.6 mmol), 4,4,4',4',5,5,5',5'-octamethyl-2,2'-bi(1,3,2-dioxaborolane) (bispinacolato bisboronate, 0.719 g, 2.83 mmol), potassium acetate (0.76 g, 7.7 mmol) and [1,1'-bis(diphenylphosphino)ferrocene]dichloropalladium(II) in complex with dichloromethane (1:1) (0.21 g, 0.26 mmol) under a nitrogen atmosphere. The combined mixture was diluted with dimethylsulfoxide (8.5 mL) and heated at 85° C. for 12 h. The reaction mixture was then cooled to room temperature and diluted with water and dichloromethane. The phases were partitioned and the aqueous portion was extracted thrice with dichloromethane. The organic layers were combined, dried over MgSO4, filtered and concentrated. The residue was purified by flash column chromatography to afford 232 as a protio-dehalogenated byproduct (66 mg, 7% yield). MS(ESI+) m/z 310.2 (M+H+), calcd. 310.4. 1H NMR (500 MHz, DMSO) δ 8.41 (dd, J=8.0, 1.6 Hz, 1H), 7.89 (s, 1H), 7.33 (dd, J=11.0, 4.3 Hz, 1H), 7.16 (t, J=7.6 Hz, 1H), 7.07 (d, J=8.1 Hz, 1H), 5.83 (dt, J=13.0, 6.6 Hz, 1H), 4.51 (q, J=5.6 Hz, 4H), 2.26 (s, 3H), 1.46 (d, J=6.6 Hz, 6H)

Example 233

2-(1-Isopropyl-1H-1,2,4-triazol-5-yl)-5,6-dihydroimidazo[1,2-d]pyrido[4,3-f][1,4]oxazepine 233

A mixture of 10-chloro-2-(1-isopropyl-1H-1,2,4-triazol-5-yl)-5,6-dihydroimidazo[1,2-d]pyrido[4,3-f][1,4]oxazepine (82.7 mg, 0.250 mmol), palladium on carbon 10% (0.1:0.9, Palladium:carbon black, 83 mg) and triethylamine (0.104 mL, 0.750 mmol) in 5.0 ml of ethanol and 5.0 ml of tetrahydrofuran (5.0 mL, 62 mmol) was hydrogenated at 1 atm for 3 hours. The catalyst was filtered out, the filtrate concentrated, the residue purified by RP HPLC, acetonitrile gradient to give 233. Yield 32 mg (43%). MS(ESI+): 297.2. 1H NMR (500 MHz, DMSO) δ 8.40 (s, 1H), 8.30 (d, J=5.2, 1H), 8.25 (d, J=5.2, 1H), 8.08 (s, 1H), 7.94 (s, 1H), 5.87 (dt, J=13.0, 6.6, 1H), 4.60 (dd, J=13.1, 5.5, 4H), 1.49 (d, J=6.6, 6H).

Example 234

2-(1-Isopropyl-1H-1,2,4-triazol-5-yl)-10-(4-methylpiperazin-1-yl)-5,6-dihydroimidazo[1,2-d]pyrido[4,3-f][1,4]oxazepine 234

A mixture of 10-chloro-2-(1-isopropyl-1H-1,2,4-triazol-5-yl)-5,6-dihydroimidazo[1,2-d]pyrido[4,3-f][1,4]oxazepine (132 mg, 0.400 mmol), 1-methyl-piperazine (88.7 uL, 0.800 mmol), palladium acetate (44.9 mg, 0.200 mmol), 2,8,9-tri-i-butyl-2,5,8,9-tetraaza-1-phosphabicyclo[3.3.3]undecane (71.0 uL, 0.200 mmol) and Sodium tert-butoxide (38.4 mg, 0.400 mmol) in 1,4-Dioxane (8.0 mL) was degassed. The reaction was microwaved on 200 watts, 120° C. for 30 minutes. The mixture was filtered and the filtrate concentrated in vacuum. The residue was partitioned between water and ethyl acetate. The organic extracts were washed with water, brine and dried over MgSO4 and concentrated in vacuum. The residue was purified on 4 g silica column using 5-10% gradient of methanol containing 1% of ammonia in DCM to give 234. Yield 50 mg (30%). MS: 395.2. 1H NMR (500 MHz, DMSO) δ 8.04 (s, 1H), 8.03 (s, 1H), 7.94 (s, 1H), 7.63 (s, 1H), 5.69 (dt, J=13.3, 6.6, 1H), 4.61-4.53 (m, 2H), 4.49-4.41 (m, 2H), 3.41 (s, 4H), 2.45 (s, 4H), 2.23 (s, 3H), 1.50 (d, J=6.6, 6H).

Example 235

2-(1-isopropyl-3-methyl-1H-1,2,4-triazol-5-yl)-9-(pyrimidin-5-yl)-5,6-dihydrobenzo[f]imidazo[1,2-d][1,4]oxazepine 235

8-Bromo-2-(2-isopropyl-5-methyl-2H-[1,2,4]triazol-3-yl)-4,5-dihydro-6-oxa-1,3a-diaza-benzo[e]azulene was reacted under palladium catalyzed, Suzuki conditions with 5-(4,4,5,5-Tetramethyl-[1,3,2]dioxaborolan-2-yl)-pyrimidine to give 235. MS(ESI+) 388.2. 1H NMR (500 MHz, DMSO) δ 9.24-9.20 (m, 3H), 8.54 (d, J=8.4, 1H), 7.96 (s, 1H), 7.65 (dd, J=8.4, 1.4, 1H), 7.58 (d, J=1.2, 1H), 5.96-5.71 (m, 1H), 4.57 (s, 4H), 2.26 (s, 3H), 1.48 (d, J=6.6, 6H)

Example 236

9-(5-fluoropyridin-3-yl)-2-(1-isopropyl-3-methyl-1H-1,2,4-triazol-5-yl)-5,6-dihydrobenzo[f]imidazo[1,2-d][1,4]oxazepine 236

8-Bromo-2-(2-isopropyl-5-methyl-2H-[1,2,4]triazol-3-yl)-4,5-dihydro-6-oxa-1,3a-diaza-benzo[e]azulene was reacted under palladium catalyzed, Suzuki conditions with 3-Fluoro-5-(4,4,5,5-tetramethyl-[1,3,2]dioxaborolan-2-yl)-pyridine to give 236. MS(ESI+) 405.2. 1H NMR (500 MHz, DMSO) δ 8.89 (s, 1H), 8.61 (d, J=2.6, 1H), 8.52 (d, J=8.4, 1H), 8.19-8.14 (m, 1H), 7.96 (s, 1H), 7.63 (dd, J=8.3, 1.3, 1H), 7.54 (d, J=1.4, 1H), 5.89-5.80 (m, 1H), 4.57 (s, 4H), 2.26 (s, 3H), 1.48 (d, J=6.6, 6H)

Example 237

2-(3-amino-1-isopropyl-1H-1,2,4-triazol-5-yl)-5,6-dihydrobenzo[f]imidazo[1,2-d][1,4]oxazepine-9-carbonitrile 237

5-(8-Bromo-4,5-dihydro-6-oxa-1,3a-diaza-benzo[e]azulen-2-yl)-1-isopropyl-1H-[1,2,4]triazol-3-ylamine was reacted with zinc cyanide to give 237 after reverse phase HPLC. LCMS: 336

Example 238

N-(5-(2-(1-isopropyl-3-methyl-1H-1,2,4-triazol-5-yl)-5,6-dihydrobenzo[f]imidazo[1,2-d][1,4]oxazepin-9-yl)pyridin-2-yl)acetamide 238

8-Bromo-2-(2-isopropyl-5-methyl-2H-[1,2,4]triazol-3-yl)-4,5-dihydro-6-oxa-1,3a-diaza-benzo[e]azulene was reacted under palladium catalyzed, Suzuki conditions with N-[5-(4,4,5,5-Tetramethyl-[1,3,2]dioxaborolan-2-yl)-pyridin-2-yl]-acetamide to give 238. MS(ESI+) 444.2. 1H NMR (500 MHz, DMSO) δ 10.63 (s, 1H), 8.72 (s, 1H), 8.48 (d, J=8.4, 1H), 8.17 (s, 2H), 7.93 (s, 1H), 7.55 (dd, J=8.4, 1.4, 1H), 7.43 (d, J=1.4, 1H), 5.89-5.80 (m, 1H), 4.55 (s, 4H), 2.26 (s, 3H), 2.12 (s, 3H), 1.47 (d, J=6.6, 6H)

Example 239

9-Chloro-2-(1-isopropyl-1H-1,2,4-triazol-5-yl)-5,6-dihydrobenzo[f][1,2,4]triazolo[1,5-d][1,4]oxazepine 239

Step 1: Methyl-9-chloro-5,6-dihydrobenzo[f][1,2,4]triazolo[1,5-d][1,4]oxazepine-2-carboxylate

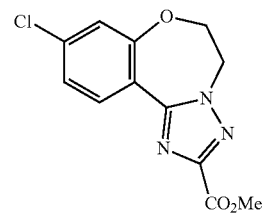 [SMILES: COC(=O)c1nc2n(n1)CCOc1cc(Cl)ccc1-2]

To methyl 1-(2-(2-bromo-5-chlorophenoxy)ethyl)-1H-1,2,4-triazole-3-carboxylate in acetonitrile (10.00 mL, 191.5 mmol) was added cesium carbonate (0.9036 g, 2.773 mmol) in a microwave flask with stirbar. The mixture was degassed by bubbling nitrogen by syringe. Tetraethylammonium chloride (0.2298 g, 1.387 mmol), palladium acetate (0.1556 g, 0.6933 mmol), and copper(I) iodide (0.02641 g, 0.1387 mmol) were added, respectively, and the vessel was sealed by crimping. Next, the flask was heated while stirring to 165° C. for 18 min in the microwave. Once the reaction was cooled to room temperature, the crude was filtered through celite, concentrated, and purified by silica gel chromatography, to give Methyl-9-chloro-5,6-dihydrobenzo[f][1,2,4]triazolo[1,5-d][1,4]oxazepine-2-carboxylate in 15% yield. 1H NMR (400 MHz, CDCl3) δ 8.59 (d, J=2.6 Hz, 1H), 7.34 (dd, J=8.8, 2.7 Hz, 1H), 7.04 (d, J=8.8 Hz, 1H), 4.75 (m, 2H), 4.53 (m, 2H), 4.05 (s, 3H). LRMS m/z Calcd. for C12H10ClN3O3: 279.04107, found: 280.0 [M+1].

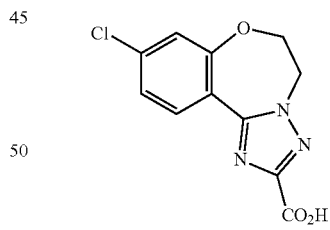

Step 2

Methyl-9-chloro-5,6-dihydrobenzo[f][1,2,4]triazolo[1,5-d][1,4]oxazepine-2-carboxylate (0.144 g, 0.515 mmol) was dissolved in 3:2:1 THF:MeOH:H2O (5.0 mL), and treated with 4 N aqueous LiOH (0.644 mL). The mixture was stirred for 30 min at 25° C. The reaction was quenched with 1 N aq. HCl (10 mL) and the solution was extracted with EtOAc (3×20 mL). The combined organic extracts were dried with Na2SO4 and concentrated in vacuo to give 9-Chloro-5,6-dihydrobenzo[f][1,2,4]triazolo[1,5-d][1,4]oxazepine-2-carboxylic acid (89% yield)

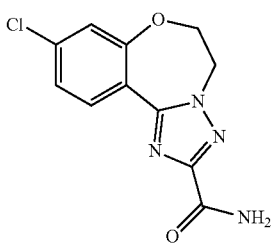 [SMILES: NC(=O)c1nc2n(n1)CCOc1cc(Cl)ccc1-2]

Step 3

To 9-Chloro-5,6-dihydrobenzo[f][1,2,4]triazolo[1,5-d][1,4]oxazepine-2-carboxylic acid (0.137 g, 0.515 mmol) in N,N-dimethylformamide (1.20 mL, 15.4 mmol) was added N,N,N',N'-tetramethyl-O-(7-azabenzotriazol-1-yl)uronium hexafluorophosphate (0.587 g, 1.54 mmol) and 6-chloro-1-hydroxybenzotriazole (0.262 g, 1.54 mmol). The mixture was stirred vigorously, and NH4Cl (0.220 g, 4.12 mmol) was added. After 10 minutes, N,N-diisopropylethylamine (0.359 mL, 2.06 mmol) was added. The reaction was stirred at room temperature for 3 hours. Then, the reaction was concentrated, taken to dryness, and washed with water. The crude product was purified by a silica gel plug, eluting with DCM/MeOH, and then by reverse phase HPLC to give 9-Chloro-5,6-dihydrobenzo[f][1,2,4]triazolo[1,5-d][1,4]oxazepine-2-carboxamide (5.3% yield)

Step 4

To 9-Chloro-5,6-dihydrobenzo[f][1,2,4]triazolo[1,5-d][1,4]oxazepine-2-carboxamide (0.0053 g, 0.020 mmol) in toluene (0.160 mL, 1.50 mmol) was added 1,1-dimethoxy-N,N-dimethylmethanamine (0.0150 mL, 0.113 mmol), and the mixture was heated in a sealed flask to 102° C. for 2 hours while stirring. Next, the reaction mixture was cooled and concentrated to dryness, and isopropylhydrazine hydrochloride (0.00376 g, 0.0340 mmol) and acetic acid (0.0938 g, 1.56 mmol) were added and the reaction was sealed and heated to 102° C. overnight while stirring. Then, the reaction was concentrated to dryness and taken up in DMF, and purification by reverse phase HPLC gave 239 in 98% yield. 1H NMR (500 MHz, CDCl3) δ 8.56 (d, J=2.6 Hz, 1H), 8.02 (s, 1H), 7.35 (dd, J=8.8, 2.6 Hz, 1H), 7.06 (d, J=8.8 Hz, 1H), 5.84-5.66 (m, 1H), 4.84-4.70 (m, 2H), 4.62-4.47 (m, 2H), 1.61 (s, 6H). LRMS m/z Calcd. for C15H15ClN6O: 330.09959. found: 331.1 [M+1].

Example 240

9-bromo-2-(1-isopropyl-3-(methylthio)-1H-1,2,4-triazol-5-yl)-5,6-dihydrobenzo[f]imidazo[1,2-d][1,4]oxazepine 240

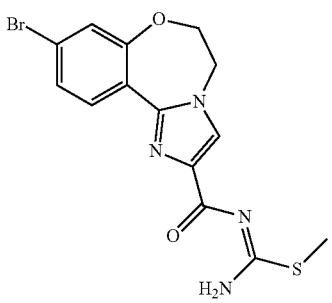 [SMILES: CS/C(N)=N/C(=O)c1cn2c(n1)-c1ccc(Br)cc1OCC2]

1-(8-Bromo-4,5-dihydro-6-oxa-1,3a-diaza-benzo[e]azulene-2-carbonyl)-2-methyl-isothiourea (27 mg, 0.068 mmol) was heated with isopropylhydrazine hydrochloride (23 mg, 0.20 mmol) in acetic acid (0.9 mL) at 100° C. overnight. The mixture was concentrated and the crude residue purified by reverse-phase HPLC to give 240. LCMS EI: 422.1

Example 241

5-(9-(5-fluoropyridin-3-yl)-5,6-dihydrobenzo[f]imidazo[1,2-d][1,4]oxazepin-2-yl)-1-isopropyl-1H-1,2,4-triazol-3-amine 241

5-(8-Bromo-4,5-dihydro-6-oxa-1,3a-diaza-benzo[e]azulen-2-yl)-1-isopropyl-1H-[1,2,4]triazol-3-ylamine was reacted with 3-fluoro-5-(4,4,5,5-tetramethyl-1,3,2-dioxaborolan-2-yl)pyridine were reacted under Suzuki palladium coupling conditions. The crude product was purified by reverse phase HPLC to give 241. LCMS: 406.2

Example 242

2-(1-isopropyl-1H-1,2,4-triazol-5-yl)-9-(1-(tetrahydro-2H-pyran-2-yl)-1H-imidazol-5-yl)-5,6-dihydrobenzo[f]imidazo[1,2-d][1,4]oxazepine 242

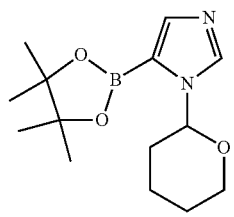 [SMILES: CC1(C)OB(c2cncn2C2CCCCO2)OC1(C)C]

1-(Tetrahydro-2H-pyran-2-yl)-5-(4,4,5,5-tetramethyl-1,3,2-dioxaborolan-2-yl)-1H-imidazole was prepared by hydrogen with palladium reduction of 2-chloro-1-(tetrahydro-2H-pyran-2-yl)-5-(4,4,5,5-tetramethyl-1,3,2-dioxaborolan-2-yl)-1H-imidazole.

To a mixture of 9-bromo-2-(1-isopropyl-1H-1,2,4-triazol-5-yl)-5,6-dihydrobenzo[f]imidazo[1,2-d][1,4]oxazepine 250 mg, 0.67 mmol) and 1-(tetrahydro-2H-pyran-2-yl)-5-(4,4,5,5-tetramethyl-1,3,2-dioxaborolan-2-yl)-1H-imidazole (204 mg, 0.73 mmol) in dry DMF (2.5 mL) under nitrogen was added CsF (254 mg, 1.68 mmol), CuI (13 mg, 0.067 mmol) and Pd(PPh3)4 (39 mg, 0.034 mmol). The reaction mixture was heated at 130° C. for 40 min under microwave. Cooled to room temperature, the resulting mixture was poured into water and extracted with EtOAc. Dried organics over sodium sulfate and purified by pre-TLC (100% EtOAc) to give 242 as a yellow solid (49.3 mg, yield: 17%). 1H NMR (DMSO-d6, 400 MHz): δ 8.49 (d, J=8.4 Hz, 1H), 8.11 (s, 1H), 7.97 (s, 1H), 7.92 (s 1H), 7.28 (dd, J1=1.6 Hz, J2=8.4 Hz, 1H), 7.18 (d, J=6.8 Hz, 2H), 5.92-5.89 (m, 1H), 5.19 (d, J=9.2 Hz, 1H), 4.55-4.52 (m, 4H), 4.04 (d, J=11.2 Hz, 1H), 3.60-3.56 (m, 1H), 2.29-1.90 (m, 3H), 1.58-1.48 (m, 9H). MS: (ESI, m/z)=446 [M+H]+

Example 243

3-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide 243

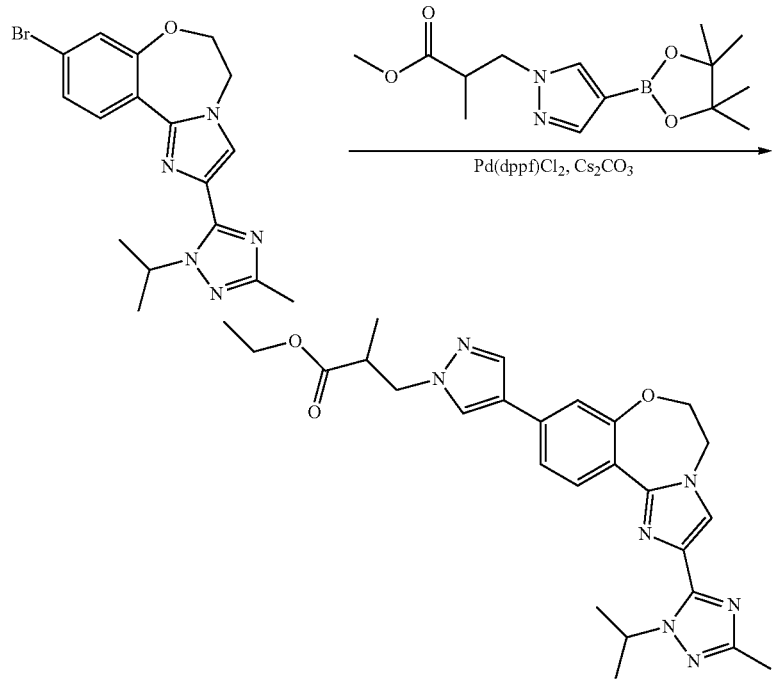

9-bromo-2-(1-isopropyl-3-methyl-1H-1,2,4-triazol-5-yl)-5,6-dihydrobenzo[f]imidazo[1,2-d][1,4]oxazepine 411 and ethyl 2-methyl-3-(4-(4,4,5,5-tetramethyl-1,3,2-dioxaborolan-2-yl)-1H-pyrazol-1-yl)propanoate were reacted under Suzuki palladium coupling conditions to give ethyl 3-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoate LC/MS(ESI+): m/z 490 (M+H), which was hydrolyzed with lithium hydroxide in water then the corresponding acid was treated with ammonium chloride, HATU, diisopropylethylamine, and DMF to give 243. LC/MS(ESI+): m/z 461 (M+H). 1H NMR (500 MHz, DMSO) δ 8.35 (d, J=8.4, 1H), 8.15 (s, 1H), 7.95 (s, 1H), 7.86 (s, 1H), 7.36 (dd, J=8.4, 1.7, 2H), 7.25 (d, J=1.7, 1H), 6.83 (s, 1H), 5.82 (dt, J=13.2, 6.6, 1H), 4.51 (s, 4H), 4.30 (dd, J=13.5, 7.6, 1H), 4.02 (dd, J=13.5, 7.0, 1H), 2.91 (dd, J=14.3, 7.1, 1H), 2.25 (s, 3H), 1.47 (d, J=6.6, 5H), 1.01 (d, J=7.0, 3H)

Example 244

2-(1-isopropyl-3-methyl-1H-1,2,4-triazol-5-yl)-9-(pyridin-3-yl)-5,6-dihydrobenzo[f]imidazo[1,2-d][1,4]oxazepine 244

8-Bromo-2-(2-isopropyl-5-methyl-2H-[1,2,4]triazol-3-yl)-4,5-dihydro-6-oxa-1,3a-diaza-benzo[e]azulene was reacted with 3-(4,4,5,5-Tetramethyl-[1,3,2]dioxaborolan-2-yl)-pyridine to give 244. MS(ESI+) 387.2

Example 245

5-(2-(1-isopropyl-3-methyl-1H-1,2,4-triazol-5-yl)-5,6-dihydrobenzo[f]imidazo[1,2-d][1,4]oxazepin-9-yl)-N,N-dimethylpyrimidin-2-amine 245

8-Bromo-2-(2-isopropyl-5-methyl-2H-[1,2,4]triazol-3-yl)-4,5-dihydro-6-oxa-1,3a-diaza-benzo[e]azulene was reacted with Dimethyl-[5-(4,4,5,5-tetramethyl-[1,3,2]dioxaborolan-2-yl)-pyrimidin-2-yl]-amine to give 245. MS(ESI+) 431.2

Example 246

5-(5,6-dihydrobenzo[f]imidazo[1,2-d][1,4]oxazepin-2-yl)-1-isopropyl-N-methyl-1H-1,2,4-triazol-3-amine 246

5-(9-bromo-5,6-dihydrobenzo Wimidazo[1,2-d][1,4]oxazepin-2-yl)-1-isopropyl-N-methyl-1H-1,2,4-triazol-3-amine was hydrogenated in the presence of 10% Pd on carbon to give 246 after reverse phase HPLC. LCMS: 325.2

Example 247

N-isopropyl-2-(4-(2-(1-isopropyl-1H-1,2,4-triazol-5-yl)-5,6-dihydrobenzo[f]imidazo[1,2-d][1,4]oxazepin-9-yl)piperidin-1-yl)acetamide 247

To a suspension of 2-(2-isopropyl-2H-[1,2,4]triazol-3-yl)-8-piperidin-4-yl-4,5-dihydro-6-oxa-1,3a-diaza-benzo[e]azulene trifluoroacetic acid salt (350 mg, 0.71 mmol) in THF was added potassium carbonate (245 mg, 1.78 mmol) followed by N-isopropyl-2-chloroacetamide (106 mg, 0.78 mmol) and the reaction mixture stirred for 18 h at RT then heated at 50° C. for 2 h. The resultant mixture was concentrated in vacuo and the residue subjected to flash chromatography (SiO2, gradient 0 to 5% MeOH in DCM to give 247 as a white solid (180 mg, 53%). $^1$H NMR δ (ppm) (DMSO-d6): 8.28 (1 H, d, J=8.28 Hz), 7.86 (1 H, d, J=0.63 Hz), 7.85 (1 H, s), 7.40 (1 H, d, J=8.18 Hz), 7.03 (1 H, dd, J=8.36, 1.77 Hz), 6.89 (1H, d, J=1.72 Hz), 5.88-5.79 (1 H, m), 4.48-4.41 (4 H, m), 3.89-3.83 (1 H, m), 2.89-2.79 (4 H, m), 2.13 (2 H, td, J=10.70, 4.11 Hz), 1.74-1.64 (4 H, m), 1.43 (6 H, d, J=6.60 Hz), 1.04 (6 H, d, J=6.59 Hz). 1 Proton obscured by solvent peak. LCMS: RT=2.94 min, M+H+ =478

Example 248

2-(4-(2-(1-isopropyl-1H-1,2,4-triazol-5-yl)-5,6-dihydrobenzo[f]imidazo[1,2-d][1,4]oxazepin-9-yl)piperidin-1-yl)-N,2-dimethylpropanamide 248

A biphasic mixture of 50% aqueous sodium hydroxide (2 mL) and DCM (2.5 mL) was treated with 2-bromo-2,N-dimethyl-propionamide (121 mg, 0.67 mmol), tetrabutylammonium bromide (118 mg, 0.37 mmol) and a solution of 2-(2-isopropyl-2H-[1,2,4]triazol-3-yl)-8-piperidin-4-yl-4,5-dihydro-6-oxa-1,3a-diaza-benzo[e]azulene trifluoroacetic acid salt (300 mg, 0.61 mmol) in DCM (1 mL). The resultant mixture was stirred at RT for 3 h before the addition of further tetrabutylammonium bromide (118 mg, 0.37 mmol) and stirring at RT for 18 h. The reaction mixture was diluted with DCM and washed with water. The combined aqueous extracts were washed with DCM and the combined organic extracts dried (MgSO4), filtered and concentrated in vacuo. The resultant residue was subjected to flash chromatography (SiO2, gradient 0 to 5% MeOH in DCM) followed by trituration in diethyl ether to give 248 as a cream solid (120 mg, 41%). $^1$H NMR δ (ppm) (DMSO-d6): 8.27 (1 H, d, J=8.26 Hz), 7.86 (1 H, d, J=0.63 Hz), 7.85 (1 H, s), 7.64 (1 H, m), 7.02 (1 H, dd, J=8.34, 1.75 Hz), 6.91 (1 H, d, J=1.70 Hz), 5.88-5.78 (1 H, m), 4.48-4.42 (4 H, m), 2.74 (2 H, d, J=10.86 Hz), 2.59 (3 H, d, J=4.75 Hz), 2.17-2.08 (2 H, m), 1.75-1.69 (4 H, m), 1.43 (6 H, d, J=6.60 Hz), 1.05 (6 H, s). 1 Proton obscured by solvent peak. LCMS: RT=2.78 min, M+H+=478

Example 249

2-(4-(2-(1-isopropyl-1H-1,2,4-triazol-5-yl)-5,6-dihydrobenzo[f]imidazo[1,2-d][1,4]oxazepin-9-yl)piperidin-1-yl)-N,N-dimethylethanesulfonamide 249

2-(2-isopropyl-2H-[1,2,4]triazol-3-yl)-8-piperidin-4-yl-4,5-dihydro-6-oxa-1,3a-diaza-benzo[e]azulene trifluoroacetic acid salt was reacted with N,N-dimethylethenesulfonamide to give 249 as a white solid. $^1$H NMR δ (ppm) (DMSO-d6): 8.28 (1 H, d, J=8.29 Hz), 7.86 (1 H, d, J=0.63 Hz), 7.85 (1 H, s), 7.01 (1 H, dd, J=8.37, 1.77 Hz), 6.85 (1 H, d, J=1.72 Hz), 5.88-5.80 (1 H, m), 4.48-4.42 (4 H, m), 3.23-3.15 (2 H, m), 2.95 (2 H, d, J=11.09 Hz), 2.74 (6 H, s), 2.68-2.60 (2 H, m), 2.09-1.98 (2 H, m), 1.73 (2 H, d, J=12.61 Hz), 1.64-1.55 (2 H, m), 1.43 (6 H, d, J=6.61 Hz). 1 Proton obscured by solvent peak. LCMS: RT=2.90 M+H+=513

Example 250

2-(4-(2-(1-isopropyl-3-methyl-1H-1,2,4-triazol-5-yl)-5,6-dihydrobenzo[f]imidazo[1,2-d][1,4]oxazepin-9-yl)piperidin-1-yl)acetamide 250

4-[2-(2-Isopropyl-5-methyl-2H-[1,2,4]triazol-3-yl)-4,5-dihydro-6-oxa-1,3a-diaza-benzo[e]azulen-8-yl]-piperidine-1-carboxylic acid tert-butyl ester was prepared from 8-bromo-2-(2-isopropyl-2H-[1,2,4]triazol-3-yl)-4,5-dihydro-6-oxa-1,3a-diaza-benzo[e]azulene (500 mg, 1.12 mmol) and 4-piperidine-1-carboxylic acid tert-butyl ester zinc iodide (1.68 mmol) to give 4-[2-(2-Isopropyl-5-methyl-2H-[1,2,4]triazol-3-yl)-4,5-dihydro-6-oxa-1,3a-diaza-benzo[e]azulen-8-yl]-piperidine-1-carboxylic acid tert-butyl ester (569 mg, 100%). LCMS: RT=4.79 min, M+H+=493.

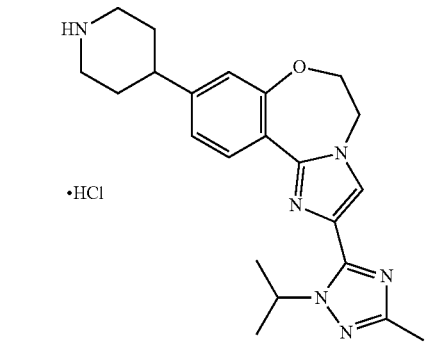 [SMILES: Cl ; Cc1nc(-c2cn3c(n2)-c2ccc(C4CCNCC4)cc2OCC3)n(C(C)C)n1]

To a solution of 4-[2-(2-isopropyl-5-methyl-2H-[1,2,4]triazol-3-yl)-4,5-dihydro-6-oxa-1,3a-diaza-benzo[e]azulen-8-yl]-piperidine-1-carboxylic acid tert-butyl ester (569 mg, 1.16 mmol) in dioxane (15 mL) and methanol (5 mL) was added 4M HCl in dioxane (15 mL) and the reaction mixture stirred for 20 h at RT before being concentrated in vacuo. The resultant residue was triturated in a mixture of diethyl ether and methanol to give 2-(2-Isopropyl-5-methyl-2H-[1,2,4]triazol-3-yl)-8-piperidin-4-yl-4,5-dihydro-6-oxa-1,3a-diaza-benzo[e]azulene Hydrochloride as a tan solid (212 mg, 43%). LCMS: RT=2.34/2.66 min, M+H+=393.

A mixture of 2-(2-isopropyl-5-methyl-2H-[1,2,4]triazol-3-yl)-8-piperidin-4-yl-4,5-dihydro-6-oxa-1,3a-diaza-benzo [e]azulene hydrochloride (120 mg, 0.28 mmol) in DMF (1.5 mL) was treated with potassium carbonate (97 mg, 0.7 mmol) followed by bromo acetamide (43 mg, 0.336 mmol)

and stirred at RT for 18 h. The reaction mixture was diluted with ethyl acetate/methanol and washed with water, the organic layer dried (Na2SO4), filtered and concentrated in vacuo. The resultant solid residue was recrystallised from methanol to give 250 as a white solid (51 mg, 41%). ¹H NMR δ (ppm) (DMSO-d6): 8.27 (1 H, d, J=8.28 Hz), 7.81 (1 H, s), 7.16 (1 H, s), 7.07 (1 H, s), 7.01 (1 H, dd, J=8.36, 1.78 Hz), 6.87 (1 H, d, J=1.72 Hz), 5.81-5.73 (1 H, m), 4.45-4.41 (4 H, m), 2.89-2.82 (2 H, m), 2.83 (2 H, s), 2.20 (3 H, s), 2.16-2.07 (2 H, m), 1.72-1.66 (4 H, m), 1.40 (6 H, d, J=6.61 Hz). 1 Proton obscured by solvent peak. LCMS: RT=2.97 [M+H]+=450

Example 251

2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoic acid 251

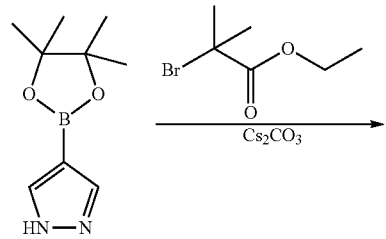

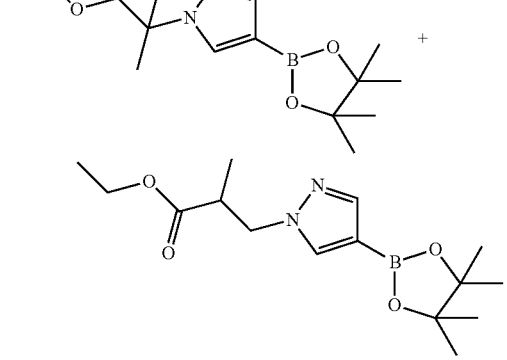

To a solution of 4,4,5,5-tetramethyl-2-(1H-pyrazol-4-yl)-1,3,2-dioxaborolane (5 g, 0.03 mol) and Cesium Carbonate (10 g, 0.03 mol) in DMF (50 mL) was added Ethyl 2-bromoisobutyrate (4.2 mL, 0.03 mol). The reaction was heated to 110° C. and stirred overnight. The reaction was cooled to room temperature, diluted with H2O, extracted the aqueous layer with EtOAc (2×) and the combined organic portions were washed with brine, dried over MgSO4, filtered and concentrated in vacuo. The crude product was a mixture of two isomers which was then separated by triturating with hexane to isolate the desired product ethyl 2-methyl-2-(4-(4,4,5,5-tetramethyl-1,3,2-dioxaborolan-2-yl)-1H-pyrazol-1-yl)propanoate. LC/MS(ESI+): m/z 309 (M+H). 1H NMR (400 MHz, CDCl3) δ 7.89 (d, J=4.1, 1H), 7.84 (s, 1H), 4.22-4.08 (m, 2H), 1.85 (d, J=7.6, 6H), 1.36-1.31 (m, 12H), 1.20 (td, J=7.1, 2.8, 3H).

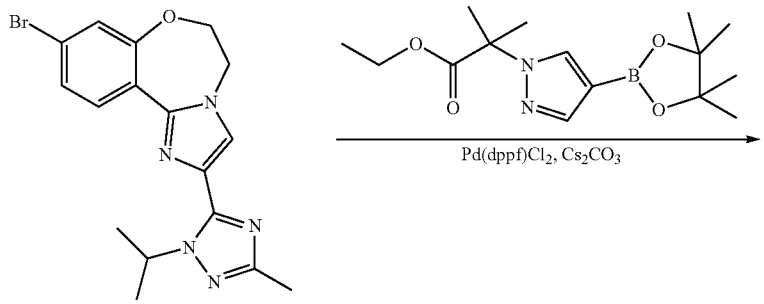

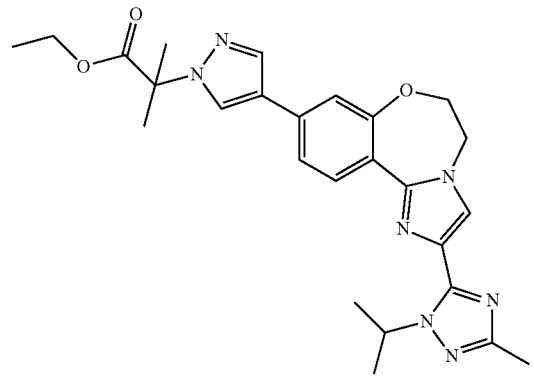

9-Bromo-2-(1-isopropyl-3-methyl-1H-1,2,4-triazol-5-yl)-5,6-dihydrobenzo[f]imidazo[1,2-d][1,4]oxazepine 411 and ethyl 2-methyl-2-(4-(4,4,5,5-tetramethyl-1,3,2-dioxaborolan-2-yl)-1H-pyrazol-1-yl)propanoate were coupled under Suzuki conditions to give ethyl 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoate. LC/MS(ESI+): m/z 490 (M+H)

Ethyl 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoate (750 mg, 0.0015 mol) was treated with 1 M of LiOH/H2O (1.6 mL) in MeOH (10 mL). The reaction was allowed to stirred at room temperature for 2 hours. The mixture was acidified by 10% citric acid aqueous solution was until PH=5, extracted with EtOAc twice, dried with MgSO4, and concentrated in vacuo. The crude was purified by Prep HPLC to provide 251. LC/MS(ESI+): m/z 462 (M+H). 1H NMR (500 MHz, DMSO) δ 8.44 (s, 1H), 8.36 (d, J=8.4, 1H), 7.97 (s, 1H), 7.86 (s, 1H), 7.44 (dd, J=8.4, 1.7, 1H), 7.35 (d, J=1.7, 1H), 5.82 (dt, J=13.1, 6.6, 1H), 4.52 (s, 3H), 2.25 (s, 2H), 1.78 (s, 4H), 1.45 (t, J=13.9, 4H)

Example 252

1-(4-(2-(1-isopropyl-3-methyl-1H-1,2,4-triazol-5-yl)-5,6-dihydrobenzo[f]imidazo[1,2-d][1,4]oxazepin-9-yl)-1H-imidazol-1-yl)-2-methylpropan-2-ol 252

2-(2-Isopropyl-5-methyl-2H-[1,2,4]triazol-3-yl)-8-(4,4,5,5-tetramethyl-[1,3,2]dioxaborolan-2-yl)-4,5-dihydro-6-oxa-1,3a-diaza-benzo[e]azulene was reacted with 1-(4-Bromo-imidazol-1-yl)-2-methyl-propan-2-ol to give 252. MS(ESI+) 448.3

Example 253

5-(9-fluoro-5,6-dihydrobenzo[f]imidazo[1,2-d][1,4]oxazepin-2-yl)-1-isopropyl-1H-1,2,4-triazol-3-amine 253

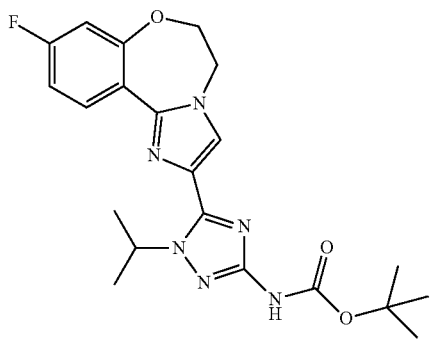 [SMILES: CC(C)n1nc(NC(=O)OC(C)(C)C)nc1-c1cn2c(n1)-c1ccc(F)cc1OCC2]

tert-Butyl 5-(9-fluoro-5,6-dihydrobenzo[f]imidazo[1,2-d][1,4]oxazepin-2-yl)-1-isopropyl-1H-1,2,4-triazol-3-ylcarbamate (0.200 mg, 0.47 mmol) was dissolved in 1,2-Dichloroethane (3 mL, 40 mmol) and trifluoroacetic acid (3 mL, 40 mmol) was added. The reaction mixture was stirred at room temperature for 1.5 hours. Complete reaction was confirmed by LCMS and the reaction mixture concentrated in vacuo. The crude solid was purified by HPLC to give 253 (18.3 mg, 12% yield)

Example 254

2-(4-(2-(3-methyl-1H-1,2,4-triazol-5-yl)-5,6-dihydrobenzo[f]imidazo[1,2-d][1,4]oxazepin-9-yl)-1H-pyrazol-1-yl)ethanol 254

8-Bromo-2-(5-methyl-2H-[1,2,4]triazol-3-yl)-4,5-dihydro-6-oxa-1,3a-diaza-benzo[e]azulene was reacted with 1-[2-(Tetrahydro-pyran-2-yloxy)-ethyl]-4-(4,4,5,5-tetramethyl-[1,3,2]dioxaborolan-2-yl)-1H-pyrazole under microwave conditions to give 254. MS(ESI+) 378.2

Example 255

2-(4-(2-(1-isopropyl-1H-1,2,4-triazol-5-yl)-5,6-dihydrobenzo[f]imidazo[1,2-d][1,4]oxazepin-9-yl)-2-methyl-1H-imidazol-1-yl)ethanol 255

Compound 256 (90 mg, 0.18 mmol) was dissolved in 3 mL of methanol and HCl-methanol (3 ml, 4M) was added dropwise at 0° C. The mixture was allowed to warm up to room temperature slowly and stirred at room temperature for 2 hours, concentrated. The residue was washed with EtOAc to give 65 mg of 255 as HCl salt. Yield=82%. 1H NMR (CDCl3, 400 MHz): δ8.65-8.61 (m, 2 H), 8.17 (s, 1 H), 8.00 (s, 1 H), 7.52-7.48 (m, 2 H), 5.81-5.78 (m, 1 H), 4.68-4.60 (m, 4 H), 4.31-4.29 (m, 2 H), 3.95-3.92 (m, 2 H), 2.74 (s, 3 H), 1.65 (d, J=1.2 Hz, 6 H). LC-MS: m/z=404 [M+H+]

Example 256

2-(1-isopropyl-1H-1,2,4-triazol-5-yl)-9-(2-methyl-1-(2-(tetrahydro-2H-pyran-2-yloxy)ethyl)-1H-imidazol-4-yl)-5,6-dihydrobenzo[f]imidazo[1,2-d][1,4]oxazepine 256

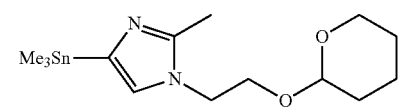

4-Iodo-2-methyl-1-(2-(tetrahydro-2H-pyran-2-yloxy)ethyl)-1H-imidazole was prepared by reaction of 4-iodo-2-methyl-1H-imidazole, Cs2CO3, and 2-(2-Bromo-ethoxy)-tetrahydro-pyran in DMF. To a mixture of 4-Iodo-2-methyl-1-(2-(tetrahydro-2H-pyran-2-yloxy)ethyl)-1H-imidazole (500 mg, 1.9 mmol) in DCM (10 mL) was added ethylmagnesium bromide (0.7 ml, 3 mol/L, 2.2 mmol) at −78° C. The temperature of the mixture was allowed to warm up to about 10° C. slowly and cooled again. Trimethyltin chloride (2.2 ml, 1 mol/1, 2.2 mmol) was added dropwise at −78° C. After the addition, the temperature was allowed to slowly warm up to room temperature. The reaction mixture was pouted into saturate NH4Cl solution, then extracted with DCM, The organic was washed with water twice, dried over anhydrous Na2SO4, concentrated to give 0.44 g of 2-methyl-1-(2-(tetrahydro-2H-pyran-2-yloxy)ethyl)-4-(trimethyl stannyl)-1H-imidazole. Yield=63%. 1H NMR (CDCl3, 400 MHz): δ 7.04 (s, 1 H, ArH), 3.71 (s, 2 H), 2.43 (s, 3 H), 1.24-1.20 (m, 6 H), 0.88 (s, 9 H), 0.29 (s, 6 H), 0.06 (s, 9 H). LC-MS: m/z=375 [M+H+]

A mixture of 9-bromo-2-(1-isopropyl-1H-1,2,4-triazol-5-yl)-5,6-dihydrobenzo[f]imidazo[1,2-d][1,4]oxazepine (300 mg, 0.8 mmol), Pd(PPh3)4 (93 mg, 0.08 mmol), 2-methyl-1-(2-(tetrahydro-2H-pyran-2-yloxy)ethyl)-4-(trimethylstannyl)-1H-imidazole (600 mg, 1.6 mmol) in dioxane (2 ml) was bubbled with N2 for about 2 min and then stirred at 120° C. for 35 min under the irradiation of microwave. Filtered, concentrated and purified by pre-TLC (EtOAc) to give 130 mg of 256. Yield=32%. 1H NMR (CDCl3, 400 MHz): δ 8.44-8.42 (m, 1 H, ArH), 7.81 (s, 1 H), 7.58 (s, 1 H), 7.48-7.46 (m, 1 H), 7.42 (d, J=1.6 Hz, 1 H), 7.19 (s, 1 H), 4.51-4.95 (m, 1 H), 4.45-4.44 (t, 1 H), 4.39-4.38 (m, 2 H), 4.38-4.37 (m, 2 H), 4.07-4.04 (m, 2 H), 4.00-4.97 (m, 1 H), 3.63-3.54 (m, 2 H), 3.40-3.36 (m, 1 H), 2.49 (s, 3 H), 1.76-1.60 (m, 4 H), 1.48-1.47 (m, 2 H) LC-MS: m/z=504 [M+H+]

Example 257

5-(2-(1-isopropyl-3-methyl-1H-1,2,4-triazol-5-yl)-5,6-dihydrobenzo[f]imidazo[1,2-d][1,4]oxazepin-9-yl)pyrimidin-2-amine 257

8-Bromo-2-(2-isopropyl-5-methyl-2H-[1,2,4]triazol-3-yl)-4,5-dihydro-6-oxa-1,3a-diaza-benzo[e]azulene was reacted with 5-(4,4,5,5-tetramethyl-[1,3,2]dioxaborolan-2-yl)-pyrimidin-2-ylamine to give 257. MS(ESI+) 403.2

Example 258

5-(2-(1-isopropyl-3-methyl-1H-1,2,4-triazol-5-yl)-5,6-dihydrobenzo[f]imidazo[1,2-d][1,4]oxazepin-10-yl)pyridin-2(1H)-one 258

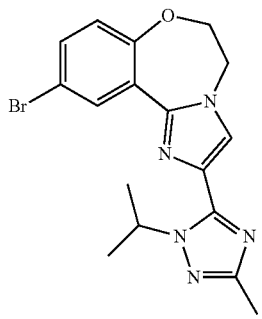 [SMILES: Cc1nc(-c2cn3c(n2)-c2cc(Br)ccc2OCC3)n(C(C)C)n1]

10-bromo-2-(1-isopropyl-3-methyl-1H-1,2,4-triazol-5-yl)-5,6-dihydrobenzo[f]imidazo[1,2-d][1,4]oxazepine was reacted with 6-fluoropyridin-3-ylboronic acid to give 10-(6-fluoropyridin-3-yl)-2-(1-isopropyl-3-methyl-1H-1,2,4-triazol-5-yl)-5,6-dihydrobenzo[f]imidazo[1,2-d][1,4]oxazepine (0.121 g, 39%). 1H NMR (500 MHz, DMSO) δ 8.67 (d, J=2.4, 1H), 8.52 (d, J=2.6, 1H), 8.25 (td, J=8.2, 2.7, 1H), 7.92 (s, 1H), 7.68 (dd, J=8.5, 2.5, 1H), 7.31 (dd, J=8.4, 2.8, 1H), 7.19 (d, J=8.5, 1H), 5.69 (dt, J=13.3, 6.6, 1H), 4.56 (s, 4H), 2.26 (s, 3H), 1.47 (d, J=6.6, 6H). MS (ESI+): m/z 405.2 (M+H)

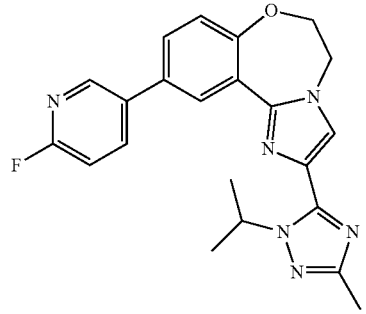 [SMILES: Cc1nc(-c2cn3c(n2)-c2cc(-c4ccc(F)nc4)ccc2OCC3)n(C(C)C)n1]

10-(6-Fluoropyridin-3-yl)-2-(1-isopropyl-3-methyl-1H-1,2,4-triazol-5-yl)-5,6-dihydrobenzo[f]imidazo[1,2-d][1,4]oxazepine was hydrolyzed with HCl to give 258 (0.028 g, 25%). 1H NMR (500 MHz, DMSO) δ 11.76 (s, 1H), 8.50 (d, J=2.4, 1H), 7.90 (s, 1H), 7.78 (dd, J=9.5, 2.8, 1H), 7.64 (s, 1H), 7.52 (dd, J=8.5, 2.5, 1H), 7.10 (d, J=8.5, 1H), 6.47 (d, J=9.5, 1H), 5.70 (dt, J=13.2, 6.5, 1H), 4.52 (q, J=5.8, 4H), 2.26 (s, 3H), 1.48 (d, J=6.6, 6H). MS (ESI+): m/z 403.2 (M+H).

Example 261

N-(azetidin-3-yl)-2-(1-isopropyl-1H-1,2,4-triazol-5-yl)-5,6-dihydroimidazo[1,2-d]pyrido[4,3-f][1,4]oxazepin-10-amine 261

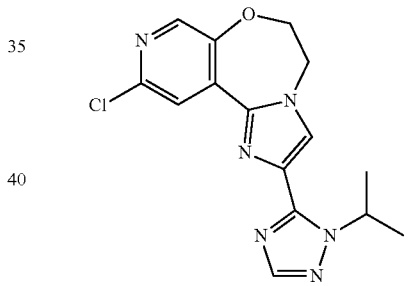

A solution of 10-chloro-2-(1-isopropyl-1H-1,2,4-triazol-5-yl)-5,6-dihydroimidazo[1,2-d]pyrido[4,3-f][1,4]oxazepine (90.0 mg, 0.272 mmol), tert-butyl 3-aminoazetidine-1-carboxylate (46.9 mg, 0.272 mmol), Palladium Acetate (6.11 mg, 0.0272 mmol), XPhos (13.0 mg, 0.0272 mmol), and Sodium-tert-butoxide (52.3 mg, 0.544 mmol) in 1,4-Dioxane (1.50 mL, 19.2 mmol) was heated in microwave at 115 C for 20 min. The reaction was filtered thru celite then rinsed with EtOAc. The filtrate was washed with water and brine. The organic layer was dried Na2SO4, concentrated to give crude intermediate tert-butyl 3-(2-(1-isopropyl-1H-1,2,4-triazol-5-yl)-5,6-dihydroimidazo[1,2-d]pyrido[4,3-f][1,4]oxazepin-10-ylamino)azetidine-1-carboxylate which was dissolved in DCM (10.0 mL). Trifluoroacetic Acid (0.419 mL, 5.44 mmol) was added and the reaction was stirred 3 h. The reaction was concentrated and submitted rHPLC purification to give 261. MS: (ESI+)=367.2. 1H NMR (500 MHz, DMSO) δ 8.29 (s, 1H), 8.23 (s, 1H), 7.98 (s, 1H), 7.79 (s, 1H), 5.74 (dt, J=13.1, 6.5 Hz, 2H), 4.73-4.60 (m, 3H), 4.58-4.51 (m, 2H), 4.43 (dd, J=12.7, 6.9 Hz, 2H), 4.24 (dt, J=15.9, 5.6 Hz, 1H), 2.77 (m, J=34.8, 13.1, 5.3 Hz, 2H), 1.50 (d, J=6.6, 2.9 Hz, 6H)

Example 262

3-(2-(1-isopropyl-1H-1,2,4-triazol-5-yl)-5,6-dihydroimidazo[1,2-d]pyrido[4,3-f][1,4]oxazepin-10-ylamino)propane-1,2-diol 262

A solution of 10-chloro-2-(1-isopropyl-1H-1,2,4-triazol-5-yl)-5,6-dihydroimidazo[1,2-d]pyrido[4,3-f][1,4]oxazepine (90.0 mg, 0.272 mmol), (2,2-dimethyl-1,3-dioxolan-4-yl)methanamine (0.0353 mL, 0.272 mmol), Palladium Acetate (6.11 mg, 0.0272 mmol), XPhos (13.0 mg, 0.0272 mmol), and Sodium-tert-butoxide (52.3 mg, 0.544 mmol) in 1,4-Dioxane (1.50 mL, 19.2 mmol) was heated in microwave at 115° C. for 20 min. The reaction was filtered thru celite then rinsed with EtOAc. The filtrate was washed water, brine. The organic layer was dried Na2SO4, concentrated to give intermediate N-((2,2-dimethyl-1,3-dioxolan-4-yl)methyl)-2-(1-isopropyl-1H-1,2,4-triazol-5-yl)-5,6-dihydroimidazo[1,2-d]pyrido[4,3-f][1,4]oxazepin-10-amine to which was added 4.00 M of Hydrogen chloride in dioxane (5.00 mL). The reaction was stirred 3 h. The reaction was concentrated and submitted HPLC purification to give 262. MS: (ESI+)=386.2. 1H NMR (500 MHz, DMSO) δ 7.99 (s, 1H), 7.92 (s, 1H), 7.85 (s, 1H), 7.44 (s, 1H), 6.36 (s, 1H), 5.86 (dt, J=13.2, 6.6 Hz, 1H), 4.78 (d, J=4.8 Hz, 1H), 4.61-4.46 (m, 3H), 4.46-4.33 (m, 2H), 3.64 (dd, J=11.4, 5.3 Hz, 1H), 3.47-3.34 (m, 3H), 3.21-3.10 (m, 1H), 1.49 (d, J=6.6 Hz, 6H)

Example 263

3-(2-(1-isopropyl-3-methyl-1H-1,2,4-triazol-5-yl)-5,6-dihydrobenzo[f]imidazo[1,2-d][1,4]oxazepin-10-yl)pyridin-2(1H)-one 263

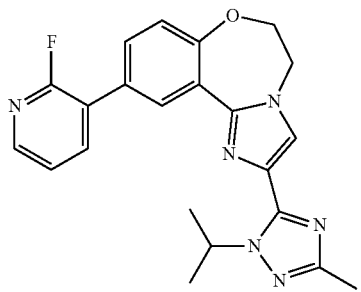 [SMILES: Cc1nc(-c2cn3c(n2)-c2cc(-c4cccnc4F)ccc2OCC3)n(C(C)C)n1]

Following the procedure for 203, 10-(2-fluoropyridin-3-yl)-2-(1-isopropyl-3-methyl-1H-1,2,4-triazol-5-yl)-5,6-dihydrobenzo[f]imidazo[1,2-d][1,4]oxazepine was prepared 0.756 g, 62%. 1H NMR (500 MHz, DMSO) δ 8.73 (s, 1H), 8.24 (d, J=4.7, 1H), 8.20-8.10 (m, 1H), 7.91 (s, 1H), 7.60 (d, J=9.4, 1H), 7.55-7.45 (m, 1H), 7.20 (d, J=8.5, 1H), 5.70 (dt, J=13.2, 6.6, 1H), 4.57 (s, 4H), 2.26 (s, 3H), 1.45 (d, J=6.6, 6H). MS (ESI(+)): m/z 405.2 (M+H)

10-(2-fluoropyridin-3-yl)-2-(1-isopropyl-3-methyl-1H-1,2,4-triazol-5-yl)-5,6-dihydrobenzo[f]imidazo[1,2-d][1,4]oxazepine was hydrolyzed with HCl to give 263 (0.412 g, 70% yield). 1H NMR (500 MHz, DMSO) δ 11.80 (s, 1H), 8.86 (d, J=2.3, 1H), 7.88 (s, 1H), 7.66 (ddd, J=9.0, 7.7, 2.2, 2H), 7.37 (d, J=5.0, 1H), 7.06 (d, J=8.5, 1H), 6.31 (t, J=6.6, 1H), 5.73 (dt, J=13.2, 6.6, 1H), 4.61-4.47 (m, 4H), 2.25 (s, 3H), 1.45 (d, J=6.6, 6H). MS (ESI(+)): m/z 403.2 (M+H).

Example 265

1-(4-(2-(1-isopropyl-1H-1,2,4-triazol-5-yl)-5,6-dihydrobenzo[f]imidazo[1,2-d][1,4]oxazepin-9-yl)-2-methyl-1H-imidazol-1-yl)-2-methylpropan-2-ol 265

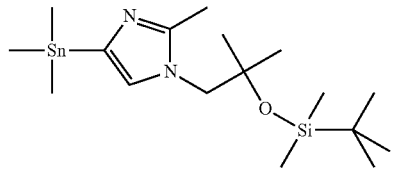 [SMILES: Cc1n[c]([Sn]([CH3])([CH3])[CH3])cn1CC(C)(C)O[Si](C)(C)C(C)(C)C]

1-(2-(tert-butyldimethylsilyloxy)-2-methylpropyl)-4-iodo-2-methyl-1H-imidazole was prepared by reaction of 1-(4-iodo-2-methyl-1H-imidazol-1-yl)-2-methylpropan-2-ol, lutidine, tert-butyldimethylsilyl trimethylsulfonate (TBSOTf) in DCM.

To a mixture of 1-(2-(tert-butyldimethylsilyloxy)-2-methylpropyl)-4-iodo-2-methyl-1H-imidazole (1.5 g, 3.8 mmol) in DCM (15 mL) was added ethylmagnesium bromide (1.9 mL, 3 mol/L, 5.7 mmol) at −78° C. The temperature of the mixture was allowed to warm up to about 10° C. slowly and cooled again. Trimethyltin chloride (6.5 ml, 1 mol/L, 6.5 mmol) was added dropwise at −78° C. After the addition, the temperature was allowed to slowly warm up to room temperature. The reaction mixture was pouted into saturate NH4Cl solution, then extracted with DCM, The organic was washed with water twice, dried over anhydrous Na2SO4, concentrated to give 0.44 g of 1-(2-(tert-butyldimethylsilyloxy)-2-methylpropyl)-2-methyl-4-(trimethylstannyl)-1H-imidazole. Yield=63%. 1H NMR (CDCl3, 400 MHz): δ 7.04 (s, 1 H, ArH), 3.74 (s, 2 H), 2.43 (s, 3 H), 1.24-1.20 (m, 6 H), 0.88 (s, 9 H), 0.29 (s, 6 H), 0.03 (s, 8 H). LC-MS: m/z=375 [M+H+]

To a mixture of 9-bromo-2-(1-isopropyl-1H-1,2,4-triazol-5-yl)-5,6-dihydrobenzo[f]imidazo[1,2-d][1,4]oxazepine (300 mg, 0.8 mmol), Pd(PPh3)4 (93 mg, 0.08 mmol), 1-(2-(tert-butyldimethylsilyloxy)-2-methylpropyl)-2-methyl-4-(trimethylstannyl)-1H-imidazole (690 mg, 1.6 mmol) in dioxane (2 mL) was bubbled with N2 for about 2 min and then stirred at 120° C. for 35 min under the irradition of microwave. Filtered, concentrated and purified by pre-TLC (pure EtOAc) to give 160 mg of 9-(1-(2-(tert-butyldimethylsilyloxy)-2-methylpropyl)-2-methyl-1H-imidazol-4-yl)-2-(1-isopropyl-1H-1,2,4-triazol-5-yl)-5,6-dihydrobenzo[f]imidazo[1,2-d][1,4]oxazepine. Yield=46%. LC-MS: m/z=548 [M+H+]

9-(1-(2-(tert-Butyldimethylsilyloxy)-2-methylpropyl)-2-methyl-1H-imidazol-4-yl)-2-(1-isopropyl-1H-1,2,4-triazol-5-yl)-5,6-dihydrobenzo Wimidazo[1,2-d][1,4]oxazepine (110 mg, 0.196 mmol) was dissolved in 5 mL of THF, tetrabutylammonium fluoride (TBAF, 102 mg, 0.392 mmol) was added at 0° C. The temperature was allowed to warm up to room temperature slowly and stirred at room temperature for over night. Concentrated, the residue was portioned with EtOAc-water to give 30 mg of 265. Yield=36%. 1 H NMR (CDCl3, 400 MHz): δ 8.48 (d, J=8.0 Hz, 1 H), 7.87 (s, 1 H), 7.64 (s, 1 H), 7.51-7.47 (m, 2 H), 7.26 (s, 1 H), 6.03-5.99 (m, 1 H), 4.51-4.43 (m, 4 H), 3.85 (s, 1 H), 2.47 (s, 3 H), 1.65-1.56 (m, 6 H), 1.28-1.26 (m, 6 H). LC-MS: m/z=433 [M+H+]

Example 269

3-(2-(1-isopropyl-1H-1,2,4-triazol-5-yl)-5,6-dihydroimidazo[1,2-d]pyrido[4,3-f][1,4]oxazepin-10-yl)pyridin-2(1H)-one 269

To a solution of 10-(2-fluoropyridin-3-yl)-2-(1-isopropyl-1H-1,2,4-triazol-5-yl)-5,6-dihydroimidazo[1,2-d]pyrido[4,3-f][1,4]oxazepine (0.087 g, 0.22 mmol) in 1,2-Dimethoxyethane (3.00 mL, 28.9 mmol) was added 10% aqueous HCl (3 mL). The reaction was allowed to stir and heat at 80° C. overnight. The reaction was allowed to cool to room temperature and concentrated under reduced pressure to give 269, analyzed by rHPLC. MS: (ESI+)=390.2. 1H NMR (500 MHz, DMSO) δ 9.76 (s, 1H), 8.45-8.39 (m, 2H), 8.04 (s, 1H), 7.93 (s, 1H), 7.47 (dd, J=6.1, 2.1 Hz, 1H), 6.37 (t, J=6.7 Hz, 1H), 5.91 (dt, J=13.3, 6.7 Hz, 2H), 5.91 (dt, J=13.3, 6.7 Hz, 1H), 4.61 (dd, J=13.1, 5.5 Hz, 4H), 1.52 (d, J=6.6 Hz, 6H).

Example 270

2-(5-(9-cyclopropyl-5,6-dihydrobenzo[f]imidazo[1,2-d][1,4]oxazepin-2-yl)-3-methyl-1H-1,2,4-triazol-1-yl)propan-1-ol 270

A microwave vial was charged with a solution of 2-[5-(8-Bromo-4,5-dihydro-6-oxa-1,3a-diaza-benzo[e]azulen-2-yl)-3-methyl-[1,2,4]triazol-1-yl]-propan-1-ol (0.140 g, 0.000346 mol) and Potassium phosphate (0.220 g, 0.00104 mol) in Tetrahydrofuran (2.0 mL) and Water (2.0 mL). The mixture was thoroughly purged with N2. 2-cyclopropyl-4,4,5,5-tetramethyl-1,3,2-dioxaborolane (0.189 mL, 0.00104 mol) and Tetrakis(triphenylphosphine)palladium(0) (0.0400 g, 0.0000346 mol) were added and the vial was sealed immediately. The reaction was heated in the microwave to 120° C. for 20 minutes. The reaction was diluted with methylene chloride and filtered through celite. Saturated NH4Cl was added and the mixture was extracted 3 times with methylene chloride. The organic layers were combined, dried with MgSO4 and concentrated. The crude was purified by reverse-phase HPLC to give 35 mg of 270 as a white solid. MS(ESI+) 366.2. 1H NMR (500 MHz, DMSO) δ 8.26 (d, J=8.3 Hz, 1H), 7.82 (s, 1H), 6.86 (dd, J=8.4, 1.7 Hz, 1H), 6.75 (d, J=1.7 Hz, 1H), 5.73-5.57 (m, 1H), 4.85 (t, J=5.4 Hz, 1H), 4.50-4.43 (m, 4H), 3.76 (ddd, J=10.7, 7.5, 6.0 Hz, 1H), 3.68-3.62 (m, 1H), 2.24 (s, 3H), 1.97-1.85 (m, 1H), 1.39 (d, J=6.7 Hz, 3H), 1.02-0.93 (m, 2H), 0.75-0.67 (m, 2H)

Example 271

2-(1-isopropyl-1H-1,2,4-triazol-5-yl)-9-(2-methyl-1H-imidazol-5-yl)-5,6-dihydrobenzo[f]imidazo[1,2-d][1,4]oxazepine 271

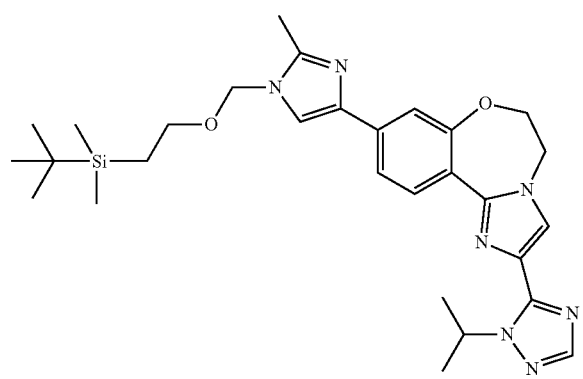 [SMILES: Cc1nc(-c2ccc3c(c2)OCCn2cc(-c4ncnn4C(C)C)nc2-3)cn1COCC[Si](C)(C)C(C)(C)C]

Following the procedure for 265, a mixture of 9-bromo-2-(1-isopropyl-1H-1,2,4-triazol-5-yl)-5,6-dihydrobenzo[f]imidazo[1,2-d][1,4]oxazepine and a mixture of regioisomers 2-methyl-1-((2-(trimethylsilyl)ethoxy)methyl)-4-(trimethyl stannyl)-1H-imidazole and 2-methyl-1-((2-(trimethylsilyl)ethoxy)methyl)-5-(trimethyl stannyl)-1H-imidazole were reacted to give 9-(1-((2-(tert-butyldimethylsilyl)ethoxy)methyl)-2-methyl-1H-imidazol-4-yl)-2-(1-isopropyl-1H-1,2,4-triazol-5-yl)-5,6-dihydrobenzo Wimidazo[1,2-d][1,4]oxazepine which was dissolved (360 mg, 0.71 mmol) in ethanol (3 mL). To the mixture was added HCl-methanol (3 mL, 4 mol/L) dropwise at 0° C. After 30 minutes, the temperature was allowed to warm up to 70° C. and stirred for over night. Concentrated, the residue was basified with TEA, then purified by per-TLC to give 240 mg of 271. Yield=91%. 1H NMR (MeOD, 400 MHz): δ 8.72 (s, 1 H), 8.60 (d, J=4.4 Hz, 1 H), 8.19 (s, 1 H), 7.87 (s, 1 H), 7.51 (d, J=2.0 Hz, 1 H), 7.46 (s, 1 H), 5.72-5.72 (m, 1 H), 4.65-4.64 (m, 2 H), 4.60-4.59 (m, 2 H), 2.68 (s, 3 H), 1.63-1.62 (d, J=6.8 Hz, 6 H). LC-MS: m/z=376 [M+H+]

Example 272

1-(4-(2-(1-isopropyl-1H-1,2,4-triazol-5-yl)-5,6-dihydrobenzo[f]imidazo[1,2-d][1,4]oxazepin-9-yl)-1-methyl-1H-imidazol-2-yl)-2-methylpropan-2-ol 272

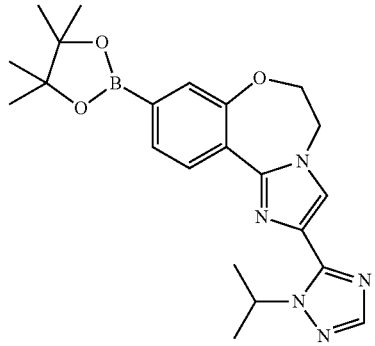 [SMILES: CC(C)n1ncnc1-c1cn2c(n1)-c1ccc(B3OC(C)(C)C(C)(C)O3)cc1OCC2]

To a mixture of 9-bromo-2-(1-isopropyl-1H-1,2,4-triazol-5-yl)-5,6-dihydrobenzo[f]imidazo[1,2-d][1,4]oxazepine (500 mg, 1.336 mmol) and 4,4,4',4',5,5,5',5'-octamethyl-2,2'-bi(1,3,2-dioxaborolane) (509 mg, 2.004 mmol) in dry DMF (4 mL) under nitrogen was added KOAc (393 mg, 4.01 mmol) and Pd(dppf)Cl2 (50 mg, 0.067 mmol). The reaction mixture was heated at 120° C. for 20 min under microwave. Cooled to room temperature and concentrated, the crude product was purified by column chromatography (hexanes/EtOAc=3:1-1:2) to give 2-(1-isopropyl-1H-1,2,4-triazol-5-yl)-9-(4,4,5,5-tetramethyl-1,3,2-dioxaborolan-2-yl)-5,6-dihydrobenzo[f]imidazo[1,2-d][1,4]oxazepineas a yellow solid (275 mg, yield: 49%). LCMS: (ESI, m/z)=422 [M+H]+

To a mixture of 2-(1-isopropyl-1H-1,2,4-triazol-5-yl)-9-(4,4,5,5-tetramethyl-1,3,2-dioxaborolan-2-yl)-5,6-dihydrobenzo[f]imidazo[1,2-d][1,4]oxazepine (200 mg, 0.48 mmol) and 1-(4-bromo-1-methyl-1H-imidazol-2-yl)-2-methyl-propan-2-ol (166 mg, 0.71 mmol) in dry DMF (2 mL) under nitrogen was added CsF (180 mg, 1.19 mmol), CuI (9 mg, 0.048 mmol) and Pd(PPh3)4 (27 mg, 0.024 mmol). The reaction mixture was heated at 130° C. for 40 min under microwave. Cooled to room temperature, the resulting mixture was poured into water and extracted with EtOAc. Dried organics over sodium sulfate and purified by pre-HPLC to give 272 as a white solid (34.9 mg, yield: 16%). 1H NMR (DMSO-d6, 400 MHz): δ 8.51 (s, 1H), 7.90 (s, 1H), 7.86 (s, 1H), 7.23-7.11 (m, 3H), 5.93-5.89 (m, 1H), 4.54-4.52 (m, 4H), 3.74-3.66 (m, 5H), 1.46 (dd, J=6.4 Hz, 6H), 1.24 (brs, 6H). MS: (ESI, m/z)=448 [M+H]+

Example 273

1-(4-(2-(3-(hydroxymethyl)-1-isopropyl-1H-1,2,4-triazol-5-yl)-5,6-dihydrobenzo[f]imidazo[1,2-d][1,4]oxazepin-9-yl)-1H-pyrazol-1-yl)-2-methylpropan-2-ol 273

Following the procedures as Example 182, Suzuki reaction of (5-(9-bromo-5,6-dihydrobenzo[f]imidazo[1,2-d][1,4]oxazepin-2-yl)-1-isopropyl-1H-1,2,4-triazol-3-yl)methanol and 2-methyl-1-(4-(4,4,5,5-tetramethyl-1,3,2-dioxaborolan-2-yl)-1H-pyrazol-1-yl)propan-2-ol provided 273. LCMS: Rt=2.33 min, [M+H]=464

Example 274

N-tert-butyl-2-(4-(2-(1-isopropyl-1H-1,2,4-triazol-5-yl)-5,6-dihydrobenzo[f]imidazo[1,2-d][1,4]oxazepin-9-yl)piperidin-1-yl)acetamide 274

To a suspension of 2-(2-isopropyl-2H-[1,2,4]triazol-3-yl)-8-piperidin-4-yl-4,5-dihydro-6-oxa-1,3a-diaza-benzo[e]azulene trifluoroacetic acid salt (300 mg, 0.61 mmol) in THF (5 mL) was added potassium carbonate (295 mg, 2.13 mmol) and N-tert-butyl-2-chloroacetamide (100 mg, 0.67 mmol). The mixture was stirred for 5 days before being diluted with DCM and washed with water (2×30 mL). The organic phase was dried (MgSO4) and concentrated in vacuo. The resultant residue was triturated in diethyl ether, affording 274 as a cream solid (169 mg, 0.34 mmol, 56%). LCMS: RT=3.12 min, [M+H]+=492. ¹H NMR δ (ppm) (DMSO-d): 8.29 (1 H, d, J=8.29 Hz), 7.86 (1 H, d, J=0.63 Hz), 7.85 (1 H, s), 7.15 (1 H, s), 7.03 (1 H, dd, J=8.36, 1.77 Hz), 6.89 (1 H, d, J=1.71 Hz), 5.90-5.80 (1 H, m), 4.48-4.41 (4 H, m), 2.85 (2 H, d, J=11.24 Hz), 2.81 (2 H, s), 2.20-2.09 (2 H, m), 1.78-1.67 (2 H, m), 1.70-1.58 (2 H, m), 1.44 (6 H, d, J=6.60 Hz), 1.25 (9 H, s). 1 H obscured by solvent.

Example 275

2-(4-(2-(1-isopropyl-3-methyl-1H-1,2,4-triazol-5-yl)-5,6-dihydrobenzo[f]imidazo[1,2-d][1,4]oxazepin-9-yl)piperidin-1-yl)-N-methylacetamide 275

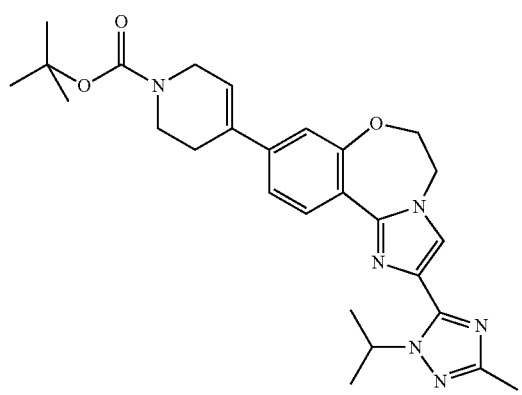 [SMILES: Cc1nc(-c2cn3c(n2)-c2ccc(C4=CCN(C(=O)OC(C)(C)C)CC4)cc2OCC3)n(C(C)C)n1]

A suspension of 8-bromo-2-(2-isopropyl-5-methyl-2H-[1,2,4]triazol-3-yl)-4,5-dihydro-6-oxa-1,3a-diaza-benzo[e]azulene (1.2 g, 3.09 mmol), 4-(4,4,5,5-tetramethyl-[1,3,2]dioxaborolan-2-yl)-3,6-dihydro-2H-pyridine-1-carboxylic acid tert-butyl ester (1.8 g, 5.82 mmol), PdCl2dppf.DCM (339 mg, 0.46 mmol) and potassium carbonate (1.9 g, 13.9 mmol) in DMF (10 mL) was degassed and then heated at 90° C. under an atmosphere of nitrogen for 1.5 h. The cooled reaction mixture was diluted with ethyl acetate and water, the aqueous extracted with ethyl acetate and combined organic extracts dried (Na2SO4), filtered and concentrated in vacuo. The resultant residue was subjected to flash chromatography (SiO2, gradient 0 to 100% ethyl acetate in cyclohexane, 1% TEA in final eluent) to give 4-[2-(2-Isopropyl-5-methyl-2H-[1,2,4]triazol-3-yl)-4,5-dihydro-6-oxa-1,3a-diaza-benzo[e]azulen-8-yl]-3,6-dihydro-2H-pyridine-1-carboxylic acid tert-butyl ester as a tan foam (1.5 g, 99%). LCMS: RT=3.77 min, [M+H]+=491

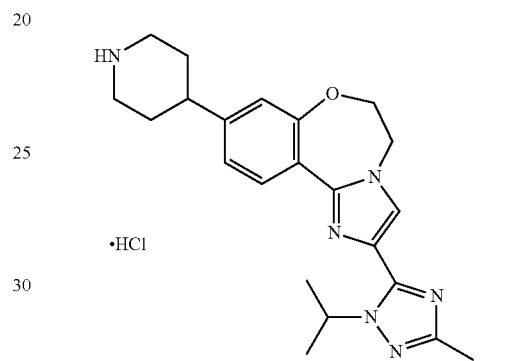

A solution of 4-[2-(2-isopropyl-5-methyl-2H-[1,2,4]triazol-3-yl)-4,5-dihydro-6-oxa-1,3a-diaza-benzo[e]azulen-8-yl]-3,6-dihydro-2H-pyridine-1-carboxylic acid tert-butyl ester (1.5 g, 3.06 mmol) in IMS (15 mL) was degassed then treated with palladium on carbon (10% palladium, 50% water, 450 mg) and the reaction mixture stirred at RT under an atmosphere of hydrogen for 18 h then at 40° C. for 8 h then RT for 18 h. Further palladium on carbon was added (10% palladium, 50% water, 450 mg) and stirring continued at 40° C. for 8 h before filtering through a pad of Celite® and removal of solvent in vacuo. The resultant residue was dissolved in methanol (5 mL) and treated with 3M HCl in methanol (10 mL) and stirred at RT for 1.5 h before concentrating in vacuo. The resultant residue was triturated in diethyl ether to give 2-(2-Isopropyl-5-methyl-2H-[1,2,4]triazol-3-yl)-8-piperidin-4-yl-4,5-dihydro-6-oxa-1,3a-diaza-benzo[e]azulene hydrochloride as a yellow solid (1.26 g, 79%). ¹H NMR 400 MHz (DMSO-d6) δ: 9.03 (2 H, s), 8.37 (1 H, d, J=8.31 Hz), 8.17 (1 H, s), 7.06 (1 H, dd, J=8.37, 1.7 Hz), 6.92 (1 H, d, J=1.7 Hz), 5.78 (1 H, m), 4.54 (4 H, d, J=17.19 Hz), 3.35 (2 H, d, J=12.43 Hz), 2.98 (2 H, m), 2.87 (1 H, m), 2.38 (2 H, s), 2.08-1.78 (4 H, m), 1.49 (6 H, d, J=6.57 Hz)

To a suspension of 2-(2-isopropyl-5-methyl-2 H-[1,2,4]triazol-3-yl)-8-piperidin-4-yl-4,5-dihydro-6-oxa-1,3a-diaza-benzo[e]azulene hydrochloride (150 mg, 0.35 mmol) was added triethylamine (107 μL, 0.77 mmol) followed by 2-chloro-N-methylacetamide (41 mg, 0.38 mmol). The resultant mixture was stirred overnight before the addition of tetrabutylammonium iodide (13 mg, 0.04 mmol) and the reaction stirred for 24 hours. The mixture was washed with water then extracted with 10% MeOH in DCM (×5). The combined organic layers were dried (MgSO4), concentrated in vacuo and purified by flash column chromatography (SiO2, gradient 0-10% MeOH in DCM) twice to afford 275 (23 mg, 0.05 mmol, 14%). LCMS: RT=2.63 min, [M+H]+ =464. $^1$H NMR δ (ppm)(CDCl3): 8.42 (1 H, d, J=8.30 Hz), 7.59 (1 H, s), 7.00 (1 H, dd, J=8.35, 1.83 Hz), 6.88 (1 H, d, J=1.79 Hz), 5.91-5.81 (1 H, m), 4.48-4.44 (2 H, m), 4.42-4.36 (2 H, m), 3.13-2.91 (4 H, m), 2.85 (3 H, d, J=4.98 Hz), 2.56-2.48 (1 H, m), 2.39 (3 H, s), 2.33 (2 H, s), 1.87 (2 H, s), 1.78 (2 H, s), 1.54 (6 H, d, J=6.65 Hz). NH not observed.

Alternatively, to a suspension of 2-(2-isopropyl-2H-[1,2,4]triazol-3-yl)-8-piperidin-4-yl-4,5-dihydro-6-oxa-1,3a-diaza-benzo[e]azulene trifluoroacetic acid salt (300 mg, 0.61 mmol) in THF (5 mL) was added triethylamine (291 µL, 2.10 mmol) and 2-bromo-N-methylacetamide (102 mg, 0.67 mmol). The mixture was stirred for 2 hours before the addition of potassium carbonate (169 mg, 1.22 mmol) then for a further 2 hours. The reaction was diluted with DCM and washed with water (2×20 mL), dried (MgSO4) and concentrated in vacuo. The resultant residue was triturated with diethyl ether giving 275 as a cream solid (156 mg, 0.35 mmol, 57%). LCMS: RT=2.62 min, [M+H]+=450. $^1$H NMR δ (ppm) (DMSO-d6): 8.29 (1 H, d, J=8.27 Hz), 7.86 (1 H, s), 7.85 (1 H, s), 7.66 (1 H, s), 7.02 (1 H, dd, J=8.33, 1.76 Hz), 6.88 (1H, d, J=1.71 Hz), 5.89-5.79 (1 H, m), 4.49-4.42 (4 H, m), 2.88 (2H, s), 2.84 (2 H, d, J=10.90 Hz), 2.59 (3 H, d, J=4.73 Hz), 2.13 (2 H, s), 1.77-1.67 (4 H, m), 1.44 (6 H, d, J=6.60 Hz). 1 H obscured by solvent Example 276

N-ethyl-2-(4-(2-(1-isopropyl-3-methyl-1H-1,2,4-triazol-5-yl)-5,6-dihydrobenzo[f]imidazo[1,2-d][1,4]oxazepin-9-yl)piperidin-1-yl)acetamide 276

To a suspension of 2-(2-isopropyl-5-methyl-2H-[1,2,4]triazol-3-yl)-8-piperidin-4-yl-4,5-dihydro-6-oxa-1,3a-diaza-benzo[e]azulene hydrochloride (150 mg, 0.35 mmol) in DCM (2 mL) was added triethylamine (107 µL, 0.77 mmol). The resultant mixture was stirred for 10 minutes before the addition of 2-chloro-N-ethyl-acetamide (46 mg, 0.38 mmol) and tetrabutylammonium iodide (13 mg, 0.04 mmol). The reaction was stirred at RT for 4 days before the reaction was washed with sodium hydrogen carbonate solution (sat. aq.). The aqueous phase was extracted with 10% MeOH in DCM (×3) and the combined organic layers dried (Na2SO4) then concentrated in vacuo. The resultant residue was purified by flash column chromatography (SiO2, gradient 0-10% MeOH in DCM) affording 276 (91 mg, 0.19 mmol, 55%). LCMS: RT=2.75 min, [M+H]+=478. $^1$H NMR δ (ppm) (CDCl3): 8.43 (1 H, d, J=8.29 Hz), 7.59 (1 H, s), 7.16 (1 H, s), 7.00 (1 H, dd, J=8.34, 1.81 Hz), 6.88 (1 H, d, J=1.76 Hz), 5.91-5.80 (1 H, m), 4.48-4.44 (2 H, m), 4.42-4.37 (2 H, m), 3.37-3.26 (2 H, m), 3.06-2.88 (4 H, m), 2.57-2.47 (1 H, m), 2.38 (3 H, s), 2.30 (2H, s), 1.87 (2 H, d, J=12.74 Hz), 1.76 (2 H, s), 1.54 (6 H, d, J=6.65 Hz), 1.15 (3 H, t, J=7.26 Hz).

Example 277

N-isopropyl-2-(4-(2-(1-isopropyl-3-methyl-1H-1,2,4-triazol-5-yl)-5,6-dihydrobenzo[f]imidazo[1,2-d][1,4]oxazepin-9-yl)piperidin-1-yl)acetamide 277

To a suspension of 2-(2-isopropyl-5-methyl-2H-[1,2,4]triazol-3-yl)-8-piperidin-4-yl-4,5-dihydro-6-oxa-1,3a-diaza-benzo[e]azulene hydrochloride (150 mg, 0.35 mmol) in DCM (2 mL) was added triethylamine (107 µL, 0.77 mmol). The resultant mixture was stirred for 10 minutes before the addition of 2-chloro-N-isopropyl-acetamide (52 mg, 0.38 mmol) and tetrabutylammonium iodide (13 mg, 0.04 mmol). The reaction was stirred at RT for 4 days before the reaction was washed with sodium hydrogen carbonate solution (sat. aq.). The aqueous phase was extracted with 10% MeOH in DCM (×3) and the combined organic layers dried (Na2SO4) then concentrated in vacuo. The resultant residue was purified by flash column chromatography (SiO2, gradient 0-10% MeOH in DCM) affording 277 (88 mg, 0.18 mmol, 51%). LCMS: RT=2.85 min, [M+H]+=492. $^1$H NMR δ (ppm) (CDCl3): 8.43 (1 H, d, J=8.29 Hz), 7.59 (1 H, s), 7.01 (1 H, dd, J=8.34, 1.82 Hz), 6.97 (1 H, s), 6.89 (1 H, d, J=1.76 Hz), 5.92-5.82 (1 H, m), 4.48-4.44 (2 H, m), 4.42-4.38 (2 H, m), 4.13-4.02 (1 H, m), 3.10-2.85 (4 H, m), 2.58-2.46 (1 H, m), 2.38 (3 H, s), 2.35-2.20 (2 H, m), 1.94-1.84 (2 H, s), 1.81-1.68 (2 H, m), 1.54 (6 H, d, J=6.64 Hz), 1.16 (6H, d, J=6.55 Hz)

Example 278

2-(4-(2-(1-isopropyl-1H-1,2,4-triazol-5-yl)-5,6-dihydrobenzo[f]imidazo[1,2-d][1,4]oxazepin-9-yl)piperidin-1-yl)-N,N-dimethylacetamide 278

To a suspension of 2-(2-isopropyl-2H-[1,2,4]triazol-3-yl)-8-piperidin-4-yl-4,5-dihydro-6-oxa-1,3a-diaza-benzo[e]azulene trifluoroacetic acid salt (300 mg, 0.61 mmol) in THF (5 mL) was added potassium carbonate (295 mg, 2.13 mmol) and 2-chloro-N,N-dimethylacetamide (82 mg, 0.67 mmol). The reaction was stirred for 4 hours before being diluted with DCM and the mixture washed with water (2×30 mL), dried (MgSO4) and concentrated in vacuo. The resultant residue was purified by flash column chromatography (SiO2, gradient 0-5% MeOH in DCM). The resultant material was triturated with diethyl ether then petroleum ether to give 278 as a white solid (85 mg, 0.17 mmol, 29%). LCMS: RT=2.72 min, [M+H]+=464. $^1$H NMR δ (ppm)(DMSO-d): 8.28 (1 H, d, J=8.29 Hz), 7.86 (1 H, d, J=0.64 Hz), 7.85 (1 H, s), 7.01 (1 H, dd, J=8.35, 1.78 Hz), 6.86 (1 H, d, J=1.73 Hz), 5.89-5.79 (1H, m), 4.48-4.41 (4H, m), 3.10 (2 H, s), 3.00 (3 H, s), 2.89 (2 H, d, J=10.79 Hz), 2.77 (3 H, s), 2.11 (2 H, dd, J=12.35, 10.20 Hz), 1.71 (2 H, d, J=12.52 Hz), 1.61 (2 H, td, J=12.15, 3.73 Hz), 1.44 (6 H, d, J=6.60 Hz). 1 H obscured by solvent.

Alternatively, a solution of 2-(2-isopropyl-2H-[1,2,4]triazol-3-yl)-8-piperidin-4-yl-4,5-dihydro-6-oxa-1,3a,9-triaza-benzo[e]azulene hydrochloride (66 mg, 0.12 mmol), in DCM (1 mL), methanol (1 mL) and TEA (0.07 mL) was treated with N,N-dimethyl-2-chloroacetamide (17 mg, 0.14 mmol) and TBAI (5 mg) and then stirred at RT for 48 h then 30° C. for 18 h. The reaction mixture was concentrated in vacuo and the residue partitioned between DCM and water. The aqueous layer was extracted three times with DCM the 10% methanol in DCM, the combined organic extracts dried using a phase separation cartridge before being concentrated in vacuo. The resultant residue was subjected to flash chromatography (SiO2, gradient 0 to 10% methanol in DCM) to give 278 as a white solid (34 mg, 61%). LCMS: RT=2.26 min, [M+H]+ 465. $^1$H NMR 400 MHz (DMSO-d6) δ: 9.43 (1 H, s), 7.96 (1 H, s), 7.92 (1 H, s), 6.91 (1 H, s), 5.91-5.90 (1 H, m), 4.60-4.58 (4 H, m), 3.15 (2 H, s), 3.06 (3 H, s), 2.93 (2 H, d, J=11.06 Hz), 2.82 (3 H, s), 2.63 (1 H, m), 2.15-2.14 (2 H, m), 1.82-1.69 (4 H, m), 1.50 (6 H, d, J=6.60 Hz)

Example 279

2-(4-(2-(1-isopropyl-1H-1,2,4-triazol-5-yl)-5,6-dihydrobenzo[f]imidazo[1,2-d][1,4]oxazepin-9-yl)piperidin-1-yl)-N-methylacetamide 279

Following the procedures for Example 278, 2-(2-isopropyl-2H-[1,2,4]triazol-3-yl)-8-piperidin-4-yl-4,5-dihydro-6-oxa-1,3a,9-triaza-benzo[e]azulene hydrochloride was reacted with N-dimethyl-2-chloroacetamide to give 279. LCMS: RT=2.62 min, [M+H]=450

Example 280

2-(1-isopropyl-1H-1,2,4-triazol-5-yl)-4,5-dihydrobenzo[b][1,2,4]triazolo[1,5-d][1,4]oxazepine 280 (88)

To amide 87 (0.0485 g, 0.211 mmol) in toluene (1.68 mL, 15.8 mmol) was added 1,1-dimethoxy-N,N-dimethylmethanamine (0.158 mL, 1.19 mmol), and the mixture was heated in a sealed flask to 102° C. for 2 hours while stirring (FIG. 18). Next, the reaction mixture was cooled and concentrated to dryness, and isopropylhydrazine hydrochloride (0.0396 g, 0.358 mmol) and acetic acid (0.934 mL, 16.4 mmol) were added and the reaction was sealed and heated to 102° C. overnight while stirring. Then, the reaction was concentrated to dryness and taken up in DMF, and preparative HPLC (acetonitrile/water) gave 280 in 42% yield. 1H NMR (500 MHz, CDCl3) δ 8.23 (d, J=8.2 Hz, 1H), 8.02 (s, 1H), 7.30 (dd, J=15.6, 7.8 Hz, 2H), 7.23 (d, J=7.4 Hz, 1H), 7.20 (d, J=7.9 Hz, 1H), 5.77-5.69 (m, 1H), 4.51 (t, J=5.6 Hz, 2H), 3.56 (t, J=5.6 Hz, 2H), 1.60 (d, J=6.6 Hz, 6H). LRMS m/z Calcd. for C12H16N6O: 296.13856, found: 297.1 [M+1].

Example 281

10-fluoro-2-(1-isopropyl-3-methyl-1H-1,2,4-triazol-5-yl)-5,6-dihydrobenzo[f]imidazo[1,2-d][1,4]oxazepine 281

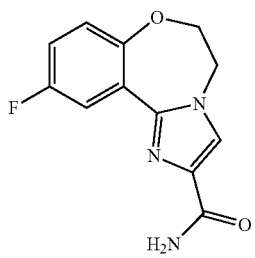 [SMILES: NC(=O)c1cn2c(n1)-c1cc(F)ccc1OCC2]

10-Fluoro-5,6-dihydrobenzo[f]imidazo[1,2-d][1,4]oxazepine-2-carboxamide from Example 90 (0.2 g, 0.81 mmol), dimethylacetamide-dimethyacetal (0.36 mL, 2.4 mmol), and toluene (10 mL, 90 mmol) were combined in a round bottom flask with a vigreux condensation column attached. Heated at 95° C. for more than 24 hours and concentrated in vacuo. The residue was dissolved in acetic acid and isopropylhydrazine hydrochloride (0.11 g, 0.97 mmol) was added and heated at 95° C. with a vigreux condensation column attached for four hours. Complete reaction by LCMS. Concentrated in vacuo and purified by HPLC to give 281 (67.7 mg, 26% yield, M+1 328.1)

Example 282

9-(1,2-dimethyl-1H-imidazol-4-yl)-2-(1-isopropyl-1H-1,2,4-triazol-5-yl)-5,6-dihydrobenzo[f]imidazo[1,2-d][1,4]oxazepine 282

To a 100 mL round bottom flask charged with NaH (12 mg, 0.5 mmol) was added DMF (6 mL) dropwise, followed by 271 (100 mg, 0.25 mmol). After stirring for about 1 hour, iodomethane (48 mg, 0.33 mmol) was added dropwise at 0° C. in THF. Then the mixture was allowed to warm up to room temperature slowly and stirred for 2 hours. The reaction mixture was poured into water, extracted with EtOAc, the organic phase was dried over anhydrous Na2SO4, concentrated, then purified by pre-TLC (EtOAc) to give 50 mg (52% Yield) of 282. 1H NMR (CDCl3, 400 MHz): δ 8.48 (d, J=8.0 Hz, 1 H), 7.87 (s, 1 H), 7.64 (s, 1 H), 7.48-7.44 (m, 2 H), 7.14 (s, 1 H), 6.04-5.98 (m, 1 H), 4.51-4.43 (m, 4 H), 3.62 (s, 3 H), 2.45 (s, 3 H),1.60 (d, J=6.8 Hz, 6 H), and 15 mg (16% yield) of the regioisomer 9-(1,2-dimethyl-1H-imidazol-5-yl)-2-(1-isopropyl-1H-1,2,4-triazol-5-yl)-5,6-dihydrobenzo[f]imidazo[1,2-d][1,4]oxazepine 291 1H NMR (CDCl3, 400 MHz): δ8.57 (d, J=8.0 Hz, 1 H), 7.87 (s, 1 H), 7.87 (s, 1 H), 7.69 (s, 1 H), 7.16 (d, J=6.8 Hz, 1 H), 7.06-7.04 (m, 2 H), 6.02-5.96 (m, 1 H), 4.54-4.52 (m, 2 H), 4.48-4.47 (m, 2 H), 3.59 (s, 3 H), 2.46 (s, 3 H), 1.60 (d, J=6.8 Hz, 6 H). LC-MS: m/z=389 [M+H+].

Example 285

2-(4-(2-(1,3-dimethyl-1H-1,2,4-triazol-5-yl)-5,6-dihydrobenzo[f]imidazo[1,2-d][1,4]oxazepin-9-yl)-1H-pyrazol-1-yl)ethanol 285

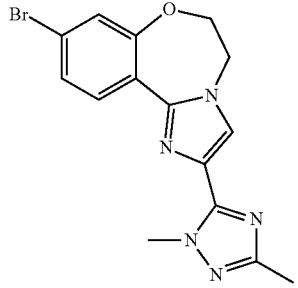 [SMILES: Cc1nc(-c2cn3c(n2)-c2ccc(Br)cc2OCC3)n(C)n1]

8-Bromo-4,5-dihydro-6-oxa-1,3a-diaza-benzo[e]azulene-2-carboxylic acid amide was reacted with dimethylacetamide-dimethylacetal in toluene, followed by dissolution in acetic acid and treatment with methylhydrazine hydrochloride to give 8-Bromo-2-(2,5-dimethyl-2H-[1,2,4]triazol-3-yl)-4,5-dihydro-6-oxa-1,3a-diaza-benzo[e]azulene. MS(ESI+) 360.0/362.0

To a microwave vial was added 8-Bromo-2-(2,5-dimethyl-2H-[1,2,4]triazol-3-yl)-4,5-dihydro-6-oxa-1,3a-diaza-benzo[e]azulene (0.150 g, 0.000416 mol) and Potassium acetate (0.123 g, 0.00125 mol) in Acetonitrile (2.0 mL) and Water (2.0 mL). The solution was thoroughly purged with N2. 1-[2-(Tetrahydro-pyran-2-yloxy)-ethyl]-4-(4,4,5,5-tetramethyl-[1,3,2]dioxaborolan-2-yl)-1H-pyrazole (0.148 g, 0.000458 mol) and Tetrakis(triphenylphosphine)palladium (0) (0.0481 g, 0.0000416 mol) were added and the vial was immediately sealed. The reaction was heated in the microwave to 140° C. for 20 minutes. The mixture was partitioned between saturated NH4Cl and methylene chloride and extracted 3 times with methylene chloride. The organic phases were combined, dried with MgSO4, and concentrated. The crude was dissolved in methylene chloride (5.0 mL) and hydrogen chloride (0.00125 mol, 4N in dioxane, 0.31 mL) was added dropwise. The reaction was stirred at room temperature for 1 hour. The mixture was concentrated and partitioned between saturated sodium bicarbonate and methylene chloride and extracted 3 times with methylene chloride. Most of the product precipitated in the aqueous phase—the mixture was filtered and submitted to reverse-phase HPLC, then recrystallized in EtOH/MeOH to afford 24 mg 285 as a white solid. MS(ESI+) 392.2. 1H NMR (500 MHz, DMSO) δ 8.40 (d, J=8.4 Hz, 1H), 8.22 (s, 1H), 7.94 (s, 1H), 7.88 (s, 1H), 7.36 (dd, J=8.4, 1.7 Hz, 1H), 7.27 (d, J=1.7 Hz, 1H), 4.90 (t, J=5.3 Hz, 1H), 4.54-4.48 (m, 4H), 4.21 (s, 3H), 4.16 (t, J=5.7 Hz, 2H), 3.77 (q, J=5.6 Hz, 2H), 2.24 (s, 3H)

Example 286

2-(1-isopropyl-1H-1,2,4-triazol-5-yl)-9-(1-(2-methoxyethyl)piperidin-4-yl)-5,6-dihydrobenzo[f]imidazo[1,2-d][1,4]oxazepine 286

To a solution of 2-(2-isopropyl-2H-[1,2,4]triazol-3-yl)-8-piperidin-4-yl-4,5-dihydro-6-oxa-1,3a-diaza-benzo[e]azulene trifluoroacetic acid salt (300 mg, 0.61 mmol) in DMF (3.5 mL) were added potassium carbonate (290 mg, 2.10 mmol) and 1-bromo-2-methoxy-ethane (93 mg, 0.67 mmol). The resultant reaction mixture was stirred at 60° C. for 4 hours before being cooled to RT and diluted with DCM. The mixture was washed sequentially with sodium hydrogen carbonate solution (sat. aq.), water and brine then dried (MgSO4) and concentrated in vacuo. The resultant residue was purified by flash column chromatography (SiO2, gradient 0-8% MeOH in DCM) and triturated with petroleum ether to afford 286 as a white solid (127 mg, 0.29 mmol, 48%). LCMS: RT=3.02 min, [M+H]=437. $^1$H NMR δ (ppm) (DMSO-d6): 8.28 (1 H, d, J=8.28 Hz), 7.86 (1 H, d, J=0.62 Hz), 7.85 (1 H, s), 7.01 (1H, dd, J=8.36, 1.77 Hz), 6.85 (1 H, d, J=1.72 Hz), 5.90-5.80 (1 H, m), 4.45 (4 H, m), 3.40 (2H, t, J=5.89 Hz), 3.20 (3 H, s), 2.93 (2 H, d, J=11.11 Hz), 2.01 (2 H, dd, J=12.41, 10.21 Hz), 1.70 (2 H, d, J=12.52 Hz), 1.58 (2 H, ddd, J=24.42, 12.21, 3.61 Hz), 1.44 (6 H, d, J=6.60 Hz). 3H obscured by solvent.

Example 287

2-(4-(2-(1-isopropyl-1H-1,2,4-triazol-5-yl)-5,6-dihydrobenzo[f]imidazo[1,2-d][1,4]oxazepin-9-yl)piperidin-1-yl)-2-methylpropanamide 287

To 2-{4-[2-(2-isopropyl-2H-[1,2,4]triazol-3-yl)-4,5-dihydro-6-oxa-1,3a-diaza-benzo[e]azulen-8-yl]-piperidin-1-yl}-2-methyl-propionitrile (312 mg, 0.70 mmol) was added concentrated sulfuric acid (3.5 mL). The resultant mixture was stirred for 3.5 hours at RT before being poured onto ice and basified with sodium carbonate. The aqueous mixture was extracted with 10% MeOH in DCM (×5). The combined organic layers were dried (Na2SO4) and concentrated in vacuo. The resultant residue was purified by flash column chromatography (SiO2, gradient 0-10% MeOH in DCM), then triturated with diethyl ether (×3), to afford 287 (196 mg, 0.42 mmol, 60%). LCMS: RT=2.67 min, [M+H]+=464. $^1$H NMR δ (ppm)(DMSO-d): 8.27 (1 H, d, J=8.27 Hz), 7.86 (1H, d, J=0.63 Hz), 7.85 (1 H, s), 7.17 (1 H, d, J=3.55 Hz), 7.03 (1 H, dd, J=8.34, 1.74 Hz), 6.91-6.89 (2 H, m), 5.89-5.79 (1 H, m), 4.48-4.41 (4 H, m), 2.80 (2 H, d, J=10.82 Hz), 2.17-2.09 (2 H, m), 1.77-1.60 (4 H, m), 1.44 (6 H, d, J=6.60 Hz), 1.05 (6 H, s). 1H obscured by solvent.

Example 288

2-(4-(2-(1-isopropyl-3-methyl-1H-1,2,4-triazol-5-yl)-5,6-dihydrobenzo[f]imidazo[1,2-d][1,4]oxazepin-9-yl)piperidin-1-yl)ethanol 288

To a suspension of 2-(2-isopropyl-5-methyl-2H-[1,2,4]triazol-3-yl)-8-piperidin-4-yl-4,5-dihydro-6-oxa-1,3a-diazabenzo[e]azulene hydrochloride (100 mg, 0.23 mmol) in DMF (2 mL) was added sodium phosphate dibasic (107 mg, 0.75 mmol), triethylamine (2 drops) and 2-(2-bromo-ethoxy)-tetrahydro-pyran (38 μL, 0.25 mmol). The resultant mixture was stirred overnight at RT before a further addition of triethylamine (100 μL) was made. The reaction was stirred at 50° C. for 5 hours then allowed to stand at RT over the weekend. The reaction was heated to 50° C. and stirred overnight before the addition of 2-(2-bromo-ethoxy)-tetrahydro-pyran (38 μL, 0.25 mmol) and potassium iodide (10 mg, 0.06 mmol) then stirred overnight at 55° C. The solution was cooled and loaded onto a SCX-2 cartridge, washed with MeOH then eluted with 2M NH3 in MeOH. The resultant residue was purified by flash column chromatography (SiO2, gradient 0-10% MeOH in DCM) this gave 288 (31 mg, 0.07 mmol, 31%). LCMS: RT=2.59 min, [M+H]+ 437. $^1$H NMR δ (ppm) (CDCl3): 8.42 (1 H, d, J=8.30 Hz), 7.58 (1 H, s), 7.00 (1 H, dd, J=8.34, 1.83 Hz), 6.88 (1 H, d, J=1.78 Hz), 5.93-5.83 (1 H, m), 4.46-4.43 (2 H, m), 4.41-4.37 (2 H, m), 3.70 (2 H, t, J=5.19 Hz), 3.17 (2 H, d, J=11.24 Hz), 2.68 (2 H, t, J=5.17 Hz), 2.62-2.50 (1 H, m), 2.38 (3 H, s), 2.36-2.27 (2 H, m), 2.05-1.85 (4 H, m), 1.54 (6 H, d, J=6.65 Hz). OH not observed Example 289

2-(4-(2-(1-isopropyl-3-methyl-1H-1,2,4-triazol-5-yl)-5,6-dihydrobenzo[f]imidazo[1,2-d][1,4]oxazepin-9-yl)piperidin-1-yl)-2-methylpropanamide 289

To 2-{4-[2-(2-isopropyl-5-methyl-2H-[1,2,4]triazol-3-yl)-4,5-dihydro-6-oxa-1,3a-diaza-benzo[e]azulen-8-yl]-piperidin-1-yl}-2-methyl-propionitrile (140 mg, 0.31 mmol) was added concentrated sulfuric acid (1.75 mL). The mixture was stirred at RT for 3.5 hours before the reaction was diluted with ice and neutralised with sodium carbonate. The aqueous mixture was extracted with 10% MeOH in DCM (×5) before the organic phase was dried (MgSO4) and concentrated in vacuo. The resultant residue was purified by flash column chromatography (SiO2, gradient 0-10% MeOH in DCM). The material was triturated with diethyl ether before being purified by reverse phase HPLC (C18, gradient 20-70% MeOH/0.1% formic acid in water/0.1% formic acid). The resultant residue was taken up into MeOH (1.2 mL) and treated with 0.2 M HCl in diethyl ether. The solution was concentrated in vacuo affording 289 (14 mg, 0.03 mmol, 9%). LCMS: RT=2.65 min, [M+H]+=478. $^1$H NMR δ (ppm) (DMSO-d6): 9.50 (1 H, m), 8.33 (1 H, d, J=8.29 Hz), 7.97 (1 H, s), 7.93 (1 H, s), 7.86 (1 H, s), 7.02 (1 H, dd, J=8.36, 1.75 Hz), 6.87 (1 H, d, J=1.71 Hz), 5.78-5.71 (1 H, m), 4.50-4.44 (4 H, m), 3.19-3.04 (2H, m), 2.91-2.80 (1 H, m), 2.25 (3 H, s), 2.12 (2 H, d, J=13.49 Hz), 1.98 (2 H, d, J=13.54 Hz), 1.51 (6 H, s), 1.43 (6 H, d, J=6.59 Hz). 2H obscured by solvent.

Example 290

1-(5-(2-(1-isopropyl-1H-1,2,4-triazol-5-yl)-5,6-dihydrobenzo[f]imidazo[1,2-d][1,4]oxazepin-9-yl)-1H-imidazol-2-yl)-2-methylpropan-2-ol 290

Step 1

To a solution of imidazole (81.6 g, 1.2 mol) in dry THF (2.5 L) was slowly added NaH (86.4 g, 3.6 mol) in small portions at −78° C. After all NaH was added, the mixture was stirred at −78° C. for 30 min, and 2-chloro-tetrahydro-pyran solution, prepared by hydrogen chloride gas treatment of dihydropyran, was added to the reaction mixture dropwise. The mixture was slowly warmed to r.t. and it was stirred at r.t. for 2 h. Methanol was added to quench the excess NaH. The mixture was concentrated with a rotary evaporator. Water was added and it was extract with EtOAc (500 mL×3), dried over MgSO4, and purified by neutral Al$_2$O$_3$ column chromatography (petroleum ether 5 L, petroleum ether:CH2Cl2=10:1, petroleum ether:CH2Cl2=3:1, CH2Cl2 and EtOAc). The last four fractions were pooled and concentrated to give 1-(tetrahydro-pyran-2-yl)-1H-imidazole (140 g, 76%). 1H NMR (CDCl3): δ 7.65 (s, 1H), 7.08 (s, 1H), 7.05 (s, 1H), 5.20 (dd, J=2.6, 9.5 Hz, 1H), 4.05-4.02 (m, 1H), 3.68-3.62 (m, 1H), 2.01-1.89 (m, 3H), 1.69-1.60 (m, 3H)

Step 2: 2-methyl-1-[1-(tetrahydro-pyran-2-yl)-1H-imidazol-2-yl]-propan-2-ol

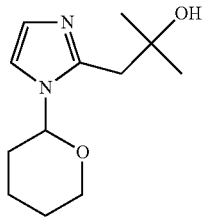 [SMILES: CC(C)(O)Cc1nccn1C1CCCCO1]

To the solution of 1-(tetrahydro-pyran-2-yl)-1H-imidazole (7.6 g, 50 mmol) in dry THF (500 ml) at −78° C. was added n-BuLi solution (2.5 M in hexanes, 25 mL, 60 mmol, 1.2 equiv). The reaction mixture was slowly warmed to 0° C. and stirred at 0° C. for 30 min. After it was cooled to −78° C., 2,2-dimethyloxirane (7.2 g, 100 mmol) was added and it was stirred for 1 h. The reaction mixture was warmed to r.t. slowly and stirred at r.t. overnight. MeOH was added and the reaction mixture was concentrated by a rotary evaporator. Water (30 ml) was added and it was extracted with CH2Cl2 (15 ml×3). The organic layer was dried over MgSO4, concentrated, and purified by neutral Al2O3 column chromatography (CH2Cl2:MeOH=100:1) to give 8 gm of 2-methyl-1-[1-(tetrahydro-pyran-2-yl)-1H-imidazol-2-yl]-propan-2-ol (75%). 1H NMR (CDCl3): δ 7.04 (s, 1H), 6.95 (s, 1H), 5.13 (dd, J=2.6, 9.5 Hz, 1H), 4.05-4.02 (m, 1H), 3.68-3.62 (m, 1H), 2.82 (d, J=12.0 Hz, 2H), 2.01-1.89 (m, 4H), 1.92 (m, 1H), 1.69-1.60 (m, 3H), 1.24 (m, 6H)

Step 3: 1-[4-bromo-1-(tetrahydro-pyran-2-yl)-1H-imidazol-2-yl]-2-methyl-propan-2-ol

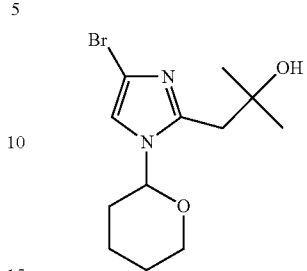

To a solution of 2-methyl-1-[1-(tetrahydro-pyran-2-yl)-1H-imidazol-2-yl]-propan-2-ol (1.12 g, 5 mmol) in DMF (10 mL) at −78° C. was added NBS (0.72 g, 4 mmol) in DMF (pre-cooled to −78° C.). The reaction mixture was warmed to r.t. slowly and stirred at r.t. overnight. The solvent was removed under vacuum and purified by neutral Al2O3 column chromatography (CH2Cl2: MeOH=100:1) to give 0.5 gm of 1-[4-bromo-1-(tetrahydro-pyran-2-yl)-1H-imidazol-2-yl]-2-methyl-propan-2-ol (34%). 1H NMR (CDCl3, 400 MHz): δ 7.03 (s, 1H), 5.13 (dd, J=2.6, 9.6 Hz, 1H), 4.05-4.02 (m, 1H), 3.68-3.62 (m, 1H), 2.82 (d, J=12.0 Hz, 2H), 2.01-1.89 (m, 4H), 1.92 (m, 1H), 1.69-1.60 (m, 3H), 1.24 (m, 6H)

Step 4: 2-(1-isopropyl-1H-1,2,4-triazol-5-yl)-9-(4,4,5,5-tetramethyl-1,3,2-dioxaborolan-2-yl)-5,6-dihydrobenzo[f]imidazo[1,2-d][1,4]oxazepine

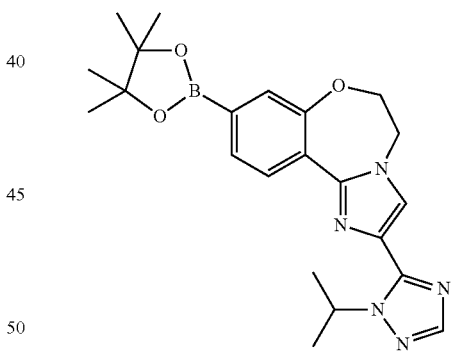

To a mixture of 9-bromo-2-(1-isopropyl-1H-1,2,4-triazol-5-yl)-5,6-dihydrobenzo Wimidazo[1,2-d][1,4]oxazepine (500 mg, 1.3 mmol) and 4,4,5,5,4',4',5',5'-octamethyl-[2,2']bi[1,3,2]dioxaborolanyl (509 mg, 2.0 mmol) in dry DMF (4 mL) under nitrogen was added KOAc (393 mg, 4.0 mmol) and Pd(dppf)Cl2 (50 mg, 0.067 mmol). The reaction mixture was heated at 120° C. for 20 min in a microwave reactor. After it was cooled to room temperature and concentrated, the crude product was purified by column chromatography (hexanes/EtOAc=3:1 to 1:2) to give 2-(1-isopropyl-1H-1,2,4-triazol-5-yl)-9-(4,4,5,5-tetramethyl-1,3,2-dioxaborolan-2-yl)-5,6-dihydrobenzo[f]imidazo[1,2-d][1,4]oxazepine as a yellow solid (275 mg, 49%). LCMS: (ESI), m/z 422 [M+H]+

Step 5: 1-[4-[2-(2-isopropyl-2H-[1,2,4]triazol-3-yl)-4,5-dihydro-6-oxa-1,3a-diaza-benzo[e]azulen-8-yl]-1-(tetrahydro-pyran-2-yl)-1H-imidazol-2-yl]-2-methyl-propan-2-ol

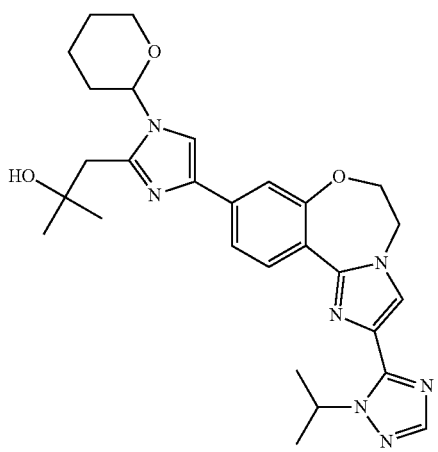 [SMILES: CC(C)n1ncnc1-c1cn2c(n1)-c1ccc(-c3cn(C4CCCCO4)c(CC(C)(C)O)n3)cc1OCC2]

To a mixture of 2-(1-isopropyl-1H-1,2,4-triazol-5-yl)-9-(4,4,5,5-tetramethyl-1,3,2-dioxaborolan-2-yl)-5,6-dihydrobenzo[f]imidazo[1,2-d][1,4]oxazepine (600 mg, 1.42 mmol) and 1-(4-bromo-1-(tetrahydro-pyran-2-yl)-1H-imidazol-2-yl)-2-methyl-propan-2-ol (648 mg, 2.1 mmol) in dry DMF (6 mL) under nitrogen was added CsF (534 mg, 3.53 mmol), CuI (27 mg, 0.14 mmol) and Pd(PPh3)4 (81 mg, 0.07 mmol). The reaction mixture was heated at 120° C. for 20 min in a microwave reactor. It was filtered, concentrated and purified by column chromatography (DCM/MeOH=20:1) to give 1-[4-[2-(2-isopropyl-2H-[1,2,4]triazol-3-yl)-4,5-dihydro-6-oxa-1,3a-diaza-benzo[e]azulen-8-yl]-1-(tetrahydro-pyran-2-yl)-1H-imidazol-2-yl]-2-methyl-propan-2-ol as brown oil (1.1 g). LCMS: (ESI, m/z)=518 [M+H]+.

Step 6

To a solution of 1-[4-[2-(2-isopropyl-2H-[1,2,4]triazol-3-yl)-4,5-dihydro-6-oxa-1,3a-diaza-benzo[e]azulen-8-yl]-1-(tetrahydro-pyran-2-yl)-1H-imidazol-2-yl]-2-methyl-propan-2-ol (735 mg, 1.42 mmol) in EtOH (15 mL) was added a solution of hydrogen chloride in MeOH (7.1 mL, 28.4 mmol). The reaction mixture was heated at reflux for 5 h, cooled to r.t. and concentrated. Saturated NaHCO3 solution was added slowly and the reaction mixture was extracted with EtOAc. The combined organic layer was dried over Na2SO4, filtered and concentrated. The crude product was purified by prep-TLC (DCM:MeOH=8:1) to give 290 as a yellow solid (74 mg, 12%). 1H NMR (CDCl3, 400 MHz): δ 8.44 (d, J=8.4 Hz, 1H), 7.89 (s, 1H), 7.58 (s, 1H), 7.43-7.36 (m, 2H), 7.28 (s, 1H), 5.95-5.91 (m, 1H), 4.45-4.02 (m, 4H), 2.97 (s, 2H), 1.60 (d, J=6.8 Hz, 6H), 1.30 (s, 6H). MS: (ESI, m/z)=434 [M+H]+.

Example 291

9-(1,2-dimethyl-1H-imidazol-5-yl)-2-(1-isopropyl-1H-1,2,4-triazol-5-yl)-5,6-dihydrobenzo[f]imidazo[1,2-d][1,4]oxazepine 291

Step 1: 4-iodo-2-methyl-1-((2-(trimethylsilyl)ethoxy)methyl)-1H-imidazole and 5-iodo-2-methyl-1-((2-(trimethylsilyl)ethoxy)methyl)-1H-imidazole

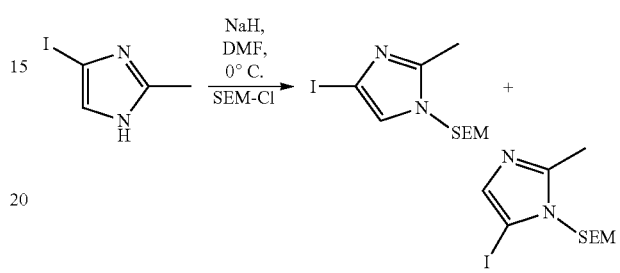

To NaH (1.84 g, 76.6 mmol) in a 100 mL of round bottom flask was added DMF (10 mL) dropwise, 4-iodo-2-methyl-1H-imidazole (8 g, 38.3 mmol) was added. After it was stirred for about 1 hour, 2-(trimethylsilyl)ethoxymethyl chloride (5.36 g, 45.9 mmol) was added dropwise at 0° C. The temperature was allowed to warm up to r.t. slowly, and stirred at r.t. for 2 h. The reaction mixture was poured into water and extracted with EtOAc. The organic phase was dried over anhydrous Na2SO4, concentrated, and purified by column chromatography (hexanes/EtOAc=5:1) to give a mixture of 4-iodo-2-methyl-1-((2-(trimethylsilyl)ethoxy)methyl)-1H-imidazole and 5-iodo-2-methyl-1-((2-(trimethylsilyl)ethoxy)methyl)-1H-imidazole which was used directly for next step (7.8 g, 63%). LC-MS m/z 339 [M+H+]

Step 2: 2-methyl-1-((2-(trimethylsilyl)ethoxy)methyl)-4-(trimethyl stannyl)-1H-imidazole and 2-methyl-1-((2-(trimethylsilyl)ethoxy)methyl)-5-(trimethyl stannyl)-1H-imidazole

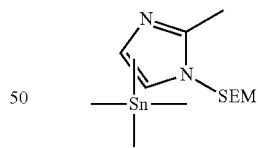

To a mixture of 4-iodo-2-methyl-1-((2-(trimethylsilyl)ethoxy)methyl)-1H-imidazole and 5-iodo-2-methyl-1-((2-(trimethylsilyl)ethoxy)methyl)-1H-imidazole (1.29 g, 3.8 mmol) in DCM (15 mL) was added ethylmagnesium bromide (1.9 mL, 3 mol/L, 5.7 mmol) at −78° C. The temperature of the mixture was allowed to warm up to about 10° C. slowly. After it was cooled to −78° C., trimethyltin chloride (6.5 ml, 1 mol/L, 6.5 mmol) was added dropwise. After the temperature was allowed to slowly warm up to room temperature and the reaction mixture was pouted into saturate NH4Cl solution and extracted with DCM. The organic was washed with water twice, dried over anhydrous Na2SO4, and concentrated to give the mixture of 2-methyl-1-((2-(trimethylsilyl)ethoxy)methyl)-4-(trimethyl stannyl)-1H- imidazole and 2-methyl-1-((2-(trimethylsilyl)ethoxy)methyl)-5-(trimethyl stannyl)-1H-imidazole (1.0 g, 70%). LC-MS m/z 377 [M+H+]

Step 3: 2-(1-isopropyl-1H-1,2,4-triazol-5-yl)-9-(2-methyl-1-((2-(trimethylsilyl)ethoxy)methyl)-1H-imidazol-4-yl)-5,6-dihydrobenzo[f]imidazo[1,2-d][1,4]oxazepine

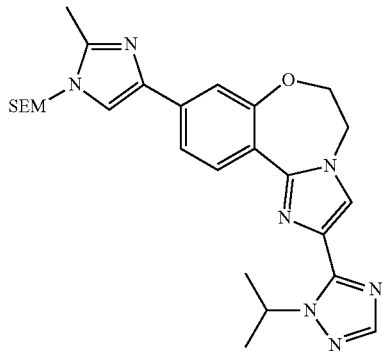 [SMILES: Cc1nc(-c2ccc3c(c2)OCCn2cc(-c4ncnn4C(C)C)nc2-3)cn1COCC[Si](C)(C)C]

A mixture of 9-bromo-2-(1-isopropyl-1H-1,2,4-triazol-5-yl)-5,6-dihydrobenzo[f]imidazo[1,2-d][1,4]oxazepine 194 (300 mg, 0.8 mmol), Pd(PPh3)4 (93 mg, 0.08 mmol), a mixture of 2-methyl-1-((2-(trimethylsilyl)ethoxy)methyl)-4-(trimethyl stannyl)-1H-imidazole and 2-methyl-1-((2-(trimethylsilyl)ethoxy)methyl)-5-(trimethyl stannyl)-1H-imidazole (600 mg, 1.6 mmol) in dioxane (2 mL) was bubbled with N2 for about 2 min and then it was stirred at 120° C. for 35 min under the microwave irradiation. It was filtered, concentrated and purified by prep-TLC (EtOAc) to give 2-(1-isopropyl-1H-1,2,4-triazol-5-yl)-9-(2-methyl-1-((2-(trimethylsilyl)ethoxy)methyl)-1H-imidazol-4-yl)-5,6-dihydrobenzo[f]imidazo[1,2-d][1,4]oxazepine (238 mg, 59%). LC-MS m/z 506 [M+H+]

Step 4: 2-(1-isopropyl-1H-1,2,4-triazol-5-yl)-9-(2-methyl-1H-imidazol-4-yl)-5,6-dihydrobenzo[f]imidazo[1,2-d][1,4]oxazepine 271

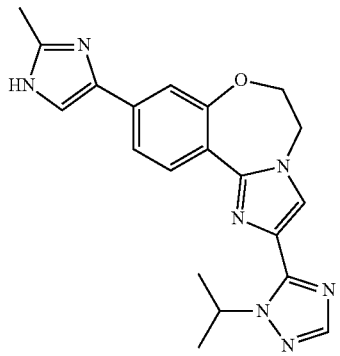 [SMILES: Cc1nc(-c2ccc3c(c2)OCCn2cc(-c4ncnn4C(C)C)nc2-3)c[nH]1]

A solution of HCl in MeOH (4 mol/L, 3 mL, 12 mmol) was added dropwise to a solution of 2-(1-isopropyl-1H-1,2,4-triazol-5-yl)-9-(2-methyl-1-((2-(trimethylsilyl)ethoxy)methyl)-1H-imidazol-4-yl)-5,6-dihydrobenzo Wimidazo[1,2-d][1,4]oxazepine 271 (360 mg, 0.71 mmol) in ethanol (3 mL) at 0° C. After 30 min, the temperature was allowed to warm up to 70° C. and stirred at 70° C. overnight. It was concentrated, basified with TEA, and purified by prep-TLC to give 2-(1-isopropyl-1H-1,2,4-triazol-5-yl)-9-(2-methyl-1H-imidazol-4-yl)-5,6-dihydrobenzo[f]imidazo[1,2-d][1,4]oxazepine 271 (240 mg, 91%). 1H NMR (MeOD, 400 MHz): δ 8.72 (s, 1H), 8.60 (d, J=4.4 Hz, 1H), 8.19 (s, 1H), 7.87 (s, 1H), 7.51 (d, J=2.0 Hz, 1H), 7.46 (s, 1H), 5.72-5.72 (m, 1H), 4.65-4.64 (m, 2H), 4.60-4.59 (m, 2H), 2.68 (s, 3H), 1.63-1.62 (d, J=6.8 Hz, 6H). LC-MS m/z 376 [M+H+]

Step 5

Following the procedures for Example 282, to sodium hydride NaH (12 mg, 0.5 mmol) in a 100 mL round bottom flask was added DMF (6 mL) dropwise 2-(1-isopropyl-1H-1,2,4-triazol-5-yl)-9-(2-methyl-1H-imidazol-4-yl)-5,6-dihydrobenzo[f]imidazo[1,2-d][1,4]oxazepine 271 (100 mg, 0.25 mmol) was added. After it was stirred for 1 h, iodomethane (48 mg, 0.33 mmol) in THF was added dropwise at 0° C. The mixture was allowed to warm up to room temperature slowly and stirred for 2 hours. The reaction mixture was poured into water, extracted with EtOAc. The organic phase was dried over anhydrous Na2SO4, concentrated, and purified by prep-TLC (EtOAc) to give 282 (50 mg, 51%) and 291 (15 mg, 15%). 1H NMR (CDCl3, 400 MHz): δ 8.57 (d, J=8.0 Hz, 1H), 7.87 (s, 1H), 7.87 (s, 1H), 7.69 (s, 1H), 7.16 (d, J=6.8 Hz, 1H), 7.06-7.04 (m, 2H), 6.02-5.96 (m, 1H), 4.54-4.52 (m, 2H), 4.48-4.47 (m, 2H), 3.59 (s, 3H), 2.46 (s, 3H), 1.60 (d, J=6.8 Hz, 6H). LC-MS m/z 389 [M+H+]

Example 292

1-(4-(2-(1-isopropyl-1H-1,2,4-triazol-5-yl)-5,6-dihydrobenzo[f]imidazo[1,2-d][1,4]oxazepin-9-yl)piperidin-1-yl)-2-methylpropan-2-ol 292

To a stirred suspension of 2-(2-isopropyl-2H-[1,2,4]triazol-3-yl)-8-piperidin-4-yl-4,5-dihydro-6-oxa-1,3a-diazabenzo[e]azulene trifluoro acetate (300 mg, 0.61 mmol) in THF (8 mL) was added lithium perchlorate (65 mg, 0.61 mmol) and DIPEA (0.21 mL, 1.21 mmol) followed by 1,2-epoxy-2-methylpropane (0.54 mL, 0.81 mmol) and the mixture stirred at RT for 5 h before the addition of water (2.5 mL). After stirring for a further 18 h then DIPEA (0.16 mL, 0.92 mmol) added and the mixture heated at 45° C. for 5 h then at RT for 72 h. The reaction mixture was diluted with DCM and washed with water before being dried (MgSO4), filtered and concentrated in vacuo. The resultant residue was subjected to flash chromatography (SiO2, preconditioned with 25% TEA in DCM, gradient 0 to 5% methanol in DCM) then freeze dried from methanol/water and triturated in petroleum ether to give 292 as a cream solid (92 mg, 34%). LCMS: RT=2.76 min, [M+H]+=451. 1H NMR 400 MHz (DMSO-d) δ: 8.32 (1 H, d, J=8.28 Hz), 7.90 (2 H, d, J=2.80 Hz), 7.05 (1 H, dd, J=8.35, 1.77 Hz), 6.90 (1 H, d, J=1.70 Hz), 7.27-4.48 (1 H, m), 4.49 (4 H, q, J=5.87 Hz), 4.03 (1 H, s), 3.04 (2 H, d, J=10.80 Hz), 2.46 (1 H, s), 2.23 (4 H, s), 1.70 (4 H, s), 1.48 (6 H, d, J=6.59 Hz), 1.10 (6 H, s)

Example 293

2-(4-(2-(1-isopropyl-1H-1,2,4-triazol-5-yl)-5,6-dihydrobenzo[f]imidazo[1,2-d][1,4]oxazepin-9-yl)piperidin-1-yl)ethanol 293

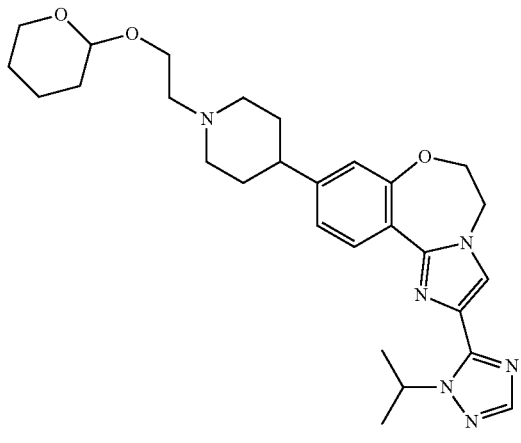 [SMILES: CC(C)n1ncnc1-c1cn2c(n1)-c1ccc(C3CCN(CCOC4CCCCO4)CC3)cc1OCC2]

To a stirred suspension of 2-(2-isopropyl-2H-[1,2,4]triazol-3-yl)-8-piperidin-4-yl-4,5-dihydro-6-oxa-1,3a-diaza-benzo[e]azulene trifluoro acetate (300 mg, 0.61 mmol) in DMF (3.5 mL) was added potassium carbonate (290 mg, 2.1 mmol) and 2-(2-bromoethoxy)tetrahydro-2H-pyran and the mixture heated at 60° C. for 18 h before being diluted with DCM. The resultant solution was washed with saturated aqueous sodium hydrogen carbonate, water and then brine before being dried (MgSO4), filtered and concentrated in vacuo. The resultant residue was subjected to flash chromatography (SiO2, gradient 0 to 8% methanol in DCM) to give 2-(2-Isopropyl-2H-[1,2,4]triazol-3-yl)-8-{1-[2-(tetrahydro-pyran-2-yloxy)-ethyl]-piperidin-4-yl}-4,5-dihydro-6-oxa-1,3a-diaza-benzo[e]azulene as a cream solid (147 mg, 48%). 1H NMR 400 MHz (CDCl3) δ: 8.44 (1 H, d, J=8.29 Hz), 7.87 (1 H, s), 7.63 (1 H, s), 7.04 (1 H, dd, J=8.33, 1.81 Hz), 6.92 (1 H, d, J=1.75 Hz), 6.01-6.00 (1 H, m), 4.63 (1 H, t, J=3.54 Hz), 4.46-4.45 (4 H, m), 3.92-3.91 (2 H, m), 3.65 (1 H, m), 3.57-3.49 (1 H, m), 3.15 (2 H, m), 2.73 (2 H, m), 2.53 (1 H, m), 2.25 (2 H, m), 1.87 (5 H, m), 1.73-1.69 (3 H, m), 1.60 (8 H, m).

A solution of 2-(2-isopropyl-2H-[1,2,4]triazol-3-yl)-8-{1-[2-(tetrahydro-pyran-2-yloxy)-ethyl]-piperidin-4-yl}-4,5-dihydro-6-oxa-1,3a-diaza-benzo[e]azulene (371 mg, 0.73 mmol) in methanol (3.5 mL) was treated with 4N HCl in dioxane (3.5 mL) and the mixture stirred for 45 min before being concentrated in vacuo. The resultant residue was re subjected to the reaction conditions as before and stirred for 1 h at RT before being concentrated in vacuo. The resultant residue was partitioned between DCM/saturated aqueous sodium hydrogen carbonate, the aqueous extracted twice with DCM and the combined organic extracts washed with brine and then dried (Na2SO4), filtered and concentrated in vacuo. The resultant residue was subjected to flash chromatography (SiO2, column preconditioned with 1% TEA in DCM, gradient 0 to 7% methanol in DCM) to give 293 as a yellow foam (94 mg, 30%). LCMS: RT=2.61 min, [M+H]+=423. ¹H NMR 400 MHz (DMSO-d) δ: 8.32 (1 H, d, J=8.28 Hz), 7.89 (2 H, d, J=1.96 Hz), 7.05 (1 H, dd, J=8.31, 1.76 Hz), 6.89 (1 H, d, J=1.71 Hz), 5.88-5.87 (1 H, m), 4.49 (4 H, q, J=5.91 Hz), 3.53 (2 H, t, J=7.21 Hz), 3.03 (2 H, d, J=11.27 Hz), 2.52 (3 H, m), 2.16 (2 H, t, J=11.38 Hz), 1.76 (2 H, d, J=12.61 Hz), 1.67 (2 H, d, J=12.75 Hz), 1.47 (6 H, d, J=6.60 Hz)

Example 294

2-(1-isopropyl-1H-1,2,4-triazol-5-yl)-9-(tetrahydro-2H-pyran-4-yl)-5,6-dihydrobenzo[f]imidazo[1,2-d][1,4]oxazepine 294

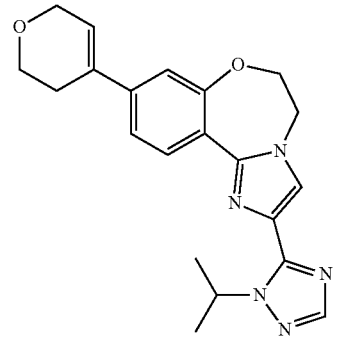 [SMILES: CC(C)n1ncnc1-c1cn2c(n1)-c1ccc(C3=CCOCC3)cc1OCC2]

A mixture of trifluoro-methanesulfonic acid 3,6-dihydro-2H-pyran-4-yl ester (125 mg, 0.54 mmol), 8-(5,5-dimethyl-[1,3,2]dioxaborinan-2-yl)-2-(2-isopropyl-2H-[1,2,4]triazol-3-yl)-4,5-dihydro-6-oxa-1,3a-diaza-benzo[e]azulene (200 mg, 0.491 mmol), PdCl2dppf.DCM (41 mg, 0.05 mmol, 10 mol %), cesium carbonate (400 mg, 1.23 mmol), DME (2 mL) and water (0.2 mL) was heated at 80° C. for 90 min. The cooled reaction mixture was diluted with DCM, filtered and concentrated in vacuo. The resultant residue was subjected to flash chromatography (SiO2, gradient 0 to 100% ethyl acetate in cyclohexane) to give 8-(3,6-Dihydro-2H-pyran-4-yl)-2-(2-isopropyl-2H-[1,2,4]triazol-3-yl)-4,5-dihydro-6-oxa-1,3a-diaza-benzo[e]azulene (73 mg, 39%). LCMS RT=4.36, [M+H]+=378.

A mixture of 8-(3,6-dihydro-2H-pyran-4-yl)-2-(2-isopropyl-2H-[1,2,4]triazol-3-yl)-4,5-dihydro-6-oxa-1,3a-diaza-benzo[e]azulene (73 mg, 0.19 mmol), 20% palladium hydroxide on carbon (50 mg) and ethyl acetate (10 mL) was degassed then stirred at RT for 72 h under an atmosphere of hydrogen. The reaction mixture was filtered, the filtrate concentrated in vacuo and the residue triturated in cyclohexane to give 294 as a white solid (51 mg, 71%). LCMS: RT=4.30 min, [M+H]+=380 ¹H NMR 400 MHz (DMSO-d) δ: 8.34 (1 H, d, J=8.29 Hz), 7.91 (2 H, d, J=1.36 Hz), 7.08 (1 H, dd, J=8.34, 1.79 Hz), 6.92 (1 H, d, J=1.73 Hz), 5.90-5.89 (1 H, m), 4.50 (4 H, q, J=5.58 Hz), 3.96-3.95 (2 H, m), 3.44 (2 H, td, J=11.21, 3.01 Hz), 2.77-2.76 (1 H, m), 1.73-1.66 (4 H, m), 1.49 (6 H, d, J=6.60 Hz)

Example 295 methyl 2-(2-ethoxyphenyl)-5,6-dihydrobenzo[f]imidazo[1,2-d][1,4]oxazepine-9-carboxylate 295

Methyl 2-iodo-5,6-dihydrobenzo[f]imidazo[1,2-d][1,4]oxazepine-9-carboxylate (80 mg, 1 eq), 2-ethoxyphenylboronic acid (66 mg, 1.75 eq), and tetrakis(triphenylphosphine)palladium (10 mg, 0.05 eq), in 1.0 M aqueous sodium carbonate (1.0 mL) and acetonitrile (1.0 mL) were heated to 140° C. for 10 min in a sealed microwave reactor. The crude reaction mixture was concentrated and purified using reverse phase HPLC to yield 295 (9 mg). ESI-MS 365.1 (M)+

Example 296 methyl 2-(3-isopropylphenyl)-5,6-dihydrobenzo[f]imidazo[1,2-d][1,4]oxazepine-9-carboxylate 296

Methyl 2-iodo-5,6-dihydrobenzo[f]imidazo[1,2-d][1,4]oxazepine-9-carboxylate (80 mg, 1 eq), 3-isopropylphenylboronic acid (65 mg, 1.75 eq), and tetrakis(triphenylphosphine)palladium (10 mg, 0.05 eq), in 1.0 M aqueous sodium carbonate (1.0 mL) and acetonitrile (1.0 mL) were heated to 140° C. for 10 min in a sealed microwave reactor. The crude reaction mixture was concentrated and purified using reverse phase HPLC to yield 296 (4 mg). ESI-MS: 363.1 (M)+

Example 297 methyl 2-(2-ethylphenyl)-5,6-dihydrobenzo[f]imidazo[1,2-d][1,4]oxazepine-9-carboxylate 297

Methyl 2-iodo-5,6-dihydrobenzo[f]imidazo[1,2-d][1,4]oxazepine-9-carboxylate (80 mg, 1 eq), 2-ethylphenylboronic acid (60 mg, 1.75 eq), and tetrakis(triphenylphosphine)palladium (10 mg, 0.05 eq), in 1.0 M aqueous sodium carbonate (1.0 mL) and acetonitrile (1.0 mL) were heated to 140° C. for 10 min in a sealed microwave reactor. The crude reaction mixture was concentrated and purified using reverse phase HPLC to yield 297 (11 mg). ESI-MS: 349.1 (M)+

Example 298 methyl 2-(2-isopropylphenyl)-5,6-dihydrobenzo[f]imidazo[1,2-d][1,4]oxazepine-9-carboxylate 298

Methyl 2-iodo-5,6-dihydrobenzo[f]imidazo[1,2-d][1,4]oxazepine-9-carboxylate (80 mg, 1 eq), 2-isopropylphenylboronic acid (65 mg, 1.75 eq), and tetrakis(triphenylphosphine)palladium (10 mg, 0.05 eq), in 1.0 M aqueous sodium carbonate (1.0 mL) and acetonitrile (1.0 mL) were heated to 140° C. for 10 min in a sealed microwave reactor. The crude reaction mixture was concentrated and purified using reverse phase HPLC to yield 298 (23 mg). ESI-MS: 363.1 (M)+.

Example 299 methyl 2-(3-(trifluoromethyl)phenyl)-5,6-dihydrobenzo[f]imidazo[1,2-d][1,4]oxazepine-9-carboxylate 299

Methyl 2-iodo-5,6-dihydrobenzo[f]imidazo[1,2-d][1,4]oxazepine-9-carboxylate (80 mg, 1 eq), 3-(trifluoromethyl)phenylboronic acid (76 mg, 1.75 eq), and tetrakis(triphenylphosphine)palladium (10 mg, 0.05 eq), in 1.0 M aqueous sodium carbonate (1.0 mL) and acetonitrile (1.0 mL) were heated to 140° C. for 10 min in a sealed microwave reactor. The crude reaction mixture was concentrated and purified using reverse phase HPLC to yield 299 (34 mg). ESI-MS: 389.1 (M)+

Example 300

2-(2-(1-isopropyl-3-methyl-1H-1,2,4-triazol-5-yl)-5,6-dihydrobenzo[f]imidazo[1,2-d][1,4]oxazepin-9-yl)acetamide 300

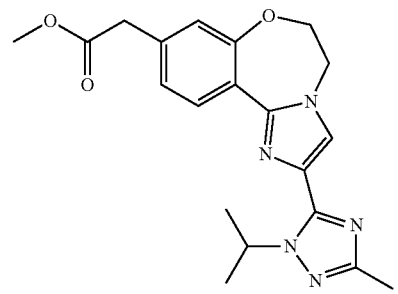

A mixture of 194 mg (0.500 mmol) of 9-bromo-2-(1-isopropyl-3-methyl-1H-1,2,4-triazol-5-yl)-5,6-dihydrobenzo[f]imidazo[1,2-d][1,4]oxazepine 411, 0.436 mL (2.00 mmol) of 1-(tert-butyldimethylsilyloxy)-1-methoxyethene, 19.6 mg (0.025 mmol) of dichlorobis(tri-o-tolylphosphine)palladium(II) (19.6 mg, 0.0250 mmol) and 309 mg (1.00 mmol) of tributyltin fluoride (309 mg, 1.00 mmol) in 3.0 ml of tetrahydrofuran was degassed and then heated for 18 hours at 80° C. The mixture was filtered through Celite, the filtrate mixed with 10 ml of water, the mixture was acidified to pH2 and extracted with ethyl acetate. The organic phases were combined, dried with MgSO4 and concentrated. The residue was purified by flash chromatography (0-5% gradient of methanol in dichloromethane) to afford 98 mg of Methyl 2-(2-(1-isopropyl-1H-1,2,4-triazol-5-yl)-5,6-dihydrobenzo[f]imidazo[1,2-d][1,4]oxazepin-9-yl)acetate (51%). M/z 382.2. calc. 381. 18

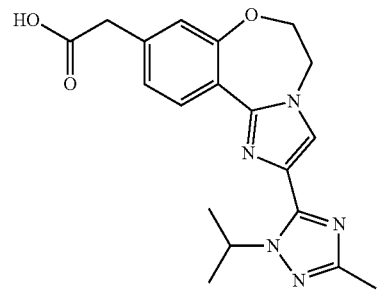 [SMILES: Cc1nc(-c2cn3c(n2)-c2ccc(CC(=O)O)cc2OCC3)n(C(C)C)n1]

A mixture of 98 mg (0.257 mmol) of methyl 2-(2-(1-isopropyl-1H-1,2,4-triazol-5-yl)-5,6-dihydrobenzo[f]imidazo[1,2-d][1,4]oxazepin-9-yl)acetate and 2.0 ml of 1.0 M of aqueous lithium hydroxide in 6 ml of methanol/tetrahydrofuram (1:1) mixture was stirred at 50° C. for 3 hours. The mixture was concentrated and acidified to pH 3 by careful addition of 1 N aqueous hydrogen chloride. The precipitate was collected and dried in high vacuum for 18 hours to give 2-(2-(1-isopropyl-3-methyl-1H-1,2,4-triazol-5-yl)-5,6-dihydrobenzo[f]imidazo[1,2-d][1,4]oxazepin-9-yl)acetic acid. Yield 58 mg. M/z 368.2, calc 367.16

A mixture of 58 mg (0.158 mmol) of 2-(2-(1-isopropyl-3-methyl-1H-1,2,4-triazol-5-yl)-5,6-dihydrobenzo[f]imidazo[1,2-d][1,4]oxazepin-9-yl)acetic acid, 76 mg (0.20 mmol) of N,N,N',N'-Tetramethyl-O-(7-azabenzotriazol-1- yl)uronium Hexafluorophosphate, (HATU, 16 mg, 0.30 mmol) of ammonium chloride and 28 uL (0.200 mmol) of Triethylamine in N,N-3.0 ml of Dimethylformamide was stirred for 40 min. The mixture was concentrated in vacuum and triturated with 10 ml of water. The solid was collected and purified by RP HPLC (acetonitrile gradient) to give 300. Yield 8.1 mg. M/z 367.2, calc. 366.18. 1H NMR (500 MHz, DMSO) δ 8.30 (d, J=8.2, 1H), 7.86 (s, 1H), 7.44 (s, 1H), 7.04 (d, J=8.3, 1H), 6.96 (s, 1H), 6.88 (s, 1H), 5.80 (dt, J=13.1, 6.5, 1H), 4.49 (q, J=6.2, 4H), 3.38 (s, 2H), 2.25 (s, 3H), 1.45 (d, J=6.6, 6H)

Example 301

2-(5-(2-(1-isopropyl-1H-1,2,4-triazol-5-yl)-5,6-dihydrobenzo[f]imidazo[1,2-d][1,4]oxazepin-9-yl)-2-methyl-1H-imidazol-1-yl)ethanol 301

Step 1: Preparation of 4,5-diiodo-2-methyl-1H-imidazole

To a rapidly stirred solution of 2-methyl-1H-imidazole (40.0 g, 0.49 mol) in DMF (250 mL) was added NIS (119 g, 0.51 mol) in small portions at 0° C. The temperature of the mixture was allowed to warm up to r.t. slowly and stirred at r.t. for 4 hours. The reaction mixture was poured into a saturate Na2CO3 solution, and keep the solution pH>7. The solid was filtered and dried to give 4,5-diiodo-2-methyl-1H-imidazole (112 g, 68.7%). ESI-MS, m/z 335 [M+H+]

Step 2: 4-iodo-2-methyl-1H-imidazole

A mixture of 4,5-diiodo-2-methyl-1H-imidazole (40.0 g, 119.4 mmol) and Na2SO3 (120.4 g, 0.96 mmol) in DMF (250 mL) was stirred at 110° C. under N2 overnight. The solid was filtered off, and the filtrate was concentrated and poured into water, extracted with EtOAc. The combined organic layer was washed with water, dried over Na2SO4, concentrated and purified by silica gel chromatography to give 4-iodo-2-methyl-1H-imidazole (15.3 g, 61%)

Step 3: 4-iodo-2-methyl-1-(2-(tetrahydro-2H-pyran-2-yloxy)ethyl)-1H-imidazole and 5-iodo-2-methyl-1-(2-(tetrahydro-2H-pyran-2-yloxy)ethyl)-1H-imidazole

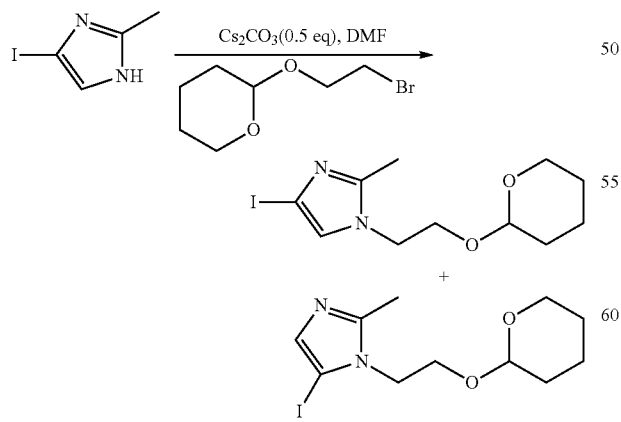

A mixture of 4-iodo-2-methyl-1H-imidazole (1.0 g, 4.8 mmol), Cs2CO3 (0.78 g, 2.4 mmol), 2-(2-Bromo-ethoxy)-tetrahydro-pyran (1.5 g, 6.0 mmol) in DMF (10 mL) was stirred at 70° C. for 4 h. The reaction mixture was concentrated, poured into water, extracted with EtOAc. The combined organic layer was washed with brine and concentrated. It was purified by chromatography to give the mixture of 4-iodo-2-methyl-1-(2-(tetrahydro-2H-pyran-2-yloxy)ethyl)-1H-imidazole (0.6 g, 37%) which was contaminated with some of 5-iodo-2-methyl-1-(2-(tetrahydro-2H-pyran-2-yloxy)ethyl)-1H-imidazole that was difficult to separate. 1H NMR (CDCl3, 400 MHz): δ 6.97 (s, 1H), 4.54 (t, J=3.2 Hz, 1H), 3.95-3.94 (m, 2H), 3.93-3.91 (m, 1H), 3.60-3.56 (m, 2H), 3.48-3.43 (m, 1H), 2.40 (s, 1H), 1.75-1.54 (m, 6H). LC-MS: m/z 337 [M+H+]

Step 4: 2-methyl-1-(2-(tetrahydro-2H-pyran-2-yloxy)ethyl)-4-(trimethylstannyl)-1H-imidazole and 2-methyl-1-(2-(tetrahydro-2H-pyran-2-yloxy)ethyl)-5-(trimethylstannyl)-1H-imidazole To a mixture of 4-iodo-2-methyl-1-(2-(tetrahydro-2H-pyran-2-yloxy)ethyl)-1H-imidazole and 5-iodo-2-methyl-1-(2-(tetrahydro-2H-pyran-2-yloxy)ethyl)-1H-imidazole (500 mg, 1.9 mmol) in DCM (10 mL) was added ethyl magnesium bromide (0.7 ml, 3 mol/L, 2.2 mmol) at −78° C. The mixture was allowed to warm up to about 10° C. slowly. After cooled to −78° C. again, trimethyltin chloride (2.2 mL, 1 mol/L, 2.2 mmol) was added dropwise. After addition, the mixture was allowed to slowly warm up to room temperature. The reaction mixture was poured into a saturate NH4Cl solution, and extracted with DCM. The combined organic layer was washed with water twice, dried over anhydrous Na2SO4 and concentrated to give 2-methyl-1-(2-(tetrahydro-2H-pyran-2-yloxy)ethyl)-4-(trimethylstannyl)-1H-imidazole (0.44 g, 63%) 1H NMR (CDCl3, 400 MHz): δ 6.93 (s, 1H), 4.54-4.53 (m, 1H), 4.05-4.03 (m, 2H), 3.97-3.93 (m, 1H), 3.61-3.59 (m, 2H), 3.45-3.39 (m, 1H), 2.44 (s, 3H), 1.66-1.47 (m, 6H), 0.26 (s, 9H). LC-MS, m/z 375 [M+H+], which was contaminated with some 2-methyl-1-(2-(tetrahydro-2H-pyran-2-yloxy)ethyl)-5-(trimethylstannyl)-1H-imidazole.

Step 5: 2-(1-isopropyl-1H-1,2,4-triazol-5-yl)-9-(2-methyl-1-(2-(tetrahydro-2H-pyran-2-yloxy)ethyl)-1H-imidazol-5-yl)-5,6-dihydrobenzo[f]imidazo[1,2-d][1,4]oxazepine (left below) and 2-(1-isopropyl-1H-1,2,4-triazol-5-yl)-9-(2-methyl-1-(2-(tetrahydro-2H-pyran-2-yloxy)ethyl)-1H-imidazol-4-yl)-5,6-dihydrobenzo[f]imidazo[1,2-d][1,4]oxazepine (right below)

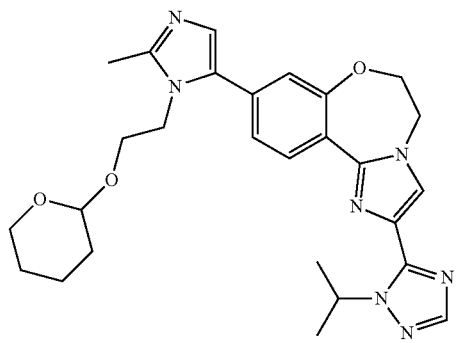

-continued

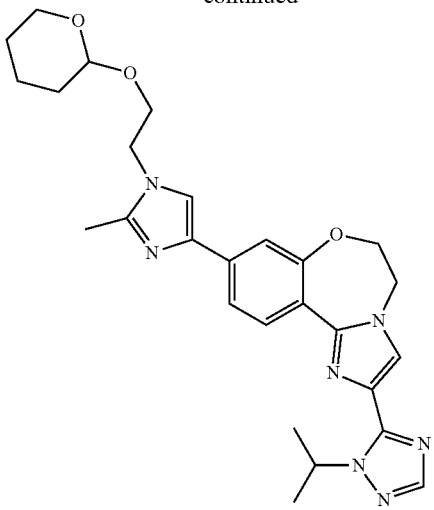

A mixture of 9-bromo-2-(1-isopropyl-1H-1,2,4-triazol-5-yl)-5,6-dihydrobenzo[f]imidazo[1,2-d][1,4]oxazepine 194 (300 mg, 0.8 mmol), Pd(PPh3)4 (93 mg, 0.08 mmol), and 2-methyl-1-(2-(tetrahydro-2H-pyran-2-yloxy)ethyl)-4-(trimethylstannyl)-1H-imidazole (600 mg, 1.6 mmol) in dioxane (2 mL) was bubbled with N2 for about 2 min. The mixture was then stirred at 120° C. for 35 min under microwave irradiation. The mixture was filtered, concentrated and purified by prep-TLC (EtOAc) to give the mixture of 2-(1-isopropyl-1H-1,2,4-triazol-5-yl)-9-(2-methyl-1-(2-(tetrahydro-2H-pyran-2-yloxy)ethyl)-1H-imidazol-5-yl)-5,6-dihydrobenzo[f]imidazo[1,2-d][1,4]oxazepine (left above) and 2-(1-isopropyl-1H-1,2,4-triazol-5-yl)-9-(2-methyl-1-(2-(tetrahydro-2H-pyran-2-yloxy)ethyl)-1H-imidazol-4-yl)-5,6-dihydrobenzo[f]imidazo[1,2-d][1,4]oxazepine (right above) (total 130 mg, 32%). 1H NMR (CDCl3, 400 MHz): δ 8.44-8.42 (m, 1H), 7.81 (s, 1H), 7.58 (s, 1H), 7.48-7.46 (m, 1H), 7.42 (d, J=1.6 Hz, 1H), 7.19 (s, 1H), 4.51-4.95 (m, 1H), 4.45-4.44 (t, 1H), 4.39-4.38 (m, 2H), 4.38-4.37 (m, 2H), 4.07-4.04 (m, 2H), 4.00-4.97 (m, 1H), 3.63-3.54 (m, 2H), 3.40-3.36 (m, 1H), 2.49 (s, 3H), 1.76-1.6 (m, 4H), 1.48-1.47 (m, 2H). LC-MS, m/z 504 [M+H+]

Step 6

The mixture of 2-(1-isopropyl-1H-1,2,4-triazol-5-yl)-9-(2-methyl-1-(2-(tetrahydro-2H-pyran-2-yloxy)ethyl)-1H-imidazol-5-yl)-5,6-dihydrobenzo[f]imidazo[1,2-d][1,4]oxazepine (left above) and 2-(1-isopropyl-1H-1,2,4-triazol-5-yl)-9-(2-methyl-1-(2-(tetrahydro-2H-pyran-2-yloxy)ethyl)-1H-imidazol-4-yl)-5,6-dihydrobenzo[f]imidazo[1,2-d][1,4]oxazepine (right above) (90 mg, 0.18 mmol) was dissolved in methanol (3 mL) and a HCl solution in MeOH (4 mol/L, 3.0 mL) was added dropwise at 0° C. The mixture was allowed to warm up to room temperature slowly and stirred at room temperature for 2 h. It was concentrated and the residue was washed with EtOAc to give 255 (65 mg, 72%) and 301 (20 mg, 21%) as HCl salts. 301: 1H NMR (CDCl3, 400 MHz): δ 8.54 (d, J=8.4 Hz, 1H), 7.85 (s, 1H), 7.66 (s, 1H), 7.24 (d, J=8.4 Hz, 2H), 7.11 (s, 1H), 6.89 (s, 1 H), 6.04-5.95 (m, 1H), 4.51-4.45 (m, 4H), 4.12-4.06 (m, 2H), 3.78-3.74 (m, 2H), 2.44 (s, 3H), 1.60 (d, J=6.4 Hz, 6H). LC-MS m/z 420 [M+H+]

Example 302

1-(4-(2-(1-isopropyl-3-(methoxymethyl)-1H-1,2,4-triazol-5-yl)-5,6-dihydrobenzo[f]imidazo[1,2-d][1,4]oxazepin-9-yl)-1H-pyrazol-1-yl)-2-methylpropan-2-ol 302

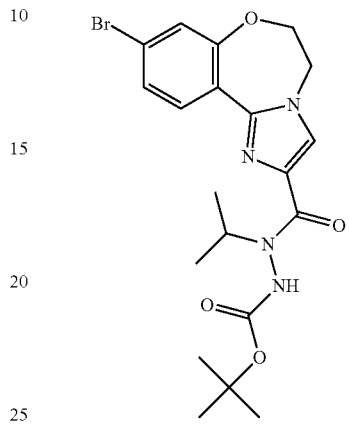

Step 1

To a mixture of 8-bromo-4,5-dihydro-6-oxa-1,3a-diaza-benzo[e]azulene-2-carboxylic acid (1.92 g, 6.2 mmol) and N'-isopropyl-hydrazinecarboxylic acid tert-butyl ester (1.30 g, 7.5 mmol) in DMF (20 mL) at 0° C. was added DIPEA (2.70 mL, 15.5 mmol) and HATU (3.54 g, 9.3 mmol). The reaction mixture was stirred for 7 h at RT before the addition of DMF (40 mL) and stirring overnight. The reaction mixture was concentrated in vacuo and the resultant residue partitioned between DCM and water. The aqueous phase was extracted with DCM (×2) before the combined organic extracts were washed sequentially with 10% citric acid solution, saturated sodium bicarbonate solution then brine, dried (Na2SO4) and concentrated in vacuo. The resultant residue was subjected to flash chromatography (SiO2, gradient 0-90% ethyl acetate in cyclohexane) to give N'-(8-Bromo-4,5-dihydro-6-oxa-1,3a-diaza-benzo[e]azulene-2-carbonyl)-N'-isopropyl-hydrazinecarboxylic acid tert-butyl ester as a white solid (3.02 g, quantitative yield). LCMS RT=4.76 min, [M+H]+=465/467. ¹H NMR 400 MHz (DMSO-d6) δ: 8.62 (1 H, s), 8.40 (1 H, d, J=8.59 Hz), 7.69 (1 H, s), 7.23-7.22 (2 H, m), 4.81 (1 H, s), 4.44 (4 H, s), 1.32 (9 H, s), 1.13 (6 H, d, J=6.64 Hz)

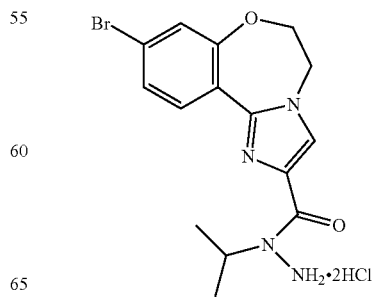

Step 2

A solution of N'-(8-bromo-4,5-dihydro-6-oxa-1,3a-diaza-benzo[e]azulene-2-carbonyl)-N'-isopropyl-hydrazinecarboxylic acid tert-butyl ester (2.71 g, 5.83 mmol) in methanol (52 mL) was treated with 4N HCl in dioxane (5.83 mL, 23.3 mmol). The reaction mixture was stirred at 50° C. overnight before the reaction was concentrated in vacuo and the resultant residue triturated with diethyl ether to give 8-Bromo-4,5-dihydro-6-oxa-1,3a-diaza-benzo[e]azulene-2-carboxylic acid N-isopropyl-hydrazide dihydrochloride as a pale yellow foam (2.69 g, quantitative yield). LCMS RT=4.17 min, [M+H]+=365/367

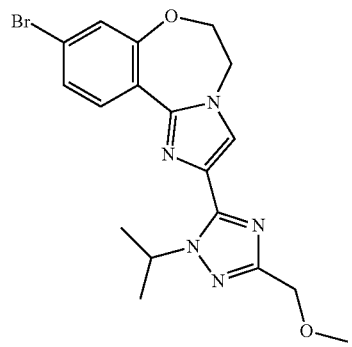

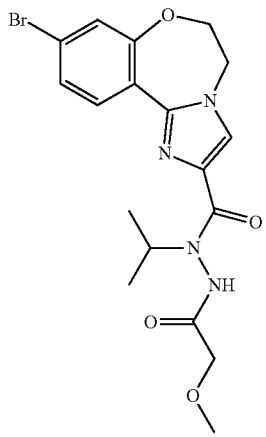 [SMILES: COCC(=O)NN(C(=O)c1cn2c(n1)-c1ccc(Br)cc1OCC2)C(C)C]

Step 3

A suspension of 8-bromo-4,5-dihydro-6-oxa-1,3a-diaza-benzo[e]azulene-2-carboxylic acid N-isopropyl-hydrazide dihydrochloride (2.69 g, 6.1 mmol) in DCM (61 mL) was treated with TEA (3.84 mL, 27.6 mmol). The resultant solution was cooled to 0° C. before methoxyacetyl chloride (1.12 mL, 12.3 mmol) was added dropwise and the reaction stirred at 0° C. for 1.75 h. The reaction was quenched with saturated sodium bicarbonate solution and the phases separated. The aqueous phase was extracted with DCM (×2) before the combined organic phases were washed sequentially with 10% citric acid solution, saturated sodium bicarbonate solution and brine. The organic solution was dried (Na2SO4), concentrated in vacuo and the resultant solid was triturated with diethyl ether to give 8-Bromo-4,5-dihydro-6-oxa-1,3a-diaza-benzo[e]azulene-2-carboxylic acid N-isopropyl-N'-(2-methoxy-acetyl)-hydrazide as an off-white solid (2.29 g, 5.24 mmol, 86%). LCMS RT=4.29 min, [M+H]+=437/439. $^1$H NMR 400 MHz (DMSO-d) δ: 9.61 (1 H, s), 8.29 (1 H, d, J=8.63 Hz), 7.71 (1 H, s), 7.27 (1 H, dd, J=8.64, 2.06 Hz), 7.21 (1 H, d, J=2.06 Hz), 4.84 (1 H, t, J=6.91 Hz), 4.45 (4 H, s), 3.92 (2 H, s), 3.33 (3 H, s), 1.15 (6 H, d, J=6.66 Hz)

Step 4

8-Bromo-4,5-dihydro-6-oxa-1,3a-diaza-benzo[e]azulene-2-carboxylic acid N-isopropyl-N'-(2-methoxy-acetyl)-hydrazide (1.00 g, 2.29 mmol) was suspended in phosphorus (V) oxychloride (23 mL) then stirred at 100° C. for 18 h. The reaction mixture was concentrated in vacuo and the residue then azeotroped with toluene (×3) giving a brown solid. To the brown solid was added acetic acid (23 mL) and ammonium chloride (1.76 g, 22.9 mmol), the resultant mixture was stirred at 125° C. for 2.5 h then further ammonium chloride (0.88 g, 11.4 mmol) added, the reaction was stirred at 125° C. for 1 h, then concentrated in vacuo. The resultant residue was treated with water and extracted with DCM (×3). The combined organic extracts were washed with saturated aqueous sodium bicarbonate solution then followed by brine then dried (Na2SO4) and concentrated in vacuo. The resultant solid was triturated with diethyl ether to give 8-Bromo-2-(2-isopropyl-5-methoxymethyl-2H-[1,2,4]triazol-3-yl)-4,5-dihydro-6-oxa-1,3a-diaza-benzo[e]azulene as a light brown solid (0.73 g, 1.74 mmol, 76%). LCMS RT=4.95 min, [M+H]+=418/420. $^1$H NMR 400 MHz (DMSO-d6) δ: 8.29 (1 H, d, J=8.65 Hz), 7.93 (1 H, s), 7.31 (1 H, dd, J=8.66, 2.05 Hz), 7.25 (1 H, d, J=2.05 Hz), 5.79-5.78 (1 H, m), 4.49 (4 H, s), 4.33 (2 H, s), 3.27 (3 H, s), 1.43 (6 H, d, J=6.60 Hz)

Step 5

A mixture of 8-bromo-2-(2-isopropyl-5-methoxymethyl-2H-[1,2,4]triazol-3-yl)-4,5-dihydro-6-oxa-1,3a-diaza-benzo[e]azulene (100 mg, 0.24 mmol), 2-methyl-1-[4-(4,4,5,5-tetramethyl-[1,3,2]dioxaborolan-2-yl)-pyrazol-1-yl]-propan-2-ol (127 mg, 0.48 mmol), PdCl2(dppf).DCM (9.8 mg, 0.012 mmol), cesium carbonate (234 mg, 0.72 mmol), DME (1.6 mL), water (0.27 mL) and IMS (0.5 mL) was degassed and then heated at 140° C. for 20 min using microwave irradiation. The reaction mixture was partitioned between DCM and water, the aqueous extracted twice with DCM and the combined organic extracts washed with brine then dried (Na2SO4), filtered and concentrated in vacuo. The resultant residue was subjected to RPHPLC (C18 column, gradient 5 to 95% methanol in water+0.1% HCO2H) to give 302 as a white solid (40 mg, 35%). LCMS: RT=3.77 min, [M+H]+ 478. $^1$H NMR 400 MHz (DMSO-D) δ: 8.37 (1 H, d, J=8.38 Hz), 8.17 (1 H, s), 7.94 (2 H, d, J=7.28 Hz), 7.40 (1 H, dd, J=8.37, 1.80 Hz), 7.28 (1 H, d, J=1.77 Hz), 5.89-5.88 (1 H, m), 4.74 (1 H, s), 4.53 (4 H, m), 4.38 (2 H, s), 4.04 (2 H, s), 3.32 (3 H, s), 1.49 (6 H, d, J=6.60 Hz), 1.10 (6 H, s).

Example 303

(3R,4R)-4-(2-(1-isopropyl-1H-1,2,4-triazol-5-yl)-5,6-dihydrobenzo[f]imidazo[1,2-d][1,4]oxazepin-9-yl)piperidin-3-ol 303

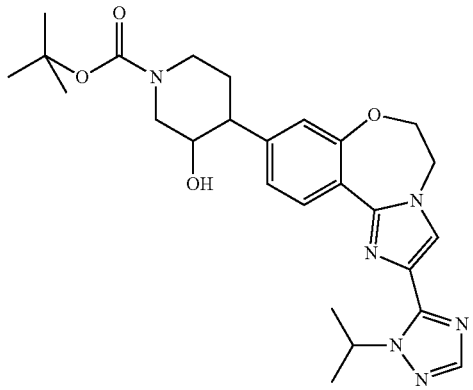 [SMILES: CC(C)n1ncnc1-c1cn2c(n1)-c1ccc(C3CCN(C(=O)OC(C)(C)C)CC3O)cc1OCC2]

4-[2-(2-Isopropyl-2H-[1,2,4]triazol-3-yl)-4,5-dihydro-6-oxa-1,3a-diaza-benzo[e]azulen-8-yl]-3,6-dihydro-2H-pyridine-1-carboxylic acid tert-butyl ester (1.05 g, 2.21 mmol) was partially dissolved in dry diethyleneglycol dimethyl ether (25 mL) and a solution of borane/THF complex (1M in THF, 13.2 mL, 13.2 mmol) was added dropwise. After stirring briefly at room temperature, the mixture was allowed to stand for 16 h. The mixture was then cooled in ice, and water (2 mL), 2M sodium hydroxide (6.5 mL) and 35% hydrogen peroxide (1.7 mL, 16.24 mmol) were added dropwise in sequence. The mixture was heated at 50° C. for 6 h, then cooled, diluted with water (approx. 45 mL) and extracted three times with ethyl acetate. The combined organic extracts were dried (Na2SO4) and concentrated. The resultant residue was subjected to flash chromatography (SiO2, gradient 0-8.5% methanol in DCM) to give the crude product (0.78 g, 71%), containing approx. 20% of 4-hydroxypiperidine isomer which was recrystallised twice from ethyl acetate/methanol to give racemic-trans-3-Hydroxy-4-[2-(2-isopropyl-2H-[1,2,4]triazol-3-yl)-4,5-dihydro-6-oxa-1,3a-diaza-benzo[e]azulen-8-yl]-piperidine-1-carboxylic acid tert-butyl ester containing <5% of the cis isomer (0.38 g). LCMS RT=4.44, [M+H]+=495. $^1$H NMR 400 MHz (DMSO-d6) δ: 8.39 (1 H, d, J=8.25 Hz), 7.89 (1 H, s), 7.47 (1 H, d, J=2.62 Hz), 7.03 (1 H, dd, J=8.29, 1.80 Hz), 6.77 (1 H, s), 6.07-5.99 (1 H, m), 4.37-4.37 (6 H, m), 4.19-4.18 (1 H, m), 3.73-3.73 (1 H, m), 2.66-2.66 (3 H, m), 1.81-1.81 (1 H, m), 1.61 (6 H, d, J=6.01 Hz), 1.50 (9 H, s)

To a solution of trans-racemic-3-hydroxy-4-[2-(2-isopropyl-2H-[1,2,4]triazol-3-yl)-4,5-dihydro-6-oxa-1,3a-diaza-benzo[e]azulen-8-yl]-piperidine-1-carboxylic acid tert-butyl ester (180 mg, 0.36 mmol) in DCM (1 mL) and methanol (0.6 mL) was added 4M HCl in dioxane (1.6 mL) slowly and the reaction mixture stirred at RT for 2.5 hr before being concentrated in vacuo. The resultant residue was triturated in diethyl ether to give 4-(2-(1-isopropyl-1H-1,2,4-triazol-5-yl)-5,6-dihydrobenzo[f]imidazo[1,2-d][1,4]oxazepin-9-yl)piperidin-3-ol which was resolved to give the (3R,4R) enantiomer 303 as a white solid (172 mg, quantitative). LCMS: RT=2.41 min, [M+H]+ 395. $^1$H NMR 400 MHz (DMSO-d6) δ: 9.30 (1 H, br, s), 9.10 (1 H, br, s), 8.36 (1 H, d, J=8.28 Hz), 8.10 (1 H, br, s), 8.06 (1 H, s), 7.04 (1 H, d, J=8.38 Hz), 6.91 (1 H, s), 5.87 (1 H, m), 4.53 (4 H, d, J=8.12 Hz), 3.90 (1 H, br, m), 3.25 (2 H, m), 2.78 (1 H, m), 2.52 (2 H, m), 1.80 (2 H, m), 1.50 (1 H, d, J=6.58 Hz)

Example 304 racemic-trans-2-(3-hydroxy-4-(2-(1-isopropyl-1H-1,2,4-triazol-5-yl)-5,6-dihydrobenzo[f]imidazo[1,2-d][1,4]oxazepin-9-yl)piperidin-1-yl)-N,N-dimethylacetamide 304

Following the procedure for Example 330, trans-racemic-4-[2-(2-isopropyl-2H-[1,2,4]triazol-3-yl)-4,5-dihydro-6-oxa-1,3a-diaza-benzo[e]azulen-8-yl]-piperidin-3-ol hydrochloride (0.15 g, 0.35 mmol) was reacted with N,N-dimethyl-2-chloroacetamide (46 mg, 0.38 mmol) to give 304 (135 mg, 80%). LCMS: RT=2.50 min, [M+H]+=480. 1H NMR 400 MHz (CDCl3) δ: 8.40 (1 H, d, J=8.26 Hz), 7.86 (1 H, s), 7.43 (1 H, s), 7.08-7.03 (1 H, m), 6.82 (1 H, d, J=1.72 Hz), 6.02 (1 H, m), 4.38 (4 H, m), 4.10 (1H, br, m), 3.38 (2 H, m), 3.31 (2 H, m), 3.09 (3 H, s), 3.00 (1H, m), 2.98 (3 H, s), 2.47 (2H, m), 1.86 (2 H, m), 1.60 (6 H, dd, J=6.59, 2.76 Hz)

Example 305

2-(5-(9-bromo-5,6-dihydrobenzo[f]imidazo[1,2-d][1,4]oxazepin-2-yl)-1-isopropyl-1H-1,2,4-triazol-3-yl)acetamide 305

8-Bromo-2-iodo-4,5-dihydro-6-oxa-1,3a-diaza-benzo[e]azulene with 2-Carbamimidoyl-acetamide hydrochloride and isopropylhydrazine hydrochloride were reacted following Example 420. The crude product was purified by reverse phase HPLC to give 305 (29 mg obtained). LCMS: 433.0. 1H NMR (500 MHz, DMSO) δ 8.33 (d, J=8.6 Hz, 1H), 7.95 (s, 1H), 7.39 (s, 1H), 7.35 (dd, J=8.7, 2.0 Hz, 1H), 7.29 (d, J=2.0 Hz, 1H), 6.97 (s, 1H), 5.79 (dt, J=13.2, 6.6 Hz, 1H), 4.53 (s, 4H), 3.45 (s, 2H), 1.47 (d, J=6.6 Hz, 6H)

Example 306

5-(2-(1-isopropyl-1H-1,2,4-triazol-5-yl)-5,6-dihydroimidazo[1,2-d]pyrido[4,3-f][1,4]oxazepin-10-yl)pyridin-2(1H)-one 306

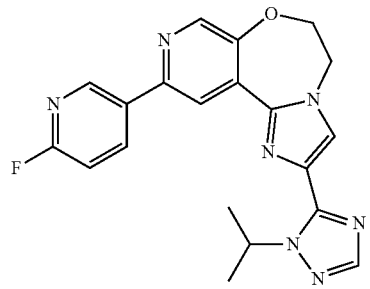 [SMILES: CC(C)n1ncnc1-c1cn2c(n1)-c1cc(-c3ccc(F)nc3)ncc1OCC2]

10-Chloro-2-(1-isopropyl-1H-1,2,4-triazol-5-yl)-5,6-dihydroimidazo[1,2-d]pyrido[4,3-f][1,4]oxazepine (85.0 mg, 0.257 mmol) dissolved in Acetonitrile (2 mL, 50 mmol) and Water (2 mL, 100 mmol) with dissolved Potassium acetate (85.5 mg, 0.871 mmol). Degas by bubbling nitrogen for 5 min. 2-Fluoropyridine-5-boronic acid (47.1 mg, 0.334 mmol) was added, then Tetrakis(triphenylphosphine)palladium(0) (4.0E1 mg, 0.035 mmol). The reaction was microwaved at 145 C 35 min, cooled to RT, and extracted with ethyl acetate. Combined organics were concentrated to give fluoro intermediate, 10-(6-fluoropyridin-3-yl)-2-(1-isopropyl-1H-1,2,4-triazol-5-yl)-5,6-dihydroimidazo[1,2-d]pyrido[4,3-f][1,4]oxazepine, which was dissolved in 1,2-Dimethoxyethane (3.00 mL, 28.9 mmol). 10% aqueous HCl (3 mL) was added. The reaction was allowed to stir and heat at 80° C. overnight. The reaction was allowed to cool to room temperature and concentrated under reduced pressure to give 306, analyzed by rHPLC. MS: (ESI+)=390.1

Example 307

4-(2-(1-isopropyl-1H-1,2,4-triazol-5-yl)-5,6-dihydroimidazo[1,2-d]pyrido[4,3-f][1,4]oxazepin-10-yl)piperazin-2-one 307

A solution of 10-chloro-2-(1-isopropyl-1H-1,2,4-triazol-5-yl)-5,6-dihydroimidazo[1,2-d]pyrido[4,3-f][1,4]oxazepine (80.0 mg, 0.242 mmol), Piperazin-2-one (48.4 mg, 0.484 mmol), XPhos (23.0 mg, 0.0484 mmol), and Sodium-tert-butoxide (46.5 mg, 0.484 mmol) in was heated in microwave at 125 C for 30 min. The reaction was filtered thru celite then rinsed with EtOAc. The filtrate was washed water, brine. The organic layer was dried Na2SO4, concentrated to give 307, analyzed by rHPLC. MS: (ESI+)=395.2. 1H NMR (500 MHz, DMSO) δ 8.06 (s, 1H), 8.03 (d, J=5.7 Hz, 2H), 7.93 (s, 1H), 7.59 (s, 1H), 5.72 (dt, J=13.1, 6.6 Hz, 1H), 4.62-4.52 (m, 2H), 4.51-4.39 (m, 2H), 3.94 (s, 2H), 3.73-3.62 (m, 2H), 3.37-3.30 (m, 2H), 1.51 (d, J=6.6 Hz, 6H).

Example 308

2-(4-(2-(1-isopropyl-3-(methoxymethyl)-1H-1,2,4-triazol-5-yl)-5,6-dihydrobenzo[f]imidazo[1,2-d][1,4]oxazepin-9-yl)piperidin-1-yl)acetamide 308

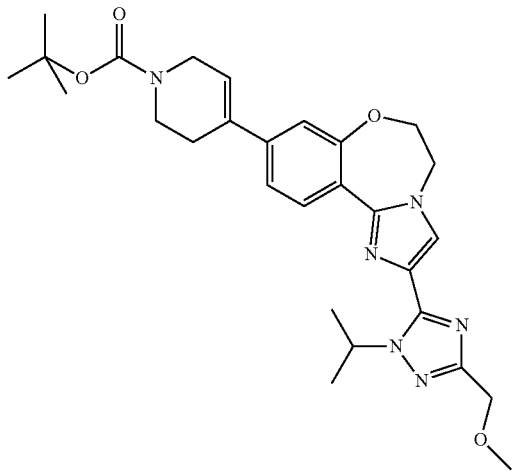 [SMILES: COCc1nc(-c2cn3c(n2)-c2ccc(C4=CCN(C(=O)OC(C)(C)C)CC4)cc2OCC3)n(C(C)C)n1]

Step 1

8-Bromo-2-(2-isopropyl-5-methoxymethyl-2H-[1,2,4]triazol-3-yl)-4,5-dihydro-6-oxa-1,3a-diaza-benzo[e]azulene (250 mg, 0.60 mmol), 3,6-dihydro-2H-pyridine-1-N-Boc-4-boronic acid pinacol ester (370 mg, 1.20 mmol), cesium carbonate (585 mg, 1.79 mmol) and 1,1'-bis(diphenylphosphino)ferrocenepalladium (ii) dichloride, dichloromethane (24 mg, 0.03 mmol) were suspended in DME (4.0 mL), IMS (1.3 mL) and water (0.68 mL) and the reaction mixture purged with argon. The reaction mixture was heated using microwave irradiation in a sealed tube at 140° C. for 20 min. The reaction mixture was washed with water, extracted with DCM (2×15 mL) and the combined organics were washed with brine, dried (Na2SO4) then concentrated in vacuo. The resultant residue was subjected to flash chromatography (SiO2, eluting with 5% methanol in DCM) to yield 4-[2-(2-Isopropyl-5-methoxymethyl-2H-[1,2,4]triazol-3-yl)-4,5-dihydro-6-oxa-1,3a-diaza-benzo[e]azulen-8-yl]-3,6-dihydro-2H-pyridine-1-carboxylic acid tert-butyl ester as a brown foam (224 mg, 72%). LCMS: RT=5.08 min, [M+H]+=521

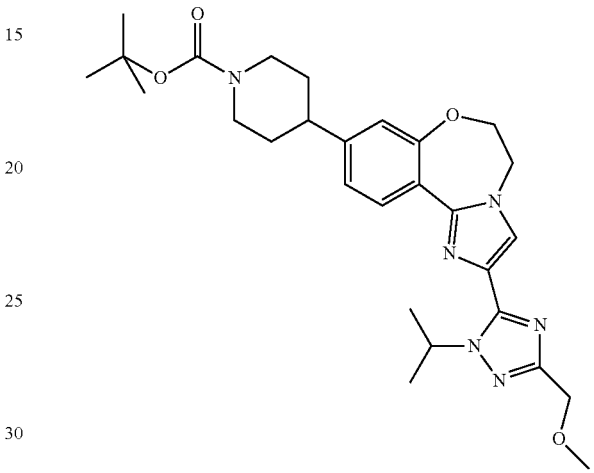

Step 2

To a solution of 4-[2-(2-isopropyl-5-methoxymethyl-2H-[1,2,4]triazol-3-yl)-4,5-dihydro-6-oxa-1,3a-diaza-benzo[e]azulen-8-yl]-3,6-dihydro-2H-pyridine-1-carboxylic acid tert-butyl ester (224 mg, 0.43 mmol) in IMS (3 mL) was added a catalytic amount of palladium on carbon (10% by wt) and the reaction mixture stirred under an atmosphere of hydrogen at 50° C. for 16 h. The reaction mixture was filtered and the solids washed with IMS (10 mL). The filtrate was concentrated in vacuo and the resultant residue subjected to flash chromatography (SiO2, eluting with 2% MeOH in DCM) to yield 4-[2-(2-Isopropyl-5-methoxymethyl-2H-[1,2,4]triazol-3-yl)-4,5-dihydro-6-oxa-1,3a-diaza-benzo[e]azulen-8-yl]-piperidine-1-carboxylic acid tert-butyl ester as a yellow oil (162 mg, 72%). LCMS: RT=5.05 min, [M+H]+=523

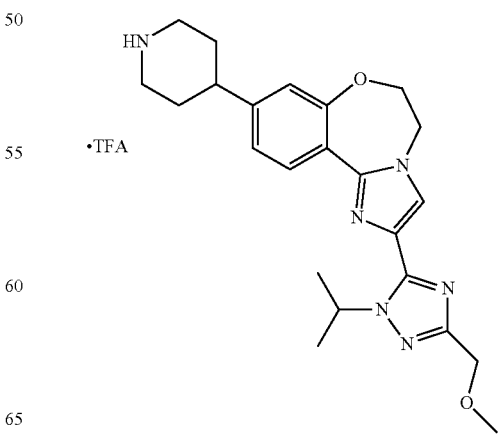

Step 3

To a solution of 4-[2-(2-isopropyl-5-methoxymethyl-2H-[1,2,4]triazol-3-yl)-4,5-dihydro-6-oxa-1,3a-diaza-benzo[e]azulen-8-yl]-piperidine-1-carboxylic acid tert-butyl ester (158 mg, 0.30 mmol) in DCM (1.5 mL) was added trifluoroacetic acid (1.5 mL, 20.2 mmol) and the reaction mixture stirred at RT for 30 min. The reaction mixture was concentrated in vacuo and the residue azeotroped with ether. The resultant oil was triturated with diethyl ether to give 2-(2-Isopropyl-5-methoxymethyl-2H-[1,2,4]triazol-3-yl)-8-piperidin-4-yl-4,5-dihydro-6-oxa-1,3a-diaza-benzo[e]azulene trifluoroacetate salt as a solid which was collected by filtration (103 mg, 64%). LCMS RT=3.03 min, [M+H]+=423. $^1$H NMR 400 MHz (DMSO-d) δ: 8.56 (1 H, s), 8.33 (1 H, d, J=8.33 Hz), 7.90 (1 H, s), 7.00 (1 H, dd, J=8.38, 1.78 Hz), 6.85 (1 H, d, J=1.73 Hz), 5.81-5.80 (1 H, m), 4.46 (4 H, d, J=2.51 Hz), 4.33 (2 H, s), 3.34 (2 H, d, J=12.58 Hz), 3.27 (3 H, s), 2.98-2.95 (2 H, m), 2.82 (1 H, t, J=11.91 Hz), 1.93 (2 H, d, J=13.66 Hz), 1.75 (2 H, t, J=12.95 Hz), 1.44 (6 H, d, J=6.60 Hz)

Step 4

A suspension of 2-(2-isopropyl-5-methoxymethyl-2H-[1,2,4]triazol-3-yl)-8-piperidin-4-yl-4,5-dihydro-6-oxa-1,3a-diaza-benzo[e]azulene trifluoroacetate salt (99 mg, 0.18 mmol) in THF (1.8 mL) was treated with 2-bromoacetamide (109 mg, 0.2 mmol) followed by potassium carbonate (56 mg, 0.41 mmol) and the reaction mixture stirred at RT before being diluted with DCM and water. The aqueous layer was extracted twice with DCM and the combined organic extracts washed with saturated aqueous sodium bicarbonate followed by brine then dried (Na2SO4), filtered and concentrated in vacuo. The resultant residue was dissolved in methanol, the solution cooled to 0° C. and treated with water to form a precipitate which was filtered off and washed with cold methanol/water to give a white solid. The solid was azeotroped with methanol then diethyl ether to give 308 as a white solid (38 mg, 43%). LCMS: RT=2.66 min, [M+H]+=480. $^1$H NMR 400 MHz (DMSO-d6) δ: 8.39 (1 H, d, J=8.32 Hz), 8.16 (1 H, s), 7.09-7.08 (1 H, m), 6.97 (1 H, s), 5.76-5.74 (1 H, m), 4.58 (4 H, d, J=14.42 Hz), 4.51 (2 H, s), 3.96 (2 H, s), 3.60 (2 H, d, J=11.71 Hz), 3.37 (3 H, s), 3.20 (2 H, m), 2.86 (1 H, m), 2.03 (4 H, m), 1.53 (6 H, d, J=6.57 Hz)

Example 309

2-(1-isopropyl-3-(methoxymethyl)-1H-1,2,4-triazol-5-yl)-5,6-dihydrobenzo[f]imidazo[1,2-d][1,4]oxazepine 309

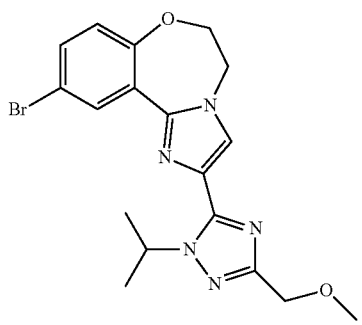 [SMILES: COCc1nc(-c2cn3c(n2)-c2cc(Br)ccc2OCC3)n(C(C)C)n1]

Step 1

A mixture of 9-bromo-2-iodo-4,5-dihydro-6-oxa-1,3a-diaza-benzo[e]azulene (2.00 g, 5.1 mmol), 2-methoxy-acetamidine hydrochloride (0.76 g, 6.1 mmol) and TEA (5.00 mL, 35.9 mmol) in DMF (38 mL) was evacuated and refilled with nitrogen (×3). The reaction was treated with Xantphos (0.15 g, 0.26 mmol) and palladium (II) acetate (57 mg, 0.26 mmol) before the reaction was purged with carbon monoxide gas and the reaction stirred at 60° C. for 3.5 h. The reaction mixture was cooled to RT, purged with nitrogen then treated with isopropyl-hydrazine hydrochloride (1.70 g, 15.0 mmol) and acetic acid (19 mL). After stirring at 60° C. for 1.5 h the reaction was diluted with ethyl acetate (350 mL). The solution was washed with 1N NaOH (2×50 mL) followed by brine (50 mL), then dried (Na2SO4) and concentrated in vacuo. The resultant residue was subjected to flash chromatography (SiO2, gradient 0-3% methanol in DCM) then triturated with diethyl ether to afford 9-Bromo-2-(2-isopropyl-5-methoxymethyl-2H-[1,2,4]triazol-3-yl)-4,5-dihydro-6-oxa-1,3a-diaza-benzo[e]azulene as a pale pink solid (0.85 g, 2.0 mmol, 40%). LCMS RT=4.95 min, [M+H]+=418/420. $^1$H NMR 400 MHz (DMSO-d6) δ: 8.44 (1 H, d, J=2.57 Hz), 7.94 (1 H, s), 7.43 (1 H, dd, J=8.74, 2.58 Hz), 6.99 (1 H, d, J=8.74 Hz), 5.72-5.63 (1 H, m), 4.49 (4 H, d, J=3.06 Hz), 4.33 (2 H, s), 3.27 (3 H, s), 1.44 (6 H, d, J=6.60 Hz).

Step 2

To a suspension of 9-bromo-2-(2-isopropyl-5-methoxymethyl-2H-[1,2,4]triazol-3-yl)-4,5-dihydro-6-oxa-1,3a-diaza-benzo[e]azulene (0.85 g, 2.0 mmol) in IMS (20 mL) was added DCM (6 mL). The mixture was degassed with nitrogen before being treated with palladium on carbon (10% palladium, 50% water, 350 mg). The vessel was evacuated and refilled with hydrogen and stirred at RT 18 h before further catalyst was added and the reaction stirred for 72 h. The reaction was filtered then concentrated in vacuo to give 309 as a pale yellow solid (0.73 g, quantitative yield). LCMS RT=4.55 min, [M+H]+=340. $^1$H NMR 400 MHz (DMSO-d6) δ: 8.37 (2 H, dd, J=9.88, 1.75 Hz), 7.30 (1 H, ddd, J=7.93, 7.18, 1.70 Hz), 7.12-7.12 (1 H, m), 7.03 (1 H, dd, J=8.19, 1.22 Hz), 5.83-5.74 (1 H, m), 4.48-4.47 (4 H, m), 4.36 (2 H, s), 3.28 (3 H, s), 1.45 (6 H, d, J=6.60 Hz)

Example 313

9-bromo-2-(3-cyclopropyl-1-isopropyl-1H-1,2,4-triazol-5-yl)-5,6-dihydrobenzo[f]imidazo[1,2-d][1,4]oxazepine 313

8-Bromo-2-iodo-4,5-dihydro-6-oxa-1,3a-diaza-benzo[e]azulene with Cyclopropanecarboxamidine hydrochloride and isopropylhydrazine hydrochloride were reacted following Example 420. The crude product was purified by reverse phase HPLC to give 313 (75 mg obtained). LCMS: 414.0. 1H NMR (400 MHz, DMSO) δ 8.30 (m, H), 7.90 (s, 1H), 7.35 (dd, J=8.7, 2.0 Hz, 1H), 7.29 (d, J=2.0 Hz, 1H), 5.75 (dt, J=13.2, 6.6 Hz, 1H), 4.51 (m. 4H), 2.02-1.91 (m, 1H), 1.45 (d, J=6.6 Hz, 6H), 0.93-0.85 (m, 2H), 0.84-0.77 (m, 12H)

Example 314

9-(1-ethylpiperidin-4-yl)-2-(1-isopropyl-1H-1,2,4-triazol-5-yl)-5,6-dihydrobenzo[f]imidazo[1,2-d][1,4]oxazepine 314

To a stirred suspension of 2-(2-isopropyl-2H-[1,2,4]triazol-3- yl)-8-piperidin-4-yl-4,5-dihydro-6-oxa-1,3a-diazabenzo[e]azulene trifluoro acetate (189 mg, 0.37 mmol) in DCE (3 mL) was added acetic acid (3 drops, catalytic) acetaldehyde (0.023 mL, 0.41 mmol) and sodium triazetoxyborohydride (94 mg, 0.44 mmol). After stirring for 2 h at RT DCM was added and the mixture washed with saturated aqueous sodium hydrogen carbonate, water and then brine before being dried (MgSO4), filtered and concentrated in vacuo. The resultant residue was subjected to flash chromatography (SiO2, gradient 0 to 20% methanol in DCM) then freeze dried from methanol/water and triturated in petroleum ether to give 314 as a brown solid (18 mg, 12%). LCMS: RT=2.73 min, [M+H]+=407. $^1$H NMR 400 MHz (DMSO-d) δ: 8.32 (1 H, d, J=8.29 Hz), 7.90 (2 H, d, J=2.38 Hz), 7.06 (1 H, d, J=8.41 Hz), 6.90 (1 H, s), 5.90-5.89 (1 H, m), 4.49 (4 H, d, J=7.47 Hz), 2.97 (2 H, d, J=10.98 Hz), 2.34 (2 H, q, J=7.20 Hz), 1.95 (2 H, t, J=11.47 Hz), 1.76 (2 H, d, J=12.54 Hz), 1.72-1.54 (3 H, m), 1.48 (6 H, d, J=6.59 Hz), 1.02 (3 H, t, J=7.20 Hz)

Example 315

(5-(5,6-dihydrobenzo[f]imidazo[1,2-d][1,4]oxazepin-2-yl)-1-isopropyl-1H-1,2,4-triazol-3-yl)methanol 315

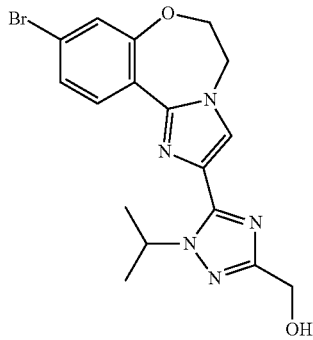 [SMILES: CC(C)n1nc(CO)nc1-c1cn2c(n1)-c1ccc(Br)cc1OCC2]

A solution of 8-bromo-2-(2-isopropyl-5-methoxymethyl-2H-[1,2,4]triazol-3-yl)-4,5-dihydro-6-oxa-1,3a-diaza-benzo[e]azulene 309 (280 mg, 0.67 mmol) in 48% aqueous HBr (4.19 mL) was heated at 100° C. for 4 h before cooling to RT. The solution was neutralized by the addition of 1M aqueous sodium carbonate and then extracted with DCM, the organic layer washed with water then dried (Na2SO4), filtered and concentrated in vacuo to give [5-(8-Bromo-4,5-dihydro-6-oxa-1,3a-diaza-benzo[e]azulen-2-yl)-1-isopropyl-1H-[1,2,4]triazol-3-yl]-methanol as a cream solid (162 mg, 60%). LCMS RT=4.74 min, [M+H]+=404. $^1$H NMR 400 MHz (DMSO-d) δ: 8.30 (1 H, d, J=8.65 Hz), 7.91 (1 H, s), 7.33 (1 H, dd, J=8.65, 2.06 Hz), 7.27 (1 H, d, J=2.03 Hz), 5.82-5.75 (1 H, m), 5.18 (1 H, t, J=6.03 Hz), 4.51 (4 H, s), 4.40 (2 H, d, J=5.99 Hz), 1.44 (6 H, d, J=6.60 Hz)

A solution of [5-(8-bromo-4,5-dihydro-6-oxa-1,3a-diaza-benzo[e]azulen-2-yl)-1-isopropyl-1 H-[1,2,4]triazol-3-yl]-methanol (67 mg, 0.17 mmol) in IMS was degassed then treated with Pd/C (10% wt. 120 mg) before being stirred at RT under an atmosphere of hydrogen for 18 h. The reaction mixture was filtered through Celite®, washing with DCM, the filtrate concentrated in vacuo. The resultant residue was subjected to flash chromatography (SiO2, gradient 0 to 7% methanol in DCM) to give 315 as a white solid (13 mg, 24%). LCMS: RT=3.79 min, [M+H]+=326. $^1$H NMR 400 MHz (DMSO-d) δ: 8.42 (1 H, dd, J=8.03, 1.74 Hz), 7.91 (1 H, s), 7.33 (1 H, ddd, J=8.16, 7.12, 1.77 Hz), 7.16-7.16 (1 H, m), 7.06 (1 H, dd, J=8.18, 1.21 Hz), 5.86 (1 H, t, J=6.61 Hz), 5.21 (1 H, t, J=6.03 Hz), 4.52 (4 H, q, J=5.81 Hz), 4.42 (2 H, d, J=6.00 Hz), 1.48 (6 H, d, J=6.61 Hz)

Example 316

3-(2-(1-isopropyl-3-methyl-1H-1,2,4-triazol-5-yl)-5,6-dihydrobenzo[f]imidazo[1,2-d][1,4]oxazepin-9-yl)propanamide 316

Step 1: (E)-methyl 3-(2-(1-isopropyl-3-methyl-1H-1,2,4-triazol-5-yl)-5,6-dihydrobenzo[f]imidazo[1,2-d][1,4]oxazepin-9-yl)acrylate

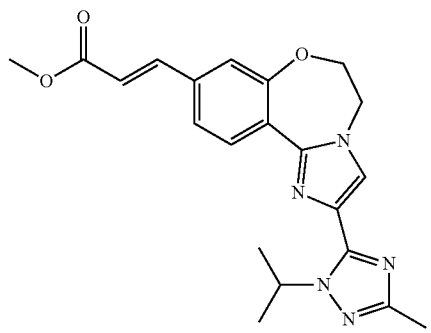

A mixture of 0.194 g (0.500 mmol) of 9-bromo-2-(1-isopropyl-3-methyl-1H-1,2,4-triazol-5-yl)-5,6-dihydrobenzo[f]imidazo[1,2-d][1,4]oxazepine 411, 0.180 mL (2.00 mmol) of methyl acrylate, 22.4 mg (0.0999 mmol) of palladium acetate, 122 mg (0.400 mmol) of tri-o-tolylphosphine and 0.278 mL, (2.00 mmol) of triethylamine in 4.0 ml of N,N-Dimethylformamide was heated at 100° C. for 6 hours. The mixture was concentrated in vacuum and partitioned between ethyl acetate and water. The organic extracts were washed with dilute aqueous HCl, water, brine, dried over Na2SO4 and concentrated in vacuum. The residue was purified on 4 g silica column eluting with heptane-ethyl acetate gradient to give (E)-methyl 3-(2-(1-isopropyl-3-methyl-1H-1,2,4-triazol-5-yl)-5,6-dihydrobenzo[f]imidazo[1,2-d][1,4]oxazepin-9-yl)acrylate. Yield 0.11 g. M/z 394.2, calc. 393.18

Step 2: Methyl 3-(2-(1-isopropyl-3-methyl-1H-1,2,4-triazol-5-yl)-5,6-dihydrobenzo[f]imidazo[1,2-d][1,4]oxazepin-9-yl)propanoate

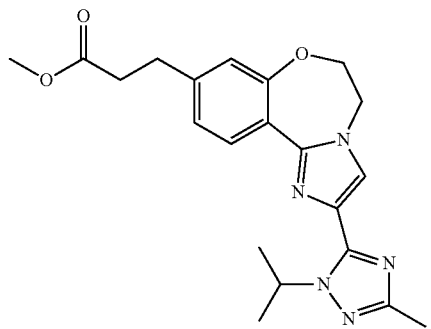

A solution of 0.11 g (0.28 mmol) of (E)-methyl 3-(2-(1-isopropyl-3-methyl-1H-1,2,4-triazol-5-yl)-5,6-dihydrobenzo[f]imidazo[1,2-d][1,4]oxazepin-9-yl)acrylate in 5 ml of THF/ethanol mixture was subjected to hydrogenation over 100 mg of 10% Pd—C for 4 hours. The mixture was filtered through celite; the filtrate was concentrated in vacuum to give Methyl 3-(2-(1-isopropyl-3-methyl-1H-1,2,4-triazol-5-yl)-5,6-dihydrobenzo[f]imidazo[1,2-d][1,4]oxazepin-9-yl)propanoate. Yield 96 mg. M/z 396.2, calc. 395.20

Step 3: 3-(2-(1-isopropyl-3-methyl-1H-1,2,4-triazol-5-yl)-5,6-dihydrobenzo[f]imidazo[1,2-d][1,4]oxazepin-9-yl)propanoic acid

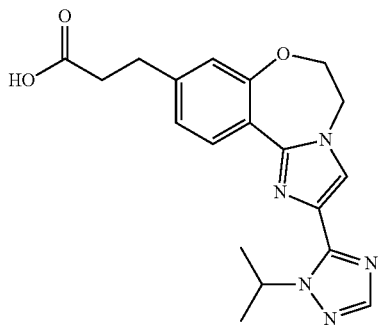 [SMILES: CC(C)n1ncnc1-c1cn2c(n1)-c1ccc(CCC(=O)O)cc1OCC2]

Methyl 3-(2-(1-isopropyl-3-methyl-1H-1,2,4-triazol-5-yl)-5,6-dihydrobenzo[f]imidazo[1,2-d][1,4]oxazepin-9-yl)propanoate was treated with lithium hydroxide to give 3-(2-(1-isopropyl-3-methyl-1H-1,2,4-triazol-5-yl)-5,6-dihydrobenzo[f]imidazo[1,2-d][1,4]oxazepin-9-yl)propanoic acid. M/z 382.2, calc. 381.18

Step 4

Following the procedures of Example 300, 2-(2-(1-isopropyl-3-methyl-1H-1,2,4-triazol-5-yl)-5,6-dihydrobenzo[f]imidazo[1,2-d][1,4]oxazepin-9-yl)propanoate, ammonium chloride, and HATU were reacted to give 316. M/z 381.1, calc. 380.20. 1H NMR (400 MHz, DMSO) δ 8.29 (d, J=8.2, 1H), 7.85 (s, 1H), 7.28 (s, 1H), 7.00 (d, J=8.3, 1H), 6.89 (s, 1H), 6.75 (s, 1H), 5.81 (dt, J=13.1, 6.4, 1H), 4.48 (s, 4H), 2.80 (t, J=7.5, 2H), 2.36 (dd, J=16.8, 9.2, 2H), 2.25 (s, 3H), 1.45 (d, J=6.5, 6H)

Example 317

9-chloro-2-(1-isopropyl-1H-1,2,4-triazol-5-yl)-5,6-dihydroimidazo[1,2-d]pyrido[3,4-f][1,4]oxazepine 317

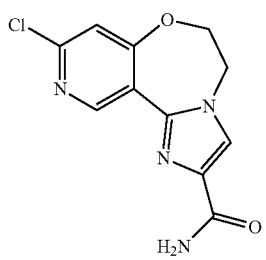 [SMILES: NC(=O)c1cn2c(n1)-c1cnc(Cl)cc1OCC2]

A mixture of [9-chloro-5,6-dihydroimidazo[1,2-d]pyrido[3,4-f][1,4]oxazepine-2-carboxamide (0.520 g, 1.96 mmol) and 1,1-Dimethoxy-N,N-dimethylmethanamine (1.305 mL, 9.824 mmol) in Toluene (28.2 mL, 265 mmol) was heated under reflux for 1 hour. LCMS: no stm, major peak m/z 320.1. After cooling, the intermediate was concentrated. A mixture of the intermediate and isopropylhydrazine hydrochloride (0.4345 g, 3.929 mmol) in Acetic acid (18 mL, 320 mmol) was heated at 85° C. for 3 hours. The mixture was cooled and filtered from an insoluble impurity. The mother liquor was concentrated in vacuum. The residue was diluted with EtOAc then washed with water and brine. The organic layer was dried Na2SO4, filtered, and concentrated to give 317 (264). MS: (ESI+)=331.0. 1H NMR (400 MHz, DMSO) δ 9.29 (s, 1H), 7.97 (d, J=24.4 Hz, 1H), 7.94 (s, 1H), 7.31-7.19 (m, 1H), 5.85 (dq, J=13.0, 6.4 Hz, 1H), 4.66 (dd, J=5.2, 2.5 Hz, 2H), 4.63-4.54 (m, 2H), 1.48 (d, J=6.6 Hz, 6H).

Example 318

1-(5-(5,6-dihydrobenzo[f]imidazo[1,2-d][1,4]oxazepin-2-yl)-1-isopropyl-1H-1,2,4-triazol-3-yl)-N,N-dimethylmethanamine 318

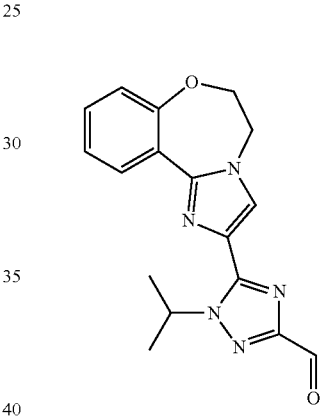

A suspension of [5-(8-bromo-4,5-dihydro-6-oxa-1,3a-diaza-benzo[e]azulen-2-yl)-1-isopropyl-1H-[1,2,4]triazol-3-yl]-methanol 315 (166 mg, 0.51 mmol) in DCM (5 mL) was treated with Dess-Martin periodinane (DMP, 238 mg, 0.56 mmol) and resultant solution stirred at RT for 2 h under an atmosphere of nitrogen. The reaction was quenched by the addition of sodium thiosulphate (620 mg in 1 mL water) before the addition of further water and extracted twice with DCM. The combined organic extracts were washed with water then dried (Na2SO4), filtered and concentrated in vacuo to give 5-(4,5-Dihydro-6-oxa-1,3a-diaza-benzo[e]azulen-2-yl)-1-isopropyl-1H-[1,2,4]triazole-3-carbaldehyde as a cream solid (170 mg, quantitative). LCMS: RT=4.30 min, [M+H]+ 324. ¹H NMR 400 MHz (DMSO-d6) δ: 9.91 (1 H, s), 8.43 (1 H, dd, J=8.06, 1.78 Hz), 8.11 (1 H, s), 7.34-7.34 (1 H, m), 7.17-7.17 (1 H, m), 7.07 (1 H, dd, J=8.17, 1.23 Hz), 6.03 (1 H, m), 4.57-4.48 (4 H, m), 1.55 (6 H, d, J=6.60 Hz)

A mixture of 5-(4,5-dihydro-6-oxa-1,3a-diaza-benzo[e]azulen-2-yl)-1-isopropyl-1H-[1,2,4]triazole-3-carbaldehyde (85 mg, 0.26 mmol), acetic acid (catalytic, 2 drops), 4 Å molecular sieves and dimethylamine hydrochloride (24 mg, 0.29 mmol) in THF (5 mL) was stirred at RT for 10 min before the addition of sodium triacetoxyborohydride (66 mg, 0.31 mmol). After stirring at RT for a further 18 h the reaction mixture was diluted with DCM, the organic layer washed with saturated aqueous sodium bicarbonate followed by water and then brine, then dried (Na2SO4), filtered and concentrated in vacuo. The resultant residue was subjected to RPHPLC (C18 column, gradient 5 to 98% methanol in water+0.1% HCO2H) to give 318 as a white solid (13 mg, 14%). LCMS: RT=3.18 min, [M+H]+353. $^1$H NMR 400 MHz (DMSO-d6) δ: 8.45 (1 H, dd, J=8.02, 1.76 Hz), 7.97 (1 H, s), 7.39-7.32 (1 H, m), 7.19-7.19 (1 H, m), 7.09 (1 H, dd, J=8.15, 1.25 Hz), 5.89 (1 H, m), 4.54 (4 H, d, J=2.46 Hz), 3.47 (2 H, s), 2.24 (6 H, s), 1.51 (6 H, d, J=6.59 Hz)

Example 319 racemic-cis-2-(3-hydroxy-4-(2-(1-isopropyl-1H-1,2,4-triazol-5-yl)-5,6-dihydrobenzo[f]imidazo[1,2-d][1,4]oxazepin-9-yl)piperidin-1-yl)-N,N-dimethylacetamide 319

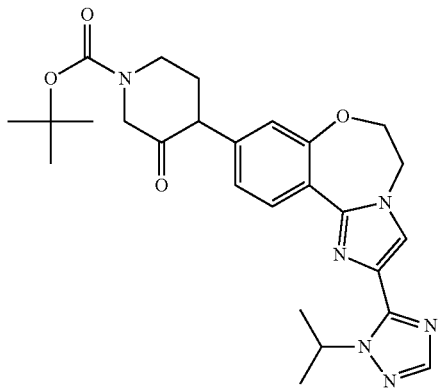 [SMILES: CC(C)n1ncnc1-c1cn2c(n1)-c1ccc(C3CCN(C(=O)OC(C)(C)C)CC3=O)cc1OCC2]

Step 1

Racemic-trans-3-Hydroxy-4-[2-(2-isopropyl-2H-[1,2,4]triazol-3-yl)-4,5-dihydro-6-oxa-1,3a-diaza-benzo[e]azulen-8-yl]-piperidine-1-carboxylic acid tert-butyl ester from Example 328 (containing approx. 24% of 4-hydroxypiperidine isomer, 0.32 g, 0.65 mmol) was dissolved in DCM (15 mL) and cooled in an ice-bath. Dess-Martin periodinane (0.3 M in DCM, 4.33 mL, 1.3 mmol) was added dropwise, the mixture was stirred at 0-10° C. for 7 h, then refrigerated for 16 h. Aqueous sodium bisulphate and sodium bicarbonate (10 mL each) were added and the mixture was stirred at room temperature for 15 min. The phases were separated and the aqueous phase was extracted twice with DCM. Combined organic extracts were washed with brine, dried (Na2SO4) and concentrated in vacuo. The resultant residue was subjected to flash chromatography (SiO2, gradient 0-5% methanol in DCM) then trituration with ether to give 4-[2-(2-Isopropyl-2H-[1,2,4]triazol-3-yl)-4,5-dihydro-6-oxa-1,3a-diaza-benzo[e]azulen-8-yl]-3-oxo-piperidine-1-carboxylic acid tert-butyl ester (86 mg). Additional product was recovered from the trituration liquor (59 mg). Total yield 145 mg (45%). LCMS RT=3.53, [M+H]+=493, [M+H+MeOH]+=525.

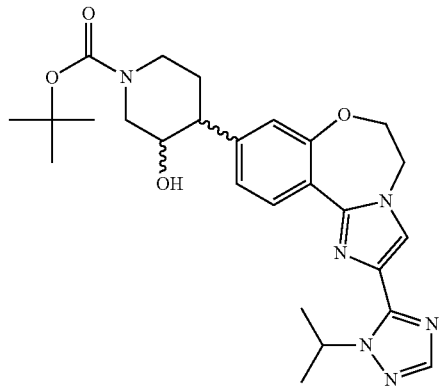 [SMILES: CC(C)n1ncnc1-c1cn2c(n1)-c1ccc(C3CCN(C(=O)OC(C)(C)C)CC3O)cc1OCC2]

Step 2

A solution of 4-[2-(2-isopropyl-2H-[1,2,4]triazol-3-yl)-4,5-dihydro-6-oxa-1,3a-diaza-benzo[e]azulen-8-yl]-3-oxo-piperidine-1-carboxylic acid tert-butyl ester (145 mg, 0.29 mmol) in dry THF (10 mL) was cooled to −78 C and a solution of lithium tri-sec-butylborohydride in THF (L-Selectride®, 1M, 0.30 mL, 0.30 mmol) was added dropwise. The mixture was stirred at −78° C. for 1 h, then aqueous sodium bicarbonate was added dropwise. After warming to room temperature, the mixture was extracted three times with ethyl acetate. The combined organic extracts were dried (Na2SO4), filtered and concentrated in vacuo. The resultant residue was subjected to flash chromatography (SiO2, gradient 0-5% methanol in DCM) to give racemic-cis-3-hydroxy-4-[2-(2-isopropyl-2H-[1,2,4]triazol-3-yl)-4,5-dihydro-6-oxa-1,3a-diaza-benzo[e]azulen-8-yl]-piperidine-1-carboxylic acid tert-butyl ester (92 mg, 64%). LCMS RT=3.39, [M+H]+=495.

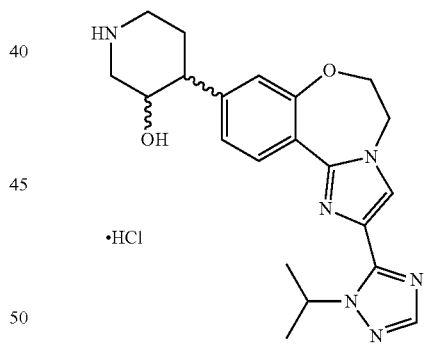

Step 3

To a solution of racemic-cis-3-hydroxy-4-[2-(2-isopropyl-2H-[1,2,4]triazol-3-yl)-4,5-dihydro-6-oxa-1,3a-diaza-benzo[e]azulen-8-yl]-piperidine-1-carboxylic acid tert-butyl ester (92 mg, 0.186 mmol) in DCM (0.5 mL) and methanol (0.3 mL) was added slowly a solution of hydrogen chloride in dioxane (4M, 0.8 mL). The mixture was stirred at room temperature for 2 h 20 min, then concentrated in vacuo. The resultant residue was triturated twice with ether and dried under vacuum to give racemic-cis-4-[2-(2-Isopropyl-2H-[1,2,4]triazol-3-yl)-4,5-dihydro-6-oxa-1,3a-diaza-benzo[e]azulen-8-yl]-piperidin-3-ol hydrochloride (86 mg, 108%). LCMS RT=1.93, [M+H]+=395.

Step 4 cis-racemic-4-[2-(2-isopropyl-2H-[1,2,4]triazol-3-yl)-4,5-dihydro-6-oxa-1,3a-diaza-benzo[e]azulen-8-yl]-piperidin-3-ol hydrochloride (86 mg, 0.19 mmol) was reacted with N,N-dimethyl-2-chloroacetamide (26 mg, 0.21 mmol) to give 319 (51 mg, 57%). LCMS: RT=2.58 min, [M+H]+=480. ¹H NMR 400 MHz (DMSO-d) δ: 8.29 (1 H, d, J=8.29 Hz), 7.90-7.90 (2 H, m), 7.08 (1 H, dd, J=8.37, 1.72 Hz), 6.98 (1 H, d, J=1.65 Hz), 5.89-5.88 (1 H, m), 4.56-4.41 (4 H, m), 4.08 (1 H, br), 3.79 (1 H, br), 3.17 (2H, m), 3.06 (3 H, s), 2.88 (2 H, m), 2.82 (3 H, s), 2.62 (1 H, m), 2.39 (1 H, m), 2.22 (2 H, m), 1.53 (1 H, m), 1.48 (6 H, d, J=6.61 Hz)

Example 320 racemic-cis-2-(3-hydroxy-4-(2-(1-isopropyl-1H-1,2,4-triazol-5-yl)-5,6-dihydrobenzo[f]imidazo[1,2-d][1,4]oxazepin-9-yl)piperidin-1-yl)-N,N-dimethylacetamide 320

Following the procedures for Example 330, cis-racemic-4-[2-(2-isopropyl-2H-[1,2,4]triazol-3-yl)-4,5-dihydro-6-oxa-1,3a-diaza-benzo[e]azulen-8-yl]-piperidin-3-ol hydrochloride (86 mg, 0.19 mmol) was reacted with N,N-dimethyl-2-chloroacetamide (26 mg, 0.21 mmol) to give 320 (51 mg, 57%). LCMS: RT=2.58 min, [M+H]+=480. ¹H NMR 400 MHz (DMSO-d6) δ: 8.29 (1 H, d, J=8.29 Hz), 7.90-7.90 (2 H, m), 7.08 (1 H, dd, J=8.37, 1.72 Hz), 6.98 (1 H, d, J=1.65 Hz), 5.89-5.88 (1 H, m), 4.56-4.41 (4 H, m), 4.08 (1 H, br), 3.79 (1 H, br), 3.17 (2 H, m), 3.06 (3 H, s), 2.88 (2 H, m), 2.82 (3 H, s), 2.62 (1 H, m), 2.39 (1 H, m), 2.22 (2 H, m), 1.53 (1 H, m), 1.48 (6 H, d, J=6.61 Hz)

Example 321

2-((1R,3r,5S)-3-(2-(1-isopropyl-1H-1,2,4-triazol-5-yl)-5,6-dihydrobenzo[f]imidazo[1,2-d][1,4]oxazepin-9-yl)-8-azabicyclo[3 0.2.1]octan-8-yl)acetamide 321

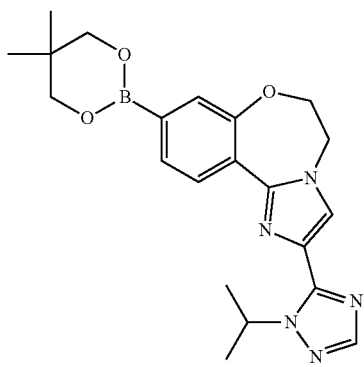 [SMILES: CC(C)n1ncnc1-c1cn2c(n1)-c1ccc(B3OCC(C)(C)CO3)cc1OCC2]

Step 1

A vessel was charged with 8-bromo-2-(2-isopropyl-2H-[1,2,4]triazol-3-yl)-4,5-dihydro-6-oxa-1,3a-diaza-benzo[e]azulene (1.00 g, 2.67 mmol, bis(neopentyl glycolato)diboron (905 mg, 4.01 mmol), potassium acetate (918 mg, 9.35 mmol) and dioxane (12 mL) before the vessel was sealed and degassed with nitrogen for 10 min. To the reaction was added PdCl2dppf.DCM (109 mg, 0.13 mmol, 5 mol %) and the reaction purged with nitrogen before being stirred at 90° C. for 65 h. The reaction mixture was cooled to RT then diluted with DCM (200 mL) and treated with activated carbon. The mixture was filtered and the filtrate was washed with water, dried (Na2SO4) and concentrated in vacuo to give 8-(5,5-Dimethyl-[1,3,2]dioxaborinan-2-yl)-2-(2-isopropyl-2H-[1,2,4]triazol-3-yl)-4,5-dihydro-6-oxa-1,3a-diaza-benzo[e]azulene (1.00 g, 2.46 mmol, 92%). LCMS RT=3.79 min, [M–HCC(CH3)2CH+H]+=340

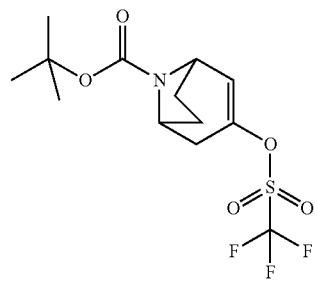 [SMILES: CC(C)(C)OC(=O)N1C2C=C(OS(=O)(=O)C(F)(F)F)CC1CC2]

Step 2

To a solution of 3-oxo-8-aza-bicyclo[3.2.1]octane-8-carboxylic acid tert-butyl ester (500 mg, 2.22 mmol) in THF (5 mL) at −78° C. was added 1M LiHMDS in THF (2.44 mL, 2.44 mmol) dropwise. The resulting mixture was stirred at −78° C. for 1 h before the addition of a solution of N-phenylbis(trifluoromethanesulfonimide) (872 mg, 2.44 mmol) in THF (5 mL) dropwise. The reaction mixture was stirred at −78° C. for 4 h before being quenched with saturated sodium bicarbonate solution. The mixture was extracted with ethyl acetate, dried (MgSO4) and concentrated in vacuo before being subjected to flash chromatography (SiO2, gradient 0-40% ethyl acetate in cyclohexane). The resultant residue was further purified by flash chromatography (SiO2, gradient 0-100% DCM in cyclohexane) to give 3-trifluoromethanesulfonyloxy-8-aza-bicyclo[3.2.1]oct-2-ene-8-carboxylic acid tert-butyl ester (402 mg, 0.56 mmol, 25%). 1H NMR 400 MHz (CDCl3) δ: 6.11 (1 H, s), 4.48 (2 H, m), 3.02 (1 H, m), 2.26 (1 H, m), 2.13 (1 H, m), 2.09 (1 H, m), 2.04 (1 H, m), 2.03 (1 H, s), 1.48 (9 H, s)

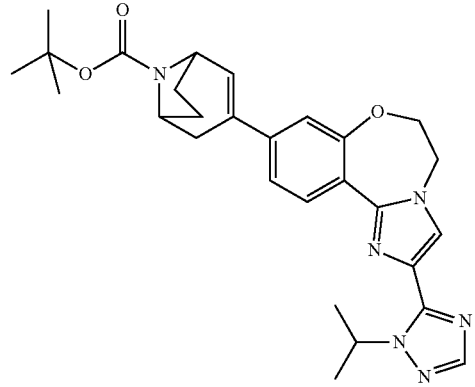 [SMILES: CC(C)n1ncnc1-c1cn2c(n1)-c1ccc(C3=CC4CCC(C3)N4C(=O)OC(C)(C)C)cc1OCC2]

Step 3

A vessel was charged with 8-(5,5-dimethyl-[1,3,2]dioxaborinan-2-yl)-2-(2-isopropyl-2H-[1,2,4]triazol-3-yl)-4,5-dihydro-6-oxa-1,3a-diaza-benzo[e]azulene (237 mg, 0.56 mmol), PdCl2dppf.DCM (46 mg, 0.06 mmol, 10 mol %) and cesium carbonate (456 mg, 1.40 mmol) before being evacuated and refilled with nitrogen. To the resultant mixture was added a solution of 3-trifluoromethanesulfonyloxy-8-aza-bicyclo[3.2.1]oct-2-ene-8-carboxylic acid tert-butyl ester (402 mg, 0.56 mmol) in DME (2 mL), followed by water (0.2 mL). The reaction was evacuated and refilled with nitrogen before being stirred at 110° C. for 1.5 h. The reaction mixture was partitioned between ethyl acetate and water, the organic phase was separated, dried (MgSO4) and concentrated in vacuo. The resultant residue was subjected to flash chromatography (SiO2, gradient 0-100% ethyl acetate in cyclohexane) to give 3-[2-(2-Isopropyl-2H-[1,2,4]triazol-3-yl)-4,5-dihydro-6-oxa-1,3a-diaza-benzo[e]azulen-8-yl]-8-aza-bicyclo[3.2.1]oct-2-ene-8-carboxylic acid tert-butyl ester as a colourless oil (177 mg, 0.35 mmol, 63%). LCMS RT=4.84 min, [M+H]+=503

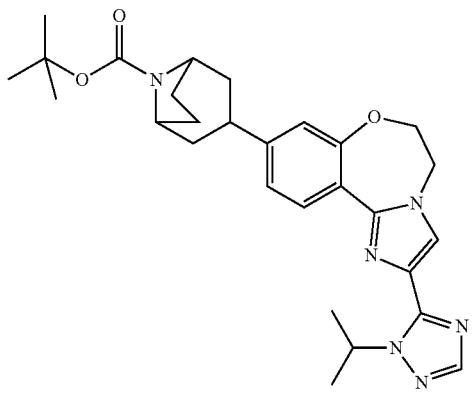 [SMILES: CC(C)n1ncnc1-c1cn2c(n1)-c1ccc(C3CC4CCC(C3)N4C(=O)OC(C)(C)C)cc1OCC2]

Step 4

To a degassed solution of 3-[2-(2-isopropyl-2H-[1,2,4]triazol-3-yl)-4,5-dihydro-6-oxa-1,3a-diaza-benzo[e]azulen-8-yl]-8-aza-bicyclo[3.2.1]oct-2-ene-8-carboxylic acid tert-butyl ester (176 mg, 0.35 mmol) in acetic acid (7 mL) was added palladium hydroxide on carbon (20% palladium, 50% water, 62 mg). The vessel was evacuated and refilled with hydrogen gas (×3) before the reaction was stirred at RT for 100 h. The reaction mixture was filtered through a pad of Celite®, washing with ethyl acetate, the filtrate concentrated in vacuo to give a mixture of endo/exo-3-[2-(2-isopropyl-2H-[1,2,4]triazol-3-yl)-4,5-dihydro-6-oxa-1,3a-diaza-benzo[e]azulen-8-yl]-8-aza-bicyclo[3.2.1]octane-8-carboxylic acid tert-butyl ester as a black gum (177 mg, 0.35 mmol, quantitative yield). LCMS RT=4.83 min, [M+H]+ 505

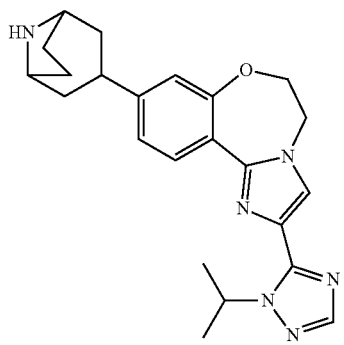 [SMILES: CC(C)n1ncnc1-c1cn2c(n1)-c1ccc(C3CC4CCC(C3)N4)cc1OCC2]

Step 5

To a solution of 3-[2-(2-isopropyl-2H-[1,2,4]triazol-3-yl)-4,5-dihydro-6-oxa-1,3a-diaza-benzo[e]azulen-8-yl]-8-aza-bicyclo[3.2.1]octane-8-carboxylic acid tert-butyl ester (177 mg, 0.35 mmol) in dioxane (10 mL) was added 4M HCl in dioxane (5 mL) and methanol (5 mL). The resultant mixture was stirred at RT for 18 h before being concentrated in vacuo. The resultant residue was taken up into methanol and loaded onto a SCX-2 cartridge, eluting with methanol then 2M NH3 in methanol. The basic fractions were concentrated in vacuo to give a mixture of endo/exo-8-(8-aza-bicyclo[3.2.1]oct-3-yl)-2-(2-isopropyl-2H-[1,2,4]triazol-3-yl)-4,5-dihydro-6-oxa-1,3a-diaza-benzo[e]azulene as a brown glass (91 mg, 0.22 mmol, 64%). LCMS RT=2.77 min and 2.91 min, [M+H]+=405

Step 6

A solution of endo/exo-8-(8-aza-bicyclo[3.2.1]oct-3-yl)-2-(2-isopropyl-2H-[1,2,4]triazol-3-yl)-4,5-dihydro-6-oxa-1,3a-diaza-benzo[e]azulene (91 mg, 0.22 mmol) in DCM (1 mL) was treated with TEA (38 L, 0.27 mmol) followed by bromoacetamide (37 mg, 0.27 mmol) and the reaction mixture stirred at RT for 22 h before being concentrated in vacuo. The resultant residue was subjected to flash chromatography (SiO2, gradient 0 to 7% 2M NH3 (methanol) in DCM) and endo/exo isomers separated by RPHPLC (C6-phenyl column, gradient 5 to 25% acetonitrile in water+ 0.1% HCO2H over 20 min) to give 321 and 322 as white solids (3 mg and 13 mg of 1st and 2nd eluting isomers respectively). 1st eluting isomer was assigned as 321: LCMS: RT=2.64 min, [M+H]+=462. 1H NMR 400 MHz (CDCl3) δ: 8.45 (1 H, d, J=8.40 Hz), 8.10 (1H, br), 7.97 (1 H, br), 7.89 (1 H, s), 7.67 (1 H, s), 7.14 (1 H, d, J=8.52 Hz), 7.02 (1 H, s), 5.99 (1 H, m), 5.81 (1 H, br), 4.49-4.47 (4 H, m), 3.49 (2 H, s), 3.19 (3 H, m), 2.66-2.56 (2 H, m), 2.04-1.96 (4 H, m), 1.66 (2 H, m), 1.59 (6 H, d, J=6.63 Hz)

Example 322

2-((1R,3S,5S)-3-(2-(1-isopropyl-1H-1,2,4-triazol-5-yl)-5,6-dihydrobenzo[f]imidazo[1,2-d][1,4]oxazepin-9-yl)-8-azabicyclo[3.2.1]octan-8-yl)acetamide 322

Following the procedures for Example 321, 2nd eluting isomer was assigned as 322: LCMS: RT=2.70 min, [M+H]+ =462. 1H NMR 400 MHz (CDCl3) δ: 8.45 (1 H, d, J=8.31 Hz), 8.02 (1H, br), 7.88 (1 H, d, J=0.67 Hz), 7.74 (1 H, br), 7.66 (1 H, s), 7.06 (1 H, dd, J=8.35, 1.82 Hz), 6.93 (1 H, d, J=1.77 Hz), 5.99-5.98 (1 H, m), 5.75 (1 H, br), 4.47-4.46 (4 H, m), 3.42 (2 H, m), 3.16 (2 H, s), 2.92-2.90 (1 H, m), 2.10-2.08 (2 H, m), 2.00 (2 H, t, J=12.82 Hz), 1.82-1.81 (4 H, m), 1.59 (6 H, d, J=6.63 Hz)

Example 323

2-(1-isopropyl-1H-1,2,4-triazol-5-yl)-9-(4-methyl-piperazin-1-yl)-5,6-dihydroimidazo[1,2-d]pyrido[3,2-f][1,4]oxazepine 323

A solution of 9-chloro-2-(1-isopropyl-1H-1,2,4-triazol-5-yl)-5,6-dihydroimidazo[1,2-d]pyrido[3,2-f][1,4]oxazepine (66.0 mg, 0.200 mmol), 1-methyl-Piperazine, (88.5 uL, 0.798 mmol) and Triethylamine (167 uL, 1.20 mmol) in N,N-Dimethylacetamide (3.00 mL, 32.3 mmol) was heated in microwave at 160 C for 20 min. The reaction was filtered thru celite then rinsed with EtOAc. The filtrate was washed water, brine. The organic layer was dried Na2SO4, concentrated. The crude product was purified by rHPLC to give 323. MS: (ESI+)=395.2. 1H NMR (400 MHz, DMSO) δ 8.50 (d, J=8.7 Hz, 1H), 7.88 (s, 1H), 7.80 (s, 1H), 6.72 (d, J=8.8 Hz, 1H), 5.88 (dt, J=13.2, 6.7 Hz, 1H), 4.49 (m, 4H), 3.61-3.48 (m, 4H), 2.42-2.34 (m, 4H), 2.21 (s, 3H), 1.47 (d, J=6.6 Hz, 6H)

Example 324

4-(2-(1-isopropyl-1H-1,2,4-triazol-5-yl)-5,6-dihydroimidazo[1,2-d]pyrido[3,2-f][1,4]oxazepin-9-yl)piperazin-2-one 324

Following the procedures in Example 323, 9-chloro-2-(1-isopropyl-1H-1,2,4-triazol-5-yl)-5,6-dihydroimidazo[1,2-d]pyrido[3,2-f][1,4]oxazepine and piperazin-2-one were reacted to give 324. MS: (ESI+)=395.1. 1H NMR (400 MHz, DMSO) δ 8.55 (d, J=8.7 Hz, 1H), 8.10 (s, 1H), 7.88 (s, 1H), 7.81 (s, 1H), 6.70 (d, J=8.8 Hz, 1H), 5.88 (dt, J=13.2, 6.6 Hz, 1H), 4.60-4.40 (m, 4H), 4.06 (s, J=8.0 Hz, 2H), 3.84-3.68 (m, 2H), 1.47 (d, J=6.6 Hz, 6H).

Example 325

4-(2-(1-isopropyl-1H-1,2,4-triazol-5-yl)-5,6-dihydroimidazo[1,2-d]pyrido[3,4-f][1,4]oxazepin-9-yl)piperazin-2-one 325

A solution of 9-chloro-2-(1-isopropyl-1H-1,2,4-triazol-5-yl)-5,6-dihydroimidazo[1,2-d]pyrido[3,4-f][1,4]oxazepine 317 (55.0 mg, 0.166 mmol), piperazin-2-one (0.110 g, 1.10 mmol) and triethylamine (0.275 mL, 1.97 mmol) in N-methylpyrrolidinone (3.00 mL, 31.1 mmol) was heated at 150° C. for 2d. The reaction was filtered thru celite then rinsed with EtOAc. The filtrate was washed water and brine. The organic layer was dried Na2SO4, concentrated to give 325, analyzed by rHPLC. MS: (ESI+)=395.1. 1H NMR (400 MHz, DMSO) δ 8.55 (d, J=8.7 Hz, 1H), 8.10 (s, 1H), 7.88 (s, 1H), 7.81 (s, 1H), 6.70 (d, J=8.8 Hz, 1H), 5.88 (dt, J=13.2, 6.6 Hz, 1H), 4.63-4.30 (m, 4H), 4.06 (d, J=8.0 Hz, 2H), 3.81-3.63 (m, 2H), 1.47 (d, J=6.6 Hz, 6H).

Example 327

4-(2-(1-isopropyl-3-methyl-1H-1,2,4-triazol-5-yl)-5,6-dihydrobenzo[f]imidazo[1,2-d][1,4]oxazepin-10-yl)pyridin-2(1H)-one 327

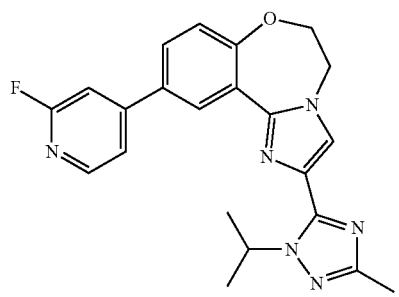 [SMILES: Cc1nc(-c2cn3c(n2)-c2cc(-c4ccnc(F)c4)ccc2OCC3)n(C(C)C)n1]

Following the procedure for 203, was prepared by substituting 2-fluoropyridin-3-ylboronic acid with 2-fluoropyridin-4-ylboronic acid to give 10-(2-fluoropyridin-4-yl)-2-(1-isopropyl-3-methyl-1H-1,2,4-triazol-5-yl)-5,6-dihydrobenzo[f]imidazo[1,2-d][1,4]oxazepine (0.242 g, 24%, MS (ESI(+)): m/z 404.9 (M+H), which was treated with 10% aq. HCl to give 327 (0.141 g, 59%). 1H NMR (400 MHz, DMSO) δ 11.53 (s, 1H), 8.72 (d, J=2.2, 1H), 7.93 (s, 1H), 7.67 (dd, J=8.5, 2.3, 1H), 7.49 (d, J=6.9, 1H), 7.15 (d, J=8.6, 1H), 6.55 (s, 1H), 6.48 (d, J=6.2, 1H), 5.70 (dt, J=13.2, 6.7, 1H), 4.56 (s, 4H), 2.26 (s, 3H), 1.49 (d, J=6.6, 6H). MS (ESI(+)): m/z 403.1 (M+H).

Example 328

(3R,4S)-4-(2-(1-isopropyl-3-methyl-1H-1,2,4-triazol-5-yl)-5,6-dihydrobenzo[f]imidazo[1,2-d][1,4]oxazepin-9-yl)piperidin-3-ol 328

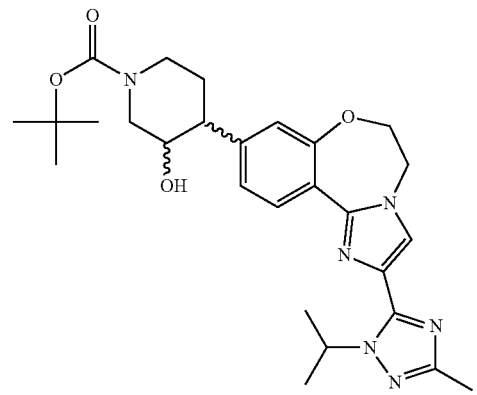 [SMILES: Cc1nc(-c2cn3c(n2)-c2ccc(C4CCN(C(=O)OC(C)(C)C)CC4O)cc2OCC3)n(C(C)C)n1]

Step 1

4-[2-(2-Isopropyl-5-methyl-2H-[1,2,4]triazol-3-yl)-4,5-dihydro-6-oxa-1,3a-diaza-benzo[e]azulen-8-yl]-3,6-dihydro-2H-pyridine-1-carboxylic acid tert-butyl ester (0.60 g, 1.22 mmol) was partially dissolved in dry diethyleneglycol dimethyl ether (14 mL) and a solution of borane/THF complex (1M in THF, 7.29 mL, 7.29 mmol) was added dropwise. After stirring briefly at room temperature, the mixture was allowed to stand for 16 h. The mixture was then cooled in ice, and water (1.1 mL), 2M sodium hydroxide (3.6 mL) and 35% hydrogen peroxide (0.94 mL, 8.98 mmol) were added dropwise in sequence. The mixture was heated at 50° C. for 8 h, then cooled, diluted with water (approximately 30 mL) and extracted three times with ethyl acetate. The combined organic extracts were dried (Na2SO4), filtered and concentrated in vacuo. The resultant residue was subjected to flash chromatography (SiO2, gradient 0-10% methanol in DCM) to give racemic-trans-3-Hydroxy-4-[2-(2-isopropyl-5-methyl-2H-[1,2,4]triazol-3-yl)-4,5-dihydro-6-oxa-1,3a-diaza-benzo[e]azulen-8-yl]-piperidine-1-carboxylic acid tert-butyl ester (0.46 g, 74%), containing approx. 20% of 4-hydroxypiperidine isomer. LCMS RT=4.48, [M+H]+=509.

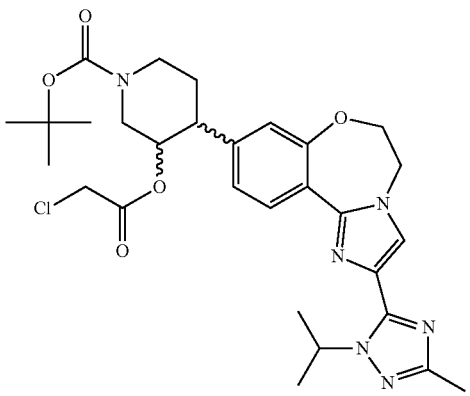 [SMILES: Cc1nc(-c2cn3c(n2)-c2ccc(C4CCN(C(=O)OC(C)(C)C)CC4OC(=O)CCl)cc2OCC3)n(C(C)C)n1]

Step 2

Racemic-trans-3-Hydroxy-4-[2-(2-isopropyl-5-methyl-2H-[1,2,4]triazol-3-yl)-4,5-dihydro-6-oxa-1,3a-diaza-benzo[e]azulen-8-yl]-piperidine-1-carboxylic acid tert-butyl ester (0.215 g, 0.42 mmol) was suspended in dry THF (10 mL) and triphenylphosphine (0.22 g, 0.85 mmol) and chloroacetic acid (82 mg, 0.85 mmol) were added. Diethyl azodicarboxylate (0.133 mL, 0.85 mmol) was added dropwise and the mixture was stirred at room temperature for 24 h. The mixture was concentrated and the resultant residue was subjected to flash chromatography (SiO2, gradient 0-10% methanol in DCM). The resultant impure material was dissolved in dry DCM (5 mL) and triphenylphosphine, chloroacetic acid and diethyl azodicarboxylate were added (quantities as above). The mixture was stirred at room temperature for 16 hr, then concentrated in vacuo, the crude product was triturated with ether and the liquor was concentrated. The resultant residue was subjected to flash chromatography (SiO2, gradient 0-5% methanol in DCM) to give impure racemic-cis-3-(2-Chloro-acetoxy)-4-[2-(2-isopropyl-5-methyl-2H-[1,2,4]triazol-3-yl)-4,5-dihydro-6-oxa-1,3a-diaza-benzo[e]azulen-8-yl]-piperidine-1-carboxylic acid tert-butyl ester (0.297 g), which was used in the subsequent step without further purification. LCMS RT=4.61, [M+H]+=585/587.

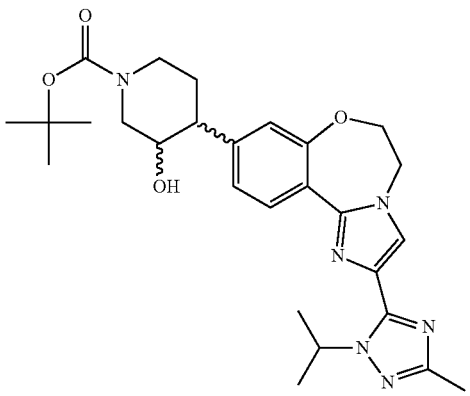 [SMILES: Cc1nc(-c2cn3c(n2)-c2ccc(C4CCN(C(=O)OC(C)(C)C)CC4O)cc2OCC3)n(C(C)C)n1]

Step 3

A solution of impure racemic-cis-3-(2-chloro-acetoxy)-4-[2-(2-isopropyl-5-methyl-2H-[1,2,4]triazol-3-yl)-4,5-dihydro-6-oxa-1,3a-diaza-benzo[e]azulen-8-yl]-piperidine-1-carboxylic acid tert-butyl ester (0.297 g) in dioxane (5 mL) was stirred with aqueous sodium hydroxide (1M, 4.2 mL) at room temperature for 16 h, followed by heating at 50° C. for approx. 24 h. The cooled mixture was extracted three times with ethyl acetate, the combined organic extracts were dried (Na2SO4), filtered and concentrated in vacuo. The resultant residue was subjected to flash chromatography (SiO2, gradient 0-5% methanol in DCM) to give racemic-cis-3-Hydroxy-4-[2-(2-isopropyl-5-methyl-2H-[1,2,4]triazol-3-yl)-4,5-dihydro-6-oxa-1,3a-diaza-benzo[e]azulen-8-yl]-piperidine-1-carboxylic acid tert-butyl ester (17 mg). LCMS RT=4.50, [M+H]+ 509

To a solution of cis-racemic-3-hydroxy-4-[2-(2-isopropyl-2H-[1,2,4]triazol-3-yl)-4,5-dihydro-6-oxa-1,3a-diaza-benzo[e]azulen-8-yl]-piperidine-1-carboxylic acid tert-butyl ester (17 mg, 0.36 mmol) in DCM (1 mL) and methanol (0.6 mL) was added 4M HCl in dioxane (1.5 mL) slowly and the reaction mixture stirred at RT for 2.5 h before being concentrated in vacuo. The resultant residue was triturated in diethyl ether to give racemic cis-4-(2-(1-isopropyl-3-methyl-1H-1,2,4-triazol-5-yl)-5,6-dihydrobenzo[f]imidazo[1,2-d][1,4]oxazepin-9-yl)piperidin-3-ol which was resolved as the (3R,4S) enantiomer 328 as a white solid (10 mg, 67%). MS RT 2.47, [M+H]+=409. $^1$H NMR (DMSO-d6) δ: 8.92 (1H, br, d), 8.33 (1 H, d, J=8.30 Hz), 7.97 (1 H, s), 7.08 (1 H, d, J=8.36 Hz), 6.96 (1 H, d, J=1.66 Hz), 5.79 (1 H, t, J=6.59 Hz), 4.50 (4 H, d, J=7.99 Hz), 4.06 (1 H, s), 3.27 (2 H, m), 3.17 (2 H, m), 2.97 (2 H, d, J=14.58 Hz), 2.32-2.27 (1H, m), 2.29 (3 H, s), 1.74 (1 H, d, J=13.43 Hz), 1.46 (6 H, d, J=6.59 Hz)

Example 329

2-(4-(2-(1-isopropyl-3-methyl-1H-1,2,4-triazol-5-yl)-5,6-dihydrobenzo[f]imidazo[1,2-d][1,4]oxazepin-9-yl)piperidin-1-yl)-N,N-dimethylacetamide 329

A suspension of 2-(2-isopropyl-5-methyl-2H-[1,2,4]triazol-3-yl)-8-piperidin-4-yl-4,5-dihydro-6-oxa-1,3a-diaza-benzo[e]azulene hydrochloride (310 mg, 0.72 mmol) in DCM (6 mL) and TEA (0.3 mL, 2.16 mmol) was sonicated and stirred before adding N,N-dimethyl-2-chloroacetamide (98 mg, 0.8 mmol) and TBAI (28 mg, 0.072 mmol) and the reaction mixture stirred for 72 h at RT before being concentrated in vacuo. The resultant residue was partitioned between water and DCM and the aqueous extracted five times with DCM, the combined organic extracts dried (Na2SO4), filtered and concentrated in vacuo. The resultant residue was subjected to flash chromatography (SiO2, gradient 0 to 10% methanol in DCM) then triturated in diethyl ether to give 329 as a white solid (129 mg, 38%). LCMS: RT=2.71 min, [M+H]+=478. 1H NMR 400 MHz (CDCl3) δ: 8.44 (1 H, d, J=8.30 Hz), 7.61 (1 H, s), 7.04 (1 H, d, J=8.43 Hz), 6.91 (1 H, s), 5.91 (1 H, t, J=6.63 Hz), 4.45 (4 H, d, J=14.92 Hz), 3.39 (2 H, m), 3.11 (2 H, m), 3.10 (3 H, s), 2.99 (1 H, m), 2.98 (3 H, s), 2.54 (2 H, m), 2.41 (3 H, s), 1.90 (4 H, s), 1.57 (6 H, d, J=6.65 Hz)

Example 330 trans-racemic-2-(3-hydroxy-4-(2-(1-isopropyl-1H-1,2,4-triazol-5-yl)-5,6-dihydrobenzo[f]imidazo[1,2-d][1,4]oxazepin-9-yl)piperidin-1-yl)-N,2-dimethylpropanamide 330

A mixture of trans-racemic-4-[2-(2-isopropyl-2H-[1,2,4]triazol-3-yl)-4,5-dihydro-6-oxa-1,3a-diaza-benzo[e]azulen-8-yl]-piperidin-3-ol hydrochloride (199 mg, 0.46 mmol), 2-bromo-2-methyl-N-methyl propionamide (83 mg, 0.46 mmol), NaOH (2 mL, 50% aqueous solution), TBAB (16 mg, 0.05 mmol) and DCM (2.5 mL) was stirred vigorously at RT for 7.5 h. The phases were separated and the aqueous layer extracted three times with 10% methanol in DCM, the combined organic extracts washed with brine then dried (Na2SO4), filtered and concentrated in vacuo. The resultant residue was subjected to flash chromatography (SiO2, gradient 0 to 10% methanol in DCM) to give 330 (84 mg, 37%). LCMS: RT=2.54 min, [M+H]+=494. 1H NMR 400 MHz (CDCl3) δ: 8.44 (1 H, d, J=8.23 Hz), 7.87 (1 H, s), 7.48 (1 H, s), 7.17 (1 H, br), 7.08 (1 H, m), 6.86 (1 H, s), 6.03-6.01 (1 H, m), 4.77-4.07 (4 H, m), 3.82 (1 H, br), 3.17 (1 H, m), 2.86 (3 H, d, J=4.98 Hz), 2.85 (2H, m), 2.46 (1 H, m), 2.27 (1 H, m), 2.18 (1 H, m), 1.90 (1 H, m), 1.70 (1 H, m), 1.61 (6 H, m), 1.27 (6 H, d, J=10.69 Hz)

Example 331

2-(4-(2-(1-isopropyl-1H-1,2,4-triazol-5-yl)-5,6-dihydroimidazo[1,2-d]pyrido[3,4-f][1,4]oxazepin-9-yl) piperazin-1-yl)-N,N-dimethylacetamide 331

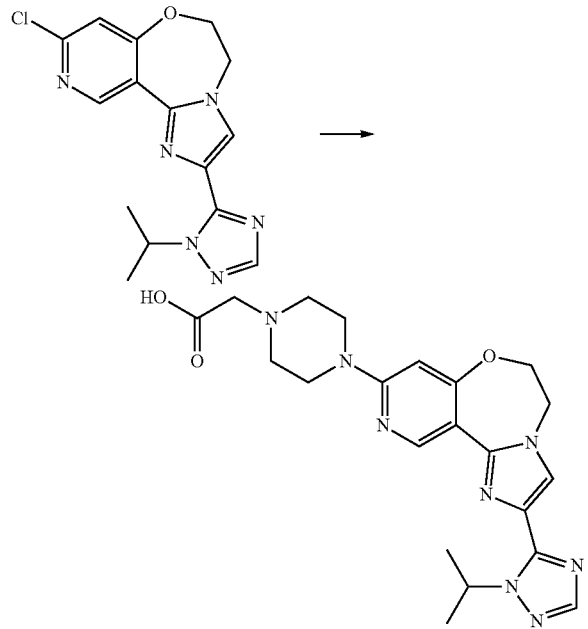

A solution of 9-chloro-2-(1-isopropyl-1H-1,2,4-triazol-5-yl)-5,6-dihydroimidazo[1,2-d]pyrido[3,4-f][1,4]oxazepine 317 (80.0 mg, 0.242 mmol), ethyl 2-(piperazin-1-yl)acetate (0.275 g, 1.60 mmol) and Triethylamine (0.400 mL, 2.87 mmol) in N-Methylpyrrolidinone (4.36 mL, 45.2 mmol) was heated at 150° C. for 2 days. The reaction was filtered thru celite then rinsed with EtOAc. The filtrate was washed water, brine. The organic layer was dried Na2SO4, concentrated. To a solution of crude ethy ester intermediate in Tetrahydrofuran (3.00 mL, 37.0 mmol) and Water (3.00 mL, 166 mmol) was added Lithium hydroxide hydrate (0.0406 g, 0.967 mmol). The reaction was stirred at r.t. The reaction was quenched with water then wash EtOAc. The aqueous layer was concentrated to give 2-(4-(2-(1-isopropyl-1H-1,2, 4-triazol-5-yl)-5,6-dihydroimidazo[1,2-d]pyrido[3,4-f][1,4] oxazepin-9-yl)piperazin-1-yl)acetic acid which was carried to next reaction. MS: (ESI+)=439.2

2-(4-(2-(1-Isopropyl-1H-1,2,4-triazol-5-yl)-5,6-dihydroimidazo[1,2-d]pyrido[3,4-f][1,4]oxazepin-9-yl)piperazin-1-yl)acetic acid (0.050 g, 0.00011 mol) dissolved in N,N-Dimethylformamide (1.79 mL, 0.0231 mol) and treated sequentially with N,N-Diisopropylethylamine (0.119 mL, 0.000686 mol) Dimethylamine hydrochloride (0.0373 g, 0.000457 mol) then N,N,N',N'-Tetramethyl-O-(7-azabenzotriazol-1-yl)uronium Hexafluorophosphate (0.0521 g, 0.000137 mol). Stir at r.t. 2 h. Add sat. sodium bicarbonate, extract with ethyl acetate. Dry organics over sodium sulfate and concentrate to give 331, analyzed by rHPLC. MS: (ESI+)=466.2. 1H NMR (400 MHz, DMSO) δ 9.10 (s, 1H), 7.89 (s, 1H), 7.84 (s, 1H), 6.34 (s, 1H), 6.01-5.79 (m, 1H), 4.50 (d, J=10.0 Hz, 4H), 3.53 (s, 4H), 3.18 (s, 2H), 3.03 (s, 3H), 2.82 (s, 3H), 1.47 (d, J=6.5 Hz, 6H).

Example 332

2-(4-(2-(1-isopropyl-1H-1,2,4-triazol-5-yl)-5,6-dihydroimidazo[1,2-d]pyrido[3,4-f][1,4]oxazepin-9-yl) piperazin-1-yl)acetamide 332

2-(4-(2-(1-Isopropyl-1H-1,2,4-triazol-5-yl)-5,6-dihydroimidazo[1,2-d]pyrido[3,4-f][1,4]oxazepin-9-yl)piperazin-1-yl)acetic acid from Example 331 (0.050 g, 0.11 mmol) dissolved in N,N-Dimethylformamide (1.79 mL, 0.0231 mol) and treated sequentially with N,N-Diisopropylethylamine (0.119 mL, 0.686 mmol) Ammonium chloride (0.0244 g, 0.457 mmol) then N,N,N',N'-Tetramethyl-O-(7-azabenzotriazol-1-yl)uronium Hexafluorophosphate (0.0521 g, 0.137 mmol). Stir at r.t. 2 h. Add sat. sodium bicarbonate, extract with ethyl acetate. Dry organics over sodium sulfate and concentrate to give 332, analyzed by rHPLC. MS: (ESI+)=466.2. 1H NMR (400 MHz, DMSO) δ 9.11 (s, 1H), 7.89 (s, 1H), 7.85 (s, 1H), 7.20 (s, 2H), 6.35 (s, 1H), 5.93 (dt, J=13.7, 7.0 Hz, 1H), 4.50 (d, J=10.4 Hz, 4H), 3.57 (s, 5H), 2.91 (s, 2H), 1.47 (d, J=6.5 Hz, 6H).

Example 333

2-(1-isopropyl-1H-1,2,4-triazol-5-yl)-5,6-dihydroimidazo[1,2-d]pyrido[3,2-f][1,4]oxazepin-9(8H)-one 333

A solution of 9-chloro-5,6-dihydroimidazo[1,2-d]pyrido [3,2-f][1,4]oxazepine-2-carboxamide (55.0 mg, 0.166 mmol) in Sulfuric acid (0.70 mL, 13 mmol) and Water (0.70 mL, 39 mmol) was heated at 125 C for 2 h. The reaction was diluted with water, neutralized 1M NaOH then extracted EtOAc. The organic layer was dried Na2SO4, concentrated to give 333 after rHPLC purification. MS: (ESI+)=313.0

Example 334

2-(4-(2-(1-isopropyl-1H-1,2,4-triazol-5-yl)-5,6-dihydroimidazo[1,2-d]pyrido[3,2-f][1,4]oxazepin-9-yl) piperazin-1-yl)-N-methylacetamide 334

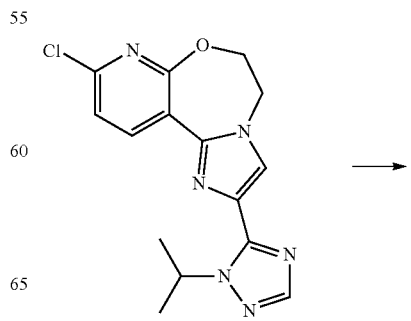

-continued

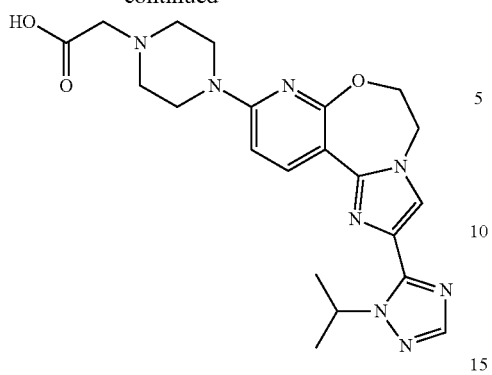

A solution of 9-chloro-2-(1-isopropyl-1H-1,2,4-triazol-5-yl)-5,6-dihydroimidazo[1,2-d]pyrido[3,2-f][1,4]oxazepine (150.0 mg, 0.4535 mmol), ethyl 2-(piperazin-1-yl)acetate (0.275 g, 1.60 mmol) and Triethylamine (0.400 mL, 2.87 mmol) in N-Methylpyrrolidinone (4.36 mL, 45.2 mmol) was heated at 150 C for 2d. The reaction was diluted with EtOAc then wash with water and brine. The organic layer was dried Na2SO4, concentrated to give intermediate ethyl ester which was dissolved in Tetrahydrofuran (8.00 mL, 98.6 mmol) and Water (8.00 mL, 444 mmol). Lithium hydroxide hydrate (0.07612 g, 1.814 mmol) was added. The reaction was stirred at room temp. and then quenched with water and washed with EtOAc. The aqueous layer was concentrated to give 2-(4-(2-(1-isopropyl-1H-1,2,4-triazol-5-yl)-5,6-dihydroimidazo[1,2-d]pyrido[3,2-f][1,4]oxazepin-9-yl)piperazin-1-yl)acetic acid. MS: (ESI+)=439.4

2-(4-(2-(1-Isopropyl-1H-1,2,4-triazol-5-yl)-5,6-dihydroimidazo[1,2-d]pyrido[3,2-f][1,4]oxazepin-9-yl)piperazin-1-yl)acetic acid (0.050 g, 0.00011 mol) was dissolved in N,N-Dimethylformamide (1.79 mL, 0.0231 mol) and treated sequentially with N,N-Diisopropylethylamine (0.119 mL, 0.000686 mol) 2.00 M of Methylamine in Tetrahydrofuran (0.228 mL) then N,N,N',N'-Tetramethyl-O-(7-azabenzotriazol-1-yl)uronium Hexafluorophosphate (0.0521 g, 0.000137 mol). Stir at r.t. 2 h. Add sat. sodium bicarbonate, extract with ethyl acetate. Dry organics over sodium sulfate and concentrate to give 334, analyzed by rHPLC. MS: (ESI+)=452.2

Example 335

2-(4-(2-(1-isopropyl-1H-1,2,4-triazol-5-yl)-5,6-dihydroimidazo[1,2-d]pyrido[3,2-f][1,4]oxazepin-9-yl) piperazin-1-yl)-N,N-dimethylacetamide 335

2-(4-(2-(1-isopropyl-1H-1,2,4-triazol-5-yl)-5,6-dihydroimidazo[1,2-d]pyrido[3,2-f][1,4]oxazepin-9-yl)piperazin-1-yl)acetic acid from Example 334 (0.050 g, 0.00011 mol) dissolved in N,N-Dimethylformamide (1.79 mL, 0.0231 mol) and treated sequentially with N,N-Diisopropylethylamine (0.119 mL, 0.000686 mol) Dimethylamine hydrochloride (0.0373 g, 0.000457 mol) then N,N,N',N'-Tetramethyl-O-(7-azabenzotriazol-1-yl)uronium Hexafluorophosphate (0.0521 g, 0.137 mmol). Stir at r.t. 2 h. Add sat. sodium bicarbonate, extract with ethyl acetate. Dry organics over sodium sulfate and concentrated to give 335, analyzed by rHPLC. MS: (ESI+)=466.3

Example 336

2-(2-(1-isopropyl-1H-1,2,4-triazol-5-yl)-5,6-dihydrobenzo[f]imidazo[1,2-d][1,4]oxazepin-9-yl)acetic acid 336

Step 1 methyl 2-(2-(1-isopropyl-1H-1,2,4-triazol-5-yl)-5,6-dihydrobenzo[f]imidazo[1,2-d][1,4]oxazepin-9-yl) acetate

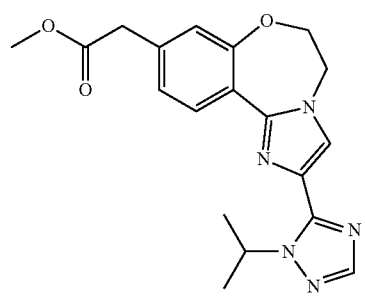 [SMILES: COC(=O)Cc1ccc2c(c1)OCCn1cc(-c3ncnn3C(C)C)nc1-2]

Following the procedures of Example 300, 9-bromo-2-(1-isopropyl-1H-1,2,4-triazol-5-yl)-5,6-dihydrobenzo[f]imidazo[1,2-d][1,4]oxazepine 194 and 1-(tert-butyldimethylsilyloxy)-1-methoxyethene were reacted to give methyl 2-(2-(1-isopropyl-1H-1,2,4-triazol-5-yl)-5,6-dihydrobenzo[f]imidazo[1,2-d][1,4]oxazepin-9-yl)acetate. M/z 368.2, calc. 367.16

Step 2

Methyl 2-(2-(1-isopropyl-1H-1,2,4-triazol-5-yl)-5,6-dihydrobenzo[f]imidazo[1,2-d][1,4]oxazepin-9-yl) acetate and lithium hydroxide were reacted to give 336. M/z 354.1, calc. 353.15

Example 337

1-((2-(1-isopropyl-1H-pyrazol-5-yl)-5,6-dihydrobenzo[f]imidazo[1,2-d][1,4]oxazepin-9-yl)methyl) urea 337

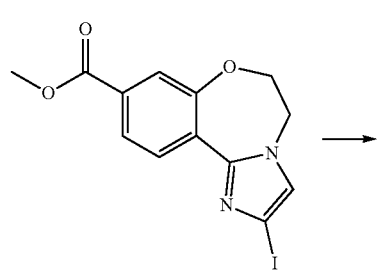

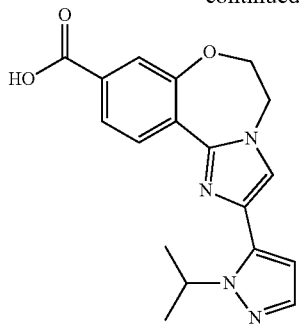

Methyl 2-iodo-5,6-dihydrobenzo[f]imidazo[1,2-d][1,4]oxazepine-9-carboxylate (0.6 g, 2.0 mmol), prepared according to Example 40, 1-isopropyl-5-(4,4,5,5-tetramethyl-1,3,2-dioxaborolan-2-yl)-1H-pyrazole (0.477 mmol, 2.02 mmol) and bis(triphenylphosphine)palladium(II) chloride (0.059 g, 0.084 mmol) were combined in a 35-mL microwaveable vessel. Subsequently, potassium carbonate (1.0 M in water, 5 mL) and acetonitrile (5 mL) were added. The reaction vessel was then subjected to microwave irradiation at 140° C. for 20 min. The mixture was diluted further with EtOAc and the product was isolated via acid-base extraction to provide 0.3 g (50% yield) of 2-(1-isopropyl-1H-pyrazol-5-yl)-5,6-dihydrobenzo[f]imidazo[1,2-d][1,4]oxazepine-9-carboxylic acid.

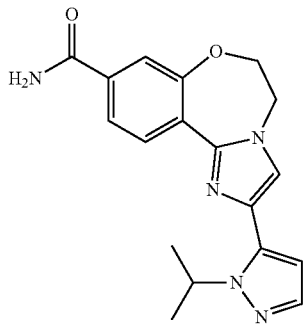 [SMILES: CC(C)n1nccc1-c1cn2c(n1)-c1ccc(C(N)=O)cc1OCC2]

2-(1-isopropyl-1H-pyrazol-5-yl)-5,6-dihydrobenzo[f]imidazo[1,2-d][1,4]oxazepine-9-carboxylic acid (0.3 g, 0.9 mmol) was dissolved in tetrahydrofuran (3 mL) and ammonium chloride (0.19 g, 3.6 mmol) and N,N-diisopropylethylamine (0.31 mL, 1.8 mmol) were added followed by N,N,N',N'-tetramethyl-O-(7-azabenzotriazol-1-yl)uranium hexafluorophosphate (HATU) (0.37 g, 0.98 mmol) lastly and the resulting mixture was stirred at ambient temperature for 2 h. The reaction was complete as indicated by LCMS analysis. The reaction mixture was then diluted with saturated aqueous sodium bicarbonate solution and extracted with EtOAc twice. The combined organic layers were washed once with brine and dried over Na2SO4. The liquid was filtered and concentrated to dryness. The crude residue was carried on to the subsequent reaction without further purification steps applied. This provided 0.3 g (quantitative) of 2-(1-isopropyl-1H-pyrazol-5-yl)-5,6-dihydrobenzo[f]imidazo[1,2-d][1,4]oxazepine-9-carboxamide. MS(ESI+) m/z 338.1 (M+H+), calcd. 338.4

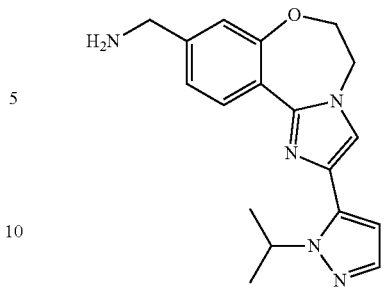

Lithium tetrahydroaluminate (0.047 g, 1.3 mmol) was suspended in tetrahydrofuran (8 mL) and cooled to 0° C. A solution of 2-(1-isopropyl-1H-pyrazol-5-yl)-5,6-dihydrobenzo[f]imidazo[1,2-d][1,4]oxazepine-9-carboxamide (0.3 g, 0.9 mmol) in tetrahydrofuran (2 mL) was added and the reaction mixture was stirred at cold temperature for 10 min. The flask was gradually brought to room temperature and stirred for 16 h. The reaction was quenched by pouring into a mixture of diethyl ether and saturated aqueous Rochelle's salt solution (1:1). The mixture containing significant emulsion was stirred very vigorously until the phases separated (ca. 2 h). The phases were partitioned and the aqueous layer was extracted numerous times with EtOAc. The combined organic layers were dried over MgSO4, filtered and concentrated to give (0.15 g, 0.46 mmol) (2-(1-isopropyl-1H-pyrazol-5-yl)-5,6-dihydrobenzo[f]imidazo[1,2-d][1,4]oxazepin-9-yl)methanamine (MS(ESI+) m/z 323.1 (M+H+), calcd. 323.4) which was dissolved in glacial acetic acid (0.8 mL) and water (5 mL). A solution of potassium cyanate (0.114 g, 1.41 mmol) in water was added dropwise. N,N-dimethylformamide (3 mL) was added to help with dissolution. The resulting reaction mixture was stirred at room temperature for 12 h. Subsequently, the reaction was heated at 50° C. for 3 h. The mixture was cooled to room temperature and filtered to provide 0.02 g (10% yield) of 337. MS(ESI+) m/z 367.1 (M+H+), calcd. 367.4. 1H NMR (400 MHz, DMSO) δ 8.53 (s, 5H), 8.33 (d, J=8.2 Hz, 1H), 7.61 (d, J=3.7 Hz, 1H), 7.43 (s, 1H), 7.01 (d, J=8.7 Hz, 1H), 6.91 (s, 1H), 6.63 (s, 1H), 6.38 (s, 1H), 5.62 (s, 2H), 5.42 (s, 7H), 4.47 (s, 3H), 4.17 (d, J=5.8 Hz, 2H), 1.44 (d, J=6.4 Hz, 6H)

Example 338

(2S)-1-(2-(1-isopropyl-1H-1,2,4-triazol-5-yl)-5,6-dihydroimidazo[1,2-d]pyrido[3,4-f][1,4]oxazepin-9-yl)pyrrolidine-2-carboxamide 338

Following the procedures of Example 339, 2-(2-isopropyl-2H-[1,2,4]triazol-3-yl)-4,5-dihydro-6-oxa-1,3a,9-triazabenzo[e]azulen-8-ol from Example 93 and L-prolinamide, were reacted and the crude product subjected to flash chromatography (SiO2, gradient 0 to 8% methanol in DCM) then recrystallisation from methanol to give 338 as a white solid (115 mg, 44%). LCMS: RT=2.48 min, [M+H]+ 409. $^1$H NMR 400 MHz (DMSO-d6) δ: 9.06 (1 H, s), 7.88 (1 H, s), 7.83 (1 H, s), 7.33 (1 H, br), 6.92 (1 H, br), 5.97-5.96 (1 H, m), 5.94 (1 H, s), 4.53-4.45 (4 H, m), 4.30 (1 H, d, J=8.51 Hz), 3.59 (1 H, s), 3.37 (1 H, d, J=9.93 Hz), 2.18 (1 H, m), 1.95 (3 H, m), 1.47 (6 H, dd, J=6.59, 3.43 Hz)

Example 339

1-(2-(1-isopropyl-1H-1,2,4-triazol-5-yl)-5,6-dihydroimidazo[1,2-d]pyrido[3,4-f][1,4]oxazepin-9-yl)piperidine-4-carboxamide 339

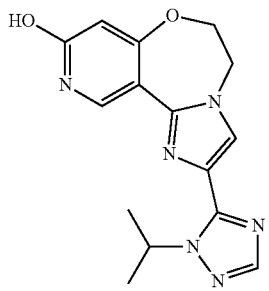 [SMILES: CC(C)n1ncnc1-c1cn2c(n1)-c1cnc(O)cc1OCC2]

2-(2-Isopropyl-2H-[1,2,4]triazol-3-yl)-4,5-dihydro-6-oxa-1,3a,9-triaza-benzo[e]azulen-8-ol from Example 93 was treated with sodium hydride, (1.2 eq.) and the reaction mixture stirred at RT or 40 C for 15 min to 1.25 h before the addition of benzenebis(trifluoromethane) sulfonamide (1.2 eq.). Stirring was continued at RT until complete consumption of pyridone was seen (TLC or LCMS) then piperidine-4-carboxylic acid amide was added (1 to 2.5 eq.) and the reaction mixture heated at 70 to 100 C until no further reaction was seen. The crude products were isolated by removal of solvent in vacuo, precipitation from the reaction mixture by addition of water, addition of water and extraction with ethyl acetate or DCM, or by using an Isolute SCX-2 cartridge and the crude product recrystallised from methanol to give 339 as a white solid (161 mg, 60%). LCMS: RT=2.41 min, [M+H]+ 423. $^1$H NMR 400 MHz (DMSO-d6) δ: 9.10 (1 H, s), 7.88 (1 H, d, J=0.65 Hz), 7.83 (1 H, s), 7.27 (1 H, s), 6.76 (1 H, s), 6.34 (1 H, s), 5.93-5.92 (1 H, m), 4.51-4.49 (4 H, m), 4.31 (2 H, d, J=13.19 Hz), 2.94-2.81 (2 H, m), 2.38-2.35 (1 H, m), 1.73 (2 H, m), 1.53 (2 H, dd, J=12.25, 3.87 Hz), 1.47 (6 H, d, J=6.60 Hz)

Example 340

1-(2-(1-isopropyl-1H-1,2,4-triazol-5-yl)-5,6-dihydroimidazo[1,2-d]pyrido[3,4-f][1,4]oxazepin-9-yl)piperidin-4-ol 340

Following the procedures of Example 339, 2-(2-isopropyl-2H-[1,2,4]triazol-3-yl)-4,5-dihydro-6-oxa-1,3a,9-triaza-benzo[e]azulen-8-ol from Example 93 and 4-hydroxypiperidine, the crude product was recrystallised from methanol to give 340 as a white solid (106 mg, 42%). LCMS: RT=2.48 min, [M+H]+=396. $^1$H NMR 400 MHz (DMSO-d6) δ: 9.09 (1 H, s), 7.88 (1 H, d, J=0.64 Hz), 7.83 (1 H, s), 6.33 (1 H, s), 5.97-5.88 (1 H, m), 4.69 (1 H, d, J=4.26 Hz), 4.49-4.48 (4 H, m), 4.03-3.99 (2 H, m), 3.75-3.67 (1 H, m), 3.14-3.13 (2 H, m), 1.80-1.71 (2 H, m), 1.47 (6 H, d, J=6.60 Hz), 1.34-1.33 (2 H, m)

Example 341

2-(1-isopropyl-1H-1,2,4-triazol-5-yl)-9-morpholino-5,6-dihydroimidazo[1,2-d]pyrido[3,4-f][1,4]oxazepine 341

Following the procedures of Example 339, 2-(2-isopropyl-2H-[1,2,4]triazol-3-yl)-4,5-dihydro-6-oxa-1,3a,9-triaza-benzo[e]azulen-8-ol from Example 93 and morpholine, the crude product was recrystallised from methanol to give 341 as a white solid (107 mg, 44%). LCMS: RT=3.12 min, [M+H]+ 382. $^1$H NMR 400 MHz (DMSO-d) δ: 9.14 (1 H, s), 7.90 (1 H, d, J=0.63 Hz), 7.86 (1 H, s), 6.36 (1 H, s), 5.93-5.92 (1 H, m), 4.57-4.48 (4 H, m), 3.70 (4 H, t, J=4.74 Hz), 3.50 (4 H, t, J=4.74 Hz), 1.49 (6 H, d, J=6.60 Hz)

Example 342

N-isopropyl-2-(4-(2-(1-isopropyl-1H-1,2,4-triazol-5-yl)-5,6-dihydroimidazo[1,2-d]pyrido[3,4-f][1,4]oxazepin-9-yl)piperazin-1-yl)acetamide 342

Following the procedures of Example 331, 342 was prepared. MS: (ESI+)=480.2

Example 343

1-(2-(1-isopropyl-1H-1,2,4-triazol-5-yl)-5,6-dihydroimidazo[1,2-d]pyrido[3,2-f][1,4]oxazepin-9-yl)azetidine-3-carboxamide 343

A solution of 9-chloro-5,6-dihydroimidazo[1,2-d]pyrido[3,2-f][1,4]oxazepine-2-carboxamide (45.0 mg, 0.136 mmol), azetidine-3-carboxylic acid (30.0 mg, 0.297 mmol) and Triethylamine (0.300 mL, 2.15 mmol) in Isopropyl alcohol (1.00 mL, 13.1 mmol) was heated at 150 C for 2 days. The reaction was diluted with water then washed with EtOAc. The aqueous layer was acidified then extracted with EtOAc. The organic layer was dried Na2SO4, concentrated to give carboxylic acid intermediate, 1-(2-(1-isopropyl-1H-1,2,4-triazol-5-yl)-5,6-dihydroimidazo[1,2-d]pyrido[3,2-f][1,4]oxazepin-9-yl)azetidine-3-carboxylic acid (MS: (ESI+) 396.1) which was dissolved (0.060 g, 0.00015 mol) in N,N-Dimethylformamide (2.37 mL, 0.0306 mol) and treated sequentially with N,N-Diisopropylethylamine (0.158 mL, 0.000910 mol) Ammonium chloride (0.0325 g, 0.607 mmol) then N,N,N',N'-Tetramethyl-O-(7-azabenzotriazol-1-yl)uronium Hexafluorophosphate (HATU, 0.0692 g, 0.000182 mol). Stirred at RT 2 hr. Add sat. sodium bicarbonate, extract with ethyl acetate. Dry organics over sodium sulfate and concentrated to give 343, analyzed by rHPLC. MS: (ESI+)=395.1. 1H NMR (400 MHz, DMSO) δ 8.50 (d, J=8.5 Hz, 1H), 7.88 (s, 1H), 7.80 (s, 1H), 7.50 (s, 1H), 7.04 (s, 1H), 6.28 (d, J=8.5 Hz, 1H), 5.96-5.76 (m, 1H), 4.48 (d, J=10.2 Hz, 4H), 4.09 (t, J=8.3 Hz, 2H), 3.98 (t, J=6.9 Hz, 2H), 3.44 (dd, J=14.5, 7.4 Hz, 1H), 1.46 (d, J=6.5 Hz, 6H).

Examples 344 and 345

(2S)-2-(2-(1-isopropyl-1H-1,2,4-triazol-5-yl)-5,6-dihydrobenzo[f]imidazo[1,2-d][1,4]oxazepin-9-yl)propanamide 344 and (2R)-2-(2-(1-isopropyl-1H-1,2,4-triazol-5-yl)-5,6-dihydrobenzo[f]imidazo[1,2-d][1,4]oxazepin-9-yl)propanamide 345

A degassed mixture of 187 mg (0.500 mmol) of 9-bromo-2-(1-isopropyl-1H-1,2,4-triazol-5-yl)-5,6-dihydrobenzo[f]imidazo[1,2-d][1,4]oxazepine 194, 320.6 mg (2.000 mmol) of (1-trimethylsilyloxy)-1-methoxyprop-1-ene, 19.4 mg (0.025 mmol) of bromo(tri-t-butylphosphine)palladium dimer and 154.5 mg (0.500 mmol) of tributyltin fluoride in 4.0 ml of 1,4-dioxane was heated for 18 hours at 105° C. After a work up a mixture of saturated and unsaturated esters was separated from a product of debromination by column chromatography eluting with 1-4% gradient of methanol in dichloromethane. 98 mg of the above mixture and 100 mg of 10% Pd-Carbon in 12 ml of ethanol was hydrogenated at 1 atm for 3 hours. The mixture was filtered, the filtrate concentrated in vacuum giving 80 mg of pure methyl 2-(2-(1-isopropyl-1H-1,2,4-triazol-5-yl)-5,6-dihydrobenzo[f]imidazo[1,2-d][1,4]oxazepin-9-yl)propanoate. M/z 382.1, calc. 381.18

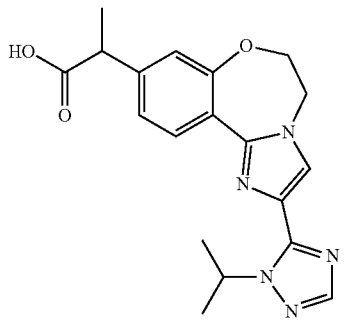 [SMILES: CC(C(=O)O)c1ccc2c(c1)OCCn1cc(-c3ncnn3C(C)C)nc1-2]

Methyl 2-(2-(1-isopropyl-1H-1,2,4-triazol-5-yl)-5,6-dihydrobenzo[f]imidazo[1,2-d][1,4]oxazepin-9-yl)propanoate and lithium hydroxide were reacted to give 2-(2-(1-isopropyl-1H-1,2,4-triazol-5-yl)-5,6-dihydrobenzo[f]imidazo[1,2-d][1,4]oxazepin-9-yl)propanoic acid. M/z 368.2, calc. 367.16, which was reacted with ammonium chloride and HATU following the procedure of Example 215 to give a racemic mixture of enantiomers 344 and 345. M/z 367.1, calc. 366.18. 1H NMR (400 MHz, DMSO) δ 8.32 (d, J=8.3, 1H), 7.90 (s, 2H), 7.41 (s, 1H), 7.10 (d, J=8.5, 1H), 7.00 (s, 1H), 6.87 (s, 1H), 5.88 (dt, J=12.5, 6.2, 1H), 4.50 (d, J=4.7, 4H), 3.57 (q, J=6.9, 1H), 1.48 (d, J=6.5, 6H), 1.31 (d, J=6.9, 3H)

Example 348

2-(1-isopropyl-3-methyl-1H-1,2,4-triazol-5-yl)-9-(oxetan-3-yl)-5,6-dihydrobenzo[f]imidazo[1,2-d][1,4]oxazepine 348

Generation of boronic acid: A solution of 2-(2-Isopropyl-5-methyl-2H-[1,2,4]triazol-3-yl)-8-(4,4,5,5-tetramethyl-[1,3,2]dioxaborolan-2-yl)-4,5-dihydro-6-oxa-1,3a-diaza-benzo[e]azulene (Example 57, 0.495 g, 0.00114 mol) and Sodium periodate (0.730 g, 0.00341 mol) in a 4:1 mixture of Tetrahydrofuran (7.38 mL) and Water (1.84 m) was stirred at room temperature for 30 minutes. Aqueous Hydrogen chloride (0.000796 mol, 1N, 0.8 mL) was added and the reaction was stirred at room temperature overnight. The mixture was diluted with water and extracted 3 times with methylene chloride. The organic layers were combined, dried with MgSO4 and concentrated. The crude material was carried forward without further purification.

To a CEM microwave vial was added the crude boronic acid (0.154 g, 0.437 mmol), Nickel(II)iodide (0.0186 g, 0.0596 mmol), trans-2-Aminocyclohexanol hydrochloride (0.00904 g, 0.0596 mmol) and Sodium hexamethyldisilazane (0.477 mmol, 2M in THF, 0.24 mL), in degassed Isopropyl alcohol (0.91 mL) and Dimethyl sulfoxide (1.5 mL). The mixture was continuously purged with nitrogen. 3-iodooxetane (0.0731 g, 0.398 mmol) in Isopropyl alcohol (0.21 mL) was added and the vial was capped immediately. The reaction was heated to 85° C. in the microwave for 25 minutes. About 50% conversion to product was observed by LC/MS—protodeboronation was also observed. The mixture was diluted with methylene chloride and filtered through celite. Water was added and the mixture was extracted 3 times with methylene chloride. The crude was loaded as a solid onto silica gel and purified by flash chromatography (50% EtOAc in hexanes), and re-purified by reverse-phase HPLC to give 25.8 mg of 348 as a white solid. MS(ESI+) 366.1. 1H NMR (400 MHz, DMSO) δ 8.40 (d, J=8.2 Hz, 1H), 7.89 (s, 1H), 7.22 (d, J=8.3 Hz, 1H), 7.06 (s, 1H), 5.93-5.73 (m, 1H), 4.94 (t, J=7.0 Hz, 2H), 4.63 (t, J=6.2 Hz, 2H), 4.55-4.46 (m, 4H), 4.33-4.18 (m, 1H), 2.25 (s, 3H), 1.46 (d, J=6.4 Hz, 6H)

Example 351

2-(2-(1-isopropyl-1H-1,2,4-triazol-5-yl)-5,6-dihydrobenzo[f]imidazo[1,2-d][1,4]oxazepin-9-yl)acetamide 351

Following the procedures of Example 215, 2-(2-(1-isopropyl-1H-1,2,4-triazol-5-yl)-5,6-dihydrobenzo[f]imidazo[1,2-d][1,4]oxazepin-9-yl)acetic acid, ammonium chloride, and HATU were reacted to give 351. M/z 353.1, calc. 352.16. 1H NMR (400 MHz, DMSO) δ 8.32 (d, J=8.3, 1H), 7.91 (s, 2H), 7.48 (s, 1H), 7.04 (d, J=8.2, 1H), 6.97 (s, 1H), 6.92 (s, 1H), 5.95-5.81 (m, 1H), 4.50 (d, J=5.8, 4H), 3.38 (s, 2H), 1.48 (d, J=6.5, 6H)

Example 352

N-hydroxy-2-(2-(1-isopropyl-1H-1,2,4-triazol-5-yl)-5,6-dihydrobenzo[f]imidazo[1,2-d][1,4]oxazepin-9-yl)acetamide 352

Following the procedures of Example 316, 2-(2-(1-isopropyl-1H-1,2,4-triazol-5-yl)-5,6-dihydrobenzo[f]imidazo[1,2-d][1,4]oxazepin-9-yl)acetic acid and hydroxylamine were reacted to give 352. M/z 369.1, calc. 368.16. 1H NMR (400 MHz, DMSO) δ 10.69 (s, 1H), 8.88 (s, 1H), 8.32 (d, J=8.2, 1H), 7.92 (d, J=2.9, 2H), 7.04 (d, J=8.2, 1H), 6.97 (s, 1H), 5.95-5.81 (m, 1H), 4.50 (d, J=5.7, 4H), 3.29 (s, 2H), 1.48 (d, J=6.6, 6H)

Example 353

(9-(1-(2-hydroxy-2-methylpropyl)-1H-pyrazol-4-yl)-5,6-dihydrobenzo[f]imidazo[1,2-d][1,4]oxazepin-2-yl)(S-dioxothiomorpholino)methanone 353

Following the procedures in the Examples herein, amide coupling and Suzuki coupling gave 353. MS(ESI+): 486.1

Example 354

1-((2-(1-(2,4-difluorophenyl)-3-methyl-1H-1,2,4-triazol-5-yl)-5,6-dihydrobenzo[f]imidazo[1,2-d][1,4]oxazepin-9-yl)methyl)urea 354

C-{2-[2-(2,4-Difluoro-phenyl)-5-methyl-2H-[1,2,4]triazol-3-yl]-4,5-dihydro-6-oxa-1,3a-diaza-benzo[e]azulen-8-yl}-methylamine in acetic acid and water was reacted with potassium cyanate in water to give 354. MS(ESI+) 452.1. 1H NMR (400 MHz, DMSO) δ 7.89 (s, 1H), 7.68 (td, J=8.7, 6.2 Hz, 1H), 7.62-7.54 (m, 2H), 7.32-7.25 (m, 1H), 6.87-6.80 (m, 2H), 6.44 (t, J=6.1 Hz, 1H), 5.57 (br, 2H), 4.49-4.38 (m, 4H), 4.12 (d, J=6.1 Hz, 2H), 2.35 (s, 3H)

Example 355

(2-(1-(2,4-difluorophenyl)-3-methyl-1H-1,2,4-triazol-5-yl)-5,6-dihydrobenzo[f]imidazo[1,2-d][1,4]oxazepin-9-yl)methanamine 355

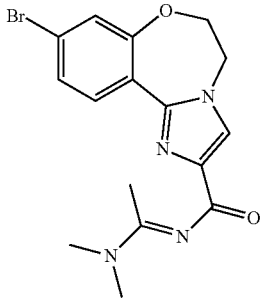 [SMILES: C/C(=N\C(=O)c1cn2c(n1)-c1ccc(Br)cc1OCC2)N(C)C]

To a solution of 8-Bromo-4,5-dihydro-6-oxa-1,3a-diaza-benzo[e]azulene-2-carboxylic acid amide (5.00 g, 0.0162 mol) in Toluene (85 mL) was added Dimethylacetamide-dimethylacetal (7.23 mL, 0.0487 mol). The reaction was stirred at 95° C. for 4 h. The toluene was removed in vacuo and the crude 8-Bromo-4,5-dihydro-6-oxa-1,3a-diaza-benzo[e]azulene-2-carboxylic acid [1-dimethylamino-eth-(E)-ylidene]-amide was carried forward without further purification. MS(ESI+) 377.1/379.1

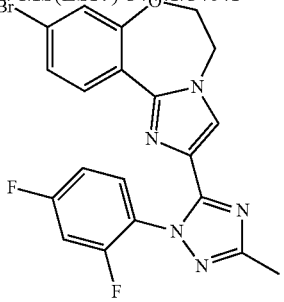

8-Bromo-4,5-dihydro-6-oxa-1,3a-diaza-benzo[e]azulene-2-carboxylic acid [1-dimethylamino-eth-(E)-ylidene]-amide (0.0162 mol) was dissolved in Acetic acid (50 mL). 2,4-Difluorophenylhydrazine hydrochloride (3.52 g, 0.0195 mol) was added and the reaction was stirred at 95° C. overnight. The acetic acid was removed in vacuo. The crude was loaded as a solid onto silica gel and purified by flash chromatography (4-10% methanol in methylene chloride) to afford 3.662 g 8-Bromo-2-[2-(2,4-difluoro-phenyl)-5-methyl-2H-[1,2,4]triazol-3-yl]-4,5-dihydro-6-oxa-1,3a-diaza-benzo[e]azulene as an orange solid. MS(ESI+) 458.0/460.0

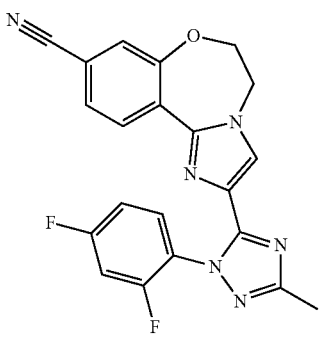 [SMILES: Cc1nc(-c2cn3c(n2)-c2ccc(C#N)cc2OCC3)n(-c2ccc(F)cc2F)n1]

8-Bromo-2-[2-(2,4-difluoro-phenyl)-5-methyl-2H-[1,2,4]triazol-3-yl]-4,5-dihydro-6-oxa-1,3a-diaza-benzo[e]azulene was reacted with zinc cyanide, and Tetrakis(triphenylphosphine)palladium(0) in DMF under microwave irradiation at 60 W for 30 minutes (Tmax=175° C.) to give 2-[2-(2,4-difluoro-phenyl)-5-methyl-2H-[1,2,4]triazol-3-yl]-4,5-dihydro-6-oxa-1,3a-diaza-benzo[e]azulene-8-carbonitrile. MS(ESI+) 405.1

To 2-[2-(2,4-Difluoro-phenyl)-5-methyl-2H-[1,2,4]triazol-3-yl]-4,5-dihydro-6-oxa-1,3a-diaza-benzo[e]azulene-8-carbonitrile in tetrahydrofuran was added Lithium tetrahydroaluminate (1M in THF), dropwise at 0° C. The reaction was stirred for 2 hours and quenched with saturated Na2SO4 until H2 evolution ceased. MgSO4 was added and the whole was diluted with copious amounts of methylene chloride, filtered over celite, and concentrated in vacuo. The crude was purified by flash chromatography (1-15% MeOH in DCM spiked with Et3N) to afford to give 355. MS(ESI+) 409.1. 1H NMR (400 MHz, DMSO) δ 7.89 (s, 1H), 7.68 (td, J=8.7, 6.2 Hz, 1H), 7.64-7.52 (m, 2H), 7.32-7.25 (m, 1H), 6.95 (s, 1H), 6.91 (dd, J=8.2, 1.2 Hz, 1H), 4.48-4.38 (m, 4H), 3.66 (s, 2H), 2.35 (s, 3H).

Example 356

9-(1-(2-(dimethylamino)-2-oxoethyl)piperidin-4-yl)-N-(2-hydroxyethyl)-N-isopropyl-5,6-dihydrobenzo[f]imidazo[1,2-d][1,4]oxazepine-2-carboxamide 356

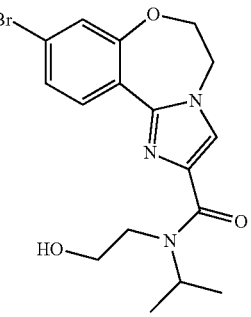

Step 1

A sealed flask containing 8-bromo-2-iodo-4,5-dihydro-6-oxa-1,3a-diaza-benzo[e]azulene (500 mg, 1.28 mmol), palladium (II) chloride (6 mg, 0.03 mmol) and 4,5-bis(diphenylphosphino)-9,9-dimethylxanthene (15 mg, 0.03 mmol) was flushed with CO. 2-Isopropylamino ethanol (172 mg, 1.67 mmol), and TEA (0.53 mL, 3.8 mmol) were added as a solution in toluene (2.5 mL) and the reaction mixture heated at 100° C. for 3.5 h. The reaction mixture was washed with water and extracted with ethyl acetate (2×30 mL). The combined organic extracts were washed with brine, dried (Na2SO4) and concentrated in vacuo. The resultant residue was subjected to flash chromatography (SiO2, gradient 2-3% methanol in DCM) to yield 8-Bromo-4,5-dihydro-6-oxa-1,3a-diaza-benzo[e]azulene-2-carboxylic acid (2-hydroxy-ethyl)-isopropyl-amide (123 mg, 23%). LCMS: RT=3.11 min, [M+H]+=394/396

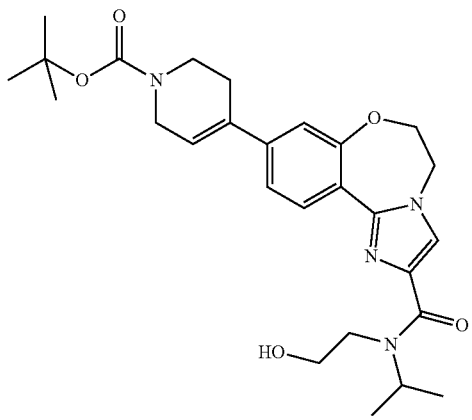 [SMILES: CC(C)N(CCO)C(=O)c1cn2c(n1)-c1ccc(C3=CCN(C(=O)OC(C)(C)C)CC3)cc1OCC2]

Step 2

8-Bromo-4,5-dihydro-6-oxa-1,3a-diaza-benzo[e]azulene-2-carboxylic acid (2-hydroxy-ethyl)-isopropyl-amide (114 mg, 0.28 mmol), 3,6-dihydro-2H-pyridine-1-N-Boc-4-boronic acid pinacol ester (129 mg, 0.62 mmol), potassium carbonate (96 mg, 0.69 mmol) and PdCl2dppf.DCM (20 mg, 0.02 mmol) were suspended in DMF (1.5 mL), and the reaction mixture purged with argon. The reaction mixture was heated at 100° C. for 3 h. The reaction mixture was washed with water, extracted with ethyl acetate (2×15 mL) and the combined organic extracts washed with brine, dried (Na2SO4) and concentrated in vacuo. The resultant residue was subjected to flash chromatography (SiO2, gradient 0-2% MeOH in DCM) to yield 4-{2-[(2-Hydroxy-ethyl)-isopropyl-carbamoyl]-4,5-dihydro-6-oxa-1,3a-diaza-benzo[e]azulen-8-yl}-3,6-dihydro-2H-pyridine-1-carboxylic acid tert-butyl ester (115 mg, 80%). LCMS: RT=3.48 min, [M+H]+=497

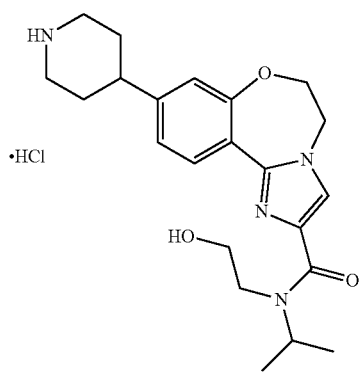 [SMILES: Cl ; CC(C)N(CCO)C(=O)c1cn2c(n1)-c1ccc(C3CCNCC3)cc1OCC2]

Step 3: 8-Piperidin-4-yl-4,5-dihydro-6-oxa-1,3a-diaza-benzo[e]azulene-2-carboxylic acid (2-hydroxy-ethyl)-isopropyl-amide hydrochloride To a solution of 4-{2-[(2-hydroxy-ethyl)-isopropyl-carbamoyl]-4,5-dihydro-6-oxa-1,3a-diaza-benzo[e]azulen-8-yl}-3,6-dihydro-2H-pyridine-1-carboxylic acid tert-butyl ester (112 mg, 0.23 mmol) in IMS (3 mL) was added hydrochloric acid (2 mL, 2M, 4.0 mmol) and palladium on carbon (20 mg, 10% by wt) added. The reaction mixture was stirred under an atmosphere of hydrogen at 50° C. for 4.5 h. The reaction mixture was filtered and the solids washed with IMS (10 mL). The filtrate was concentrated in vacuo and azeotroped with acetonitrile to yield 8-piperidin-4-yl-4,5-dihydro-6-oxa-1,3a-diaza-benzo[e]azulene-2-carboxylic acid (2-hydroxy-ethyl)-isopropyl-amide hydrochloride as a thick oil (110 mg). LCMS: RT=0.32 min, [M+H]+=399

To a stirred mixture of 8-piperidin-4-yl-4,5-dihydro-6-oxa-1,3a-diaza-benzo[e]azulene-2-carboxylic acid (2-hydroxy-ethyl)-isopropyl-amide hydrochloride (127 mg, 0.23 mmol) in DMF (2 mL) was added potassium carbonate (127 mg, 0.92 mmol), N,N-dimethyl-2-chloroacetamide (36 mg, 0.3 mmol) and KI (catalytic) and stirring continued at RT for 72 h before concentrating in vacuo. The resultant residue was diluted with ethyl acetate and washed with water followed by brine, then dried (Na2SO4), filtered and concentrated in vacuo. The resultant residue was passed down an Isolute SCX-2 cartridge eluting with DCM/methanol then 2M NH3 in methanol. Basic fractions were combined and concentrated in vacuo, the residue subjected to RPHPLC (C18 column, gradient 5 to 95% CH3CN in water+0.1% HCO2H) to give 356 as a colourless glass (22 mg, 20%). LCMS: RT=1.90 min, [M+H]+=484 1H NMR 400 MHz (CDCl3) δ: 8.42 (2 H, s), 8.20 (1H, br, s), 8.34 (1 H, d, J=8.32 Hz), 7.81 (1 H, s), 7.04 (1 H, dd, J=8.40, 1.77 Hz), 6.90 (1 H, d, J=1.69 Hz), 4.63 (2 H, m), 4.45-4.44 (4 H, m), 3.38 (3 H, m), 3.32 (2 H, m), 3.16 (2 H, d, J=11.21 Hz), 3.11 (3 H, s), 2.99 (3 H, s), 2.56 (1 H, m), 2.48 (2 H, m), 1.87 (4 H, m), 1.42 (6 H, d, J=6.46 Hz)

Example 357

2-(1-isopropyl-1H-1,2,4-triazol-5-yl)-9-(1-isopropylpiperidin-4-yl)-5,6-dihydrobenzo[f]imidazo[1,2-d][1,4]oxazepine 357

A suspension of 2-(2-isopropyl-2H-[1,2,4]triazol-3-yl)-8-piperidin-4-yl-4,5-dihydro-6-oxa-1,3a-diaza-benzo[e]azulene trifluoro acetate (250 mg, 0.51 mmol) in DCE (5 mL) was added acetone (0.06 mL, 0.77 mmol) and 4 Å molecular sieves was stirred under an atmosphere of argon for 10 min before adding sodium triacetoxy borohydride (216 mg, 1.02 mmol) and stirring for 18 h at RT. Further acetone (0.06 mL) and sodium triacetoxyborohydride (216 mg) were added and stirring continued for a further 24 h. The reaction mixture was diluted with DCM and saturated aqueous sodium hydrogen carbonate and the organic layer washed with water followed by brine and then dried (MgSO4), filtered and concentrated in vacuo. The resultant solid was subjected to RPHPLC (gradient 20 to 70% methanol in water+0.1% HCO2H) to give 357 as a yellow solid (17 mg, 8%). LCMS: RT=2.81 min, [M+H]+=421. 1H NMR 400 MHz (DMSO-d) δ: 8.37-8.26 (1 H, m), 7.90-7.89 (2 H, m), 7.05 (1 H, dd, J=8.33, 1.81 Hz), 6.89 (1 H, d, J=1.73 Hz), 5.89-5.88 (1 H, m), 4.49-4.48 (4 H, m), 2.91 (2 H, d, J=10.95 Hz), 2.76-2.75 (1 H, m), 2.46 (1 H, s), 2.26 (2 H, t, J=11.38 Hz), 1.78 (2 H, d, J=12.43 Hz), 1.64 (2 H, td, J=12.20, 3.68 Hz), 1.48 (6 H, d, J=6.60 Hz), 1.01 (6 H, d, J=6.57 Hz)

Example 358

2-(4-(2-(1-isopropyl-3-methyl-1H-1,2,4-triazol-5-yl)-5,6-dihydrobenzo[f]imidazo[1,2-d][1,4]oxazepin-9-yl)piperidin-1-yl)-2-methylpropan-1-ol 358

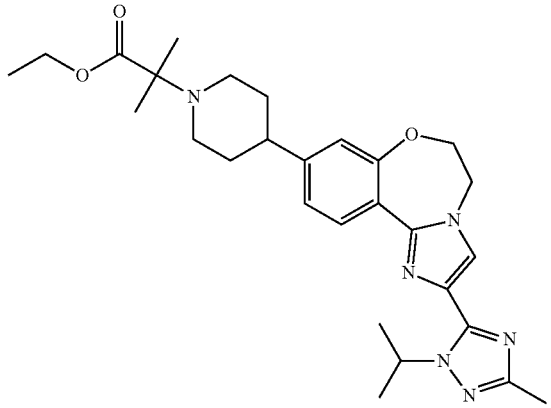 [SMILES: CCOC(=O)C(C)(C)N1CCC(c2ccc3c(c2)OCCn2cc(-c4nc(C)nn4C(C)C)nc2-3)CC1]

A mixture of 2-(2-isopropyl-5-methyl-2H-[1,2,4]triazol-3-yl)-8-piperidin-4-yl-4,5-dihydro-6-oxa-1,3a-diaza-benzo[e]azulene hydrochloride (100 mg, 0.255 mmol), 2-bromo-2-methyl-propionic acid ethyl ester (45 uL, 0.31 mmol), cesium carbonate (187 mg, 0.57 mmol) and DMF (0.5 mL) was heated at 70° C. for 3 h the then stirred at RT for 18 h then heated again at 70° C. for 4 h before concentrating in vacuo. The resultant residue was subjected to flash chromatography (SiO2, gradient 0 to 5% methanol in DCM) to give 2-{4-[2-(2-Isopropyl-5-methyl-2H-[1,2,4]triazol-3-yl)-4,5-dihydro-6-oxa-1,3a-diaza-benzo[e]azulen-8-yl]-piperidin-1-yl}-2-methyl-propionic acid ethyl ester (47 mg, 36%). LCMS RT=2.24, [M+H]+=507.

A solution of 2-{4-[2-(2-Isopropyl-5-methyl-2H-[1,2,4]triazol-3-yl)-4,5-dihydro-6-oxa-1,3a-diaza-benzo[e]azulen-8-yl]-piperidin-1-yl}-2-methyl-propionic acid ethyl ester (47 mg, 0.092 mmol) in anhydrous THF (3 mL) was cooled to 0° C. and treated with lithium aluminium hydride (1M solution in THF, 0.3 mL, 0.3 mmol), the mixture stirred and allowed to warm to RT before quenching by the addition of saturated aqueous sodium hydrogen carbonate. The resultant mixture was extracted twice with ethyl acetate, the combined organic extracts dried (Na2SO4), filtered and concentrated in vacuo. The resultant residue was subjected to RPHPLC (C18 column, gradient 0 to 60% methanol in water+0.1% formic acid) to give 358 as a white solid (20 mg, 47%). LCMS: RT=2.74 min, [M+H]+=465. $^1$H NMR 400 MHz (DMSO-d) δ: 8.33 (1 H, d, J=8.28 Hz), 8.26 (1 H, s), 7.87 (1 H, s), 7.05 (1 H, dd, J=8.35, 1.77 Hz), 6.90 (1 H, d, J=1.71 Hz), 5.82-5.81 (1 H, m), 4.49 (4 H, m), 3.38 (2 H, s), 3.21 (2 H, d, J=11.33 Hz), 2.58 (1 H, t, J=11.87 Hz), 2.47 (2 H, d, J=11.47 Hz), 2.26 (3 H, s), 1.85 (2 H, d, J=12.54 Hz), 1.72 (2 H, m), 1.46 (6 H, d, J=6.60 Hz), 1.07 (6 H, s)

Example 359

2-(4-(2-(1-isopropyl-1H-1,2,4-triazol-5-yl)-5,6-dihydrobenzo[f]imidazo[1,2-d][1,4]oxazepin-9-yl)piperidin-1-yl)-2-methylpropan-1-ol 359

Following the procedures of Example 358, 2-(2-isopropyl-2H-[1,2,4]triazol-3-yl)-8-piperidin-4-yl-4,5-dihydro-6-oxa-1,3a-diaza-benzo[e]azulene trifluoro acetate (103 mg) was converted to 359, a white solid (6.6 mg, 2% overall yield). LCMS: RT=2.73 min, [M+H]+=451. $^1$H NMR 400 MHz (DMSO-d) δ: 8.33 (1 H, d, J=8.28 Hz), 7.91 (2 H, d, J=2.06 Hz), 7.06 (1 H, dd, J=8.35, 1.76 Hz), 6.90 (1 H, d, J=1.71 Hz), 5.90 (1 H, t, J=6.60 Hz), 4.50 (4 H, dd, J=11.70, 5.85 Hz), 3.34 (2 H, br, m), 3.13 (2 H, d, J=11.26 Hz), 2.55 (1 H, m), 2.35 (2 H, t, J=11.38 Hz), 1.81 (2 H, d, J=12.50 Hz), 1.64 (2 H, d, J=12.44 Hz), 1.49 (6 H, d, J=6.60 Hz), 1.02 (6 H, s)

Example 360

4-(2-(1-isopropyl-1H-1,2,4-triazol-5-yl)-5,6-dihydrobenzo[f]imidazo[1,2-d][1,4]oxazepin-9-yl)pyrazolidine-3,5-dione 360

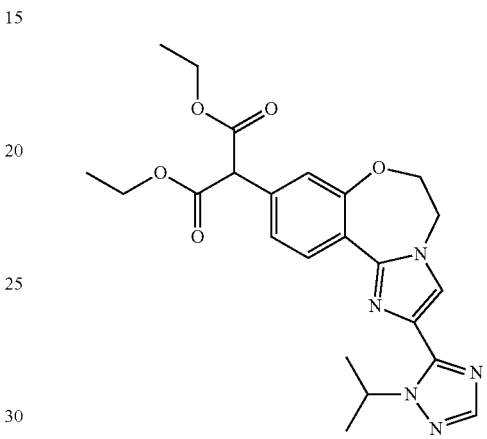

A mixture of 9-bromo-2-(1-isopropyl-1H-1,2,4-triazol-5-yl)-5,6-dihydrobenzo[f]imidazo[1,2-d][1,4]oxazepine 194 (1410 mg (3.77 mmol), diethyl malonate (2.00 mL (13.2 mmol), palladium (II) acetate (42.3 mg, 0.188 mmol), 2-dicyclohexylphosphino-2'-(N,N-dimethylamino)biphenyl (148 mg, 0.377 mmol) and potassium phosphate (2.80 g, 13.2 mmol) in 6.0 ml of 1,4-Dioxane was degassed and heated for 24 hours at 100° C. The mixture was concentrated in vacuum and the residue purified on 24 g silica column eluting with 1% of MeOH in EtOAc to give diethyl 2-(2-(1-isopropyl-1H-1,2,4-triazol-5-yl)-5,6-dihydrobenzo[f]imidazo[1,2-d][1,4]oxazepin-9-yl)malonate. Yield 974 mg. M/z 454.3, calc. 453.20

A mixture of 181 mg (0.40 mmol) of diethyl 2-(2-(1-isopropyl-1H-1,2,4-triazol-5-yl)-5,6-dihydrobenzo[f]imidazo[1,2-d][1,4]oxazepin-9-yl)malonate and 0.314 mL (10.0 mmol) of hydrazine in 4.0 ml of Ethanol was heated at 75° C. for 18 hours. The mixture was concentrated, the residue triturated with acetic acid. A precipitate was filtered off, washed with acetic acid, ethyl ether and recrystallized from ethyl ether/ethanol mixture to give 360. Yield 59 mg (37.5%). M/z 394.1, calc. 393.15. 1H NMR (400 MHz, DMSO) δ 10.20 (s, 2H), 8.29 (d, J=8.6, 1H), 7.89 (d, J=12.9, 2H), 7.70 (d, J=8.5, 1H), 7.63 (s, 1H), 5.93 (dt, J=13.1, 6.7, 1H), 4.48 (d, J=7.2, 4H), 1.49 (d, J=6.6, 6H)

Example 361

2-(1-isopropyl-1H-1,2,4-triazol-5-yl)-9-(1-(2,2,2-trifluoroethyl)piperidin-4-yl)-5,6-dihydrobenzo[f]imidazo[1,2-d][1,4]oxazepine 361

A suspension of 2-(2-isopropyl-2H-[1,2,4]triazol-3-yl)-8-piperidin-4-yl-4,5-dihydro-6-oxa-1,3a-diaza-benzo[e]azulene trifluoro acetate (250 mg, 0.51 mmol) in THF (5 mL)

was treated with TEA and the mixture flushed with argon. 2,2,2-trifluoroethyl trifluoromethane sulfonate (0.15 mL, 1.02 mmol) was added and the mixture stirred at RT for 72 h. The reaction mixture was partitioned between DCM and water, the organic layer washed with saturated aqueous sodium hydrogen carbonate followed by brine and then dried (MgSO4), filtered and concentrated in vacuo. The resultant residue was dissolved in 1.25 M HCl in methanol then concentrated in vacuo to give a solid which was triturated in IPA then diethyl ether. The resultant solid was subjected to RPHPLC (C18 column, gradient 10 to 98% methanol in water+0.1% HCO2H) to give 361 as a white solid (49 mg, 23%). LCMS: RT=4.59 min, [M+H]+=461. 1H NMR 400 MHz (DMSO-d6) δ: 8.33 (1 H, d, J=8.29 Hz), 7.91-7.91 (2 H, m), 7.08 (1 H, dd, J=8.36, 1.79 Hz), 6.92 (1 H, m), 5.91-5.90 (1 H, m), 4.51 (4 H, q, J=5.90 Hz), 3.21 (2 H, q, J=10.30 Hz), 3.03 (2 H, d, J=11.25 Hz), 2.45 (3 H, m), 1.76 (2 H, m), 1.69-1.67 (2 H, m), 1.49 (6 H, d, J=6.60 Hz)

Example 363

1-((2-(1-(2,4-difluorophenyl)-3-methyl-1H-1,2,4-triazol-5-yl)-5,6-dihydrobenzo[f]imidazo[1,2-d][1,4]oxazepin-9-yl)methylamino)-2-methylpropan-2-ol 363

To a slurry of C-{2-[2-(2,4-Difluoro-phenyl)-5-methyl-2H-[1,2,4]triazol-3-yl]-4,5-dihydro-6-oxa-1,3a-diaza-benzo[e]azulen-8-yl}-methylamine (0.150 g, 0.000367 mol) and Cesium Carbonate (0.0335 g, 0.000103 mol) in Methanol (0.5 mL) was added Isobutylene Oxide (0.0359 mL, 0.000404 mol). The flask was sealed and heated to 70° C. for 2 hours.

The mixture was diluted with diethyl ether and water was added. The mixture was extracted 3 times with diethyl ether. The organic phases were combined, dried with MgSO4 and concentrated to give 11.2 mg of 363 as a white solid (6.4% yield). MS(ESI+) 481.2. 1H NMR (400 MHz, DMSO) δ 7.89 (s, 1H), 7.68 (td, J=8.6, 6.0 Hz, 1H), 7.63-7.51 (m, 2H), 7.29 (td, J=8.2, 1.5 Hz, 1H), 6.94 (s, 1H), 6.90 (dd, J=8.3, 1.3 Hz, 1H), 4.47-4.38 (m, 4H), 4.20 (s, 1H), 3.67 (s, 2H), 2.35 (s, 3H), 2.33 (s, 2H), 1.08 (s, 6H)

Example 364

2-(1-isopropyl-1H-1,2,4-triazol-5-yl)-5,6-dihydroimidazo[1,2-d]pyrido[3,4-f][1,4]oxazepine 364

A solution of 9-chloro-2-(1-isopropyl-1H-1,2,4-triazol-5-yl)-5,6-dihydroimidazo[1,2-d]pyrido[3,4-f][1,4]oxazepine 317 (35.0 mg, 0.106 mmol) in Methanol (1.91 mL, 47.1 mmol) was added Triethylamine (0.0147 mL, 0.106 mmol) and Palladium (0.0113 g, 0.0106 mmol). The reaction was stirred overnight at room temperature under H2 atm. The reaction was filtered thru celite. The solute was concentrated then diluted with EtOAc, wash with H2O. The organic layer was dried Na2SO4, concentrated. The crude product was purified by isco column to give 364. MS: (ESI+)=297.1. 1H NMR (400 MHz, DMSO) δ 9.49 (s, 1H), 8.36 (d, J=5.7 Hz, 1H), 7.99 (s, 1H), 7.92 (s, 1H), 7.05 (d, J=5.7 Hz, 1H), 5.90 (dt, J=13.2, 6.5 Hz, 1H), 4.59 (dt, J=26.2, 13.1 Hz, 4H), 1.50 (d, J=6.6 Hz, 6H)

Example 365

(2R)-1-(2-(1-isopropyl-1H-1,2,4-triazol-5-yl)-5,6-dihydroimidazo[1,2-d]pyrido[3,4-f][1,4]oxazepin-9-yl)pyrrolidine-2-carboxamide 365

A solution of 9-chloro-2-(1-isopropyl-1H-1,2,4-triazol-5-yl)-5,6-dihydroimidazo[1,2-d]pyrido[3,4-f][1,4]oxazepine 317 (25.0 mg, 0.0756 mmol), R-Prolinamide (0.0570 g, 0.499 mmol) and Triethylamine (0.125 mL, 0.897 mmol) in N-Methylpyrrolidinone (1.36 mL, 14.1 mmol) was heated at 150 C for 2d. The reaction was filtered thru celite then rinsed with EtOAc. The filtrate was washed water, brine. The organic layer was dried Na2SO4, concentrated to give 365, analyzed by rHPLC. MS: (ESI+) 409.2

Example 366

2-(1-isopropyl-1H-1,2,4-triazol-5-yl)-9-(pyrrolidin-1-yl)-5,6-dihydroimidazo[1,2-d]pyrido[3,4-f][1,4]oxazepine 366

Following the procedures for Example 365, 366 was prepared. MS: (ESI+)=366.2. 1H NMR (400 MHz, DMSO) δ 9.08 (s, 1H), 7.88 (s, 1H), 7.82 (s, 1H), 5.94 (dd, J=13.6, 6.9 Hz, 1H), 4.61-4.32 (m, 4H), 3.40 (d, J=6.3 Hz, 4H), 1.95 (t, J=6.5 Hz, 4H), 1.48 (d, J=6.6 Hz, 6H)

Example 367

2-(1-isopropyl-1H-1,2,4-triazol-5-yl)-N-methyl-5,6-dihydroimidazo[1,2-d]pyrido[3,2-f][1,4]oxazepin-9-amine 367

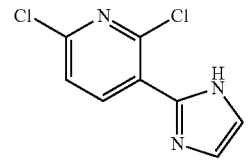 [SMILES: Clc1ccc(-c2ncc[nH]2)c(Cl)n1]

A mixture of 1.936 g (11.00 mmol) of 2,6-dichloronicotinaldehyde, 6.384 g (44.00 mmol) of aqueous ethanedial and aqueous Ammonia (4.996 g, 88.00 mmol) in 60 ml of methanol was stirred for 3 hours. The mixture was concentrated in vacuum and acidified to pH<1 with 200 ml of 0.5 N aq HCl. The aqueous solution was extracted with ethyl acetate (3×30 ml). The organic extracts were discarded while aqueous was basified by addition of sat NaHCO3. The mixture was extracted with ethyl acetate (3×30 ml), combined organic extracts were washed with water, brine, dried and concentrated in vacuum to give 2,6-dichloro-3-(1H-imidazol-2-yl)pyridine (crude 0.85 g, yield 36%) M/z 214.0, calc. 212.99. 1H NMR (500 MHz, DMSO) δ 12.51 (s, 1H), 8.31 (d, J=8.1, 1H), 7.74-7.63 (m, 1H), 7.26 (s, 2H)

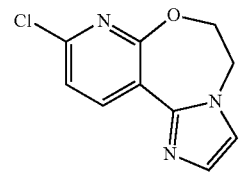 [SMILES: Clc1ccc2c(n1)OCCn1ccnc1-2]

A mixture of 0.856 g (4.00 mmol) of 2,6-dichloro-3-(1H-imidazol-2-yl)pyridine, 704 mg (8.00 mmol) of ethylene carbonate and 2930 mg (9.00 mmol) of cesium carbonate was heated in 25.0 ml of N,N-dimethylformamide for 13 hours at 90° C. The mixture was filtered, the filtrate concentrated in high vacuum, the residue purified on 10 g of silica column eluting with 80% of ethyl acetate in heptane to give 9-chloro-5,6-dihydroimidazo[1,2-d]pyrido[3,2-f][1,4]

oxazepine. Yield 0.359 g (41%). M/z 222.0, calc. 221.04. 1H NMR (500 MHz, CDCl3) δ 8.84 (d, J=8.2, 1H), 7.18 (s, 1H), 7.15 (d, J=8.2, 1H), 7.02 (s, 1H), 4.63-4.57 (m, 2H), 4.47-4.41 (m, 2H)

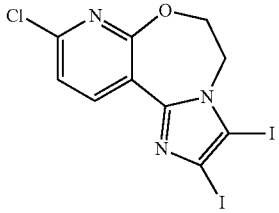 [SMILES: Clc1ccc2c(n1)OCCn1c-2nc(I)c1I]

A mixture of 0.359 g (1.62 mmol) of 9-chloro-5,6-dihydroimidazo[1,2-d]pyrido[3,2-f][1,4]oxazepine and 0.913 g (4.06 mmol) of N-iodosuccinimide in 20.0 ml N,N-dimethylformamide was heated at 80° C. for 60 hours. The mixture was concentrated in vacuum, the residue partitioned between ethyl acetate (40 ml) and 0.1 M aq Na2CO3. The organic extracts were washed with 5% aqueous Na2S2O5, water, brine, dried over Na2SO4 and concentrated in vacuum to give 9-chloro-2,3-diiodo-5,6-dihydroimidazo[1,2-d]pyrido[3,2-f][1,4]oxazepine. Yield 0.644 (84%). M/z 473.9, calc. 472.83. 1H NMR (500 MHz, CDCl3) δ 8.85 (d, J=8.2, 1H), 7.19 (s, 1H), 7.16 (d, J=8.2, 1H), 7.03 (s, 1H), 4.60 (dd, J=9.9, 5.8, 2H), 4.47-4.42 (m, 2H)

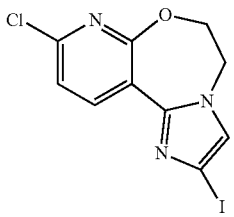 [SMILES: Clc1ccc2c(n1)OCCn1cc(I)nc1-2]

2.0 M of Isopropylmagnesium Chloride in tetrahydrofuran (0.782 mL) was added dropwise to a solution of 0.644 g (1.36 mmol) of 9-chloro-2,3-diiodo-5,6-dihydroimidazo[1,2-d]pyrido[3,2-f][1,4]oxazepine in 12 ml of tetrahydrofuran at −10° C. The mixture was allowed to warm to 15° C. The mixture then was quenched by addition of 20 ml of sat. aqueous NH4Cl and extracted with ethyl acetate. The organic extracts were washed with water, brine, dried over Na2SO4 and concentrated to give 9-chloro-2-iodo-5,6-dihydroimidazo[1,2-d]pyrido[3,2-f][1,4]oxazepine. Yield 448 mg (98%). M/z 348.2, calc. M 346.93. 1H NMR (400 MHz, CDCl3) δ 8.83 (d, J=8.2, 1H), 7.16 (dd, J=14.0, 5.9, 1H), 7.10 (s, 1H), 4.61-4.54 (m, 2H), 4.41 (dd, J=5.0, 2.9, 2H)

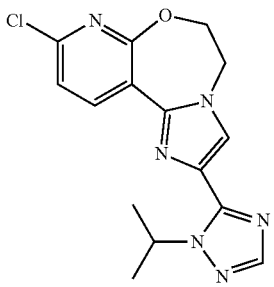 [SMILES: CC(C)n1ncnc1-c1cn2c(n1)-c1ccc(Cl)nc1OCC2]

Following the procedures of Examples herein, including Examples 20-22, 9-chloro-2-iodo-5,6-dihydroimidazo[1,2-d]pyrido[3,2-f][1,4]oxazepine was converted to 9-chloro-2-(1-isopropyl-1H-1,2,4-triazol-5-yl)-5,6-dihydroimidazo[1,2-d]pyrido[3,2-f][1,4]oxazepine. A mixture of 110 mg (0.33 mmol) of 9-chloro-2-(1-isopropyl-1H-1,2,4-triazol-5-yl)-5,6-dihydroimidazo[1,2-d]pyrido[3,2-f][1,4]oxazepine, 87 mg (1.3 mmol) of methylammonium chloride and 0.23 ml (1.3 mmol) of N,N-diisopropylethylamine in 3.0 ml of N-methylpyrrolidinone was microwaved for 90 min at 170° C. NMP was removed under high vacuum, the residue was basified with 1 M Na2CO3 and partitioned between ethyl acetate and water. The organic extracts were washed with 5% aqueous citric acid, water, brine, dried over MgSO4 and concentrated. The residue was purified by RP HPLC (acetonitrile gradient) to give 367. Yield 12 mg. M/z 326.3, calc. 325.17. 1H NMR (400 MHz, DMSO) δ 8.37 (d, J=8.6, 1H), 7.88 (s, 1H), 7.77 (s, 1H), 6.96 (s, 1H), 6.34 (d, J=8.6, 1H), 5.88 (dt, J=13.0, 6.5, 1H), 4.46 (d, J=9.2, 4H), 2.78 (d, J=2.9, 3H), 1.46 (d, J=6.6, 6H)

Example 368

(2S,4R)-4-hydroxy-1-(2-(1-isopropyl-3-methyl-1H-1,2,4-triazol-5-yl)-5,6-dihydroimidazo[1,2-d]pyrido[3,4-f][1,4]oxazepin-9-yl)pyrrolidine-2-carboxamide 368

Following the procedures of Example 339, 2-(2-isopropyl-5-methyl-2H-[1,2,4]triazol-3-yl)-4,5-dihydro-6-oxa-1,3a,9-triaza-benzo[e]azulen-8-ol and 4-trans-hydroxy-1-prolinamide were reacted and the crude product recrystallised from IMS to give 368 as a white solid (86 mg, 53%). LCMS: RT=2.19 min, [M+H]+ 439. ¹H NMR 400 MHz (DMSO-d6) δ: 9.02 (1 H, s), 7.77 (1 H, s), 7.40 (1 H, br), 6.90 (1 H, br), 5.90 (1 H, s), 5.87-5.85 (1 H, m), 5.05 (1 H, d, J=3.93 Hz), 4.52-4.41 (4 H, m), 4.39 (1 H, m), 4.31 (1 H, m), 3.66 (1 H, dd, J=10.60, 4.98 Hz), 2.22 (3 H, s), 2.16-2.10 (1 H, m), 2.00-1.99 (1 H, m), 1.43 (6 H, dd, J=6.59, 2.86 Hz)

Example 369

(2S)-1-(2-(1-isopropyl-3-methyl-1H-1,2,4-triazol-5-yl)-5,6-dihydroimidazo[1,2-d]pyrido[3,4-f][1,4]oxazepin-9-yl)pyrrolidine-2-carboxamide 369

Following the procedures of Example 339, 2-(2-isopropyl-5-methyl-2H-[1,2,4]triazol-3-yl)-4,5-dihydro-6-oxa-1,3a,9-triaza-benzo[e]azulen-8-ol and L-prolinamide, were reacted and the crude product recrystallised from IMS to give 369 as a white solid (130 mg, 67%). LCMS: RT=2.48 min, [M+H]+=423. ¹H NMR 400 MHz (DMSO-d6) δ: 9.06 (1 H, s), 7.80 (1 H, s), 7.35 (1 H, br), 6.94 (1 H, br), 5.96 (1 H, s), 5.90-5.88 (1 H, m), 4.50 (4H, d, J=17.28 Hz), 4.32 (1 H, m), 3.61 (1 H, m), 3.45 (1 H, m)), 2.26 (2 H, s), 2.24-2.15 (1 H, m), 1.98-1.97 (3 H, m), 1.47 (6 H, dd, J=6.59, 3.27 Hz)

Example 370

1-(2-(1-isopropyl-1H-1,2,4-triazol-5-yl)-5,6-dihydroimidazo[1,2-d]pyrido[3,4-f][1,4]oxazepin-9-yl)azetidin-3-ol 370

Following the procedures of Example 339, 2-(2-isopropyl-2H-[1,2,4]triazol-3-yl)-4,5-dihydro-6-oxa-1,3a,9-triaza-benzo[e]azulen-8-ol from Example 93 and 3-hydroxyazetidine hydrochloride with added DIPEA (2.2 eq.), were reacted and the crude product subjected to flash chromatography (SiO2, gradient 0 to 8% methanol in DCM) then recrystallisation from IMS to give 370 as pale green crystals (16 mg, 14%). LCMS: RT=2.26 min, [M+H]+ 368. $^1$H NMR 400 MHz (DMSO-d6) δ: 9.09 (1 H, s), 7.90 (1 H, d, J=0.63 Hz), 7.84 (1 H, s), 5.95-5.94 (1 H, m), 5.91 (1 H, s), 5.70 (1 H, d, J=6.40 Hz), 4.59 (1 H, s), 4.55-4.47 (4 H, m), 4.18 (2 H, t, J=7.66 Hz), 3.70 (2 H, dd, J=8.85, 4.66 Hz), 1.48 (6 H, d, J=6.60 Hz)

Example 371

(3R)-1-(2-(1-isopropyl-1H-1,2,4-triazol-5-yl)-5,6-dihydroimidazo[1,2-d]pyrido[3,4-f][1,4]oxazepin-9-yl)pyrrolidin-3-ol 371

Following the procedures of Example 339, 2-(2-isopropyl-2H-[1,2,4]triazol-3-yl)-4,5-dihydro-6-oxa-1,3a,9-triazabenzo[e]azulen-8-ol from Example 93 and (R)-prolinol hydrochloride with added DIPEA (2.2 eq.), were reacted and the crude product recrystallised from methanol to give 371 as a green solid (46 mg, 34%). LCMS: RT=2.26 min, [M+H]+=382. $^1$H NMR 400 MHz (DMSO-d6) δ: 9.09 (1 H, s), 7.88 (1 H, d, J=0.63 Hz), 7.82 (1 H, s), 5.97-5.96 (1 H, m), 5.94 (1 H, s), 4.97 (1 H, d, J=3.62 Hz), 4.49-4.48 (4 H, m), 4.39 (1 H, s), 3.53-3.42 (3 H, m), 2.02-2.00 (1 H, m), 1.90-1.87 (1 H, m), 1.48 (6 H, d, J=6.60 Hz)

Example 372

(1-(2-(1-isopropyl-1H-1,2,4-triazol-5-yl)-5,6-dihydroimidazo[1,2-d]pyrido[3,4-f][1,4]oxazepin-9-yl)piperidin-4-yl)methanol 372

Following the procedures of Example 339, 2-(2-isopropyl-2H-[1,2,4]triazol-3-yl)-4,5-dihydro-6-oxa-1,3a,9-triazabenzo[e]azulen-8-ol from Example 93 and 4-piperidine methanol, were reacted and the crude product subjected to flash chromatography (SiO2, gradient 0 to 8% methanol in DCM) then recrystallisation from methanol to give 372 as a white solid (69 mg, 48%). LCMS: RT=2.57 min, [M+H]+=410. $^1$H NMR 400 MHz (DMSO-d6) δ: 9.10 (1 H, s), 7.90 (1 H, s), 7.84 (1 H, s), 6.32 (1 H, s), 5.99-5.90 (1 H, m), 4.54-4.44 (5 H, m), 4.34 (2 H, d, J=13.11 Hz), 3.28 (2 H, t, J=5.64 Hz), 2.84 (2 H, t, J=12.55 Hz), 1.71 (2 H, d, J=13.74 Hz), 1.65 (1 H, m), 1.49 (6 H, d, J=6.60 Hz), 1.13 (2 H, t, J=12.33 Hz)

Example 373

(2S,4S)-4-fluoro-1-(2-(1-isopropyl-1H-1,2,4-triazol-5-yl)-5,6-dihydroimidazo[1,2-d]pyrido[3,4-f][1,4]oxazepin-9-yl)pyrrolidine-2-carboxamide 373

Following the procedures of Example 339, 2-(2-isopropyl-2H-[1,2,4]triazol-3-yl)-4,5-dihydro-6-oxa-1,3a,9-triazabenzo[e]azulen-8-ol from Example 93 and 4-cis-fluoro-L-prolinamide hydrochloride with added DIPEA (2.2 eq.), were reacted and the crude product recrystallised from IMS to give 373 as a white solid (56 mg, 22%). LCMS: RT=2.59 min, [M+H]+=427. $^1$H NMR 400 MHz (DMSO-d6) δ: 9.05 (1 H, s), 7.84 (1 H, d, J=0.63 Hz), 7.80 (1 H, s), 7.11 (1 H, s), 6.92 (1 H, s), 5.93-5.91 (2 H, m), 5.42 (1 H, s), 5.29 (1 H, s), 4.46-4.44 (5 H, m), 3.83-3.54 (2 H, m), 2.28 (1 H, dd, J=20.28, 14.80 Hz), 1.43 (6 H, dd, J=6.59, 3.60 Hz)

Example 374

(2S,4R)-4-hydroxy-1-(2-(1-isopropyl-1H-1,2,4-triazol-5-yl)-5,6-dihydroimidazo[1,2-d]pyrido[3,4-f][1,4]oxazepin-9-yl)pyrrolidine-2-carboxamide 374

Following the procedures of Example 339, 2-(2-isopropyl-2H-[1,2,4]triazol-3-yl)-4,5-dihydro-6-oxa-1,3a,9-triazabenzo[e]azulen-8-ol from Example 93 and 4-trans-hydroxy-1-prolinamide were reacted and the crude product subjected to flash chromatography (SiO2, gradient 0 to 10% methanol in DCM) to give 374 as a white solid (56 mg, 27%). LCMS: RT=2.16 min, [M+H]+=425. $^1$H NMR 400 MHz (DMSO-d6) δ: 9.05 (1 H, s), 7.88 (1 H, s), 7.83 (1 H, s), 7.42 (1 H, br), 6.92 (1 H, br), 5.95 (1 H, m), 5.92 (1 H, s), 5.07 (1 H, d, J=3.93 Hz), 4.50-4.49 (4 H, m), 4.40 (1 H, m), 4.32 (1 H, m), 3.67 (1 H, t, J=5.33 Hz), 2.16 (1 H, m), 2.04 (1 H, m), 1.47 (6 H, dd, J=6.59, 3.01 Hz)

Example 375

(2S)-1-(2-(1-isopropyl-1H-1,2,4-triazol-5-yl)-5,6-dihydrobenzo[f]imidazo[1,2-d][1,4]oxazepin-9-yl)pyrrolidine-2-carboxamide 375

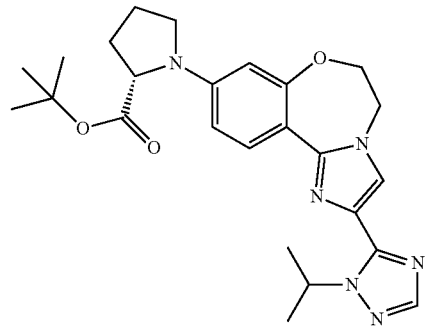 [SMILES: CC(C)n1ncnc1-c1cn2c(n1)-c1ccc(N3CCC[C@H]3C(=O)OC(C)(C)C)cc1OCC2]

A degassed mixture of 374 mg, (1.00 mmol) of 9-bromo-2-(1-isopropyl-1H-1,2,4-triazol-5-yl)-5,6-dihydrobenzo[f]imidazo[1,2-d][1,4]oxazepine 194, 342.5 mg, (2.000 mmol) of L-Proline tert-Butyl Ester, 26 mg, (0.050 mmol) of Bis(tri-t-butylphosphine)palladium and 192 mg, (2.00 mmol) of Sodium tert-butoxide in Toluene (10.0 mL, 93.9 mmol) was heated at 95° C. for 24 hours. The same quantity of L-Proline tert-Butyl Ester, Sodium tert-butoxide and the catalyst were added and the mixture was heated for 6 hours at 115° C. until no starting bromide remains in the reaction mixture. The mixture was concentrated in vacuum, the residue distributed between ethyl acetate and 5% aqueous citric acid. The organic extracts were washed with water, sat. NaHCO3, water, brine, dried over MgSO4 and purified on a silica gel 12 g column eluting with 4% Methanol in DCM to give (S)-tert-butyl 1-(2-(1-isopropyl-1H-1,2,4-triazol-5-yl)-5,6-dihydrobenzo[f]imidazo[1,2-d][1,4]oxazepin-9-yl)pyrrolidine-2-carboxylate. Yield 153 mg (55-60% purity, the product is contaminated with debromination byproduct). M/z 465.2, calc. 464.25

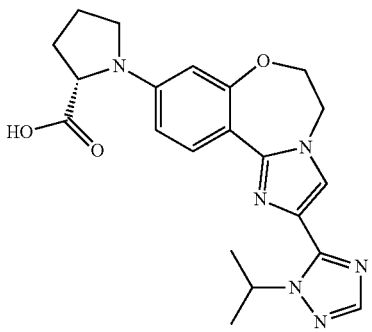 [SMILES: CC(C)n1ncnc1-c1cn2c(n1)-c1ccc(N3CCC[C@H]3C(=O)O)cc1OCC2]

Trifluoroacetic acid (3 ml) was added to a mixture of 153 mg of (S)-tert-butyl 1-(2-(1-isopropyl-1H-1,2,4-triazol-5-yl)-5,6-dihydrobenzo[f]imidazo[1,2-d][1,4]oxazepin-9-yl)pyrrolidine-2-carboxylate and 0.2 ml of triethylsilane in 5 ml of dichloromethane. The reaction mixture was stirred for 3 hours. The mixture was concentrated, the residue partitioned between 1 M aq. Na2CO3 and ethyl ether. The aqueous layer was extracted with ethyl acetate two more times. The organic layers were discarded, the aqueous solution neutralized to pH 6. A precipitate was collected, washed with water, dried in high vacuum for 36 hours to give (S)-1-(2-(1-isopropyl-1H-1,2,4-triazol-5-yl)-5,6-dihydrobenzo[f]imidazo[1,2-d][1,4]oxazepin-9-yl)pyrrolidine-2-carboxylic acid. Yield 55 mg. M/z 409.3, calc. 408.19

A mixture of 55 mg (0.135 mmol) of (S)-1-(2-(1-isopropyl-1H-1,2,4-triazol-5-yl)-5,6-dihydrobenzo[f]imidazo[1,2-d][1,4]oxazepin-9-yl)pyrrolidine-2-carboxylic acid, N,N,N',N'-Tetramethyl-O-(7-azabenzotriazol-1-yl)uronium Hexafluorophosphate (57.0 mg, 0.150 mmol), N,N-Diisopropylethylamine (52.2 uL, 0.300 mmol) and Ammonium chloride (8.02 mg, 0.150 mmol) in N,N-Dimethylacetamide (3.0 mL, 32 mmol) was stirred for 1 hour. The mixture was concentrated in vacuum, the residue triturated with water, 0.01 N aq HCL, water, dried in vacuum and subjected to RP HPLC and then chiral purification to give 375. Yield 12 mg. M/z 408.2, calc. 407.21. 1H NMR (400 MHz, DMSO) δ 8.19 (d, J=8.9, 1H), 7.87 (s, 1H), 7.77 (s, 1H), 7.40 (s, 1H), 7.04 (s, 1H), 6.36 (dd, J=9.0, 2.4, 1H), 6.07 (d, J=2.4, 1H), 5.91 (dq, J=13.3, 6.5, 1H), 4.44 (d, J=6.5, 4H), 4.01-3.93 (m, 1H), 3.57 (t, J=7.0, 1H), 3.24 (d, J=9.0, 1H), 2.23 (dd, J=12.1, 6.9, 1H), 1.98 (dd, J=14.8, 11.3, 3H), 1.47 (dd, J=6.6, 3.3, 6H)

Example 376

(2R)-1-(2-(1-isopropyl-1H-1,2,4-triazol-5-yl)-5,6-dihydrobenzo[f]imidazo[1,2-d][1,4]oxazepin-9-yl)pyrrolidine-2-carboxamide 376

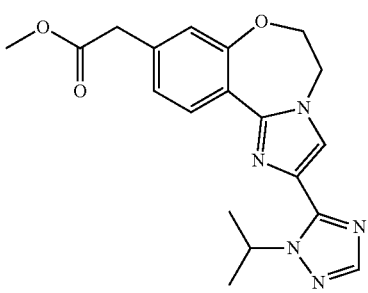 [SMILES: COC(=O)Cc1ccc2c(c1)OCCn1cc(-c3ncnn3C(C)C)nc1-2]

Following the procedures of Example 316, 9-bromo-2-(1-isopropyl-1H-1,2,4-triazol-5-yl)-5,6-dihydrobenzo[f]imidazo[1,2-d][1,4]oxazepine 194 and 1-(tert-butyldimethylsilyloxy)-1-methoxyethene were reacted to give methyl 2-(2-(1-isopropyl-1H-1,2,4-triazol-5-yl)-5,6-dihydrobenzo[f]imidazo[1,2-d][1,4]oxazepin-9-yl)acetate. M/z 368.2, calc. 367.16

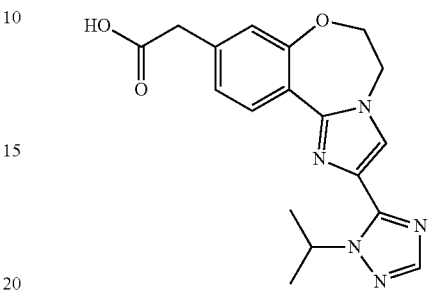

Methyl 2-(2-(1-isopropyl-1H-1,2,4-triazol-5-yl)-5,6-dihydrobenzo[f]imidazo[1,2-d][1,4]oxazepin-9-yl)acetate and lithium hydroxide were reacted to give 2-(2-(1-isopropyl-1H-1,2,4-triazol-5-yl)-5,6-dihydrobenzo[f]imidazo[1,2-d][1,4]oxazepin-9-yl)acetic acid. M/z 354.1, calc. 353.15

2-(2-(1-Isopropyl-1H-1,2,4-triazol-5-yl)-5,6-dihydrobenzo[f]imidazo[1,2-d][1,4]oxazepin-9-yl)acetic acid and ammonia were reacted to give 376. M/z 353.1, calc. 352.16. 1H NMR (400 MHz, DMSO) δ 8.32 (d, J=8.3, 1H), 7.91 (s, 2H), 7.48 (s, 1H), 7.04 (d, J=8.2, 1H), 6.97 (s, 1H), 6.92 (s, 1H), 5.95-5.81 (m, 1H), 4.50 (d, J=5.8, 4H), 3.38 (s, 2H), 1.48 (d, J=6.5, 6H)

Example 377

(2S)-1-(2-(1-isopropyl-1H-imidazol-2-yl)-5,6-dihydroimidazo[1,2-d]pyrido[3,4-f][1,4]oxazepin-9-yl)pyrrolidine-2-carboxamide 377

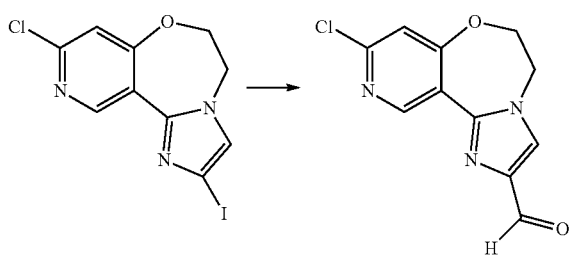 [SMILES: Clc1cc2c(cn1)-c1nc(I)cn1CCO2 ; O=Cc1cn2c(n1)-c1cnc(Cl)cc1OCC2]

Ethylmagnesium bromide (3.0 M in Et2O, 100 mmol, 33.3 mL) was added dropwise to a solution of 9-chloro-2-iodo-5,6-dihydroimidazo[1,2-d]pyrido[3,4-f][1,4]oxazepine (10.0 g, 28.8 mmol) in tetrahydrofuran (173 mL) at −20° C. The mixture was maintained at this temperature 20 min and then allowed to warm to ambient temperature for a 1 hr period. At this point, the reaction was re-cooled to −20° C. and N,N-dimethylformamide (8.9 mL, 115 mmol) was added to the mixture. Stirring was continued for 16 h before quenching with saturated aqueous ammonium chloride solution (220 mL) and further dilution with EtOAc (250 mL). The phases were separated and the aqueous layer was extracted twice with EtOAc. The combined organic portions were washed once with brine, dried over MgSO4, filtered and concentrated in vacuo. This provided 7.08 g (98% yield) of 9-chloro-5,6-dihydroimidazo[1,2-d]pyrido[3,4-f][1,4]oxazepine-2-carbaldehyde as a yellow solid in >95% purity as determined by analytical HPLC. MS(ESI+): m/z 249.8 (M+H+), calc. 249.65

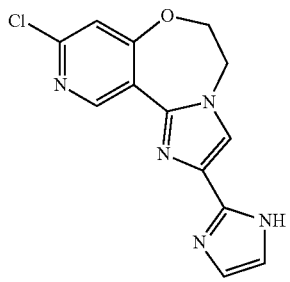 [SMILES: Clc1cc2c(cn1)-c1nc(-c3ncc[nH]3)cn1CCO2]

To a 100-mL round-bottomed flask was combined 9-chloro-5,6-dihydroimidazo[1,2-d]pyrido[3,4-f][1,4]oxazepine-2-carbaldehyde (1.1 g, 4.4 mmol), 40% aqueous solution of ethanedial (2.1 mL, 18.0 mmol), ammonium hydroxide (2.55 mL, 65.5 mmol) and methanol (10.5 mL). The resulting reaction mixture was stirred together at room temperature for 6 h. At the end of this period, the mixture was evaporated to dryness and the oily residue was purified by flash column chromatography (0-100% EtOAc in dichloromethane, slow gradient) to provide 1.13 g (86% yield) of 9-chloro-2-(1H-imidazol-2-yl)-5,6-dihydroimidazo[1,2-d]pyrido[3,4-f][1,4]oxazepine.

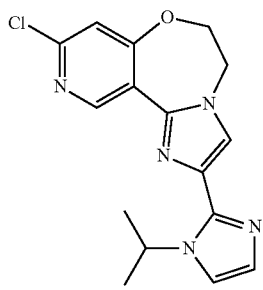 [SMILES: CC(C)n1ccnc1-c1cn2c(n1)-c1cnc(Cl)cc1OCC2]

To a solution of 9-chloro-2-(1H-imidazol-2-yl)-5,6-dihydroimidazo[1,2-d]pyrido[3,4-f][1,4]oxazepine (0.402 g, 1.4 mmol) in N,N-dimethylformamide (9.6 mL) was added Cs2CO3 (0.6 g, 2.0 mmol) followed by isopropyl iodide (0.2 mL, 2 mmol). The reaction mixture was heated at 50° C. for a 20 h period. The mixture was subsequently cooled to room temperature and diluted with water and EtOAc. The mixture was extracted twice with EtOAc, dried over MgSO4, filtered and concentrated. The resultant residue was purified by flash column chromatography (0-10% MeOH in dichloromethane). This procured 0.22 g (48% yield) of 9-chloro-2-(1-isopropyl-1H-imidazol-2-yl)-5,6-dihydroimidazo[1,2-d]pyrido[3,4-f][1,4]oxazepine which was combined with L-prolinamide (0.152 g, 1.33 mmol) in N,N-dimethylacetamide (6.7 mL) and sealed in a pressure vessel. The mixture was heated at 150° C. was heated for 40 h at which point an additional amount of L-prolinamide (0.152 g, 1.33 mmol) was added and the mixture was continued to be heated for 12 h. Only 50% conversion was observed at the end of this period and heating was discontinued and the material was purified by rp-HPLC eluting with 0.1% NH4OH in acetonitrile to provide 19.8 mg (8% yield) of 377. MS(ESI+) m/z 408.2 (M+H+), calcd. 408.5. 1H NMR (400 MHz, DMSO) δ 9.03 (s, 1H), 7.58 (s, 1H), 7.43-7.26 (m, 2H), 6.89 (d, J=1.0 Hz, 2H), 5.94 (s, 1H), 5.72 (dt, J=13.6, 6.8 Hz, 1H), 4.56-4.38 (m, 4H), 4.29 (d, J=8.0 Hz, 1H), 3.59 (s, 1H), 2.17 (d, J=8.9 Hz, 1H), 1.98 (dd, J=31.1, 24.1 Hz, 4H), 1.44 (d, J=4.2 Hz, 6H).

Example 378

(2S)-1-(2-(1-(2,4-difluorophenyl)-1H-1,2,4-triazol-5-yl)-5,6-dihydroimidazo[1,2-d]pyrido[3,4-f][1,4]oxazepin-9-yl)pyrrolidine-2-carboxamide 378

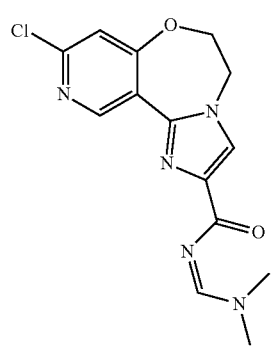 [SMILES: CN(C)/C=N\C(=O)c1cn2c(n1)-c1cnc(Cl)cc1OCC2]

To a solution of 8-Chloro-4,5-dihydro-6-oxa-1,3a,9-triaza-benzo[e]azulene-2-carboxylic acid amide (2.40 g, 0.00907 mol) in Toluene (40 mL) was added 1,1-Dimethoxy-N,N-dimethylmethanamine (4.82 mL, 0.0363 mol). The flask was sealed and heated to 95° C. for 8 h. The reaction was deemed complete by TLC. The solvent was removed in vacuo to give 8-Chloro-4,5-dihydro-6-oxa-1,3a,9-triaza-benzo[e]azulene-2-carboxylic acid 1-dimethylamino-methylideneamide which was used crude. MS(ESI+) 320.1

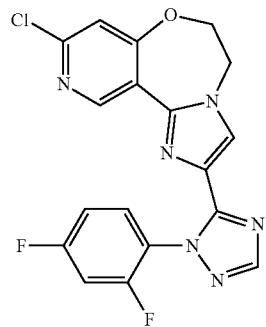 [SMILES: Fc1ccc(-n2ncnc2-c2cn3c(n2)-c2cnc(Cl)cc2OCC3)c(F)c1]

8-Chloro-4,5-dihydro-6-oxa-1,3a,9-triaza-benzo[e]azulene-2-carboxylic acid 1-dimethylamino-methylideneamide (0.00907 mol) was dissolved in Acetic acid (36 mL). 2,4-Difluorophenylhydrazine hydrochloride (1.965 g, 0.01088 mol) was added and the reaction was stirred at 95° C. for 2.5 hours. The AcOH was removed in vacuo. The crude was triturated in iPrOH to afford 2.828 g (78% yield over 2 steps) of 8-Chloro-2-[2-(2,4-difluoro-phenyl)-2H-[1,2,4]triazol-3-yl]-4,5-dihydro-6-oxa-1,3a,9-triaza-benzo[e]azulene as a light brown powder clean by 1H NMR. MS(ESI+) 401.1

A solution of 8-Chloro-2-[2-(2,4-difluoro-phenyl)-2H-[1,2,4]triazol-3-yl]-4,5-dihydro-6-oxa-1,3a,9-triaza-benzo[e]azulene (0.200 g, 0.499 mmol), L-prolinamide (0.171 g, 0.00150 mol) and Triethylamine (0.417 mL, 0.00299 mol) in N-Methylpyrrolidinone (5 mL) under N2 was heated to 150° C. overnight. The mixture was diluted with dichloromethane. Saturated NH4Cl was added and the mixture was extracted 3 times with dichloromethane. The organic phases were combined, dried with Na2SO4 and concentrated. The crude was purified by reverse-phase HPLC to obtain 94 mg (39% yield) of 378 as a light pink solid. MS(ESI+) 479.2. 1H NMR (400 MHz, DMSO) δ 8.35 (s, 1H), 8.18 (s, 1H), 7.86 (s, 1H), 7.69 (td, J=8.7, 6.0 Hz, 1H), 7.62-7.53 (m, 1H), 7.35-7.26 (m, 2H), 6.92 (br, 1H), 5.84 (s, 1H), 4.47-4.36 (m, 4H), 4.24 (d, J=7.4 Hz, 1H), 3.62-3.53 (m, 1H), 3.42-3.32 (m, 1H), 2.24-2.08 (m, 1H), 2.02-1.83 (m, 3H)

Example 379

(2R)-2-(2-(1-isopropyl-3-methyl-1H-1,2,4-triazol-5-yl)-5,6-dihydrobenzo[f]imidazo[1,2-d][1,4]oxazepin-9-yl)pyrrolidine-1-carboxamide 379 and Example 380

(2S)-2-(2-(1-isopropyl-3-methyl-1H-1,2,4-triazol-5-yl)-5,6-dihydrobenzo[f]imidazo[1,2-d][1,4]oxazepin-9-yl)pyrrolidine-1-carboxamide 380

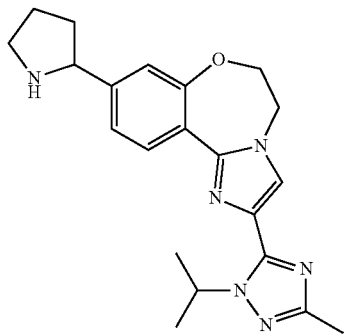 [SMILES: Cc1nc(-c2cn3c(n2)-c2ccc(C4CCCN4)cc2OCC3)n(C(C)C)n1]

To a solution of N-(tert-Butoxycarbonyl)pyrrolidine (1.02 mL, 0.00584 mol) and N,N,N',N'-Tetramethylethylenediamine (0.881 mL, 0.00584 mol) in anhydrous 2-Methoxy-2-methylpropane (12 mL) at −78° C. was added sec-Butyllithium (0.00584 mol, 1.4M in cyclohexane, 4.17 mL). The reaction was stirred for 3 hours at −78° C. A solution of Zinc dichloride (0.00350 mol, 0.5 M in THF, 7.0 mL) was added dropwise with rapid stirring and was stirred at −78° C. for 30 minutes. The reaction was then warmed to room temperature and stirred an additional 30 minutes. To a N2-filled flask containing 8-Bromo-2-(2-isopropyl-5-methyl-2H-[1,2,4]triazol-3-yl)-4,5-dihydro-6-oxa-1,3a-diaza-benzo[e]azulene (0.900 g, 0.00232 mol), Palladium Acetate (0.0260 g, 0.116 mmol) and Tri-t-butylphosphonium tetrafluoroborate (0.0420 g, 0.000145 mol) was added the zinc chloride pyrrolidine solution (1.25 equiv., 0.243M, 11.9 mL). The reaction was heated to 90° C. overnight. An incomplete conversion to product was observed by LC/MS. The mixture was diluted with dichloromethane and filtered through celite. Saturated NH4Cl was added and the mixture was extracted 3 times with dichloromethane. The organic layers were combined, dried with Na2SO4 and concentrated. The crude was redissolved in Methylene chloride (4.5 mL). Trifluoroacetic Acid (5.5 mL) was added and the reaction was stirred at room temperature for 30 minutes, then concentrated. The crude was purified by reverse-phase HPLC and the enantiomers were separated by chiral SFC to obtain 10 mg of each enantiomer of 2-(2-Isopropyl-5-methyl-2H-[1,2,4]triazol-3-yl)-8-pyrrolidin-2-yl-4,5-dihydro-6-oxa-1,3a-diaza-benzo[e]azulene as a white solid. MS(ESI+) 379.2

To a solution of 2-(2-Isopropyl-5-methyl-2H-[1,2,4]triazol-3-yl)-8-pyrrolidin-2-yl-4,5-dihydro-6-oxa-1,3a-diazabenzo[e]azulene (0.009 g, 0.00002 mol) in Acetic acid (4.06 uL, 0.0713 mmol) and water (0.13 mL) was added a solution of Potassium cyanate (0.00579 g, 0.0713 mmol) in water (0.13 mL) dropwise. N,N-Dimethylformamide (0.13 mL, 0.0017 mol) was added to solubilize the reagents. The reaction was stirred at 50° C. overnight, cooled down, filtered, and rinsed with cold water. The crude was purified by precipitation in MeOH/water to give 10 mg of each enantiomer 379 and 380. MS(ESI+) 422.2. 1H NMR (400 MHz, DMSO) δ 8.32 (d, J=8.3 Hz, 1H), 7.85 (s, 1H), 6.95 (dd, J=8.3, 1.6 Hz, 1H), 6.79 (d, J=1.3 Hz, 1H), 5.90-5.76 (m, 1H), 5.69 (br, 2H), 4.89 (dd, J=7.9, 1.3 Hz, 1H), 4.53-4.44 (m, 4H), 3.58-3.49 (m, 1H), 3.42-3.34 (m, 1H), 2.25 (s, 3H), 2.25-2.17 (m, 1H), 1.92-1.65 (m, 3H), 1.45 (dd, J=6.6, 3.9 Hz, 6H).

Example 381

(2S)-4,4-difluoro-1-(2-(1-isopropyl-1H-1,2,4-triazol-5-yl)-5,6-dihydroimidazo[1,2-d]pyrido[3,4-f][1,4]oxazepin-9-yl)pyrrolidine-2-carboxamide 381

Following the procedures of Example 339, 2-(2-isopropyl-2H-[1,2,4]triazol-3-yl)-4,5-dihydro-6-oxa-1,3a,9-triazabenzo[e]azulen-8-ol from Example 93 and 4,4-difluoro-L-prolinamide hydrochloride with added DIPEA (2.2 eq.) were reacted and the crude product subjected to RPHPLC (C18 column, gradient 5 to 95% acetonitrile in water+0.1% HCO2H) then recrystallisation from IMS to give 381 as a white solid (24 mg, 11%). LCMS: RT=3.21 min, [M+H]+=445. 1H NMR 400 MHz (DMSO-d6) δ: 9.11 (1 H, s), 7.90 (1 H, d, J=0.64 Hz), 7.87 (1 H, s), 7.53 (1 H, br), 7.14 (1 H, br), 6.08 (1 H, s), 5.99-5.91 (1 H, m), 4.61 (1 H, dd, J=9.53, 4.24 Hz), 4.58-4.49 (4 H, m), 4.00-3.98 (2 H, m), 2.91-2.90 (1 H, m), 2.45 (1 H, dd, J=13.51, 4.18 Hz), 1.49 (6 H, dd, J=6.59, 3.35 Hz)

Example 382

(2S,4S)-4-fluoro-1-(2-(1-isopropyl-3-methyl-1H-1,2,4-triazol-5-yl)-5,6-dihydroimidazo[1,2-d]pyrido[3,4-f][1,4]oxazepin-9-yl)pyrrolidine-2-carboxamide 382

Following the procedures of Example 339, 2-(2-isopropyl-5-methyl-2H-[1,2,4]triazol-3-yl)-4,5-dihydro-6-oxa-1,3a,9-triaza-benzo[e]azulen-8-ol and 4-cis-fluoro-L-prolinamide hydrochloride with added TEA (2.5 eq.), were reacted and the crude product recrystallised from IMS/DCM to give 382 as a white solid (68 mg, 42%). LCMS: RT=2.58 min, [M+H]+ 441. 1H NMR 400 MHz (DMSO-d6) δ: 9.04 (1 H, s), 7.76 (1 H, s), 7.10 (1 H, s), 6.91 (1 H, s), 5.95 (1 H, s), 5.87-5.80 (1 H, m), 5.42 (1 H, s), 5.29 (1 H, s), 4.49-4.36 (5 H, m), 3.74-3.73 (2 H, m), 2.46-2.45 (1 H, m), 2.20 (3 H, s), 1.40 (6 H, dd, J=6.59, 3.37 Hz)

Example 383

(2S)-4,4-difluoro-1-(2-(1-isopropyl-3-methyl-1H-1,2,4-triazol-5-yl)-5,6-dihydroimidazo[1,2-d]pyrido[3,4-f][1,4]oxazepin-9-yl)pyrrolidine-2-carboxamide 383

Following the procedures of Example 339, 2-(2-isopropyl-5-methyl-2H-[1,2,4]triazol-3-yl)-4,5-dihydro-6-oxa-1,3a,9-triaza-benzo[e]azulen-8-ol and 4,4-difluoro-L-prolinamide hydrochloride with added TEA (2.5 eq.) were reacted and the crude product subjected to flash chromatography (SiO2, gradient 0 to 5% methanol in DCM) to give 383 as a white solid (29 mg, 17%). LCMS: RT=3.14 min, [M+H]+=459. $^1$H NMR 400 MHz (DMSO-d6) δ: 9.09 (1 H, s), 7.85 (1 H, d, J=0.64 Hz), 7.55 (1 H, br), 7.15 (1 H, br), 6.05 (1 H, s), 5.93-5.81 (1 H, m), 4.61 (1 H, dd, J=9.53, 4.24 Hz), 4.58-4.49 (4 H, m), 4.00-3.98 (2 H, m), 2.91-2.90 (1 H, m), 2.45 (1 H, dd, J=13.51, 4.18 Hz), 2.25 (3H, s), 1.49 (6 H, dd, J=6.59, 3.35 Hz)

Example 384

(2S,4S)-4-hydroxy-1-(2-(1-isopropyl-1H-1,2,4-triazol-5-yl)-5,6-dihydroimidazo[1,2-d]pyrido[3,4-f][1,4]oxazepin-9-yl)pyrrolidine-2-carboxamide 384

Following the procedures of Example 339, 2-(2-isopropyl-2H-[1,2,4]triazol-3-yl)-4,5-dihydro-6-oxa-1,3a,9-triaza-benzo[e]azulen-8-ol from Example 93 and 4-cis-hydroxy-1-prolinamide were reacted and the crude product recrystallised from IMS to give 384 as a white solid (75 mg, 28%). LCMS: RT=2.32 min, [M+H]+ 425. $^1$H NMR 400 MHz (DMSO-d6) δ: 9.08 (1 H, s), 7.90 (1H, d, J=0.63 Hz), 7.85 (1 H, s), 7.47 (1 H, br), 7.13 (1H, br), 6.00 (1 H, s), 5.95-5.94 (1 H, m), 5.28 (1 H, d, J=6.27 Hz), 4.51 (4 H, d, J=11.64 Hz), 4.32 (2 H, m), 3.60 (1 H, m), 3.50 (1 H, m), 2.42 (1 H, t, J=4.54 Hz), 1.94 (1 H, d, J=13.24 Hz), 1.49 (6 H, dd, J=6.59, 2.75 Hz)

Example 385

(2S,4S)-4-hydroxy-1-(2-(1-isopropyl-3-methyl-1H-1,2,4-triazol-5-yl)-5,6-dihydroimidazo[1,2-d]pyrido[3,4-f][1,4]oxazepin-9-yl)pyrrolidine-2-carboxamide 385

Following the procedures of Example 339, 2-(2-isopropyl-5-methyl-2H-[1,2,4]triazol-3-yl)-4,5-dihydro-6-oxa-1,3a,9-triaza-benzo[e]azulen-8-ol and 4-cis-hydroxy-1-prolinamide were reacted and the crude product recrystallised from IMS to give 385 as a white solid (74 mg, 46%). LCMS: RT=2.34 min, [M+H]+ 439. $^1$H NMR 400 MHz (DMSO-d6) δ: 9.05 (1 H, s), 7.79 (1 H, s), 7.45 (1 H, br), 7.11 (1 H, br), 5.98 (1 H, s), 5.90-5.84 (1 H, m), 5.27 (1 H, d, J=6.27 Hz), 4.48 (4 H, m), 4.31-4.28 (2 H, m), 3.59 (1 H, dd, J=10.61, 4.77 Hz), 3.48 (1 H, d, J=10.45 Hz), 2.40-2.38 (1 H, m), 2.24 (3 H, s), 1.93 (1 H, d, J=13.06 Hz), 1.45 (6 H, dd, J=6.59, 2.55 Hz)

Example 386

2-(1-isopropyl-1H-imidazol-2-yl)-5,6-dihydroimidazo[1,2-d]pyrido[3,4-f][1,4]oxazepine 386

9-Chloro-2-(1-isopropyl-1H-imidazol-2-yl)-5,6-dihydroimidazo[1,2-d]pyrido[3,4-f][1,4]oxazepine (0.044 g, 0.13 mmol), prepared according to Example 377, was taken up in ethanol (5 mL) and 20% palladium hydroxide on carbon (19 mg, 0.03 mmol), and glacial acetic acid (0.2 mL) were added. The mixture was subjected to evacuation under reduced pressure and recycled with an H2 atmosphere. This process was repeated twice. Finally, the reaction was placed under an H2 atmosphere and allowed to stir at ambient temperature 2 h. At the end of this period the mixture was filtered through a pad of Celite® and concentrated in vacuo. The residue was purified by rp-HPLC (0.1% NH4OH in acetonitrile) to provide 13 mg (39% yield) of 386. MS(ESI+) m/z 296.1 (M+H+), calcd. 295.3. 1H NMR (400 MHz, DMSO) δ 9.47 (s, 1H), 8.33 (d, J=5.6 Hz, 1H), 7.74 (s, 1H), 7.33 (d, J=1.1 Hz, 1H), 7.03 (d, J=5.6 Hz, 1H), 6.92 (d, J=0.9 Hz, 1H), 5.66 (dq, J=13.3, 6.6 Hz, 1H), 4.57 (td, J=7.9, 3.5 Hz, 4H), 1.38 (d, J=6.6 Hz, 6H)

Example 387

(5-(9-chloro-5,6-dihydroimidazo[1,2-d]pyrido[3,4-f][1,4]oxazepin-2-yl)-1-(2,2,2-trifluoroethyl)-1H-1,2,4-triazol-3-yl)methanol 387

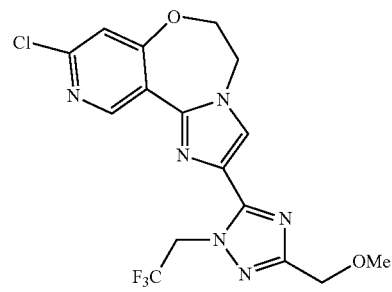 [SMILES: COCc1nc(-c2cn3c(n2)-c2cnc(Cl)cc2OCC3)n(CC(F)(F)F)n1]

A suspension of 8-Chloro-2-[5-methoxymethyl-2-(2,2,2-trifluoro-ethyl)-2H-[1,2,4]triazol-3-yl]-4,5-dihydro-6-oxa-1,3a,9-triaza-benzo[e]azulene (500 mg, 1.20 mmol) in 48% aqueous HBr (2.1 mL) was sealed and heated at 100° C. for 3 h while carefully monitoring by LCMS. The mixture was cooled to room temperature and poured over a cold solution of 10% KOH. The solid was collect by filtration (~90% purity by LCMS and 1H NMR analysis). The solid was used in subsequent steps without purification. A small amount was purified by HPLC to give 17 mg of 387. LCMS: 401.0. 1H NMR (400 MHz, DMSO) δ 9.27 (s, 1H), 8.11 (s, 1H), 7.24 (s, 1H), 5.81 (q, J=8.9 Hz, 2H), 5.34 (t, J=6.0 Hz, 1H), 4.71-4.57 (m, 4H), 4.46 (d, J=6.0 Hz, 2H).

Example 388

(2R)-1-(2-(1-isopropyl-1H-1,2,4-triazol-5-yl)-5,6-dihydroimidazo[1,2-d]pyrido[3,4-f][1,4]oxazepin-9-yl)-2,5-dihydro-1H-pyrrole-2-carboxamide 388

A solution of 2.64 g (8.00 mmol) of 9-chloro-2-(1-isopropyl-1H-1,2,4-triazol-5-yl)-5,6-dihydroimidazo[1,2-d]pyrido[3,4-f][1,4]oxazepine 317 in 250 ml of glacial acetic acid was placed into 350 ml glass pressure vessel. The vessel was closed and the mixture was heated for 64 hours at 155° C. The mixture was cooled down to room temperature. White precipitate appeared. The mixture was concentrated to 50 ml volume in vacuum, the solid material was filtered out, washed with acetic acid, ethyl ether and dried on air. Weight 1.68 g. The above product was stirred with 15 ml of sat NaHCO3 for 1 hour, filtered out, washed with 2×10 ml of water, dissolved in THF/water (10:1) mixture and concentrated. The residue was dried in high vacuum for 18 hours to give 2-(1-Isopropyl-1H-1,2,4-triazol-5-yl)-5,6-dihydroimidazo[1,2-d]pyrido[3,4-f][1,4]oxazepin-9(10H)-one. Yield 1.12 g (45%). M/z 313.1, calc. 312.13. 1H NMR (400 MHz, DMSO) δ 11.79 (s, 1H), 8.41 (s, 1H), 7.89 (s, 1H), 7.82 (s, 1H), 5.84 (s, 1H), 5.78 (dt, J=13.2, 6.6, 1H), 4.57-4.51 (m, 2H), 4.50-4.45 (m, 2H), 1.45 (d, J=6.6, 6H)

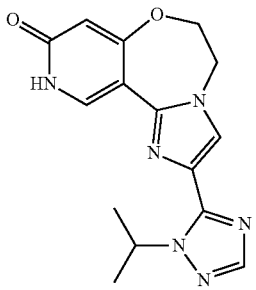 [SMILES: CC(C)n1ncnc1-c1cn2c(n1)-c1c[nH]c(=O)cc1OCC2]

Sodium hydride (192 mg (4.80 mmol) of 60% suspension of in mineral oil) was added to a suspension of 600 mg (1.92 mmol) of 2-(1-isopropyl-1H-1,2,4-triazol-5-yl)-5,6-dihydroimidazo[1,2-d]pyrido[3,4-f][1,4]oxazepin-9(10H)-one in 5.0 ml of dimethylformamide and the mixture was heated at 45° C. for 1 hour. N-Phenylbis(trifluoromethanesulphonimide) (1373 mg, 3.842 mmol) was added and the above reaction mixture was heated at 45° C. for 20 hours. The mixture was partitioned between ethyl acetate and 5% citric acid, the organic extracts were washed with water (×2), brine, dried over MgSO4 and concentrated. The residue was purified on a 12 g silica column eluting 2-(1-isopropyl-1H-1,2,4-triazol-5-yl)-5,6-dihydroimidazo[1,2-d]pyrido[3,4-f][1,4]oxazepin-9-yl trifluoromethanesulfonate with 4% MeOH in DCM. Yield 560 mg (66%). M/z 445.2, calc. 444.08

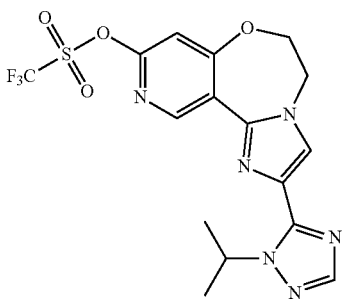 [SMILES: CC(C)n1ncnc1-c1cn2c(n1)-c1cnc(OS(=O)(=O)C(F)(F)F)cc1OCC2]

A mixture of 134 mg (0.30 mmol) of 2-(1-isopropyl-1H-1,2,4-triazol-5-yl)-5,6-dihydroimidazo[1,2-d]pyrido[3,4-f][1,4]oxazepin-9-yl trifluoromethanesulfonate, (R)-2,5-dihydro-1H-pyrrole-2-carboxamide (84.1 mg, 0.750 mmol) and N,N-diisopropylethylamine (61.0 uL, 0.350 mmol) in N,N-Dimethylacetamide (3.0 mL, 32 mmol) was heated for 18 hours at 80° C. The mixture was concentrated in high vacuum, the residue triturated with 5% aqueous citric acid. The precipitate was filtered out, washed with aq. citric acid, water, dried in vacuum and purified by RP HPLC (acetonitrile gradient) to give 388. Yield 28 mg. M/z 407.2, calc. 406.19. 1H NMR (400 MHz, DMSO) δ 9.08 (s, 1H), 7.88 (s, 1H), 7.84 (s, 1H), 7.38 (s, 1H), 6.98 (s, 1H), 6.13 (dd, J=6.2, 1.9, 1H), 6.02-5.88 (m, 3H), 4.97 (s, 1H), 4.52 (dd, J=9.3, 7.1, 4H), 4.39-4.18 (m, 2H), 1.48 (dd, J=6.6, 2.5, 6H)

Example 389

(2S)-1-(2-(1-isopropyl-1H-1,2,4-triazol-5-yl)-5,6-dihydroimidazo[1,2-d]pyrido[3,4-f][1,4]oxazepin-9-yl)-2,5-dihydro-1H-pyrrole-2-carboxamide 389

Following the procedures in Example 388, 2-(1-isopropyl-1H-1,2,4-triazol-5-yl)-5,6-dihydroimidazo[1,2-d]pyrido[3,4-f][1,4]oxazepin-9-yl trifluoromethanesulfonate and (S)-2,5-dihydro-1H-pyrrole-2-carboxamide were reacted to give 389. M/z 407.2, calc. 406.19. 1H NMR (400 MHz, DMSO) δ 9.08 (s, 1H), 7.88 (s, 1H), 7.84 (s, 1H), 7.38 (s, 1H), 6.98 (s, 1H), 6.13 (dd, J=6.2, 1.9, 1H), 6.02-5.88 (m, 3H), 4.97 (s, 1H), 4.52 (dd, J=9.3, 7.1, 4H), 4.39-4.18 (m, 2H), 1.48 (dd, J=6.6, 2.5, 6H)

Example 390

(5-(9-(pyrrolidin-1-yl)-5,6-dihydroimidazo[1,2-d]pyrido[3,4-f][1,4]oxazepin-2-yl)-1-(2,2,2-trifluoroethyl)-1H-1,2,4-triazol-3-yl)methanol 390

(5-(9-chloro-5,6-dihydroimidazo[1,2-d]pyrido[3,4-f][1,4]oxazepin-2-yl)-1-(2,2,2-trifluoroethyl)-1H-1,2,4-triazol-3-yl)methanol 387 was reacted with pyrrolidine to give 390 (13 mg) as a colorless solid. LCMS: 436.1. 1H NMR (400 MHz, DMSO) δ 9.05 (s, 1H), 7.93 (s, 1H), 5.95 (s, 1H), 5.84 (q, J=8.9 Hz, 2H), 5.32 (t, J=6.1 Hz, 1H), 4.50 (m, 4H), 4.45 (d, J=6.0 Hz, 2H), 3.41 (m, 4H), 1.95 (m, 4H)

Example 391

(2S)-1-(2-(1-(3,5-difluorophenyl)-3-methyl-1H-1,2,4-triazol-5-yl)-5,6-dihydroimidazo[1,2-d]pyrido[3,4-f][1,4]oxazepin-9-yl)pyrrolidine-2-carboxamide 391

(S)-1-(2-Iodo-4,5-dihydro-6-oxa-1,3a,9-triaza-benzo[e]azulen-8-yl)-pyrrolidine-2-carboxylic acid amide with acetamidine hydrochloride and 3,5-difluorophenylhydrazine hydrochloride were reacted following Example 420. The crude product was purified by reverse phase HPLC to give 391 (13 mg, 11% yield). LCMS: 493.2. 1H NMR (400 MHz, DMSO) δ 8.58 (s, 1H), 7.82 (s, 1H), 7.45 (m, 3H), 7.32 (s, 1H), 6.91 (s, 1H), 5.87 (s, 1H), 4.45 (m, 4H), 4.25 (d, J=7.8 Hz, 1H), 3.59 (m, 1H), 3.42-3.31 (m, 1H), 2.34 (s, 3H), 2.22-2.09 (m, 1H), 2.00-1.86 (m, 3H).

Example 392

(2S)-2-(2-(1-isopropyl-1H-1,2,4-triazol-5-yl)-5,6-dihydroimidazo[1,2-d]pyrido[3,4-f][1,4]oxazepin-9-ylamino)propanamide 392

A solution containing 9-chloro-2-(1-isopropyl-1H-1,2,4-triazol-5-yl)-5,6-dihydroimidazo[1,2-d]pyrido[3,4-f][1,4]oxazepine 317 (0.1 g, 0.3 mmol), prepared according to Example 377, and L-alaninamide HCl (0.15 g, 1.21 mmol) in N,N-dimethylacetamide (1 mL) was heated at 90° C. for 16 h. The crude reaction mixture was directly purified by rp-HPLC to provide 8 mg (7% yield) of 392. MS(ESI+) m/z 383.1 (M+H+), calcd. 383.2. 1H NMR (400 MHz, DMSO) δ 8.99 (s, 1H), 7.88 (s, 1H), 7.81 (s, 1H), 7.30 (s, 1H), 6.90 (s, 1H), 6.81 (d, J=7.4 Hz, 1H), 6.12 (s, 1H), 5.92 (dt, J=13.1, 6.5 Hz, 1H), 4.47 (q, J=5.8 Hz, 4H), 4.37-4.21 (m, 1H), 1.47 (dd, J=6.6 Hz, 6H), 1.25 (d, J=7.0 Hz, 3H)

Example 393

(2S)-1-(2-(1-isopropyl-1H-1,2,4-triazol-5-yl)-5,6-dihydroimidazo[1,2-d]pyrido[3,4-f][1,4]oxazepin-9-yl)-3,3-dimethylpyrrolidine-2-carboxamide 393

Following the procedures of Example 388, 2-(1-isopropyl-1H-1,2,4-triazol-5-yl)-5,6-dihydroimidazo[1,2-d]pyrido[3,4-f][1,4]oxazepin-9-yl trifluoromethanesulfonate and (S)-3,3-dimethylpyrrolidine-2-carboxamide were reacted to give 393. M/z 437.2, calc. 436.23. 1H NMR (400 MHz, DMSO) δ 9.05 (s, 1H), 7.88 (s, 1H), 7.82 (s, 1H), 7.40 (s, 1H), 6.97 (s, 1H), 5.95 (dd, J=14.5, 7.9, 2H), 4.49 (dd, J=14.6, 5.6, 4H), 3.90 (s, 1H), 3.63 (t, J=8.5, 1H), 3.43 (d, J=7.8, 1H), 1.96 (dd, J=21.1, 9.3, 1H), 1.68 (dd, J=11.9, 5.8, 1H), 1.48 (dd, J=6.6, 3.6, 6H), 1.08 (d, J=6.9, 6H)

Example 394

(5-(9-(dimethylamino)-5,6-dihydroimidazo[1,2-d]pyrido[3,4-f][1,4]oxazepin-2-yl)-1-(2,2,2-trifluoroethyl)-1H-1,2,4-triazol-3-yl)methanol 394

(5-(9-chloro-5,6-dihydroimidazo[1,2-d]pyrido[3,4-f][1,4]oxazepin-2-yl)-1-(2,2,2-trifluoroethyl)-1H-1,2,4-triazol-3-yl)methanol 387 was reacted with dimethylamine-HCl to give 394 (11 mg) as a colorless solid. LCMS: 410.1. 1H NMR (400 MHz, DMSO) δ 9.06 (s, 1H), 7.94 (s, 1H), 6.13 (s, 1H), 5.84 (q, J=8.9 Hz, 2H), 5.32 (t, J=6.1 Hz, 1H), 4.50 (m, 4H), 4.45 (d, J=6.0 Hz, 2H), 3.05 (s, 6H)

Example 395

(2S,3S)-3-hydroxy-1-(2-(1-isopropyl-3-methyl-1H-1,2,4-triazol-5-yl)-5,6-dihydroimidazo[1,2-d]pyrido[3,4-f][1,4]oxazepin-9-yl)pyrrolidine-2-carboxamide 395

Following the procedures of Example 339, 2-(2-isopropyl-5-methyl-2H-[1,2,4]triazol-3-yl)-4,5-dihydro-6-oxa-1,3a,9-triaza-benzo[e]azulen-8-ol and 3-trans-hydroxy-1-prolinamide were reacted and the crude product recrystallised from Industrial Methylated Spirits (IMS) to give 395 as a white solid (63 mg, 39%). LCMS: RT=2.23 min, [M+H]+ 439. ¹H NMR 400 MHz (DMSO-d6) δ: 9.07 (1 H, s), 7.80 (1 H, s), 7.38 (1 H, br), 7.02 (1 H, br), 5.97 (1 H, s), 5.91-5.90 (1 H, m), 5.27 (1 H, d, J=3.77 Hz), 4.50 (5 H, m), 4.35 (1 H, t, J=5.08 Hz), 4.27 (2 H, m), 3.65 (1 H, m), 2.25 (3 H, s), 2.07 (1 H, m), 1.89 (1 H, m), 1.46 (6 H, dd, J=6.60, 3.78 Hz)

Example 396

(2S,3R)-3-hydroxy-1-(2-(1-isopropyl-3-methyl-1H-1,2,4-triazol-5-yl)-5,6-dihydroimidazo[1,2-d]pyrido[3,4-f][1,4]oxazepin-9-yl)pyrrolidine-2-carboxamide 396

Following the procedures of Example 339, 2-(2-isopropyl-5-methyl-2H-[1,2,4]triazol-3-yl)-4,5-dihydro-6-oxa-1,3a,9-triaza-benzo[e]azulen-8-ol and 3-cis-hydroxy-1-prolinamide were reacted and the crude product recrystallised from IMS then triturated in hot IMS to give 396 as a white solid (37 mg, 23%). LCMS: RT=2.29 min, [M+H]+ 439. ¹H NMR 400 MHz (DMSO-d6) δ: 9.04 (1 H, s), 7.78 (1 H, s), 7.17 (1 H, br), 6.91 (1 H, br), 5.91 (1 H, s), 5.88 (1 H, m), 5.22 (1 H, d, J=4.70 Hz), 4.47 (4 H, m), 4.24 (1 H, m), 3.64 (1 H, m), 3.37 (1 H, m), 2.24 (3 H, s), 2.07 (2 H, m), 2.02 (1 H, m), 1.44 (6 H, dd, J=6.59, 3.11 Hz)

Example 397

(2S,3R)-3-hydroxy-1-(2-(1-isopropyl-1H-1,2,4-triazol-5-yl)-5,6-dihydroimidazo[1,2-d]pyrido[3,4-f][1,4]oxazepin-9-yl)pyrrolidine-2-carboxamide 397

Following the procedures of Example 339, 2-(2-isopropyl-2H-[1,2,4]triazol-3-yl)-4,5-dihydro-6-oxa-1,3a,9-triaza-benzo[e]azulen-8-ol from Example 93 and 3-cis-hydroxy-1-prolinamide were reacted and the crude product subjected to RPHPLC (C18 column, gradient 15 to 55% methanol in water+0.1% HCO2H) to give 397 as a white powder (11 mg, 6%). LCMS: RT=2.28 min, [M+H]+ 425. ¹H NMR 400 MHz (DMSO-d6) δ: 9.08 (1 H, s), 7.91 (1 H, d, J=0.63 Hz), 7.85 (1 H, s), 7.20 (1 H, br), 6.94 (1 H, br), 6.00-5.98 (1 H, m), 5.94 (1 H, s), 5.25 (1 H, d, J=4.81 Hz), 4.51-4.50 (4 H, m), 4.47 (1 H, m), 4.27 (1 H, m), 3.68 (1 H, m), 3.41 (1 H, m), 2.09-2.08 (1 H, m), 2.04-2.01 (1 H, m), 1.50 (6 H, dd, J=6.59, 3.26 Hz)

Example 398

(2S,3S)-3-hydroxy-1-(2-(1-isopropyl-1H-1,2,4-triazol-5-yl)-5,6-dihydroimidazo[1,2-d]pyrido[3,4-f][1,4]oxazepin-9-yl)pyrrolidine-2-carboxamide 398

Following the procedures of Example 339, 2-(2-isopropyl-2H-[1,2,4]triazol-3-yl)-4,5-dihydro-6-oxa-1,3a,9-triaza-benzo[e]azulen-8-ol from Example 93 and 3-trans-hydroxy-1-prolinamide were reacted and the crude product subjected to RPHPLC (C18 column, gradient 15 to 55% methanol in water+0.1% HCO2H) to give 398 as a white powder (63 mg, 39%). LCMS: RT=2.20 min, [M+H]+ 425. ¹H NMR 400 MHz (DMSO-d6) δ: 9.09 (1 H, s), 7.91 (1 H, d, J=0.63 Hz), 7.86 (1 H, s), 7.40 (1 H, br), 7.04 (1 H, br), 5.99 (1 H, m), 5.89 (1 H, s), 5.29 (1 H, d, J=3.76 Hz), 4.53 (4 H, m), 4.29 (1 H, m), 4.21 (1 H, br), 3.66 (1 H, d, J=m) 3.50 (1 H, m), 2.13-2.02 (1 H, m), 1.91 (1 H, dd, J=12.83, 6.39 Hz), 1.50 (6 H, dd, J=6.59, 3.95 Hz)

Example 399

(2S)-1-(2-(3-methyl-1-(2,2,2-trifluoroethyl)-1H-1,2,4-triazol-5-yl)-5,6-dihydroimidazo[1,2-d]pyrido[3,4-f][1,4]oxazepin-9-yl)pyrrolidine-2-carboxamide 399

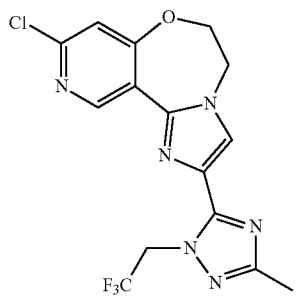 [SMILES: Cc1nc(-c2cn3c(n2)-c2cnc(Cl)cc2OCC3)n(CC(F)(F)F)n1]

Following the procedures of Example 378, 8-Chloro-4,5-dihydro-6-oxa-1,3a,9-triaza-benzo[e]azulene-2-carboxylic acid 1-dimethylamino-methylideneamide was reacted with trifluoroethylhydrazine to give 8-Chloro-2-[5-methyl-2-(2,2,2-trifluoro-ethyl)-2H-[1,2,4]triazol-3-yl]-4,5-dihydro-6-oxa-1,3a,9-triaza-benzo[e]azulene (MS(ESI+) 385.1/387.1) which was reacted with L-prolineamide to give 399. MS(ESI+) 463.2. 1H NMR (400 MHz, DMSO) δ 9.02 (s, 1H), 7.92 (s, 1H), 7.33 (s, 1H), 6.91 (s, 1H), 5.94 (s, 1H), 5.86-5.72 (m, 2H), 4.55-4.54 (m, 4H), 4.35-4.26 (m, 1H), 3.65-3.56 (m, 1H), 3.43-3.35 (m, 1H), 2.28 (s, 3H), 2.22-2.10 (m, 1H), 2.04-1.90 (m, 3H)

Example 400

(2S,4R)-4-fluoro-1-(2-(1-isopropyl-3-methyl-1H-1,2,4-triazol-5-yl)-5,6-dihydroimidazo[1,2-d]pyrido[3,4-f][1,4]oxazepin-9-yl)pyrrolidine-2-carboxamide 400

Following the procedures of Example 339, 2-(2-isopropyl-5-methyl-2H-[1,2,4]triazol-3-yl)-4,5-dihydro-6-oxa-1,3a,9-triaza-benzo[e]azulen-8-ol and 4-trans-fluoro-L-prolinamide were reacted and the crude product recrystallised from IMS to give 400 as a white solid (53 mg, 33%). LCMS: RT=2.77 min, [M+H]+ 441. ¹H NMR 400 MHz (DMSO-d6) δ: 9.01 (1 H, s), 7.75 (1 H, s), 7.51 (1 H, s), 7.00 (1 H, s), 5.96 (1 H, s), 6.00-5.66 (1 H, m), 5.46 (1 H, s), 5.33 (1 H, s), 4.45-4.44 (4 H, m), 4.34 (1 H, t, J=8.00 Hz), 3.86 (1 H, s), 3.71 (1 H, ddd, J=36.66, 12.73, 3.36 Hz), 2.53-2.52 (1 H, m), 2.20 (3 H, s), 1.40 (6 H, dd, J=6.59, 2.53 Hz)

Example 401

(2S,4R)-4-fluoro-1-(2-(1-isopropyl-1H-1,2,4-triazol-5-yl)-5,6-dihydroimidazo[1,2-d]pyrido[3,4-f][1,4]oxazepin-9-yl)pyrrolidine-2-carboxamide 401

Following the procedures of Example 339, 2-(2-isopropyl-5-methyl-2H-[1,2,4]triazol-3-yl)-4,5-dihydro-6-oxa-1,3a,9-triaza-benzo[e]azulen-8-ol and 4-trans-fluoro-L-prolinamide were reacted and the crude product recrystallised from IMS to give a white solid. The mother liquors were concentrated in vacuo and the residue subjected to flash chromatography (SiO2, gradient 0 to 10% methanol in DCM) and pure products combined to give 401 as a white solid (45 mg, 28%). LCMS: RT=2.80 min, [M+H]+=427. ¹H NMR 400 MHz (DMSO-d6) δ: 9.02 (1 H, s), 7.84 (1 H, d, J=0.63 Hz), 7.80 (1 H, s), 7.51 (1 H, s), 7.00 (1 H, s), 5.97 (1 H, s), 5.90-5.89 (1 H, m), 5.46 (1 H, s), 5.33 (1 H, s), 4.50-4.43 (4 H, m), 4.34 (1 H, t, J=8.09 Hz), 3.73-3.72 (1 H, m), 2.53-2.52 (1 H, m), 2.13-2.12 (1 H, m), 1.43 (6 H, dd, J=6.59, 2.68 Hz).

Example 402

(2S)-1-(2-(1-isopropyl-1H-1,2,4-triazol-5-yl)-5,6-dihydroimidazo[1,2-d]pyrido[3,4-f][1,4]oxazepin-9-yl)-2-methylpyrrolidine-2-carboxamide 402

Following the procedures for Examples 339 and 408, 2-(2-isopropyl-5-methyl-2H-[1,2,4]triazol-3-yl)-4,5-dihydro-6-oxa-1,3a,9-triaza-benzo[e]azulen-8-ol and (S)-2-methyl-pyrollidine-2-carboxylic acid amide were reacted. The crude product was passed down a Isolute SCX-2 column, eluting with methanol then 2M NH3 in methanol. The basic fractions were concentrated in vacuo and the resultant residue subjected to reverse phase HPLC (C18 column, gradient 15 to 75% Methanol in water+0.1% HCO2H). The appropriate fractions were evaporated to dryness, passed down an Isolute NH2 column, eluting with methanol then further triturated in diethyl ether to give 402 as a white solid. LCMS: RT=2.79 min, [M+H]+=423. ¹H NMR 400 MHz (CD3OD) δ: 9.14 (1 H, s), 7.93 (1 H, s), 7.69 (1 H, s), 6.05 (1 H, s), 5.99 (1 H, m), 4.51-4.50 (4 H, m), 3.70 (1 H, m), 3.57 (1 H, m), 3.50 (1 H, m), 2.36-2.33 (1 H, m), 2.10-2.08 (2 H, m), 1.63 (3 H, s), 1.56 (6 H, dd, J=6.63, 2.34 Hz)

Example 403

1-isopropyl-4-(2-(1-isopropyl-1H-1,2,4-triazol-5-yl)-5,6-dihydrobenzo[f]imidazo[1,2-d][1,4]oxazepin-9-yl)piperidine-3-carboxamide 403

Step 1: 1-Isopropyl-4-[2-(2-isopropyl-2H-[1,2,4]triazol-3-yl)-4,5-dihydro-6-oxa-1,3a-diaza-benzo[e]azulen-8-yl]-2,3,6-tetrahydro-pyridine-3-carboxylic acid amide

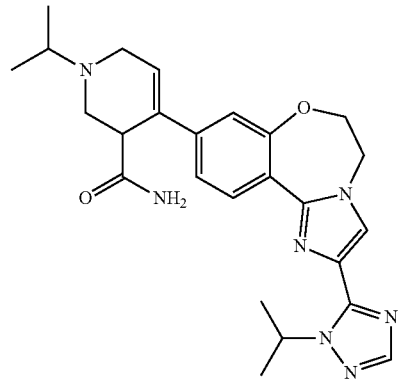 [SMILES: CC(C)N1CC=C(c2ccc3c(c2)OCCn2cc(-c4ncnn4C(C)C)nc2-3)C(C(N)=O)C1]

To a solution of from 4-[2-(2-isopropyl-2H[1,2,4]triazol-3-yl)-4,5-dihydro-6-oxa-1,3a-diaza-benzo[e]azulen-8-yl]-1,2,5,6-tetrahydro-pyridine-3-carboxylic acid amide (0.40 g, 0.87 mmol) in DCM (2 mL) and methanol (2 mL) over molecular sieves (4 Å) was added acetone (0.26 mL, 3.48 mmol) and acetic acid (50 µl). The reaction mixture was stirred at RT for 1 h before sodium triacetoxyborohydride (0.73 g, 3.48 mmol) was added. The reaction mixture was stirred at RT for 48 h. Further quantities of acetone (0.26 mL, 3.48 mmol) and sodium triacetoxyborohydride (0.73 g, 3.48 mmol) were added and the reaction mixture stirred at RT for 16 h. The reaction mixture was diluted with saturated aqueous sodium bicarbonate solution and extracted with 10% methanol in DCM (3×30 mL). The combined organic extracts were dried (Na2SO4) and concentrated in vacuo. The resultant residue was subjected to flash chromatography (SiO2, gradient 0 to 10% methanol in DCM) to give 1-Isopropyl-4-[2-(2-isopropyl-2H-[1,2,4]triazol-3-yl)-4,5-dihydro-6-oxa-1,3a-diaza-benzo[e]azulen-8-yl]-2,3,6-tetrahydro-pyridine-3-carboxylic acid amide (153 mg, 38%). ¹H NMR 300 MHz (CDCl3) δ: 8.48 (1 H, d, J=8.49 Hz), 7.87 (1 H, s), 7.84 (1H, br, s), 7.63 (1 H, s), 7.35 (1 H, dd, J=8.52, 1.97 Hz), 7.24 (1H, s), 6.28 (1H, m), 6.00 (1 H, m), 5.20 (1H, br, m), 4.48-4.46 (4 H, m), 3.51 (1 H, m), 3.15 (1H, m), 2.85 (1H, m), 2.88 (1H, m), 2.65 (1H, m), 1.59 (6 H, dd, J=6.70, 5.29 Hz), 1.12 (6 H, dd, J=6.53, 2.65 Hz).

Step 2

To a solution of 1-isopropyl-4-[2-(2-isopropyl-2H-[1,2,4]triazol-3-yl)-4,5-dihydro-6-oxa-1,3a-diaza-benzo[e]azulen-8-yl]-1,2,5,6-tetrahydro-pyridine-3-carboxylic acid amide (153 mg, 0.33 mmol) in IMS (denatured ethanol) (10 mL) was added platinum (IV) oxide (15 mg, 0.06 mmol). The reaction mixture was heated at 50° C. under an atmosphere of hydrogen. The reaction mixture was cooled to RT, filtered through Celite® and the filtrate concentrated in vacuo. The resultant residue was subjected to flash chromatography (SiO2, gradient 10 to 20% methanol in DCM) to give 403 (80 mg, 52%). LCMS: RT=2.61 min, [M+H]+=464. $^1$H NMR 400 MHz (DMSO-d6) δ: 8.38 (1 H, d, J=8.33 Hz), 8.15 (1 H, s), 8.04 (1 H, s), 7.04 (1 H, dd, J=8.35, 1.82 Hz), 6.89 (1 H, d, J=1.72 Hz), 5.86 (1 H, m), 4.57-4.48 (4 H, m), 3.57 (2 H, t, J=12.74 Hz), 3.42 (1 H, m), 3.31 (1 H, m), 3.25 (1 H, m), 3.22 (1 H, m), 3.04 (1 H, s), 2.60 (1 H, d, J=13.63 Hz), 1.96 (1 H, s), 1.50 (6 H, dd, J=6.59, 3.63 Hz), 1.30 (3H, d, J=6.70 Hz), 1.22 (3 H, d, J=6.70 Hz)

Example 404

2-(2-(1-isopropyl-1H-1,2,4-triazol-5-yl)-5,6-dihydroimidazo[1,2-d]pyrido[3,4-f][1,4]oxazepin-9-ylamino)acetamide 404

Following the procedure for Example 339, 2-(2-isopropyl-2H-[1,2,4]triazol-3-yl)-4,5-dihydro-6-oxa-1,3a,9-triaza-benzo[e]azulen-8-ol from Example 93 and glycinamide hydrochloride salt in NMP were heated at 85° C. for 20 h. The reaction mixture was cooled and loaded onto an Isolute SCX-2 cartridge, washed with methanol and eluted with 2M ammonia in methanol and appropriate fractions concentrated in vacuo. The resultant residue was subjected to flash chromatography (SiO2, gradient 0 to 10% 2M ammonia in methanol in DCM). The solid was recrystallised from methanol to give 404 as a white solid (19 mg, 8%). LCMS: RT=2.14 min, [M+H]+=369. $^1$H NMR 400 MHz (DMSO-d6) δ: 9.01 (1 H, s), 7.90 (1 H, d, J=0.63 Hz), 7.82 (1 H, s), 7.32 (1 H, br, s), 7.01 (1 H, br, s), 6.11 (1 H, s), 5.97-5.88 (1 H, m), 4.49-4.48 (4 H, m), 3.84 (2 H, d, J=4.26 Hz), 1.48 (6 H, d, J=6.60 Hz)

Example 405

(2S)-1-(2-(1-isopropyl-1H-1,2,4-triazol-5-yl)-5,6-dihydroimidazo[1,2-d]pyrido[3,4-f][1,4]oxazepin-9-yl)-N-methylpyrrolidine-2-carboxamide 405

Following the procedures of Example 388, 2-(1-isopropyl-1H-1,2,4-triazol-5-yl)-5,6-dihydroimidazo[1,2-d]pyrido[3,4-f][1,4]oxazepin-9-yltrifluoromethanesulfonate and (S)—N-methylpyrrolidine-2-carboxamide were reacted to give 405. M/z 423.2, calc. 422.22. 1H NMR (400 MHz, DMSO) δ 9.06 (s, 1H), 7.88 (s, 1H), 7.83 (s, 1H), 7.74 (d, J=4.3, 1H), 5.95 (p, J=6.7, 2H), 4.58-4.41 (m, 4H), 4.35 (d, J=8.5, 1H), 3.67-3.57 (m, 1H), 3.41-3.33 (m, 1H), 2.57 (d, J=4.6, 3H), 2.15 (dd, J=10.8, 7.7, 1H), 1.94 (d, J=6.6, 3H), 1.47 (dd, J=6.6, 2.4, 6H)

Example 406

(2S,3S)-1-(2-(1-isopropyl-1H-1,2,4-triazol-5-yl)-5,6-dihydroimidazo[1,2-d]pyrido[3,4-f][1,4]oxazepin-9-yl)-3-methylpyrrolidine-2-carboxamide 406

Following the procedures of Example 388, 2-(1-isopropyl-1H-1,2,4-triazol-5-yl)-5,6-dihydroimidazo[1,2-d]pyrido[3,4-f][1,4]oxazepin-9-yltrifluoromethanesulfonate and (2S,3S)-3-methylpyrrolidine-2-carboxamide were reacted to give 406. M/z 432.2, calc., calc. 422.22. 1H NMR (400 MHz, DMSO) δ 9.05 (s, 1H), 7.88 (s, 1H), 7.82 (s, 1H), 7.36 (s, 1H), 6.91 (s, 1H), 6.57 (s, 1H), 6.01-5.88 (m, 2H), 4.49 (d, J=8.8, 4H), 3.88 (s, 1H), 3.55 (t, J=6.7, 2H), 2.32 (dd, J=10.3, 6.4, 1H), 2.18-2.09 (m, 1H), 1.59 (dd, J=12.0, 5.7, 1H), 1.48 (dd, J=6.6, 2.9, 6H), 1.10 (d, J=6.9, 3H)

Example 407

(2S,4R)-1-(2-(1-isopropyl-1H-1,2,4-triazol-5-yl)-5,6-dihydroimidazo[1,2-d]pyrido[3,4-f][1,4]oxazepin-9-yl)-4-methoxypyrrolidine-2-carboxamide 407

Following the procedure for Examples 339 and 408, 2-(2-isopropyl-5-methyl-2H-[1,2,4]triazol-3-yl)-4,5-dihydro-6-oxa-1,3a,9-triaza-benzo[e]azulen-8-ol and (2S,4R)-4-methoxy-pyrrolidine-2-carboxylic acid amide were reacted. The reaction mixture was diluted with water passed down an SCX-2 cartridge, washed with DCM, ethyl acetate and methanol and products eluted with 2M ammonia in methanol. Appropriate fractions were concentrated in vacuo and the resultant residue was triturated in diethyl ether and methanol, filtered and dried to give 407 as beige solid (45 mg, 32%). LCMS: RT=2.60 min, [M+H]+=439. $^1$H NMR 400 MHz (CDCl3) δ: 9.27 (1 H, s), 7.83 (1 H, s), 7.57 (1 H, s), 6.79 (1 H, br, s), 6.00 (1 H, s), 5.98 (1 H, m), 5.29 (1 H, br, s), 4.65 (1 H, dd, J=8.28, 4.87 Hz), 4.49-4.47 (2 H, m), 4.39-4.34 (2 H, m), 4.23 (1 H, t, J=5.53 Hz), 3.74 (1 H, dd, J=10.34, 5.70 Hz), 3.51-3.46 (1 H, m), 3.36 (3 H, s), 2.52-2.51 (1 H, m), 2.24-2.23 (1 H, m), 1.55-1.54 (6 H, m)

Example 408

(2S,3S)-1-(2-(1-isopropyl-1H-1,2,4-triazol-5-yl)-5,6-dihydroimidazo[1,2-d]pyrido[3,4-f][1,4]oxazepin-9-yl)-3-methoxypyrrolidine-2-carboxamide 408

Step 1: (2S,3S)-2-Carbamoyl-3-methoxy-pyrrolidine-1-carboxylic acid tert-butyl ester

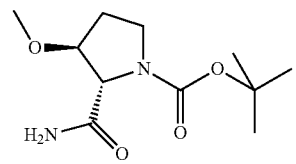 [SMILES: CO[C@H]1CCN(C(=O)OC(C)(C)C)[C@@H]1C(N)=O]

(2S,3S)-3-Methoxy-pyrrolidine-1,2-dicarboxylic acid 1-tert-butyl ester 2-methyl ester (518 mg, 2.0 mmol) was stirred in 7M ammonia in methanol (5 mL) for 4 days. The reaction mixture was concentrated in vacuo and the residue was subjected to flash chromatography (SiO2, gradient 0 to 6% methanol in DCM) to give (2S,3S)-2-Carbamoyl-3-methoxy-pyrrolidine-1-carboxylic acid tert-butyl ester (153 mg, 31%). $^1$H NMR 400 MHz (DMSO-d6) δ: 7.54 (1 H, br, s), 7.09 (1 H, br, s), 4.09-4.00 (1 H, m), 3.78 (1 H, m), 3.47 (1 H, m), 3.26 (3 H, s), 1.93 (3 H, m), 1.37 (9 H, s)

Step 2: (2S,3S)-3-Methoxy-pyrrolidine-2-carboxylic acid amide hydrochloride salt

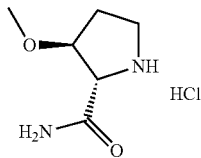

(2S,3S)-2-Carbamoyl-3-methoxy-pyrrolidine-1-carboxylic acid tert-butyl ester (120 mg, 0.49 mmol) was stirred in hydrochloric acid (5 mL, 3M in methanol) and methanol for 4 h. The reaction mixture was concentrated in vacuo and the residue triturated in diethyl ether and methanol to give (2S,3S)-3-Methoxy-pyrrolidine-2-carboxylic acid amide hydrochloride salt as a white solid (69 mg, 38%). $^1$H NMR 400 MHz (DMSO-d6) δ: 8.28 (1 H, br, s), 7.82 (1 H, br, s), 4.23 (1 H, m), 4.11-4.10 (1 H, m), 3.37 (1H, m), 3.35 (3 H, s), 3.19-3.16 (1 H, m), 2.07 (1 H, m), 1.84-1.83 (1 H, m)

Step 3

Following the procedure for Example 339, 2-(2-isopropyl-5-methyl-2H-[1,2,4]triazol-3-yl)-4,5-dihydro-6-oxa-1,3a,9-triaza-benzo[e]azulen-8-ol and (2S,3S)-3-methoxy-pyrrolidine-2-carboxylic acid amide with added triethylamine were reacted. The crude product was washed with water, filtered then triturated in diethyl ether and methanol to give 408 as a white solid (40 mg, 27%). LCMS: RT=2.68 min, [M+H]+=439. $^1$H NMR 400 MHz (CDCl3) δ: 9.31 (1 H, s), 7.86 (1 H, s), 7.59 (1 H, s), 6.99 (1 H, br, s), 6.08 (1 H, s), 6.03 (1 H, m), 5.37 (1 H, br, s), 4.67 (1 H, s), 4.53-4.49 (2 H, m), 4.40-4.39 (2 H, m), 4.29 (1 H, m), 3.62-3.57 (1 H, m), 3.52-3.51 (1 H, m), 3.39 (3 H, s), 2.23 (2 H, m), 1.57 (6 H, dd, J=6.68, 3.32 Hz)

Example 409

(2S)-1-(2-(1-cyclohexyl-1H-1,2,4-triazol-5-yl)-5,6-dihydroimidazo[1,2-d]pyrido[3,4-f][1,4]oxazepin-9-yl)pyrrolidine-2-carboxamide 409

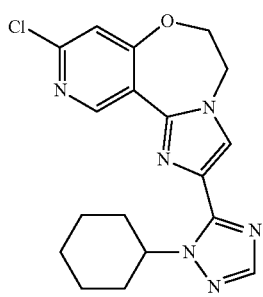 [SMILES: Clc1cc2c(cn1)-c1nc(-c3ncnn3C3CCCCC3)cn1CCO2]

Following the procedures of Example 378, 8-Chloro-4,5-dihydro-6-oxa-1,3a,9-triaza-benzo[e]azulene-2-carboxylic acid 1-dimethylamino-methylideneamide was reacted with cyclohexylhydrazine hydrochloride to give 8-Chloro-2-(2-cyclohexyl-2H-[1,2,4]triazol-3-yl)-4,5-dihydro-6-oxa-1,3a,9-triaza-benzo[e]azulene (MS(ESI+) 371.2/373.2) which was reacted with L-prolineamide to give 409. MS(ESI+) 449.2.

Example 410

(2S)-1-(2-(1-(2-chlorophenyl)-1H-1,2,4-triazol-5-yl)-5,6-dihydroimidazo[1,2-d]pyrido[3,4-f][1,4]oxazepin-9-yl)pyrrolidine-2-carboxamide 410

Following the procedures of Example 378, 8-Chloro-4,5-dihydro-6-oxa-1,3a,9-triaza-benzo[e]azulene-2-carboxylic acid 1-dimethylamino-methylideneamide was reacted with 2-chlorophenylhydrazine hydrochloride to give 8-chloro-2-[2-(2-chloro-phenyl)-2H-[1,2,4]triazol-3-yl]-4,5-dihydro-6-oxa-1,3a,9-triaza-benzo[e]azulene (MS(ESI+) 399.1/401.1) which was reacted with L-prolineamide to give 410. MS(ESI+) 477.1. 1H NMR (400 MHz, DMSO) δ 8.26 (s, 1H), 8.15 (s, 1H), 7.79 (s, 1H), 7.72 (dd, J=8.0, 1.1 Hz, 1H), 7.66-7.52 (m, 3H), 7.29 (br, 1H), 6.91 (br, 1H), 5.83 (s, 1H), 4.45-4.38 (m, 4H), 4.23 (d, J=7.7 Hz, 1H), 3.61-3.53 (s, 1H), 3.40-3.32 (m, 1H), 2.23-2.06 (m, 1H), 2.02-1.84 (m, 3H)

Example 413

(5-(9-(dimethylamino)-5,6-dihydroimidazo[1,2-d]pyrido[3,4-f][1,4]oxazepin-2-yl)-1-isopropyl-1H-1,2,4-triazol-3-yl)methanol 413

8-Chloro-2-iodo-4,5-dihydro-6-oxa-1,3a,9-triaza-benzo[e]azulene with 2-methoxyacetamidine hydrochloride and isopropylhydrazine hydrochloride were reacted following Example 420 to give 8-Chloro-2-(2-isopropyl-5-methoxymethyl-2H-[1,2,4]triazol-3-yl)-4,5-dihydro-6-oxa-1,3a,9-triaza-benzo[e]azulene after collection by filtration (1.42 g, 66% yield)

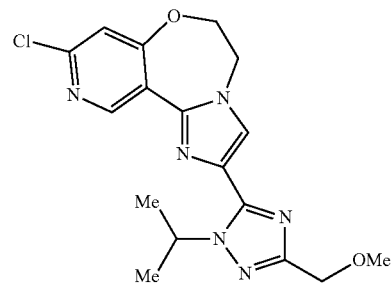 [SMILES: COCc1nc(-c2cn3c(n2)-c2cnc(Cl)cc2OCC3)n(C(C)C)n1]

8-Chloro-2-[5-methoxymethyl-2-(2,2,2-trifluoro-ethyl)-2H-[1,2,4]triazol-3-yl]-4,5-dihydro-6-oxa-1,3a,9-triaza-benzo[e]azulene was reacted with 48% aqueous HBr to give [5-(8-Chloro-4,5-dihydro-6-oxa-1,3a,9-triaza-benzo[e]azulen-2-yl)-1-isopropyl-1H-[1,2,4]triazol-3-yl]-methanol after purification by FCC (CH2Cl2/MeOH), 29% isolated yield.

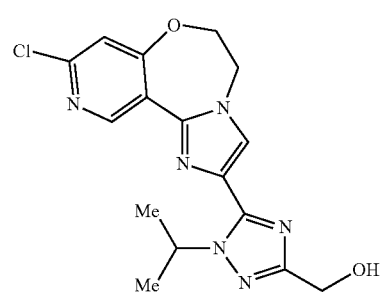 [SMILES: CC(C)n1nc(CO)nc1-c1cn2c(n1)-c1cnc(Cl)cc1OCC2]

[5-(8-Chloro-4,5-dihydro-6-oxa-1,3a,9-triaza-benzo[e]azulen-2-yl)-1-isopropyl-1H-[1,2,4]triazol-3-yl]-methanol was reacted with dimethylamine-HCl to give 413 (10 mg) as a colorless solid. LCMS: 370.2. 1H NMR (400 MHz, DMSO) δ 9.09 (s, 1H), 7.80 (s, 1H), 6.13 (s, 1H), 5.98-5.85 (m, 1H), 5.18 (t, J=6.0 Hz, 1H), 4.56-4.44 (m, 4H), 4.41 (d, J=6.0 Hz, 2H), 3.05 (s, 6H), 1.47 (d, J=6.6 Hz, 6H)

Example 414

4-(2-(1-isopropyl-1H-1,2,4-triazol-5-yl)-5,6-dihydrobenzo[f]imidazo[1,2-d][1,4]oxazepin-9-yl)-1-methyl-1,2,5,6-tetrahydropyridine-3-carboxamide 414

Step 1: 4-Oxo-piperidine-1,3-dicarboxylic acid 1-tert-butyl ester 3-methyl ester

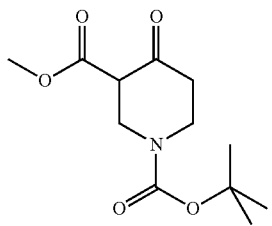 [SMILES: COC(=O)C1CN(C(=O)OC(C)(C)C)CCC1=O]

4-Oxo-piperidin-3-carboxylic acid methyl ester hydrochloride (10 g, 51.7 mmol) in water (60 mL) was cooled to 0° C. and sodium carbonate (6.0 g, 56.8 mmol) added. A solution of di-tert-butyl dicarbonate (11.3 g, 51.7 mmol) in THF (48 mL) was added dropwise over 15 min and the reaction left at 0° C. for 1 hour. Water was added, the mixture extracted with diethyl ether. The combined organic extracts were washed with 10% citric acid then saturated aqueous sodium hydrogen carbonate and then brine, dried (Na2SO4), filtered and concentrated in vacuo to give 4-Oxo-piperidine-1,3-dicarboxylic acid 1-tert-butyl ester 3-methyl ester as a yellow oil (13.42 g, 100%). $^1$H NMR 300 MHz (CDCl3) δ: 4.08 (2 H, s), 3.82 (3 H, s), 3.77 (1H, m), 3.59 (2 H, t, J=5.93 Hz), 2.40 (2 H, t, J=5.87 Hz), 1.50 (9 H, s).

Step 2: 4-Trifluoromethanesulphonyloxy-5,6-dihydro-2H-pyridine-1,3-dicaroxylic acid 1-tert-butyl ester 3-methyl ester

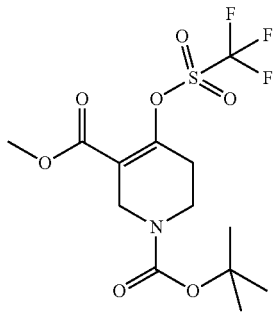 [SMILES: COC(=O)C1=C(OS(=O)(=O)C(F)(F)F)CCN(C(=O)OC(C)(C)C)C1]

A suspension of sodium hydride (0.31 g, 7.8 mmol) in THF (10 mL) at 0° C. was treated with 4-oxo-piperidine-1,3-dicarboxylic acid 1-tert-butyl ester 3-methyl ester (1.0 g, 3.9 mmol) in THF (4 mL) and stirred for 0.5 h. A solution of N-phenyl-bis(trifluoromethanesulphonamide) (1.53 g, 4.3 mmol) in THF (3 mL) was added and the reaction mixture stirred at RT for 18 h. Water was added and the THF removed in vacuo. Ethyl acetate and 10% aqueous sodium carbonate were added, the organic layer separated and then washed with 10% aqueous sodium carbonate, dried (Na2SO4), filtered and then concentrated in vacuo. The resultant residue was subjected to flash chromatography (SiO2, gradient 0 to 20% ethyl acetate in cyclohexane) to give 4-Trifluoromethanesulphonyloxy-5,6-dihydro-2H-pyridine-1,3-dicaroxylic acid 1-tert-butyl ester 3-methyl ester as yellow oil (7.98 g, 91%). $^1$H NMR 300 MHz (CDCl3) δ: 4.28 (2 H, s), 3.84 (3 H, s), 3.63 (2 H, t, J=5.74 Hz), 2.52-2.51 (2 H, m), 1.49 (9 H, s).

Step 3: 4-[2-(2-Isopropyl-2H-[1,2,4]triazol-3-yl)-4,5-dihydro-6-oxa-1,3a-diaza-benzo[e]azulen-8-yl]5,6-dihydro-2H-pyridine-1,3-dicarboxylic acid 1-tert-butyl ester 3-methyl ester

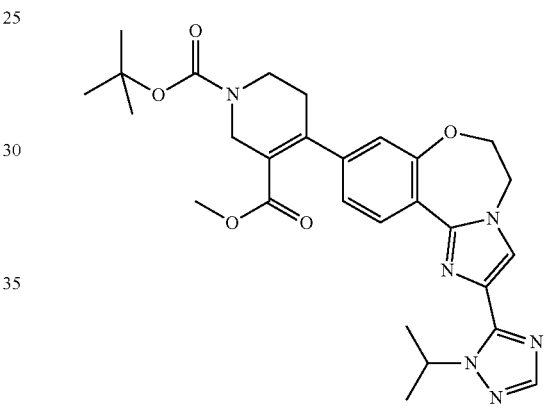

2-(2-Isopropyl-2H-[1,2,4]triazol-3-yl)-8-(4,4,5,5-tetramethyl-[1,3,2]dioxaborolan-2-yl)-4,5-dihydro-6-oxa-1,3a-diaza-benzo[e]azulene (0.20 g, 0.49 mmol), 4-trifluoromethanesulphonyloxy-piperidine-1,3-dicarboxylic acid 1-tert-butyl ester 3-methyl ester (0.29 g, 0.75 mmol), potassium acetate (0.12 g, 1.22 mmol), Pd(dppf)2Cl2.DCM (0.04 g, 0.05 mmol), DME:IMS:water 7:2:1 (5 mL), were sealed in a microwave vial and heated by microwave irradiation at 120° C. for 10 min. The reaction mixture was cooled to RT, water and DCM were added, the organic layer separated, washed with water, dried (Na2SO4), filtered and concentrated in vacuo. The resultant residue was subjected to flash chromatography (SiO2, gradient 0 to 5% methanol in DCM) to give 4-[2-(2-Isopropyl-2H-[1,2,4]triazol-3-yl)-4,5-dihydro-6-oxa-1,3a-diaza-benzo[e]azulen-8-yl]5,6-dihydro-2H-pyridine-1,3-dicarboxylic acid 1-tert-butyl ester 3-methyl ester (239 mg, 91%). $^1$H NMR 300 MHz (CDCl3) δ: 8.49 (1 H, d, J=8.30 Hz), 7.87 (1 H, d, J=0.64 Hz), 7.64 (1 H, s), 6.92 (1 H, dd, J=8.31, 1.80 Hz), 6.84 (1 H, d, J=1.77 Hz), 6.00 (1 H, m), 4.49-4.47 (4 H, m), 4.27 (2 H, s), 3.62 (2 H, t, J=5.69 Hz), 3.57 (2 H, s), 2.50 (3 H, s), 1.59 (6 H, d, J=6.63 Hz), 1.51 (9 H, s).

Step 4: 4-[2-(2-Isopropyl-2H-[1,2,4]triazol-3-yl)-4,5-dihydro-6-oxa-1,3a-diaza-benzo[e]azulen-8-yl]-5,6-dihydro-2H-pyridine-1,3-dicarboxylic acid 1-tert-butyl ester

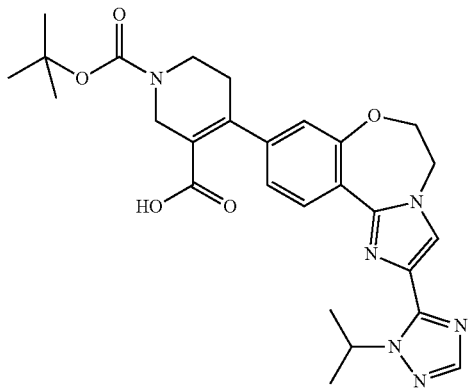 [SMILES: CC(C)n1ncnc1-c1cn2c(n1)-c1ccc(C3=C(C(=O)O)CN(C(=O)OC(C)(C)C)CC3)cc1OCC2]

4-[2-(2-Isopropyl-2H-[1,2,4]triazol-3-yl)-4,5-dihydro-6-oxa-1,3a-diaza-benzo[e]azulen-8-yl]5,6-dihydro-2H-pyridine-1,3-dicarboxylic acid 1-tert-butyl ester 3-methyl ester (0.629 g, 1.18 mmol) and lithium hydroxide monohydrate (4.8 mmol) in THF (4 mL) and water (2 mL) were heated at 60° C. overnight. The reaction mixture was cooled to RT, THF removed in vacuo and the residue acidified to pH 3 with 1M HCl. The resultant solid was filtered off, washed with water and dried. The resultant solid was subjected to flash chromatography (SiO2, gradient 0 to 10% methanol in DCM) to give 4-[2-(2-Isopropyl-2H-[1,2,4]triazol-3-yl)-4,5-dihydro-6-oxa-1,3a-diaza-benzo[e]azulen-8-yl]-5,6-dihydro-2H-pyridine-1,3-dicarboxylic acid 1-tert-butyl ester (0.31 g, 51%). $^1$H NMR 300 MHz (CDCl3) δ: 8.27 (1 H, d, J=8.34 Hz), 7.93 (1 H, s), 7.17 (1 H, s), 7.07 (1H, dd, J=8.31, 1.80 Hz), 6.55 (1 H, s), 6.10 (1 H, m), 4.40 (2 H, m), 4.14 (4 H, m), 3.67 (2 H, m), 2.50 (2H, m), 1.63 (6 H, d, J=6.58 Hz), 1.54 (9 H, s).

Step 5: 5-Carbamoyl-4-[2-(2-isopropyl-2H-[1,2,4]triazol-3-yl)-4,5-dihydro-6-oxa-1,3a-diaza-benzo[e]azulen-8-yl]-3,6-dihydro-2H-pyridine-1-carboxylic acid tert-butyl ester

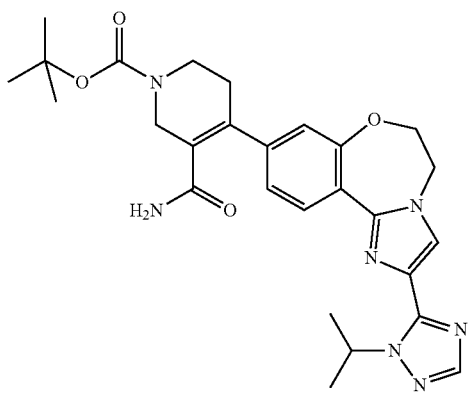 [SMILES: CC(C)n1ncnc1-c1cn2c(n1)-c1ccc(C3=C(C(N)=O)CN(C(=O)OC(C)(C)C)CC3)cc1OCC2]

4-[2-(2-isopropyl-2H[1,2,4]triazol-3-yl)-4,5-dihydro-6-oxa-1,3a-diaza-benzo[e]azulen-8- yl]-5,6-dihydro-2H-pyridine-1,3-dicarboxylic acid 1-tert-butyl ester (0.921 g, 1.77 mmol) was stirred in DMF (7 mL). EDCI (0.407 g, 2.12 mmol), HOBt (0.286 g, 2.12 mmol) and DIPEA (1.55 mL, 8.85 mmol) were added and the reaction stirred at RT for 5 min. Ammonium chloride (0.284 g, 5.31 mmol) was added and the reaction mixture stirred at RT for 18 h. Ethyl acetate and water were added, the organic layer separated and washed with water, dried (MgSO4), filtered and concentrated in vacuo to give 5-Carbamoyl-4-[2-(2-isopropyl-2H-[1,2,4]triazol-3-yl)-4,5-dihydro-6-oxa-1,3a-diaza-benzo[e]azulen-8-yl]-3,6-dihydro-2H-pyridine-1-carboxylic acid tert-butyl ester (0.917 g, 1.76 mmol). LCMS RT=3.13 min, [M+H]+=520

Step 6: 4-[2-(2-Isopropyl-2H[1,2,4]triazol-3-yl)-4,5-dihydro-6-oxa-1,3a-diaza-benzo[e]azulen-8-yl]-1,2,5,6-tetrahydro-pyridine-3-carboxylic acid amide

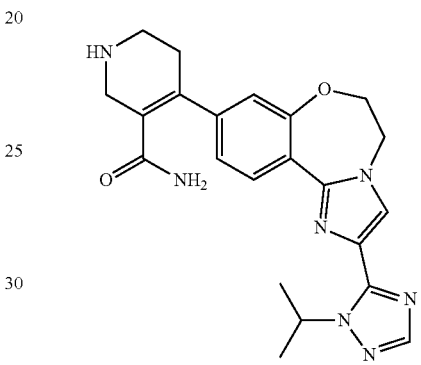

5-Carbamoyl-4-[2-(2-isopropyl-2H[1,2,4]triazol-3-yl)-4,5-dihydro-6-oxa-1,3a-diaza-benzo[e]azulen-8-yl]-3,6-dihydro-2H-pyridine-1-carboxylic acid tert-butyl ester was stirred in TFA (1 mL) and DCM (2 mL) for 2 h. The reaction mixture was concentrated in vacuo and the residue triturated with diethyl ether to give a solid. The solid was then treated with tetra allylammonium carbonate (polymer bound) (1.84 g, 4.68 mmol) in methanol and DCM for 30 min. The resin was filtered off and the filtrate concentrated in vacuo to give 4-[2-(2-Isopropyl-2H[1,2,4]triazol-3-yl)-4,5-dihydro-6-oxa-1,3a-diaza-benzo[e]azulen-8-yl]-1,2,5,6-tetrahydro-pyridine-3-carboxylic acid amide (0.40 g, 82%). $^1$H NMR 300 MHz (CDCl3) δ: 8.52-8.46 (1 H, m), 7.88 (1 H, s), 7.71-7.69 (1 H, m), 7.08 (1 H, dd, J=8.30, 1.82 Hz), 6.98 (1 H, d, J=1.79 Hz), 6.01-6.00 (1 H, m), 4.52-4.47 (4 H, m), 3.75 (2 H, s), 3.15 (2 H, t, J=5.82 Hz), 2.51 (2 H, m), 1.60 (6 H, d, J=6.62 Hz).

Step 7

To a solution of 4-[2-(2-isopropyl-2H[1,2,4]triazol-3-yl)-4,5-dihydro-6-oxa-1,3a-diaza-benzo[e]azulen-8-yl]-1,2,5,6-tetrahydro-pyridine-3-carboxylic acid amide (0.15 g, 0.35 mmol) in DCM (16 mL) and methanol (8 mL) was added formaldehyde (0.053 mL, 37% aq., 0.7 mmol), sodium triacetoxyborohydride (0.11 g, 0.52 mmol) and acetic acid (24 μL, 0.42 mmol). The reaction mixture was stirred at RT for 16 h. Sodium hydrogen carbonate (aq.) and 10% Methanol in DCM were added to the mixture and the organic fraction separated, dried (Na2SO4), filtered and concentrated in vacuo. The resultant residue was subjected to flash chromatography (SiO2, gradient 0 to 10% methanol in DCM) to give 414 (94 mg, 62%). LCMS: RT=2.31 min,

[M+H]+=434. ¹H NMR 400 MHz (DMSO-d6) δ: 8.32 (1 H, d, J=8.35 Hz), 7.92 (1 H, s), 7.91 (1 H, d, J=0.62 Hz), 7.11 (1 H, br, s), 7.08 (1 H, dd, J=8.37, 1.83 Hz), 7.02 (1 H, br, s), 6.98 (1 H, d, J=1.79 Hz), 5.94-5.86 (1 H, m), 4.53-4.46 (4 H, m), 3.15 (2 H, s), 2.61 (2 H, s), 2.46 (2 H, s), 2.35 (3 H, s), 1.48 (6 H, d, J=6.60 Hz)

Example 415

4-(2-(1-isopropyl-1H-1,2,4-triazol-5-yl)-5,6-dihydrobenzo[f]imidazo[1,2-d][1,4]oxazepin-9-yl)-1-methyl-1,2,3,6-tetrahydropyridine-3-carboxamide 415

To a solution of 4-[2-(2-isopropyl-2H[1,2,4]triazol-3-yl)-4,5-dihydro-6-oxa-1,3a-diaza-benzo[e]azulen-8-yl]-1,2,5,6-tetrahydro-pyridine-3-carboxylic acid amide from Example 414 (0.15 g, 0.35 mmol) in DCM (16 mL) and methanol (8 mL) was added formaldehyde (0.053 mL, 37% aq., 0.7 mmol), sodium triacetoxyborohydride (0.11 g, 0.52 mmol) and acetic acid (24 µL, 0.42 mmol). The reaction mixture was stirred at RT for 16 h. Sodium hydrogen carbonate (aqueous) and 10% methanol in DCM were added to the mixture and the organic fraction separated, dried (Na2SO4), filtered and concentrated in vacuo. The resultant residue was subjected to flash chromatography (SiO2, gradient 0 to 10% methanol in DCM) to give the title compound. The product was triturated with diethyl ether, filtered and dried to give the title compound (24 mg, 16%). LCMS: RT=2.39 min, [M+H]+=434. ¹H NMR 400 MHz (DMSO-d6) δ: 8.33 (1 H, d, J=8.48 Hz), 7.92 (1 H, s), 7.91 (1 H, s), 7.32 (1 H, br, s), 7.27 (1 H, dd, J=8.51, 1.92 Hz), 7.11 (1 H, d, J=1.86 Hz), 6.90 (1 H, br, s), 6.35 (1 H, d, J=3.82 Hz), 5.90-5.89 (1 H, m), 4.51-4.49 (4 H, m), 3.53 (1 H, s), 3.31 (1 H, m), 2.97 (1 H, m), 2.85 (1 H, m), 2.64 (1 H, m), 2.33 (3 H, s), 1.48 (6 H, dd, J=6.60, 3.70 Hz)

Example 416

2-(1-isopropyl-1H-1,2,4-triazol-5-yl)-N-methyl-5,6-dihydroimidazo[1,2-d]pyrido[3,4-f][1,4]oxazepin-9-amine 416

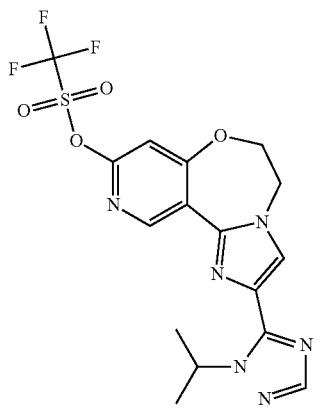 [SMILES: CC(C)N/C(=N\C=N)c1cn2c(n1)-c1cnc(OS(=O)(=O)C(F)(F)F)cc1OCC2]

A solution of trifluoro-methanesulfonic acid 2-(2-isopropyl-2H-[1,2,4]triazol-3-yl)-4,5-dihydro-6-oxa-1,3a,9-triazabenzo[e]azulen-8-yl ester (100 mg, 0.23 mmol) in NMP was treated with 2M methylamine in THF (1.8 mL, 0.9 mmol) and heated at 85° C. for 20 h then diluted with water and stirred for 4 h. The precipitate was collected by filtration and dried in vacuo to give 416 as a white solid (19.5 mg, 28%). LCMS: RT=2.26 min, [M+H]+=326. ¹H NMR 400 MHz (DMSO-d6) δ: 9.02 (1 H, s), 7.88 (1 H, s), 7.80 (1 H, s), 6.70 (1 H, br, m), 5.95 (1 H, s), 5.91-5.90 (1 H, m), 4.47 (4 H, q, J=6.12 Hz), 2.78 (3 H, d, J=4.86 Hz), 1.47 (6 H, d, J=6.60 Hz)

Example 417

(5-(9-(3,3-difluoroazetidin-1-yl)-5,6-dihydroimidazo[1,2-d]pyrido[3,4-f][1,4]oxazepin-2-yl)-1-isopropyl-1H-1,2,4-triazol-3-yl)methanol 417

[5-(8-Chloro-4,5-dihydro-6-oxa-1,3a,9-triaza-benzo[e]azulen-2-yl)-1-isopropyl-1H-[1,2,4]triazol-3-yl]-methanol was reacted with 3,3-difluoroazetidine-HCl to give 417 (23 mg) as a colorless solid. LCMS: 418.1. 1H NMR (400 MHz, DMSO) δ 9.14 (s, 1H), 7.85 (s, 1H), 6.16 (s, 1H), 5.87 (dt, J=13.2, 6.6 Hz, 1H), 5.18 (t, J=6.0 Hz, 1H), 4.60-4.47 (m, 4H), 4.41 (overlapping m, 6H), 1.47 (d, J=6.6 Hz, 6H)

Example 420

2-(3-methyl-1-(2,2,2-trifluoroethyl)-1H-1,2,4-triazol-5-yl)-9-(2-(2-methylbenzyl)pyrrolidin-1-yl)-5,6-dihydroimidazo[1,2-d]pyrido[3,4-f][1,4]oxazepine 420

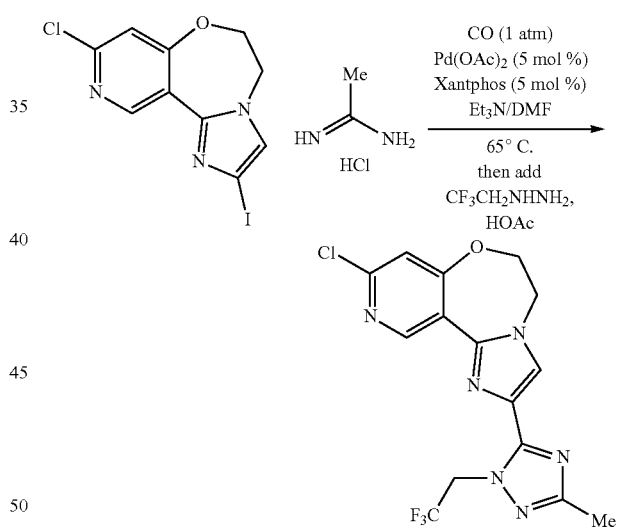

A solution of 8-Chloro-2-iodo-4,5-dihydro-6-oxa-1,3a,9-triaza-benzo[e]azulene (2.00 g, 0.58 mmol) and acetamidine hydrochloride (0.653 g, 0.69 mmol) dissolved in DMF (20 mL) and Et3N (4.0 mL) was treated with 4,5-bis(diphenylphosphino)-9,9-dimethylxanthene (Xantphos, 0.166 g, 0.029 mmol) and Pd(OAc)2 (0.0646 g, 0.029 mmol) under nitrogen atmosphere. The flask was fitted with a balloon of carbon monoxide and the reaction mixture was heated at 65° C. 2 h. After cooling to r.t. a solution of trifluoroethyl hydrazine (70% wt in H2O, 1.12 g, 0.69 mmol) in acetic acid (5 mL) was added. After 3 h at 65° C. the mixture was cooled and dilute with water. 8-Chloro-2-[5-methyl-2-(2,2,2-trifluoro-ethyl)-2H-[1,2,4]triazol-3-yl]-4,5-dihydro-6-oxa-1,3a,9-triaza-benzo[e]azulene was collected by filtration (washed with water and hexanes, dried under vacuum, 1.74 g, 78% yield). 1H NMR (400 MHz, DMSO) δ 9.26 (s, 1H), 8.10 (s, 1H), 7.24 (s, 1H), 5.76 (q, J=8.8 Hz, 2H), 4.71-4.53 (m, 4H), 2.29 (s, 3H)

A 10 mL microwave vial was charged with 8-Chloro-2-[5-methyl-2-(2,2,2-trifluoro-ethyl)-2H-[1,2,4]triazol-3-yl]-4,5-dihydro-6-oxa-1,3a,9-triaza-benzo[e]azulene (85 mg, 0.22 mmol) and 2-(2-Methyl-benzyl)-pyrrolidine (231 mg, 6 eq). 0.5 mL of NMP and 0.5 mL of triethylamine was added. The vial was sealed and heated at 160° C. for 24 h. After cooling to room temperature, the solution was purified directly by reverse phase HPLC (0.1% NH4OH/ACN). The isolated solid was further purified by chiral SFC (AD column, 35% MeOH isocratic) to give 27 mg of one enantiomer and 29 mg of 420 (48% total yield). LCMS: 524.2. 1H NMR (400 MHz, DMSO) δ 9.08 (s, 1H), 9.08 (s, 1H), 7.92 (s, 1H), 7.27-7.06 (m, 4H), 5.99 (s, 1H), 5.80 (q, J=8.9 Hz, 2H), 4.50 (m, 4H), 4.38 (br s, 1H), 3.49 (t, J=8.6 Hz, 1H), 3.15 (d, J=10.0 Hz, 1H), 2.60-2.53 (m, 1H), 2.42 (s, 3H), 2.28 (s, 3H), 2.10-1.89 (m, 2H), 1.81-1.71 (m, 2H)

Example 421

2-(3-methyl-1-(2,2,2-trifluoroethyl)-1H-1,2,4-triazol-5-yl)-9-(2-(piperidin-1-ylmethyl)pyrrolidin-1-yl)-5,6-dihydroimidazo[1,2-d]pyrido[3,4-f][1,4]oxazepine 421

[5-(8-Chloro-4,5-dihydro-6-oxa-1,3a,9-triaza-benzo[e]azulen-2-yl)-1-isopropyl-1H-[1,2,4]triazol-3-yl]-methanol was reacted with was reacted with 1-Pyrrolidin-2-ylmethyl-piperidine to give 421 after reverse phase HPLC (67 mg). LCMS: 542.2

Example 422

2-(1-(2-chlorophenyl)-1H-1,2,4-triazol-5-yl)-N,N-dimethyl-5,6-dihydroimidazo[1,2-d]pyrido[3,4-f][1,4]oxazepin-9-amine 422

Following the procedures of Examples 413 and 420, 9-bromo-2-(1-(2-chlorophenyl)-1H-1,2,4-triazol-5-yl)-5,6-dihydroimidazo[1,2-d]pyrido[3,4-f][1,4]oxazepine and dimethylamine were reacted to give 422. LC/MS(ESI+): m/z 408.1 (M+H)

Example 423

2-(1-isopropyl-3-methyl-1H-1,2,4-triazol-5-yl)-9-(1-methyl-1H-pyrazol-4-yl)-5,6-dihydrobenzo[f]imidazo[1,2-d][1,4]oxazepine 423

A microwave vial was charged with a suspension of 9-bromo-2-(1-isopropyl-3-methyl-1H-1,2,4-triazol-5-yl)-5,6-dihydrobenzo[f]imidazo[1,2-d][1,4]oxazepine 411 (0.239 mg, 0.617 mmol) in 3.0 ml ACN/1.0 mL water. To this suspension was added potassium acetate (182 mg, 1.85 mmol) and 1-methylpyrazole boronic acid pinacol ester (154 mg, 740 mmol). The reaction suspension was degassed by bubbling nitrogen through the stirred mixture via a syringe. After several minutes the syringe was removed and tetrakis(triphenylphosphine)palladium(0) (57 mg, 56 mmol) was added and the reaction vial was quickly sealed. The sealed vial was flash heated in a microwave at 150° C. for 30 minutes. The cooled reaction was diluted with EtOAc and the organic solution was washed with water×1, saline×1 and dried (Na2SO4) before concentration in vacuo. The crude residue was purified by preparative RP-HPLC to give 132 mg of 423 (55% theoretical yield). 1H NMR (400 MHz, DMSO) δ 8.36 (d, J=8.4 Hz, 1H), 8.20 (s, 1H), 7.90 (d, J=23.3 Hz, 2H), 7.36 (dd, J=8.4, 1.6 Hz, 1H), 7.25 (d, J=1.6 Hz, 1H), 5.83 (dt, J=13.3, 6.6 Hz, 1H), 4.51 (s, 4H), 3.87 (s, 3H), 2.25 (s, 3H), 1.47 (d, J=6.6 Hz, 6H)

Example 424

2-(3-amino-1-(2,2,2-trifluoroethyl)-1H-1,2,4-triazol-5-yl)-5,6-dihydrobenzo[f]imidazo[1,2-d][1,4]oxazepine-10-carbonitrile 424

Following the procedures of Example 425, 2-(10-bromo-5,6-dihydrobenzo[f]imidazo[1,2-d][1,4]oxazepin-2-yl)-1-(2,2,2-trifluoroethyl)-1H-imidazol-4-amine (150 mg, 0.350 mmol) was converted to 31 mg of 424 (24% theoretical yield). 1H NMR (400 MHz, DMSO) δ 8.72 (d, J=2.1 Hz, 1H), 7.94 (s, 1H), 7.76 (dd, J=8.5, 2.1 Hz, 1H), 7.24 (d, J=8.6 Hz, 1H), 5.58 (q, J=8.8 Hz, 2H), 5.48 (d, J=12.2 Hz, 2H), 4.60 (d, J=9.0 Hz, 4H)

Example 425

2-(3-amino-1-(2,2,2-trifluoroethyl)-1H-1,2,4-triazol-5-yl)-5,6-dihydrobenzo[f]imidazo[1,2-d][1,4]oxazepine-9-carbonitrile 425

A microwave vial was charged with a solution of 2-(9-bromo-5,6-dihydrobenzo[f]imidazo[1,2-d][1,4]oxazepin-2-yl)-1-(2,2,2-trifluoroethyl)-1H-imidazol-4-amine (0.200 mg, 0.466 mmol) in 1.0 ml DMF. To this solution was added zinc cyanide (160 mg, 1.4 mmol). The reaction mixture was degassed by bubbling nitrogen through the stirred mixture via a syringe. After several minutes the syringe was removed and Bis(ditertbutyl(4-dimethylaminophenyl)phosphine)dichloropalladium(II) (66 mg, 0.093 mmol) was added and the reaction vial was quickly sealed. The sealed vial was flash heated in a microwave at 125° C. for 30 minutes. The cooled reaction was diluted with EtOAc and the organic solution was washed with water×1, saline×1 and dried (Na2SO4) before concentration in vacuo. The crude residue was purified by preparative RP-HPLC to give 81 mg of 425 (38% theoretical yield). 1H NMR (400 MHz, DMSO) δ 8.51 (dd, J=11.8, 5.7 Hz, 1H), 8.07 (d, J=75.8 Hz, 1H), 7.78-7.40 (m, 2H), 5.58 (q, J=8.9 Hz, 2H), 5.50 (s, 2H)

Example 426

(2S)-2-(2-(1-isopropyl-1H-1,2,4-triazol-5-yl)-5,6-dihydroimidazo[1,2-d]pyrido[3,4-f][1,4]oxazepin-9-yloxy)propanamide 426

2-(2-isopropyl-2H-[1,2,4]triazol-3-yl)-4,5-dihydro-6-oxa-1,3a,9-triaza-benzo[e]azulen-8-ol from Example 93, (+)-tert-butyl d-lactate, diisopropylazodicarboxylate (DIAD), and triphenylphosphine were reacted in THF. The crude product was subjected to flash chromatography (SiO2, gradient 0-5% methanol in DCM) to give (S)-2-[2-(2-Isopropyl-2H-[1,2,4]triazol-3-yl)-4,5-dihydro-6-oxa-1,3a,9-triaza-benzo[e]azulen-8-yloxy]-propionic acid tert-butyl ester as a yellow oil contaminated with triphenylphosphine oxide, no further purification was undertaken (206 mg, 49% based on NMR quantification of PPh3O). LCMS: RT=3.74 min, [M+H]+=441

511

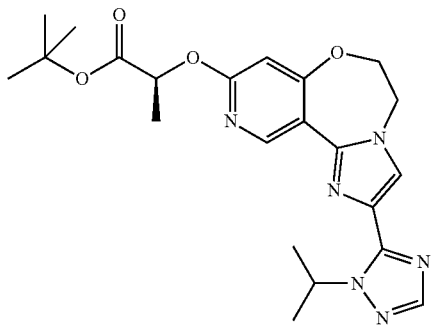 [SMILES: CC(C)n1ncnc1-c1cn2c(n1)-c1cnc(O[C@@H](C)C(=O)OC(C)(C)C)cc1OCC2]

A solution of (S)-2-[2-(2-isopropyl-2H-[1,2,4]triazol-3-yl)-4,5-dihydro-6-oxa-1,3a,9 triaza-benzo[e]azulen-8-yloxy]-propionic acid tert-butyl ester (206 mg, 0.47 mmol) in HCl in dioxane (4N, 5 mL) was heated at 50° C. for 2 h. The reaction mixture was concentrated in vacuo and the residue triturated with MeCN. The product was collected by filtration and dried in vacuo at 50° C. to yield (S)-2-[2-(2-Isopropyl-2H-[1,2,4]triazol-3-yl)-4,5-dihydro-6-oxa-1,3a,9-triaza-benzo[e]azulen-8-yloxy]-propionic acid as a beige solid (115 mg, 66%). LCMS: RT=2.72 min, [M+H]+=385

To a solution of (S)-2-[2-(2-isopropyl-2H-[1,2,4]triazol-3-yl)-4,5-dihydro-6-oxa-1,3a,9-triaza-benzo[e]azulen-8-yloxy]-propionic acid (115 mg, 0.28 mmol) in DMF (3 mL) was added HATU (128 mg, 0.34 mmol), ammonium chloride (23 mg, 0.42 mmol) and triethylamine (674, 0.42 mmol) and the reaction mixture stirred at room temperature (RT) for 5 hours. Further quantities of HATU (106 mg, 0.28 mmol), ammonium chloride (15 mg, 0.28 mmol) and triethylamine (21 µL, 0.28 mmol) were added and the reaction stirred at RT for 16 h. The reaction mixture was concentrated in vacuo, the residue dissolved in ethyl acetate (10 mL) and the mixture washed with water extracting with ethyl acetate (3×10 mL). The combined organic extracts were washed with brine, dried (MgSO4) and concentrated in vacuo. The resultant residue was subjected to reverse phase preparative HPLC (C-18 column, 10-90% MeCN in water, 0.1% formic acid, 25 min gradient) to yield 426 as a white solid (68 mg, 58%). LCMS: RT=3.07 min, [M+H]+=384; 1H NMR (400 MHz, d6-DMSO) 9.05 (1H, s), 7.87 (1H,$), 7.86 (1H, s), 7.38 (1H, s), 7.05 (1H, s), 6.41 (1H, s), 5.87 (1H, sept, J=6.6 Hz), 5.17 (1H, q, J=6.9 Hz), 4.59-4.43 (4H, m), 1.47-1.37 (9H, m)

Example 427

2-(2-(1-isopropyl-1H-1,2,4-triazol-5-yl)-5,6-dihydroimidazo[1,2-d]pyrido[3,4-f][1,4]oxazepin-9-yloxy)acetamide 427

Following the procedures of Example 426, 2-(2-isopropyl-2H-[1,2,4]triazol-3-yl)-4,5-dihydro-6-oxa-1,3a,9-triaza-benzo[e]azulen-8-ol from Example 93 and methylglycolate were reacted and the crude product was subjected to flash chromatography (SiO2, gradient 0-5% methanol in DCM) to give [2-(2-isopropyl-2H-[1,2,4]triazol-3-yl)-4,5-dihydro-6-oxa-1,3a,9-triaza-benzo[e]azulen-8-yloxy]-acetic acid methyl ester as a yellow (88 mg, 24%). LCMS: RT=3.09 min, [M+H]+=385

512

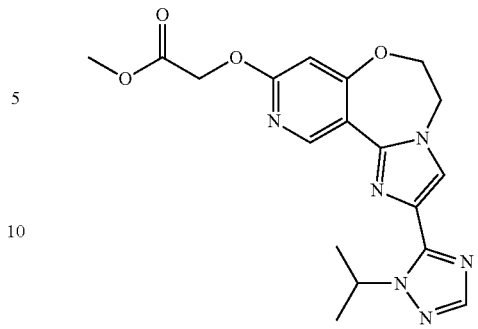

[2-(2-Isopropyl-2H-[1,2,4]triazol-3-yl)-4,5-dihydro-6-oxa-1,3a,9-triaza-benzo[e]azulen-8-yloxy]-acetic acid methyl ester (88 mg, 0.23 mmol) was dissolved in a solution of ammonia in methanol (7N, 5 mL) and the reaction mixture heated at 50° C. for 2 h, during which a white precipitate formed. The reaction mixture was concentrated in vacuo and the residue subjected to reverse phase preparative HPLC (C-18, 10-90% MeCN in water, 0.1% formic acid, 25 min gradient) to yield 427 as a white solid (42 mg, 50%). LCMS: RT=2.85 min, [M+H]+=370; 1H NMR (400 MHz, d6-DMSO) 9.07 (1H, s), 7.88 (1H, s), 7.86 (1H, s), 7.41 (1H, s), 7.18 (1H, s), 6.45 (1H, s), 5.87 (1H, sept, J=6.7 Hz), 4.66 (2H, s), 4.60-4.44 (4H, m), 1.44 (6H, d, J=6.7 Hz).

Example 428

2-(2-(1-isopropyl-1H-1,2,4-triazol-5-yl)-5,6-dihydrobenzo[f]imidazo[1,2-d][1,4]oxazepin-9-yloxy) acetamide 428

To a solution of 2-(2-isopropyl-2H-[1,2,4]triazol-3-yl)-4,5-dihydro-6-oxa-1,3a-diaza-benzo[e]azulen-8-ol 490 (80 mg, 0.26 mmol) in DMF (3 mL) was added 2-bromoacetamide (53 mg, 0.39 mmol) and cesium carbonate (109 mg, 0.33 mmol). The reaction mixture stirred at RT for 16 h before being diluted with water. The mixture was extracted with ethyl acetate (3×10 mL) and the combined organic extracts, washed with brine, dried (MgSO4) and concentrated in vacuo. The residue was subjected to flash chromatography (SiO2, gradient 0-10% methanol in DCM) to yield 428 as a white solid (61 mg, 64%). LCMS: RT=6.70 min, [M+H]+=369; 1H NMR (400 MHz, d6-DMSO) 8.28 (1H, d, J=9.8 Hz), 7.85 (1H, s), 7.82 (1H, s), 7.51 (1H, s), 7.35 (1H, s), 6.76 (1H, dd, J=9.8, 2.7 Hz), 6.54 (1H, d, J=2.7 Hz), 5.85 (1H, sept, J=6.6 Hz), 4.49-4.39 (6H, m), 1.43 (6H, d, J=6.6 Hz).

Example 429

2-(2-(1-isopropyl-1H-1,2,4-triazol-5-yl)-5,6-dihydroimidazo[1,2-d]pyrido[3,4-f][1,4]oxazepin-9-yloxy)-2-methylpropanamide 429

Following the procedures of Example 426, 2-(2-isopropyl-2H-[1,2,4]triazol-3-yl)-4,5-dihydro-6-oxa-1,3a,9-triaza-benzo[e]azulen-8-ol from Example 93 and ethyl 2-hydroxyisobutyrate were reacted and the crude product was subjected to flash chromatography (SiO2, gradient 0-5% methanol in DCM) to give 2-[2-(2-isopropyl-2H-[1,2,4] triazol-3-yl)-4,5-dihydro-6-oxa-1,3a,9-triaza-benzo[e]azulen-8-yloxy]-2-methyl-propionic acid ethyl ester as a yellow oil (103 mg, 40%). LCMS: RT=3.52 min, [M+H]+=427

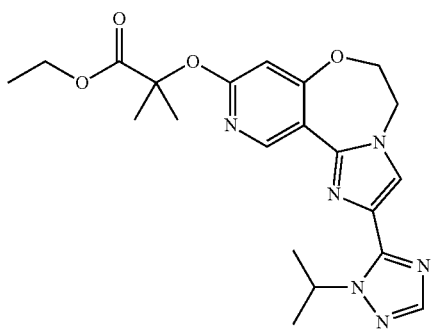 [SMILES: CCOC(=O)C(C)(C)Oc1cc2c(cn1)-c1nc(-c3ncnn3C(C)C)cn1CCO2]

To a solution of 2-[2-(2-isopropyl-2H-[1,2,4]triazol-3-yl)-4,5-dihydro-6-oxa-1,3a,9-triaza-benzo[e]azulen-8-yloxy]-2-methyl-propionic acid ethyl ester (103 mg, 0.24 mmol) in methanol (5 mL) was added water (0.5 mL) and lithium hydroxide monohydrate (19 mg, 0.48 mmol). The reaction mixture was heated at 50° C. for 16 h then HCl (1N, aq.) added until pH~4. The reaction mixture was concentrated in vacuo to give 2-[2-(2-Isopropyl-2H-[1,2,4]triazol-3-yl)-4,5-dihydro-6-oxa-1,3a,9-triaza-benzo[e]azulen-8-yloxy]-2-methyl-propionic acid as a yellow solid. LCMS: RT=2.88 min, [M+H]+=399

To a solution of 2-[2-(2-isopropyl-2H-[1,2,4]triazol-3-yl)-4,5-dihydro-6-oxa-1,3a,9-triaza-benzo[e]azulen-8-yloxy]-2-methyl-propionic acid (96 mg, 0.24 mmol) in DMF (3 mL) was added HATU (184 mg, 0.48 mmol), ammonium chloride (39 mg, 0.72 mmol) and triethyl amine (100 μL, 0.72 mmol) and the reaction mixture stirred at RT for 2 h. The reaction mixture was concentrated in vacuo, the residue dissolved in ethyl acetate (10 mL) and the mixture washed with water, extracting with ethyl acetate (3×10 mL). The combined organic extracts were washed with brine, dried (MgSO4) and concentrated in vacuo. The residue was subjected to reverse phase preparative HPLC (C-18, 10-90% MeCN in water 0.1% formic acid, 25 min gradient) to yield 429 as a white solid (38 mg, 38%). LCMS: RT=7.36 min, [M+H]+=398; 1H NMR (400 MHz, d6-DMSO) 8.99 (1H, s), 8.11 (1H, s), 7.87 (1H, s), 7.86 (1H, s), 7.16 (1H, s), 6.89 (1H, s), 6.37 (1H, s), 5.89 (1H, sept, J=6.6 Hz), 4.59-4.42 (4H, m), 1.54 (6H, s), 1.44 (6H, d, J=6.6 Hz)

Example 430

(2S,4R)-4-cyano-1-(2-(1-isopropyl-1H-1,2,4-triazol-5-yl)-5,6-dihydroimidazo[1,2-d]pyrido[3,4-f][1,4]oxazepin-9-yl)pyrrolidine-2-carboxamide 430

Following the procedure for Example 339, 2-(2-isopropyl-2H-[1,2,4]triazol-3-yl)-4,5-dihydro-6-oxa-1,3a,9-triaza-benzo[e]azulen-8-ol from Example 93 and (2S,4R)-2-carbamoyl-4-cyano-pyrrolidine-1-carboxylic acid tert-butyl ester were reacted. The crude product was subjected to flash chromatography (SiO2, gradient 0 to 10% methanol in DCM) to give 430 as an off-white solid (41 mg, 72%). LCMS: RT=2.85 min, [M+H]+=435. ¹H NMR 400 MHz (DMSO-d6) δ: 9.08 (1 H, s), 7.88 (1 H, d, J=0.63 Hz), 7.85 (1 H, s), 7.56 (1 H, br, s), 7.11 (1 H, br, s), 6.04 (1 H, s), 5.94-5.93 (1 H, m), 4.51 (4 H, d, J=15.42 Hz), 4.44 (1 H, d, J=5.97 Hz), 3.92 (1 H, dd, J=10.05, 7.55 Hz), 3.72 (1 H, t, J=8.49 Hz), 3.61-3.53 (1 H, m), 2.55-2.54 (1 H, m), 2.35 (1 H, ddd, J=12.61, 6.87, 3.63 Hz), 1.47 (6 H, dd, J=6.59, 3.21 Hz)

Example 431

5-(9-cyclopropyl-5,6-dihydrobenzo[f]imidazo[1,2-d][1,4]oxazepin-2-yl)-1-isopropyl-1H-1,2,4-triazol-3-amine 431

A microwave vial was charged with a solution of 5-(9-bromo-5,6-dihydrobenzo[f]imidazo[1,2-d][1,4]oxazepin-2-yl)-1-isopropyl-1H-1,2,4-triazol-3-amine (100 mg, 0.200 mmol) in 0.500 ml THF and 0.300 mL water. To this solution was added potassium phosphate (164 mg, 0.770 mol) and cyclopropyl boronic acid pinacol ester (308 mg, 1.48 mol). The reaction suspension was degassed by bubbling nitrogen through the stirred mixture via a syringe. After several minutes the syringe was removed and Bis(ditertbutyl(4-dimethylaminophenyl)phosphine)dichloropalladium(II) (20 mg, 0.026 mmol) was added and the reaction vial was quickly sealed. The sealed vial was flash heated in a microwave at 130° C. for 30 minutes. The cooled reaction was diluted with EtOAc and the organic solution was washed with water×1, saline×1 and dried (Na2SO4) before concentration in vacuo. The crude residue was purified by preparative RP-HPLC to give 16.7 mg of 431 (14% theoretical yield). 1H NMR (400 MHz, DMSO) δ 8.24 (d, J=8.3 Hz, 1H), 7.69 (s, 1H), 6.85 (d, J=8.4 Hz, 1H), 6.74 (s, 1H), 5.73 (dt, J=13.3, 6.8 Hz, 1H), 5.15 (s, 2H), 4.46 (d, J=2.3 Hz, 4H), 2.04-1.86 (m, 1H), 1.40 (d, J=6.6 Hz, 6H), 1.11-0.88 (m, 2H), 0.72 (q, J=4.9 Hz, 2H)

Example 435

3-(2-(1-isopropyl-1H-1,2,4-triazol-5-yl)-5,6-dihydrobenzo[f]imidazo[1,2-d][1,4]oxazepin-9-yl)-2-methylpropanamide 435

Step 1: (E)-3-[2-(2-isopropyl-2H-[1,2,4]triazol-3-yl)-4,5-dihydro-6-oxa-1,3a-diaza-benzo[e]azulen-8-yl]-2-methyl-acrylic acid methyl ester

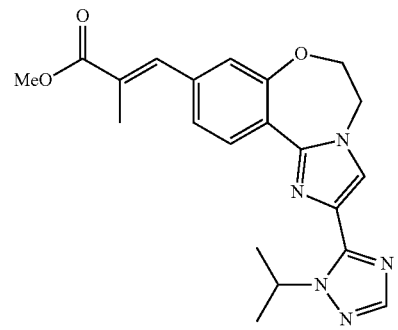 [SMILES: COC(=O)/C(C)=C/c1ccc2c(c1)OCCn1cc(-c3ncnn3C(C)C)nc1-2]

8-Bromo-2-(2-isopropyl-2H-[1,2,4]triazol-3-yl)-4,5-dihydro-6-oxa-1,3a-diaza-benzo[e]azulene 194 (300 mg, 0.80 mmol), methyl methacrylate (129 μL, 1.20 mmol), triethylamine (168 μL, 1.20 mmol), tri-o-tolyl-phosphane (49 mg, 0.16 mmol) and palladium (II) acetate (9 mg, 0.04 mmol) were suspended in DMF (5 mL) and the reaction mixture degassed by bubbling argon through the suspension. The reaction mixture was heated at 130° C. for 16 h, before cooling to RT and diluting the mixture with ethyl acetate (10 mL). The reaction mixture was washed with water, extracted with ethyl acetate (2×10 mL) and the combined organic extracts washed with brine, dried (MgSO4) then concentrated in vacuo. The resultant residue was subjected to flash chromatography (SiO2, eluting with 0-5% methanol in DCM) to yield (E)-3-[2-(2-isopropyl-2H-[1,2,4]triazol-3-yl)-4,5-dihydro-6-oxa-1,3a-diaza-benzo[e]azulen-8-yl]-2-methyl-acrylic acid methyl ester as a white solid (181 mg, 57%) LCMS: RT=3.63 min, [M+H]+=394.

Step 2: 3-[2-(2-Isopropyl-2H-[1,2,4]triazol-3-yl)-4,5-dihydro-6-oxa-1,3a-diaza-benzo[e]azulen-8-yl]-2-methyl-propionic acid methyl ester

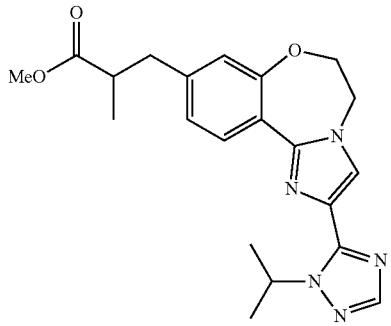 [SMILES: COC(=O)C(C)Cc1ccc2c(c1)OCCn1cc(-c3ncnn3C(C)C)nc1-2]

To a solution of (E)-3-[2-(2-isopropyl-2H-[1,2,4]triazol-3-yl)-4,5-dihydro-6-oxa-1,3a-diaza-benzo[e]azulen-8-yl]-2-methyl-acrylic acid methyl ester (181 mg, 0.46 mmol) in IMS (10 mL) was added palladium on carbon (200 mg, 10%). The reaction was stirred at RT under an atmosphere of hydrogen for 16 h. More palladium on carbon (200 mg, 10%) was added and the reaction stirred at RT under an atmosphere of hydrogen for a further 16 h. The reaction mixture was filtered and the filtrate concentrated in vacuo to give 3-[2-(2-Isopropyl-2H-[1,2,4]triazol-3-yl)-4,5-dihydro-6-oxa-1,3a-diaza-benzo[e]azulen-8-yl]-2-methyl-propionic acid methyl ester as a yellow oil (150 mg, 82%). LCMS: RT=3.40 min, [M+H]+=396.

Step 3

To a solution of 3-[2-(2-isopropyl-2H-[1,2,4]triazol-3-yl)-4,5-dihydro-6-oxa-1,3a-diaza-benzo[e]azulen-8-yl]-2-methyl-propionic acid methyl ester (150 mg, 0.38 mmol) in methanol (5 mL) and H2O (0.5 mL) was added lithium hydroxide monohydrate (30 mg, 0.76 mmol) and the reaction mixture heated at 45° C. for 72 h. The reaction mixture was concentrated in vacuo and the residue azeotroped with acetonitrile (3×10 mL). The resultant residue was suspended in DMF (3 mL) and HATU (289 mg, 0.76 mmol), ammonium chloride (61 mg, 1.14 mmol) and triethylamine (159 μL, 1.14 mmol) added. The reaction mixture was stirred at RT for 30 min. The mixture was diluted with water (15 mL) and extracted with ethyl acetate (2×10 mL). The combined organic extracts were washed with brine, dried (MgSO4) and concentrated in vacuo. The resultant residue was subjected to flash chromatography (SiO2, eluting with 0-10% methanol in DCM) to yield 435 as a white solid (61 mg, 42%). LCMS: RT=7.27 min, [M+H]+=381. ¹H NMR 400 MHz δ (DMSO-d6): 8.25 (1H, d, J=8.4 Hz), 7.86 (1H, s), 7.85 (1H, s), 7.21 (1H, br s), 6.93 (1H, dd, J=8.4, 1.8 Hz), 6.83 (1H, d, J=1.8 Hz), 6.66 (1H, br s), 5.85 (1H, sept, J=6.7 Hz), 4.50-4.39 (4H, m), 2.86-2.74 (1H, m), 2.56-2.42 (2H, m), 1.44 (6H, d, J=6.7 Hz), 0.97 (3H, d, J=6.6 Hz)

Example 436

(2S)-2-(2-(1-isopropyl-1H-1,2,4-triazol-5-yl)-5,6-dihydrobenzo[f]imidazo[1,2-d][1,4]oxazepin-9-yloxy)propanamide 436

Following the procedures of Example 426, 2-(2-isopropyl-2H-[1,2,4]triazol-3-yl)-4,5-dihydro-6-oxa-1,3a-diaza-benzo[e]azulen-8-ol 490 and (+)-tert-butyl d-lactate were reacted and the crude product was subjected to flash chromatography (SiO2, gradient 0-7% methanol in DCM) to give (S)-2-[2-(2-Isopropyl-2H-[1,2,4]triazol-3-yl)-4,5-dihydro-6-oxa-1,3a-diaza-benzo[e]azulen-8-yloxy]-propionic acid tert-butyl ester as a yellow solid (70 mg, 62%). LCMS: RT=3.76 min, [M+H]+=440.

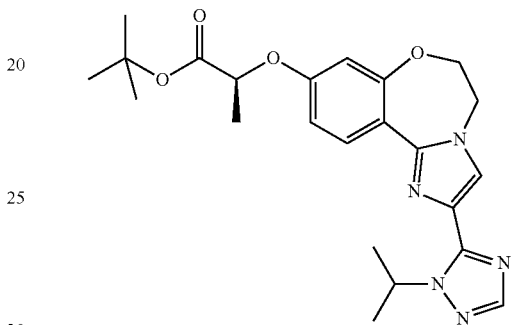

To a solution of (S)-2-[2-(2-isopropyl-2H-[1,2,4]triazol-3-yl)-4,5-dihydro-6-oxa-1,3a-diaza-benzo[e]azulen-8-yloxy]-propionic acid tert-butyl ester (64 mg, 0.15 mmol) in DCM (10 mL) was added TFA (0.5 mL) and the reaction mixture stirred at RT for 16 h. The reaction mixture was concentrated in vacuo and the crude carboxylic acid 512 dissolved in DMF (2 mL). HATU (130 mg, 0.34 mmol), ammonium chloride (27 mg, 0.51 mmol) and triethylamine (71 μL, 0.51 mmol) were added and the reaction mixture stirred at RT for 1 hour. The reaction mixture was concentrated in vacuo, the residue dissolved in ethyl acetate (10 mL) and the mixture washed with water extracting with ethyl acetate (3×10 mL). The combined organic extracts were washed with brine, dried (MgSO4) and concentrated in vacuo. The resultant residue was subjected to flash chromatography (SiO2 gradient 0-10% methanol in ethyl acetate) to yield 436 as a white solid (50 mg, 90%). LCMS: RT=3.07 min; [M+H]+=383, 1H NMR (400 MHz, d6-DMSO) 8.26 (1H, d, J=8.6 Hz), 7.81 (1H, s), 7.85 (1H, s), 7.51 (1H, s), 7.21 (1H, s), 6.72 (1H, dd, J=8.6, 2.6 Hz), 6.49 (1H, d, J=2.6 Hz), 5.85 (1H, sept, J=6.6 Hz), 4.62 (1H, q, J=6.6 Hz), 4.55-4.36 (4H, m), 1.47-1.36 (9H, m)

Alternatively, to a solution of (R)-2-hydroxy-propionamide (10 g, 0.11 mmol) and triethylamine (17.2 mL, 0.12 mmol) in THF (130 mL) at 0° C. was added dropwise, methanesulfonyl chloride (9.56 mL, 0.12 mmol) causing a thick white precipitate to form. The reaction mixture was stirred at RT for 2 hours. The reaction mixture was diluted with water (150 mL) and extracted with ethyl acetate (3×50 mL). The combined organic extracts were washed with brine, dried (MgSO4) and concentrated in vacuo. The resultant residue was triturated with TBME to yield methanesulfonic acid (R)-1-carbamoyl-ethyl ester as a white solid (13.1 g, 70%). 1H NMR (400 MHz, d6-DMSO) 7.56 (1H, br s), 7.41 (1H, br s), 4.91 (1H, t, J=6.6 Hz), 3.23 (3H, s), 1.44 (3H, d, J=6.6 Hz)

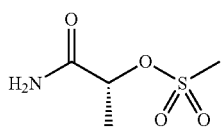

2-(2-Isopropyl-2H-[1,2,4]triazol-3-yl)-4,5-dihydro-6-oxa-1,3a-diaza-benzo[e]azulen-8-ol 490 (100 mg, 0.32 mmol), methanesulfonic acid (R)-1-carbamoyl-ethyl ester (64 mg, 0.38 mmol) and potassium carbonate (67 mg, 0.48 mmol) were suspended in DMF (3 mL) and the reaction mixture stirred at RT for 24 h then at 50° C. for 16 h. The reaction mixture was diluted with water (15 mL) and extracted with ethyl acetate (3×10 mL). The combined organic extracts were washed with brine, dried (MgSO4) and concentrated in vacuo. The resultant residue was subjected flash chromatography (SiO2 gradient 0-10% methanol in ethyl acetate) to yield 436 as a white solid (59 mg, 48%). LCMS: RT=3.07 min; [M+H]+=383; 1H NMR (400 MHz, d6-DMSO) 8.26 (1H, d, J=8.6 Hz), 7.81 (1H,$), 7.85 (1H, s), 7.51 (1H, s), 7.21 (1H, s), 6.72 (1H, dd, J=8.6, 2.6 Hz), 6.49 (1H, d, J=2.6 Hz), 5.85 (1H, sept, J=6.6 Hz), 4.62 (1H, q, J=6.6 Hz), 4.55-4.36 (4H, m), 1.47-1.36 (9H, m). ee>99% (chiralpak IC, 1 mL/min, 20% ethanol in heptane, 50 min run)

Example 438

2-(1-isopropyl-3-(methoxymethyl)-1H-1,2,4-triazol-5-yl)-9-methyl-5,6-dihydrobenzo[f]imidazo[1,2-d][1,4]oxazepine 438

2-(1-isopropyl-3-methyl-1H-1,2,4-triazol-5-yl)-5,6-dihydroimidazo[1,2-d]pyrido[3,4-f][1,4]oxazepin-9-yl trifluoromethanesulfonate from Example 463, (97 mg, 0.22 mmol) was dissolved in N-methylpyrrolidinone (1.4 mL) and treated with (1H-pyrazol-5-yl)methanamine hydrochloride (138 mg, 0.88 mmol) and triethylamine (0.24 mL, 1.8 mmol). The reaction mixture was heated at 120° C. overnight. The mixture was diluted with water and 20% MeOH in DCM and the layers separated. The aqueous phase was extracted into DCM/MeOH (3×), dried over sodium sulfate, filtered, and concentrated in vacuo. The crude residue was purified via HPLC to afford 438 as a white solid (20 mg, 29%). LC/MS(ESI+): m/z 392 (M+H). 1H NMR (400 MHz, DMSO) δ 12.57 (s, 1H), 9.03 (s, 1H), 7.88 (s, 1H), 7.80 (s, 1H), 7.54 (s, 1H), 7.07 (t, J=5.6 Hz, 1H), 6.14 (d, J=2.0 Hz, 1H), 6.09 (s, 1H), 5.93 (m, 1H), 4.46 (m, 6H), 1.47 (d, J=6.6 Hz, 6H)

Example 440

2-(1-isopropyl-3-(methoxymethyl)-1H-1,2,4-triazol-5-yl)-9-methyl-5,6-dihydrobenzo[f]imidazo[1,2-d][1,4]oxazepine 440

Following the procedures for Example 481, 9-bromo-2-(1-isopropyl-3-(methoxymethyl)-1H-1,2,4-triazol-5-yl)-5,6-dihydrobenzo[f]imidazo[1,2-d][1,4]oxazepine (0.640 mmol) was converted to 440. MS: (ESI+)=354.1

Example 442

5-(10-cyclopropyl-5,6-dihydrobenzo[f]imidazo[1,2-d][1,4]oxazepin-2-yl)-1-(2,2,2-trifluoroethyl)-1H-1,2,4-triazol-3-amine 442

Following the procedures of Example 431, 5-(10-bromo-5,6- dihydrobenzo[f]imidazo[1,2-d][1,4]oxazepin-2-yl)-1-(2,2,2-trifluoroethyl)-1H-1,2,4-triazol-3-amine (150 mg, 0.350 mmol) was converted to 8.4 mg of 442 (6.4% theoretical yield). 1H NMR (400 MHz, DMSO) δ 8.72 (d, J=2.1 Hz, 1H), 7.94 (s, 1H), 7.76 (dd, J=8.5, 2.1 Hz, 1H), 7.24 (d, J=8.6 Hz, 1H), 5.73 (dt, J=13.3, 6.8 Hz, 1H), 5.15 (s, 2H), 4.46 (d, J=2.3 Hz, 4H), 2.04-1.86 (m, 1H), 1.40 (d, J=6.6 Hz, 6H), 1.11-0.88 (m, 2H), 0.72 (q, J=4.9 Hz, 2H)

Example 443

2-(1-isopropyl-3-methyl-1H-1,2,4-triazol-5-yl)-5,6-dihydrobenzo[f]imidazo[1,2-d][1,4]oxazepine-9-carbonitrile 443

A microwave vial was charged with a solution of 9-bromo-2-(1-isopropyl-3-methyl-1H-1,2,4-triazol-5-yl)-5,6-dihydrobenzo[f]imidazo[1,2-d][1,4]oxazepine 411 (0.300 mg, 0.699 mmol) in 2.0 ml DMF. To this solution was added zinc cyanide (250 mg, 2.1 mmol). The reaction mixture was degassed by bubbling nitrogen through the stirred mixture via a syringe. After several minutes the syringe was removed and Bis(di-tert-butyl(4-dimethylaminophenyl)phosphine)dichloropalladium(II) (100 mg, 0.140 mmol) was added and the reaction vial was quickly sealed. The sealed vial was flash heated in a microwave at 125° C. for 30 minutes. The cooled reaction was diluted with EtOAc and the organic solution was washed with water×1, saline×1 and dried (Na2SO4) before concentration in vacuo. The crude residue was purified by preparative RP-HPLC to give 156 mg of 443 (59% theoretical yield) 1H NMR (400 MHz, DMSO) δ 8.55 (d, J=8.2 Hz, 1H), 8.02 (s, 1H), 7.74-7.46 (m, 2H), 5.79 (dt, J=13.1, 6.6 Hz, 1H), 4.57 (s, 4H), 2.29 (d, J=28.5 Hz, 3H), 1.46 (d, J=6.6 Hz, 6H)

Example 444

2-(2-(1-isopropyl-1H-1,2,4-triazol-5-yl)-5,6-dihydrobenzo[f]imidazo[1,2-d][1,4]oxazepin-9-ylamino)acetamide 444

Step 1: [2-(2-Isopropyl-2H-[1,2,4]triazol-3-yl)-4,5-dihydro-6-oxa-1,3a-diaza-benzo[e]azulen-8-ylamino]-acetic acid methyl ester

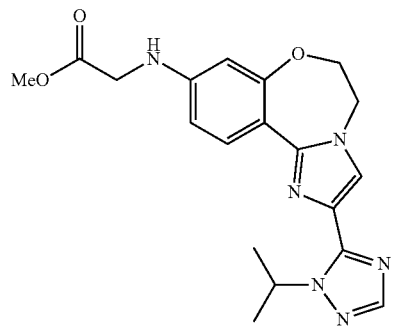 [SMILES: COC(=O)CNc1ccc2c(c1)OCCn1cc(-c3ncnn3C(C)C)nc1-2]

8-Bromo-2-(2-isopropyl-2H-[1,2,4]triazol-3-yl)-4,5-dihydro-6-oxa-1,3a-diaza-benzo[e]azulene (1.0 g, 2.7 mmol), glycine (2.0 g, 27 mmol), copper (I) iodide (0.2 g, 1.08 mmol), trans-4-hydroxy-(L)-proline (0.14 g, 1.08 mmol) and potassium phosphate (1.14 g, 5.4 mmol) in DMSO (10 mL) were heated under nitrogen at 80° C. for 18 h. The reaction mixture was cooled to RT, concentrated in vacuo, loaded onto an SCX-2 cartridge, washed with methanol and eluted with 2M ammonia in methanol. Basic fractions were combined and concentrated in vacuo and the resultant residue was subjected to flash chromatography (SiO2, gradient 0 to 10% methanol in DCM) to give [2-(2-Isopropyl-2H-[1,2,4]triazol-3-yl)-4,5-dihydro-6-oxa-1,3a-diaza-benzo[e]azulen-8-ylamino]-acetic acid methyl ester (0.407 g, 39% total). $^1$H NMR 400 MHz (CDCl3) δ: 8.32 (1 H, d, J=8.78 Hz), 7.55 (1 H, s), 7.26 (1 H, s), 6.46 (1 H, dd, J=8.79, 2.45 Hz), 6.18 (1 H, d, J=2.42 Hz), 6.00 (1 H, m), 4.46-4.45 (2 H, m), 4.41-4.35 (2 H, m), 3.94 (2 H, d, J=5.39 Hz), 3.80 (3 H, s), 1.59 (6 H, t, J=6.88 Hz).

Step 2: [2-(2-Isopropyl-2H-[1,2,4]triazol-3-yl)-4,5-dihydro-6-oxa-1,3a-diaza-benzo[e]azulen-8-ylamino]-acetic acid lithium salt

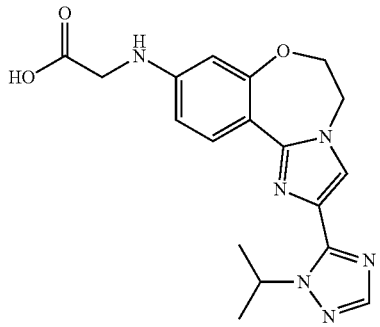 [SMILES: CC(C)n1ncnc1-c1cn2c(n1)-c1ccc(NCC(=O)O)cc1OCC2]

To a solution of [2-(2-isopropyl-2H-[1,2,4]triazol-3-yl)-4,5-dihydro-6-oxa-1,3a-diaza-benzo[e]azulen-8-ylamino]-acetic acid methyl ester (407 mg, 0.43 mmol) in dioxane (1 mL) and water (1 mL) was added lithium hydroxide monohydrate (36 mg, 0.86 mmol) and the reaction mixture stirred at RT for 18 h. Water was added and the reaction mixture extracted with DCM. The aqueous phase was filtered and concentrated in vacuo to give [2-(2-Isopropyl-2H-[1,2,4]triazol-3-yl)-4,5-dihydro-6-oxa-1,3a-diaza-benzo[e]azulen-8-ylamino]-acetic acid lithium salt (130 mg, 81%). LCMS: RT=2.30 min, [M+H]+=369.

Step 3

A mixture of [2-(2-isopropyl-2H-[1,2,4]triazol-3-yl)-4,5-dihydro-6-oxa-1,3a-diaza-benzo[e]azulen-8-ylamino]-acetic acid lithium salt (130 mg, 0.35 mmol), 1-ethyl-3-(3-dimethylaminopropyl)carbodiimide (82 mg, 0.42 mmol), 1-hydroxybenzotriazole hydrate (55 mg, 0.42 mmol) and DIPEA (0.42 mL, 1.4 mmol) in DMF (2 mL) was stirred at RT for 5 min before ammonium chloride (55 mg, 1.05 mmol) was added and the reaction stirred at RT for 18 h. The mixture was concentrated in vacuo and the resultant residue triturated with water. The solid was filtered off, washed with water then dried in vacuo. The resultant residue was subjected to flash chromatography (SiO2, gradient 0 to 10% methanol in DCM) to give 444 (48 mg, 37%). LCMS: RT=2.10 min, [M+H]+=368. $^1$H NMR 400 MHz (DMSO-d6) δ: 8.12 (1 H, d, J=8.80 Hz), 7.88 (1 H, d, J=0.63 Hz), 7.77 (1 H, s), 7.37 (1 H, br, s), 7.11 (1 H, br, s), 6.45 (1 H, dd, J=8.84, 2.36 Hz), 6.32 (1 H, br, t), 6.10 (1 H, d, J=2.33 Hz), 5.92 (1 H, m), 4.42 (4 H, m), 3.63 (2 H, d, J=5.84 Hz), 1.47 (6 H, d, J=6.60 Hz)

Example 445

2-(2-(1-isopropyl-1H-1,2,4-triazol-5-yl)-5,6-dihydrobenzo[f]imidazo[1,2-d][1,4]oxazepin-9-yl)ethanesulfonamide 445

Step 1: (E)-2-[2-(2-Isopropyl-2H-[1,2,4]triazol-3-yl)-4,5-dihydro-6-oxa-1,3a-diaza-benzo[e]azulen-8-yl]-ethenesulfonic acid amide

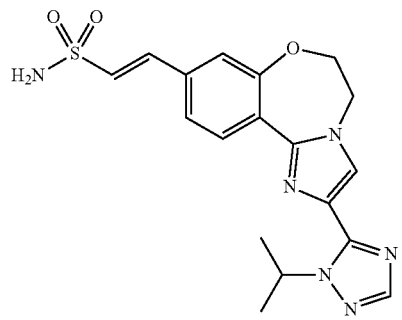 [SMILES: CC(C)n1ncnc1-c1cn2c(n1)-c1ccc(/C=C/S(N)(=O)=O)cc1OCC2]

8-Bromo-2-(2-isopropyl-2H-[1,2,4]triazol-3-yl)-4,5-dihydro-6-oxa-1,3a-diaza-benzo[e]azulene 194 (400 mg, 1.07 mmol), ethenesulfonic acid amide (172 mg, 1.60 mmol), triethylamine (223 µL, 1.60 mmol), tri-o-tolyl-phosphane (65 mg, 0.21 mmol) and palladium (II) acetate (12 mg, 0.05 mmol) were suspended in DMF (5 mL) and the reaction mixture degassed by bubbling argon through the suspension. The reaction mixture was heated at 130° C. for 16 h, before cooling to RT and diluting the mixture with ethyl acetate (10 mL). The resultant mixture was washed with water, extracted with ethyl acetate (2×10 mL) and the combined organic extracts washed with brine, dried (MgSO4) then concentrated in vacuo. The resultant residue was subjected to flash chromatography (SiO2, eluting with 0-10% methanol in DCM) to yield the title compound as a white solid (151 mg, 35%) LCMS: RT=2.69 min, [M+H]+=401.

Step 2

To a solution of (E)-2-[2-(2-isopropyl-2H-[1,2,4]triazol-3-yl)-4,5-dihydro-6-oxa-1,3a-diaza-benzo[e]azulen-8-yl]-ethenesulfonic acid amide (151 mg, 0.38 mmol) in DCM (5 mL) and IMS (2 mL) was added 10% palladium on carbon (150 mg, 10%). The reaction mixture was stirred at RT under an atmosphere of hydrogen for 16 h. The reaction mixture was filtered and the filtrate concentrated in vacuo. The resultant residue was subjected to reverse phase preparative HPLC (C18, eluting with 10-90% acetonitrile in H2O, 0.1% formic acid, 25 min gradient) to yield 445 as a white solid (74 mg, 49%). LCMS: RT=3.24 min, [M+H]+=403. $^1$H NMR 400 MHz δ (DMSO-d6): 8.29 (1H, d, J=8.7 Hz), 7.87 (1H, s), 7.86 (1H, s), 7.02 (1H, dd, J=8.5, 1.8 Hz), 6.93 (1H, d, J=1.8 Hz), 6.83 (2H, br s), 5.84 (1H, sept, J=6.6 Hz), 4.52-4.41 (4H, m), 3.27-3.20 (2H, m), 3.02-2.92 (2H, m), 1.44 (6H, d, J=6.6 Hz)

Example 446

(R)-2-(2-(1-isopropyl-1H-1,2,4-triazol-5-yl)-5,6-dihydroimidazo[1,2-d]pyrido[3,4-f][1,4]oxazepin-9-yloxy)propanamide 446

Following the procedures of Example 426, 2-(2-isopropyl-2H-[1,2,4]triazol-3-yl)-4,5-dihydro-6-oxa-1,3a,9-triazabenzo[e]azulen-8-ol from Example 93 and ethyl-(L)-lactate were reacted and the crude product was subjected to flash chromatography (SiO2, gradient 0-5% methanol in DCM) to give (R)-2-[2-(2-Isopropyl-2H-[1,2,4]triazol-3-yl)-4,5-dihydro-6-oxa-1,3a,9-triaza-benzo[e]azulen-8-yloxy]-propionic acid ethyl ester as a yellow oil contaminated with triphenylphosphine oxide, no further purification was undertaken (70 mg, 29% based on NMR quantification of PPh3O). LCMS: RT=3.38 min, [M+H]+=413

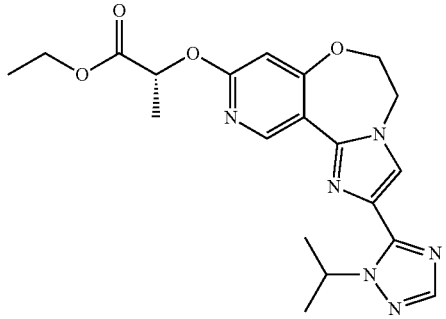 [SMILES: CCOC(=O)[C@@H](C)Oc1cc2c(cn1)-c1nc(-c3ncnn3C(C)C)cn1CCO2]

To a solution of (R)-2-[2-(2-isopropyl-2H-[1,2,4]triazol-3-yl)-4,5-dihydro-6-oxa-1,3a,9-triaza-benzo[e]azulen-8-yloxy]-propionic acid ethyl ester (70 mg, 0.17 mmol) in methanol (5 mL) and water (1 mL) was added lithium hydroxide monohydrate (23 mg, 0.58 mmol) and the reaction mixture stirred at 50° C. for 1 h. The reaction mixture was concentrated in vacuo and the resultant residue azeotroped with acetonitrile (3×20 mL). The residue was dissolved in DMF (3 mL), HATU (220 mg, 0.58 mmol), ammonium chloride (46 mg, 0.86 mmol) and triethylamine (120 µL, 0.86 mmol) added and the reaction mixture stirred at RT for 1.5 h. The reaction mixture was diluted with ethyl acetate, washed with water, extracting with ethyl acetate (3×15 mL). The combined organic extracts were washed with brine, dried (MgSO4) and concentrated in vacuo. The residue was subjected to reverse phase preparative HPLC (C-18, 10-90% MeCN in water 0.1% formic acid, 25 min gradient) to yield 446 as a white solid (28 mg, 43%). LCMS: RT=3.07 min, [M+H]+=384; 1H NMR (400 MHz, d6-DMSO) 9.05 (1H, s), 7.87 (1H, s), 7.86 (1H, s), 7.38 (1H, br s), 7.05 (1H, br s), 6.41 (1H, s), 5.87 (1H, sept, J=6.6 Hz), 5.17 (1H, q, J=6.8 Hz), 4.60-4.43 (4H, m), 1.50-1.34 (9H, m)

Example 447

9-(difluoromethyl)-2-(1-isopropyl-3-methyl-1H-1,2,4-triazol-5-yl)-5,6-dihydrobenzo[f]imidazo[1,2-d][1,4]oxazepine 447

Step 1: 2-(1-isopropyl-3-methyl-1H-1,2,4-triazol-5-yl)-9-vinyl-5,6-dihydrobenzo[f]imidazo[1,2-d][1,4]oxazepine

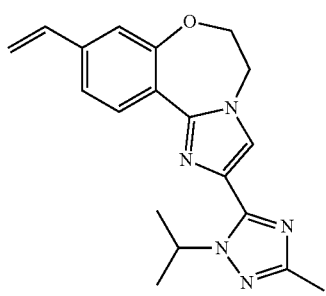 [SMILES: C=Cc1ccc2c(c1)OCCn1cc(-c3nc(C)nn3C(C)C)nc1-2]

9-bromo-2-(1-isopropyl-3-methyl-1H-1,2,4-triazol-5-yl)-5,6-dihydrobenzo[f]imidazo[1,2-d][1,4]oxazepine 411 (0.5 g, 0.001 mol) and vinyltrifluoroborane/potassium hydride (0.34 g, 0.0026 mol) was dissolved in THF (5 mL) and 1 mL H2O (Tremblay-Morin et al (2006) Tetrahedron Letters 47(18):3043-3046). Cesium Carbonate (1.2 g, 0.0039 mol) was added and mixture was degassed with N2 for 10 minutes. Tetrakis(triphenylphosphine)palladium(0) (0.074 g, 0.064 mmol) was added. The reaction vessel was sealed and was heated at 110 C in an oil bath overnight. The reaction mixture was cooled to room temperature and the seal was removed. The crude product was isolated from an aqueous workup using H2O and brine. The crude product was purified using flash column chromatography (0-10% MeOH in DCM) to give 2-(1-isopropyl-3-methyl-1H-1,2,4-triazol-5-yl)-9-vinyl-5,6-dihydrobenzo[f]imidazo[1,2-d][1,4]oxazepine (0.300 g, 89% yield Step 2: 2-(1-isopropyl-3-methyl-1H-1,2,4-triazol-5-yl)-5,6-dihydrobenzo[f]imidazo[1,2-d][1,4]oxazepine-9-carbaldehyde

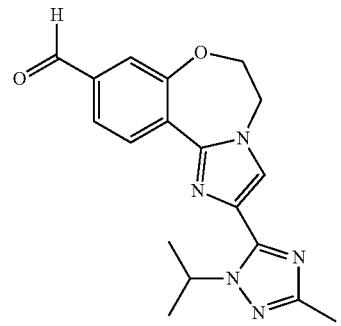 [SMILES: Cc1nc(-c2cn3c(n2)-c2ccc(C=O)cc2OCC3)n(C(C)C)n1]

2-(1-isopropyl-3-methyl-1H-1,2,4-triazol-5-yl)-9-vinyl-5,6-dihydrobenzo[f]imidazo[1,2-d][1,4]oxazepine (0.300 g, 0.000894 mol) was dissolved in THF (20 mL) and H2O (10 mL). Osmium tetroxide (0.550 mL, 0.0716 mmol, 4% wt in water) was added followed by Sodium metaperiodate (0.383 g, 0.00179 mol). The reaction was stirred overnight at room temperature. The reaction was quenched using saturated sodium thiosulfate. 2-(1-isopropyl-3-methyl-1H-1,2,4-triazol-5-yl)-5,6-dihydrobenzo[f]imidazo[1,2-d][1,4]oxazepine-9-carbaldehyde (0.302 g, 95.1% yield) was isolated using an aqueous workup and carried on without further purification Step 3

2-(1-isopropyl-3-methyl-1H-1,2,4-triazol-5-yl)-5,6-dihydrobenzo[f]imidazo[1,2-d][1,4]oxazepine-9-carbaldehyde (0.289 g, 0.000857 mol) was dissolved in DCM (3 mL) at room temperature. Bis(2-methoxyethyl)aminosulfur trifluoride (0.368 mL, 0.00171 mol) was added followed by Ethanol (0.005 mL, 0.0000857 mol). The reaction was stirred overnight. The reaction was quenched using saturated NaHCO3. The crude product was isolated using an aqueous workup and purified via reverse phase chromatography to give 447 (0.0855 g, 27.8% yield)

Example 452

2-(2-(1-isopropyl-1H-1,2,4-triazol-5-yl)-5,6-dihydroimidazo[1,2-d]pyrido[3,4-f][1,4]oxazepin-9-yloxy)-3-methylbutanamide 452

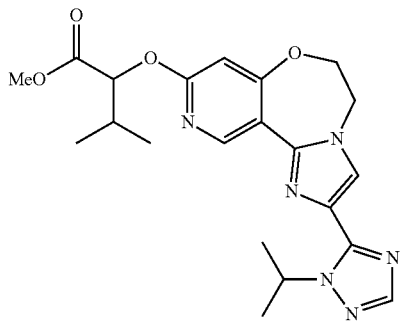 [SMILES: COC(=O)C(Oc1cc2c(cn1)-c1nc(-c3ncnn3C(C)C)cn1CCO2)C(C)C]

Following the procedures of Example 426, 2-(2-isopropyl-2H-[1,2,4]triazol-3-yl)-4,5-dihydro-6-oxa-1,3a,9-triaza-benzo[e]azulen-8-ol from Example 93 and 2-hydroxy-3-methyl-butyric acid methyl ester were reacted and subjected to flash chromatography (SiO2, gradient 0-5% methanol in ethyl acetate) to give racemic 2-[2-(2-Isopropyl-2H-[1,2,4]triazol-3-yl)-4,5-dihydro-6-oxa-1,3a,9-triaza-benzo[e]azulen-8-yloxy]-3-methyl-butyric acid methyl ester as a yellow oil (160 mg, 58%). LCMS: RT=3.60 min, [M+H]+=427

To a solution of 2-[2-(2-isopropyl-2H-[1,2,4]triazol-3-yl)-4,5-dihydro-6-oxa-1,3a,9-triaza-benzo[e]azulen-8-yloxy]-3-methyl-butyric acid methyl ester (160 mg, 0.38 mmol) in methanol (5 mL) and water (1 mL) was added lithium hydroxide monohydrate (18 mg, 0.45 mmol) and the reaction mixture stirred at 50° C. for 2 h. The reaction mixture was concentrated in vacuo and the resultant residue azeotroped with acetonitrile (3×20 mL). The residue was dissolved in DMF (3 mL), HATU (286 mg, 0.75 mmol), ammonium chloride (60 mg, 1.12 mmol) and triethylamine (157 μL, 1.12 mmol) added and the reaction mixture stirred at RT for 1 h. The reaction mixture was diluted with ethyl acetate, washed with water, extracting with ethyl acetate (3×15 mL). The combined organic extracts were washed with brine, dried (MgSO4) and concentrated in vacuo. The residue was subjected to reverse phase preparative HPLC (C-18, 10-90% MeCN in water 0.1% formic acid, 25 min gradient) to yield 452 as a white solid (28 mg, 43%). LCMS: RT=3.61 min, [M+H]+=412; 1H NMR (400 MHz, d6-DMSO) 9.04 (1H, s), 7.87 (1H s), 7.86 (1H, s), 7.31 (1H, br s), 7.08 (1H, br s), 6.43 (1H, s), 5.86 (1H, sept, J=6.56 Hz), 4.97 (1H, d, J=4.91 Hz), 4.61-4.43 (4H, m), 2.21-2.08 (1H, m), 1.43 (6H, dd, J=6.6, 3.6 Hz), 0.94 (6H, dd, J=6.6 Hz, 1.5 Hz)

Example 453

2-(1-isopropyl-1H-1,2,4-triazol-5-yl)-5,6-dihydroimidazo[1,2-d]pyrido[3,4-f][1,4]oxazepin-9-amine 453

Step 1: (3,4-Dimethoxy-benzyl)-[2-(2-isopropyl-2H-[1,2,4]triazol-3-yl)-4,5-dihydro-6-oxa-1,3a,9-triaza-benzo[e]azulen-8-yl]-amine

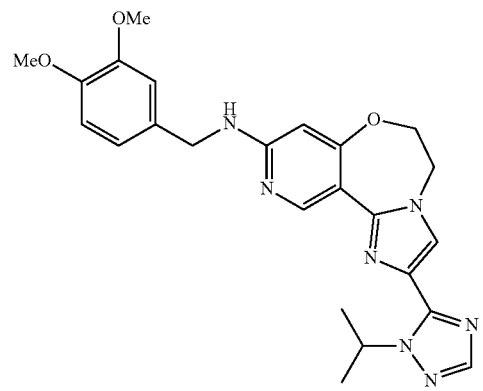 [SMILES: COc1ccc(CNc2cc3c(cn2)-c2nc(-c4ncnn4C(C)C)cn2CCO3)cc1OC]

Following the procedure for Example 339, 2-(2-isopropyl-2H-[1,2,4]triazol-3-yl)-4,5-dihydro-6-oxa-1,3a,9-triaza-benzo[e]azulen-8-ol from Example 93 and 3,4-methoxybenzylamine in NMP were reacted with heating at 85° C. for 18 hours. Water was added to the reaction mixture and the precipitate filtered off and dried to give (3,4-Dimethoxy-benzyl)-[2-(2-isopropyl-2H-[1,2,4]triazol-3-yl)-4,5-dihydro-6-oxa-1,3a,9-triaza-benzo[e]azulen-8-yl]-amine as a white solid (378 mg, 51%). 1H NMR 400 MHz (DMSO-d6) δ: 8.99 (1 H, s), 7.87 (1 H, d, J=0.63 Hz), 7.79 (1 H, s), 7.22 (1 H, br, s), 6.94 (1 H, d, J=1.86 Hz), 6.85-6.84 (2 H, m), 6.01 (1 H, s), 5.91 (1 H, m), 4.45 (4 H, d, J=5.45 Hz), 4.40 (2 H, d, J=5.98 Hz), 3.72 (3 H, s), 3.70 (3 H, s), 1.45 (6 H, d, J=6.60 Hz).

Step 2

A solution of (3,4-dimethoxy-benzyl)-[2-(2-isopropyl-2H-[1,2,4]triazol-3-yl)-4,5-dihydro-6-oxa-1,3a,9-triaza-benzo[e]azulen-8-yl]-amine (378 mg, 0.82 mmol) and TFA (15 mL) was heated at 40° C. for 5 h. The reaction mixture was concentrated in vacuo and the residue loaded onto an SCX-2 cartridge, washing with methanol and eluting with 2M ammonia in methanol. Basic fractions were combined and then concentrated in vacuo. The resultant residue was subjected to flash chromatography (SiO2, gradient 0 to 10% methanol in DCM) to give 453 as a white solid (140 mg, 55% total). LCMS: RT=2.09 min, [M+H]+=312. 1H NMR 400 MHz (DMSO-d6) δ: 8.93 (1 H, s), 7.88 (1 H, s), 7.80 (1 H, s), 6.19 (2 H, br, s), 5.98 (1 H, s), 5.90-5.88 (1 H, m), 4.49-4.43 (4 H, m), 1.47 (6 H, d, J=6.61 Hz)

Example 454

2-(1-isopropyl-3-methyl-1H-1,2,4-triazol-5-yl)-10-(1-methyl-1H-pyrazol-4-yl)-5,6-dihydrobenzo[f]imidazo[1,2-d][1,4]oxazepine 454

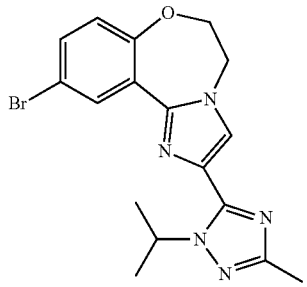 [SMILES: Cc1nc(-c2cn3c(n2)-c2cc(Br)ccc2OCC3)n(C(C)C)n1]

A microwave vial was charged with a suspension of 10-bromo-2-(1-isopropyl-3-methyl-1H-1,2,4-triazol-5-yl)-5,6-dihydrobenzo[f]imidazo[1,2-d][1,4]oxazepine (0.160 mg, 0.412 mmol) in 0.861 ml ACN/0.400 mL water. To this suspension was added potassium acetate (182 mg, 0.00185 mol) and 1-methylpyrazole boronic acid pinacol ester (107 mg, 515 mmol). The reaction suspension was degassed by bubbling nitrogen through the stirred mixture via a syringe. After several minutes the syringe was removed and tetrakis(triphenylphosphine)palladium(0) (38 mg, 33 mmol) was added and the reaction vial was quickly sealed. The sealed vial was flash heated in a microwave at 150° C. for 30 minutes. The cooled reaction was diluted with EtOAc and the organic solution was washed with water×1, saline×1 and dried (Na2SO4) before concentration in vacuo. The crude residue was purified by preparative RP-HPLC to give 132 mg of 454 (55% theoretical yield). MS: (ESI+)=390.2

Example 455

2-(1-isopropyl-3-methyl-1H-1,2,4-triazol-5-yl)-5,6-dihydrobenzo[f]imidazo[1,2-d][1,4]oxazepine-10-carbonitrile 455

A microwave vial was charged with a solution of 10-bromo-2-(1-isopropyl-3-methyl-1H-1,2,4-triazol-5-yl)-5,6-dihydrobenzo[f]imidazo[1,2-d][1,4]oxazepine (0.200 mg, 0.466 mmol) in 1.4 ml DMF. To this solution was added zinc cyanide (160 mg, 1.4 mmol). The reaction mixture was degassed by bubbling nitrogen through the stirred mixture via a syringe. After several minutes the syringe was removed and Bis(ditertbutyl(4-dimethylaminophenyl)phosphine)dichloropalladium(II) (66 mg, 0.093 mmol) was added and the reaction vial was quickly sealed. The sealed vial was flash heated in a microwave at 150° C. for 30 minutes. The cooled reaction was diluted with EtOAc and the organic solution was washed with water×1, saline×1 and dried (Na2SO4) before concentration in vacuo. The crude residue was purified by preparative RP-HPLC to give 455. MS: (ESI+)=335.1

Example 458

2-(2-(1-isopropyl-3-methyl-1H-1,2,4-triazol-5-yl)-5,6-dihydroimidazo[1,2-d]pyrido[3,4-f][1,4]oxazepin-9-ylamino)acetamide 458

Step 1: Trifluoro-methanesulphonic acid 2-(2-isopropyl-5-methyl-2H-[1,2,4]triazol-3-yl)-4,5-dihydro-6-oxa-1,3a,9-triaza-benzo[e]azulen-8-yl ester

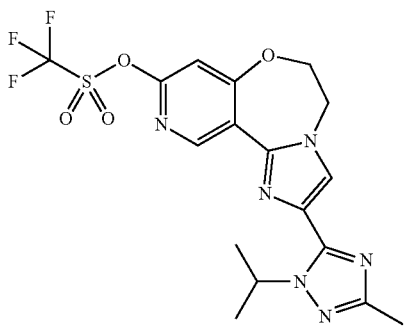 [SMILES: Cc1nc(-c2cn3c(n2)-c2cnc(OS(=O)(=O)C(F)(F)F)cc2OCC3)n(C(C)C)n1]

Following the procedure described for trifluoro-methanesulfonic acid 2-(2-isopropyl-2H-[1,2,4]triazol-3-yl)-4,5-dihydro-6-oxa-1,3a,9-triaza-benzo[e]azulen-8-yl ester to give Trifluoro-methanesulphonic acid 2-(2-isopropyl-5-methyl-2H-[1,2,4]triazol-3-yl)-4,5-dihydro-6-oxa-1,3a,9-triaza-benzo[e]azulen-8-yl ester (174 mg, 79% total). LCMS: RT=3.56 min, [M+H]+=459. $^1$H NMR 400 MHz (DMSO-d6) δ: 9.49 (1 H, s), 7.67 (1 H, s), 6.83 (1 H, s), 5.86-5.80 (1 H, m), 4.63-4.62 (2 H, m), 4.50-4.46 (2 H, m), 2.40 (3 H, s), 1.55 (6 H, d, J=6.64 Hz).

Step 2

A mixture of trifluoro-methanesulphonic acid 2-(2-isopropyl-5-methyl-2H-[1,2,4]triazol-3-yl)-4,5-dihydro-6-oxa-1,3a,9-triaza-benzo[e]azulen-8-yl ester (174 mg, 0.38 mmol), 2-amino-acetamide (281 mg, 3.8 mmol) and NMP (2 mL) was heated at 85° C. for 18 hours. The reaction mixture was treated with water and stirred, the precipitate formed collected by filtration. The aqueous filtrate was passed down an Isolute SCX-2 cartridge washing with methanol and eluting with 2M ammonia in methanol. Appropriate fractions were combined and concentrated in vacuo, the resultant residue subjected to flash chromatography (SiO2, gradient 0 to 10% methanol in DCM) to give 458 (24 mg, 17%). LCMS: RT=2.18 min, [M+H]+=383. $^1$H NMR 400 MHz (DMSO-d6) δ: 9.00 (1 H, s), 7.78 (1 H, s), 7.31 (1 H, br, s), 7.00 (1 H, br, s), 6.94 (1 H, br, t), 6.10 (1 H, s), 5.85 (1 H, m), 4.47 (4 H, m), 3.83 (2 H, d, J=5.85 Hz), 2.25 (3 H, s), 1.45 (6 H, d, J=6.61 Hz)

Example 459

1-(2-(1-isopropyl-1H-1,2,4-triazol-5-yl)-5,6-dihydrobenzo[f]imidazo[1,2-d][1,4]oxazepin-9-yl)piperidine-2-carboxamide 459

Step 1: 1-[2-(2-Isopropyl-2H-[1,2,4]triazol-3-yl)-4,5-dihydro-6-oxa-1,3a-diaza-benzo[e]azulen-8-yl]-piperidine-2-carboxylic acid

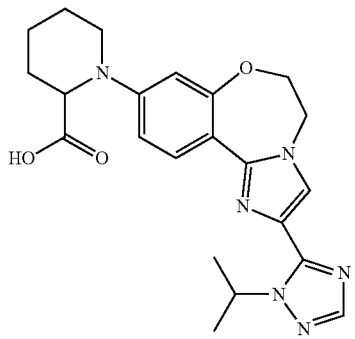 [SMILES: CC(C)n1ncnc1-c1cn2c(n1)-c1ccc(N3CCCCC3C(=O)O)cc1OCC2]

9-bromo-2-(1-isopropyl-1H-1,2,4-triazol-5-yl)-5,6-dihydrobenzo[f]imidazo[1,2-d][1,4]oxazepine 194 (1.01 g, 2.7 mmol), methyl picolinate (3.86 g, 27.0 mmol), copper (I) iodide (0.2 g, 1.08 mmol), trans-4-hydroxy(L)proline (0.14 g, 1.08 mmol) and potassium phosphate (1.14 g, 5.4 mmol) in DMSO (10 mL) were heated at 80° C. for 24 hours. The cooled reaction mixture was loaded onto an Isolute SCX-2 cartridge, washed with methanol and eluted with 2M ammonia in methanol. The resultant residue was triturated with diethyl ether to afford 1-[2-(2-Isopropyl-2H-[1,2,4]triazol-3-yl)-4,5-dihydro-6-oxa-1,3a-diaza-benzo[e]azulen-8-yl]-piperidine-2-carboxylic acid (1.04 g, 87% total). LCMS: RT=2.94 min, [M+H]+=423.

Step 2

A mixture of 1-[2-(2-Isopropyl-2H-[1,2,4]triazol-3-yl)-4,5-dihydro-6-oxa-1,3a-diaza-benzo[e]azulen-8-yl]-piperidine-2-carboxylic acid (1.15 g, 2.73 mmol), EDCI (0.58 g, 3.0 mmol), HOBt (0.41 g, 3.0 mmol) and DIPEA (2.34 mL, 13.65 mmol) in DMF was stirred at RT (2 mL) for 5 min before ammonium chloride (0.44 g, 8.18 mmol) was added and the reaction mixture stirred for 18 h. The reaction mixture was concentrated in vacuo and the resultant residue triturated with water before being subjected to flash chromatography (SiO2, gradient 0 to 10% methanol in DCM) to give 459 as a white solid (0.08 g, 6%). LCMS: RT=3.48 min, [M+H]+=422. $^1$H NMR 400 MHz (DMSO-d6) δ: 8.18 (1 H, d, J=9.06 Hz), 7.89 (1 H, d, J=0.63 Hz), 7.80 (1 H, s), 7.31 (1 H, br, s), 7.01 (1 H, br, s), 6.72 (1 H, dd, J=9.16, 2.60 Hz), 6.40 (1 H, d, J=2.54 Hz), 5.92-5.91 (1 H, m), 4.44-4.43 (4 H, m), 4.39 (1 H, m), 3.60 (1 H, d, J=12.44 Hz), 3.39-3.32 (1 H, m), 2.06 (1 H, d, J=13.57 Hz), 1.75 (2 H, m), 1.58 (3 H, m), 1.48 (6 H, dd, J=6.60, 2.59 Hz)

Example 463

2-(1-isopropyl-3-methyl-1H-1,2,4-triazol-5-yl)-5,6-dihydroimidazo[1,2-d]pyrido[3,4-f][1,4]oxazepin-9-amine 463

Step 1: 2-(1-isopropyl-3-methyl-1H-1,2,4-triazol-5-yl)-5,6-dihydroimidazo[1,2-d]pyrido[3,4-f][1,4]oxazepin-9-yl trifluoromethanesulfonate

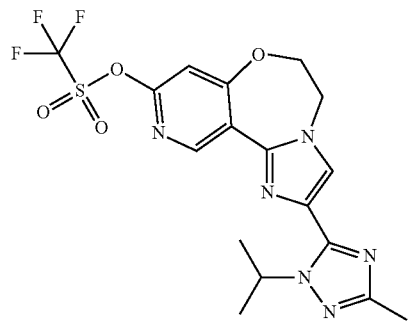 [SMILES: Cc1nc(-c2cn3c(n2)-c2cnc(OS(=O)(=O)C(F)(F)F)cc2OCC3)n(C(C)C)n1]

2-(1-isopropyl-3-methyl-1H-1,2,4-triazol-5-yl)-5,6-dihydroimidazo[1,2-d]pyrido[3,4-f][1,4]oxazepin-9-ol (280 mg, 0.87 mmol) was dissolved in N, N-dimethylacetamide (2.3 mL) and treated with N-(5-chloro-2-pyridyl) triflimide (720 mg, 1.8 mmol) and triethylamine (0.61 mL, 4.4 mmol). The mixture was stirred overnight at 60° C. The reaction mixture was diluted with 1N HCl and ethyl acetate. The layers were separated and the aqueous phase was extracted into ethyl acetate (4×). The combined organics were washed with brine (1×), dried over MgSO4, filtered, and absorbed onto celite for purification by flash chromatography [4 g, 0-100% EtOAc in heptane; removes large impurity] followed by a second purification eluting with 0-20% MeOH in DCM to afford 2-(1-isopropyl-3-methyl-1H-1,2,4-triazol-5-yl)-5,6-dihydroimidazo[1,2-d]pyrido[3,4-f][1,4]oxazepin-9-yl trifluoromethanesulfonate as a dark viscous oil (285 mg, 71%). 1H NMR (400 MHz, DMSO) δ 9.29 (d, J=11.2 Hz, 1H), 7.99 (d, J=6.2 Hz, 1H), 7.36 (s, 1H), 5.82 (hept, J=6.7 Hz, 1H), 4.76-4.68 (m, 4H), 2.26 (s, 3H), 1.45 (t, J=7.8 Hz, 6H)

Step 2: N-(3,4-dimethoxybenzyl)-2-(1-isopropyl-3-methyl-1H-1,2,4-triazol-5-yl)-5,6-dihydroimidazo[1,2-d]pyrido[3,4-f][1,4]oxazepin-9-amine

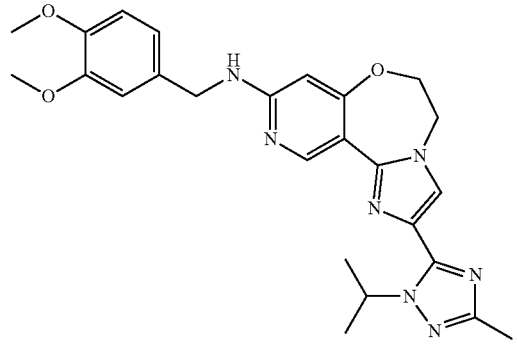

2-(1-isopropyl-3-methyl-1H-1,2,4-triazol-5-yl)-5,6-dihydroimidazo[1,2-d]pyrido[3,4-f][1,4]oxazepin-9-yl trifluoromethanesulfonate (790 mg, 1.7 mmol) was dissolved in N-methylpyrrolidinone (11 mL) and treated with veratrylamine (1.0 mL, 6.9 mmol) and triethylamine (1.9 mL, 14 mmol). The reaction mixture was heated at 120° C. overnight. The mixture was diluted with water and 20% MeOH in DCM and the layers separated. The aqueous phase was extracted into DCM/MeOH (3×), dried over sodium sulfate, filtered, and absorbed onto celite for purification by flash chromatography to afford N-(3,4-dimethoxybenzyl)-2-(1-isopropyl-3-methyl-1H-1,2,4-triazol-5-yl)-5,6-dihydroimidazo[1,2-d]pyrido[3,4-f][1,4]oxazepin-9-amine as a light yellow solid (190 mg, 23%). 1H NMR (400 MHz, DMSO) δ 8.99 (s, 1H), 7.75 (s, 1H), 6.95 (d, J=1.5 Hz, 1H), 6.92 (s, 1H), 6.88 (s, 1H), 6.02 (s, 1H), 5.85 (hept, J=6.6 Hz, 1H), 4.65 (s, 1H), 4.50-4.36 (m, 6H), 3.73 (s, 6H), 2.24 (s, 3H), 1.44 (d, J=6.6 Hz, 6H)

Step 3

N-(3,4-dimethoxybenzyl)-2-(1-isopropyl-3-methyl-1H-1,2,4-triazol-5-yl)-5,6-dihydroimidazo[1,2-d]pyrido[3,4-f][1,4]oxazepin-9-amine (190 mg, 0.40 mmol) was dissolved in TFA (3.0 mL) and heated at 65° C. for 30 min. The reaction mixture was cooled to ambient temperature and concentrated to dryness in vacuo. The crude residue was purified via HPLC to afford 463 as a white solid (40 mg, 31%). LC/MS(ESI+): m/z 326 (M+H). 1H NMR (400 MHz, DMSO) δ 8.92 (s, 1H), 7.76 (s, 1H), 6.19 (s, 2H), 5.98 (s, 1H), 5.88-5.76 (m, 1H), 4.45 (dd, J=14.4, 5.6 Hz, 4H), 2.24 (s, 3H), 1.44 (d, J=6.6 Hz, 6H)

Example 466

8-(2-(1-isopropyl-1H-1,2,4-triazol-5-yl)-5,6-dihydroimidazo[1,2-d]pyrido[3,4-f][1,4]oxazepin-9-yl)-3,8-diazabicyclo[3.2.1]octan-2-one 466

Step 1: 3,8-Diaza-bicyclo[3.2.1]octan-2-one

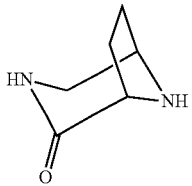

To a solution of 2-oxo-3,8-diazabicyclo[3.2.1]octane-8-carboxylic acid tert-butyl ester (108 mg, 0.48 mmol) in DCM (0.5 mL) at 0° C. was added dropwise, TFA (0.5 ml) and the reaction mixture stirred for 30 min. The reaction was warmed to RT and stirred for 1 h before being concentrated in vacuo and triturated with diethyl ether. The resultant residue was subjected to flash chromatography (Isolute NH2, 50% methanol in DCM) to give 3,8-Diaza-bicyclo[3.2.1]octan-2-one as a white solid (69 mg, quantitative). LCMS: RT=0.32 min, [M+H]+=127. 1H NMR 400 MHz (DMSO-d6) δ: 7.02 (1 H, br, s), 3.53 (1 H, m), 3.24 (1 H, dd, J=11.00, 4.14 Hz), 2.80-2.79 (1 H, m), 2.77 (1 H, m), 1.78 (3 H, m), 1.57-1.56 (1 H, m).

Step 2

To a suspension of 2-(2-Isopropyl-2H-[1,2,4]triazol-3-yl)-4,5-dihydro-6-oxa-1,3a,9-triaza-benzo[e]azulen-8-ol from Example 93 (137 mg, 0.44 mmol) in NMP (1.2 mL) was added sodium hydride (60% in mineral oil, 21 mg, 0.53 mmol). The reaction mixture was stirred at RT for 45 min, then at 45° C. for 45 min then cooled to RT. Phenyl trifluorosulphonimide (189 mg, 0.53 mmol) was added and the reaction stirred at RT for 1 h. 3,8-diaza-bicyclo[3.2.1]octan-2-one (69 mg, 0.48 mmol) and triethylamine (77 μL, 0.44 mmol) were added and the reaction mixture heated at 100° C. for 72 h then 120° C. for 7 h. The reaction mixture was cooled to RT, quenched with water and the resulting solid filtered and dried in vacuo. The resultant solid was loaded onto an Isolute SCX-2 cartridge, washed with methanol and eluted with 2M ammonia in methanol. Basic fractions were combined and concentrated in vacuo, the resultant residue was subjected to flash chromatography (SiO2, gradient 0 to 10% methanol in DCM) to give 466 (54 mg, 29%). LCMS: RT=2.33 min, [M+H]+=421. 1H NMR 300 MHz (DMSO-d6) δ: 9.13 (1 H, s), 7.88 (2 H, d, J=8.29 Hz), 7.19 (1 H, br, s), 6.42 (1 H, s), 5.95 (1 H, m), 4.53 (4 H, d, J=10.45 Hz), 4.50 (1 H, m), 3.49 (1 H, m), 3.17 (1 H, d, J=5.21 Hz), 2.98 (1 H, m), 2.05-2.20 (2 H, m), 1.99 (1 H, m), 1.95-1.98 (1 H, m), 1.48 (6 H, dd, J=6.57, 2.41 Hz)

Example 467

3-methyl-2-(2-(1-(2,2,2-trifluoroethyl)-1H-1,2,4-triazol-5-yl)-5,6-dihydrobenzo[f]imidazo[1,2-d][1,4]oxazepin-9-yloxy)butanamide 467

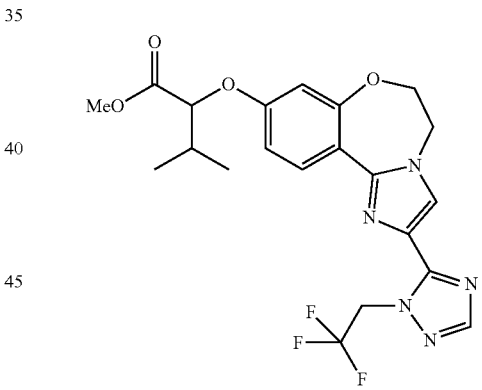

Following the procedures of Example 426, 2-[2-(2,2,2-trifluoro-ethyl)-2H-[1,2,4]triazol-3-yl]-4,5-dihydro-6-oxa-1,3a-diaza-benzo[e]azulen-8-ol and 2-hydroxy-3-methyl-butyric acid methyl ester were reacted and the crude product was subjected to flash chromatography (SiO2, gradient 0-10% methanol in ethyl acetate) to give racemic 3-Methyl-2-{2-[2-(2,2,2-trifluoro-ethyl)-2H-[1,2,4]triazol-3-yl]-4,5-dihydro-6-oxa-1,3a-diaza-benzo[e]azulen-8-yloxy}-butyric acid methyl ester as a yellow oil contaminated with triphenylphosphine oxide. LCMS: RT=3.70 min, [M+H]+=466

To a solution of 3-methyl-2-{2-[2-(2,2,2-trifluoro-ethyl)-2H-[1,2,4]triazol-3-yl]-4,5-dihydro-6-oxa-1,3a-diaza-benzo[e]azulen-8-yloxy}-butyric acid methyl ester in methanol (5 mL) was added water (0.5 mL) and lithium hydroxide monohydrate (22 mg, 0.57 mmol). The reaction mixture was heated at 50° C. for 16 h then HCl (1N, aqueous) added until pH~4. The reaction mixture was concentrated in vacuo. The resultant residue was dissolved in DMF (3 mL) and HATU (220 mg, 0.57 mmol), ammonium chloride (46 mg, 0.86 mmol) and triethylamine (120 µL, 0.86 mmol) added. The reaction mixture was stirred at RT for 1 h before being concentrated in vacuo. The residue was dissolved in ethyl acetate (10 mL) and the mixture washed with water, extracting with ethyl acetate (3×10 mL). The combined organic extracts were washed with brine, dried (MgSO4) and concentrated in vacuo. The resultant residue was subjected to flash chromatography (SiO2, gradient 0-10% methanol in ethyl acetate) to give 467 as a white solid (121 mg, 36%). LCMS: RT=4.05 min, [M+H]+=451; 1H NMR (400 MHz, d6-DMSO) 8.22 (1H, d, J=8.3 Hz), 8.03 (1H, s), 7.96 (1H, s), 7.47 (1H, br s), 7.25 (1H, br s), 6.74 (1H, dd, J=8.3, 2.5 Hz), 6.51 (1H, d, J=2.5 Hz), 5.86 (2H, q, J=8.9 Hz), 4.50-4.40 (4H, m), 4.22 (1H, dd, J=6.2 Hz), 2.08 (1H, oct, J=6.3 Hz), 0.96 (3H, d, J=6.3 Hz), 0.94 (3H, d, J=6.4 Hz)

Example 468

2-(1-(2,2,2-trifluoroethyl)-1H-1,2,4-triazol-5-yl)-5,6-dihydrobenzo[f]imidazo[1,2-d][1,4]oxazepin-9-ol 468

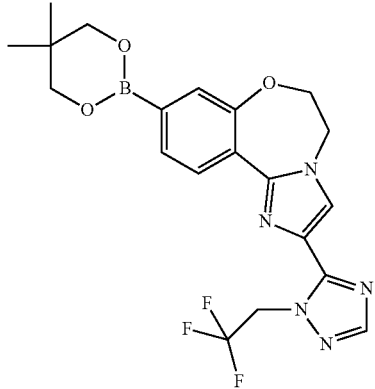 [SMILES: CC1(C)COB(c2ccc3c(c2)OCCn2cc(-c4ncnn4CC(F)(F)F)nc2-3)OC1]

8-Bromo-2-[2-(2,2,2-trifluoro-ethyl)-2H-[1,2,4]triazol-3-yl]-4,5-dihydro-6-oxa-1,3a-diaza-benzo[e]azulene (2 g, 4.8 mmol), bis(neopentylglycolato)diborane (1.64 g, 7.2 mmol), 1,1'-bis(diphenylphosphino)ferrocenepalladium(ii) dichloride dichloromethane (197 mg, 0.24 mmol) and potassium acetate (1.66 g, 16.9 mmol) were suspended in dioxane (25 mL) and the mixture degassed by bubbling argon through the mixture. The reaction mixture was heated at 90° C. for 2 h before cooling to RT and diluting with DCM (50 mL). Charcoal was added and the mixture stirred at RT for 5 min. The mixture was filtered and the filtrate washed with water, extracting with DCM (3×20 mL). The combined organic extracts were washed with brine, dried (MgSO4) and concentrated in vacuo. The resultant residue was triturated with diethyl ether, filtered and dried in vacuo at 50° C. to give 8-(5,5-Dimethyl-[1,3,2]dioxaborinan-2-yl)-2-[2-(2,2,2-trifluoro-ethyl)-2H-[1,2,4]triazol-3-yl]-4,5-dihydro-6-oxa-1,3a-diaza-benzo[e]azulene as a beige solid (1.7 g, 79%). LCMS: RT=2.64 min, [M+H]+=380

To a solution of 8-(5,5-dimethyl-[1,3,2]dioxaborinan-2-yl)-2-[2-(2,2,2-trifluoro-ethyl)-2H-[1,2,4]triazol-3-yl]-4,5-dihydro-6-oxa-1,3a-diaza-benzo[e]azulene (1.7 g, 3.8 mmol) in IMS was added hydroxylamine hydrochloride (1.58 g, 22.8 mmol) and sodium hydroxide (1.22 g, 30.4 mmol). The reaction mixture was stirred at RT for 18 h before being diluted with water (100 mL). The reaction mixture was concentrated in vacuo to remove the IMS. The solid which formed was collected by filtration and dried in vacuo to yield 468 as a beige solid (1.1 g, 85%). LCMS: RT=2.81 min, [M+H]+=352

Example 472

2-methyl-2-(2-(1-(2,2,2-trifluoroethyl)-1H-1,2,4-triazol-5-yl)-5,6-dihydrobenzo[f]imidazo[1,2-d][1,4]oxazepin-9-yloxy)propanamide 472

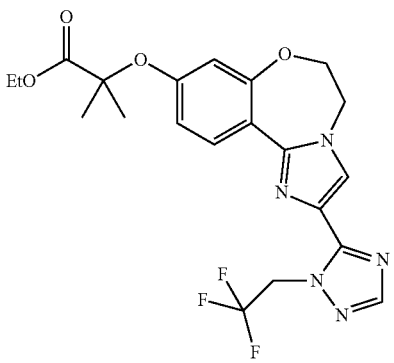 [SMILES: CCOC(=O)C(C)(C)Oc1ccc2c(c1)OCCn1cc(-c3ncnn3CC(F)(F)F)nc1-2]

Following the procedures of Example 426, 2-[2-(2,2,2-trifluoro-ethyl)-2H-[1,2,4]triazol-3-yl]-4,5-dihydro-6-oxa-1,3a-diaza-benzo[e]azulen-8-ol, 2-hydroxy-3-methyl-butyric acid methyl ester and 2-hydroxy-2-methyl-propionic acid ethyl ester were reacted and the crude product was subjected to flash chromatography (SiO2, gradient 0-10% methanol in ethyl acetate) to give 2-methyl-2-{2-[2-(2,2,2-trifluoro-ethyl)-2H-[1,2,4]triazol-3-yl]-4,5-dihydro-6-oxa-1,3a-diaza-benzo[e]azulen-8-yloxy}-propionic acid ethyl ester as a yellow oil contaminated with triphenylphosphine oxide. LCMS: RT=3.68 min, [M+H]+=466

To a solution of 2-methyl-2-{2-[2-(2,2,2-trifluoro-ethyl)-2H-[1,2,4]triazol-3-yl]-4,5-dihydro-6-oxa-1,3a-diaza-benzo[e]azulen-8-yloxy}-propionic acid ethyl ester in methanol (5 mL) was added water (2 mL) and lithium hydroxide monohydrate (25 mg, 0.62 mmol). The reaction mixture was heated at 50° C. for 30 min then HCl (1N, aqueous) added until pH~4. The reaction mixture was concentrated in vacuo. The resultant residue was dissolved in DMF (3 mL) and HATU (217 mg, 0.56 mmol), ammonium chloride (45 mg, 0.85 mmol) and triethylamine (119 µL, 0.85 mmol) added. The reaction mixture was stirred at RT for 1 h before being concentrated in vacuo. The residue was dissolved in ethyl acetate (10 mL) and the mixture washed with water, extracting with ethyl acetate (3×10 mL). The combined organic extracts were washed with brine, dried (MgSO4) and concentrated in vacuo. The resultant residue was subjected to flash chromatography (SiO2, gradient 0-10% methanol in ethyl acetate) to give 472 as a white solid (61 mg, 50%). LCMS: RT=3.74 min, [M+H]+=437; 1H NMR (400 MHz, d6-DMSO) 8.21 (1H, d, J=8.9 Hz), 8.03 (1H, s), 7.96 (1H, s), 7.52 (1H, br s), 7.25 (1H, br s), 6.68 (1H, dd, J=8.9, 2.8 Hz), 6.47 (1H, d, J=2.8 Hz), 5.85 (2H, q, J=8.9 Hz), 4.49-4.39 (4H, m), 1.44 (6H, s)

Example 475

2-(1-isopropyl-1H-1,2,4-triazol-5-yl)-9-(2-(methylsulfonyl)phenyl)-5,6-dihydrobenzo[f]imidazo[1,2-d][1,4]oxazepine 475

A solution of 8-Bromo-2-(2-isopropyl-2H-[1,2,4]triazol-3-yl)-4,5-dihydro-6-oxa-1,3a-diaza-benzo[e]azulene 194 (0.050 g, 0.13 mmol) and crushed Potassium phosphate (0.0851 g, 0.401 mmol) in N,N-Dimethylformamide (0.5 mL) was thoroughly degassed with N2. 2-Methylsulfonylphenylboronic acid (0.053 g, 0.27 mmol), Palladium Acetate (0.0015 g, 0.0067 mmol) and S-Phos (0.00686 g, 0.0167 mmol) were added and the mixture was heated in the microwave for 30 minutes at 180° C. The reaction was diluted with methylene chloride and filtered through celite. Saturated NH4Cl was added and the mixture was extracted 3 times with methylene chloride. The organic layers were combined, dried with Na2SO4 and concentrated. The crude was purified by reverse-phase HPLC to obtain 8.1 mg of 475 as a white solid. MS(ESI+) 450.1. 1H NMR (400 MHz, DMSO) δ 8.47 (d, J=8.3 Hz, 1H), 8.11 (dd, J=8.0, 1.1 Hz, 1H), 7.98 (s, 1H), 7.92 (s, 1H), 7.79 (td, J=7.5, 1.3 Hz, 1H), 7.70 (td, J=7.8, 1.3 Hz, 1H), 7.45 (dd, J=7.5, 1.1 Hz, 1H), 7.21 (dd, J=8.3, 1.8 Hz, 1H), 7.12 (d, J=1.7 Hz, 1H), 5.93 (hept, J=6.2 Hz, 1H), 4.57 (q, J=5.7 Hz, 4H), 2.93 (s, 3H), 1.50 (d, J=6.6 Hz, 6H)

Example 476

2-(2-(1-isopropyl-1H-1,2,4-triazol-5-yl)-5,6-dihydrobenzo[f]imidazo[1,2-d][1,4]oxazepin-9-yl)benzamide 476

Following the procedures of Example 475, 8-Bromo-2-(2-isopropyl-2H-[1,2,4]triazol-3-yl)-4,5-dihydro-6-oxa-1,3a-diaza-benzo[e]azulene 194 was reacted with (2-aminocarbonylphenyl)boronic acid to give 476. MS(ESI+) 415.2. 1H NMR (400 MHz, DMSO) δ 8.42 (d, J=8.3 Hz, 1H), 7.95 (s, 1H), 7.91 (s, 1H), 7.70 (s, 1H), 7.54-7.39 (m, 4H), 7.34 (s, 1H), 7.22 (dd, J=8.3, 1.7 Hz, 1H), 7.12 (d, J=1.7 Hz, 1H), 5.93 (hept, J=6.2 Hz, 1H), 4.55 (q, J=5.7 Hz, 4H), 1.50 (d, J=6.6 Hz, 6H)

Example 477

9-(2-ethylphenyl)-2-(1-isopropyl-1H-1,2,4-triazol-5-yl)-5,6-dihydrobenzo[f]imidazo[1,2-d][1,4]oxazepine 477

Following the procedures of Example 475, 8-Bromo-2-(2-isopropyl-2H-[1,2,4]triazol-3-yl)-4,5-dihydro-6-oxa-1,3a-diaza-benzo[e]azulene 194 was reacted with 2-ethylphenylboronic acid to give 477. MS(ESI+) 400.2. 1H NMR (400 MHz, DMSO) δ 8.47 (d, J=8.2 Hz, 1H), 7.95 (s, 1H), 7.92 (s, 1H), 7.38-7.31 (m, 2H), 7.30-7.23 (m, 1H), 7.20 (d, J=7.3 Hz, 1H), 7.12 (dd, J=8.2, 1.7 Hz, 1H), 6.97 (d, J=1.6 Hz, 1H), 5.93 (hept, J=6.2 Hz, 1H), 4.65-4.41 (m, 4H), 2.61 (q, J=7.6 Hz, 2H), 1.50 (d, J=6.6 Hz, 6H), 1.07 (t, J=7.5 Hz, 3H)

Example 478

(2-(2-(1-isopropyl-1H-1,2,4-triazol-5-yl)-5,6-dihydrobenzo[f]imidazo[1,2-d][1,4]oxazepin-9-yl)phenyl)methanol 478

Following the procedures of Example 475, 8-Bromo-2-(2-isopropyl-2H- [1,2,4]triazol-3-yl)-4,5-dihydro-6-oxa-1,3a-diaza-benzo[e]azulene 194 was reacted with 2-(hydroxymethyl)phenylboronic acid to give 478. MS(ESI+) 402.1. 1H NMR (400 MHz, DMSO) δ 8.46 (d, J=8.3 Hz, 1H), 7.96 (s, 1H), 7.92 (s, 1H), 7.58 (d, J=7.7 Hz, 1H), 7.41 (td, J=7.4, 1.1 Hz, 1H), 7.38-7.32 (m, 1H), 7.28 (d, J=7.4 Hz, 1H), 7.20 (dd, J=8.3, 1.6 Hz, 1H), 7.09 (d, J=1.5 Hz, 1H), 6.02-5.83 (m, 1H), 5.16 (t, J=5.3 Hz, 1H), 4.56 (q, J=6.1 Hz, 4H), 4.45 (d, J=5.3 Hz, 2H), 1.50 (d, J=6.6 Hz, 6H)

Example 479

2-(1-isopropyl-3-methyl-1H-1,2,4-triazol-5-yl)-5,6-dihydrobenzo[f]imidazo[1,2-d][1,4]oxazepin-9-amine 479

Following Example 480, 9-bromo-2-(1-isopropyl-3-methyl-1H-1,2,4-triazol-5-yl)-5,6-dihydrobenzo[f]imidazo[1,2-d][1,4]oxazepine 411 was converted to 479 as a white solid (15 mg, 7.2%). LC/MS(ESI+): m/z 325 (M+H). 1H NMR (400 MHz, DMSO) δ 8.04 (d, J=8.6 Hz, 1H), 7.71 (s, 1H), 6.37 (dd, J=8.7, 2.0 Hz, 1H), 6.17 (d, J=2.0 Hz, 1H), 5.84 (m, 1H), 5.51 (s, 2H), 4.39 (m, 4H), 2.23 (s, 3H), 1.43 (d, J=6.6 Hz, 6H)

Example 480

2-(1-isopropyl-1H-1,2,4-triazol-5-yl)-5,6-dihydrobenzo[f]imidazo[1,2-d][1,4]oxazepin-9-amine 480

Step 1: tert-butyl 2-(1-isopropyl-1H-1,2,4-triazol-5-yl)-5,6-dihydrobenzo[f]imidazo[1,2-d][1,4]oxazepin-9-ylcarbamate

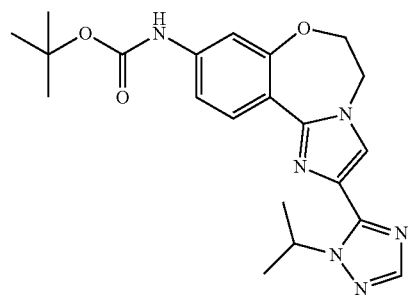 [SMILES: CC(C)n1ncnc1-c1cn2c(n1)-c1ccc(NC(=O)OC(C)(C)C)cc1OCC2]

A mixture of 9-bromo-2-(1-isopropyl-1H-1,2,4-triazol-5-yl)-5,6-dihydrobenzo[f]imidazo[1,2-d][1,4]oxazepine 194 (250 mg, 0.67 mmol), t-butyl carbamate (390 mg, 3.3 mmol), cesium carbonate (440 mg, 1.3 mmol), 4,5-bis(diphenylphosphino)-9,9-dimethylxanthene (58 mg, 0.10 mmol), and tris(dibenzylideneacetone)dipalladium(0) (46 mg, 0.05 mmol) was suspended in 1,4-dioxane (5.2 mL) and heated at 110° C. for 24 hr. The reaction mixture was cooled to ambient temperature, diluted with DCM, and filtered to remove solids. The crude mixture was absorbed onto celite for purification by flash chromatography to afford tert-butyl 2-(1-isopropyl-1H-1,2,4-triazol-5-yl)-5,6-dihydrobenzo[f]imidazo[1,2-d][1,4]oxazepin-9-ylcarbamate as a yellow crystalline solid (170 mg, 61%). 1H NMR (400 MHz, DMSO) δ 9.56 (d, J=12.5 Hz, 1H), 8.27 (d, J=8.8 Hz, 1H), 7.89 (s, 1H), 7.85 (s, 1H), 7.26 (t, J=5.8 Hz, 1H), 7.23-7.14 (m, 1H), 5.89 (hept, J=6.6 Hz, 1H), 4.52-4.42 (m, 4H), 1.47 (d, J=6.6 Hz, 6H)

Step 2 tert-butyl 2-(1-isopropyl-1H-1,2,4-triazol-5-yl)-5,6-dihydrobenzo[f]imidazo[1,2-d][1,4]oxazepin-9-ylcarbamate (170 mg, 0.40 mmol) was dissolved in DCM (3.0 mL) and treated with trifluoroacetic acid. After 10 min the solvent was removed in vacuo. The crude residue was re-dissolved in DCM and the solvent removed once again to provide a golden solid. The crude material was purified via HPLC to afford 480 as an off-white solid (32 mg, 32%). LC/MS (ESI+): m/z 311 (M+H). 1H NMR (400 MHz, DMSO) δ 8.05 (d, J=8.6 Hz, 1H), 7.87 (s, 1H), 7.75 (s, 1H), 6.38 (d, J=6.4 Hz, 1H), 6.17 (s, 1H), 5.97-5.84 (m, 1H), 5.52 (s, 2H), 4.39 (s, 4H), 1.46 (d, J=6.4 Hz, 6H)

Example 481

2-(1-isopropyl-3-methyl-1H-1,2,4-triazol-5-yl)-10-methyl-5,6-dihydrobenzo[f]imidazo[1,2-d][1,4]oxazepine 481

A microwave vial was charged with a suspension of 10-bromo-2-(1-isopropyl-3-methyl-1H-1,2,4-triazol-5-yl)-5,6-dihydrobenzo[f]imidazo[1,2-d][1,4]oxazepine (0.200 mg, 0.515 mmol) in 2.0 ml THF/0.400 mL water. To this suspension was added potassium phosphate (330 mg, 0.0015 mol) and trimethylboroxine (0.14 ml, 1.00 mmol). The reaction suspension was degassed by bubbling nitrogen through the stirred mixture via a syringe. After several minutes the syringe was removed and Bis(ditertbutyl(4-dimethylaminophenyl)phosphine)dichloropalladium(II) (18 mg, 0.02 mmol) was added and the reaction vial was quickly sealed. The sealed vial was flash heated in a microwave at 140° C. for 40 minutes. The cooled reaction was diluted with EtOAc and the organic solution was washed with water×1, saline×1 and dried (Na2SO4) before concentration in vacuo. The crude residue was purified by preparative RP-HPLC to give 481. MS: (ESI+)=324.1

Example 482

2-(1-isopropyl-3-methyl-1H-1,2,4-triazol-5-yl)-9-methyl-5,6-dihydrobenzo[f]imidazo[1,2-d][1,4]oxazepine 482

Following the procedures of Example 481, 9-bromo-2-(1-isopropyl-3-methyl-1H-1,2,4-triazol-5-yl)-5,6-dihydrobenzo[f]imidazo[1,2-d][1,4]oxazepine 411 (0.640 mmol) was converted to 482. MS: (ESI+)=324.1

Example 485

(2R)-2-(2-(1-isopropyl-1H-1,2,4-triazol-5-yl)-5,6-dihydrobenzo[f]imidazo[1,2-d][1,4]oxazepin-9-yloxy)propanamide 485

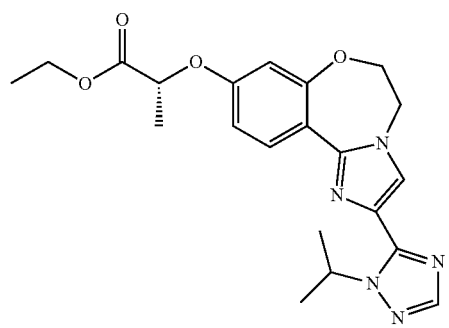 [SMILES: CCOC(=O)[C@@H](C)Oc1ccc2c(c1)OCCn1cc(-c3ncnn3C(C)C)nc1-2]

Following the procedure of Example 426, 2-(2-isopropyl-2H-[1,2,4]triazol-3-yl)-4,5-dihydro-6-oxa-1,3a-diaza-benzo[e]azulen-8-ol 490 and ethyl-1-lactate were reacted and the crude product was subjected to flash chromatography (SiO2, gradient 0-10% methanol in ethyl acetate) to give (R)-2-[2-(2-isopropyl-2H-[1,2,4]triazol-3-yl)-4,5-dihydro-6-oxa-1,3a-diaza-benzo[e]azulen-8-yloxy]-propionic acid ethyl ester as a yellow (315 mg, 66%). LCMS: RT=3.44 min, [M+H]+=412

To a solution of (R)-2-[2-(2-isopropyl-2H-[1,2,4]triazol-3-yl)-4,5-dihydro-6-oxa-1,3a-diaza-benzo[e]azulen-8-yloxy]-propionic acid ethyl ester (315 mg, 0.77 mmol) in methanol (10 mL) was added water (1 mL) and lithium hydroxide monohydrate (46 mg, 1.15 mmol). The reaction mixture was heated at 50° C. for 16 h then HCl (1N, aq.) added until pH~4. The reaction mixture was concentrated in vacuo. The resultant residue was dissolved in DMF (5 mL) and HATU (583 mg, 1.53 mmol), ammonium chloride (122 mg, 2.29 mmol) and triethylamine (320 μL, 2.29 mmol) added. The reaction mixture was stirred at RT for 1 h before being concentrated in vacuo. The residue was dissolved in ethyl acetate (10 mL) and the mixture washed with water, extracting with ethyl acetate (3×10 mL). The combined organic extracts were washed with brine, dried (MgSO4) and concentrated in vacuo. The resultant residue was subjected to flash chromatography (SiO2, gradient 0-10% methanol in ethyl acetate) and the product crystallised from acetonitrile to give 485 as a white solid (75 mg, 26%). LCMS: RT=3.25 min, [M+H]+=383

Example 486

(2S)-2-(2-(1-(2,2,2-trifluoroethyl)-1H-1,2,4-triazol-5-yl)-5,6-dihydrobenzo[f]imidazo[1,2-d][1,4]oxazepin-9-yloxy)propanamide 486

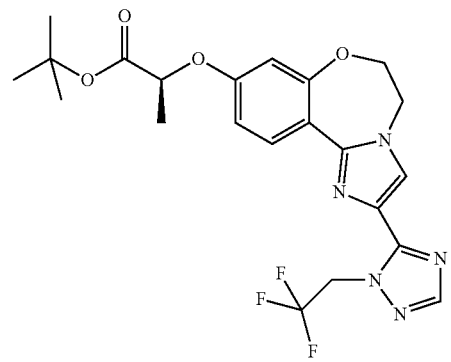 [SMILES: C[C@H](Oc1ccc2c(c1)OCCn1cc(-c3ncnn3CC(F)(F)F)nc1-2)C(=O)OC(C)(C)C]

Following the procedure of Example 426, 2-[2-(2,2,2-trifluoro-ethyl)-2H-[1,2,4]triazol-3-yl]-4,5-dihydro-6-oxa-1,3a-diaza-benzo[e]azulen-8-ol and 2-hydroxy-3-methyl-butyric acid methyl ester and (R)-2-hydroxy-propionic acid tert-butyl ester were reacted and the crude product was subjected to flash chromatography (SiO2, gradient 0-10% methanol in ethyl acetate) to give (S)-2-{2-[2-(2,2,2-Trifluoro-ethyl)-2H-[1,2,4]triazol-3-yl]-4,5-dihydro-6-oxa-1,3a-diaza-benzo[e]azulen-8-yloxy}-propionic acid tert-butyl ester as a yellow oil contaminated with triphenylphosphine oxide. LCMS: RT=3.86 min, [M+H]+=480

A solution of (S)-2-{2-[2-(2,2,2-trifluoro-ethyl)-2H-[1,2,4]triazol-3-yl]-4,5-dihydro-6-oxa-1,3a-diaza-benzo[e]azulen-8-yloxy}-propionic acid tert-butyl ester was dissolved in DCM (3 mL), TFA (0.5 mL) added and the reaction mixture stirred at RT for 16 h. The reaction mixture was concentrated in vacuo, and the residue dissolved in DMF (3 mL). HATU (217 mg, 0.56 mmol), ammonium chloride (46 mg, 0.85 mmol) and triethylamine (119 µL, 0.85 mmol) were added and the reaction mixture stirred at RT for 1 hour. The reaction mixture was concentrated in vacuo, the residue dissolved in ethyl acetate (10 mL) and the mixture washed with water extracting with ethyl acetate (3×10 mL). The combined organic extracts were washed with brine, dried (MgSO4) and concentrated in vacuo. The residue was subjected to flash chromatography (SiO2 gradient 0-10% methanol in EtOAc) then reverse phase preparative HPLC (C-18, 10-90% MeCN in water, 0.1% formic acid, 25 min gradient) then to yield 486 as a white solid (57 mg, 47%). LCMS: RT=3.52 min, [M+H]+=423; 1H NMR (400 MHz, d6-DMSO) 8.22 (1H, d, J=8.9 Hz), 8.03 (1H, s), 7.95 (1H, s), 7.51 (1H, br s), 7.22 (1H, br s), 6.73 (1H, dd, J=8.9, 2.6 Hz), 6.50 (1H, d, J=2.6 Hz), 5.86 (1H, q, J=8.9 Hz), 4.64 (1H, q, J=6.6 Hz), 4.51-4.38 (4H, m), 1.40 (1H, d, J=6.4 Hz)

Example 487

(2R)-2-(2-(1-(2,2,2-trifluoroethyl)-1H-1,2,4-triazol-5-yl)-5,6-dihydrobenzo[f]imidazo[1,2-d][1,4]oxazepin-9-yloxy)propanamide 487

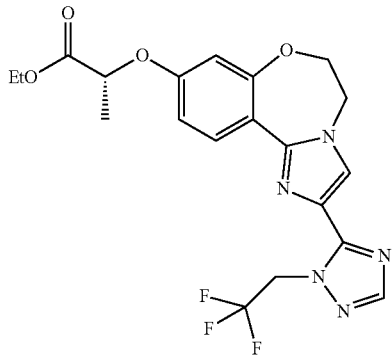 [SMILES: CCOC(=O)[C@@H](C)Oc1ccc2c(c1)OCCn1cc(-c3ncnn3CC(F)(F)F)nc1-2]

Following the procedure of Example 426, 2-[2-(2,2,2-trifluoro-ethyl)-2H-[1,2,4]triazol-3-yl]-4,5-dihydro-6-oxa-1,3a-diaza-benzo[e]azulen-8-ol, 2-hydroxy-3-methyl-butyric acid methyl ester and (S)-2-hydroxypropionic acid ethyl ester were reacted and the crude product was subjected to flash chromatography (SiO2, gradient 0-10% methanol in ethyl acetate) to give (R)-2-{2-[2-(2,2,2-Trifluoro-ethyl)-2H-[1,2,4]triazol-3-yl]-4,5-dihydro-6-oxa-1,3a-diaza-benzo[e]azulen-8-yloxy}-propionic acid ethyl ester as a yellow oil contaminated with triphenylphosphine oxide, no further purification was undertaken. LCMS: RT=3.51 min, [M+H]+=452

To a solution (R)-2-{2-[2-(2,2,2-trifluoro-ethyl)-2H-[1,2,4]triazol-3-yl]-4,5-dihydro-6-oxa-1,3a-diaza-benzo[e]azulen-8-yloxy}-propionic acid ethyl ester in methanol (3 mL) was added water (1 mL) and lithium hydroxide monohydrate (11 mg, 0.42 mmol). The reaction mixture was stirred at RT for 16 h then HCl (1N, aq.) added until pH~4. The reaction mixture was concentrated in vacuo. The resultant residue was dissolved in DMF (3 mL) and HATU (217 mg, 0.56 mmol), ammonium chloride (45 mg, 0.85 mmol) and triethylamine (119 µL, 0.85 mmol) added. The reaction mixture was stirred at RT for 1 h before being concentrated in vacuo. The residue was dissolved in ethyl acetate (10 mL) and the mixture washed with water, extracting with ethyl acetate (3×10 mL). The combined organic extracts were washed with brine, dried (MgSO4) and concentrated in vacuo. The resultant residue was subjected to flash chromatography (SiO2, gradient 0-10% methanol in ethyl acetate) to give 487 as a white solid (49 mg, 40%). LCMS: RT=3.52 min, [M+H]+=423; 1H NMR (400 MHz, d6-DMSO) 8.22 (1H, d, J=8.9 Hz), 8.03 (1H, s), 7.95 (1H, s), 7.51 (1H, br s), 7.22 (1H, br s), 6.73 (1H, dd, J=8.9, 2.6 Hz), 6.50 (1H, d, J=2.6 Hz), 5.86 (2H, q, J=8.9 Hz), 4.64 (1H, q, J=6.6 Hz), 4.51-4.38 (4H, m), 1.40 (3H, d, J=6.4 Hz)

Example 489

2-(3-methyl-1-(2,2,2-trifluoroethyl)-1H-1,2,4-triazol-5-yl)-5,6-dihydroimidazo[1,2-d]pyrido[3,4-f][1,4]oxazepin-9-amine 489

Step 1: 2-[5-Methyl-2-(2,2,2-trifluoro-ethyl)-2H-[1,2,4]triazol-3-yl]-4,5-dihydro-6-oxa-1,3a,9-triaza-benzo[e]azulen-8-ol

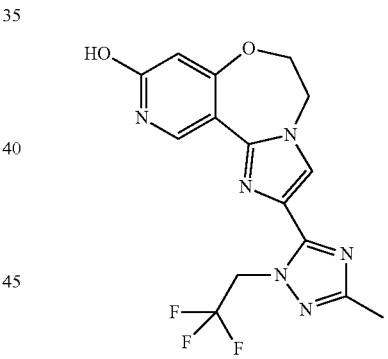

A solution of 8-chloro-2-[5-methyl-2-(2,2,2-trifluoro-ethyl)-2H-[1,2,4]triazol-3-yl]-4,5-dihydro-6-oxa-1,3a,9-tri-aza-benzo[e]azulene (4 g, 10.4 mmol) in acetic acid (100 mL) was heated to 150° C. for 65 hours. The reaction was cooled, concentrated in vacuo and loaded onto an Isolute SCX-2 cartridge, washing with methanol and eluting with 2M ammonia in methanol. Basic fractions were combined and concentrated in vacuo, the resultant residue was subjected to flash chromatography (SiO2, gradient 0 to 10% methanol in DCM) to give 2-[5-Methyl-2-(2,2,2-trifluoro-ethyl)-2H-[1,2,4]triazol-3-yl]-4,5-dihydro-6-oxa-1,3a,9-tri-aza-benzo[e]azulen-8-ol. LCMS: RT=2.25 min, [M+H]+=367.33. 1H NMR 300 MHz (DMSO-d): δ 8.40 (1 H, br, s), 7.94 (1 H, s), 5.85 (1 H, s), 5.77 (1 H, s), 5.73 (2 H, m), 4.56 (2 H, m), 4.49 (2 H, m), 2.29 (3 H, s)

Step 2: Trifluoro-methanesulphonic acid 2-[5-methyl-2-(2,2,2-trifluoro-ethyl)-2H-[1,2,4]triazol-3-yl]-4,5-dihydro-6-oxa-1,3a,9-triaza-benzo[e]azulen-8-yl ester

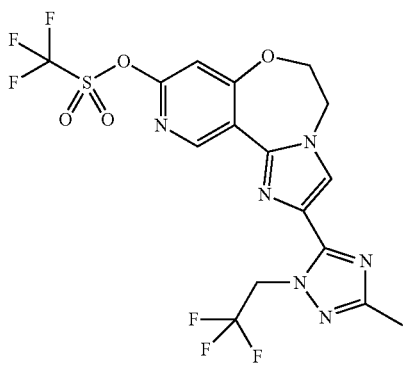 [SMILES: Cc1nc(-c2cn3c(n2)-c2cnc(OS(=O)(=O)C(F)(F)F)cc2OCC3)n(CC(F)(F)F)n1]

2-[5-methyl-2-(2,2,2-trifluoro-ethyl)-2H-[1,2,4]triazol-3-yl]-4,5-dihydro-6-oxa-1,3a,9-triaza-benzo[e]azulen-8-ol was converted to Trifluoro-methanesulphonic acid 2-[5-methyl-2-(2,2,2-trifluoro-ethyl)-2H-[1,2,4]triazol-3-yl]-4,5-dihydro-6-oxa-1,3a,9-triaza-benzo[e]azulen-8-yl ester. LCMS: RT=3.65 min, [M+H]+=499.20.

Step 3: (3,4-Dimethoxy-benzyl)-{2-[5-methyl-2-(2,2,2-trifluoro-ethyl)-2H-[1,2,4]triazol-3-yl]-4,5-dihydro-6-oxa-1,3a,9-triaza-benzo[e]azulen-8-yl}amine

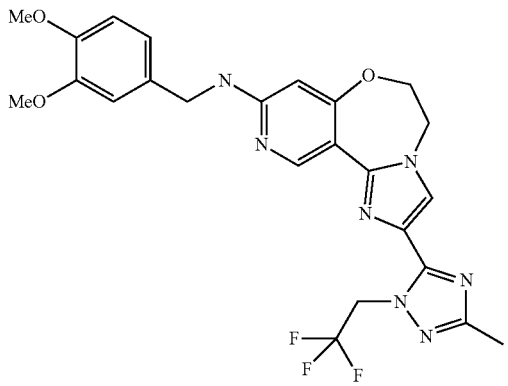 [SMILES: COc1ccc(CNc2cc3c(cn2)-c2nc(-c4nc(C)nn4CC(F)(F)F)cn2CCO3)cc1OC]

trifluoro-methanesulphonic acid 2-[5-methyl-2-(2,2,2-trifluoro-ethyl)-2H-[1,2,4]triazol-3-yl]-4,5-dihydro-6-oxa-1,3a,9-triaza-benzo[e]azulen-8-yl ester was converted to (3,4-Dimethoxy-benzyl)-{2-[5-methyl-2-(2,2,2-trifluoro-ethyl)-2H-[1,2,4]triazol-3-yl]-4,5-dihydro-6-oxa-1,3a,9-triaza-benzo[e]azulen-8-yl}amine. LCMS: RT=2.39 min, [M+H]+=516.38. $^1$H NMR 300 MHz (DMSO-d6): δ 8.95 (1 H, s), 7.89 (1 H, s), 7.25 (1 H, br, s), 6.95 (1 H, d, J=1.85 Hz), 6.86-6.86 (2H, m), 6.00 (1 H, s), 5.77 (2 H, d, J=8.90 Hz), 4.45 (4 H, d, J=5.44 Hz), 4.39 (2 H, d, J=5.99 Hz), 3.72 (3 H, s), 3.70 (3 H, s), 2.26 (3 H, s)

Step 4

(3,4-dimethoxy-benzyl)-{2-[5-methyl-2-(2,2,2-trifluoro-ethyl)-2H-[1,2,4]triazol-3-yl]-4,5-dihydro-6-oxa-1,3a,9-tri- aza-benzo[e]azulen-8-yl}amine was converted to 489 with further recrystallisation from methanol. LCMS: RT=2.41 min, [M+H]+=366.22. $^1$H NMR 400 MHz (DMSO-d6): δ 8.89 (1 H, s), 7.90 (1 H, s), 6.22 (2 H, br, s), 5.98 (1 H, s), 5.82-5.72 (2 H, m), 4.46-4.45 (4 H, m), 2.27 (3 H, s)

Example 490

2-(1-isopropyl-1H-1,2,4-triazol-5-yl)-5,6-dihydrobenzo[f]imidazo[1,2-d][1,4]oxazepin-9-ol 490

To a solution of 8-(5,5-dimethyl-[1,3,2]dioxaborinan-2-yl)-2-(2-isopropyl-2H-[1,2,4]triazol-3-yl)-4,5-dihydro-6-oxa-1,3a-diaza-benzo[e]azulene (473 mg, 1.16 mmol) in IMS (10 mL) was added hydroxylamine hydrochloride (242 mg, 0.39 mmol) and sodium hydroxide (186 mg, 4.65 mmol) and the reaction mixture stirred at RT for 18 h. Further quantities of hydroxylamine hydrochloride (242 mg, 0.39 mmol) and sodium hydroxide (186 mg, 4.65 mmol) were added and stirring continued for 3 h. The reaction mixture was diluted with ammonium chloride solution (20 mL, saturated) and extracted with ethyl acetate (3×10 mL). The combined organic extracts were dried (MgSO4), concentrated in vacuo and the resultant residue subjected to flash chromatography (SiO2, gradient 0-5% methanol in DCM) to yield 490 as a white solid (155 mg, 43%). 1H NMR (400 MHz, CDCl3) δ 8.29 (1H, d, J=8.4 Hz), 7.88 (1H, s), 7.59 (1H, s), 6.64 (1H, dd, J=8.4, 2.6 Hz), 6.48 (1H, d, J=2.6 Hz), 5.99 (1H, sept, J=6.7 Hz), 4.44-4.32 (4H, m), 1.58 (6H, d, J=6.7 Hz).

Alternatively, 8-Bromo-2-(2-isopropyl-2H-[1,2,4]triazol-3-yl)-4,5-dihydro-6-oxa-1,3a-diaza-benzo[e]azulene (9.5 g, 25.4 mmol), 2-di-tert-butylphosphino-2',4',6'-triisopropylbiphenyl (855 mg, 2.0 mmol), tris(dibenzylideneacetone)dipalladium (0) (475 mg, 0.5 mmol) and potassium hydroxide (4.2 g, 76.2 mmol) were suspended in dioxane (29 mL) and water (15 mL). The suspension was degassed with nitrogen and the reaction mixture heated at 90° C. for 1 h. The reaction mixture was diluted with water (50 mL) and extracted with ethyl acetate (20 mL). The aqueous fraction was acidified to pH~5 by addition of hydrochloric acid (1M) causing a precipitate to form. The suspension was extracted with ethyl acetate (3×15 mL). The combined organic extracts were dried (MgSO4), concentrated in vacuo. The resultant residue was triturated with diethyl ether to yield 490 as an orange solid (3.6 g, 46%). 1H NMR (400 MHz, DMSO-d6) δ 9.90 (1H, br s), 8.22 (1H, d, J=8.9 Hz), 7.88 (1H, s), 7.82 (1H, s), 6.61 (1H, dd, J=8.9, 2.6 Hz), 6.41 (1H, d, J=2.6 Hz), 5.90 (1H, sept, J=6.5 Hz), 4.49-4.39 (4H, m), 1.47 (6H, d, J=6.5 Hz)

Also alternatively,

Step 1: 4-Benzyloxy-2-fluoro-benzonitrile

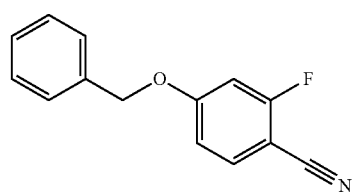 [SMILES: N#Cc1ccc(OCc2ccccc2)cc1F]

A solution of 2-fluoro-4-hydroxy-benzonitrile (80 g, 0.58 mol), potassium carbonate (162 g, 1.17 mol) and benzyl bromide (76.4 mL, 0.64 mol) and potassium iodide (9.6 g, 0.058 mol) in acetone (600 mL) was stirred at RT and a significant exothermic reaction was observed. Stirring continued for 18 h without cooling. Reaction progress was monitored by TLC analysis. The reaction mixture was diluted with H2O (600 mL) and extracted with EtOAc (500 mL×2). The combined organic extracts were washed with saturated aqueous NaCl solution (500 mL), dried over Na2SO4, filtered and concentrated in vacuo. The resultant residue was triturated in cyclohexane (300 mL) and the crystalline solid was filtered off and washed to afford 4-Benzyloxy-2-fluoro-benzonitrile (118.2 g, 90%). 1H NMR (400 MHz, CDCl3): 7.51 (1 H, dd, J=8.70, 7.48 Hz), 7.40 (5 H, m), 6.86-6.76 (2 H, m), 5.11 (2 H, s).

Step 2: 4-Benzyloxy-2-fluoro-benzamidine hydrochloride

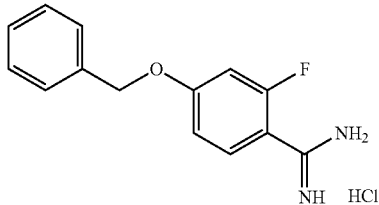 [SMILES: N=C(N)c1ccc(OCc2ccccc2)cc1F ; Cl]

A solution of 4-benzyloxy-2-fluoro-benzonitrile (84 g, 0.37 mol) in THF (450 mL) under an atmosphere of nitrogen, was cooled to −70° C. The resultant suspension was treated with a solution of 1M LiHMDS in THF (440 mL, 0.44 mol) over 10 min to reach a maximum temperature of −55° C. The reaction mixture was allowed to warm to RT and stirred for three days. Reaction progress was monitored by TLC analysis. The reaction mixture was poured onto ice/1M HCl mixture, the pH adjusted to ~1 by addition of 6M HCl and washed with EtOAc (500 mL). The organic layer was extracted with 1M HCl and the combined aqueous extracts washed with EtOAc (500 mL). The acid aqueous extracts were concentrated to low volume in vacuo and the resultant solid filtered off, washed with H2O and dried in vacuo to give 4-Benzyloxy-2-fluoro-benzamidine hydrochloride as a pale cream crystalline solid (74.5 g, 72%). 1H NMR (400 MHz, d6-DMSO): 9.30 (4 H, d, J=10.39 Hz), 7.64 (1H, t, J=8.59 Hz), 7.49-7.35 (5 H, m), 7.19 (1 H, dd, J=12.88, 2.41 Hz), 7.06 (1 H, dd, J=8.77, 2.41 Hz), 5.25 (2 H, s).

Step 3: 5-[2-(4-Benzyloxy-2-fluoro-phenyl)-1H-imidazol-4-yl]-1-isopropyl-1H-[1,2,4]triazole

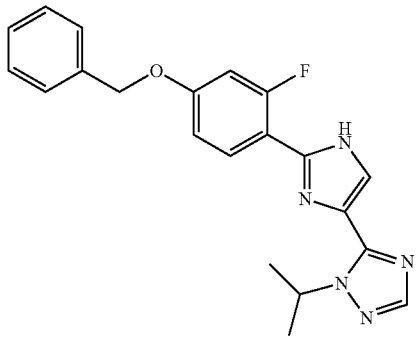 [SMILES: CC(C)n1ncnc1-c1c[nH]c(-c2ccc(OCc3ccccc3)cc2F)n1]

A solution of 4-benzyloxy-2-fluoro-benzamidine hydrochloride (74.5 g, 0.265 mol) in THF (705 mL) was treated with potassium hydrogen carbonate (106 g, 1.06 mol) and H2O (150 mL). The resultant mixture was heated to reflux to give a white suspension. Whilst maintaining gentle reflux and mechanical stirring (500 rpm) a solution of 2-chloro-1-(2-isopropyl-2H-[1,2,4]triazol-3-yl)-ethanone (50 g, 0.265 mol) was added dropwise over 40 min. The resultant suspension gradually dissolved giving a dark red mixture that was refluxed for 18 h. The mixture was cooled to RT, diluted with saturated aqueous NaCl solution (500 mL) and extracted with EtOAc (500 mL). The organic extract was washed with saturated aqueous NaCl solution, dried over Na2SO4, filtered and concentrated in vacuo to give a pink solid The solid was triturated in a mixture of MTBE/pentane (1:1 by volume, 300 mL), collected by filtration, washed with a MTBE/pentane mixture and dried in vacuo to give 5-[2-(4-Benzyloxy-2-fluoro-phenyl)-1H-imidazol-4-yl]-1-isopropyl-1H-[1,2,4]triazole as a pale pink solid (84 g, 84%). 1H NMR (400 MHz, d6-DMSO): 7.95-7.93 (2 H, m), 7.76 (1 H, s), 7.44-7.42 (5 H, m), 7.12 (1 H, dd, J=13.10, 2.52 Hz), 7.03 (1 H, dd, J=8.74, 2.47 Hz), 5.90 (1 H, m), 5.21 (2 H, s), 1.46 (6 H, d, J=6.60 Hz).

Step 4: 2-[2-(4-Benzyloxy-2-fluoro-phenyl)-4-(2-isopropyl-2H-[1,2,4]triazol-3-yl)-imidazol-1-yl]-ethanol

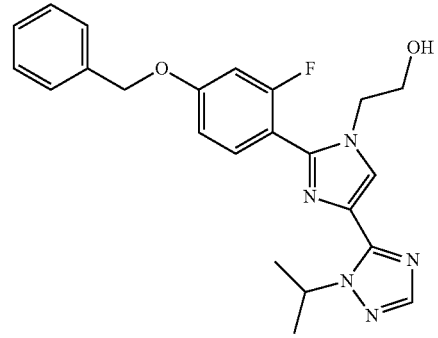 [SMILES: CC(C)n1ncnc1-c1cn(CCO)c(-c2ccc(OCc3ccccc3)cc2F)n1]

A suspension of 5-[2-(4-benzyloxy-2-fluoro-phenyl)-1H-imidazol-4-yl]-1-isopropyl-1H-[1,2,4]triazole (84 g, 0.22 mol) and [1,3]dioxolan-2-one (48 g, 0.55 mol) in toluene (100 mL) was heated at 130° C. for 7.5 h allowing some solvent to evaporate until reaction was initiated. The cooled reaction mixture was concentrated in vacuo and the residue treated with acetonitrile (50 mL), stirred, sonicated and cooled in an ice bath. The resultant solid was collected by filtration, washed with cold acetonitrile then diethyl ether and dried in vacuo at 60° C. to give 2-[2-(4-Benzyloxy-2-fluoro-phenyl)-4-(2-isopropyl-2H-[1,2,4]triazol-3-yl)-imidazol-1-yl]-ethanol (65.2 g, 70%). 1H NMR (400 MHz, CDCl3): 8.04 (1 H, s), 7.80 (1 H, d, J=0.71 Hz), 7.43-7.41 (6 H, m), 6.89 (1 H, dd, J=8.59, 2.50 Hz), 6.79 (1 H, dd, J=11.73, 2.47 Hz), 5.93-5.92 (1 H, m), 5.11 (2 H, s), 4.02 (2 H, t, J=4.93 Hz), 3.89 (2 H, t, J=4.96 Hz), 1.49 (6 H, d, J=6.61 Hz). LCMS: RT=3.30 min, [M+H]+=422.

Step 5: 8-Benzyloxy-2-(2-isopropyl-2H-[1,2,4]triazol-3-yl)-4,5-dihydro-6-oxa-1,3a-diaza-benzo[e]azulene

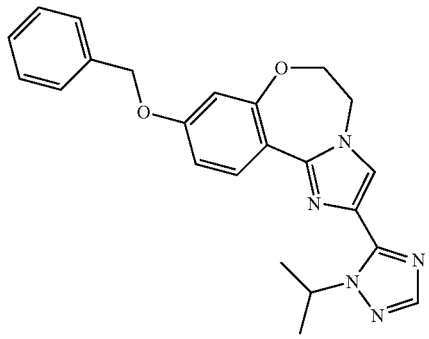 [SMILES: CC(C)n1ncnc1-c1cn2c(n1)-c1ccc(OCc3ccccc3)cc1OCC2]

A solution of 2-[2-(4-benzyloxy-2-fluoro-phenyl)-4-(2-isopropyl-2H-[1,2,4]triazol-3-yl)-imidazol-1-yl]-ethanol (25.0 g, 59.31 mmol) in DMF (890 mL) was treated with sodium hydride (3.51 g, 94.89 mmol) by portionwise addition. The resultant mixture was stirred for 23 h at RT and quenched with ice and H2O. The precipitate was collected by filtration, washed with H2O and dried in vacuo at 60° C. to give 8-Benzyloxy-2-(2-isopropyl-2H-[1,2,4]triazol-3-yl)-4,5-dihydro-6-oxa-1,3a-diaza-benzo[e]azulene as an off-white solid (13.9 g, 58%). 1H NMR (400 MHz, CDCl3): 8.43 (1 H, d, J=8.97 Hz), 7.87 (1 H, s), 7.63 (1 H, s), 7.41-7.39 (5 H, m), 6.82 (1 H, dd, J=8.98, 2.58 Hz), 6.64 (1 H, d, J=2.55 Hz), 6.00 (1 H, m), 5.10 (2 H, s), 4.50-4.48 (2 H, m), 4.42-4.41 (2 H, m), 1.59 (6 H, d, J=6.63 Hz). LCMS: RT=3.80 min, [M+H]+=402.

Step 6

A solution of 8-benzyloxy-2-(2-isopropyl-2H-[1,2,4]triazol-3-yl)-4,5-dihydro-6-oxa-1,3a-diaza-benzo[e]azulene in a mixture of EtOAc (350 mL) and IMS (150 mL), under argon atmosphere, was treated with Pd/C. The atmosphere was exchanged with hydrogen and the resultant reaction mixture was stirred at RT for 20 h. The hydrogen atmosphere was exchanged with argon, the reaction mixture was diluted with DCM (~60 mL), filtered through a pad of Celite and washed with a mixture of DCM/IMS (9:1 by volume). The resultant solution was concentrated in vacuo to give the title compound as an off-white solid (9.42 g, 51%). More material was recovered by thorough washing of the Celite residue to provide 490 in 83% total yield. 1H NMR (400 MHz, d6-DMSO): 8.22 (1 H, d, J=8.81 Hz), 7.89 (1 H, s), 7.82 (1 H, s), 6.61 (1 H, dd, J=8.80, 2.44 Hz), 6.41 (1 H, d, J=2.41 Hz), 5.95-5.86 (1 H, m), 4.45 (4 H, m), 1.47 (6 H, d, J=6.60 Hz). LCMS: RT=2.52 min, [M+H]+=312

Example 492

9-(difluoromethoxy)-2-(1-isopropyl-1H-1,2,4-triazol-5-yl)-5,6-dihydrobenzo[f]imidazo[1,2-d][1,4]oxazepine Following the procedures of the Examples herein, 9-bromo-2-(1-isopropyl-1H-1,2,4-triazol-5-yl)-5,6-dihydrobenzo[f]imidazo[1,2-d][1,4]oxazepine 194 and difluoromethanol were reacted to give 492. LC/MS(ESI+): m/z 362.1 (M+H)

Example 493

2-(1-(2,2,2-trifluoroethyl)-1H-1,2,4-triazol-5-yl)-5,6-dihydrobenzo[f]imidazo[1,2-d][1,4]oxazepin-9-amine 493

To a mixture of 2-(1-(2,2,2-trifluoroethyl)-1H-1,2,4-triazol-5-yl)-5,6-dihydrobenzo[f]imidazo[1,2-d][1,4]oxazepine-9-carboxylic acid (170 mg, 0.45 mmol) and triethylamine (95 uL, 0.68 mmol), in DMF (3.5 mL), was added diphenylphosphonic azide (146 uL, 0.68 mmol) at ambient temperature. After 3 h, water (0.45 mL) was added and the reaction mixture was heated at 100° C. After 1 h, the mixture was diluted with ethyl acetate and sat. NaHCO3. The aqueous layer was extracted into ethyl acetate (3×), and the combined organics were filtered through a plug of celite and concentrated in vacuo. The crude residue was purified by preparative HPLC to afford 493 as a white solid (85 mg, 54%). LC/MS (ESI+): m/z 351 (M+H). 1H NMR (400 MHz, DMSO) δ 8.05 (s, 1H), 8.01 (d, J=8.7 Hz, 1H), 7.89 (s, 1H), 6.38 (dd, J=8.7, 2.2 Hz, 1H), 6.18 (d, J=2.2 Hz, 1H), 5.92 (q, J=8.9 Hz, 2H), 5.56 (s, 2H), 4.41 (dd, J=12.3, 5.6 Hz, 4H)

Example 494

(2S)-2-(2-(1-(2,2,2-trifluoroethyl)-1H-1,2,4-triazol-5-yl)-5,6-dihydrobenzo[f]imidazo[1,2-d][1,4]oxazepin-9-yloxy)butanamide 494

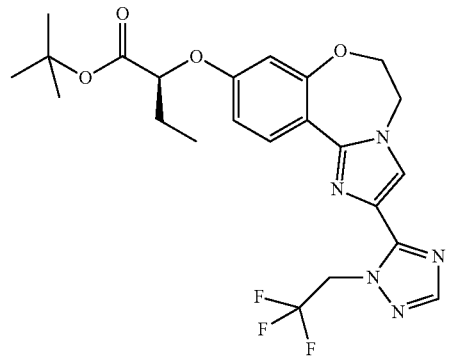

Following the procedure of Example 426, 2-[2-(2,2,2-trifluoro-ethyl)-2H-[1,2,4]triazol-3-yl]-4,5-dihydro-6-oxa-1,3a-diaza-benzo[e]azulen-8-ol, 2-hydroxy-3-methyl-butyric acid methyl ester and (S)-2-hydroxy-butyric acid tert-butyl ester were reacted and the crude product was subjected to flash chromatography (SiO2, gradient 0-10% methanol in ethyl acetate) to give (S)-2-{2-[2-(2,2,2-Trifluoro-ethyl)-2H-[1,2,4]triazol-3-yl]-4,5-dihydro-6-oxa-1,3a-diaza-benzo[e]azulen-8-yloxy}-butyric acid tert-butyl ester as a yellow oil contaminated with triphenylphosphine oxide, no further purification was undertaken. LCMS: RT=4.05 min, [M+H]+=494

To a solution of (S)-2-{2-[2-(2,2,2-trifluoro-ethyl)-2H-[1,2,4]triazol-3-yl]-4,5-dihydro-6-oxa-1,3a-diaza-benzo[e]azulen-8-yloxy}-butyric acid tert-butyl ester in DCM (3 mL) was added TFA (0.5 mL) and the reaction mixture stirred at RT for 16 h. The reaction mixture was concentrated in vacuo, and the residue dissolved in DMF (3 mL). HATU (217 mg, 0.56 mmol), ammonium chloride (46 mg, 0.85 mmol) and triethylamine (119 µL, 0.85 mmol) were added and the reaction mixture stirred at RT for 1 hour. The reaction mixture was concentrated in vacuo, the residue dissolved in ethyl acetate (10 mL) and the mixture washed with water extracting with ethyl acetate (3×10 mL). The combined organic extracts were washed with brine, dried (MgSO4) and concentrated in vacuo. The residue was subjected to flash chromatography (SiO2 gradient 0-10% methanol in EtOAc) then reverse phase preparative HPLC (C-18 column, 10-90% MeCN in water, 0.1% formic acid, 25 min gradient) to yield 494 as a white solid (49 mg, 39%). LCMS: RT=3.78 min, [M+H]+=437; 1H NMR (400 MHz, d6-DMSO) 8.22 (1H, d, J=8.9 Hz), 8.03 (1H, s), 7.96 (1H, s), 7.50 (1H, br s), 7.24 (1H, br s), 6.74 (1H, dd, J=8.9, 2.5 Hz), 6.51 (1H, d, J=2.5 Hz), 5.86 (2H, q, J=8.9 Hz), 4.52-4.39 (5H, m), 1.79 (2H, pent, J=7.2 Hz), 0.92 (3H, t, J=7.2 Hz)

Example 495

(2R)-2-(2-(1-(2,2,2-trifluoroethyl)-1H-1,2,4-triazol-5-yl)-5,6-dihydrobenzo[f]imidazo[1,2-d][1,4]oxazepin-9-yloxy)butanamide 495

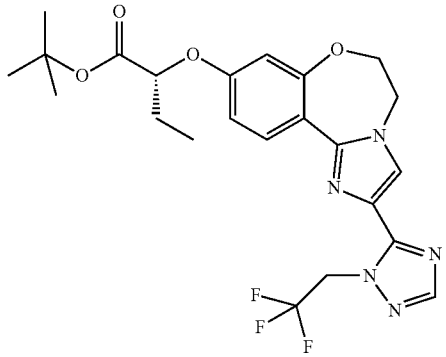 [SMILES: CC[C@@H](Oc1ccc2c(c1)OCCn1cc(-c3ncnn3CC(F)(F)F)nc1-2)C(=O)OC(C)(C)C]

Following the procedure for Example 426, 2-[2-(2,2,2-trifluoro-ethyl)-2H-[1,2,4]triazol-3-yl]-4,5-dihydro-6-oxa-1,3a-diaza-benzo[e]azulen-8-ol, 2-hydroxy-3-methyl-butyric acid methyl ester and (S)-2-hydroxy-butyric acid tert-butyl ester were reacted and the crude product was subjected to flash chromatography (SiO2, gradient 0-10% methanol in ethyl acetate) to give (R)-2-{2-[2-(2,2,2-Trifluoro-ethyl)-2H-[1,2,4]triazol-3-yl]-4,5-dihydro-6-oxa-1,3a-diaza-benzo[e]azulen-8-yloxy}-butyric acid tert-butyl ester as a yellow oil contaminated with triphenylphosphine oxide. LCMS: RT=4.05 min, [M+H]+=494

To a solution of (R)-2-{2-[2-(2,2,2-trifluoro-ethyl)-2H-[1,2,4]triazol-3-yl]-4,5-dihydro-6-oxa-1,3a-diaza-benzo[e]azulen-8-yloxy}-butyric acid tert-butyl ester in DCM (3 mL) was added TFA (0.5 mL) and the reaction mixture stirred at RT for 16 h. The reaction mixture was concentrated in vacuo, and the residue dissolved in DMF (3 mL). HATU (217 mg, 0.56 mmol), ammonium chloride (46 mg, 0.85 mmol) and triethylamine (119 µL, 0.85 mmol) were added and the reaction mixture stirred at RT for 1 hour. The reaction mixture was concentrated in vacuo, the residue dissolved in ethyl acetate (10 mL) and the mixture washed with water extracting with ethyl acetate (3×10 mL). The combined organic extracts were washed with brine, dried (MgSO4) and concentrated in vacuo. The residue was subjected to flash chromatography (SiO2 gradient 0-10% methanol in EtOAc) then reverse phase preparative HPLC (C-18 column, 10-90% MeCN in water, 0.1% formic acid, 25 min gradient) to yield 495 as a white solid (60 mg, 48%). LCMS: RT=3.78 min, [M+H]+=437; 1H NMR (400 MHz, d6-DMSO) 8.22 (1H, d, J=8.9 Hz), 8.03 (1H, s), 7.96 (1H, s), 7.50 (1H, br s), 7.24 (1H, br s), 6.74 (1H, dd, J=8.9, 2.5 Hz), 6.51 (1H, d, J=2.5 Hz), 5.86 (2H, q, J=8.9 Hz), 4.52-4.39 (5H, m), 1.79 (2H, pent, J=7.2 Hz), 0.92 (3H, t, J=7.2 Hz)

Example 496

2-(2-(1-(2,2,2-trifluoroethyl)-1H-1,2,4-triazol-5-yl)-5,6-dihydroimidazo[1,2-d]pyrido[3,4-f][1,4]oxazepin-9-ylamino)acetamide 496

Step 1: Trifluoro-methanesulphonic acid 2-[2-(2,2,2-trifluoroethyl)-2H-[1,2,4]triazol-3-yl]-4,5-dihydro-6-oxa-1.3a,9-triaza-benzo[e]azulen-8-yl ester

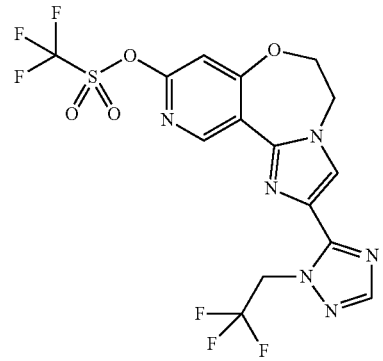 [SMILES: O=S(=O)(Oc1cc2c(cn1)-c1nc(-c3ncnn3CC(F)(F)F)cn1CCO2)C(F)(F)F]

2-[2-(2,2,2-trifluoro-ethyl)-2H-[1,2,4]triazol-3-yl]-4,5-dihydro-6-oxa-1,3a,9-triaza-benzo[e]azulen-8-ol was converted to Trifluoro-methanesulphonic acid 2-[2-(2,2,2-trifluoroethyl)-2H-[1,2,4]triazol-3-yl]-4,5-dihydro-6-oxa-1.3a,9-triaza-benzo[e]azulen-8-yl ester. LCMS: RT=3.65 min, [M+H]+=485.12.

Step 2 trifluoro-methanesulphonic acid 2-[2-(2,2,2-trifluoroethyl)-2H-[1,2,4]triazol-3-yl]-4,5-dihydro-6-oxa-1.3a,9-triaza-benzo[e]azulen-8-yl ester was converted to 496. LCMS: RT=2.33 min, [M+H]+=409.02. $^1$H NMR 400 MHz (DMSO-d6): δ 8.97 (1 H, s), 8.05 (1 H, s), 7.96 (1 H, s), 7.31 (1 H, br, s), 6.99 (1 H, br, s), 6.95 (1 H, br, t, J=5.89 Hz), 6.10 (1 H, s), 5.88 (2 H, q, J=8.86 Hz), 4.48 (4 H, s), 3.84 (2 H, d, J=5.85 Hz)

Example 499

9-ethyl-2-(1-isopropyl-3-methyl-1H-1,2,4-triazol-5-yl)-5,6-dihydrobenzo[f]imidazo[1,2-d][1,4]oxazepine 499

2-(1-isopropyl-3-methyl-1H-1,2,4-triazol-5-yl)-9-vinyl-5,6-dihydrobenzo[f]imidazo[1,2-d][1,4]oxazepine from Example 447 (0.300 g, 0.894 mmol) was dissolved in ethanol (5 mL) and purged with N2. 10% Palladium on Carbon (0.1:0.9, Palladium:carbon black, 0.0952 g) was added. The resulting suspension was placed under vacuum followed by addition of H2 at atm pressure. This process was repeated three times to saturate the catalyst. The reaction was stirred for 18 hours at room temperature. The reaction mixture was filtered and concentrated to dryness. The crude product was purified using reverse phase chromatography to give 499 (0.189 g, 62.9% yield).

Example 501

(2S)-3-methyl-2-(2-(1-(2,2,2-trifluoroethyl)-1H-1,2,4-triazol-5-yl)-5,6-dihydrobenzo[f]imidazo[1,2-d][1,4]oxazepin-9-yloxy)butanamide 501

Following the procedures of Examples 426 and 467, 2-[2-(2,2,2-trifluoro-ethyl)-2H-[1,2,4]triazol-3-yl]-4,5-dihydro-6-oxa-1,3a-diaza-benzo[e]azulen-8-ol and 2S-hydroxy-3-methyl-butyric acid methyl ester were converted to 501.

Example 502

(2R)-3-methyl-2-(2-(1-(2,2,2-trifluoroethyl)-1H-1,2,4-triazol-5-yl)-5,6-dihydrobenzo[f]imidazo[1,2-d][1,4]oxazepin-9-yloxy)butanamide 502

Following the procedures of Examples 426 and 467, 2-[2-(2,2,2-trifluoro-ethyl)-2H-[1,2,4]triazol-3-yl]-4,5-dihydro-6-oxa-1,3a-diaza-benzo[e]azulen-8-ol and 2R-hydroxy-3-methyl-butyric acid methyl ester were converted to 502.

Example 513

(2S)-3-hydroxy-2-(2-(1-(2,2,2-trifluoroethyl)-1H-1,2,4-triazol-5-yl)-5,6-dihydrobenzo[f]imidazo[1,2-d][1,4]oxazepin-9-yloxy)propanamide 513

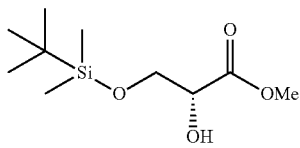

To a solution of (R)-2,2-dimethyl-[1,3]dioxolane-4-carboxylic acid methyl ester (2.5 g, 15.6 mmol) in methanol (15 mL) was added HCl in dioxane (4N, 5 mL, 20 mmol) and the reaction mixture was stirred at RT for 5 h. The reaction mixture was concentrated in vacuo, the resultant residue dissolved in THF (20 mL) and imidazole (1.28 g, 18.7 mmol) and tert-butylchlorodimethylsilane (2.47 g, 16.4 mmol) added. The reaction mixture was stirred at RT for 16 h. The reaction mixture was diluted with ethyl acetate (10 mL) and the mixture washed with water extracting with ethyl acetate (3×10 mL). The combined organic extracts were washed with brine, dried (MgSO4) and concentrated in vacuo. The residue was subjected to flash chromatography (SiO2 gradient 0-50% EtOAc in cyclohexane) to yield (R)-3-(tert-butyl-dimethyl-silanyloxy)-2-hydroxy-propionic acid methyl ester as a colorless oil (2.29 g, 63%). 1H NMR (400 MHz, CDCl3) 4.26-4.20 (1H, m), 3.93 (1H, dd, J=10.1, 3.4 Hz), 3.86 (1H, dd, J=10.1, 2.8 Hz), 3.79 (3H, s), 3.01 (1H, d, J=7.8 Hz), 0.88 (9H, s), 0.06 (3H, s), 0.04 (3H, s)

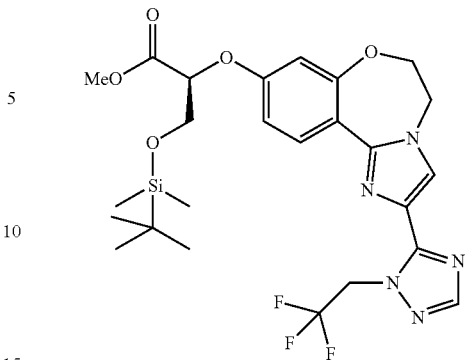

Following the procedures of Example 426, 2-[2-(2,2,2-trifluoro-ethyl)-2H-[1,2,4]triazol-3-yl]-4,5-dihydro-6-oxa-1,3a-diaza-benzo[e]azulen-8-ol and (R)-3-(tert-butyl-dimethyl-silanyloxy)-2-hydroxy-propionic acid methyl ester were reacted and the crude product was subjected to flash chromatography (SiO2, gradient 0-10% methanol in ethyl acetate) to give (S)-3-(tert-Butyl-dimethyl-silanyloxy)-2-{2-[2-(2,2,2-trifluoro-ethyl)-2H-[1,2,4]triazol-3-yl]-4,5-dihydro-6-oxa-1,3a-diaza-benzo[e]azulen-8-yloxy}-propionic acid methyl ester as a yellow oil contaminated with triphenylphosphine oxide. LCMS: RT=4.48 min, [M+H]+=568

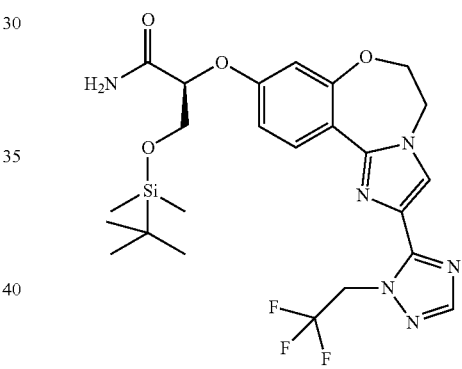

(S)-3-(tert-Butyl-dimethyl-silanyloxy)-2-{2-[2-(2,2,2-trifluoro-ethyl)-2H-[1,2,4]triazol-3-yl]-4,5-dihydro-6-oxa-1,3a-diaza-benzo[e]azulen-8-yloxy}-propionic acid methyl ester was dissolved in ammonia in methanol (7 N, 10 mL) and the reaction mixture stirred at RT for 48 hr. The reaction mixture was concentrated in vacuo and the resultant residue subjected to flash chromatography (SiO2, gradient 0-5% methanol in ethyl acetate) to give (S)-3-(tert-Butyl-dimethyl-silanyloxy)-2-{2-[2-(2,2,2-trifluoro-ethyl)-2H-[1,2,4]triazol-3-yl]-4,5-dihydro-6-oxa-1,3a-diaza-benzo[e]azulen-8-yloxy}-propionamide as a yellow oil (101 mg, 49% over 2 steps). LCMS: RT=3.78 min, [M+H]=553

To a solution of (S)-3-(tert-butyl-dimethyl-silanyloxy)-2-{2-[2-(2,2,2-trifluoro-ethyl)-2H-[1,2,4]triazol-3-yl]-4,5-dihydro-6-oxa-1,3a-diaza-benzo[e]azulen-8-yloxy}-propionamide (101 mg, 0.18 mmol) in THF (5 mL) was added TBAF (0.22 mL, 1M solution in THF, 0.22 mmol) and the reaction mixture was stirred at RT for 2 hr. The reaction mixture was diluted with ethyl acetate (10 mL) and water (10 mL) added. A white precipitate formed which was collected by filtration and dried in vacuo to yield 513 as a white solid (45 mg, 56%). LCMS: RT=2.98 min, [M+H]+=439; 1H NMR (400 MHz, d6-DMSO) 8.23 (1H, d, J=8.7 Hz), 8.03 (1H, s), 7.96

(1H, s), 7.50 (1H, br s), 7.30 (1H, br s), 6.77 (1H, dd, J=8.9, 2.7 Hz), 6.54 (1H, d, J=2.6 Hz), 5.86 (2H, q, J=8.9 Hz), 5.09 (1H, t, J=5.8 Hz), 4.54 (1H, t, J=4.9 Hz), 4.50-4.41 (4H, m), 3.74-3.67 (2H, m)

Example 524

N-((3-aminooxetan-3-yl)methyl)-2-(1-isopropyl-1H-1,2,4-triazol-5-yl)-5,6-dihydrobenzo[f]imidazo[1,2-d][1,4]oxazepin-9-amine 524

Following the procedures of Example 551, 9-bromo-2-(1-isopropyl-1H-1,2,4-triazol-5-yl)-5,6-dihydrobenzo[f]imidazo[1,2-d][1,4]oxazepine 194 and 3-(aminomethyl)oxetan-3-amine were reacted to give 524. LC/MS(ESI+): m/z 396.3 (M+H)

Example 525

(3-amino-1-(2-(1-isopropyl-1H-1,2,4-triazol-5-yl)-5,6-dihydrobenzo[f]imidazo[1,2-d][1,4]oxazepin-9-yl)azetidin-3-yl)methanol 525

Following the procedures of Example 551, 9-bromo-2-(1-isopropyl-1H-1,2,4-triazol-5-yl)-5,6-dihydrobenzo[f]imidazo[1,2-d][1,4]oxazepine 194 and (3-aminoazetidin-3-yl)methanol were reacted to give 525. LC/MS(ESI+): m/z 396.2 (M+H)

Example 526

2-(2-(1-(2,2,2-trifluoroethyl)-1H-1,2,4-triazol-5-yl)-5,6-dihydrobenzo[f]imidazo[1,2-d][1,4]oxazepin-9-ylamino)acetamide 526

Step 1: 2-{2-[2-(2,2,2-Trifluoro-ethyl)-2H-[1,2,4]-triazol-3-yl]-4,5-dihydro-6-oxa-1,3a-diaza-benzo[e]azulen-8-ylamino}-acetic acid tert-butyl ester

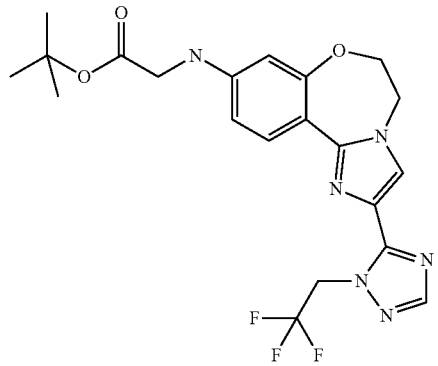 [SMILES: CC(C)(C)OC(=O)CNc1ccc2c(c1)OCCn1cc(-c3ncnn3CC(F)(F)F)nc1-2]

8-bromo-2-[4-(2,2,2-trifluoro-ethyl)-4H-[1,2,4]triazol-3-yl]-4,5-dihydro-6-oxa-1,3a-diaza-benzo[e]azulene was converted to 2-{2-[2-(2,2,2-Trifluoro-ethyl)-2H-[1,2,4]-triazol-3-yl]-4,5-dihydro-6-oxa-1,3a-diaza-benzo[e]azulen-8-ylamino}-acetic acid tert-butyl ester. LCMS: RT=3.62 min, [M+H]+=465. ¹H NMR 300 MHz (CHCl-d):δ 8.24 (1 H, d, J=8.78 Hz), 7.95 (1 H, s), 7.73 (1 H, s), 6.45 (1 H, dd, J=8.81, 2.43 Hz), 6.18 (1 H, d, J=2.40 Hz), 5.75 (2 H, d, J=8.45 Hz), 4.49-4.45 (4 H, m), 3.83 (2 H, d, J=5.03 Hz), 1.51 (9H, s)

Step 2: 2-{2-[2-(2,2,2-Trifluoro-ethyl)-2H-[1,2,4]-triazol-3-yl]-4,5-dihydro-6-oxa-1,3a-diaza-benzo[e]azulen-8-ylamino}-acetic acid trifluoroacetate salt

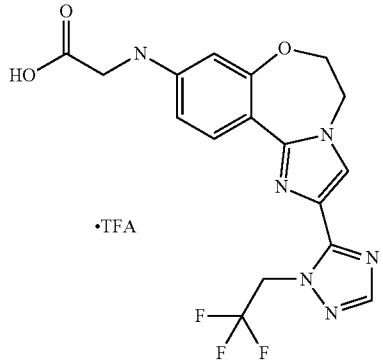 [SMILES: O=C(O)CNc1ccc2c(c1)OCCn1cc(-c3ncnn3CC(F)(F)F)nc1-2]

2-{2-[2-(2,2,2-trifluoro-ethyl)-2H-[1,2,4]-triazol-3-yl]-4,5-dihydro-6-oxa-1,3a-diaza-benzo[e]azulen-8-ylamino}-acetic acid tert-butyl ester was converted to 2-{2-[2-(2,2,2-Trifluoro-ethyl)-2H-[1,2,4]-triazol-3-yl]-4,5-dihydro-6-oxa-1,3a-diaza-benzo[e]azulen-8-ylamino}-acetic acid trifluoroacetate salt. LCMS (110165625): RT=2.72 min, [M+H]+=409.

Step 3

Following the amidation procedure in Example 529, 2-{2-[2-(2,2,2-trifluoro-ethyl)-2H-[1,2,4]-triazol-3-yl]-4,5-dihydro-6-oxa-1,3a-diaza-benzo[e]azulen-8-ylamino}-acetic acid trifluoroacetate salt was converted to 526. LCMS: RT=3.07 min, [M+H]+=408. ¹H NMR 400 MHz (DMSO-d6):δ 8.05 (1 H, s), 7.91 (1 H, s), 7.37 (1 H, br, s), 7.11 (1 H, br, s), 6.46 (1 H, dd, J=8.85, 2.35 Hz), 6.35 (1 H, t, J=5.89 Hz), 6.10 (1 H, d, J=2.31 Hz), 5.92 (2 H, q, J=8.88 Hz), 4.44 (4 H, q, J=5.80 Hz), 3.64 (2 H, d, J=5.86 Hz)

Example 528 cis-2-(2-(1-(2,2,2-trifluoroethyl)-1H-1,2,4-triazol-5-yl)-5,6-dihydrobenzo[f]imidazo[1,2-d][1,4]oxazepin-9-yl)cyclopropanecarboxamide 528

Following the procedures in Example 530, 2-{2-[2-(2,2,2-trifluoro-ethyl)-2H-[1,2,4]-triazol-3-yl]-4,5-dihydro-6-oxa-1,3a-diaza-benzo[e]azulen-8-yl}-cyclopropanecarboxylic acid was amidated to give the racemic mixture from which 528 was isolated. LCMS: RT=3.51 min, [M+H]+=419. ¹H NMR 400 MHz (DMSO-d6):δ 8.21 (1 H, d, J=8.31 Hz), 8.08 (1 H, s), 8.04 (1 H, s), 7.44 (1 H, br, s), 7.02 (1 H, dd, J=8.37, 1.75 Hz), 6.89 (1 H, d, J=1.67 Hz), 6.65 (1 H, br, s), 5.95-5.85 (2 H, m), 4.56-4.41 (4 H, m), 2.38-2.38 (1 H, m), 2.03 (1 H, td, J=8.50, 6.06 Hz), 1.48 (1 H, q, J=5.80 Hz), 1.18 (1 H, td, J=8.18, 4.41 Hz)

Example 529

(2S)-2-(2-(1-(2,2,2-trifluoroethyl)-1H-1,2,4-triazol-5-yl)-5,6-dihydrobenzo[f]imidazo[1,2-d][1,4]oxazepin-9-ylamino)propanamide 529

Step 1: (S)-2-{2-[2-(2,2,2-Trifluoro-ethyl-2H-[1,2,4]triazol-3-yl]-4,5-dihydro-6-oxa-1,3a-diaza-benzo[e]azulen-8-ylamino}-propionic acid tert-butyl ester

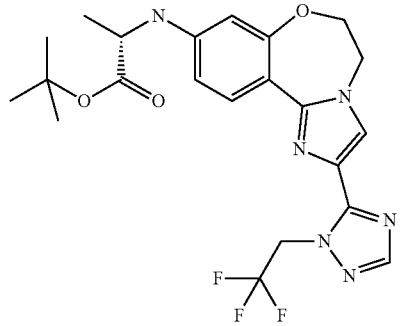 [SMILES: C[C@H](Nc1ccc2c(c1)OCCn1cc(-c3ncnn3CC(F)(F)F)nc1-2)C(=O)OC(C)(C)C]

A vessel was charged with 8-bromo-2-[4-(2,2,2-trifluoro-ethyl)-4H-[1,2,4]triazol-3-yl]-4,5-dihydro-6-oxa-1,3a-diaza-benzo[e]azulene (200 mg, 0.48 mmol), alanine tert-butyl ester hydrochloride (434 mg, 2.4 mmol), cesium carbonate (1.25 g, 3.84 mmol), 1,3-diisopropylimidazolium chloride (20 mg, 0.1 mmol) and DME (2 mL), evacuated and refilled with argon. Bis(1,5-cyclooctadiene)rhodium tetrafluoroborate complex (20 mg, 0.05 mmol) was added and degassing repeated before the reaction mixture was heated at 90° C. for 18 hours. The reaction mixture was concentrated in vacuo, water and 10% methanol in DCM were added and the organic layer separated, dried (MgSO4), filtered and concentrated in vacuo. The resultant residue was subjected to flash chromatography (SiO2, gradient 5-100% ethyl acetate in cyclohexane) to give (S)-2-{2-[2-(2,2,2-Trifluoro-ethyl-2H-[1,2,4]triazol-3-yl]-4,5-dihydro-6-oxa-1,3a-diaza-benzo[e]azulen-8-ylamino}-propionic acid tert-butyl ester (150 mg, 65%). LCMS: RT=3.74 min, [M+H]+=479. $^1$H NMR 300 MHz (DMSO-d):δ 8.22 (1 H, d, J=8.79 Hz), 7.92 (1 H, s), 7.62 (1 H, s), 6.44 (1 H, dd, J=8.81, 2.44 Hz), 6.20 (1 H, d, J=2.40 Hz), 5.73 (2 H, t, J=8.31 Hz), 4.42-4.41 (4 H, m), 4.01 (1 H, m), 2.04 (3 H, s), 1.47 (9 H, s).

Step 2: (S)-2-{2-[2-(2,2,2-Trifluoro-ethyl-2H-[1,2,4]triazol-3-yl]-4,5-dihydro-6-oxa-1,3a-diaza-benzo[e]azulen-8-ylamonio}-propionic acid trifluoroacetate salt

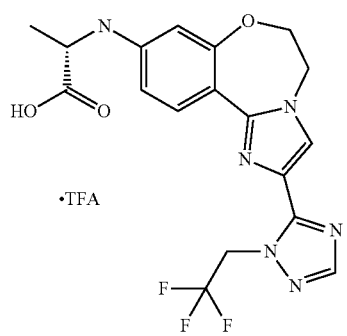 [SMILES: C[C@H](Nc1ccc2c(c1)OCCn1cc(-c3ncnn3CC(F)(F)F)nc1-2)C(=O)O]

(S)-2-{2-[2-(2,2,2-trifluoro-ethyl-2H-[1,2,4]triazol-3-yl]-4,5-dihydro-6-oxa-1,3a-diaza-benzo[e]azulen-8-ylamonio}-propionic acid tert-butyl ester was converted to (S)-2-{2-[2-(2,2,2-Trifluoro-ethyl-2H-[1,2,4]triazol-3-yl]-4,5-dihydro-6-oxa-1,3a-diaza-benzo[e]azulen-8-ylamonio}-propionic acid trifluoroacetate salt. LCMS: RT=2.86 min, [M+H]+=423.

Step 3

HATU (179 mg, 0.47 mmol), ammonium chloride (50 mg, 0.942 mmol) and triethylamine (0.22 mL, 1.57 mmol) were added to a solution of (S)-2-{2-[2-(2,2,2-trifluoro-ethyl-2H-[1,2,4]triazol-3-yl]-4,5-dihydro-6-oxa-1,3a-diaza-benzo[e]azulen-8-ylamonio}-propionic acid trifluoroacetate salt (168 mg, 0.314 mmol) in DMF (3 mL) and stirred for 18 hours. The reaction mixture was concentrated in vacuo and the residue treated with ethyl acetate and water, the organics layer separated, dried (Na2SO4), filtered and concentrated in vacuo. The resultant residue was subjected to flash chromatography (SiO2, gradient 0 to 10% methanol in DCM), then trituration in water to give 529 (39 mg, 30%). LCMS: RT=3.23 min, [M+H]+=422. $^1$H NMR 400 MHz (DMSO-d6):δ 8.05 (1 H, s), 7.91 (1 H, s), 7.40 (1 H, br, s), 7.01 (1 H, br, s), 6.46 (1 H, dd, J=8.86, 2.33 Hz), 6.25 (1 H, d, J=7.11 Hz), 6.13 (1 H, d, J=2.29 Hz), 5.92 (2 H, q, J=8.89 Hz), 4.46-4.39 (4 H, m), 3.81 (1 H, t, J=6.96 Hz), 1.32 (3 H, d, J=6.87 Hz)

Example 530 trans-2-(2-(1-(2,2,2-trifluoroethyl)-1H-1,2,4-triazol-5-yl)-5,6-dihydrobenzo[f]imidazo[1,2-d][1,4]oxazepin-9-yl)cyclopropanecarboxamide 530

Step 1: 2-(4,4,5,5-Tetramethyl-[1,3,2]dioxaborolan-2-yl)-cyclopropanecarboxylic acid ethyl ester

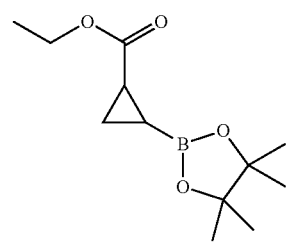 [SMILES: CCOC(=O)C1CC1B1OC(C)(C)C(C)(C)O1]

Ethyl diazoacetate (3.49 g, 61.3 mmol) was added over 20 minutes to a stirred suspension of palladium (II) acetate (61 mmol) and vinylboronic acid pinacol ester (1.9 g, 12.26 mmol) in diethyl ether (30 mL) and stirred for 2 hours. The reaction was concentrated in vacuo and the residues distilled under vacuum (100-140° C. at 0.5-1 mbar) to afford 2-(4,4,5,5-Tetramethyl-[1,3,2]dioxaborolan-2-yl)-cyclopropanecarboxylic acid ethyl ester (3.08 g, quant.) as a 4:6 mix of products, cis/trans isomers. $^1$H NMR 300 MHz (CHCl3-d): δ 4.26-4.25 (0.8 H, m), 4.12-4.12 (1.2 H, m), 1.83-1.82 (0.4 H, m), 1.76-1.75 (0.6 H, m), 1.28-1.27 (6 H, m), 1.26 (6 H, m), 1.22 (3 H, m), 1.16-1.05 (0.8 H, m), 1.01-1.00 (1.2 H, m), 0.58 (0.6 H, ddd, J=10.25, 7.44, 5.18 Hz), 0.41-0.41 (0.4 H, m)

Step 2: Racemic cis/trans-2-{2-[2-(2,2,2-Trifluoro-ethyl)-2H-[1,2,4]-triazol-3-yl]-4,5-dihydro-6-oxa-1,3a-diaza-benzo[e]azulen-8-yl}-cyclopropanecarboxylic acid ethyl ester

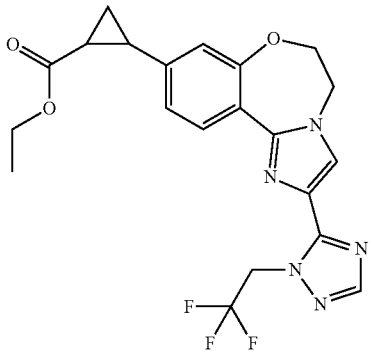 [SMILES: CCOC(=O)C1CC1c1ccc2c(c1)OCCn1cc(-c3ncnn3CC(F)(F)F)nc1-2]

A vessel was charged with 8-bromo-2-[4-(2,2,2-trifluoro-ethyl)-4H-[1,2,4]triazol-3-yl)-4,5-dihydro-6-oxa-1,3a-diaza-benzo[e]azulene (500 mg, 1.2 mmol), 2-(4,4,5,5-tetramethyl-[1,3,2]dioxaborolan-2-yl)-cyclopropanecarboxylic acid ethyl ester (300 mg, 1.25 mmol), PdCl2dppf.DCM (92.5 mg, 0.125 mmol, 10 mol %), cesium carbonate (3.88 g, 11.9 mmol), 1,4-dioxane (10 mL) and water (2.5 mL). The reaction vessel was evacuated and refilled with nitrogen before being stirred at 110° C. for 18 hours. The reaction mixture was concentrated in vacuo and the residue diluted with water before adjusting to pH 6 with 1M HCl. The mixture was extracted with ethyl acetate and the combined organic extracts were dried (MgSO4), filtered and concentrated in vacuo. The resultant residue was subjected to flash chromatography (SiO2, gradient 0-5% methanol in DCM) to give Racemic cis/trans-2-{2-[2-(2,2,2-Trifluoro-ethyl)-2H-[1,2,4]-triazol-3-yl]-4,5-dihydro-6-oxa-1,3a-diaza-benzo[e]azulen-8-yl}-cyclopropanecarboxylic acid ethyl ester (265 mg, 49%) as a 1:1 mix of products. LCMS RT=3.58/3.68 min, [M+H]+=448. $^1$H NMR 300 MHz (CHCl3-d): δ 8.34 (1 H, dd, J=8.33, 3.28 Hz), 7.94 (1 H, s), 7.70 (1 H, d, J=2.72 Hz), 7.06 (0.5 H, m), 6.98 (0.5 H, s), 6.88 (0.5 H, m) 6.79 (0.5 H, d, J=1.82 Hz), 5.73 (2 H, d, J=8.37 Hz), 4.46 (4 H, d, J=7.93 Hz), 4.18-4.17 (2 H, m), 3.95 (1 H, dd, J=7.12, 1.58 Hz), 2.11 (0.5 H, m), 1.94 (0.5 H, m), 1.72 (1H, m), 1.37 (1 H, m), 1.29 (1.5 H, t, J=7.14 Hz), 1.07 (1.5 H, t, J=7.12 Hz)

Step 3: Racemic cis/trans-2-{2-[2-(2,2,2-Trifluoro-ethyl)-2H-[1,2,4]-triazol-3-yl]-4,5-dihydro-6-oxa-1,3a-diaza-benzo[e]azulen-8-yl}-cyclopropanecarboxylic acid

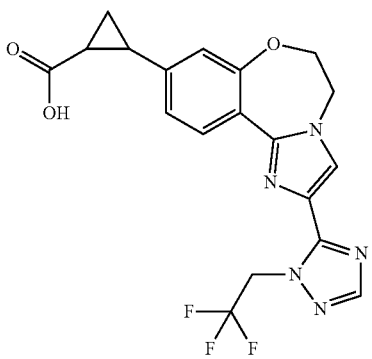 [SMILES: O=C(O)C1CC1c1ccc2c(c1)OCCn1cc(-c3ncnn3CC(F)(F)F)nc1-2]

2-{2-[2-(2,2,2-trifluoro-ethyl)-2H-[1,2,4-triazol-3-yl]-4,5-dihydro-6-oxa-1,3a-diaza-benzo[e]azulen-8-yl}-cyclopropanecarboxylic acid ethyl ester was converted to a 1:1 mix of Racemic cis/trans-2-{2-[2-(2,2,2-Trifluoro-ethyl)-2H-[1,2,4]-triazol-3-yl]-4,5-dihydro-6-oxa-1,3a-diaza-benzo[e]azulen-8-yl}-cyclopropanecarboxylic acid. LCMS: RT=3.01 min, [M+H]+=420. $^1$H NMR 300 MHz (CHCl3-d): δ $^1$H NMR δ (ppm) (CHCl-d): 8.34 (0.5 H, d, J=8.33 Hz), 8.29 (0.5 H, d, J=8.30 Hz), 7.96 (0.5 H, s), 7.95 (0.5 H, s), 7.73 (0.5 H, s), 7.68 (0.5 H, s), 7.08 (0.5 H, m), 6.93 (0.5 H, s), 6.87 (0.5 H, m), 6.78 (0.5 H, s), 5.72 (2 H, m), 4.45 (2 H, m), 4.26 (2 H, m), 2.56 (1H, m), 2.18 (0.5 H, m), 1.94 (0.5 H, m), 1.70 (1H, m), 1.41 (1H, m)

Step 4

Following the amidation procedure from Example 529, 2-{2-[2-(2,2,2-trifluoro-ethyl)-2H-[1,2,4]-triazol-3-yl]-4,5-dihydro-6-oxa-1,3a-diaza-benzo[e]azulen-8-yl}-cyclopropanecarboxylic acid was converted to 530 after separation of cis diastereomer (528). LCMS: RT=3.47 min, [M+H]+=419. $^1$H NMR 400 MHz (DMSO-d6): δ 8.25 (1 H, d, J=8.34 Hz), 8.07 (1 H, s), 8.04 (1 H, s), 7.57 (1 H, br, s), 6.94 (1H, br, s), 6.92 (1 H, d, J=3.76 Hz), 6.81 (1 H, d, J=1.78 Hz), 5.89 (2 H, q, J=8.88 Hz), 4.54-4.44 (4 H, m), 2.25-2.19 (1 H, m), 1.89 (1 H, dt, J=8.50, 4.71 Hz), 1.34-1.33 (1 H, m), 1.24-1.23 (1 H, m)

Example 538

(2S)-1-(2-(1-(2,2,2-trifluoroethyl)-1H-1,2,4-triazol-5-yl)-5,6-dihydrobenzo[f]imidazo[1,2-d][1,4]oxazepin-9-yl)azetidine-2-carboxamide 538

Step 1: (S)-1-{2-[2-(2,2,2-Trifluoro-ethyl)-2H-[1,2,4]triazol-3-yl]-4,5-dihydro-6-oxa-1,3a-diaza-benzo[e]azulen-8-yl}-azetidine-2-carboxylic acid

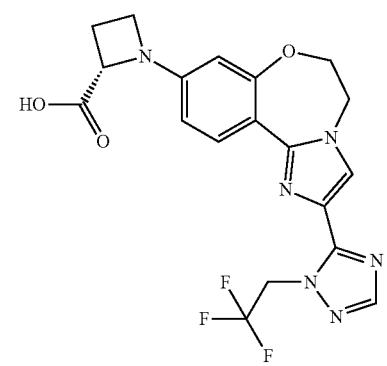 [SMILES: O=C(O)[C@@H]1CCN1c1ccc2c(c1)OCCn1cc(-c3ncnn3CC(F)(F)F)nc1-2]

8-bromo-2-[2-(2,2,2-trifluoro-ethyl)-2H-[1,2,4]triazol-3-yl]-4,5-dihydro-6-oxa-1,3a-diaza-benzo[e]azulene was converted to (S)-1-{2-[2-(2,2,2-Trifluoro-ethyl)-2H-[1,2,4]triazol-3-yl]-4,5-dihydro-6-oxa-1,3a-diaza-benzo[e]azulen-8-yl}-azetidine-2-carboxylic acid. LCMS: RT=2.97 min, [M+H]+=435.

Step 2

Following the amidation procedure in Example 529, (S)-1-{2-[2-(2,2,2-trifluoro-ethyl)-2H-[1,2,4]triazol-3-yl]-4, 5-dihydro-6-oxa-1,3a-diaza-benzo[e]azulen-8-yl}-azetidine-2-carboxylic acid was converted to 538. LCMS: RT=3.40 min, [M+H]+=434. 1H NMR 400 MHz (MeOD):δ 8.17 (1 H, d, J=8.76 Hz), 8.05 (1 H, s), 7.94 (1 H, s), 7.52 (1 H, s), 7.23 (1 H, s), 6.28 (1 H, dd, J=8.77, 2.35 Hz), 5.99 (1 H, d, J=2.31 Hz), 5.93-5.86 (2 H, m), 4.45-4.44 (4 H, m), 4.30 (1 H, dd, J=8.77, 6.81 Hz), 3.92-3.91 (1 H, m), 3.71-3.70 (1 H, m), 2.32-2.30 (1 H, m)

Example 539

(2S)-2-(2-(1-isopropyl-1H-1,2,4-triazol-5-yl)-5,6-dihydrobenzo[f]imidazo[1,2-d][1,4]oxazepin-9-ylamino)propanamide 539

Step 1: (S)-2-[2-(2-Isopropyl-2H-[1,2,4]triazol-3-yl)-4,5-dihydro-6-oxa-1,3a-diaza-benzo[e]azulen-8-ylamino]-propionic acid

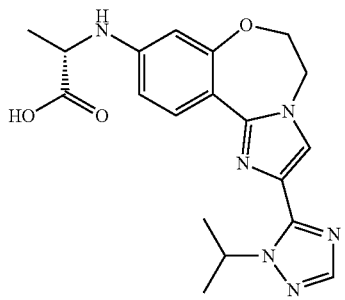 [SMILES: CC(C)n1ncnc1-c1cn2c(n1)-c1ccc(N[C@@H](C)C(=O)O)cc1OCC2]

A mixture of 8-bromo-2-(2-isopropyl-2H-[1,2,4]triazol-3-yl)-4,5-dihydro-6-oxa-1,3a-diaza-benzo[e]azulene 194 (0.72 g, 1.69 mmol), alanine tert-butyl ester hydrochloride (1.52 g, 8.4 mmol), Rh(COD)2.BF4 (0.07 g, 0.18 mmol), diisopropylimidazolium hydrochloride (0.07 g, 0.35 mmol) and cesium carbonate (4.38 g, 13.4 mmol) in DME (7 mL) was heated at 90° C. under an argon atmosphere for 16 h. The reaction mixture was concentrated in vacuo and the resultant residue partitioned between DCM and water. The aqueous phase was acidified with 1M HCl, extracted with 10% methanol in DCM and the combined organic extracts dried (Na2SO4) and concentrated in vacuo to give (S)-2-[2-(2-Isopropyl-2H-[1,2,4]triazol-3-yl)-4,5-dihydro-6-oxa-1,3a-diaza-benzo[e]azulen-8-ylamino]-propionic acid (0.27 g, 33%). LCMS: RT=2.47 min, [M+H]+=383.

Step 2

Following the amidation procedure in Example 529, (S)-2-[2-(2-isopropyl-2H-[1,2,4]triazol-3-yl)-4,5-dihydro-6-oxa-1,3a-diaza-benzo[e]azulen-8-ylamino]-propionic acid was converted to 539. LCMS: RT=2.77 min, [M+H]+=382. 1 H NMR 400 MHz (MeOD):δ 8.10 (1 H, d, J=8.80 Hz), 7.87 (1 H, d, J=0.64 Hz), 7.76 (1 H, s), 7.39 (1 H, s), 7.01 (1 H, s), 6.44 (1 H, dd, J=8.85, 2.34 Hz), 6.21 (1 H, d, J=7.11 Hz), 6.12 (1 H, d, J=2.30 Hz), 5.91-5.90 (1 H, m), 4.42-4.41 (4 H, m), 3.82-3.75 (1 H, m), 1.47 (6 H, dd, J=6.59, 1.77 Hz), 1.32 (3 H, d, J=6.87 Hz)

Example 542

(2S)-3-methoxy-2-(2-(1-(2,2,2-trifluoroethyl)-1H-1,2,4-triazol-5-yl)-5,6-dihydrobenzo[f]imidazo[1,2-d][1,4]oxazepin-9-ylamino)propanamide 542

Step 1: (S)-3-Methoxy-2-{2-[2-(2,2,2-trifluoro-ethyl)-2H-[1,2,4]triazol-3-yl]-4,5-dihydro-6-oxa-1,3a-diaza-benzo[e]azulen-8-ylamino}-propionic acid

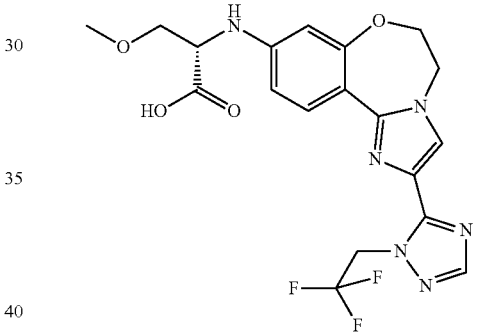

8-bromo-2-[2-(2,2,2-trifluoro-ethyl)-2H-[1,2,4]triazol-3-yl]-4,5-dihydro-6-oxa-1,3a-diaza-benzo[e]azulene and (S)-2-amino-3-methoxypropanoic acid hydrochloride were reacted to form (S)-3-Methoxy-2-{2-[2-(2,2,2-trifluoro-ethyl)-2H-[1,2,4]triazol-3-yl]-4,5-dihydro-6-oxa-1,3a-diaza-benzo[e]azulen-8-ylamino}-propionic acid. LCMS: RT=2.89 min, [M+H]+=453

Step 2

Following the amidation procedure in Example 529, (S)-3-methoxy-2-{2-[2-(2,2,2-trifluoro-ethyl)-2H-[1,2,4]triazol-3-yl]-4,5-dihydro-6-oxa-1,3a-diaza-benzo[e]azulen-8-ylamino}-propionic acid were reacted to give 542. LCMS: RT=3.29 min, [M+H]+=452. 1H NMR 400 MHz (MeOD):δ 8.07 (1 H, s), 8.05 (1 H, s), 7.91 (1 H, s), 7.45 (1 H, s), 7.15 (1 H, s), 6.52 (1 H, dd, J=8.89, 2.36 Hz), 6.21-6.20 (2 H, m), 5.91 (2 H, q, J=8.88 Hz), 4.45-4.43 (4 H, m), 4.00-3.99 (1 H, m), 3.57 (2 H, d, J=5.63 Hz), 3.29 (3 H, s)

Example 543

(2S)-1-(2-(1-(2,2,2-trifluoroethyl)-1H-1,2,4-triazol-5-yl)-5,6-dihydrobenzo[f]imidazo[1,2-d][1,4]oxazepin-9-yl)piperazine-2-carboxamide 543

Step 1: (S)-4-{2-[2-(2,2,2-Trifluoro-ethyl)-2H-[1,2,4]triazol-3-yl]-4,5-dihydro-6-oxa-1,3a-diaza-benzo[e]azulen-8-yl}-piperazine-1,3-dicarboxylic acid 1-benzyl ester

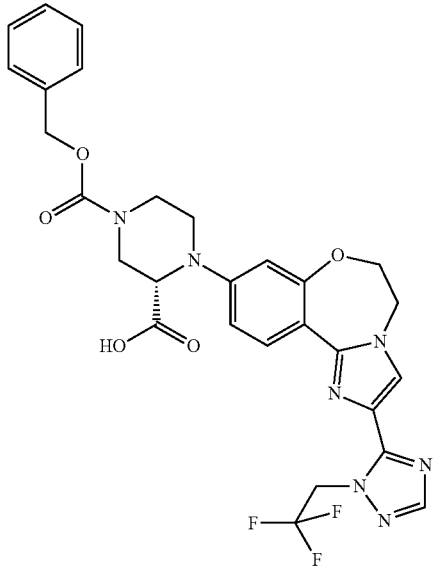 [SMILES: O=C(O)[C@@H]1CN(C(=O)OCc2ccccc2)CCN1c1ccc2c(c1)OCCn1cc(-c3ncnn3CC(F)(F)F)nc1-2]

8-bromo-2-[2-(2,2,2-trifluoro-ethyl)-2H-[1,2,4]triazol-3-yl]-4,5-dihydro-6-oxa-1,3a-diaza-benzo[e]azulene and (S)-piperazine-1,3-dicarboxylic acid 1-benzyl ester was converted to (S)-4-{2-[2-(2,2,2-Trifluoro-ethyl)-2H-[1,2,4]triazol-3-yl]-4,5-dihydro-6-oxa-1,3a-diaza-benzo[e]azulen-8-yl}-piperazine-1,3-dicarboxylic acid 1-benzyl ester. LCMS: RT=3.50 min, [M+H]+=598.

Step 2: (S)-3-Carbamoyl-4-{2-[2-(2,2,2-trifluoro-ethyl)-2H-[1,2,4]triazol-3-yl]-4,5-dihydro-6-oxa-1,3a-diaza-benzo[e]azulen-8-yl}-piperazine-1-carboxylic acid benzyl ester

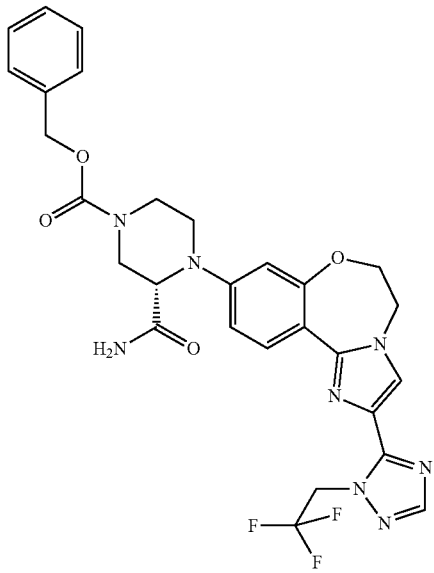 [SMILES: NC(=O)[C@@H]1CN(C(=O)OCc2ccccc2)CCN1c1ccc2c(c1)OCCn1cc(-c3ncnn3CC(F)(F)F)nc1-2]

(S)-4-{2-[2-(2,2,2-trifluoro-ethyl)-2H-[1,2,4]triazol-3-yl]-4,5-dihydro-6-oxa-1,3a-diaza-benzo[e]azulen-8-yl}-piperazine-1,3-dicarboxylic acid 1-benzyl ester was converted to (S)-3-Carbamoyl-4-{2-[2-(2,2,2-trifluoro-ethyl)-2H-[1,2,4]triazol-3-yl]-4,5-dihydro-6-oxa-1,3a-diaza-benzo[e]azulen-8-yl}-piperazine-1-carboxylic acid benzyl ester. LCMS: RT=3.27 min, [M+H]+=597.

Step 3

A mixture of (S)-3-carbamoyl-4-{2-[2-(2,2,2-trifluoro-ethyl)-2H-[1,2,4]triazol-3-yl]-4,5-dihydro-6-oxa-1,3a-diaza-benzo[e]azulen-8-yl}-piperazine-1-carboxylic acid benzyl ester (0.03 g) and 10% Pd/C (0.014 g) in IMS (5 mL) was stirred under an atmosphere of hydrogen at RT for 64 h. The reaction mixture was filtered through Celite® and the filtrate concentrated in vacuo. The resultant residue was subjected to flash chromatography (SiO2, gradient 0 to 20% methanol in DCM) to give 543 (0.005 g, 20%). LCMS: RT=2.49 min, [M+H]+ 463. 1H NMR 400 MHz (MeOD):δ 8.28 (1 H, d, J=9.03 Hz), 8.00 (1 H, s), 7.78 (1 H, s), 6.79 (1 H, dd, J=9.09, 2.63 Hz), 6.56 (1 H, d, J=2.58 Hz), 5.83 (2 H, q, J=8.50 Hz), 4.50-4.43 (3 H, m), 4.30 (1 H, t, J=3.89 Hz), 3.52-3.45 (2 H, m), 3.38 (1 H, dd, J=13.28, 3.28 Hz), 3.34 (1 H, s), 3.13-3.10 (2 H, m), 2.96-2.88 (1 H, m)

Example 547

(2-(1-isopropyl-1H-1,2,4-triazol-5-yl)-5,6-dihydrobenzo[f]imidazo[1,2-d][1,4]oxazepin-9-yl)methyl carbamate 547

To a solution of [2-(2-isopropyl-2H-[1,2,4]triazol-3-yl)-4,5-dihydro-6-oxa-1,3a-diaza-benzo[e]azulen-8-yl]-methanol (0.10 g, 0.31 mmol) in THF (1 mL) cooled to −78° C. was added trichloroacetyl isocyanate (40 μL, 0.47 mmol). The resultant mixture was allowed to warm to 0° C. before triethylamine (0.17 mL) and water (0.3 mL) were added and the mixture stirred at RT for 16 h. The reaction mixture was diluted with water and extracted with ethyl acetate. The combined organic phases were dried (Na2SO4) and concentrated in vacuo. The resultant residue was subjected to flash chromatography (SiO2, gradient 0 to 10% methanol in DCM) to give 547 (0.095 g, 83%). LCMS: RT=3.34 min, [M+H]+=369. 1H-NMR 400 MHz (DMSO-d6):δ 8.39 (1 H, d, J=8.24 Hz), 7.92-7.92 (2 H, m), 7.11 (1 H, dd, J=8.30, 1.71 Hz), 7.02 (1 H, d, J=1.63 Hz), 5.88-5.87 (1 H, m), 4.99 (2 H, s), 4.55-4.49 (4 H, m), 3.29 (2 H, s), 1.48 (6 H, d, J=6.60 Hz)

Example 548

(2S)-1-(2-(3-methyl-1-(2,2,2-trifluoroethyl)-1H-1,2,4-triazol-5-yl)-5,6-dihydrobenzo[f]imidazo[1,2-d][1,4]oxazepin-9-yl)pyrrolidine-2-carboxamide 548

Step 1: (S)-1-{2-[5-Methyl-2-(2,2,2-trifluoro-ethyl)-2H-[1,2,4]triazol-3-yl]-4,5-dihydro-6-oxa-1,3a-diaza-benzo[e]azulen-8-yl}-pyrrolidine-2-carboxylic acid

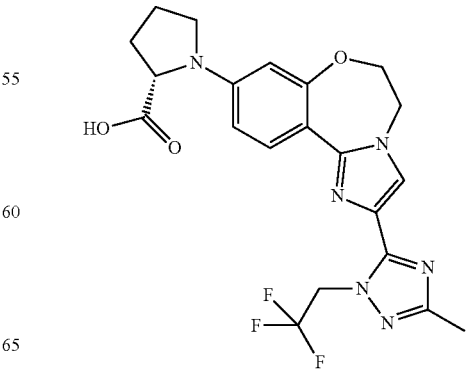

8-bromo-2-[5-methyl-2-(2,2,2-trifluoro-ethyl)-2H-[1,2,4]triazol-3-yl]-4,5-dihydro-6-oxa-1,3a-diaza-benzo[e]azulene and L-proline were reacted to give (S)-1-{2-[5-Methyl-2-(2,2,2-trifluoro-ethyl)-2H-[1,2,4]triazol-3-yl]-4,5-dihydro-6-oxa-1,3a-diaza-benzo[e]azulen-8-yl}-pyrrolidine-2-carboxylic acid. LCMS: RT=3.06 min, [M+H]+=463.

Step 2

Following the amidation procedure in Example 529, (S)-1-{2-[5-methyl-2-(2,2,2-trifluoro-ethyl)-2H-[1,2,4]triazol-3-yl]-4,5-dihydro-6-oxa-1,3a-diaza-benzo[e]azulen-8-yl}-pyrrolidine-2-carboxylic acid was converted to 548. LCMS: RT=3.60 min, [M+H]+ 462. 1H NMR 400 MHz (DMSO-d6):δ 8.14 (1 H, d, J=8.92 Hz), 7.88 (1 H, s), 7.42 (1 H, s), 7.06 (1 H, s), 6.37 (1 H, dd, J=8.97, 2.45 Hz), 6.06 (1 H, d, J=2.40 Hz), 5.81 (2 H, q, J=8.90 Hz), 4.48-4.40 (4 H, m), 3.98-3.97 (1 H, m), 3.58-3.56 (1 H, m), 2.28 (2 H, s), 2.23-2.21 (1 H, m), 1.98-1.96 (3 H, m)

Example 549

2-cyclopropyl-2-(2-(1-isopropyl-1H-1,2,4-triazol-5-yl)-5,6-dihydrobenzo[f]imidazo[1,2-d][1,4]oxazepin-9-yloxy)acetamide 549

Step 1: Cyclopropyl-[2-(2-isopropyl-2H-[1,2,4]triazol-3-yl)-4,5-dihydro-6-oxa-1,3a-diaza-benzo[e]azulen-8-yloxy]-acetic acid methyl ester

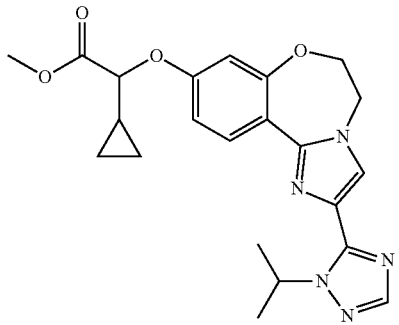 [SMILES: COC(=O)C(Oc1ccc2c(c1)OCCn1cc(-c3ncnn3C(C)C)nc1-2)C1CC1]

A mixture of 2-(2-isopropyl-2H-[1,2,4]triazol-3-yl)-4,5-dihydro-6-oxa-1,3a-diaza-benzo[e]azulen-8-ol 490 (0.20 g, 0.64 mmol), cyclopropyl-hydroxy-acetic acid methyl ester (0.253 g, 1.28 mmol), triphenylphopshine (0.205 g, 1.28 mmol) and DIAD (252 µL, 1.28 mmol) in dioxane (6 mL) was stirred at RT for 18 h then concentrated in vacuo. The resultant residue was subjected to flash chromatography (SiO2, gradient 0 to 10% methanol in TBME) to give Cyclopropyl-[2-(2-isopropyl-2H-[1,2,4]triazol-3-yl)-4,5-dihydro-6-oxa-1,3a-diaza-benzo[e]azulen-8-yloxy]-acetic acid methyl ester (0.068 g, 25%). LCMS: RT=3.43 min, [M+H]+=424.

Step 2

A solution of cyclopropyl-[2-(2-isopropyl-2H-[1,2,4]triazol-3-yl)-4,5-dihydro-6-oxa-1,3a-diaza-benzo[e]azulen-8-yloxy]-acetic acid methyl ester (0.068 g, 0.16 mmol) and 7M ammonia in methanol (20 mL) was stirred at RT for 18 h then concentrated in vacuo. The resultant residue was subjected to flash chromatography (SiO2, gradient 0 to 10% methanol in ethyl acetate) to give 549 (0.033 g, 50%). LCMS: RT=3.52 min, [M+H]+=409. 1H NMR 400 MHz (DMSO-d6):δ 8.28 (1 H, d, J=8.97 Hz), 7.89 (1 H, d, J=0.64 Hz), 7.85 (1 H, s), 7.54 (1 H, s), 7.25 (1 H, s), 6.73 (1 H, dd, J=8.99, 2.59 Hz), 6.49 (1 H, d, J=2.57 Hz), 5.89-5.88 (1 H, m), 4.52-4.44 (4 H, m), 3.97 (1 H, d, J=8.20 Hz), 1.48 (3 H, d, J=1.16 Hz), 1.46 (3 H, d, J=1.16 Hz), 1.26-1.25 (1 H, m), 0.61-0.54 (3 H, m), 0.44-0.43 (1 H, m)

Example 550

2-cyclopropyl-2-(2-(1-isopropyl-1H-1,2,4-triazol-5-yl)-5,6-dihydrobenzo[f]imidazo[1,2-d][1,4]oxazepin-9-yloxy)acetamide 550

Step 1: (S)-2-{[2-(2-Isopropyl-2H-[1,2,4]triazol-3-yl)-4,5-dihydro-6-oxa-1,3a-diaza-benzo[e]azulen-8-yl]-methyl-amino}-propionic acid tert-butyl ester

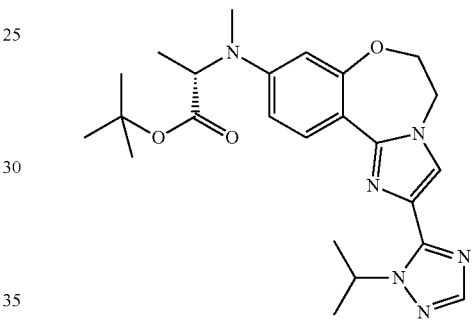

To a solution of (S)-2-[2-(2-isopropyl-2H-[1,2,4]triazol-3-yl)-4,5-dihydro-6-oxa-1,3a-diaza-benzo[e]azulen-8-ylamino]-propionic acid tert-butyl ester (0.24 g, 0.55 mmol) in DCE (7 mL) was added aqueous formaldehyde (4.4 mL, 55.4 mmol, 37% solution) and sodium triacetoxyborohydride (7.2 g, 34.0 mmol) portion wise over 58 h. The resulting mixture was then washed with saturated aqueous sodium carbonate and the aqueous phase extracted with further DCM. The combined organic phases were dried (Na2SO4) and concentrated in vacuo to give (S)-2-{[2-(2-Isopropyl-2H-[1,2,4]triazol-3-yl)-4,5-dihydro-6-oxa-1,3a-diaza-benzo[e]azulen-8-yl]-methyl-amino}-propionic acid tert-butyl ester (0.24 g, 97%). LCMS: RT=3.81 min, [M+H]+=453.

Step 2

(S)-2-{[2-(2-Isopropyl-2H-[1,2,4]triazol-3-yl)-4,5-dihydro-6-oxa-1,3a-diaza-benzo[e]azulen-8-yl]-methyl-amino}-propionic acid tert-butyl ester (0.24 g, 0.53 mmol) and TFA (2.5 mL) in DCM (2.5 mL) was stirred at RT for 5 h then concentrated in vacuo. The resultant residue was triturated with diethyl ether and pentane to give 550 (0.269 g, quant.). LCMS: RT=2.70 min, [M+H]+=397

Example 551

(2S)-1-(2-(1-isopropyl-1H-1,2,4-triazol-5-yl)-5,6-dihydrobenzo[f]imidazo[1,2-d][1,4]oxazepin-9-yl)azetidine-2-carboxamide 551

Step 1: (S)-1-[2-(2-Isopropyl-2H-[1,2,4]triazol-3-yl)-4,5-dihydro-6-oxa-,3a-diaza-benzo[e]azulen-8-yl]-azetidine-2-carboxylic acid

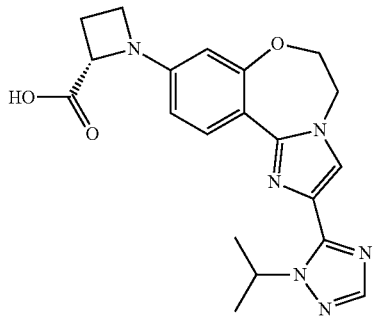 [SMILES: CC(C)n1ncnc1-c1cn2c(n1)-c1ccc(N3CC[C@H]3C(=O)O)cc1OCC2]

A mixture of 9-bromo-2-(1-isopropyl-1H-1,2,4-triazol-5-yl)-5,6-dihydrobenzo[f]imidazo[1,2-d][1,4]oxazepine 194 (0.27 g, 0.72 mmol), (L)-azetidine-2-carboxylic acid (0.73 g, 7.2 mmol), copper (I) iodide (0.057 g, 0.3 mmol) and potassium phosphate (1.83 g, 8.64 mmol) in DMSO (6 mL) was heated under argon at 80° C. for 18 h. The reaction mixture was cooled to RT, filtered through Celite® then loaded onto an SCX-2 cartridge, washed with dioxane and eluted with 2M ammonia in methanol. Basic fractions were combined and concentrated in vacuo and the resultant residue was subjected to flash chromatography (C18, gradient 20 to 60% methanol (containing 0.2M ammonia) in water) to give (S)-1-[2-(2-Isopropyl-2H-[1,2,4]triazol-3-yl)-4,5-dihydro-6-oxa-3a-diaza-benzo[e]azulen-8-yl]-azetidine-2-carboxylic acid (0.158 g, 56%). LCMS: RT=2.60 min, [M+H]+=395.

Step 2

Following the amidation procedure in Example 529, (S)-1-[2-(2-isopropyl-2H-[1,2,4]triazol-3-yl)-4,5-dihydro-6-oxa-,3a-diaza-benzo[e]azulen-8-yl]-azetidine-2-carboxylic acid was converted to 551. LCMS: RT=3.01 min, [M+H]+=394. 1H NMR 400 MHz (DMSO-d6):δ 8.22 (1 H, d, J=8.74 Hz), 7.88 (1 H, d, J=0.64 Hz), 7.80 (1 H, s), 7.53 (1 H, s), 7.24 (1 H, s), 6.27 (1 H, dd, J=8.76, 2.35 Hz), 5.99 (1 H, d, J=2.32 Hz), 5.91-5.90 (1 H, m), 4.47-4.43 (4 H, m), 4.30 (1 H, dd, J=8.76, 6.88 Hz), 3.93-3.92 (1 H, m), 3.71 (1 H, q, J=7.77 Hz), 2.54-2.46 (1 H, m), 2.34-2.27 (1 H, m), 1.48 (3 H, d, J=3.26 Hz), 1.46 (3 H, d, J=3.28 Hz)

Example 552

1-((2-(1-isopropyl-1H-1,2,4-triazol-5-yl)-5,6-dihydrobenzo[f]imidazo[1,2-d][1,4]oxazepin-9-yl)methyl)-1-methylurea 552

Step 1: 2-(2-Isopropyl-2H-[1,2,4]triazol-3-yl)-4,5-dihydro-6-oxa-1,3a-diaza-benzo[e]azulene-8-carbaldehyde

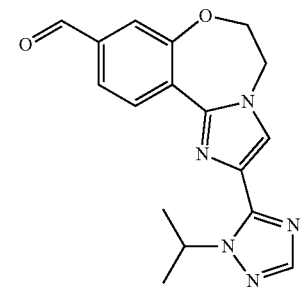 [SMILES: CC(C)n1ncnc1-c1cn2c(n1)-c1ccc(C=O)cc1OCC2]

A solution of [2-(2-isopropyl-2H-[1,2,4]triazol-3-yl)-4,5-dihydro-6-oxa-1,3a-diaza-benzo[e]azulen-8-yl]-methanol (0.294 g, 0.91 mmol) and Dess-Martin periodinane (3.32 mL, 1.0 mmol, 3M solution in DCM) in DCM (15 mL) was stirred at RT for 1.5 h then washed with 1M sodium hydroxide. The aqueous phase was extracted with DCM and the combined organic extracts dried (Na2SO4) and concentrated in vacuo to give 2-(2-Isopropyl-2H-[1,2,4]triazol-3-yl)-4,5-dihydro-6-oxa-1,3a-diaza-benzo[e]azulene-8-carbaldehyde (0.35 g, quant.). LCMS: RT=3.07 min, [M+H]+=324.

Step 2: [2-(2-Isopropyl-2H-[1,2,4]triazol-3-yl)-4,5-dihydro-6-oxa-1,3a-diaza-benzo[e]azulen-8-ylmethyl]-methyl-amine

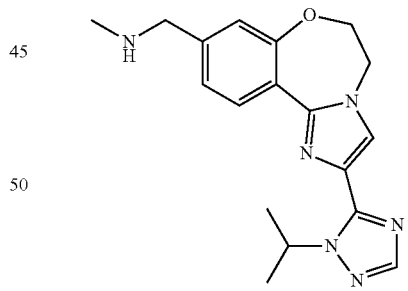

A mixture of 2-(2-Isopropyl-2H-[1,2,4]triazol-3-yl)-4,5-dihydro-6-oxa-1,3a-diaza-benzo[e]azulene-8-carbaldehyde (0.35, 0.90 mmol), methylamine (0.9 mL, 1.80 mmol, 2M solution in THF) and 4 Å molecular sieves in CHCl3 were stirred at RT for 1.5 h before sodium triacetoxyborohydride (0.57 g, 2.7 mmol) was added. The resultant mixture was stirred for 16 h then washed with saturated aqueous sodium bicarbonate. The aqueous phase was extracted with 10% methanol in DCM and the combined organic phases dried (Na2SO4) and concentrated in vacuo. The resultant residue was subjected to flash chromatography (SiO2, gradient 0 to 20% methanol in DCM) to give [2-(2-Isopropyl-2H-[1,2,4]

triazol-3-yl)-4,5-dihydro-6-oxa-1,3a-diaza-benzo[e]azulen-8-ylmethyl]-methyl-amine (109 mg, 36%). LCMS: RT=1.90 min, [M+H]+=339

Step 3

A solution of [2-(2-isopropyl-2H-[1,2,4]triazol-3-yl)-4,5-dihydro-6-oxa-1,3a-diaza-benzo[e]azulen-8-ylmethyl]-methyl-amine (0.106 g, 0.31 mmol) and trimethylsilyl isocyanate (87 µL, 0.56 mmol) in DCM (4 mL) was stirred at RT for 1.5 h then washed with water. The aqueous phase was extracted with DCM and the combined organics dried (Na2SO4) and concentrated in vacuo. The resultant residue was triturated with diethyl ether to give 552 (0.101 g, 85%). LCMS: RT 3.07 min, [M+H]+=382. 1H NMR 400 MHz (DMSO-d6):δ 8.36 (1 H, d, J=8.23 Hz), 7.90-7.90 (2 H, m), 6.99 (1 H, dd, J=8.28, 1.71 Hz), 6.86 (1 H, d, J=1.63 Hz), 5.96 (2 H, s), 5.89-5.88 (1 H, m), 4.53-4.47 (4 H, m), 4.39 (2 H, s), 2.76 (3 H, s), 1.48 (6 H, d, J=6.60 Hz)

Example 553

(2S)-1-(2-(3-methyl-1-(2,2,2-trifluoroethyl)-1H-1,2,4-triazol-5-yl)-5,6-dihydrobenzo[f]imidazo[1,2-d][1,4]oxazepin-9-yl)azetidine-2-carboxamide 553

Step 1: (S)-1-{2-[5-Methyl-2-(2,2,2-trifluoro-ethyl)-2H-[1,2,4]triazol-3-yl]-4,5-dihydro-6-oxa-1,3a-diaza-benzo[e]azulen-8-yl}-azetidine-2-carboxylic acid

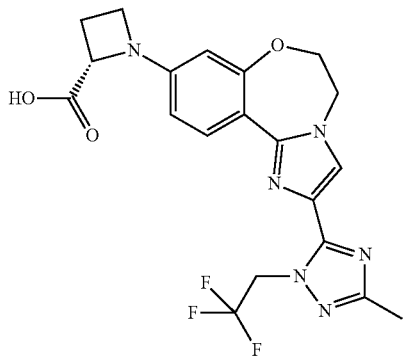 [SMILES: Cc1nc(-c2cn3c(n2)-c2ccc(N4CC[C@H]4C(=O)O)cc2OCC3)n(CC(F)(F)F)n1]

Following the procedure in Example 551, 8-bromo-2-[5-methyl-2-(2,2,2-trifluoro-ethyl)-2H-[1,2,4]triazol-3-yl]-4,5-dihydro-6-oxa-1,3a-diaza-benzo[e]azulene and (L)-azetidine-2-carboxylic acid were reacted to give (S)-1-{2-[5-Methyl-2-(2,2,2-trifluoro-ethyl)-2H-[1,2,4]triazol-3-yl]-4,5-dihydro-6-oxa-1,3a-diaza-benzo[e]azulen-8-yl}-azetidine-2-carboxylic acid. LCMS: RT=2.93 min, [M+H]+=449

Step 2

Following the amidation procedure in Example 529, (S)-1-{2-[5-Methyl-2-(2,2,2-trifluoro-ethyl)-2H-[1,2,4]triazol-3-yl]-4,5-dihydro-6-oxa-1,3a-diaza-benzo[e]azulen-8-yl}-azetidine-2-carboxylic acid was converted to 553. LCMS: RT=3.45 min, [M+H]+=448. 1H NMR 400 MHz (DMSO-d6):δ 8.15 (1 H, d, J=8.75 Hz), 7.89 (1 H, s), 7.53 (1 H, s), 7.23 (1 H, s), 6.27 (1H, dd, J=8.78, 2.35 Hz), 5.98 (1 H, d, J=2.31 Hz), 5.81-5.79 (2 H, m), 4.43-4.42 (3 H, m), 4.30 (1 H, dd, J=8.76, 6.83 Hz), 3.93-3.92 (1 H, m), 3.71 (1 H, q, J=7.78 Hz), 2.36-2.29 (1 H, m), 2.27 (3 H, s)

Example 555

2-(1-isopropyl-1H-1,2,4-triazol-5-yl)-10-phenyl-5,6-dihydrobenzo[f]imidazo[1,2-d][1,4]oxazepine 555

A mixture of 10-bromo-2-(1-isopropyl-1H-1,2,4-triazol-5-yl)-5,6-dihydrobenzo[f]imidazo[1,2-d][1,4]oxazepine (0.5 mmol), phenylboronic acid (200 mg, 0.75 mmol), Cs2CO3 (490 mg, 1.5 mmol) was stirred in dioxane and water (5:1, 3.0 mL) followed by the addition of Pd(dppf)Cl2 (30 mg). The reaction mixture was bubbled with N2 gas for 10 min, the reaction tube was sealed, and the contents were stirred at 130° C. under microwave irradiation for 30 min. The mixture was filtered through celite and the filtrate was concentrated and purified with prep-HPLC to give 555 (19.8 mg, 12%). 1H-NMR (DMSO, 400 MHz): δ 8.70 (s, 1H), 7.93 (d, J=14.4 Hz, 2H), 7.61-7.66 (m, 3H), 7.46-7.50 (m, 2H), 7.34-7.38 (m, 1H), 7.14 (d, J=8.4 Hz, 2H), 5.75-5.79 (m, 1H), 4.54-4.56 (m, 4H), 1.50 (d, J=7.6 Hz, 6H)

Example 556

1-isopropyl-5-(10-phenyl-5,6-dihydrobenzo[f]imidazo[1,2-d][1,4]oxazepin-2-yl)-1H-1,2,4-triazol-3-amine 556

A mixture of 5-(10-bromo-5,6-dihydrobenzo[f]imidazo[1,2-d][1,4]oxazepin-2-yl)-1-isopropyl-1H-1,2,4-triazol-3-amine (0.5 mmol), phenylboronic acid (200 mg, 0.75 mmol), Cs2CO3 (490 mg, 1.5 mmol) was stirred in dioxane and water (5:1, 3.0 mL) followed by the addition of Pd(dppf)Cl2 (30 mg). The reaction mixture was bubbled with N2 gas for 10 min, the reaction tube was sealed, and the contents were stirred at 130° C. under microwave irradiation for 30 min. The mixture was filtered through celite and the filtrate was concentrated and purified with prep-HPLC to give 556 (31 mg, 18%). 1H-NMR (DMSO, 400 MHz): δ 8.68 (s, 1H), 8.16 (s, 1H), 7.64-7.68 (m, 3H), 7.38-7.50 (m, 2H), 7.34-7.37 (m, 1H), 7.17 (d, J=8.4 Hz, 2H), 5.49-5.55 (m, 1H), 4.54-4.60 (m, 4H), 1.46 (d, J=6.8 Hz, 6H)

Example 557

2-(1-isopropyl-1H-1,2,4-triazol-5-yl)-10-(pyrimidin-5-yl)-5,6-dihydrobenzo[f]imidazo[1,2-d][1,4]oxazepine 557

A mixture of 10-bromo-2-(1-isopropyl-1H-1,2,4-triazol-5-yl)-5,6-dihydrobenzo[f]imidazo[1,2-d][1,4]oxazepine (0.5 mmol), pyrimidin-5-ylboronic acid (200 mg, 0.75 mmol), Cs2CO3 (490 mg, 1.5 mmol) was stirred in dioxane and water (5:1, 3.0 mL) followed by the addition of Pd(dppf)Cl2 (30 mg). The reaction mixture was bubbled with N2 gas for 10 min, the reaction tube was sealed, and the contents were stirred at 130° C. under microwave irradiation for 30 min. The mixture was filtered through celite and the filtrate was concentrated and purified with prep-HPLC to give 557 (39 mg, 13%). 1H-NMR (CDCl3, 400 MHz): δ 9.23 (s, 1H), 9.01 (s, 2H), 8.78 (s, 1H), 7.89 (s, 1H), 7.69 (s, 1H), 7.53-7.53 (d, J=2.4 Hz 1H), 7.52-7.51 (d, J=2.4 Hz 1H), 5.90-5.83 (m, 1H), 4.58-4.56 (m, 2H), 4.53-4.51. MS (ESI) m/z 374.17 [M+H+]

Example 558

1-isopropyl-5-(10-(pyrimidin-5-yl)-5,6-dihydrobenzo[f]imidazo[1,2-d][1,4]oxazepin-2-yl)-1H-1,2,4-triazol-3-amine 558

A mixture of 5-(10-bromo-5,6-dihydrobenzo[f]imidazo[1,2-d][1,4]oxazepin-2-yl)-1-isopropyl-1H-1,2,4-triazol-3-amine (0.5 mmol), pyrimidin-5-ylboronic acid (200 mg, 0.75 mmol), Cs2CO3 (490 mg, 1.5 mmol) was stirred in dioxane and water (5:1, 3.0 mL) followed by the addition of Pd(dppf)Cl2 (30 mg). The reaction mixture was bubbled with N2 gas for 10 min, the reaction tube was sealed, and the contents were stirred at 130° C. under microwave irradiation for 30 min. The mixture was filtered through celite and the filtrate was concentrated and purified with prep-HPLC to give 558 (65.8 mg, 16.9%). 1H-NMR (CDCl3, 400 MHz): δ 9.22 (s, 1H), 9.00 (s, 2H), 8.77 (s, 1H), 7.582 (s, 1H), 7.53-7.52 (d, J=2.4 Hz, 1H), 7.50-7.50 (d, J=2.4 Hz, 1H), 5.74-5.68 (m, 1H), 4.57-4.55 (m, 2H), 4.49-4.48 (m, 2H), 4.05 (s, 2H). MS (ESI) m/z 389.18 [M+H+]

Example 559

1-(2-chlorophenyl)-5-(10-(pyrimidin-5-yl)-5,6-dihydrobenzo[f]imidazo[1,2-d][1,4]oxazepin-2-yl)-1H-1,2,4-triazol-3-amine 559

A mixture of 5-(10-bromo-5,6-dihydrobenzo[f]imidazo[1,2-d][1,4]oxazepin-2-yl)-1-(2-chlorophenyl)-1H-1,2,4-triazol-3-amine (0.5 mmol), pyrimidin-5-ylboronic acid (200 mg, 0.75 mmol), Cs2CO3 (490 mg, 1.5 mmol) was stirred in dioxane and water (5:1, 3.0 mL) followed by the addition of Pd(dppf)Cl2 (30 mg). The reaction mixture was bubbled with N2 gas for 10 min, the reaction tube was sealed, and the contents were stirred at 130° C. under microwave irradiation for 30 min. The mixture was filtered through celite and the filtrate was concentrated and purified with prep-HPLC to give 559 (38.2 mg, 8.3%). 1H-NMR (CDCl3, 400 MHz): δ 9.22 (s, 1H), 8.79 (s, 2H), 8.01 (s, 1H), 7.55-7.42 (m, 6H) 7.00-7.07 (d, J=8 Hz, 1H), 4.45 (s, 2H), 4.41 (s, 2H), 4.258 (s, 2H). MS (ESI) m/z 457.12 [M+H+]

Example 560

10-(4-chlorophenyl)-2-(1-isopropyl-1H-1,2,4-triazol-5-yl)-5,6-dihydrobenzo[f]imidazo[1,2-d][1,4]oxazepine 560

A mixture of 10-bromo-2-(1-isopropyl-1H-1,2,4-triazol-5-yl)-5,6-dihydrobenzo[f]imidazo[1,2-d][1,4]oxazepine (0.5 mmol), 4-chlorophenylboronic acid (200 mg, 0.75 mmol), Cs2CO3 (490 mg, 1.5 mmol) was stirred in dioxane and water (5:1, 3.0 mL) followed by the addition of Pd(dppf)Cl2 (30 mg). The reaction mixture was bubbled with N2 gas for 10 min, the reaction tube was sealed, and the contents were stirred at 130° C. under microwave irradiation for 30 min. The mixture was filtered through celite and the filtrate was concentrated and purified with prep-HPLC to give 560 (40.5 mg, 10%). 1H NMR (CDCl3, 400 MHz): δ 8.7-8.7 (d, J=2.4 Hz, 1H), 7.96 (s, 1H), 7.90 (s, 1H) 7.57-7.43 (m, 5H), 7.15-7.13 (d, J=8.8 Hz, 1H), 5.94 (m, 1H), 4.56-4.54 (d, J=5.6 Hz, 2H), 4.56-4.54 (d, J=5.6 Hz, 2H), 1.62 (s, 6H). MS (ESI) m/z 406.14 [M+H+]

Example 561

5-(10-(4-chlorophenyl)-5,6-dihydrobenzo[f]imidazo[1,2-d][1,4]oxazepin-2-yl)-1-isopropyl-1H-1,2,4-triazol-3-amine 561

A mixture of 5-(10-bromo-5,6-dihydrobenzo[f]imidazo[1,2-d][1,4]oxazepin-2-yl)-1-isopropyl-1H-1,2,4-triazol-3-amine (0.5 mmol), 4-chlorophenylboronic acid (200 mg, 0.75 mmol), Cs2CO3 (490 mg, 1.5 mmol) was stirred in dioxane and water (5:1, 3.0 mL) followed by the addition of Pd(dppf)Cl2 (30 mg). The reaction mixture was bubbled with N2 gas for 10 min, the reaction tube was sealed, and the contents were stirred at 130° C. under microwave irradiation for 30 min. The mixture was filtered through celite and the filtrate was concentrated and purified with prep-HPLC to give 561 (76.4 mg, 18.1%). 1H NMR (CDCl3, 400 MHz): δ 8.71-8.69 (d, J=2.4 Hz, 1H), 7.63 (s, 1H), 7.56-7.43 (m, 5H), 7.12-7.10 (d, J=8.8 Hz, 1H), 5.75 (m, 1H), 4.52-4.51 (d, J=5.6 Hz, 2H), 4.46-4.45 (d, J=5.6 Hz, 2H), 4.13 (s, 2H), 1.53-1.51 (s, J=6.4 Hz, 6H). MS (ESI) m/z 420.15 [M+H+]

Example 562

10-(4-chlorophenyl)-2-(1-(2-chlorophenyl)-1H-1,2,4-triazol-5-yl)-5,6-dihydrobenzo[f]imidazo[1,2-d][1,4]oxazepine 562

A mixture of 10-bromo-2-(1-(2-chlorophenyl)-1H-1,2,4-triazol-5-yl)-5,6-dihydrobenzo[f]imidazo[1,2-d][1,4]oxazepine (0.5 mmol), 4-chlorophenylboronic acid (200 mg, 0.75 mmol), Cs2CO3 (490 mg, 1.5 mmol) was stirred in dioxane and water (5:1, 3.0 mL) followed by the addition of Pd(dppf)Cl2 (30 mg). The reaction mixture was bubbled with N2 gas for 10 min, the reaction tube was sealed, and the contents were stirred at 130° C. under microwave irradiation for 30 min. The mixture was filtered through celite and the filtrate was concentrated and purified with prep-HPLC to give 562 (79.7 mg, 16.8%). 1H NMR (CDCl3, 400 MHz): δ 8.12 (s, 1H), 8.02 (s, 1H), 8.01 (s, 1H), 7.66-7.52 (dd, J=16 Hz, 2H), 7.46-7.04 (m, 7H), 7.04-7.02 (d, J=8 Hz, 1H), 7.11-7.09 (d, J=8 Hz, 1H), 4.46-4.44 (d, J=8 Hz, 4H). MS (ESI) m/z 474.08 [M+H+]

Example 563

2-(1-(2-chlorophenyl)-1H-1,2,4-triazol-5-yl)-10-phenyl-5,6-dihydrobenzo[f]imidazo[1,2-d][1,4]oxazepine 563

A mixture of 10-bromo-2-(1-(2-chlorophenyl)-1H-1,2,4-triazol-5-yl)-5,6-dihydrobenzo[f]imidazo[1,2-d][1,4]oxazepine (0.5 mmol), phenylboronic acid (200 mg, 0.75 mmol), Cs2CO3 (490 mg, 1.5 mmol) was stirred in dioxane and water (5:1, 3.0 mL) followed by the addition of Pd(dppf)Cl2 (30 mg). The reaction mixture was bubbled with N2 gas for 10 min, the reaction tube was sealed, and the contents were stirred at 130° C. under microwave irradiation for 30 min. The mixture was filtered through celite and the filtrate was concentrated and purified with prep-HPLC to give 563 (82 mg, 38%). 1H-NMR (DMSO, 400 MHz): δ 8.18 (s, 1H), 8.01 (s, 1H), 7.89 (s, 1H), 7.38-7.70 (m, 10H), 7.14 (d, J=7.6 Hz, 1H), 4.45-4.51 (m, 4H)

Example 564

1-(2-chlorophenyl)-5-(10-phenyl-5,6-dihydrobenzo[f]imidazo[1,2-d][1,4]oxazepin-2-yl)-1H-1,2,4-triazol-3-amine 564

A mixture of 5-(10-bromo-5,6-dihydrobenzo[f]imidazo[1,2-d][1,4]oxazepin-2-yl)-1-(2-chlorophenyl)-1H-1,2,4-triazol-3-amine (0.5 mmol), phenylboronic acid (200 mg, 0.75 mmol), Cs2CO3 (490 mg, 1.5 mmol) was stirred in dioxane and water (5:1, 3.0 mL) followed by the addition of Pd(dppf)Cl2 (30 mg). The reaction mixture was bubbled with N2 gas for 10 min, the reaction tube was sealed, and the contents were stirred at 130° C. under microwave irradiation for 30 min. The mixture was filtered through celite and the filtrate was concentrated and purified with prep-HPLC to give 564 (47 mg, 21%). 1H-NMR (DMSO, 400 MHz): δ 7.90 (s, 1H), 8.89 (s, 1H), 7.38-7.70 (m, 10H), 7.03 (d, J=10.8 Hz, 1H), 5.48 (s, 2H), 4.43-4.49 (m, 4H)

Example 565

2-(1-(2-chlorophenyl)-1H-1,2,4-triazol-5-yl)-10-(pyrimidin-5-yl)-5,6-dihydrobenzo[f]imidazo[1,2-d][1,4]oxazepine 565

A mixture of 10-bromo-2-(1-(2-chlorophenyl)-1H-1,2,4-triazol-5-yl)-5,6-dihydrobenzo[f]imidazo[1,2-d][1,4]oxazepine (0.5 mmol), pyrimidin-5-ylboronic acid (200 mg, 0.75 mmol), Cs2CO3 (490 mg, 1.5 mmol) was stirred in dioxane and water (5:1, 3.0 mL) followed by the addition of Pd(dppf)Cl2 (30 mg). The reaction mixture was bubbled with N2 gas for 10 min, the reaction tube was sealed, and the contents were stirred at 130° C. under microwave irradiation for 30 min. The mixture was filtered through celite and the filtrate was concentrated and purified with prep-HPLC to give 565 (283 mg, 64.2%). 1H NMR (CDCl3, 400 MHz): δ 9.25 (s, 1H), 8.81 (s, 2H), 8.09-8.01 (m, 2H), 7.54 (s, 1H), 7.19-7.47 (m, 3H), 7.43-7.41 (dd, J=8 Hz, 2H), 7.11-7.09 (d, J=8 Hz, 1H), 4.47-4.45 (d, J=8 Hz, 4H), MS (ESI) m/z 442.11 [M+H+]

Example 566

1-(2-chlorophenyl)-5-(10-(4-chlorophenyl)-5,6-dihydrobenzo[f]imidazo[1,2-d][1,4]oxazepin-2-yl)-1H-1,2,4-triazol-3-amine 566

A mixture of 5-(10-bromo-5,6-dihydrobenzo[f]imidazo[1,2-d][1,4]oxazepin-2-yl)-1-(2-chlorophenyl)-1H-1,2,4-triazol-3-amine (0.5 mmol), 4-chlorophenylboronic acid (200 mg, 0.75 mmol), Cs2CO3 (490 mg, 1.5 mmol) was stirred in dioxane and water (5:1, 3.0 mL) followed by the addition of Pd(dppf)Cl2 (30 mg). The reaction mixture was bubbled with N2 gas for 10 min, the reaction tube was sealed, and the contents were stirred at 130° C. under microwave irradiation for 30 min. The mixture was filtered through celite and the filtrate was concentrated and purified with prep-HPLC to give 566 (200 mg, 42.2%). 1H NMR (CDCl3, 400 MHz): δ 8.06 (s, 1H), 7.56-7.37 (m, 10H), 7.03-7.00 (d, J=8.0 Hz, 2H) 4.44 (s, 2H), 4.39 (s, 2H), 4.21 (s, 2H). MS (ESI) m/z 474.08 [M+H+]

Example 567

9-(4-chlorophenyl)-2-(1-isopropyl-1H-1,2,4-triazol-5-yl)-5,6-dihydrobenzo[f]imidazo[1,2-d][1,4]oxazepine 567

To a mixture of 9-bromo-2-(1-isopropyl-1H-1,2,4-triazol-5-yl)-5,6-dihydrobenzo[f]imidazo[1,2-d][1,4]oxazepine 194 (300 mg, 0.80 mmol), 4-chlorophenylboronic acid (188 mg, 1.21 mmol), Pd(dppf)Cl2 (65 mg, 0.080 mmol) and Cs2CO3 (314 mg, 0.96 mmol) in a microwave reaction tube, dioxane/H2O (5 ml) was added and argon was bubbled through. The reaction mixture was heated under microwave irradiation at 130 C for 30 min. The reaction mixture was filtered, concentrated, and purified by HPLC to give 567 (68.4 mg, 21%). 1H NMR (DMSO, 400 MHz) δ 8.46 (d, J=8.8 Hz, 1H), 7.94 (s, 1H), 7.90 (s, 1H), 7.74 (d, J=6.4 Hz, 2H), 7.51-7.46 (m, 3H), 2.34 (s, 1H), 5.95-5.84 (m, 1H), 4.53 (s, 4H), 1.46 (d, J=6.8 Hz, 6H). LCMS (ESI): m/z 406.0 (M+H+)

Example 568

9-(4-chlorophenyl)-2-(1-(2-chlorophenyl)-1H-1,2,4-triazol-5-yl)-5,6-dihydrobenzo[f]imidazo[1,2-d][1,4]oxazepine 568

Step 1: 9-bromo-N-formyl-5,6-dihydrobenzo[f]imidazo[1,2-d][1,4]oxazepine-2-carboxamide

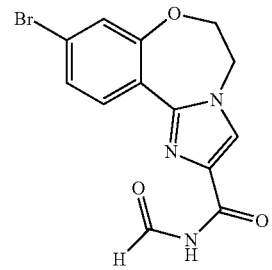 [SMILES: O=CNC(=O)c1cn2c(n1)-c1ccc(Br)cc1OCC2]

9-bromo-2-iodo-5,6-dihydrobenzo[f]imidazo[1,2-d][1,4]oxazepine, from Example 43, (1.0 g, 2.56 mmol), Pd(dppf)Cl2 (104 mg, 0.128 mmol) and DMAP (363 mg, 2.56 mmol) were combined in a flask, and HCONH2 (30 ml) was added. The resulting mixture was stirred at 70° C. for 5 h. The reaction mixture was cooled to room temperature, diluted with EtOAc, and filtered. The solid was collected to give 9-bromo-N-formyl-5,6-dihydrobenzo[f]imidazo[1,2-d][1,4]oxazepine-2-carboxamide (400 mg, 46%). LCMS (ESI) m/z 335.8 (M+H+)

Step 2: 9-bromo-2-(1-(2-chlorophenyl)-1H-1,2,4-triazol-5-yl)-5,6-dihydrobenzo[f]imidazo[1,2-d][1,4]oxazepine

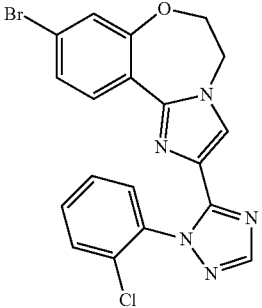 [SMILES: Clc1ccccc1-n1ncnc1-c1cn2c(n1)-c1ccc(Br)cc1OCC2]

To a solution of 9-bromo-N-formyl-5,6-dihydrobenzo[f]imidazo[1,2-d][1,4]oxazepine-2-carboxamide (350 mg, 1.04 mmol) in HOAc (10 ml) was added (2-chlorophenyl)hydrazine hydrochloride (557 mg, 3.13 mmol) in one portion. The resulting mixture was stirred at 80° C. for 4 h. The reaction mixture was cooled to room temperature and concentrated. The residue was dissolved in MeOH and purified by chromatography on silica gel (Hexanes: EtOAc=10:1-1:1) to give 9-bromo-2-(1-(2-chlorophenyl)-1H-1,2,4-triazol-5-yl)-

5,6-dihydrobenzo[f]imidazo[1,2-d][1,4]oxazepine (300 mg, 65%). LCMS (ESI): m/z 443.7 (M+H+)

Step 3

9-bromo-2-(1-(2-chlorophenyl)-1H-1,2,4-triazol-5-yl)-5,6-dihydrobenzo[f]imidazo[1,2-d][1,4]oxazepine (300 mg, 0.88 mmol), 4-chlorophenylboronic acid (188 mg, 1.20 mmol), Cs2CO3 (314 mg, 0.96 mmol) and dioxane/water (3:1, 5 ml) were combined in a tube. Pd(dppf)Cl2 (65 mg, 0.08 mmol) was added and N2 was bubbled through the solution. The mixture was heated in the microwave reactor at 130° C. for 30 min. The reaction mixture was filtered. The filtrate was concentrated, and purified by HPLC to give 568 (86 mg, 20%). 1H NMR (DMSO, 400 MHz) δ 8.17 (s, 1H), 7.88 (s, 1H), 7.70 (d, J=8.4 Hz, 3H), 7.64-7.60 (m, 3H), 7.54 (d, J=6.8 Hz, 1H), 7.46 (d, J=8.4 Hz, 2H), 7.25-7.20 (m, 2H), 4.44 (s, 4H). LCMS (ESI): m/z 470.0 (M+H+)

Example 569

5-(9-(4-chlorophenyl)-5,6-dihydrobenzo[f]imidazo[1,2-d][1,4]oxazepin-2-yl)-1-isopropyl-1H-1,2,4-triazol-3-amine 569

Step 1: methyl 9-bromo-5,6-dihydrobenzo[f]imidazo[1,2-d][1,4]oxazepine-2-carboxylate

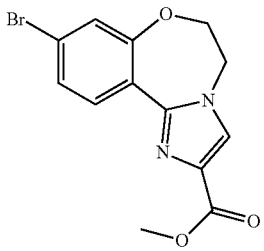 [SMILES: COC(=O)c1cn2c(n1)-c1ccc(Br)cc1OCC2]

9-Bromo-2-iodo-5,6-dihydrobenzo[f]imidazo[1,2-d][1,4]oxazepine (5.0 g, 12.8 mmol), Pd(dppf)Cl2 (0.52 g, 0.64 mmol) and DMAP (1.82 g, 12.8 mmol) were mixed in MeOH (150 ml). The reaction mixture was stirred at 60° C. overnight. The reaction mixture was cooled to room temperature, and filtered. The solid was collected to give methyl 9-bromo-5,6-dihydrobenzo[f]imidazo[1,2-d][1,4]oxazepine-2-carboxylate with a purity of 94% (3.5 g). 1H NMR (DMSO, 400 MHz) δ 8.27 (d, J=8.4 Hz, 1H), 8.05 (s, 1H), 7.28 (d, J=8.8 Hz, 1H), 7.24 (s, 1H), 4.46 (s, 4H), 3.74 (s, 3H). LCMS (ESI) m/z 324.7 (M+H+)

Step 2: 9-bromo-5,6-dihydrobenzo[f]imidazo[1,2-d][1,4]oxazepine-2-carboxylic acid

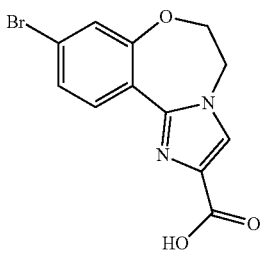 [SMILES: O=C(O)c1cn2c(n1)-c1ccc(Br)cc1OCC2]

methyl 9-bromo-5,6-dihydrobenzo[f]imidazo[1,2-d][1,4]oxazepine-2-carboxylate (3.5 g, 10.8 mmol) and LiOH (0.52 g, 21.7 mmol) were dissolved in a mixture of THF:H2O (1:1, 150 mL). After the resulting mixture was stirred at 70° C. for 2 h, the water phase of the reaction mixture was separated, adjusted to pH 4.0 and extracted with EtOAc (100 mL×4). The organic phase was pooled and concentrated to give product (3.0 g, 90.5%). LCMS (ESI): m/z 310.6 (M+H+)

Step 3: methyl N'-9-bromo-5,6-dihydrobenzo[f]imidazo[1,2-d][1,4]oxazepine-2-carbonyl-N-Boc-carbamimidothioate

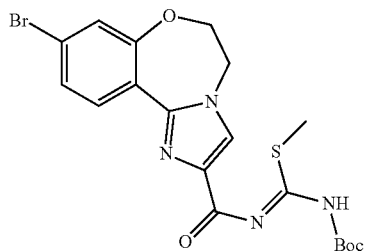 [SMILES: CS/C(=N\C(=O)c1cn2c(n1)-c1ccc(Br)cc1OCC2)NC(=O)OC(C)(C)C]

9-Bromo-5,6-dihydrobenzo[f]imidazo[1,2-d][1,4]oxazepine-2-carboxylic acid (3.2 g, 10.4 mmol), methyl N-Boc-carbamimidothioate (4.7 g, 12.4 mmol), HATU (5.0 g, 26.0 mmol) and DIPEA (6.7 g, 52.1 mmol) were dissolved in DCM (200 mL). After the resulting mixture was stirred at room temperature for 2 h, the reaction mixture was concentrated and methanol (50 mL) was added and filtered. The solid was collected to give methyl N'-9-bromo-5,6-dihydrobenzo[f]imidazo[1,2-d][1,4]oxazepine-2-carbonyl-N-Boc-carbamimidothioate (3.0 g, 60%). 1H NMR (DMSO, 400 MHz) δ 12.84 (s, 1H), 8.31 (s, 1H), 8.18 (s, 1H), 7.32-7.27 (m, 2H), 5.72 (s, 1H), 4.49 (s, 4H), 2.30 (s, 3H), 1.49 (s, 9H)

Step 4: 5-(9-bromo-5,6-dihydrobenzo[f]imidazo[1,2-d][1,4]oxazepin-2-yl)-1-isopropyl-1H-1,2,4-triazol-3-amine

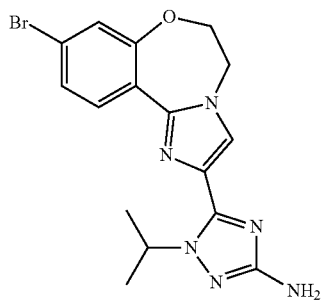 [SMILES: CC(C)n1nc(N)nc1-c1cn2c(n1)-c1ccc(Br)cc1OCC2]

To a mixture of methyl N'-9-bromo-5,6-dihydrobenzo[f]imidazo[1,2-d][1,4]oxazepine-2-carbonyl-N-Boc-carbamimidothioate (1.2 g, 2.5 mmol) and isopropylhydrazine hydrochloride (0.55 g, 5 mmol) in DMF (50 mL), DIPEA (3.2 g, 25 mmol) was added. The resulting mixture was stirred at 120° C. overnight. The reaction mixture was concentrated, and MeOH (30 mL) was added. The solid was collected to give 5-(9-bromo-5,6-dihydrobenzo[f]imidazo

[1,2-d][1,4]oxazepin-2-yl)-1-isopropyl-1H-1,2,4-triazol-3-amine (430 mg, 49%). 1H NMR (DMSO, 400 MHz) δ 8.28 (d, J=8.4 Hz, 1H), 7.57 (s, 1H), 7.33 (d, J=8.4 Hz, 1H), 7.26 (s, 1H), 5.69-5.66 (m, 1H), 5.35 (s, 1H), 4.49 (s, 4H), 4.10 (s, 1H), 3.14 (s, 2H), 1.37 (d, J=6.8 Hz, 6H)

Step 5

After 5-(9-bromo-5,6-dihydrobenzo[f]imidazo[1,2-d][1,4]oxazepin-2-yl)-1-isopropyl-1H-1,2,4-triazol-3-amine (400 mg, 1.03 mmol), 4-chlorophenylboronic acid (321 mg, 2.06 mmol), Pd(dppf)Cl2 (84 mg, 0.1 mmol) and Cs2CO3 (403 mg, 1.23 mmol) were combined in a tube, dioxane and water (3:1, 20 ml) was added. The mixture was bubbled with N2 for 10 min. The mixture was sealed to heat in the microwave reactor at 130° C. for 30 min. The reaction mixture was filtered. The filtrate was concentrated and purified by HPLC to give 569 (74.9 mg, 17%) 1H NMR (DMSO, 400 MHz) δ 8.44 (d, J=8.4 Hz, 1H), 7.74 (d, J=9.2 Hz, 3H), 7.51-7.46 (m, 3H), 7.34 (s, 1H), 7.75-7.72 (m, 1H), 5.19 (s, 2H), 4.51 (s, 4H), 1.39 (d, J=6.8 Hz, 6H). LCMS (ESI) m/z 421.0 (M+H+)

Example 570

1-(2-chlorophenyl)-5-(9-(4-chlorophenyl)-5,6-dihydrobenzo[f]imidazo[1,2-d][1,4]oxazepin-2-yl)-1H-1,2,4-triazol-3-amine 570

Step 1: 5-(9-Bromo-5,6-dihydrobenzo[f]imidazo[1,2-d][1,4]oxazepin-2-yl)-1-(2-chlorophenyl)-1H-1,2,4-triazol-3-ylcarbamic acid

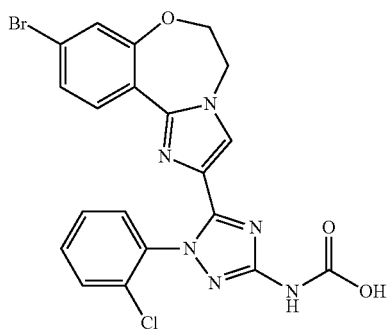 [SMILES: O=C(O)Nc1nc(-c2cn3c(n2)-c2ccc(Br)cc2OCC3)n(-c2ccccc2Cl)n1]

CH3COOH (50 ml) was added to a mixture of methyl N'-9-bromo-5,6-dihydrobenzo[f]imidazo[1,2-d][1,4]oxazepine-2-carbonyl-N-Boc-carbamimidothioate, from Example 569, (1.0 g, 2.08 mmol) and (2-chlorophenyl)hydrazine hydrochloride (0.74 g, 4.16 mmol). The resulting mixture was stirred at 120° C. overnight. The reaction mixture was concentrated and purified by silica gel chromatography (Hexanes: EtOAc, 3:1-1:1) to give 5-(9-Bromo-5,6-dihydrobenzo[f]imidazo[1,2-d][1,4]oxazepin-2-yl)-1-(2-chlorophenyl)-1H-1,2,4-triazol-3-ylcarbamic acid (630 mg, 60%). 1H NMR (DMSO, 400 MHz) δ 10.60 (s, 1H), 7.76 (s, 1H), 7.70-7.68 (m, 1H), 7.63-7.60 (m, 2H), 7.52-7.52 (m, 1H), 7.48-7.46 (m, 1H), 7.18 (s, 1H), 7.10-7.07 (m, 1H), 5.45 (s, 1H), 4.42 (s, 4H)

Step 2: 1-(2-chlorophenyl)-5-(9-(4-chlorophenyl)-5,6-dihydrobenzo[f]imidazo[1,2-d][1,4]oxazepin-2-yl)-1H-1,2,4-triazol-3-ylcarbamic acid

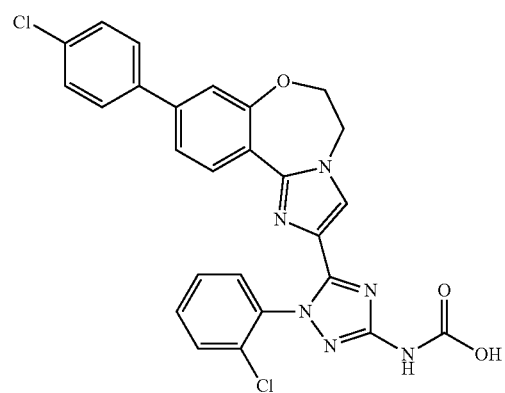 [SMILES: O=C(O)Nc1nc(-c2cn3c(n2)-c2ccc(-c4ccc(Cl)cc4)cc2OCC3)n(-c2ccccc2Cl)n1]

5-(9-Bromo-5,6-dihydrobenzo[f]imidazo[1,2-d][1,4]oxazepin-2-yl)-1-(2-chlorophenyl)-1H-1,2,4-triazol-3-ylcarbamic acid (600 mg, 1.2 mmol), 4-chlorophenylboronic acid (374 mg, 2.4 mmol), Pd(dppf)Cl2 (97.9 mg, 0.12 mmol) and Cs2CO3 (469 mg, 1.44 mmol) were dissolved in dioxane/H2O (3:1, 30 ml). The resulting mixture was bubbled with N2 for 10 min and then sealed to stir at 120° C. for 4 h under N2. The reaction mixture was filtered. The filtrate was concentrated and purified by HPLC to give 1-(2-chlorophenyl)-5-(9-(4-chlorophenyl)-5,6-dihydrobenzo[f]imidazo[1,2-d][1,4]oxazepin-2-yl)-1H-1,2,4-triazol-3-ylcarbamic acid (270 mg, 21%). 1H NMR (DMSO, 400 MHz) δ 10.65 (s, 1H), 7.74 (s, 1H), 7.70 (d, J=8.4 Hz, 3H), 7.67-7.61 (m, 3H), 7.54 (t, 1H), 7.47 (d, J=8.4 Hz, 2H), 7.27-7.22 (m, 2H), 7.45-7.43 (m, 4H)

Step 3

A solution of EtOAc/HCl (20 mL) was added to 1-(2-chlorophenyl)-5-(9-(4-chlorophenyl)-5,6-dihydrobenzo[f]imidazo[1,2-d][1,4]oxazepin-2-yl)-1H-1,2,4-triazol-3-ylcarbamic acid (270 mg, 0.6 mmol) in EtOAc (10 mL) in portions. The resulting mixture was stirred at 50° C. for 5 h. The reaction mixture was filtered and the solid was collected to give 570 (100 mg, 34%). 1H NMR (DMSO, 400 MHz) δ 7.73-7.69 (m, 5H), 7.63-7.61 (m, 2H), 7.55-7.52 (m, 1H), 7.48 (dd, J=2.0, 6.8 Hz, 2H), 7.28-7.25 (m, 2H), 4.80-4.30 (b, 2H), 4.45 (s, 4H). LCMS (ESI) m/z 489.1 (M+H+)

Example 901 p110α (alpha) PI3K Binding Assay

Binding Assays: Initial polarization experiments were performed on an Analyst HT 96-384 (Molecular Devices Corp, Sunnyvale, Calif.). Samples for fluorescence polarization affinity measurements were prepared by addition of 1:3 serial dilutions of p110 alpha PI3K (Upstate Cell Signaling Solutions, Charlottesville, Va.) starting at a final concentration of 20 ug/mL in polarization buffer (10 mM tris pH 7.5, 50 mM NaCl, 4 mM MgCl2, 0.05% Chaps, and 1 mM DTT) to 10 mM PIP2 (Echelon-Inc., Salt Lake City, Utah) final concentration. After an incubation time of 30 minutes at room temperature, the reactions were stopped by the addition of GRP-1 and PIP3-TAMRA probe (Echelon- Inc., Salt Lake City, Utah) 100 nM and 5 nM final concentrations respectively. Read with standard cut-off filters for the rhodamine fluorophore (λex=530 nm; λem=590 nm) in 384-well black low volume Proxiplates (PerkinElmer, Wellesley, Mass.) Fluorescence polarization values were plotted as a function of the protein concentration, and the EC50 values were obtained by fitting the data to a 4-parameter equation using KaleidaGraph software (Synergy software, Reading, Pa.). This experiment also establishes the appropriate protein concentration to use in subsequent competition experiments with inhibitors.

Inhibitor IC50 values were determined by addition of the 0.04 mg/mL p110 alpha PI3K (final concentration) combined with PIP2 (10 mM final concentration) to wells containing 1:3 serial dilutions of the antagonists in a final concentration of 25 mM ATP (Cell Signaling Technology, Inc., Danvers, Mass.) in the polarization buffer. After an incubation time of 30 minutes at room temperature, the reactions were stopped by the addition of GRP-1 and PIP3-TAMRA probe (Echelon-Inc., Salt Lake City, Utah) 100 nM and 5 nM final concentrations respectively. Read with standard cut-off filters for the rhodamine fluorophore (λex=530 nm; λem=590 nm) in 384-well black low volume proxi plates (PerkinElmer, Wellesley, Mass.) Fluorescence polarization values were plotted as a function of the antagonist concentration, and the IC50 values were obtained by fitting the data to a 4-parameter equation in Assay Explorer software (MDL, San Ramon, Calif.).

Alternatively, inhibition of PI3K was determined in a radiometric assay using purified, recombinant enzyme and ATP at a concentration of 1 uM. The Formula I compound was serially diluted in 100% DMSO. The kinase reaction was incubated for 1 hr at room temperature, and the reaction was terminated by the addition of PBS. IC50 values were subsequently determined using sigmoidal dose-response curve fit (variable slope).

Example 902

In Vitro Cell Proliferation Assay

Efficacy of Formula I compounds was measured by a cell proliferation assay employing the following protocol (Promega Corp. Technical Bulletin TB288; Mendoza et al (2002) Cancer Res. 62:5485-5488):

1. An aliquot of 100 μl of cell culture containing about 104 cells (PC3, Detroit562, or MDAMB361.1) in medium was deposited in each well of a 384-well, opaque-walled plate.
2. Control wells were prepared containing medium and without cells.
3. The compound was added to the experimental wells and incubated for 3-5 days.
4. The plates were equilibrated to room temperature for approximately 30 minutes.
5. A volume of CellTiter-Glo Reagent equal to the volume of cell culture medium present in each well was added.
6. The contents were mixed for 2 minutes on an orbital shaker to induce cell lysis.
7. The plate was incubated at room temperature for 10 minutes to stabilize the luminescence signal.
8. Luminescence was recorded and reported in graphs as RLU=relative luminescence units.

Alternatively, cells were seeded at optimal density in a 96 well plate and incubated for 4 days in the presence of test compound. Alamar Blue™ was subsequently added to the assay medium, and cells were incubated for 6 hr before reading at 544 nm excitation, 590 nm emission. EC50 values were calculated using a sigmoidal dose response curve fit. The term EC50 refers to the half maximal effective concentration and is the concentration at which a drug induces a response halfway between the baseline and maximum after some specified exposure time. It is commonly used as a measure of drug potency.

The anti-proliferative effects of Formula I exemplary compounds were measured by the CellTiter-Glo® Assay against various tumor cell lines, including the following:

| Cell line | Tissue Type | Mutation Status | EC50 (μmole) 107 | EC50 (μmole) 180 | EC50 (μmole) 186 | EC50 (μmole) 196 | EC50 (μmole) 207 |
|---|---|---|---|---|---|---|---|
| AU565 | Breast | WT | 0.259 | 0.230 | 0.47 | 0.152 | 3.729 |
| BT474 | Breast | PI3K(amped | | | 0.324 | 0.086 | 1.678 |
| CAL120 | Breast | WT | | 2.121 | | | |
| CAL51 | Breast | PI3K/PTEN | | 0.672 | | | |
| EFM19-2A | Breast | WT | | 0.146 | | | |
| EVSA-T | Breast | PTEN | 1.406 | 2.035 | 1.997 | 1.123 | 1.769 |
| HCC1954 | Breast | PI3K | | 0.168 | 0.420 | 0.128 | 3.388 |
| KPL4 | Breast | PI3K | | 0.039 | 0.088 | 0.016 | 1.364 |
| MCF7 | Breast | PI3K | | 0.121 | | | |
| MDA-MB-231 | Breast | K-RAS | | 10 | | | |
| MDA-MB-361.1 | Breast | PI3K | 1.050 | 0.214 | 0.710 | 0.178 | 10 |
| MFM223 | Breast | PI3K | | 0.439 | 1.099 | 0.211 | 7.253 |
| SKBR3 | Breast | WT | | 0.144 | 0.860 | | |
| T47D | Breast | PI3K | | 0.123 | 0.133 | 0.045 | 0.762 |
| Colo205 | Colon | B-Raf | | 0.259 | | | |
| HCT116 | Colon | PI3K/KRAS | | 1.02 | | | |
| KM12 | Colon | PTEN | | | | 4.687 | 10 |
| MDST8 | Colon | PTEN | | | | 4.009 | 7.789 |
| RKO | Colon | PI3K | | 2.5 | | | |
| LN229 | Glioma | PI3K | | 0.869 | | | |
| U87MG | Glioma | PTEN | | 0.787 | | 1.019 | 5.769 |
| H1703 | Lung(NSCLC) | WT | | 0.225 | | 0.136 | |
| H2122 | Lung(NSCLC) | K-RAS | | 0.515 | 2.948 | 0.366 | 10 |
| H520 | Lung(NSCLC) | PTEN | | | | 0.264 | 1.287 |
| 537MEL | Melanoma | PTEN | | 2.433 | | | |

-continued

| Cell line | Tissue Type | Mutation Status | EC50 (µmole) 107 | EC50 (µmole) 180 | EC50 (µmole) 186 | EC50 (µmole) 196 | EC50 (µmole) 207 |
|---|---|---|---|---|---|---|---|
| A2058 | Melanoma | PTEN | | 10 | | 9.24 | |
| A375 | Melanoma | B-Raf | | 10 | | 10 | |
| IGROV1 | Ovarian | PI3K | | 0.06 | | | |
| TOV21GX1 | Ovarian | PI3K/PTEN | | 3.592 | | | |
| PC3 | Prostate | PTEN | 0.999 | 0.769 | 1.300 | 0.864 | 0.762 |

Example 903

Caco-2 Permeability

Caco-2 cells are seeded onto Millipore Multiscreen plates at 1×105 cells/cm2, and cultured for 20 days. Assessment of compound permeability is subsequently conducted. The compounds are applied to the apical surface (A) of cell monolayers and compound permeation into the basolateral (B) compartment is measured. This is performed in the reverse direction (B-A) to investigate active transport. A permeability coefficient value, Papp, for each compound, a measure of the rate of permeation of the compound across the membrane, is calculated. Compounds are grouped into low (Papp</=1.0×106 cm/s) or high (Papp>1=1.0×106 cm/s) absorption potential based on comparison with control compounds with established human absorption.

For assessment of a compound's ability to undergo active efflux, the ratio of basolateral (B) to apical (A) transport compared with A to B was determined. Values of B-A/A-B>/=1.0 indicate the occurrence of active cellular efflux.

Example 904

Hepatocyte Clearance

Suspensions of cryopreserved human hepatocytes are used. Incubations are performed at compound concentration of 1 mM or 3 µM at a cell density of 0.5×106 viable cells/mL. The final DMSO concentration in the incubation is about 0.25%. Control incubations are also performed in the absence of cells to reveal any non-enzymatic degradation. Duplicate samples (50 µL) are removed from the incubation mixture at 0, 5, 10, 20, 40 and 60 minutes (control sample at 60 minutes only) and added to methanol containing internal standard (100 µL)—to terminate the reaction. Tolbutamide, 7-hydroxycoumarin, and testosterone may be used as control compounds. Samples are centrifuged and the supernatants at each time point pooled for analysis by LC-MSMS. From a plot of ln peak area ratio (parent compound peak area/internal standard peak area) against time, intrinsic clearance (CLint) is calculated as follows: CLint (µl/min/million cells)=V×k, where k is the elimination rate constant, obtained from the gradient of ln concentration plotted against time; V is a volume term derived from the incubation volume and is expressed as uL 106 cells-1.

Example 905

Cytochrome P450 Inhibition

Formula I compounds may be screened against CYP450 targets (1A2, 2C9, 2C19, 2D6, 3A4) at about 10 concentrations in duplicate, with a top concentration of about 100 uM. Standard inhibitors (furafylline, sulfaphenazole, tranylcypromine, quinidine, ketoconazole) may be used as controls. Plates may be read using a BMG LabTechnologies PolarStar in fluorescence mode.

Example 906

Cytochrome P450 Induction

Freshly isolated human hepatocytes from a single donor may be cultured for about 48 hr prior to addition of Formula I compound at three concentrations and incubated for 72 hr. Probe substrates for CYP3A4 and CYP1A2 are added for 30 minutes and 1 hr before the end of the incubation. At 72 hr, cells and media are removed and the extent of metabolism of each probe substrate quantified by LC-MS/MS. The experiment is controlled by using inducers of the individual P450s incubated at one concentration in triplicate.

Example 907

Plasma Protein Binding

Solutions of Formula I compound (Sum, 0.5% final DMSO concentration) are prepared in buffer and 10% plasma (v/v in buffer). A 96 well HT dialysis plate is assembled so that each well is divided in two by a semipermeable cellulose membrane. The buffer solution is added to one side of the membrane and the plasma solution to the other side; incubations are then conducted at 37° C. over 2 hr in triplicate. The cells are subsequently emptied, and the solutions for each batch of compounds are combined into two groups (plasma-free and plasma-containing) then analyzed by LC-MSMS using two sets of calibration standards for plasma-free (6 points) and plasma-containing solutions (7 points). The fraction unbound value for the compound is calculated.

Example 908 hERG Channel Blockage

Formula I compounds are evaluated for ability to modulate rubidium efflux from HEK-294 cells stably expressing hERG potassium channels using established flux methodology. Cells are prepared in medium containing RbCl, plated into 96-well plates and grown overnight to form monolayers. The efflux experiment is initiated by aspirating the media and washing each well with 3×100 µL of pre-incubation buffer (containing low [K+]) at room temperature. Following the final aspiration, 50 µL of working stock (2×) compound is added to each well and incubated at room temperature for 10 minutes. Stimulation buffer 50 µL (containing high [K+]) is then added to each well giving the final test compound concentrations. Cell plates are then incubated at room temperature for a further 10 minutes. Supernatant 80

μL from each well is then transferred to equivalent wells of a 96-well plate and analyzed via atomic emission spectroscopy. The compound is screened as 10pt duplicate IC50 curves, n=2, from a top concentration of 100 μM.

Example 909

In Vivo Tumor Xenograft

Animals suitable for transgenic experiments can be obtained from standard commercial sources. Groups of Taconic nude mice (were implanted subcutaneously in the hind flank with MDA-MB-361.1 (PI3K mutant) breast cancer cells. Mouse xenografts were dosed daily for 21 days with drug or vehicle. Tumor sizes were recorded twice weekly over the course of the study. Mouse body weights were also recorded twice weekly, and the mice were observed regularly. Tumor volume was measured in two dimensions (length and width) using Ultra Cal-IV calipers (Model 54-10-111; Fred V. Fowler Co., Inc.; Newton, Mass.) and analyzed using Excel v.11.2 (Microsoft Corporation; Redmond, Wash.). Tumor inhibition graphs were plotted using KaleidaGraph, Version 3.6 (Synergy Software; Reading, Pa.). The tumor volume was calculated with formula: Tumor size (mm3)=(longer measurement×shorter measurement2)×0.5

Animal body weights were measured using an Adventurera Pro AV812 scale (Ohaus Corporation; Pine Brook, N.J.). Graphs were generated using KaleidaGraph Version 3.6. Percent weight change was calculated using formula: Group percent weight change=(1−(initial weight/new weight))×100.

Mice whose tumor volume exceeded 2000 mm3 or whose body weight loss was >20% of their starting weight were promptly euthanized according to regulatory guidance.

The percent tumor growth inhibition (% INH) at the end of study (EOS) was calculated using formula: % INH=100× (EOS mean volume of tumors in animals given vehicle—EOS mean volume of tumors in animals given the drug)/ EOS mean volume of tumors in animals given vehicle.

Tumor incidence (TI) was determined based on the number of measurable tumors remaining in each group at the end of the study. A partial response (PR) was defined as a >50% but <100% reduction in tumor volume, compared with the starting tumor volume, observed on any day of the study. A complete response (CR) was defined as a 100% reduction in tumor volume, compared with the initial tumor volume, observed on any day of the study. Data were analyzed and p-values were determined using the Dunnett's test with JMP statistical software, version 5.1.2 (SAS Institute; Cary, N.C.). Individual tumor volumes at end of study and mean tumor volume ±SEM values were calculated using JMP statistical software, version 5.1.2. Body weight data were graphed based on the mean percentage of change from initial body weights ±SEM.

Example 910

Phospho AKT Induction Assay

In a 6-well tissue culture plate cells were seeded at 5×105 cells per well overnight. Cells were treated with an EC80 of the Formula I compound. Following treatment, cells were washed once with cold PBS and lysed in 1× Cell Extraction Buffer from Biosource (Carlsbad, Calif.) supplemented with protease inhibitors (Roche, Mannheim, Germany), 1 mM PMSF, and Phosphatase Inhibitor Cocktails 1 and 2 from Sigma (St. Louis, Mo.). Determination of protein concentration was performed using the Pierce BCA Protein Assay Kit (Rockford, Ill.). Levels of pAkt (Ser473) and total Akt were assessed using bead kits from Biosource (Carlsbad, Calif.) and the Luminex Bio-Plex system (Bio-Rad, Hercules, Calif.).

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

We claim:

1. A compound selected from Formula I:

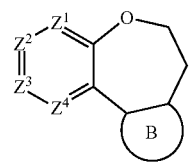

stereoisomers, geometric isomers, tautomers, and pharmaceutically acceptable salts thereof, wherein:

$Z^1$ is $CR^1$ or N;
$Z^2$ is $CR^2$ or N;
$Z^3$ is $CR^3$ or N;
$Z^4$ is $CR^4$ or N;
B is a pyrazolyl, imidazolyl, or triazolyl ring fused to the benzoxepin ring and selected from the structures:

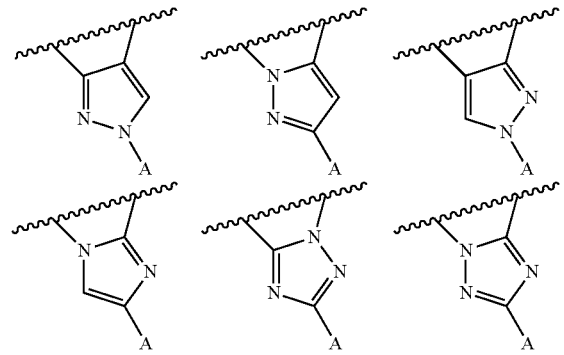

$R^1$, $R^2$, $R^3$, and $R^4$ are independently selected from H, F, Cl, Br, I, —CN, —COR$^{10}$, —CO$_2$R$^{10}$, —C(=O)N (R$^{10}$)OR$^{11}$, —C(=NR$^{10}$)NR$^{10}$R$^{11}$, —C(=O) NR$^{10}$R$^{11}$, —NO$_2$, —NR$^{10}$R$^{11}$, —NR$^{12}$C(=O)R$^{10}$, —NR$^{12}$C(=O)OR$^{11}$, —NR$^{12}$C(=O)NR$^{10}$R$^{11}$, —NR$^{12}$C(=O)(C$_1$-C$_{12}$ alkylene)NR$^{10}$R$^{11}$, —NR$^{12}$ (C$_1$-C$_{12}$ alkylene)NR$^{10}$R$^{11}$, —NR$^{12}$(C$_1$-C$_{12}$ alkylene) OR$^{10}$, —NR$^{12}$(C$_1$-C$_{12}$ alkylene)C(=O)NR$^{10}$R$^{11}$, —OR$^{10}$, —SR$^{10}$, —S(O)$_2$R$^{10}$,
—C(=O)NR$^{10}$(C$_1$-C$_{12}$ alkylene)NR$^{10}$R$^{11}$,
—C(=O)NR$^{10}$(C$_1$-C$_{12}$ alkylene)NR$^{10}$C(=O)OR$^{11}$,
—C(=O)NR$^{10}$(C$_1$-C$_{12}$ alkylene)NR$^{10}$C(=O)R$^{11}$,
—C(=O)NR$^{10}$(C$_1$-C$_{12}$ alkylene)R$^{10}$,
$C_1$-$C_{12}$ alkyl,
$C_2$-$C_8$ alkenyl,
$C_2$-$C_8$ alkynyl,
$C_3$-$C_{12}$ carbocyclyl,
$C_2$-$C_{20}$ heterocyclyl,
$C_6$-$C_{20}$ aryl, $C_1$-$C_{20}$ heteroaryl, —($C_3$-$C_{12}$ carbocyclyl)-($C_1$-$C_{12}$ alkyl),
—($C_2$-$C_{20}$ heterocyclyl)-($C_1$-$C_{12}$ alkyl),
—($C_6$-$C_{20}$ aryl)-($C_1$-$C_{12}$ alkyl),
—($C_1$-$C_{20}$ heteroaryl)-($C_1$-$C_{12}$ alkyl),
—($C_1$-$C_{12}$ alkylene)-($C_3$-$C_{12}$ carbocyclyl),
—($C_1$-$C_{12}$ alkylene)-($C_2$-$C_{20}$ heterocyclyl),
—($C_1$-$C_{12}$ alkylene)-($C_2$-$C_{20}$ heterocyclyl)-($C_2$-$C_{20}$ heterocyclyl),
—($C_1$-$C_{12}$ alkylene)-($C_2$-$C_{20}$ heterocyclyl)-($C_3$-$C_{12}$ carbocyclyl),
—($C_1$-$C_{12}$ alkylene)-($C_2$-$C_{20}$ heterocyclyl)-C(=O)—($C_2$-$C_{20}$ heterocyclyl),
—($C_1$-$C_{12}$ alkylene)-($C_1$-$C_{20}$ heteroaryl),
—($C_1$-$C_{12}$ alkylene)-($C_2$-$C_{20}$ heterocyclyl)-($C_1$-$C_{12}$ alkyl),
—($C_1$-$C_{12}$ alkylene)-($C_6$-$C_{20}$ aryl)-($C_1$-$C_{12}$ alkyl),
—($C_1$-$C_{12}$ alkylene)-($C_1$-$C_{20}$ heteroaryl)-($C_1$-$C_{12}$ alkyl),
—($C_1$-$C_{12}$ alkylene)-C(=O)—($C_2$-$C_{20}$ heterocyclyl),
—($C_1$-$C_{12}$ alkylene)C(=O)OR$^{10}$,
—($C_1$-$C_{12}$ alkylene)C(=O)NR$^{10}$R$^{11}$,
—($C_1$-$C_{12}$ alkylene)-NR$^{10}$R$^{11}$,
—($C_1$-$C_{12}$ alkylene)NR$^{12}$C(=O)R$^{10}$,
—($C_1$-$C_{12}$ alkylene)OR$^{10}$,
—($C_1$-$C_{12}$ alkylene)-NR$^{10}$—($C_1$-$C_{12}$ alkylene)-($C_1$-$C_{20}$ heteroaryl),
—($C_1$-$C_{12}$ alkylene)-NR$^{10}$—($C_1$-$C_{12}$ alkylene)-($C_1$-$C_{20}$ heterocyclyl),
—($C_1$-$C_{12}$ alkylene)-NR$^{10}$—($C_1$-$C_{12}$ alkylene)-NHC(=O)—($C_1$-$C_{20}$ heteroaryl),
—($C_1$-$C_{12}$ alkylene)-($C_2$-$C_{20}$ heterocyclyl)-NR$^{10}$R$^{11}$, and
—($C_1$-$C_{12}$ alkylene)-($C_2$-$C_{20}$ heterocyclyl)-($C_1$-$C_{12}$ alkyl)-NR$^{10}$R$^{11}$, where alkyl, alkenyl, alkynyl, alkylene, carbocyclyl, heterocyclyl, aryl, and heteroaryl are optionally substituted with one or more groups independently selected from F, Cl, Br, I, R$^{10}$, —SR$^{10}$, —S(O)$_2$R$^{10}$, —S(O)$_2$NR$^{10}$R$^{11}$, —NR$^{10}$R$^{11}$, —NR$^{12}$C(O)R$^{10}$, —CO$_2$R$^{10}$, —C(O)R$^{10}$, —CONR$^{10}$R$^{11}$, oxo, and —OR$^{10}$;

A is selected from the structures:

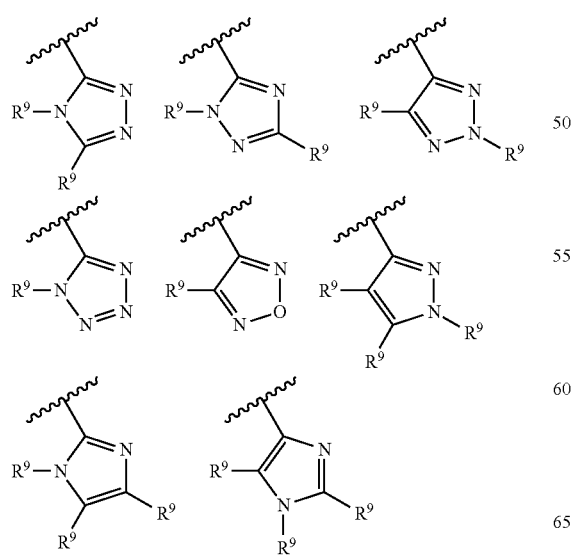

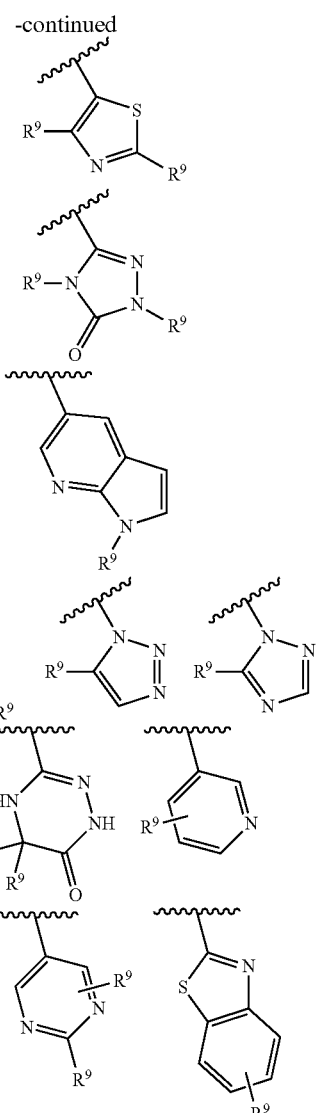

where R$^9$ is independently selected from H, F, Cl, Br, I, —CH$_3$, —CH$_2$CH$_3$, —CH(CH$_3$)$_2$, —C(CH$_3$)$_3$, —CH$_2$CH(CH$_3$)$_2$, —CH$_2$OH, —CH$_2$CO$_2$H, —CH(CH$_3$)CH$_2$OCH$_3$, —CN, —CF$_3$, —CH$_2$CF$_3$, —CH$_2$NH$_2$, —CH$_2$CH$_2$NH$_2$, —C(=O)CH$_3$, —CH$_2$C(=O)NHCH$_3$, —C(=O)NHCH$_3$, —CO$_2$H, —CH$_2$CO$_2$CH$_3$, —NH$_2$, —OH, —OCH$_3$, —SCH$_3$, —S(O)$_2$CH$_3$, cyclopropyl, cyclopropylmethyl, 1-methylpiperid-4-yl, 4-methylpiperazin-1-yl, 4-morpholinyl, morpholin-4-yl-ethyl, benzyl, and phenyl, where benzyl and phenyl are optionally substituted with one or more groups selected from F, Cl, Br, I, —CH$_2$OH, —CH$_2$CO$_2$H, —CN, —CH$_2$NH$_2$, —CH$_3$, —C(=O)CH$_3$, —C(=O)NHCH$_3$, —CO$_2$H, —CH$_2$CO$_2$CH$_3$, —NH$_2$, —OCH$_3$, —S(O)$_2$CH$_3$, 1-methylpiperid-4-yl, 4-methylpiperazin-1-yl, and 4-morpholinyl; and where the wavy line indicates the site of attachment;

R$^5$ is selected from H, and C$_1$-C$_{12}$ alkyl, optionally substituted with one or more groups independently selected from F, Cl, Br, I, —CN, —CO$_2$H, —CONH$_2$, —CONHCH$_3$, —NH$_2$, —NO$_2$, —N(CH$_3$)$_2$, —NHCOCH$_3$, —NHS(O)$_2$CH$_3$, —OH, —OCH$_3$, —OCH$_2$CH$_3$, —S(O)$_2$NH$_2$, and —S(O)$_2$CH$_3$;

R$^6$ is selected from C$_1$-C$_{12}$ alkyl, C$_3$-C$_{12}$ carbocyclyl, C$_2$-C$_{20}$ heterocyclyl, C$_1$-C$_{20}$ heteroaryl, and C$_6$-C$_{20}$ aryl, each optionally substituted with one or more groups independently selected from F, Cl, Br, I, —CH$_3$, —CH$_2$OH, —CH$_2$C$_6$H$_5$, —CN, —CF$_3$, —CO$_2$H, —C(O)CH$_3$, —NH$_2$, —NO$_2$, —N(CH$_3$)$_2$, —NHCOCH$_3$, —NHS(O)$_2$CH$_3$, —OH, oxo, —OCH$_3$, —OCH$_2$CH$_3$, —S(O)$_2$NH$_2$, —S(O)$_2$CH$_3$, —C(=O)NR$^{10}$(C$_1$-C$_{12}$ alkylene)NR$^{10}$R$^{11}$, phenyl, pyridinyl, tetrahydro-furan-2-yl, 2,3-dihydro-benzofuran-2-yl, 1-isopropyl-pyrrolidin-3-ylmethyl, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, —C≡CR$^{13}$, —CH=CHR$^{13}$, and —C(=O)NR$^{10}$R$^{11}$;

or R$^5$ and R$^6$ together with the nitrogen atom to which they are attached form C$_2$-C$_{20}$ heterocyclyl or C$_1$-C$_{20}$ heteroaryl, optionally substituted with one or more groups selected from F, Cl, Br, I, CH$_3$, C(CH$_3$)$_3$, —CH$_2$OH, —CH$_2$CH$_2$OH, —CH$_2$C$_6$H$_5$, pyridin-2-yl, 6-methyl-pyridin-2-yl, pyridin-4-yl, pyridin-3-yl, pyrimidin-2-yl, pyrazin-2-yl, tetrahydro-furan-carbonyl, 2-methoxy-phenyl, benzoyl, cyclopropylmethyl, (tetrahydrofuran-2-yl)methyl, 2,6-dimethyl-morpholin-4-yl, 4-methyl-piperazine-carbonyl, pyrrolidine-1-carbonyl, cyclopropanecarbonyl, 2,4-difluoro-phenyl, pyridin-2-ylmethyl, morpholin-4-yl, —CN, —CF$_3$, —CO$_2$H, —CONH$_2$, —CONHCH$_3$, —CON(CH$_3$)$_2$, —COCF$_3$, —COCH$_3$, —COCH(CH$_3$)$_2$, —NO$_2$, NHCH$_3$, —N(CH$_3$)$_2$, —N(CH$_2$CH$_3$)$_2$, —NHCOCH$_3$, —NCH$_3$COCH$_3$, —NHS(O)$_2$CH$_3$, —OH, —OCH$_3$, —OCH$_2$CH$_3$, —CH$_2$OCH$_3$, —CH$_2$CH$_2$OCH$_3$, —CH$_2$S(O)$_2$NHCH$_3$, —CH$_2$S(O)$_2$CH$_2$CH$_3$, —S(O)$_2$NHCH$_3$, —S(O)$_2$CH$_2$CH$_3$, —S(O)$_2$NH$_2$, —S(O)$_2$N(CH$_3$)$_2$ and —S(O)$_2$CH$_3$;

R$^{10}$, R$^{11}$ and R$^{12}$ are independently selected from H, C$_1$-C$_{12}$ alkyl, —(C$_1$-C$_{12}$ alkylene)-(C$_2$-C$_{20}$ heterocyclyl), —(C$_1$-C$_{12}$ alkylene)-(C$_6$-C$_{20}$ aryl), —(C$_1$-C$_{12}$ alkylene)-(C$_3$-C$_{12}$ carbocyclyl), C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl, each of which are optionally substituted with one or more groups independently selected from F, Cl, Br, I, —CH$_3$, —CH$_2$CH$_3$, —CH(CH$_3$)$_2$, —CH$_2$OH, —CH$_2$OCH$_3$, —CH$_2$CH$_2$OH, —C(CH$_3$)$_2$OH, —CH$_2$C(CH$_3$)$_2$OH, —CH$_2$CH(CH$_3$)OH, —CH$_2$CO$_2$H, —CH$_2$CO$_2$CH$_3$, —CH$_2$NH$_2$, —(CH$_2$)$_2$N(CH$_3$)$_2$, —CH$_2$C$_6$H$_5$, —CN, —CF$_3$, —CO$_2$H, —C(O)CH$_3$, —C(O)CH(OH)CH$_3$, —CO$_2$CH$_3$, —CONH$_2$, —CONHCH$_3$, —CON(CH$_3$)$_2$, —C(CH$_3$)$_2$CONH$_2$, —NH$_2$, —NO$_2$, —N(CH$_3$)$_2$, —N(CH$_3$)C(CH$_3$)$_2$CONH$_2$, —N(CH$_3$)CH$_2$CH$_2$S(O)$_2$CH$_3$, —NHCOCH$_3$, —NHS(O)$_2$CH$_3$, =O (oxo), —OH, —OCH$_3$, —OCH$_2$CH$_3$, —OCH$_2$CH$_2$OH, —OP(O)(OH)$_2$, —SCH$_3$, —S(O)$_2$CH$_3$, —S(O)$_2$NH$_2$, —S(O)$_2$N(CH$_3$)$_2$, —CH$_2$S(O)$_2$NHCH$_3$, —CH$_2$S(O)$_2$CH$_2$CH$_3$, —S(O)$_2$NHCH$_3$, —S(O)$_2$CH$_2$CH$_3$, pyrrolidin-1-yl, 2-oxopyrrolidin-1-yl, cyclopropyl, cyclopentyl, oxetanyl, 4-methylpiperazin-1-yl, and 4-morpholinyl;

or R$^{10}$ and R$^{11}$ together with the nitrogen atom to which they are attached form a C$_2$-C$_{20}$ heterocyclyl ring or C$_1$-C$_{20}$ heteroaryl each of which are optionally substituted with one or more groups independently selected from F, Cl, Br, I, —CH$_3$, —CH$_2$OH, —CH$_2$C$_6$H$_5$, —CN, —CF$_3$, —CO$_2$H, —CONH$_2$, —CONHCH$_3$, —NO$_2$, —N(CH$_3$)$_2$, —NHCOCH$_3$, —NHS(O)$_2$CH$_3$, —OH, oxo, —OCH$_3$, —OCH$_2$CH$_3$, —S(O)$_2$NH$_2$, —S(O)$_2$CH$_3$, —CH(CH$_3$)$_2$, —CH$_2$CF$_3$, —CH$_2$CH$_2$OH and —C(CH$_3$)$_2$OH; and R$^{13}$ is selected from H, F, Cl, Br, I, —CH$_3$, —CH$_2$CH$_3$, —CN, —CF$_3$, —CH$_2$N(CH$_3$)$_2$, —CH$_2$OH, —CO$_2$H, —CONH$_2$, —CON(CH$_3$)$_2$, —NO$_2$, and —S(O)$_2$CH$_3$.

2. The compound of claim 1 having Formula Ia:

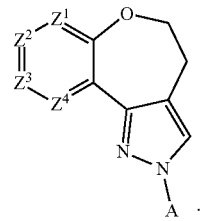

Ia

3. The compound of claim 1 having Formula Ib:

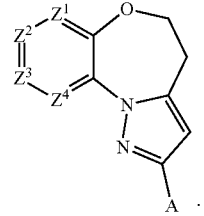

Ib

4. The compound of claim 1 having Formula Ic:

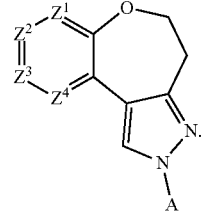

Ic

5. The compound of claim 1 having Formula Ie:

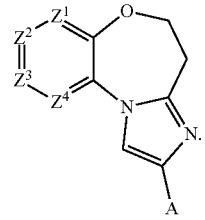

Ie

6. The compound of claim 1 having Formula If:

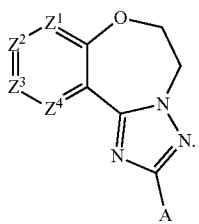

If

7. The compound of claim 1 having Formula Ig:

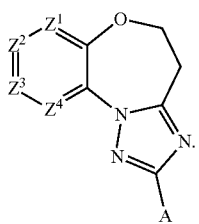

Ig

8. A compound selected from Formula I:

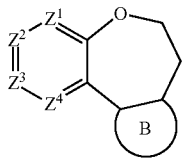

stereoisomers, geometric isomers, tautomers, and pharmaceutically acceptable salts thereof, wherein:
$Z^1$ is $CR^1$ or N;
$Z^2$ is $CR^2$ or N;
$Z^3$ is $CR^3$ or N;
$Z^4$ is $CR^4$ or N;
B is a pyrazolyl, imidazolyl, or triazolyl ring fused to the benzoxepin ring and selected from the structures:

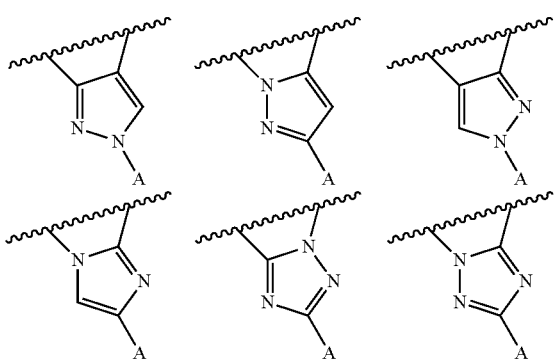

$R^1$, $R^2$, $R^3$, and $R^4$ are independently selected from H, F, Cl, Br, I, —CN, —$COR^{10}$, —$CO_2R^{10}$, —C(=O)N($R^{10}$)$OR^{11}$, —C(=$NR^{10}$)$NR^{10}R^{11}$, —$NO_2$, —$NR^{10}R^{11}$, —$NR^{12}C$(=O)$R^{10}$, —$NR^{12}C$(=O)$OR^{11}$, —$NR^{12}C$(=O)$NR^{10}R^{11}$, —$NR^{12}C$(=O)($C_1$-$C_{12}$alkylene)$NR^{10}R^{11}$, —$NR^{12}$($C_1$-$C_{12}$ alkylene)$NR^{10}R^{11}$, —$NR^{12}$($C_3$-$C_{12}$ alkylene)$OR^{10}$, —$NR^{12}$($C_1$-$C_{12}$ alkylene)C(=O)$NR^{10}R^{11}$, —$OR^{10}$, —$SR^{10}$, —S(O)$_2R^{10}$,
—C(=O)$NR^{10}$($C_1$-$C_{12}$alkylene)$NR^{10}R^{11}$,
—C(=O)$NR^{10}$($C_1$-$C_{12}$alkylene)$NR^{10}C$(=O)$OR^{11}$,
—C(=O)$NR^{10}$($C_1$-$C_{12}$alkylene)$NR^{10}C$(=O)$R^{11}$,
—C(=O)$NR^{10}$($C_1$-$C_{12}$ alkylene)$R^{10}$,
$C_1$-$C_{12}$ alkyl,
$C_2$-$C_8$ alkenyl,
$C_2$-$C_8$ alkynyl,
$C_3$-$C_{12}$ carbocyclyl,
$C_2$-$C_{20}$ heterocyclyl,
$C_6$-$C_{20}$ aryl,
$C_1$-$C_{20}$ heteroaryl,
—($C_3$-$C_{12}$ carbocyclyl)-($C_1$-$C_{12}$ alkyl),
—($C_2$-$C_{20}$ heterocyclyl)-($C_1$-$C_{12}$ alkyl),
—($C_6$-$C_{20}$ aryl)-($C_1$-$C_{12}$ alkyl),
—($C_1$-$C_{20}$ heteroaryl)-($C_1$-$C_{12}$ alkyl),
—($C_1$-$C_{12}$ alkylene)-($C_3$-$C_{12}$ carbocyclyl),
—($C_1$-$C_{12}$ alkylene)-($C_2$-$C_{20}$ heterocyclyl),
—($C_1$-$C_{12}$ alkylene)-($C_2$-$C_{20}$ heterocyclyl)-($C_2$-$C_{20}$ heterocyclyl),
—($C_1$-$C_{12}$ alkylene)-($C_2$-$C_{20}$ heterocyclyl)-($C_3$-$C_{12}$ carbocyclyl),
—($C_1$-$C_{12}$ alkylene)-($C_2$-$C_{20}$ heterocyclyl)-C(=O)—($C_2$-$C_{20}$ heterocyclyl),
—($C_1$-$C_{12}$ alkylene)-($C_1$-$C_{20}$ heteroaryl),
—($C_1$-$C_{12}$ alkylene)-($C_2$-$C_{20}$ heterocyclyl)-($C_1$-$C_{12}$ alkyl),
—($C_1$-$C_{12}$ alkylene)-($C_6$-$C_{20}$ aryl)-($C_1$-$C_{12}$ alkyl),
—($C_1$-$C_{12}$ alkylene)-($C_1$-$C_{20}$ heteroaryl)-($C_1$-$C_{12}$ alkyl),
—($C_1$-$C_{12}$ alkylene)-C(=O)—($C_2$-$C_{20}$ heterocyclyl),
—($C_1$-$C_{12}$ alkylene)C(=O)$OR^{10}$,
—($C_1$-$C_{12}$ alkylene)C(=O)$NR^{10}R^{11}$,
—($C_1$-$C_{12}$ alkylene)-$NR^{10}R^{11}$,
—($C_1$-$C_{12}$ alkylene)$NR^{10}C$(=O)$R^{10}$,
—($C_1$-$C_{12}$ alkylene)$OR^{10}$,
—($C_1$-$C_{12}$ alkylene)-$NR^{10}$—($C_1$-$C_{12}$ alkylene)-($C_1$-$C_{20}$ heteroaryl),
—($C_1$-$C_{12}$ alkylene)-$NR^{10}$—($C_1$-$C_{12}$ alkylene)-($C_1$-$C_{20}$ heterocyclyl),
—($C_1$-$C_{12}$ alkylene)-$NR^{10}$—($C_1$-$C_{12}$ alkylene)-NHC(=O)—($C_1$-$C_{20}$ heteroaryl),
—($C_1$-$C_{12}$ alkylene)-($C_2$-$C_{20}$ heterocyclyl)-$NR^{10}R^{11}$, and
—($C_1$-$C_{12}$ alkylene)-($C_2$-$C_{20}$ heterocyclyl)-($C_1$-$C_{12}$ alkyl)-$NR^{10}R^{11}$,
where alkyl, alkenyl, alkynyl, alkylene, carbocyclyl, heterocyclyl, aryl, and heteroaryl are optionally substituted with one or more groups independently selected from F, Cl, Br, I, $R^{10}$, —$SR^{10}$, —S(O)$_2R^{10}$, —S(O)$_2NR^{10}R^{11}$, —$NR^{10}R^{11}$, —$NR^{12}C$(O)$R^{10}$, —$CO_2R^{10}$, —,C(O)$R^{10}$, —$CONR^{10}R^{11}$, oxo, and —$OR^{10}$;
A is selected from the structures:

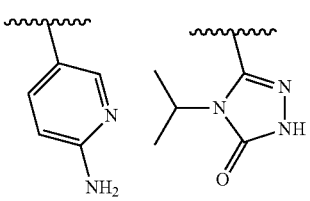

585
-continued
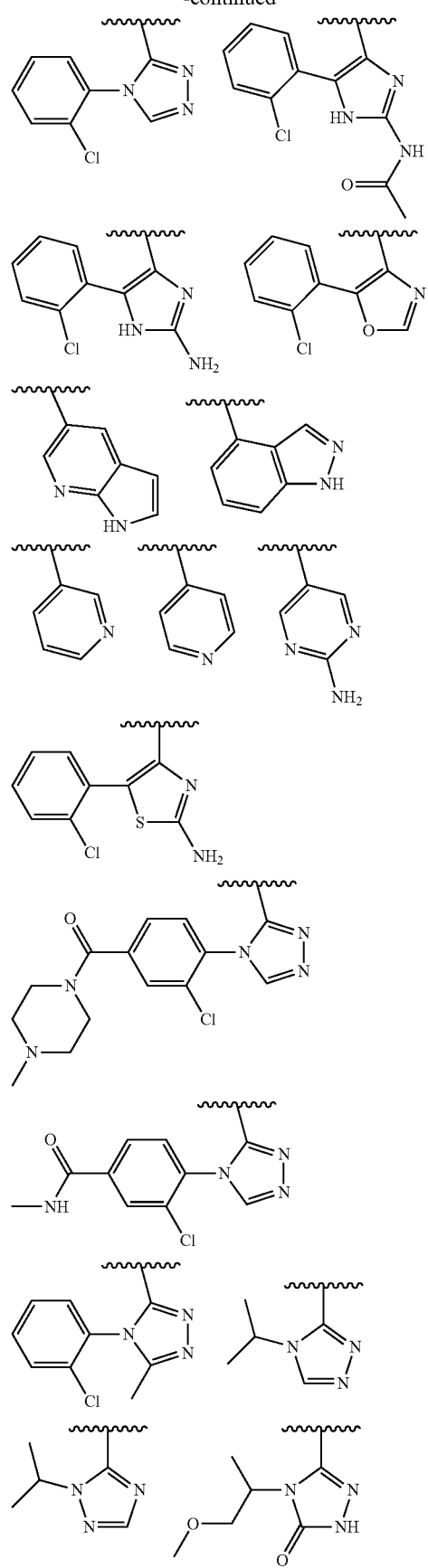
586
-continued
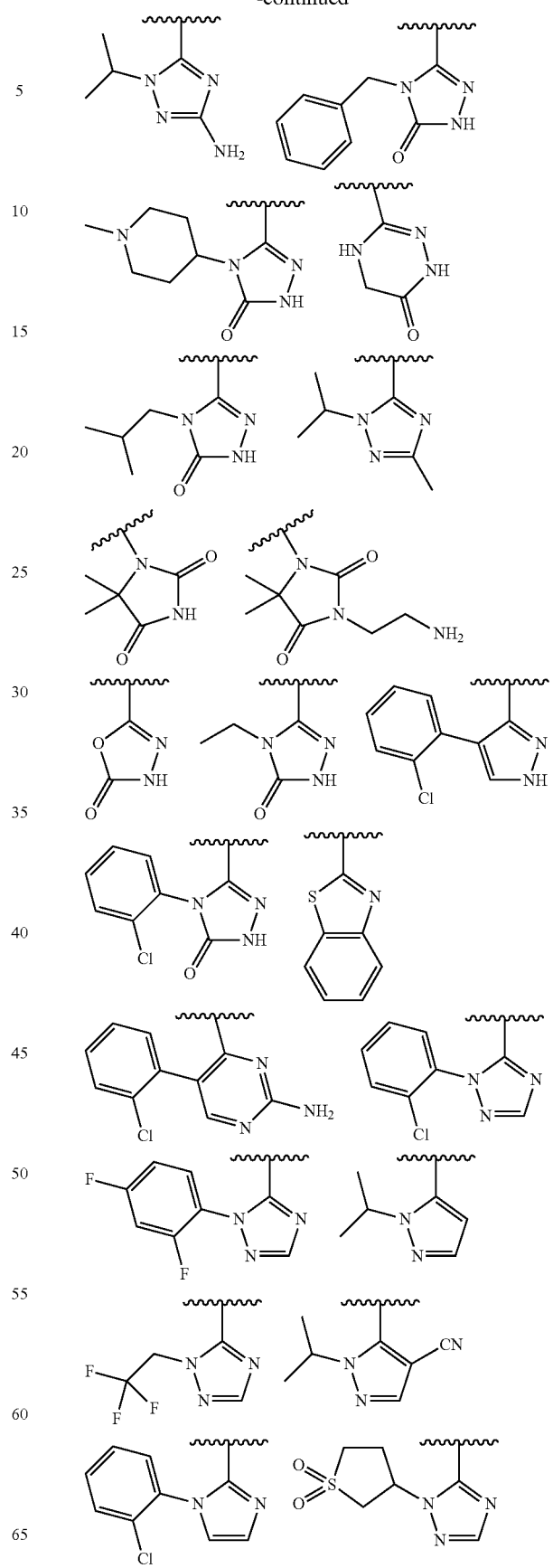

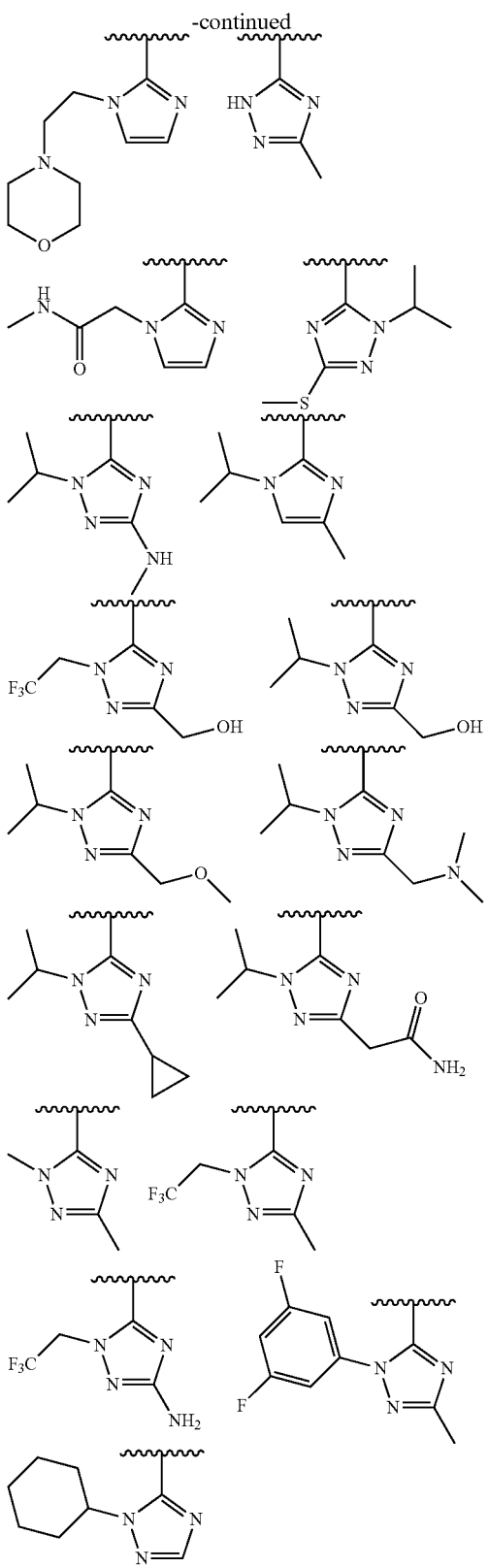

where the wavy line indicates the site of attachment;
R$^5$ is selected from H, and C$_1$-C$_{12}$ alkyl, optionally substituted with one or more groups independently selected from F, Cl, Br, I, —CN, —CO$_2$H, —CONH$_2$, —CONHCH$_3$, —NH$_2$, —NO$_2$, —N(CH$_3$)$_2$, —NHCOCH$_3$, —NHS(O)$_2$CH$_3$, —OH, —OCH$_3$, —OCH$_2$CH$_3$, —S(O)$_2$NH$_2$, and —S(O)$_2$CH$_3$;

R$^6$ is selected from C$_1$-C$_{12}$ alkyl, C$_3$-C$_{12}$ carbocyclyl, C$_2$-C$_{20}$ heterocyclyl, C$_1$-C$_{20}$ heteroaryl, and C$_6$-C$_{20}$ aryl, each optionally substituted with one or more groups independently selected from F, Cl, Br, I, —CH$_3$, —CH$_2$OH, —CH$_2$C$_6$H$_5$, —CN, —CF$_3$, —CO$_2$H, —C(O)CH$_3$, —NH$_2$, —NO$_2$, —N(CH$_3$)$_2$, —NHCOCH$_3$, —NHS(O)$_2$CH$_3$, —OH, oxo, —OCH$_3$, —OCH$_2$CH$_3$, —S(O)$_2$NH$_2$, —S(O)$_2$CH$_3$, —C(=O)NR$^{10}$(C$_1$-C$_{12}$ alkylene)NR$^{10}$R$^{11}$, phenyl, pyridinyl, tetrahydro-furan-2-yl, 2,3-dihydro-benzofuran-2-yl, 1-isopropyl-pyrrolidin-3-ylmethyl, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, —C=CR$^{13}$, —CH=CHR$^{13}$, and —C(=O)NR$^{10}$R$^{11}$;

or R$^5$ and R$^6$ together with the nitrogen atom to which they are attached form C$_2$-C$_{20}$ heterocyclyl or C$_1$-C$_{20}$ heteroaryl, optionally substituted with one or more groups selected from F, Cl, Br, I, CH$_3$, C(CH$_3$)$_3$, —CH$_2$OH, —CH$_2$CH$_2$OH, —CH$_2$C$_6$H$_5$, pyridin-2-yl, 6-methyl-pyridin-2-yl, pyridin-4-yl, pyridin-3-yl, pyrimidin-2-yl, pyrazin-2-yl, tetrahydro-furan-carbonyl, 2-methoxy-phenyl, benzoyl, cyclopropylmethyl, (tetrahydrofuran-2-yl)methyl, 2,6-dimethyl-morpholin-4-yl, 4-methyl-piperazine-carbonyl, pyrrolidine-1-carbonyl, cyclopropanecarbonyl, 2,4-difluoro-phenyl, pyridin-2-ylmethyl, morpholin-4-yl, —CN, —CF$_3$, —CO$_2$H, —CONH$_2$, —CONHCH$_3$, —CON(CH$_3$)$_2$, —COCF$_3$, —COCH$_3$, —COCH(CH$_3$)$_2$, —NO$_2$, NHCH$_3$, —N(CH$_3$)$_2$, —N(CH$_2$CH$_3$)$_2$, —NHCOCH$_3$, —NCH$_3$COCH$_3$, —NHS(O)$_2$CH$_3$, —OH, —OCH$_3$, —OCH$_2$CH$_3$, —CH$_2$OCH$_3$, —CH$_2$CH$_2$OCH$_3$, —CH$_2$S(O)$_2$NHCH$_3$, —CH$_2$S(O)$_2$CH$_2$CH$_3$, —S(O)$_2$NHCH$_3$, —S(O)$_2$CH$_2$CH$_3$, —S(O)$_2$NH$_2$, —S(O)$_2$N(CH$_3$)$_2$ and —S(O)$_2$CH$_3$;

R$^{10}$, R$^{11}$ and R$^{12}$ are independently selected from H, C$_1$-C$_{12}$ alkyl, —(C$_1$-C$_{12}$ alkylene)-(C$_2$-C$_{20}$ heterocyclyl), —(C$_1$-C$_{12}$ alkylene)-(C$_6$-C$_{20}$ aryl), —(C$_1$-C$_{12}$ alkylene)-(C$_3$-C$_{12}$ carbocyclyl), C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl, each of which are optionally substituted with one or more groups independently selected from F, Cl, Br, I, —CH$_3$, —CH$_2$CH$_3$, —CH(CH$_3$)$_2$, —CH$_2$OH, —CH$_2$OCH$_3$, —CH$_3$CH$_2$OH, —C(CH$_3$)$_2$OH, —CH$_2$C(CH$_3$)$_2$OH, —CH$_2$CH(CH$_3$)OH, —CH$_2$CO$_2$H, —CH$_2$CO$_2$CH$_3$, —CH$_3$NH$_2$, —(CH$_3$)$_2$N(CH$_3$)$_2$, —CH$_2$C$_6$H$_5$, —CN, —CF$_3$, —CO$_2$H, —C(O)CH$_3$, —C(O)CH(OH)CH$_3$, —CO$_2$CH$_3$, —CONH$_2$, —CONHCH$_3$, —CON(CH$_3$)$_2$, —C(CH$_3$)$_2$CONH$_2$, —NH$_2$, —NO$_2$, —N(CH$_3$)$_2$, —N(CH$_3$)C(CH$_3$)$_2$CONH$_2$, —N(CH$_3$)CH$_2$CH$_2$S(O)$_2$CH$_3$, —NHCOCH$_3$, —NHS(O)$_2$CH$_3$, =O (oxo), —OH, —OCH$_3$, —OCH$_2$CH$_3$, —OCH$_2$CH$_2$OH, —OP(O)(OH)$_2$, —SCH$_3$, —S(O)$_2$CH$_3$, —S(O)$_2$NH$_2$, —S(O)$_2$N(CH$_3$)$_2$, —CH$_2$S(O)$_2$NHCH$_3$, —CH$_2$S(O)$_2$CH$_2$CH$_3$, —S(O)$_2$NHCH$_3$, —S(O)$_2$CH$_2$CH$_3$, pyrrolidin-1-yl, 2-oxopyrrolidin-1-yl, cyclopropyl, cyclopentyl, oxetanyl, 4-methylpiperazin-1-yl, and 4-morpholinyl;

or R$^{10}$ and R$^{11}$ together with the nitrogen atom to which they are attached form a C$_2$-C$_{20}$ heterocyclyl ring or C$_1$-C$_{20}$ heteroaryl each of which are optionally substituted with one or more groups independently selected from F, Cl, Br, I, —CH$_3$, —CH$_2$OH, —CH$_2$C$_6$H$_5$, —CN, —CF$_3$, —CO$_2$H, —CONH$_2$, —CONHCH$_3$, —NO$_2$, —N(CH$_3$)$_2$, —NHCOCH$_3$, —NHS(O)$_2$CH$_3$, —OH, oxo, —OCH$_3$, —OCH$_2$CH$_3$, —S(O)$_2$NH$_2$, —S(O)$_2$CH$_3$, —CH(CH$_3$)$_2$, —CH$_2$CF$_3$, —CH$_2$CH$_2$OH and —C(CH$_3$)$_2$OH; and R$^{13}$ is selected from H, F, Cl, Br, I, —CH$_3$, —CH$_2$CH$_3$, —CN, —CF$_3$, —CH$_2$N(CH$_3$)$_2$, —CH$_3$OH, —CO$_2$H, —CONH$_2$, —CON(CH$_3$)$_2$, —NO$_2$, and —S(O)$_2$CH$_3$.

\* \* \* \* \*